US012528818B2

(12) United States Patent
Wang et al.

(10) Patent No.: US 12,528,818 B2
(45) Date of Patent: Jan. 20, 2026

(54) COMPOSITIONS AND METHODS FOR INHIBITION OF RAS

(71) Applicants: Leidos Biomedical Research, Inc., Frederick, MD (US); Lawrence Livermore National Security, LLC, Livermore, CA (US); TheRas, Inc., South San Francisco, CA (US)

(72) Inventors: Bin Wang, Dallas, TX (US); Rui Xu, Dallas, TX (US); Eli Wallace, Loveland, CO (US); Zuhui Zhang, Millbrae, CA (US); David Michael Turner, Frederick, MD (US); Anna Elzbieta Maciag, Frederick, MD (US); Dhirendra Kumar Simanshu, Frederick, MD (US); Albert Hay Wah Chan, Frederick, MD (US); Tao Liao, Frederick, MD (US); Christopher John Brassard, Frederick, MD (US); Yue Yang, Foster City, CA (US); Paola Bisignano, San Francisco, CA (US); Felice Lightstone, Fremont, CA (US)

(73) Assignees: Leidos Biomedical Research, Inc., Frederick, MD (US); Lawrence Livermore National Security, LLC, Livermore, CA (US); TheRas, Inc., South San Francisco, CA (US)

( * ) Notice: Subject to any disclaimer, the term of this patent is extended or adjusted under 35 U.S.C. 154(b) by 0 days.

(21) Appl. No.: 19/196,683

(22) Filed: May 1, 2025

(65) Prior Publication Data

US 2025/0270225 A1 Aug. 28, 2025

Related U.S. Application Data

(63) Continuation of application No. 18/291,432, filed as application No. PCT/US2022/037992 on Jul. 22, 2022.

(60) Provisional application No. 63/329,237, filed on Apr. 8, 2022, provisional application No. 63/225,407, filed on Jul. 23, 2021.

(51) Int. Cl.

| | |
|---|---|
| ***C07D 239/80*** | (2006.01) |
| ***A61K 31/517*** | (2006.01) |
| ***A61K 31/551*** | (2006.01) |
| ***C07D 409/04*** | (2006.01) |
| ***C07D 409/14*** | (2006.01) |
| ***C07D 413/14*** | (2006.01) |
| ***C07D 417/04*** | (2006.01) |
| ***C07D 417/14*** | (2006.01) |
| ***C07D 471/08*** | (2006.01) |
| ***C07D 471/10*** | (2006.01) |
| ***C07D 487/04*** | (2006.01) |
| ***C07D 487/10*** | (2006.01) |
| ***C07D 519/00*** | (2006.01) |

(52) U.S. Cl.

CPC .......... *C07D 487/10* (2013.01); *A61K 31/517* (2013.01); *A61K 31/551* (2013.01); *C07D 409/04* (2013.01); *C07D 409/14* (2013.01); *C07D 413/14* (2013.01); *C07D 417/04* (2013.01); *C07D 417/14* (2013.01); *C07D 471/08* (2013.01); *C07D 471/10* (2013.01); *C07D 487/04* (2013.01); *C07D 519/00* (2013.01)

(58) Field of Classification Search

CPC ............................ C07D 239/80; A61K 31/517

USPC ...................................... 544/283; 514/252.17

See application file for complete search history.

(56) References Cited

U.S. PATENT DOCUMENTS

| | | | |
|---|---|---|---|
| 9,840,516 | B2 | 12/2017 | Li et al. |
| 10,023,588 | B2 | 7/2018 | Ostrem et al. |
| 10,111,874 | B2 | 10/2018 | Janes et al. |
| 10,246,424 | B2 | 4/2019 | Li et al. |
| 10,414,757 | B2 | 9/2019 | Li et al. |
| 11,008,334 | B2 | 5/2021 | Ostrem et al. |
| 11,603,376 | B2 | 3/2023 | Ostrem et al. |
| 11,718,630 | B2 | 8/2023 | Ostrem et al. |
| 11,891,402 | B2 | 2/2024 | Ostrem et al. |
| 12,116,375 | B2 | 10/2024 | Ostrem et al. |
| 2023/0002382 | A1 | 1/2023 | Xie et al. |
| 2023/0174526 | A1 | 6/2023 | Wan et al. |
| 2023/0365563 | A1 | 11/2023 | Zhang et al. |
| 2024/0109893 | A1 | 4/2024 | Tian et al. |

(Continued)

FOREIGN PATENT DOCUMENTS

| | | | |
|---|---|---|---|
| CN | 112110918 | A | 12/2020 |
| CN | 113754653 | A | 12/2021 |
| CN | 113 999 226 | A | 2/2022 |

(Continued)

OTHER PUBLICATIONS

Garske, A. L. et al., Chemical genetic strategy for targeting protein kinases based on covalent complementarity, PNAS, 108(37):15046-15052 (2011).

International Search Report for PCT/US2022/037992, filed Jul. 22, 2022, 8 pages, (mailed Jan. 23, 2023).

Invitation to Pay Additional Fees for PCT/US2022/037992, filed Jul. 22, 2022, 13 pages, (mailed Dec. 1, 2022).

Written Opinion for PCT/US2022/037992, filed Jul. 22, 2022, 10 pages, (mailed Jan. 23, 2023).

(Continued)

*Primary Examiner* — Charanjit Aulakh

(74) *Attorney, Agent, or Firm* — Choate, Hall & Stewart LLP; Kristen C. Buteau; Lauren E. Markham

(57) ABSTRACT

Provided herein are compounds, or salts, esters, tautomers, prodrugs, zwitterionic forms, or stereoisomers thereof, as well as pharmaceutical compositions comprising the same. Also provided herein are methods of using the same in modulating (e.g., inhibiting) KRAS (e.g., KRAS having a G12C mutation) and treating diseases or disorders such as cancers in subjects in need thereof.

16 Claims, No Drawings

(56) References Cited

U.S. PATENT DOCUMENTS

| | | | |
|---|---|---|---|
| 2024/0300964 | A1 | 9/2024 | Wang et al. |
| 2025/0154133 | A1 | 5/2025 | Li et al. |

FOREIGN PATENT DOCUMENTS

| | | | | |
|---|---|---|---|---|
| CN | 115433179 A | 12/2022 | | |
| WO | WO-2013/155223 A1 | 10/2013 | | |
| WO | WO-2014/152588 A1 | 9/2014 | | |
| WO | WO-2015/054572 A1 | 4/2015 | | |
| WO | WO-2016/044772 A1 | 3/2016 | | |
| WO | WO-2016/049568 A1 | 3/2016 | | |
| WO | WO-2016/164675 A1 | 10/2016 | | |
| WO | WO-2017/087528 A1 | 5/2017 | | |
| WO | WO-2017/100546 A1 | 6/2017 | | |
| WO | WO-2017/172979 A1 | 10/2017 | | |
| WO | WO-2018/218069 A1 | 11/2018 | | |
| WO | WO-2018/218070 A2 | 11/2018 | | |
| WO | WO-2020/081282 A1 | 4/2020 | | |
| WO | WO-2020/097537 A2 | 5/2020 | | |
| WO | WO-2021/108683 A1 | 6/2021 | | |
| WO | WO-2021/129820 A1 | 7/2021 | | |
| WO | WO-2021/218110 A1 | 11/2021 | | |
| WO | WO-2022/002018 A1 | 1/2022 | | |
| WO | WO-2022/002102 A1 | 1/2022 | | |
| WO | WO-2022/047260 A1 | 3/2022 | | |
| WO | WO-2022/061251 A1 | 3/2022 | | |
| WO | WO-2022/068921 A1 | 4/2022 | | |
| WO | WO-2022/083616 A1 | 4/2022 | | |
| WO | WO-2022/093856 A1 | 5/2022 | | |
| WO | WO-2022/105855 A1 | 5/2022 | | |
| WO | WO-2022/119748 A1 | 6/2022 | | |
| WO | WO-2022/135470 A1 | 6/2022 | | |
| WO | WO 2022/148422 A1 | 7/2022 | | |
| WO | WO-2022/156792 A1 | 7/2022 | | |
| WO | WO 2022/177917 A2 * | 8/2022 | ........... | A61K 31/517 |
| WO | WO-2022/251576 A1 | 12/2022 | | |
| WO | WO-2022/261154 A1 | 12/2022 | | |
| WO | WO-2023/004102 A2 | 1/2023 | | |
| WO | WO-2023/018699 A1 | 2/2023 | | |
| WO | WO-2023/133181 A1 | 7/2023 | | |
| WO | WO-2023/133183 A1 | 7/2023 | | |
| WO | WO-2023/141300 A1 | 7/2023 | | |
| WO | WO-2023/150284 A2 | 8/2023 | | |
| WO | WO-2023/179703 A1 | 9/2023 | | |
| WO | WO-2023/215801 A1 | 11/2023 | | |
| WO | WO-2023/225252 A1 | 11/2023 | | |
| WO | WO-2024/030633 A1 | 2/2024 | | |
| WO | WO-2024/030647 A1 | 2/2024 | | |
| WO | WO-2024/158778 A1 | 8/2024 | | |
| WO | WO-2025/117828 A1 | 6/2025 | | |

OTHER PUBLICATIONS

Ebright, R. Y. et al., Response and Resistance to RAS Inhibition in Cancer, Cancer Discov., 15(7):1325-1349 (2025).

International Search Report for PCT/US2022/016487, 9 pages (mailed Aug. 19, 2022).

International Search Report for PCT/US2023/010172, 4 pages (mailed May 11, 2023).

International Search Report for PCT/US2023/010176, 4 pages (mailed May 11, 2023).

International Search Report for PCT/US2023/029520, 7 pages (mailed Dec. 21, 2023).

International Search Report for PCT/US2023/029537, 5 pages (mailed Nov. 23, 2023).

International Search Report for PCT/US2024/012559, 11 pages (mailed Jun. 21, 2024).

International Search Report for PCT/US2024/057867, 4 pages (mailed Mar. 5, 2025).

Maciag, A. E. et al. Discovery of BBO-8520, a First-In-Class Direct and Covalent Dual Inhibitor of GTP-Bound (ON) and GDP-Bound (OFF) KRASG12C, Cancer Discov., 579-594 (2025).

McGregor, L. M. et al. Expanding the Scope of Electrophiles Capable of Targeting K-Ras Oncogenes, Biochem., 56(25):3178-3183 (2017).

Mei, R. et al., Oxazolinyl-Assisted C-H Amidation by Cobalt (III) Catalysis, ACS Catalysis, 6(2):793-797 (2016).

Ostrem, J. M. et al., K-Ras(G12C) inhibitors allosterically control GTP affinity and effector interactions, Nature, 503(7477):548-551 (2013).

Rosell, R. et al., KRAS G12C-mutant driven non-small cell lung cancer (NSCLC), Crit. Rev. Oncol. Hem., 195(104228):1-19 (2024).

Uras, I. Z. et al., Targeting KRAS Mutant Non-Small-Cell Lung Cancer: Past, Present and Future, Int. J. Mol. Sci., 21:4325-4355 (2020).

Wouters, R. et al., A Scaffold-Hopping Strategy toward the Identification of Inhibitors of Cyclin G Associated Kinase, ChemMedChem, 14(2):237-254 (2018).

Written Opinion for PCT/US2022/016487, 25 pages (mailed Aug. 19, 2022).

Written Opinion for PCT/US2023/010172, filed Jan. 5, 2023, 6 pages (mailed May 11, 2023).

Written Opinion for PCT/US2023/010176, 6 pages (mailed May 11, 2023).

Written Opinion for PCT/US2023/029520, 14 pages (mailed Dec. 21, 2023).

Written Opinion for PCT/US2023/029537, 9 pages (mailed Nov. 23, 2023).

Written Opinion for PCT/US2024/012559, 12 pages (mailed Jun. 21, 2024).

Written Opinion for PCT/US2024/057867, 13 pages (mailed Mar. 5, 2025).

Xu, J. et al., Atroposelective Negishi Coupling Optimization Guided by Multivariate Linear Regression Analysis: Asymmetric Synthesis of KRAS G12C Covalent Inhibitor GDC-6036, Jrnl. Ameri. Chem. Soc., 144(45):20955-20963 (2022).

Zhou, Z. and Westover, K. D., Beyond First-Generation KRAS Inhibitors: BBO-8520 Tests the Dual Mechanism Hypothesis, Cancer Discov., 455-457 (2025).

* cited by examiner

COMPOSITIONS AND METHODS FOR INHIBITION OF RAS

RELATED APPLICATIONS

This application claims priority to and benefit of U.S. Application No. 63/225,407, filed Jul. 23, 2021, and U.S. Application No. 63/329,237, filed Apr. 8, 2022, the entire contents of each of which are hereby incorporated by reference.

STATEMENT AS TO RIGHTS TO INVENTIONS MADE UNDER FEDERALLY SPONSORED RESEARCH AND DEVELOPMENT

This invention was made with government support under (1) Contract No.: 75N91019D00024 awarded by the National Institutes of Health and (2) Contract No. DE-AC52-07NA27344 awarded by the United States Department of Energy. The government has certain rights in the invention.

BACKGROUND

RAS mutations occur in approximately 20-30% of human cancers, including the majority of pancreatic ductal adenocarcinoma (PDAC), half of colorectal cancers, and a third of all lung cancers. With the highest RAS mutation frequencies seen with the top three causes of cancer deaths in the United States (lung, colorectal, and pancreatic cancer), the development of anti-RAS therapies is a major priority and a major challenge for cancer research. RAS proteins did not appear to present suitable pockets to which drugs could bind, except for the GDP/GTP binding site. Unfortunately, RAS proteins bind to these nucleotides with very high (picomolar) affinities, making the development of effective nucleotide analogs virtually impossible. Attempts to block pathways downstream of RAS with a hope to provide clinical benefit for patients suffering from RAS-driven cancers have been generally disappointing.

The three RAS genes (HRAS, NRAS, and KRAS) encode four 188-189 amino acid proteins that share 82%-90% amino acid sequence identity and near-identical structural and biochemical properties. However, they are differentially expressed, and mutated with different frequencies in cancer. KRAS is the most frequently mutated oncogene in cancer, and KRAS mutation is commonly associated with poor prognosis and resistance to therapy. Significant cancer type preferences exist among the RAS genes. KRAS mutations predominate in lung, colorectal, and pancreatic cancer, whereas NRAS mutations predominate in cutaneous melanomas and acute myelogenous leukemia, and HRAS mutations are found in bladder and head and neck squamous cell carcinomas.

An estimated over 600,000 Americans will die from cancer in 2021, corresponding to more than 1600 deaths per day (Cancer Facts and Figures 2021). The greatest number of deaths are from cancers of the lung, prostate, and colorectum in men, and cancers of the lung, breast, and colorectum in women. Almost one-quarter of all cancer deaths are due to lung cancer, 82% of which is directly caused by cigarette smoking. The 5-year survival rate for lung cancer patients is only about 20%.

KRAS is mutationally activated in lung cancer, and Glycine-to-Cysteine (G12C) mutations account for the majority of codon 12 mutations associated with cigarette smoking. A significant percentage of colorectal cancers are also driven by KRAS G12C mutations.

Early clinical data for allele-specific covalent KRAS G12C inhibitors show some effectiveness, at least in lung cancer. Those KRAS G12C inhibitors (e.g., Amgen Inc.'s sotorasib and Mirati Therapeutics. Inc.'s adagrasib) target inactive (GDP)-bound protein, and their effectiveness is enabled by high (comparable to wild type (WT) KRAS) intrinsic GTP hydrolysis rate of KRAS G12C mutant. Clinical data for these agents have shown that though most patients with KRAS G12C mutant non-small cell lung cancer (NSCLC) experience clinical benefit from selective KRAS G12C inhibition, patients with colorectal cancer bearing the same mutation rarely respond.

The cause of limited efficacy of KRAS G12C (GDP) inhibitors in colorectal cancers has been investigated. Unlike NSCLC cell lines, KRAS G12C colorectal cancer models have high basal receptor tyrosine kinase (RTK) activation and are responsive to growth factor stimulation. In colorectal cancer lines, KRAS G12C inhibition induces higher phospho-ERK rebound than in NSCLC cells. Also, it has been reported that KRAS G12C-GDP inhibitors induce transcription of new KRAS G12C that is in GTP-bound conformation, and insensitive to KRAS G12C inactive state inhibitors.

Therefore, there is a need for improved KRAS G12C inhibitors.

SUMMARY

The present disclosure provides compounds, as well as compositions and kits comprising the same, and methods of using the same in the treatment of diseases and disorders such as cancers. In some embodiments, the present disclosure provides KRAS G12C inhibitors targeting both active GTP-bound protein and inactive GDP-bound protein, which inhibitors may provide therapeutic advantages over KRAS G12C-GDP inhibitors. In some embodiments, compounds provided herein have inhibitory activity against a KRAS protein comprising a glycine to cysteine mutation at codon 12 (e.g., a G12C mutation) in both its active and inactive conformations. In some embodiments, compounds provided herein are useful in the treatment of cancers, such as cancers characterized by a KRAS G12C mutation.

In an aspect, the present disclosure provides compositions comprising compounds represented by one of Formulas AA (e.g., Formula IA, IC, ID, or IE), BB (e.g., Formula IB), CC (e.g., Formula IIA, IIC, or IID), and DD (e.g., Formula IIB):

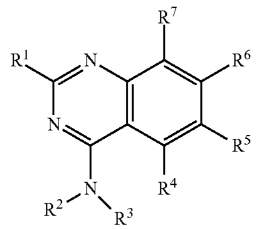
(AA)

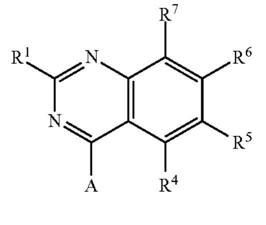
(BB)

-continued (CC)

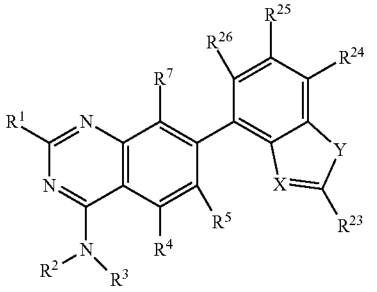

(DD)

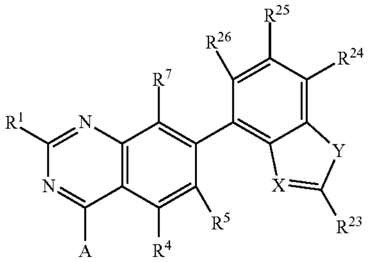

or a salt, ester, tautomer, prodrug, zwitterionic form, or stereoisomer thereof, wherein A, X, Y, $R^1$, $R^2$, $R^3$, $R^4$, $R^5$, $R^6$, $R^7$, $R^{23}$, $R^{24}$, $R^{25}$, and $R^{26}$ are as provided herein. In some embodiments, a compound provided herein, or a salt, ester, tautomer, zwitterionic form, or stereoisomer thereof, can modulate (e.g., inhibit) the activity of a KRAS protein, such as a KRAS protein having a G12C mutation. In some embodiments, a compound provided herein, or a salt, ester, tautomer, zwitterionic form, or stereoisomer thereof, includes an electrophilic moiety E, as provided herein. In some embodiments, a compound provided herein, or a salt, ester, tautomer, zwitterionic form, or stereoisomer thereof, is capable of interacting covalently with a cysteine at the 12 position of the KRAS protein (e.g., a G12C mutation). In some embodiments, a compound provided herein, or a salt, ester, tautomer, zwitterionic form, or stereoisomer thereof, is capable of binding a KRAS protein in an active ("GTP-bound") conformation. In some embodiments, a compound provided herein, or a salt, ester, tautomer, zwitterionic form, or stereoisomer thereof, is capable of binding a KRAS protein in an inactive ("GDP-bound") conformation.

In another aspect, the present disclosure provides a pharmaceutical composition comprising a compound provided herein (e.g., a compound represented by one of Formulas AA, BB, CC, and DD, or any other formula set forth herein), or a salt, ester, tautomer, prodrug, zwitterionic form, or stereoisomer thereof, together with a pharmaceutically acceptable carrier.

In a further aspect, the present disclosure provides a method of inhibition of KRAS activity in a human or animal subject for the treatment of a disease such as cancer, including pancreatic cancer (e.g., pancreatic ductal adenocarcinoma (PDAC)), colorectal cancer, and lung cancer, using, e.g., a compound provided herein (e.g., a compound represented by one of Formulas AA, BB, CC, and DD, or any other formula set forth herein), or a salt, ester, tautomer, prodrug, zwitterionic form, or stereoisomer thereof, or a pharmaceutical composition comprising the same.

In another aspect, the present disclosure provides a use of a compound provided herein (e.g., a compound represented by one of Formulas AA, BB, CC, and DD, or any other formula set forth herein), or a salt, ester, tautomer, zwitterionic form, or stereoisomer thereof, in the manufacture of a medicament for the treatment of a disease, disorder, or condition (e.g., a cancer) ameliorated, treated, inhibited, or reduced by inhibition of KRAS, including KRAS having a G12C mutation. In some embodiments, the disease, disorder, or condition is pancreatic cancer (e.g., pancreatic ductal adenocarcinoma (PDAC)), colorectal cancer, or lung cancer.

In a further aspect, the present disclosure provides a compound as provided herein (e.g., a compound represented by one of Formulas AA, BB, CC, and DD, or any other formula set forth herein), or a salt, ester, tautomer, zwitterionic form, or stereoisomer thereof, for use as a medicament. In some embodiments, the medicament is used in the treatment of a disease, disorder, or condition (e.g., a cancer). In some embodiments, the disease, disorder, or condition is pancreatic cancer (e.g., pancreatic ductal adenocarcinoma (PDAC)), colorectal cancer, or lung cancer.

DETAILED DESCRIPTION

The present disclosure provides compounds (e.g., compounds of Formulas IA, IA1, IA2, IB, IC, IC1, IC2, IC3, IC4, IC5, IC6, ID, ID1, IE, II, IIA, IIA1, IIA2, IIB, IIC, and IID), which compounds may possess useful KRAS inhibitory activity, and may be used in the treatment or prophylaxis of a disease, disorder, or condition in which KRAS plays an active role. In particular, certain compounds provided herein may possess useful inhibitory activity of KRAS having a G12C mutation, which KRAS protein is in an active (GTP-bound) or inactive (GDP-bound) conformation. Certain compounds provided herein may be capable of inhibiting both active and inactive forms of KRAS. The present disclosure also provides pharmaceutical compositions comprising one or more compounds provided herein together with a pharmaceutically acceptable carrier, as well as methods of making and using the compounds and compositions. The present disclosure also provides methods for inhibiting KRAS, including KRAS having a G12C mutation, which KRAS is in an active or inactive conformation. In an aspect, the present disclosure provides a method for treating a disorder mediated by KRAS including a KRAS having a G12C mutation in a subject in need of such treatment, which method comprises administering to the subject a therapeutically effective amount of a compound or composition provided herein. Also provided herein is the use of certain compounds provided herein in the manufacture of a medicament for the treatment of a disease, disorder, or condition ameliorated, treated, inhibited, or reduced by inhibition of KRAS, including KRAS having a G12C mutation. In some embodiments, the disease, disorder, or condition is a cancer (e.g., as described herein).

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

"About," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

"Acyl," as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —$C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

"Alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

"Alkynyl" refers to either a straight chain or branched-chain hydrocarbon having at least 2 carbon atoms and at least one triple bond and having the number of carbon atom indicated (i.e., $C_{2-6}$ means to two to six carbons). Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, and 1,3,5-hexatriynyl.

"Alkoxy," as used herein, alone or in combination, refers to an alkyl ether radical, wherein the term alkyl is as described herein. Examples of suitable alkyl ether radicals include methoxy, ethoxy, n-propoxy, isopropoxy, n-butoxy, iso-butoxy, sec-butoxy, tert-butoxy, and the like.

"Alkyl," as used herein, alone or in combination, refers to a straight-chain or branched-chain alkyl radical containing from 1 to 20 carbon atoms (e.g., $C_{1-20}$ alkyl). In certain embodiments, said alkyl will comprise from 1 to 10 carbon atoms (e.g., $C_{1-10}$ alkyl). In further embodiments, said alkyl will comprise from 1 to 8 carbon atoms (e.g., $C_{1-8}$ alkyl). In further embodiments, said alkyl will comprise from 1 to 6 carbon atoms (e.g., $C_{1-6}$ alkyl). In further embodiments, said alkyl will comprise from 1 to 3 carbon atoms (e.g., $C_{1-3}$ alkyl). Alkyl groups are unsubstituted or substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl, and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

"Alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino, and the like.

"Alkylthio," as used herein, alone or in combination, refers to an alkyl thioether (R-S-) radical wherein the term alkyl is as described herein and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

"Amido" and "carbamoyl," as used herein, alone or in combination, refer to an amino group as described herein attached to the parent molecular moiety through a carbonyl group, or vice versa. The "amido" group as used herein incudes a "C-amido" and "N-amido" groups. The term "C-amido" as used herein, alone or in combination, refers to a —C(O)N(RR') group with R and R' as defined herein or as defined by the specifically enumerated "R" groups designated. In some embodiments, the "amido" group includes —$C(O)NH_2$, $C_{1-4}$alkylamido, and di($C_{1-4}$alkyl)amido. The term "$C_{1-4}$alkylamido", as used herein, refers to —C(O)NH($C_{1-4}$alkyl), wherein $C_{1-4}$alkyl is as defined herein. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

"Amino," as used herein, alone or in combination, refers to —NRR', wherein R and R' are independently selected from hydrogen, alkyl, acyl, heteroalkyl, aryl, cycloalkyl, heteroaryl, and heterocycloalkyl, any of which may themselves be unsubstituted or substituted. Additionally, R and R' may combine to form a heterocycloalkyl, which is unsubstituted or substituted. An "amino" group may be a primary amine (e.g., —$NH_2$), secondary or di-substituted amine (e.g., —NHR where R is not hydrogen), or tertiary or tri-substituted amine (e.g., —NRR' where neither R nor R' is hydrogen).

"Aryl," as used herein, alone or in combination, means a carbocyclic aromatic system containing one, two, or three rings wherein such polycyclic ring systems are fused together. The term "aryl" embraces aromatic groups such as phenyl, naphthyl, anthracenyl, and phenanthryl. An aryl moiety may include, for example, between 5 to 20 carbon atoms, such as between 5 to 12 carbon atoms, such as 5 or 6 carbon atoms.

"Arylalkenyl" or "aralkenyl," as used herein, alone or in combination, refers to an aryl group attached to the parent molecular moiety through an alkenyl group.

"Arylalkoxy" or "aralkoxy," as used herein, alone or in combination, refers to an aryl group attached to the parent molecular moiety through an alkoxy group.

"Arylalkyl" or "aralkyl," as used herein, alone or in combination, refers to an aryl group attached to the parent molecular moiety through an alkyl group.

"Aryloxy," as used herein, alone or in combination, refers to an aryl group attached to the parent molecular moiety through an oxy.

"Carbamate," as used herein, alone or in combination, refers to an ester of carbamic acid (—NHCOO—) which may be attached to the parent molecular moiety from either the nitrogen or acid end, and which is unsubstituted or substituted as defined herein.

"O-carbamyl" as used herein, alone or in combination, refers to a —OC(O)NRR' group, with R and R' as defined herein.

"N-carbamyl" as used herein, alone or in combination, refers to a ROC(O)NR'— group, with R and R' as defined herein.

"Carbonyl," as used herein, when alone includes formyl [—C(O)H] and in combination is a —C(O)— group.

"Carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

"Cyano," as used herein, alone or in combination, refers to —CN.

"Cycloalkyl," or, alternatively, "carbocycle," as used herein, alone or in combination, refers to a saturated or partially saturated monocyclic, bicyclic, or tricyclic alkyl group wherein each cyclic moiety contains from 3 to 12 carbon atom ring members and which may optionally be a benzo fused ring system which is unsubstituted or substituted as defined herein. A carbocycle may comprise a bridged ring system and/or a spiro ring system (e.g., a system including two rings sharing a single carbon atom). The term "cycloalkenyl" refers to a cycloalkyl group having one or two double bonds. In certain embodiments, said cycloalkyl (or cycloalkenyl) will comprise from 5 to 7 carbon atoms. Examples of such groups include cyclopropyl, cyclobutyl, cyclopentyl, cyclohexyl, cycloheptyl, cyclobutenyl, cyclopentenyl, cyclohexenyl, tetrahydronapthyl, indanyl, octahydronaphthyl, 2,3-dihydro-1H-indenyl, adamantyl, and the like. "Bicyclic" and "tricyclic" as used herein are intended to include both fused ring systems, such as decahydronaphthalene and octahydronaphthalene, as well as the multicyclic (multicentered) saturated or partially unsaturated type. The latter type of isomer is exemplified in general by bicyclo[1,1,1]pentane, camphor, adamantane, and bicyclo[3,2,1]octane.

"Ester," as used herein, alone or in combination, refers to a carboxy group bridging two moieties linked at carbon atoms.

"Ether," as used herein, alone or in combination, refers to an oxy group bridging two moieties linked at carbon atoms.

"Halo," or "halogen," as used herein, alone or in combination, refers to fluorine, chlorine, bromine, or iodine.

"Haloalkoxy," as used herein, alone or in combination, refers to a haloalkyl group attached to the parent molecular moiety through an oxygen atom.

"Haloalkyl," as used herein, alone or in combination, refers to an alkyl radical having the meaning as described herein wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro, or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene ($—CF_2—$), chloromethylene (—CHCl—) and the like.

"Heteroalkyl," as used herein, alone or in combination, refers to a stable straight or branched hydrocarbon chain, fully saturated or containing from 1 to 3 degrees of unsaturation, consisting of the stated number of carbon atoms and from one to three heteroatoms selected from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, $—CH_2—NH—OCH_3$.

"Heteroaryl," as used herein, alone or in combination, refers to a 3- to 15-membered aromatic monocyclic ring, or a fused monocyclic, bicyclic, or tricyclic ring system in which at least one of the fused rings is aromatic, which ring or ring system contains at least one atom selected from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, imidazolyl, pyrazolyl, pyridyl, pyrimidinyl, pyrazinyl, pyridazinyl, triazolyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, phenanthrolinyl, dibenzofuranyl, acridinyl, phenanthridinyl, xanthenyl and the like.

"Heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently selected from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. A heterocycle may comprise a bridged ring system and/or a spiro ring system (e.g., a system including two rings sharing a single atom, such as a single carbon atom). "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups are unsubstituted or substituted unless specifically prohibited.

"Hydrazinyl" as used herein, alone or in combination, refers to two amino groups joined by a single bond, i.e., —N—N—.

"Hydroxy," as used herein, alone or in combination, refers to —OH.

"Hydroxyalkyl," as used herein, alone or in combination, refers to a hydroxy group attached to the parent molecular moiety through an alkyl group.

"Iminohydroxy," as used herein, alone or in combination, refers to =N(OH) and =N—O—.

"Lower amino," as used herein, alone or in combination, refers to —NRR', wherein R and R' are independently selected from hydrogen and lower alkyl, either of which is unsubstituted or substituted.

"Mercaptyl" as used herein, alone or in combination, refers to an RS— group, where R is as defined herein.

"Nitro," as used herein, alone or in combination, refers to —$NO_2$.

"Oxy" or "oxa," as used herein, alone or in combination, refer to —O—.

"Oxo," as used herein, alone or in combination, refers to =O.

"Perhaloalkoxy" refers to an alkoxy group where all of the hydrogen atoms are replaced by halogen atoms.

"Perhaloalkyl" as used herein, alone or in combination, refers to an alkyl group where all of the hydrogen atoms are replaced by halogen atoms.

"Ring," or equivalently, "cycle," as used herein, in reference to a chemical structure or portion thereof, means a group in which every atom is a member of a common cyclic structure. A ring can be saturated or unsaturated, including aromatic, unless otherwise provided, and may have between 3 and 9 members. If the ring is a heterocycle, it may contain between 1 and 4 heteroatoms or heteroatom-comprising groups selected from B, N, O, S, C(O), and $S(O)_m$, wherein m is 0, 1, or 2. Unless specifically prohibited, a ring is unsubstituted or substituted. Two or more rings may be fused together (e.g., they may share a bond and two common atoms). Two or more rings may be linked together in a spiro arrangement such that only a single atom is shared between two rings. Two or more rings may also or alternatively be configured in a bridged arrangement such that three or more atoms are shared between two or more rings.

"Sulfonate," "sulfonic acid," and "sulfonic," as used herein, alone or in combination, refer to the —$SO_3H$ group and its anion as the sulfonic acid is used in salt formation.

"Sulfanyl," as used herein, alone or in combination, refers to —S—.

"Sulfinyl," as used herein, alone or in combination, refers to —S(O)—.

"Sulfonyl," as used herein, alone or in combination, refers to —$S(O)_2$—.

"N-sulfonamido" refers to a $RS(=O)_2NR'$— group with R and R' as defined herein.

"S-sulfonamido" refers to a —$S(=O)_2NRR'$, group, with R and R' as defined herein.

"Tautomer", as use herein, alone or in combination, refers to one of two or more isomers that rapidly interconvert. Generally, this interconversion is sufficiently fast so that an individual tautomer is not isolated in the absence of another tautomer. The ratio of the amount of tautomers can be dependent on solvent composition, ionic strength, and pH, as well as other solution parameters. The ratio of the amount of tautomers can be different in a particular solution and in the microenvironment of a biomolecular binding site in said solution. Examples of tautomers that are well known in the art include keto/enol, enamine/imine, and lactam/lactim tautomers. Examples of tautomers that are well known in the art also include 2-hydroxypyridine/2(1H)-pyridone and 2-aminopyridine/2(1H)-iminopyridone tautomers.

"Thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

"Thiol," as used herein, alone or in combination, refers to an —SH group.

"Thiocarbonyl," as used herein, when alone includes thioformyl —C(S)H and in combination is a —C(S)— group.

"N-thiocarbamyl" refers to an ROC(S)NR'— group, with R and R' as defined herein.

"O-thiocarbamyl" refers to a —OC(S)NRR' group, with R and R' as defined herein.

"Thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As described herein, groups may be substituted or unsubstituted (e.g., "optionally substituted"). Unless otherwise specified, any group may be substituted with one or more substituents, such as one or more substituents provided herein. Examples of substituents that may substitute a group include, but are not limited to, one or more substituents independently selected from the following groups or a particular designated set of groups, alone or in combination: alkyl (e.g., $C_{1-20}$ alkyl, such as $C_{1-10}$ alkyl, such as $C_{1-6}$ alkyl, such as $C_{1-3}$ alkyl), alkenyl (e.g., $C_{2-20}$ alkenyl, such as $C_{2-10}$ alkenyl, such as $C_{2-6}$ alkenyl), alkynyl (e.g., $C_{2-20}$ alkynyl, such as $C_{2-10}$ alkynyl, such as $C_{2-6}$ alkynyl), alkanoyl (e.g., $C_{1-20}$ alkanoyl, such as $C_{1-10}$ alkanoyl, such as $C_{1-6}$ alkanoyl), heteroalkyl (e.g., a heteroalkyl moiety including 1-20 carbon atoms and 1-6 heteroatoms, such as a heteroalkyl moiety including 1-6 carbon atoms and 1-3 heteroatoms), haloalkyl (e.g., a halo-substituted $C_{1-20}$ alkyl, such as a halo-substituted $C_{1-10}$ alkyl, a halo-substituted $C_{1-6}$ alkyl), haloalkenyl (e.g., a halo-substituted $C_{2-20}$ alkenyl, such as a halo-substituted $C_{2-6}$ alkenyl), haloalkynyl (e.g., a halo-substituted $C_{2-20}$ alkynyl, such as a halo-substituted $C_{2-6}$ alkynyl), perhaloalkyl (e.g., $C_{1-20}$ perhaloalkyl, such as $C_{1-6}$ perhaloalkyl, such as $C_{1-3}$ perhaloalkyl), perhaloalkoxy (e.g., $C_{1-20}$ perhaloalkoxy, such as $C_{1-6}$ perhaloalkoxy), phenyl, aryl (e.g., $C_{5-20}$ aryl, such as $C_{5-10}$ aryl, such as $C_{5-6}$ aryl), aryloxy (e.g., $C_{5-20}$ aryloxy, such as $C_{5-10}$ aryloxy, such as $C_{5-6}$ aryloxy), alkoxy (e.g., $C_{1-20}$ alkoxy, such as $C_{1-10}$ alkoxy, such as $C_{1-6}$ alkoxy), haloalkoxy (e.g., $C_{1-20}$ haloalkoxy, such as $C_{1-10}$ haloalkoxy, such as $C_{1-6}$ haloalkoxy), oxo, acyloxy (e.g., an acyloxy group including 1-20 carbon atoms, such as 1-10 carbon atoms, such as 1-6 carbon atoms), carbonyl (e.g., C(O) or C=O), carboxyl (e.g., C(O)O), alkylcarbonyl (e.g., $C_{1-20}$ alkylcarbonyl, such as $C_{1-10}$ alkylcarbonyl, such as $C_{1-6}$ alkylcarbonyl, such as $C_{1-3}$ alkylcarbonyl), carboxyester (e.g., C(O)OR where R is, e.g., alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein), carboxamido, cyano (e.g., CN), hydrogen, halogen (e.g., iodine, bromine, chlorine, or fluorine), hydroxy, amino (e.g., NR'R" where R' and R" are independently, e.g., hydrogen, alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein), alkylamino (e.g., NR'R" where R' is alkyl (e.g., $C_{1-20}$ alkyl, such as $C_{1-10}$ alkyl, such as $C_{1-6}$ alkyl, such as $C_{1-3}$ alkyl) and R" is, e.g., hydrogen, alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein), arylamino (e.g., NR'R" where R' is aryl (e.g., $C_{5-20}$ aryl, such as $C_{5-10}$ aryl, such as $C_{5-6}$ aryl) and R" is, e.g., hydrogen, alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein), amido (e.g., C(O)NR'R" where R' and R" are independently, e.g., hydrogen, alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein), nitro (e.g., $NO_2$), thiol (e.g., SH), alkylthio (e.g., $C_{1-20}$ alkyl substituted with a thiol group, such as $C_{1-10}$ alkyl substituted with a thiol group, such as $C_{1-6}$ alkyl substituted with a thiol group, such as $C_{1-3}$ alkyl substituted with a thiol group), haloalkylthio (e.g., $C_{1-20}$ haloalkylthio, such as $C_{1-10}$ haloalkylthio, such as $C_{1-6}$ haloalkylthio, such as $C_{1-3}$ haloalkylthio), perhaloalkylthio (e.g., $C_{1-20}$ perhaloalkylthio, such as $C_{1-10}$ perhaloalkylthio, such as $C_{1-6}$ perhaloalkylthio, such as $C_{1-3}$ perhaloalkylthio), arylthiol (e.g., $C_{5-20}$ arylthiol, such as $C_{5-10}$ arylthiol, such as $C_{5-6}$ arylthiol), sulfonate (e.g., $S(O)_2OR$ where R is, e.g., alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein), sulfonic acid (e.g., $S(O)_2OH$), trisubstituted silyl (e.g., SiR'R"R* where R', R", and R* are independently selected from, e.g., alkyl (e.g., $C_{1-20}$ alkyl, such as $C_{1-10}$ alkyl, such as $C_{1-6}$ alkyl, such as $C_{1-3}$ alkyl), alkenyl (e.g., (e.g., $C_{2-20}$ alkenyl, such as $C_{2-10}$ alkenyl, such as $C_{2-6}$ alkenyl), or alkynyl (e.g., $C_{2-20}$ alkynyl, such as $C_{2-10}$ alkynyl, such as $C_{2-6}$ alkynyl), any of which may be substituted by any group provided herein; in some cases, a trisubstituted silyl can be trimethylsilyl), $N_3$, $SCH_3$, $C(O)CH_3$, $CO_2CH_3$, $CO_2H$, pyridinyl, thiophene, furanyl, carbamate, and urea. Additional groups may also be contemplated. Where structurally feasible, two substituents may be joined together to form a fused five-, six-, or seven-membered carbocyclic or heterocyclic ring consisting of zero to three heteroatoms (e.g., N, O, S, etc.), for example forming methylenedioxy or ethylenedioxy. An unsubstituted or substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "unsubstituted or substituted with."

The terms R, R', R", R*, etc., appearing by themselves and without a number designation, unless otherwise defined, refer to a moiety selected from hydrogen, alkyl, cycloalkyl, heteroalkyl, aryl, heteroaryl and heterocycloalkyl, any of which is unsubstituted or substituted (e.g., as described herein). Such R and R' groups should be understood to be unsubstituted or substituted as defined herein. Whether an R group has a number designation or not, every R group, including R, R' and $R^n$ where n=(1, 2, 3, . . . n), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

"Bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

Asymmetric centers may exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, atropisomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds provided herein may comprise conformational isomers, which compounds comprise groups that can orient in different conformations in relation to another moiety. Additionally, the compounds disclosed herein can exist in unsolvated as well as solvated forms with pharmaceutically acceptable solvents such as water, ethanol, and the like. In general, the solvated forms are considered equivalent to the unsolvated forms.

"Combination therapy" means the administration of two or more therapeutic agents to treat a therapeutic condition or disorder described in the present disclosure. Such administration encompasses co-administration of these therapeutic agents in a substantially simultaneous manner, such as in a single dose unit (e.g., capsule) having a fixed ratio of active ingredients or in multiple, separate dose units (e.g., capsules) for each active ingredient. In addition, such administration also encompasses use of each type of therapeutic agent in a sequential manner. In either case, the treatment regimen will provide beneficial effects of the drug combination in treating the conditions or disorders described herein.

"KRAS inhibitor" is used herein to refer to a compound that exhibits an $IC_{50}$ with respect to KRAS activity of no more than about 100 μM and more typically not more than about 50 μM, as measured in the assays described generally herein, such as level of covalent modification to Cys12 in KRAS G12C as measured using a matrix assisted laser desorption ionization-time of flight mass spectrometry (MALDI-TOF MS) assay, and/or a KRAS G12C protein-effector protein interaction disruption assay. "$IC_{50}$" is that concentration of inhibitor which reduces the activity of an enzyme (e.g., KRAS) to half-maximal level. Certain compounds disclosed herein have been discovered to exhibit inhibition against KRAS. In certain embodiments, compounds exhibit an $IC_{50}$ with respect to KRAS (e.g., KRAS having a G12C mutation) of no more than about 50 μM; in further embodiments, compounds exhibit an $IC_{50}$ with respect to KRAS (e.g., KRAS having a G12C mutation) of no more than about 10 μM; in yet further embodiments, compounds exhibit an $IC_{50}$ with respect to KRAS (e.g., KRAS having a G12C mutation) of not more than about 1 μM; in yet further embodiments, compounds exhibit an $IC_{50}$ with respect to KRAS (e.g., KRAS having a G12C mutation) of not more than about 200 nanomolar (nM), as measured in the KRAS assay described herein. In some embodiments, compounds exhibit an $IC_{50}$ with respect to KRAS (e.g., KRAS having a G12C mutation) of less than about 50 μM, such as less than about 40 μM, 30 μM, 20 μM, 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, or less. In certain embodiments, compounds exhibit an $IC_{50}$ with respect to KRAS (e.g., KRAS having a G12C mutation) of less than about 1 μM, such as less than about 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, or less. In some embodiments, a KRAS inhibitor has inhibitory activity against KRAS having a G12C mutation that exceeds its inhibitory activity against KRAS having another mutation, such as a G12D, G12R, G12S, G12A, or G12V mutation. For example, in some embodiments, a KRAS inhibitor provided herein has at least two-fold, five-fold, ten-fold, twenty-fold, thirty-fold, forty-fold, fifty-fold, one hundred-fold, or higher inhibitory activity against KRAS having a G12C mutation relative to KRAS having another mutation such as a G12D, G12R, G12S, G12A, or G12V mutation. In some embodiments, a KRAS inhibitor provided herein has greater inhibitory activity against KRAS having a G12C mutation than against KRAS having a G12D mutation. In some embodiments, a KRAS inhibitor provided herein has greater inhibitory activity against KRAS having a G12C mutation than against KRAS having a G12R mutation. In some embodiments, a KRAS inhibitor provided herein has greater inhibitory activity against KRAS having a G12C mutation than against an KRAS having a G12S mutation. In some embodiments, a KRAS inhibitor provided herein has greater inhibitory activity against KRAS having a G12C mutation than against KRAS having a G12A mutation. In some embodiments, a KRAS inhibitor provided herein has greater inhibitory activity against KRAS having a G12C mutation than against KRAS having a G12V mutation. In some embodiments, a KRAS inhibitor provided herein has greater inhibitory activity against active ("GTP-bound") KRAS having a G12C mutation than against an inactive ("GDP-bound") KRAS having a G12C mutation. In some embodiments, a KRAS inhibitor provided herein has lower inhibitory activity against active ("GTP-bound") KRAS having a G12C mutation than against an inactive ("GDP-bound") KRAS having a G12C mutation. In some embodiments, a KRAS inhibitor provided herein has inhibitory activity against both active ("GTP-bound") and inactive ("GDP-bound") KRAS having a G12C mutation. In some embodiments, a KRAS inhibitor provided herein has similar inhibitory activity against active ("GTP-bound") and inactive ("GDP-bound") KRAS having a G12C mutation. In some embodiments, a KRAS inhibitor provided herein has inhibitory activity against a K-RAS4a splice variant. In some embodiments, a KRAS inhibitor provided herein has inhibitory activity against a K-RAS4b splice variant. In some embodiments, a KRAS inhibitor provided herein has inhibitory activity against both K-RAS4a and K-RAS4b splice variants.

"Therapeutically effective amount" refers to an amount of a compound or of a pharmaceutical composition useful for treating or ameliorating an identified disease, disorder, or condition, or for exhibiting a detectable therapeutic or inhibitory effect. The exact amounts will depend on the purpose of the treatment and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

"Treat," "treating," and "treatment" refer to any indicia of success in the treatment or amelioration of an injury, pathology, disease, disorder, or condition, including any objective or subjective parameter such as abatement; remission; diminishing of symptoms or making the injury, pathology, disease, disorder, or condition more tolerable to the patient; slowing in the rate of degeneration or decline; making the final point of degeneration less debilitating; and/or improving a patient's physical or mental well-being. The treatment or amelioration of symptoms can be based on objective or subjective parameters, including the results of a physical examination, neuropsychiatric exams, and/or a psychiatric evaluation. Treatment may also be preemptive in nature; i.e., it may include prevention of a disease, disorder, or condition, prevention of onset of one or more symptoms of a disease, disorder, or condition, and/or prevention of escalation of a disease, disorder, or condition. Prevention of a disease, disorder, or condition may involve complete protection from disease, and/or prevention of disease progression (e.g., to a later stage of the disease, disorder, or condition). For example, prevention of a disease may not mean complete foreclosure of any effect related to the diseases at any level, but instead may mean prevention of the symptoms of a disease, disorder, or condition to a clinically significant or detectable level.

"Patient" or "subject" refers to a living organism suffering from or prone to a disease, disorder, or condition that can be treated by administration of a compound or pharmaceutical composition as provided herein. Non-limiting examples include humans, rats, mice, rabbits, hamsters, guinea pigs, hamsters, cats, dogs, non-human primates (e.g., monkeys), goats, pigs, sheep, cows, deer, horses, and other non-mammalian animals. Examples of mammals that can be treated by administration of a compound or pharmaceutical composition provided herein include, for example, rodents (e.g., rats, mice, squirrels, guinea pigs, hamsters, etc.), lagomorphs (e.g., rabbits, hares, etc.), primates (e.g., monkeys, apes, etc.), bovines (e.g., cattle), odd-toed ungulates (e.g., horses), even-toed ungulates (e.g., bovines such as cattle, ovine such as sheep, caprine such as goats, porcine such as pigs, etc.), and marsupials (e.g., kangaroo, wallaby, wallaroo, sugar glider, etc.). In some embodiments, the patient or subject is human. In some embodiments, the patient or subject is a companion animal such as a cat or dog. In some embodiments, the patient or subject is a farm animal such as a goat, sheep, cow, pig, or horse. In some embodiments, the patient or subject is an exotic animal such as a primate (e.g., monkey), marsupial (e.g., kangaroo, wallaby, wallaroo, sugar glider, etc.), or a non-domesticated or hybrid cat or dog.

"Composition," as used herein, is intended to encompass a product comprising the specified ingredients in the specified amounts, as well as any product, which results, directly or indirectly, from combination of the specified ingredients in the specified amounts. By "pharmaceutically acceptable" it is meant the carrier, diluent, or excipient must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present disclosure include, but are not limited to, binders, fillers, disintegrants, lubricants, coatings, sweeteners, flavors, and colors. One of skill in the art will recognize that other pharmaceutical excipients are useful in the present disclosure.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug.

The compounds disclosed herein can exist as therapeutically acceptable salts (also referred to herein as "pharmaceutically acceptable salts"). The present disclosure includes compounds provided herein in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The terms "therapeutically acceptable salt" and "pharmaceutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and NN'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

"KRAS G12C-positive cancer" refers to a cancer characterized by a KRAS G12C mutation.

"Jointly therapeutically effective amount" as used herein means the amount at which the therapeutic agents, when given separately (in a chronologically staggered manner, especially a sequence-specific manner) to a warm-blooded animal, especially to a human to be treated, show an (additive, but preferably synergistic) interaction (joint therapeutic effect). Whether this is the case can be determined inter alia by following the blood levels, showing that both compounds are present in the blood of the human to be treated at least during certain time intervals.

"Synergistic effect" as used herein refers to an effect of at least two therapeutic agents: a KRAS G12C inhibitor, as defined herein, and an additional agent, which additional agent may be an agent configured to treat a disease, disorder, or condition or a symptom thereof. The effect can be, for example, slowing the symptomatic progression of a proliferative disease, such as cancer, particularly lung cancer, or symptoms thereof. Analogously, a "synergistically effective amount" refers to the amount needed to obtain a synergistic effect.

"A," "an," or "a(n)", when used in reference to a group of substituents or "substituent group" herein, mean at least one. For example, where a compound is substituted with "an" alkyl or aryl, the compound is unsubstituted or substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Compounds

In an aspect, the present disclosure provides a compound represented by Formula IA:

(IA)

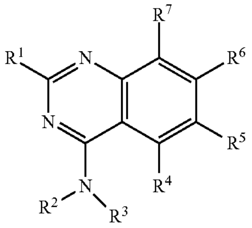

or a salt (e.g., pharmaceutically acceptable salt), ester, tautomer, prodrug, zwitterionic form, or stereoisomer thereof, wherein:

$R^1$ is selected from

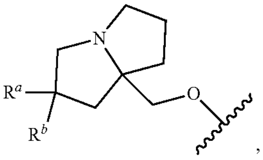
,
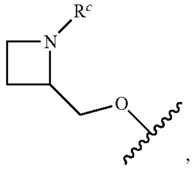
,
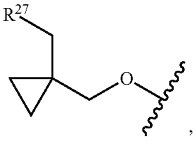
, and $—OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with $—N(R^{12})(E)$, and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is selected from H, $—OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $—OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, $—OR^{12}$, —CN, and H;

$R^8$ is selected from H and $C_{1-6}$alkyl, wherein any $C_{1-6}$alkyl is unsubstituted or substituted with one or more $R^{13}$;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from $—OR^{22}$, —CN, $—N(R^{22})_2$, and halogen;

each $R^{14}$ is independently selected from halogen, —CN, $—N(R^{12})_2$, and $C_{1-6}$alkyl, wherein any $C_{1-6}$alkyl is unsubstituted or substituted with one or more $R^{13}$;

each $R^{15}$ is independently selected from halogen, $—N(R^{12})_2$, $—N(R^{12})C(O)(C_{1-6}alkyl)$, —CN, $—OR^{12}$, and $C_{1-6}$alkyl, wherein any $C_{1-6}$alkyl is unsubstituted or substituted with one or more $R^{13}$;

each $R^{20}$ is independently selected from —OH, $—OC_{1-6}$alkyl, —CN, $—NH_2$, $—NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each E is independently selected from

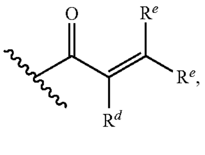
,
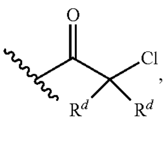
,

-continued

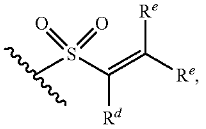, 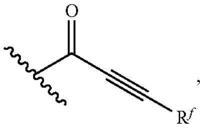,

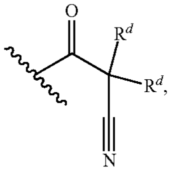, 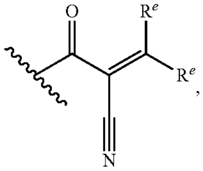,

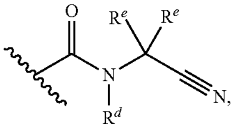, 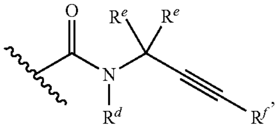,

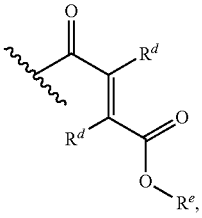, 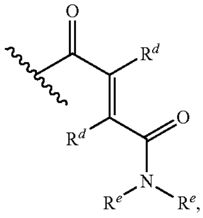,

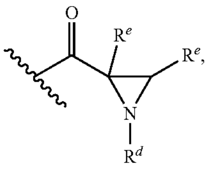, 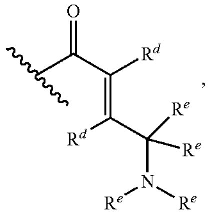, and —CN;

$R^a$ and $R^b$ are each independently selected from halogen, $C_{1-6}$ alkyl, —$OR^{12}$, and H, wherein any $C_{1-6}$alkyl is unsubstituted or is substituted with one or more $R^{13}$;

$R^c$ is selected from halogen, $C_{1-6}$ alkyl, and H;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IA, or a salt (e.g., a pharmaceutically acceptable salt) thereof.

In some embodiments, $R^1$ is —$OR^8$.

In some embodiments, $R^8$ is H. In some embodiments, $R^8$ is $C_{1-6}$alkyl, wherein any $C_{1-6}$alkyl is unsubstituted or substituted with one or more $R^{13}$. In some embodiments, $R^8$ is unsubstituted $C_{1-6}$alkyl.

In some embodiments, $R^1$ is selected from:

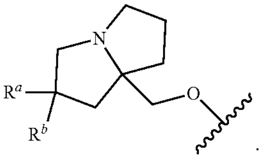.

In some embodiments, $R^a$ and $R^b$ are each independently selected from halogen, $C_{1-6}$alkyl, —$OR^2$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$.

In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

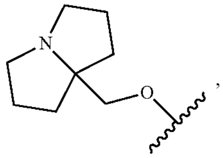, 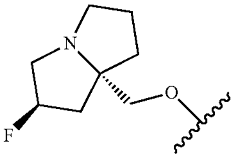,

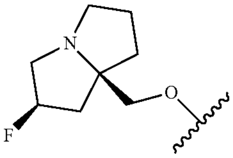, 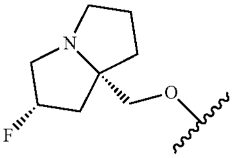,

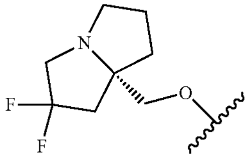, 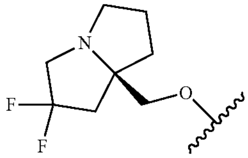,

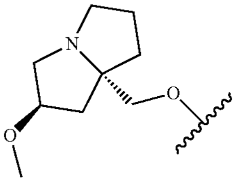, 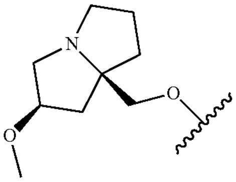,

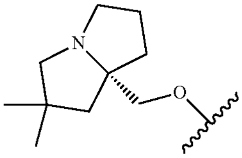, and 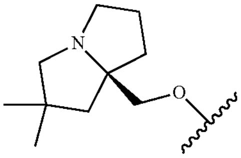.

In some embodiments, $R^1$ is selected from:

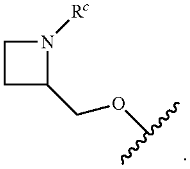.

In some embodiments, $R^c$ is methyl. In some embodiments, $R^1$ is selected from:

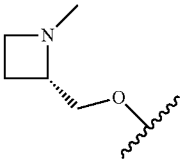 and 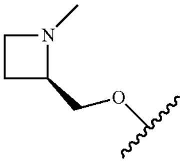.

In some embodiments, $R^1$ is selected from:

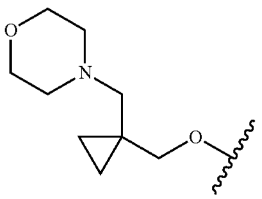

and

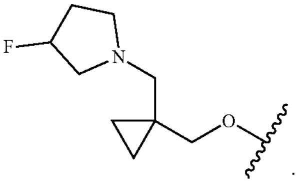

In some embodiments, $R^1$ is OH. In some embodiments, $R^8$ is —$OCH_3$, —$OCH_2CH_3$, —$OCH_2CH_2OH$, or —$OCH_2CH_2OCH_3$.

In some embodiments, $R^2$ is H. In some embodiments, $R^2$ is $C_{1-6}$ alkyl unsubstituted or substituted with one or more $R^{13}$. In some such embodiments, each $R^{13}$ is independently selected from —$OR^{22}$ (e.g., —OH) and —CN. In some embodiments, $R^2$ is selected from $C_{1-6}$ alkyl. In some embodiments, $R^2$ is selected from $C_{1-2}$ alkyl. In some embodiments $R^2$ is selected from —$CH_3$, —$CH_2CH_3$, —$CH_2CH_2OH$, —$CH_2CH_2CN$, and —$CH(CH_3)_2$. In some embodiments, $R^2$ is selected from a 3-6 membered carbocycle. In some embodiments, $R^2$ is cyclopropyl.

In some embodiments, $R^3$ is selected from $C_{1-6}$ alkyl that is substituted with —$N(R^{12})(E)$. In some embodiments, $R^3$ is $C_2$ alkyl that is substituted with —$N(R^{12})(E)$. In some embodiments, $R^3$ is $C_2$ alkyl that is substituted with —N(H)(E).

In some embodiments, $R^3$ is a 4-6 membered heterocycle that is substituted with one or more E and 0-4 $R^{10}$. In some embodiments, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is an azetidine, pyrrolidine, or piperidine, wherein the azetidine, pyrrolidine, or piperidine is substituted with one or more E and 1-2 $R^{10}$, and $R^{10}$ is $C_{1-6}$ alkyl or halogen. In some embodiments, $R^3$ is a pyrrolidine substituted with one or more E and 0-4 $R^{10}$. In some embodiments, $R^3$ is selected from:

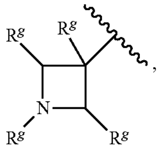

,

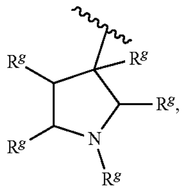

-continued

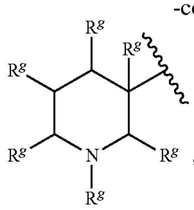

, and

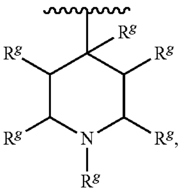

wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

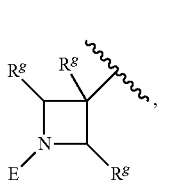

,

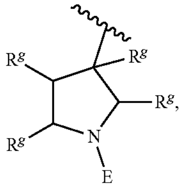

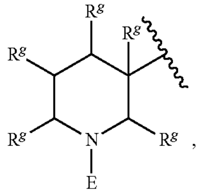

, and

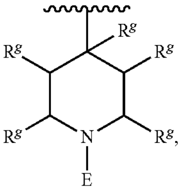

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is unsubstituted $C_{1-6}$alkyl (e.g., methyl).

In some embodiments, $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a piperazinyl ring that is substituted with one or more E and 0-4 $R^{11}$. In some embodiments, $R^2$ and $R^3$ together with the atom to which they are attached, form a piperazinyl ring that is substituted with one or more E and 1-2 $R^{11}$, and $R^{11}$ is $C_{1-6}$ alkyl. In some embodiments, $R^2$ and $R^3$, together with the atom to which they are attached, form the structure:

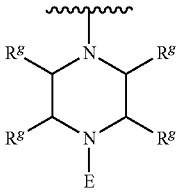
or
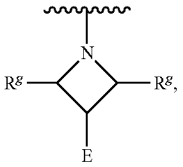

wherein each $R^g$ is independently selected from $C_{1-6}$alkyl and H, wherein any $C_{1-6}$alkyl is unsubstituted or substituted with one or more $R^{20}$, optionally wherein two $R^g$ groups, together with the atoms to which they are attached, form a 3-6 membered carbocycle or heterocycle. In some embodiments, each $R^g$ is H. In some embodiments, one or two $R^g$ groups are $C_{1-6}$alkyl (e.g., methyl). In some embodiments, $R^2$ and $R^3$, together with the atom to which they are attached, form the structure:

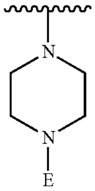
,
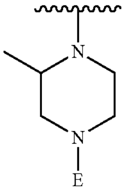
,
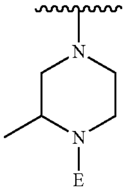
,

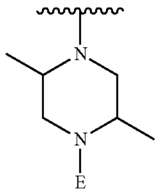
,
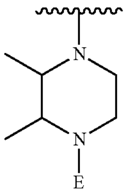
,
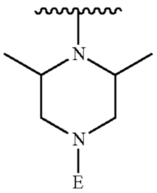
,

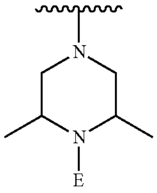
,
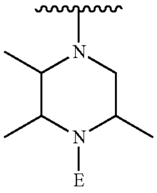
,
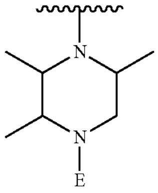
, or
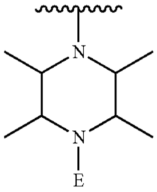
.

In some embodiments, $R^2$ and $R^3$, together with the atom to which they are attached, form a bridged piperazinyl ring that is substituted with one or more E and 0-4 $R^{11}$. In some embodiments, $R^2$ and $R^3$, together with the atom to which they are attached, form the structure:

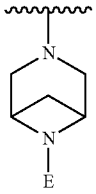
or
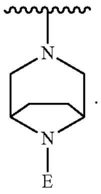
.

In some embodiments, $R^2$ and $R^3$, together with the atom to which they are attached, form a 4-8 membered bicyclic heterocycle comprising a fused ring system that is substituted with one or more E and 0-4 $R^{11}$. In some embodiments, $R^2$ and $R^3$, together with the atom to which they are attached, form a structure selected from:

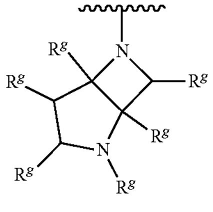
and
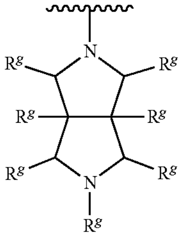
, wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a structure selected from:

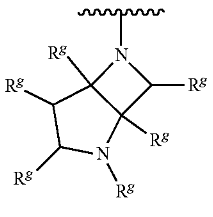
and
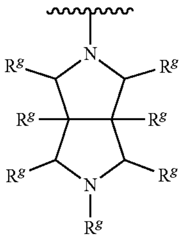
, wherein each $R^g$ is independently selected from $C_{1-6}$alkyl and H, wherein any $C_{1-6}$alkyl is unsubstituted or substituted with one or more $R^{20}$. In some embodiments, $R^2$ and $R^3$, together with the atom to which they are attached, form the structure:

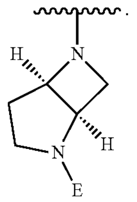

In some embodiments, each $R^g$ is H.

In some embodiments, $R^4$ is H.

In some embodiments, $R^5$ is H.

In some embodiments, $R^5$ is —CN.

In some embodiments, $R^5$ is a halogen. In some embodiments, $R^5$ is Cl. In some embodiments, $R^5$ is F.

In some embodiments, $R^5$ is selected from $C_{1-6}$alkyl that is unsubstituted or substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is $—CF_3$. In some embodiments, $R^5$ is $—CHF_2$. In some embodiments, $R^5$ is selected from $—CF_3$, $—CF_2H$, and $—CH_2CN$. In some embodiments, $R^5$ is selected from $—CH_3$, $—CH_2CH_3$, $—CF_2H$, $—CF_3$, $—CF_2CH_3$, and $—CH_2CN$. In some embodiments, $R^5$ is $C_{1-6}$alkyl that is substituted with one or more $R^{13}$, wherein each $R^{13}$ is independently selected from $—OR^{22}$, —CN, and $—N(R^{22})_2$. In some embodiments, $R^5$ is $—CH_2CN$.

In some embodiments, $R^5$ is selected from $—OR^{12}$, wherein $R^{12}$ is selected from $C_{1-6}$ alkyl and H. In some embodiments, $R^5$ is $—OCH_3$.

In some embodiments, $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$. In some embodiments, $R^5$ is selected from a 3-6 membered carbocycle and a 3-6 membered heterocycle, wherein any carbocycle or heterocycle is unsubstituted or substituted with one or more $R^{14}$. In some embodiments, $R^5$ is a 3-6 membered carbocycle unsubstituted or substituted with one or more $R^{14}$. In some embodiments, $R^5$ is a 3-4 membered carbocycle unsubstituted or substituted with one or more $R^{14}$ (e.g., one or more —CN). In some embodiments, $R^5$ is a 5-6 membered heteroaryl or phenyl unsubstituted or substituted with one or more $R^{14}$ (e.g., $C_{1-6}$alkyl). In some embodiments, $R^5$ is a pyridyl, furanyl, or imidazolyl, each unsubstituted or substituted with one or more $R^{14}$ (e.g., $C_{1-6}$alkyl). In some embodiments, $R^5$ is a furanyl. In some embodiments, $R^5$ is phenyl.

In some embodiments, $R^6$ is a 9-10 membered heteroaryl having 1-3 heteroatoms independently selected from nitrogen, oxygen, and sulfur that is substituted with one or more $R^{15}$. In some embodiments, $R^6$ is a 9-membered heteroaryl having 1-3 heteroatoms independently selected from nitrogen, oxygen, and sulfur and substituted with one or more $R^{15}$. In some such embodiments, at least one $R^{15}$ is $—N(R^{12})_2$ (e.g., $—NH_2$). In some embodiments, at least one $R^{15}$ is a halogen (e.g., F). In some embodiments, each $R^{15}$ is independently selected from halogen, —CN, and $—N(R^{12})_2$. In some embodiments, $R^6$ is substituted with at least two $R^{15}$ (e.g., at least a halogen and $—NH_2$).

In some embodiments, $R^6$ has the structure:

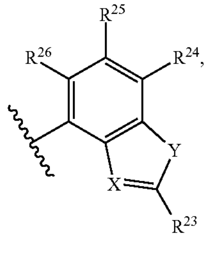

wherein X is selected from N and C—CN; Y is selected from O and S; $R^{23}$ is selected from $—N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^{25}$, and $R^{26}$ are independently selected from H, halogen, $—OR^{12}$, and $C_{1-6}$alkyl, wherein any $C_{1-6}$alkyl is unsubstituted or substituted with one or more $R^{13}$.

In some embodiments, $R^6$ is selected from:

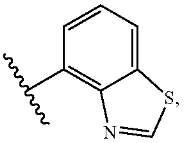
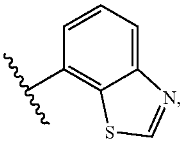
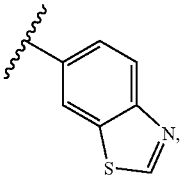
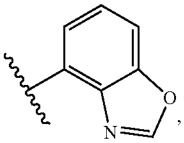
,
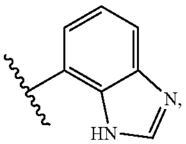
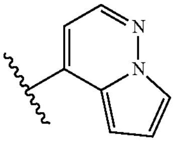
,
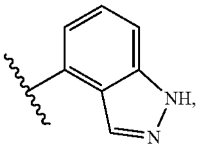
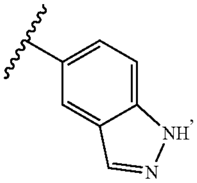
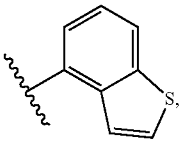
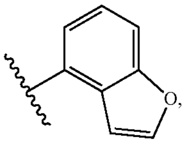
and
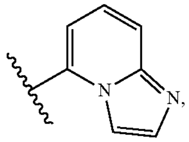

any of which is substituted with one or more $R^{15}$.

In some embodiments, $R^6$ is selected from:

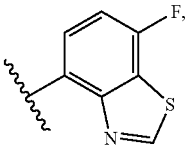
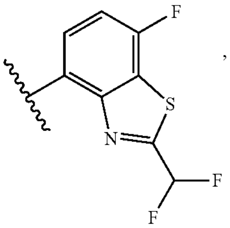
,
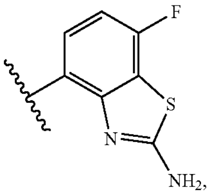
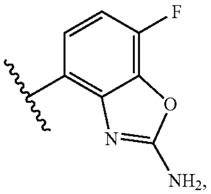

-continued
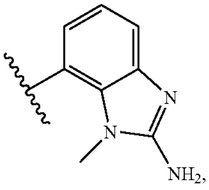,
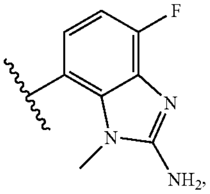,
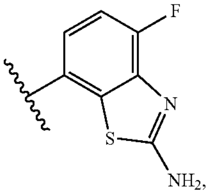,
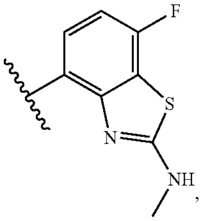,
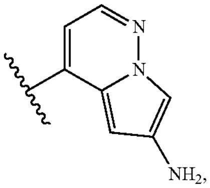,
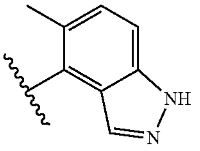,
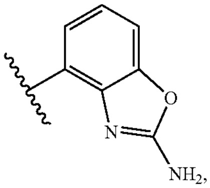,
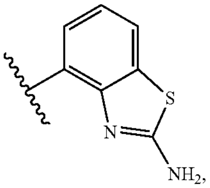,
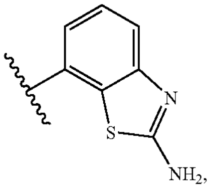,
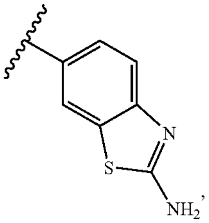,
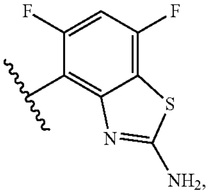,
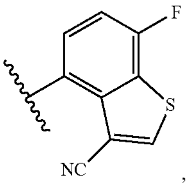,
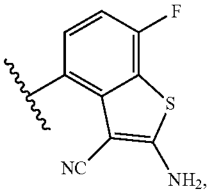,
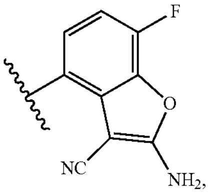, and
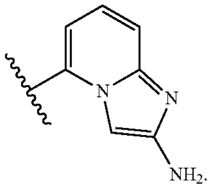.
In some embodiments, $R^6$ is selected from:
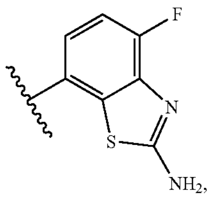,
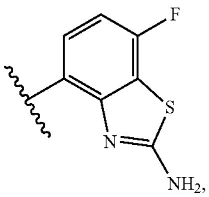,
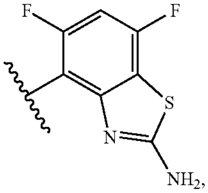,
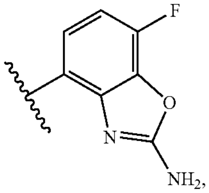,
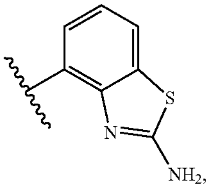,
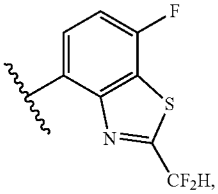,
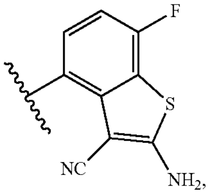,
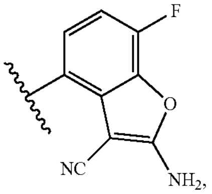, and
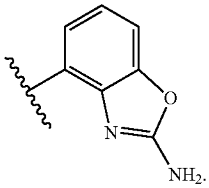.
In some embodiments, $R^6$ is
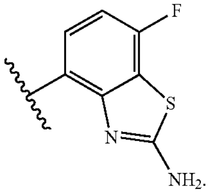 [SMILES: *c1ccc(F)c2sc(N)nc12].
In some embodiments, $R^6$ is
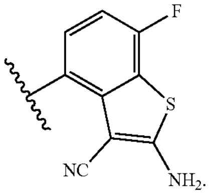 [SMILES: *c1ccc(F)c2sc(N)c(C#N)c12].
In some embodiments, $R^7$ is a halogen. In some embodiments, $R^7$ is F. In some embodiments, $R^7$ is Cl.
In some embodiments, $R^7$ is —$OR^{12}$, such as —OH. In some embodiments, $R^7$ is —$OR^{12}$, wherein $R^{12}$ is $C_{1-6}$ alkyl.

In some embodiments, $R^7$ is —CN.

In some embodiments, $R^7$ is H.

In some embodiments, each E is independently selected from:

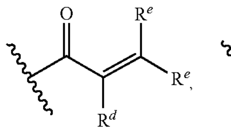,
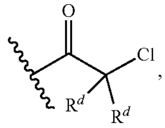, and
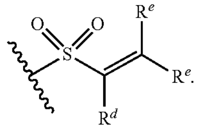.

In some embodiments, each E is:

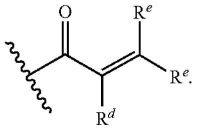.

In some embodiments, each $R^d$ and $R^e$ is H. In some embodiments, the compound has a single E.

In some embodiments, $R^4$ is H; $R^7$ is a halogen; and $R^1$ is OH. In some embodiments, $R^7$ is F. In some embodiments, $R^5$ is H. In some embodiments, $R^5$ is —$CF_3$.

In some embodiments, $R^4$ is H; $R^7$ is a halogen (e.g., F); and $R^1$ is selected from:

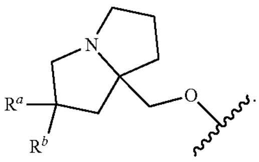.

In some embodiments, $R^a$ and $R^b$ are each independently selected from halogen, $C_{1-6}$alkyl, —$OR^2$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

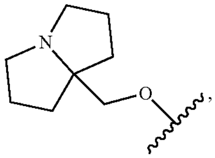,
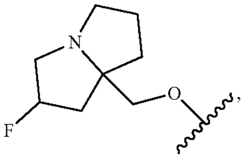,

-continued

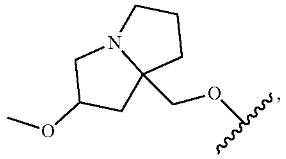,

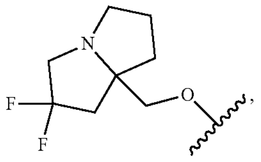, and
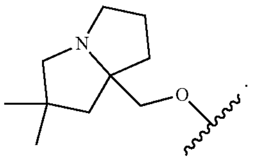.

In some embodiments, $R^1$ is selected from:

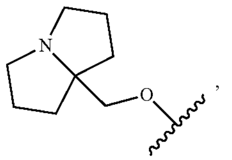,
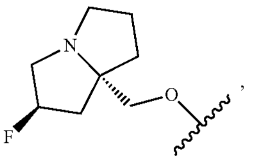,
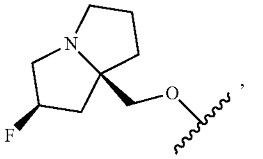,
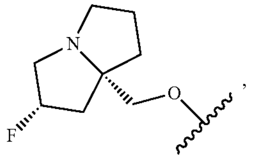,
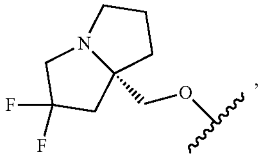,
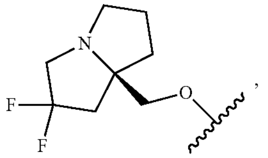,
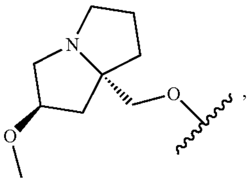,
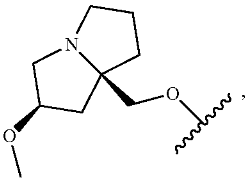,
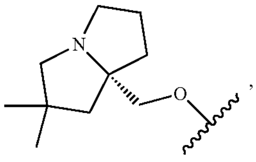, and
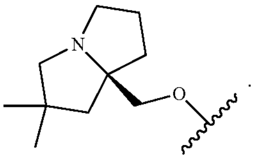.

In some embodiments, $R^7$ is F. In some embodiments, $R^5$ is H. In some embodiments, $R^5$ is —$CF_3$. In some embodiments, $R^5$ is Cl.

In some embodiments, $R^4$ is H; $R^7$ is a halogen; and $R^1$ is selected from:

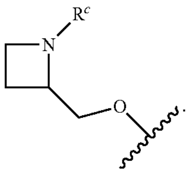.

In some embodiments, $R^c$ is methyl. In some embodiments, $R^1$ is selected from:

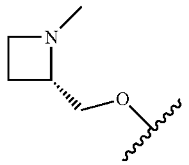

and

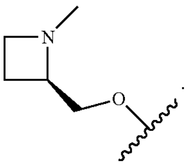

In some embodiments, $R^7$ is F. In some embodiments, $R^5$ is H. In some embodiments, $R^5$ is —$CF_3$.

In some embodiments, the present disclosure provides a compound represented by Formula IA1:

(IA1)

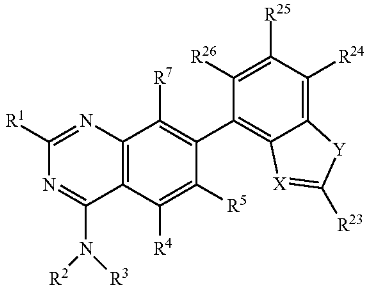

or a salt (e.g., pharmaceutically acceptable salt), ester, tautomer, prodrug, zwitterionic form, or stereoisomer thereof, wherein:

$R^1$ is selected from

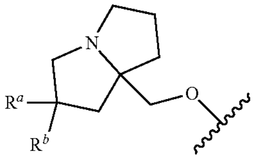

and

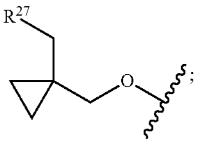

$R^2$ is $C_{1-6}$ alkyl that is unsubstituted or is substituted with one or more $R^{13}$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^{12}$, —CN, and H;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{20}$ is independently selected from —OH, —$OC_{1-6}$ alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each E is independently selected from

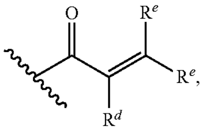

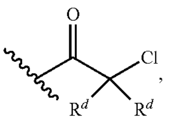

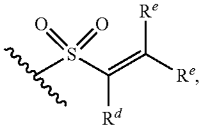

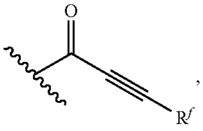

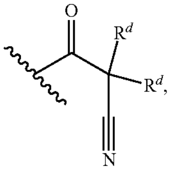

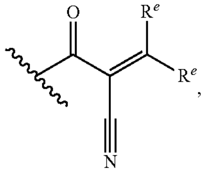

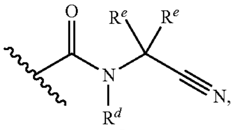

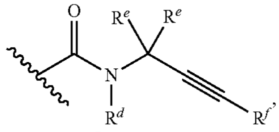

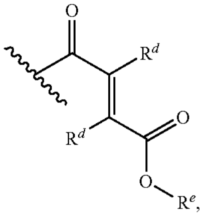

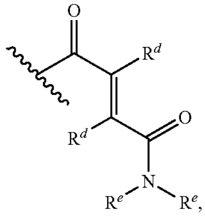

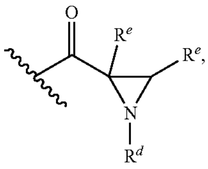

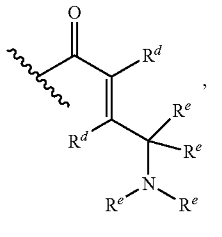

and —CN;

$R^a$ and $R^b$ are each independently selected from halogen, $C_{1-6}$ alkyl, —$OR^{12}$, and H, wherein any $C_{1-6}$alkyl is unsubstituted or is substituted with one or more $R^{13}$;

each $R^d$ and $R^e$ is independently selected from halogen, $C_{1-6}$ alkyl, and H;

each $R^f$ is independently selected from $C_{1-6}$ alkyl and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

In some embodiments, the present disclosure provides a compound of Formula IA1, or a salt (e.g., a pharmaceutically acceptable salt) thereof.

In some embodiments for a compound of Formula IA1, $R^2$ is selected from $C_{1-2}$ alkyl. In some embodiments, $R^2$ is methyl.

In some embodiments for a compound of Formula IA1, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

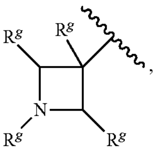
,
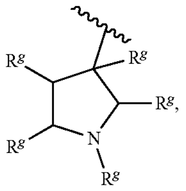
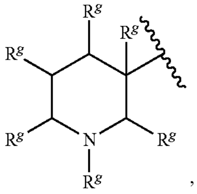
, and
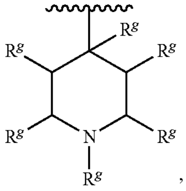
, wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, $R^3$ is selected from:

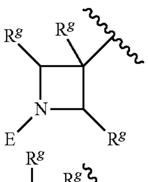
,
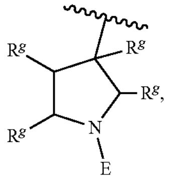
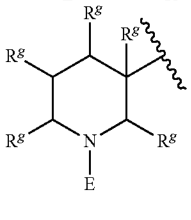
, and
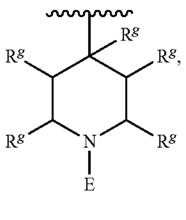

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is unsubstituted $C_{1-6}$alkyl (e.g., methyl).

In some embodiments, the present disclosure provides a compound represented by Formula IA2:

(IA2)

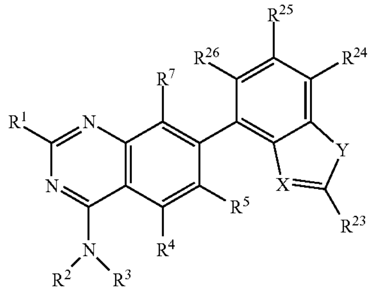

or a salt (e.g., pharmaceutically acceptable salt), ester, tautomer, prodrug, zwitterionic form, or stereoisomer thereof, wherein:

$R^1$ is selected from

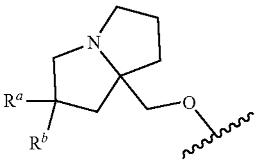
and
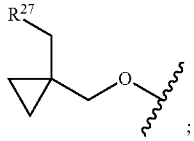
;

$R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is H;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^2$, —CN, and H;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each E is independently selected from

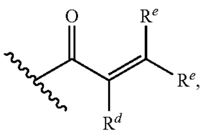

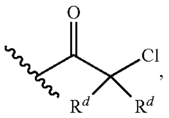

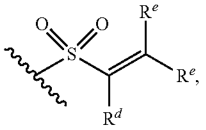

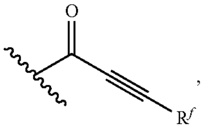

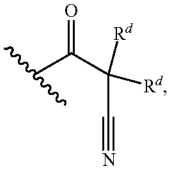

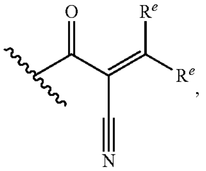

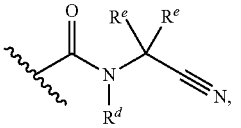

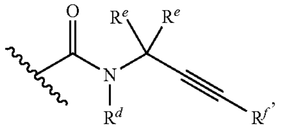

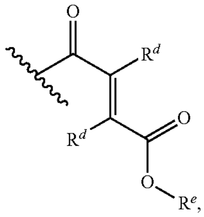

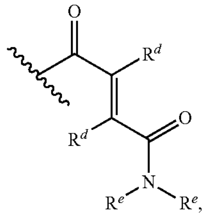

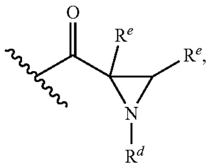

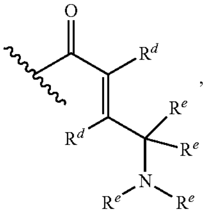

$R^a$ and $R^b$ are each independently selected from halogen, $C_{1-6}$ alkyl, —$OR^{12}$, and H, wherein any $C_{1-6}$alkyl is unsubstituted or is substituted with one or more $R^{13}$;

each $R^d$ and $R^e$ is independently selected from halogen, $C_{1-6}$ alkyl, and H;

each $R^f$ is independently selected from $C_{1-6}$ alkyl and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

In some embodiments, the present disclosure provides a compound of Formula IA2, or a salt (e.g., a pharmaceutically acceptable salt) thereof.

In some embodiments for a compound of Formula IA2, $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

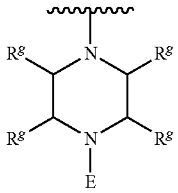

or

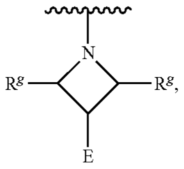

wherein each $R^g$ is independently selected from $C_{1-6}$alkyl and H, wherein any $C_{1-6}$alkyl is unsubstituted or substituted with one or more $R^{20}$, optionally wherein two $R^g$ groups, together with the atoms to which they are attached, form a 3-6 membered carbocycle or heterocycle. In some embodiments, each $R^g$ is H. In some embodiments, one or two $R^g$ groups are $C_{1-6}$alkyl (e.g., methyl). In some embodiments, $R^2$ and $R^3$, together with the atom to which they are attached, form the structure:

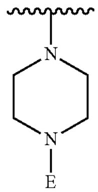,

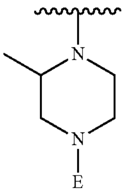,

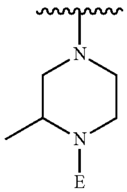,

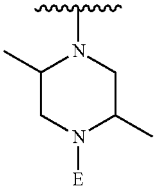,

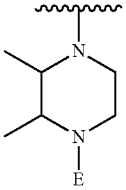,

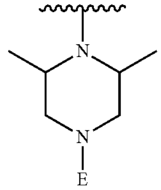,

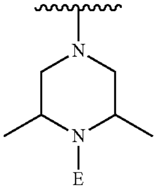,

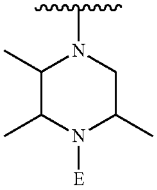,

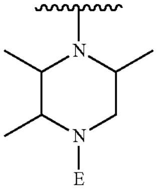, or

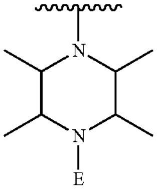.

In some embodiments, $R^2$ and $R^3$, together with the atom to which they are attached, form a bridged piperazinyl ring that is substituted with one or more E and 0-4 $R^{11}$. In some embodiments, $R^2$ and $R^3$, together with the atom to which they are attached, form the structure:

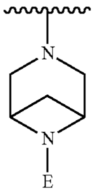

or

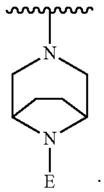

.

In some embodiments for a compound of Formula IA1 or IA2, $R^1$ is selected from:

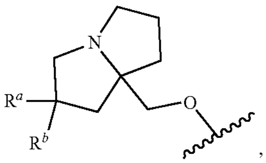

, wherein $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$ alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

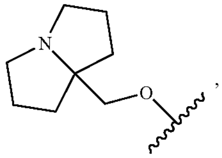

,

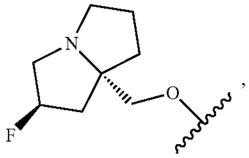

,

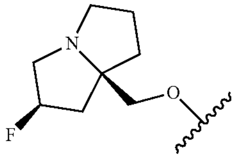

,

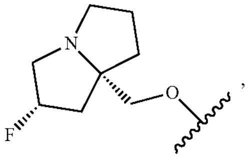

,

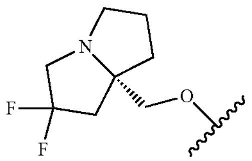

,

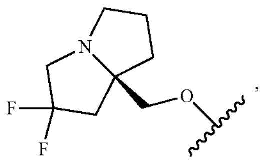

,

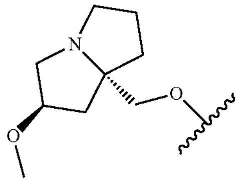

,

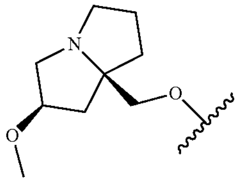

,

-continued

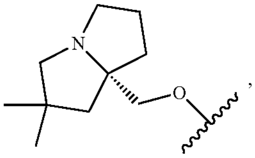

, and

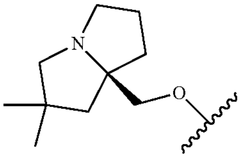

.

In some embodiments for a compound of Formula IA1 or IA2, $R^5$ is selected from $C_{1-6}$alkyl, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$. In some embodiments, $R^5$ is $C_{1-6}$alkyl substituted with —CN or one or more halogens. In some embodiments, $R^5$ is —$CF_3$. In some embodiments, $R^5$ is phenyl. In some embodiments, $R^5$ is furanyl. In some embodiments, $R^5$ is H. In some embodiments, $R^5$ is halogen (e.g., F or Cl).

In some embodiments for a compound of Formula IA1 or IA2, $R^7$ is a halogen (e.g., F). In some embodiments, $R^7$ is —CN. In some embodiments, $R^7$ is H.

In some embodiments for a compound of Formula IA1 or IA2, X is N and Y is O. In some embodiments, X is N and Y is S. In some embodiments, X is C—CN and Y is O. In some embodiments, X is C—CN and Y is S. In some embodiments, $R^{23}$ is —$NH_2$. In some embodiments, $R^{24}$ is F. In some embodiments, $R^{25}$ and $R^{26}$ are H. In some embodiments,

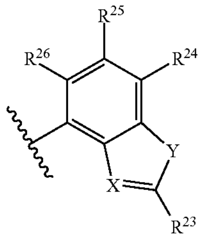

is selected from:

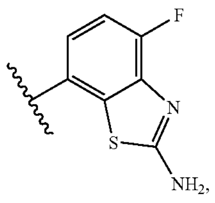

,

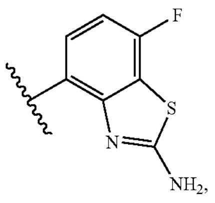

,

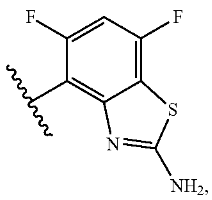

,

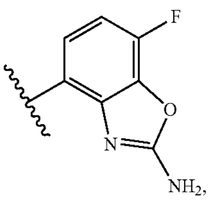

,

-continued

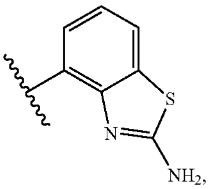
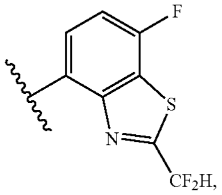
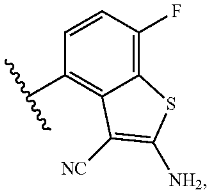
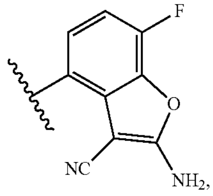
and
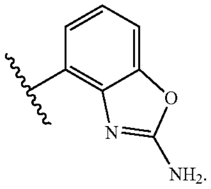

In some embodiments for a compound of Formula IA1 or IA2,

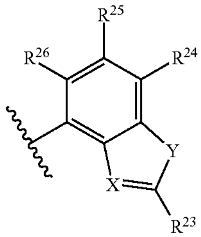
is
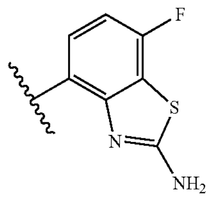

In some embodiments,

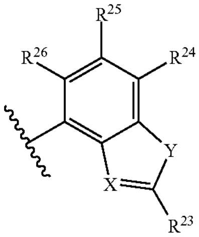
is
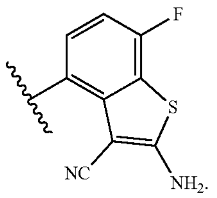

In some embodiments for a compound of Formula IA1 or IA2, each E is:

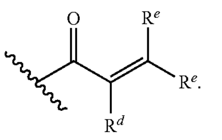

In some embodiments, each $R^d$ and $R^e$ is H. In some embodiments, the compound has a single E.

In some embodiments for a compound of Formula IA1 or IA2, $R^7$ is H and $R^5$ is $C_{1-6}$alkyl that unsubstituted or substituted with one or more $R^{13}$. In some embodiments, $R^5$ is —$CF_3$. In some embodiments, X is N and Y is S. In some embodiments, X is C—CN and Y is S.

In some embodiments for a compound of Formula IA1 or IA2, $R^7$ is a halogen and $R^5$ is $C_{1-6}$alkyl that unsubstituted or substituted with one or more $R^{13}$. In some embodiments, $R^7$ is F. In some embodiments, $R^5$ is —$CF_3$. In some embodiments, X is N and Y is S. In some embodiments, X is C—CN and Y is S.

In some embodiments for a compound of Formula IA1 or IA2, $R^7$ is a halogen and $R^5$ is H. In some embodiments, $R^7$ is F. In some embodiments, X is N and Y is S. In some embodiments, X is C—CN and Y is S.

In some embodiments for a compound of Formula IA1 or IA2, $R^7$ is a halogen and $R^5$ is a halogen. In some embodiments, $R^7$ is F. In some embodiments, $R^5$ is Cl. In some embodiments, X is N and Y is S. In some embodiments, X is C—CN and Y is S.

In another aspect, the present disclosure provides a compound represented by Formula IB:

(IB)

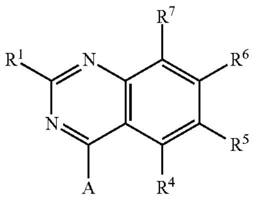

or a salt (e.g., pharmaceutically acceptable salt), ester, tautomer, prodrug, zwitterionic form, or stereoisomer thereof, wherein:

$R^1$ is selected from —$OR^8$,

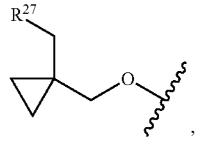
, a 4-6 membered heterocycle comprising a nitrogen atom, and H, wherein the heterocycle is unsubstituted or substituted with one or more $R^{16}$.

A is selected from

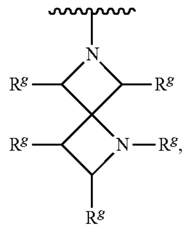
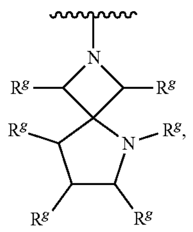

-continued

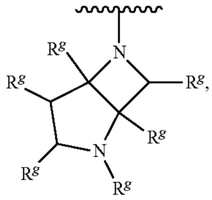

and

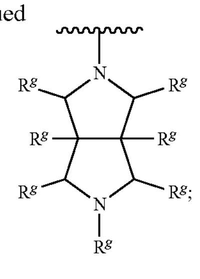

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —CN, —$OR^{12}$, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each $R^a$ and $R^b$ is independently selected from halogen, $C_{1-6}$ alkyl, —$OR^{12}$, and H, wherein any $C_{1-6}$alkyl is unsubstituted or substituted with one or more $R^{13}$;

each $R^g$ is independently selected from $C_{1-6}$alkyl, H, and E, wherein at least one $R^g$ is E, and wherein any $C_{1-6}$alkyl is unsubstituted or substituted with one or more $R^{20}$;

each E is independently selected from

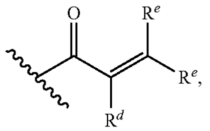

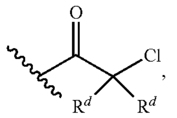

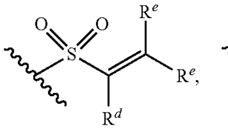

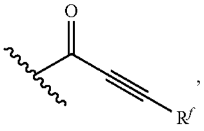

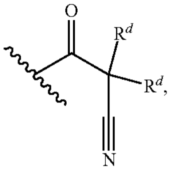

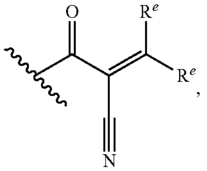

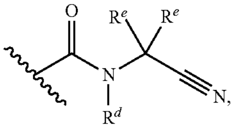

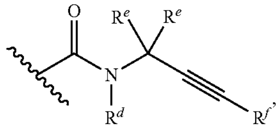

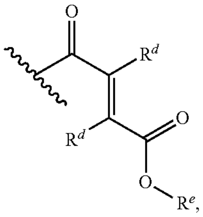

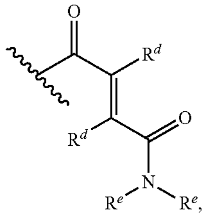

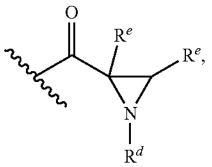

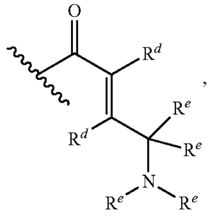

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IB, or a salt (e.g., a pharmaceutically acceptable salt) thereof.

In some embodiments, A is selected from:

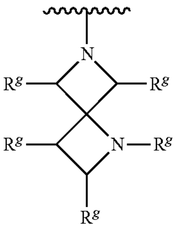

and

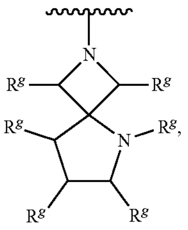

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, A is selected from:

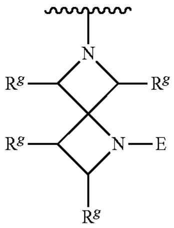
and
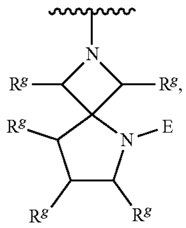

wherein each $R^g$ is independently selected from $C_{1-6}$alkyl and H, wherein any $C_{1-6}$alkyl is unsubstituted or substituted with one or more $R^{20}$. In some embodiments, each $R^g$ is H.

In some embodiments, A is selected from:

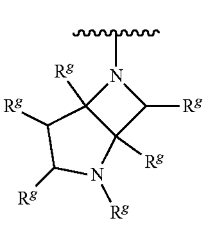
and
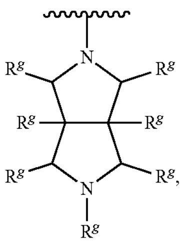

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, A is selected from:

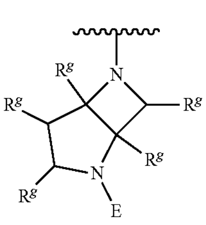
and
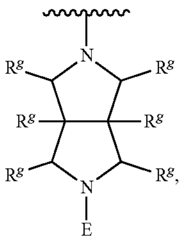

wherein each $R^g$ is independently selected from $C_{1-6}$alkyl and H, wherein any $C_{1-6}$alkyl is unsubstituted or substituted with one or more $R^{20}$. In some embodiments, each $R^g$ is H.

In some embodiments, $R^1$ is selected from —$OR^8$, wherein $R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl. In some embodiments, $R^8$ is a heterocycle or an alkylheterocycle, wherein any heterocycle contains 4-8 members and is substituted with one or more $R^a$ and/or $R^b$. In some embodiments, $R^8$ is a heterocycle that is unsubstituted or substituted with one or more $R^a$ and/or $R^b$. In some embodiments, $R^8$ is an alkylheterocycle that is unsubstituted or substituted with one or more $R^a$ and/or $R^b$. In some embodiments, $R^8$ is —$CH_2$(heterocycle), where the heterocycle is unsubstituted or substituted with one or more $R^a$ and/or $R^b$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$ and/or $R^b$, wherein the one or more $R^a$ and/or $R^b$ is a halogen (e.g., F). In some embodiments, a heterocycle or a heterocycle of an alkylheterocycle is substituted with one or more $R^a$ and/or $R^b$, wherein the one or more $R^a$ and/or $R^b$ is a $C_{1-6}$alkyl (e.g., methyl). In some embodiments, a heterocycle or a heterocycle of an alkylheterocycle is substituted with one or more $R^a$ and/or $R^b$, wherein the one or more $R^a$ and/or $R^b$ is a —$OR^{12}$ (e.g., —$OCH_3$).

In some embodiments, $R^1$ is selected from:

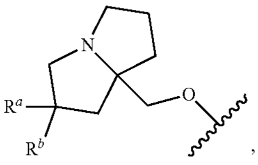
, wherein $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

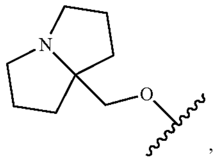
,
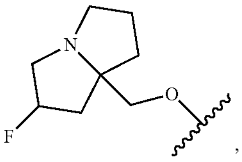
,
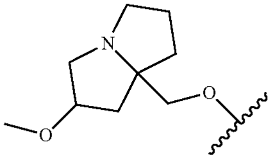
,
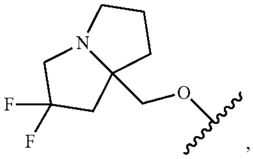
, and
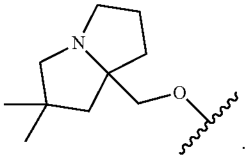
.

In some embodiments, $R^1$ is selected from:

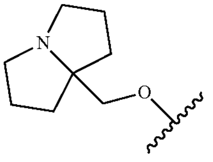
,
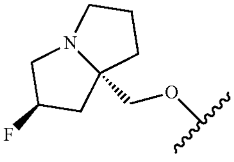
,

-continued

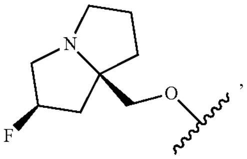

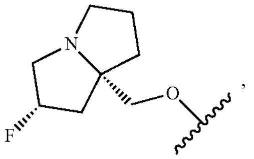

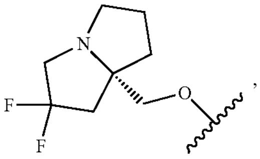

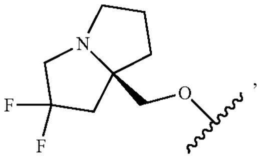

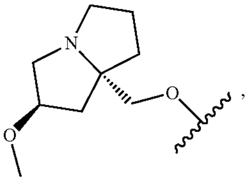

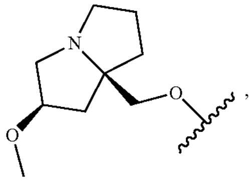

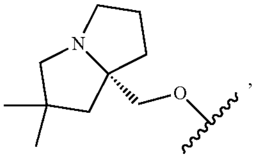

and

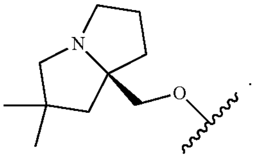

In some embodiments, $R^1$ is selected from:

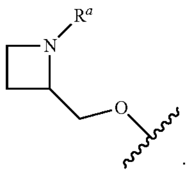

In some embodiments, $R^a$ is methyl. In some embodiments, $R^1$ is selected from:

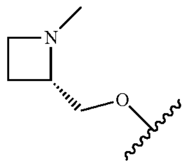

and

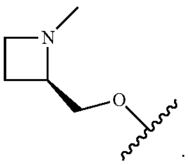

In some embodiments, $R^1$ is selected from.

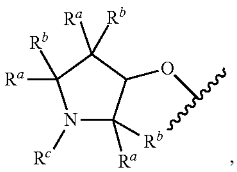

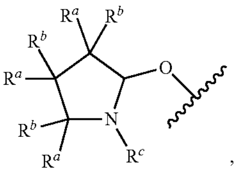

-continued

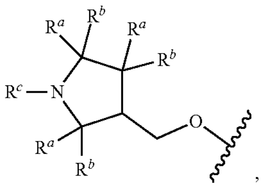

and

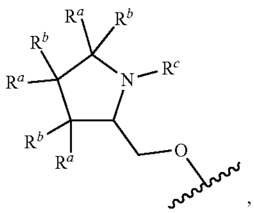

wherein each $R^a$ and $R^b$ is independently selected from halogen, $C_{1-6}$ alkyl, $—OR^{12}$, and H; and $R^c$ is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and $—OR^{12}$, and the other $R^a$ and $R^b$ groups are H. In some embodiments, one $R^a$ or $R^b$ is halogen (e.g., F). In some embodiments, two $R^a$ groups, two $R^b$ groups, or an $R^a$ and an $R^b$ are halogen (e.g., F). In some embodiments, one $R^a$ or $R^b$ is $—OR^{12}$ (e.g., $—OCH_3$ or $—CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from $—CH_3$, $—CH_2CH_2F$, $—CH_2CHF_2$, and $—CH_2CH_2CN$. In some embodiments, $R^1$ is selected from:

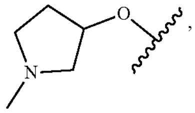

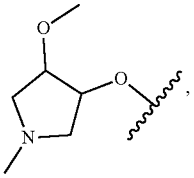

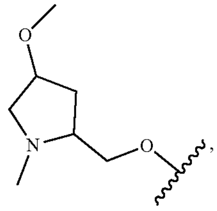

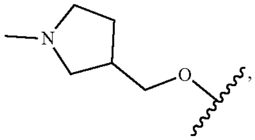

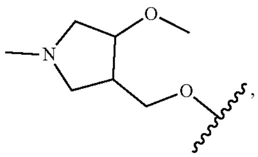

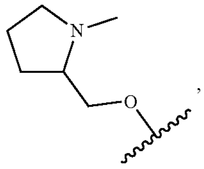

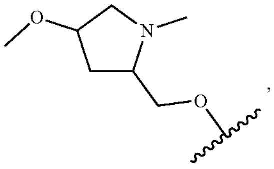

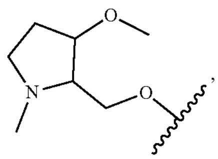

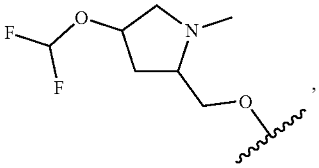

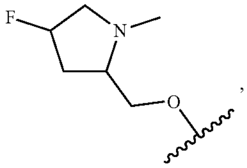

-continued

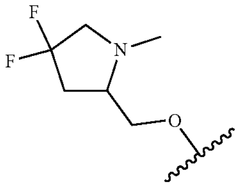,
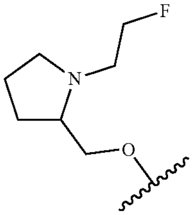,
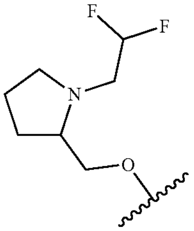,
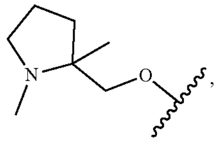,
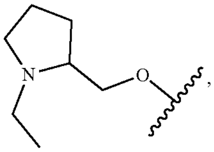,
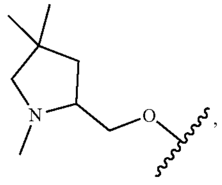,
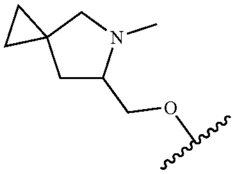, and
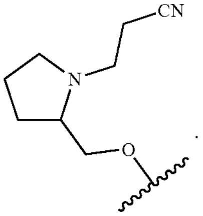.

In some embodiments, $R^1$ is selected from:

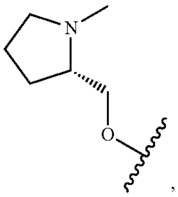,
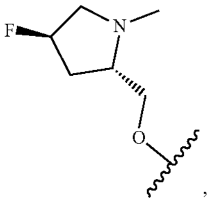,
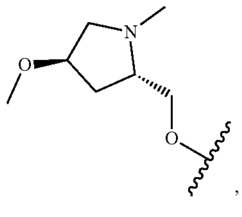, and
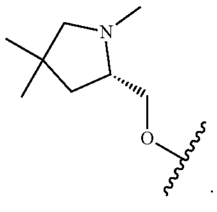.

In some embodiments, $R^1$ is selected from:

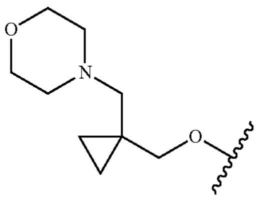 and

-continued

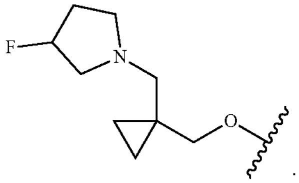.

In some embodiments, $R^1$ is selected from:

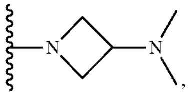,
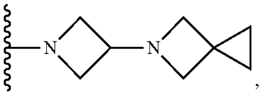,
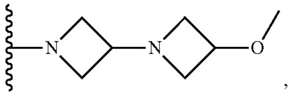,
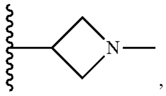, and
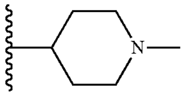.

In some embodiments, $R^4$ is H.

In some embodiments, $R^5$ is H.

In some embodiments, $R^5$ is —CN.

In some embodiments, $R^5$ is a halogen. In some embodiments, $R^5$ is Cl. In some embodiments, $R^5$ is F.

In some embodiments, $R^5$ is selected from $C_{1-6}$alkyl that is unsubstituted or substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is —$CF_3$. In some embodiments, $R^5$ is —$CHF_2$. In some embodiments, $R^5$ is selected from —$CF_3$, —$CF_2H$, and —$CH_2CN$. In some embodiments, $R^5$ is selected from —$CH_3$, —$CH_2CH_3$, —$CF_2H$, —$CF_3$, —$CF_2CH_3$, and —$CH_2CN$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$.

In some embodiments, $R^5$ is selected from —$OR^{12}$, wherein $R^{12}$ is selected from $C_{1-6}$ alkyl and H. In some embodiments, $R^5$ is —$OCH_3$.

In some embodiments, $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$. In some embodiments, $R^5$ is selected from a 3-6 membered carbocycle and a 3-6 membered heterocycle, wherein any carbocycle or heterocycle is unsubstituted or substituted with one or more $R^{14}$. In some embodiments, $R^5$ is a 3-6 membered carbocycle unsubstituted or substituted with one or more $R^{14}$. In some embodiments, $R^5$ is a 3-4 membered carbocycle unsubstituted or substituted with one or more $R^{14}$ (e.g., one or more —CN). In some embodiments, $R^5$ is a 5-6 membered heteroaryl or phenyl unsubstituted or substituted with one or more $R^{14}$ (e.g., $C_{1-6}$alkyl). In some embodiments, $R^5$ is a pyridyl, furanyl, or imidazolyl, each unsubstituted or substituted with one or more $R^{14}$ (e.g., $C_{1-6}$alkyl). In some embodiments, $R^5$ is a furanyl. In some embodiments, $R^5$ is phenyl.

In some embodiments, $R^6$ is a 9-10 membered heteroaryl having 1-3 heteroatoms independently selected from nitrogen, oxygen, and sulfur that is substituted with one or more $R^{15}$. In some embodiments, $R^6$ is a 9-membered heteroaryl having 1-3 heteroatoms independently selected from nitrogen, oxygen, and sulfur and substituted with one or more $R^{15}$. In some such embodiments, at least one $R^{15}$ is —$N(R^{12})_2$ (e.g., —$NH_2$). In some embodiments, at least one $R^{15}$ is a halogen (e.g., F). In some embodiments, each $R^{15}$ is independently selected from halogen, —CN, and —$N(R^{12})_2$. In some embodiments, $R^6$ is substituted with at least two $R^{15}$ (e.g., at least a halogen and —$NH_2$).

In some embodiments, $R^6$ has the structure:

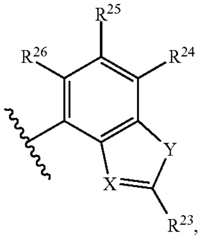

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$ and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

In some embodiments, $R^6$ is selected from:

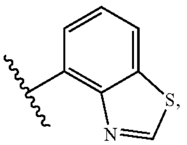
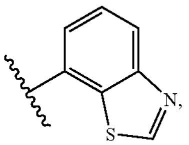
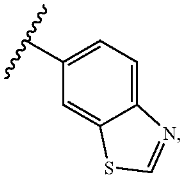
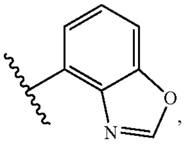
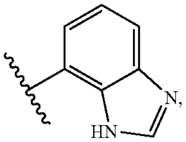
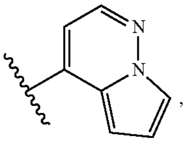
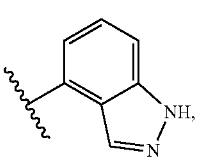
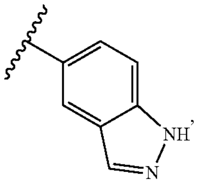
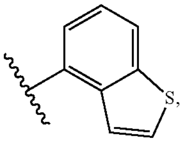
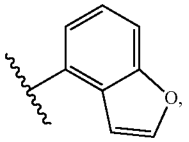
and -continued

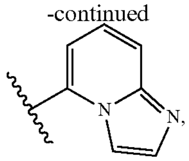

any of which is substituted with one or more $R^{15}$.

In some embodiments, $R^6$ is selected from:

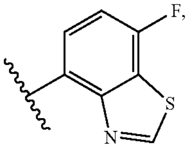
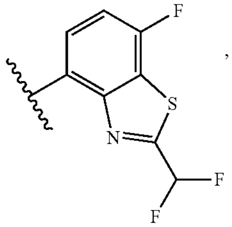
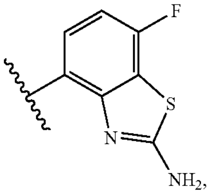
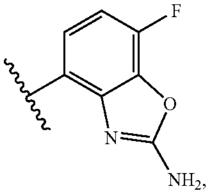 [SMILES: *c1ccc(F)c2sc(N)nc12]
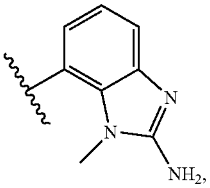
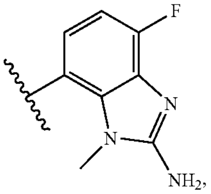
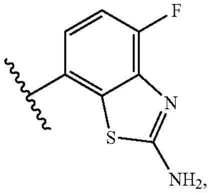
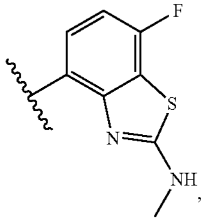
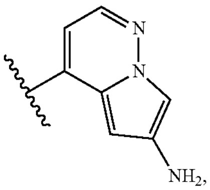
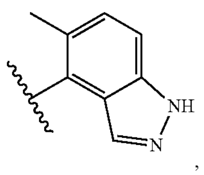
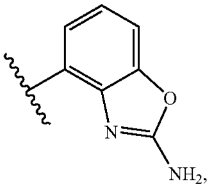
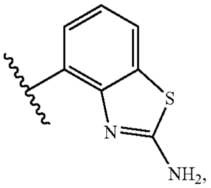
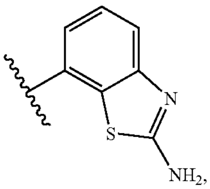
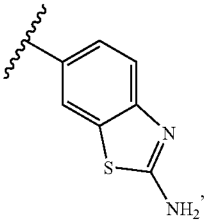

-continued

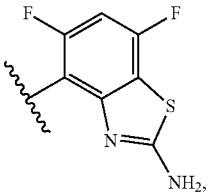

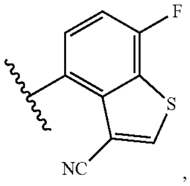

,

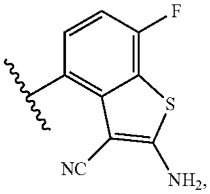

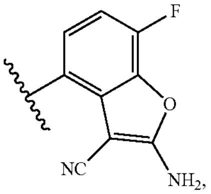

and

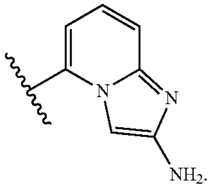

In some embodiments, $R^6$ is selected from:

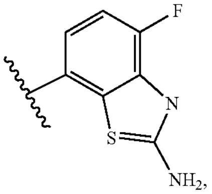

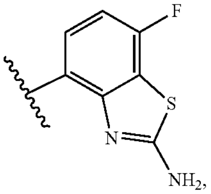

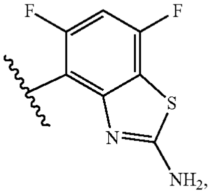

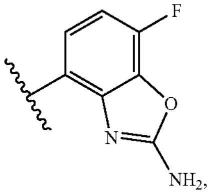

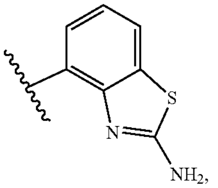

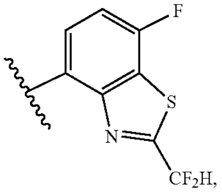

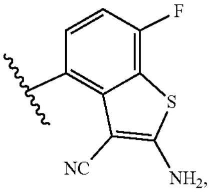

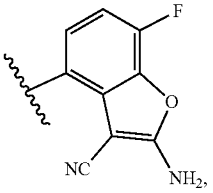

and

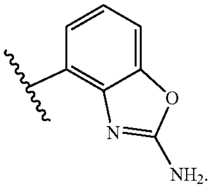

In some embodiments, $R^6$ is

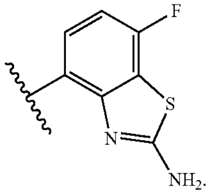

In some embodiments, $R^6$ is

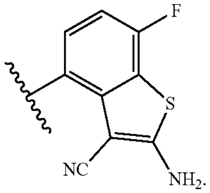 [SMILES: *c1ccc(F)c2sc(N)c(C#N)c12]

In some embodiments, $R^7$ is a halogen. In some embodiments, $R^7$ is F.

In some embodiments, $R^7$ is —$OR^{12}$, such as —OH. In some embodiments, $R^7$ is —$OR^{12}$, wherein $R^{12}$ is $C_{1-6}$ alkyl.

In some embodiments, $R^7$ is —CN.

In some embodiments, $R^7$ is H.

In some embodiments, each E is independently selected from:

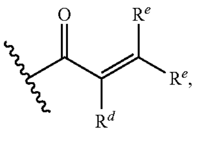

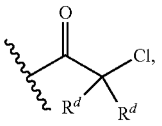

and

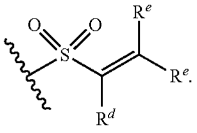

In some embodiments, each E is:

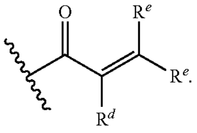

In some embodiments, each $R^d$ and $R^e$ is H. In some embodiments, the compound includes a single E.

In some embodiments, $R^4$ is H; $R^7$ is a halogen; and A is selected from:

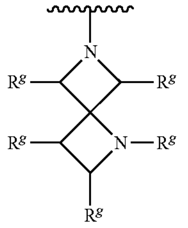

and

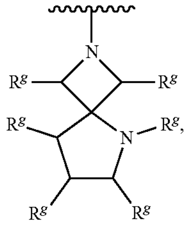

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, A is selected from:

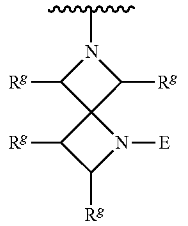

and

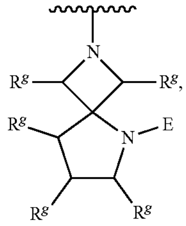

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, $R^7$ is F.

In some embodiments, $R^4$ is H; $R^7$ is a halogen; and A is selected from:

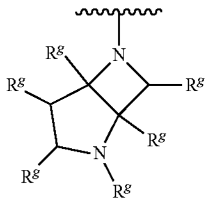

and

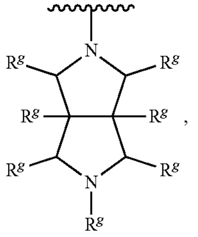

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, A is selected from:

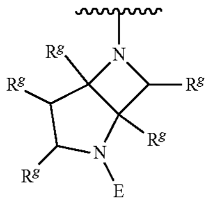

and

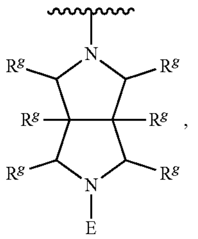

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, $R^7$ is F.

In another aspect, the present disclosure provides a compound according to Formula IC:

(IC)

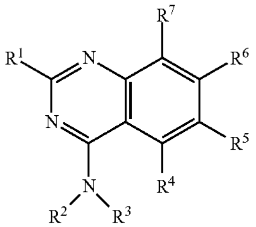

or a salt (e.g., pharmaceutically acceptable salt), ester, tautomer, prodrug, zwitterionic form, or stereoisomer thereof, wherein:

$R^1$ is selected from $-OR^8$,

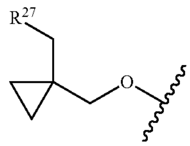

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with $-N(R^{12})(E)$, wherein the heterocycle is substituted with one or more E and 0-4 $R^{10}$, optionally wherein two $R^{10}$ groups, together with the atom or atoms to which they are attached, form a 3-6 membered carbocycle;

$R^4$ is selected from H, $-OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $-OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, $-OR^x$, —CN, and H;

$R^8$ is selected from $C_{1-6}$ alkyl, a heterocycle and an alkylheterocycle, wherein any heterocycle comprises 4-8 members and is unsubstituted or is substituted with one or more $R^a$ and/or $R^b$, wherein any $C_{1-6}$ alkyl of $R^8$ is unsubstituted or substituted with one or more $R^{20}$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$OR^{12}$, —CN, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^x$ is independently selected from $C_{1-6}$ alkyl, a 3-6 membered carbocycle, and H;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each $R^a$ and $R^b$ is independently selected from halogen, $C_{1-6}$ alkyl, —$OR^{12}$, a 3-6 membered carbocycle, and H, wherein any $C_{1-6}$ alkyl is unsubstituted or is substituted with one or more $R^{13}$;

each E is independently selected from

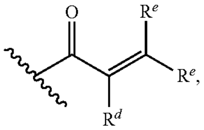,
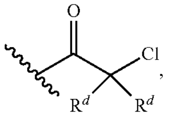,
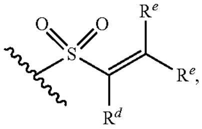,
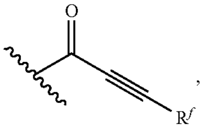,
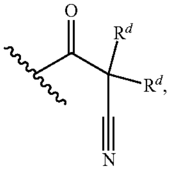,
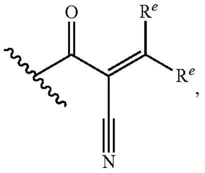,
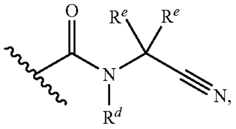,
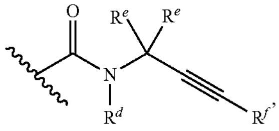,
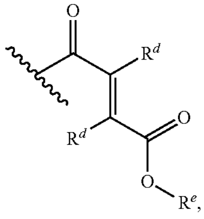,
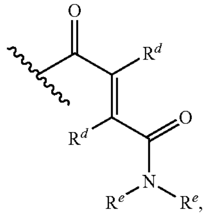, -continued

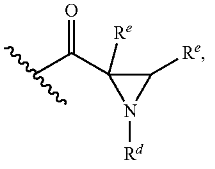,
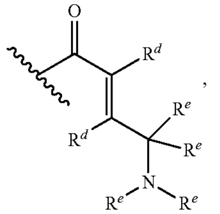, each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IC, or a salt (e.g., a pharmaceutically acceptable salt) thereof.

In some embodiments, $R^2$ is H. In some embodiments, $R^2$ is selected from $C_{1-6}$ alkyl and a 3-6 membered carbocycle. In some embodiments, $R^2$ is $C_{1-6}$ alkyl unsubstituted or substituted with one or more $R^{13}$. In some such embodiments, each $R^{13}$ is independently selected from —$OR^{22}$ (e.g., —OH) and —CN. In some embodiments, $R^2$ is methyl. In some embodiments $R^2$ is selected from —$CH_3$, —$CH_2CH_3$, —$CH_2CH_2OH$, —$CH_2CH_2CN$, and —$CH(CH_3)_2$.

In some embodiments, $R^3$ is selected from $C_{1-6}$ alkyl that is substituted with —$N(R^{12})(E)$. In some embodiments, $R^3$ is $C_2$ alkyl that is substituted with —$N(R^{12})(E)$. In some embodiments, $R^3$ is $C_2$ alkyl that is substituted with —N(H)(E).

In some embodiments, $R^3$ is a 4-6 membered heterocycle that is substituted with one or more E and 0-4 $R^{10}$, wherein the heterocycle includes one or more heteroatoms selected from N, O, and S, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes one or more heteroatoms selected from N, O, and S. In some embodiments, $R^3$ is selected from a 4-6 membered heterocycle, wherein the heterocycle contains a single heteroatom that is N, and wherein the heterocycle is substituted with one or more E and 0-4 $R^{10}$, optionally wherein two $R^{10}$ groups, together with the atom or atoms to which they are attached, form a 3-6 membered carbocycle. In some embodiments, $R^3$ is selected from a 4-6 membered heterocycle, wherein the heterocycle contains a single heteroatom that is N, and wherein the heterocycle is substituted with one or more E and 0-4 $R^{10}$. In some embodiments, $R^3$ is an azetidine, pyrrolidine, or piperidine, wherein the azetidine, pyrrolidine, or piperidine is substituted with one or more E and 0-4 $R^{10}$, optionally wherein two $R^{10}$ groups, together with the atom or atoms to which they are attached, form a 3-6 membered carbocycle. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is an azetidine, pyrrolidine, or piperidine, wherein the azetidine, pyrrolidine, or piperidine is substituted with one or more E and 1-2 $R^{10}$, and $R^{10}$ is $C_{1-6}$ alkyl or halogen. In some embodiments, $R^3$ is a pyrrolidine substituted with one or more E and 0-4 $R^{10}$. In some embodiments, $R^3$ is selected from:

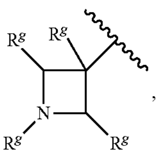
,
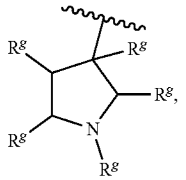
,

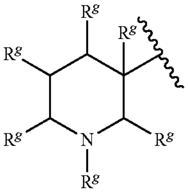
, and
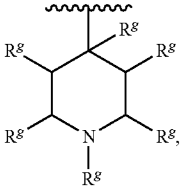
, wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

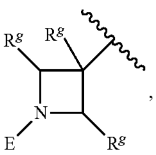
,
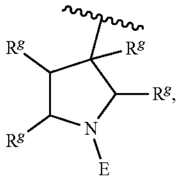
,

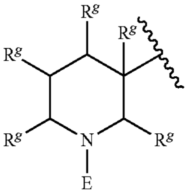
, and
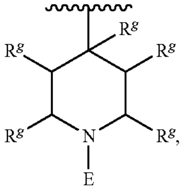
, wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In some embodiments, $R^1$ is H.

In some embodiments, $R^1$ is selected from —$OR^8$, wherein $R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl. In some embodiments, $R^8$ is a heterocycle or an alkylheterocycle, wherein any heterocycle contains 4-8 members and is substituted with one or more $R^a$ and/or $R^b$. In some embodiments, $R^8$ is a heterocycle that is unsubstituted or substituted with one or more $R^a$ and/or R. In some embodiments, $R^8$ is an alkylheterocycle that is unsubstituted or substituted with one or more $R^a$ and/or $R^b$. In some embodiments, $R^8$ is —$CH_2$(heterocycle), where the heterocycle is unsubstituted or substituted with one or more $R^a$ and/or $R^b$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$ and/or $R^b$, wherein the one or more $R^a$ and/or $R^b$ is a halogen (e.g., F). In some embodiments, a heterocycle or a heterocycle of an alkylheterocycle is substituted with one or more $R^a$ and/or $R^b$, wherein the one or more $R^a$ and/or $R^b$ is a $C_{1-6}$alkyl (e.g., methyl). In some embodiments, a heterocycle or a heterocycle of an alkylheterocycle is substituted with one or more $R^a$ and/or $R^b$, wherein the one or more $R^a$ and/or $R^b$ is a —$OR^{12}$ (e.g., —$OCH_3$).

In some embodiments, $R^1$ is selected from:

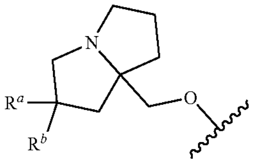
, wherein $R^a$ and $R^b$ are each independently selected from halogen, —$OR^{12}$, and H. In some embodiments, $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

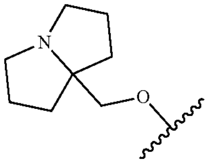
,
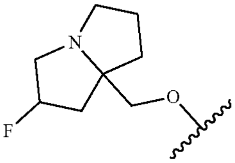
,

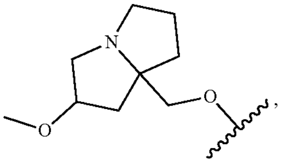
,

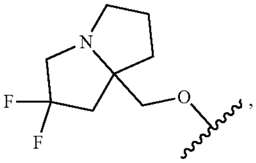
, and

-continued

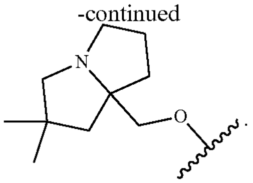

In some embodiments, $R^1$ is selected from:

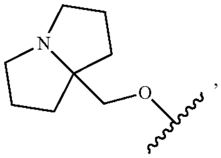
,
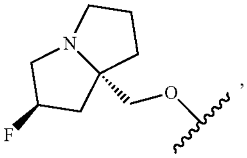
,
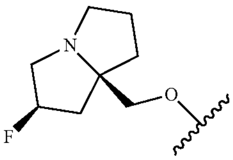
,
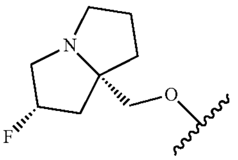
,
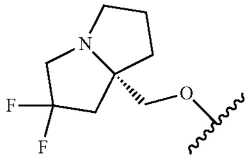
,
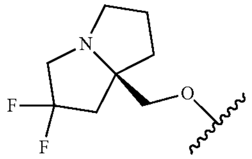
,
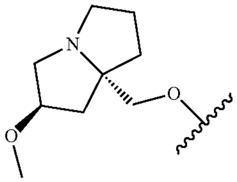
,
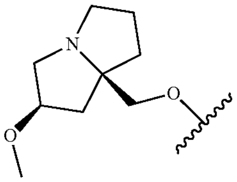
,
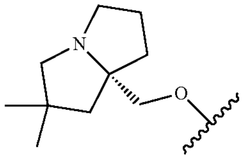
, and
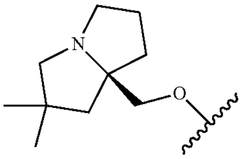
.

In some embodiments, $R^1$ is selected from:

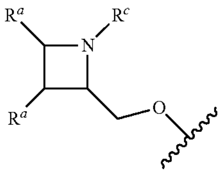
, wherein each $R^a$ is independently selected from halogen, $C_1$ alkyl, —$OR^{12}$, and H; and wherein $R^c$ is selected from $C_{1-6}$ alkyl, wherein the $C_{1-6}$ alkyl is unsubstituted or is substituted with one or more $R^{13}$. In some embodiments, $R^c$ is methyl. In some embodiments, $R^1$ is selected from:

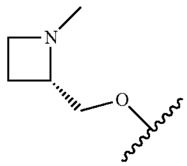
and
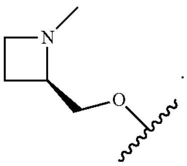
.

In some embodiments, $R^1$ is selected from:

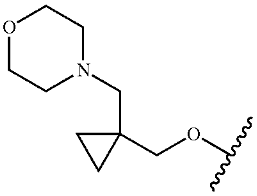
and
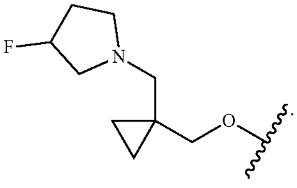
.

In some embodiments, $R^1$ is selected from:

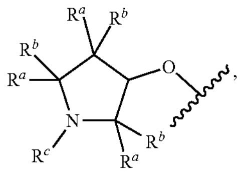
,
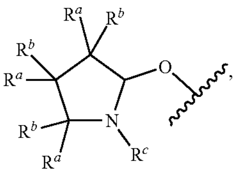
,
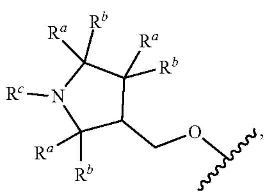
, and
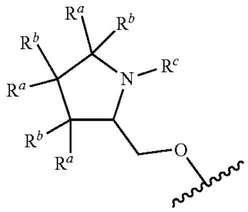

wherein each $R^a$ and $R^b$ is independently selected from halogen, $C_{1-6}$ alkyl, —$OR^{12}$, a 3-6 membered carbocycle, and H; and $R^c$ is selected from $C_{1-6}$ alkyl, wherein the $C_{1-6}$ alkyl is unsubstituted or is substituted with one or more $R^{13}$. In some embodiments, each $R^a$ and $R^b$ is independently selected from halogen, $C_{1-6}$ alkyl, —$OR^{12}$, and H. In some embodiments, one or more $R^a$ and/or $R^b$ is selected from halogen, $C_{1-6}$ alkyl, and —$OR^{12}$, and the other $R^a$ and $R^b$ groups are H. In some embodiments, one $R^a$ or $R^b$ is halogen (e.g., F). In some embodiments, two $R^a$ groups, two $R^b$ groups, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

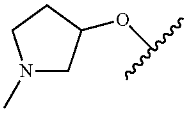,
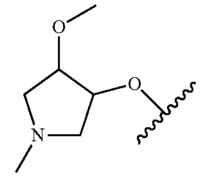,
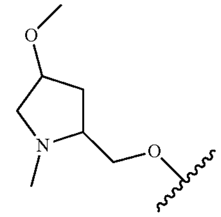,
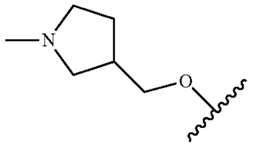,
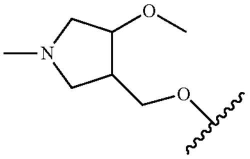,
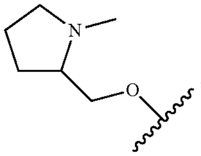,
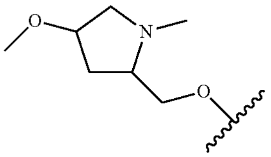,
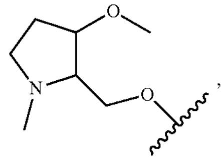,
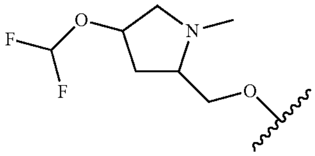,
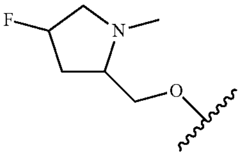,
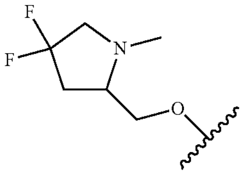,
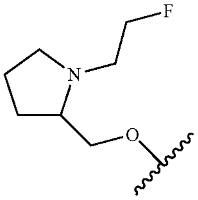,
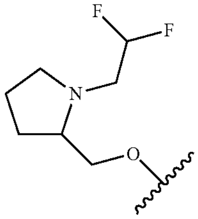,
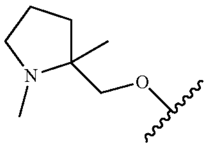,
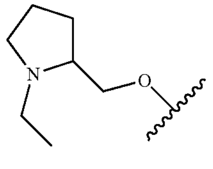,
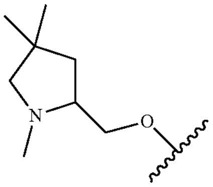,
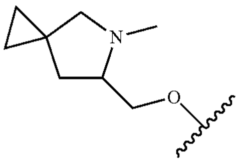, and -continued

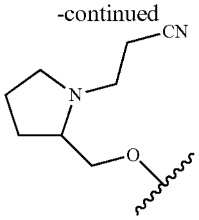.

In some embodiments, $R^1$ is selected from:

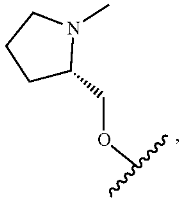,
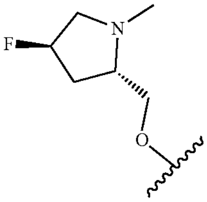,
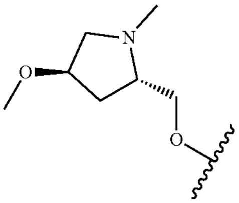, and
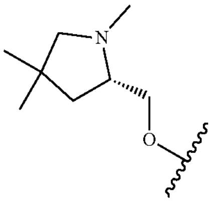.

In some embodiments, $R^1$ is a 4-6 membered heterocycle comprising a nitrogen atom, wherein the heterocycle is unsubstituted or substituted with one or more $R^{16}$. In some embodiments, $R^1$ is:

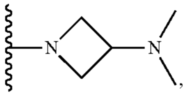,
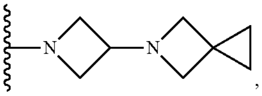,
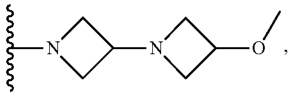,
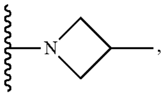, and
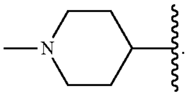.

In some embodiments, $R^4$ is H. In some embodiments, $R^4$ is $—OCH_3$.

In some embodiments, $R^5$ is H.

In some embodiments, $R^5$ is —CN.

In some embodiments, $R^5$ is a halogen. In some embodiments, $R^5$ is F. In some embodiments, $R^5$ is Cl.

In some embodiments, $R^5$ is $C_{1-6}$alkyl that is unsubstituted or substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is $—CF_3$. In some embodiments, $R^5$ is $—CHF_2$. In some embodiments, $R^5$ is selected from $—CF_3$, $—CF_2H$, and $—CH_2CN$. In some embodiments, $R^5$ is selected from $—CH_3$, $—CH_2CH_3$, $—CF_2H$, $—CF_3$, $—CF_2CH_3$, and $—CH_2CN$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$.

In some embodiments, $R^5$ is selected from —$OR^{12}$, wherein $R^{12}$ is selected from $C_{1-6}$ alkyl and H. In some embodiments, $R^5$ is —$OCH_3$.

In some embodiments, $R^5$ is selected from a 3-6 membered heterocycle, a 5-6 membered heteroaryl, phenyl, and a 3-6 membered carbocycle, wherein any carbocycle, heteroaryl, phenyl, or heterocycle is unsubstituted or substituted with one or more $R^{14}$. In some embodiments, $R^5$ is selected from a 3-6 membered heterocycle and a 3-6 membered carbocycle, wherein any carbocycle or heterocycle is unsubstituted or substituted with one or more $R^{14}$. In some embodiments, $R^5$ is a 3-6 membered carbocycle unsubstituted or substituted with one or more $R^{14}$. In some embodiments, $R^5$ is a 3-4 membered carbocycle unsubstituted or substituted with one or more $R^{14}$ (e.g., one or more —CN). In some embodiments, $R^5$ is a 5-6 membered heteroaryl or phenyl unsubstituted or substituted with one or more $R^{14}$ (e.g., $C_{1-6}$alkyl). In some embodiments, $R^5$ is a pyridyl, furanyl, or imidazolyl, each unsubstituted or substituted with one or more $R^{14}$ (e.g., $C_{1-6}$alkyl). In some embodiments, $R^5$ is a furanyl. In some embodiments, $R^5$ is phenyl.

In some embodiments, $R^7$ is a halogen. In some embodiments, $R^7$ is F. In some embodiments, $R^7$ is Cl.

In some embodiments, $R^7$ is —$OR^x$, such as OH. In some embodiments, $R^7$ is —$OR^x$, wherein $R^x$ is $C_{1-6}$ alkyl. In some embodiments, $R^7$ is —OH.

In some embodiments, $R^7$ is —CN.

In some embodiments, $R^7$ is H.

In some embodiments, $R^7$ is:

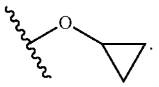 [SMILES: *OC1CC1]

In some embodiments, $R^6$ is a 9-10 membered heteroaryl having 1-3 heteroatoms independently selected from nitrogen, oxygen, and sulfur that is substituted with one or more $R^{15}$. In some embodiments, $R^6$ is a 9-membered heteroaryl having 1-3 heteroatoms independently selected from nitrogen, oxygen, and sulfur and substituted with one or more $R^{15}$. In some such embodiments, at least one $R^{15}$ is —$N(R^{12})_2$ (e.g., —$NH_2$). In some embodiments, at least one $R^{15}$ is a halogen (e.g., F). In some embodiments, each $R^{15}$ is independently selected from halogen, —CN, and —$N(R^{12})_2$. In some embodiments, $R^6$ is substituted with at least two $R^{15}$ (e.g., at least a halogen and —$NH_2$).

In some embodiments, $R^6$ has the structure:

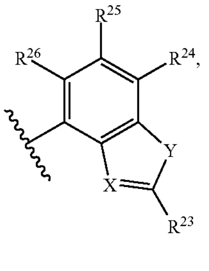

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

In some embodiments, $R^6$ is selected from:

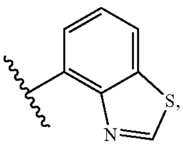
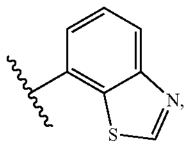
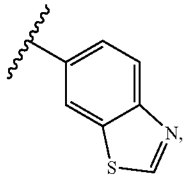
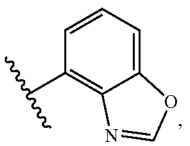
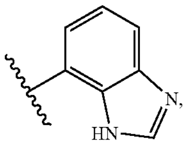
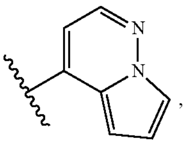
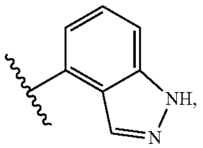
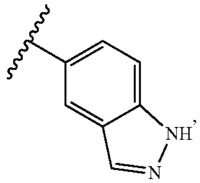
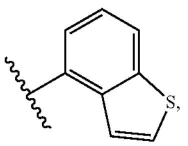
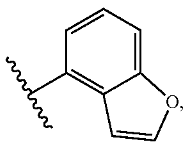
and
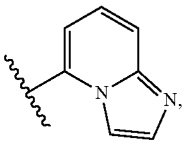

any of which is substituted with one or more $R^{15}$.

In some embodiments, $R^6$ is selected from:

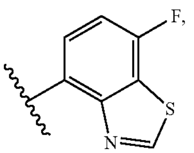
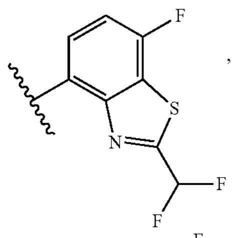
,
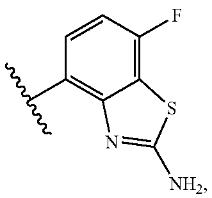
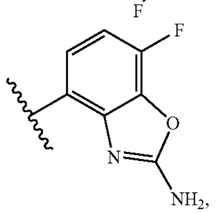

-continued
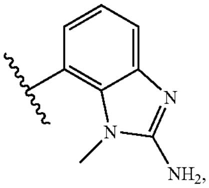
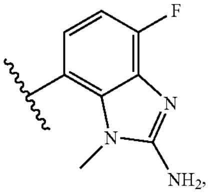
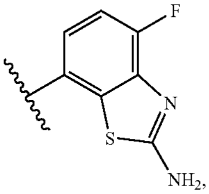
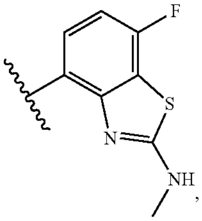
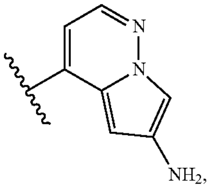
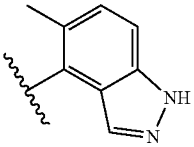
,
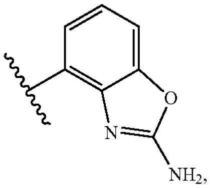
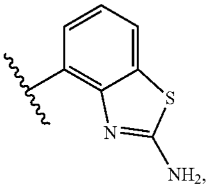
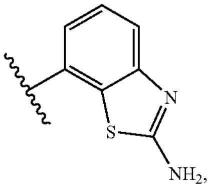
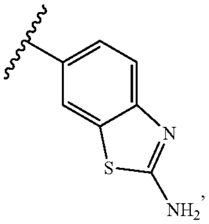
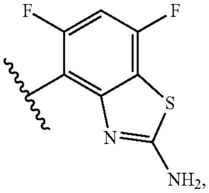
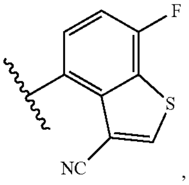
,
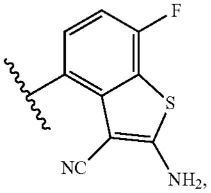
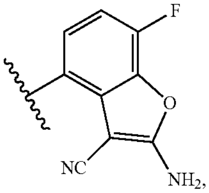
and
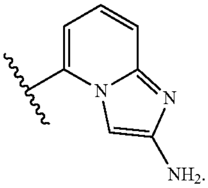
In some embodiments, $R^6$ is selected from:
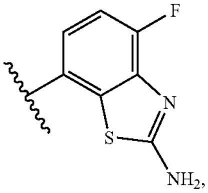
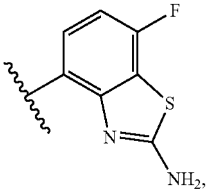
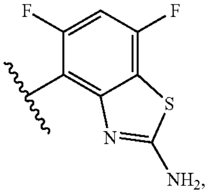
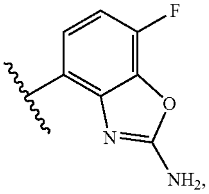
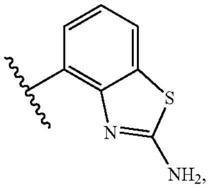
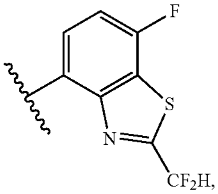
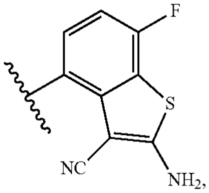
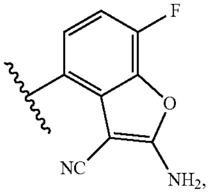
and
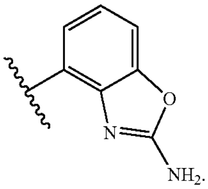
In some embodiments, $R^6$ is
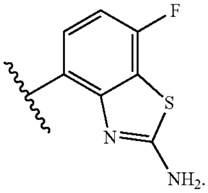 [SMILES: *c1ccc(F)c2sc(N)nc12]
In some embodiments, $R^6$ is
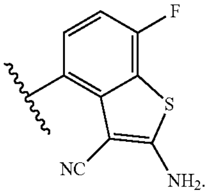

In some embodiments, each E is independently selected from:

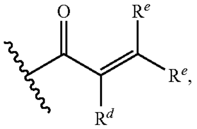
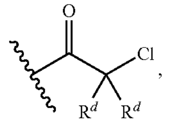
and
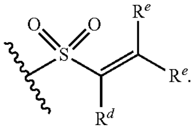

In some embodiments, each E is:

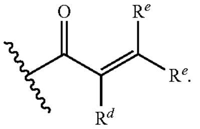

In some embodiments, each $R^d$ and $R^e$ is H. In some embodiments, the compound includes a single E.

In some embodiments, $R^4$ is H; $R^7$ is a halogen; and $R^3$ is selected from $C_{1-6}$ alkyl that is substituted with —N($R^{12}$)(E). In some embodiments, $R^3$ is $C_2$ alkyl that is substituted with —N($R^{12}$)(E). In some embodiments, $R^3$ is $C_2$ alkyl that is substituted with —N(H)(E). In some embodiments, $R^7$ is F. In some embodiments, $R^2$ is H. In some embodiments, $R^2$ is selected from $C_{1-6}$ alkyl and a 3-6 membered carbocycle. In some embodiments, $R^2$ is methyl.

In some embodiments, $R^4$ is H; $R^7$ is a halogen; and $R^3$ is selected from a 4-6 membered heterocycle, wherein the heterocycle contains a single heteroatom that is N, and wherein the heterocycle is substituted with one or more E and 0-4 $R^{10}$. In some embodiments, $R^3$ is selected from:

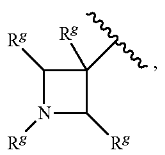
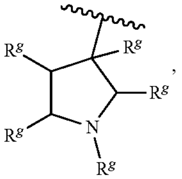
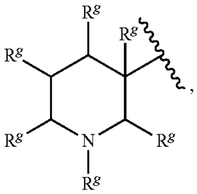
and
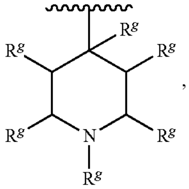

wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

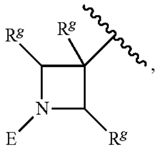
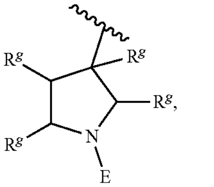
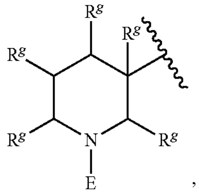
, and
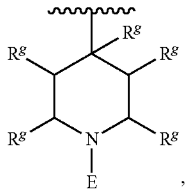

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl). In some embodiments, $R^7$ is F. In some embodiments, $R^2$ is H. In some embodiments, $R^2$ is selected from $C_{1-6}$ alkyl and a 3-6 membered carbocycle. In some embodiments, $R^2$ is methyl.

In some embodiments, the compound is a compound according to Formula IC1:

(IC1)

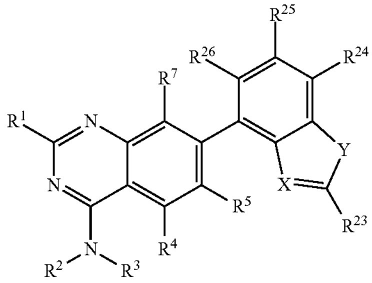

or a salt (e.g., pharmaceutically acceptable salt), ester, tautomer, prodrug, zwitterionic form, or stereoisomer thereof, wherein:

$R^1$ is —$OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^x$ is independently selected from $C_{1-6}$ alkyl, a 3-6 membered carbocycle, and H;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, a 3-6 membered carbocycle, and H, wherein any $C_{1-6}$ alkyl is unsubstituted or is substituted with one or more $R^{13}$;

each E is independently selected from

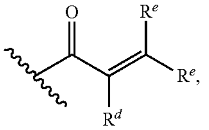 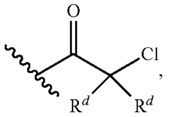

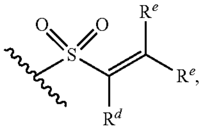 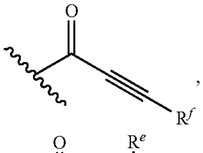

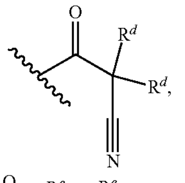 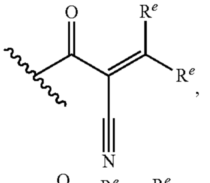

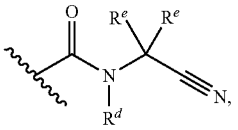 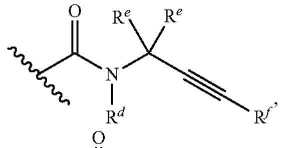

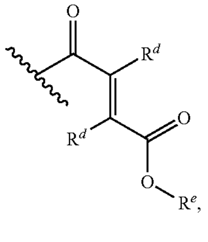 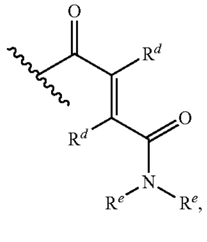

-continued

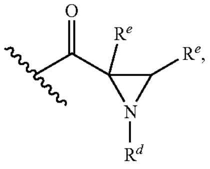 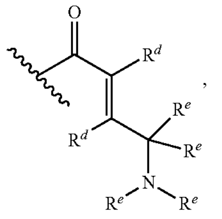

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IC1, or a salt (e.g., a pharmaceutically acceptable salt) thereof.

In some embodiments for a compound of Formula IC1, $R^2$ is selected from $C_{1-2}$ alkyl. In some embodiments, $R^2$ is methyl.

In some embodiments for a compound of Formula IC1, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

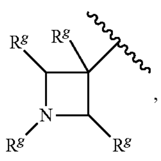 , 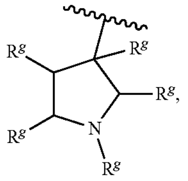

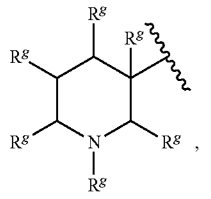 , and 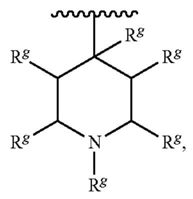

wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, $R^3$ is selected from:

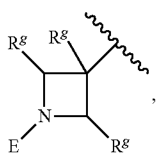 , 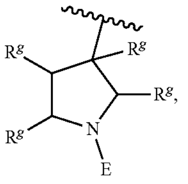

-continued

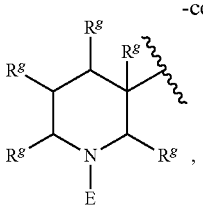

, and

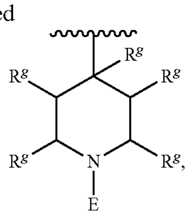

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl.

In some embodiments, the compound is a compound according to Formula IC2:

(IC2)

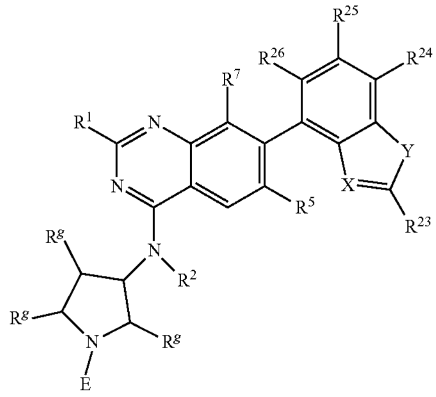

or a salt (e.g., pharmaceutically acceptable salt), ester, tautomer, prodrug, zwitterionic form, or stereoisomer thereof, wherein:

$R^1$ is —$OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^x$ is independently selected from $C_{1-6}$ alkyl, a 3-6 membered carbocycle, and H;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, a 3-6 membered carbocycle, and H, wherein any $C_{1-6}$ alkyl is unsubstituted or is substituted with one or more $R^{13}$;

each E is independently selected from

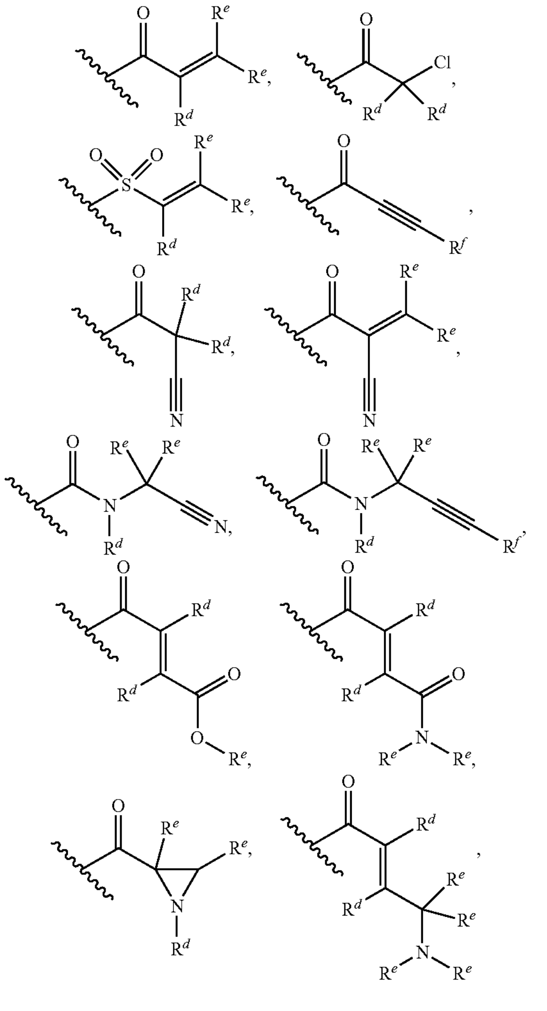

each $R^d$ and $R^e$ is independently selected from halogen, $C_{1-6}$ alkyl, and H;

each $R^f$ is independently selected from $C_{1-6}$ alkyl and H; and each $R^g$ is independently selected from $C_{1-6}$alkyl, halogen, and H, wherein any $C_{1-6}$alkyl is unsubstituted or substituted with one or more $R^{20}$.

In some embodiments, the present disclosure provides a compound of Formula IC2, or a salt (e.g., a pharmaceutically acceptable salt) thereof.

In some embodiments, the compound is a compound according to Formula IC3, IC4, or IC5:

(IC3)

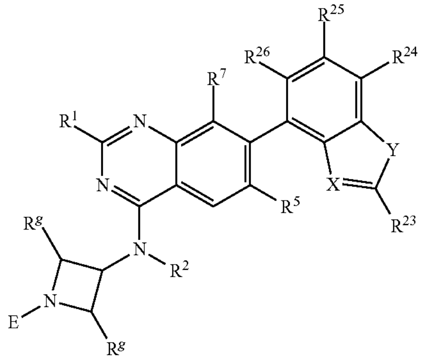

(IC4)

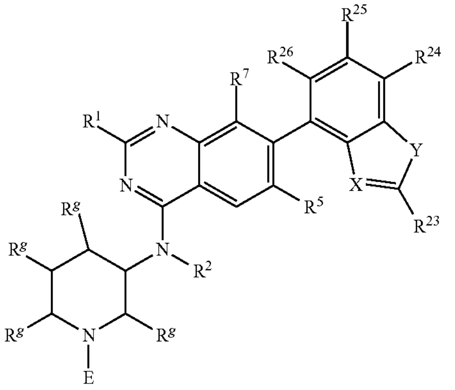

(IC5)

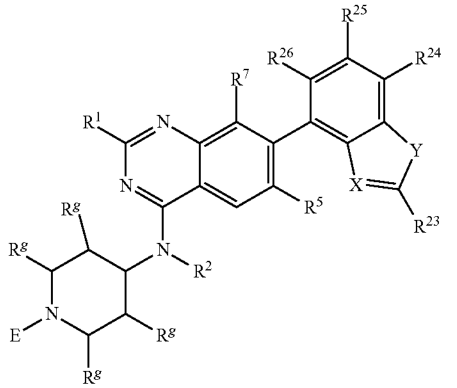

or a salt (e.g., pharmaceutically acceptable salt), ester, tautomer, prodrug, zwitterionic form, or stereoisomer thereof, wherein:

$R^1$ is —$OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^5$ is selected from H, —CN, halogen, $C_{1-6}$alkyl, —$OR^2$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^x$ is independently selected from $C_{1-6}$ alkyl, a 3-6 membered carbocycle, and H;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, a 3-6 membered carbocycle, and H, wherein any $C_{1-6}$ alkyl is unsubstituted or is substituted with one or more $R^{13}$;

each E is independently selected from

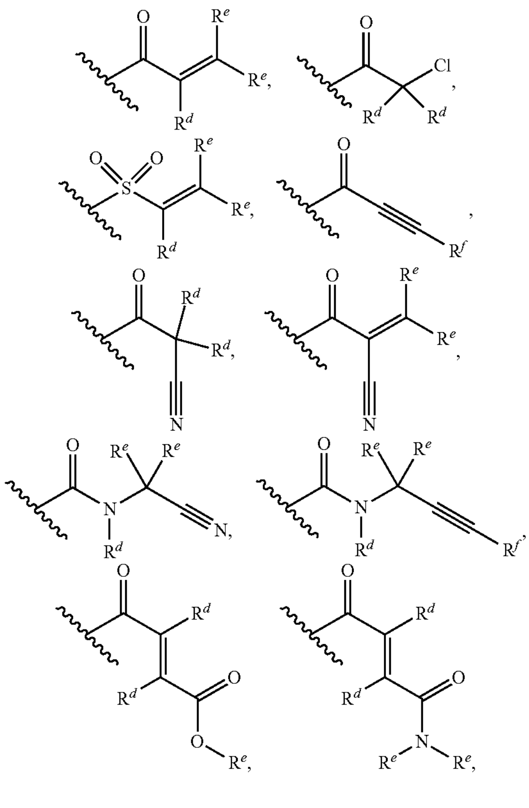

-continued

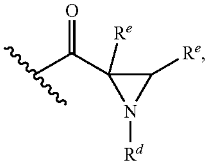

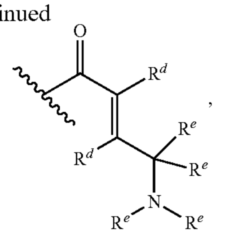

and —CN;

each $R^d$ and $R^e$ is independently selected from halogen, $C_{1-6}$ alkyl, and H;

each $R^f$ is independently selected from $C_{1-6}$ alkyl and H; and each $R^g$ is independently selected from $C_{1-6}$alkyl, halogen, and H, wherein any $C_{1-6}$alkyl is unsubstituted or substituted with one or more $R^{20}$.

In some embodiments, the present disclosure provides a compound of Formula IC3, or a salt (e.g., a pharmaceutically acceptable salt) thereof. In some embodiments, the present disclosure provides a compound of Formula IC4, or a salt (e.g., a pharmaceutically acceptable salt) thereof. In some embodiments, the present disclosure provides a compound of Formula IC5, or a salt (e.g., a pharmaceutically acceptable salt) thereof.

In some embodiments, the compound is a compound according to Formula IC6:

(IC6)

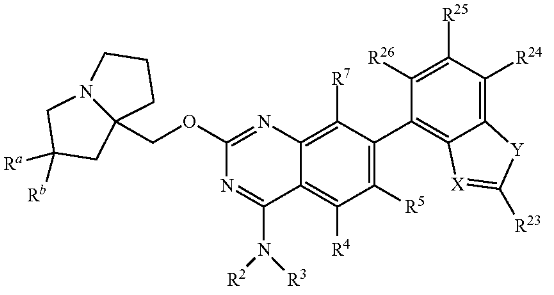

or a salt (e.g., pharmaceutically acceptable salt), ester, tautomer, prodrug, zwitterionic form, or stereoisomer thereof, wherein:

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^x$, —CN, and H;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^x$ is independently selected from $C_{1-6}$ alkyl, a 3-6 membered carbocycle, and H;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, a 3-6 membered carbocycle, and H, wherein any $C_{1-6}$ alkyl is unsubstituted or is substituted with one or more $R^{13}$;

each E is independently selected from

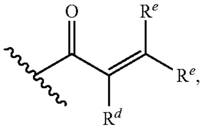

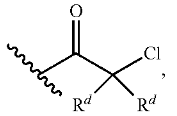

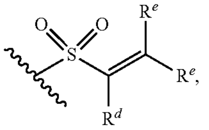

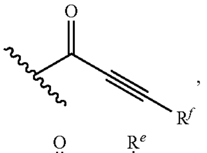

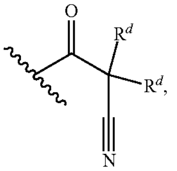

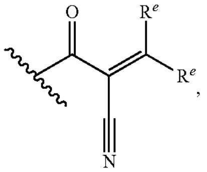

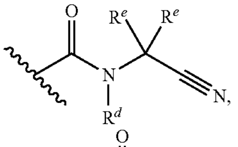

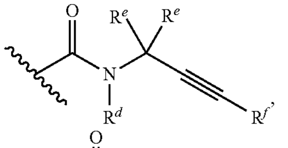

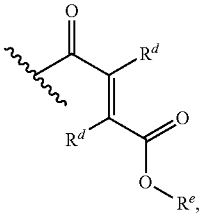

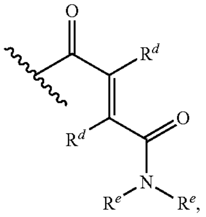

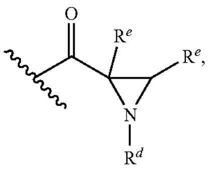

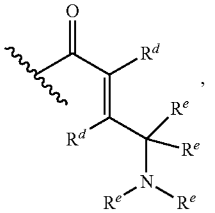

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IC6, or a salt (e.g., a pharmaceutically acceptable salt) thereof.

In some embodiments for a compound of Formula IC6, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is $—OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl.

In some embodiments for a compound of Formula IC6, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

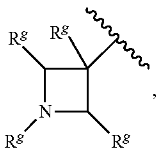
,
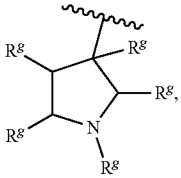

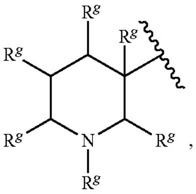
, and
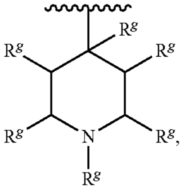

wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, $R^3$ is selected from:

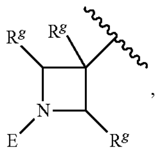
,
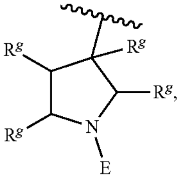

-continued

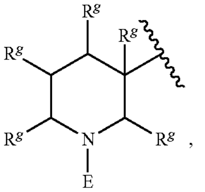
, and
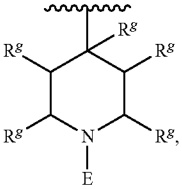

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^9$ is $C_{1-6}$alkyl.

In some embodiments for a compound of Formula IC1, IC2, IC3, IC4, IC5, or IC6, $R^2$ is $C_{1-2}$ alkyl. In some embodiments, $R^2$ is methyl. In some embodiments, $R^2$ is ethyl.

In some embodiments for a compound of Formula IC1, IC2, IC3, IC4, IC5, or IC6, $R^1$ is selected from:

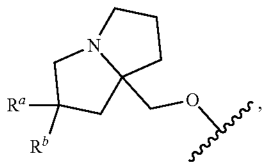
, wherein $R^a$ and $R^b$ are each independently selected from halogen, $C_{1-6}$alkyl, $—OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is $—OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

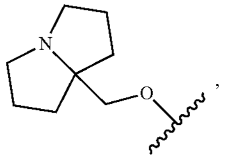
,
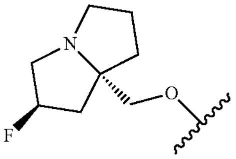
,

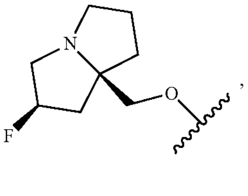
,
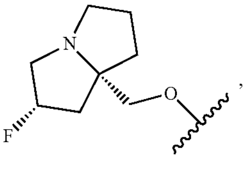
,

-continued

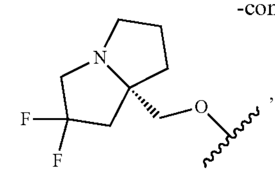

,

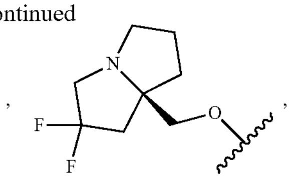

,

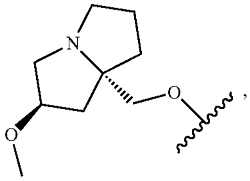

,

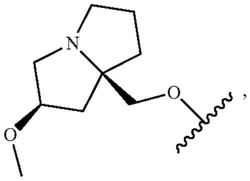

,

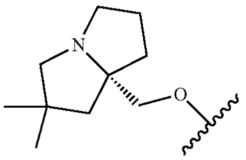

, and

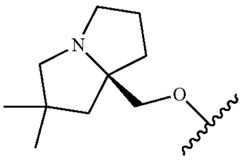

.

In some embodiments for a compound of Formula IC1, IC2, IC3, IC4, IC5, or IC6, $R^5$ is selected from $C_{1-6}$alkyl, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$. In some embodiments, $R^5$ is $C_{1-6}$alkyl substituted with —CN or one or more halogens. In some embodiments, $R^5$ is —$CF_3$. In some embodiments, $R^5$ is phenyl. In some embodiments, $R^5$ is furanyl. In some embodiments, $R^5$ is H. In some embodiments, $R^5$ is halogen (e.g., F or Cl).

In some embodiments for a compound of Formula IC1, IC2, IC3, IC4, IC5, or IC6, $R^7$ is a halogen (e.g., F). In some embodiments, $R^7$ is —CN. In some embodiments, $R^7$ is H.

In some embodiments for a compound of Formula IC1, IC2, IC3, IC4, IC5, or IC6, X is N and Y is O. In some embodiments, X is N and Y is S. In some embodiments, X is C—CN and Y is O. In some embodiments, X is C—CN and Y is S. In some embodiments, $R^{23}$ is —$NH_2$. In some embodiments, $R^{24}$ is F.

In some embodiments, $R^{25}$ and $R^{26}$ are H. In some embodiments,

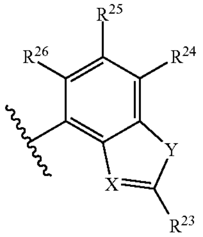

is selected from:

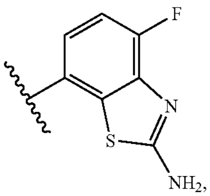

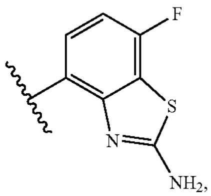

-continued

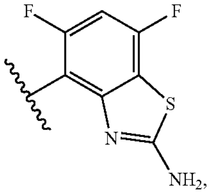

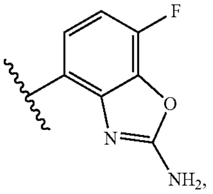

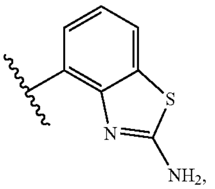

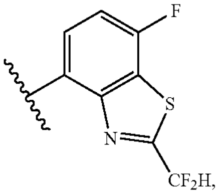

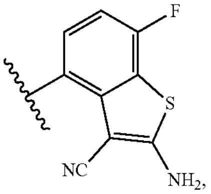

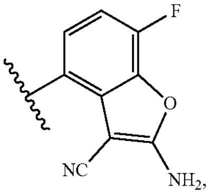

and

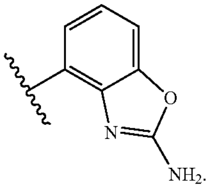

In some embodiments for a compound of Formula IC1, IC2, IC3, IC4, IC5, or IC6,

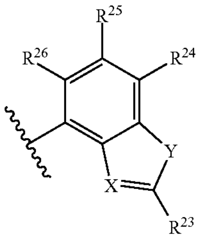

is

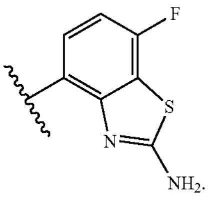 [SMILES: *c1ccc(F)c2sc(N)nc12]

In some embodiments,

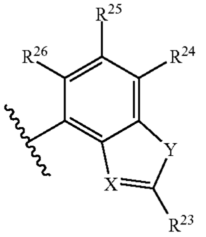

is

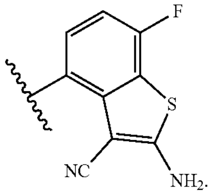

In some embodiments for a compound of Formula IC1, IC2, IC3, IC4, IC5, or IC6, each E is:

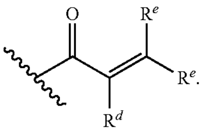

In some embodiments, each $R^d$ and $R^e$ is H. In some embodiments, the compound has a single E.

In some embodiments for a compound of Formula IC1, IC2, IC3, IC4, IC5, or IC6, $R^7$ is H and $R^5$ is $C_{1-6}$alkyl that is unsubstituted or substituted with one or more $R^{13}$. In some embodiments, $R^5$ is —$CF_3$. In some embodiments, X is N and Y is S. In some embodiments, X is C—CN and Y is S.

In some embodiments for a compound of Formula IC1, IC2, IC3, IC4, IC5, or IC6, $R^7$ is a halogen and $R^5$ is $C_{1-6}$alkyl that is unsubstituted or substituted with one or more $R^{13}$. In some embodiments, $R^7$ is F. In some embodiments, $R^5$ is —$CF_3$. In some embodiments, X is N and Y is S. In some embodiments, X is C—CN and Y is S.

In some embodiments for a compound of Formula IC1, IC2, IC3, IC4, IC5, or IC6, $R^7$ is a halogen and $R^5$ is H. In some embodiments, $R^7$ is F. In some embodiments, X is N and Y is S. In some embodiments, X is C—CN and Y is S.

In some embodiments for a compound of Formula IC1, IC2, IC3, IC4, IC5, or IC6, $R^7$ is a halogen and $R^5$ is a halogen. In some embodiments, $R^7$ is F. In some embodiments, $R^5$ is Cl. In some embodiments, X is N and Y is S. In some embodiments, X is C—CN and Y is S.

In another aspect, the present disclosure provides a compound according to Formula ID:

(ID)

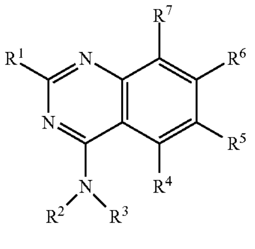

or a salt (e.g., pharmaceutically acceptable salt), ester, tautomer, prodrug, zwitterionic form, or stereoisomer thereof, wherein:

$R^1$ is selected from —$OR^8$,

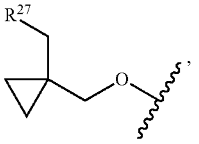

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle, wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from —CN, $C_{2-6}$alkynyl, $C_{1-6}$alkyl, a 3-6 membered carbocycle, a 5-6 membered heteroaryl, phenyl, and a 3-6 membered heterocycle, wherein any $C_{1-6}$alkyl is unsubstituted or is substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$N(R^{12})C(O)(C_{1-6}alkyl)$, —$OR^{12}$, —CN, and $C_{1-6}$alkyl, wherein any $C_{1-6}$alkyl is unsubstituted or substituted with one or more $R^{13}$;

each $R^{16}$ is independently selected from halogen, —N$(R^2)_2$, $C_{1-6}$alkyl, —$OR^{12}$, and 3-6 membered heterocycle, wherein any $C_{1-6}$alkyl is unsubstituted or substituted with one or more $R^{13}$ and wherein any heterocycle is unsubstituted or substituted with one or more $R^{20}$;

each $R^x$ is independently selected from $C_{1-6}$ alkyl, a 3-6 membered carbocycle, and H;

each $R^{20}$ is independently selected from —OH, —$OC_{1-6}$ alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

each E is independently selected from

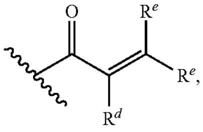, 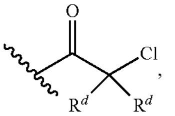, 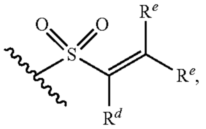, 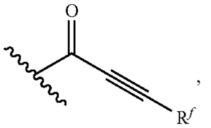, 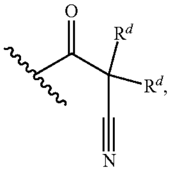, 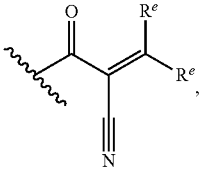, 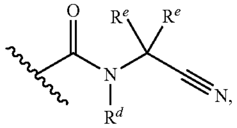, 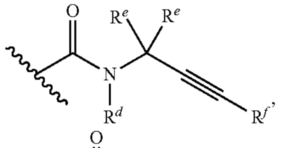, 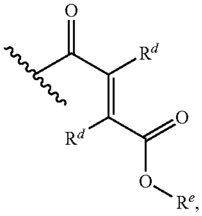, 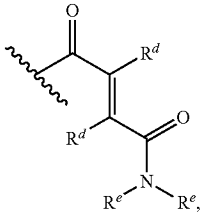, 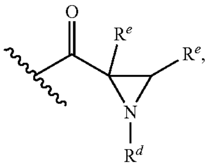, 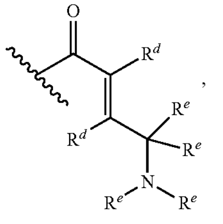, and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula ID, or a salt (e.g., a pharmaceutically acceptable salt) thereof.

In some embodiments, $R^5$ is —CN.

In some embodiments, $R^5$ is selected from $C_{2-6}$alkynyl. In some embodiments, $R^5$ is $C_2$alkynyl.

In some embodiments, $R^5$ is $C_{1-6}$alkyl that is unsubstituted or is substituted with one or more $R^{13}$. In some embodiments, $R^5$ is $C_{1-6}$alkyl that is substituted with —CN. In some embodiments, $R^5$ is $C_{1-6}$alkyl that is substituted with —CN and one or more $R^{13}$. In some embodiments, $R^5$ is $C_{1-6}$alkyl that is substituted with —CN and one or more $R^{13}$, wherein each $R^{13}$ is independently selected from —$OR^{22}$, —CN, and —$N(R^{22})_2$. In some embodiments, $R^5$ is —$CH_2CN$. In some embodiments, $R^5$ is $C_{1-6}$alkyl that is substituted with one or more halogen. In some embodiments, $R^5$ is —$CF_3$.

In some embodiments, $R^5$ is selected from a 3-6 membered carbocycle that is unsubstituted or substituted with one or more $R^{14}$. In some embodiments, $R^5$ is selected from a cyclobutyl that is unsubstituted or substituted with one or more $R^{14}$. In some embodiments, $R^5$ is selected from a phenyl that is unsubstituted or substituted with one or more $R^{14}$. In some embodiments, $R^5$ is selected from a 3-6 membered heterocycle that is unsubstituted or substituted with one or more $R^{14}$. In some embodiments, $R^5$ is selected from a 5-6 membered heteroaryl that is unsubstituted or substituted with one or more $R^{14}$. In some embodiments, $R^5$ is selected from a 5-6 membered heterocycle or heteroaryl that includes one or two heteroatoms selected from O and N and is unsubstituted or substituted with one or more $R^{14}$. In some embodiments, $R^5$ is selected from a 5-6 membered heterocycle that includes one or two heteroatoms selected from O and N and is unsubstituted or substituted with one or more $R^{14}$. In some embodiments, $R^5$ is selected from furanyl, pyridinyl, and pyrazolyl that is unsubstituted or is substituted with one or more $R^{14}$. In some embodiments, $R^5$ is selected from:

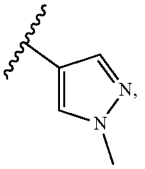, 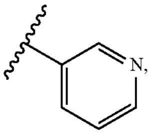, and 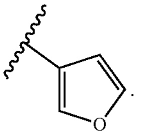.

In some embodiments, $R^5$ is:

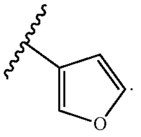 [SMILES: *c1ccoc1].

In some embodiments, $R^1$ is H.

In some embodiments, $R^1$ is selected from —$OR^8$, wherein $R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl. In some embodiments, $R^8$ is a heterocycle or an alkylheterocycle, wherein any heterocycle contains 4-8 members and is substituted with one or more $R^a$. In some embodiments, $R^8$ is a heterocycle that is unsubstituted or substituted with one or more $R^a$. In some embodiments, $R^8$ is an alkylheterocycle that is unsubstituted or substituted with one or more $R^a$. In some embodiments, $R^8$ is —$CH_2$(heterocycle), where the heterocycle is unsubstituted or substituted with one or more $R^a$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$, wherein the one or more $R^a$ is a halogen (e.g., F). In some embodiments, a heterocycle or a heterocycle of an alkylheterocycle is substituted with one or more $R^a$, wherein the one or more $R^a$ is a $C_{1-6}$alkyl (e.g., methyl). In some embodiments, a heterocycle or a heterocycle of an alkylheterocycle is substituted with one or more $R^a$, wherein the one or more $R^a$ is a —$OR^{12}$ (e.g., —$OCH_3$).

In some embodiments, $R^1$ is selected from:

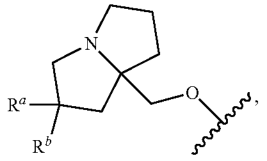

wherein $R^a$ and $R^b$ are each independently selected from halogen, —$OR^{12}$, and H. In some embodiments, $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

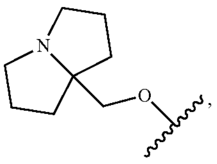

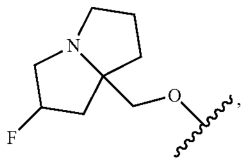

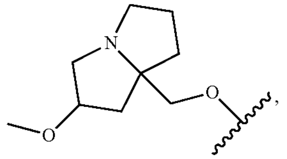

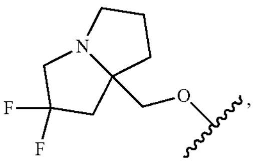

and

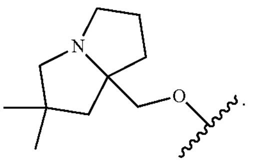

In some embodiments, $R^1$ is selected from:

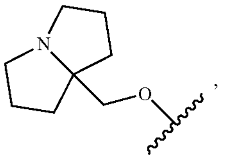

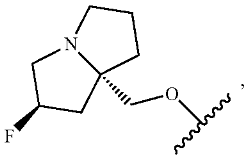

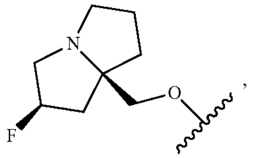

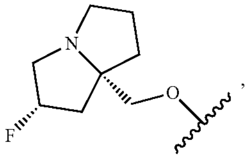

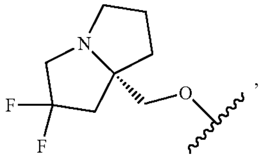

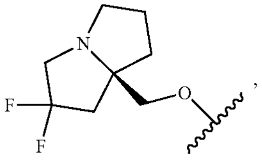

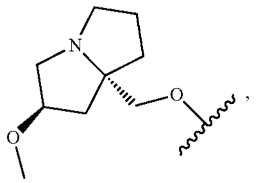

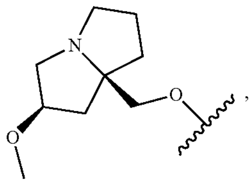

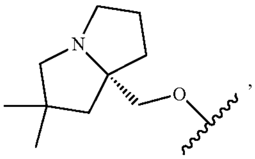

and

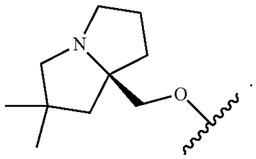

In some embodiments, $R^1$ is selected from:

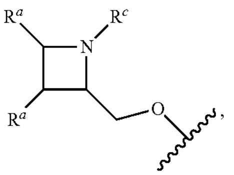

wherein each $R^a$ is independently selected from halogen, $C_{1-6}$ alkyl, —$OR^{12}$, and H; and wherein $R^c$ is selected from $C_{1-6}$ alkyl, wherein the $C_{1-6}$ alkyl is unsubstituted or is substituted with one or more $R^{13}$. In some embodiments, $R^c$ is methyl. In some embodiments, $R^1$ is selected from:

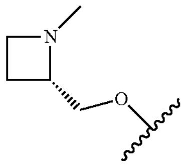

and

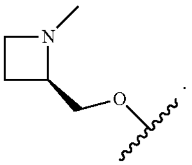

In some embodiments, $R^1$ is selected from:

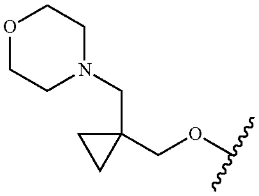

and

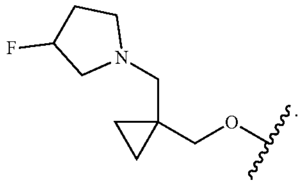

In some embodiments, $R^1$ is selected from:

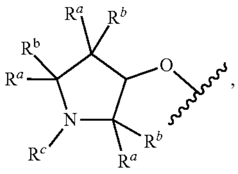

,

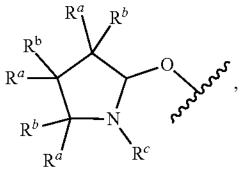

,

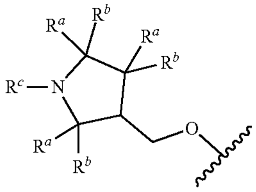

, and

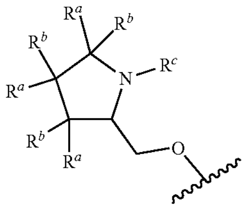

, wherein each $R^a$ and $R^b$ is independently selected from halogen, $C_{1-6}$ alkyl, —$OR^{12}$, and H; and $R^c$ is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and —$OR^{12}$, and the other $R^a$ and $R^b$ groups are H. In some embodiments, one $R^a$ or $R^b$ is halogen (e.g., F). In some embodiments, two $R^a$ groups, two $R^b$ groups, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

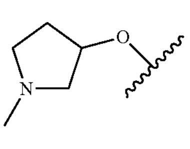

,

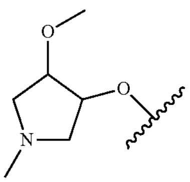

,

-continued

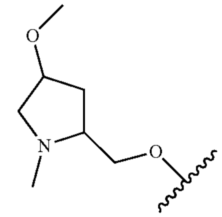

,

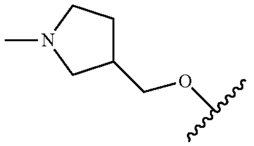

,

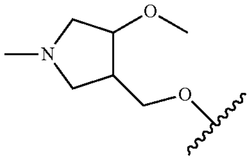

,

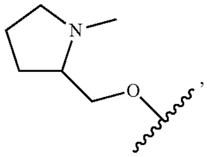

,

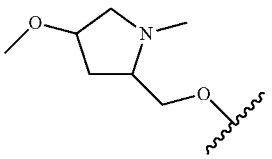

,

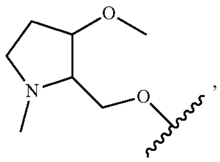

,

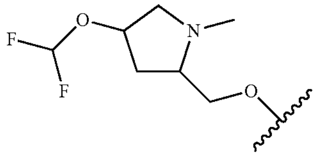

,

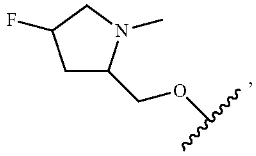

,

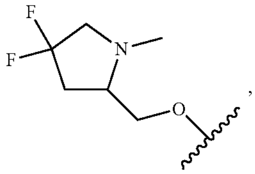

,

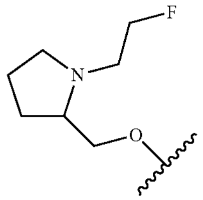

,

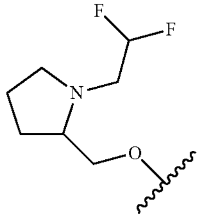

,

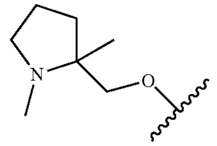

,

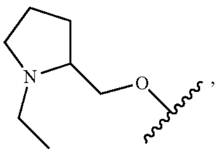

,

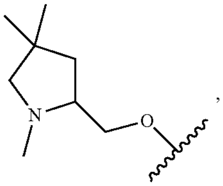

,

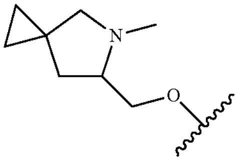

, and

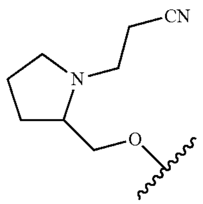

.

In some embodiments, $R^1$ is selected from:

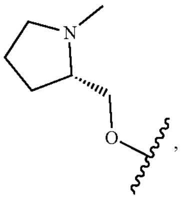, 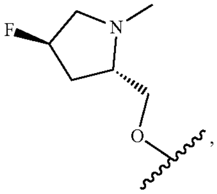, 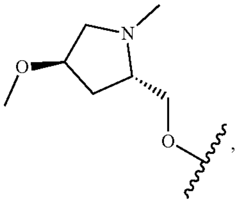, and 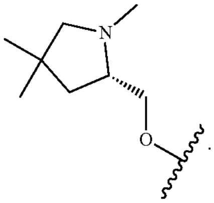.

In some embodiments, $R^1$ is selected from:

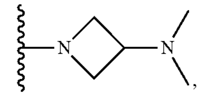, 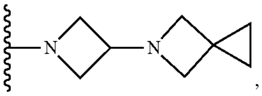, 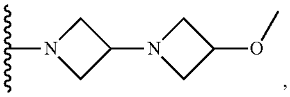, 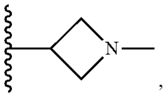, and 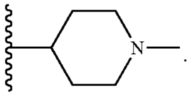.

In some embodiments, $R^2$ is H. In some embodiments, $R^2$ is $C_{1-6}$ alkyl unsubstituted or substituted with one or more $R^{13}$. In some such embodiments, each $R^{13}$ is independently selected from —$OR^{22}$ (e.g., —OH) and —CN. In some embodiments, $R^2$ is selected from $C_{1-6}$ alkyl. In some embodiments $R^2$ is selected from —$CH_3$, —$CH_2CH_3$, —$CH_2CH_2OH$, —$CH_2CH_2CN$, and —$CH(CH_3)_2$. In some embodiments, $R^2$ is selected from a 3-6 membered carbocycle.

In some embodiments, $R^3$ is a 4-6 membered heterocycle that is substituted with one or more E and 0-4 $R^{10}$, wherein the heterocycle includes one or more heteroatoms selected from N, O, and S, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$, optionally wherein two $R^{10}$ groups, together with the atom or atoms to which they are attached, form a 3-6 membered carbocycle. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

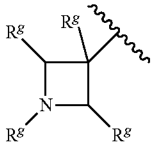, 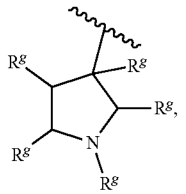 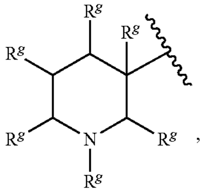, and 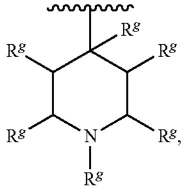

wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

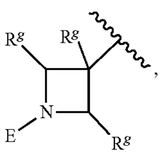, 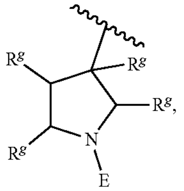 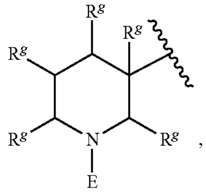, and 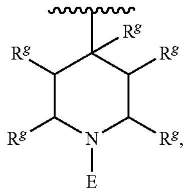

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In some embodiments, $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

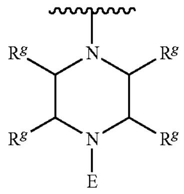 or 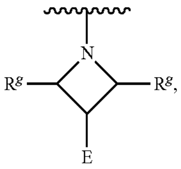

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, one or two $R^g$ are $C_{1-6}$alkyl (e.g., methyl). In some embodiments, $R^2$ and $R^3$, together with the atom to which they are attached, form the structure:

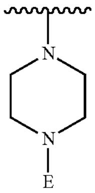, 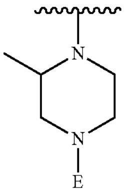, 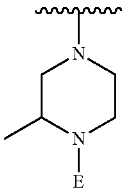,

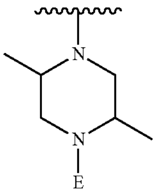, 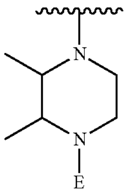, 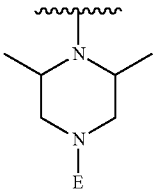,

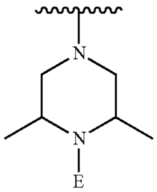, 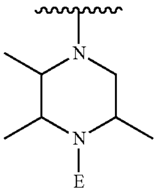, 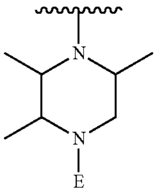, or

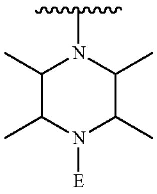.

In some embodiments, $R^2$ and $R^3$, together with the atom to which they are attached, form a 4-8 membered bicyclic heterocycle comprising a fused ring system that is substituted with one or more E and 0-4 $R^{11}$. In some embodiments, $R^2$ and $R^3$, together with the atom to which they are attached, form a structure selected from:

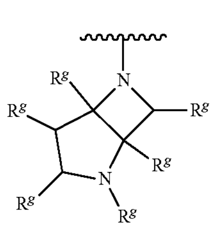 and 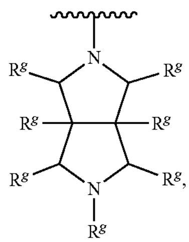

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a structure selected from:

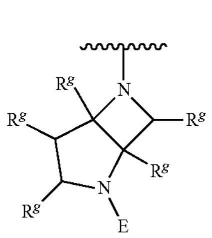 and 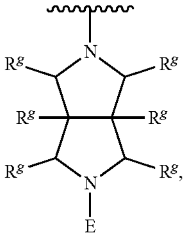

wherein each $R^g$ is independently selected from $C_{1-6}$alkyl and H, wherein any $C_{1-6}$alkyl is unsubstituted or substituted with one or more $R^{20}$. In some embodiments, $R^2$ and $R^3$, together with the atom to which they are attached, form the structure:

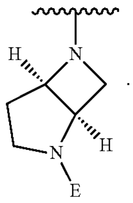.

In some embodiments, $R^4$ is H.

In some embodiments, $R^6$ is a 9-10 membered heteroaryl having 1-3 heteroatoms independently selected from nitrogen, oxygen, and sulfur that is substituted with one or more $R^{15}$. In some embodiments, $R^6$ is a 9-membered heteroaryl having 1-3 heteroatoms independently selected from nitrogen, oxygen, and sulfur and substituted with one or more $R^{15}$. In some such embodiments, at least one $R^{15}$ is —$N(R^{12})_2$ (e.g., —$NH_2$). In some embodiments, at least one $R^{15}$ is a halogen (e.g., F). In some embodiments, each $R^{15}$ is independently selected from halogen, —CN, and —$N(R^{12})_2$. In some embodiments, $R^6$ is substituted with at least two $R^{15}$ (e.g., at least a halogen and —$NH_2$).

In some embodiments, $R^6$ has the structure:

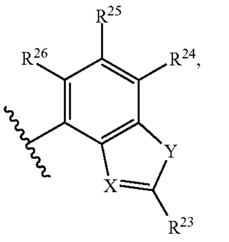

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^2$, and $R^{26}$ are independently selected from H, halogen, —$OR^{12}$, and $C_{1-6}$alkyl, wherein any $C_{1-6}$alkyl is unsubstituted or substituted with one or more $R^{13}$.

In some embodiments, $R^6$ is selected from:

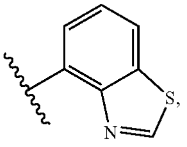
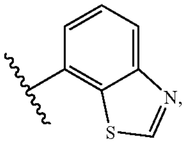
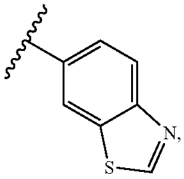
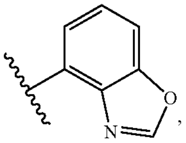
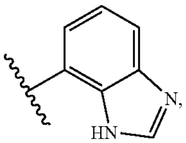
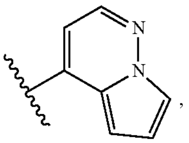
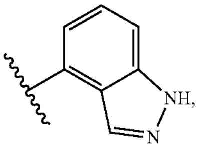
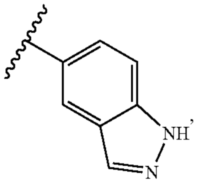
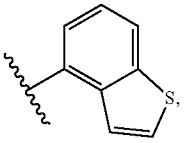
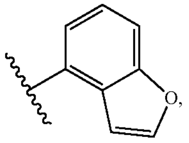
and
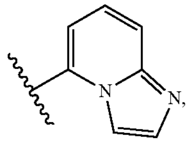

any of which is substituted with one or more $R^{15}$.

In some embodiments, $R^6$ is selected from:

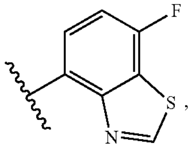
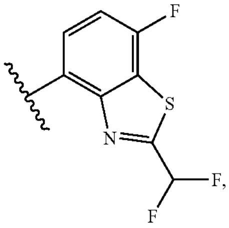
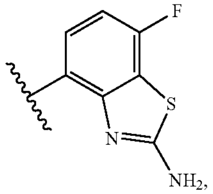
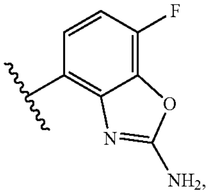
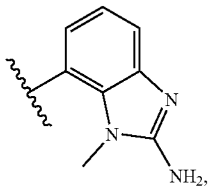
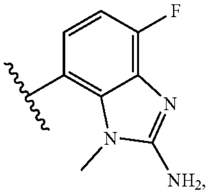
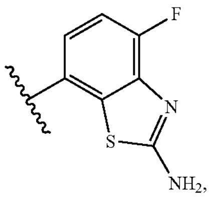
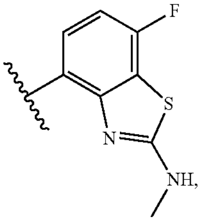
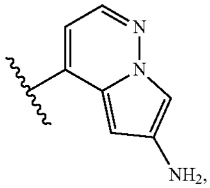
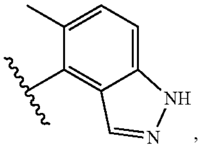
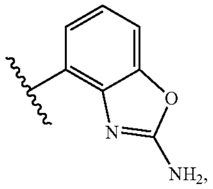
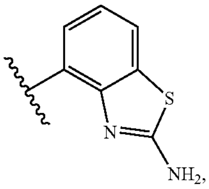
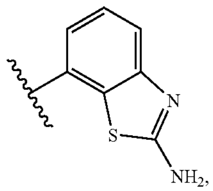
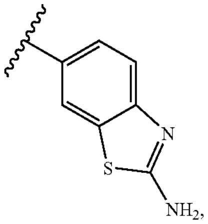
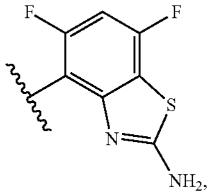
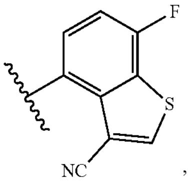
, -continued

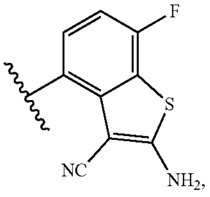 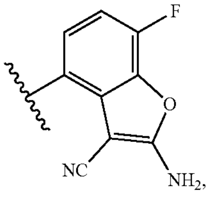 and

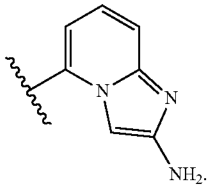

In some embodiments, $R^6$ is selected from:

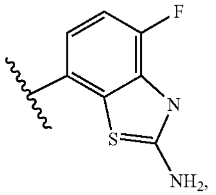 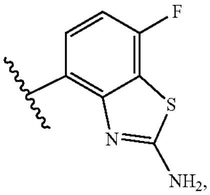

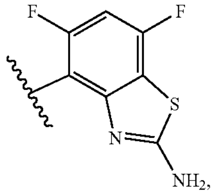 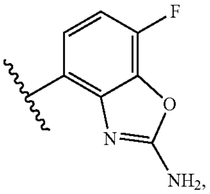

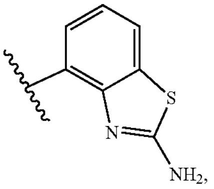 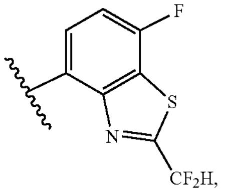

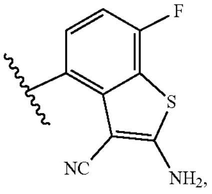 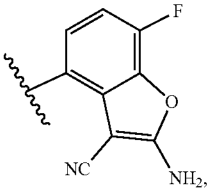 and

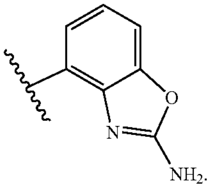

In some embodiments, $R^6$ is

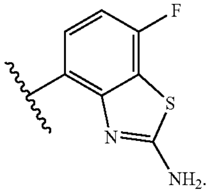 [SMILES: *c1ccc(F)c2sc(N)nc12]

In some embodiments, $R^6$ is

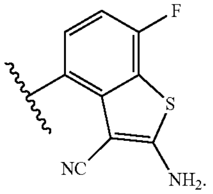 [SMILES: *c1ccc(F)c2sc(N)c(C#N)c12]

In some embodiments, $R^7$ is a halogen. In some embodiments, $R^7$ is F. In some embodiments, $R^7$ is Cl.

In some embodiments, $R^7$ is —$OR^x$, such as OH. In some embodiments, $R^7$ is —$OR^x$, wherein $R^x$ is $C_{1-6}$ alkyl.

In some embodiments, $R^7$ is —CN.

In some embodiments, $R^7$ is H.

In some embodiments, each E is independently selected from:

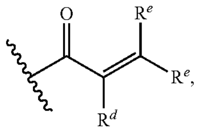 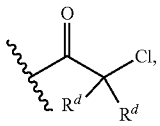 and

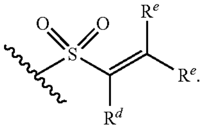

In some embodiments, each E is:

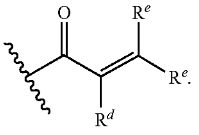

In some embodiments, each $R^d$ and $R^e$ is H. In some embodiments, the compound includes a single E.

In some embodiments, $R^4$ is H; $R^7$ is a halogen; and $R^5$ is selected from $C_{2-6}$alkynyl. In some embodiments, $R^5$ is $C_2$alkynyl. In some embodiments, $R^7$ is F.

In some embodiments, $R^4$ is H; $R^7$ is a halogen; and $R^5$ is $C_{1-6}$alkyl that is unsubstituted or substituted with one or more $R^{13}$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$. In some embodiments, $R^7$ is F.

In some embodiments, $R^4$ is H; $R^7$ is a halogen; and $R^5$ is selected from a 3-6 membered carbocycle that is unsubstituted or substituted with one or more $R^{14}$. In some embodiments, $R^5$ is selected from selected from a cyclobutyl that is unsubstituted or substituted with one or more $R^{14}$. In some embodiments, $R^5$ is selected from selected from a phenyl that is unsubstituted or substituted with one or more $R^{14}$. In some embodiments, $R^7$ is F.

In some embodiments, $R^4$ is H; $R^7$ is a halogen; and $R^5$ is selected from a 3-6 membered heterocycle that is unsubstituted or substituted with one or more $R^{14}$. In some embodiments, $R^5$ is selected from a 5-6 membered heterocycle that includes one or two heteroatoms selected from O and N is unsubstituted or substituted with one or more $R^{14}$.

In some embodiments, $R^4$ is H; $R^7$ is a halogen; and $R^5$ is selected from a 5-6 membered heteroaryl that is unsubstituted or substituted with one or more $R^{14}$. In some embodiments, $R^5$ is selected from furanyl, pyridinyl, and pyrazolyl that is unsubstituted or is substituted with one or more $R^{14}$. In some embodiments, $R^5$ is selected from:

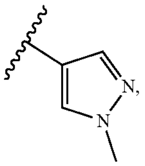 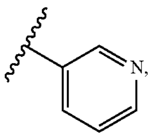 and 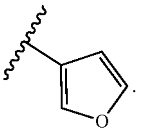

In some embodiments, $R^5$ is:

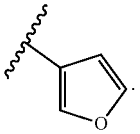

In some embodiments, $R^7$ is F.

In some embodiments, $R^4$ is H; $R^7$ is a halogen; and $R^5$ is $C_{1-6}$alkyl that is unsubstituted or substituted with one or more $R^{13}$. In some embodiments, $R^7$ is F. In some embodiments, $R^5$ is —$CF_3$.

In some embodiments, $R^4$ is H; $R^7$ is a halogen; and $R^5$ is H. In some embodiments, $R^7$ is F.

In some embodiments, $R^4$ is H; $R^7$ is a halogen; and $R^5$ is a halogen. In some embodiments, $R^7$ is F. In some embodiments, $R^5$ is Cl.

In some embodiments, the compound is a compound according to Formula ID1:

(ID1)

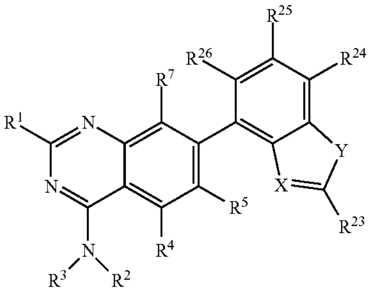

or a salt (e.g., pharmaceutically acceptable salt), ester, tautomer, prodrug, zwitterionic form, or stereoisomer thereof, wherein:

$R^1$ is —$OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle, wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle;

$R^4$ is H;

$R^5$ is selected from $C_{2-6}$alkynyl, $C_{1-6}$alkyl, a 3-6 membered carbocycle, a 5-6 membered heteroaryl, phenyl, and a 3-6 membered heterocycle, wherein any $C_{1-6}$alkyl is substituted with —CN, and wherein any carbocycle, heteroaryl, phenyl, or heterocycle is unsubstituted or substituted with one or more $R^{14}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^x$ is independently selected from $C_{1-6}$ alkyl, a 3-6 membered carbocycle, and H;

each $R^{20}$ is independently selected from —OH, —$OC_{1-6}$ alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

each E is independently selected from

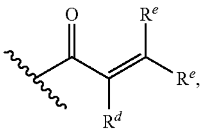 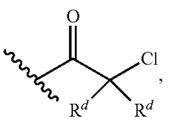

-continued

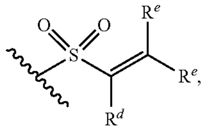,
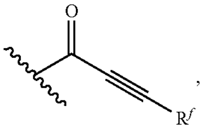,
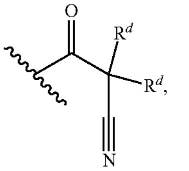,
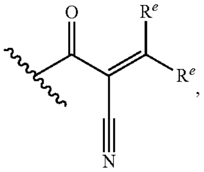,
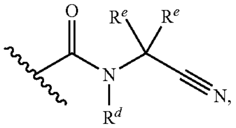,
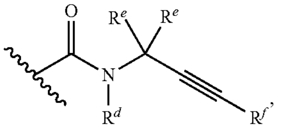,
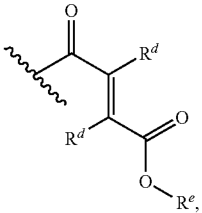,
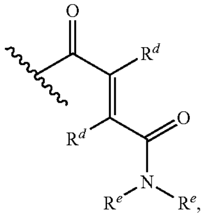,
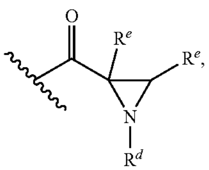,
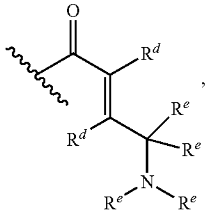, and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula ID1, or a salt (e.g., a pharmaceutically acceptable salt) thereof.

In some embodiments for a compound of Formula ID1, $R^2$ is selected from $C_{1-2}$ alkyl. In some embodiments, $R^2$ is methyl. In some embodiments, $R^2$ is ethyl.

In some embodiments for a compound of Formula ID1, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

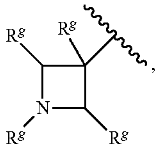,
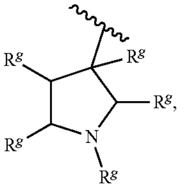,

-continued

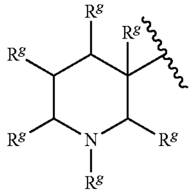, and
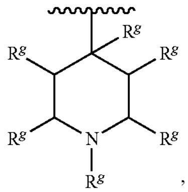, wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, $R^3$ is selected from:

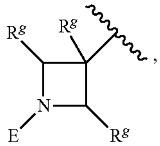,
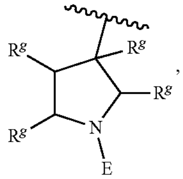,
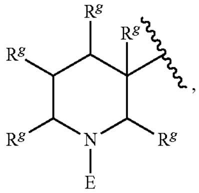, and
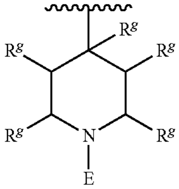, wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In some embodiments for a compound of Formula ID1, $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle. In some embodiments, $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

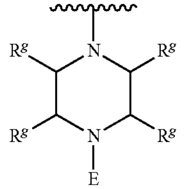 or
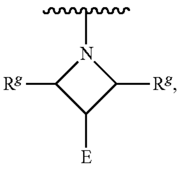, wherein each $R^g$ is independently selected from $C_{1-6}$alkyl and H, wherein any $C_{1-6}$alkyl is unsubstituted or substituted with one or more $R^{20}$, optionally wherein two $R^g$ groups, together with the atoms to which they are attached, form a 3-6 membered carbocycle. In some embodiments, each $R^g$ is H. In some embodiments, one or two $R^9$ groups are $C_{1-6}$alkyl (e.g., methyl). In some embodiments, $R^2$ and $R^3$, together with the atom to which they are attached, form the structure:

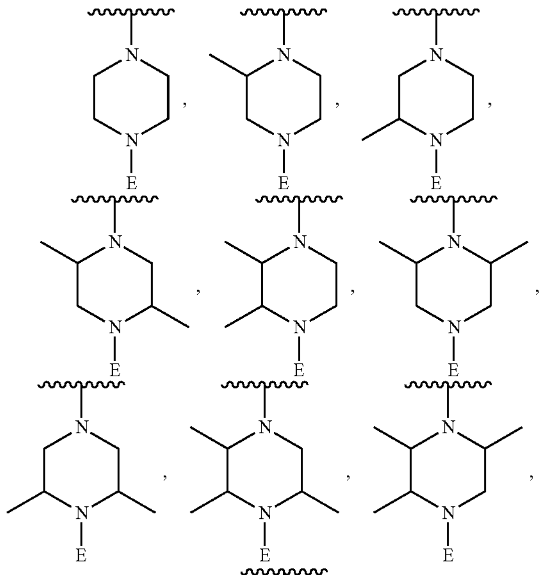

or

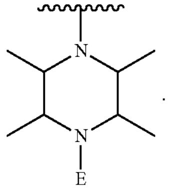

In some embodiments, $R^2$ and $R^3$, together with the atom to which they are attached, form a bridged piperazinyl ring that is substituted with one or more E and 0-4 $R^{11}$. In some embodiments, $R^2$ and $R^3$, together with the atom to which they are attached, form the structure:

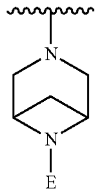

or

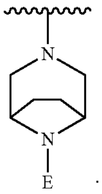

In some embodiments for a compound of Formula ID1, $R^1$ is selected from:

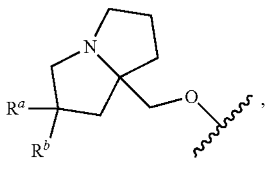

wherein $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, each of $R^a$ and $R^b$ is F. In some embodiments, each of $R^a$ and $R^b$ is methyl. In some embodiments, $R^b$ is methyl. In some embodiments, $R^1$ is selected from:

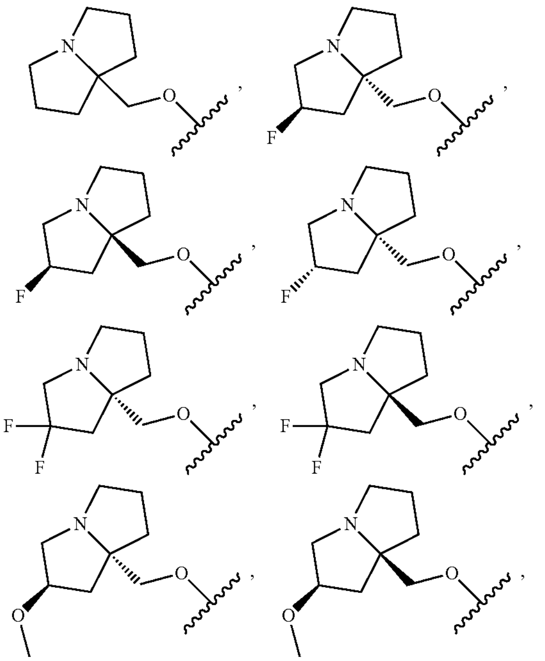

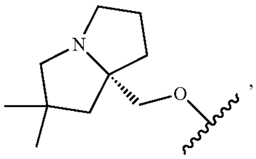

and

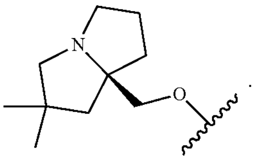

In some embodiments for a compound of Formula ID1, $R^5$ is selected from $C_{1-6}$alkyl substituted with —CN. In some embodiments, $R^5$ is selected from a 3-6 membered carbocycle and phenyl, wherein any carbocycle or phenyl is unsubstituted or substituted with one or more $R^{14}$. In some embodiments, $R^5$ is phenyl. In some embodiments, $R^5$ is selected from a 5-6 membered heteroaryl and a 3-6 membered heterocycle, wherein any heteroaryl or heterocycle is unsubstituted or substituted with one or more $R^{14}$. In some embodiments, $R^5$ is furanyl.

In some embodiments for a compound of Formula ID1, $R^7$ is a halogen (e.g., F or Cl). In some embodiments, $R^7$ is —CN. In some embodiments, $R^7$ is H.

In some embodiments for a compound of Formula ID1, X is N and Y is O. In some embodiments, X is N and Y is S. In some embodiments, X is C—CN and Y is O. In some embodiments, X is C—CN and Y is S. In some embodiments, $R^{23}$ is —$NH_2$. In some embodiments, $R^{24}$ is F. In some embodiments, $R^{25}$ and $R^{26}$ are H. In some embodiments,

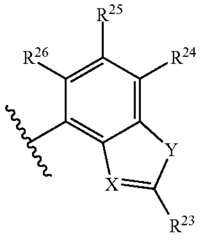

is selected from:

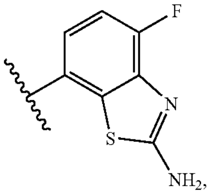,
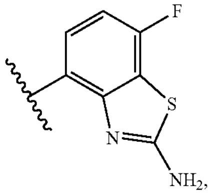,
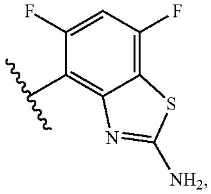,
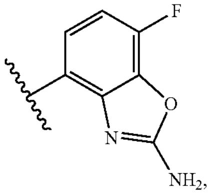,
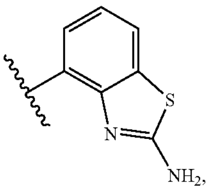,
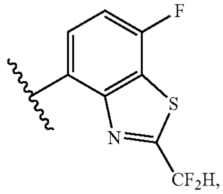,
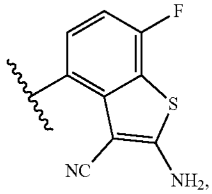,
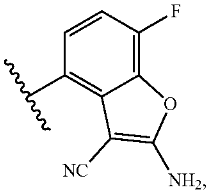, and
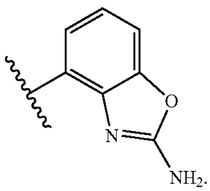.

In some embodiments,

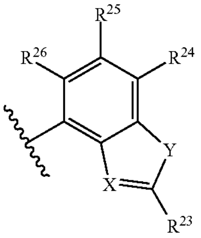 is 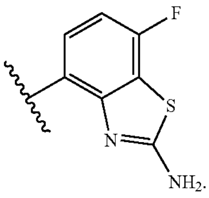.

In some embodiments,

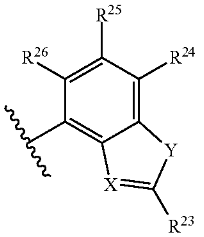 is 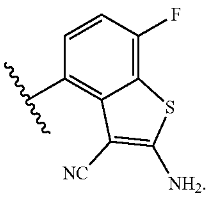.

In some embodiments for a compound of Formula ID1, each E is:

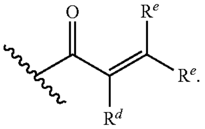.

In some embodiments, each $R^d$ and $R^e$ is H. In some embodiments, the compound has a single E.

In some embodiments for a compound of Formula ID1, $R^7$ is H and $R^5$ is $C_{1-6}$alkyl that is substituted with —CN. In some embodiments, X is N and Y is S. In some embodiments, X is C—CN and Y is S.

In some embodiments for a compound of Formula ID1, $R^7$ is a halogen and $R^5$ is $C_{1-6}$alkyl substituted with —CN. In some embodiments, $R^7$ is F. In some embodiments, X is N and Y is S. In some embodiments, X is C—CN and Y is S.

In some embodiments for a compound of Formula ID1, $R^7$ is H and $R^5$ is selected from a 3-6 membered carbocycle and phenyl, wherein any carbocycle or phenyl is unsubstituted or substituted with one or more $R^{14}$. In some embodiments, $R^5$ is phenyl. In some embodiments, X is N and Y is S. In some embodiments, X is C—CN and Y is S.

In some embodiments for a compound of Formula ID1, $R^7$ is a halogen and $R^5$ is selected from a 3-6 membered carbocycle and phenyl, wherein any carbocycle or phenyl is unsubstituted or substituted with one or more $R^{14}$. In some embodiments, $R^5$ is phenyl. In some embodiments, $R^7$ is F. In some embodiments, X is N and Y is S. In some embodiments, X is C—CN and Y is S.

In some embodiments for a compound of Formula ID1, $R^7$ is H and $R^5$ is selected from a 5-6 membered heteroaryl and a 3-6 membered heterocycle, wherein any heteroaryl or heterocycle is unsubstituted or substituted with one or more $R^{14}$. In some embodiments, $R^5$ is furanyl. In some embodiments, X is N and Y is S. In some embodiments, X is C—CN and Y is S.

In some embodiments for a compound of Formula ID1, $R^7$ is a halogen and $R^5$ is selected from a 5-6 membered heteroaryl and a 3-6 membered heterocycle, wherein any heteroaryl or heterocycle is unsubstituted or substituted with one or more $R^{14}$. In some embodiments, $R^5$ is furanyl. In some embodiments, $R^7$ is F. In some embodiments, X is N and Y is S. In some embodiments, X is C—CN and Y is S.

In another aspect, the present disclosure provides a compound according to Formula IE:

(IE)

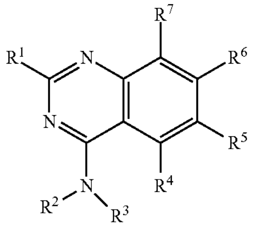

or a salt (e.g., pharmaceutically acceptable salt), ester, tautomer, prodrug, zwitterionic form, or stereoisomer thereof, wherein:

$R^1$ is selected from —$OR^8$,

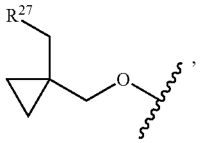

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is —OH;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$OR^{12}$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$.

each $R^{28}$ is independently selected from $C_{1-6}$alkyl and halogen;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

each E is independently selected from

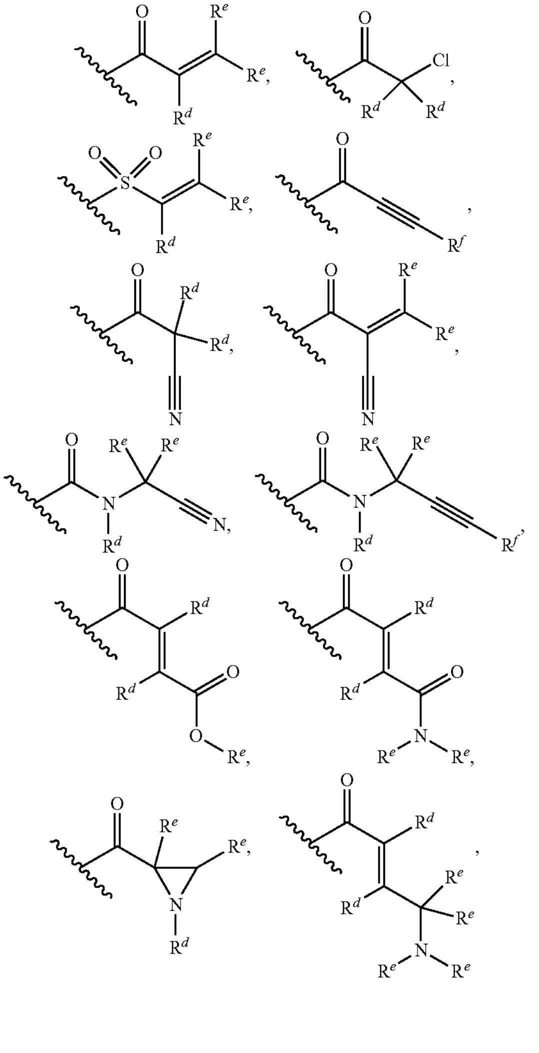

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IE, or a salt (e.g., a pharmaceutically acceptable salt) thereof.

In some embodiments, $R^1$ is H.

In some embodiments, $R^1$ is selected from —$OR^8$, wherein $R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl. In some embodiments, $R^8$ is a heterocycle or an alkylheterocycle, wherein any heterocycle contains 4-8 members and is substituted with one or more $R^a$ b. In some embodiments, $R^8$ is a heterocycle that is unsubstituted or substituted with one or more $R^a$. In some embodiments, $R^8$ is an alkylheterocycle that is unsubstituted or substituted with one or more $R^a$. In some embodiments, $R^8$ is —$CH_2$(heterocycle), where the heterocycle is unsubstituted or substituted with one or more $R^a$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$, wherein the one or more $R^a$ is a halogen (e.g., F). In some embodiments, a heterocycle or a heterocycle of an alkylheterocycle is substituted with one or more $R^a$, wherein the one or more $R^a$ is a $C_{1-6}$alkyl (e.g., methyl). In some embodiments, a heterocycle or a heterocycle of an alkylheterocycle is substituted with one or more $R^a$, wherein the one or more $R^a$ is a —$OR^{12}$ (e.g., —$OCH_3$).

In some embodiments, $R^1$ is selected from:

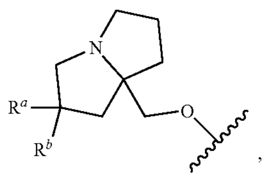

, wherein $R^a$ and $R^b$ are each independently selected from halogen, —$OR^{12}$, and H. In some embodiments, $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^1$ is selected from:

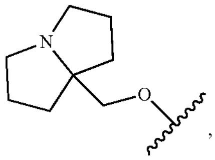

,

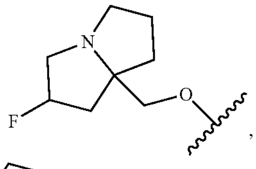

,

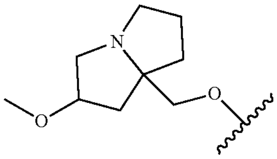

,

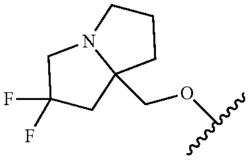

, and

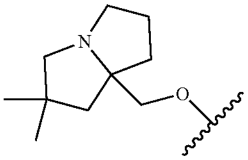

.

In some embodiments, $R^1$ is selected from:

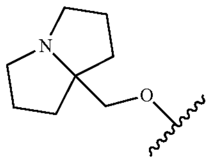

,

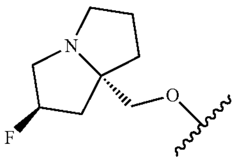

,

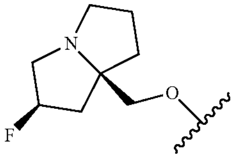

,

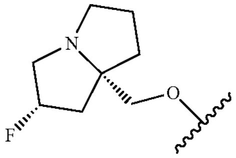

,

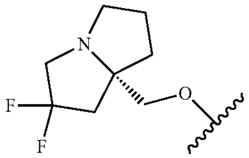

,

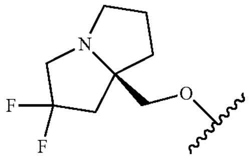

,

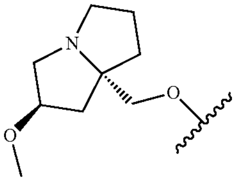

,

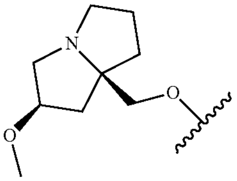

,

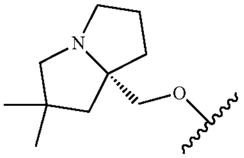

, and

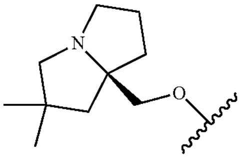

.

In some embodiments, $R^1$ is selected from:

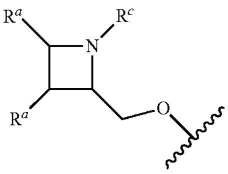

, wherein each $R^a$ is independently selected from halogen, $C_{1-6}$ alkyl, —$OR^{12}$, and H; and wherein $R^c$ is selected from $C_{1-6}$ alkyl, wherein the $C_{1-6}$ alkyl is unsubstituted or is substituted with one or more $R^{13}$. In some embodiments, $R^c$ is methyl. In some embodiments, $R^1$ is selected from:

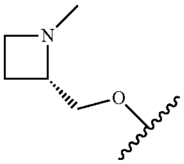
and
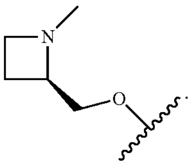
.

In some embodiments, $R^1$ is selected from:

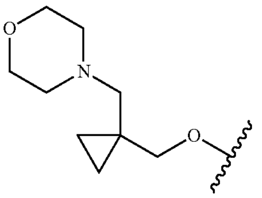
and
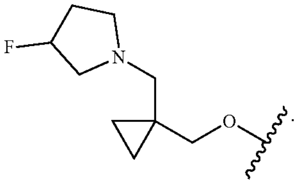
.

In some embodiments, $R^1$ is selected from:

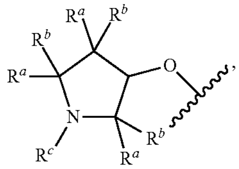
,
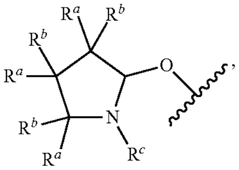
,
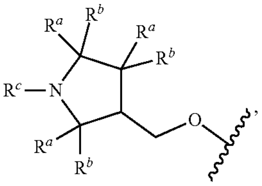
, and
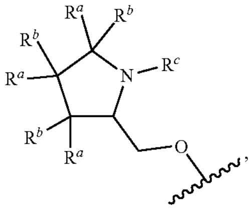
, wherein each $R^a$ and $R^b$ is independently selected from halogen, $C_{1-6}$ alkyl, —$OR^2$, and H; and $R^c$ is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and —$OR^{12}$, and the other $R^a$ and $R^b$ groups are H. In some embodiments, one $R^a$ or $R^b$ is halogen (e.g., F). In some embodiments, two $R^a$ groups, two $R^b$ groups, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

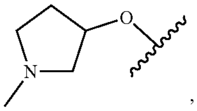
,
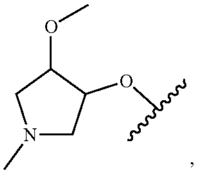
,
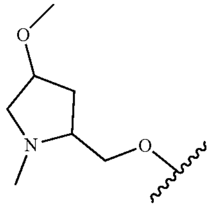
,
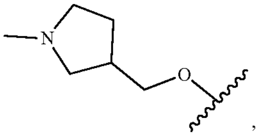
,
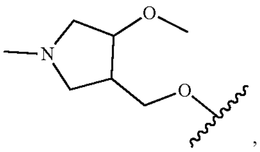
,
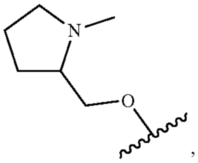
,
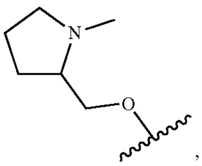
,
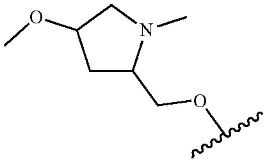
,
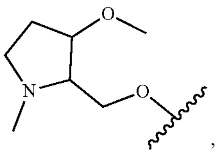
,
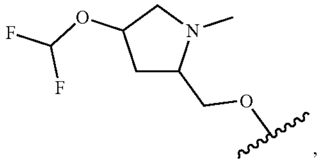
,
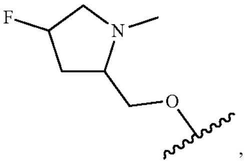
,
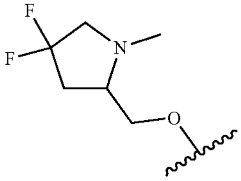
,
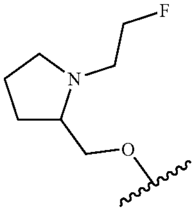
,
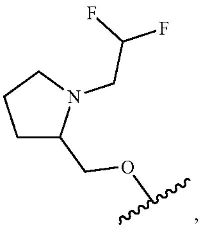
,
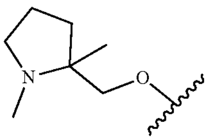
,
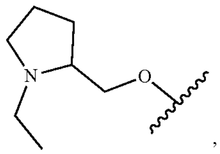
,
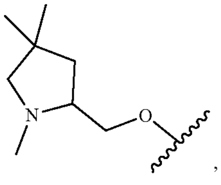
,
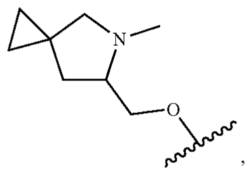
, and -continued

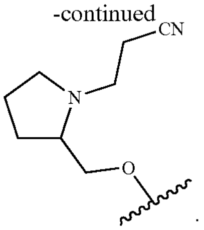

In some embodiments, $R^1$ is selected from:

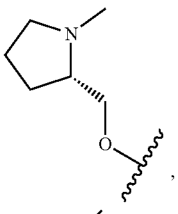
,
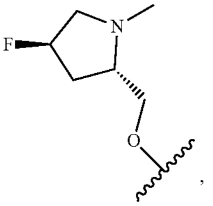
,
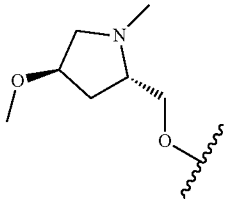
, and
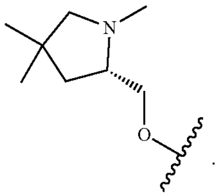
.

In some embodiments, $R^1$ is a 4-6 membered heterocycle comprising a nitrogen atom, wherein the heterocycle is unsubstituted or substituted with one or more $R^{16}$. In some embodiments, $R^1$ is:

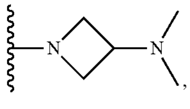
,
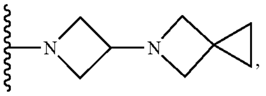
,
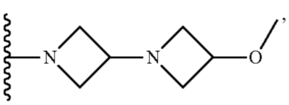
,
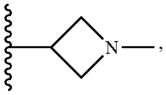
, and
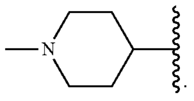
.

In some embodiments, $R^2$ is H. In some embodiments, $R^2$ is selected from $C_{1-6}$ alkyl. In some embodiments, $R^2$ is selected from $C_{1-2}$ alkyl. In some embodiments $R^2$ is selected from —$CH_3$, —$CH_2CH_3$, and —$CH(CH_3)_2$. In some embodiments, $R^2$ is selected from a 3-6 membered carbocycle. In some embodiments, $R^2$ is cyclopropyl.

In some embodiments, $R^3$ is selected from $C_{1-6}$ alkyl that is substituted with —$N(R^{12})(E)$. In some embodiments, $R^3$ is selected from $C_2$ alkyl that is substituted with —$N(R^{12})(E)$. In some embodiments, $R^3$ is selected from $C_2$ alkyl that is substituted with —N(H)(E).

In some embodiments, $R^3$ is a 4-6 membered heterocycle that is substituted with one or more E and 0-4 $R^{10}$. In some embodiments, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, at least one $R^{10}$ is a halogen (e.g., F). In some embodiments, at least one $R^{10}$ is $C_{1-6}$alkyl (e.g., methyl). In some embodiments, $R^3$ is selected from:

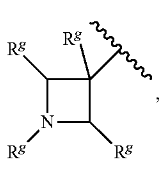
,
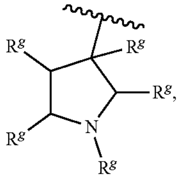

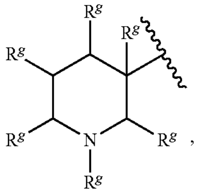
, and
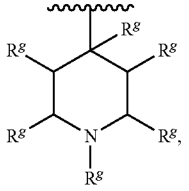

wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, $R^3$ is selected from:

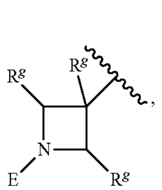
,
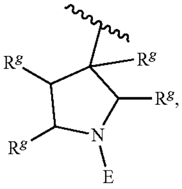

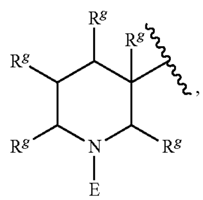
, and
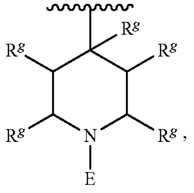

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

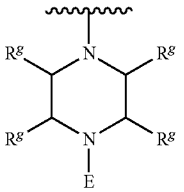

or

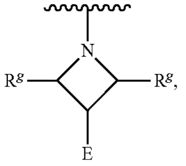

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, one or two $R^g$ groups are $C_{1-6}$alkyl (e.g., methyl). In some embodiments, $R^2$ and $R^3$, together with the atom to which they are attached, form the structure:

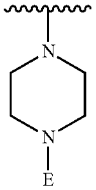
,
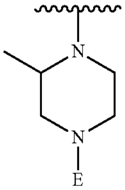
,
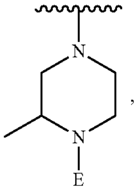
,
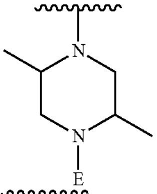
,
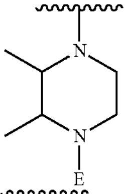
,
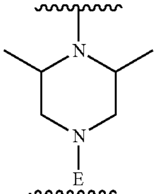
,
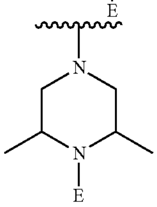
,
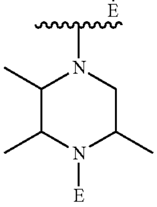
,
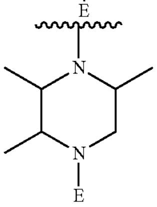
, or
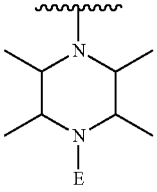
.

In some embodiments, $R^2$ and $R^3$, together with the atom to which they are attached, form a bridged piperazinyl ring that is substituted with one or more E and 0-4 $R^{11}$. In some embodiments, $R^2$ and $R^3$, together with the atom to which they are attached, form the structure:

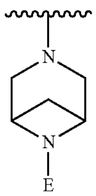

or

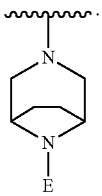
.

In some embodiments, $R^2$ and $R^3$, together with the atom to which they are attached, form a 4-8 membered bicyclic heterocycle comprising a fused ring system that is substituted with one or more E and 0-4 $R^{11}$. In some embodiments, $R^2$ and $R^3$, together with the atom to which they are attached, form a structure selected from:

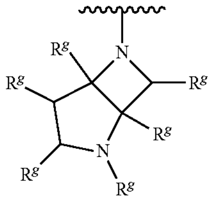

and

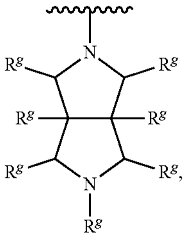

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a structure selected from:

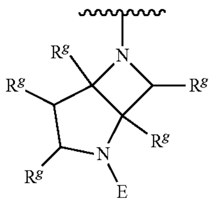

and

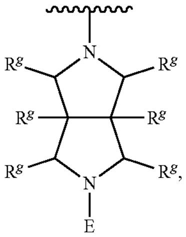

wherein each $R^g$ is independently selected from $C_{1-6}$alkyl and H, wherein any $C_{1-6}$alkyl is unsubstituted or substituted with one or more $R^{20}$. In some embodiments, $R^2$ and $R^3$, together with the atom to which they are attached, form the structure:

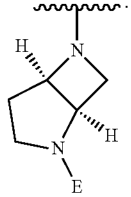
.

In some embodiments, each $R^g$ is H.

In some embodiments, $R^4$ is H.

In some embodiments, $R^5$ is H.

In some embodiments, $R^5$ is —CN.

In some embodiments, $R^5$ is a halogen. In some embodiments, $R^5$ is Cl. In some embodiments, $R^5$ is F.

In some embodiments, $R^5$ is selected from $C_{1-6}$alkyl that is unsubstituted or substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is —$CF_3$. In some embodiments, $R^5$ is —$CHF_2$. In some embodiments, $R^5$ is selected from —$CF_3$, —$CF_2H$, and —$CH_2CN$. In some embodiments, $R^5$ is selected from —$CH_3$, —$CH_2CH_3$, —$CF_2H$, —$CF_3$, —$CF_2CH_3$, and —$CH_2CN$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$.

In some embodiments, $R^5$ is selected from —$OR^{12}$, wherein $R^{12}$ is selected from $C_{1-6}$ alkyl and H. In some embodiments, $R^5$ is —$OCH_3$.

In some embodiments, $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$. In some embodiments, $R^5$ is a 3-6 membered carbocycle unsubstituted or substituted with one or more $R^{14}$. In some embodiments, $R^5$ is a 3-4 membered carbocycle unsubstituted or substituted with one or more $R^{14}$. In some embodiments, $R^5$ is a 5-6 membered heteroaryl or phenyl unsubstituted or substituted with one or more $R^{14}$ (e.g., $C_{1-6}$alkyl). In some embodiments, $R^5$ is a pyridyl, furanyl, or imidazolyl, each unsubstituted or substituted with one or more $R^{14}$ (e.g., $C_{1-6}$alkyl). In some embodiments, $R^5$ is a furanyl. In some embodiments, $R^5$ is phenyl.

In some embodiments, $R^6$ is a 9-10 membered heteroaryl having 1-3 heteroatoms independently selected from nitrogen, oxygen, and sulfur that is substituted with one or more $R^{15}$. In some embodiments, $R^6$ is a 9-membered heteroaryl having 1-3 heteroatoms independently selected from nitrogen, oxygen, and sulfur and substituted with one or more $R^{15}$. In some such embodiments, at least one $R^{15}$ is —$N(R^{12})_2$ (e.g., —$NH_2$). In some embodiments, at least one $R^{15}$ is a halogen (e.g., F). In some embodiments, each $R^{15}$ is independently selected from halogen, —CN, and —$N(R^{12})_2$. In some embodiments, $R^6$ is substituted with at least two $R^{15}$ (e.g., at least a halogen and —$NH_2$).

In some embodiments, $R^6$ has the structure:

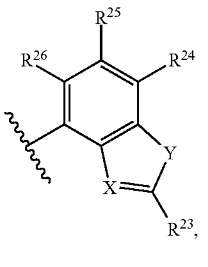

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

In some embodiments, $R^6$ is selected from:

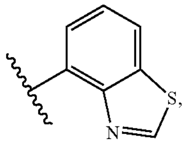
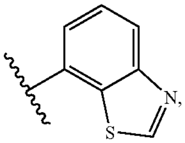
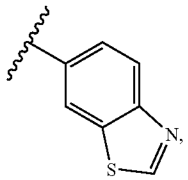
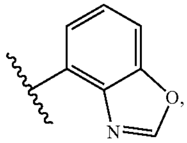
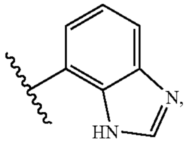
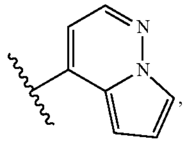
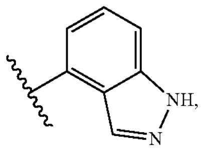
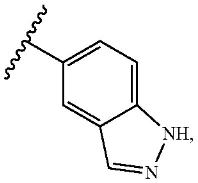
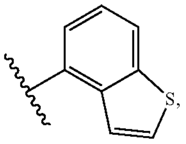
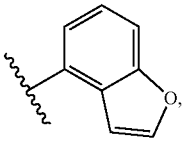
and
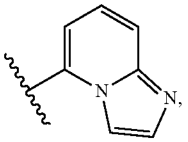

any of which is substituted with one or more $R^{15}$.

In some embodiments, $R^6$ is selected from:

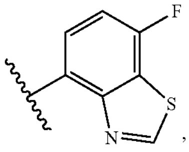
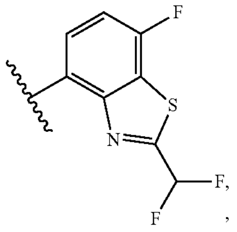
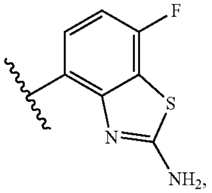
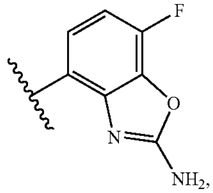
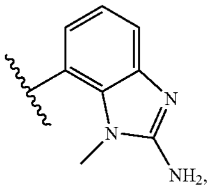
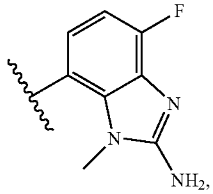

-continued
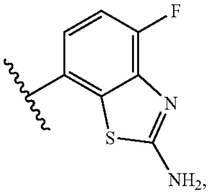
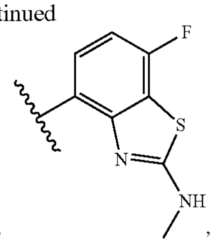
,
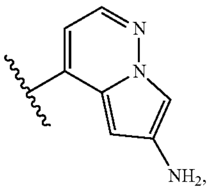
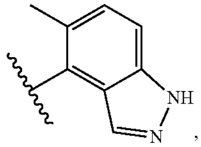
,
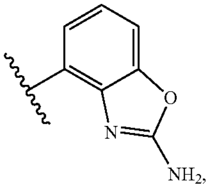
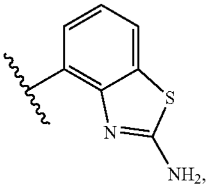
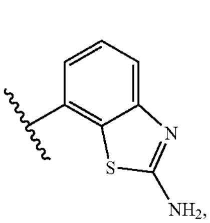
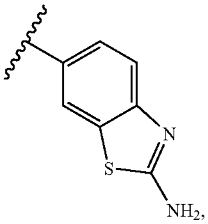
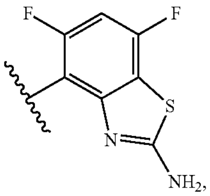
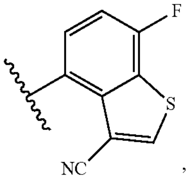
,
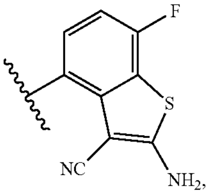
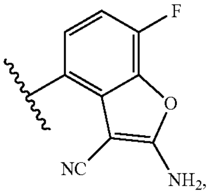
and
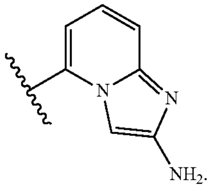
In some embodiments, $R^6$ is selected from:
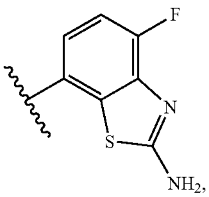
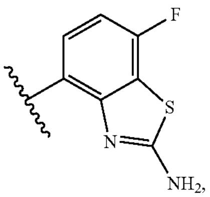
-continued
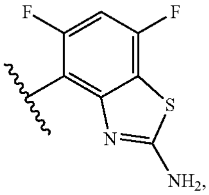
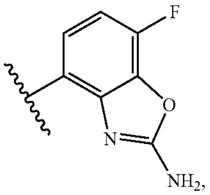 [SMILES: *c1ccc(F)c2sc(N)nc12]
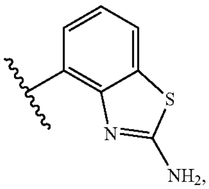
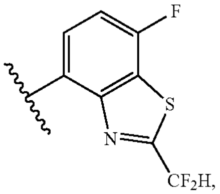
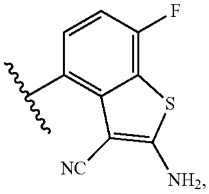
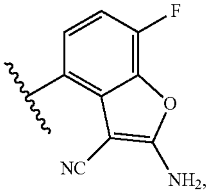
and
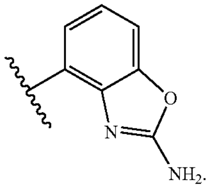
In some embodiments, $R^6$ is
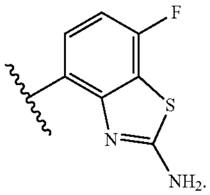
In some embodiments, $R^6$ is
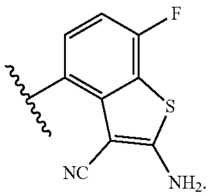 [SMILES: *c1ccc(F)c2sc(N)c(C#N)c12]
In some embodiments, each E is independently selected from:
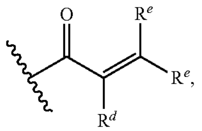
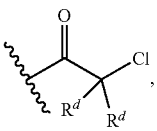
, and -continued

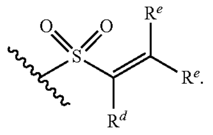

In some embodiments, each E is:

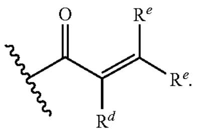

In some embodiments, each $R^d$ and $R^e$ is H. In some embodiments, the compound includes a single E.

In some embodiments, $R^4$ is H and $R^5$ is a halogen. In some embodiments, $R^5$ is Cl.

In some embodiments, $R^1$ is H, $R^4$ is H, and $R^5$ is a halogen. In some embodiments, $R^5$ is Cl.

In another aspect, the present disclosure provides a compound according to Formula II:

(II)

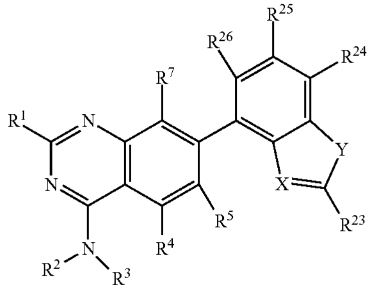

or a salt (e.g., pharmaceutically acceptable salt), ester, tautomer, prodrug, zwitterionic form, or stereoisomer thereof, wherein:

$R^1$ is selected from

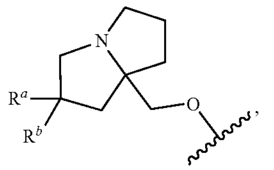,

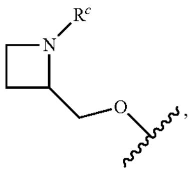,

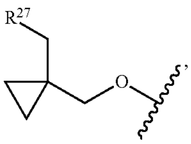,

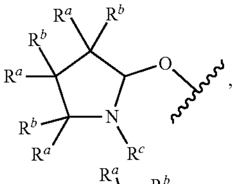,

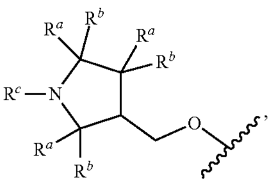,

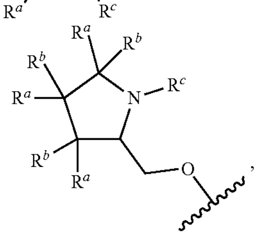,

-continued

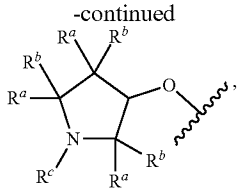,

—$OR^8$, a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^X$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$ alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —$N(R^2)C(O)(C_{1-6}alkyl)$, —$OR^{12}$, and $C_{1-6}alkyl$-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

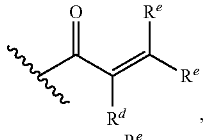
,
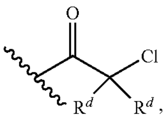

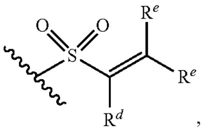
,
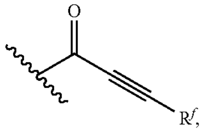

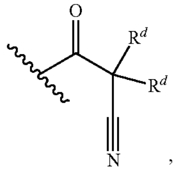
,
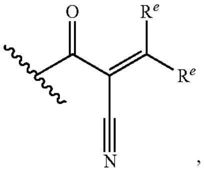
,

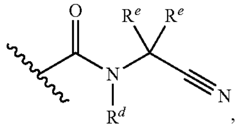
,
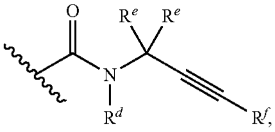

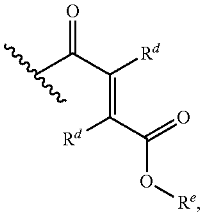

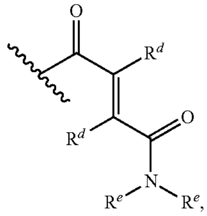

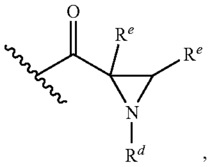
,
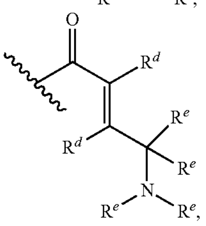

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula II, or a salt (e.g., a pharmaceutically acceptable salt) thereof.

In another aspect, the present disclosure provides a compound according to Formula IIA:

(IIA)

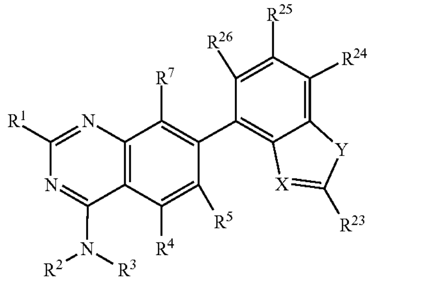

or a salt (e.g., pharmaceutically acceptable salt), ester, tautomer, prodrug, zwitterionic form, or stereoisomer thereof, wherein:

$R^1$ is selected from

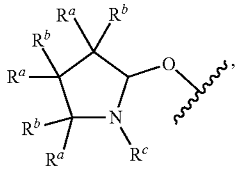
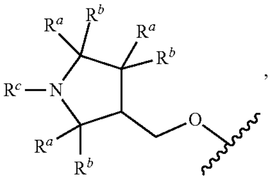
,
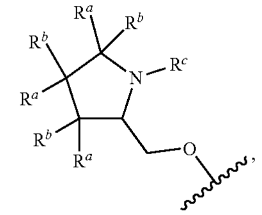
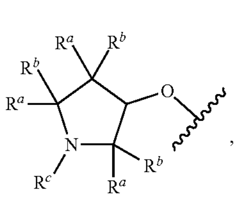
, and a 4-6 membered heterocycle comprising a nitrogen atom, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^X$, —CN, and H;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^4$ is independently selected from halogen, —CN, —$N(R^{12})_2$, and $C_{1-6}$alkyl, wherein any $C_{1-6}$ alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —$N(R^2)C(O)(C_{1-6}$alkyl), —$OR^{12}$, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

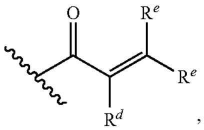
,
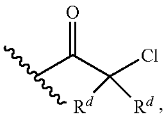
,
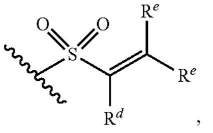
,
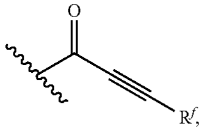
,
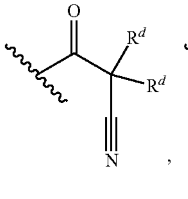
,
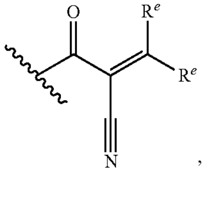
, -continued

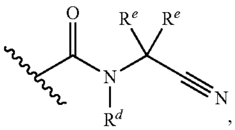
,
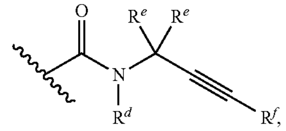
,
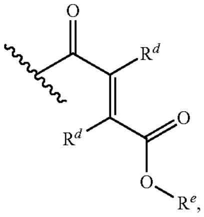
,
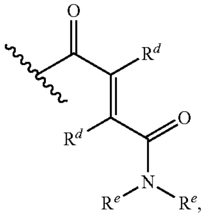
,
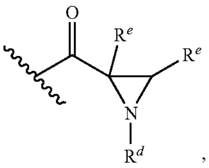
,
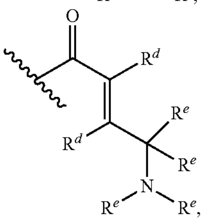
, and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IIA, or a salt (e.g., a pharmaceutically acceptable salt) thereof.

In some embodiments, $R^1$ is selected from:

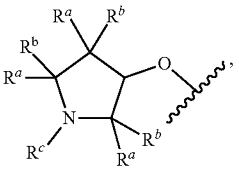
,
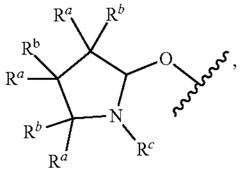
,
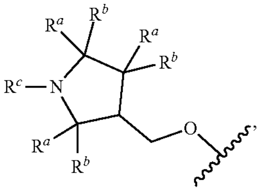
, and
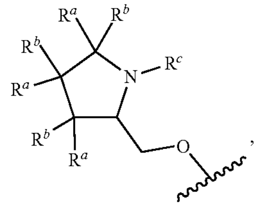
, wherein each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle; and $R^c$ is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and —$OR^{12}$, and the other $R^a$ and $R^b$ groups are H. In some embodiments, one $R^a$ or $R^b$ is halogen (e.g., F). In some embodiments, two $R^a$ groups, two $R^b$ groups, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

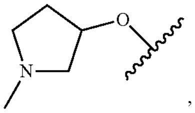, 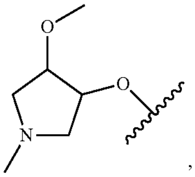,
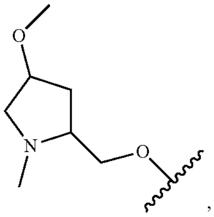, 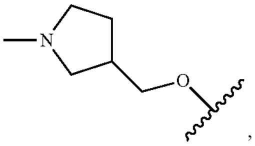,
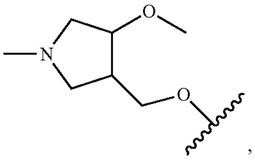, 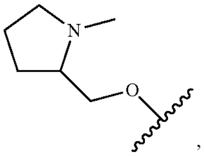,
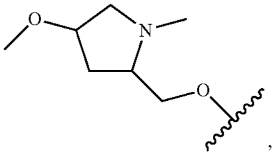, 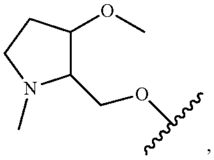,
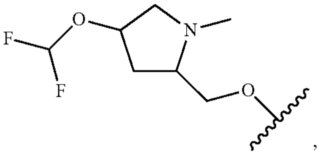, 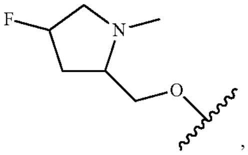,
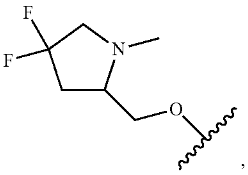, 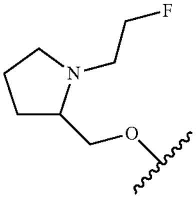,
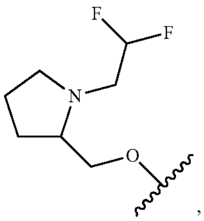, 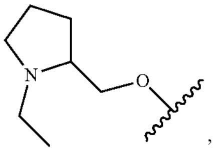,
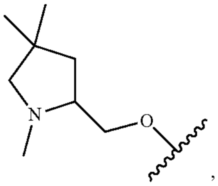, 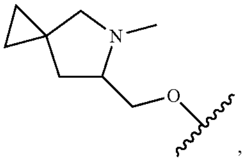, and
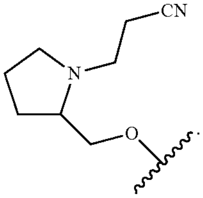
In some embodiments, $R^1$ is:
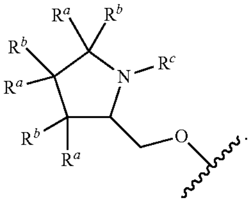
In some embodiments, $R^1$ is selected from:
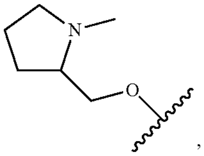, 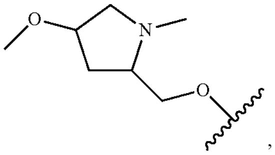,
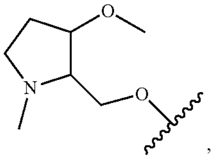, 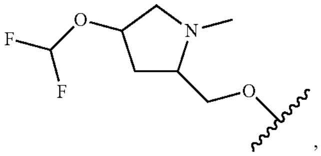,
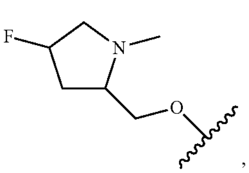, 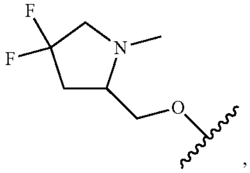,
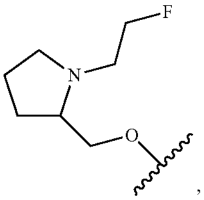, 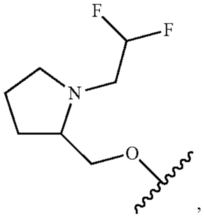,
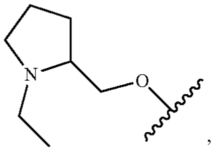, 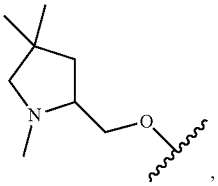,
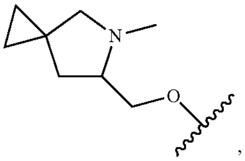, and 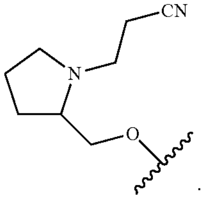.

In some embodiments, $R^1$ is selected from:

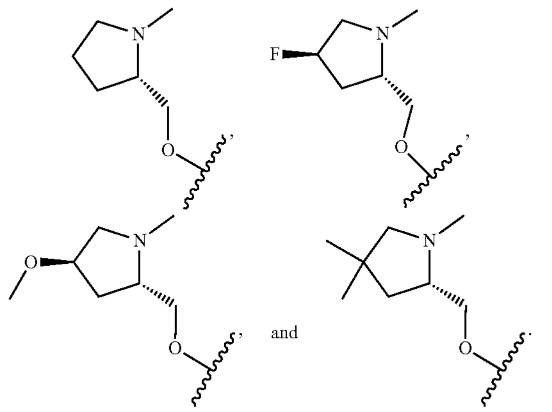

In some embodiments, $R^2$ is a 4-6 membered heterocycle comprising a nitrogen atom, wherein the heterocycle is unsubstituted or substituted with one or more $R^{16}$. In some embodiments, $R^1$ is:

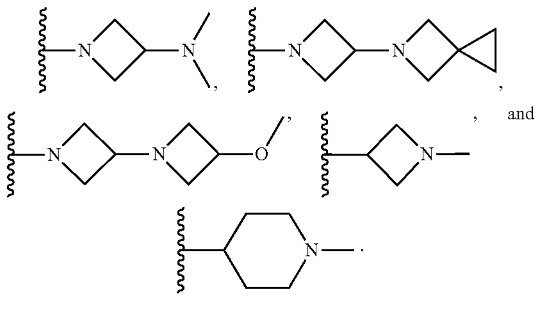

In some embodiments, $R^2$ is selected from H, $C_{1-6}$ alkyl, and a 3-6 membered carbocycle, wherein $C_{1-6}$ alkyl is unsubstituted or substituted with one or more $R^{13}$. In some embodiments, $R^2$ is selected from H, $C_{1-6}$ alkyl, and a 3-6 membered carbocycle. In some embodiments, $R^2$ is H. In some embodiments, $R^2$ is $C_{1-6}$ alkyl unsubstituted or substituted with one or more $R^{13}$. In some such embodiments, each $R^{13}$ is independently selected from —$OR^{22}$ (e.g., —OH) and —CN. In some embodiments, $R^2$ is $C_{1-6}$ alkyl. In some embodiments $R^2$ is selected from —$CH_3$, —$CH_2CH_3$, —$CH_2CH_2OH$, —$CH_2CH_2CN$, and —$CH(CH_3)_2$. In some embodiments, $R^2$ is a 3-6 membered carbocycle. In some embodiments, $R^2$ is cyclopropyl.

In some embodiments, $R^3$ is selected from $C_{1-6}$ alkyl that is substituted with —$N(R^{12})(E)$. In some embodiments, $R^3$ is selected from $C_{1-6}$ alkyl that is substituted with —N(H)(E).

In some embodiments, $R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$. In some embodiments, $R^3$ is a 4-6 membered heterocycle that is substituted with one or more E and 0-4 $R^{10}$, wherein the heterocycle includes one or more heteroatoms selected from N, O, and S, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes a single heteroatom that is N, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

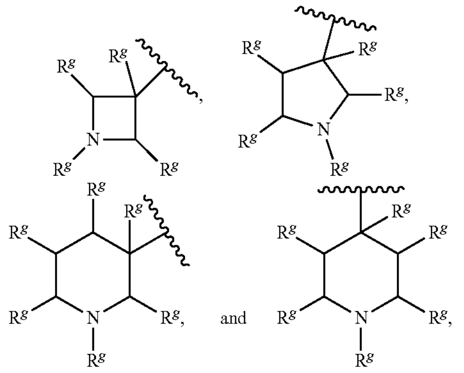

wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

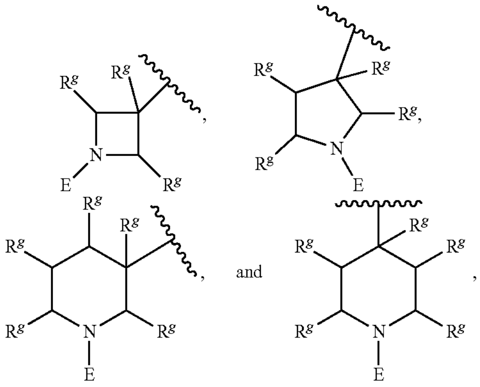

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In some embodiments, $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

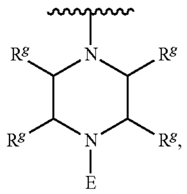

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, one or two $R^9$ groups are $C_{1-6}$alkyl (e.g., methyl). In some embodiments, $R^2$ and $R^3$, together with the atom to which they are attached, form the structure:

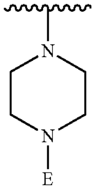, 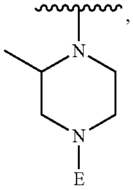, 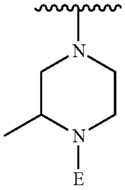, 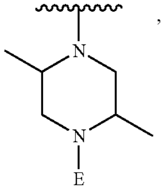,

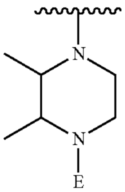, 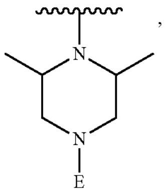, 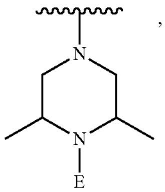,

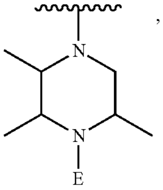, 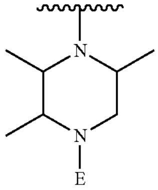, or 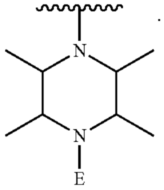.

In some embodiments, $R^2$ and $R^3$, together with the atom to which they are attached, form a 4-8 membered bicyclic heterocycle comprising a fused ring system that is substituted with one or more E and 0-4 $R^{11}$. In some embodiments, $R^2$ and $R^3$, together with the atom to which they are attached, form a 4-8 membered heterocycle comprising a spirocyclic ring system that is substituted with one or more E and 0-4 $R^{11}$. In some embodiments, $R^2$ and $R^3$, together with the atom to which they are attached, form a structure selected from:

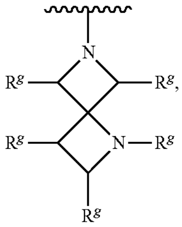 and 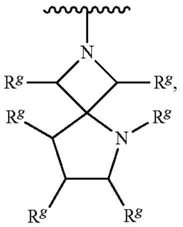

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a 4-8 membered heterocycle comprising a fused ring system that is substituted with one or more E and 0-4 $R^{11}$. In some embodiments, $R^2$ and $R^3$, together with the atom to which they are attached, form a structure selected from:

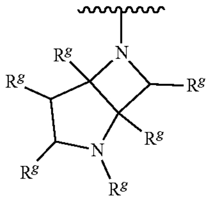 and 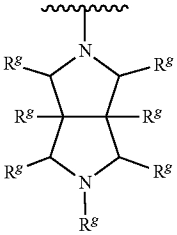, wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a structure selected from:

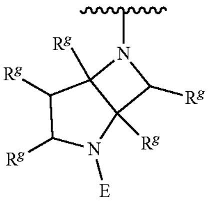 and 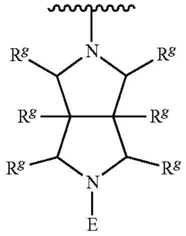, wherein each $R^g$ is independently selected from $C_{1-6}$alkyl and H, wherein any $C_{1-6}$alkyl is unsubstituted or substituted with one or more $R^{20}$. In some embodiments, $R^2$ and $R^3$, together with the atom to which they are attached, form the structure:

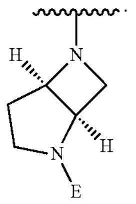

In some embodiments, $R^4$ is H.

In some embodiments, $R^5$ is H.

In some embodiments, $R^5$ is —CN.

In some embodiments, $R^5$ is a halogen. In some embodiments, $R^5$ is Cl. In some embodiments, $R^5$ is F.

In some embodiments, $R^5$ is selected from $C_{1-6}$alkyl that is unsubstituted or substituted with one or more $R^{13}$. In some embodiments, $R^5$ is selected from $C_{1-2}$alkyl that is unsubstituted or substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is —$CF_3$. In some embodiments, $R^5$ is —$CHF_2$. In some embodiments, $R^5$ is selected from —$CF_2H$, —$CF_3$, —$CH_2CN$, and —$CH_2CH_3$. In some embodiments, $R^5$ is selected from —$CH_3$, —$CH_2CH_3$, —$CF_2H$, —$CF_3$, —$CF_2CH_3$, and —$CH_2CN$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$.

In some embodiments, $R^5$ is selected from —$OR^{12}$. In some embodiments, $R^5$ is selected from —$OR^2$, wherein $R^{12}$ is selected from $C_{1-6}$ alkyl and H. In some embodiments, $R^5$ is —$OCH_3$. In some embodiments, $R^5$ is —$OCF_3$.

In some embodiments, $R^5$ is selected from a 3-6 membered carbocycle that is unsubstituted or substituted with one or more $R^{14}$. In some embodiments, $R^5$ is selected from a cyclobutyl that is unsubstituted or substituted with one or more $R^{14}$. In some embodiments, $R^5$ is selected from a phenyl that is unsubstituted or substituted with one or more $R^{14}$. In some embodiments, $R^5$ is phenyl.

In some embodiments, $R^5$ is selected from a 3-6 membered heterocycle or a 5-6 membered heteroaryl that is unsubstituted or substituted with one or more $R^{14}$. In some embodiments, $R^5$ is selected from a 3-6 membered heterocycle that is unsubstituted or substituted with one or more $R^{14}$. In some embodiments, $R^5$ is selected from a 5-6 membered heteroaryl that is unsubstituted or substituted with one or more $R^{14}$. In some embodiments, $R^5$ is selected from a 5-6 membered heterocycle or a 5-6 membered heteroaryl that includes one or two heteroatoms selected from O and N and is unsubstituted or substituted with one or more $R^{14}$. In some embodiments, $R^5$ is selected from a 5-6 membered heterocycle that includes one or two heteroatoms selected from O and N and is unsubstituted or substituted with one or more $R^{14}$. In some embodiments, $R^5$ is selected from furanyl, pyridinyl, and pyrazolyl that is unsubstituted or is substituted with one or more $R^{14}$. In some embodiments, $R^5$ is selected from:

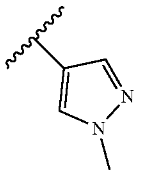
,
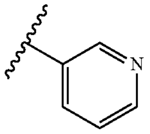
, and
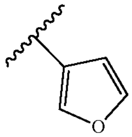
.

In some embodiments, $R^7$ is a halogen. In some embodiments, $R^7$ is F. In some embodiments, $R^7$ is Cl.

In some embodiments, $R^7$ is —$OR^X$, such as OH. In some embodiments, $R^7$ is —$OR^X$, where $R^X$ is $C_{1-6}$ alkyl.

In some embodiments, $R^7$ is —CN.

In some embodiments, $R^7$ is H.

In some embodiments, $R^7$ is:

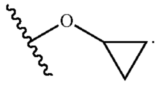 [SMILES: *OC1CC1]
.

In some embodiments, X is N. In some embodiments, X is N and Y is O. In some embodiments, X is N and Y is S.

In some embodiments, X is C—CN and Y is O. In some embodiments, X is C—CN and Y is S. In some embodiments, Y is S.

In some embodiments, $R^{23}$ is selected from —$N(R^{12})_2$. In some embodiments, $R^{23}$ is —$NH_2$.

In some embodiments, $R^{24}$ is a halogen. In some embodiments, $R^{24}$ is F.

In some embodiments, $R^8$ and $R^{26}$ are H.

In some embodiments, each E is independently selected from:

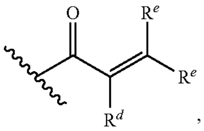
,
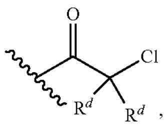
, and
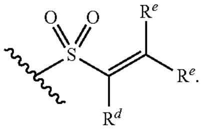
.

In some embodiments, each E is:

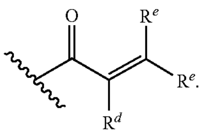
.

In some embodiments, each $R^d$ and $R^e$ is H. In some embodiments, the compound includes a single E.

In some embodiments, $R^4$ is H, $R^7$ is a halogen, and $R^1$ is:

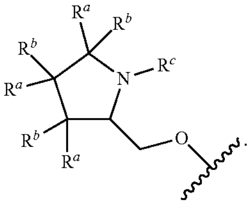

In some embodiments, $R^1$ is selected from:

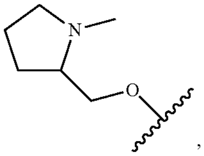,
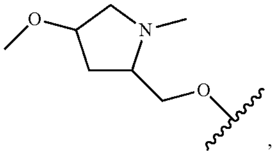,
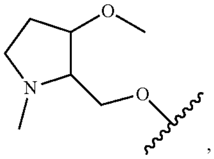,
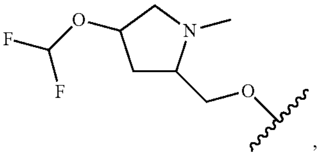,
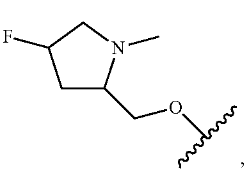,
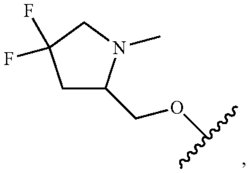,
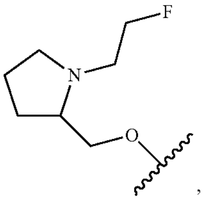,
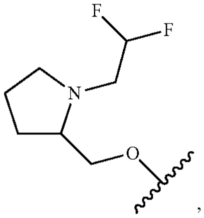,
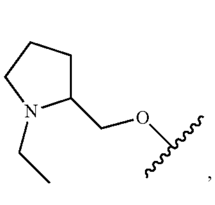,
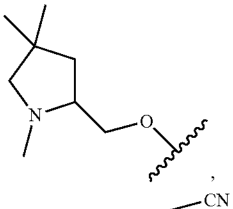,
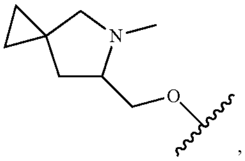, and
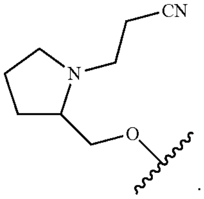.

In some embodiments, $R^1$ is selected from:

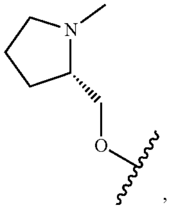,
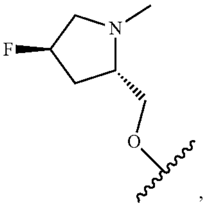,
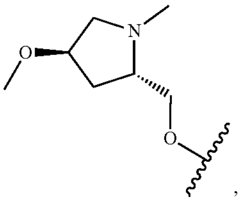, and
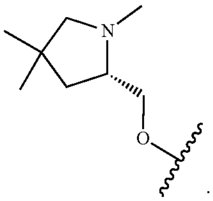.

In some embodiments, $R^7$ is F.

In some embodiments, $R^4$ is H, $R^7$ is a halogen, and $R^1$ is:

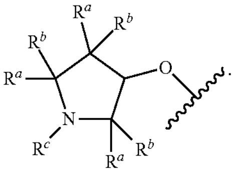

In some embodiments, $R^1$ is:

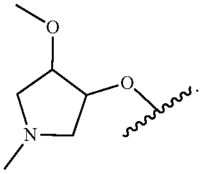 [SMILES: *OC1CN(C)CC1OC]

In some embodiments, $R^7$ is F.

In some embodiments, $R^4$ is H, $R^7$ is a halogen, and $R^1$ is a 4-6 membered heterocycle comprising a nitrogen atom, wherein the heterocycle is unsubstituted or substituted with one or more $R^{16}$. In some embodiments, $R^1$ is:

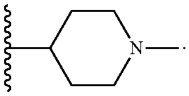

In some embodiments, $R^7$ is F.

In another aspect, the present disclosure provides a compound according to Formula IIA1:

(IIA1)

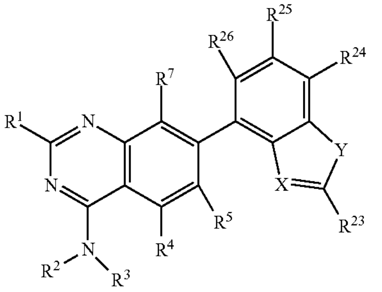

or a salt (e.g., pharmaceutically acceptable salt), ester, tautomer, prodrug, zwitterionic form, or stereoisomer thereof, wherein:

$R^1$ is selected from

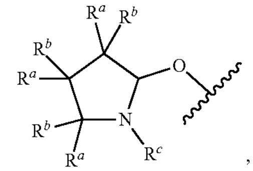
,
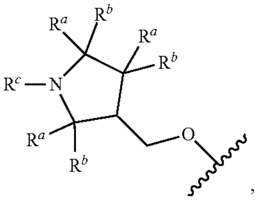
,
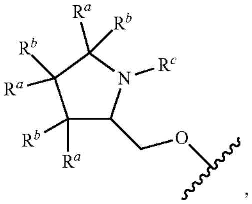
, and
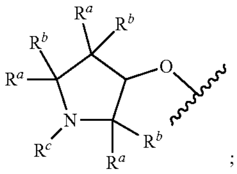
;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^X$, —CN, and H;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$ alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —$N(R^2)C(O)(C_{1-6}alkyl)$, —$OR^{12}$, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

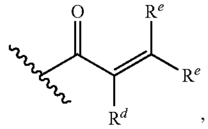
,
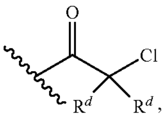
,
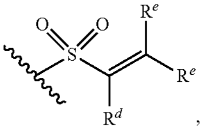
,
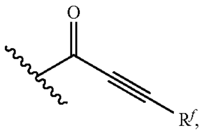
,
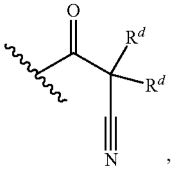
,
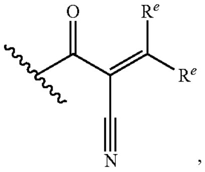
,
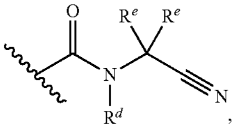
,
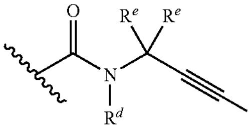
,
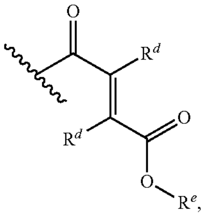
,
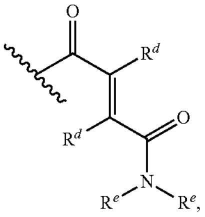
,
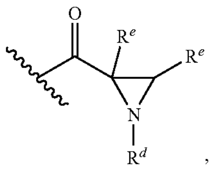
,
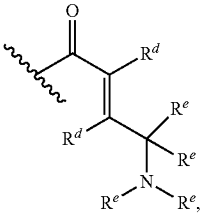
, and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IIA1, or a salt (e.g., a pharmaceutically acceptable salt) thereof.

In some embodiments, $R^2$ is H. In some embodiments, $R^2$ is $C_{1-6}$ alkyl unsubstituted or substituted with one or more $R^{13}$. In some such embodiments, each $R^{13}$ is independently selected from —$OR^{22}$ (e.g., —OH) and —CN. In some embodiments, $R^2$ is $C_{1-6}$ alkyl. In some embodiments $R^2$ is selected from —$CH_3$, —$CH_2CH_3$, —$CH_2CH_2OH$, —$CH_2CH_2CN$, and —$CH(CH_3)_2$. In some embodiments, $R^2$ is a 3-6 membered carbocycle. In some embodiments, $R^2$ is cyclopropyl.

In some embodiments, $R^3$ is a 4-6 membered heterocycle that is substituted with one or more E and 0-4 $R^{10}$. In some embodiments, $R^3$ is a 4-6 membered heterocycle that is substituted with one or more E and 0-4 $R^{10}$, wherein the heterocycle includes one or more heteroatoms selected from N, O, and S, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes a single heteroatom that is N, optionally wherein two $R^{10}$ groups, together with the atom or atoms to which they are attached, form a 3-6 membered carbocycle. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

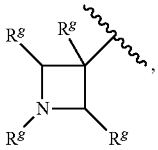,
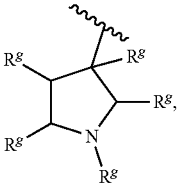,
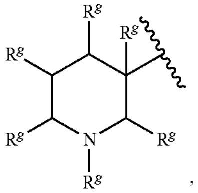, and
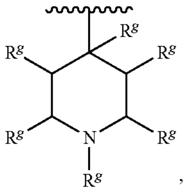, wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

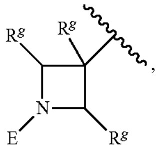,
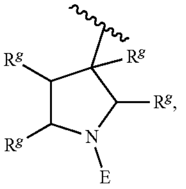

-continued

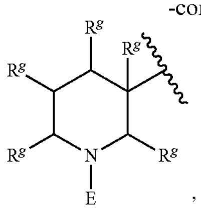, and
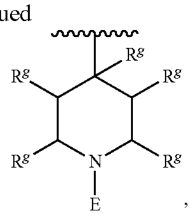, wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In another aspect, the present disclosure provides a compound according to Formula IIA2:

(IIA2)

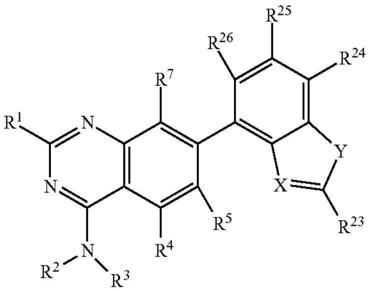

or a salt (e.g., pharmaceutically acceptable salt), ester, tautomer, prodrug, zwitterionic form, or stereoisomer thereof, wherein:

$R^1$ is selected from

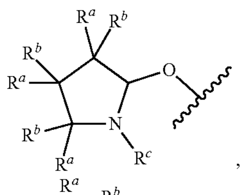,
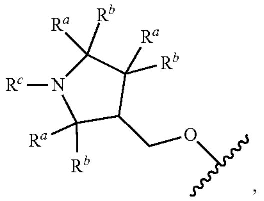,
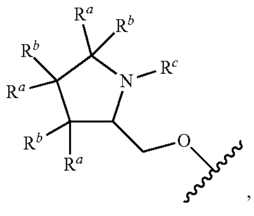, and
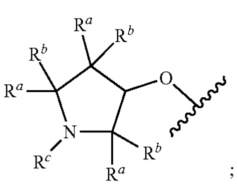;

$R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is H;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^X$, —CN, and H;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$ alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —$N(R^2)C(O)(C_{1-6}alkyl)$, —$OR^{12}$, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

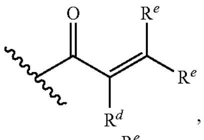,
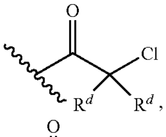,
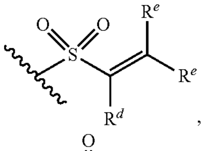,
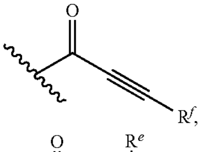,
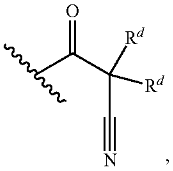,
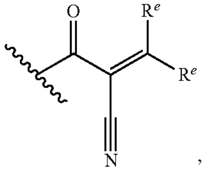,
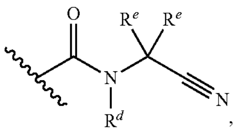,
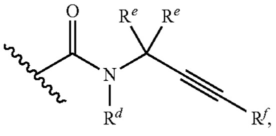, -continued

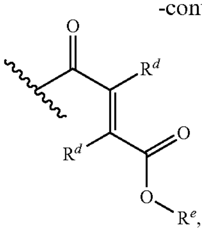
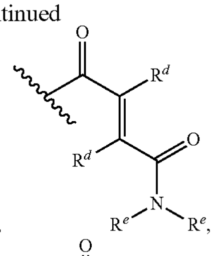
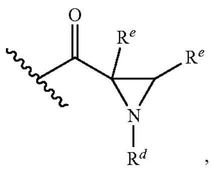,
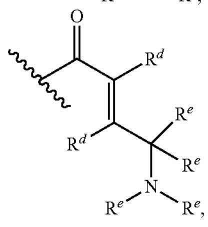

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IIA2, or a salt (e.g., a pharmaceutically acceptable salt) thereof.

In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle or heterocycle. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

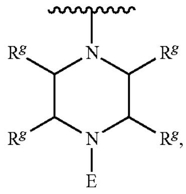

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, one or two $R^g$ groups are $C_{1-6}$alkyl (e.g., methyl). In some embodiments, $R^2$ and $R^3$, together with the atom to which they are attached, form the structure:

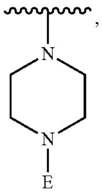,
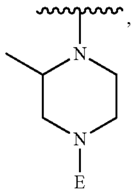,
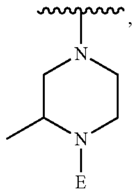,
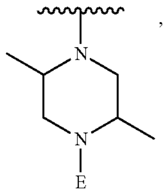,

-continued

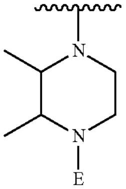,
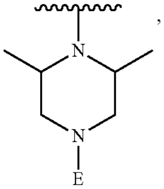,
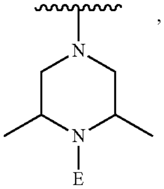,
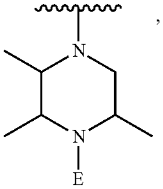,
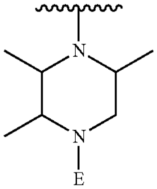, or
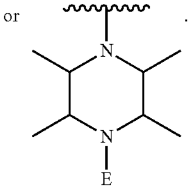.

In some embodiments for a compound of Formula IIA1 or IIA2, one $R^a$ or $R^b$ is selected from halogen, $C_{1-6}$ alkyl, and —$OR^{12}$, and the other $R^a$ and $R^b$ groups are H. In some embodiments, one $R^a$ or $R^b$ is halogen (e.g., F). In some embodiments, two $R^a$ groups, two $R^b$ groups, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

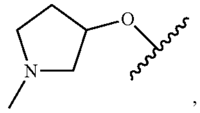,
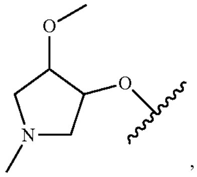,
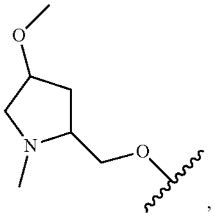,
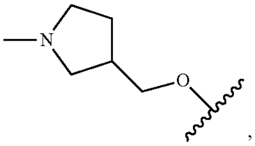,
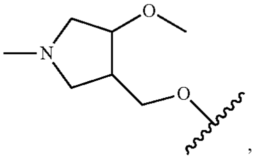,
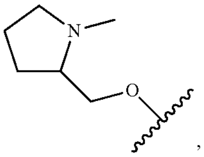,
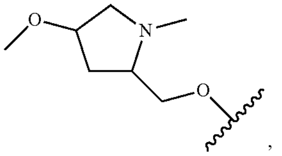,
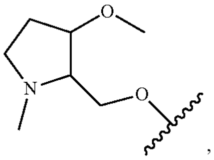,
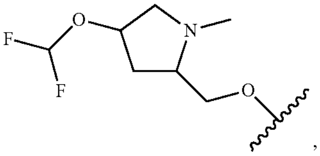,
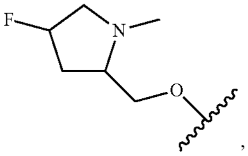, -continued

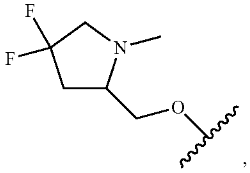,
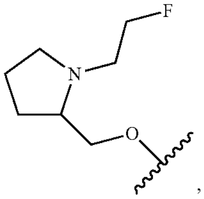,
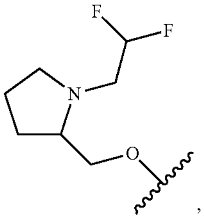,
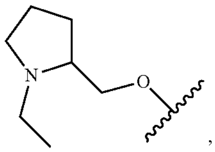,
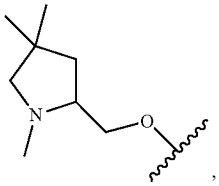,
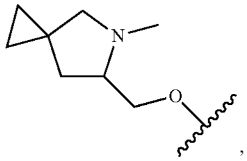, and
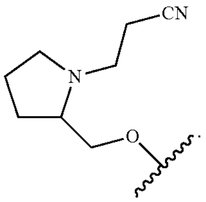.

In some embodiments for a compound of Formula IIA1 or IIA2, $R^1$ is selected from:

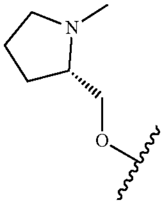,
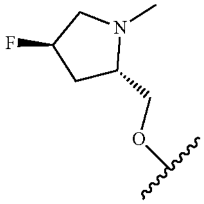,
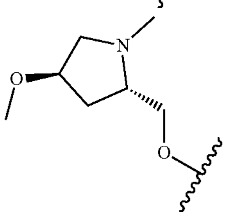, and
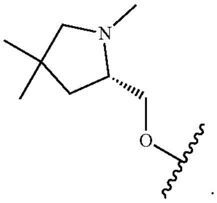.

In some embodiments for a compound of Formula IIA1 or IIA2, $R^5$ is H.

In some embodiments for a compound of Formula IIA1 or IIA2, $R^5$ is —CN.

In some embodiments for a compound of Formula IIA1 or IIA2, $R^5$ is a halogen. In some embodiments, $R^5$ is Cl. In some embodiments, $R^5$ is F.

In some embodiments for a compound of Formula IIA1 or IIA2, $R^5$ is selected from $C_{1-6}$alkyl that is unsubstituted or substituted with one or more $R^{13}$. In some embodiments, $R^5$ is selected from $C_{1-2}$alkyl that is unsubstituted or substituted with one or more $R^{13}$. In some embodiments, $R^5$ is selected from $C_{1-6}$alkyl that is unsubstituted, such as methyl or ethyl.

In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is $—CF_3$. In some embodiments, $R^5$ is $—CHF_2$. In some embodiments, $R^5$ is selected from $—CF_2H$, $—CF_3$, $—CH_2CN$, and $—CH_2CH_3$. In some embodiments, $R^5$ is selected from $—CH_3$, $—CH_2CH_3$, $—CF_2H$, $—CF_3$, $—CF_2CH_3$, and $—CH_2CN$. In some embodiments, $R^5$ is $C_{1-6}$alkyl that is substituted with one or more $R^{13}$, wherein each $R^{13}$ is independently selected from $—OR^{22}$, —CN, and $—N(R^{22})_2$. In some embodiments, $R^5$ is $—CH_2CN$.

In some embodiments for a compound of Formula IIA1 or IIA2, $R^5$ is selected from $—OR^{12}$. In some embodiments, $R^5$ is selected from $—OR^{12}$, wherein $R^{12}$ is selected from $C_{1-6}$ alkyl and H. In some embodiments, $R^5$ is $—OCH_3$. In some embodiments, $R^5$ is $—OCF_3$.

In some embodiments for a compound of Formula IIA1 or IIA2, $R^5$ is selected from a 3-6 membered carbocycle that is unsubstituted or substituted with one or more $R^{14}$. In some embodiments, $R^5$ is selected from a cyclobutyl that is unsubstituted or substituted with one or more $R^{14}$. In some embodiments, $R^5$ is selected from a phenyl that is unsubstituted or substituted with one or more $R^{14}$. In some embodiments, $R^5$ is phenyl.

In some embodiments for a compound of Formula IIA1 or IIA2, $R^5$ is selected from a 3-6 membered heterocycle or a 5-6 membered heteroaryl that is unsubstituted or substituted with one or more $R^{14}$. In some embodiments, $R^5$ is selected from a 3-6 membered heterocycle that is unsubstituted or substituted with one or more $R^{14}$. In some embodiments, $R^5$ is selected from a 5-6 membered heteroaryl that is unsubstituted or substituted with one or more $R^{14}$. In some embodiments, $R^5$ is selected from a 5-6 membered heterocycle or a 5-6 membered heteroaryl that includes one or two heteroatoms selected from O and N and is unsubstituted or substituted with one or more $R^{14}$. In some embodiments, $R^5$ is selected from a 5-6 membered heterocycle that includes one or two heteroatoms selected from O and N and is unsubstituted or substituted with one or more $R^{14}$. In some embodiments, $R^5$ is selected from furanyl, pyridinyl, and pyrazolyl that is unsubstituted or is substituted with one or more $R^{14}$.

In some embodiments for a compound of Formula IIA1 or IIA2, $R^7$ is a halogen. In some embodiments, $R^7$ is F. In some embodiments, $R^7$ is Cl.

In some embodiments for a compound of Formula IIA1 or IIA2, $R^7$ is $—OR^X$, such as —OH. In some embodiments, $R^7$ is $—OR^X$, where $R^X$ is $C_{1-6}$ alkyl.

In some embodiments for a compound of Formula IIA1 or IIA2, $R^7$ is —CN.

In some embodiments for a compound of Formula IIA1 or IIA2, $R^7$ is H.

In some embodiments for a compound of Formula IIA1 or IIA2, X is N. In some embodiments, X is N and Y is O. In some embodiments, X is N and Y is S.

In some embodiments for a compound of Formula IIA1 or IIA2, X is C—CN and Y is O. In some embodiments, X is C—CN and Y is S. In some embodiments, Y is S.

In some embodiments for a compound of Formula IIA1 or IIA2, $R^{23}$ is selected from $—N(R^{12})_2$. In some embodiments, $R^{23}$ is $—NH_2$.

In some embodiments for a compound of Formula IIA1 or IIA2, $R^{24}$ is a halogen. In some embodiments, $R^{24}$ is F.

In some embodiments for a compound of Formula IIA1 or IIA2, $R^{25}$ and $R^{26}$ are H.

In some embodiments for a compound of Formula IIA1 or IIA2, each E is independently selected from:

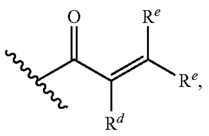
, 
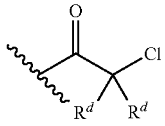
, and

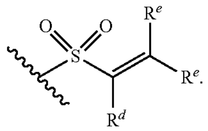

In some embodiments for a compound of Formula IIA1 or IIA2, each E is:

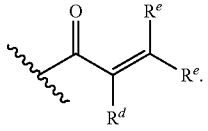

In some embodiments, each $R^d$ and $R^e$ is H. In some embodiments, the compound includes a single E.

In a further aspect, the present disclosure provides a compound according to Formula IIB:

(IIB)

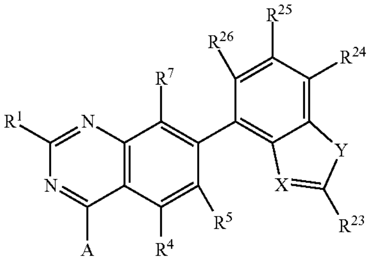

or a salt (e.g., pharmaceutically acceptable salt), ester, tautomer, prodrug, zwitterionic form, or stereoisomer thereof, wherein:

$R^1$ is selected from $—OR^8$,

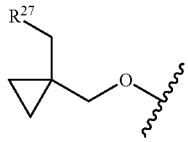
, a 4-6 membered heterocycle comprising a nitrogen atom, and H, wherein the heterocycle is unsubstituted or substituted with one or more $R^{16}$;

A is selected from:

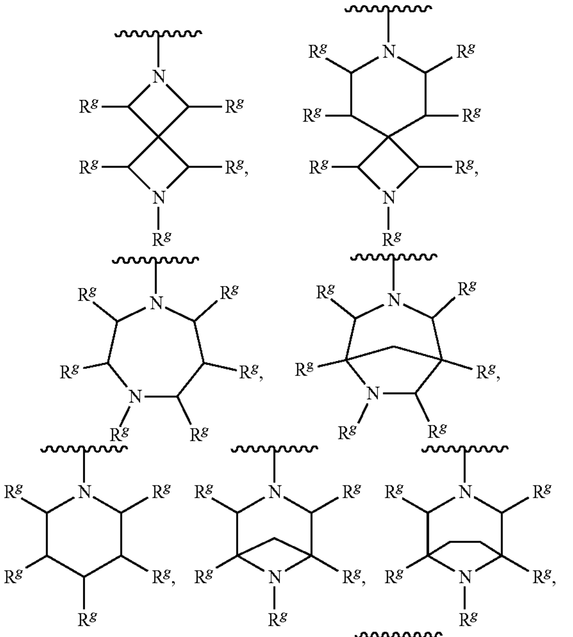

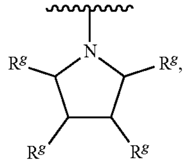 and 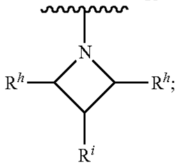

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, —$N(R^2)C(O)(C_{1-6}alkyl)$, —$OR^{12}$, and $C_{1-6}$alkyl-$N(R^{12})_2$;

$R^{24}$, $R^2$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^g$ is independently selected from $C_{1-6}$alkyl, H, and E, wherein at least one $R^g$ is E, and wherein any $C_{1-6}$alkyl is unsubstituted or substituted with one or more $R^{20}$;

each $R^h$ is independently selected from $C_{1-6}$alkyl and H;

$R^i$ is selected from —$N(R^{12})(E)$, E, and —$(C_{1-6}alkyl)E$;

$R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$;

each E is independently selected from

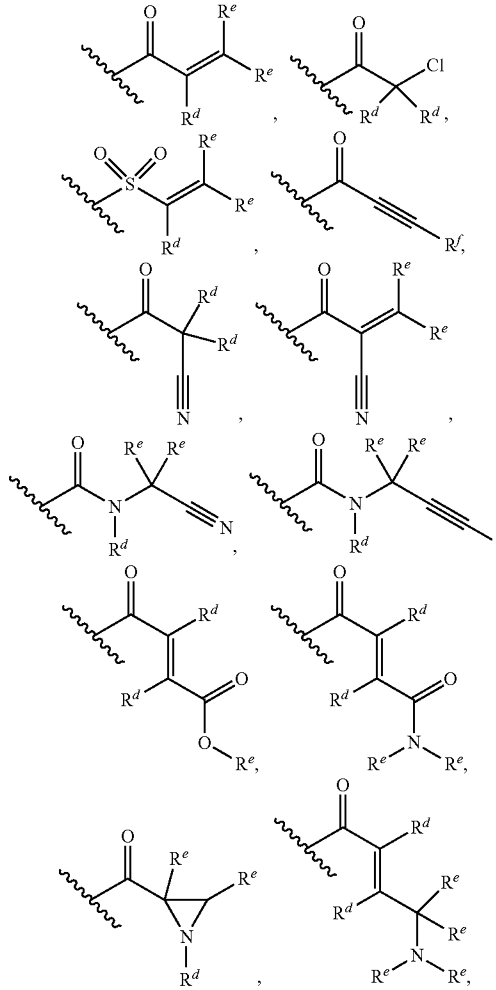

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IIB, or a salt (e.g., a pharmaceutically acceptable salt) thereof.

In some embodiments, A is selected from:

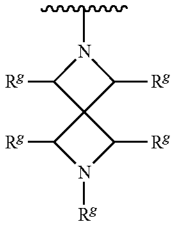

and

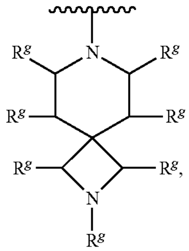

In some embodiments, only one $R^g$ is E. In some embodiments, A is selected from:

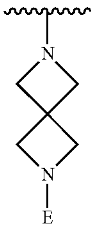

and

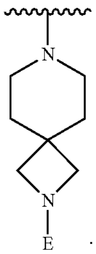

In some embodiments, A is selected from:

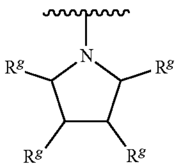

,

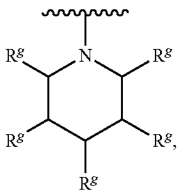

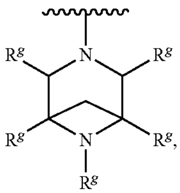

and

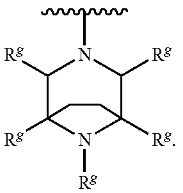

In some embodiments, only one $R^g$ is E. In some embodiments, A is selected from:

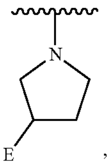

,

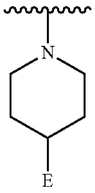

,

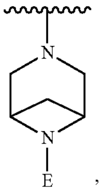

, and

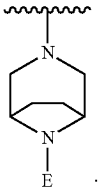

In some embodiments, A is:

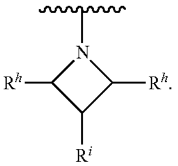

In some embodiments, A is selected from:

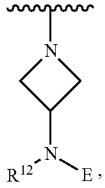

,

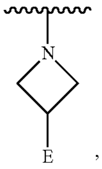

, and

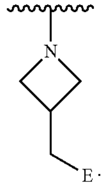

In some embodiments, A is selected from:

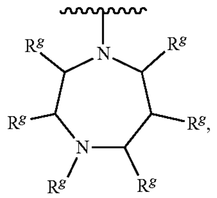

and

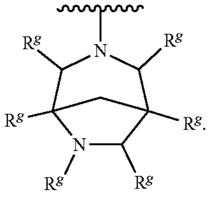

In some embodiments, A is selected from:

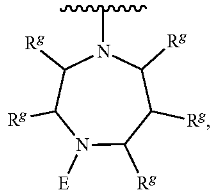

and

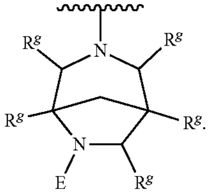

In some embodiments, $R^1$ is H.

In some embodiments, $R^1$ is —OR. In some embodiments, $R^8$ is a heterocycle that is unsubstituted or substituted with one or more $R^a$ and/or $R^b$. In some embodiments, $R^8$ is an alkylheterocycle that is unsubstituted or substituted with one or more $R^a$ and/or $R^b$. In some embodiments, $R^8$ is —$CH_2$(heterocycle), wherein the heterocycle is unsubstituted or substituted with one or more $R^a$ and/or $R^b$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$ and/or $R^b$, wherein the one or more $R^a$ and/or $R^b$ is a halogen (e.g., F). In some embodiments, a heterocycle or a heterocycle of an alkylheterocycle is substituted with one or more $R^a$ and/or $R^b$, wherein the one or more $R^a$ and/or $R^b$ is a $C_{1-6}$alkyl (e.g., methyl). In some embodiments, a heterocycle or a heterocycle of an alkylheterocycle is substituted with one or more $R^a$ and/or $R^b$, wherein the one or more $R^a$ and/or $R^b$ is a —$OR^{12}$ (e.g., —$OCH_3$).

In some embodiments, $R^1$ is selected from:

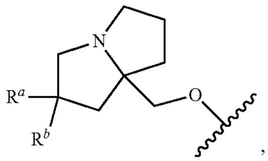
, wherein $R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$. In some embodiments, $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^b$ is methyl. In some embodiments, $R^1$ is selected from:

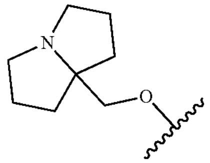
,

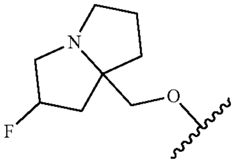
,

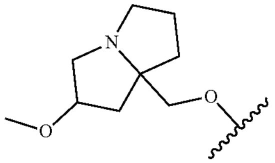
,

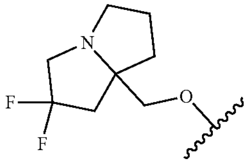
, and

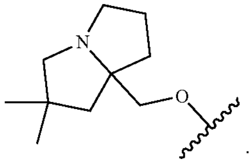
.

In some embodiments, $R^1$ is selected from:

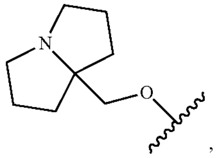
,
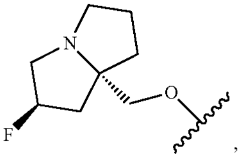
,

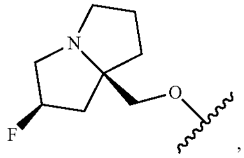
,
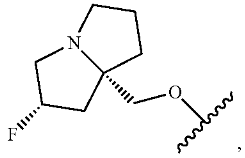
,

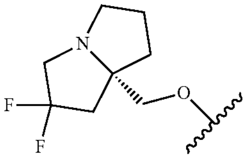
,
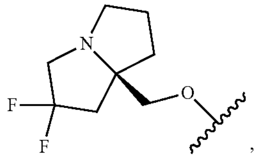
,

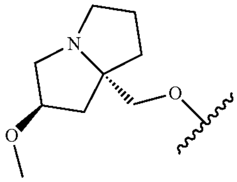
,
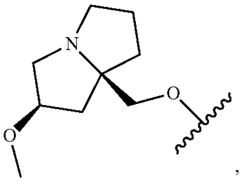
,

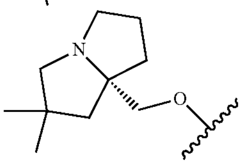
, and
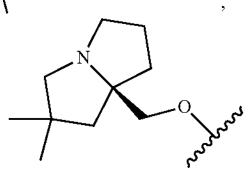
.

In some embodiments, $R^1$ is selected from:

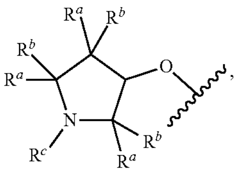
,
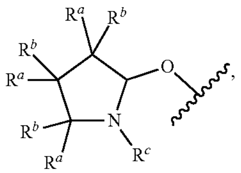
,

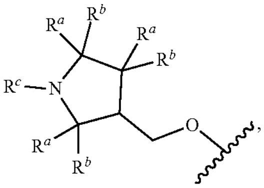
, and

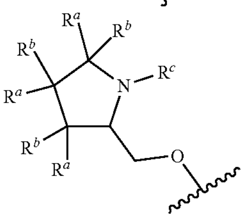

wherein each $R^a$ and $R^b$ is independently selected from halogen, $C_{1-6}$ alkyl, —$OR^{12}$, and H; and R is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and —$OR^{12}$, and the other $R^a$'s are H. In some embodiments, one $R^a$ or $R^b$ is halogen (e.g., F). In some embodiments, two $R^a$'s, two $R^b$'s, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

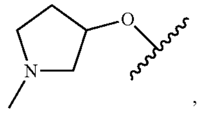
,
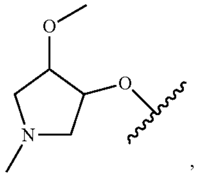
,
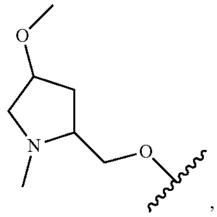
,
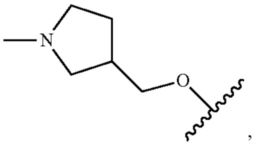
,
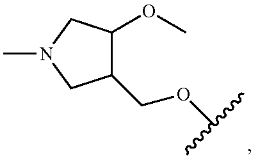
,
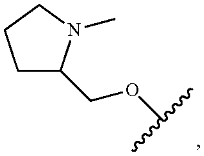
,
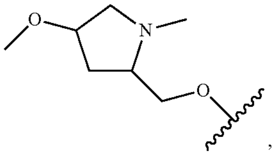
,
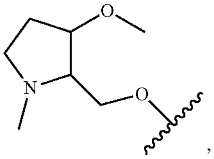
,
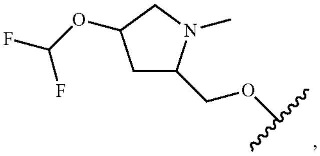
,
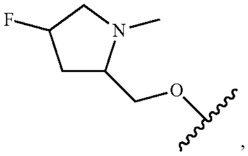
,
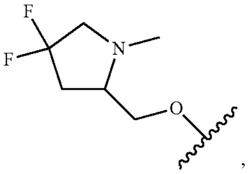
,
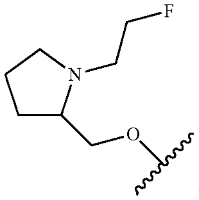
,
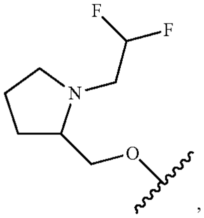
,
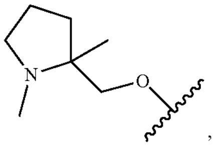
,
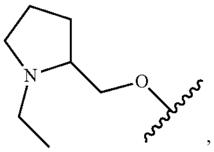
,
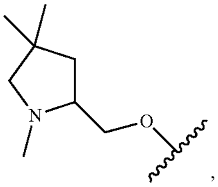
, -continued

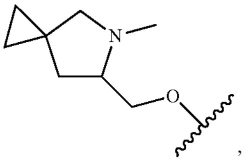
, and
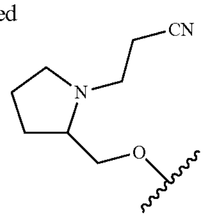
.

In some embodiments, $R^1$ is:

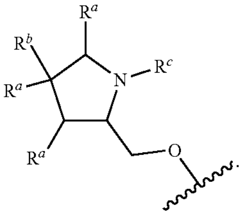

In some embodiments, $R^1$ is selected from:

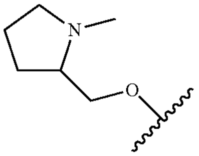
,
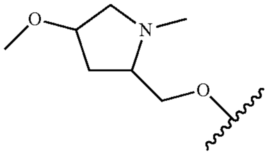
,
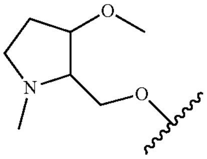
,
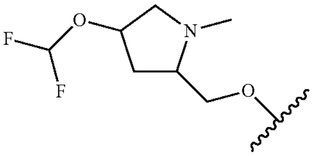
,
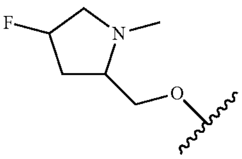
,
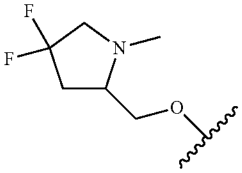
,
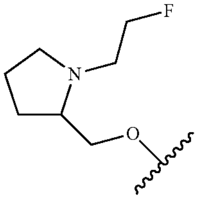
,
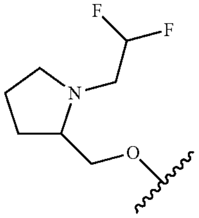
,
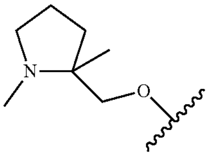
,
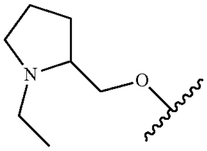
,
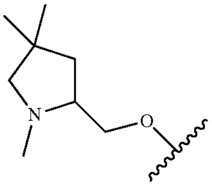
, and
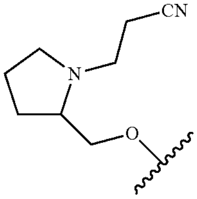
.

In some embodiments, $R^1$ is selected from

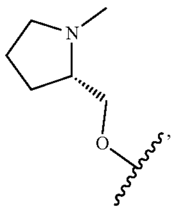,

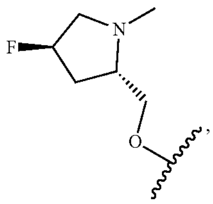,

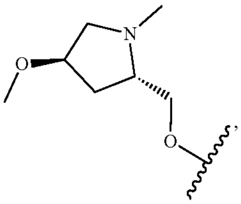, and

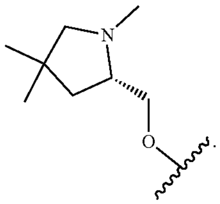.

In some embodiments, $R^1$ is selected from:

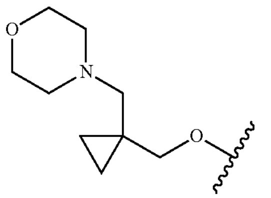 and

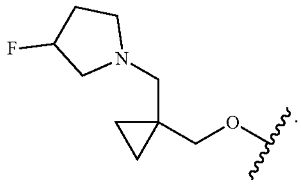.

In some embodiments, $R^1$ is selected from:

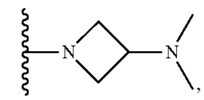,

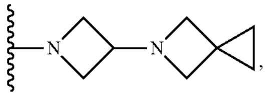,

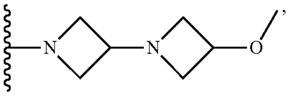,

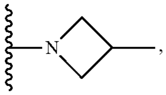, and

-continued

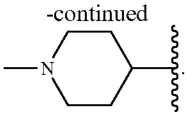.

In some embodiments, $R^4$ is H.

In some embodiments, $R^5$ is H.

In some embodiments, $R^5$ is a halogen. In some embodiments, $R^5$ is Cl. In some embodiments, $R^5$ is F.

In some embodiments, $R^5$ is —CN.

In some embodiments, $R^5$ is selected from $C_{2-6}$alkynyl. In some embodiments, $R^5$ is $C_2$alkynyl.

In some embodiments, $R^5$ is selected from $C_{1-6}$alkyl that is unsubstituted or substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is $C_{1-6}$alkyl that is substituted with one or more halogens, such as one or more fluorines. In some embodiments, $R^5$ is —$CF_3$. In some embodiments, $R^5$ is —$CHF_2$. In some embodiments, $R^5$ is selected from —$CF_3$, —$CF_2H$, and —$CH_2CN$. In some embodiments, $R^5$ is selected from —$CH_3$, —$CH_2CH_3$, —$CF_2H$, —$CF_3$, —$CF_2CH_3$, and —$CH_2CN$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$.

In some embodiments, $R^5$ is selected from —$OR^{12}$, wherein $R^{12}$ is selected from $C_{1-6}$ alkyl and H. In some embodiments, $R^5$ is —$OCH_3$.

In some embodiments, $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$. In some embodiments, $R^5$ is a 3-6 membered carbocycle unsubstituted or substituted with one or more $R^{14}$. In some embodiments, $R^5$ is a 3-4 membered carbocycle unsubstituted or substituted with one or more $R^{14}$ (e.g., one or more —CN). In some embodiments, $R^5$ is a 5-6 membered heteroaryl or phenyl unsubstituted or substituted with one or more $R^{14}$ (e.g., $C_{1-6}$alkyl). In some embodiments, $R^5$ is a pyridyl, furanyl, or imidazolyl, each unsubstituted or substituted with one or more $R^{14}$ (e.g., $C_{1-6}$alkyl). In some embodiments, $R^5$ is a furanyl. In some embodiments, $R^5$ is phenyl.

In some embodiments, $R^7$ is a halogen. In some embodiments, $R^7$ is F. In some embodiments, $R^7$ is Cl.

In some embodiments, $R^7$ is —$OR^{12}$, such as OH. In some embodiments, $R^7$ is —$OR^{12}$, where $R^{12}$ is $C_{1-6}$ alkyl.

In some embodiments, $R^7$ is —CN.

In some embodiments, $R^7$ is H.

In some embodiments, X is N and Y is O. In some embodiments, X is N and Y is S.

In some embodiments, X is C—CN and Y is O. In some embodiments, X is C—CN and Y is S.

In some embodiments, X is N.

In some embodiments, Y is S.

In some embodiments, $R^{23}$ is selected from —$N(R^{12})_2$. In some embodiments, $R^{23}$ is —$NH_2$.

In some embodiments, $R^{24}$ is a halogen. In some embodiments, $R^{24}$ is F.

In some embodiments, $R^{25}$ and $R^{26}$ are H.

In some embodiments, each E is independently selected from:

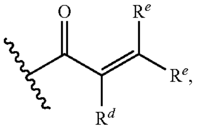

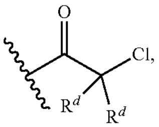

and

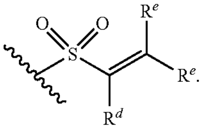

In some embodiments, each E is:

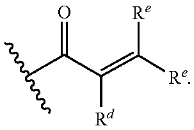

In some embodiments, each $R^d$ and $R^e$ is H. In some embodiments, the compound includes a single E.

In another aspect, the present disclosure provides a compound according to Formula IIC:

(IIC)

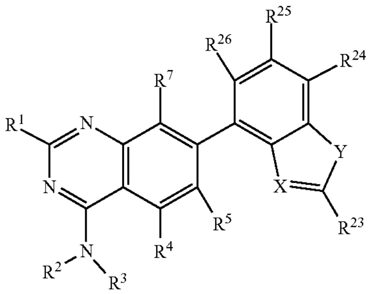

or a salt (e.g., pharmaceutically acceptable salt), ester, tautomer, prodrug, zwitterionic form, or stereoisomer thereof, wherein:

$R^1$ is selected from —$OR^8$,

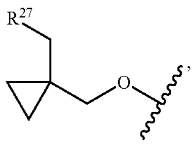

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is —$OR^Y$, wherein $R^Y$ is selected from $C_{1-6}$ alkyl;

$R^5$ is selected from halogen and H;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{16}$ is independently selected from halogen, —N$(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, —$N(R^2)C(O)(C_{1-6}alkyl)$, —$OR^{12}$, and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

$R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$;

each E is independently selected from

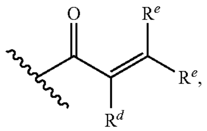

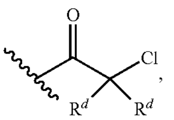

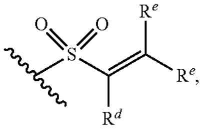

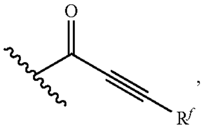

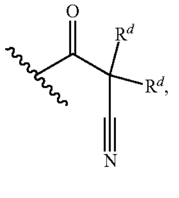

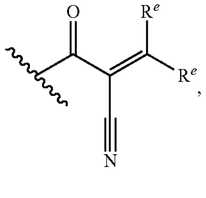

-continued

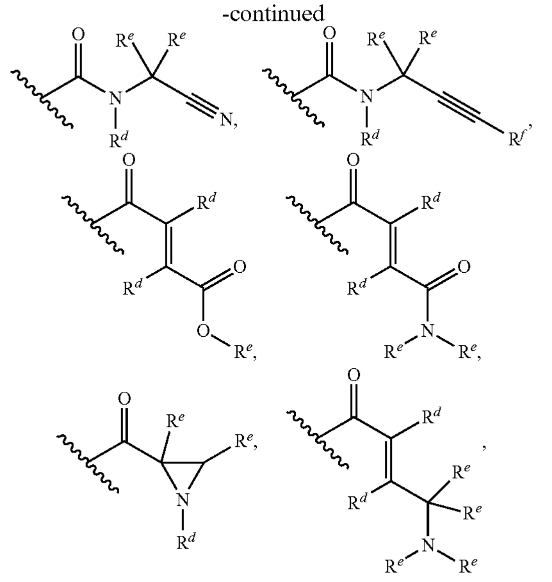

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IIC, or a salt (e.g., a pharmaceutically acceptable salt) thereof.

In some embodiments, $R^4$ is $—OCH_3$.

In some embodiments, $R^1$ is H.

In some embodiments, $R^1$ is selected from $—OR^8$, wherein $R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl. In some embodiments, $R^8$ is a heterocycle or an alkylheterocycle, wherein any heterocycle contains 4-8 members and is substituted with one or more $R^a$ and/or $R^b$. In some embodiments, $R^8$ is a heterocycle that is unsubstituted or substituted with one or more $R^a$ and/or R. In some embodiments, $R^8$ is an alkylheterocycle that is unsubstituted or substituted with one or more $R^a$ and/or $R^b$. In some embodiments, $R^8$ is $—CH_2$(heterocycle), where the heterocycle is unsubstituted or substituted with one or more $R^a$ and/or $R^b$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$ and/or $R^b$, wherein the one or more $R^a$ and/or $R^b$ is a halogen (e.g., F). In some embodiments, a heterocycle or a heterocycle of an alkylheterocycle is substituted with one or more $R^a$ and/or $R^b$, wherein the one or more $R^a$ and/or $R^b$ is a $C_{1-6}$alkyl (e.g., methyl). In some embodiments, a heterocycle or a heterocycle of an alkylheterocycle is substituted with one or more $R^a$ and/or $R^b$, wherein the one or more $R^a$ and/or $R^b$ is a $—OR^{12}$ (e.g., $—OCH_3$).

In some embodiments, $R^1$ is selected from:

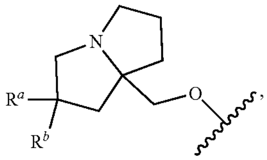

wherein $R^a$ and $R^b$ are each independently selected from halogen, $—OR^{12}$, and H. In some embodiments, $R^a$ and $R^b$ are each independently selected from halogen, $C_{1-6}$alkyl, $—OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is $—OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, $R^1$ is selected from:

In some embodiments, $R^1$ is selected from:

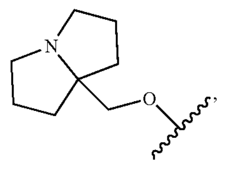

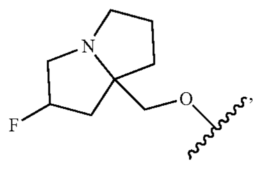

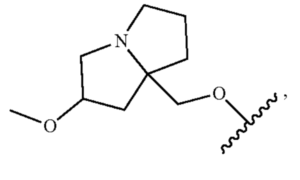

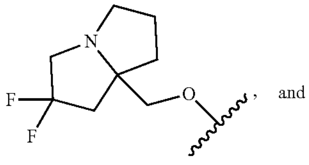

and

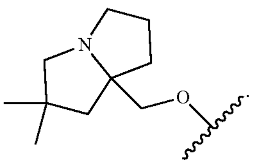

In some embodiments, $R^1$ is selected from:

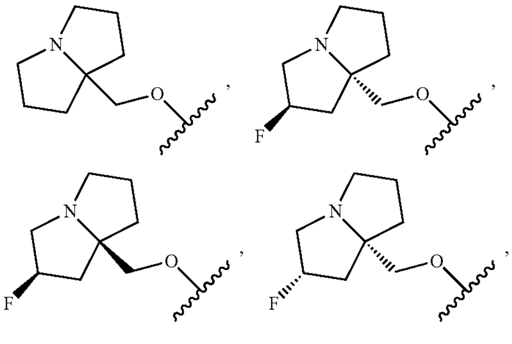

-continued

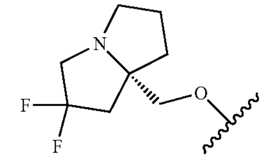 , 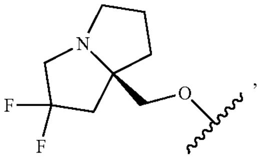 ,

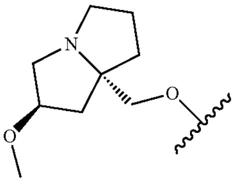 , 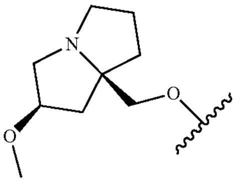 ,

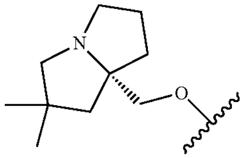 , and 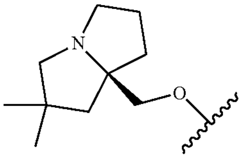 .

In some embodiments, $R^1$ is selected from:

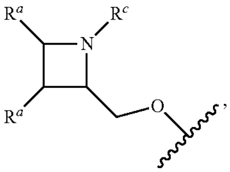 , wherein each $R^a$ is independently selected from halogen, $C_{1-6}$ alkyl, —$OR^{12}$, and H; and wherein $R^c$ is selected from $C_{1-6}$ alkyl, wherein the $C_{1-6}$ alkyl is unsubstituted or is substituted with one or more $R^{13}$. In some embodiments, $R^c$ is methyl. In some embodiments, $R^1$ is selected from:

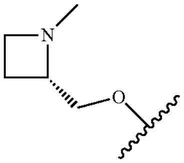 and 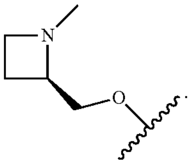 .

In some embodiments, $R^1$ is selected from:

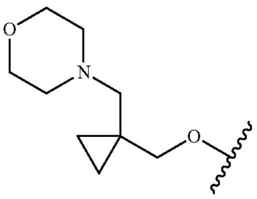 and

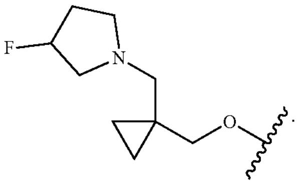 .

In some embodiments, $R^1$ is selected from:

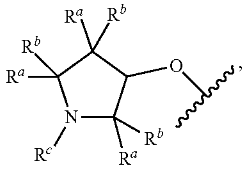 , 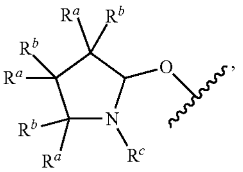 ,

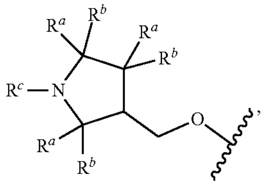 , and 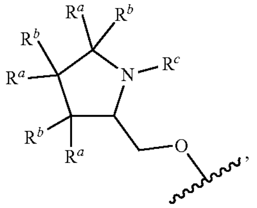 , wherein each $R^a$ and $R^b$ is independently selected from halogen, $C_{1-6}$ alkyl, —$OR^{12}$, and H; and $R^c$ is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and —$OR^{12}$, and the other $R^a$'s are H. In some embodiments, one $R^a$ or $R^b$ is halogen (e.g., F). In some embodiments, two $R^a$'s, two $R^b$'s, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$ alkyl (e.g., methyl). In some embodiments, two $R^a$'s, two $R^b$'s, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

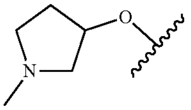 , 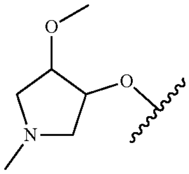 ,

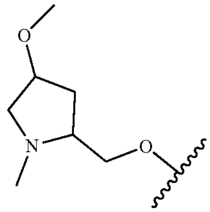 , 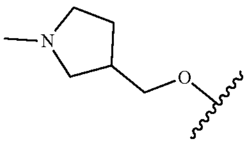 ,

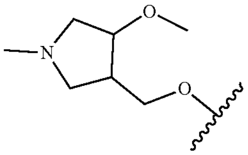 , 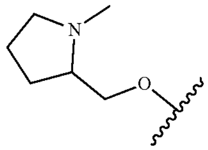 ,

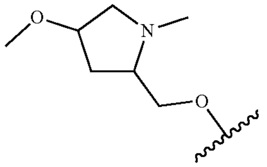 , 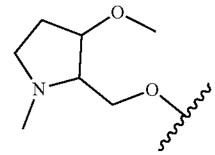 ,

-continued

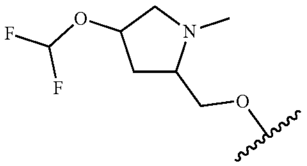
,
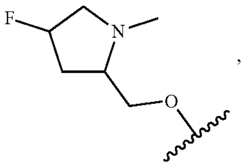
,
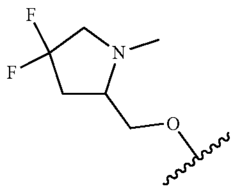
,
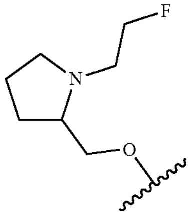
,
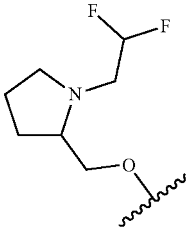
,
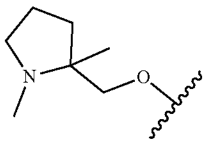
,
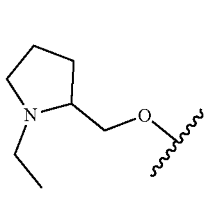
,
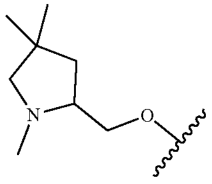
,
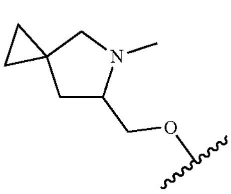
, and
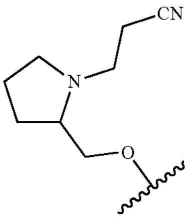
.

In some embodiments, $R^1$ is selected from:

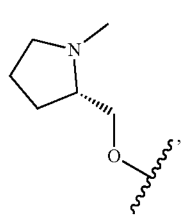
,
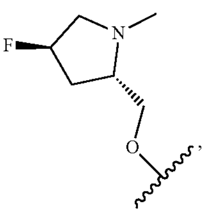
,
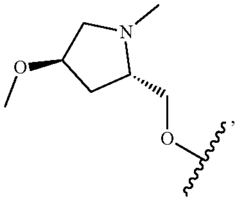
, and
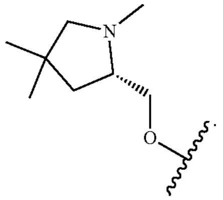
.

In some embodiments, $R^1$ is a 4-6 membered heterocycle comprising a nitrogen atom, wherein the heterocycle is unsubstituted or substituted with one or more $R^{16}$. In some embodiments, $R^1$ is:

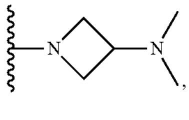
,
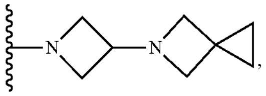
,
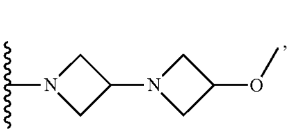
,
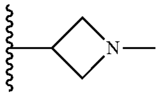
, and
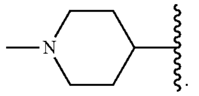
.

In some embodiments, $R^2$ is H. In some embodiments, $R^2$ is selected from $C_{1-6}$ alkyl. In some embodiments, $R^2$ is selected from $C_{1-2}$ alkyl. In some embodiments $R^2$ is selected from —$CH_3$, —$CH_2CH_3$, and —$CH(CH_3)_2$. In some embodiments, $R^2$ is selected from a 3-6 membered carbocycle. In some embodiments, $R^2$ is cyclopropyl.

In some embodiments, $R^3$ is selected from $C_{1-6}$ alkyl that is substituted with —$N(R^{12})(E)$. In some embodiments, $R^3$ is selected from $C_2$ alkyl that is substituted with —$N(R^{12})(E)$. In some embodiments, $R^3$ is selected from $C_2$ alkyl that is substituted with —N(H)(E).

In some embodiments, $R^3$ is a 4-6 membered heterocycle that is substituted with one or more E and 0-4 $R^{10}$. In some embodiments, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

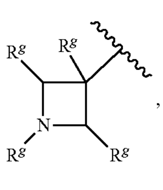
,
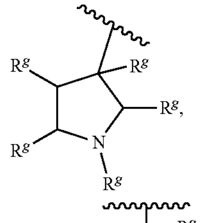
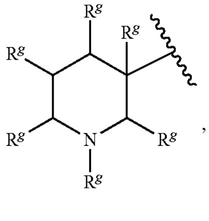
, and
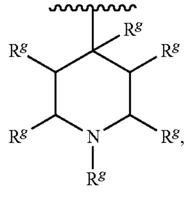

wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$. In some embodiments, $R^3$ is selected from:

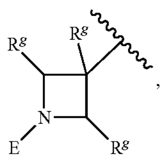
,
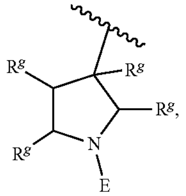

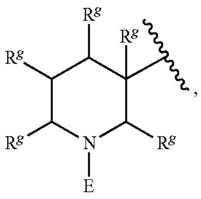
, and
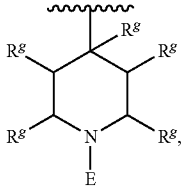

wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^9$ is $C_{1-6}$alkyl is unsubstituted or substituted with one or more $R^{20}$. In some embodiments, at least one $R^g$ is $C_{1-6}$alkyl (e.g., methyl).

In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

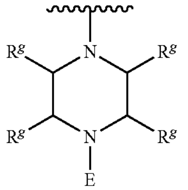
or
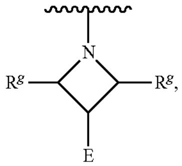

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, one or two $R^g$ groups are $C_{1-6}$alkyl (e.g., methyl). In some embodiments, $R^2$ and $R^3$, together with the atom to which they are attached, form the structure:

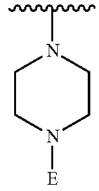
,
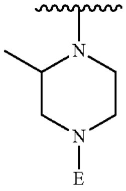
,
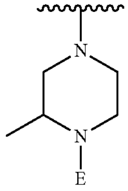
,

-continued

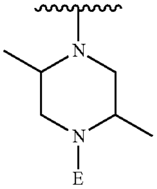
,
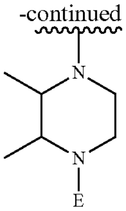
,
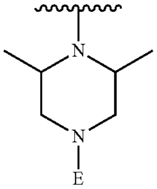
,

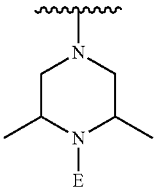
,
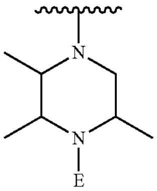
,
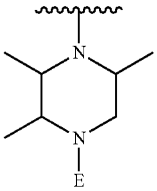
, or
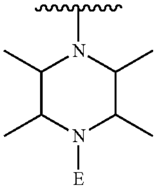
.

In some embodiments, $R^2$ and $R^3$, together with the atom to which they are attached, form a bridged piperazinyl ring that is substituted with one or more E and 0-4 $R^{11}$. In some embodiments, $R^2$ and $R^3$, together with the atom to which they are attached, form the structure:

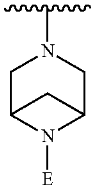
or
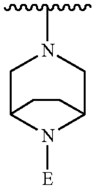
.

In some embodiments, $R^2$ and $R^3$, together with the atom to which they are attached, form a 4-8 membered bicyclic heterocycle comprising a fused ring system that is substituted with one or more E and 0-4 $R^{11}$. In some embodiments, $R^2$ and $R^3$, together with the atom to which they are attached, form a structure selected from:

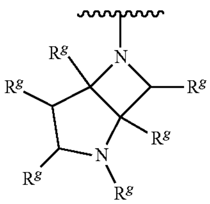
and
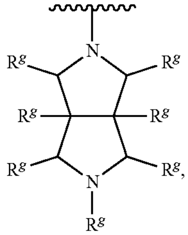

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a structure selected from:

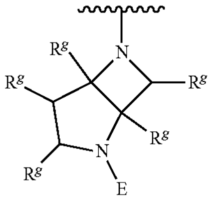

and

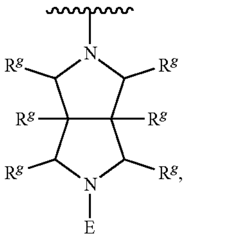

wherein each $R^g$ is independently selected from $C_{1-6}$alkyl and H, wherein any $C_{1-6}$alkyl is unsubstituted or substituted with one or more $R^{20}$. In some embodiments, $R^2$ and $R^3$, together with the atom to which they are attached, form the structure:

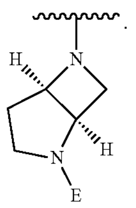

In some embodiments, each $R^g$ is H.

In some embodiments, $R^5$ is H. In some embodiments, $R^5$ is a halogen. In some embodiments, $R^5$ is Cl. In some embodiments, $R^5$ is F.

In some embodiments, $R^7$ is a halogen. In some embodiments, $R^7$ is F. In some embodiments, $R^7$ is Cl.

In some embodiments, $R^7$ is —$OR^{12}$, such as —OH. In some embodiments, $R^7$ is —$OR^{12}$, wherein $R^{12}$ is $C_{1-6}$ alkyl.

In some embodiments, $R^7$ is —CN.

In some embodiments, $R^7$ is H.

In some embodiments, X is N and Y is O. In some embodiments, X is N and Y is S.

In some embodiments, X is C—CN and Y is O. In some embodiments, X is C—CN and Y is S.

In some embodiments, X is N.

In some embodiments, Y is S.

In some embodiments, $R^{23}$ is selected from —$N(R^{12})_2$. In some embodiments, $R^{23}$ is —$NH_2$.

In some embodiments, $R^{24}$ is a halogen. In some embodiments, $R^{24}$ is F.

In some embodiments, $R^{25}$ and $R^{26}$ are H.

In some embodiments, each E is independently selected from:

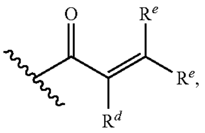

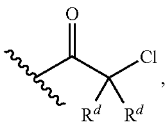

, and

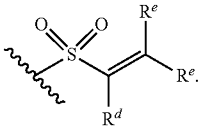

In some embodiments, each E is:

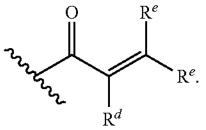

In some embodiments, each $R^d$ and $R^e$ is H. In some embodiments, the compound includes a single E.

In some embodiments, $R^4$ is —$OCH_3$ and $R^1$ is H.

In some embodiments, $R^4$ is —$OCH_3$, $R^1$ is H, $R^5$ is H, and $R^7$ is a halogen. In some embodiments, $R^7$ is F.

In a further aspect, the present disclosure provides a compound according to Formula IID:

(IID)

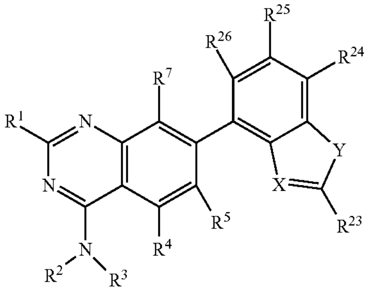

or a salt (e.g., pharmaceutically acceptable salt), ester, tautomer, prodrug, zwitterionic form, or stereoisomer thereof, wherein:

$R^1$ is selected from —$OR^8$,

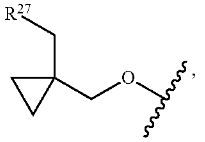

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from —CN, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, —$N(R^2)C(O)(C_{1-6}alkyl)$, —$OR^{12}$, and $C_{1-6}alkyl\text{-}N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$;

each E is independently selected from

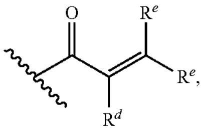

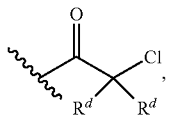

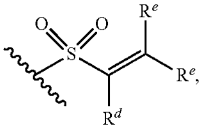

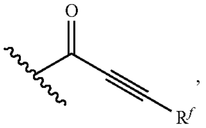

-continued

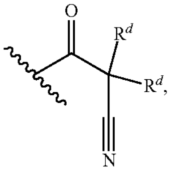

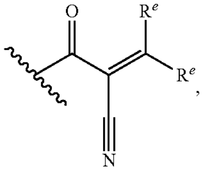

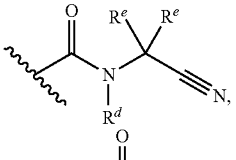

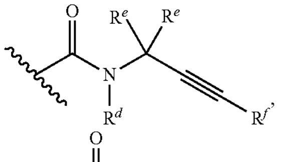

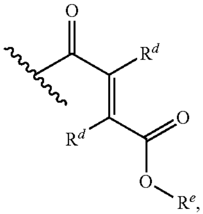

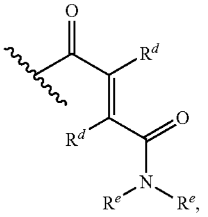

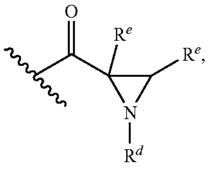

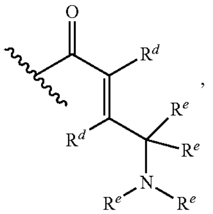

and —CN;

each $R^d$ and $R^e$ is independently selected from halogen, $C_{1-6}$ alkyl, and H; and each $R^f$ is independently selected from $C_{1-6}$ alkyl and H.

In some embodiments, the present disclosure provides a compound of Formula IID, or a salt (e.g., a pharmaceutically acceptable salt) thereof.

In some embodiments, $R^5$ is —CN.

In some embodiments, $R^5$ is selected from $C_{1-6}$alkyl that is unsubstituted or is substituted with one or more $R^{13}$. In some embodiments, $R^5$ is selected from $C_{1-6}$alkyl that is unsubstituted, such as methyl or ethyl. In some embodiments, $R^5$ is selected from $C_{1-6}$alkyl that is substituted with one or more halogens or —CN. In some embodiments, $R^5$ is selected from $C_{1-6}$alkyl that is substituted with —CN. In some embodiments, $R^5$ is selected from $C_{1-6}$alkyl that is substituted with one or more halogens, such as one or more fluorines. In some embodiments, $R^5$ is selected from —$CF_3$ and —$CF_2H$. In some embodiments, $R^5$ is selected from —$CF_3$, —$CF_2H$, and —$CH_2CN$. In some embodiments, $R^5$ is selected from —$CH_3$, —$CH_2CH_3$, —$CF_2H$, —$CF_3$, —$CF_2CH_3$, and —$CH_2CN$. In some embodiments, $R^5$ is $C_{1-6}$alkyl that is substituted with one or more $R^{13}$, wherein each $R^{13}$ is independently selected from —$OR^{22}$, —CN, and —$N(R^{22})_2$. In some embodiments, $R^5$ is —$CH_2CN$.

In some embodiments, $R^5$ is selected from —$OR^{12}$, wherein $R^{12}$ is selected from $C_{1-6}$alkyl that is unsubstituted or is substituted with one or more halogens. In some embodiments, $R^5$ is selected from —$OCF_3$ and —$OCH_3$.

In some embodiments, $R^5$ is selected from a 3-6 membered carbocycle that is unsubstituted or substituted with one or more $R^{14}$. In some embodiments, $R^5$ is selected from a cyclopropyl and cyclobutyl that is unsubstituted or substituted with one or more $R^{14}$. In some embodiments, $R^5$ is a phenyl that is unsubstituted or substituted with one or more $R^{14}$. In some embodiments, $R^5$ is phenyl.

In some embodiments, $R^5$ is selected from a 3-6 membered heterocycle and 5-6 membered heteroaryl, wherein the heterocycle or heteroaryl is unsubstituted or substituted with one or more $R^{14}$. In some embodiments, $R^5$ is selected from a 3-6 membered heterocycle that is unsubstituted or substituted with one or more $R^{14}$. In some embodiments, $R^5$ is selected from a 5-6 membered heteroaryl that is unsubstituted or substituted with one or more $R^{14}$. In some embodiments, $R^5$ is selected from a 5-6 membered heterocycle or 5-6 membered heteroaryl that includes one or two heteroatoms selected from O and N and is unsubstituted or substituted with one or more $R^{14}$. In some embodiments, $R^5$ is selected from a 5-6 membered heterocycle that includes one or two heteroatoms selected from O and N and is unsubstituted or substituted with one or more $R^{14}$. In some embodiments, $R^5$ is selected from furanyl, pyridinyl, and pyrazolyl that is unsubstituted or is substituted with one or more $R^{14}$. In some embodiments, $R^5$ is selected from:

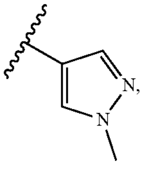,
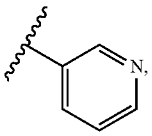, and
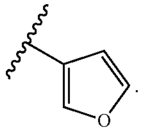.

In some embodiments, $R^5$ is:

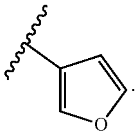.

In some embodiments, $R^1$ is H.

In some embodiments, $R^1$ is —OR. In some embodiments, $R^8$ is a heterocycle that is unsubstituted or substituted with one or more $R^a$ and/or R. In some embodiments, $R^8$ is an alkylheterocycle that is unsubstituted or substituted with one or more $R^a$ and/or $R^b$. In some embodiments, $R^8$ is —$CH_2$(heterocycle), where the heterocycle is unsubstituted or substituted with one or more $R^a$ and/or $R^b$. In some embodiments, a heterocycle or a heterocycle of an alkylheterocycle is a 4-6 membered monocyclic heterocycle having 1-2 heteroatoms independently selected from N, O, and S. In some embodiments, a heterocycle or a heterocycle of an alkylheterocycle is an 8-membered bicyclic heterocycle having 1-2 heteroatoms independently selected from N, O, and S. In some embodiments, a heterocycle or a heterocycle of an alkylheterocycle is substituted with one or more $R^a$ and/or $R^b$, wherein the one or more $R^a$ and/or $R^b$ is a halogen (e.g., F). In some embodiments, a heterocycle or a heterocycle of an alkylheterocycle is substituted with one or more $R^a$ and/or $R^b$, wherein the one or more $R^a$ and/or $R^b$ is a $C_{1-6}$alkyl (e.g., methyl). In some embodiments, a heterocycle or a heterocycle of an alkylheterocycle is substituted with one or more $R^a$ and/or $R^b$, wherein the one or more $R^a$ and/or $R^b$ is a —$OR^{12}$ (e.g., —$OCH_3$).

In some embodiments, $R^1$ is selected from:

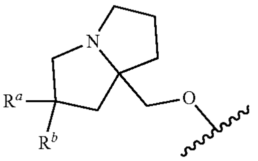

wherein $R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$. In some embodiments, $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$. In some embodiments, $R^a$ is a halogen. In some embodiments, $R^a$ is F. In some embodiments, $R^a$ is $C_{1-6}$alkyl that is unsubstituted or is substituted with one or more $R^{13}$. In some embodiments, $R^a$ is methyl. In some embodiments, $R^a$ is —$OC_{1-6}$alkyl. In some embodiments, $R^a$ is H. In some embodiments, $R^b$ is H. In some embodiments, $R^b$ is a halogen. In some embodiments, $R^b$ is F. In some embodiments, $R^b$ is $C_{1-6}$alkyl that is unsubstituted or is substituted with one or more $R^{13}$. In some embodiments, $R^b$ is methyl. In some embodiments, each of $R^a$ and $R^b$ is F. In some embodiments, each of $R^a$ and $R^b$ is methyl. In some embodiments, $R^b$ is methyl. In some embodiments, $R^1$ is selected from:

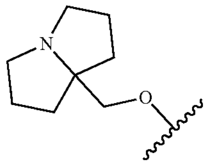,
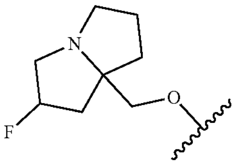,
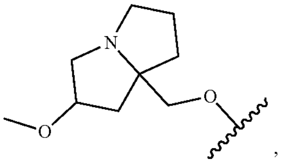,
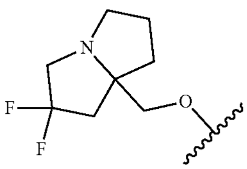, and
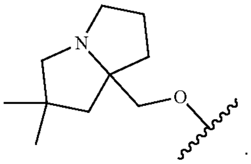.

In some embodiments, $R^1$ is selected from:

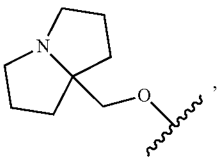,
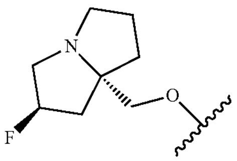,
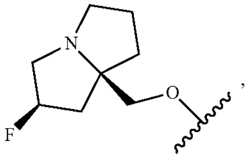,
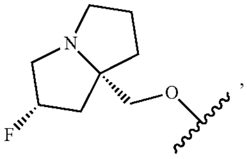,

-continued

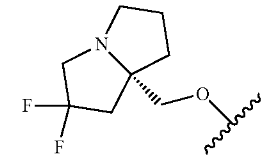,
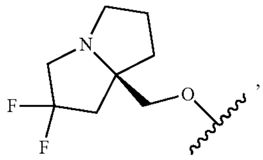,
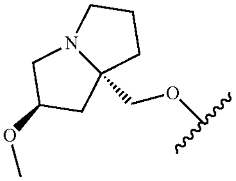,
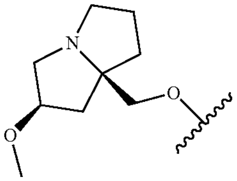,
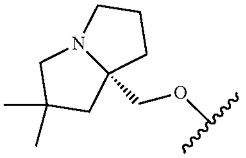, and
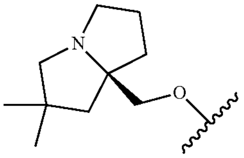.

In some embodiments, wherein $R^1$ is:

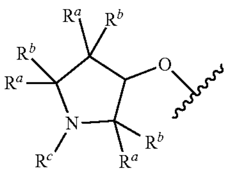,
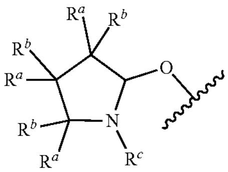,
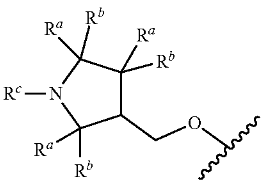, and
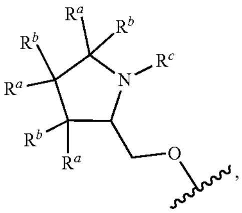, wherein each $R^a$ and $R^b$ is independently selected from halogen, $C_{1-6}$ alkyl, —$OR^{12}$, and H; and $R^c$ is selected from $C_{1-6}$ alkyl, wherein the $C_{1-6}$ alkyl is unsubstituted or is substituted with one or more $R^{13}$. In some embodiments, one $R^a$ or $R^b$ is selected from halogen, $C_{1-6}$ alkyl, and —$OR^{12}$, and the other $R^a$ and $R^b$ groups are H. In some embodiments, one $R^a$ or $R^b$ is halogen (e.g., F). In some embodiments, two $R^a$groups, two $R^b$ groups, or an $R^a$ and an $R^b$ are halogen (e.g., F). In some embodiments, one $R^a$ or $R^b$ is —$OR^{12}$ (e.g., —$OCH_3$ or —$CHF_2$). In some embodiments, one $R^a$ or $R^b$ is $C_{1-6}$alkyl (e.g., methyl). In some embodiments, two $R^a$ groups, two $R^b$ groups, or an $R^a$ and an $R^b$ are $C_{1-6}$ alkyl (e.g., methyl). In some embodiments, $R^c$ is selected from —$CH_3$, —$CH_2CH_2F$, —$CH_2CHF_2$, and —$CH_2CH_2CN$. In some embodiments, $R^1$ is selected from:

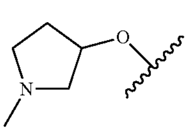,
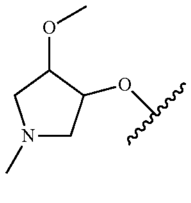,

-continued

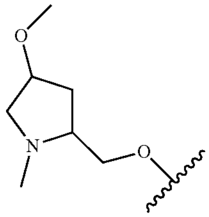,
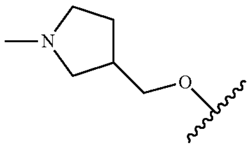,
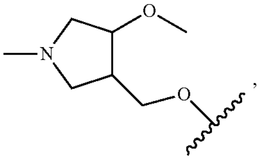,
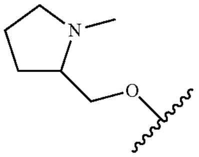,
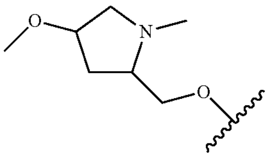,
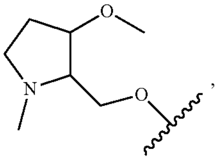,
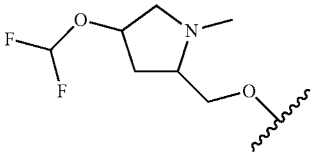,
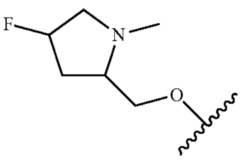,
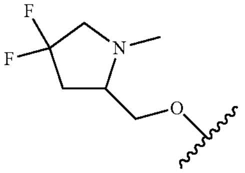,
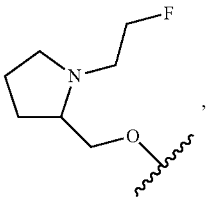,
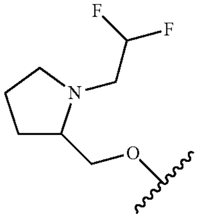,
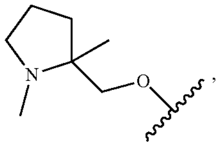,
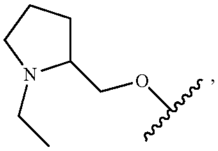,
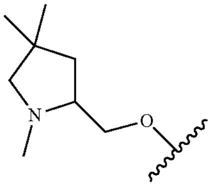,
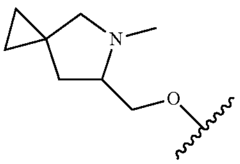, and
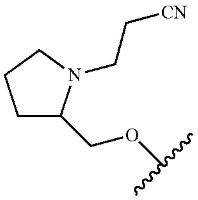.

In some embodiments, $R^1$ is selected from:

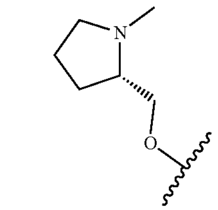,

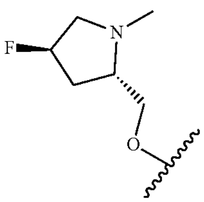,

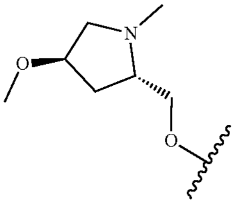, and

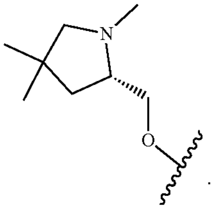.

In some embodiments, $R^1$ is selected from:

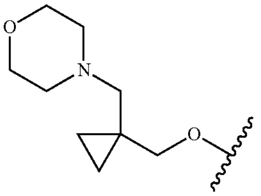 and

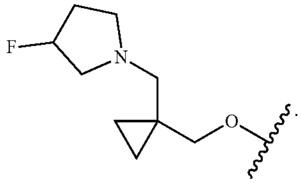.

In some embodiments, $R^1$ is a 4-6 membered heterocycle comprising a nitrogen atom, wherein the heterocycle is unsubstituted or substituted with one or more $R^{16}$. In some embodiments, $R^1$ is:

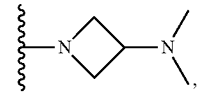,

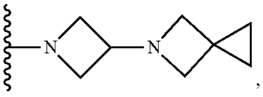,

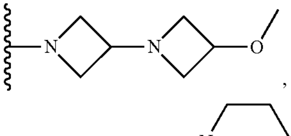,

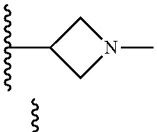, and

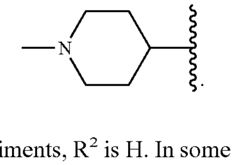.

In some embodiments, $R^2$ is H. In some embodiments, $R^2$ is selected from $C_{1-6}$ alkyl and a 3-6 membered carbocycle. In some embodiments, $R^2$ is $C_{1-6}$ alkyl. In some embodiments, $R^2$ is selected from $C_{1-2}$ alkyl. In some embodiments $R^2$ is selected from $—CH_3$, $—CH_2CH_3$, and $—CH(CH_3)_2$. In some embodiments, $R^2$ is a 3-6 membered carbocycle. In some embodiments, $R^2$ is cyclopropyl.

In some embodiments, $R^3$ is selected from $C_{1-6}$ alkyl that is substituted with $—N(R^{12})(E)$. In some embodiments, $R^3$ is selected from $C_2$ alkyl that is substituted with $—N(R^{12})(E)$. In some embodiments, $R^3$ is selected from $C_2$ alkyl that is substituted with —N(H)(E).

In some embodiments, $R^3$ is a 4-6 membered heterocycle that is substituted with one or more E and 0-4 $R^{10}$. In some embodiments, $R^3$ is a 4-6 membered heterocycle that is substituted with one or more E and 0-4 $R^{10}$, wherein the heterocycle includes one or more heteroatoms selected from N, O, and S. In some embodiments, $R^3$ is a 4-6 membered heterocycle that is substituted with one or more E and 0-4 $R^{10}$, wherein the heterocycle includes a single heteroatom that is N. In some embodiments, $R^3$ is an azetidine, pyrrolidine, or piperidine, wherein the azetidine, pyrrolidine, or piperidine is substituted with one or more E and 0-4 $R^{10}$. In some embodiments, $R^3$ is a pyrrolidine substituted with one or more E and 0-4 $R^{10}$. In some embodiments, $R^3$ is selected from:

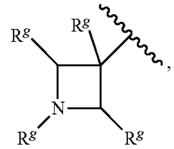,

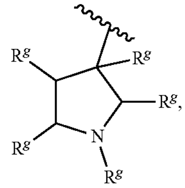,

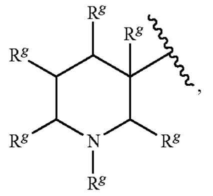, and

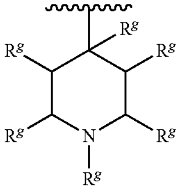, wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$. In some embodiments, each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^3$ is selected from:

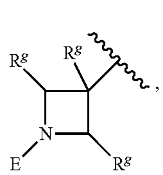,

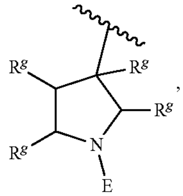,

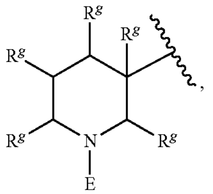, and

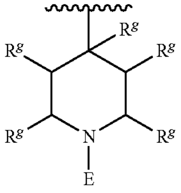, wherein each $R^g$ is independently selected from $C_{1-6}$alkyl, halogen, and H, wherein any $C_{1-6}$alkyl is unsubstituted or substituted with one or more $R^{20}$. In some embodiments, each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, at least one $R^g$ is a halogen. In some embodiments, at least one $R^g$ is F. In some embodiments, at least one $R^g$ is $C_{1-6}$alkyl that is unsubstituted or substituted with one or more $R^{20}$. In some embodiments, at least one $R^g$ is $C_{1-6}$alkyl (e.g., methyl).

In some embodiments, $R^2$ and $R^3$, together with the atom to which they are attached, form a 4-8 membered heterocycle that is substituted with one or more E and 0-4 $R^{11}$. In some embodiments, $R^2$ and $R^3$, together with the atom to which they are attached, form a piperazinyl ring that is substituted with one or more E and 0-4 $R^{11}$. In some embodiments, $R^2$ and $R^3$, together with the atom to which they are attached, form the structure:

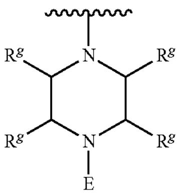
or
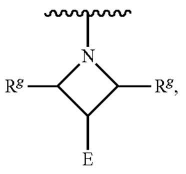

wherein each $R^g$ is independently selected from $C_{1-6}$alkyl and H, wherein any $C_{1-6}$alkyl is unsubstituted or substituted with one or more $R^{20}$. In some embodiments, each $R^g$ is H. In some embodiments, one or two $R^g$ groups are $C_{1-6}$alkyl (e.g., methyl). In some embodiments, $R^2$ and $R^3$, together with the atom to which they are attached, form the structure:

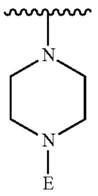
,
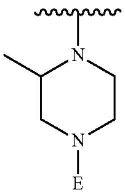
,
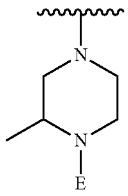
,
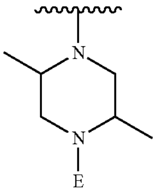
,
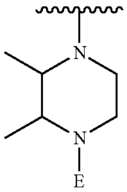
,
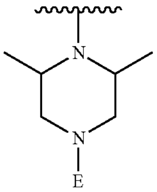
,
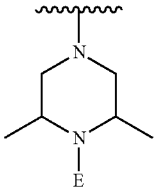
,
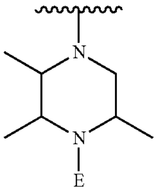
,
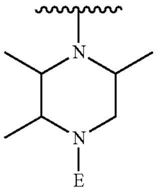
, or
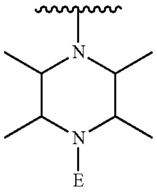
.

In some embodiments, $R^2$ and $R^3$, together with the atom to which they are attached, form a bridged piperazinyl ring that is substituted with one or more E and 0-4 $R^{11}$. In some embodiments, $R^2$ and $R^3$, together with the atom to which they are attached, form the structure:

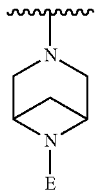
or
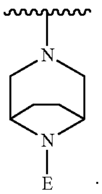
.

In some embodiments, $R^2$ and $R^3$, together with the atom to which they are attached, form a 4-8 membered bicyclic heterocycle comprising a fused ring system that is substituted with one or more E and 0-4 $R^{11}$. In some embodiments, $R^2$ and $R^3$, together with the atom to which they are attached, form a structure selected from:

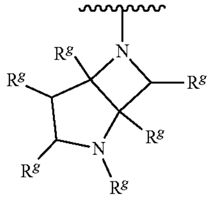
and
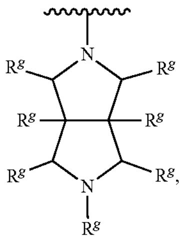

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$. In some embodiments, $R^2$ and $R^3$, together with the atom to which they are attached, form a structure selected from:

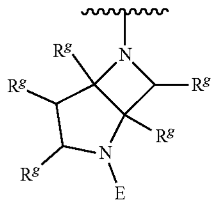
and
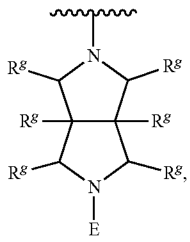

wherein each $R^g$ is independently selected from $C_{1-6}$alkyl and H, wherein any $C_{1-6}$alkyl is unsubstituted or substituted with one or more $R^{20}$. In some embodiments, $R^2$ and $R^3$, together with the atom to which they are attached, form the structure:

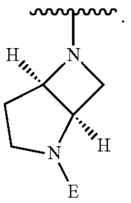

In some embodiments, each $R^g$ is H.

In some embodiments, $R^4$ is H.

In some embodiments, $R^5$ is selected from $C_{1-6}$alkyl that is unsubstituted or substituted with one or more $R^{13}$. In some embodiments, $R^5$ is selected from $C_{1-2}$alkyl that is unsubstituted or substituted with one or more $R^{13}$. In some embodiments, $R^5$ is selected from —$CF_2H$, —$CF_3$, —$CH_2CN$, and —$CH_2CH_3$.

In some embodiments, $R^5$ is selected from —$OR^{12}$. In some embodiments, $R^5$ is —$OCF_3$ or —$OCH_3$.

In some embodiments, $R^5$ is selected from a 3-6 membered carbocycle that is unsubstituted or substituted with one or more $R^{14}$. In some embodiments, $R^5$ is selected from a cyclobutyl that is unsubstituted or substituted with one or more $R^{14}$. In some embodiments, $R^5$ is selected from a phenyl that is unsubstituted or substituted with one or more $R^{14}$.

In some embodiments, $R^5$ is selected from a 3-6 membered heterocycle that is unsubstituted or substituted with one or more $R^{14}$. In some embodiments, $R^5$ is selected from a 5-6 membered heterocycle that includes one or two heteroatoms selected from O and N is unsubstituted or substituted with one or more $R^{14}$. In some embodiments, $R^5$ is selected from a 5-6 membered heteroaryl that is unsubstituted or substituted with one or more $R^{14}$. In some embodiments, $R^5$ is selected from furanyl, pyridinyl, and pyrazolyl that is unsubstituted or is substituted with one or more $R^{14}$. In some embodiments, $R^5$ is selected from:

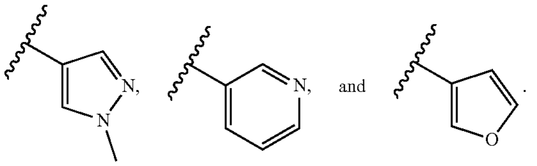

In some embodiments, $R^7$ is a halogen. In some embodiments, $R^7$ is F. In some embodiments, $R^7$ is Cl.

In some embodiments, $R^7$ is —$OR^{12}$, such as —OH. In some embodiments, $R^7$ is —$OR^{12}$, wherein $R^{12}$ is $C_{1-6}$ alkyl.

In some embodiments, $R^7$ is —CN.

In some embodiments, $R^7$ is H.

In some embodiments, X is N and Y is O. In some embodiments, X is N and Y is S.

In some embodiments, X is C—CN and Y is O. In some embodiments, X is C—CN and Y is S.

In some embodiments, X is N.

In some embodiments, Y is S.

In some embodiments, $R^{23}$ is selected from —$N(R^{12})_2$. In some embodiments, $R^{23}$ is —$NH_2$.

In some embodiments, $R^{24}$ is a halogen. In some embodiments, $R^{24}$ is F.

In some embodiments, $R^{25}$ and $R^{26}$ are H.

In some embodiments, each E is independently selected from:

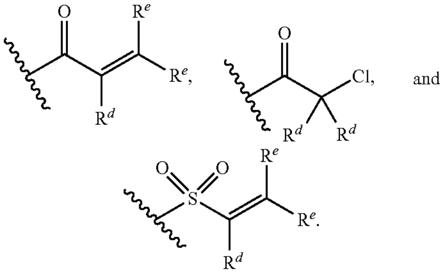

In some embodiments, each E is:

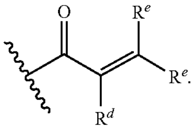

In some embodiments, each $R^d$ and $R^e$ is H. In some embodiments, the compound includes a single E.

In some embodiments, $R^4$ is H and $R^7$ is a halogen. In some embodiments, $R^7$ is F.

In some embodiments, $R^4$ is H, $R^7$ is a halogen, and $R^1$ is H. In some embodiments, $R^7$ is F.

In some embodiments, $R^4$ is H and $R^7$ is a halogen, and $R^5$ is selected from $C_{1-6}$alkyl that is unsubstituted or substituted with one or more $R^{13}$. In some embodiments, $R^5$ is selected from $C_{1-2}$alkyl that is unsubstituted or substituted with one or more $R^{13}$. In some embodiments, $R^5$ is selected from —$CF_2H$, —$CF_3$, —$CH_2CN$, and —$CH_2CH_3$. In some embodiments, $R^7$ is F.

In some embodiments, $R^4$ is H and $R^7$ is a halogen, and $R^5$ is selected from —$OR^{12}$. In some embodiments, $R^5$ is —$OCF_3$ or —$OCH_3$. In some embodiments, $R^7$ is F.

In some embodiments, $R^4$ is H and $R^7$ is a halogen, and $R^5$ is selected from a 3-6 membered carbocycle that is unsubstituted or substituted with one or more $R^{14}$. In some embodiments, $R^5$ is selected from a cyclobutyl that is unsubstituted or substituted with one or more $R^{14}$. In some embodiments, $R^5$ is selected from a phenyl that is unsubstituted or substituted with one or more $R^{14}$. In some embodiments, $R^7$ is F.

In some embodiments, $R^4$ is H and $R^7$ is a halogen, and $R^5$ is selected from a 3-6 membered heterocycle that is unsubstituted or substituted with one or more $R^{14}$. In some embodiments, $R^7$ is F. In some embodiments, $R^5$ is selected from a 5-6 membered heterocycle that includes one or two heteroatoms selected from O and N is unsubstituted or substituted with one or more $R^{14}$. In some embodiments, $R^5$ is selected from a 5-6 membered heteroaryl that is unsubstituted or substituted with one or more $R^{14}$. In some embodiments, $R^5$ is selected from furanyl, pyridinyl, and pyrazolyl that is unsubstituted or is substituted with one or more $R^{14}$. In some embodiments, $R^5$ is selected from:

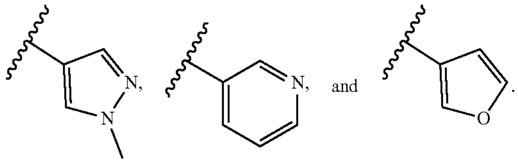

Also provided herein are embodiments wherein any embodiment described herein may be combined with any one or more of these embodiments, provided the combination is not mutually exclusive. As used herein, two embodiments are "mutually exclusive" when one is defined to be something which is different than the other. For example, an embodiment wherein two groups combine to form a ring is mutually exclusive with an embodiment in which one group is ethyl and the other group is hydrogen. Similarly, an embodiment wherein one group is $CH_2$ is mutually exclusive with an embodiment wherein the same group is NH.

In some embodiments of any of the preceding aspects, the compound is a compound included in Table 2, 3, 4, or 5 or a salt, ester, tautomer, prodrug, zwitterionic form, or stereoisomer thereof. In some embodiments, the compound is a compound included in Table 2, or a salt, ester, tautomer, prodrug, zwitterionic form, or stereoisomer thereof. In some embodiments, the compound is a compound included in Table 3, or a salt, ester, tautomer, prodrug, zwitterionic form, or stereoisomer thereof. In some embodiments, the compound is a compound included in Table 4, or a salt, ester, tautomer, prodrug, zwitterionic form, or stereoisomer thereof. In some embodiments, the compound is a compound included in Table 5, or a salt, ester, tautomer, prodrug, zwitterionic form, or stereoisomer thereof.

Also provided herein is a compound selected from Table 2, 3, 4, or 5 or any of the Examples provided herein, or a salt, ester, tautomer, prodrug, zwitterionic form, or stereoisomer thereof. In some embodiments, the present disclosure provides a compound selected from Table 2, 3, 4, or 5 or any of the Examples provided herein, or a salt thereof.

In some embodiments of any of the preceding aspects, a compound provided herein, or a salt, ester, tautomer, zwitterionic form, or stereoisomer thereof, includes an electrophilic moiety E, as provided herein. In some embodiments of any of the preceding aspects, a compound includes multiple electrophilic moieties. In some embodiments of any of the preceding aspects, a compound provided herein, or a salt, ester, tautomer, zwitterionic form, or stereoisomer thereof, is capable of interacting covalently with a cysteine (C) at the 12 position of the KRAS protein (e.g., a G12C mutation) (e.g., via an electrophilic moiety E). In some embodiments of any of the preceding aspects, a compound provided herein, or a salt, ester, tautomer, zwitterionic form, or stereoisomer thereof, is capable of reversibly interacting with a cysteine (C) at the 12 position of the KRAS protein (e.g., a G12C mutation) (e.g., via an electrophilic moiety E). In some embodiments of any of the preceding aspects, a compound provided herein, or a salt, ester, tautomer, zwitterionic form, or stereoisomer thereof, is capable of irreversibly interacting with a cysteine (C) at the 12 position of the KRAS protein (e.g., a G12C mutation) (e.g., via an electrophilic moiety E). In some embodiments of any of the preceding aspects, a compound provided herein, or a salt, ester, tautomer, zwitterionic form, or stereoisomer thereof, binds selectively to KRAS having a G12C mutation relative to KRAS having other residues at the 12 position of the P loop, such as glycine (G), valine (V), serine (S), alanine (A), and aspartic acid (D). For example, in some embodiments, a compound provided herein, or a salt, ester, tautomer, zwitterionic form, or stereoisomer thereof, demonstrates at least 1.5, 2, 3, 4, 5, 10, 20, 30, 40, 50, 60, 70, 80, 90, 100-fold, or greater selectivity for KRAS having a G12C mutation relative to KRAS having other residues at the 12 position of the P loop, such as glycine (G), valine (V), serine (S), alanine (A), and aspartic acid (D). In some embodiments of any of the preceding aspects, a compound provided herein, or a salt, ester, tautomer, zwitterionic form, or stereoisomer thereof, binds selectively to KRAS having a G12C mutation relative to wildtype KRAS. For example, in some embodiments, a compound provided herein, or a salt, ester, tautomer, zwitterionic form, or stereoisomer thereof, demonstrates at least 1.5, 2, 3, 4, 5, 10, 20, 30, 40, 50, 60, 70, 80, 90, 100-fold, or greater binding selectivity for KRAS having a G12C mutation relative to wildtype KRAS. In some embodiments of any of the preceding aspects, a compound provided herein, or a salt, ester, tautomer, zwitterionic form, or stereoisomer thereof, binds selectively to KRAS having a G12C mutation relative to other forms of RAS (e.g., HRAS and NRAS). For example, in some embodiments, a compound provided herein, or a salt, ester, tautomer, zwitterionic form, or stereoisomer thereof, demonstrates at least 1.5, 2, 3, 4, 5, 10, 20, 30, 40, 50, 60, 70, 80, 90, 100-fold, or greater binding selectivity for KRAS having a G12C mutation relative to another form of RAS (e.g., HRAS or NRAS), such as an HRAS or NRAS protein having a G12C mutation. In some embodiments of any of the preceding aspects, a compound provided herein, or a salt, ester, tautomer, zwitterionic form, or stereoisomer thereof, is capable of binding to a KRAS protein having a G12C mutation and one or more additional mutations, such as a mutation at codon 13 (to, e.g., D or C) or codon 61.

In some embodiments of any of the preceding aspects, a compound provided herein, or a salt, ester, tautomer, zwitterionic form, or stereoisomer thereof, is capable of selectively binding a KRAS protein in an active (GTP-bound) conformation. In some embodiments of any of the preceding aspects, a compound provided herein, or a salt, ester, tautomer, zwitterionic form, or stereoisomer thereof, is capable of selectively binding a KRAS protein in an inactive (GDP-bound) conformation. In some embodiments of any of the preceding aspects, a compound provided herein, or a salt, ester, tautomer, zwitterionic form, or stereoisomer thereof, is capable of selectively binding a KRAS protein in both active (GTP-bound) and inactive (GDP-bound) conformations. In some embodiments of any of the preceding aspects, a compound provided herein, or a salt, ester, tautomer, zwitterionic form, or stereoisomer thereof, has higher selectivity for a KRAS protein in its active (GTP-bound) conformation than in its inactive (GDP-bound) conformation. In some embodiments of any of the preceding aspects, a compound provided herein, or a salt, ester, tautomer, zwitterionic form, or stereoisomer thereof, has higher selectivity for a KRAS protein in its inactive (GDP-bound) conformation than in its active (GTP-bound) conformation.

Compositions

The present disclosure also provides a composition (e.g., a pharmaceutical composition) comprising a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof. In some embodiments, a provided composition comprises a compound provided herein, or a pharmaceutically acceptable salt thereof. For example, the present disclosure provides a pharmaceutical composition comprising a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, together with a pharmaceutically acceptable carrier. In some embodiments, a provided pharmaceutical composition comprises a compound provided herein or a pharmaceutically acceptable salt thereof, together with a pharmaceutically acceptable carrier.

In some embodiments, the pharmaceutical composition is formulated for oral administration. In some embodiments, the oral pharmaceutical formulation is selected from a tablet and a capsule.

In some embodiments, the pharmaceutical composition is formulated for parenteral administration. In some embodiments, the pharmaceutical composition is formulated for intravenous administration. In some embodiments, the pharmaceutical composition is formulated for subcutaneous administration.

While it may be possible for certain compounds provided herein (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID), or a salt, ester, tautomer, prodrug, zwitterionic form, or stereoisomer thereof, to be administered as the raw chemical, compounds may additionally or alternatively be provided in a pharmaceutical formulation. Accordingly, provided herein are pharmaceutical formulations which comprise one or more compounds disclosed herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration selected. Any of the well-known techniques, carriers, and excipients may be used as suitable and as understood in the art. The pharmaceutical compositions disclosed herein may be manufactured in any suitable manner known, e.g., by means of conventional mixing, dissolving, granulating, dragee-making, levigating, emulsifying, encapsulating, entrapping or compression processes.

A pharmaceutical formulation provided herein can be suitable for oral, parenteral (including subcutaneous, intradermal, intramuscular, intravenous, intraarticular, and intramedullary), intraperitoneal, transmucosal, transdermal, rectal, and topical (including dermal, buccal, sublingual, and intraocular) administration. The most suitable route may depend on, for example, the condition and disorder of the subject to which the pharmaceutical formulation will be administered. A pharmaceutical formulation can be provided in a unit dosage form. A pharmaceutical formulation can be prepared by any suitable method. A method of preparing a pharmaceutical formulation may comprise bringing a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a pharmaceutically acceptable salt, ester, amide, prodrug or solvate thereof ("active ingredient") in contact with one or more pharmaceutically acceptable carriers (e.g., accessory ingredients). In general, the formulations are prepared by uniformly and intimately bringing into association the active ingredient with liquid carriers or finely divided solid carriers or both and then, if necessary, shaping the product into the desired formulation.

Pharmaceutical formulations of compounds provided herein (e.g., compounds of any one of Formulas IA, IA1, IA2, IB, IC, IC1, IC2, IC3, IC4, IC5, IC6, ID, ID1, IE, II, IA, IIA1, IIA2, IIB, IIC, and IID in any available form (e.g., salt, ester, tautomer, prodrug, zwitterionic form, stereoisomer etc.)) may be provided as discrete units. For example, a formulation suitable for oral administration may be provided as capsules, cachets, and/or tablets containing a predetermined amount of the compound in any suitable form (e.g., the active ingredient); as a solution or suspension in a solvent (e.g., aqueous or non-aqueous solvent); as an emulsion (e.g., an oil-in-water liquid emulsion or water-in-oil liquid emulsion); or as a powder or granules. The active ingredient may additionally or alternatively be provided as a bolus, electuary, or paste.

Pharmaceutical preparations suitable for oral administration include tablets, push-fit capsules made of gelatin, as well as soft, sealed capsules made of gelatin and a plasticizer, such as glycerol or sorbitol. Tablets may be made by, for example, compression or molding, optionally with one or more accessory ingredients, such as one or more pharmaceutically acceptable excipients. Compressed tablets may be prepared by, for example, compressing in a suitable machine the active ingredient in a free-flowing form such as a powder or granules, optionally mixed with binders, inert diluents, or lubricating, surface active or dispersing agents. Molded tablets may be made by, for example, molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration. The push-fit capsules can contain the active ingredients in admixture with, for example, one or more fillers such as lactose, one or more binders such as one or more starches, and/or one or more lubricants such as talc or magnesium stearate and, optionally, one or more stabilizers. In soft capsules, the active compounds may be dissolved or suspended in suitable liquids, such as fatty oils, liquid paraffin, or liquid polyethylene glycols. Stabilizers and other elements may also be added. Dragee cores are provided with suitable coatings. For this purpose, concentrated sugar solutions may be used, which may optionally contain a gum, gelling agent, polymer, solvent, or combination thereof. Dyestuffs or pigments may be added to the tablets or dragee coatings for identification or to characterize different combinations of active compound doses.

A pharmaceutical composition comprising a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof (e.g., salt, ester, tautomer, prodrug, zwitterionic form, stereoisomer, etc.), may be formulated for parenteral administration by injection, e.g., by bolus injection or continuous infusion. Formulations for injection may be presented in unit dosage form, e.g., in ampoules, vials, or in multi-dose containers, with an added preservative. The compositions may take such forms as suspensions, solutions, or emulsions in oily or aqueous vehicles, and may contain formulating agents such as suspending, stabilizing, and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, prior (e.g., immediately prior) to use. Extemporaneous injection solutions and suspensions may be prepared from sterile powders, granules and tablets of the kind previously described.

A pharmaceutical composition comprising a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof (e.g., salt, ester, tautomer, prodrug, zwitterionic form, stereoisomer etc.), may be formulated as a solution for injection, which solution may be an aqueous or non-aqueous (oily) sterile solution and may comprise one or more antioxidants, thickening agents, suspending agents, buffers, solutes, and/or bacteriostats. The addition of one or more such additives may render the formulation isotonic with the blood of the intended recipient (e.g., subject or patient). Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described elsewhere herein, the compounds provided herein (e.g., compounds of any one of Formulas IA, IA1, IA2, IB, IC, IC1, IC2, IC3, IC4, IC5, IC6, ID, ID1, IE, II, IIA, IIA1, IIA2, IIB, IIC, and IID in any suitable form (e.g., salt, ester, tautomer, prodrug, zwitterionic form, stereoisomer, etc.)) may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical composition comprising a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID) or a form thereof (e.g., salt, ester, tautomer, prodrug, zwitterionic form, stereoisomer, etc.) that is suitable for buccal or sublingual administration may take the form of tablets, lozenges, pastilles, or gels. Such compositions may comprise the active ingredient in a flavored basis such as sucrose and acacia or tragacanth. A pharmaceutical composition comprising a compound provided herein or a form thereof (e.g., salt, ester, tautomer, prodrug, zwitterionic form, stereoisomer, etc.) that is suitable for rectal administration may be formulated as a suppository or retention enema and may comprise a medium such as, for example, cocoa butter, polyethylene glycol, or other glycerides.

Certain compounds provided herein (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID) or a form thereof (e.g., salt, ester, tautomer, prodrug, zwitterionic form, stereoisomer, etc.) may be formulated for non-systemic administration, such as topical administration. This includes the application of a compound disclosed herein, or a form thereof, externally to the epidermis or the buccal cavity and the instillation of such a compound, or a form thereof, into the ear, eye and nose, such that the compound, or a form thereof, does not significantly enter the blood stream. In contrast, systemic administration refers to oral, intravenous, intraperitoneal, and intramuscular administration.

Formulations suitable for topical administration include liquid or semi-liquid preparations suitable for penetration through the skin to the site of inflammation such as gels, liniments, lotions, creams, ointments, or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 50% w/w. In other embodiments, it may comprise from 0.1% to 1% w/w of the formulation.

For administration by inhalation, compounds (e.g., compounds of any one of Formulas IA, IA1, IA2, IB, IC, IC1, IC2, IC3, IC4, IC5, IC6, ID, ID1, IE, II, IIA, IIA1, IIA2, IIB, IIC, and IID) or forms thereof (e.g., salt, ester, tautomer, prodrug, zwitterionic form, stereoisomer, etc.) may be conveniently delivered from an insufflator, nebulizer pressurized packs, or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Alternatively, for administration by inhalation or insufflation, the compounds provided herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as described herein, or an appropriate fraction thereof, of the active ingredient (e.g., a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof).

It should be understood that in addition to the ingredients particularly described elsewhere herein, the formulations described herein may include other useful agents having regard to the type of formulation in question, for example those suitable for oral administration may include flavoring agents.

Compounds (e.g., compounds of any one of Formulas IA, IA1, IA2, IB, IC, IC1, IC2, IC3, IC4, IC5, IC6, ID, ID1, IE, II, IIA, IIA1, IIA2, IIB, IIC, and IID) or forms thereof (e.g., salt, ester, tautomer, prodrug, zwitterionic form, stereoisomer, etc.) may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

Methods

The present disclosure also provides a method of modulating KRAS (e.g., KRAS having a G12C mutation) comprising contacting KRAS with a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof. For example, the present disclosure may provide a method of altering a cell phenotype, cell proliferation, KRAS activity, biochemical output produced by active or inactive KRAS, expression of KRAS, and/or binding of KRAS with a natural binding partner. Any such feature may be monitored and may be altered upon contacting KRAS with a compound provided herein, or a form thereof. A method of modulating KRAS (e.g., KRAS having a G12C mutation) may be a mode of treatment of a disease, disorder, or condition (e.g., a cancer), a biological assay, a cellular assay, a biochemical assay, etc.

In some embodiments, a method of modulating KRAS (e.g., KRAS having a G12C mutation) comprises contacting a KRAS protein with a compound provided herein, or a salt, ester, tautomer, zwitterionic form, or stereoisomer thereof, where the KRAS protein is in the active (GTP-bound) conformation. In some embodiments, a method of modulating KRAS (e.g., KRAS having a G12C mutation) comprises contacting a KRAS protein with a compound provided herein, or a salt, ester, tautomer, zwitterionic form, or stereoisomer thereof, where the KRAS protein is in the inactive (GDP-bound) conformation. In some embodiments, contacting a KRAS protein with a compound provided herein, or a salt, ester, tautomer, zwitterionic form, or stereoisomer thereof, comprises incubating the KRAS protein with the compound or form thereof. In some embodiments, contacting a KRAS protein with a compound provided herein, or a salt, ester, tautomer, zwitterionic form, or stereoisomer thereof, comprises contacting a cell containing the KRAS protein with the compound or form thereof. In some embodiments, the cell is in a subject. In some embodiments, the subject is a human. In some embodiments, the subject is a human having a disease, disorder, or condition such as a cancer, such as a cancer characterized by a KRAS protein having a G12C mutation.

The present disclosure also provides methods of treating a disease, disorder, or condition in a subject in need thereof using a compound provided herein, (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID), or a salt, ester, tautomer, prodrug, zwitterionic form, or stereoisomer thereof. For example, the present disclosure provides a method comprising providing (e.g., administering) to a subject (e.g., patient) in need thereof an effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof. The present disclosure also provides methods of treating a disease, disorder, or condition in a subject in need thereof using a pharmaceutical composition comprising a compound provided herein, (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID), or a salt, ester, tautomer, prodrug, zwitterionic form, or stereoisomer thereof. For example, the present disclosure provides a method comprising providing (e.g., administering) to a subject (e.g., patient) in need thereof a pharmaceutical composition comprising an effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof. In some embodiments, the subject is known to have (e.g., has previously been diagnosed with) a disease, disorder, or condition such as a cancer. The disease, disorder, or condition may be a KRAS-mediated disease, such as a cancer characterized by a G12C mutation in KRAS. In some embodiments, the compound administered to the subject in need thereof according to the methods described herein is a compound described in an embodiment, example, figure, or table herein, or a stereoisomer or pharmaceutically acceptable salt thereof.

The present disclosure also provides a compound as provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, for use as a medicament, such as a medicament for the treatment of a disease, disorder, or condition (e.g., a cancer). The present disclosure also provides a compound as provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, for use in the manufacture of a medicament for the treatment of a disease, disorder, or condition (e.g., a cancer) in a subject in need thereof.

The present disclosure also provides the use of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, for the treatment of a disease, disorder, or condition (e.g., a cancer, as described herein, such as a cancer characterized by a KRAS protein having a G12C mutation) in a subject in need thereof.

The present disclosure also provides the use of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, in the manufacture of a medicament for treating a disease, disorder, or condition (e.g., a cancer, as described herein, such as a cancer characterized by a KRAS protein having a G12C mutation) in a subject in need thereof.

The present disclosure also provides a method of inhibiting KRAS (e.g., KRAS having a G12C mutation) (e.g., in a subject in need thereof) comprising contacting KRAS with a compound as provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient. In some embodiments, a method of inhibiting KRAS (e.g., KRAS having a G12C mutation) comprises contacting a KRAS protein with a compound provided herein, or a salt, ester, tautomer, zwitterionic form, or stereoisomer thereof, where the KRAS protein is in the active (GTP-bound) conformation. In some embodiments, a method of inhibiting KRAS (e.g., KRAS having a G12C mutation) comprises contacting a KRAS protein with a compound provided herein, or a salt, ester, tautomer, zwitterionic form, or stereoisomer thereof, where the KRAS protein is in the inactive (GDP-bound) conformation. In some embodiments, contacting a KRAS protein with a compound provided herein, or a salt, ester, tautomer, zwitterionic form, or stereoisomer thereof, comprises incubating the KRAS protein with the compound or form thereof. In some embodiments, contacting a KRAS protein with a compound provided herein, or a salt, ester, tautomer, zwitterionic form, or stereoisomer thereof, comprises contacting a cell containing the KRAS protein with the compound or form thereof. In some embodiments, the cell is in a subject. In some embodiments, the subject is a human. In some embodiments, the subject is a human having a disease, disorder, or condition such as a cancer, such as a cancer characterized by a KRAS protein having a G12C mutation.

The present disclosure also provides a compound as provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, for use in inhibiting KRAS (e.g., KRAS having a G12C mutation) (e.g., in a subject in need thereof). The present disclosure also provides a compound as provided herein (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, for use in the manufacture of a medicament for inhibiting KRAS (e.g., KRAS having a G12C mutation) in a subject in need thereof.

The present disclosure also provides the use of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, for inhibiting KRAS (e.g., KRAS having a G12C mutation) in a subject in need thereof.

The present disclosure also provides the use of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, or a pharmaceutical composition comprising any of the foregoing compounds and a pharmaceutically acceptable excipient, in the manufacture of a medicament for inhibiting KRAS (e.g., KRAS having a G12C mutation) in a subject in need thereof.

The present disclosure also provides a method comprising administering a therapeutically effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof to a subject (e.g., patient) (e.g., a subject in need thereof), thereby ameliorating, reducing, eliminating, ceasing, delaying the progression of, or improving one or more symptoms of the subject, such as one or more symptoms of a disease, disorder, or condition (e.g., a cancer). In some embodiments, the subject has a cancer characterized by a mutant KRAS (e.g., KRAS having a G12C mutation).

In some embodiments, administering a therapeutically effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, slows or prevents growth of a tumor. In some embodiments, administering a therapeutically effective amount of a compound provided herein (e.g., a compound of any one of Formulas IA, IA1, IA2, IB, IC, IC, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, results in shrinkage of a tumor (e.g., tumor regression). In some embodiments, administering a therapeutically effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, results in at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% regression of a tumor, such as for a period of one or more weeks (e.g., at least about 1, 2, 3, 4, 5, 6, 7, 8, 9, 10, 11, 12, or more weeks), a period of one or more months (e.g., at least about 1, 2, 3, 4, 5, 6, 7, 8, 9, 10, 11, 12, or more months), or a period of one or more years (e.g., at least about 1, 2, 3, or more years). In some embodiments, administering a therapeutically effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, stabilizes a tumor. In some embodiments, administering a therapeutically effective amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a salt, ester, tautomer, prodrug, zwitterionic form, or stereoisomer thereof, stabilizes a tumor for a period of one or more weeks (e.g., at least about 1, 2, 3, 4, 5, 6, 7, 8, 9, 10, 11, 12, or more weeks), a period of one or more months (e.g., at least about 1, 2, 3, 4, 5, 6, 7, 8, 9, 10, 11, 12, or more months), or a period of one or more years (e.g., at least about 1, 2, 3, or more years). In some embodiments, the subject has a cancer characterized by a mutant KRAS (e.g., KRAS having a G12C mutation).

In some embodiments of any of the methods, uses, and medicaments provided herein, the disease, disorder, or condition is a cancer. In some embodiments of any of the methods, uses, and medicaments provided herein, the cancer is pancreatic cancer (e.g., pancreatic ductal adenocarcinoma), lung cancer (e.g., non-small cell lung cancer), colorectal cancer (CRC), endometrial cancer, uterine carcinosarcoma, Ewing sarcoma, osteosarcoma, Rhabdomyosarcoma, adrenocortical carcinoma, neuroblastoma, Wilm tumor, retinoblastoma, skin cancer, breast cancer, prostate cancer, head and neck cancer, or ovarian cancer. In some embodiments, the cancer is pancreatic cancer (e.g., pancreatic ductal adenocarcinoma), lung cancer (e.g., non-small cell lung cancer adenocarcinoma), or colorectal cancer (CRC). In some embodiments, the cancer is pancreatic cancer (e.g., pancreatic ductal adenocarcinoma). In some embodiments, the cancer is lung cancer (e.g., non-small cell lung cancer adenocarcinoma). In some embodiments, the cancer is colorectal cancer (CRC). In some embodiments, the cancer is or comprises a solid tumor.

In some embodiments of any of the methods, uses, and medicaments provided herein, the disease, disorder, or condition is related to KRAS, such as a disorder associated with a mutation of KRAS or dysregulation of KRAS. In some embodiments, the disease, disorder, or condition is related to the KRAS gene, such as a disease, disorder, or condition associated with a mutation of the KRAS gene or dysregulation of the KRAS gene. Mutation or dysregulation of KRAS or KRAS may include mutation or dysregulation of human K-Ras4a and/or human K-Ras4b. In some embodiments, the disease, disorder, or condition is related to the KRAS (e.g., human K-Ras4a or K-Ras4b) signaling pathway activity, such as a disease, disorder, or condition related to aberrant KRAS signaling pathway activity. In some embodiments, the disease, disorder, or condition is related to mutation or dysregulation of human K-Ras4b. In some embodiments, the disease, disorder, or condition is related to aberrant K-Ras4b signaling pathway activity. In some embodiments, the disease, disorder, or condition is related to mutation or dysregulation of human K-Ras4a. In some embodiments, the disease, disorder, or condition is related to aberrant K-Ras4a signaling pathway activity.

Administration and Combination Therapy

The compounds provided herein (e.g., compounds of any one of Formulas IA, IA1, IA2, IB, IC, IC1, IC2, IC3, IC4, IC5, IC6, ID, ID1, IE, II, IIA, IIA1, IIA2, IIB, IIC, and IID) and forms thereof (e.g., salt, ester, tautomer, prodrug, zwitterionic form, stereoisomer, etc.), or compositions (e.g., pharmaceutical compositions) comprising the same, can be administered in various modes (e.g., orally, topically, or by injection). The amount of active ingredient (e.g., a compound provided herein in any suitable form thereof) administered to a subject (e.g., patient) will be the responsibility of an attendant medical provider. The specific dose level for a given subject (e.g., patient) will depend on a variety of factors including, for example, the activity of the active ingredient administered; the physical attributes of the subject (e.g., age, weight, height, body mass index, general health, co-morbidities, sex, etc.); other characteristics of the subject (e.g., diet, level of exercise, national origin, ethnicity, etc.); time of administration; route of administration; rate of excretion; drug combination; the disease, disorder, or condition being treated; and the severity of the disease, disorder, or condition being treated.

In some embodiments, a compound provided herein (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID), or a form thereof (e.g., salt, ester, tautomer, prodrug, zwitterionic form, stereoisomer, etc.) is administered in combination with an additional agent, such as an additional therapeutic agent. For example, if a subject experiences a side effect such as hypertension upon receiving a compound provided herein, or a form thereof, it may be appropriate to administer an additional agent that is effective in managing the side effect, such as an anti-hypertensive agent. In another example, the therapeutic effectiveness of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof, may be enhanced by administration of an adjuvant, which adjuvant may itself have only minimal therapeutic benefit, but in combination with another therapeutic agent may provide an enhanced overall therapeutic benefit to a subject. In a further example, the therapeutic benefit of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof, may be enhanced by administration of the compound, or a form thereof, and an additional agent (which may comprise an additional therapeutic regimen) that also provides a therapeutic benefit. For example, a compound provided herein (e.g., a compound of any one of Formulas IA, IA1, IA2, IB, IC, IC1, IC2, IC3, IC4, IC5, IC6, ID, ID1, IE, II, IA, IIA1, IIA2, IIB, IIC, and IID), or a form thereof, may be administered in combination with an additional agent that may be effective in the treatment of a disease, disorder, or condition such as a cancer. Generally, the combination of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof, and one or more additional agents (e.g., therapeutic agents) may enhance the overall benefit experienced by the subject upon either component individually. In some embodiments, the effect may be additive. In some embodiments, the effect may be synergistic.

In some embodiments, a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof (e.g., salt, ester, tautomer, prodrug, zwitterionic form, stereoisomer, etc.) is administered in combination with an anti-cancer agent (e.g., chemotherapeutic agent). An anti-cancer agent may be, for example, an alkylating agent, an antimitotic, a checkpoint inhibitor, an anti-metabolite, a plant alkaloid, a terpenoid, a cytotoxic agent, an antibiotic, a topoisomerase inhibitor, an aromatase inhibitor, an angiogenesis inhibitor, an anti-steroid, an anti-androgen, an mTOR inhibitor, monoclonal antibodies, or a tyrosine kinase inhibitor. An alkylating agent may be, for example, armustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, or cyclophosphamide (ENDOXAN). An anti-metabolite may be, for example, cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEY), methotrexate (RHEUMATREX), or raltitrexed. An antimitotic may be, for example, a taxane such as docetaxel (TAXITERE) or paclitaxel (ABRAXANE, TAXOL), or a *vinca* alkaloid such as vincristine (ONCOVIN), vinblastine, vindesine, or vinorelbine (NAVELBINE). A checkpoint inhibitor may be an anti-PD-1 or anti-PD-L1 antibody such as pembrolizumab (KEYTRUDA), nivolumab (OPDIVO), MED14736, or MPDL3280A; anti-CTLA-4 antibody ipilimumab (YERVOY); or an agent that targets LAG3 (lymphocyte activation gene 3 protein), KIR (killer cell immunoglobulin-like receptor), 4-1BB (tumor necrosis factor receptor superfamily member 9), TIM3 (T-cell immunoglobulin and mucin-domain containing-3), or 0X40 (tumor necrosis factor receptor superfamily member 4). A topoisomerase inhibitor may be, for example, camptothecin (CTP), irinotecan (CAMPTOSAR), topotecan (HYCAMTIN), teniposide (VUMON), or etoposide (EPOSIN). A cytotoxic antibiotic may be, for example, actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOYANTRONE), or plicamycin. An aromatase inhibitor may be, for example, aminoglutethimide, anastrozole (ARIMIDEX), letrozole (FEMARA), vorozole (RIYIZOR), or exemestane (AROMASIN). An angiogenesis inhibitor may be, for example, genistein, sunitinib (SUTENT), or bevacizumab (AYASTIN). An anti-steroid or anti-androgen may be, for example, aminoglutethimide (CYTADREN), bicalutamide (CASODEX), cyproterone, flutamide (EULEXIN), or nilutamide(NILANDRON). A tyrosine kinase inhibitor may be, for example, imatinib (GLEEVEC), erlotinib (TARCEVA), afatinib (GILOTRIF), lapatinib (TYKERB), sorafenib (NEXAVAR), or axitinib (INLYTA). An mTOR inhibitor may be, for example, everolimus, temsirolimus (TORISEL), or sirolimus. Monoclonal antibody may be, for example, trastuzumab (HERCEPTIN) or rituximab (RITUXAN). Additional examples of agents that may be useful in combination with a compound provided herein, or an alternative form thereof, include, but are not limited to, amsacrine; *Bacillus* Calmette-Guerin (B—C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,r'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Two or more therapeutic agents, one of which is a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID) or a form thereof, may be administered in any order or may be administered simultaneously. If administered simultaneously, the multiple therapeutic agents may be provided in a single, unified form, or in multiple forms (such as, for example, as a single pill or as two separate pills). One of the therapeutic agents may be given in multiple doses, or both may be given as multiple doses. If not administered simultaneously, the timing between the multiple doses may be any duration of time ranging from a few minutes to four weeks.

Accordingly, in another aspect, the present disclosure provides a method for treating a disease, disorder, or condition (e.g., a cancer) in a subject (e.g., a human or animal subject) in need of such treatment comprising administering to the subject an amount of a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof (e.g., salt, ester, tautomer, prodrug, zwitterionic form, stereoisomer, etc.), in combination with at least one additional agent for the treatment of the disease, disorder, or condition. In a related aspect, the present disclosure provides a composition (e.g., pharmaceutical composition) comprising a compound provided herein (e.g., a compound of any one of Formulas IA, IA1, IA2, IB, IC, IC1, IC2, IC3, IC4, IC5, IC6, ID, ID1, IE, II, IIA, IIA1, IIA2, IIB, IIC, and IID), or a form thereof (e.g., salt, ester, tautomer, prodrug, zwitterionic form, stereoisomer, etc.), and at least one additional agent for use in the treatment of a disease, disorder, or condition (e.g., a cancer).

In some embodiments, a method provided herein is used to treat a disease, disorder, or condition (e.g., a cancer) comprising administering to a subject in need thereof a therapeutically effective amount of a compound of any one of Formulas IA, IA1, IA2, IB, IC, IC1, IC2, IC3, IC4, IC5, IC6, ID, ID1, IE, II, IIA, IIA1, IIA2, IIB, IIC, and IID or a pharmaceutically acceptable salt thereof, wherein the disease, disorder, or condition is a cancer that has developed a resistance to one or more chemotherapeutic drugs and/or ionizing radiation. In some embodiments, a method provided herein is used to treat a disease, disorder, or condition (e.g., a cancer) comprising administering to a subject in need thereof a therapeutically effective amount of a compound of any one of Formulas IA, IA1, IA2, IB, IC, IC1, IC2, IC3, IC4, IC5, IC6, ID, ID1, IE, II, IIA, IIA1, IIA2, IIB, IIC, and IID or a pharmaceutically acceptable salt thereof, in combination with an additional agent, wherein the disease, disorder, or condition is a cancer that has developed a resistance to one or more chemotherapeutic drugs and/or ionizing radiation.

The compounds, compositions, and methods disclosed herein are useful for the treatment of a disease, disorder, or condition, such as a cancer. In certain embodiments, the disease is one of dysregulated cellular proliferation, including cancer. The cancer may be hormone-dependent or hormone-resistant, such as in the case of breast cancers. In certain embodiments, the cancer is or comprises a solid tumor. In other embodiments, the cancer is a lymphoma or leukemia. In certain embodiments, the cancer is a drug resistant phenotype of a cancer disclosed herein or otherwise known. Tumor invasion, tumor growth, tumor metastasis, and angiogenesis may also be treated using the compositions and methods disclosed herein. In some embodiments, the compounds, compositions, and methods provided herein are also useful in the treatment of precancerous neoplasias.

Cancers that may be treated by the methods disclosed herein include, but are not limited to, pancreatic cancer, colon cancer, rectal cancer, colorectal cancer, breast cancer, ovarian cancer, endometrial cancer, lung cancer, and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma, and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML), and lymphomas including lymphocytic, granulocytic and monocytic lymphomas. Additional types of cancers which may be treated using the compounds and methods provided herein include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor. Additional diseases and disorders that may be treated by the methods disclosed herein include, but are not limited to, diseases or disorders related to KRAS, such as diseases or disorders associated with a mutation of KRAS (e.g., KRAS G12C mutation) or dysregulation of KRAS, and diseases or disorders related to the KRAS gene, such as diseases or disorders associated with a mutation of the KRAS gene or dysregulation of the KRAS gene.

In some embodiments, the compounds, compositions, and methods provided herein are useful in the prevention and/or reduction of tumor invasion, growth, and/or metastasis.

The compounds, compositions, and methods provided herein may be useful in the treatment of humans as well as in the veterinary treatment of non-human animals including companion animals, exotic animals, and farm animals (e.g., as described herein), including mammals, rodents, and the like. For example, the compounds, compositions, and methods provided herein may be useful in the treatment of horses, dogs, or cats.

Enumerated Embodiments

The following embodiments, while non-limiting, are exemplary of certain aspects of the present disclosure:

A1. A compound represented by Formula IA:

(IA)

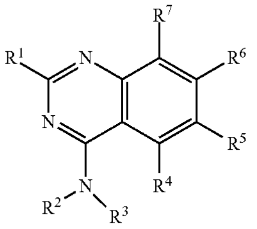

or a salt (e.g., pharmaceutically acceptable salt), ester, tautomer, prodrug, zwitterionic form, or stereoisomer thereof, wherein:

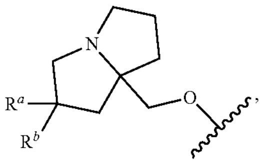

, and

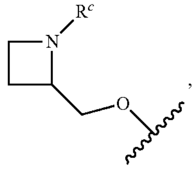

, $R^1$ is selected from R, and, and $OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is H, —$OR^{12}$, and $C_{1-6}$alkyl, wherein any $C_{1-6}$alkyl is unsubstituted or substituted with one or more $R^{13}$;

$R^5$ is selected from halogen, $C_{1-6}$alkyl, —$OR^{12}$, a 3-6 membered carbocycle, and a 3-6 membered heterocycle, wherein any $C_{1-6}$alkyl is unsubstituted or substituted with one or more $R^{13}$ and wherein any carbocycle and heterocycle is unsubstituted or substituted with one or more $R^{14}$;

$R^6$ is a bicyclic heteroaryl substituted with one or more $R^{15}$;

$R^7$ is selected from halogen, —$OR^{12}$, —CN, and H;

$R^8$ is selected from hydrogen and $C_{1-6}$alkyl, wherein any $C_{1-6}$alkyl is unsubstituted or substituted with one or more $R^{13}$;

each $R^{10}$ is independently selected from $C_{1-6}$alkyl, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{15}$ is independently selected from halogen, $N(R^{12})_2$, —CN, and $C_{1-6}$alkyl, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

E is selected from

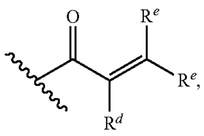

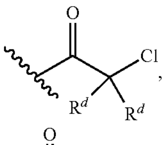

,

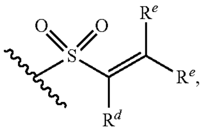

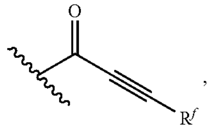

,

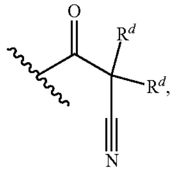

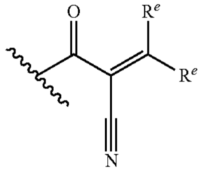

,

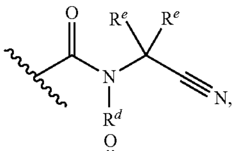

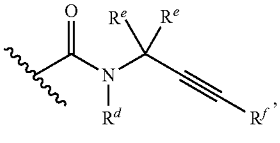

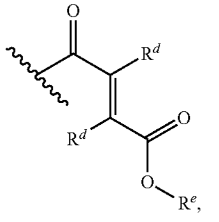

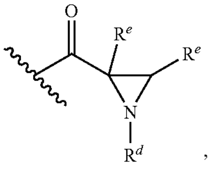

,

-continued

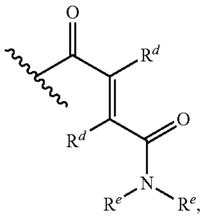
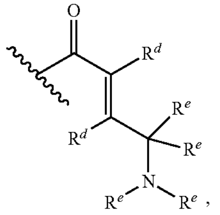

and CN;

$R^a$ and $R^b$ are each independently selected from halogen, $C_{1-6}$ alkyl, —$OR^{12}$, and H, wherein any $C_{1-6}$alkyl is unsubstituted or is substituted with one or more $R^{13}$;

$R^c$ is selected from halogen, $C_{1-6}$ alkyl, and H;

each $R^d$ and $R^e$ is independently selected from halogen, $C_{1-6}$ alkyl, and H; and each $R^f$ is independently selected from $C_{1-6}$ alkyl and H.

A2. The compound of embodiment A1, wherein $R^1$ is selected from

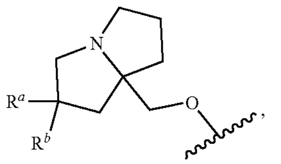

A3. The compound of embodiment A2, wherein $R^a$ is a halogen and/or wherein $R^b$ is a halogen.

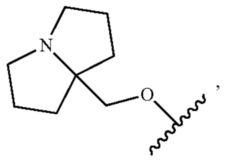
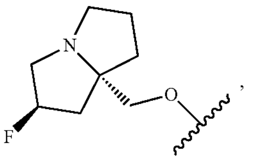
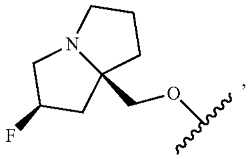
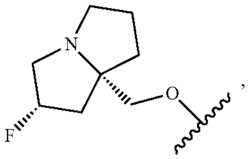
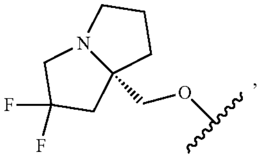
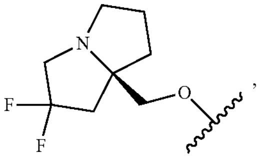
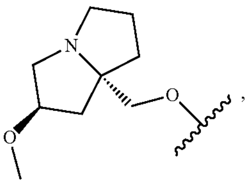
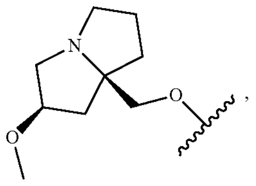

-continued

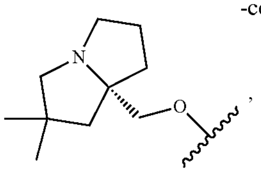
and
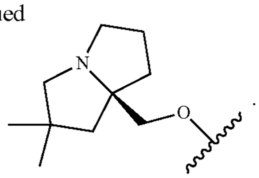

A4. The compound of embodiment A2, wherein $R^1$ is selected from

A5. The compound of embodiment A1, wherein $R^1$ is selected from

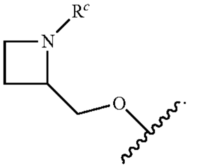

A6. The compound of embodiment A5, wherein $R^1$ is selected from

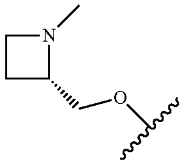
and
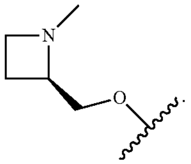

A7. The compound of embodiment A1, wherein $R^1$ is OH.

A8. The compound of any one of embodiments A1-A7, wherein $R^2$ is H.

A9. The compound of any one of embodiments A1-A7, wherein $R^2$ is selected from $C_{1-6}$ alkyl.

A10. The compound of embodiment A9, wherein $R^2$ is selected from $C_{1-2}$ alkyl.

A11. The compound of any one of embodiments A1-A7, wherein $R^2$ is selected from a 3-6 membered carbocycle.

A12. The compound of embodiment A11, wherein $R^2$ is cyclopropyl.

A13. The compound of any one of embodiments A1-A12, wherein $R^3$ is a 4-6 membered heterocycle that is substituted with one or more E and 0-4 $R^{10}$.

A14. The compound of embodiment A13, wherein $R^3$ is a 4-6 membered heterocycle that is substituted with one or more E and 0-4 $R^{10}$, wherein the heterocycle includes a single heteroatom that is N.

A15. The compound of embodiment A14, wherein $R^3$ is selected from

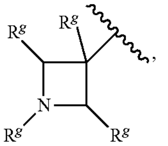
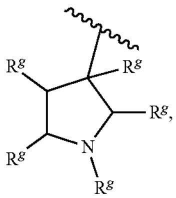

-continued

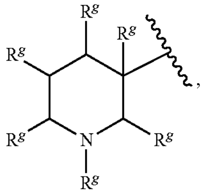, and 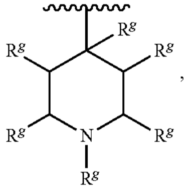, wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A16. The compound of embodiment A15, wherein $R^3$ is selected from

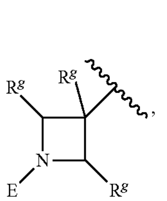, 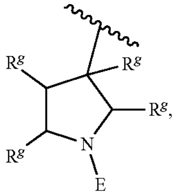

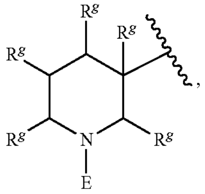, and 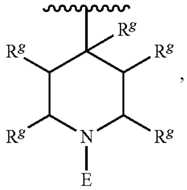, wherein each $R^g$ is independently selected from $C_{1-6}$alkyl and H, wherein any $C_{1-6}$alkyl is unsubstituted or substituted with one or more $R^{20}$.

A17. The compound of embodiment A16, wherein each $R^g$ is H.

A18. The compound of any one of embodiments A1-A7, wherein $R^2$ and $R^3$, together with the atom to which they are attached, form a 4-8 membered heterocycle.

A19. The compound of embodiment A18, wherein $R^2$ and $R^3$, together with the atom to which they are attached, form a piperazinyl ring that is substituted with one or more E and 0-4 $R^{11}$.

A20. The compound of embodiment A19, wherein $R^2$ and $R^3$, together with the atom to which they are attached, form the structure

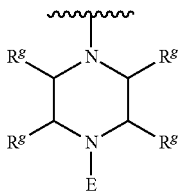 or 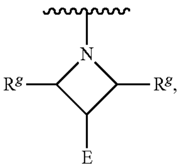

wherein each $R^g$ is independently selected from $C_{1-6}$alkyl and H, wherein any $C_{1-6}$alkyl is unsubstituted or substituted with one or more $R^{20}$.

A21. The compound of embodiment A20, wherein each $R^g$ is H.

A22. The compound of embodiment A20, wherein $R^2$ and $R^3$, together with the atom to which they are attached, form the structure

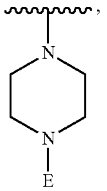, 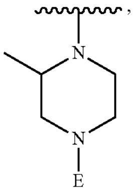, 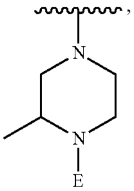,

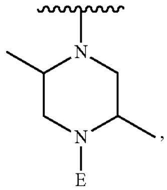, 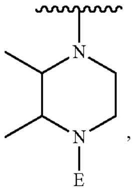, 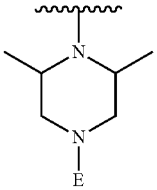,

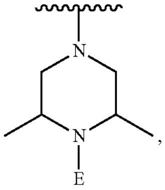, 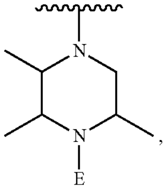, 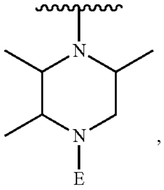, or

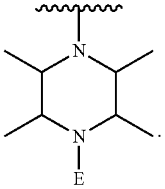.

A23. The compound of embodiment A18, wherein $R^2$ and $R^3$, together with the atom to which they are attached, form a bridged piperazinyl ring that is substituted with one or more E and 0-4 $R^{11}$.

A24. The compound of embodiment A23, wherein $R^2$ and $R^3$, together with the atom to which they are attached, form the structure

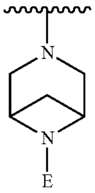 or 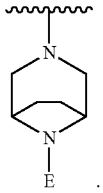.

A25. The compound of embodiment A18, wherein $R^2$ and $R^3$, together with the atom to which they are attached, form a 4-8 membered bicyclic heterocycle comprising a fused ring system that is substituted with one or more E and 0-4 $R^{11}$.

A26. The compound of embodiment A25, wherein $R^2$ and $R^3$, together with the atom to which they are attached, form a structure selected from:

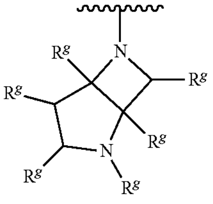

and

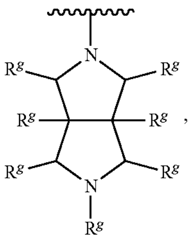

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A27. The compound of embodiment A26, wherein $R^2$ and $R^3$, together with the atom to which they are attached, form a structure selected from:

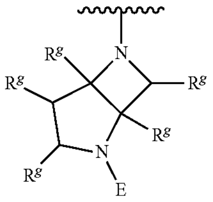

and

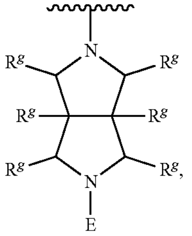

wherein each $R^g$ is independently selected from $C_{1-6}$alkyl and H, wherein any $C_{1-6}$alkyl is unsubstituted or substituted with one or more $R^{20}$.

A28. The compound of embodiment A27, wherein $R^2$ and $R^3$, together with the atom to which they are attached, form the structure

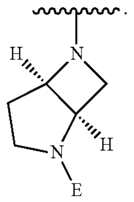

A29. The compound of embodiment A28, wherein each $R^g$ is H.

A30. The compound of any one of embodiments A1-A29, wherein $R^4$ is H.

A31. The compound of any one of embodiments A1-A30, wherein $R^5$ is a halogen.

A32. The compound of embodiment A31, wherein $R^5$ is Cl.

A33. The compound of any one of embodiments A1-A30, wherein $R^5$ is selected from $C_{1-6}$alkyl that is unsubstituted or substituted with one or more $R^{13}$.

A34. The compound of embodiment A33, wherein $R^5$ is $C_{1-6}$alkyl that is substituted with one or more halogens.

A35. The compound of embodiment A34, wherein $R^5$ is $CF_3$.

A36. The compound of embodiment A33, wherein $R^5$ is $C_{1-6}$alkyl that is substituted with one or more $R^{13}$, wherein each $R^{13}$ is independently selected from —$OR^{22}$, —CN, and —$N(R^{22})_2$.

A37. The compound of embodiment A36, wherein $R^5$ is $CH_2CN$.

A38. The compound of any one of embodiments A1-A30, wherein $R^5$ is selected from —$OR^{12}$, wherein $R^{12}$ is selected from $C_{1-6}$ alkyl and H.

A39. The compound of embodiment A38, wherein $R^5$ is —$OCH_3$.

A40. The compound of any one of embodiments A1-A30, wherein $R^5$ is selected from a 3-6 membered carbocycle and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$.

A41. The compound of any one of embodiments A1-A40, wherein $R^6$ is selected from

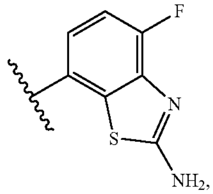

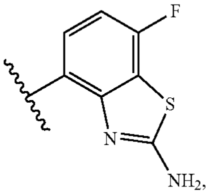

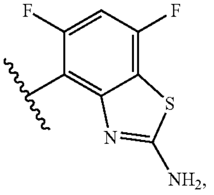

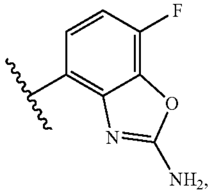

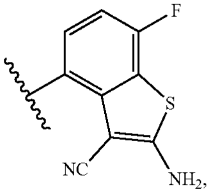

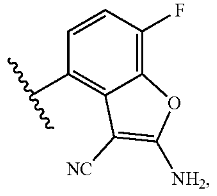

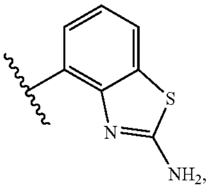

and

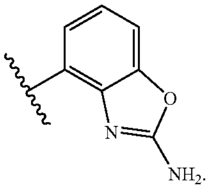

A42. The compound of any one of embodiments A1-A41, wherein $R^7$ is a halogen.

A43. The compound of embodiment A42, wherein $R^7$ is F.

A44. The compound of any one of embodiments A1-A43, wherein each E is independently selected from

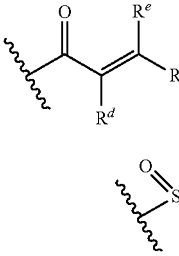

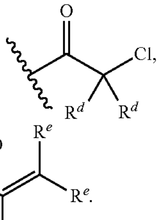

and

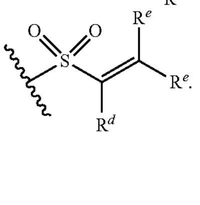

A45. The compound of embodiment A44, wherein each E is

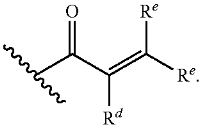

A46. The compound of embodiment A45, wherein each $R^d$ and $R^e$ is H.

A47. A compound represented by Formula IB:

(IB)

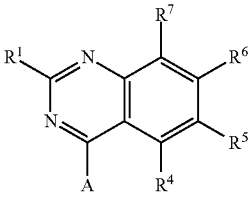

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

A is selected from

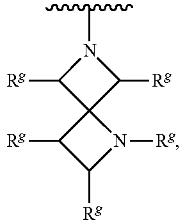

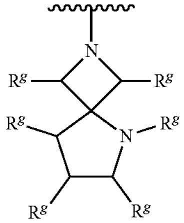

,

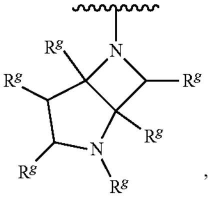

, and

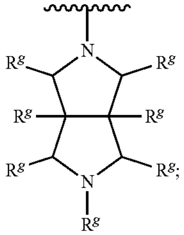

$R^4$ is H, —$OR^{12}$, and $C_{1-6}$alkyl, wherein any $C_{1-6}$alkyl is unsubstituted or substituted with one or more $R^{13}$;

$R^5$ is selected from halogen, $C_{1-6}$alkyl, a 3-6 membered carbocycle, and a 3-6 membered heterocycle, wherein any $C_{1-6}$alkyl is unsubstituted or substituted with one or more $R^{13}$ and wherein any carbocycle and heterocycle is unsubstituted or substituted with one or more $R^{14}$;

$R^6$ is a bicyclic heteroaryl substituted with one or more $R^{15}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ or $R^b$, and wherein an alkyl moiety of any alkylheterocycle is selected from $C_{1-6}$ alkyl;

each $R^{12}$ is independently selected from $C_{1-6}$alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{15}$ is independently selected from halogen, $N(R^{12})_2$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^a$ and $R^b$ is independently selected from halogen, $C_{1-6}$ alkyl, —$OR^{12}$, and H, wherein any $C_{1-6}$alkyl is unsubstituted or substituted with one or more $R^{13}$;

each $R^g$ is independently selected from $C_{1-6}$alkyl, H, and E, wherein at least one $R^g$ is E, and wherein any $C_{1-6}$alkyl is unsubstituted or substituted with one or more $R^{20}$;

E is selected from

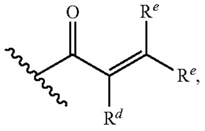

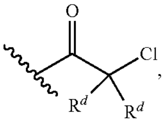

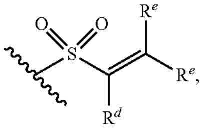

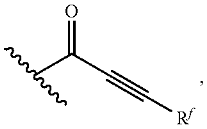

,

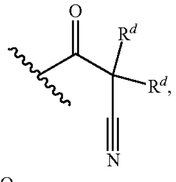

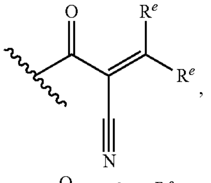

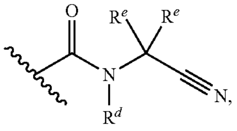

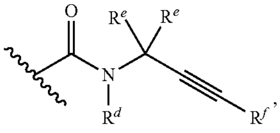

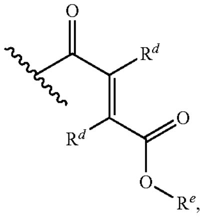

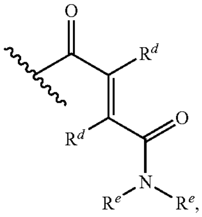

-continued

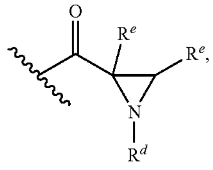

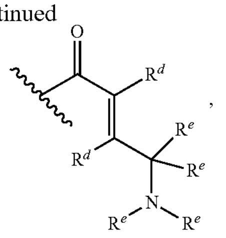

, and CN;

each $R^d$ and $R^e$ is independently selected from halogen, $C_{1-6}$ alkyl, and H; and each $R^f$ is independently selected from $C_{1-6}$ alkyl and H.

A48. The compound of embodiment A47, wherein A is selected from

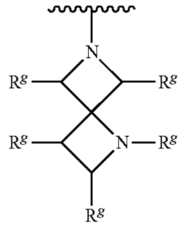

and

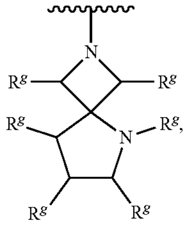

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A49. The compound of embodiment A48, wherein A is selected from

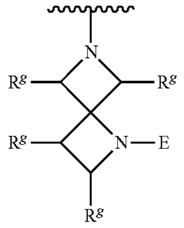

and

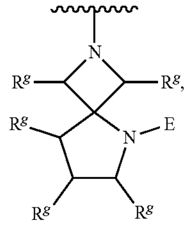

wherein each $R^g$ is independently selected from $C_{1-6}$alkyl and H, wherein any $C_{1-6}$alkyl is unsubstituted or substituted with one or more $R^{20}$.

A50. The compound of embodiment A49, wherein each $R^g$ is H.

A51. The compound of embodiment A47, wherein A is selected from

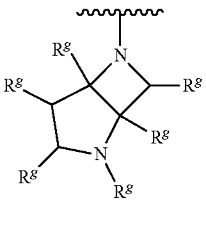

and

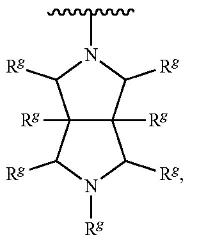

each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A52. The compound of embodiment A51, wherein A is selected from

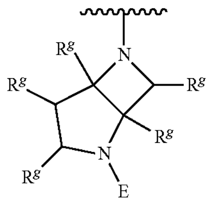

and

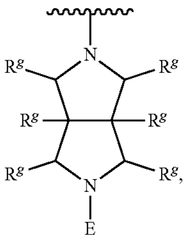

wherein each $R^g$ is independently selected from $C_{1-6}$alkyl and H, wherein any $C_{1-6}$alkyl is unsubstituted or substituted with one or more $R^{20}$.

A53. The compound of embodiment A52, wherein each $R^g$ is H.

A54. The compound of any one of embodiments A47-A53, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$ or $R^b$, and wherein an alkyl moiety of any alkylheterocycle is selected from $C_{1-6}$ alkyl.

A55. The compound of embodiment A54, wherein $R^8$ is a heterocycle or an alkylheterocycle, wherein any heterocycle contains 4-8 members and is substituted with one or more $R^a$ or $R^b$.

A56. The compound of embodiment A54 or A55, wherein $R^1$ is selected from

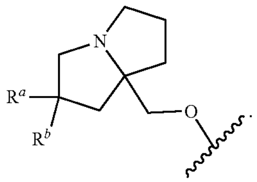

A57. The compound of embodiment A56, wherein $R^a$ is a halogen and/or $R^b$ is a halogen.

A58. The compound of embodiment A56, wherein $R^1$ is selected from

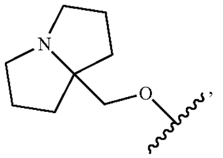

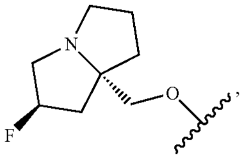

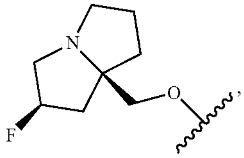

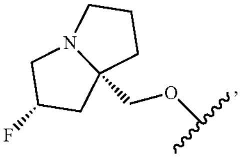

-continued
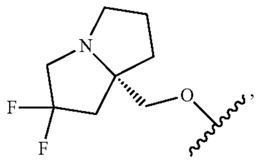
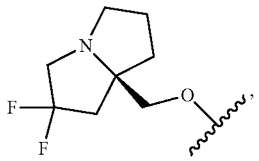
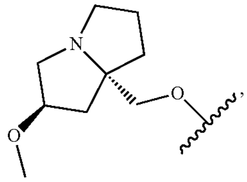
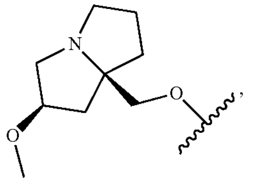
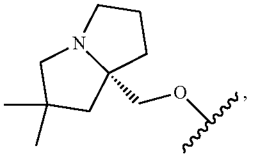
and
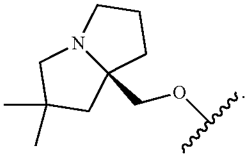
A59. The compound of embodiment A54 or A55, wherein $R^1$ is selected from
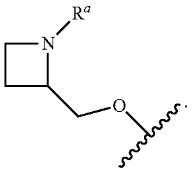
A60. The compound of embodiment A59, wherein $R^1$ is selected from
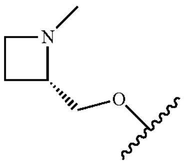
and
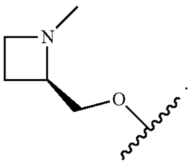
A61. The compound of embodiment A54 or A55, wherein $R^1$ is selected from
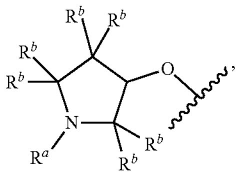
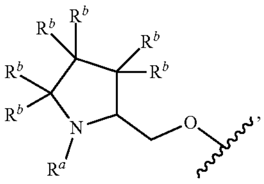
and
-continued
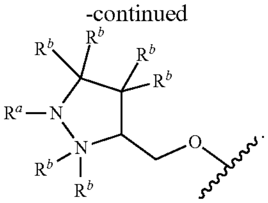
A62. The compound of embodiment A61, wherein $R^1$ is selected from
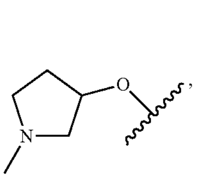
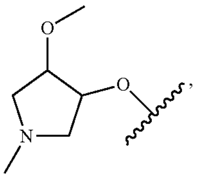
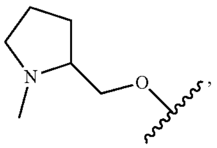
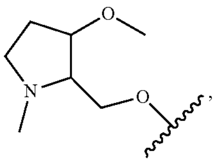
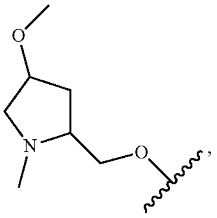
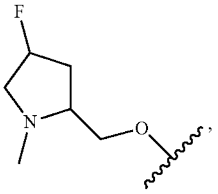
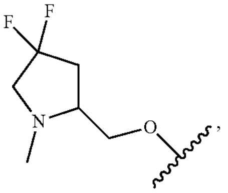
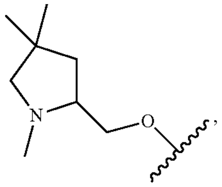
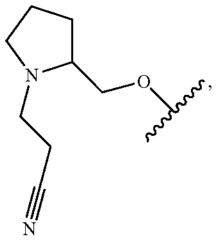
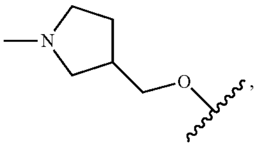
and
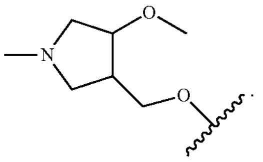

A63. The compound of embodiment A61, wherein $R^1$ is selected from

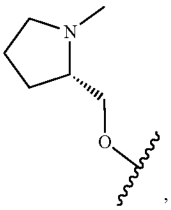
,
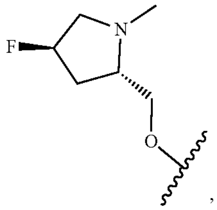
,
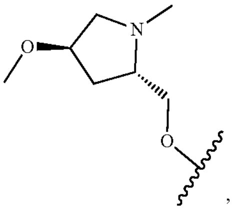
, and
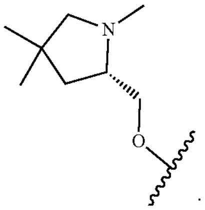
.

A64. The compound of any one of embodiments A47-A63, wherein $R^4$ is H.

A65. The compound of any one of embodiments A47-A64, wherein $R^5$ is a halogen.

A66. The compound of embodiment A65, wherein $R^5$ is F.

A67. The compound of any one of embodiments A47-A64, wherein $R^5$ is selected from $C_{1-6}$alkyl that is unsubstituted or substituted with one or more $R^{13}$.

A68. The compound of embodiment A67, wherein $R^5$ is $C_{1-6}$alkyl that is substituted with one or more halogens.

A69. The compound of embodiment A68, wherein $R^5$ is $CF_3$.

A70. The compound of any one of embodiments A47-A64, wherein $R^5$ is selected from a 3-6 membered carbocycle and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$.

A71. The compound of embodiment A70, wherein $R^5$ is a furan.

A72. The compound of any one of embodiments A47-A71, wherein $R^6$ is selected from

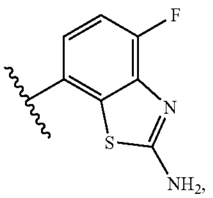
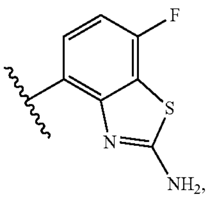
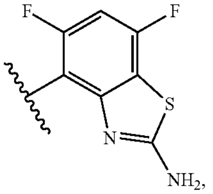
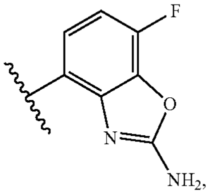
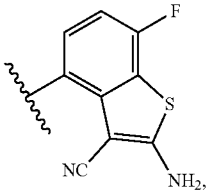
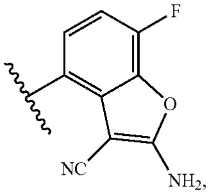

-continued

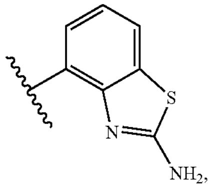
and
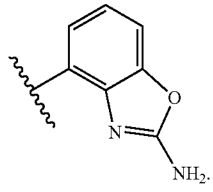

A73. The compound of any one of embodiments A47-A72, wherein $R^7$ is a halogen.

A74. The compound of embodiment A73, wherein $R^7$ is F.

A75. The compound of any one of embodiments A47-A74, wherein each E is independently selected from

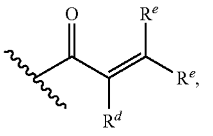
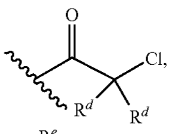
and
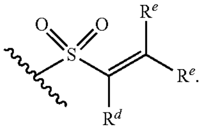

A76. The compound of embodiment A75, wherein each E is

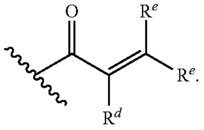

A77. The compound of embodiment A76, wherein each $R^d$ and $R^e$ is H.

A78. A compound according to Formula IC:

(IC)

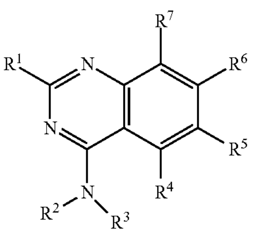

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, wherein the heterocycle contains a single heteroatom that is N, and wherein the heterocycle is substituted with one or more E and 0-4 $R^{10}$;

$R^4$ is H, —$OR^{12}$, and $C_{1-6}$alkyl, wherein any $C_{1-6}$alkyl is unsubstituted or substituted with one or more $R^{13}$;

$R^5$ is selected from H, halogen, $C_{1-6}$alkyl, a 3-6 membered carbocycle, and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$;

$R^6$ is a bicyclic heteroaryl substituted with one or more $R^5$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{15}$ is independently selected from halogen, $N(R^{12})_2$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^X$ is independently selected from $C_{1-6}$ alkyl, a 3-6 membered carbocycle, and H;

each $R^{22}$ is independently selected from $C_{1-6}$ alkyl, $C_{2-6}$ alkenyl, and H;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

E is selected from

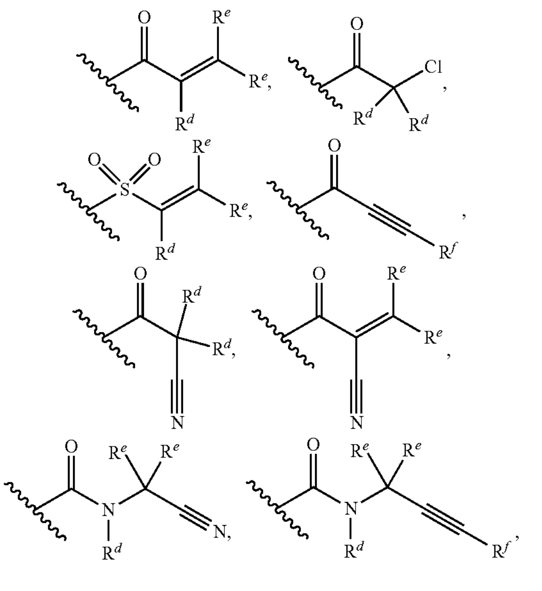

-continued

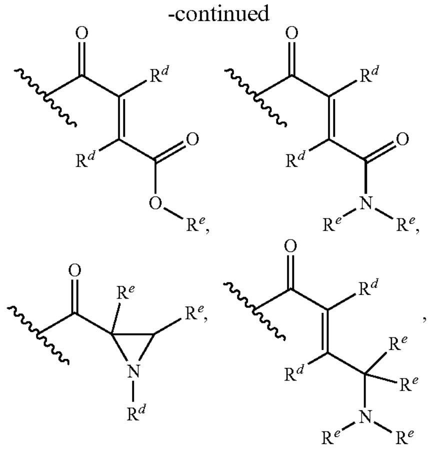

and CN;

each $R^d$ and $R^e$ is independently selected from halogen, $C_{1-6}$ alkyl, and H; and each $R^f$ is independently selected from $C_{1-6}$ alkyl and H.

A79. The compound of embodiment A78, wherein $R^2$ is H.

A80. The compound of embodiment A78, wherein $R^2$ is selected from $C_{1-6}$ alkyl and a 3-6 membered carbocycle.

A81. The compound of embodiment A80, wherein $R^2$ is methyl.

A82. The compound of any one of embodiments A78-A81, wherein $R^3$ is selected from $C_{1-6}$ alkyl that is substituted with —$N(R^{12})(E)$.

A83. The compound of embodiment A82, wherein $R^3$ is $C_2$ alkyl that is substituted with —$N(R^{12})(E)$.

A84. The compound of embodiment A83, wherein $R^3$ is $C_2$ alkyl that is substituted with —N(H)(E).

A85. The compound of any one of embodiments A78-A81, wherein $R^3$ is selected from a 4-6 membered heterocycle, wherein the heterocycle contains a single heteroatom that is N, and wherein the heterocycle is substituted with one or more E and 0-4 $R^{10}$.

A86. The compound of embodiment A85, wherein $R^3$ is selected from

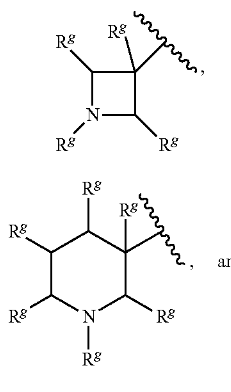

and

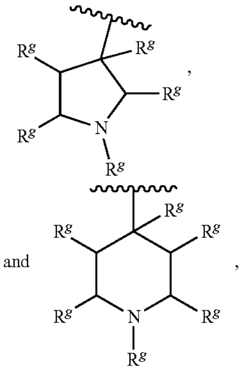

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A87. The compound of embodiment A86, wherein $R^3$ is selected from

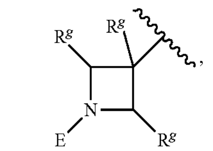
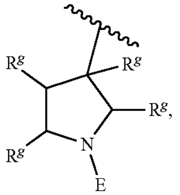
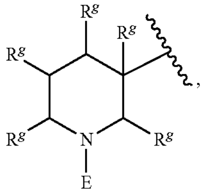
and
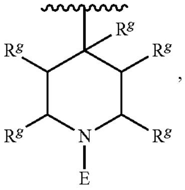

wherein each $R^g$ is independently selected from $C_{1-6}$alkyl and H, wherein any $C_{1-6}$alkyl is unsubstituted or substituted with one or more $R^{20}$.

A88. The compound of embodiment A87, wherein each $R^g$ is H.

A89. The compound of any one of embodiments A78-A88, wherein $R^1$ is H.

A90. The compound of any one of embodiments A78-A88, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$ or $R^b$, and wherein an alkyl moiety of any alkylheterocycle is selected from $C_{1-6}$ alkyl.

A91. The compound of embodiment A90, wherein $R^8$ is a heterocycle or an alkylheterocycle, wherein any heterocycle contains 4-8 members and is substituted with one or more $R^a$ or $R^b$.

A92. The compound of embodiment A90 or A91, wherein $R^1$ is selected from

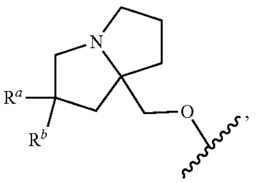

wherein $R^a$ and $R^b$ are each independently selected from halogen, $C_{1-6}$ alkyl, —$OR^{12}$, and H, wherein any $C_{1-6}$ alkyl is unsubstituted or is substituted with one or more $R^{13}$.

A93. The compound of embodiment A92, wherein $R^1$ is selected from:

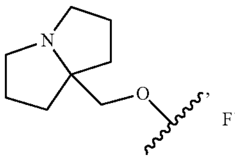
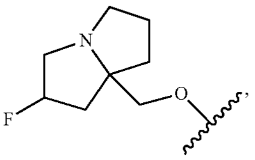

-continued

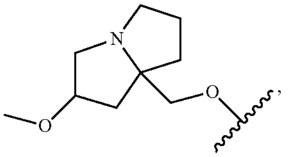
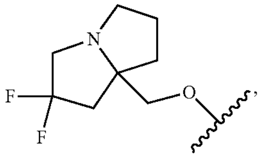
and
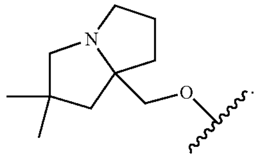

A94. The compound of embodiment A92, wherein $R^1$ is selected from

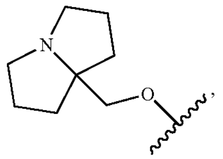
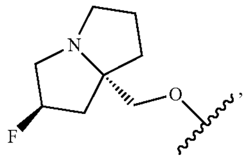
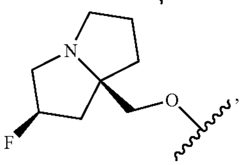
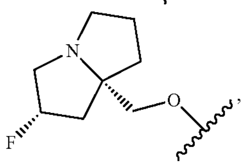
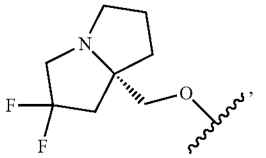
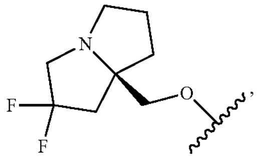
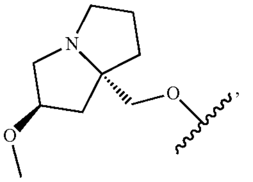
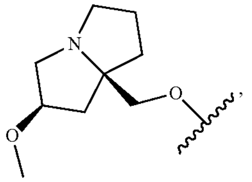
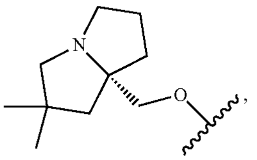
and
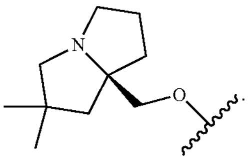

A95. The compound of embodiment A90 or A91, wherein $R^1$ is selected from

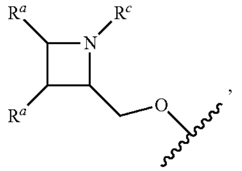

wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

A96. The compound of embodiment A95, wherein $R^1$ is selected from

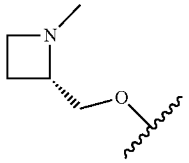 and 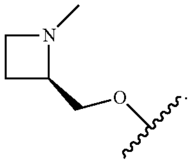.

A97. The compound of embodiment A90 or A91, wherein $R^1$ is selected from:

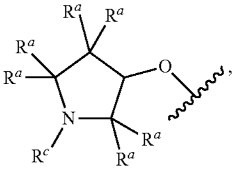, 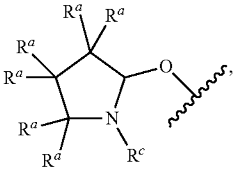,

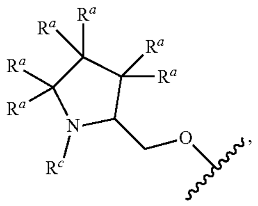, and

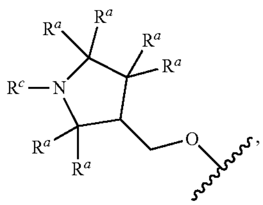, wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

A98. The compound of embodiment A97, wherein $R^1$ is selected from

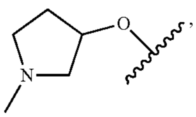, 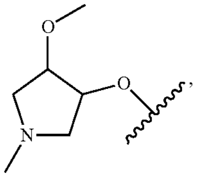,

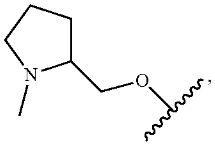, 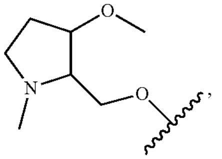,

-continued

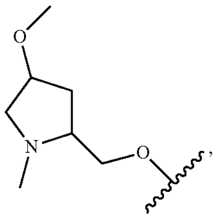, 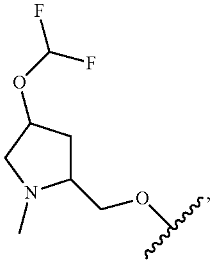,

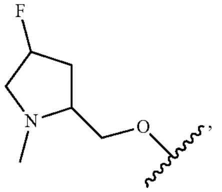, 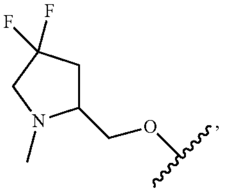,

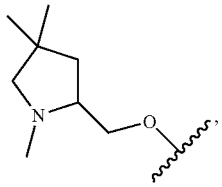, 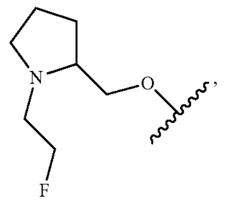,

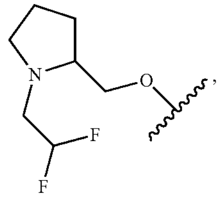, 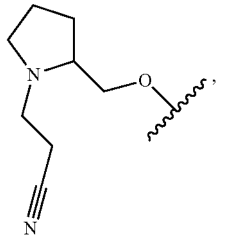,

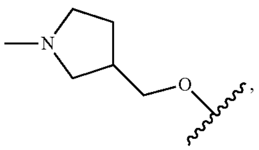, and 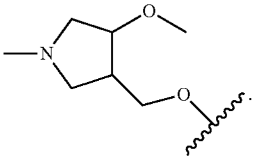.

A99. The compound of embodiment A97, wherein $R^1$ is selected from

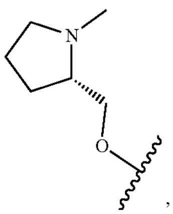, 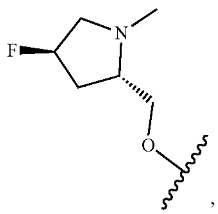,

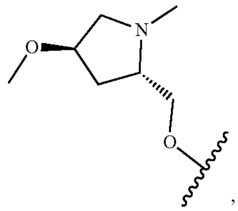, and 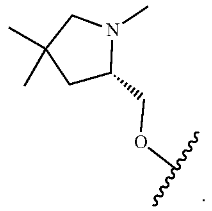.

A100. The compound of any one of embodiments A78-A88, wherein $R^1$ is a 4-6 membered heterocycle comprising a nitrogen atom, wherein the heterocycle is unsubstituted or substituted with one or more $R^{16}$.

A101. The compound of embodiment A100, wherein $R^1$ is

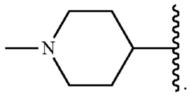 [SMILES: *C1CCN(C)CC1]

A102. The compound of any one of embodiments A78-A101, wherein $R^4$ is H.

A103. The compound of any one of embodiments A78-A101, wherein $R^4$ is —$OCH_3$.

A104. The compound of any one of embodiments A78-A103, wherein $R^5$ is H.

A105. The compound of any one of embodiments A78-A103, wherein $R^5$ is a halogen.

A106. The compound of embodiment A105, wherein $R^5$ is Cl.

A107. The compound of any one of embodiments A78-A103, wherein $R^5$ is $C_{1-6}$alkyl that is unsubstituted or substituted with one or more $R^{13}$.

A108. The compound of embodiment A107, wherein $R^5$ is $C_{1-6}$alkyl that is substituted with one or more halogens.

A109. The compound of embodiment A108, wherein $R^5$ is $CF_3$.

A110. The compound of embodiment A107, wherein $R^5$ is $C_{1-6}$alkyl that is substituted with one or more $R^{13}$, wherein each $R^{13}$ is independently selected from —$OR^{22}$, —CN, and —$N(R^{22})_2$.

A111. The compound of embodiment A110, wherein $R^5$ is $CH_2CN$.

A112. The compound of any one of embodiments A78-A103, wherein $R^5$ is a 3-6 membered heterocycle that is unsubstituted or substituted with one or more $R^{14}$.

A113. The compound of embodiment A112, wherein $R^5$ is a furan.

A114. The compound of any one of embodiments A78-A113, wherein $R^7$ is a halogen.

A115. The compound of embodiment A114, wherein $R^7$ is F.

A116. The compound of any one of embodiments A78-A113, wherein $R^7$ is —OH.

A117. The compound of any one of embodiments A78-A113, wherein $R^7$ is

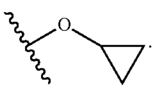 [SMILES: *OC1CC1]

A118. The compound of any one of embodiments A78-A117, wherein $R^6$ is selected from

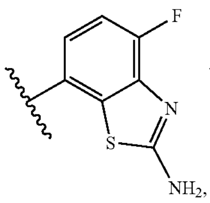

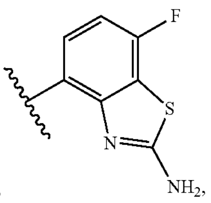

-continued

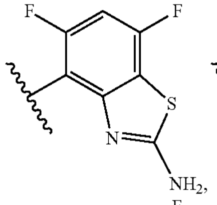

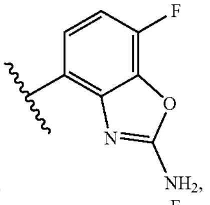

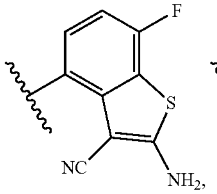

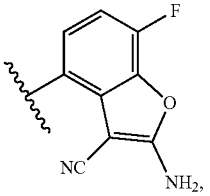

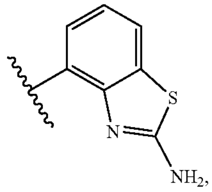

and

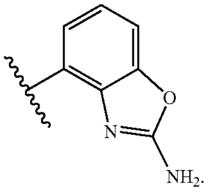

A119. The compound of any one of embodiments A78-A118, wherein each E is independently selected from

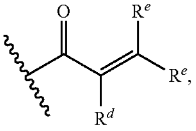

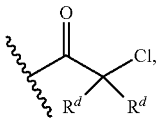

and

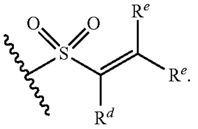

A120. The compound of embodiment A119, wherein each E is

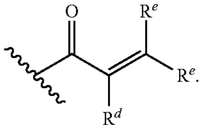

A121. The compound of embodiment A120, wherein each $R^d$ and $R^e$ is H.

A122. A compound according to Formula ID:

(ID)

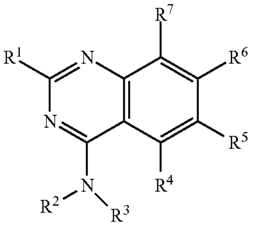

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

$R^2$ is selected from H, $C_{1-6}$ alkyl, and a 3-6 membered carbocycle;

$R^3$ is a 4-6 membered heterocycle, wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is H, —$OR^{12}$, and $C_{1-6}$alkyl, wherein any $C_{1-6}$alkyl is unsubstituted or substituted with one or more $R^{13}$;

$R^5$ is selected from $C_{2-6}$alkynyl, $C_{1-6}$alkyl, a 3-6 membered carbocycle, and a 3-6 membered heterocycle, wherein any $C_{1-6}$alkyl is substituted with CN, and wherein any carbocycle and heterocycle is unsubstituted or substituted with one or more $R^{14}$;

$R^6$ is a bicyclic heteroaryl substituted with one or more $R^{15}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{15}$ is independently selected from halogen, $N(R^{12})_2$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^X$ is independently selected from $C_{1-6}$ alkyl, a 3-6 membered carbocycle, and H;

each $R^{22}$ is independently selected from $C_{1-6}$ alkyl, $C_{2-6}$ alkenyl, and H;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

E is selected from

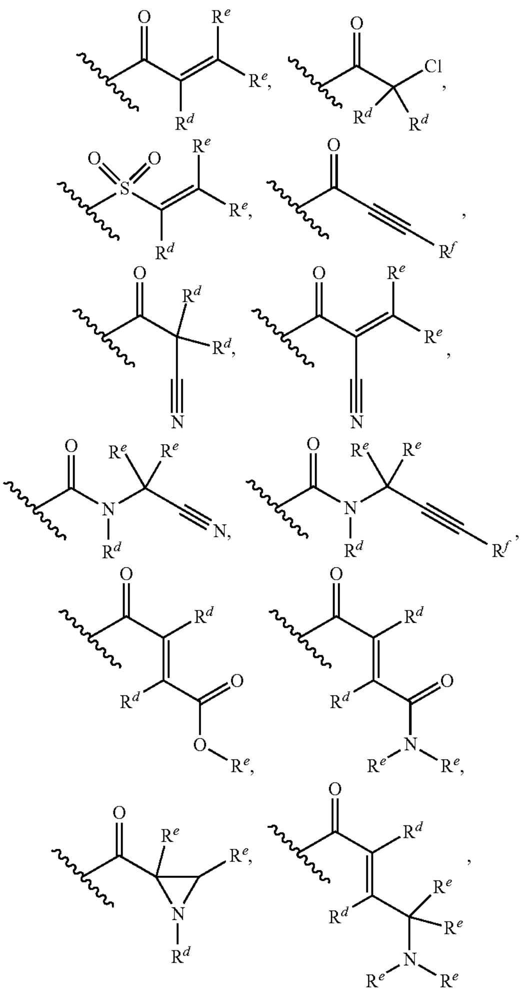

and CN;

each $R^d$ and $R^e$ is independently selected from halogen, $C_{1-6}$ alkyl, and H; and each $R^f$ is independently selected from $C_{1-6}$ alkyl and H.

A123. The compound of embodiment A122, wherein $R^5$ is selected from $C_{2-6}$alkynyl.

A124. The compound of embodiment A123, wherein $R^5$ is $C_2$alkynyl.

A125. The compound of embodiment A122, wherein $R^5$ is $C_{1-6}$alkyl that is unsubstituted or substituted with one or more $R^{13}$.

A126. The compound of embodiment A125, wherein $R^5$ is $C_{1-6}$alkyl that is substituted with one or more $R^{13}$, wherein each $R^{13}$ is independently selected from —$OR^{22}$, —CN, and —$N(R^{22})_2$.

A127. The compound of embodiment A126, wherein $R^5$ is $CH_2CN$.

A128. The compound of embodiment A122, wherein $R^5$ is selected from a 3-6 membered carbocycle that is unsubstituted or substituted with one or more $R^{14}$.

A129. The compound of embodiment A128, wherein $R^5$ is selected from selected from a cyclobutyl that is unsubstituted or substituted with one or more $R^{14}$.

A130. The compound of embodiment A128, wherein $R^5$ is selected from selected from a phenyl that is unsubstituted or substituted with one or more $R^{14}$.

A131. The compound of embodiment A122, wherein $R^5$ is selected from a 3-6 membered heterocycle that is unsubstituted or substituted with one or more $R^{14}$.

A132. The compound of embodiment A131, wherein $R^5$ is selected from a 5-6 membered heterocycle that includes one or two heteroatoms selected from O and N is unsubstituted or substituted with one or more $R^{14}$.

A133. The compound of embodiment A132, wherein $R^5$ is selected from furan, pyridine, and pyrazole that is unsubstituted or is substituted with one or more $R^{14}$.

A134. The compound of embodiment A133, wherein $R^5$ is selected from

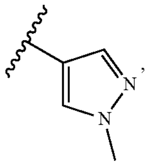, 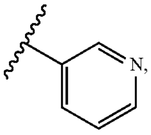, and 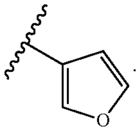.

A135. The compound of any one of embodiments A122-A134, wherein $R^1$ is H.

A136. The compound of any one of embodiments A122-A134, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$ or $R^b$, and wherein an alkyl moiety of any alkylheterocycle is selected from $C_{1-6}$ alkyl.

A137. The compound of embodiment A136, wherein $R^8$ is a heterocycle or an alkylheterocycle, wherein any heterocycle contains 4-8 members and is substituted with one or more $R^a$ or $R^b$.

A138. The compound of embodiment A136 or A137, wherein $R^1$ is selected from

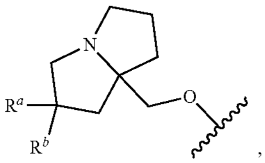, wherein $R^a$ and $R^b$ are each independently selected from halogen, $C_{1-6}$ alkyl, —$OR^{12}$, and H, wherein any $C_{1-6}$ alkyl is unsubstituted or is substituted with one or more $R^{13}$.

A139. The compound of embodiment A138, wherein $R^1$ is selected from:

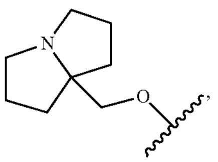, 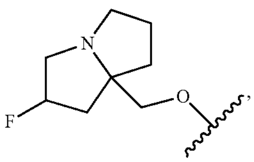, 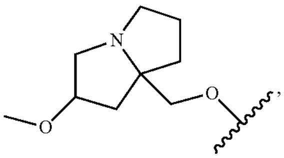,

-continued

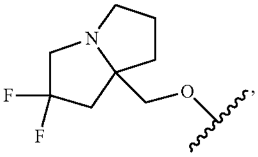, and 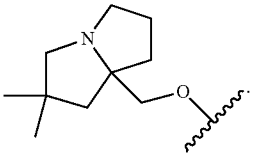.

A140. The compound of embodiment A138, wherein $R^1$ is selected from

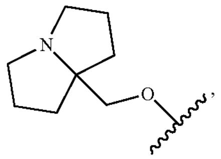, 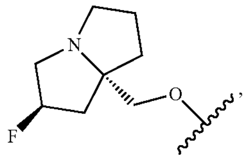, 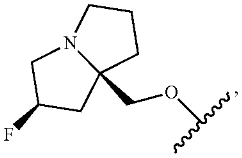, 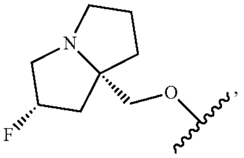, 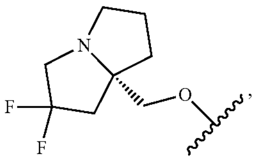, 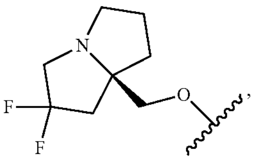, 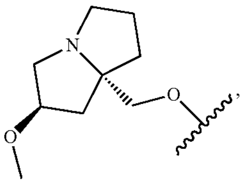, 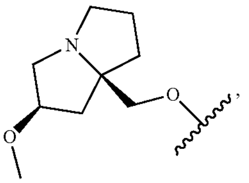, 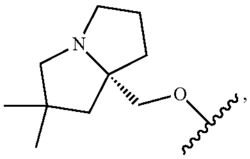, and 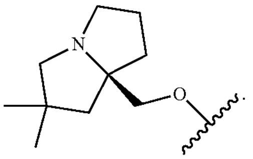.

A141. The compound of embodiment A136 or A137, wherein $R^1$ is selected from

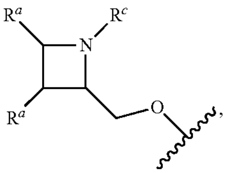, wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

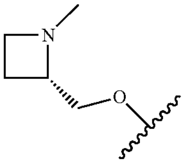 and 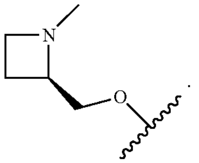.

A143. The compound of embodiment A136 or A137, wherein $R^1$ is selected from:

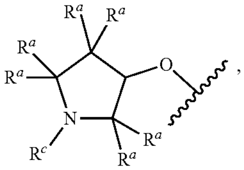

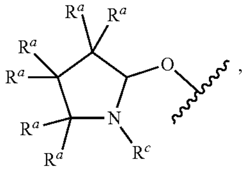

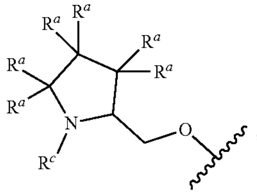

and

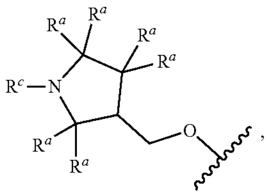

wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

A144. The compound of embodiment A143, wherein $R^1$ is selected from

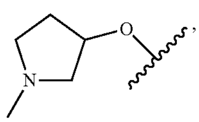

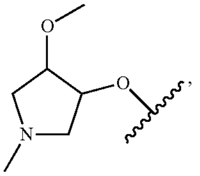

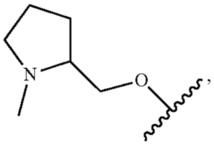

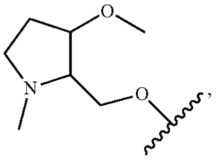

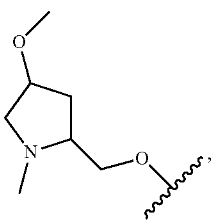

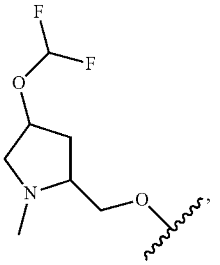

-continued

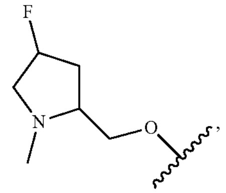

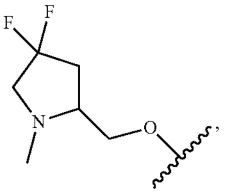

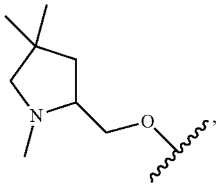

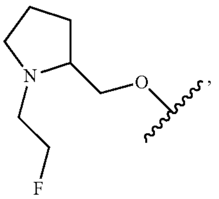

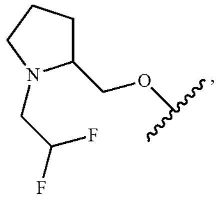

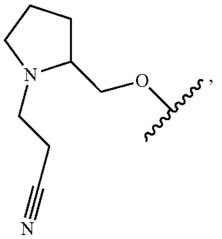

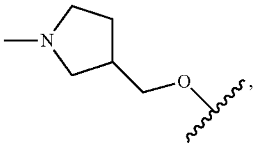

and

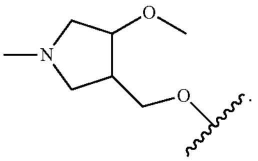.

A145. The compound of embodiment A143, wherein $R^1$ is selected from

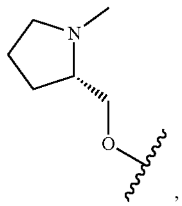,

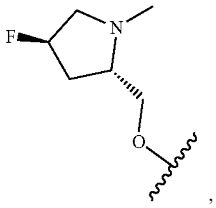,

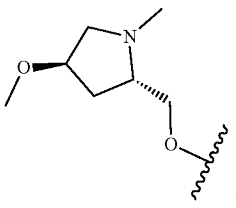, and

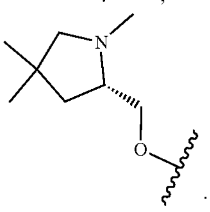.

A146. The compound of any one of embodiments A122-A145, wherein $R^2$ is H.

A147. The compound of any one of embodiments A122-A146, wherein $R^3$ is a 4-6 membered heterocycle that is substituted with one or more E and 0-4 $R^{10}$, wherein the heterocycle includes a single heteroatom that is N.

A148. The compound of embodiment A147, wherein $R^3$ is selected from

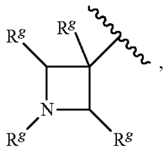
,
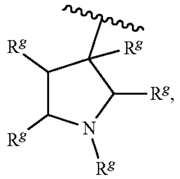

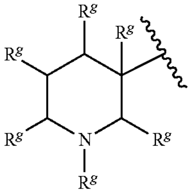
, and
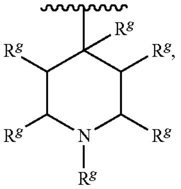

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A149. The compound of embodiment A148, wherein $R^3$ is selected from

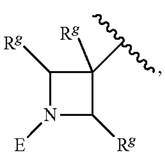
,
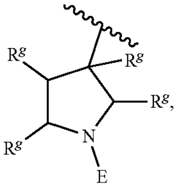

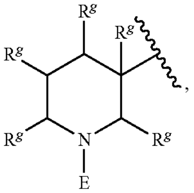
, and
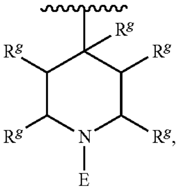

wherein each $R^g$ is independently selected from $C_{1-6}$alkyl and H, wherein any $C_{1-6}$alkyl is unsubstituted or substituted with one or more $R^{20}$.

A150. The compound of embodiment A149, wherein each $R^g$ is H.

A151. The compound of any one of embodiments A122-A145, wherein $R^2$ and $R^3$, together with the atom to which they are attached, form a 4-8 membered heterocycle that is substituted with one or more E and 0-4 $R^{11}$.

A152. The compound of embodiment A151, wherein $R^2$ and $R^3$, together with the atom to which they are attached, form a piperazinyl ring that is substituted with one or more E and 0-4 $R^{11}$.

A153. The compound of embodiment A152, wherein $R^2$ and $R^3$, together with the atom to which they are attached, form the structure

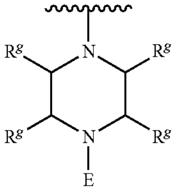
or
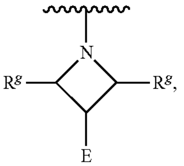

wherein each $R^g$ is independently selected from $C_{1-6}$alkyl and H, wherein any $C_{1-6}$alkyl is unsubstituted or substituted with one or more $R^{20}$.

A154. The compound of embodiment A153, wherein each $R^g$ is H.

A155. The compound of embodiment A153, wherein $R^2$ and $R^3$, together with the atom to which they are attached, form the structure

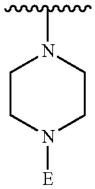
,
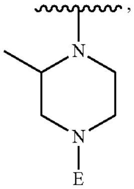
,
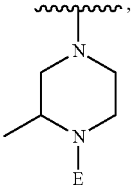
,

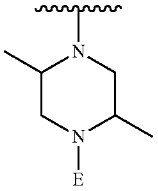
,
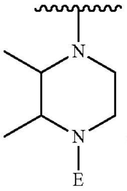
,
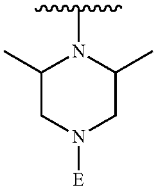
,

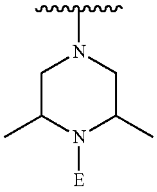
,
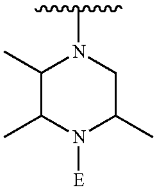
,
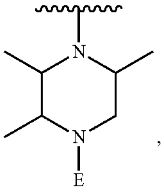
, or

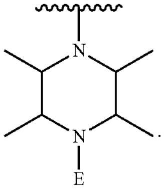
.

A156. The compound of embodiment A151, wherein $R^2$ and $R^3$, together with the atom to which they are attached, form a 4-8 membered bicyclic heterocycle comprising a fused ring system that is substituted with one or more E and 0-4 $R^{11}$.

A157. The compound of embodiment A156, wherein $R^2$ and $R^3$, together with the atom to which they are attached, form a structure selected from:

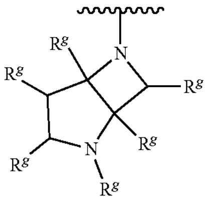
and
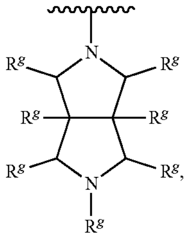

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A158. The compound of embodiment A157, wherein $R^2$ and $R^3$, together with the atom to which they are attached, form a structure selected from:

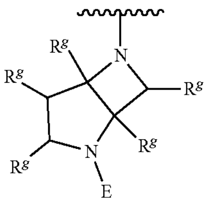
and
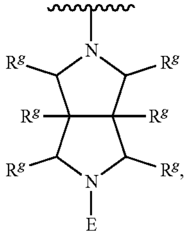

wherein each $R^g$ is independently selected from $C_{1-6}$alkyl and H, wherein any $C_{1-6}$alkyl is unsubstituted or substituted with one or more $R^{20}$.

A159. The compound of embodiment A158, wherein $R^2$ and $R^3$, together with the atom to which they are attached, form the structure

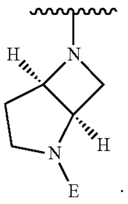

A160. The compound of any one of embodiments A122-A159, wherein $R^4$ is H.

A161. The compound of any one of embodiments A122-A160, wherein $R^6$ is selected from

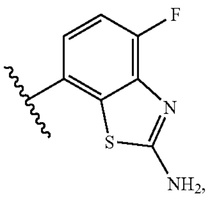
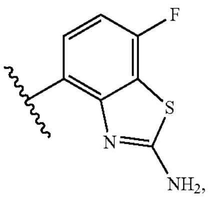

-continued

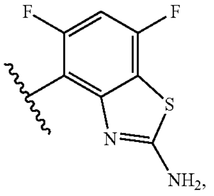
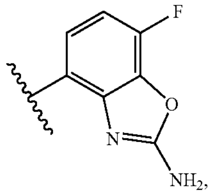
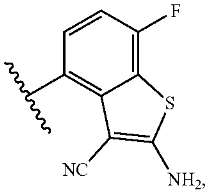
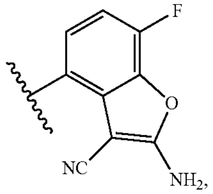
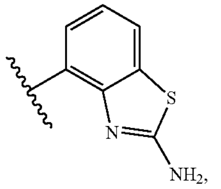
and
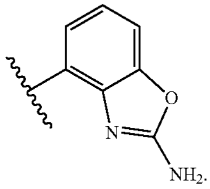

A162. The compound of any one of embodiments A122-A161, wherein $R^7$ is a halogen.

A163. The compound of embodiment A162, wherein $R^7$ is F.

A164. The compound of any one of embodiments A122-A163, wherein each E is independently selected from

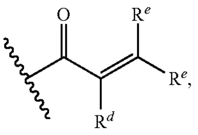
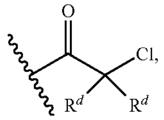
and
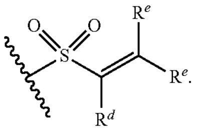

A165. The compound of embodiment A164, wherein each E is

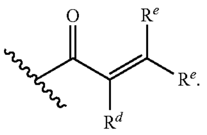

A166. The compound of embodiment A165, wherein each $R^d$ and $R^e$ is H.

A167. A compound according to Formula IE:

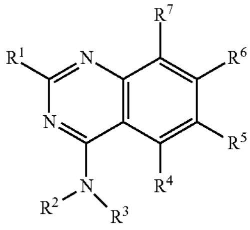

(IE)

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is H, —$OR^{12}$, and $C_{1-6}$alkyl, wherein any $C_{1-6}$alkyl is unsubstituted or substituted with one or more $R^{13}$;

$R^5$ is selected from halogen, $C_{1-6}$alkyl, a 3-6 membered carbocycle, and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$;

$R^6$ is a bicyclic heteroaryl substituted with one or more $R^{15}$;

$R^7$ is —OH;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{15}$ is independently selected from halogen, $N(R^{12})_2$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^{22}$ is independently selected from $C_{1-6}$ alkyl, $C_{2-6}$ alkenyl, and H;

E is selected from

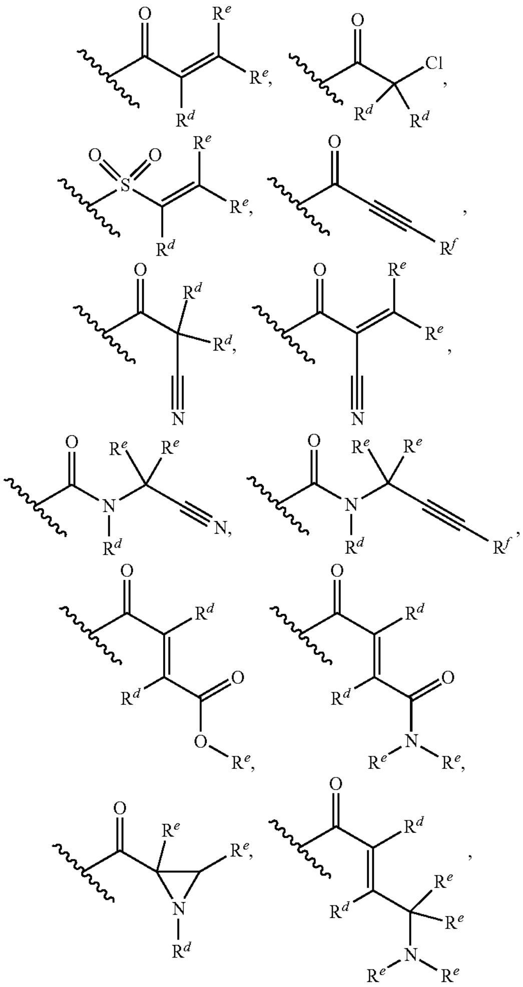

and CN;

each $R^d$ and $R^e$ is independently selected from halogen, $C_{1-6}$ alkyl, and H; and each $R^f$ is independently selected from $C_{1-6}$ alkyl and H.

A168. The compound of embodiment A167, wherein $R^1$ is H.

A169. The compound of embodiment A167 or A168, wherein $R^2$ is H.

A170. The compound of any one of embodiments A167-A169, wherein $R^3$ is selected from $C_{1-6}$ alkyl that is substituted with —$N(R^{12})(E)$.

A171. The compound of embodiment A170, wherein $R^3$ is selected from $C_2$ alkyl that is substituted with —$N(R^{12})(E)$.

A172. The compound of embodiment A171, wherein $R^3$ is selected from $C_2$ alkyl that is substituted with —N(H)(E).

A173. The compound of embodiment A167 or A168, wherein $R^2$ and $R^3$, together with the atom to which they are attached, form a 4-8 membered heterocycle that is substituted with one or more E and 0-4 $R^{11}$.

A174. The compound of embodiment A173, wherein $R^2$ and $R^3$, together with the atom to which they are attached, form a piperazinyl ring that is substituted with one or more E and 0-4 $R^{11}$.

A175. The compound of embodiment A174, wherein $R^2$ and $R^3$, together with the atom to which they are attached, form the structure

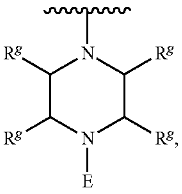

wherein each $R^g$ is independently selected from $C_{1-6}$alkyl and H, wherein any $C_{1-6}$alkyl is unsubstituted or substituted with one or more $R^{20}$.

A176. The compound of embodiment A175, wherein each $R^g$ is H.

A177. The compound of embodiment A175, wherein $R^2$ and $R^3$, together with the atom to which they are attached, form the structure

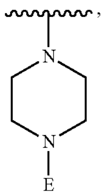, 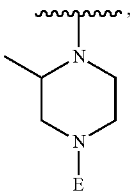, 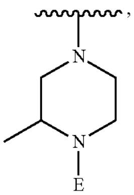, 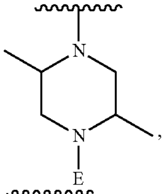, 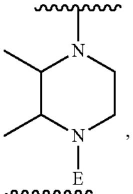, 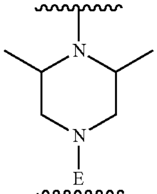, 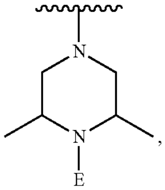, 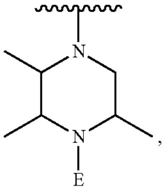, 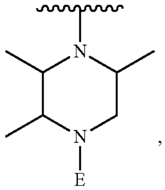, or 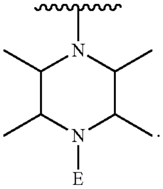.

A178. The compound of any one of embodiments A167-A177, wherein $R^4$ is Ha

A179. The compound of any one of embodiments A167-A178, wherein $R^5$ is a halogen.

A180. The compound of embodiment A179, wherein $R^5$ is Cl.

A181. The compound of any one of embodiments A167-A180, wherein $R^6$ is selected from

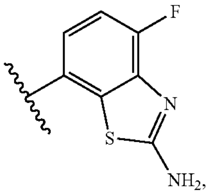 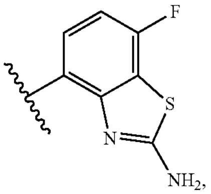 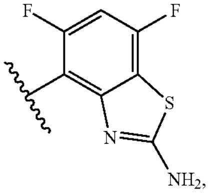 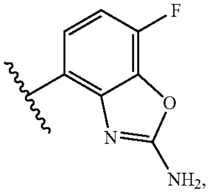 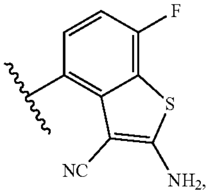 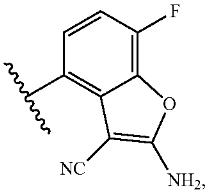 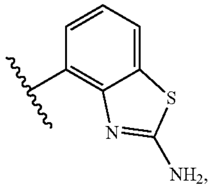 and 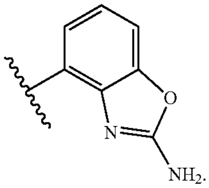

A182. The compound of any one of embodiments A167-A181, wherein each E is independently selected from

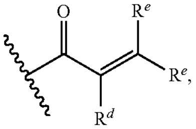 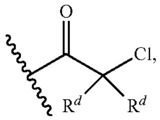 and 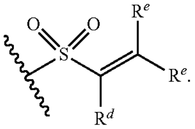

A183. The compound of embodiment A182, wherein each E is

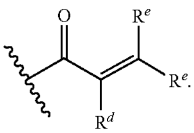

A184. The compound of embodiment A183, wherein each $R^d$ and $R^e$ is H.

A185. A compound according to Formula IIA:

(IIA)

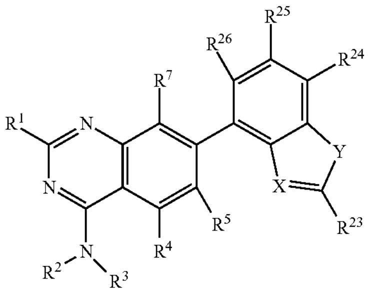

or a salt (e.g., pharmaceutically acceptable salt), ester, tautomer prodrug, zwitterionic form, or stereoisomer thereof, wherein.

$R^1$ is selected from

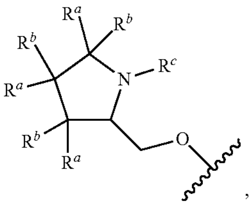
,
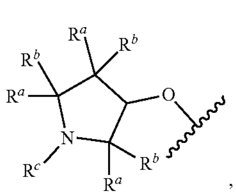
, and a 4-6 membered heterocycle comprising a nitrogen atom, wherein a heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^2)(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is H, —$OR^{12}$, and $C_{1-6}$alkyl, wherein any $C_{1-6}$alkyl is unsubstituted or substituted with one or more $R^{13}$;

$R^5$ is selected from halogen, $C_{1-6}$alkyl, $C_{2-6}$alkynyl, —$OR^{12}$, a 3-6 membered carbocycle, and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$;

$R^7$ is selected from halogen, —$OR^X$, —CN, and H;

each $R^{10}$ is independently selected from $C_{1-6}$alkyl, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$ and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^X$ is independently selected from $C_{1-6}$ alkyl, a 3-6 membered carbocycle, and H;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

E is selected from

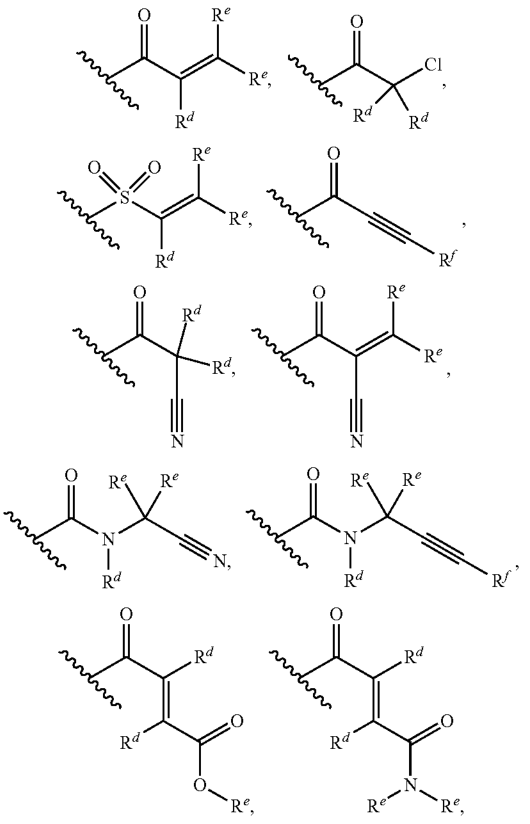

-continued

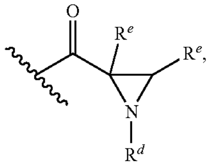

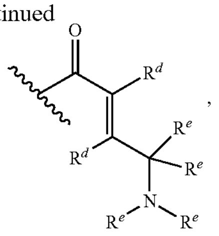

and CN;

each $R^d$ and $R^e$ is independently selected from halogen, $C_{1-6}$ alkyl, and H; and each $R^f$ is independently selected from $C_{1-6}$ alkyl and H.

A186. The compound of embodiment A185, wherein $R^1$ is

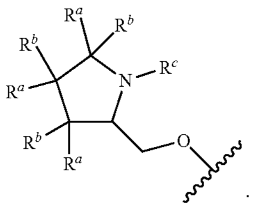

A187. The compound of embodiment A186, wherein $R^1$ is selected from:

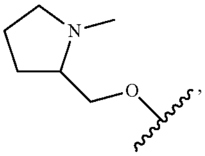

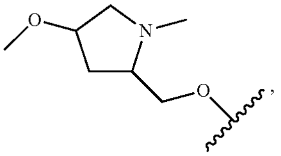

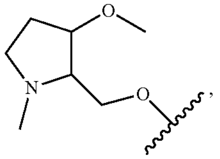

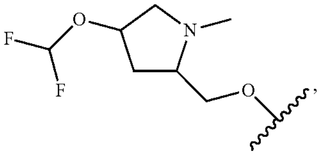

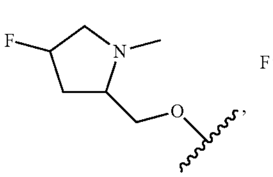

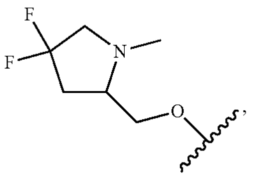

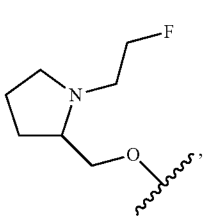

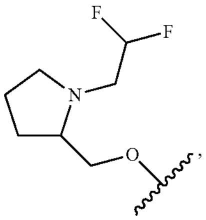

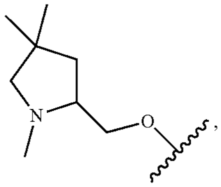

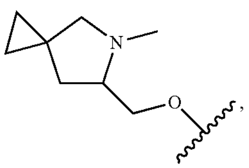

and

-continued

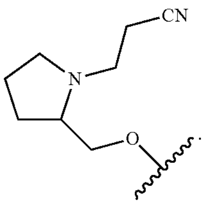

A188. The compound of embodiment A186, wherein $R^1$ is selected from

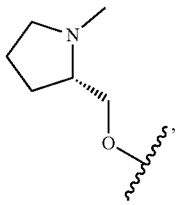

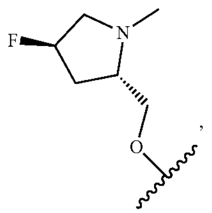

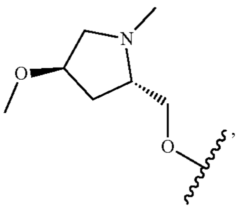

and

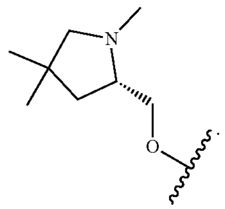

A189. The compound of embodiment A185, wherein $R^1$ is

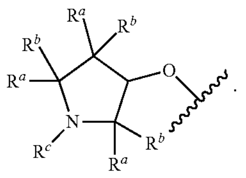

A190. The compound of embodiment A189, wherein $R^1$ is

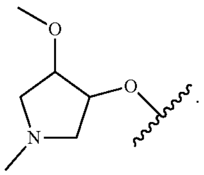 [SMILES: *OC1CN(C)CC1OC]

A191. The compound of embodiment A185, wherein $R^1$ is a 4-6 membered heterocycle comprising a nitrogen atom, and H, wherein the heterocycle is unsubstituted or substituted with one or more $R^{16}$.

A192. The compound of embodiment A191, wherein $R^1$ is

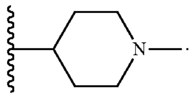

A193. The compound of any one of embodiments A185-A192, wherein $R^2$ is selected from H, $C_{1-6}$ alkyl, and a 3-6 membered carbocycle.

A194. The compound of embodiment A193, wherein $R^2$ is H.

A195. The compound of any one of embodiments A185-A194, wherein $R^3$ is selected from $C_{1-6}$ alkyl that is substituted with —N($R^{12}$)(E).

A196. The compound of embodiment A195, wherein $R^3$ is selected from $C_{1-6}$ alkyl that is substituted with —N(H)(E).

A197. The compound of any one of embodiments A185-A194, wherein $R^3$ is a 4-6 membered heterocycle that is substituted with one or more E and 0-4 $R^{10}$.

A198. The compound of embodiment A197, wherein $R^3$ is a 4-6 membered heterocycle that is substituted with one or more E and 0-4 $R^{10}$, wherein the heterocycle includes a single heteroatom that is N.

A199. The compound of embodiment A198, wherein $R^3$ is selected from

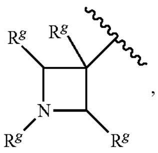
,
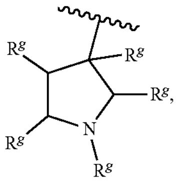

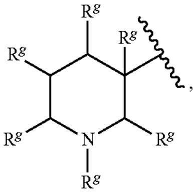
, and
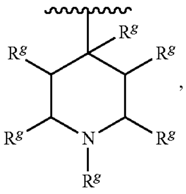
,

Wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A200. The compound of embodiment A199, wherein $R^3$ is selected from

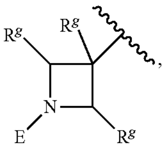
,
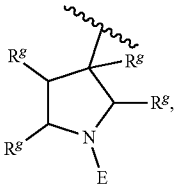

-continued

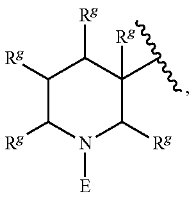
, and
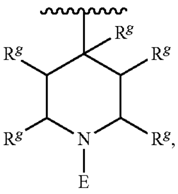

wherein each $R^g$ is independently selected from $C_{1-6}$alkyl and H, wherein any $C_{1-6}$alkyl is unsubstituted or substituted with one or more $R^{20}$.

A201. The compound of embodiment A200, wherein each $R^g$ is H.

A202. The compound of any one of embodiments A185-A192, wherein $R^2$ and $R^3$, together with the atom to which they are attached, form a 4-8 membered heterocycle that is substituted with one or more E and 0-4 $R^{11}$.

A203. The compound of embodiment A202, wherein $R^2$ and $R^3$, together with the atom to which they are attached, form a piperazinyl ring that is substituted with one or more E and 0-4 $R^{11}$.

A204. The compound of embodiment A203, wherein $R^2$ and $R^3$, together with the atom to which they are attached, form the structure

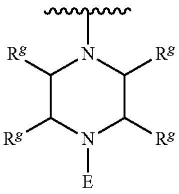
, wherein each $R^g$ is independently selected from $C_{1-6}$alkyl and H, wherein any $C_{1-6}$alkyl is unsubstituted or substituted with one or more $R^{20}$.

A205. The compound of embodiment A204, wherein each $R^g$ is H.

A206. The compound of embodiment A204, wherein $R^2$ and $R^3$, together with the atom to which they are attached, form the structure:

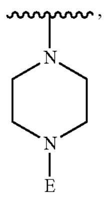
,
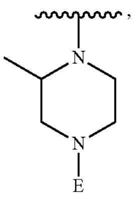
,
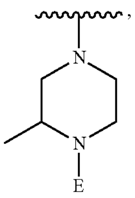
,
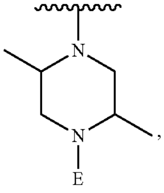
,
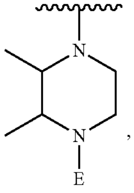
,
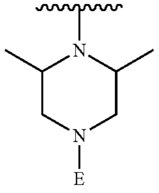
, -continued

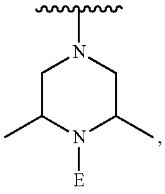
,
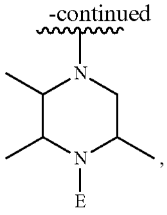
,
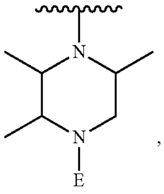
, or
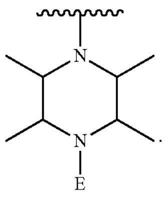
.

A207. The compound of embodiment A202, wherein $R^2$ and $R^3$, together with the atom to which they are attached, form a 4-8 membered bicyclic heterocycle comprising a fused ring system that is substituted with one or more E and 0-4 $R^{11}$.

A208. The compound of embodiment A207, wherein $R^2$ and $R^3$, together with the atom to which they are attached, form a structure selected from:

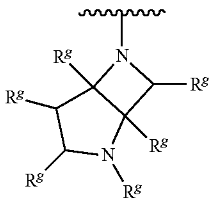
and
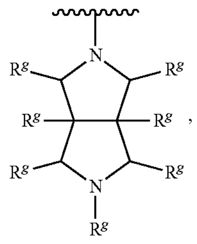
, wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A209. The compound of embodiment A208, wherein $R^2$ and $R^3$, together with the atom to which they are attached, form a structure selected from:

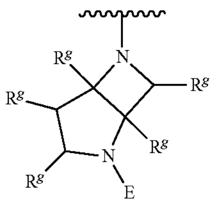
and
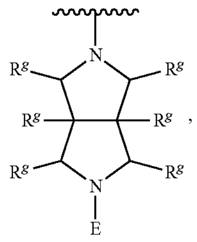
, wherein each $R^g$ is independently selected from $C_{1-6}$alkyl and H, wherein any $C_{1-6}$alkyl is unsubstituted or substituted with one or more $R^2$.

A210. The compound of embodiment A209, wherein $R^2$ and $R^3$, together with the atom to which they are attached, form the structure

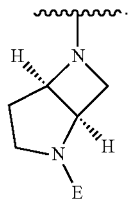
.

A211. The compound of embodiment A202, wherein $R^2$ and $R^3$, together with the atom to which they are attached, form a 4-8 membered heterocycle comprising a spirocyclic ring system that is substituted with one or more E and 0-4 $R^{11}$.

A212. The compound of embodiment A211, wherein $R^2$ and $R^3$, together with the atom to which they are attached, form a structure selected from:

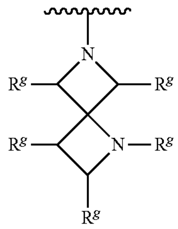
and
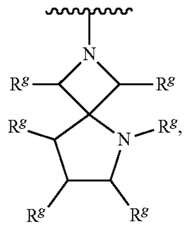

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A213. The compound of any one of embodiments A185-A212, wherein $R^4$ is H.

A214. The compound of any one of embodiments A185-A213, wherein $R^5$ is a halogen.

A215. The compound of embodiment A214, wherein $R^5$ is Cl.

A216. The compound of any one of embodiments A185-A213, wherein $R^5$ is selected from $C_{1-6}$alkyl that is unsubstituted or substituted with one or more $R^{13}$.

A217. The compound of embodiment A216, wherein $R^5$ is selected from $C_{1-2}$alkyl that is unsubstituted or substituted with one or more $R^{13}$.

A218. The compound of embodiment A217, wherein $R^5$ is selected from $-CF_2H$, $-CF_3$, $-CH_2CN$, and $-CH_2CH_3$.

A219. The compound of any one of embodiments A185-A213, wherein $R^5$ is selected from $-OR^{12}$.

A220. The compound of embodiment A219, wherein $R^5$ is $-OCF_3$.

A221. The compound of any one of embodiments A185-A213, wherein $R^5$ is selected from a 3-6 membered carbocycle that is unsubstituted or substituted with one or more $R^{14}$.

A222. The compound of embodiment A221, wherein $R^5$ is selected from selected from a cyclobutyl that is unsubstituted or substituted with one or more $R^{14}$.

A223. The compound of embodiment A221, wherein $R^5$ is selected from selected from a phenyl that is unsubstituted or substituted with one or more $R^{14}$.

A224. The compound of any one of embodiments A185-A213, wherein $R^5$ is selected from a 3-6 membered heterocycle that is unsubstituted or substituted with one or more $R^{14}$.

A225. The compound of embodiment A224, wherein $R^5$ is selected from a 5-6 membered heterocycle that includes one or two heteroatoms selected from O and N is unsubstituted or substituted with one or more $R^{14}$.

A226. The compound of embodiment A225, wherein $R^5$ is selected from furan, pyridine, and pyrazole that is unsubstituted or is substituted with one or more $R^{14}$.

A227. The compound of embodiment A225 or A226, wherein $R^5$ is selected from

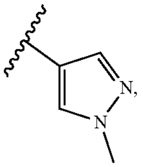 , 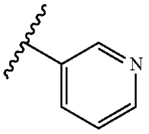 , and 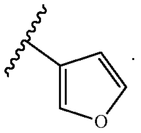 .

A228. The compound of any one of embodiments A185-A227, wherein $R^7$ is a halogen.

A229. The compound of embodiment A228, wherein $R^7$ is F.

A230. The compound of any one of embodiments A185-A227, wherein $R^7$ is

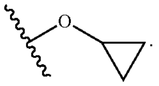

A231. The compound of any one of embodiments A185-A230, wherein X is N.

A232. The compound of any one of embodiments A185-A231, wherein Y is S.

A233. The compound of any one of embodiments A185-A232, wherein $R^{23}$ is selected from —$N(R^{12})_2$.

A234. The compound of embodiment A233, wherein $R^{23}$ is —$NH_2$.

A235. The compound of any one of embodiments A185-A234, wherein $R^{24}$ is a halogen.

A236. The compound of embodiment A235, wherein $R^{24}$ is F.

A237. The compound of any one of embodiments A185-A236, wherein $R^{25}$ and $R^{26}$ are H.

A238. The compound of any one of embodiments A185-A237, wherein each E is independently selected from

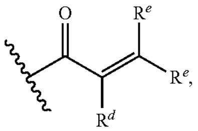

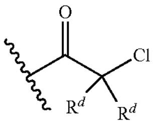 , and 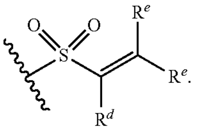

A239. The compound of embodiment A238, wherein each E is

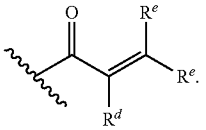

A240. The compound of embodiment A239, wherein each $R^a$ and $R^c$ is H.

A241. A compound according to Formula IIB:

(IIB)

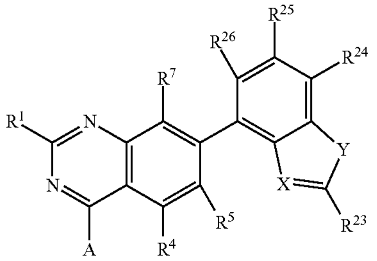

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

A is selected from:

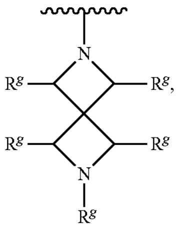 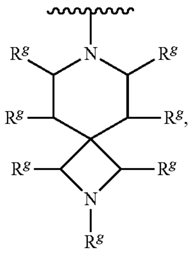

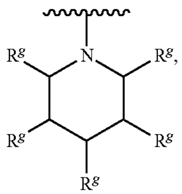 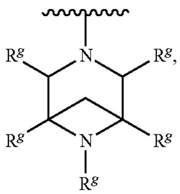

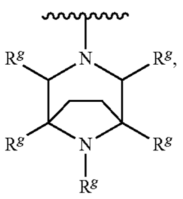 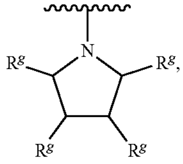 and

-continued

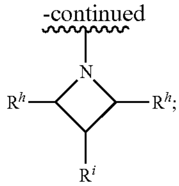

$R^4$ is H, —$OR^{12}$, and $C_{1-6}$alkyl, wherein any $C_{1-6}$alkyl is unsubstituted or substituted with one or more $R^{13}$;

$R^5$ is selected from halogen, $C_{1-6}$alkyl, $C_{2-6}$alkynyl, —$OR^{12}$, a 3-6 membered carbocycle, and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —$N(R^2)_2$, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, and —$OR^{12}$, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$ and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^g$ is independently selected from $C_{1-6}$alkyl, H, and E, wherein at least one $R^g$ is E, and wherein any $C_{1-6}$alkyl is unsubstituted or substituted with one or more $R^{20}$;

each $R^h$ is independently selected from $C_{1-6}$alkyl and H;

$R^i$ is selected from —$N(R^{12})(E)$, E, and —($C_{1-6}$alkyl)E;

each $R^a$ and $R^b$ are each independently selected from halogen, —$OR^2$, $C_{1-6}$alkyl, and H, wherein any $C_{1-6}$alkyl is unsubstituted or is substituted with one or more $R^{13}$;

E is selected from

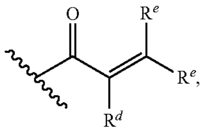

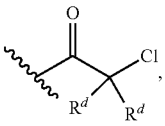

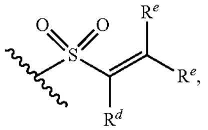

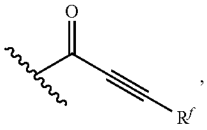

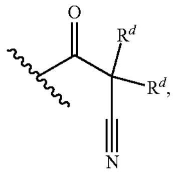

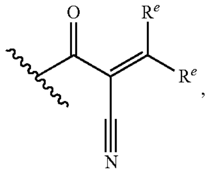

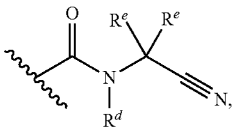

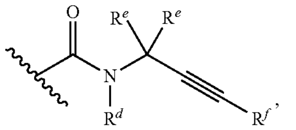

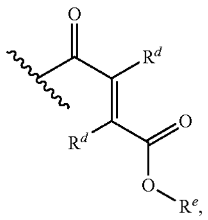

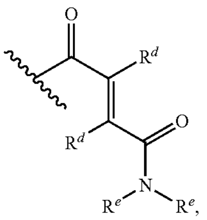

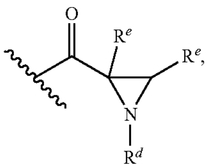

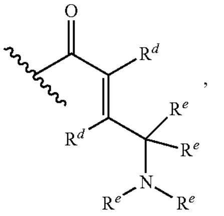

and CN;

each $R^d$ and $R^e$ is independently selected from halogen, $C_{1-6}$ alkyl, and H; and each $R^f$ is independently selected from $C_{1-6}$ alkyl and H.

A242. The compound of embodiment A241, wherein A is selected from

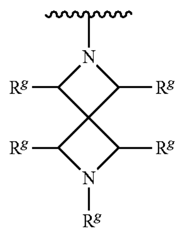

and

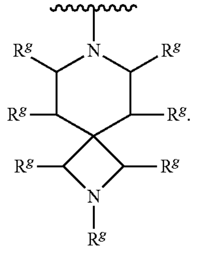

A243. The compound of embodiment A242, wherein A is selected from

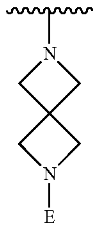

and

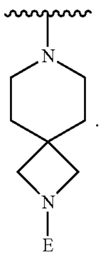

A244. The compound of embodiment A241, wherein A is selected from

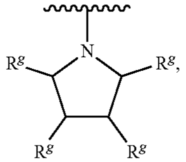

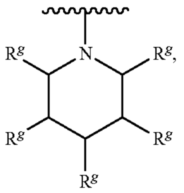

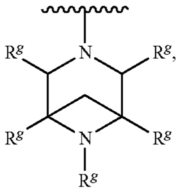

and

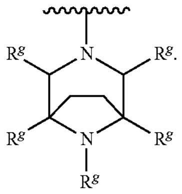

A245. The compound of embodiment A244, wherein A is selected from

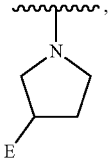

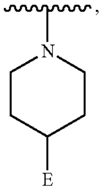

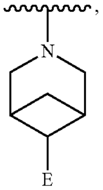

and

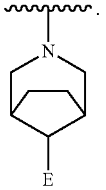

A246. The compound of embodiment A241, wherein A is

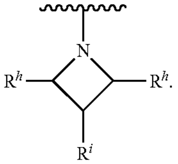

A247. The compound of embodiment A246, wherein A is selected from

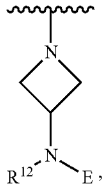

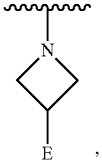

and

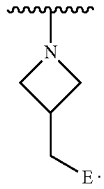

A248. The compound of any one of embodiments A241-A247, wherein $R^1$ is H.

A249. The compound of any one of embodiments A241-A247, wherein $R^1$ is selected from

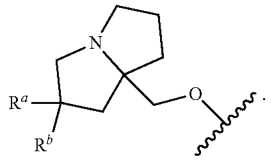

A250. The compound of embodiment A249, wherein $R^a$ is a halogen and/or $R^b$ is a halogen.

A251. The compound of embodiment A249, wherein $R^1$ is selected from

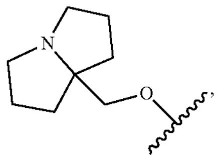

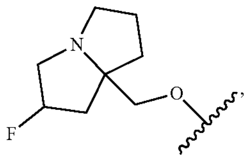

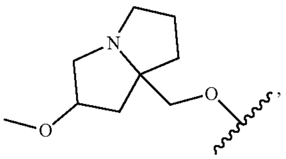

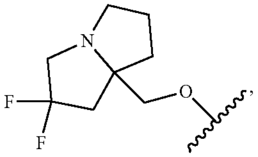

and

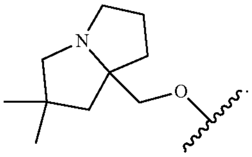

A252. The compound of embodiment A249, wherein $R^1$ is selected from

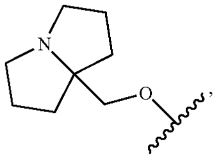

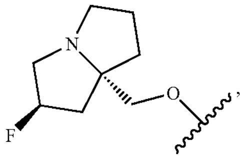

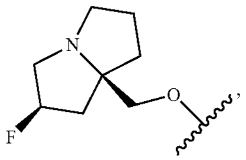

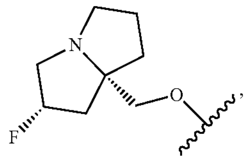

-continued

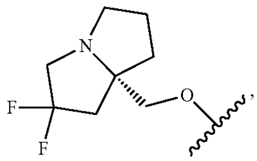
,
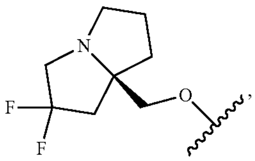
,
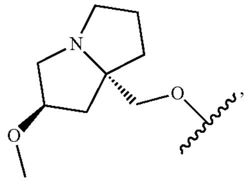
,
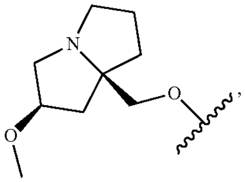
,
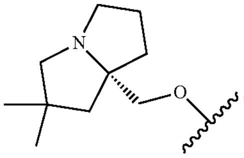
, and
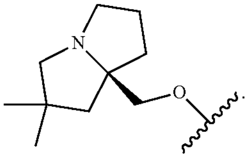
.

A253. The compound of any one of embodiments A241-A247, wherein $R^1$ is

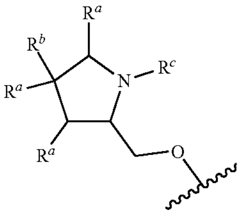
, wherein each $R^a$ and $R^b$ is independently selected from halogen, $C_{1-6}$ alkyl, —$OR^{12}$, and H; and $R^c$ is selected from $C_{1-6}$ alkyl, wherein any $C_{1-6}$ alkyl is unsubstituted or is substituted with one or more $R^{13}$.

A254. The compound of embodiment A253, wherein $R^1$ is selected from:

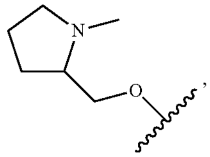
,
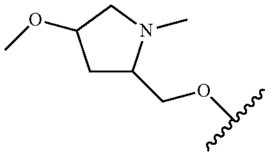
,
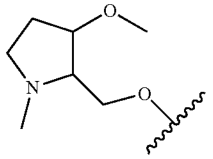
,
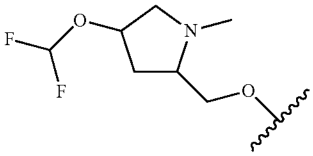
,
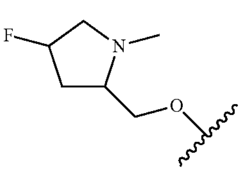
,
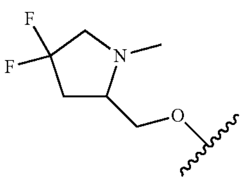
, -continued

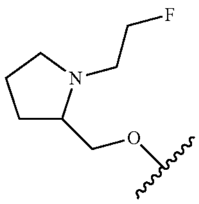
,
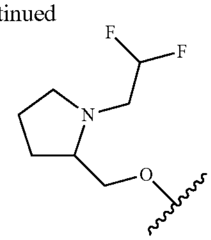
,
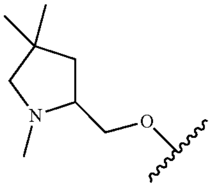
, and
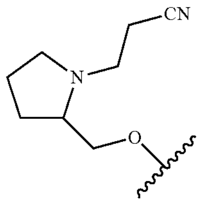
.

A255. The compound of embodiment A254, wherein $R^1$ is selected from

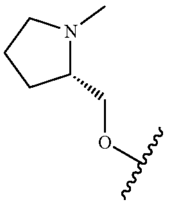
,
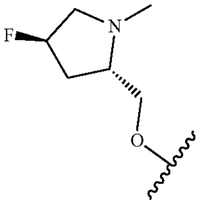
,
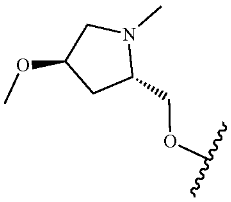
, and
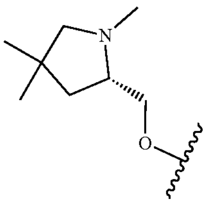
.

A256. The compound of any one of embodiments A241-A255, wherein $R^4$ is H.

A257. The compound of any one of embodiments A241-A256, wherein $R^5$ is a halogen.

A258. The compound of embodiment A257, wherein $R^5$ is Cl.

A259. The compound of any one of embodiments A241-A258, wherein $R^7$ is a halogen.

A260. The compound of embodiment A259, wherein $R^7$ is F.

A261. The compound of any one of embodiments A241-A260, wherein X is N.

A262. The compound of any one of embodiments A241-A261, wherein Y is S.

A263. The compound of any one of embodiments A241-A262, wherein $R^{23}$ is selected from —$N(R^{12})_2$.

A264. The compound of embodiment A263, wherein $R^{23}$ is —$NH_2$.

A265. The compound of any one of embodiments A241-A264, wherein $R^{24}$ is a halogen.

A266. The compound of embodiment A265, wherein $R^{24}$ is F.

A267. The compound of any one of embodiments A241-A266, wherein $R^{25}$ and $R^{26}$ are H.

A268. The compound of any one of embodiments A241-A267, wherein each E is independently selected from

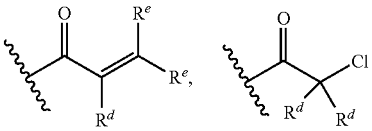

and

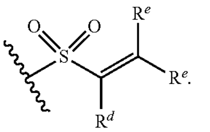

A269. The compound of embodiment A268, wherein each E is

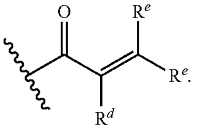

A270. The compound of embodiment A269, wherein each $R^d$ and $R^e$ is H.

A271. A compound according to Formula IIC:

(IIC)

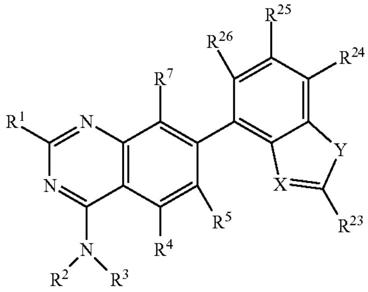

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is —$OR^Y$, wherein $R^Y$ is selected from $C_{1-6}$ alkyl;

$R^5$ is selected from halogen and H;

$R^7$ is selected from halogen, —$OR^{12}$, —CN, and H;

each $R^{10}$ is independently selected from $C_{1-6}$alkyl, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$ and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

E is selected from

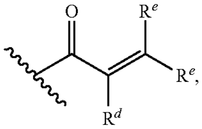
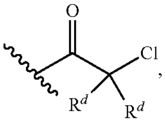
,
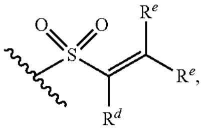
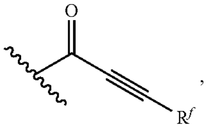
,
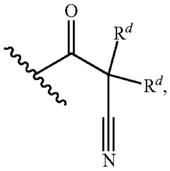
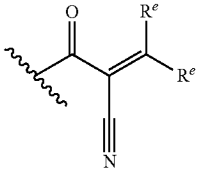
,
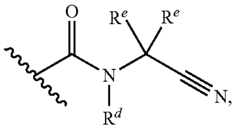
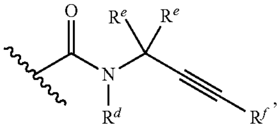
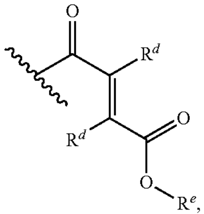
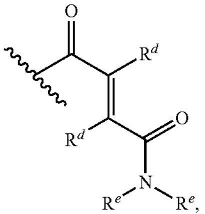
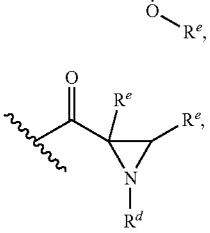
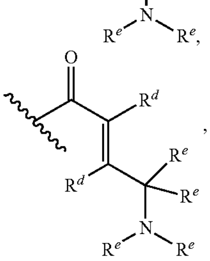
, and CN;

each $R^d$ and $R^e$ is independently selected from halogen, $C_{1-6}$ alkyl, and H; and each $R^f$ is independently selected from $C_{1-6}$ alkyl and H.

A272. The compound of embodiment A271, wherein $R^4$ is —$OCH_3$.

A273. The compound of embodiment A271 or A272, wherein $R^1$ is H.

A274. The compound of any one of embodiments A271-A273, wherein $R^2$ is H.

A275. The compound of any one of embodiments A271-A273, wherein $R^2$ and $R^3$, together with the atom to which they are attached, form a 4-8 membered heterocycle that is substituted with one or more E and 0-4 $R^{11}$.

A276. The compound of embodiment A275, wherein $R^2$ and $R^3$, together with the atom to which they are attached, form a piperazinyl ring that is substituted with one or more E and 0-4 $R^{11}$.

A277. The compound of embodiment A276, wherein $R^2$ and $R^3$, together with the atom to which they are attached, form the structure

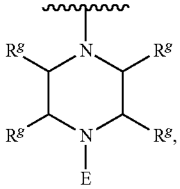

wherein each $R^g$ is independently selected from $C_{1-6}$alkyl and H, wherein any $C_{1-6}$alkyl is unsubstituted or substituted with one or more $R^{20}$.

A278. The compound of embodiment A277, wherein each $R^g$ is H.

A279. The compound of embodiment A277, wherein $R^2$ and $R^3$, together with the atom to which they are attached, form the structure:

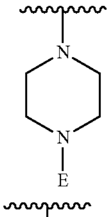, 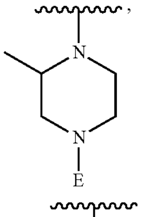, 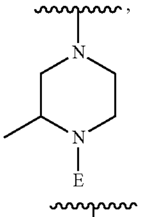, 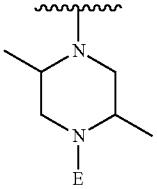, 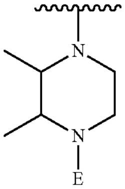, 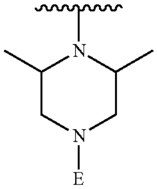, 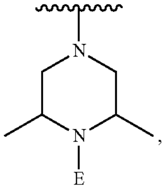, 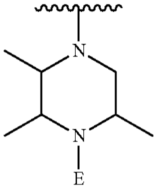, 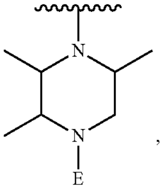, or -continued

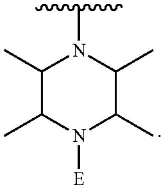.

A280. The compound of any one of embodiments A271-A279, wherein $R^5$ is H.

A281. The compound of any one of embodiments A271-A279, wherein $R^5$ is a halogen.

A282. The compound of embodiment A281, wherein $R^5$ is Cl.

A283. The compound of any one of embodiments A271-A282, wherein $R^7$ is a halogen.

A284. The compound of embodiment A283, wherein $R^7$ is F.

A285. The compound of any one of embodiments A271-A284, wherein X is N.

A286. The compound of any one of embodiments A271-A285, wherein Y is S.

A287. The compound of any one of embodiments A271-A286, wherein $R^{23}$ is selected from —$N(R^{12})_2$.

A288. The compound of embodiment A287, wherein $R^{23}$ is —$NH_2$.

A289. The compound of any one of embodiments A271-A288, wherein $R^{24}$ is a halogen.

A290. The compound of embodiment A289, wherein $R^{24}$ is F.

A291. The compound of any one of embodiments A271-A290, wherein $R^{25}$ and $R^{26}$ are H.

A292. The compound of any one of embodiments A271-A291, wherein each E is independently selected from

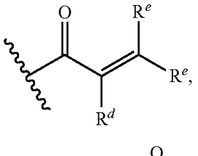, 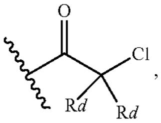, and

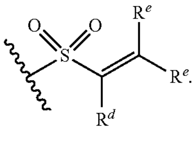.

A293. The compound of embodiment A292, wherein each E is

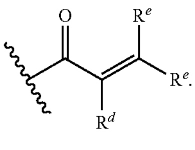.

A294. The compound of embodiment A293, wherein each $R^d$ and $R^e$ is H.

A295. A compound according to Formula IID:

(IIA)

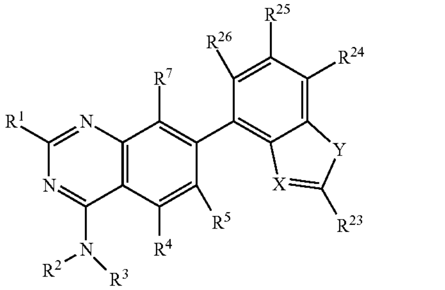

or a salt (e.g., pharmaceutically acceptable salt), ester, tautomer, prodrug, zwitterionic form, or stereoisomer thereof, wherein:

$R^1$ is selected from —$OR^8$, a 4-6 membered heterocycle comprising a nitrogen atom, and H, wherein a heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is H, —$OR^{12}$, and $C_{1-6}$alkyl, wherein any $C_{1-6}$alkyl is unsubstituted or substituted with one or more $R^{13}$;

$R^5$ is selected from $C_{1-6}$alkyl, —$OR^{12}$, a 3-6 membered carbocycle, and a 3-6 membered heterocycle, wherein any $C_{1-6}$alkyl is unsubstituted or substituted with one or more $R^{13}$, and wherein any carbocycle and heterocycle is unsubstituted or substituted with one or more $R^{14}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ or $R^b$, and wherein an alkyl moiety of any alkylheterocycle is selected from $C_{1-6}$ alkyl;

each $R^{10}$ is independently selected from $C_{1-6}$alkyl, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, $N(R^{12})_2$, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, and —$OR^{12}$, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{23}$ is selected from —$N(R^{12})_2$ and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$;

E is selected from

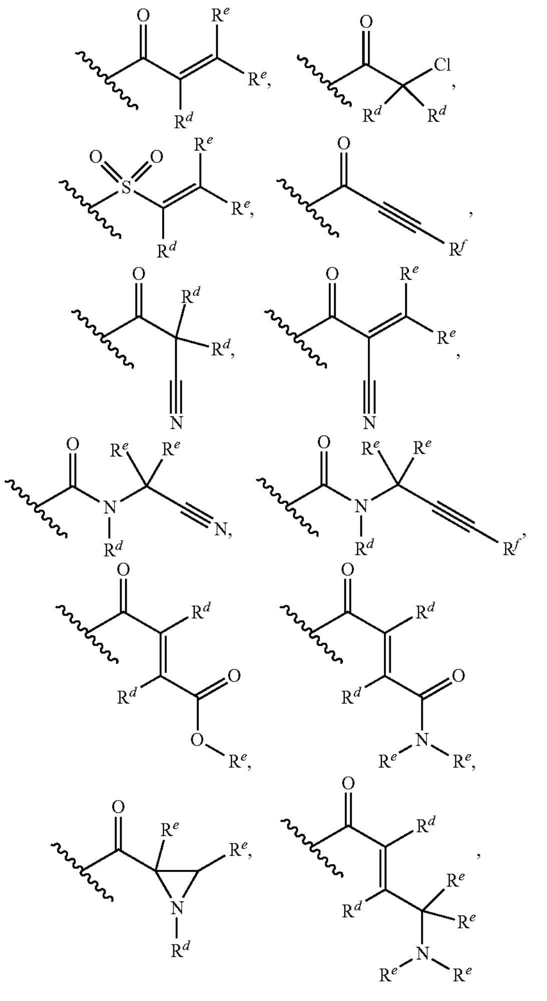

and CN;

each $R^d$ and $R^c$ is independently selected from halogen, $C_{1-6}$ alkyl, and H; and each $R^f$ is independently selected from $C_{1-6}$ alkyl and H.

A296. The compound of embodiment A295, wherein $R^5$ is selected from $C_{1-6}$alkyl that is unsubstituted or is substituted with one or more $R^{13}$.

A297. The compound of embodiment A296, wherein $R^5$ is selected from $C_{1-2}$alkyl that is unsubstituted or is substituted with one or more $R^{13}$.

A298. The compound of embodiment A297, wherein $R^5$ is selected from —$CF_2H$, —$CF_3$, —$CH_2CN$, and —$CH_2CH_3$.

A299. The compound of embodiment A295, wherein $R^8$ is selected from —$OR^{12}$, wherein $R^{12}$ is selected from $C_{1-6}$alkyl that is unsubstituted or is substituted with one or more halogens.

A300. The compound of embodiment A299, wherein $R^5$ is selected from —$OCF_3$ and —$OCH_3$.

A301. The compound of embodiment A295, wherein $R^5$ is selected from a 3-6 membered carbocycle that is unsubstituted or substituted with one or more $R^{14}$.

A302. The compound of embodiment A301, wherein $R^5$ is selected from selected from a cyclopropyl or cyclobutyl that is unsubstituted or substituted with one or more $R^{14}$.

A303. The compound of embodiment A301, wherein $R^5$ is selected from selected from a phenyl that is unsubstituted or substituted with one or more $R^{14}$.

A304. The compound of embodiment A295, wherein $R^5$ is selected from a 3-6 membered heterocycle that is unsubstituted or substituted with one or more $R^{14}$.

A305. The compound of embodiment A304, wherein $R^5$ is selected from a 5-6 membered heterocycle that includes one or two heteroatoms selected from O and N is unsubstituted or substituted with one or more $R^{14}$.

A306. The compound of embodiment A305, wherein $R^5$ is selected from furan, pyridine, and pyrazole that is unsubstituted or is substituted with one or more $R^{14}$.

A307. The compound of embodiment A305 or A306, wherein $R^5$ is selected from

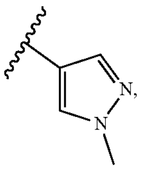 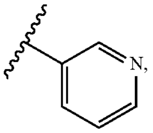 and 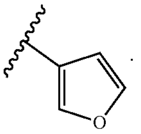.

A308. The compound ofany one of embodiments A295-A307, wherein $R^1$ is H.

A309. The compound of any one of embodiments A295-A307, wherein $R^1$ is selected from

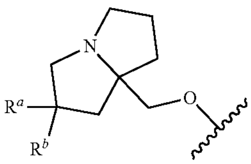, wherein $R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$.

A310. The compound of embodiment A309, wherein $R^a$ is a halogen and/or $R^b$ is a halogen.

A311. The compound of embodiment A309, wherein $R^1$ is selected from:

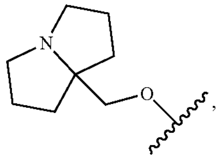, 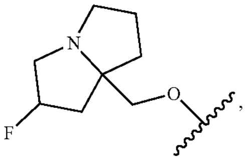,

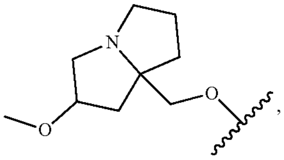,

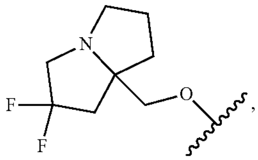, and 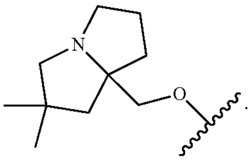.

A312. The compound of embodiment A309, wherein $R^1$ is selected from:

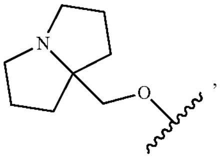, 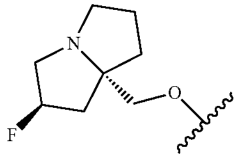,

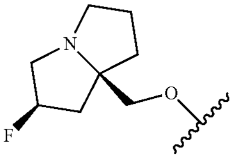, 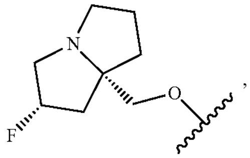,

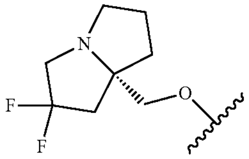, 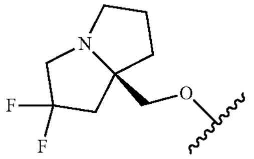,

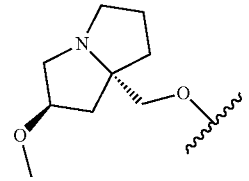, 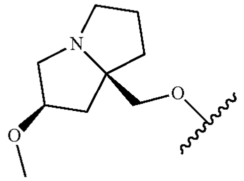,

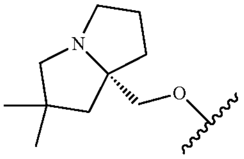, and 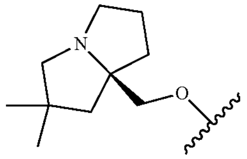.

A313. The compound of any one of embodiments A295-A307, wherein $R^1$ is

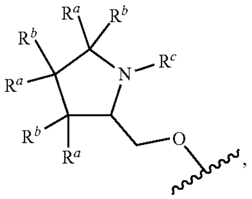

wherein each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle; and $R^c$ is selected from $C_{1-6}$ alkyl, wherein any $C_{1-6}$ alkyl is unsubstituted or is substituted with one or more $R^{13}$.

A314. The compound of embodiment A313, wherein $R^1$ is selected from:

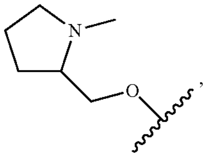
,
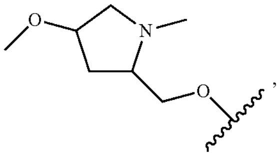
,
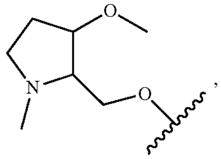
,
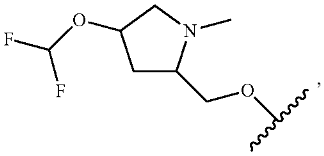
,
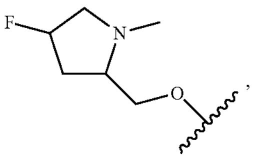
,
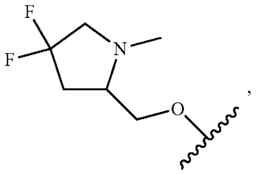
,
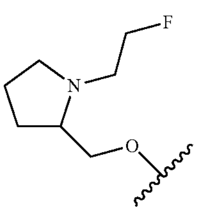
,
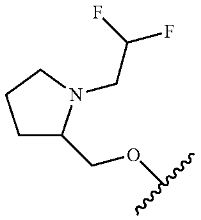
,
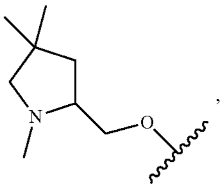
,
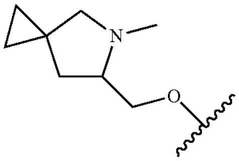
, and
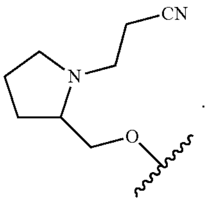
.

A315. The compound of embodiment A313, wherein $R^1$ is selected from

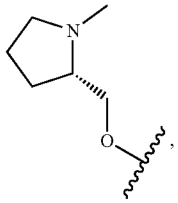
,
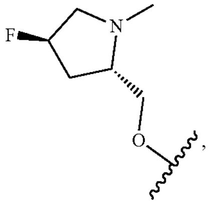
,
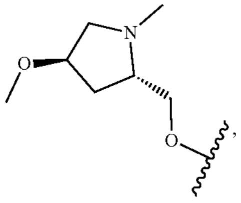
, and
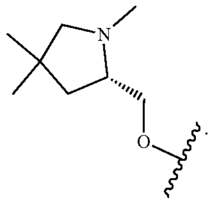
.

A316. The compound of any one of embodiments A295-A315, wherein $R^2$ is H.

A317. The compound of any one of embodiments A295-A315, wherein $R^2$ is selected from $C_{1-6}$ alkyl and a 3-6 membered carbocycle.

A318. The compound of any one of embodiments A295-A317, wherein $R^3$ is a 4-6 membered heterocycle that is substituted with one or more E and 0-4 $R^{10}$.

A319. The compound of embodiment A318, wherein $R^3$ is selected from

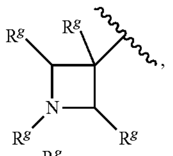
,
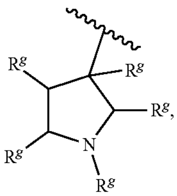
,
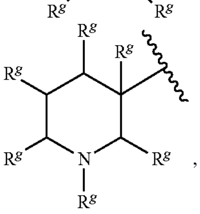
, and
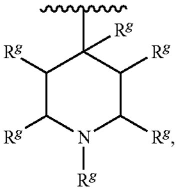
, wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A320. The compound of embodiment A319, wherein $R^3$ is selected from

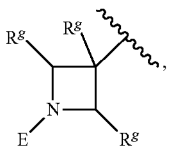
,
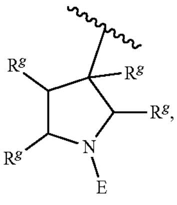
,

-continued

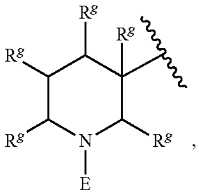

, and

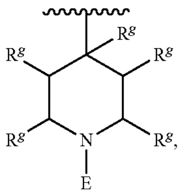

wherein each $R^g$ is independently selected from $C_{1-6}$alkyl and H, wherein any $C_{1-6}$alkyl is unsubstituted or substituted with one or more $R^{20}$.

A321. The compound of embodiment A320, wherein each $R^g$ is H.

A322. The compound of any one of embodiments A295-A315, wherein $R^2$ and $R^3$, together with the atom to which they are attached, form a 4-8 membered heterocycle that is substituted with one or more E and 0-4 $R^{11}$.

A323. The compound of embodiment A322, wherein $R^2$ and $R^3$, together with the atom to which they are attached, form a piperazinyl ring that is substituted with one or more E and 0-4 $R^{11}$.

A324. The compound of embodiment A323, wherein $R^2$ and $R^3$, together with the atom to which they are attached, form the structure

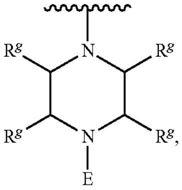

wherein each $R^g$ is independently selected from $C_{1-6}$alkyl and H, wherein any $C_{1-6}$alkyl is unsubstituted or substituted with one or more $R^{20}$.

A325. The compound of embodiment A324, wherein each $R^g$ is H.

A326. The compound of embodiment A324, wherein $R^2$ and $R^3$, together with the atom to which they are attached, form the structure:

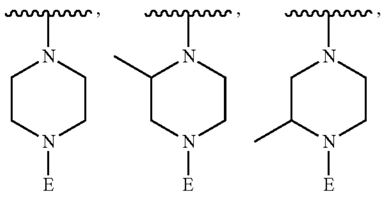

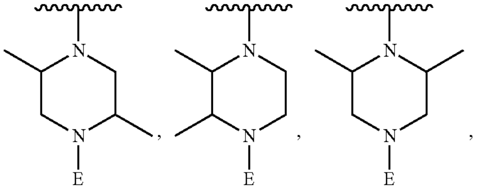

-continued

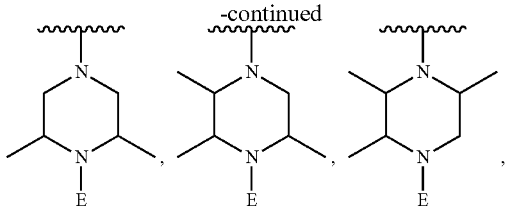

, or

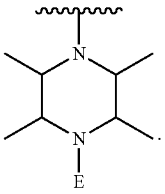

A327. The compound of embodiment A322, wherein $R^2$ and $R^3$, together with the atom to which they are attached, form a 4-8 membered bicyclic heterocycle comprising a fused ring system that is substituted with one or more E and 0-4 $R^{11}$.

A328. The compound of embodiment A327, wherein $R^2$ and $R^3$, together with the atom to which they are attached, form a structure selected from:

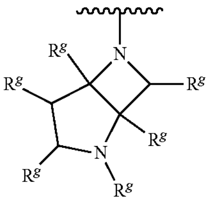

and

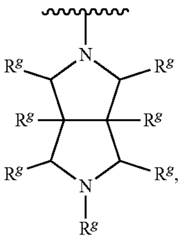

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

A329. The compound of embodiment A328, wherein $R^2$ and $R^3$, together with the atom to which they are attached, form a structure selected from:

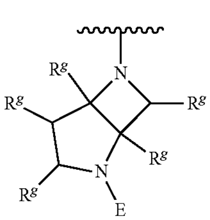

and

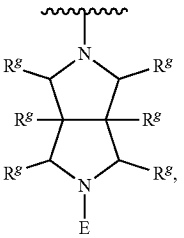

wherein each $R^g$ is independently selected from $C_{1-6}$alkyl and H, wherein any $C_{1-6}$alkyl is unsubstituted or substituted with one or more $R^{20}$.

A330. The compound of embodiment A329, wherein $R^2$ and $R^3$, together with the atom to which they are attached, form the structure

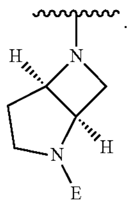

A331. The compound of any one of embodiments A295-A330, wherein $R^4$ is H.

A332. The compound of any one of embodiments A295-A331, wherein $R^7$ is a halogen.

A333. The compound of embodiment A332, wherein $R^7$ is F.

A334. The compound of any one of embodiments A295-A333, wherein X is N.

A335. The compound of any one of embodiments A295-A334, wherein Y is S.

A336. The compound of any one of embodiments A295-A335, wherein $R^{23}$ is selected from $—N(R^{12})_2$.

A337. The compound of embodiment A336, wherein $R^{23}$ is $—NH_2$.

A338. The compound of any one of embodiments A295-A337, wherein $R^{24}$ is a halogen.

A339. The compound of embodiment A338, wherein $R^{24}$ is F.

A340. The compound of any one of embodiments A295-A339, wherein $R^{25}$ and $R^{26}$ are H.

A341. The compound of any one of embodiments A295-A340, wherein each E is independently selected from

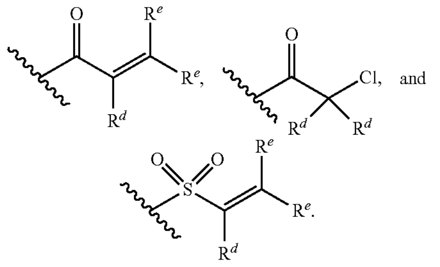

A342. The compound of embodiment A341, wherein each E is

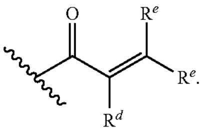

A343. The compound of embodiment A342, wherein each $R^d$ and $R^e$ is H.

A344. A compound shown in Table 2, or a salt (e.g., pharmaceutically acceptable salt), ester, tautomer, prodrug, zwitterionic form, or stereoisomer thereof.

A345. A pharmaceutical composition comprising a compound of any one of embodiments A1-A344, or a salt (e.g., pharmaceutically acceptable salt), ester, tautomer, prodrug, zwitterionic form, or stereoisomer thereof, and a pharmaceutically acceptable excipient.

A346. A compound of any one of embodiments A1-A344, or a salt (e.g., pharmaceutically acceptable salt), ester, tautomer, prodrug, zwitterionic form, or stereoisomer thereof, for use as a medicament.

A347. The compound of embodiment A346, wherein the medicament is useful in the prevention or treatment of a disease, disorder, or condition ameliorated by the inhibition of KRAS having a G12C mutation.

A348. The compound of embodiment A346 or A347, wherein the medicament is useful in the prevention or treatment of a cancer.

A349. The compound of embodiment A348, wherein the cancer is selected from the group consisting of pancreatic cancer, colorectal cancer, and lung cancer.

A350. A compound of any one of embodiments A1-A344, or a salt (e.g., pharmaceutically acceptable salt), ester, tautomer, prodrug, zwitterionic form, or stereoisomer thereof, for use in the treatment of a disease, disorder, or condition.

A351. The compound of embodiment A350, wherein the disease, disorder, or condition is a cancer.

A352. The compound of embodiment A351, wherein the cancer is selected from the group consisting of pancreatic cancer, colorectal cancer, and lung cancer.

A353. The compound of any one of embodiments A350-A352, wherein the compound is used in the treatment of a disease, disorder, or condition in a subject in need thereof.

A354. A compound of any one of embodiments A1-A344, or a salt (e.g., pharmaceutically acceptable salt), ester, tautomer, prodrug, zwitterionic form, or stereoisomer thereof, for use in the manufacture of a medicament.

A355. The compound of embodiment A354, wherein the medicament is useful in the prevention or treatment of a disease, disorder, or condition ameliorated by the inhibition of KRAS having a G12C mutation.

A356. The compound of embodiment A354 or A355, wherein the medicament is useful in the treatment of a cancer.

A357. The compound of embodiment A356, wherein the cancer is selected from the group consisting of pancreatic cancer, colorectal cancer, and lung cancer.

A358. A method, comprising administering a therapeutically effective amount of a compound of any one of embodiments A1-A344, or a salt (e.g., pharmaceutically acceptable salt), ester, tautomer, prodrug, zwitterionic form, or stereoisomer thereof, to a subject in need thereof.

A359. The method of embodiment A358, wherein the subject has a disease, disorder, or condition ameliorated by the inhibition of KRAS having a G12C mutation.

A360. The method of embodiment A358 or A359, wherein the subject has a cancer.

A361. The method of embodiment A360, wherein the subject was previously diagnosed with the cancer.

A362 The method of embodiment A360, wherein the subject has previously undergone a treatment regimen for the cancer.

A363. The method of embodiment A360, wherein the subject has previously entered remission from the cancer.

A364. The method of any one of embodiments A360-A363, wherein the cancer is selected from the group consisting of pancreatic cancer, colorectal cancer, and lung cancer.

A365. The method of any one of embodiments A358-A364, wherein the compound, or the salt, ester, tautomer, prodrug, zwitterionic form, or stereoisomer thereof, is administered in combination with an additional therapeutic agent.

A366. The use of a compound of any one of embodiments A1-A344, or a salt (e.g., pharmaceutically acceptable salt), ester, tautomer, prodrug, zwitterionic form, or stereoisomer thereof, for the manufacture of a medicament for the treatment of a cancer.

A367. The use of embodiment A366, wherein the cancer is selected from the group consisting of pancreatic cancer, colorectal cancer, and lung cancer.

A368. A method, comprising contacting a KRAS protein with a compound of any one of embodiments A1-A344, or a salt (e.g., pharmaceutically acceptable salt), ester, tautomer, prodrug, zwitterionic form, or stereoisomer thereof.

A369. The method of embodiment A368, wherein contacting the KRAS protein with the compound modulates KRAS.

A370. The method of embodiment A368 or A369, wherein the KRAS protein has a G12C mutation.

A371. The method of any one of embodiments A368-A370, wherein the KRAS protein is in an active state.

A372. The method of any one of embodiments A368-A370, wherein the KRAS protein is in an inactive state.

The following embodiments, while non-limiting, are exemplary of certain aspects of the present disclosure:

B1. A compound represented by Formula IA:

(IA)

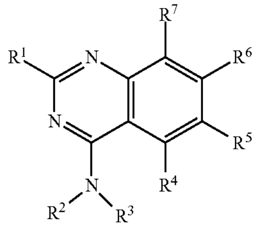

or a salt (e.g., pharmaceutically acceptable salt) thereof, wherein:

$R^1$ is selected from

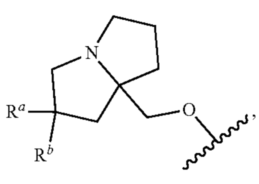

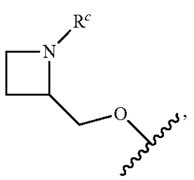

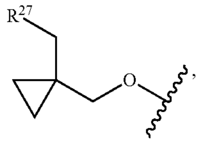

and —$OR^8$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, —$OR^{12}$, —CN, and H;

$R^8$ is selected from H and $C_{1-6}$alkyl, wherein any $C_{1-6}$alkyl is unsubstituted or substituted with one or more $R^{13}$;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$N(R^{12})C(O)(C_{1-6}alkyl)$, —CN, —$OR^{12}$, and $C_{1-6}$alkyl, wherein any $C_{1-6}$alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each E is independently selected from

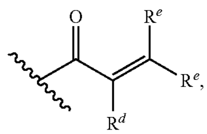

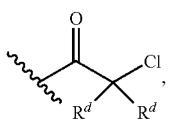

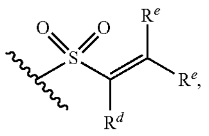

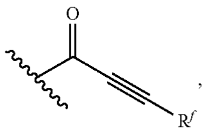

-continued

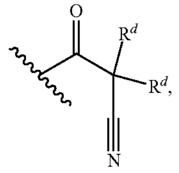 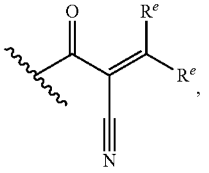

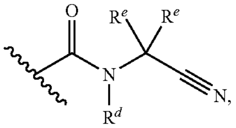 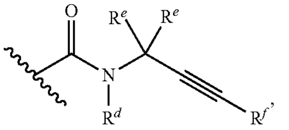

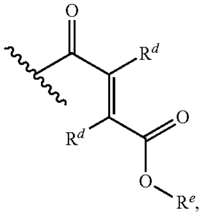 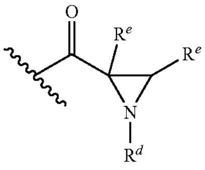 ,

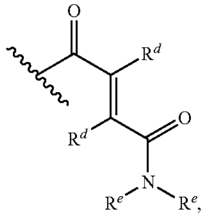 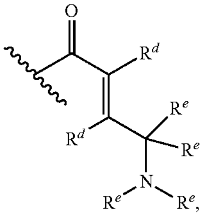

$R^a$ and $R^b$ are each independently selected from halogen, $C_{1-6}$ alkyl, —$OR^{12}$, and H, wherein any $C_{1-6}$alkyl is unsubstituted or is substituted with one or more $R^{13}$;

$R^c$ is selected from halogen, $C_{1-6}$ alkyl, and H;

each $R^d$ and $R^e$ is independently selected from halogen, $C_{1-6}$ alkyl, and H; and each $R^f$ is independently selected from $C_{1-6}$ alkyl and H.

B2. The compound of embodiment B1, wherein $R^1$ is selected from

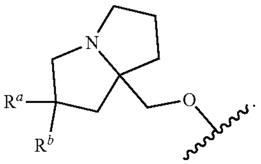

B3. The compound of embodiment B2, wherein $R^a$ is a halogen and/or wherein $R^b$ is a halogen.

B4. The compound of embodiment B2, wherein $R^1$ is selected from

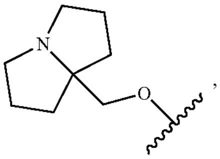 , 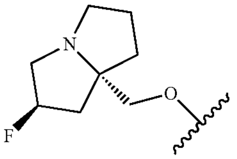 ,

-continued

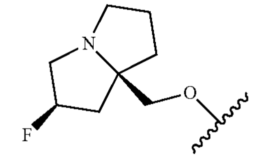 , 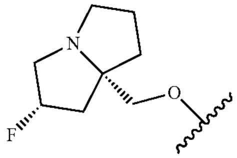 ,

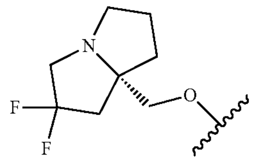 , 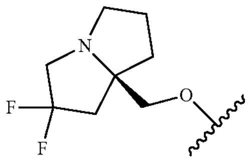 ,

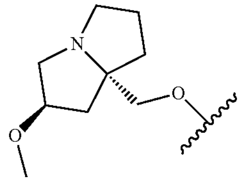 , 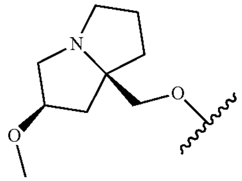 ,

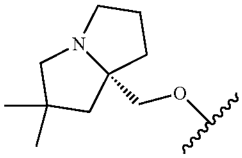 , and 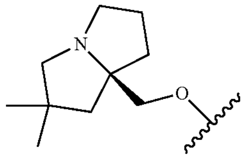 .

B5. The compound of embodiment B1, wherein $R^1$ is selected from

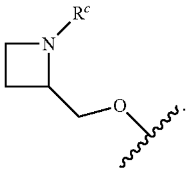

B6. The compound of embodiment B5, wherein $R^1$ is selected from

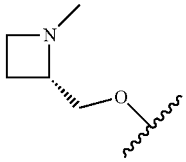 and 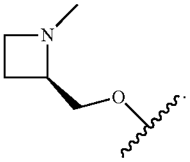

B7. The compound of embodiment B1, wherein $R^1$ is selected from

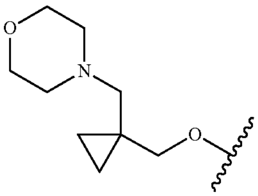 and

-continued

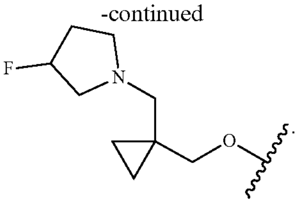

B8. The compound of embodiment B1, wherein $R^1$ is —$OR^8$, wherein $R^g$ is selected from H and $C_{1-6}$alkyl, wherein any $C_{1-6}$alkyl is unsubstituted or substituted with one or more $R^{13}$.

B9. The compound of embodiment B8, wherein $R^1$ is OH.

B10. The compound of any one of embodiments B1-B9, wherein $R^2$ is H.

B111. The compound of any one of embodiments B1-B9, wherein $R^2$ is selected from $C_{1-6}$ alkyl that is unsubstituted or is substituted with one or more $R^{13}$.

B12. The compound of embodiment B11, wherein $R^2$ is selected from $C_{1-2}$ alkyl that is unsubstituted or is substituted with one or more $R^{13}$.

B13. The compound of embodiment B12, wherein $R^2$ is selected from methyl and ethyl.

B14. The compound of any one of embodiments B1-B9, wherein $R^2$ is selected from a 3-6 membered carbocycle.

B15. The compound of embodiment B14, wherein $R^2$ is cyclopropyl.

B16. The compound of any one of embodiments B1-B15, wherein $R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle.

B17. The compound of embodiment B16, wherein $R^3$ is a 4-6 membered heterocycle that is substituted with one or more E and 0-4 $R^{10}$, wherein the heterocycle includes one or more heteroatoms selected from N, O, and S, optionally wherein two $R^{10}$ groups, together with the atom or atoms to which they are attached, form a 3-6 membered carbocycle.

B18. The compound of embodiment B17, wherein $R^3$ is a 4-6 membered heterocycle that is substituted with one or more E and 0-4 $R^{10}$, wherein the heterocycle includes a single heteroatom that is N, optionally wherein two $R^{10}$ groups, together with the atom or atoms to which they are attached, form a 3-6 membered carbocycle.

B19. The compound of embodiment B18, wherein $R^3$ is an azetidine, pyrrolidine, or piperidine, wherein the azetidine, pyrrolidine, or piperidine is substituted with one or more E and 0-4 $R^{10}$, optionally wherein two $R^{10}$ groups, together with the atom or atoms to which they are attached, form a 3-6 membered carbocycle.

B20. The compound of embodiment B18 or B19, wherein $R^3$ is selected from

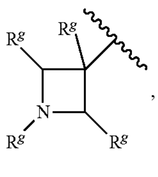

,

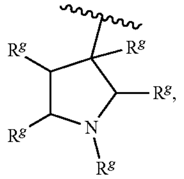

-continued

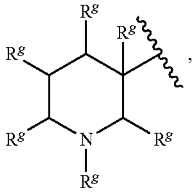

, and

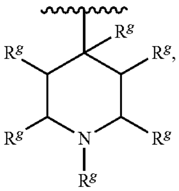

wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$.

B21. The compound of embodiment B20, wherein $R^3$ is selected from

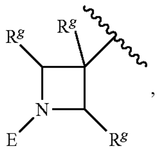

,

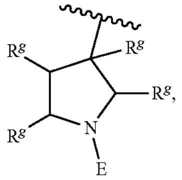

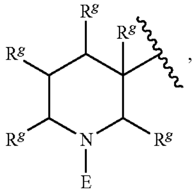

, and

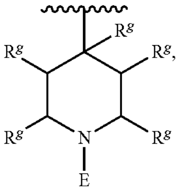

wherein each $R^g$ is independently selected from $C_{1-6}$alkyl, halogen, and H, wherein any $C_{1-6}$alkyl is unsubstituted or substituted with one or more $R^{20}$.

B22. The compound of embodiment B21, wherein each $R^g$ is H.

B23. The compound of embodiment B21, wherein at least one $R^g$ is a halogen.

B24. The compound of embodiment B21 or B23, wherein at least one $R^g$ is $C_{1-6}$alkyl that is unsubstituted or substituted with one or more $R^{20}$.

B25. The compound of embodiment B24, wherein at least one $R^g$ is methyl.

B26. The compound of any one of embodiments B1-B9, wherein $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle.

B27. The compound of embodiment B26, wherein $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle or heterocycle.

B28. The compound of embodiment B26, wherein $R^2$ and $R^3$, together with the atom to which they are attached, form the structure

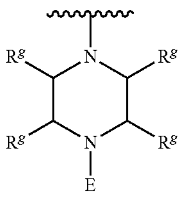

or

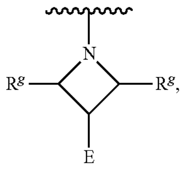

wherein each $R^g$ is independently selected from $C_{1-6}$alkyl and H, wherein any $C_{1-6}$alkyl is unsubstituted or substituted with one or more $R^{20}$, optionally wherein two $R^g$ groups, together with the atoms to which they are attached, form a 3-6 membered carbocycle or heterocycle.

B29. The compound of embodiment B28, wherein each $R^g$ is H.

B30. The compound of embodiment B28, wherein at least one $R^g$ is $C_{1-6}$alkyl that is unsubstituted or substituted with one or more $R^{20}$.

B31. The compound of embodiment B30, wherein at least one $R^g$ is methyl.

B32. The compound of embodiment B28, wherein $R^2$ and $R^3$, together with the atom to which they are attached, form the structure

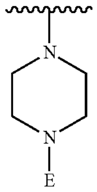,
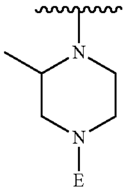,
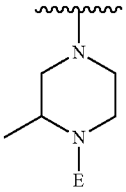,
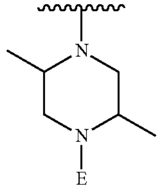,
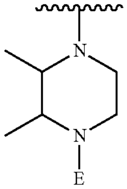,
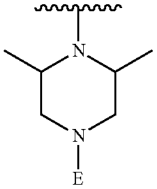,
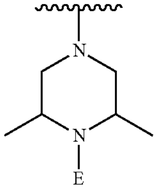,
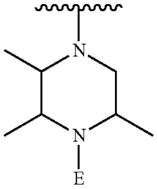,
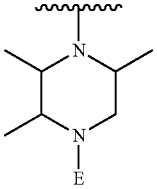, or
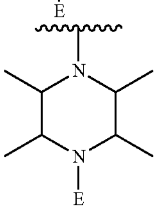.

B33. The compound of embodiment B26, wherein $R^2$ and $R^3$, together with the atom to which they are attached, form a bridged piperazinyl ring that is substituted with one or more E and 0-4 $R^{11}$.

B34. The compound of embodiment B33, wherein $R^2$ and $R^3$, together with the atom to which they are attached, form the structure

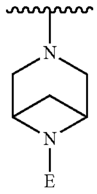

or

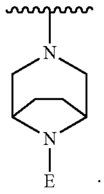.

B35. The compound of embodiment B26, wherein $R^2$ and $R^3$, together with the atom to which they are attached, form a 4-8 membered bicyclic heterocycle comprising a fused ring system that is substituted with one or more E and 0-4 $R^{11}$.

B36. The compound of embodiment B35, wherein $R^2$ and $R^3$, together with the atom to which they are attached, form a structure selected from:

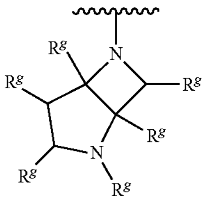

and

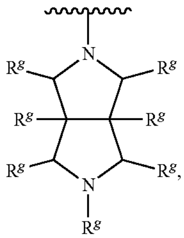

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

B37. The compound of embodiment B36, wherein $R^2$ and $R^3$, together with the atom to which they are attached, form a structure selected from:

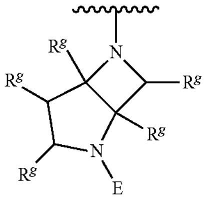

and

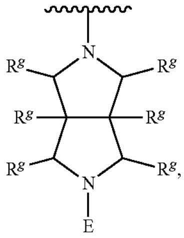

wherein each $R^g$ is independently selected from $C_{1-6}$alkyl and H, wherein any $C_{1-6}$alkyl is unsubstituted or substituted with one or more $R^{20}$.

B38. The compound of embodiment B37, wherein $R^2$ and $R^3$, together with the atom to which they are attached, form the structure

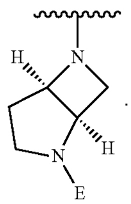.

B39. The compound of embodiment B37, wherein each $R^g$ is H.

B40. The compound of any one of embodiments B1-B39, wherein $R^4$ is H.

B41. The compound of any one of embodiments B1-B40, wherein $R^5$ is a halogen.

B42. The compound of embodiment B41, wherein $R^5$ is Cl.

B43. The compound of any one of embodiments B1-B40, wherein $R^5$ is selected from $C_{1-6}$alkyl that is unsubstituted or substituted with one or more $R^{13}$.

B44. The compound of embodiment B43, wherein $R^5$ is $C_{1-6}$alkyl that is substituted with one or more halogens.

B45. The compound of embodiment B44, wherein $R^5$ is $—CHF_2$ or $—CF_3$.

B46. The compound of embodiment B43, wherein $R^5$ is $C_{1-6}$alkyl that is substituted with one or more $R^{13}$, wherein each $R^{13}$ is independently selected from $—OR^{22}$, —CN, and $—N(R^{22})_2$.

B47. The compound of embodiment B46, wherein $R^5$ is $—CH_2CN$.

B48. The compound of any one of embodiments B1-B40, wherein $R^5$ is selected from $—OR^{12}$, wherein $R^{12}$ is selected from $C_{1-6}$ alkyl and H.

B49. The compound of embodiment B48, wherein $R^5$ is $—OCH_3$.

B50. The compound of any one of embodiments B1-B40, wherein $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$.

B51. The compound of embodiment B50, wherein $R^5$ is a furanyl.

B52. The compound of embodiment B50, wherein $R^5$ is a phenyl.

B53. The compound of any one of embodiments B1-B52, wherein $R^6$ is a 9-10 membered heteroaryl having 1-3 heteroatoms independently selected from nitrogen, oxygen, and sulfur that is substituted with one or more $R^{15}$.

B54. The compound of any one of embodiments B1-B53, wherein $R^6$ has the structure:

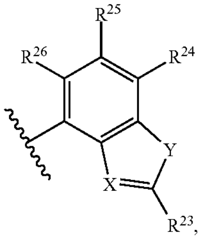

wherein X is selected from N and C—CN; Y is selected from O and S; $R^{23}$ is selected from $—N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^2$, and $R^{26}$ are independently selected from H, halogen, $—OR^{12}$, and $C_{1-6}$alkyl, wherein any $C_{1-6}$alkyl is unsubstituted or substituted with one or more $R^{13}$.

B55. The compound of any one of embodiments B1-B54, wherein $R^6$ is selected from:

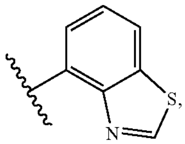
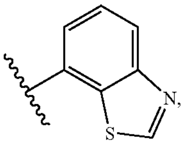
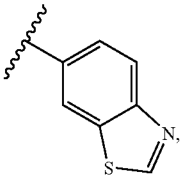
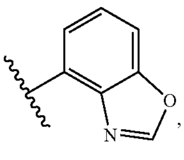,
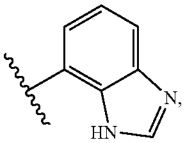
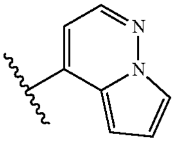,
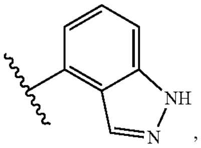,
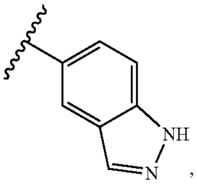,
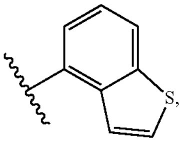
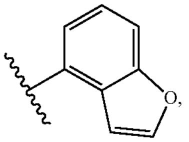 and
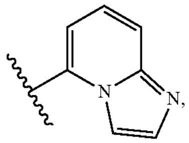

any of which is substituted with one or more $R^{15}$.

B56. The compound of any one of embodiments B1-B55, wherein $R^6$ is selected from:

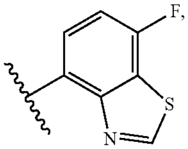
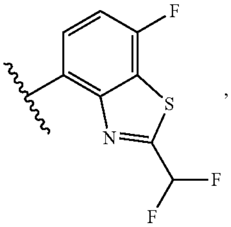,
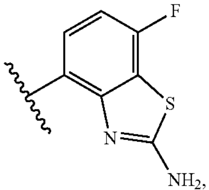
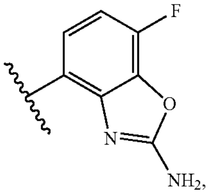

-continued

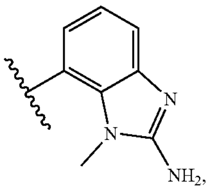
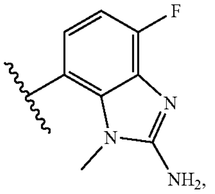
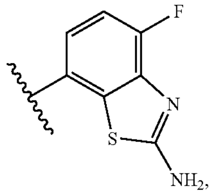
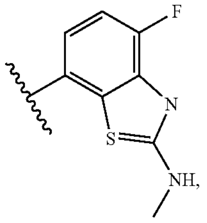
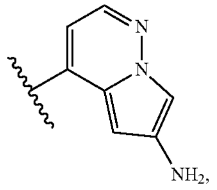
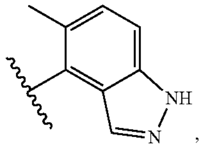
,
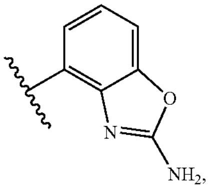
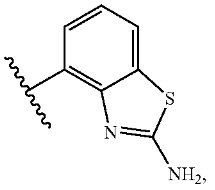
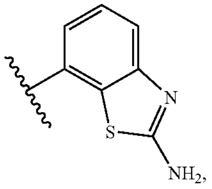
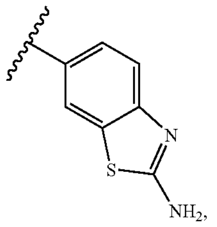
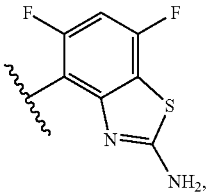
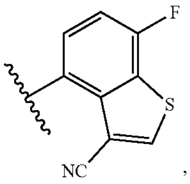
,
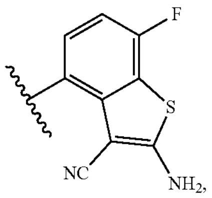
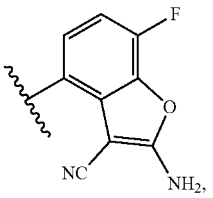
and
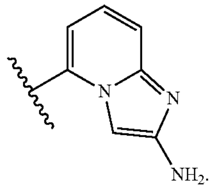

B57. The compound of any one of embodiments B1-B56, wherein $R^6$ is selected from

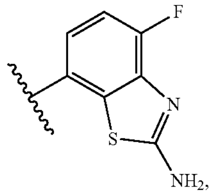
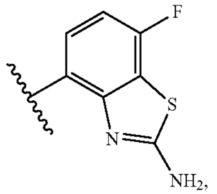
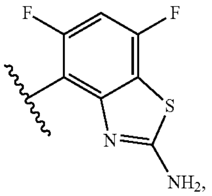
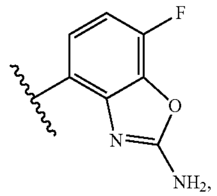
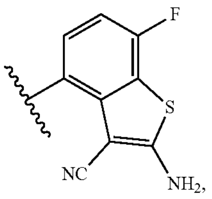
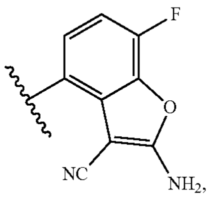
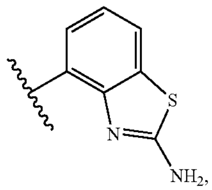
and
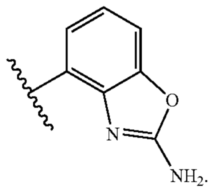

B58. The compound of any one of embodiments B1-B57, wherein $R^7$ is a halogen.

B59. The compound of embodiment B58, wherein $R^7$ is F.

B60. The compound of any one of embodiments B1-B57, wherein $R^7$ is —$OR^{12}$.

B61. The compound of any one of embodiments B1-B57, wherein $R^7$ is —CN.

B62. The compound of any one of embodiments B1-B57, wherein $R^7$ is H.

B63. The compound of any one of embodiments B1-B62, wherein each E is independently selected from

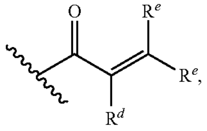
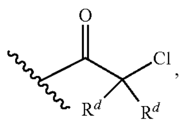
and
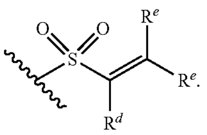

B64. The compound of embodiment B63, wherein each E is

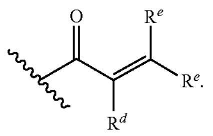

B65. The compound of embodiment B64, wherein each $R^d$ and $R^e$ is H.

B66. The compound of any one of embodiments B1-B65, wherein the compound is a compound according to Formula IA1:

(IA1)

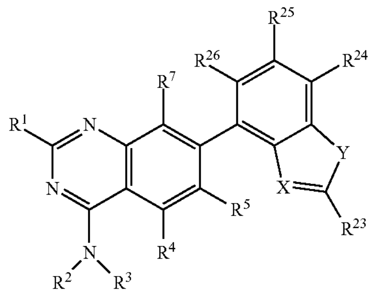

or a salt (e.g., a pharmaceutically acceptable salt) thereof, wherein:

$R^1$ is selected from

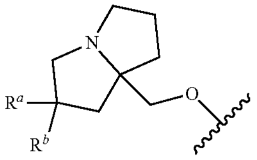

and

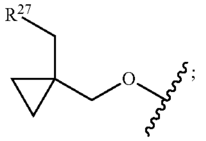

$R^2$ is $C_{1-6}$ alkyl that is unsubstituted or is substituted with one or more $R^{13}$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B67. The compound of any one of embodiments B1-B65, wherein the compound is a compound according to Formula IA2:

(IA2)

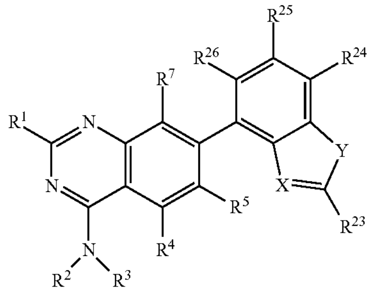

or a salt (e.g., a pharmaceutically acceptable salt) thereof, wherein:

$R^1$ is selected from

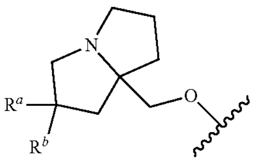

and

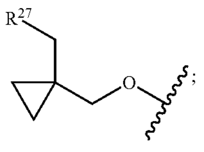

$R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B68. A compound according to Formula IC:

(IC)

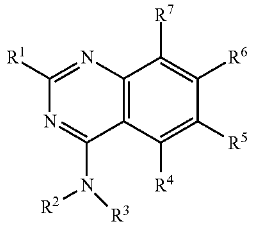

or a salt (e.g., pharmaceutically acceptable salt) thereof, wherein:

$R^1$ is selected from —$OR^8$,

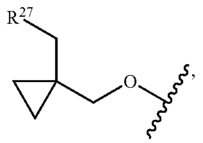

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with —$N(R^{12})(E)$, wherein the heterocycle is substituted with one or more E and 0-4 $R^{10}$, optionally wherein two $R^{10}$ groups, together with the atom or atoms to which they are attached, form a 3-6 membered carbocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$OR^{12}$, —CN, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^x$ is independently selected from $C_{1-6}$ alkyl, a 3-6 membered carbocycle, and H;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ and $R^b$ is independently selected from halogen, $C_{1-6}$ alkyl, —$OR^{12}$, a 3-6 membered carbocycle, and H, wherein any $C_{1-6}$ alkyl is unsubstituted or is substituted with one or more $R^{13}$;

each E is independently selected from

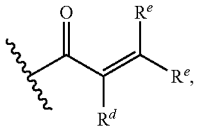 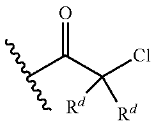 ,

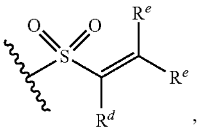 , 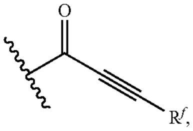

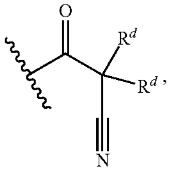 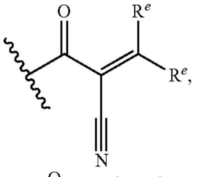

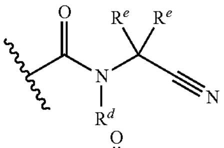 , 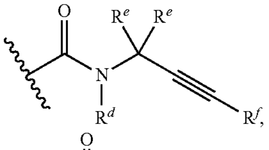

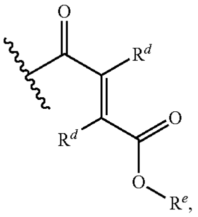 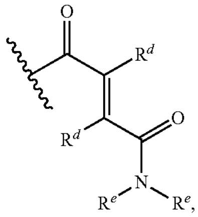

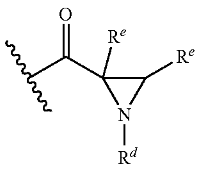 , 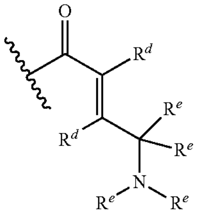

and —CN;

each $R^d$ and $R^e$ is independently selected from halogen, $C_{1-6}$ alkyl, and H; and each $R^f$ is independently selected from $C_{1-6}$ alkyl and H.

B69. The compound of embodiment B68, wherein $R^2$ is H.

B70. The compound of embodiment B68, wherein $R^2$ is selected from $C_{1-6}$ alkyl.

B71. The compound of embodiment B70, wherein $R^2$ is methyl.

B72. The compound of embodiment B68, wherein $R^2$ is selected from a 3-6 membered carbocycle.

B73. The compound of any one of embodiments B68-B72, wherein $R^3$ is selected from $C_{1-6}$ alkyl that is substituted with —$N(R^{12})(E)$.

B74. The compound of embodiment B73, wherein $R^3$ is $C_2$ alkyl that is substituted with —$N(R^{12})(E)$.

B75. The compound of embodiment B74, wherein $R^3$ is $C_2$ alkyl that is substituted with —N(H)(E).

B76. The compound of any one of embodiments B68-B72, wherein $R^3$ is selected from a 4-6 membered heterocycle, wherein the heterocycle includes one or more heteroatoms selected from N, O, and S, and wherein the heterocycle is substituted with one or more E and 0-4 $R^{10}$, optionally wherein two $R^{10}$ groups, together with the atom or atoms to which they are attached, form a 3-6 membered carbocycle.

B77. The compound of embodiment B76, wherein $R^3$ is selected from a 4-6 membered heterocycle, wherein the heterocycle includes a single heteroatom that is N, and wherein the heterocycle is substituted with one or more E and 0-4 $R^{10}$, optionally wherein two $R^{10}$ groups, together with the atom or atoms to which they are attached, form a 3-6 membered carbocycle.

B78. The compound of embodiment B77, wherein $R^3$ is selected from

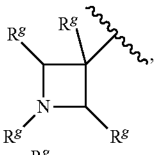
,
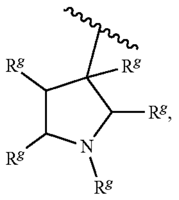
,
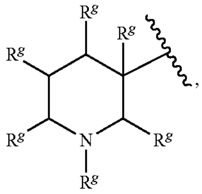
, and
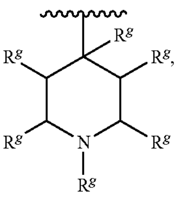
, wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$.

B79. The compound of embodiment B78, wherein $R^3$ is selected from

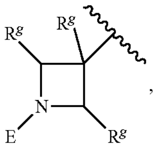
,
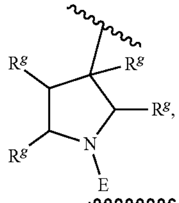
,
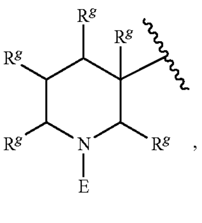
, and
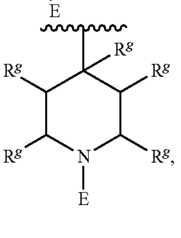
, wherein each $R^g$ is independently selected from $C_{1-6}$alkyl, halogen, and H, wherein any $C_{1-6}$alkyl is unsubstituted or substituted with one or more $R^{20}$.

B80. The compound of embodiment B79, wherein each $R^g$ is H.

B81. The compound of embodiment B79, wherein at least one $R^g$ is a halogen.

B82. The compound of embodiment B79 or B80, wherein at least one $R^g$ is selected from $C_{1-6}$alkyl that is unsubstituted or substituted with one or more $R^{20}$.

B83. The compound of embodiment B82, wherein at least one $R^g$ is methyl.

B84. The compound of any one of embodiment B68-B83, wherein $R^1$ is H.

B85. The compound of any one of embodiments B68-B83, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl.

B86. The compound of embodiment B85, wherein $R^8$ is a heterocycle or an alkylheterocycle, wherein any heterocycle contains 4-8 members and is substituted with one or more $R^a$ and/or $R^b$.

B87. The compound of embodiment B86, wherein the heterocycle or the heterocycle of the alkylheterocycle is a 4-8 membered heterocycle containing 1-2 heteroatoms independently selected from N, O, and S.

B88. The compound of any one of embodiments B85-B87, wherein $R^1$ is selected from

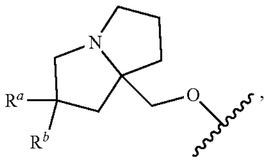
, wherein $R^a$ and $R^b$ are each independently selected from halogen, $C_{1-6}$ alkyl, —$OR^{12}$, and H, wherein any $C_{1-6}$ alkyl is unsubstituted or is substituted with one or more $R^{13}$.

B89. The compound of embodiment B88, wherein $R^1$ is selected from:

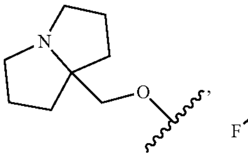
,
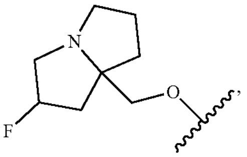
,
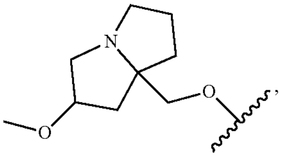
,
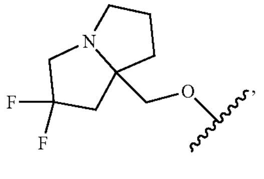
, and
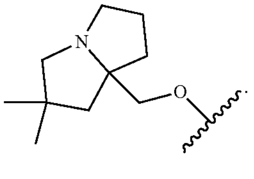
.

B90. The compound of embodiment B88, wherein $R^1$ is selected from

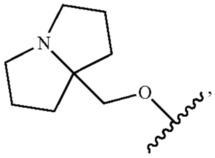,
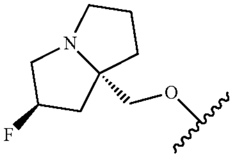,
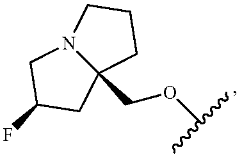,
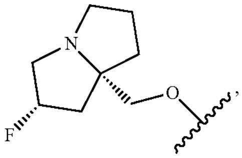,
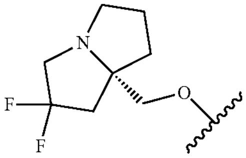,
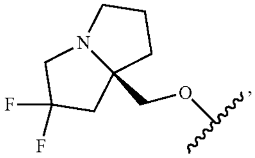,
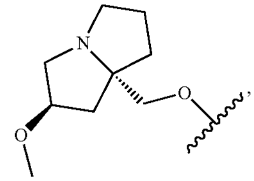,
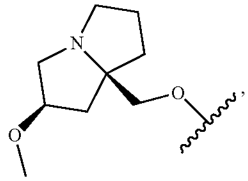,
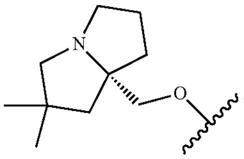, and
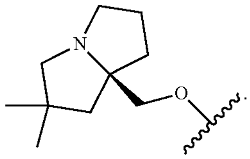.

B91. The compound of any one of embodiments B85-B87, wherein $R^1$ is selected from

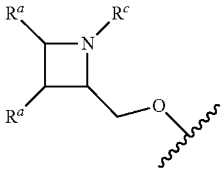, wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

B92. The compound of embodiment B91, wherein $R^1$ is selected from

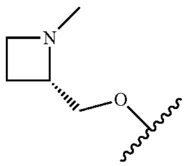
and
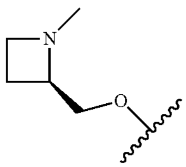.

B93. The compound of any one of embodiments B85-B87, wherein $R^1$ is selected from:

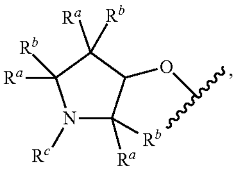,
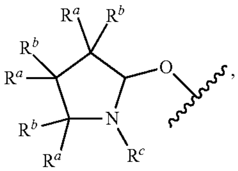,
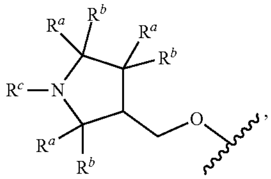, and
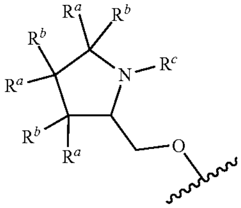, wherein each $R^a$ and $R^b$ is independently selected from halogen, $C_{1-6}$ alkyl, —$OR^{12}$, and H; and wherein $R^c$ is selected from $C_{1-6}$ alkyl and a 3-6 membered carbocycle, wherein any $C_{1-6}$ alkyl is unsubstituted or is substituted with one or more $R^{13}$.

B94. The compound of embodiment B93, wherein $R^1$ is selected from

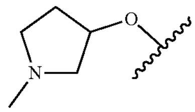,
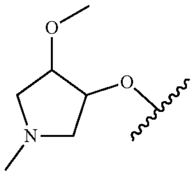,
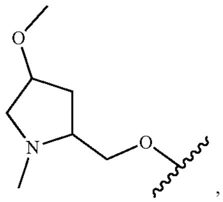,
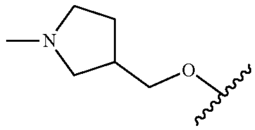,
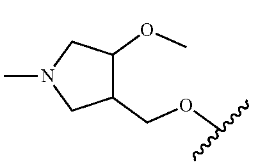,
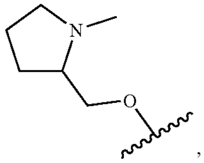,
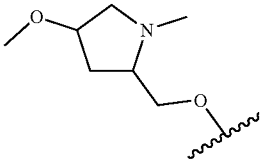,
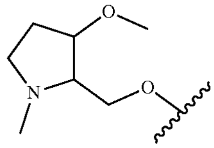,
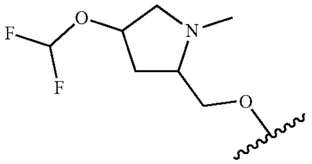,
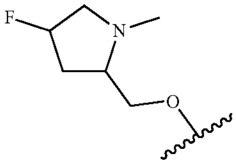, -continued

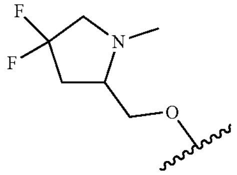,

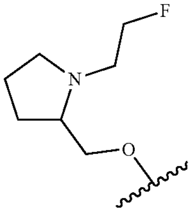,

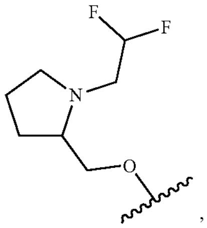,

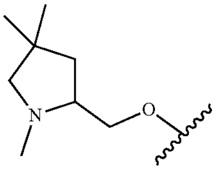,

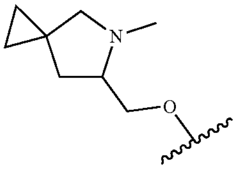, and

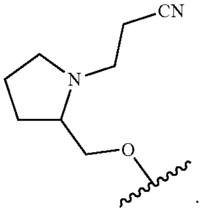.

B95. The compound of embodiment B94, wherein $R^1$ is selected from

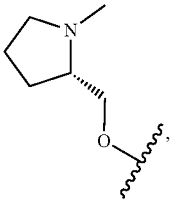,

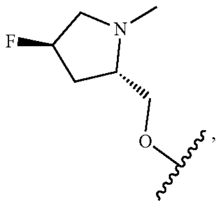,

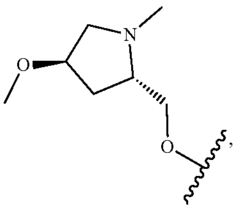, and

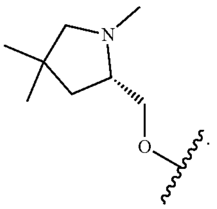.

B96. The compound of any one of embodiments B68-B83, wherein $R^1$ is a 4-6 membered heterocycle comprising a nitrogen atom, wherein the heterocycle is unsubstituted or substituted with one or more $R^{16}$.

B97. The compound of embodiment B96, wherein $R^1$ is selected from

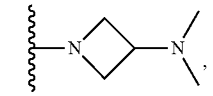,

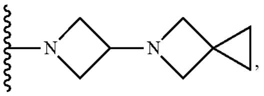,

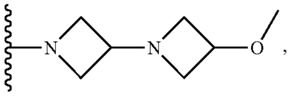,

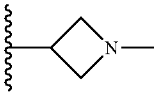, and

-continued

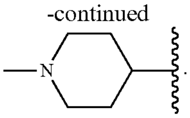.

B98. The compound of any one of embodiments B68-B97, wherein $R^4$ is H.

B99. The compound of any one of embodiments B68-B97, wherein $R^4$ is —$OCH_3$.

B100. The compound of any one of embodiments B68-B99, wherein $R^5$ is H.

B101. The compound of any one of embodiments B68-B99, wherein $R^5$ is a halogen.

B102. The compound of embodiment B101, wherein $R^5$ is Cl.

B103. The compound of any one of embodiments B68-B99, wherein $R^5$ is —CN.

B104. The compound of any one of embodiments B68-B99, wherein $R^5$ is $C_{1-6}$alkyl that is unsubstituted or substituted with one or more $R^{13}$.

B105. The compound of embodiment B104, wherein $R^5$ is $C_{1-6}$alkyl that is substituted with one or more halogens.

B106. The compound of embodiment B105, wherein $R^5$ is —$CHF_2$ or —$CF_3$.

B107. The compound of embodiment B104, wherein $R^5$ is $C_{1-6}$alkyl that is substituted with one or more $R^{13}$, wherein each $R^{13}$ is independently selected from —$OR^{22}$, —CN, and —$N(R^{22})_2$.

B108. The compound of embodiment B107, wherein $R^5$ is —$CH_2CN$.

B109. The compound of any one of embodiments B68-B99, wherein $R^5$ is selected from a 3-6 membered heterocycle, a 5-6 membered heteroaryl, phenyl, and a 3-6 membered carbocycle, wherein any carbocycle, heteroaryl, phenyl, or heterocycle is unsubstituted or substituted with one or more $R^{14}$.

B110. The compound of embodiment B109, wherein $R^5$ is selected from a 3-6 membered heterocycle and a 5-6 membered heteroaryl, wherein any heterocycle or heteroaryl is unsubstituted or substituted with one or more $R^{14}$.

B111. The compound of embodiment B110, wherein $R^5$ is furanyl.

B112. The compound of embodiment B109, wherein $R^5$ is selected from phenyl and a 3-6 membered carbocycle, wherein any carbocycle or phenyl is unsubstituted or substituted with one or more $R^{14}$.

B113. The compound of embodiment B112, wherein $R^5$ is phenyl.

B114. The compound of any one of embodiments B68-B113, wherein $R^7$ is a halogen.

B115. The compound of embodiment B114, wherein $R^7$ is F.

B116. The compound of any one of embodiments B68-B113, wherein $R^7$ is —OH.

B117. The compound of any one of embodiments B68-B113, wherein $R^7$ is

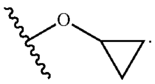.

B118. The compound of any one of embodiments B68-B113, wherein $R^7$ is H.

B119. The compound of any one of embodiments B68-B113, wherein $R^7$ is —CN.

B120. The compound of any one of embodiments B68-B119, wherein $R^6$ is a 9-10 membered heteroaryl having 1-3 heteroatoms independently selected from nitrogen, oxygen, and sulfur that is substituted with one or more $R^{15}$.

B121. The compound of any one of embodiments B68-B120, wherein $R^6$ has the structure:

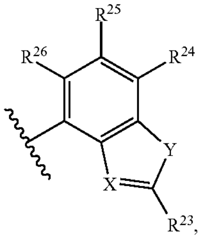

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B122. The compound of any one of embodiments B68-B121, wherein $R^6$ is selected from:

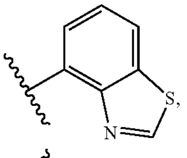
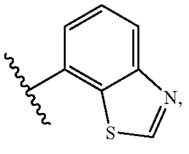
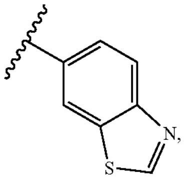
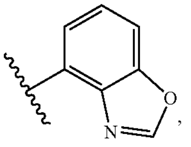
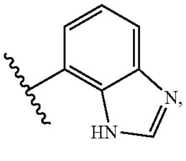
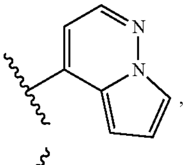
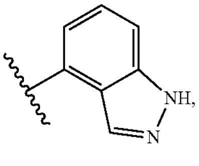
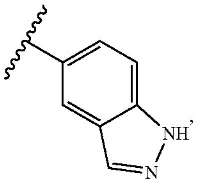
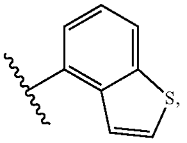
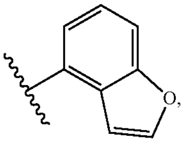
and -continued

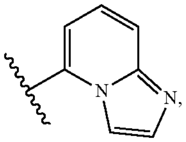

any of which is substituted with one or more $R^{15}$.

B123. The compound of any one of embodiments B68-B122, wherein $R^6$ is selected from:

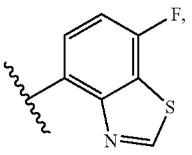
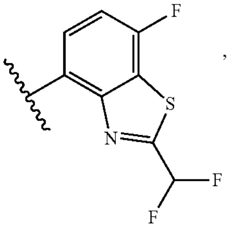
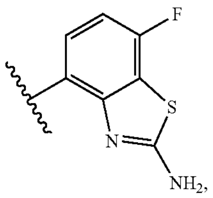
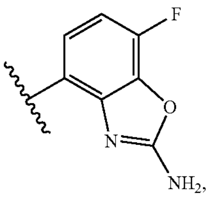
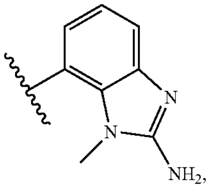
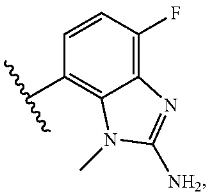
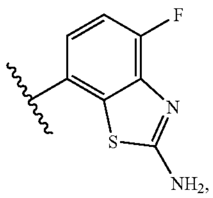
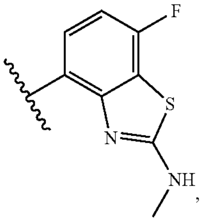
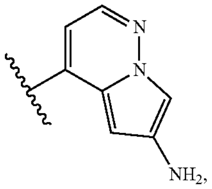
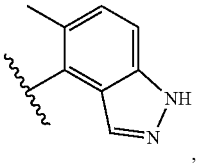
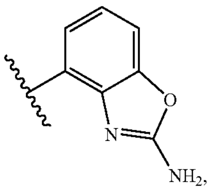
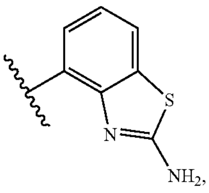

-continued

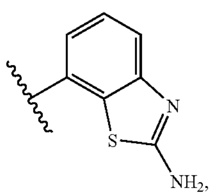 , 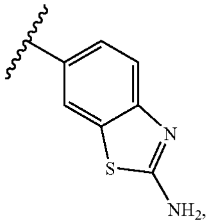 ,

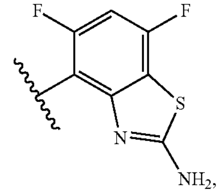 , 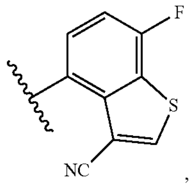 ,

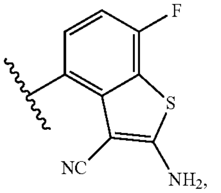 , 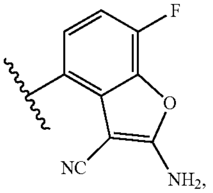 , and

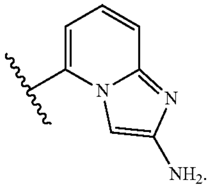 .

B124. The compound of any one of embodiments B68-B123, wherein $R^6$ is selected from

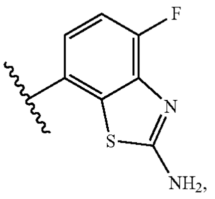 , 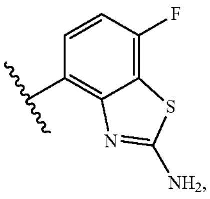 ,

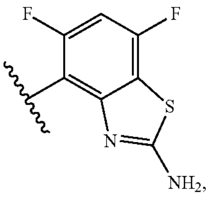 , 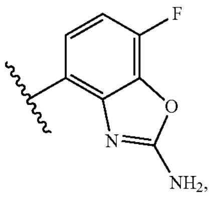 ,

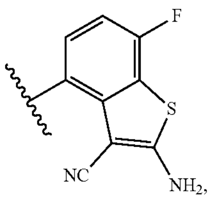 , 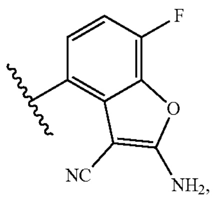 ,

-continued

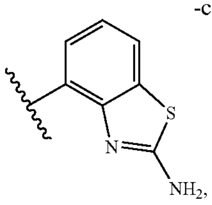 , and 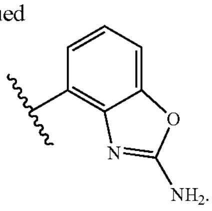 .

B125. The compound of any one of embodiments B68-B124, wherein each E is independently selected from

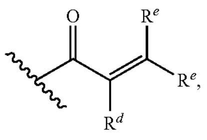 , 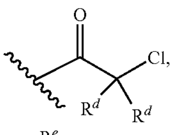 , and

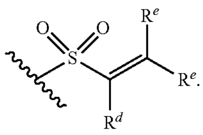 .

B126. The compound of embodiment B125, wherein each E is

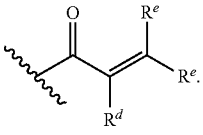 .

B127. The compound of embodiment B126, wherein each $R^d$ and $R^e$ is H.

B128. The compound of any one of embodiments B68-B127, wherein the compound is a compound according to Formula IC1:

(IC1)

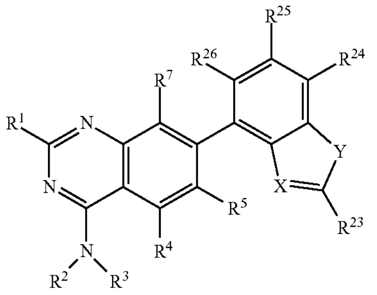

or a salt (e.g., a pharmaceutically acceptable salt) thereof, wherein:

$R^1$ is —$OR^8$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B129. The compound of any one of embodiments B68-B127, wherein the compound is a compound according to Formula IC2:

(IC2)

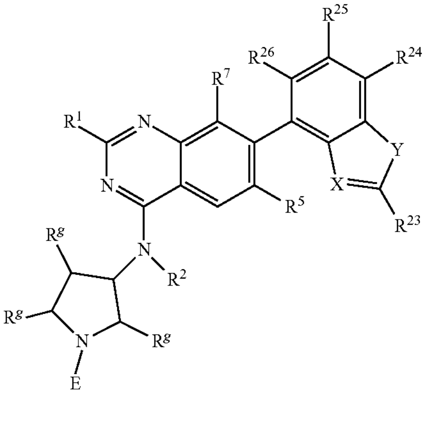

or a salt (e.g., a pharmaceutically acceptable salt) thereof, wherein:

$R^1$ is —$OR^8$;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$; and each $R^g$ is independently selected from $C_{1-6}$alkyl, halogen, and H, wherein any $C_{1-6}$alkyl is unsubstituted or substituted with one or more $R^{20}$.

B130. A compound represented by Formula IB:

(IB)

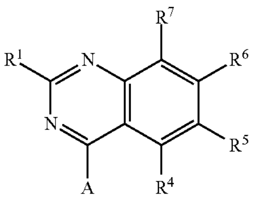

or a salt (e.g., pharmaceutically acceptable salt) thereof, wherein:

$R^1$ is selected from —$OR^8$,

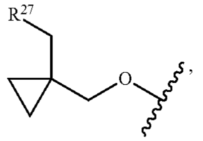

a 4-6 membered heterocycle comprising a nitrogen atom, and H, wherein the heterocycle is unsubstituted or substituted with one or more $R^{16}$;

A is selected from

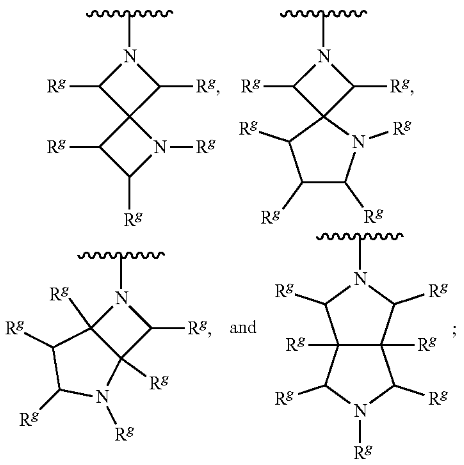

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —CN, —$OR^{12}$, and $C_{1-6}$alkyl, wherein any $C_{1-6}$alkyl is unsubstituted or substituted with one or more $R^{13}$;

each $R^{16}$ is independently selected from halogen, $—N(R^{12})_2$, $C_{1-6}$alkyl, $—OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, $—OC_{1-6}$alkyl, —CN, $—NH_2$, $—NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ and $R^b$ is independently selected from halogen, $C_{1-6}$ alkyl, $—OR^{12}$, and H, wherein any $C_{1-6}$alkyl is unsubstituted or substituted with one or more $R^{13}$;

each $R^g$ is independently selected from $C_{1-6}$alkyl, H, and E, wherein at least one $R^g$ is E, and wherein any $C_{1-6}$alkyl is unsubstituted or substituted with one or more $R^{20}$;

each E is independently selected from

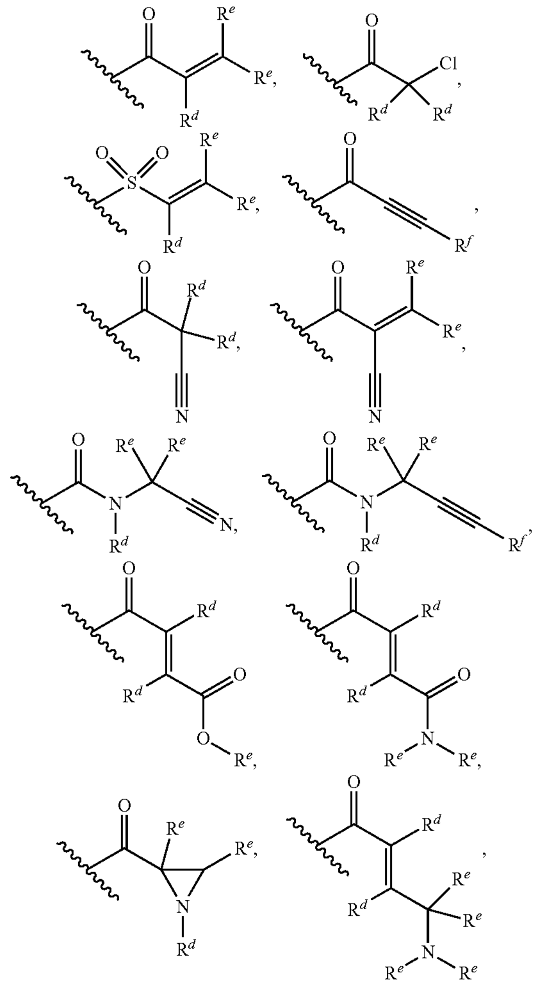

and —CN;

each $R^d$ and $R^e$ is independently selected from halogen, $C_{1-6}$ alkyl, and H; and each $R^f$ is independently selected from $C_{1-6}$ alkyl and H.

B131. The compound of embodiment B130, wherein A is selected from

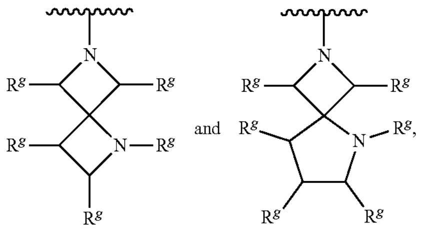

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

B132. The compound of embodiment B130, wherein A is selected from

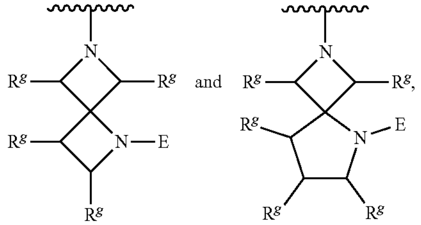

wherein each $R^g$ is independently selected from $C_{1-6}$alkyl and H, wherein any $C_{1-6}$alkyl is unsubstituted or substituted with one or more $R^{20}$.

B133. The compound of embodiment B132, wherein each $R^g$ is H.

B134. The compound of embodiment B130, wherein A is selected from

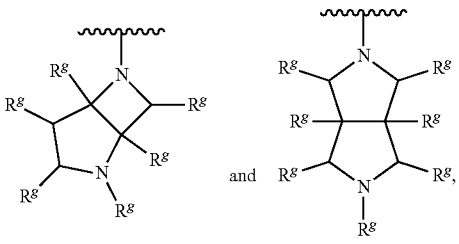

wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

B135. The compound of embodiment B134, wherein A is selected from

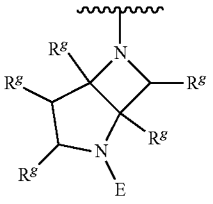 and 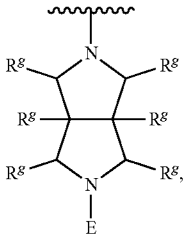

wherein each $R^g$ is independently selected from $C_{1-6}$alkyl and H, wherein any $C_{1-6}$alkyl is unsubstituted or substituted with one or more $R^{20}$.

B136. The compound of embodiment B135, wherein each $R^g$ is H.

B137. The compound of any one of embodiments B130-B136, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl.

B138. The compound of embodiment B137, wherein $R^8$ is a heterocycle or an alkylheterocycle, wherein any heterocycle contains 4-8 members and is substituted with one or more $R^a$ and/or $R^b$.

B139. The compound of embodiment B137 or B138, wherein $R^1$ is selected from

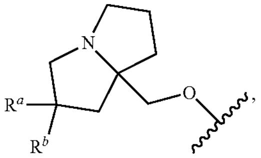

wherein $R^a$ and $R^b$ are each independently selected from halogen, $C_{1-6}$alkyl, —$OR^{12}$, and H, wherein any $C_{1-6}$alkyl is unsubstituted or is substituted with one or more $R^{13}$.

B140. The compound of embodiment B139, wherein $R^a$ is a halogen and/or $R^b$ is a halogen.

B141. The compound of embodiment B139, wherein $R^1$ is selected from

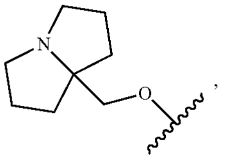 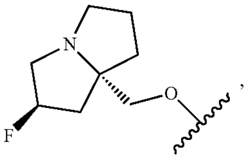

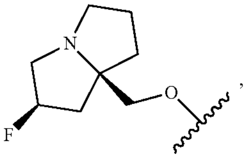 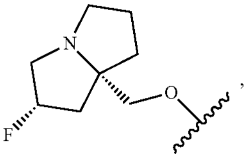

-continued

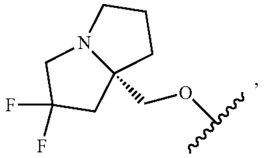 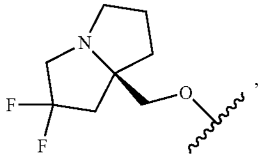

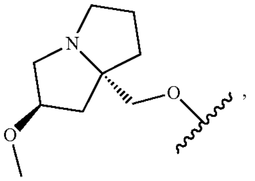 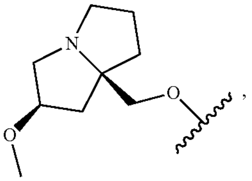

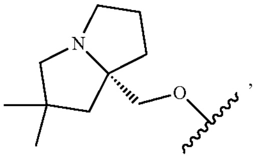 and 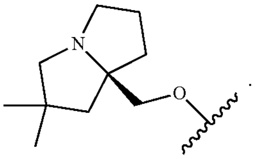

B142. The compound of embodiment B137 or B138, wherein $R^1$ is selected from

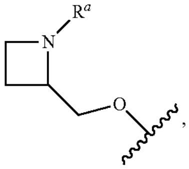

wherein $R^a$ is selected from halogen, $C_{1-6}$alkyl, —$OR^{12}$, and H, wherein any $C_{1-6}$alkyl is unsubstituted or is substituted with one or more $R^{13}$.

B143. The compound of embodiment B142, wherein $R^1$ is selected from

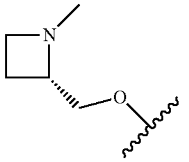 and 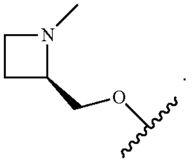

B144. The compound of embodiment B138 or B139, wherein $R^1$ is selected from

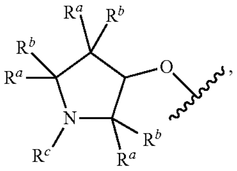 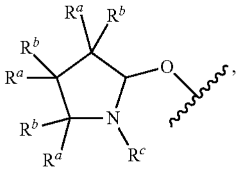

-continued

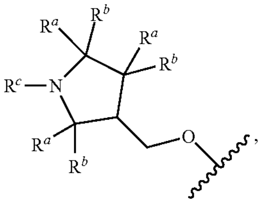, and 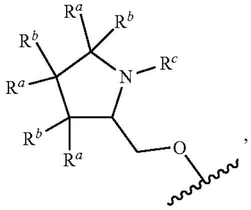, wherein each $R^a$ and $R^b$ is independently selected from halogen, $C_{1-6}$ alkyl, —$OR^{12}$, and H; and $R^c$ is selected from $C_{1-6}$ alkyl, wherein the $C_{1-6}$ alkyl is unsubstituted or is substituted with one or more $R^{13}$.

B145. The compound of embodiment B144, wherein $R^1$ is selected from:

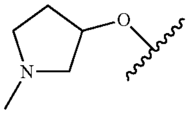, 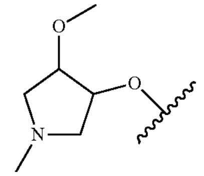, 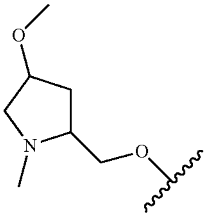, 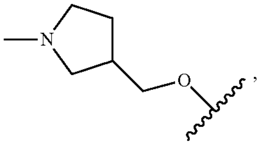, 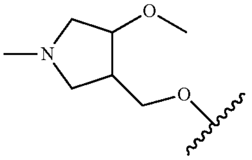, 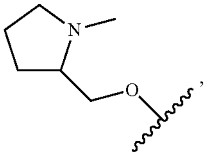, 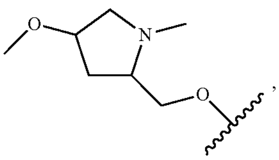, 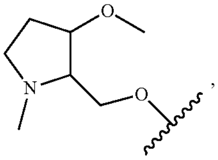, 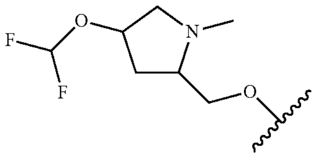, 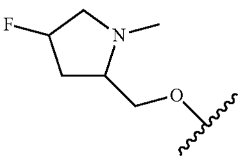, 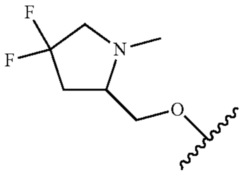, 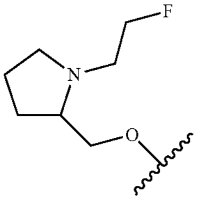, 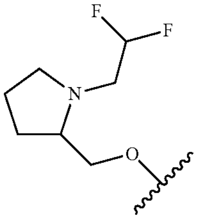, -continued

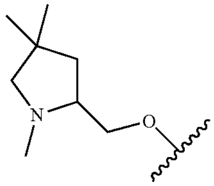, 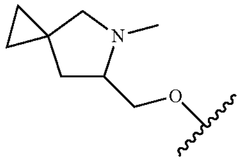, and 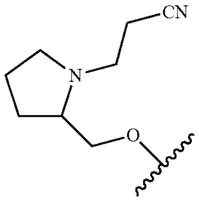.

B146. The compound of embodiment B145, wherein $R^1$ is selected from

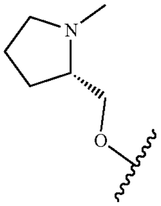, 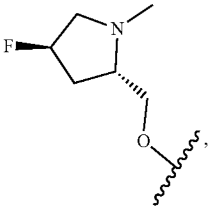, 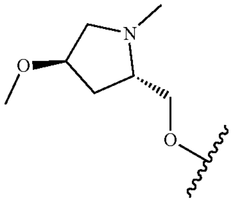, and 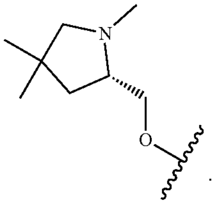.

B147. The compound of any one of embodiments B130-B146, wherein $R^4$ is H.

B148. The compound of any one of embodiments B130-B147, wherein $R^5$ is a halogen.

B149. The compound of embodiment B148, wherein $R^5$ is F.

B150. The compound of any one of embodiments B130-B147, wherein $R^5$ is H.

B151. The compound of any one of embodiments B130-B147, wherein $R^5$ is —CN.

B152. The compound of any one of embodiments B130-B147, wherein $R^5$ is selected from $C_{1-6}$alkyl that is unsubstituted or substituted with one or more $R^{13}$.

B153. The compound of embodiment B152, wherein $R^5$ is $C_{1-6}$alkyl that is substituted with one or more halogens.

B154. The compound of embodiment B153, wherein $R^5$ is —$CHF_2$ or —$CF_3$.

B155. The compound of any one of embodiments B130-B147, wherein $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$.

B156. The compound of embodiment B155, wherein $R^5$ is a furanyl.

B157. The compound of embodiment B155, wherein $R^5$ is a phenyl.

B158. The compound of any one of embodiments B130-B157, wherein $R^6$ is a 9-10 membered heteroaryl having 1-3 heteroatoms independently selected from nitrogen, oxygen, and sulfur that is substituted with one or more $R^{14}$.

B159. The compound of any one of embodiments B130-B158, wherein $R^6$ has the structure:

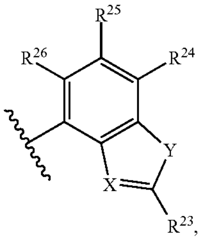

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B160. The compound of any one of embodiments B130-B159, wherein $R^6$ is selected from:

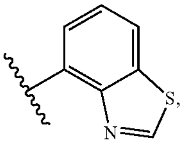
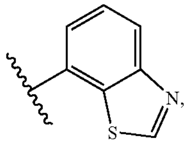
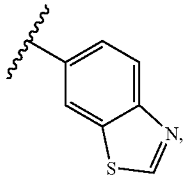
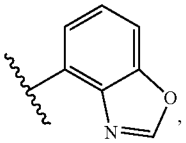
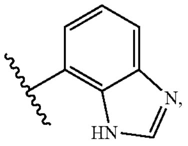
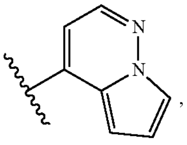
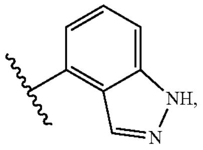
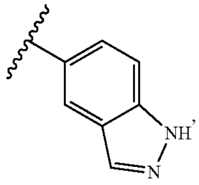
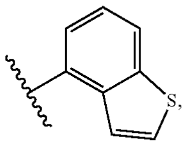
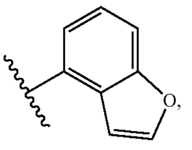
and -continued

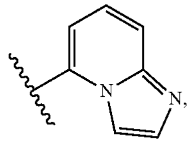

any of which is substituted with one or more $R^{15}$.

B161. The compound of any one of embodiments B130-B160, wherein $R^6$ is selected from:

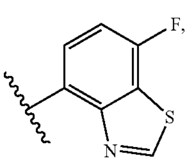
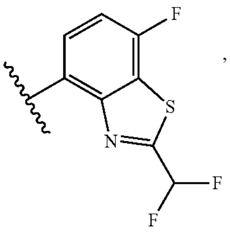
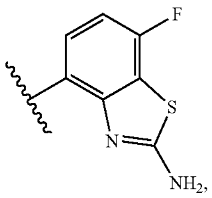
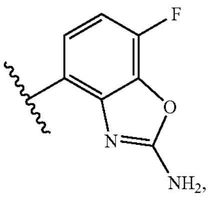
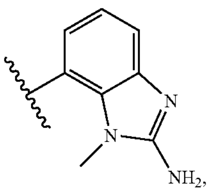
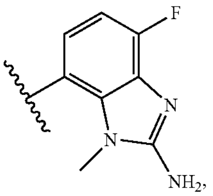
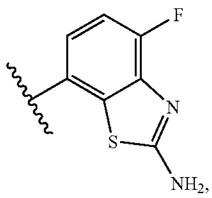
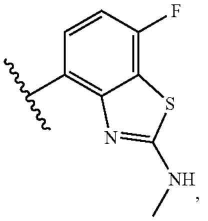
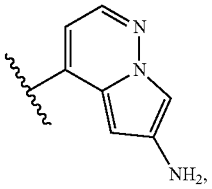
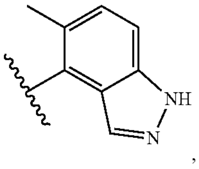
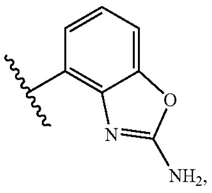
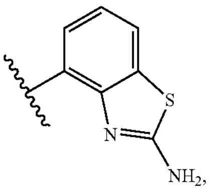

-continued

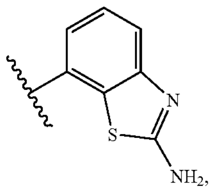
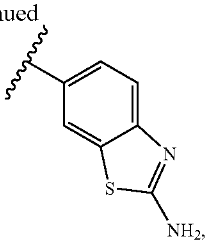
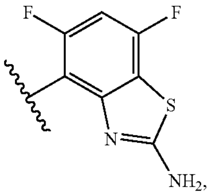
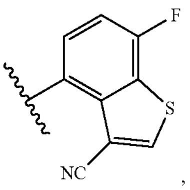
,
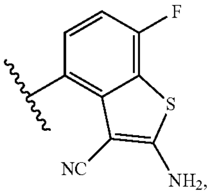
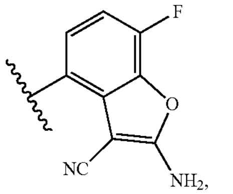
and
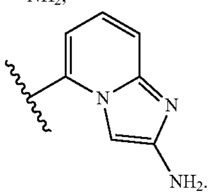

B162. The compound of any one of embodiments B130-B161, wherein $R^6$ is selected from

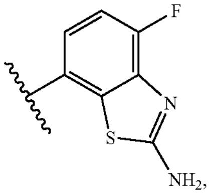
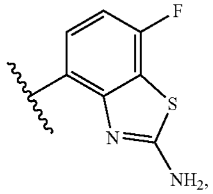
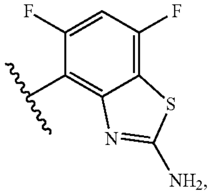
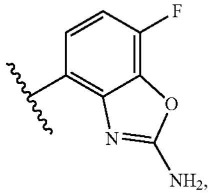
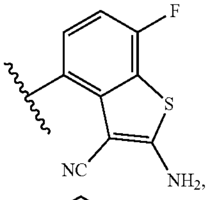
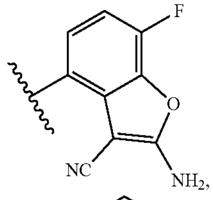
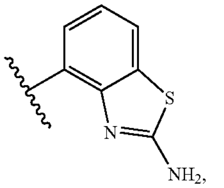
and
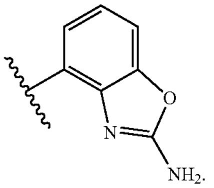

B163. The compound of any one of embodiments B130-B162, wherein $R^7$ is a halogen.

B164. The compound of embodiment B163, wherein $R^7$ is F.

B165. The compound of any one of embodiments B130-B162, wherein $R^7$ is H.

B166. The compound of any one of embodiments B130-B162, wherein $R^7$ is —CN.

B167. The compound of any one of embodiments B130-B162, wherein $R^7$ is $—OR^{12}$.

B168. The compound of any one of embodiments B130-B167, wherein each E is independently selected from

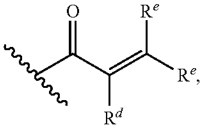
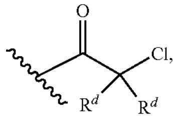
and
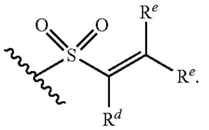

B169. The compound of embodiment B168, wherein each E is

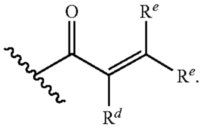

B170. The compound of embodiment B169, wherein each $R^d$ and $R^e$ is H.

B171. A compound according to Formula ID:

(ID)

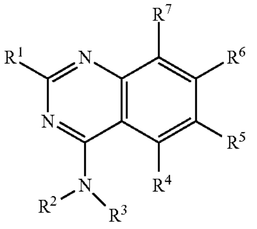

or a salt (e.g., pharmaceutically acceptable salt) thereof, wherein:

$R^1$ is selected from $—OR^8$,

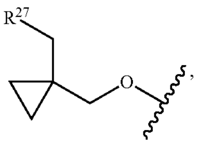

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle, wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from —CN, $C_{2-6}$alkynyl, $C_{1-6}$alkyl, a 3-6 membered carbocycle, a 5-6 membered heteroaryl, phenyl, and a 3-6 membered heterocycle, wherein any $C_{1-6}$alkyl is unsubstituted or is substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^{15}$;

$R^7$ is selected from halogen, —$OR^x$, —CN, and H;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$ alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$N(R^{12})C(O)(C_{1-6}alkyl)$, —$OR^{12}$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^x$ is independently selected from $C_{1-6}$ alkyl, a 3-6 membered carbocycle, and H;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

each E is independently selected from

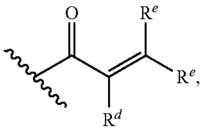
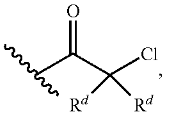
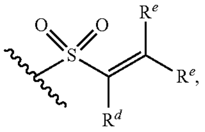
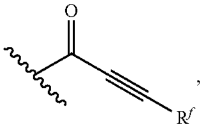
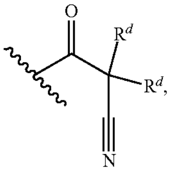
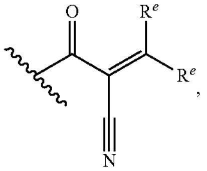
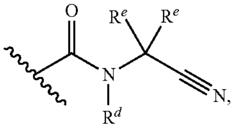
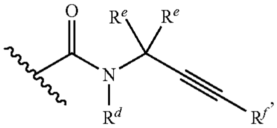
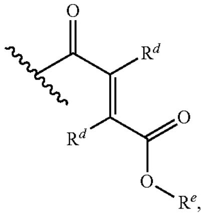
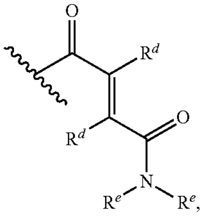
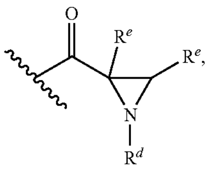
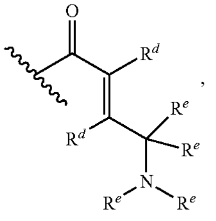

and —CN;

each $R^d$ and $R^e$ is independently selected from halogen, $C_{1-6}$ alkyl, and H; and each $R^f$ is independently selected from $C_{1-6}$ alkyl and H.

B172. The compound of embodiment B171, wherein $R^5$ is selected from $C_{2-6}$alkynyl.

B173. The compound of embodiment B172, wherein $R^5$ is $C_2$alkynyl.

B174. The compound of embodiment B171, wherein $R^5$ is $C_{1-6}$alkyl that is unsubstituted or substituted with one or more $R^{13}$.

B175. The compound of embodiment B174, wherein $R^5$ is $C_{1-6}$alkyl that is substituted with one or more $R^{13}$, wherein each $R^{13}$ is independently selected from —$OR^{22}$, —CN, and —$N(R^{22})_2$.

B176. The compound of embodiment B175, wherein $R^5$ is $C_{1-6}$alkyl that is substituted with —CN.

B177. The compound of embodiment B176, wherein $R^5$ is —$CH_2CN$.

B178. The compound of embodiment B171, wherein $R^5$ is selected from a 3-6 membered carbocycle and a phenyl, wherein any carbocycle or phenyl is unsubstituted or substituted with one or more $R^{14}$.

B179. The compound of embodiment B178, wherein $R^5$ is selected from a cyclobutyl that is unsubstituted or substituted with one or more $R^{14}$.

B180. The compound of embodiment B178, wherein $R^5$ is selected from a phenyl that is unsubstituted or substituted with one or more $R^{14}$.

B181. The compound of embodiment B171, wherein $R^5$ is selected from a 3-6 membered heterocycle and a 5-6 membered heteroaryl, wherein any heterocycle or heteroaryl is unsubstituted or substituted with one or more $R^{14}$.

B182. The compound of embodiment B181, wherein $R^5$ is selected from a 5-6 membered heterocycle or heteroaryl that includes one or two heteroatoms selected from O and N and is unsubstituted or substituted with one or more $R^{14}$.

B183. The compound of embodiment B182, wherein $R^5$ is selected from furanyl, pyridinyl, and pyrazolyl that is unsubstituted or is substituted with one or more $R^{14}$.

B184. The compound of embodiment B183, wherein $R^5$ is selected from

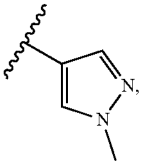, 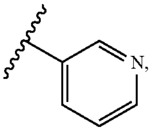, and 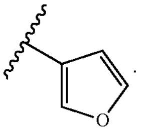.

B185. The compound of any one of embodiments B171-B184, wherein $R^1$ is H.

B186. The compound of any one of embodiments B171-B184, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl.

B187. The compound of embodiment B186, wherein $R^8$ is a heterocycle or an alkylheterocycle, wherein any heterocycle contains 4-8 members and is substituted with one or more $R^a$.

B188. The compound of embodiment B186 or B187, wherein $R^1$ is selected from

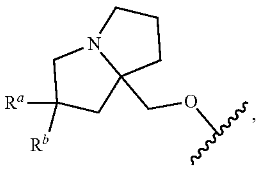, wherein $R^a$ and $R^b$ are each independently selected from halogen, $C_{1-6}$ alkyl, —$OR^{12}$, and H, wherein any $C_{1-6}$ alkyl is unsubstituted or is substituted with one or more $R^{13}$.

B189. The compound of embodiment B188, wherein $R^1$ is selected from:

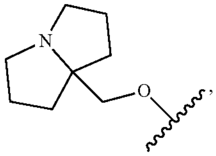, 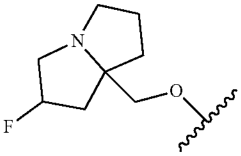,

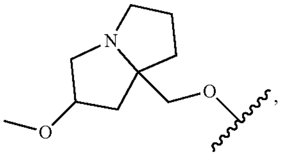,

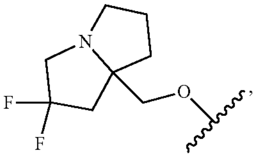, and 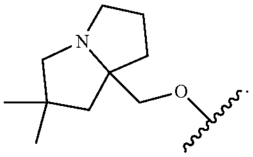.

B190. The compound of embodiment B188, wherein $R^1$ is selected from

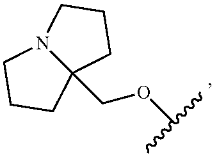, 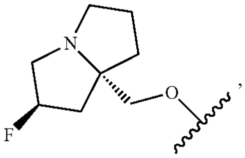,

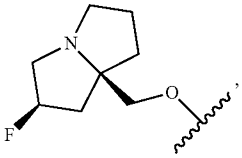, 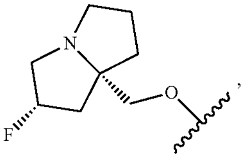,

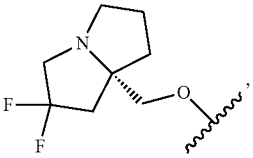, 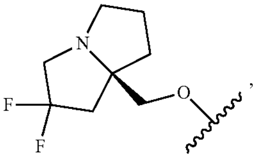,

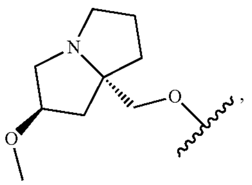, 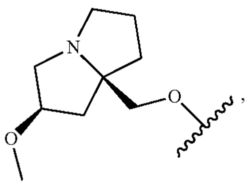,

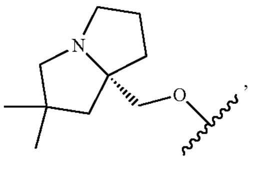, and 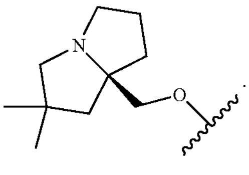.

B191. The compound of embodiment B186 or B187, wherein $R^1$ is selected from

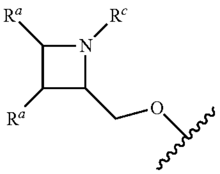, wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

B192. The compound of embodiment B191, wherein $R^1$ is selected from

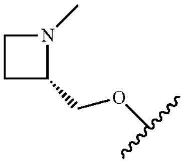 and 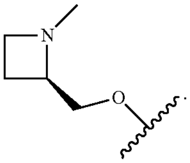.

B193. The compound of embodiment B186 or B187, wherein $R^1$ is selected from:

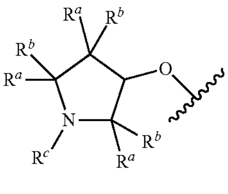, 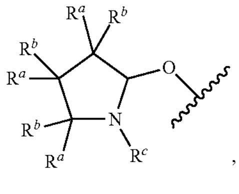,

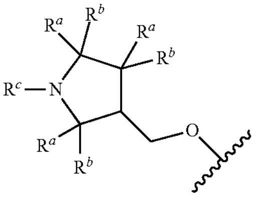, and

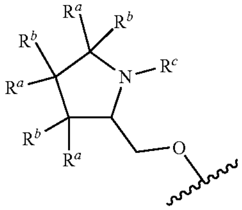, wherein each $R^a$ and $R^b$ is independently selected from halogen, $C_{1-6}$ alkyl, —$OR^{12}$, and H; and $R^c$ is selected from $C_{1-6}$ alkyl, wherein the $C_{1-6}$ alkyl is unsubstituted or is substituted with one or more $R^{13}$.

B194. The compound of embodiment B193, wherein $R^1$ is selected from

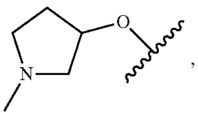, 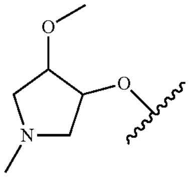,

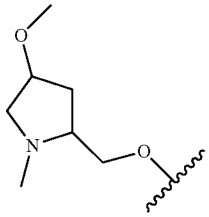, 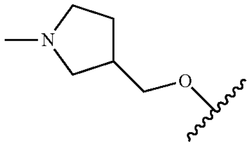,

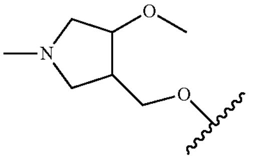, 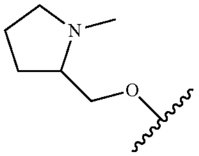,

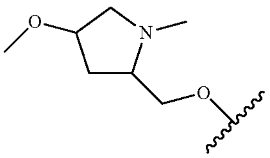, 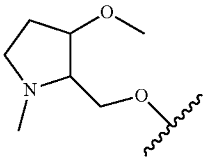,

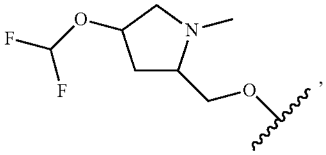,

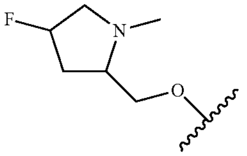, 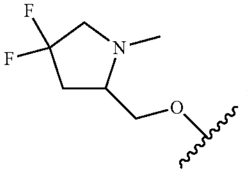,

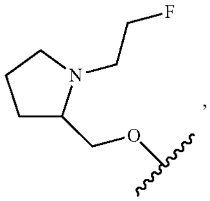, 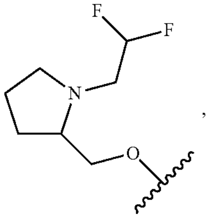,

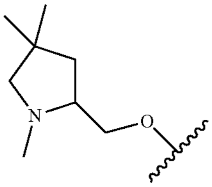, 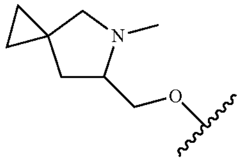, and

-continued

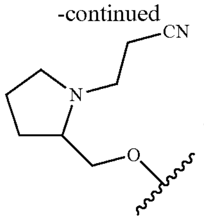

.

B195. The compound of embodiment B193, wherein $R^1$ is selected from

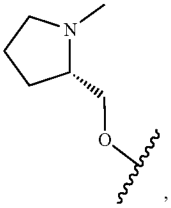

,

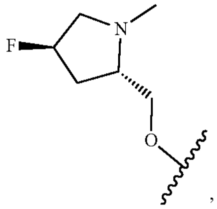

,

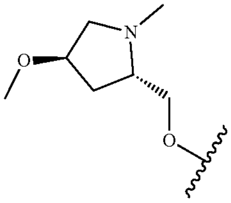

, and

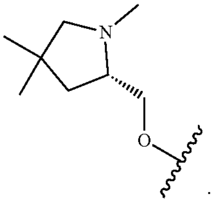

.

B196. The compound of any one of embodiments B171-B184, wherein $R^1$ is selected from

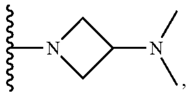

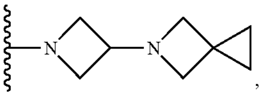

,

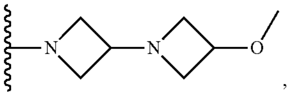

,

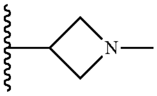

, and

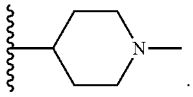

.

B197. The compound of any one of embodiments B171-B196, wherein $R^2$ is H.

B198. The compound of any one of embodiments B171-B196, wherein $R^2$ is $C_{1-6}$ alkyl.

B199. The compound of embodiment B198, wherein $R^2$ is methyl.

B200. The compound of any one of embodiments B171-B196, wherein $R^2$ is a 3-6 membered carbocycle.

B201. The compound of any one of embodiments B171-B200, wherein $R^3$ is a 4-6 membered heterocycle that is substituted with one or more E and 0-4 $R^{10}$, wherein the heterocycle includes one or more heteroatoms selected from N, O, and S, optionally wherein two $R^{10}$ groups, together with the atom or atoms to which they are attached, form a 3-6 membered carbocycle.

B202. The compound of embodiment B200, wherein $R^3$ is a 4-6 membered heterocycle that is substituted with one or more E and 0-4 $R^{10}$, wherein the heterocycle includes a single heteroatom that is N, optionally wherein two $R^{10}$ groups, together with the atom or atoms to which they are attached, form a 3-6 membered carbocycle.

B203. The compound of embodiment B202, wherein $R^3$ is selected from

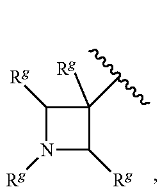

,

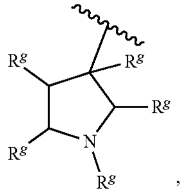

,

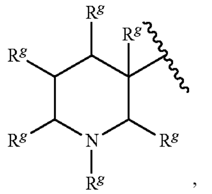

, and

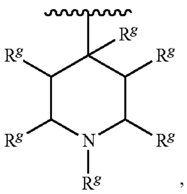

, wherein each $R^g$ is independently selected from $C_{1-6}$alkyl, halogen, H, and E, wherein at least one $R^g$ is E, and wherein any $C_{1-6}$alkyl is unsubstituted or substituted with one or more $R^{20}$.

B204. The compound of embodiment B203, wherein $R^3$ is selected from

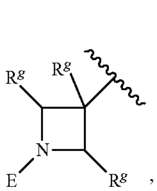

,

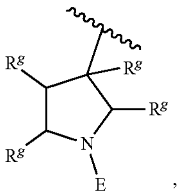

,

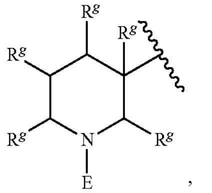

, and

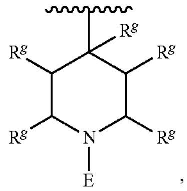

, wherein each $R^g$ is independently selected from $C_{1-6}$alkyl, halogen, and H, wherein any $C_{1-6}$alkyl is unsubstituted or substituted with one or more $R^{20}$.

B205. The compound of embodiment B204, wherein each $R^g$ is H.

B206. The compound of any one of embodiments B171-B196, wherein $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle.

B207. The compound of embodiment B206, wherein $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle.

B208. The compound of embodiment B207, wherein $R^2$ and $R^3$, together with the atom to which they are attached, form the structure

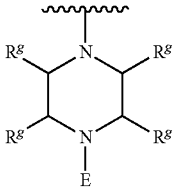

or

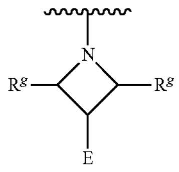

, wherein each $R^g$ is independently selected from $C_{1-6}$alkyl and H, wherein any $C_{1-6}$alkyl is unsubstituted or substituted with one or more $R^{20}$.

B209. The compound of embodiment B208, wherein each $R^g$ is H.

B210. The compound of embodiment B208, wherein $R^2$ and $R^3$, together with the atom to which they are attached, form the structure

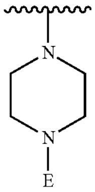

,

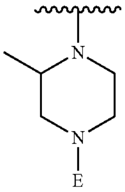

,

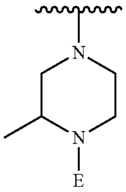

,

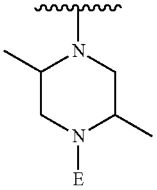

,

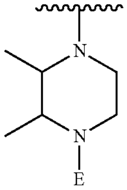

,

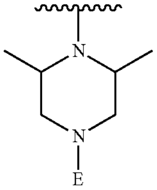

,

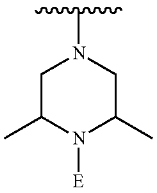

,

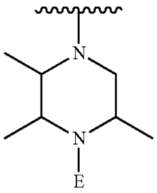

,

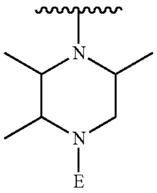

, or

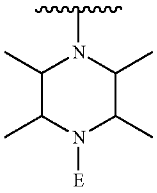

.

B211. The compound of embodiment B206, wherein $R^2$ and $R^3$, together with the atom to which they are attached, form a 4-8 membered bicyclic heterocycle comprising a fused ring system that is substituted with one or more E and 0-4 $R^{11}$.

B212. The compound of embodiment B211, wherein $R^2$ and $R^3$, together with the atom to which they are attached, form a structure selected from:

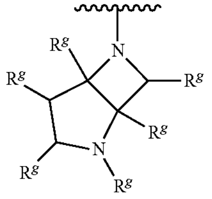

and

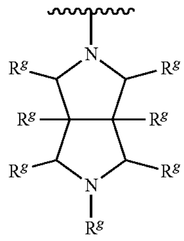

, wherein each $R^g$ is independently selected from $C_{1-6}$alkyl, H, and E, wherein at least one $R^g$ is E, and wherein any $C_{1-6}$alkyl is unsubstituted or substituted with one or more $R^{20}$.

B213. The compound of embodiment B212, wherein $R^2$ and $R^3$, together with the atom to which they are attached, form a structure selected from:

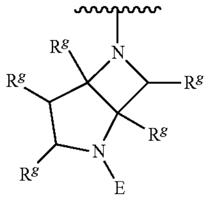

and

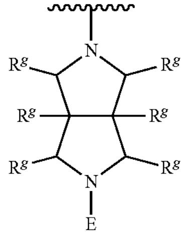

, wherein each $R^g$ is independently selected from $C_{1-6}$alkyl and H, wherein any $C_{1-6}$alkyl is unsubstituted or substituted with one or more $R^{20}$.

B214. The compound of embodiment B213, wherein $R^2$ and $R^3$, together with the atom to which they are attached, form the structure

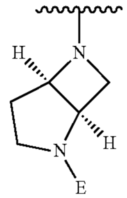

.

B215. The compound of any one of embodiments B171-B214, wherein $R^4$ is H.

B216. The compound of any one of embodiments B171-B215, wherein $R^6$ is a 9-10 membered heteroaryl having 1-3 heteroatoms independently selected from nitrogen, oxygen, and sulfur that is substituted with one or more $R^{15}$.

B217. The compound of any one of embodiments B171-B216, wherein $R^6$ has the structure:

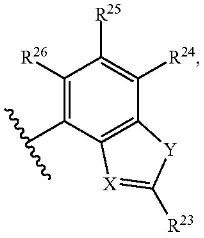

wherein X is selected from N and C—CN; Y is selected from O and S; $R^{23}$ is selected from —N($R^{12}$)$_2$, $C_{1-6}$alkyl, and $C_{1-6}$alkyl-N($R^{22}$)$_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B218. The compound of any one of embodiments B171-B217, wherein $R^6$ is selected from:

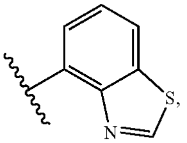 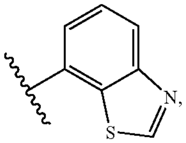

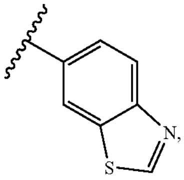 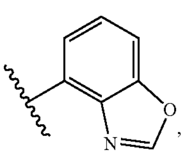

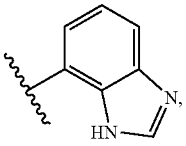 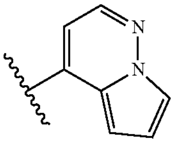

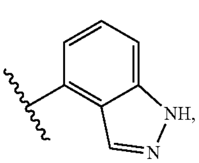 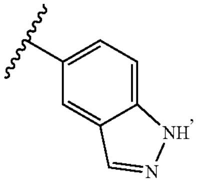

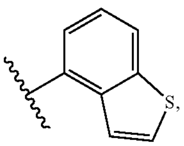 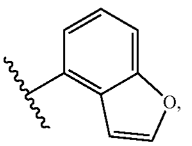 and

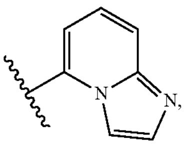

any of which is substituted with one or more $R^5$.

B219. The compound of any one of embodiments B171-B218, wherein $R^6$ is selected from:

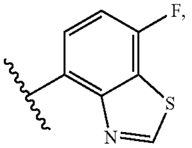 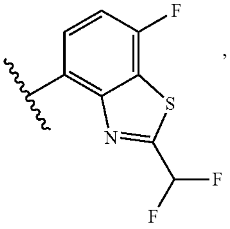 ,

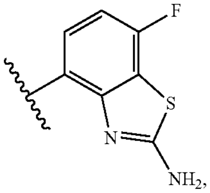 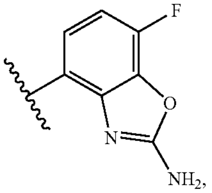

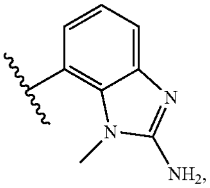 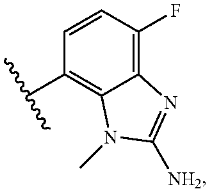

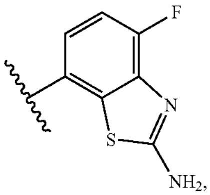 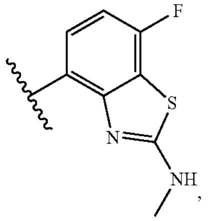

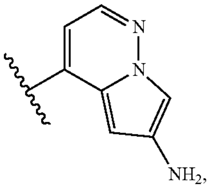 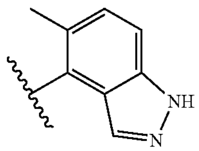 ,

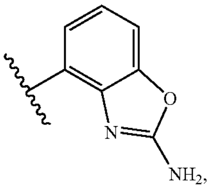 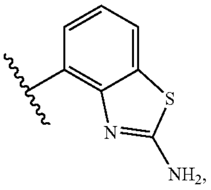

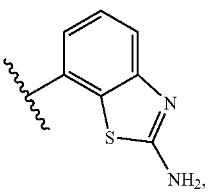 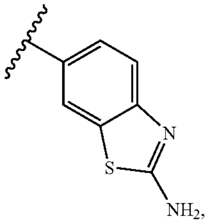

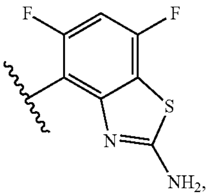 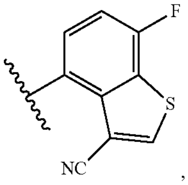 ,

-continued

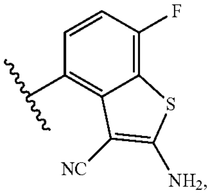 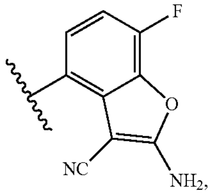 and

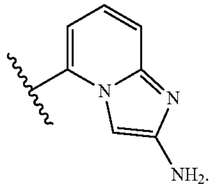

B220. The compound of any one of embodiments B171-B219, wherein $R^6$ is selected from

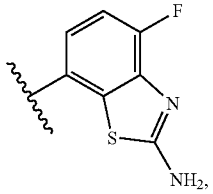 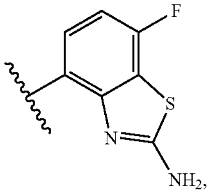

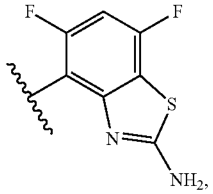 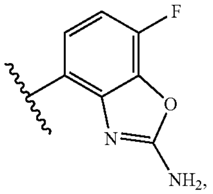

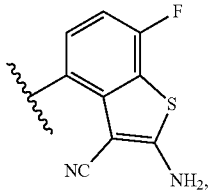 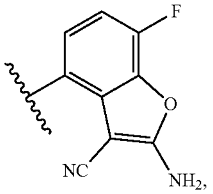

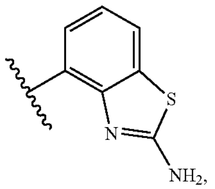 and 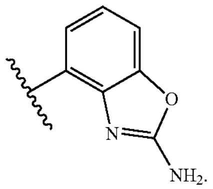

B221. The compound of any one of embodiments B171-B220, wherein $R^7$ is a halogen.

B222. The compound of embodiment B221, wherein $R^7$ is F.

B223. The compound of any one of embodiments B171-B220, wherein $R^7$ is H.

B224. The compound of any one of embodiments B171-B220, wherein $R^7$ is —CN.

B225. The compound of any one of embodiments B171-B220, wherein $R^7$ is —$OR^x$.

B226. The compound of any one of embodiments B171-B225, wherein each E is independently selected from

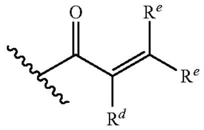 , 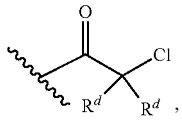 , and

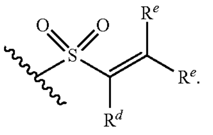

B227. The compound of embodiment B226, wherein each E is

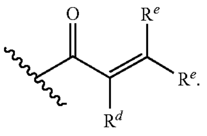

B228. The compound of embodiment B227, wherein each $R^d$ and $R^e$ is H.

B229. The compound of any one of embodiments B171-B228, wherein the compound is a compound according to Formula ID1:

(ID1)

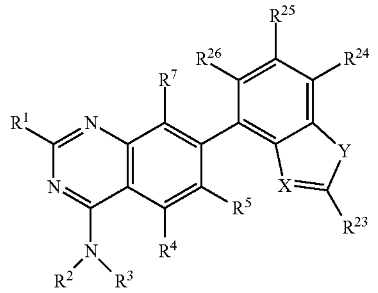

or a salt (e.g., a pharmaceutically acceptable salt) thereof, wherein:

$R^1$ is —$OR^8$;

$R^4$ is H;

$R^5$ is selected from $C_{2-6}$alkynyl, $C_{1-6}$alkyl, a 3-6 membered carbocycle, a 5-6 membered heteroaryl, phenyl, and a 3-6 membered heterocycle, wherein any $C_{1-6}$alkyl is substituted with —CN, and wherein any carbocycle, heteroaryl, phenyl, or heterocycle is unsubstituted or substituted with one or more $R^{14}$;

X is selected from N and C—CN;

Y is selected from O and S;

$R^{23}$ is selected from —$N(R^{12})_2$, $C_{1-6}$alkyl, and $C_{1-6}$alkyl-$N(R^{12})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B230. A compound according to Formula IE:

(IE)

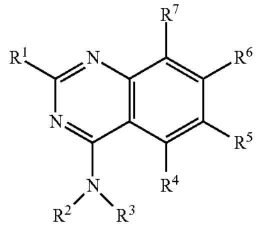

or a salt (e.g., pharmaceutically acceptable salt) thereof, wherein:

$R^1$ is selected from —$OR^8$,

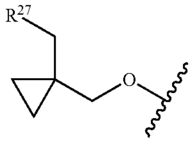, a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^6$ is a bicyclic heteroaryl substituted with one or more $R^5$;

$R^7$ is —OH;

$R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —$N(R^{12})_2$, and $C_{1-6}$alkyl, wherein any $C_{1-6}$alkyl is unsubstituted or substituted with one or more $R^{13}$;

each $R^{15}$ is independently selected from halogen, —$N(R^{12})_2$, —$OR^{12}$, —CN, and $C_{1-6}$alkyl, wherein any $C_{1-6}$alkyl is unsubstituted or substituted with one or more $R^{13}$;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ is independently selected from halogen, $C_{1-6}$ alkyl, —$OR^{12}$, and H, wherein any $C_{1-6}$ alkyl is unsubstituted or is substituted with one or more $R^{13}$;

each E is independently selected from

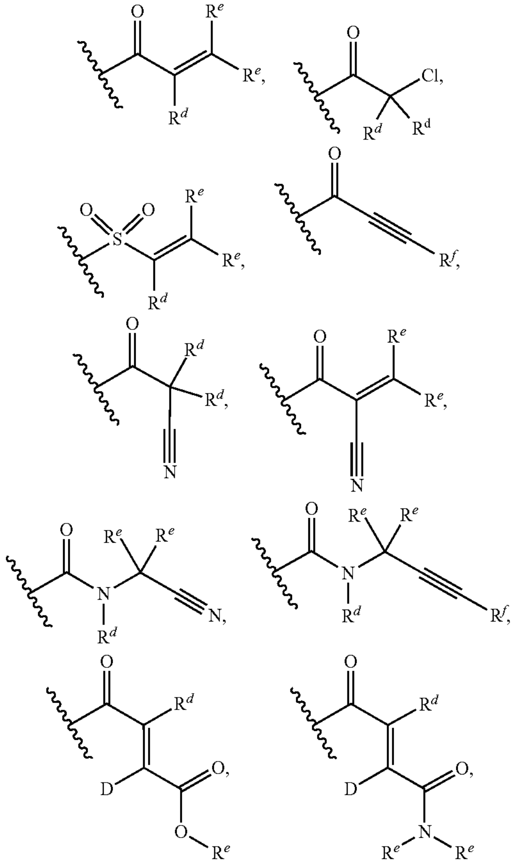

-continued

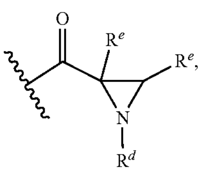

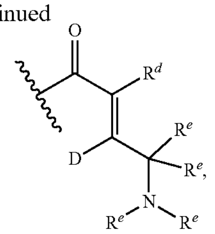

and —CN;

each $R^d$ and $R^e$ is independently selected from halogen, $C_{1-6}$ alkyl, and H; and each $R^f$ is independently selected from $C_{1-6}$ alkyl and H.

B231. The compound of embodiment B230, wherein $R^1$ is H.

B232. The compound of embodiment B230, wherein $R^1$ is selected from —$OR^8$, wherein $R^8$ is selected from a heterocycle and an alkylheterocycle, wherein any heterocycle comprises 4-8 members and is unsubstituted or is substituted with one or more $R^a$, and wherein an alkyl moiety of any alkylheterocycle is selected from $C_{1-6}$ alkyl.

B233. The compound of embodiment B232, wherein $R^8$ is a heterocycle or an alkylheterocycle, wherein any heterocycle contains 4-8 members and is substituted with one or more $R^a$.

B234. The compound of embodiment B232 or B233, wherein $R^1$ is selected from

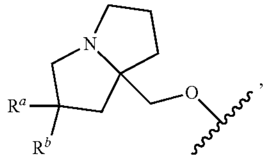

wherein $R^a$ and $R^b$ are each independently selected from halogen, $C_{1-6}$ alkyl, —$OR^{12}$, and H, wherein any $C_{1-6}$ alkyl is unsubstituted or is substituted with one or more $R^{13}$.

B235. The compound of embodiment B234, wherein $R^1$ is selected from:

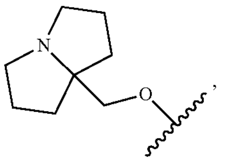

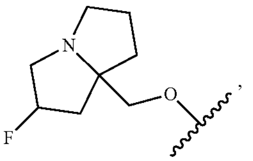

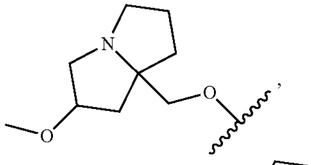

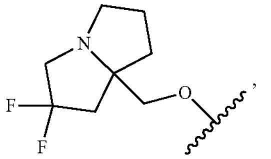

and

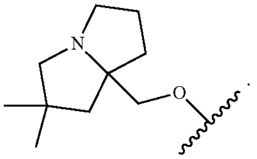

B236. The compound of embodiment B234, wherein $R^1$ is selected from

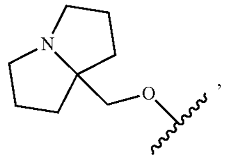

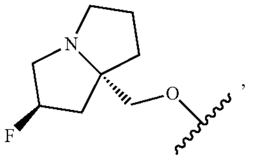

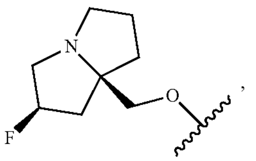

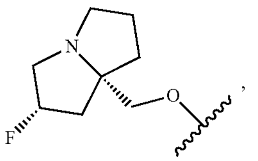

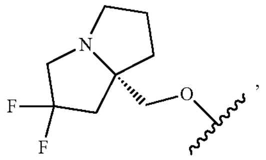

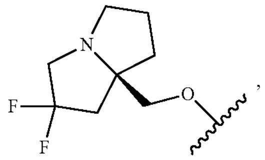

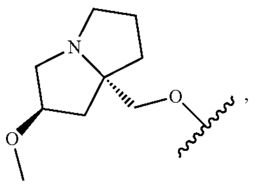

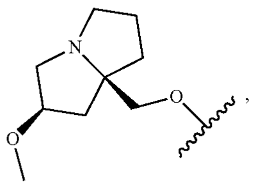

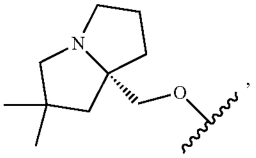

and

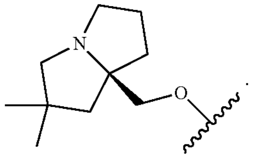

B237. The compound of embodiment B232 or B233, wherein $R^1$ is selected from

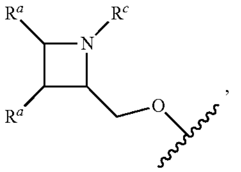

wherein each $R^a$ is independently selected from halogen, $C_{1-6}$ alkyl, —$OR^{12}$, and H; and wherein $R^c$ is selected from $C_{1-6}$ alkyl, wherein any $C_{1-6}$ alkyl is unsubstituted or is substituted with one or more $R^{13}$.

B238. The compound of embodiment B237, wherein $R^1$ is selected from

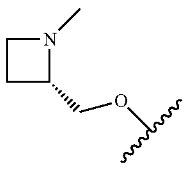

and

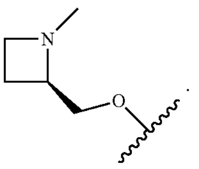

B239. The compound of embodiment B232 or B233, wherein $R^1$ is selected from:

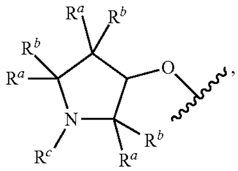,
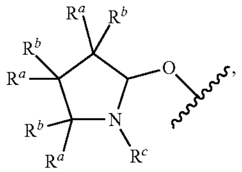,
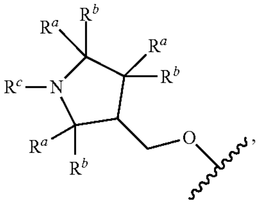, and
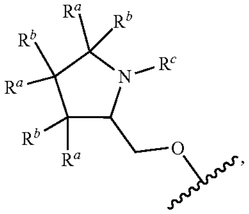, wherein each $R^a$ and $R^b$ is independently selected from halogen, $C_{1-6}$ alkyl, $-OR^{12}$, and H; and $R^c$ is selected from $C_{1-6}$ alkyl, wherein the $C_{1-6}$ alkyl is unsubstituted or is substituted with one or more $R^{13}$.

B240. The compound of embodiment B239, wherein $R^1$ is selected from

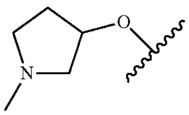,
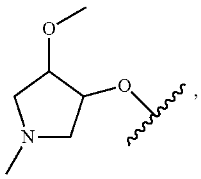,
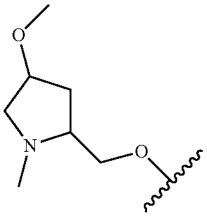,
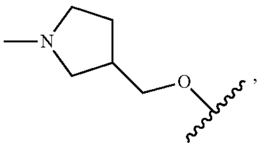,
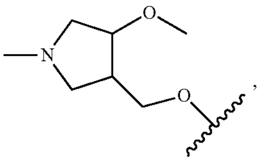,
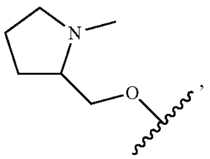,
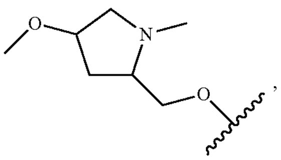,
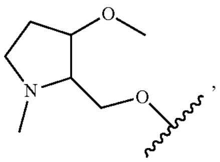, -continued

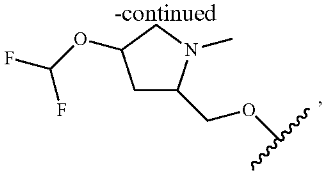,
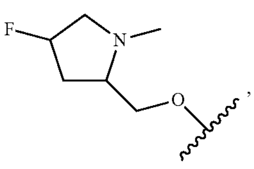,
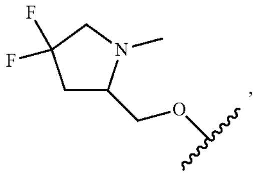,
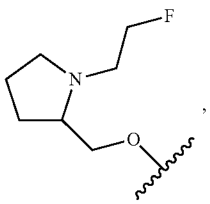,
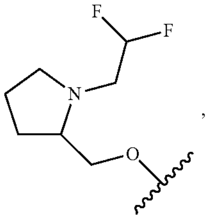,
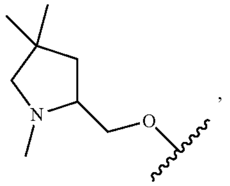,
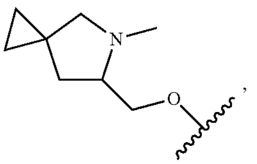, and
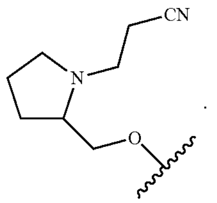 [SMILES: *OCC1CCCN1CCC#N].

B241. The compound of embodiment B240, wherein $R^1$ is selected from

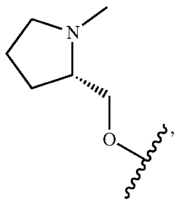,
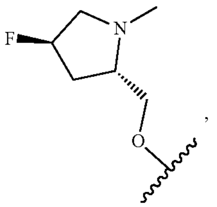,
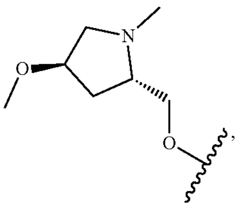, and
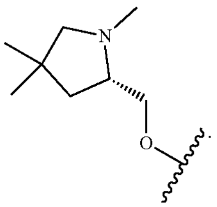.

B242. The compound of embodiment B230, wherein $R^1$ is selected from

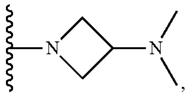,
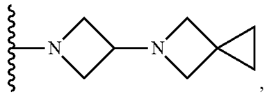,
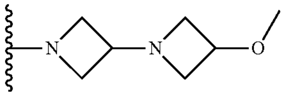,
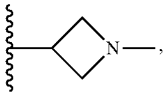, and
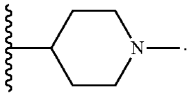.

B243. The compound of any one of embodiments B230-B242, wherein $R^2$ is H.

B244. The compound of any one of embodiments B3230-B3242, wherein $R^2$ is $C_{1-6}$ alkyl.

B245. The compound of any one of embodiments B230-B244, wherein $R^3$ is selected from $C_{1-6}$ alkyl that is substituted with —N($R^{12}$)(E).

B246. The compound of embodiment B245, wherein $R^3$ is selected from $C_2$ alkyl that is substituted with —N($R^{12}$)(E).

B247. The compound of embodiment B246, wherein $R^3$ is selected from $C_2$ alkyl that is substituted with —N(H)(E).

B248. The compound of any one of embodiments B230-B244, wherein $R^3$ is a 4-6 membered heterocycle that is substituted with one or more E and 0-4 $R^{10}$.

B249. The compound of embodiment B248, wherein $R^3$ is a 4-6 membered heterocycle containing one or more heteroatoms selected from O, N, and S, wherein the heterocycle is substituted with one or more E and 0-4 $R^{10}$.

B250. The compound of embodiment B249, wherein $R^3$ is a 4-6 membered heterocycle containing a single heteroatom that is N, wherein the heterocycle is substituted with one or more E and 0-4 $R^{10}$.

B251. The compound of embodiment B250, wherein $R^3$ is an azetidine, pyrrolidine, or piperidine, wherein the azetidine, pyrrolidine, or piperidine is substituted with one or more E and 0-4 $R^{10}$.

B252. The compound of any one of embodiments B248-B251, wherein at least one $R^{10}$ is a halogen.

B253. The compound of any one of embodiments B248-B252, wherein at least one $R^{10}$ is a methyl.

B254. The compound of any one of embodiments B230-B242, wherein $R^2$ and $R^3$, together with the atom to which they are attached, form a 4-8 membered heterocycle that is substituted with one or more E and 0-4 $R^{11}$.

B255. The compound of embodiment B254, wherein $R^2$ and $R^3$, together with the atom to which they are attached, form a piperazinyl ring that is substituted with one or more E and 0-4 $R^{11}$.

B256. The compound of embodiment B254, wherein $R^2$ and $R^3$, together with the atom to which they are attached, form the structure

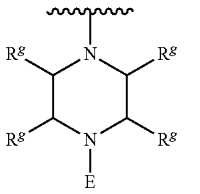
or
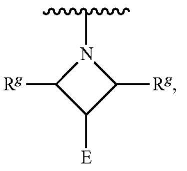, wherein each $R^g$ is independently selected from $C_{1-6}$alkyl and H, wherein any $C_{1-6}$alkyl is unsubstituted or substituted with one or more $R^{20}$.

B257. The compound of embodiment B256, wherein each $R^g$ is H.

B258. The compound of embodiment B257, wherein $R^2$ and $R^3$, together with the atom to which they are attached, form the structure

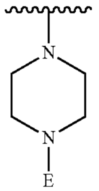,
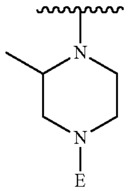,
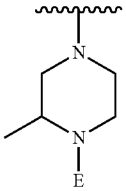,
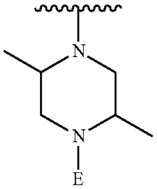,
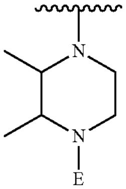,
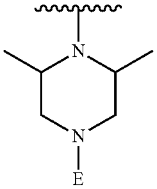,
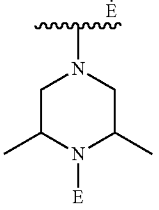,
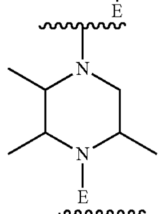,
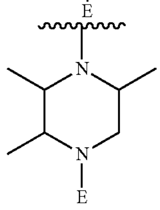, or
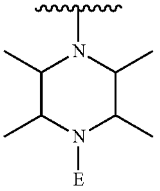.

B259. The compound of any one of embodiments B230-B258, wherein $R^4$ is H.

B260. The compound of any one of embodiments B230-B259, wherein $R^5$ is a halogen.

B261. The compound of embodiment B260, wherein $R^5$ is Cl.

B262. The compound of any one of embodiments B230-B259, wherein $R^5$ is H.

B263. The compound of any one of embodiments B230-B259, wherein $R^5$ is —CN.

B264. The compound of any one of embodiments B230-B259, wherein $R^5$ is selected from $C_{1-6}$alkyl that is unsubstituted or substituted with one or more $R^{13}$.

B265. The compound of embodiment B264, wherein $R^5$ is selected from —$CH_3$, —$CH_2CH_3$, —$CF_2H$, —$CF_3$, —$CF_2CH_3$, and —$CH_2CN$.

B266. The compound of any one of embodiments B230-B259, wherein $R^5$ is selected from —$OR^{12}$, wherein $R^{12}$ is selected from $C_{1-6}$ alkyl and H.

B267. The compound of any one of embodiments B230-B259, wherein $R^5$ is selected from a 3-6 membered carbocycle, a 5-6 membered heteroaryl, phenyl, and a 3-6 membered heterocycle, wherein any carbocycle, heteroaryl, phenyl, or heterocycle is unsubstituted or substituted with one or more $R^{14}$.

B268. The compound of embodiment B267, wherein $R^5$ is furanyl.

B269. The compound of embodiment B267, wherein $R^5$ is phenyl.

B270. The compound of any one of embodiments B230-B269, wherein $R^6$ is a 9-10 membered heteroaryl having 1-3 heteroatoms independently selected from nitrogen, oxygen, and sulfur that is substituted with one or more $R^{15}$.

B271. The compound of any one of embodiments B230-B270, wherein $R^6$ has the structure:

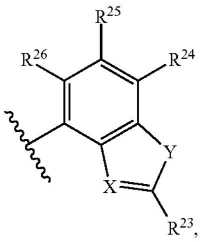

wherein X is selected from N and C—CN; Y is selected from O and S; $R^{23}$ is selected from —$N(R^{12})_2$, $C_{1-6}$alkyl, and $C_{1-6}$alkyl-$N(R^{22})_2$, wherein any $C_{1-6}$alkyl is unsubstituted or substituted with one or more $R^{13}$; and $R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$.

B272. The compound of any one of embodiments B230-B271, wherein $R^6$ is selected from:

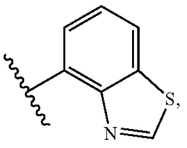
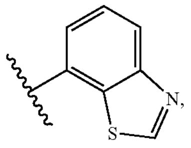
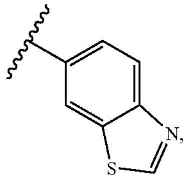
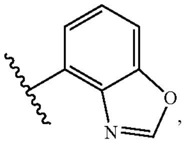
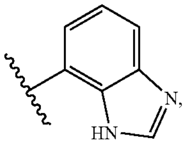
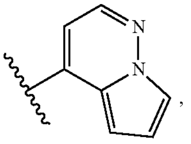
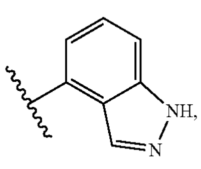
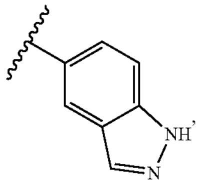
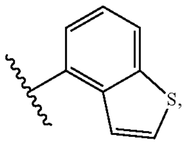
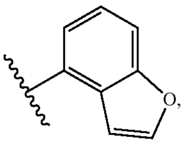

and

-continued

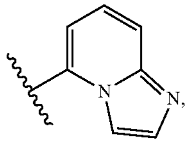

any of which is substituted with one or more $R^{15}$.

B273. The compound of any one of embodiments B230-B272, wherein $R^6$ is selected from:

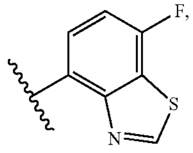
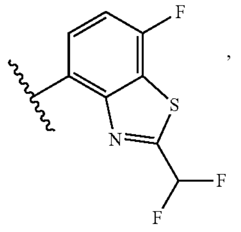
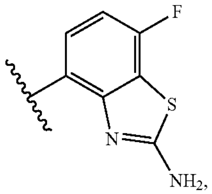
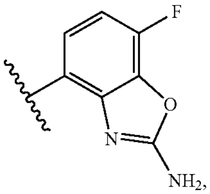
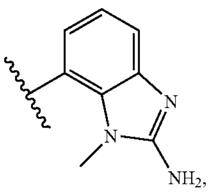
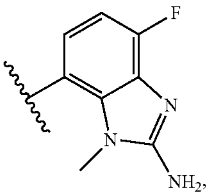
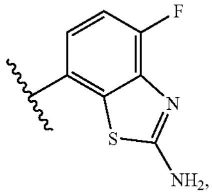
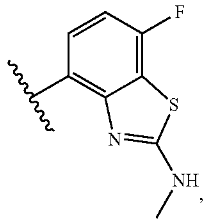
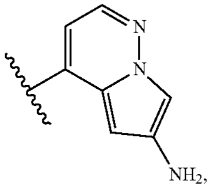
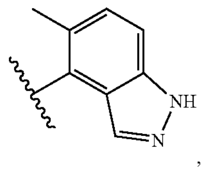
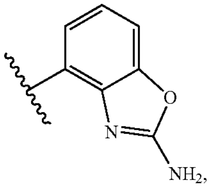
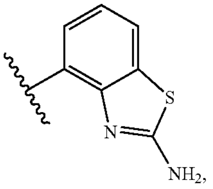

-continued

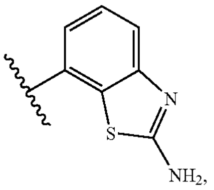

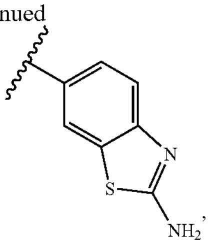

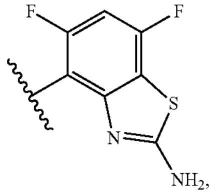

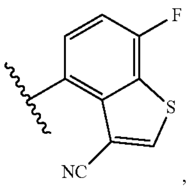

,

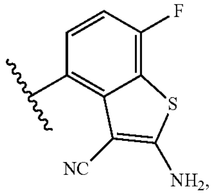

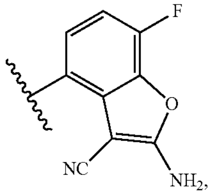

and

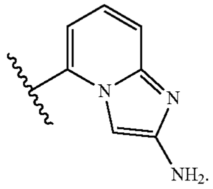

B274. The compound of any one of embodiments B230-B273, wherein $R^6$ is selected from

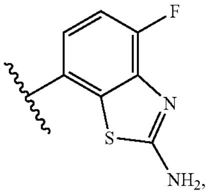

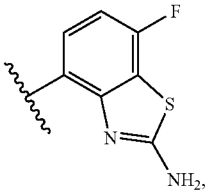

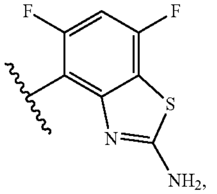

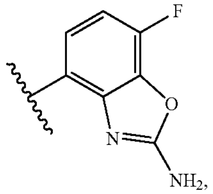

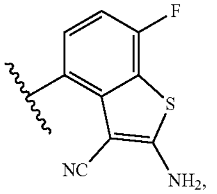

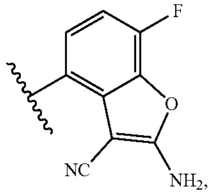

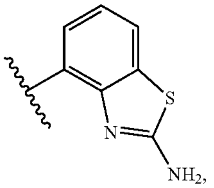

and

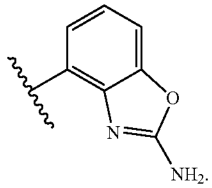

B275. The compound of any one of embodiments B230-B274, wherein each E is independently selected from

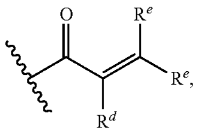

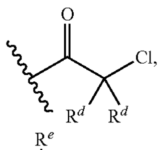

and

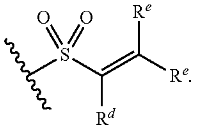

B276. The compound of embodiment B275, wherein each E is

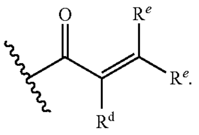

B277. The compound of embodiment B276, wherein each $R^d$ and $R^e$ is H.

B278. A compound according to Formula IIA:

(IIA)

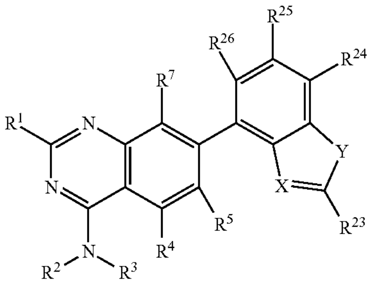

or a salt (e.g., pharmaceutically acceptable salt), wherein:

$R^1$ is selected from

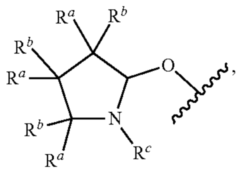

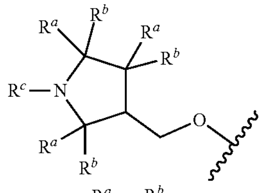

,

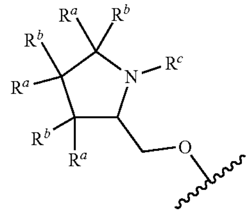

,

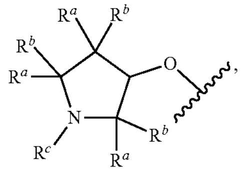

and a 4-6 membered heterocycle comprising a nitrogen atom, wherein the heterocycle is unsubstituted or substituted with one or more $R^{16}$;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is selected from $C_{1-6}$ alkyl and a 4-6 membered heterocycle, wherein the $C_{1-6}$ alkyl is substituted with —N($R^{12}$)(E), and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^X$, —CN, and H;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$ alkyl is unsubstituted or substituted with one or more $R^{13}$;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —N($R^2$)C(O)($C_{1-6}$alkyl), —$OR^{12}$, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

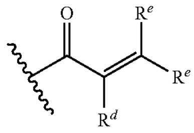,
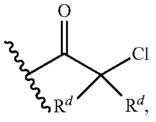
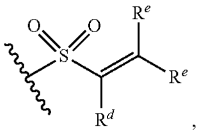,
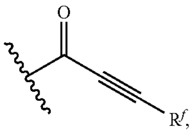
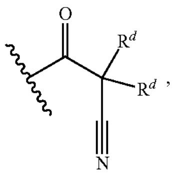,
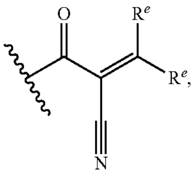
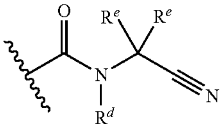,
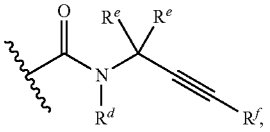
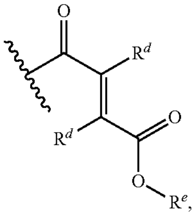
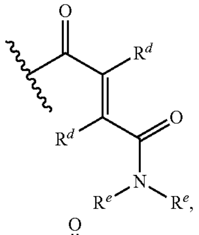
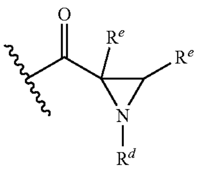,
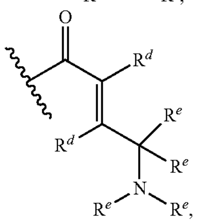

and —CN;

each $R^d$ and $R^e$ is independently selected from halogen, $C_{1-6}$ alkyl, and H; and each $R^f$ is independently selected from $C_{1-6}$ alkyl and H.

B279. A compound according to Formula IIA1:

(IIA1)

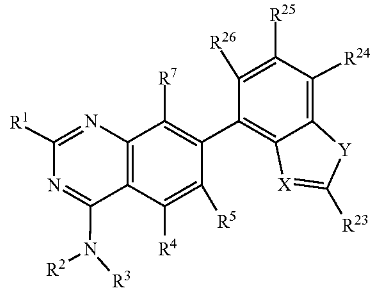

or a salt (e.g., pharmaceutically acceptable salt) thereof, wherein:

$R^1$ is selected from

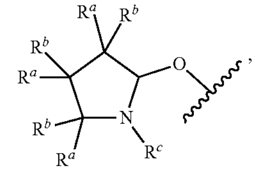,

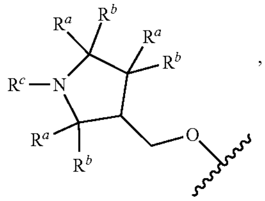,

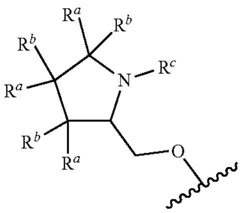, and

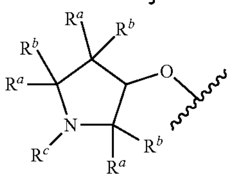;

$R^2$ is selected from H, $C_{1-6}$ alkyl, and a 3-6 membered carbocycle, wherein any $C_{1-6}$ alkyl is unsubstituted or is substituted with one or more $R^{13}$;

$R^3$ is a 4-6 membered heterocycle that is substituted with one or more E and 0-4 $R^{10}$, optionally wherein two $R^{10}$ groups, together with the atom or atoms to which they are attached, form a 3-6 membered carbocycle;

$R^4$ is H;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^X$, —CN, and H;

each $R^{10}$ is independently selected from $C_{1-6}$alkyl and halogen, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$ alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —$N(R^2)C(O)(C_{1-6}alkyl)$, —$OR^{12}$, and $C_{1-6}alkyl\text{-}N(R^2)_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

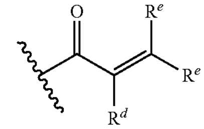,

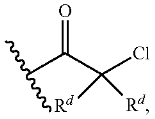,

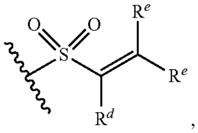,

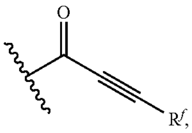,

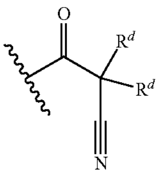,

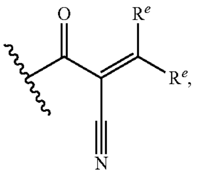,

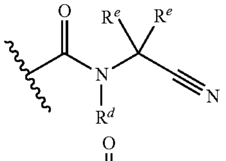,

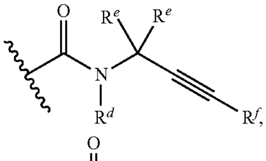,

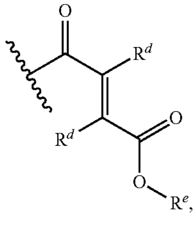,

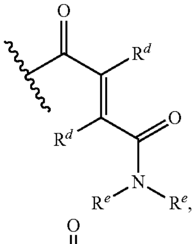,

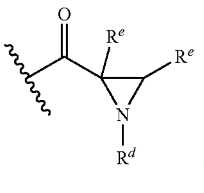,

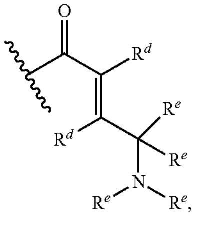, and —CN;

each $R^d$ and $R^e$ is independently selected from halogen, $C_{1-6}$ alkyl, and H; and each $R^f$ is independently selected from $C_{1-6}$ alkyl and H.

B280. The compound of embodiment B279, wherein $R^2$ is $C_{1-6}$ alkyl unsubstituted or substituted with one or more $R^{13}$.

B281. The compound of embodiment B280, wherein $R^2$ is selected from $—CH_3$, $—CH_2CH_3$, and $—CH(CH_3)_2$.

B282. The compound of any one of embodiments B279-B281, wherein $R^3$ is a 4-6 membered heterocycle that is substituted with one or more E and 0-4 $R^{10}$, wherein the heterocycle includes one or more heteroatoms selected from N, O, and S.

B283. The compound of embodiment B282, wherein $R^3$ is a 4-6 membered heterocycle that is substituted with one or more E and 0-4 $R^{10}$, wherein the heterocycle includes a single heteroatom that is N.

B284. The compound of embodiment B283, wherein $R^3$ is an azetidine, pyrrolidine, or piperidine, wherein the azetidine, pyrrolidine, or piperidine is substituted with one or more E and 0-4 $R^{10}$.

B285. The compound of any one of embodiments B279-B284, wherein $R^3$ is selected from:

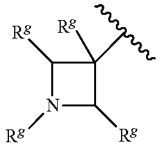,
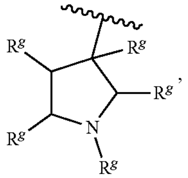,
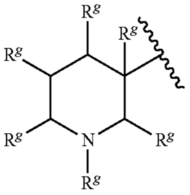, and
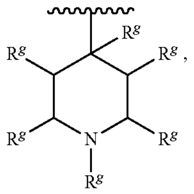, wherein each $R^g$ is independently selected from $C_{1-6}$alkyl, H, halogen, and E, wherein at least one $R^g$ is E, and wherein any $C_{1-6}$alkyl is unsubstituted or substituted with one or more $R^{20}$.

B286. The compound of embodiment B285, wherein $R^3$ is selected from:

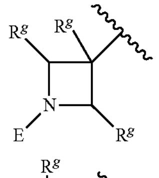,
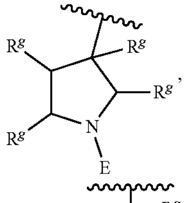,
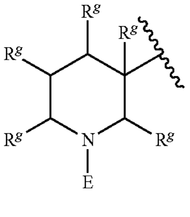, and
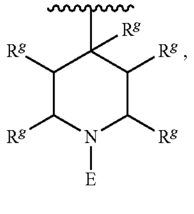, wherein each $R^g$ is independently selected from $C_{1-6}$alkyl, halogen, and H, wherein any $C_{1-6}$alkyl is unsubstituted or substituted with one or more $R^{20}$.

B287. The compound of embodiment B286, wherein at least one $R^g$ is a halogen.

B288. A compound according to Formula IIA2:

(IIA2)

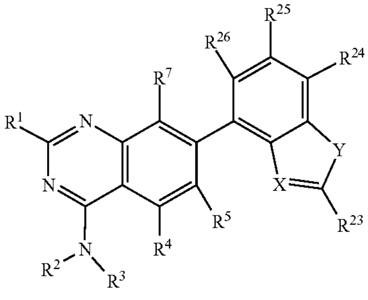

or a salt (e.g., pharmaceutically acceptable salt) thereof, wherein:

$R^1$ is selected from

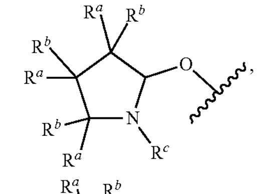,
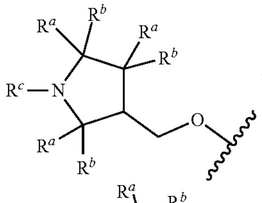,
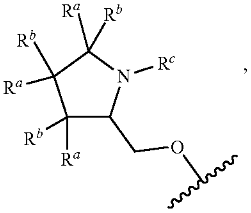, and
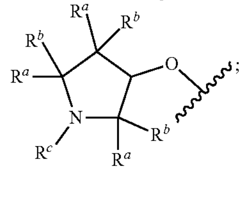;

$R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle or heterocycle;

$R^4$ is H;

$R^5$ is selected from H, —CN, halogen, $C_{1-6}$alkyl, $C_{2-6}$alkynyl, $—OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, $—OR^X$, —CN, and H;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from $—OR^{22}$, —CN, $—N(R^{22})_2$, and halogen;

each $R^{14}$ is independently selected from halogen, —CN, $—N(R^{12})_2$, and $C_{1-6}$alkyl, wherein any $C_{1-6}$ alkyl is unsubstituted or substituted with one or more $R^{13}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

each $R^X$ is independently selected from $C_{1-6}$ alkyl, a 3-6 membered carbocycle, and H;

X is selected from N and C—CN;

Y is selected from O and S;

$R^{23}$ is selected from —$N(R^{12})_2$, $C_{1-6}$alkyl, —$N(R^2)C(O)(C_{1-6}$alkyl), —$OR^{12}$, and $C_{1-6}$alkyl-$N(R^{12})_2$, wherein any $C_{1-6}$alkyl is unsubstituted or substituted with one or more $R^{13}$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

each $R^a$ and $R^b$ is independently selected from halogen, $C_{1-6}$ alkyl, —$OR^{12}$, and H, or an $R^a$ and $R^b$ connected to the same atom, together with the atom to which they are attached, form a $C_{3-6}$ carbocycle;

$R^c$ is selected from $C_{1-6}$ alkyl, wherein the $C_{1-6}$ alkyl is unsubstituted or is substituted with one or more $R^{13}$;

each E is independently selected from

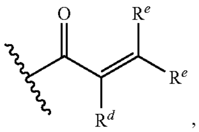
,
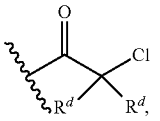
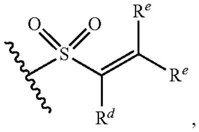
,
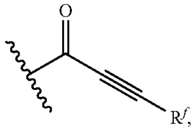
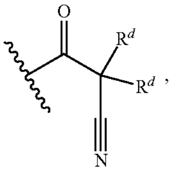
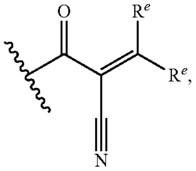
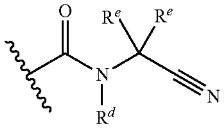
,
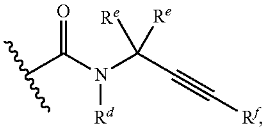
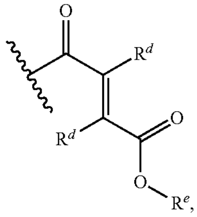
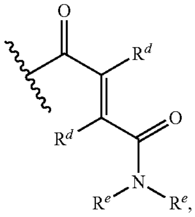
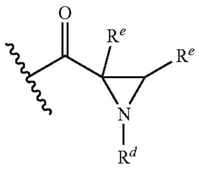
,
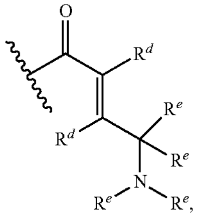

and —CN;

each $R^d$ and $R^e$ is independently selected from halogen, $C_{1-6}$ alkyl, and H; and each $R^f$ is independently selected from $C_{1-6}$ alkyl and H.

B289. The compound of embodiment B288, wherein $R^2$ and $R^3$, together with the atom to which they are attached, form a 4-8 membered heterocycle that is substituted with one or more E and 0-4 $R^{11}$.

B290. The compound of embodiment B288, wherein $R^2$ and $R^3$, together with the atom to which they are attached, form a piperazinyl ring that is substituted with one or more E and 0-4 $R^{11}$, optionally wherein two $R^{11}$ groups, together with the atom or atoms to which they are attached, form a 3-6 membered carbocycle or heterocycle.

B291. The compound of any one of embodiments B288-B290, wherein $R^2$ and $R^3$, together with the atom to which they are attached, form the structure:

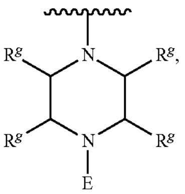

wherein each $R^g$ is independently selected from $C_{1-6}$alkyl and H, wherein any $C_{1-6}$alkyl is unsubstituted or substituted with one or more $R^{20}$.

B292. The compound of embodiment B291, wherein at least one $R^g$ is $C_{1-6}$alkyl that is unsubstituted or substituted with one or more $R^{20}$.

B293. The compound of any one of embodiments B279-B292, wherein one and only one $R^a$ or $R^b$ is selected from halogen, $C_{1-6}$ alkyl, and —$OR^{12}$, and the remaining $R^a$'s and $R^a$'s are H.

B294. The compound of any one of embodiments B279-B293, wherein $R^1$ is selected from:

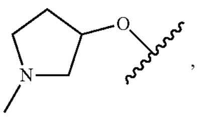
,
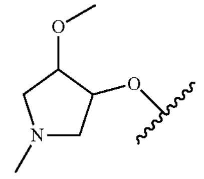
,
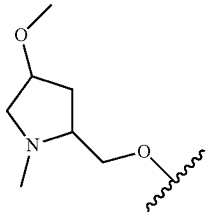
,
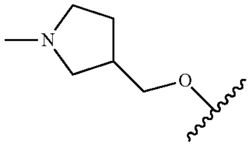
,
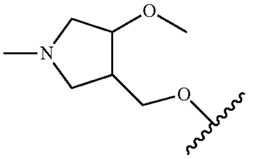
,
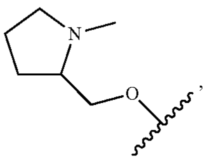
,
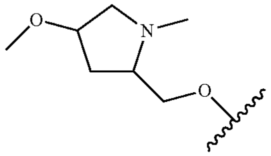
,
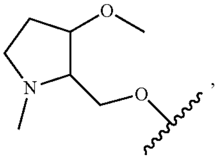
, -continued

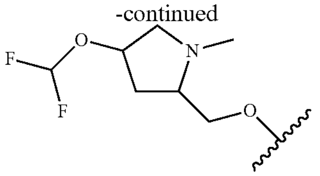

,

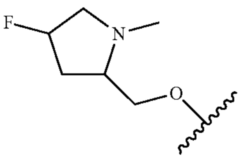

,

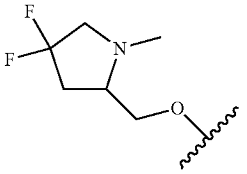

,

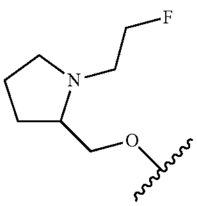

,

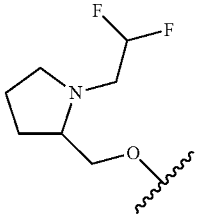

,

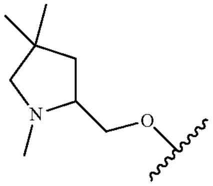

,

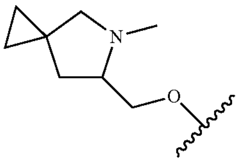

, and

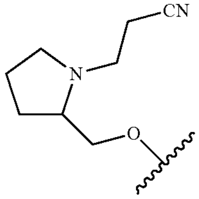

.

B295. The compound of any one of embodiments B279-B294, wherein $R^5$ is selected from $C_{1-6}$alkyl that is unsubstituted or substituted with one or more $R^{13}$.

B296. The compound of embodiment B295, wherein $R^5$ is selected from $C_{1-6}$alkyl that is substituted with one or more halogens or —CN.

B297. The compound of embodiment B296, wherein $R^5$ is selected from —$CF_2H$, —$CF_3$, —$CH_2CN$, and —$CH_2CH_3$.

B298. The compound of any one of embodiments B279-B297, wherein $R^7$ is a halogen.

B299. The compound of any one of embodiments B279-B297, wherein $R^7$ is —CN.

B300. The compound of any one of embodiments B279-B297, wherein $R^7$ is H.

B301. The compound of any one of embodiments B279-B298, wherein X is N.

B302. The compound of any one of embodiments B279-B298, wherein X is C—CN.

B303. The compound of any one of embodiments B279-B302, wherein Y is O.

B304. The compound of any one of embodiments B279-B303, wherein Y is S.

B305. The compound of any one of embodiments B279-B304, wherein $R^{23}$ is selected from —$N(R^{12})_2$.

B306. The compound of embodiment B305, wherein $R^{23}$ is —$NH_2$.

B307. The compound of any one of embodiments B279-B306, wherein $R^{24}$ is a halogen.

B308. The compound of embodiment B307, wherein $R^{24}$ is F.

B309. The compound of any one of embodiments B279-B308, wherein $R^{25}$ and $R^{26}$ are H.

B310. The compound of any one of embodiments B279-B309, wherein each E is independently selected from

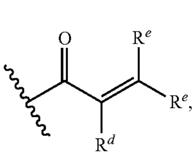

,

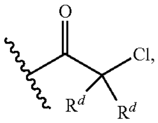

, and

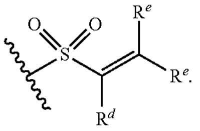

.

B311. The compound of embodiment B310, wherein each E is:

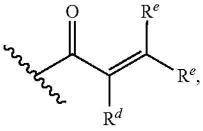

, wherein each $R^d$ and $R^e$ is H.

B312. A compound according to Formula IIB:

(IIB)

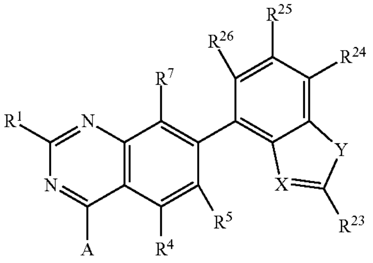

or a salt (e.g., pharmaceutically acceptable salt) thereof, wherein:

$R^1$ is selected from —$OR^8$,

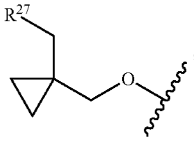

, a 4-6 membered heterocycle comprising a nitrogen atom, and H, wherein the heterocycle is unsubstituted or substituted with one or more $R^{16}$;

A is selected from:

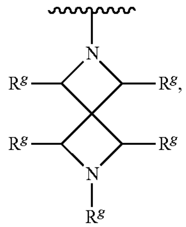
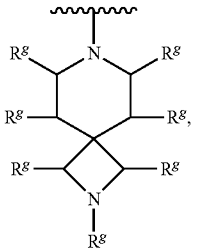
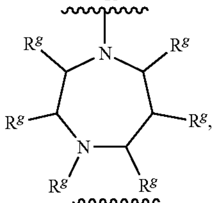
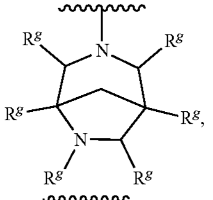
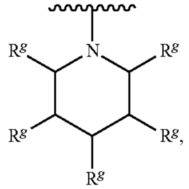
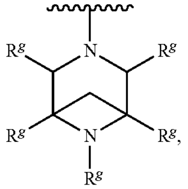
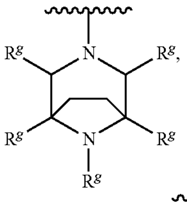
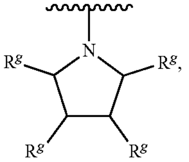
and
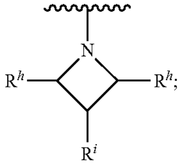

$R^4$ is selected from H, —$OR^{12}$, and $C_{1-6}$alkyl, wherein any $C_{1-6}$alkyl is unsubstituted or substituted with one or more $R^{13}$;

$R^5$ is selected from H, —CN, halogen, $C_{1-6}$alkyl, $C_{2-6}$alkynyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^2)_2$, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, —$N(R^2)C(O)(C_{1-6}alkyl)$, —$OR^{12}$, and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^g$ is independently selected from $C_{1-6}$alkyl, H, and E, wherein at least one $R^g$ is E, and wherein any $C_{1-6}$alkyl is unsubstituted or substituted with one or more $R^{20}$;

each $R^h$ is independently selected from $C_{1-6}$alkyl and H;

$R^i$ is selected from —$N(R^{12})(E)$, E, and —$(C_{1-6}alkyl)E$;

$R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$;

each E is independently selected from

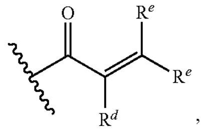
,
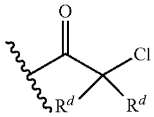
,
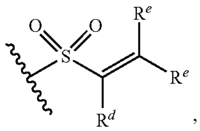
,
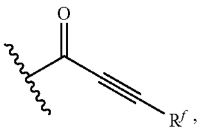
,
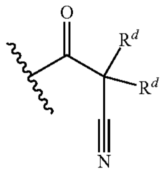
,
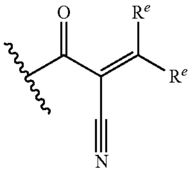
,
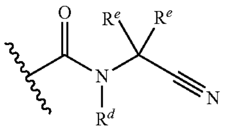
,
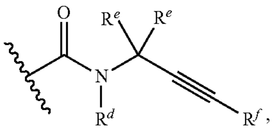
, -continued

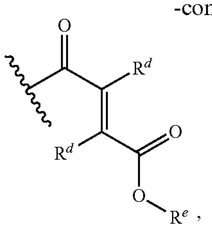

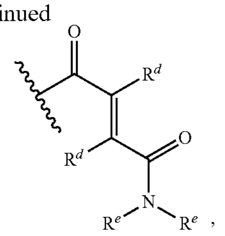

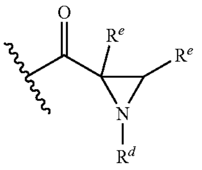

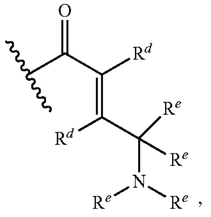

and —CN;

each $R^d$ and $R^e$ is independently selected from halogen, $C_{1-6}$ alkyl, and H; and each $R^f$ is independently selected from $C_{1-6}$ alkyl and H.

B313. A compound according to Formula IIC:

(IIC)

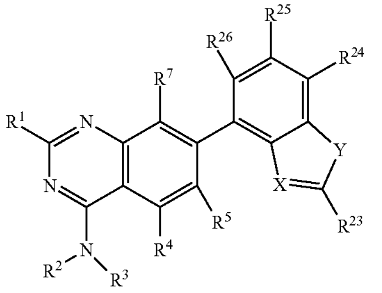

or a salt (e.g., pharmaceutically acceptable salt) thereof, wherein:

$R^1$ is selected from —$OR^8$,

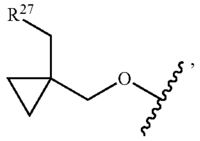

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$;

or $R^2$ and $R^3$, together with the atom to which they are attached, form a 4-8 membered heterocycle that is substituted with one or more E and 0-4 $R^{11}$;

$R^4$ is —$OR^Y$, wherein $R^Y$ is selected from $C_{1-6}$ alkyl;

$R^5$ is selected from halogen and H;

$R^7$ is selected from halogen, —$OR^{12}$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{16}$ is independently selected from halogen, —$N(R^{12})_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, —$N(R^2)C(O)(C_{1-6}alkyl)$, —$OR^{12}$, and $C_{1-6}$alkyl-$N(R^{12})_2$;

$R^{24}$, $R^{25}$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

$R^a$ and $R^b$ are each independently selected from halogen, —$OR^{12}$, $C_{1-6}$alkyl, and H, wherein any $C_{1-6}$alkyl is unsubstituted or is substituted with one or more $R^{13}$;

each E is independently selected from

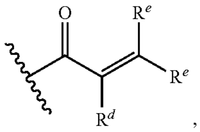

,

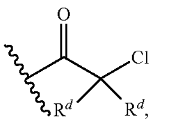

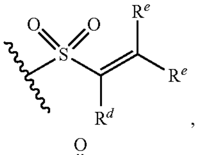

,

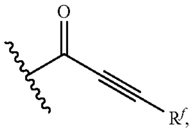

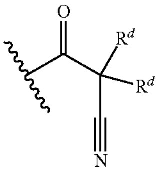

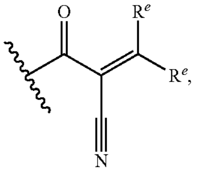

-continued

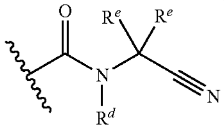
,
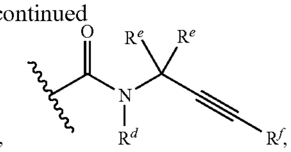

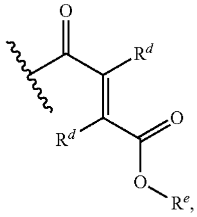

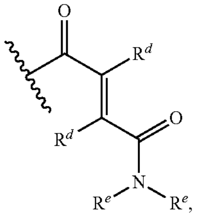

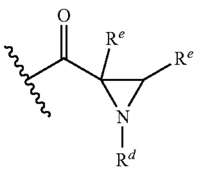
,
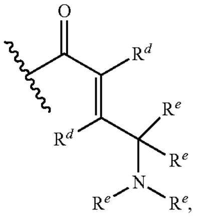

and —CN;

each $R^d$ and $R^e$ is independently selected from halogen, $C_{1-6}$ alkyl, and H; and each $R^f$ is independently selected from $C_{1-6}$ alkyl and H.

B314. A compound according to Formula IID:

(IID)

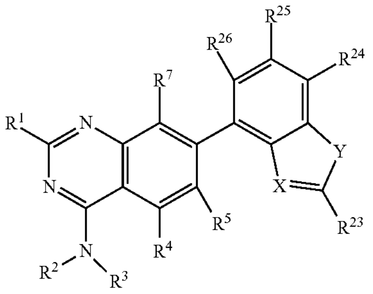

or a salt (e.g., pharmaceutically acceptable salt) thereof, wherein:

$R^1$ is selected from —$OR^8$,

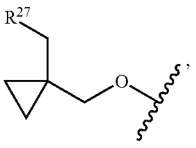

a 4-6 membered heterocycle comprising a nitrogen atom, and H, wherein the heterocycle is unsubstituted or substituted with one or more $R^{16}$;

$R^2$ is selected from H, $C_{1-6}$ alkyl, and a 3-6 membered carbocycle;

$R^3$ is selected from $C_{1-6}$ alkyl and a 4-6 membered heterocycle, wherein the $C_{1-6}$ alkyl is substituted with —$N(R^{12})(E)$, and wherein the heterocycle is substituted with one or more E and 0-4 $R^{10}$, optionally wherein two $R^{10}$ groups, together with the atom or atoms to which they are attached, form a 3-6 membered carbocycle;

or $R^2$ and $R^3$, together with the atom to which they are attached, form a 4-8 membered heterocycle that is substituted with one or more E and 0-4 $R^{11}$, optionally wherein two $R^{11}$ groups, together with the atom or atoms to which they are attached, form a 3-6 membered carbocycle;

$R^4$ is selected from H, —$OR^{12}$, and $C_{1-6}$alkyl, wherein any $C_{1-6}$alkyl is unsubstituted or substituted with one or more $R^{13}$;

$R^5$ is selected from —CN, $C_{1-6}$alkyl, —$OR^{12}$, a 3-6 membered carbocycle, a 5-6 membered heteroaryl, phenyl, and a 3-6 membered heterocycle, wherein any $C_{1-6}$alkyl is unsubstituted or substituted with one or more $R^{13}$, and wherein any carbocycle, heteroaryl, phenyl, or heterocycle is unsubstituted or substituted with one or more $R^{14}$;

$R^7$ is selected from halogen, —$OR^2$, —CN, and H;

$R^8$ is selected from a heterocycle and an alkylheterocycle, wherein any heterocycle comprises 4-8 members and is unsubstituted or is substituted with one or more $R^a$ and/or $R^b$, and wherein an alkyl moiety of any alkylheterocycle is selected from $C_{1-6}$ alkyl;

each $R^{10}$ is independently selected from $C_{1-6}$alkyl and halogen, wherein any $C_{1-6}$alkyl is unsubstituted or substituted with one or more $R^{20}$;

each $R^{11}$ is independently selected from $C_{1-6}$alkyl, wherein any $C_{1-6}$alkyl is unsubstituted or substituted with one or more $R^{20}$;

each $R^{12}$ is independently selected from $C_{1-6}$ alkyl, $C_{2-6}$ alkenyl, and H, wherein any $C_{1-6}$alkyl or $C_{2-6}$ alkenyl is unsubstituted or substituted with one or more $R^{13}$;

each $R^{13}$ is independently selected from —$OR^{22}$, —CN, —$N(R^{22})_2$, and halogen;

each $R^{14}$ is independently selected from halogen, —CN, —$N(R^{12})_2$, and $C_{1-6}$alkyl, wherein any $C_{1-6}$alkyl is unsubstituted or substituted with one or more $R^{13}$;

each $R^{16}$ is independently selected from halogen, —$N(R^2)_2$, $C_{1-6}$alkyl, —$OR^{12}$, and 3-6 membered heterocycle, wherein any $C_{1-6}$alkyl is unsubstituted or substituted with one or more $R^{13}$ and any heterocycle is unsubstituted or substituted with one or more $R^{20}$;

each $R^{20}$ is independently selected from —OH, —$OC_{1-6}$alkyl, —CN, —$NH_2$, —$NHC_{1-6}$alkyl, and halogen;

each $R^{22}$ is independently selected from $C_{1-6}$ alkyl, $C_{2-6}$ alkenyl, and H;

X is selected from N and C—CN;

Y is selected from O and S;

$R^{23}$ is selected from —$N(R^{12})_2$, —$N(R^2)C(O)(C_{1-6}alkyl)$, —$OR^{12}$, and $C_{1-6}$alkyl-$N(R^{12})_2$;

$R^{24}$, $R^2$, and $R^{26}$ are independently selected from H, halogen, —$OR^{12}$, and $C_{1-6}$alkyl, wherein any $C_{1-6}$alkyl is unsubstituted or substituted with one or more $R^{13}$;

$R^{27}$ is a 3-6 membered heterocycle including one or more heteroatoms selected from N, O, and S, wherein the heterocycle is unsubstituted or substituted with one or more $R^{28}$;

each $R^{28}$ is independently selected from $C_{1-6}$alkyl and halogen;

each $R^a$ and $R^b$ are each independently selected from halogen, —$OR^2$, $C_{1-6}$alkyl, and H, wherein any $C_{1-6}$alkyl is unsubstituted or is substituted with one or more $R^{13}$;

each E is independently selected from

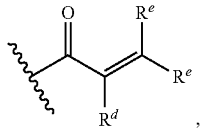
,
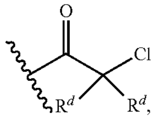

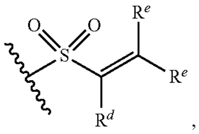
,
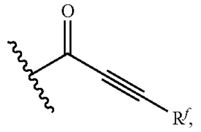

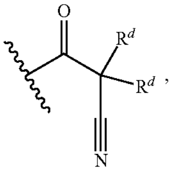
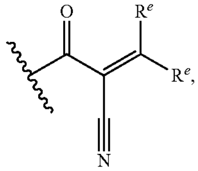

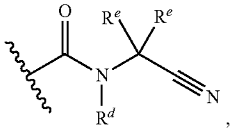
,
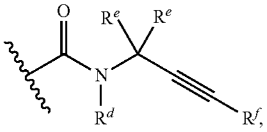

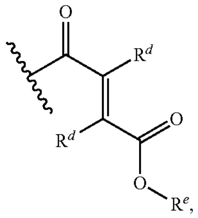
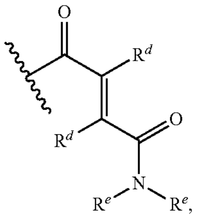

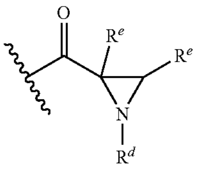
,
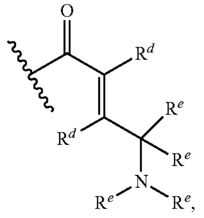

and —CN;

each $R^d$ and $R^e$ is independently selected from halogen, $C_{1-6}$ alkyl, and H; and each $R^f$ is independently selected from $C_{1-6}$ alkyl and H.

B315. A compound shown in Table 2, or a salt (e.g., pharmaceutically acceptable salt) thereof.

B316. A compound shown in Table 4, or a salt (e.g., pharmaceutically acceptable salt) thereof.

B317. A pharmaceutical composition comprising a compound of any one of embodiments B1-B316, or a salt (e.g., pharmaceutically acceptable salt) thereof, and a pharmaceutically acceptable excipient.

B318. A compound of any one of embodiments B1-B316, or a salt (e.g., pharmaceutically acceptable salt) thereof, for use as a medicament.

B319. The compound of embodiment B318, wherein the medicament is useful in the prevention or treatment of a disease, disorder, or condition ameliorated by the inhibition of KRAS having a G12C mutation.

B320. The compound of embodiment B318 or B319, wherein the medicament is useful in the prevention or treatment of a cancer.

B321. The compound of embodiment B320, wherein the cancer is selected from the group consisting of pancreatic cancer, colorectal cancer, and lung cancer.

B322. A compound of any one of embodiments B1-B316, or a salt (e.g., pharmaceutically acceptable salt) thereof, for use in the treatment of a disease, disorder, or condition.

B323. The compound of embodiment B322, wherein the disease, disorder, or condition is a cancer.

B324. The compound of embodiment B323, wherein the cancer is selected from the group consisting of pancreatic cancer, colorectal cancer, and lung cancer.

B325. The compound of any one of embodiments B322-B324, wherein the compound is used in the treatment of a disease, disorder, or condition in a subject in need thereof.

B326. A compound of any one of embodiments B1-B316, or a salt (e.g., pharmaceutically acceptable salt) thereof, for use in the manufacture of a medicament.

B327. The compound of embodiment B326, wherein the medicament is useful in the prevention or treatment of a disease, disorder, or condition ameliorated by the inhibition of KRAS having a G12C mutation.

B328. The compound of embodiment B326 or B327, wherein the medicament is useful in the treatment of a cancer.

B329. The compound of embodiment B328, wherein the cancer is selected from the group consisting of pancreatic cancer, colorectal cancer, and lung cancer.

B330. A method, comprising administering a therapeutically effective amount of a compound of any one of embodiments B1-B316, or a salt (e.g., pharmaceutically acceptable salt) thereof, to a subject in need thereof.

B331. The method of embodiment B330, wherein the subject has a disease, disorder, or condition ameliorated by the inhibition of KRAS having a G12C mutation.

B332. The method of embodiment B330 or B331, wherein the subject has a cancer.

B333. The method of embodiment B332, wherein the subject was previously diagnosed with the cancer.

B334. The method of embodiment B332, wherein the subject has previously undergone a treatment regimen for the cancer.

B335. The method of embodiment B332, wherein the subject has previously entered remission from the cancer.

B336. The method of any one of embodiments B332-B335, wherein the cancer is selected from the group consisting of pancreatic cancer, colorectal cancer, and lung cancer.

B337. The method of any one of embodiments B330-B336, wherein the compound, or the salt thereof, is administered in combination with an additional therapeutic agent.

B338. The use of a compound of any one of embodiments B1-B317, or a salt (e.g., pharmaceutically acceptable salt) thereof, for the manufacture of a medicament for the treatment of a cancer.

B339. The use of embodiment B338, wherein the cancer is selected from the group consisting of pancreatic cancer, colorectal cancer, and lung cancer.

B340. A method, comprising contacting a KRAS protein with a compound of any one of embodiments B1-B317, or a salt (e.g., pharmaceutically acceptable salt) thereof.

B341. The method of embodiment B340, wherein contacting the KRAS protein with the compound modulates KRAS.

B342. The method of embodiment B340 or B341, wherein the KRAS protein has a G12C mutation.

B343. The method of any one of embodiments B340-B342, wherein the KRAS protein is in an active (GTP-bound) state.

B344. The method of any one of embodiments B340-B342, wherein the KRAS protein is in an inactive (GDP-bound) state.

B345. The method of any one of embodiments B340-B344, wherein the KRAS protein is located within a cell.

B346. The method of embodiment B345, wherein the cell is located within a subject.

B347. The method of embodiment B346, wherein the subject is a human.

B348. The method of embodiment B346 or B347, wherein the subject has a cancer.

B349. The method of embodiment B348, wherein the cancer is selected from the group consisting of pancreatic cancer, colorectal cancer, and lung cancer.

B350. A method of inhibiting the function of a KRAS protein having a G12C mutation, comprising contacting the KRAS protein with a compound of any one of embodiments B1-B317, or a salt (e.g., pharmaceutically acceptable salt) thereof.

B351. The method of embodiment B350, wherein the KRAS protein is in an active (GTP-bound) state.

B352. The method of embodiment B350, wherein the KRAS protein is in an inactive (GDP-bound) state.

B353. The method of any one of embodiments B350-B352, wherein the KRAS protein is located within a cell.

B354. The method of embodiment B353, wherein the cell is located within a subject.

B355. The method of embodiment B354, wherein the subject is a human.

B356. The method of embodiment B354 or B355, wherein the subject has a cancer.

B357. The method of embodiment B356, wherein the cancer is selected from the group consisting of pancreatic cancer, colorectal cancer, and lung cancer.

B358. A compound capable of inhibiting a KRAS protein with a G12C mutation in both its active (GTP-bound) and inactive (GDP-bound) state.

B359. The compound of embodiment B358, wherein the compound:

(i) demonstrates modification of ≥70%, 50%≤modification <70%, or 10%≤modification <50% of GppNHp-KRAS G12C, GTP-KRAS G12C, or GDP-KRAS G12C in the assay of Biological Example 1 (e.g., a Matrix-Assisted Laser Desorption Ionization-Time of Flight Mass Spectrometry (MALDI-TOF MS) analysis of covalent modification of Cys12 in GppNHp, GTP or GDP-loaded KRAS4b (amino acids 1-169) G12C/C118S);

(ii) has $IC_{50}$≤0.5 μM, 0.5 μM≤$IC_{50}$≤5 μM, or 5 μM≤$IC_{50}$≤20 μM in the assay of Biological Example 2 (e.g., a protein:protein interaction (PPI) Homogenous Time Resolved Fluorescence (HTRF) analysis of Avi-KRAS G12C Q25A (amino acids 1-169) GppNHp/3xFLAG-PI3K CA (157-299), Avi-KRAS G12C (amino acids 1-169) GppNHp/RAF1 RBD-3xFLAG (52-151)); and/or (iii) has $IC_{50}$≤0.1 μM; B: 0.1 μM<$IC_{50}$≤1 μM; C: $IC_{50}$>1 μM in the assay of Biological Example 3 (e.g., cell-based pERK).

B360. The compound of embodiment B358 or B359, wherein the compound is capable of irreversibly binding the KRAS protein.

B361. The compound ofany one of embodiments B358-B360, wherein the compound is capable of reversibly binding the KRAS protein.

B362. The compound ofany one of embodiments B358-B361, wherein the compound is a compound according to any one of embodiments B1-B317.

EXAMPLES

Selected abbreviations used in the preceding sections and the Examples are summarized in Table 1.

TABLE 1

Abbreviations.

| Abbreviation | Term |
|---|---|
| MeCN | acetonitrile |
| cm | centimeter |
| ° C. | degrees Celsius |
| ° K. | degrees Kelvin |
| BINAP | [1,1'-Binaphthalene]-2,2'-diyl)bis(diphenylphosphane) |
| DCM | dichloromethane |
| DIEA | N,N-diisopropylethylamine (Hunig's base) |
| DMF | dimethylformamide |
| DMSO | dimethyl sulfoxide |
| ESI | electrospray ion-mass spectrometry |
| EtOH | ethanol |
| EtOAc | ethyl acetate |
| g | gram |
| Hz | hertz |
| HATU | Hexafluorophosphate azabenzotriazole tetramethyl uronium |
| HPLC | high performance liquid chromatography |
| HTRF | homogenous time-resolved fluorescence |
| h | hour |
| kDa | kilodalton |
| LC | liquid chromatography |
| LCMS | liquid chromatography-mass spectrometry |
| L | liter |
| MS | mass spectra |
| MHz | megahertz |
| MeOH | methanol |
| MTBE | methyl tert-butyl ether |
| μg | microgram |
| μL | microliter |
| μM | micromolar |
| μm | micron |
| μs | microsecond |
| mg | milligram |
| mL | milliliter |
| mm | millimeter |
| mM | millimolar |
| mmol | millimole |
| min | minute |
| M | molar |
| nL | nanoliter |
| nm | nanometer |
| NCS | N-chlorosuccinimide |
| NMP | N-methyl-2-pyrrolidone |
| PE:EA | Petroleum ether:ethyl acetate |
| ppm | parts per million |
| PTLC | preparative thin layer chromatography |
| $^1$HNMR | proton nuclear magnetic resonance |
| RBD | receptor binding domain |
| RP | reverse phase |
| rpm | revolutions per minute |

TABLE 1-continued

| Abbreviations. | |
|---|---|
| Abbreviation | Term |
| SPR | surface plasmon resonance |
| THF | tetrahydrofuran |
| TMS | tetramethylsilane |
| TLC | thin layer chromatography |
| $SOCl_2$ | thionyl chloride |
| TEA | triethylamine |
| TFA | trifluoroacetic acid |
| TCEP | tris(2-carboxyethyl)phosphine |
| UV | ultraviolet |
| UV/Vis | ultraviolet/visible |

Materials and Methods

Preparative thin layer chromatography (PTLC) separations described herein were typically performed on 20×20 cm plates (500-μm thick silica gel).

Chromatographic purifications were typically performed using Biotage Isolera One automated system running Biotage Isolera One 2.0.6 software (Biotage LLC, Charlotte, NC). Flow rates were the default values specified for the column in use. Reverse phase chromatography was performed using elution gradients of water and acetonitrile on KP-C18-HS Flash+columns (Biotage LLC) of various sizes. Typical loading was between 1:50 and 1:1000 crude sample: RP $SiO_2$ by weight. Normal phase chromatography was performed using elution gradients of various solvents (e.g., hexane, ethyl acetate, methylene chloride, methanol, acetone, chloroform, MTBE, etc.). The columns were SNAP Cartridges containing KP-SIL or SNAP Ultra (25 pm spherical particles) of various sizes (Biotage LLC). Typical loading was between 1:10 to 1:150 crude sample: $SiO_2$ by weight. Alternatively, silica gel chromatography was performed on a Biotage Horizon flash chromatography system.

$^1$HNMR analyses of intermediates and exemplified compounds were typically performed on a Bruker Ascend TM 400 spectrometer (operating at 400 MHz), Bruker Ascend 700 MHz Advance Neo Spectrometer (Bruker-Biospin) or Bruker Advance ultrashield 300/54 (operating at 300 MHz) at 298° K following standard operating procedure suggested by manufacturer. Reference frequency was set using TMS as an internal standard. Chemical shift values (δ) are reported in parts per million (ppm) with splitting patterns abbreviated to: s (singlet), br. s (broad singlet), d (doublet), dd (double doublet), t (triplet), and m (multiplet). The coupling constant (J) is given in Hz. Typical deuterated solvents were utilized as indicated in the individual examples.

LCMS analysis were typically performed using one of the following conditions:

(1) LCMS spectra were taken on an Agilent Technologies 6120B Quadrupole spectrometer. The mobile phase for the LC was acetonitrile (A) with 0.1% formic acid, and water (B) with 0.1% formic acid, and the eluent gradient was from 5-95% A in 6.0 min, 5%-40% A in 6.0 min, 80-100% A in 6.0 min. using a poroshell 120 EC-C18 50 mm×3.0 mm×2.7 μm capillary column; Flow Rate: 0.7 mL/min. Mass spectra (MS) were measured by electrospray ion-mass spectroscopy (ESI). All temperatures are in degrees Celsius (° C.) unless otherwise noted.

(2) LCMS spectra were taken on an Agilent Technologies 1290-6420 Triple Quadrupole spectrometer: The mobile phase for the LC was acetonitrile (A) with 0.05% formic acid, and water (B) with 0.05% formic acid, and the eluent gradient was from 5-95% A in 5.0 min, using a ZORBAX SB—C18 50 mm×2.1 mm×1.8 m capillary column; Flow Rate: 0.3 mL/min. Mass spectra (MS) were measured by electrospray ion-mass spectroscopy (ESI). All temperatures are in degrees Celsius unless otherwise noted.

(3) LC-MS analysis was performed using an Agilent 6120b single quadrupole mass spectrometer with an Agilent 1260 infinity II chromatography separations module and Agilent 1260 infinity II photodiode array detector controlled by Agilent Chemstation software. The HPLC column used was an Agilent ZORBAX Eclipse XDB-C18 4.6 mm×150 mm×3.5 m RapidResol column with a mobile phase of water (0.1% formic acid)/MeCN (0.1% formic acid) and a gradient of 5-95% MeCN over 10 minutes at a flow rate of 1 mL/min. Accurate mass data was obtained using a Thermo Fisher extractive plus EMR orbitrap LCMS system. Exact mass values were calculated by ChemCalc.

(4) LCMS spectra were taken on an alliance Waters 2695 coupled to a dual absorbance detector waters 2487 and a waters micro mass ZQ-2000 single quadrupole spectrometer. The mobile phase for the LC was acetonitrile (A) and water (B) with 0.01% formic acid, and the eluent gradient was from 5-100% A in 10.0 minute using a Kromasil 100-5-C18 150 mm×4.6 mm×5 m column. Mass spectra (MS) were measured by electrospray ion-mass spectroscopy (ESI). All temperatures are in degrees Celsius unless otherwise noted.

Typically, analytical HPLC mass spectrometry conditions were as follows:

LC1: Agilent Technologies 1260 Infinity coupled, Column: poroshell 120 EC-C18 150 mm×4.6 mm×4 m; Temperature: 40° C.; Eluent: 5:95 v/v acetonitrile/water+0.02% trifluoroacetic acid in 20 min; Flow Rate: 1.2 mL/min; Detection: VWD, 190-600 nm.

LC2: C18-Reverse phase preparative HPLC was performed using a Waters purification system with 2489 UV/Vis detector, 2545 Gradient module, and Fraction collector III controlled by Waters Chromescope v1.6. The preparative HPLC column used was a Waters XBridge® Prep C18 5 μm OBD™ 19×250 mm column with a mobile phase of water/MeCN or water (0.1% TFA)/MeCN (0.1% TFA).

Preparative HPLC were carried out with one of the following two conditions:

Condition 1: GILSON Preparative HPLC System; Column: Ultimate XB—C18, 21.2 mm×250 mm, 5 μm; Mobile phase: Water with 0.10% trifluoroacetic acid; MeCN with 0.1% trifluoroacetic acid; Method: 15 minutes gradient elution; Initial organic: 10% to 30%; Final organic: 60% to 80%; UV1: 240; UV2: 230; Flow: 15 ml/min.

Condition 2: C18-Reverse phase preparative HPLC was performed using a Waters purification system with 2489 UV/Vis detector, 2545 Gradient module, and Fraction collector III controlled by Waters Chromescope v1.6. The preparative HPLC column used was a Waters XBridge® Prep C18 5 μm OBD™ 19×250 mm column with a mobile phase of water/MeCN or water (0.1% TFA)/MeCN (0.1% TFA).

Compound names were generated with ChemDraw Professional.

The compounds provided herein, including in various forms such as salts, esters, tautomers, prodrugs, zwitterionic forms, stereoisomers, etc., may be prepared according to various methods including those set forth in the following examples.

Synthetic Example 1: Synthesis of 1-(3-((7-(2-amino-7-fluorobenzo[d]thiazol-4-yl)-6-chloro-8-fluoroquinazolin-4-yl)amino)azetidin-1-yl)prop-2-en-1-one (Compound 4)

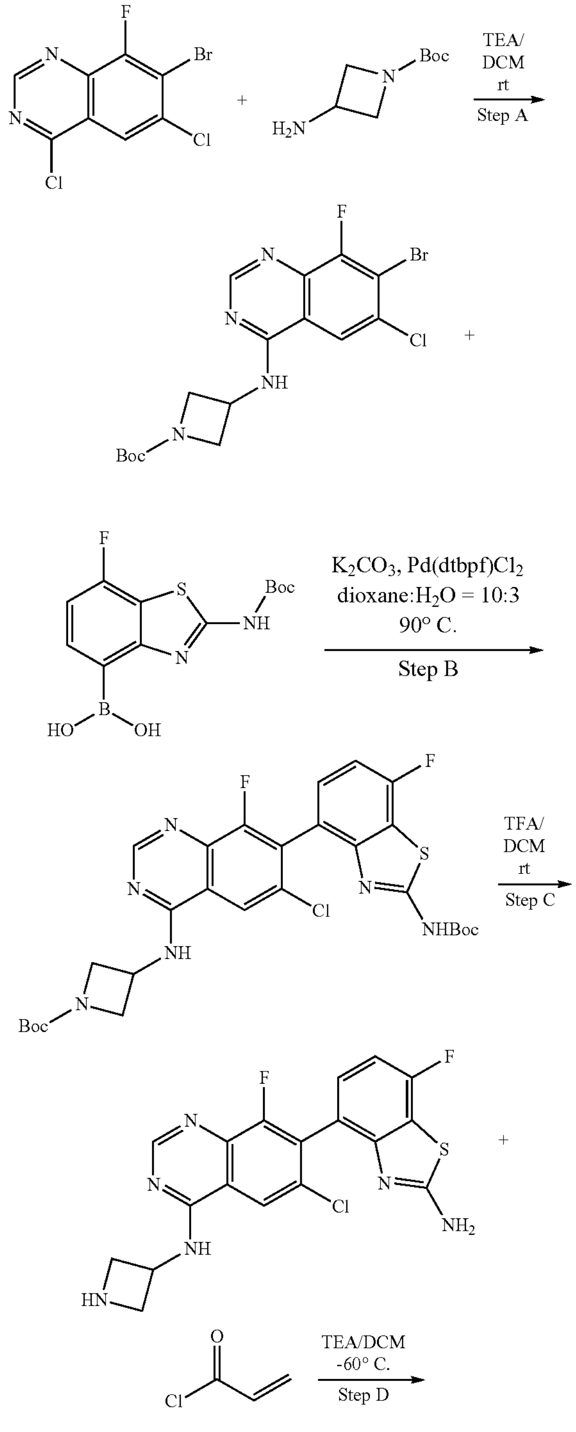

-continued

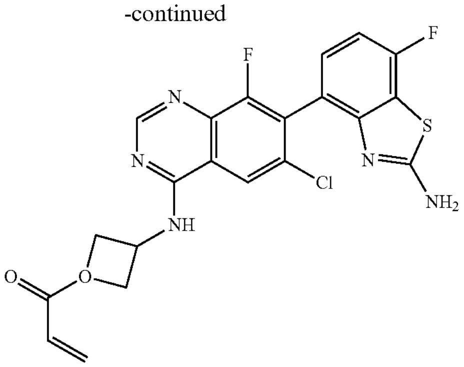

Compound 4

Step A: Preparation of tert-butyl 3-((7-bromo-6-chloro-8-fluoroquinazolin-4-yl)amino)azetidine-1-carboxylate: To a solution of 7-bromo-4,6-dichloro-8-fluoroquinazoline (50 mg, 0.17 mmol) in DCM (5 mL) was added tert-butyl 3-aminoazetidine-1-carboxylate (35.1 mg, 0.2 mmol) and TEA (34.2 mg, 0.34 mmol). The mixture was stirred at ambient temperatures for 2 hours. The reaction mixture was quenched with water (20 mL) and extracted with EtOAc (3×20 mL). The combined organic layer was washed with brine (15 mL), dried over sodium sulfate, filtered, and concentrated under reduced pressure, the residue was purified by flash column chromatography on silica gel (petroleum ether/ethyl acetate=4:1 to 1:1) to give of tert-butyl 3-((7-bromo-6-chloro-8-fluoroquinazolin-4-yl)amino)azetidine-1-carboxylate (66 mg, 90%).

Step B: Preparation of tert-butyl 3-((7-(2-((tert-butoxycarbonyl)amino)-7-fluorobenzo[d]thiazol-4-yl)-6-chloro-8-fluoroquinazolin-4-yl)amino)azetidine-1-carboxylate: The mixture of tert-butyl 3-((7-bromo-6-chloro-8-fluoroquinazolin-4-yl)amino)azetidine-1-carboxylate (66 mg, 0.15 mmol), (2-((tert-butoxycarbonyl)amino)-7-fluorobenzo[d]thiazol-4-yl)boronic acid (53.5 mg, 0.17 mmol), Pd(tbdpf)$Cl_2$ (16.1 mg, 0.02 mmol), potassium carbonate (75.8 mg, 0.36 mmol) in dioxane (2 mL) and water (0.3 mL) was stirred at 90° C. for 3 hours under Argon. Once cooled to ambient temperature, the mixture was filtrated through celite, washed with ethyl acetate. The filtrate was concentrated under reduced pressure. The residue was purified with preparative-TLC (DCM:MeOH=10:1) to give tert-butyl 3-((7-(2-((tert-butoxycarbonyl)amino)-7-fluorobenzo[d]thiazol-4-yl)-6-chloro-8-fluoroquinazolin-4-yl)amino)azetidine-1-carboxylate (28 mg, 29%).

Step C: Preparation of 4-(4-(azetidin-3-ylamino)-6-chloro-8-fluoroquinazolin-7-yl)-7-fluorobenzo[d]thiazol-2-amine: To a stirred solution of tert-butyl 3-((7-(2-((tert-butoxycarbonyl)amino)-7-fluorobenzo[d]thiazol-4-yl)-6-chloro-8-fluoroquinazolin-4-yl)amino)azetidine-1-carboxylate (28 mg, 0.037 mmol) in DCM (3 mL) was added TFA (1 mL) at 0° C. The mixture was stirred at 0° C. for 2 hours. The mixture was concentrated under reduced pressure and purified by preparative-HPLC to give 4-(4-(azetidin-3-ylamino)-6-chloro-8-fluoroquinazolin-7-yl)-7-fluorobenzo[d]thiazol-2-amine (9.2 mg, 31%) as bis trifluoroacetic acid salt. LCMS ESI (+) m/z 419 (M+H). $^1$HNMR(400 MHz, $CD_3OD$): δ 8.59 (s, 1H), 8.28 (s, 1H), 7.26 (t, J=8.4 Hz, 1H), 7.02 (t, J=8.8 Hz, 1H), 5.10-5.13 (m, 4H), 4.31-4.38 (m, 1H).

Step D: Preparation of 1-(3-((7-(2-amino-7-fluorobenzo[d]thiazol-4-yl)-6-chloro-8-fluoroquinazolin-4-yl)amino)azetidin-1-yl)prop-2-en-1-one: To a solution of 4-[4-(azetidin-3-ylamino)-6-chloro-8-fluoro-quinazolin-7-yl]-7-fluoro-1,3-benzothiazol-2-amine (21.0 mg, 0.050 mmol) in DCM (2 mL) was added triethylamine (0.069 mL, 0.49 mmol) and acryloyl chloride (0.0032 mL, 0.040 mmol) at−60° C., the mixture was stirred at −60° C. for 30 minutes. The reaction was quenched with water and extracted with ethyl acetate (40 mL). The organic layer was washed with sodium bicarbonate aqueous solution and brine, dried over sodium sulfate, filtered, and concentrated under reduced pressure. The residue was purified by preparative RPHPLC to give 1-[3-[[7-(2-amino-7-fluoro-1,3-benzothiazol-4-yl)-6-chloro-8-fluoro-quinazolin-4-yl]amino]azetidin-1-yl]prop-2-en-1-one (3.0 mg, 12% yield). LCMS ESI (+) m/z 473.1 (M+H). $^1$HNMR (400 MHz, $CD_3OD$) δ 8.57 (s, 1H), 8.33 (s, 1H), 7.26 (t, J=6.8 Hz, 1H), 7.02 (t, J=9.2 Hz, 1H), 4.28-6.48 (m, 2H), 5.79 (d, J=10.4 Hz, 1H), 4.51-4.60 (m, 3H), 4.37-4.41 (m, 1H), 4.21-4.25 (m, 1H).

Synthetic Example 2: 1-(3-((7-(2-amino-7-fluorobenzo[d]thiazol-4-yl)-6-chloro-8-fluoroquinazolin-4-yl)amino)azetidin-1-yl)-2-chloroethan-1-one (Compound 5)

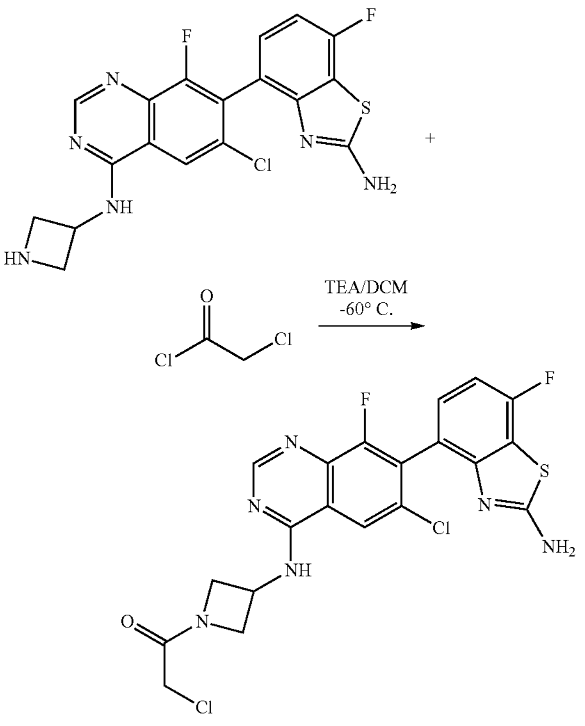

Compound 5

Preparation of 1-(3-((7-(2-amino-7-fluorobenzo[d]thiazol-4-yl)-6-chloro-8-fluoroquinazolin-4-yl)amino)azetidin-1-yl)-2-chloroethan-1-one: To a solution of 4-[4-(azetidin-3-ylamino)-6-chloro-8-fluoro-quinazolin-7-yl]-7-fluoro-1,3-benzothiazol-2-amine (42 mg, 0.10 mmol) in DCM was added triethylamine (1.0 mL, 7.2 mmol) and the mixture was stirred at −60° C. for 30 minutes. A solution of 2-chloroacetyl chloride (0.0080 mL, 0.10 mmol) in DCM was added dropwise to the mixture and then the mixture was stirred at −60° C. for 1 hour. The reaction was quenched with water and extracted with EtOAc (40 mL), the organic layer was washed with water and brine, dried over sodium sulfate, filtered, and concentrated under reduced pressure. The product was purified by preparative RP-HPLC to afford 1-[3-[[7-(2-amino-7-fluoro-1,3-benzothiazol-4-yl)-6-chloro-8-fluoro-quinazolin-4-yl]amino]azetidin-1-yl]-2-chloro-ethanone (11 mg, 21%). LCMS ESI (+) m/z 495.1 (M+H). $^1$HNMR (400 MHz, $CD_3OD$) δ 8.80 (s, 1H), 8.52 (s, 1H), 7.29 (dd, J=8.8, 5.6 Hz, 1H), 7.04 (t, J=8.4 Hz, 1H), 5.12-5.27 (m, 1H), 4.80-4.87 (m, 1H), 4.41-4.56 (m, 2H), 4.24-4.28 (m, 1H), 4.10-4.19 (m, 2H).

Synthetic Example 3: Synthesis of 4-(6-chloro-8-fluoro-4-((1-(vinylsulfonyl)azetidin-3-yl)amino)quinazolin-7-yl)-7-fluorobenzo[d]thiazol-2-amine (Compound 6)

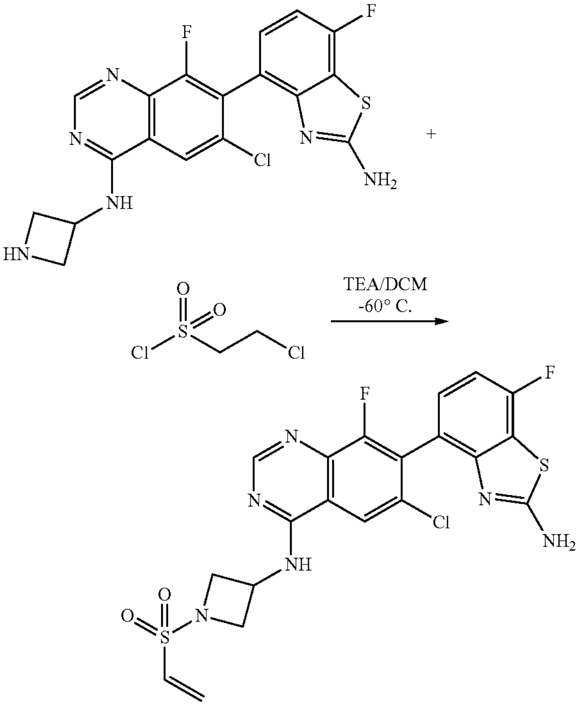

Compound 6

Preparation of 4-(6-chloro-8-fluoro-4-((1-(vinylsulfonyl)azetidin-3-yl)amino)quinazolin-7-yl)-7-fluorobenzo[d]thiazol-2-amine: To a solution of 4-[4-(azetidin-3-ylamino)-6-chloro-8-fluoro-quinazolin-7-yl]-7-fluoro-1,3-benzothiazol-2-amine (20 mg, 0.048 mmol) in DCM (2 mL) was added triethylamine (1.0 mL, 7.2 mmol) and the mixture was stirred at −60° C. for 30 minutes. A solution of 2-chloro-ethane-1-sulfonyl chloride (7.8 mg, 0.048 mmol) in DCM (1 mL) was added dropwise to the mixture and then the mixture was stirred at −60° C. for 1 hour. The reaction was quenched with water and extracted with EtOAc (40 mL), the organic layer was washed with water and brine, dried over sodium sulfate, filtered, and concentrated under reduced pressure. The residue obtained was purified by preparative RP-HPLC to afford 4-[6-chloro-8-fluoro-4-[(1-vinylsulfonylazetidin-3-yl)amino]quinazolin-7-yl]-7-fluoro-1,3-benzothiazol-2-amine (5.6 mg, 22%). LCMS ESI (+) m/z 509.1 (M+H). $^1$HNMR (400 MHz, $CD_3OD$) δ 8.25 (s, 1H), 8.05 (s, 1H), 7.22 (dd, J=8.0, 5.6 Hz, 1H), 6.99 (t, J=8.4 Hz, 1H), 6.66-6.73 (m, 1H), 6.18 (d, J=16.8 Hz, 1H), 6.0 (d, J=10 Hz, 1H), 4.58-4.62 (m, 3H), 4.45-4.51 (m, 1H), 4.32-4.37 (m, 1H).

Synthetic Example 4: Synthesis of N-[2-[[7-(2-amino-7-fluoro-1,3-benzothiazol-4-yl)-6-chloro-8-fluoro-quinazolin-4-yl]amino]propyl]-N-methyl-but-2-ynamide (Compound 18)

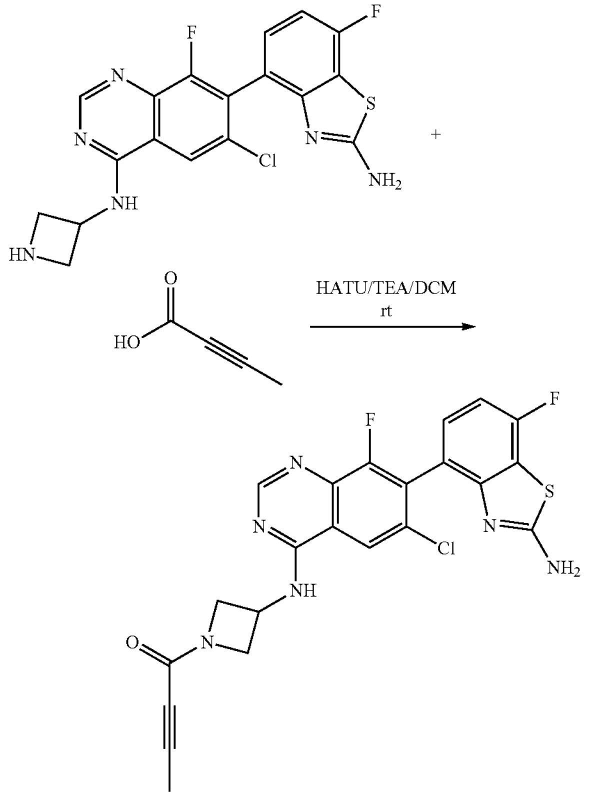

Compound 18

Preparation of 4-(6-chloro-8-fluoro-4-((1-(vinylsulfonyl)azetidin-3-yl)amino)quinazolin-7-yl)-7-fluorobenzo[d]thiazol-2-amine: To the solution of but-2-ynoic acid (7.7 mg, 0.091 mmol) and TEA (0.058 mL, 0.41 mmol) in DCM (1 mL) was added HATU (47 mg, 0.12 mmol) at ambient temperature. The mixture was stirred at ambient temperature for 20 minutes, followed by the addition of a solution of N2-[7-(2-amino-7-fluoro-1,3-benzothiazol-4-yl)-6-chloro-8-fluoro-quinazolin-4-yl]-N1-methyl-propane-1,2-diamine (36 mg, 0.083 mmol) in DCM (1 mL). The mixture was stirred at ambient temperature for 2 hours. Water (10 mL) and DCM (15 mL) were added. The organic layer was separated, washed with saturated brine solution, dried over sodium sulfate, filtered, and concentrated under reduced pressure. The residue was purified by preparative RP-HPLC to give N-[2-[[7-(2-amino-7-fluoro-1,3-benzothiazol-4-yl)-6-chloro-8-fluoro-quinazolin-4-yl]amino]propyl]-N-methyl-but-2-ynamide (10 mg, 25%). LCMS ESI (+) m/z 485.1 (M+H). $^1$HNMR (400 MHz, $CD_3OD$) δ 8.55 (s, 1H), 8.30 (d, J=1.4 Hz, 1H), 7.24 (dd, J=8.3, 5.7 Hz, 1H), 7.00 (t, J=8.8 Hz, 1H), 5.02-5.07 (m, 1H), 4.65-4.74 (m, 1H), 4.44-4.51 (m, 1H), 4.27-4.34 (m, 1H), 4.09-4.17 (m, 1H), 2.04 (s, 3H).

Synthetic Example 5: Synthesis of 1-[3-[[7-(2-amino-7-fluoro-1,3-benzothiazol-4-yl)-6-chloro-8-fluoro-quinazolin-4-yl]amino]azetidin-1-yl]-2-fluoro-prop-2-en-1-one (Compound 19)

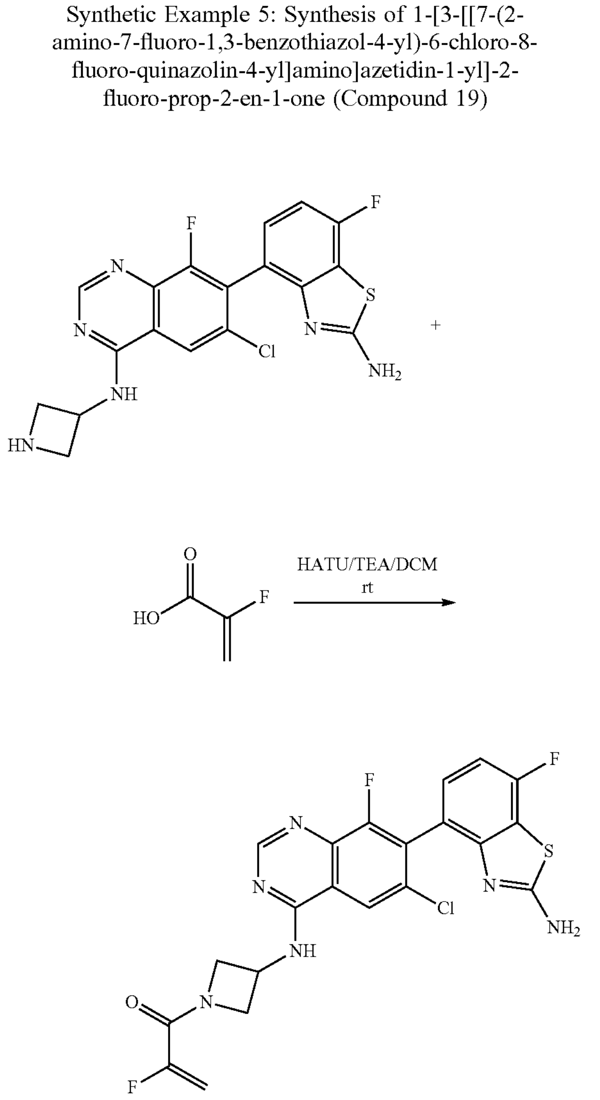

Compound 19

Preparation of 1-[3-[[7-(2-amino-7-fluoro-1,3-benzothiazol-4-yl)-6-chloro-8-fluoro-quinazolin-4-yl]amino]azetidin-1-yl]-2-fluoro-prop-2-en-1-one: To a solution of 2-fluoroprop-2-enoic acid (8.5 mg, 0.094 mmol) in DCM (3 mL) were added triethylamine (86 mg, 0.85 mmol) and HATU (49 mg, 0.13 mmol), the mixture was stirred at ambient temperature for 30 minutes. A solution of N'-[7-(2-amino-7-fluoro-1,3-benzothiazol-4-yl)-6-chloro-8-fluoro-quinazolin-4-yl]ethane-1,2-diamine in DCM was added to the mixture and stirred at ambient temperature for 2 hours. The reaction was quenched with water and extracted with ethyl acetate (40 mL). The organic layer was washed with water and brine, dried over sodium sulfate, filtered, and concentrated under reduced pressure. The residue was purified by preparative RP-HPLC to afford 1-[3-[[7-(2-amino-7-fluoro-1,3-benzothiazol-4-yl)-6-chloro-8-fluoro-quinazolin-4-yl]amino]azetidin-1-yl]-2-fluoro-prop-2-en-1-one (9.3 mg, 23%). LCMS ESI (+) m/z 491.1 (M+H). $^1$HNMR (400 MHz, $CD_3OD$) δ 8.81 (s, 1H), 8.53 (s, 1H), 7.29 (dd, J=8.4, 5.2 Hz, 1H), 7.04 (t, J=8.8 Hz, 1H), 5.60 (dd, J=47.2, 3.6 Hz, 1H), 5.23-5.28 (m, 2H), 4.90-4.95 (m, 1H), 4.56-4.64 (m, 2H), 4.28-4.32 (m, 1H).

Synthetic Example 6: Synthesis of 1-[3-[[7-(2-amino-7-fluoro-1,3-benzothiazol-4-yl)-6-chloro-8-fluoro-quinazolin-4-yl]amino]azetidin-1-yl]-2-chloro-propan-1-one (Compound 20)

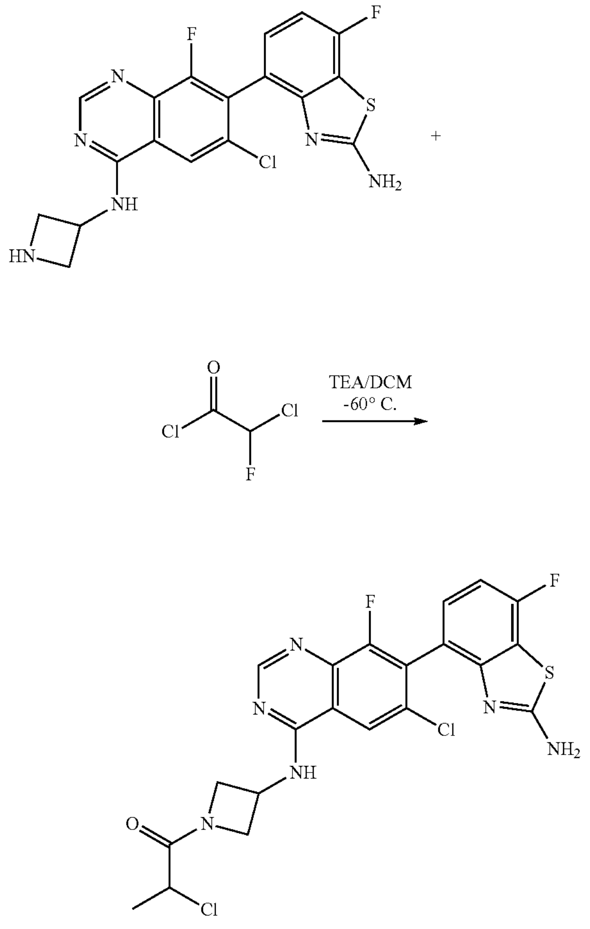

Compound 20

Preparation of 1-[3-[[7-(2-amino-7-fluoro-1,3-benzothiazol-4-yl)-6-chloro-8-fluoro-quinazolin-4-yl]amino]azetidin-1-yl]-2-chloro-propan-1-one: To a solution of 4-[4-(azetidin-3-ylamino)-6-chloro-8-fluoro-quinazolin-7-yl]-7-fluoro-1,3-benzothiazol-2-amine (36 mg, 0.086 mmol) in DCM (3 mL) was added triethylamine (0.12 mL, 0.85 mmol) and the mixture was stirred at −60° C. for 10 minutes. A solution of 2-chloropropanoyl chloride (0.0069 mL, 0.069 mol) in DCM was added dropwise to the mixture and stirred at −60° C. for 30 minutes. The reaction was quenched with water and extracted with EtOAc (40 mL), the organic layer was washed with water and brine, dried over sodium sulfate, filtered, and concentrated under reduced pressure. The residue was purified by preparative RP-HPLC to afford 1-[3-[[7-(2-amino-7-fluoro-1,3-benzothiazol-4-yl)-6-chloro-8-fluoro-quinazolin-4-yl]amino]azetidin-1-yl]-2-chloro-propan-1-one (11 mg, 25%). LCMS ESI (+) m/z 509.1 (M+H). $^1$HNMR (400 MHz, $CD_3OD$) δ 8.82 (s, 1H), 8.54 (d, J=12 Hz, 1H), 7.31 (dd, J=8.4, 5.2 Hz, 1H), 7.06 (t, J=8.8 Hz, 1H), 5.25-5.29 (m, 1H), 4.80-4.85 (m, 1H), 4.53-4.64 (m, 3H), 4.25-4.31 (m, 1H), 1.63 (d, J=6.8 Hz, 3H).

Synthetic Example 7: Synthesis of 1-[3-[[7-(2-amino-7-fluoro-1,3-benzothiazol-4-yl)-6-chloro-8-fluoro-quinazolin-4-yl]amino]azetidin-1-yl]-2-chloro-2-fluoro-ethanone (Compound 21)

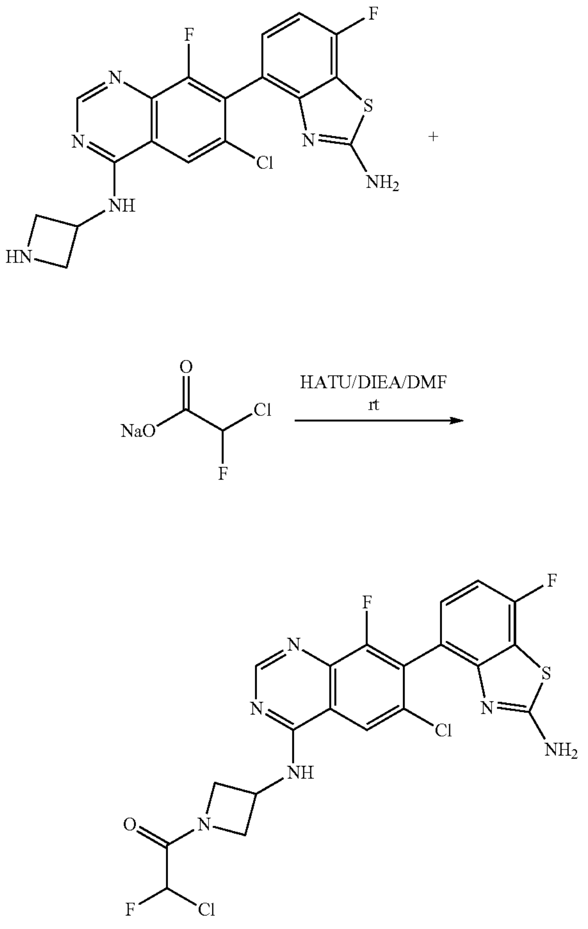

Compound 21

Preparation of 1-[3-[[7-(2-amino-7-fluoro-1,3-benzothiazol-4-yl)-6-chloro-8-fluoro-quinazolin-4-yl]amino]azetidin-1-yl]-2-chloro-2-fluoro-ethanone: To the solution of (2-chloro-2-fluoro-acetyl)oxysodium (15 mg, 0.12 mmol) in DMF (2 mL) was added HATU (54 mg, 0.14 mmol) and DIEA (0.024 mL, 0.14 mmol) at ambient temperature and stirred for 20 minutes, a solution of 4-[4-(azetidin-3-ylamino)-6-chloro-8-fluoro-quinazolin-7-yl]-7-fluoro-1,3-benzothiazol-2-amine (40 mg, 0.096 mmol) in DMF (0.5 mL) was added and the mixture was stirred at ambient temperature for 2 hours. Water and ethyl acetate were added. The organic layer was separated, washed with brine, dried (sodium sulfate), filtered, and concentrated under reduced pressure. The residue was purified by preparative RP-HPLC to give 1-[3-[[7-(2-amino-7-fluoro-1,3-benzothiazol-4-yl)-6-chloro-8-fluoro-quinazolin-4-yl]amino]azetidin-1-yl]-2-chloro-2-fluoro-ethanone (2.2 mg, 4%). LCMS ESI (+) m/z 513.1 (M+H). $^1$HNMR (400 MHz, $CD_3OD$) δ 8.67 (s, 1H), 8.22 (d, J=1.2 Hz, 1H), 7.26 (ddd, J=8.4, 5.4, 1.3 Hz, 1H), 7.04 (td, J=8.8, 2.0 Hz, 1H), 6.56 (dd, J=49.6, 2.0 Hz, 1H), 4.91-4.95 (m, 2H), 4.69-4.73 (m, 1H), 3.71-3.82 (m, 2H).

Synthetic Example 8: Synthesis of 1-[3-[[7-(2-amino-7-fluoro-1,3-benzothiazol-4-yl)-6-chloro-8-fluoro-quinazolin-4-yl]amino]azetidin-1-yl]prop-2-yn-1-one (Compound 22)

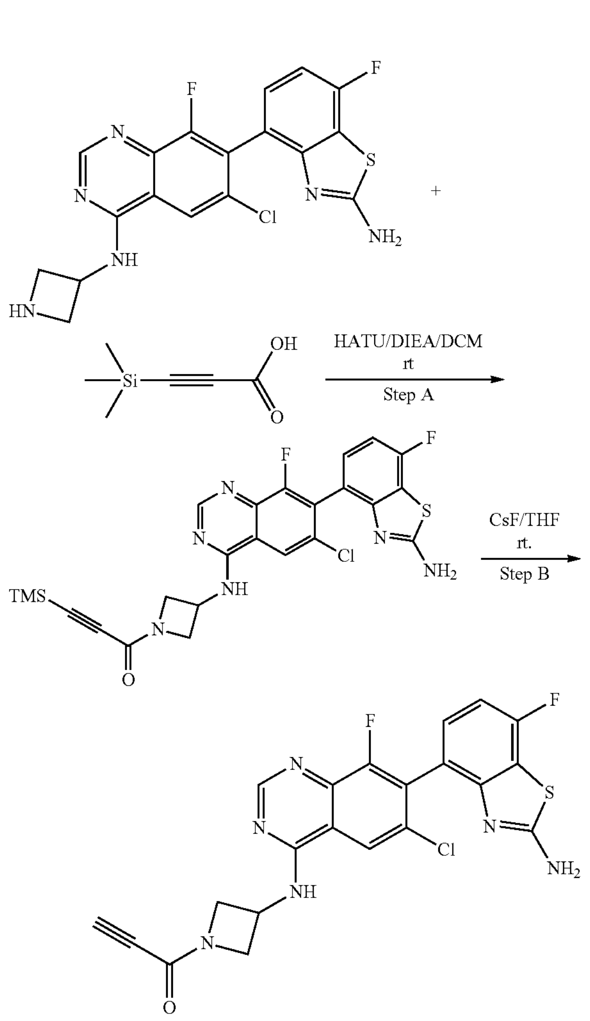

Compound 22

Step A: Preparation of 1-[3-[[6-chloro-8-fluoro-7-(7-fluoro-1,3-benzothiazol-4-yl)quinazolin-4-yl]amino]azetidin-1-yl]-3-trimethylsilyl-prop-2-yn-1-one: To the solution of 3-trimethylsilylprop-2-ynoic acid (18 mg, 0.13 mmol) in DCM (2 mL) was added HATU (56 mg, 0.15 mmol) and DIEA (38 mg, 0.30 mmol) at ambient temperature and stirred at this temperature for 20 minutes. A solution of N-(azetidin-3-yl)-6-chloro-8-fluoro-7-(7-fluoro-1,3-benzothiazol-4-yl)quinazolin-4-amine (40 mg, 0.099 mmol) in DCM (0.5 mL) was added and stirred ambient temperature for 2 hours. Brine and ethyl acetate were added. The organic layer was separated, washed with brine, dried (sodium sulfate), filtered, and concentrated under reduced pressure. The residue was purified by preparative TLC (50% EtOAc in petroleum ether) to give 1-[3-[[6-chloro-8-fluoro-7-(7-fluoro-1,3-benzothiazol-4-yl)quinazolin-4-yl]amino]azetidin-1-yl]-3-trimethylsilyl-prop-2-yn-1-one (23 mg, 37%) as a white solid. LCMS ESI (+) m/z 543.1 (M+H).

Step B: Preparation of 1-[3-[[7-(2-amino-7-fluoro-1,3-benzothiazol-4-yl)-6-chloro-8-fluoro-quinazolin-4-yl]amino]azetidin-1-yl]prop-2-yn-1-one: To a solution of 1-[3-[[7-(2-amino-7-fluoro-1,3-benzothiazol-4-yl)-6-chloro-8-fluoro-quinazolin-4-yl]amino]azetidin-1-yl]-3-trimethylsilyl-prop-2-yn-1-one (23 mg, 0.034 mmol) in THF (3 mL) was added cesium fluoride (9.4 mg, 0.068 mmol) at ambient temperature and stirred at this temperature for 40 minutes. Water (5 mL) and ethyl acetate (15 mL) were added. The organic layer was separated, dried (sodium sulfate), filtered and concentrated under reduced pressure. The crude product was purified by preparative RP-HPLC to give 1-[3-[[7-(2-amino-7-fluoro-1,3-benzothiazol-4-yl)-6-chloro-8-fluoro-quinazolin-4-yl]amino]azetidin-1-yl]prop-2-yn-1-one (2.2 mg, 13%) as a white solid. LCMS ESI (+) m/z 471.1 (M+H). $^{1}$HNMR(400 MHz, $CDCl_3$) δ 7.96 (d, J=4.8 Hz, 1H), 7.80 (s, 1H), 7.21-7.24 (m, 1H), 6.99 (t, J=9.2 Hz, 1H), 5.37-5.46 (br, 2H), 4.52-4.61 (m, 1H), 4.21-4.29 (m, 1H), 3.91-3.97 (m, 1H), 3.64-3.73 (m, 2H), 2.83 (d, J=6.0 Hz, 1H).

Synthetic Example 9: Synthesis of 1-(3-((7-(2-amino-7-fluorobenzo[d]thiazol-4-yl)-6-chloro-8-fluoro-2-(((S)-1-methylpyrrolidin-2-yl)methoxy)quinazolin-4-yl)amino)azetidin-1-yl)prop-2-en-1-one (Compound 23)

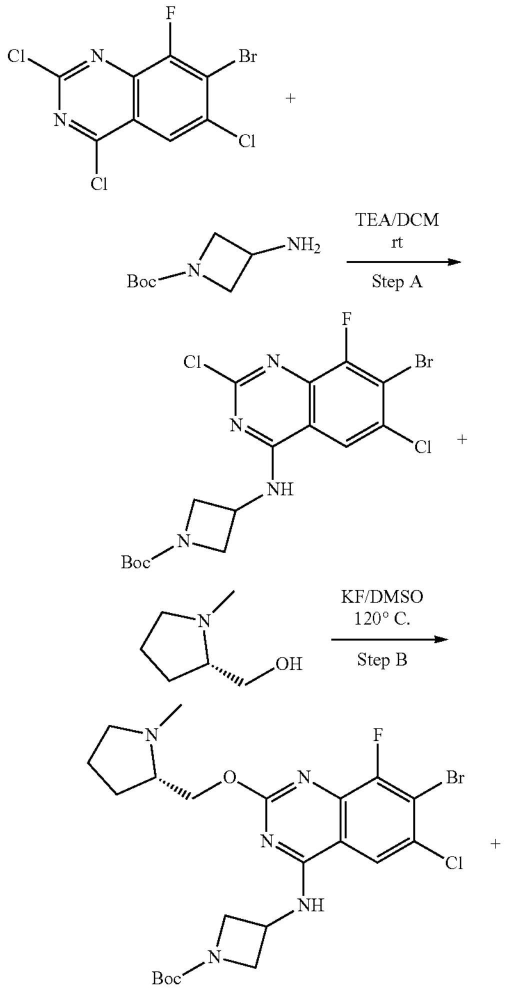

-continued

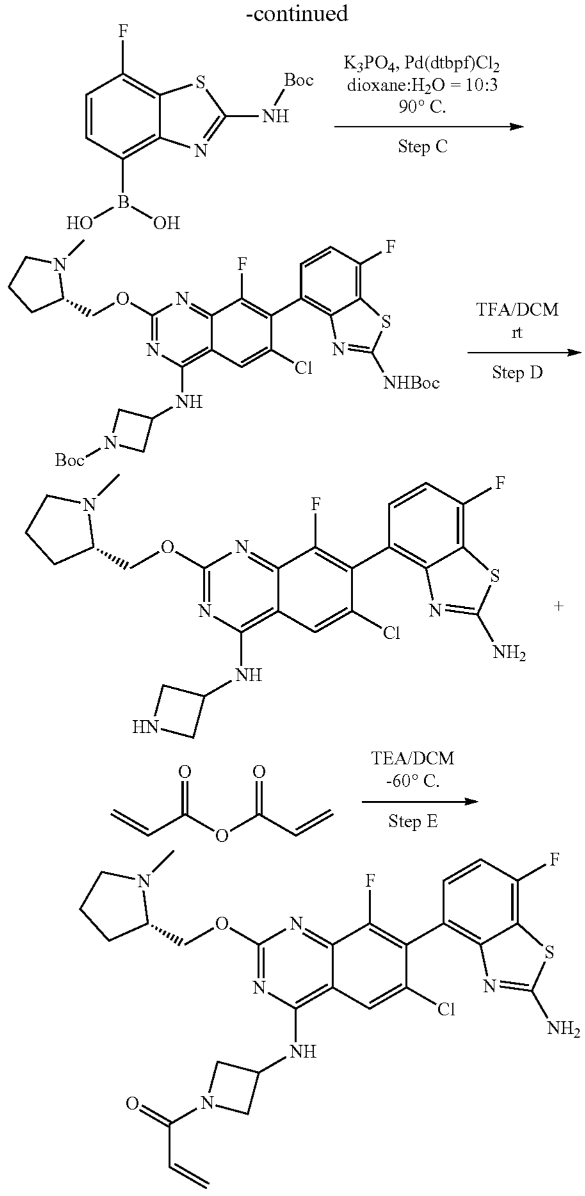

Compound 23

Step A: Preparation of tert-butyl 3-((7-bromo-2,6-dichloro-8-fluoroquinazolin-4-yl)amino)azetidine-1-carboxylate: To a solution of 7-bromo-2,4,6-trichloro-8-fluoroquinazoline (300 mg, 0.91 mmol) in DCM (50 mL) was added triethyl amine (276 mg, 2.72 mmol) and tert-butyl 3-aminoazetidine-1-carboxylate (188 mg, 1.09 mmol) at ambient temperature and the mixture was stirred at ambient temperature overnight. Water was added and the mixture was extracted with ethyl acetate (40 mL×3). The combined organic layers were washed with brine, dried over sodium sulfate, filtered, and concentrated under reduced pressure. The residue obtained was purified by flash column chromatography on silica gel 3:1 petroleum ether/ethyl acetate to give tert-butyl 3-((7-bromo-2,6-dichloro-8-fluoroquinazolin-4-yl)amino)azetidine-1-carboxylate (310 mg, 73%). LCMS ESI (+) m/z 465 (M+H).

Step B: Preparation of tert-butyl (S)-3-((7-bromo-6-chloro-8-fluoro-2-((1-methylpyrrolidin-2-yl)methoxy)quinazolin-4-yl)amino)azetidine-1-carboxylate: A solution of 3-((7-bromo-2,6-dichloro-8-fluoroquinazolin-4-yl)amino)azetidine-1-carboxylate (320 mg, 0.69 mmol), (S)-(1-methylpyrrolidin-2-yl)methanol (237 mg, 2.06 mol) and potassium fluoride (319 mg, 5.49 mmol) in DMSO (6 mL) was stirred at 118° C. for 6 hours under nitrogen atmosphere. Once cooled to ambient temperature, it was diluted with water (40 mL) and extracted with ethyl acetate (80 mL). The organic phase was isolated, dried over sodium sulfate, filtered, and concentrated under reduced pressure. The residue obtained was purified by flash column chromatography on silica gel 50:1 DCM/Methanol to give the product tert-butyl (S)-3-((7-bromo-6-chloro-8-fluoro-2-((1-methylpyrrolidin-2-yl)methoxy)quinazolin-4-yl)amino)azetidine-1-carboxylate (102 mg, 27%). LCMS ESI (+) m/z 544 (M+H).

Step C: Preparation of tert-butyl 3-((7-(2-((tert-butoxycarbonyl)amino)-7-fluorobenzo[d]thiazol-4-yl)-6-chloro-8-fluoro-2-(((S)-1-methylpyrrolidin-2-yl)methoxy)quinazolin-4-yl)amino)azetidine-1-carboxylate: To a solution of tert-butyl (S)-3-((7-bromo-6-chloro-8-fluoro-2-((1-methylpyrrolidin-2-yl)methoxy)quinazolin-4-yl)amino)azetidine-1-carboxylate (70 mg, 0.10 mmol) in (1, 4-dioxane/$H_2O$=10 mL/3 mL) was added potassium phosphate tribasic (41 mg, 0.19 mmol), (2-((tert-butoxycarbonyl)amino)-7-fluorobenzo[d]thiazol-4-yl)boronic acid (39 mg, 0.13 mmol) and dichloro[1,1'-bis(di-t-butylphosphino)ferrocene]palladium(II) (6 mg, 0.01 mmol) at ambient temperature. The mixture was warmed to 95° C. and stirred at this temperature for 2 hours. Once cooled to ambient temperature, the reaction mixture was concentrated under reduced pressure. It was diluted with water (20 mL) and extracted with ethyl acetate (40 mL). The organic phase was dried over sodium sulfate, filtered and concentrated under reduced pressure. The residue obtained was purified by preparative-TLC 50:1 DCM/Methanol to give tert-butyl 3-((7-(2-((tert-butoxycarbonyl)amino)-7-fluorobenzo[d]thiazol-4-yl)-6-chloro-8-fluoro-2-(((S)-1-methylpyrrolidin-2-yl)methoxy)quinazolin-4-yl)amino)azetidine-1-carboxylate (35 mg, 48%). LCMS ESI (+) m/z 731 (M+H).

Step D: Preparation of 4-(4-(azetidin-3-ylamino)-6-chloro-8-fluoro-2-(((S)-1-methylpyrrolidin-2-yl)methoxy)quinazolin-7-yl)-7-fluorobenzo[d]thiazol-2-amine: To a solution of 3-((7-(2-((tert-butoxycarbonyl)amino)-7-fluorobenzo[d]thiazol-4-yl)-6-chloro-8-fluoro-2-(((S)-1-methylpyrrolidin-2-yl)methoxy)quinazolin-4-yl)amino)azetidine-1-carboxylate (15 mg, 0.02 mmol) in DCM (3 mL) was added TFA (1 mL) and the mixture was stirred at ambient temperature for 1 hour. The mixture was concentrated under reduced pressure. The residue was purified by preparative-HPLC to give 4-(4-(azetidin-3-ylamino)-6-chloro-8-fluoro-2-(((S)-1-methylpyrrolidin-2-yl)methoxy)quinazolin-7-yl)-7-fluorobenzo[d]thiazol-2-amine (5 mg, 28%) as trifluoro acetic acid salt. LCMS ESI (+) m/z 532 (M+H).

Step E: Preparation of 1-(3-((7-(2-amino-7-fluorobenzo[d]thiazol-4-yl)-6-chloro-8-fluoro-2-(((S)-1-methylpyrrolidin-2-yl)methoxy)quinazolin-4-yl)amino)azetidin-1-yl)prop-2-en-1-one: To a solution of 4-(4-(azetidin-3-ylamino)-6-chloro-8-fluoro-2-(((S)-1-methylpyrrolidin-2-yl)methoxy)quinazolin-7-yl)-7-fluorobenzo[d]thiazol-2-amine (23 mg, 0.04 mmol) in dry DCM (3 mL) was added TEA (40 mg, 0.4 mmol) under nitrogen atmosphere. Then the mixture was cooled to −60° C. Acrylic anhydride (6.3 mg, 0.05 mmol) in dry DCM (1 mL) was added at −60° C. After addition, the reaction mixture was warmed to ambient temperature and stirred for 1 hour. The mixture was quenched with saturated sodium bicarbonate solution (2 mL) and diluted with water (10 mL). The product was extracted with EtOAc (10 mL×3). The combined organic layers were washed with brine (10 mL), dried (sodium sulfate), filtered, and concentrated under reduced pressure. The residue was purified by preparative RP-HPLC to give 1-(3-((7-(2-amino-7-fluorobenzo[d]thiazol-4-yl)-6-chloro-8-fluoro-2-(((S)-1-methylpyrrolidin-2-yl)methoxy)quinazolin-4-yl)amino)azetidin-1-yl)prop-2-en-1-one (7 mg, 21%) as solid. LCMS ESI (+) m/z 586.2 (M+H). $^1$HNMR (400 MHz, $CD_3OD$) δ 8.22 (s, 1H), 7.20-7.23 (m, 1H), 6.99 (t, J=8.8 Hz, 1H), 6.37-6.43 (m, 1H), 6.26-6.31 (m, 1H), 5.76-5.79 (dd, J=10.0, 1.2 Hz, 1H), 4.99-5.05 (m, 1H), 4.76 (t, J=8.8 Hz, 1H), 4.66-4.69 (m, 1H), 4.49-4.56 (m, 2H), 4.41-4.44 (m, 1H), 4.21-4.25 (m, 1H), 3.34-3.50 (m, 2H), 2.85-2.92 (m, 4H), 2.23-2.32 (m, 1H), 1.91-2.06 (m, 3H).

Synthetic Example 10: Synthesis of (S)-1-(4-(7-(2-amino-7-fluorobenzo[d]thiazol-4-yl)-8-fluoro-2-((1-methylpyrrolidin-2-yl)methoxy)pyrido[4,3-d]pyrimidin-4-yl)piperazin-1-yl)prop-2-en-1-one (Compound 33)

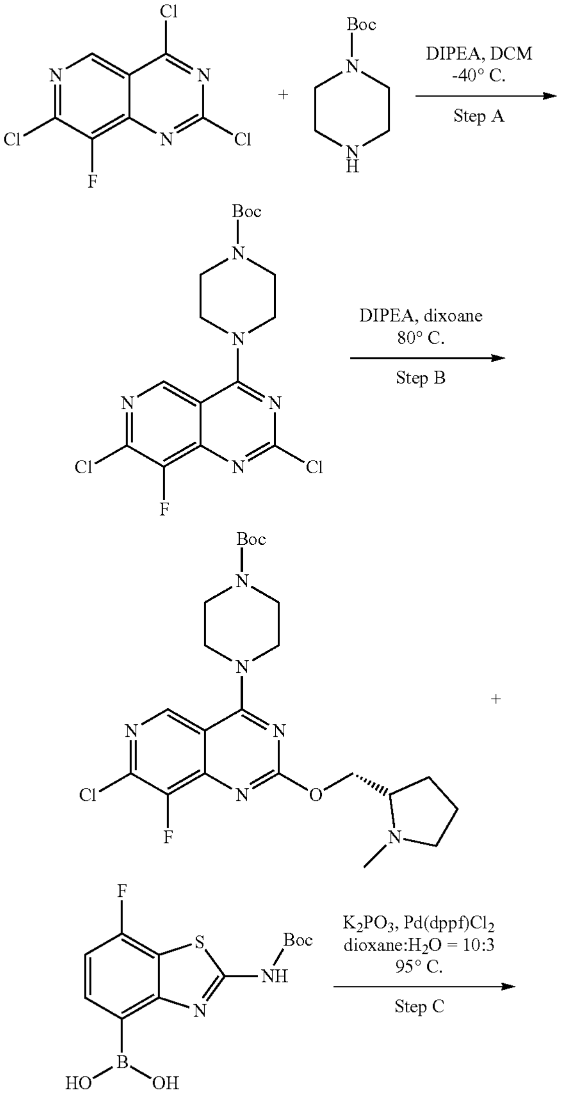

-continued

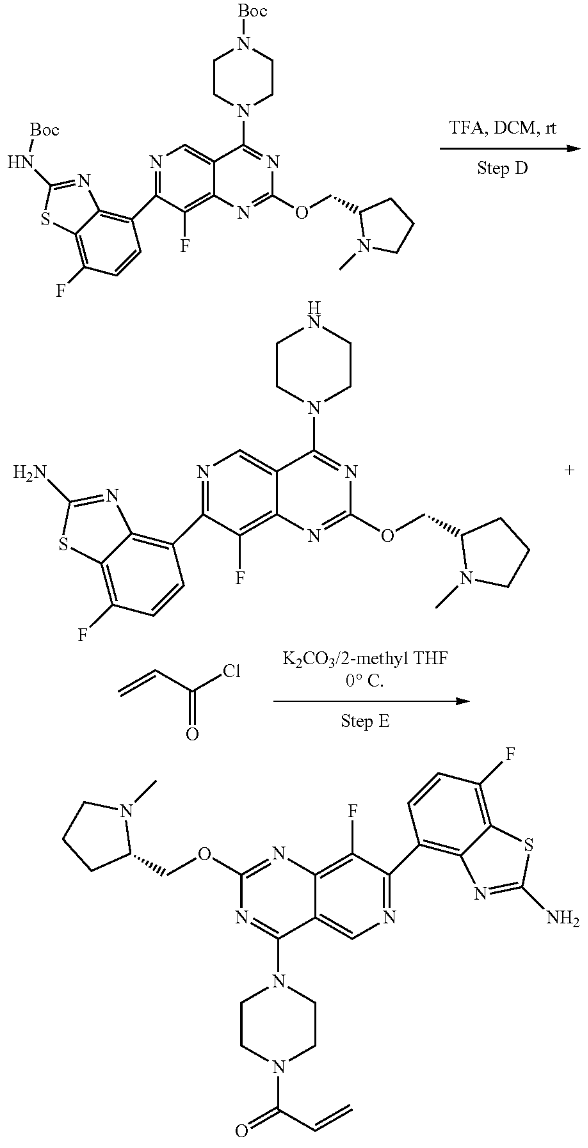

Compound 33

Step A: Preparation of tert-butyl 4-(2,7-dichloro-8-fluoropyrido[4,3-d]pyrimidin-4-yl)piperazine-1-carboxylate: To a mixture of 2,4,7-trichloro-8-fluoropyrido[4,3-d]pyrimidine (WO2020146613) (1.0 g, 4.0 mol) in DCM (20 mL) at −45° C. was added N-ethyl-N-isopropylpropan-2-amine (2.1 mL, 12 mmol) followed by tert-butyl piperazine-1-carboxylate (0.89 g, 4.8 mmol) and stirred at this temperature for 10 minutes. The reaction was quenched with ethyl acetate and saturated aqueous $NaHCO_3$. The organic layer was separated, dried with $Na_2SO_4$, filtered and evaporated under reduced pressure. The residue was purified by flash column chromatography on silica gel with ethyl acetate in hexane (10% to 50%) to provide tert-butyl 4-(2,7-dichloro-8-fluoropyrido[4,3-d]pyrimidin-4-yl)piperazine-1-carboxylate (0.90 g, 56%) as solid. LCMS ESI (+) m/z 402 (M+H). $^1$HNMR (300 MHz, $CDCl_3$) δ 8.90 (s, 1H), 4.27-3.92 (m, 4H), 3.87-3.45 (m, 4H), 1.52 (s, 9H).

Step B: Preparation of (S)-tert-butyl 4-(7-chloro-8-fluoro-2-((1-methylpyrrolidin-2-yl)methoxy)pyrido[4,3-d]pyrimidin-4-yl)piperazine-1-carboxylate: To a mixture of tert-butyl 4-{2,7-dichloro-8-fluoropyrido[4,3-d]pyrimidin-4-yl}piperazine-1-carboxylate (0.80 g, 2.0 mmol) and [(2S)-1-methylpyrrolidin-2-yl]methanol (0.46 g, 4.0 mmol) in p-dioxane (16 mL) was added N-ethyl-N-isopropylpropan-2-amine (1.0 mL, 5.6 mmol) and stirred at 80° C. for 4 hours. After cooled to ambient temperature, solvent was removed under reduced pressure. The residue obtained was purified using silica gel column chromatography with ethyl acetate in MeOH (0% to 10%) to provide (S)-tert-butyl 4-(7-chloro-8-fluoro-2-((1-methylpyrrolidin-2-yl)methoxy)pyrido[4,3-d]pyrimidin-4-yl)piperazine-1-carboxylate (0.48 g, 50%). $^{1}$HNMR (300 MHz, $CDCl_3$) δ 8.77 (s, 1H), 4.55 (dd, J=10.8, 4.7 Hz, 1H), 4.36 (dd, J=10.8, 6.6 Hz, 1H), 4.05-3.82 (m, 4H), 3.79-3.31 (m, 4H), 3.23-2.82 (m, 1H), 2.74 (m, 1H), 2.51 (s, 3H), 2.31 (dd, J=17.6, 8.5 Hz, 1H), 2.15-2.01 (m, 1H), 1.82 (m, 3H), 1.59 (s, 9H).

Step C: Preparation of (S)-tert-butyl 4-(7-(2-((tert-butoxycarbonyl)amino)-7-fluorobenzo[d]thiazol-4-yl)-8-fluoro-2-((1-methylpyrrolidin-2-yl)methoxy)pyrido[4,3-d]pyrimidin-4-yl)piperazine-1-carboxylate: A mixture of tert-butyl 4-(7-chloro-8-fluoro-2-{[(2S)-1-methylpyrrolidin-2-yl]methoxy}pyrido[4,3-d]pyrimidin-4-yl)piperazine-1-carboxylate (0.15 g, 0.31 mmol), 2-{[(tert-butoxy)carbonyl]amino}-7-fluoro-1,3-benzothiazol-4-yl)boronic acid (0.20 g, 0.624 mmol) and cesium carbonate (0.20 g, 0.62 mmol) in p-dioxane_(4.3 mL) and water (0.86 mL) was degassed with argon followed by the addition of Pd(dppf)$Cl_2$ (0.046 g, 0.062 mmol) then degassed again. The reaction mixture was stirred at 95° C. for 3 hours then cooled down to ambient temperature. The resulting mixture was diluted with ethyl acetate and brine and the organic layer was separated. The organic layer was dried over $Na_2SO_4$, filtered and concentrated under reduced pressure. The crude was purified using silica gel column chromatography with DCM in MeOH (0% to 10%) to provide (S)-tert-butyl 4-(7-(2-((tert-butoxycarbonyl)amino)-7-fluorobenzo[d]thiazol-4-yl)-8-fluoro-2-((1-methylpyrrolidin-2-yl)methoxy)pyrido[4,3-d]pyrimidin-4-yl)piperazine-1-carboxylate (0.090 g, 40%). LCMS ESI (+) m/z 713 (M+H). $^{1}$HNMR (300 MHz, $CDCl_3$) δ 9.07 (s, 1H), 7.72 (dd, J=8.6, 5.4 Hz, 1H), 7.15 (t, J=8.7 Hz, 1H), 4.59 (m, 1H), 4.41 (m, 1H), 3.99 (m, 4H), 3.68 (m, 4H), 3.17 (m, 1H), 2.77 (m, 1H), 2.54 (s, 3H), 2.32 (m, 1H), 2.07 (m, 1H), 1.83 (m, 3H), 1.58 (s, 9H), 1.53 (s, 9H).

Step D: Preparation of 7-fluoro-4-(8-fluoro-2-{[(2S)-1-methylpyrrolidin-2-yl]methoxy}-4-(piperazin-1-yl)pyrido[4,3-d]pyrimidin-7-yl)-1,3-benzothiazol-2-amine: To the tert-butyl (S)-4-(7-(2-((tert-butoxycarbonyl)amino)-7-fluorobenzo[d]thiazol-4-yl)-8-fluoro-2-((1-methylpyrrolidin-2-yl)methoxy)pyrido[4,3-d]pyrimidin-4-yl)piperazine-1-carboxylate (18 mg, 0.025 mmol) in DCM (2 ml) was added TFA (0.5 mL) and the reaction mixture was stirred at ambient temperature for 3 hours. The resulting mixture was evaporated under reduce pressure. The resulting solid was triturated with ether for 30 minutes and solid was collected and dried to give 7-fluoro-4-(8-fluoro-2-{[(2S)-1-methylpyrrolidin-2-yl]methoxy}-4-(piperazin-1-yl)pyrido[4,3-d]pyrimidin-7-yl)-1,3-benzothiazol-2-amine (0.015 g, 95%) as TFA salt. LCMS ESI (+) m/z 513 (M+H).

Step E: Preparation of (S)-1-(4-(7-(2-amino-7-fluorobenzo[d]thiazol-4-yl)-8-fluoro-2-((1-methylpyrrolidin-2-yl)methoxy)pyrido[4,3-d]pyrimidin-4-yl)piperazin-1-yl)prop-2-en-1-one: To a mixture of 7-fluoro-4-(8-fluoro-2-{[(2S)-1-methylpyrrolidin-2-yl]methoxy}-4-(piperazin-1-yl)pyrido[4,3-d]pyrimidin-7-yl)-1,3-benzothiazol-2-amine bis (trifluoroacetic acid) (80 mg, 0.11 mmol) in 2-methyloxolane (1.1 mL) was added potassium carbonate (60 mg, 0.43 mmol) followed by the addition of a 0.5 M solution of prop-2-enoyl chloride (0.24 mL, 0.12 mmol) in 2-methyloxolane at −78° C. The reaction was followed by HPLC after 1 hour (no progression). Therefore 1 mL of water was added to the reaction followed by the addition of 60 μL of 0.5 M solution of prop-2-enoyl chloride (0.24 mL, 0.13 mmol) at 0° C. in order to complete the reaction. The resulting reaction mixture was diluted with water and extracted twice with EtOAc. The organic layers were combined, dried over sodium sulfate, filtered, and evaporated under reduced pressure. The crude material was purified on a 12 g column with a gradient from 0% to 30% MeOH in DCM to provide (S)-1-(4-(7-(2-amino-7-fluorobenzo[d]thiazol-4-yl)-8-fluoro-2-((1-methylpyrrolidin-2-yl)methoxy)pyrido[4,3-d]pyrimidin-4-yl)piperazin-1-yl)prop-2-en-1-one (0.016 g, 26%). LCMS ESI (+) m/z 567.3 (M+H). $^{1}$H NMR (300 MHz, $CD_3OD$) δ 9.13 (s, 1H), 7.49 (dd, J=8.5, 5.5 Hz, 1H), 7.03 (t, J=8.8 Hz, 1H), 6.83 (dd, J=16.7, 10.6 Hz, 1H), 6.30 (dd, J=16.8, 1.9 Hz, 1H), 5.83 (dd, J=10.6, 1.8 Hz, 1H), 4.52 (m, 2H), 4.18 (m, 4H), 4.03 (m, 4H), 3.12 (dd, J=9.5, 4.5 Hz, 1H), 2.83 (d, J=7.9 Hz, 1H), 2.55 (s, 3H), 2.40 (dd, J=17.8, 8.9 Hz, 1H), 2.14 (dd, J=11.2, 6.0 Hz, 1H), 2.01-1.44 (m, 3H).

Synthetic Example 11: Synthesis of 3-((7-(2-amino-7-fluorobenzo[d]thiazol-4-yl)-6-chloro-8-fluoro-2-(((S)-1-methylpyrrolidin-2-yl)methoxy)quinazolin-4-yl)amino)azetidine-1-carbonitrile (Compound 40)

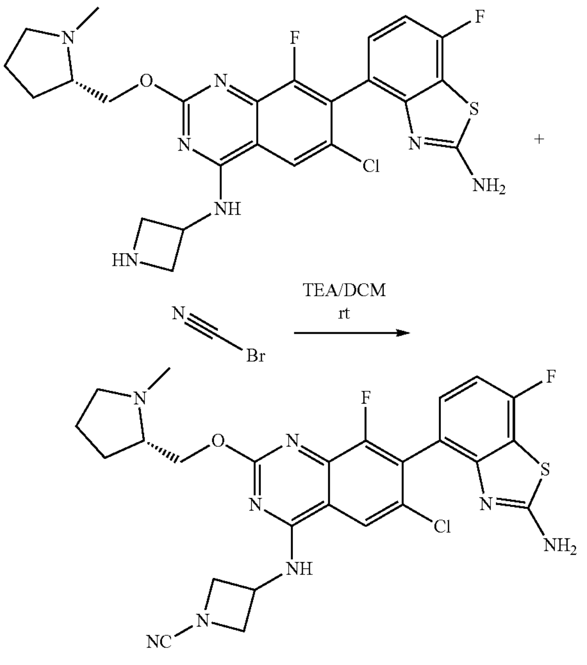

Compound 40

Preparation of 3-((7-(2-amino-7-fluorobenzo[d]thiazol-4-yl)-6-chloro-8-fluoro-2-(((S)-1-methylpyrrolidin-2-yl)methoxy)quinazolin-4-yl)amino)azetidine-1-carbonitrile: To a solution of 4-(4-(azetidin-3-ylamino)-6-chloro-8-fluoro-2-(((S)-1-methylpyrrolidin-2-yl)methoxy)quinazolin-7-yl)-7-fluorobenzo[d]thiazol-2-amine (120 mg, crude), TEA (19 mg, 0.19 mmol) in DCM (4 mL) was added a solution of cyanic bromide (22 mg, 0.21 mmol) in DCM (1 mL) at −70° C. After addition, the mixture was warmed to ambient temperature and stirred at ambient temperature for 2 hours. The reaction was quenched with aqueous sodium bicarbonate solution and extracted with DCM (5 mL×3). The combined organic layer was washed with water and brine, dried over sodium sulfate, filtered, and concentrated under reduced pressure. The residue was purified by preparative RP-HPLC to give 3-((7-(2-amino-7-fluorobenzo[d]thiazol-4-yl)-6-chloro-8-fluoro-2-(((S)-1-methylpyrrolidin-2-yl)methoxy)quinazolin-4-yl)amino)azetidine-1-carbonitrile (15.8 mg, 19%). LCMS ESI (+) m/z 557.3 (M+H). $^1$HNMR (400 MHz, $CD_3OD$) δ 8.23 (s, 1H), 7.19-7.23 (m, 1H), 6.99 (t, J=8.8 Hz, 1H), 5.03-5.13 (m, 1H), 4.74 (dt, J=12.9, 3.4 Hz, 1H), 4.49-4.68 (m, 3H), 4.39 (dd, J=8.1, 6.0 Hz, 2H), 3.50-3.68 (m, 2H), 2.95-3.08 (m, 1H), 2.93 (s, 3H), 2.22-2.33 (m, 1H), 1.94-2.15 (m, 3H).

Synthetic Example 12: Synthesis of 1-(4-(7-(2-amino-7-fluorobenzo[d]thiazol-4-yl)-8-fluoro-6-(trifluoromethyl)quinazolin-4-yl)piperazin-1-yl)prop-2-en-1-one (Compound 42)

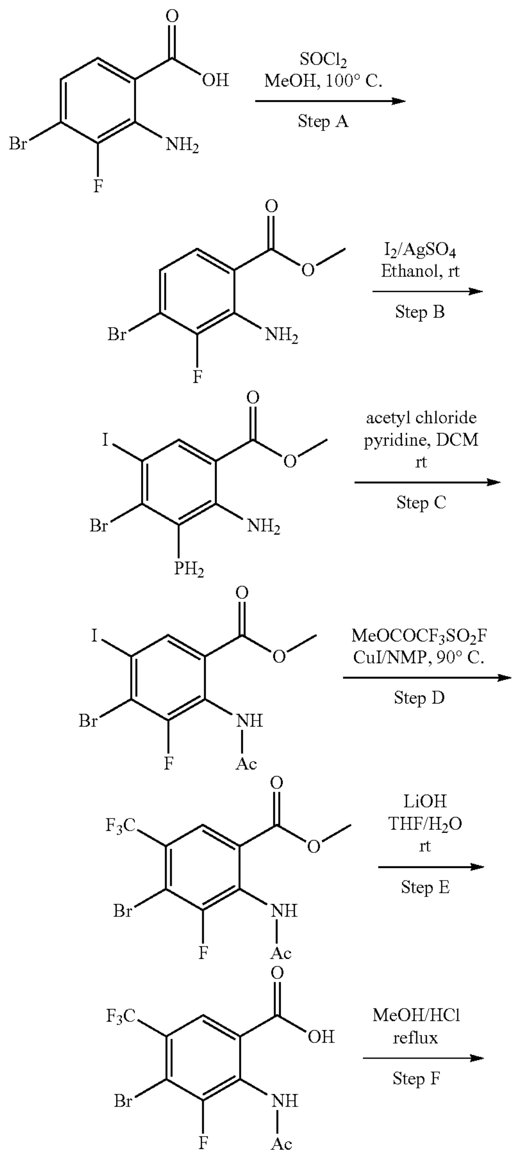

-continued

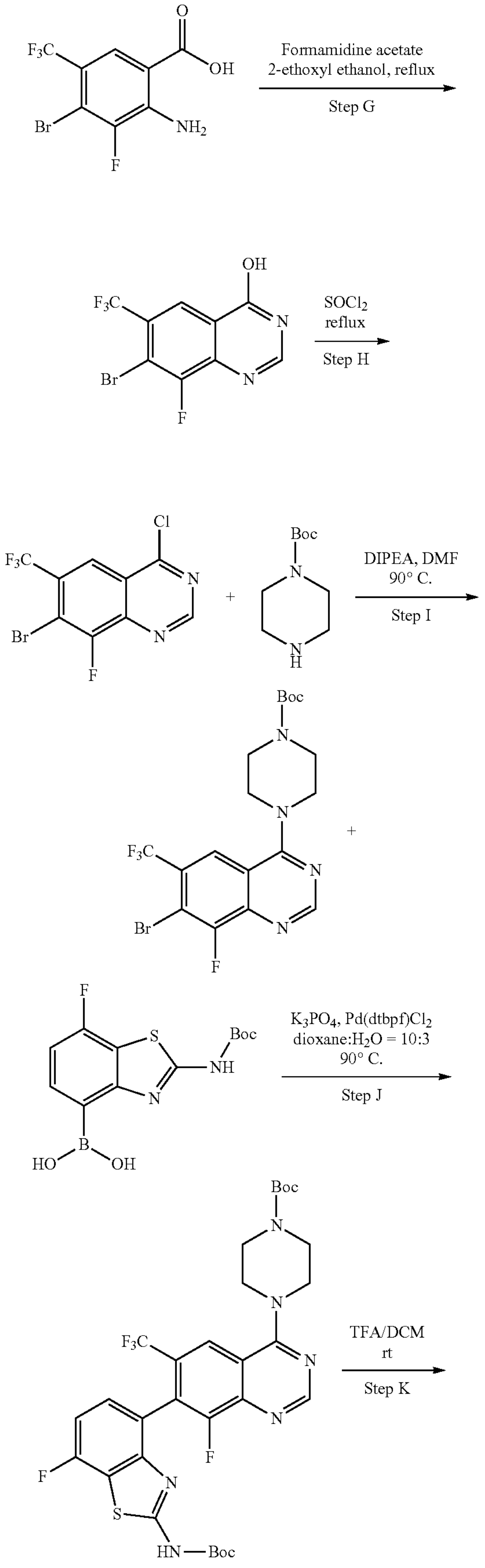

-continued

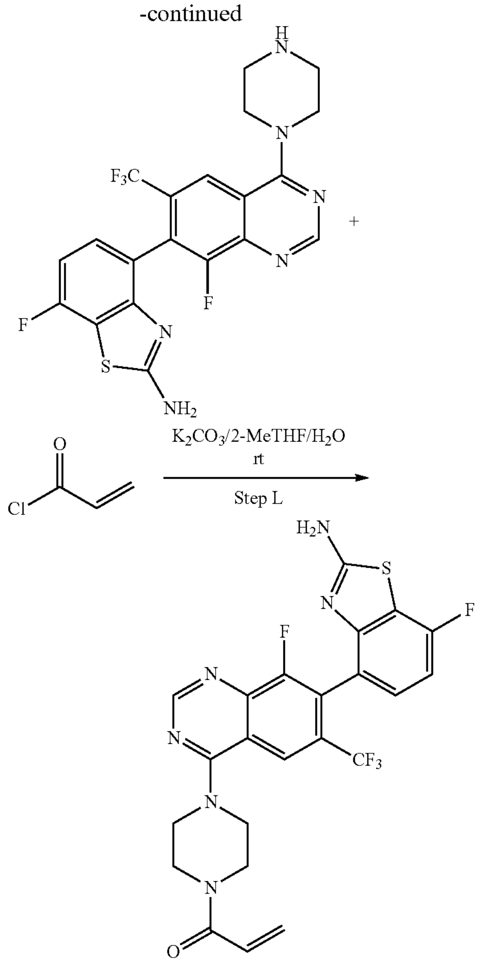

Compound 42

Step A: Preparation of methyl 2-amino-4-bromo-3-fluorobenzoate: To stirring solution of 2-amino-4-bromo-3-fluorobenzoic acid (5.0 g, 21.4 mmol) in MeOH (30 mL) was added dropwise thionyl chloride (15.6 ml, 21 mmol) at 0° C. under argon. The resulting mixture was heated to 100° C. for 16 hours. The solvent was evaporated, and the residue was dissolved in ethyl acetate (100 mL). The organic layer was washed with a saturated aqueous $NaHCO_3$ solution then dried over $Na_2SO_4$, filtered and concentrated under vacuum. The resulting crude material was purified by silica gel column chromatography using EtOAc in hexanes (0% to 20%) as eluent to give methyl 2-amino-4-bromo-3-fluorobenzoate (5.0 g, 94%) as a solid. LCMS ESI (+) m/z 249 (M+H). $^1$HNMR (300 MHz, $CDCl_3$) δ 7.53 (dd, J=8.8, 1.8 Hz, 1H), 6.78 (dd, J=8.8, 6.3 Hz, 1H), 5.93 (s, 1H), 3.90 (s, 1H).

Step B: Preparation of methyl 2-amino-4-bromo-3-fluoro-5-iodobenzoate: To a mixture of iodine (7.16 g, 28 mmol) and silver sulfate (5.3 g, 17 mmol) in EtOH (200 mL), methyl 2-amino-4-bromo-3-fluorobenzoate (5.0 g, 20 mmol) was added and the resulting mixture was stirred at ambient temperature for 45 minutes. The solid was filtered off and washed with DCM, and the filtrate was concentrated under vacuum. The residue was dissolved in DCM and washed with 10% sodium thiosulphate solution, brine and the resulting organic solution was dried over $Na_2SO_4$, filtered and concentrated under vacuum to give methyl 2-amino-4-bromo-3-fluoro-5-iodobenzoate: the title compound (6.66 g, 88% yield) as a yellow solid. LCMS ESI (+) m/z 373 (M+H). $^1$HNMR (300 MHz, $CDCl_3$) δ 8.14 (d, J=1.9 Hz, 1H), 5.94 (s, 2H), 3.91 (s, 3H).

Step C: Preparation of methyl 2-acetamido-4-bromo-3-fluoro-5-iodobenzoate: The methyl 2-amino-4-bromo-3-fluoro-5-iodobenzoate (3.50 g, 9.4 mmol) and pyridine (2.3 ml, 28 mmol) were dissolved in DCM at 0° C. Acetyl chloride (0.79 ml, 11 mmol) was added and the reaction was warmed to ambient temperature and stirred at this temperature for 16 hours. The reaction mixture was concentrated under vacuum and the residue obtained was purified by silica gel column chromatography using ethyl acetate in hexanes (0% to 30%) as eluent to give methyl 2-acetamido-4-bromo-3-fluoro-5-iodobenzoate (2.7 g, 69%) as solid. LCMS ESI (+) m/z 417 (M+H). $^1$HNMR (300 MHz, $CDCl_3$) δ 8.87 (s, 1H), 8.25 (s, 1H), 3.95 (s, 3H), 2.26 (s, 3H).

Step D: Preparation of methyl 2-acetamido-4-bromo-3-fluoro-5-(trifluoromethyl)benzoate: To a stirred solution of methyl 4-bromo-2-acetamido-3-fluoro-5-iodobenzoate (1.0 g, 2.4 mmol) and methyl fluorosulfonyldifluoroacetate (0.92 g, 0.72 mmol) in NMP (22.0 mL) at ambient temperature, CuI (0.14 g, 0.73 mmol) was added and the resulting mixture was stirred at 80° C. for 16 hours. Once cooled to ambient temperature, the mixture was quenched with water and extracted with ethyl acetate. The organic layer was dried over $Na_2SO_4$, filtered, concentrated and the crude material was purified by silica gel column chromatography using ethyl acetate in hexanes (0% to 20%) as eluent to give methyl 2-acetamido-4-bromo-3-fluoro-5-(trifluoromethyl) benzoate (0.64 g, 74%) as solid. LCMS ESI (+) m/z 358 (M+H). $^1$HNMR (300 MHz, $CDCl_3$) δ 9.23 (s, 1H), 8.10 (s, 1H), 3.93 (s, 3H), 2.28 (s, 3H).

Step E: Preparation of 2-Acetamido-4-bromo-3-fluoro-5-(trifluoromethyl)benzoic acid: Methyl 4-bromo-2-acetamido-3-fluoro-5-(trifluoromethyl)benzoate (3.4 g, 9.49 mmol) was dissolved in THF (56 ml) and water (14 ml) at ambient temperature, then LiOH (0.91 g, 38 mmol) was added. The resulting mixture was stirred at 80° C. for 2 hours. The reaction was diluted with water, acidified with 2M HCl to adjust to a pH ~4 and then extracted with ethyl acetate (2×25 mL). The organic layer was washed with brine, dried over $Na_2SO_4$, filtered and concentrated in vacuum to afford 4-bromo-2-acetamido-3-fluoro-5-(trifluoromethyl)benzoic acid as solid (3.0 g, 92%). $^1$HNMR (300 MHz, $CD_3OD$) δ 8.10 (s, 1H), 8.01 (s, 1H), 2.21 (s, 3H).

Step F: Preparation of 2-Amino-4-bromo-3-fluoro-5-(trifluoromethyl)benzoic acid: 4-Bromo-2-acetamido-3-fluoro-5-(trifluoromethyl)benzoic acid (0.50 g, 1.45 mmol) was dissolved in a 3 M solution of HCl in MeOH (0.064 mL, 1.74 mmol) and refluxed at 80° C. for 2 hours. Once cooled to ambient temperature, the reaction mixture was concentrated under vacuum to provide 2-amino-4-bromo-3-fluoro-5-(trifluoromethyl)benzoic acid as solid (0.40 g, 91%). LCMS ESI (−) m/z 300 (M−H). $^1$HNMR (300 MHz, $CD_3OD$) δ 7.86 (s, 1H).

Step G: Preparation of 7-Bromo-8-fluoro-6-(trifluoromethyl)quinazolin-4-ol: A mixture of 2-amino-4-bromo-3-fluoro-5-(trifluoromethyl)benzoic acid (0.4 g, 1.32 mmol) and formamidine acetate (0.28 g, 2.65 mmol) in 2-ethoxy ethanol (15 mL) was stirred at reflux for 16 hours. Once cooled to ambient temperature, the mixture was concentrated in vacuum. Water was added and extracted with DCM. The organic layer was washed with brine, dried over $Na_2SO_4$, filtered, and concentrated under vacuum. The crude material was purified by silica gel column chromatography and eluted with 10% MeOH in DCM to provide 7-Bromo- 8-fluoro-6-(trifluoromethyl)quinazolin-4-ol (0.2 g, 48%) as solid. LCMS ESI (+) m/z 311 (M+H). $^1$HNMR (300 MHz, $CDCl_3$) δ=8.45 (s, 1H), 8.30 (s, 1H).

Step H: Preparation of 7-Bromo-4-chloro-8-fluoro-6-(trifluoromethyl)quinazoline: 7-bromo-8-fluoro-6-(trifluoromethyl)quinazolin-4-ol (0.15 g, 0.48 mmol) was dissolved in thionyl chloride (7.5 mL, 103 mmol) and the reaction mixture stirred at refluxed for 1 hour. Once cooled to ambient temperature, the crude was concentrated under vacuum to remove excess thionyl chloride and dried to give 7-Bromo-4-chloro-8-fluoro-6-(trifluoromethyl)quinazoline (0.15 g, 97%) as solid. $^1$HNMR (300 MHz, $CDCl_3$) δ=9.22 (s, 1H), 8.47 (s, 1H).

Step I: Preparation of tert-butyl 4-(7-bromo-8-fluoro-6-(trifluoromethyl)quinazolin-4-yl)piperazine-1-carboxylate: To a solution of 7-Bromo-4-chloro-8-fluoro-6-(trifluoromethyl)quinazoline (1.70 g, 5.16 mmol) and DIEA (2.7 mL, 15.5 mmol) in DMF (10 ml) at ambient temperature was added N-Boc piperazine (1.92 g, 10.3 mmol). The resulting mixture was stirred at 90° C. for 1 hour. Once cooled to ambient temperature, the crude material was diluted with ethyl acetate (50 mL) and washed with water (50 mL). The organic layer was dried over $Na_2SO_4$, filtered, and concentrated under vacuum. The residue obtained was purified by silica gel column chromatography and eluted with ethyl acetate in hexane (0% to 30%) to provide tert-butyl 4-(7-bromo-8-fluoro-6-(trifluoromethyl)quinazolin-4-yl)piperazine-1-carboxylate (2.0 g, 81%) as solid. LCMS ESI (+) m/z 479 (M+H). $^1$HNMR (300 MHz, $CDCl_3$) δ 8.82 (s, 1H), 8.02 (s, 1H), 3.94-3.81 (m, 4H), 3.70-3.60 (m, 4H), 1.50 (s, 9H).

Step J: Preparation of tert-butyl 4-(7-(2-((tert-butoxycarbonyl)amino)-7-fluorobenzo[d]thiazol-4-yl)-8-fluoro-6-(trifluoromethyl)quinazolin-4-yl)piperazine-1-carboxylate: The tert-butyl 4-[7-bromo-8-fluoro-6-(trifluoromethyl)quinazolin-4-yl]piperazine-1-carboxylate (150 mg, 0.31 mmol), (2-{[(tert-butoxy)carbonyl]amino}-7-fluoro-1,3-benzothiazol-4-yl)boronic acid) (195 mg, 0.63 mmol) and potassium phosphate (21 mg, 0.63 mmol) were dissolved in 1,4-dioxane (1 mL) and water (0.3 mL). The resulting mixture was purged with Argon for 10 minutes then charged with the [5-(di-tert-butylphosphanyl)cyclopenta-1,3-dien-1-yl][2-(di-tert-butylphosphanyl)cyclopenta-2,4-dien-1-yl] iron dichloropalladium (20 mg, 0.031 mmol). The reaction mixture was stirred at 90° C. for 7 hours. Once cooled to ambient temperature, the resulting mixture was diluted with water and filter through a pad of celite, washed with ethyl acetate. The organic layers were dried over $Na_2SO_4$, filtered, and the solvent was evaporated in vacuum. The crude material was purified by silica gel column chromatography and eluted with ethyl acetate in hexane (0% to 30%) to provide tert-butyl 4-(7-(2-((tert-butoxycarbonyl)amino)-7-fluorobenzo[d]thiazol-4-yl)-8-fluoro-6-(trifluoromethyl)quinazolin-4-yl)piperazine-1-carboxylate (50 mg, 24%). LCMS ESI (+) m/z 667 (M+H). $^1$HNMR (300 MHz, $CDCl_3$) δ 8.85 (s, 1H), 8.11 (s, 1H), 8.00 (s, 1H), 7.34-7.28 (m, 1H), 7.10 (t, J=8.5 Hz, 1H), 3.90 (d, J=5.6 Hz, 4H), 3.69 (d, J=6.0 Hz, 4H), 1.52 (d, J=4.7 Hz, 18H).

Step K: Preparation of 7-fluoro-4-(8-fluoro-4-(piperazin-1-yl)-6-(trifluoromethyl)quinazolin-7-yl)benzo[d]thiazol-2-amine: The tert-butyl 4-[7-(2-{[(tert-butoxy)carbonyl]amino}-7-fluoro-1,3-benzothiazol-4-yl)-8-fluoro-6-(trifluoromethyl)quinazolin-4-yl]piperazine-1-carboxylate) (15 mg, 0.015 mmol) was dissolved in a DCM (1 mL) and cooled down to 0° C. TFA (1.0 mL, 13 mmol) was added dropwise under argon and the reaction mixture was warmed up to ambient temperature and stirred for 1 hour. The resulting mixture was concentrated under vacuum and the residue obtained was triturated with chloroform and filtered to provide 7-fluoro-4-(8-fluoro-4-(piperazin-1-yl)-6-(trifluoromethyl)quinazolin-7-yl)benzo[d]thiazol-2-amine (12 mg, 77%) as a TFA salt. LCMS ESI (+) m/z 467 (M+H).

Step L: Preparation of 1-(4-(7-(2-amino-7-fluorobenzo[d]thiazol-4-yl)-8-fluoro-6-(trifluoromethyl)quinazolin-4-yl)piperazin-1-yl)prop-2-en-1-one: To the 7-fluoro-4-[8-fluoro-4-(piperazin-1-yl)-6-(trifluoromethyl)quinazolin-7-yl]-1,3-benzothiazol-2-amine; bis(trifluoroacetic acid) (44.0 mg, 0.063 mmol) in 2-Me-THF (0.5 mL) and water (0.5 mL) was added potassium carbonate (35.0 mg, 0.25 mmol) and the solution was cooled to −5° C. under argon. 0.5 M stock solution in Me-THF of acryloyl chloride (0.14 mL, 0.070 mmol) was added at −5° C. The reaction mixture was warmed to ambient temperature and stirred for 15 minutes. The reaction mixture was extracted with water (2 mL) and EtOAc (2×5 mL). The organic layers were combined, dried over anhydrous $Na_2SO_4$, filtered and concentrated under vacuum. The crude material was purified by silica gel chromatography by eluting with (0-10%) MeOH in DCM to give 1-(4-(7-(2-amino-7-fluorobenzo[d]thiazol-4-yl)-8-fluoro-6-(trifluoromethyl)quinazolin-4-yl)piperazin-1-yl)prop-2-en-1-one (10.0 mg, 30%) as solid. LCMS ESI (+) m/z 521 (M+H). $^1$H NMR (300 MHz, $CD_3OD$): δ 8.74 (s, 1H), 8.30 (s, 1H), 7.28-7.18 (m, 1H), 7.04-6.95 (m, 1H), 6.84 (dd, J=16.8, 10.6 Hz, 1H), 6.30 (dd, J=16.8, 1.9 Hz, 1H), 5.83 (dd, J=10.6, 1.9 Hz, 1H), 4.13 (m, 4H), 3.95 (m, 4H). Synthetic Example 13: Synthesis of 1-(3-((7-(2-amino-7-fluorobenzo[d]thiazol-4-yl)-6-chloro-8-fluoro-2-((tetrahydro-1H-pyrrolizin-7a(5H)-yl)methoxy)quinazolin-4-yl)amino)azetidin-1-yl)prop-2-en-1-one (Compound 49)

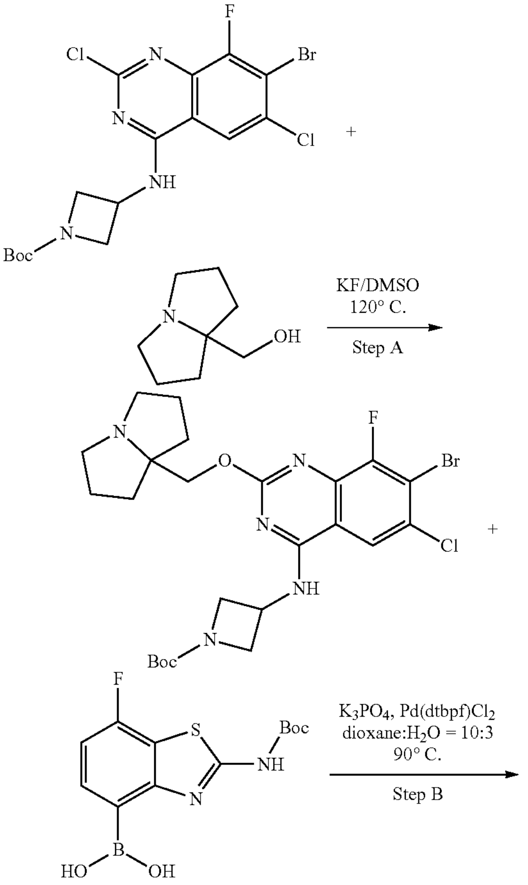

-continued

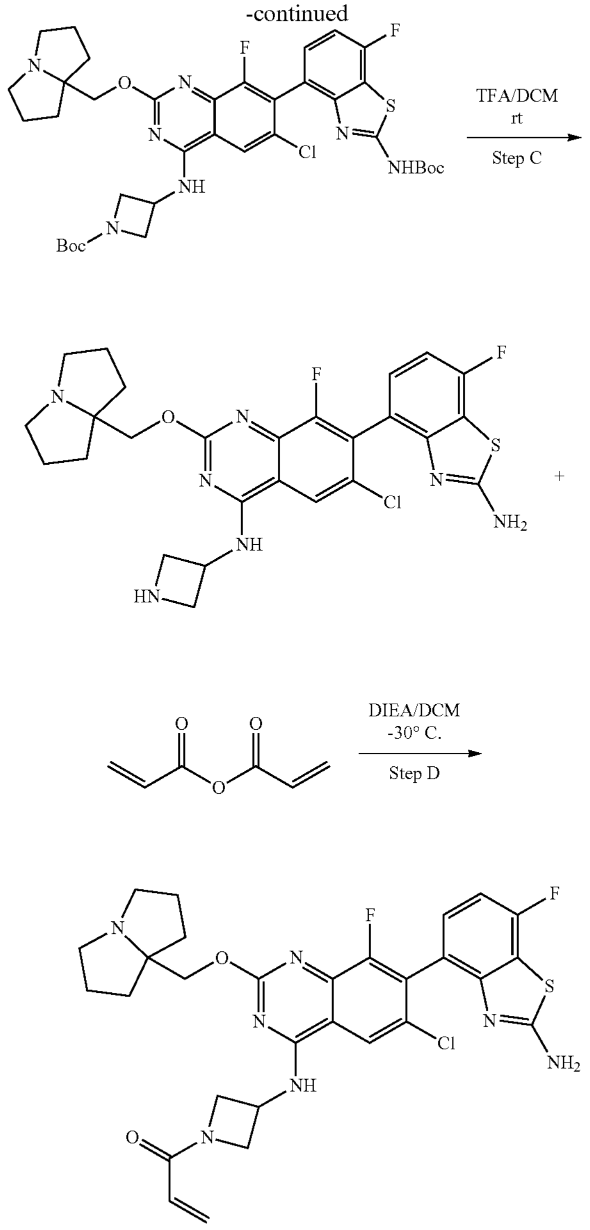

Compound 49

Step A: Preparation of butyl 3-[[7-bromo-6-chloro-8-fluoro-2-(1,2,3,5,6,7-hexahydropyrrolizin-8-ylmethoxy) quinazolin-4-yl]amino]azetidine-1-carboxylate: To tert-butyl 3-[(7-bromo-2,6-dichloro-8-fluoro-quinazolin-4-yl) amino]azetidine-1-carboxylate (0.20 g, 0.43 mmol) in DMSO (2.7 mL) was added 1,2,3,5,6,7-hexahydropyrrolizin-8-ylmethanol (0.24 g, 1.72 mmol) and KF (0.20 g, 3.43 mmol) at room temperature under Ar. The mixture was warmed to 120° C. and stirred for 2 hours at 120° C. Once cooled to room temperature, brine and ethyl acetate were added. The organic layer was separated, washed with brine, dried (sodium sulfate), filtered, and concentrated under reduced pressure. The residue was purified by flash chromatography on silica gel eluting with 5% MeOH in DCM to give tert-butyl 3-[[7-bromo-6-chloro-8-fluoro-2-(1,2,3,5,6,7-hexahydropyrrolizin-8-ylmethoxy)quinazolin-4-yl] amino]azetidine-1-carboxylate (113 mg, 46%) as an oil. LCMS ESI (+) m/z 570.1 (M+H).

Step B: Preparation of tert-butyl 3-[[7-[2-(tert-butoxycarbonylamino)-7-fluoro-1,3-benzothiazol-4-yl]-6-chloro-8-fluoro-2-(1,2,3,5,6,7-hexahydropyrrolizin-8-ylmethoxy) quinazolin-4-yl]amino]azetidine-1-carboxylate: To tert-butyl 3-[[7-bromo-6-chloro-8-fluoro-2-(1,2,3,5,6,7-hexahydropyrrolizin-8-ylmethoxy)quinazolin-4-yl]amino] azetidine-1-carboxylate (80 mg, 0.14 mmol) in 1,4-dioxane (2.5 mL) and water (0.80 mL) was added [2-(tert-butoxycarbonylamino)-7-fluoro-1,3-benzothiazol-4-yl]boronic acid (66 mg, 0.21 mmol), $K_3PO_4$ (89 mg, 0.42 mmol) and Pd(dtbpf)$Cl_2$ (9.1 mg, 0.014 mmol) at room temperature under Ar. The mixture was warmed to 90° C. and stirred at 90° C. for 1 hour. Once cooled to ambient temperature, brine and ethyl acetate were added. The organic layer was separated, washed with brine, dried (sodium sulfate), filtered, and concentrated under reduced pressure. The residue was purified by preparative TLC to give tert-butyl 3-[[7-[2-(tert-butoxycarbonylamino)-7-fluoro-1,3-benzothiazol-4-yl]-6-chloro-8-fluoro-2-(1,2,3,5,6,7-hexahydropyrrolizin-8-ylmethoxy)quinazolin-4-yl]amino]azetidine-1-carboxylate (82 mg, 60%) as a solid. LCMS ESI (+) m/z 758.3 (M+H).

Step C: Preparation of 4-[4-(azetidin-3-ylamino)-6-chloro-8-fluoro-2-(1,2,3,5,6,7-hexahydropyrrolizin-8-ylmethoxy)quinazolin-7-yl]-7-fluoro-1,3-benzothiazol-2-amine: To tert-butyl 3-[[7-[2-(tert-butoxycarbonylamino)-7-fluoro-1,3-benzothiazol-4-yl]-6-chloro-8-fluoro-2-(1,2,3,5,6,7-hexahydropyrrolizin-8-ylmethoxy)quinazolin-4-yl] amino]azetidine-1-carboxylate (82 mg, 0.084 mmol) in DCM (3 mL) was added trifluoroacetic acid (1.5 mL, 19.5 mmol) at ambient temperature under Ar. The mixture was stirred at ambient temperature for 2 hours. The mixture was concentrated to reduced pressure and the residue was purified by preparative HPLC to give 4-[4-(azetidin-3-ylamino)-6-chloro-8-fluoro-2-(1,2,3,5,6,7-hexahydropyrrolizin-8-ylmethoxy)quinazolin-7-yl]-7-fluoro-1,3-benzothiazol-2-amine (11 mg, 23%). LCMS ESI (+) m/z 558.3 (M+H). $^1$HNMR (400 MHz, $CD_3OD$) δ 8.24 (s, 1H), 7.24 (dd, J=8.4, 5.4 Hz, 1H), 7.03 (t, J=8.8 Hz, 1H), 5.13-5.28 (m, 1H), 4.58-4.70 (m, 2H), 4.42-4.53 (m, 2H), 4.33-4.38 (m, 2H), 3.64-3.74 (m, 2H), 3.25-3.30 (m, 2H), 2.26-2.38 (m, 2H), 2.17-2.27 (m, 2H), 2.05-2.17 (m, 4H).

Step D: Preparation of 4-(4-(azetidin-3-ylamino)-6-chloro-8-fluoro-2-(((S)-1-methylpyrrolidin-2-yl)methoxy) quinazolin-7-yl)-7-fluorobenzo[d]thiazol-2-amine: A solution of prop-2-enoyl prop-2-enoate (5.1 mg, 0.040 mmol) in DCM (0.1 mL) was added dropwise to the mixture of 4-[4-(azetidin-3-ylamino)-6-chloro-8-fluoro-2-(1,2,3,5,6,7-hexahydropyrrolizin-8-ylmethoxy)quinazolin-7-yl]-7-fluoro-1,3-benzothiazol-2-amine (28 mg, 0.050 mmol) and N,N-diisopropylethylamine (0.026 mL, 0.15 mmol) in DCM (8 mL) at −30° C. under Ar. The mixture was stirred at −30° C. for 1 hour. Water and ethyl acetate were added. The organic layer was separated, washed with brine, dried (sodium sulfate), filtered, and concentrated under reduced pressure. The residue was purified by preparative RP-HPLC to give 1-[3-[[7-(2-amino-7-fluoro-1,3-benzothiazol-4-yl)-6-chloro-8-fluoro-2-(1,2,3,5,6,7-hexahydropyrrolizin-8-ylmethoxy)quinazolin-4-yl]amino]azetidin-1-yl]prop-2-en-1-one (2.4 mg, 7%) as a solid. LCMS ESI (+) m/z 612.3 (M+H). $^1$HNMR (400 MHz, $CD_3OD$) δ 8.28 (s, 1H), 7.24 (dd, J=8.4, 5.4 Hz, 1H), 7.02 (t, J=8.8 Hz, 1H), 6.41 (dd, J=16.9, 10.2 Hz, 1H), 6.29 (dd, J=17.0, 1.5 Hz, 1H), 5.79 (dd, J=10.1 and 1.5 Hz, 1H), 5.00-5.08 (m, 1H), 4.77 (t, J=8.4 Hz, 1H), 4.58-4.68 (m, 2H), 4.45-4.56 (m, 2H), 4.21-4.32 (m, 3H), 3.64-3.74 (m, 2H), 1.98-2.40 (m, 8H).

Synthetic Example 14: Synthesis of 1-(4-(7-(2-amino-7-fluorobenzo[d]thiazol-4-yl)-6-chloro-8-fluoro-2-(1-methylpiperidin-4-yl)quinazolin-4-yl)piperazin-1-yl)prop-2-en-1-one (Compound 59)

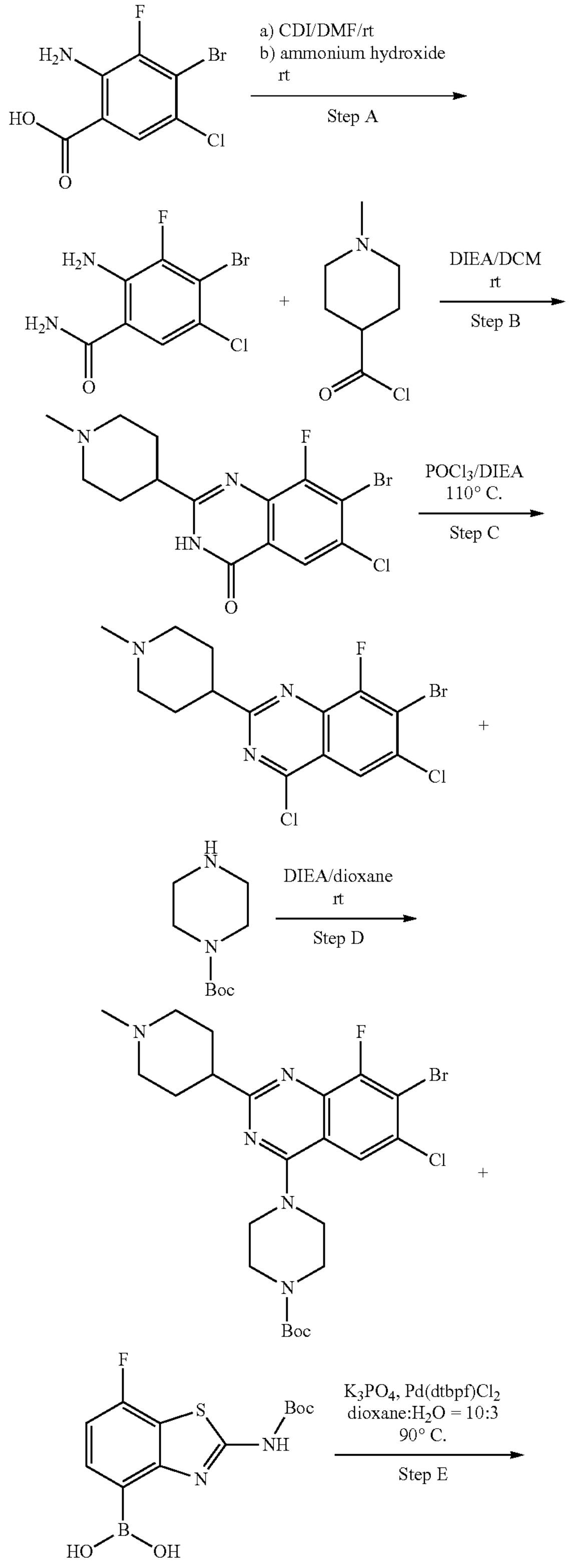

-continued

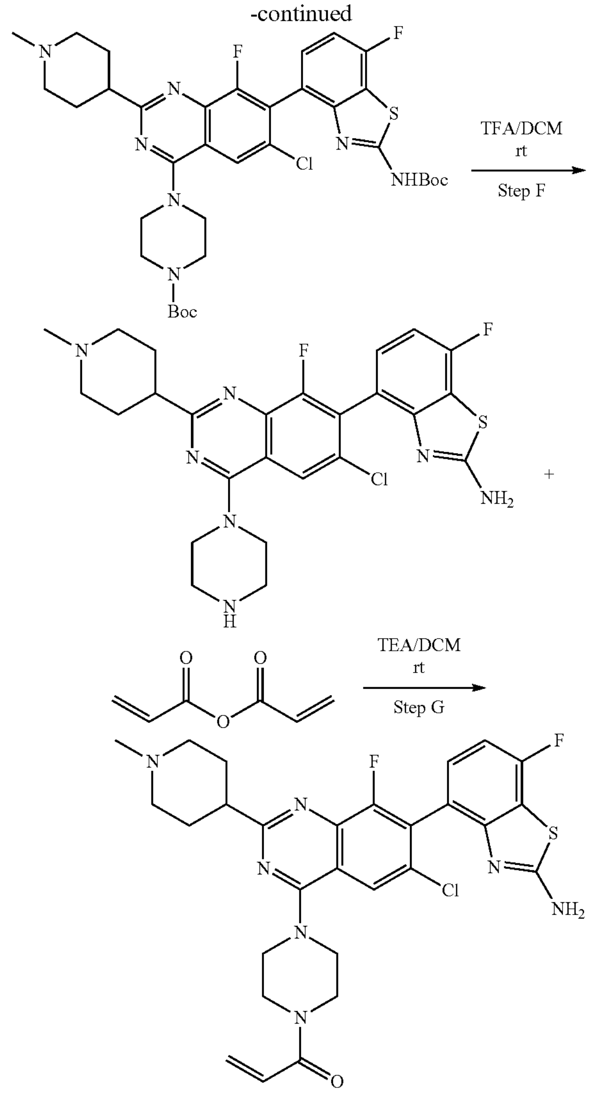

Compound 59

Step A: Preparation of 2-amino-4-bromo-5-chloro-3-fluorobenzamide: To a solution of 2-amino-4-bromo-5-chloro-3-fluorobenzoic acid (2.0 g, 7.51 mmol) in DMF (20 mL) was added CDI (1.82 g, 11.2 mmol) at ambient temperature and stirred at this temperature for 30 minutes. The mixture was poured into 37% ammonium hydroxide (10 mL) and stirred at ambient temperature for additional 1 hour. The mixture was diluted with water (100 mL) and extracted twice with ethyl acetate. The combined organics were dried over sodium sulfate, filtered, and concentrated under reduced pressure to give 2-amino-4-bromo-5-chloro-3-fluorobenzamide (1.86 g, 92%).

Step B: Preparation of 7-bromo-6-chloro-8-fluoro-2-(1-methylpiperidin-4-yl)quinazolin-4(3H)-one: To a solution of 2-amino-4-bromo-5-chloro-3-fluorobenzamide (2.0 g, 7.54 mmol) in DCM (20 mL) was added 1-methylpiperidine-4-carbonyl chloride (3.64 g, 22.6 mmol) and DIEA (3.8 g, 30.1 mmol) at ambient temperature and stirred at ambient temperature for 5 hours. The reaction mixture was quenched by addition of water and extracted with DCM. The organic layer was washed with brine, dried over Na2SO4, filtered, and concentrated under reduced pressure. The residue obtained was purified by flash column chromatography on silica gel (DCM/MeOH=10/1 with 1% TEA) to give 7-bromo-6-chloro-8-fluoro-2-(1-methylpiperidin-4-yl)quinazolin-4(3H)-one (2.8 g, 99%). LCMS ESI (+) m/z 374.0 (M+H).

Step C: Preparation of 7-bromo-4,6-dichloro-8-fluoro-2-(1-methylpiperidin-4-yl)quinazoline: A solution of 7-bromo-6-chloro-8-fluoro-2-(1-methylpiperidin-4-yl)quinazolin-4(3H)-one (1.0 g, 2.68 mmol) in $POCl_3$ (10 mL) and DIEA (1 mL) was stirred at 110° C. for 3 hours. Once cooled to ambient temperature, solvent is removed under reduced pressure to give crude 7-bromo-4,6-dichloro-8-fluoro-2-(1-methylpiperidin-4-yl)quinazoline. LCMS ESI (+) m/z 394.0 (M+H).

Step D: Preparation of tert-butyl-4-(7-bromo-6-chloro-8-fluoro-2-(1-methylpiperidin-4-yl)quinazolin-4-yl)piperazine-1-carboxylate: To a solution of 7-bromo-4,6-dichloro-8-fluoro-2-(1-methylpiperidin-4-yl)quinazoline (600 mg 1.53 mmol) in dioxane (6 mL) was added DIEA (587 mg, 4.59 mmol) and tert-butyl piperazine-1-carboxylate(343 mg 1.8 mmol) at ambient temperature. The mixture was warmed to 100° C. and stirred at 100° C. for 12 hours. Once cooled to ambient temperature, the mixture was diluted with water (30 mL) and the mixture was extracted twice with ethyl acetate. The combined organics were dried over sodium sulfate, filtered, and concentrated under reduced pressure. The residue was purified by preparative TLC (DCM/MeOH=10/1) to give tert-butyl-4-(7-bromo-6-chloro-8-fluoro-2-(1-methylpiperidin-4-yl)quinazolin-4-yl)piperazine-1-carboxylate (78 mg, 9%) as a solid. LCMS ESI (+) m/z 544.2 (M+H).

Step E: Preparation of tert-butyl 4-(7-(2-((tert-butoxycarbonyl)amino)-7-fluorobenzo[d]thiazol-4-yl)-6-chloro-8-fluoro-2-(1-methylpiperidin-4-yl)quinazolin-4-yl)piperazine-1-carboxylate: To a solution of 4-(7-bromo-6-chloro-8-fluoro-2-(1-methylpiperidin-4-yl)quinazolin-4-yl) piperazine-1-carboxylate (78 mg, 0.14 mmol) and (2-((tert-butoxycarbonyl)amino)-7-fluorobenzo[d]thiazol-4-yl) boronic acid (67 mg, 0.21 mmol) in dioxane (1 mL) and water (0.3 mL) were added $Pd(dtbpf)Cl_2$ (10 mol %) and $K_3PO_4$ (44.5 mg, 0.21 mmol) at ambient temperature. The resulting mixture was stirred at 90° C. for 2 hours. Once cooled to ambient temperature, the mixture was filtered through Celite. The filtrate was concentrated under reduced pressure and purified by preparative TLC (DCM/MeOH=15/1) to give tert-butyl 4-(7-(2-((tert-butoxycarbonyl)amino)-7-fluorobenzo[d]thiazol-4-yl)-6-chloro-8-fluoro-2-(1-methylpiperidin-4-yl)quinazolin-4-yl)piperazine-1-carboxylate (32 mg 30%). LCMS ESI (+) m/z 730.3 (M+H).

Step F: Preparation of 4-(6-chloro-8-fluoro-2-(1-methylpiperidin-4-yl)-4-(piperazin-1-yl)quinazolin-7-yl)-7-fluorobenzo[d]thiazol-2-amine: To a solution of tert-butyl 4-(7-(2-((tert-butoxycarbonyl)amino)-7-fluorobenzo[d]thiazol-4-yl)-6-chloro-8-fluoro-2-(1-methylpiperidin-4-yl)quinazolin-4-yl)piperazine-1-carboxylate(32 mg, 0.043 mmol) in DCM (3 mL) was added trifluoroacetic acid (1 mL) at ambient and stirred at this temperature for 2 hours. Solvent was removed under reduced pressure to give 4-(6-chloro-8-fluoro-2-(1-methylpiperidin-4-yl)-4-(piperazin-1-yl)quinazolin-7-yl)-7-fluorobenzo[d]thiazol-2-amine (36 mg) as TFA salt. LCMS ESI (+) m/z 530.2 (M+H).

Step G: Preparation of 1-(4-(7-(2-amino-7-fluorobenzo[d]thiazol-4-yl)-6-chloro-8-fluoro-2-(1-methylpiperidin-4-yl)quinazolin-4-y)piperazin-1-yl)prop-2-en-1-one: To a stirred solution of 1-(4-(7-(2-amino-7-fluorobenzo[d]thiazol-4-yl)-6-chloro-8-fluoro-2-(1-methylpiperidin-4-yl)quinazolin-4-yl)piperazin-1-yl)prop-2-en-1-one (18 mg 0.03 mmol) in DCM (2 mL) was added TEA (9.09 mg, 0.09 mmol) and acrylic anhydride (4.28 mg, 0.03 mmol) at ambient temperature and stirred at this temperature for 2 hours. The mixture was poured into water, extracted with ethyl acetate. The organic layer was washed with sodium bicarbonate solution and brine solution, dried over sodium sulfate, filtered, and concentrated under reduced pressure. The residue was purified by preparative RP-HPLC to afford 1-(4-(7-(2-amino-7-fluorobenzo[d]thiazol-4-yl)-6-chloro-8-fluoro-2-(1-methylpiperidin-4-yl)quinazolin-4-yl)piperazin-1-yl)prop-2-en-1-one (2.3 mg, 10%). LCMS ESI (+) m/z 584.2 (M+H). $^1$HNMR (400 MHz, $CD_3OD$) δ 8.00 (s, 1H), 7.23 (dd, J=8.4, 5.5 Hz, 1H), 7.00 (t, J=8.8 Hz, 1H), 6.76-6.89 (m, 1H), 6.28 (d, J=16.8 Hz, 1H), 5.81 (d, J=12.1 Hz, 1H), 3.81-4.10 (m, 8H), 3.31-3.50 (m, 3H), 3.01-3.16 (m, 1H), 2.86-3.00 (m, 1H), 2.74 (s, 3H), 2.10-2.33 (m, 4H).

Synthetic Example 15: Synthesis of 1-(4-(7-(2-amino-7-fluorobenzo[d]thiazol-4-yl)-6-chloro-8-fluoro-2-(1-methylpiperidin-4-yl)quinazolin-4-yl) piperazin-1-yl)prop-2-en-1-one (Compound 69)

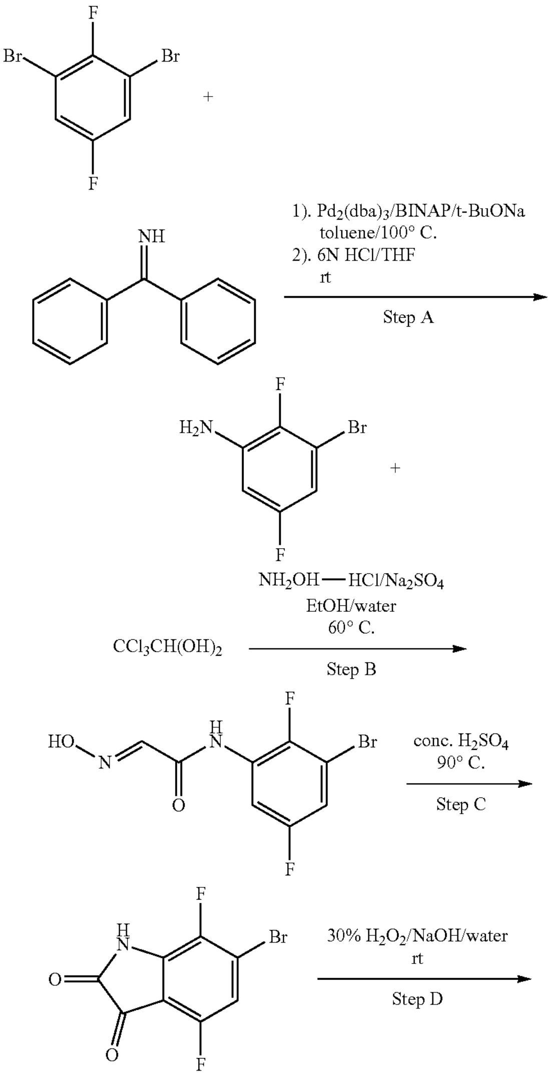

-continued

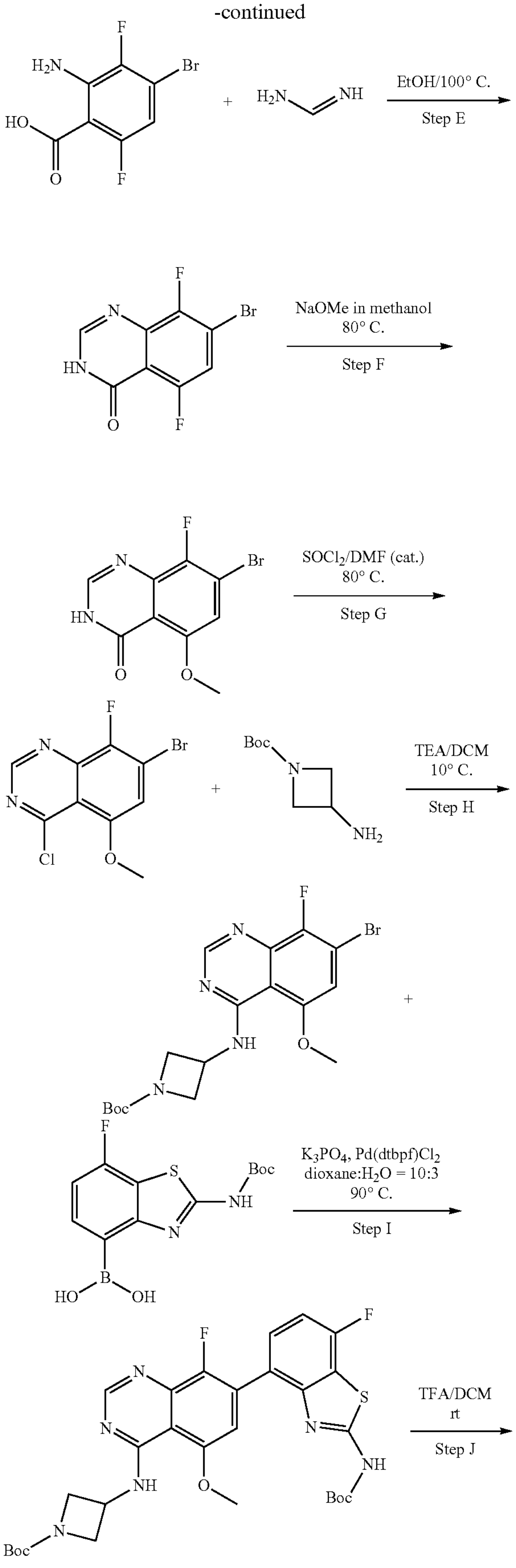

-continued

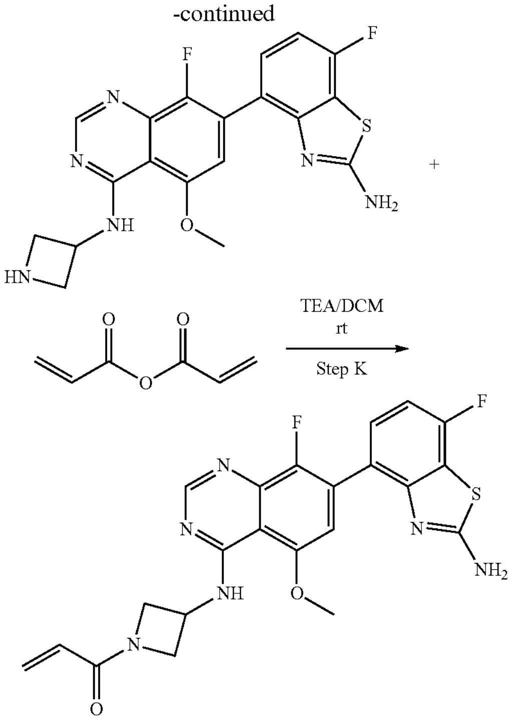

Compound 69

Step A: Preparation of 3-bromo-2,5-difluoroaniline: A mixture of 1,3-dibromo-2,5-difluorobenzene (30 g, 110.3 mmol), diphenylmethanimine (16 g, 88.23 mmol), t-NaOBu (15.8 g, 165.4 mmol), BINAP (10.3 g, 16.5 mmol) in Toluene (100 mL) was sparged with Argon and charged with $Pd_2(dba)_3$ (5.05 g, 5.51 mmol). The reaction was stirred at 100° C. for 2 hours. Once cooled to ambient temperature, it was concentrated under reduced pressure to afford a brown-red solid. The solid was dissolved in THF (100 mL) and aqueous 6.0 N HCl solution (50 mL) was added at ambient temperature and stirred for 1.5 hours at ambient temperature. The pH of reaction mixture was adjusted to ~9 with aqueous 1.0 M NaOH. It was extracted with ethyl acetate. The organic layer was separated, washed with brine, dried over sodium sulfate, filtered, and concentrated under reduced pressure. The residue was purified by flash chromatography on silica gel (petroleum ether/ethyl acetate=100:1) to give 3-bromo-2,5-difluoroaniline (14.3 g, 62%).

Step B: Preparation of (E)-N-(3-bromo-2,5-difluorophenyl)-2-(hydroxyimino)acetamide: The mixture of 3-bromo-2,5-difluoroaniline (14.3 g, 69.1 mmol), 2,2,2-trichloroethane-1,1-diol (17.1 g, 241.8 mmol), hydroxylamine hydrochloride (14.3 g, 69.1 mmol) and $Na_2SO_4$ (78.5 g, 552.7 mmol) in water (300 mL)/EtOH (42 mL)/HCl (9.8 mL) was stirred at 60° C. for 5 hours. Once cooled to ambient temperature. The precipitate was collected by filtration and washed with water, then dried under vacuum to give (E)-N-(3-bromo-2,5-difluorophenyl)-2-(hydroxyimino)acetamide (14 g, 72%). LCMS ESI (+) m/z 279 (M+H).

Step C: Preparation of 6-bromo-4,7-difluoroindoline-2,3-dione: (E)-N-(3-bromo-2,5-difluorophenyl)-2-(hydroxyimino)acetamide (14 g, 50.4 mmol) in conc. $H_2SO_4$ (90 mL) was stirred at 90° C. for 1 hour. The reaction mixture was cooled to ambient temperature and slowly added to ice water with stirring. The precipitate was collected by filtration and washed with water, then dried under vacuum to give 6-bromo-4,7-difluoroindoline-2,3-dione (8.3 g, 62%). LCMS ESI (+) m/z 260.0 (M+H).

Step D: Preparation of 2-amino-4-bromo-3,6-difluorobenzoic acid: 30% hydrogen peroxide (16.2 ml, 159.6 mmol) was added dropwise to 6-bromo-4,7-difluoroindoline-2,3-dione (8.3 g, 31.9 mmol) in 2M sodium hydroxide solution (143 mL, 287.3 mmol) at ambient temperature and stirred at this temperature for 16 hours. The reaction mixture was quenched with saturated sodium sulfite solution, and the mixture was neutralized to pH ~7. The resulting brown precipitate was filtered off and the remaining solution was acidified to pH ~2 with hydrochloric acid. The resulting cream precipitate was collected by filtration and washed with water, then dried under vacuum to give 2-amino-4-bromo-3,6-difluorobenzoic acid (7 g, 87%). LCMS ESI (+) m/z 250 (M+H).

Step E: Preparation of 7-bromo-5,8-difluoroquinazolin-4(3H)-one: A solution of formamide acetate (34.8 g, 334.7 mmol) and 2-amino-4-bromo-3,6-difluorobenzoic acid (7 g, 27.9 mmol) in EtOH (110 mL) was stirred at 100° C. for 16 hours. The reaction mixture was evaporated to dryness and poured into water. The precipitate was collected by filtration and washed with water, then dried under vacuum to give 7-bromo-5,8-difluoroquinazolin-4(3H)-one (6.5 g, 89%). LCMS ESI (+) m/z 261 (M+H).

Step F: Preparation of 7-bromo-8-fluoro-5-methoxyquinazolin-4(3H)-one: 7-bromo-5,8-difluoroquinazolin-4(3H)-one (6.5 g, 24.9 mmol) in DMF (30 mL) was added to sodium methanolate (10.7 g, 249.0 mmol) in MeOH (100 mL) at 0° C. After addition, the reaction mixture was warmed to 80° C. and stirred at 80° C. for 16 hours. Once cooled to ambient temperature, the reaction mixture was evaporated to dryness under reduced pressure. Water was added and solid formed was collected by filtration, washed with water, then dried under vacuum to give 7-bromo-8-fluoro-5-methoxyquinazolin-4(3H)-one (5.8 g, 85%). LCMS ESI (+) m/z 271 (M+H).

Step G: Preparation of 7-bromo-4-chloro-8-fluoro-5-methoxyquinazoline: To a solution of 7-bromo-8-fluoro-5-methoxyquinazolin-4(3H)-one (5.8 g, 21.3 mmol) in $SOC_2$ (50 mL) was added DMF (0.5 mL) at ambient temperature. The reaction mixture was stirred at 80° C. for 3 hours. Once cooled to ambient temperature, the reaction mixture was concentrated under reduced pressure and diluted with DCM (50 mL). The mixture was poured into cold saturated sodium bicarbonate aqueous solution, the organic layer was separated, washed with brine, dried over sodium sulfate, filtered, and concentrated under deduced pressure to give crude 7-bromo-4-chloro-8-fluoro-5-methoxyquinazoline (3.8 g, 61%). LCMS ESI (+) m/z 291 (M+H).

Step H: Preparation of tert-butyl 3-((7-bromo-8-fluoro-5-methoxyquinazolin-4-yl)amino)azetidine-1-carboxylate: A mixture of 7-bromo-4-chloro-8-fluoro-5-methoxyquinazoline (1.5 g, 5.17 mmol), tert-butyl-3-aminoazetidine-1-carboxylate (1.02 g, 5.94 mmol) and DIEA (1.33 g, 10.34 mmol) in DCM (10 mL) was stirred at 10° C. for 12 hours. The mixture was concentrated under reduced pressure and purified by flash chromatography on silica gel (PE/EA=5:1 to 1:1) to give tert-butyl 3-((7-bromo-8-fluoro-5-methoxyquinazolin-4-yl)amino)azetidine-1-carboxylate (1.53 g, 60%). LCMS ESI (+) m/z 427.2 (M+H).

Step I: Preparation of tert-butyl 3-((7-(2-((tert-butoxycarbonyl)amino)-7-fluorobenzo[d]thiazol-4-yl)-8-fluoro-5-methoxyquinazolin-4-yl)amino)azetidine-1-carboxylate: A mixture of tert-butyl 3-((7-bromo-8-fluoro-5-methoxyquinazolin-4-yl)amino)azetidine-1-carboxylate (200 mg, 0.47 mmol), (2-((tert-butoxycarbonyl)amino)-7-fluorobenzo[d]thiazol-4-yl)boronic acid (162 mg, 0.52 mmol), Pd(dtbpf)$Cl_2$ (20 mg, 0.047 mmol) and $K_3PO_4$ (200 mg, 0.94 mmol) in dioxane/water (10:3) (5 mL) was stirred at 100° C. for 2 hours. Once cooled to ambient temperature, the mixture was poured into water and extracted with ethyl acetate, dried over sodium sulfate, filtered, and concentrated under reduced pressure. The residue was purified by flash chromatography on silica gel (PE/EA=5:1 to 1:1) to give tert-butyl 3-((7-(2-((tert-butoxycarbonyl)amino)-7-fluorobenzo[d]thiazol-4-yl)-8-fluoro-5-methoxyquinazolin-4-yl)amino)azetidine-1-carboxylate (290 mg, 99%). LCMS ESI (+) m/z 615.4 (M+H).

Step J: Preparation of 4-(4-(azetidin-3-ylamino)-8-fluoro-5-methoxyquinazolin-7-yl)-7-fluorobenzo[d]thiazol-2-amine: A mixture of tert-butyl 3-((7-(2-((tert-butoxycarbonyl)amino)-7-fluorobenzo[d]thiazol-4-yl)-8-fluoro-5-methoxyquinazolin-4-yl)amino)azetidine-1-carboxylate (30 mg, 0.048 mmol) in DCM (2 mL) and TFA (1 mL) was stirred at 10° C. for 1 hour. The mixture was concentrated under reduced pressure and purified by preparative HPLC to give 4-(4-(azetidin-3-ylamino)-8-fluoro-5-methoxyquinazolin-7-yl)-7-fluorobenzo[d]thiazol-2-amine (7.39 mg, 24%). LCMS ESI (+) m/z 415.0 (M+H). $^1$HNMR (400 MHz, $CD_3OD$) δ 8.73 (s, 1H), 7.45-7.50 (m, 2H), 7.02 (t, J=9.2 Hz, 1H), 5.19-5.26 (m, 1H), 4.51 (d, J=8 Hz, 4H), 4.18 (s, 3H).

Step K: Preparation of 1-(3-((7-(2-amino-7-fluorobenzo[d]thiazol-4-yl)-8-fluoro-5-methoxyquinazolin-4-yl)amino)azetidin-1-yl)prop-2-en-1-one: To a solution of 4-(4-(azetidin-3-ylamino)-8-fluoro-5-methoxyquinazolin-7-yl)-7-fluorobenzo[d]thiazol-2-amine (50 mg, 0.12 mml) and DIEA (31 mg, 0.24 mmol) in DCM (2 mL) was added acrylic anhydride (12 mg, 0.096 mmol) at −60° C. After addition, the mixture was warmed to 0° C. and stirred at 0° C. for 1 hour. The mixture was diluted with DCM, washed with saturated bicarbonate solution and brine, dried over sodium sulfate, filtered, and concentrated under reduced pressure. The residue was purified by preparative RP-HPLC to give 1-(3-((7-(2-amino-7-fluorobenzo[d]thiazol-4-yl)-8-fluoro-5-methoxyquinazolin-4-yl)amino)azetidin-1-yl)prop-2-en-1-one (20.6 mg, 30%). LCMS ESI (+) m/z 469.0 (M+H). $^1$H NMR (400 MHz, $CD_3OD$) δ 8.75 (s, 1H), 7.53 (d, J=5.2 Hz, 1H), 7.46 (t, J=6.4 Hz, 1H), 7.03 (t, J=8.8 Hz, 1H), 6.26-6.42 (m, 2H), 5.78 (dd, J=10 Hz, 2 Hz, 1H), 5.23 (m, 1H), 4.76-4.80 (m, 1H), 4.51-4.55 (m, 2H), 4.27 (dd, J=10.8 Hz, 4.8 Hz, 1H), 4.19 (s, 3H).

Synthetic Example 16: Synthesis of 1-(3-((7-(2-amino-7-fluorobenzo[d]thiazol-4-yl)-8-fluoro-6-(furan-3-yl)-2-((tetrahydro-1H-pyrrolizin-7a(5H)-yl)methoxy)quinazolin-4-yl)amino)azetidin-1-yl)prop-2-en-1-one (Compound 70)

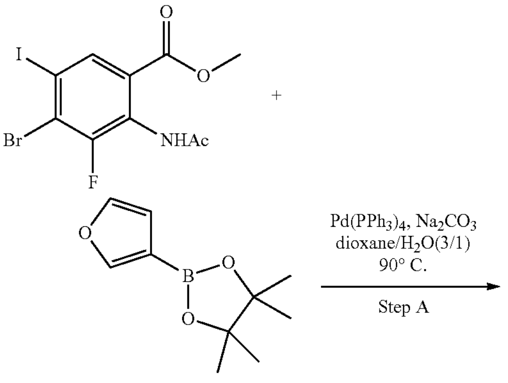

-continued

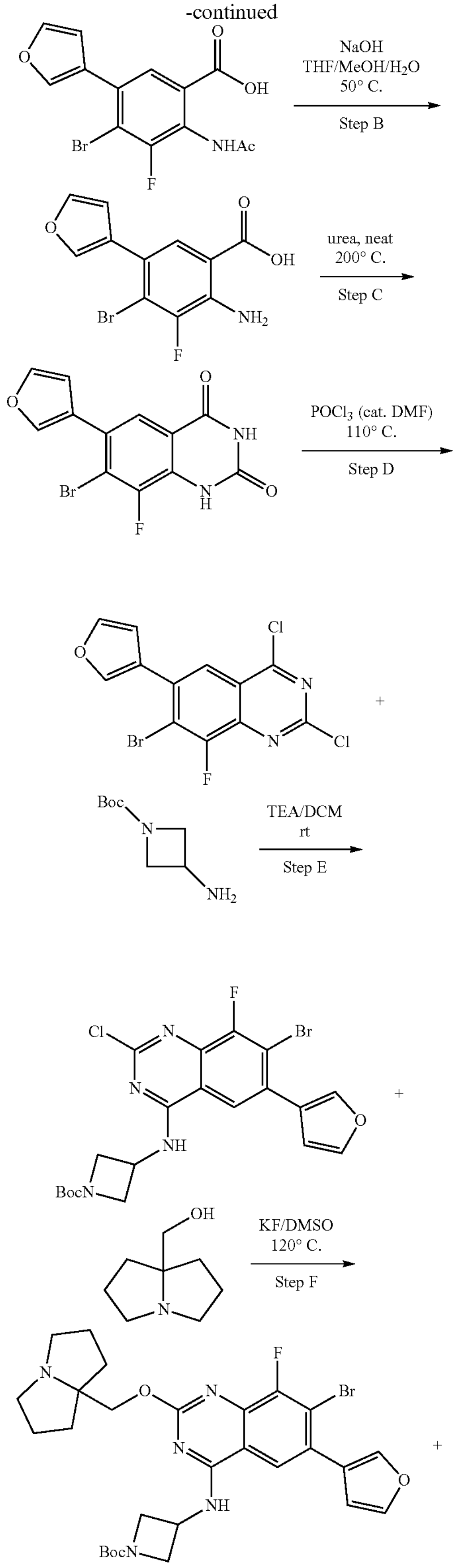

-continued

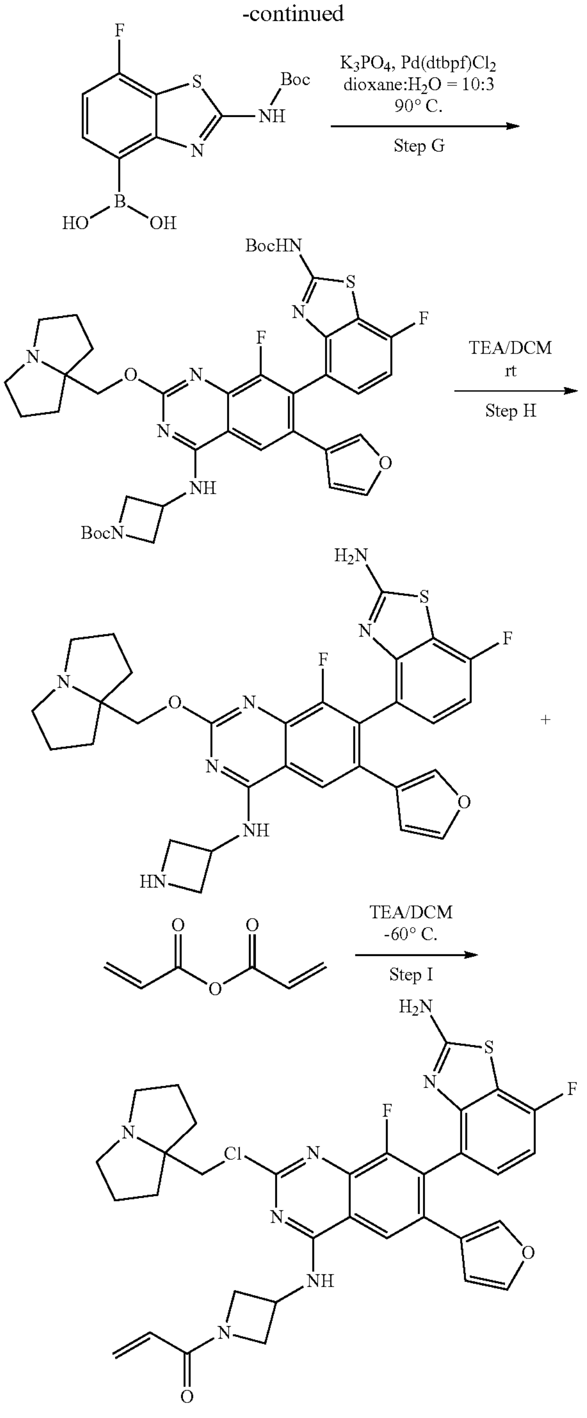

Compound 70

Step A: Preparation of 2-acetamido-4-bromo-3-fluoro-5-(3-furyl)benzoic acid: methyl 2-acetamido-4-bromo-3-fluoro-5-iodo-benzoate (5.00 g, 12.0 mmol) in 1,4-dioxane (60 mL) and water (15 mL) was added 3-furylboronic acid (1.61 g, 14.4 mmol) at room temperature under Ar. Then $Pd(PPh_3)_4$ (1.11 g, 0.96 mmol) and $Na_2CO_3$ (3.82 g, 36.1 mmol) were added under Ar. The mixture was stirred overnight at 90° C. under Ar. Once cooled to room temperature, the reaction mixture was diluted with water (50 mL) and EtOAc (50 mL) and then adjust pH to 4-5 with saturated aqueous solution of sodium hydrogen sulfate.

Organic layer was separated, washed with brine, dried (sodium sulfate), filtered and were concentrated under reduced pressure. The residue obtained was suspended in ethyl acetate and stirred for 5 minutes. Solid was collected by filtration and dried to give 2-acetamido-4-bromo-3-fluoro-5-(3-furyl)benzoic acid (3.00 g, 73%) as solid. LCMS ESI (+) m/z 342.0 (M+H).

Step B: Preparation of 2-amino-4-bromo-3-fluoro-5-(3-furyl)benzoic acid: To a solution of 2-acetamido-4-bromo-3-fluoro-5-(3-furyl)benzoic acid (3.50 g, 10.2 mmol) in THF (40 mL)/methanol (40 mL)/water (20 mL) was added NaOH (4.09 g, 102 mmol) at ambient temperature. The mixture was stirred at 50° C. for 12 hours. Once cooled to ambient temperature, organics were removed under reduced pressure. The aqueous layer was acidified with 1 N HCl to pH 3-4. The solid formed was collected by filtration and then dried to give 2-amino-4-bromo-3-fluoro-5-(3-furyl)benzoic acid (2.30 g, 75%). LCMS ESI (+) m/z 300.0 (M+H).

Step C: Preparation of 7-bromo-8-fluoro-6-(3-furyl)-1H-quinazoline-2,4-dione: 2-amino-4-bromo-3-fluoro-5-(3-furyl)benzoic acid (2.30 g, 7.66 mmol) and urea (9.21 g, 153 mmol) was placed in 50 mL round bottom flask and heated to 200° C. after mixed well. The mixture was dissolved and then solidified again. After stirred for 2 hours at 200° C., the mixture was cooled to 100° C. and water (40 mL) was added. The reaction mixture was stirred at 100° C. for 2 hours. The solid was evenly dispersed. Once cooled to room temperature, the solid was collected by filtration and dried to give 7-bromo-8-fluoro-6-(3-furyl)-1H-quinazoline-2,4-dione (1.85 g, 74%). LCMS ESI (+) m/z 325.0 (M+H).

Step D: Preparation of 7-bromo-2,4-dichloro-8-fluoro-6-(3-furyl)quinazoline: 7-bromo-8-fluoro-6-(3-furyl)-1H-quinazoline-2,4-dione (600 mg, 1.85 mmol) in phosphorus oxychloride (8.0 mL, 85.8 mmol) was added 2 drops DMF. The mixture was stirred at 110° C. for 4 hours. Once cooled to ambient temperature, phosphorus oxychloride was removed under reduced pressure. The residue was dissolved in small amount of DCM and TEA (1 mL). The mixture was directly purified by flash chromatography on silica gel eluting with 30% EtOAc in petroleum ether to give 7-bromo-2,4-dichloro-8-fluoro-6-(3-furyl)quinazoline (360 mg, 54%).

Step E: Preparation of tert-butyl 3-[[7-bromo-2-chloro-8-fluoro-6-(3-furyl)quinazolin-4-yl]amino]azetidine-1-carboxylate: To a solution of 7-bromo-2,4-dichloro-8-fluoro-6-(3-furyl)quinazoline (360 mg, 1.0 mmol) in DCM (8 mL) was added tert-butyl 3-aminoazetidine-1-carboxylate (206 mg, 1.19 mmol) and $Et_3N$ (302 mg, 2.98 mmol) at ambient temperature. The mixture was stirred at ambient temperature for 3 hours. The mixture was concentrated under reduced pressure and the residue was purified directly by flash chromatography on silica gel eluting with 30% EtOAc in petroleum ether to give tert-butyl 3-[[7-bromo-2-chloro-8-fluoro-6-(3-furyl)quinazolin-4-yl]amino]azetidine-1-carboxylate (195 mg, 39%). LCMS ESI (+) m/z 497.1 (M+H).

Step F: Preparation of tert-butyl 3-[[7-bromo-8-fluoro-6-(3-furyl)-2-(1,2,3,5,6,7-hexahydropyrrolizin-8-ylmethoxy) quinazolin-4-yl]amino]azetidine-1-carboxylate: To tert-butyl 3-[[7-bromo-2-chloro-8-fluoro-6-(3-furyl)quinazolin-4-yl]amino]azetidine-1-carboxylate (195 mg, 0.39 mmol) in DMSO (8 mL) was added 1,2,3,5,6,7-hexahydropyrrolizin-8-ylmethanol (166 mg, 1.18 mmol) and KF (182 mg, 3.13 mmol). The mixture was sealed and the stirred at 120° C. for 2 hours. Once cooled to ambient temperature, water and ethyl acetate were added. The organic layer was separated, washed with brine, dried (sodium sulfate), filtered, concentrated under reduced pressure. The residue was purified by preparative TLC (DCM/MeOH=10/1) to give tert-butyl 3-[[7-bromo-8-fluoro-6-(3-furyl)-2-(1,2,3,5,6,7-hexahydropyrrolizin-8-ylmethoxy)quinazolin-4-yl]amino]azetidine-1-carboxylate (40 mg, 17%). LCMS ESI (+) m/z 602.3 (M+H).

Step G: Preparation of tert-butyl 3-[[7-[2-(tert-butoxycarbonylamino)-7-fluoro-1,3-benzothiazol-4-yl]-8-fluoro-6-(3-furyl)-2-(1,2,3,5,6,7-hexahydropyrrolizin-8-ylmethoxy)quinazolin-4-yl]amino]azetidine-1-carboxylate: To a solution of tert-butyl 3-[[7-bromo-8-fluoro-6-(3-furyl)-2-(1,2,3,5,6,7-hexahydropyrrolizin-8-ylmethoxy)quinazolin-4-yl]amino]azetidine-1-carboxylate (40 mg, 0.0664 mmol) in 1,4-dioxane (2 mL)/water (0.60 mL) was added [2-(tert-butoxycarbonylamino)-7-fluoro-1,3-benzothiazol-4-yl]boronic acid (27 mg, 0.086 mmol), $Pd(dtbpf)Cl_2$ (3.5 mg, 0.0053 mmol) and $K_3PO_4$ (42 mg, 0.20 mmol). The mixture was bubbled with Ar for 1-2 minutes and then sealed. After that, the mixture was stirred for 1 hour at 90° C. Once cooled to ambient temperature, Water and ethyl acetate were added. The organic layer was separated, washed with brine, dried (sodium sulfate), filtered, and concentrated under reduced pressure. The residue was purified by preparative TLC (DCM/MeOH=10/1) to give tert-butyl 3-[[7-[2-(tert-butoxycarbonylamino)-7-fluoro-1,3-benzothiazol-4-yl]-8-fluoro-6-(3-furyl)-2-(1,2,3,5,6,7-hexahydropyrrolizin-8-ylmethoxy)quinazolin-4-yl]amino]azetidine-1-carboxylate (45 mg, 85%).

Step H: Preparation of 4-[4-(azetidin-3-ylamino)-8-fluoro-6-(3-furyl)-2-(1,2,3,5,6,7-hexahydropyrrolizin-8-ylmethoxy)quinazolin-7-yl]-7-fluoro-1,3-benzothiazol-2-amine: To tert-butyl 3-[[7-[2-(tert-butoxycarbonylamino)-7-fluoro-1,3-benzothiazol-4-yl]-8-fluoro-6-(3-furyl)-2-(1,2,3,5,6,7-hexahydropyrrolizin-8-ylmethoxy)quinazolin-4-yl]amino]azetidine-1-carboxylate (1.00 eq, 45 mg, 0.0570 mmol) in DCM (4 mL) was added trifluoro acetic acid (2.0 mL, 26.0 mmol) at ambient temperature and stirred at ambient temperature for 2 hours. The mixture was concentrated to under reduced pressure and the residue was purified by preparative HPLC to give 4-[4-(azetidin-3-ylamino)-8-fluoro-6-(3-furyl)-2-(1,2,3,5,6,7-hexahydropyrrolizin-8-ylmethoxy)quinazolin-7-yl]-7-fluoro-1,3-benzothiazol-2-amine (24 mg, 71%) as TFA salt. LCMS ESI (+) m/z 590.3 (M+H). $^1$HNMR (400 MHz, $CD_3OD$) δ: 8.19 (s, 1H), 7.34 (s, 1H), 7.09 (dd, J=8.3, 5.6 Hz, 1H), 7.05 (s, 1H), 6.95 (t, J=8.8 Hz, 1H), 6.25 (s, 1H), 5.19-5.27 (m, 1H), 4.63-4.71 (m, 2H), 4.48-4.53 (m, 2H), 4.36-4.41 (m, 2H), 3.65-3.71 (m, 2H), 3.23-3.28 (m, 2H), 2.01-2.36 (m, 8H).

Step I: Preparation of 1-[3-[[7-(2-amino-7-fluoro-1,3-benzothiazol-4-yl)-8-fluoro-6-(3-furyl)-2-(1,2,3,5,6,7-hexahydropyrrolizin-8-ylmethoxy)quinazolin-4-yl]amino]azetidin-1-yl]prop-2-en-1-one: To a solution of 4-[4-(azetidin-3-ylamino)-8-fluoro-6-(3-furyl)-2-(1,2,3,5,6,7-hexahydropyrrolizin-8-ylmethoxy)quinazolin-7-yl]-7-fluoro-1,3-benzothiazol-2-amine (11 mg, 0.019 mmol) and DIEA (0.017 mL, 0.093 mmol) in DCM (3 mL) was added a solution of prop-2-enoyl prop-2-enoate (1.4 mg, 0.011 mmol) in DCM at −20° C. The mixture was stirred for 15 minutes at −20° C. The reaction was quenched with water (10 mL) and extracted with ethyl acetate. The organic layer was separated, washed with brine, dried (sodium sulfate), filtered, and concentrated under reduced pressure. The residue was purified by preparative RP-HPLC to give 1-[3-[[7-(2-amino-7-fluoro-1,3-benzothiazol-4-yl)-8-fluoro-6-(3-furyl)-2-(1,2,3,5,6,7-hexahydropyrrolizin-8-ylmethoxy) quinazolin-4-yl]amino]azetidin-1-yl]prop-2-en-1-one (7.5 mg, 62%) as TFA salt. LCMS ESI (+) m/z 644.4 (M+H). $^1$HNMR (400 MHz, $CD_3OD$) δ 8.28 (s, 1H), 7.35 (s, 1H), 7.13 (dd, J=8.4, 5.2 Hz, 1H), 7.05 (s, 1H), 6.98 (t, J=8.9 Hz, 1H), 6.39-6.45 (m, 1H), 6.28-6.32 (m, 1H), 6.26 (s, 1H), 5.79 (dd, J=10.2 and 1.84 Hz, 1H), 5.08-5.15 (m, 1H), 4.72-4.80 (m, 2H), 4.65-4.73 (m, 3H), 4.50-4.56 (m, 2H), 4.32 (dd, J=10.9, 5.4 Hz, 1H), 3.67-3.72 (m, 2H), 2.08-2.38 (m, 8H).
Synthetic Example 17: Synthesis of 1-(4-(7-(2-amino-7-fluorobenzo[d]thiazol-4-yl)-8-fluoro-2-(((S)-1-methylpyrrolidin-2-yl)methoxy)-6-(trifluoromethyl)quinazolin-4-yl)piperazin-1-yl)prop-2-en-1-one (Compound 71)
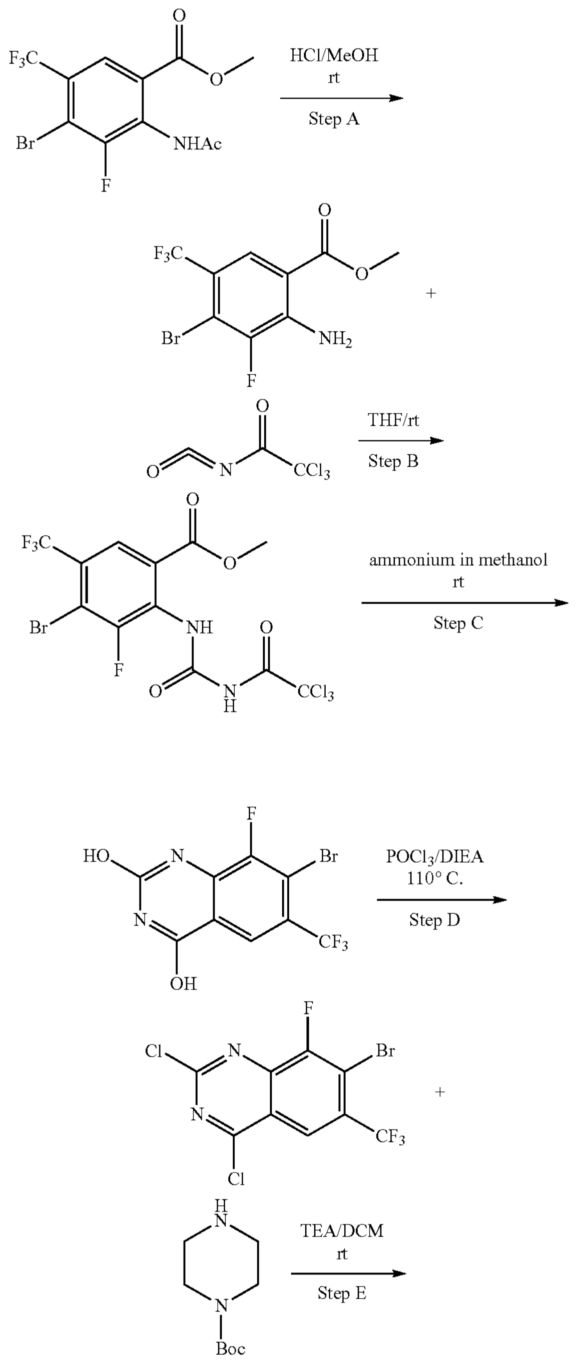
-continued
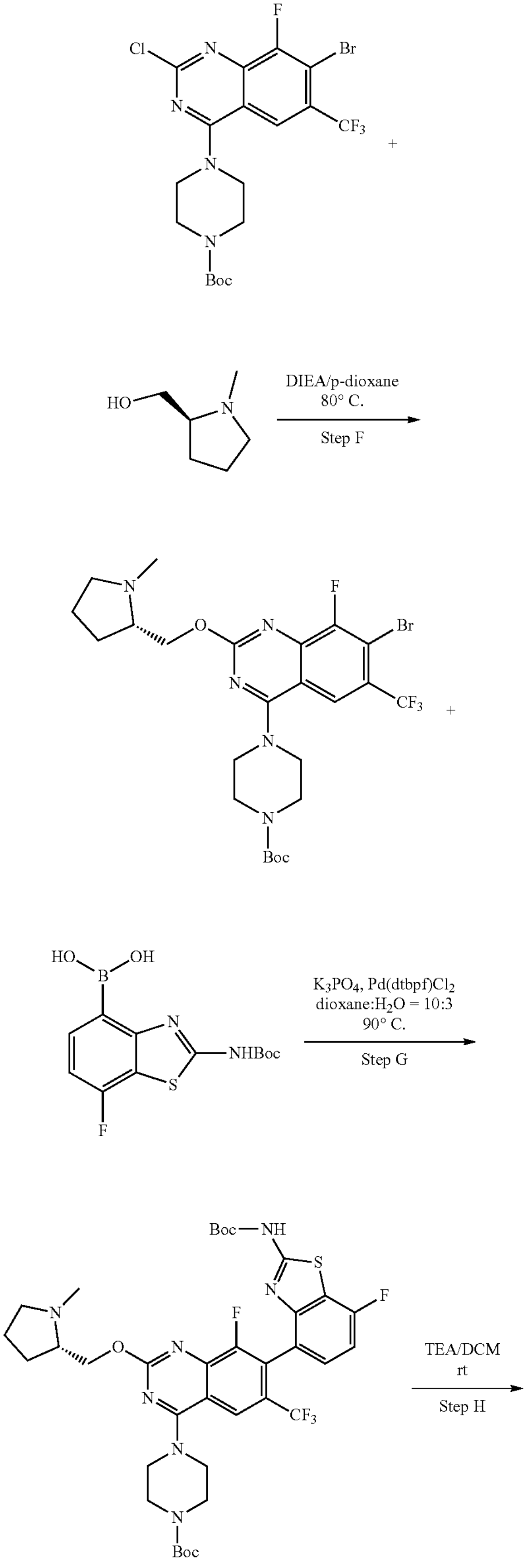

-continued

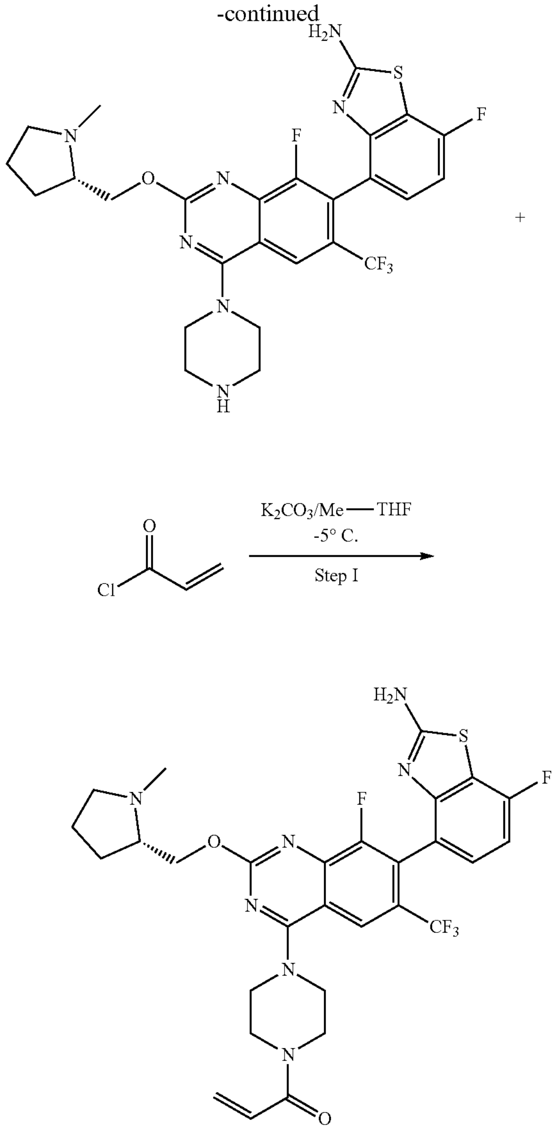

Compound 71

Step A: Preparation of 2-amino-4-bromo-3-fluoro-5-(trifluoromethyl)benzoate: A mixture of methyl 2-acetamido-4-bromo-3-fluoro-5-(trifluoromethyl)benzoate (1.20 g, 3.35 mmol) in 3 M HCl in MeOH was heated at 60° C. for 2 hours. Once cooled to ambient temperature, the solvent was evaporated, and the crude product was partitioned between EtOAc and saturated $NaHCO_3$. The organic layer was separated, dried over sodium sulfate, filtered, and evaporated to provide 2-amino-4-bromo-3-fluoro-5-(trifluoromethyl)benzoate (1.00 g, 94%) as an oil. LCMS ESI (+) m/z 316.9 (M+H). $^1$H NMR (300 MHz, $CDCl_3$) δ 8.01 (s, 1H), 6.28 (s, 2H), 3.94 (s, 3H).

Step B: Preparation of methyl 4-bromo-3-fluoro-2-(3-(2,2,2-trichloroacetyl)ureido)-5-(trifluoromethyl)benzoate: To a mixture of methyl 2-amino-4-bromo-3-fluoro-5-(trifluoromethyl)benzoate (0.80 g, 2.53 mmol) in THF (4.2 mL) was added trichloroethanecarbonyl isocyanate (0.45 mL, 3.79 mmol) at ambient temperature. After 15 minutes, the reaction mixture was evaporated, followed by the addition of MTBE and the solid formed was collected and washed with MTBE to provide methyl 4-bromo-3-fluoro-2-(3-(2,2,2-trichloroacetyl)ureido)-5-(trifluoromethyl)benzoate (0.71 g, 56%). LCMS ESI (+) m/z 529.99 (M+Na). $^1$H NMR (300 MHz, $CDCl_3$) δ 10.91 (s, 1H), 8.65 (s, 1H), 8.23 (s, 1H), 4.03 (s, 3H).

Step C: Preparation of 7-bromo-8-fluoro-6-(trifluoromethyl)quinazoline-2,4-diol: To a solution of methyl 4-bromo-3-fluoro-2-(3-(2,2,2-trichloroacetyl)ureido)-5-(trifluoromethyl)benzoate (0.71 g, 1.40 mmol) in methanol (7.0 mL) was added 7 M solution of ammonia in methanol (0.46 mL, 3.23 mmol) at ambient temperature and stirred at ambient temperature for 1 hour. The mixture was concentrated under reduced pressure to provide a solid which was co-evaporated with ether to provide 7-bromo-8-fluoro-6-(trifluoromethyl)quinazoline-2,4-diol (0.60 g, 100%) as solid LCMS ESI (+) m/z 260.0 (M+H). $^1$H NMR (300 MHz, DMSO-$d_6$) δ 8.41 (s, 1H), 8.28 (s, 1H), 7.99 (s, 1H).

Step D: Preparation of 7-bromo-2,4-dichloro-8-fluoro-6-(trifluoromethyl)quinazoline: To a stirring solution of phosphorus oxychloride (0.97 mL, 10.5 mmol) and Hunig's base (0.40 mL, 2.29 mmol) was added 7-bromo-8-fluoro-6-(trifluoromethyl)quinazoline-2,4-diol (0.15 g, 0.46 mmol) at 0° C. After addition, the resulting mixture was stirred at 110° C. for 1 hour. Once cooled down to ambient temperature, the mixture was evaporated and co-evaporated with chloroform to give 7-bromo-2,4-dichloro-8-fluoro-6-(trifluoromethyl) quinazoline which used as such for the next step. $^1$H NMR (300 MHz, $CDCl_3$) δ 8.45 (s, 1H).

Step E: Preparation of tert-butyl 4-(7-bromo-2-chloro-8-fluoro-6-(trifluoromethyl)quinazolin-4-yl)piperazine-1-carboxylate: To a mixture of 7-bromo-2,4-dichloro-8-fluoro-6-(trifluoromethyl)quinazoline (0.16 g, 0.44 mmol) in DCM (1.1 mL) at −40° C. was added Hunig's base (0.23 mL, 1.31 mmol), followed by tert-butyl piperazine-1-carboxylate (0.098 g, 0.53 mmol). The reaction mixture was brought slowly to room temperature. The resulting mixture was quenched with EtOAc and saturated $NaHCO_3$ solution. The organic layer was separated and dried with sodium sulfate, filtered, and evaporated. The crude mixture was purified with flash chromatography on silica gel eluting with 5% EtOAc in hexane to 40% EtOAc in hexane to provide tert-butyl 4-(7-bromo-2-chloro-8-fluoro-6-(trifluoromethyl) quinazolin-4-yl)piperazine-1-carboxylate(0.090 g, 40%).

Step F: Preparation of (S)-tert-butyl 4-(7-bromo-8-fluoro-2-((1-methylpyrrolidin-2-yl)methoxy)-6-(trifluoromethyl) quinazolin-4-yl)piperazine-1-carboxylate: To a mixture of tert-butyl 4-(7-bromo-2-chloro-8-fluoro-6-(trifluoromethyl) quinazolin-4-yl)piperazine-1-carboxylate (0.090 g, 0.18 mmol) and [(2S)-1-methylpyrrolidin-2-yl]methanol (0.040 g, 0.347 mmol) in p-dioxane (1.4 mL) was added Hunig's base (0.092 mL, 0.53 mmol) at ambient temperature. The reaction mixture was stirred at 80° C. for 5 hours, the reaction mixture was cooled to ambient temperature, concentrated under reduced pressure and the residue was purified by flash chromatography on silica gel eluting with 20% EtOAc in hexane to 100% EtOAc to provide (S)-tert-butyl 4-(7-bromo-8-fluoro-2-((1-methylpyrrolidin-2-yl) methoxy)-6-(trifluoromethyl)quinazolin-4-yl)piperazine-1-carboxylate (0.050 g, 48%). LCMS ESI (+) m/z 614.1 (M+Na). $^1$H NMR (300 MHz, $CDCl_3$) δ 7.95 (s, 1H), 4.57 (dd, J=10.7, 4.4 Hz, 1H), 4.36 (m, 1H), 3.85 (m, 4H), 3.67 (m, 4H), 3.12 (m, 1H), 2.73 (m, 1H), 2.52 (s, 3H), 2.31 (d, J=8.7 Hz, 1H), 2.06 (m, 1H), 1.81 (m, 3H), 1.52 (s, 9H).

Step G: Preparation of tert-butyl 4-(7-(2-((tert-butoxycarbonyl)amino)-7-fluorobenzo[d]thiazol-4-yl)-8-fluoro-2-(((S)-1-methylpyrrolidin-2-yl)methoxy)-6-(trifluoromethyl) quinazolin-4-yl)piperazine-1-carboxylate: To a stirring suspension of (S)-tert-butyl 4-(7-bromo-8-fluoro-2-((1-methylpyrrolidin-2-yl)methoxy)-6-(trifluoromethyl)quinazolin-4-yl)piperazine-1-carboxylate (0.05 g, 0.084 mmol) in 1,4 dioxane (1.0 mL), (2-{[(tert-butoxy)carbonyl]amino}-7-fluoro-1,3-benzothiazol-4-yl)boronic acid) (0.053 g, 0.17 mmol) and potassium phosphate tribasic (0.023 g, 0.17 mmol) were added, followed by water (0.24 mL) at ambient temperature. The reaction mixture was degassed with argon for 10 minutes, then Pd(dtbpf)$Cl_2$ (0.008 g, 0.012 mmol) was added and degassed again for 10 minutes. The reaction mixture was stirred at 90° C. for 90 minutes. The reaction mixture was cooled to room temperature, diluted with water and EtOAc. The organic layer was collected and dried over sodium sulfate, filtered and evaporated. The mixture was purified by flash chromatography on silica gel eluting with DCM to 8% MeOH in DCM to provide tert-butyl 4-(7-(2-((tert-butoxycarbonyl)amino)-7-fluorobenzo[d]thiazol-4-yl)-8-fluoro-2-(((S)-1-methylpyrrolidin-2-yl)methoxy)-6-(trifluoromethyl)quinazolin-4-yl)piperazine-1-carboxylate (0.040 g, 61%). LCMS ESI (+) m/z 780.2 (M+H). $^1H$ NMR (300 MHz, $CDCl_3$) δ 8.04 (s, 1H), 7.31 (s, 1H), 7.10 (t, J=9.9 Hz, 1H), 4.67-4.46 (m, 1H), 4.45-4.23 (m, 1H), 3.88 (m, 4H), 3.68 (m, 4H), 3.25-3.03 (m, 1H), 2.82-2.61 (m, 1H), 2.51 (s, 3H), 2.38-2.15 (m, 1H), 1.98 (m, 1H), 1.77 (s, 3H), 1.55 (s, 9H), 1.52 (s, 9H).

Step H: Preparation of 7-fluoro-4-(8-fluoro-2-(((S)-1-methylpyrrolidin-2-yl)methoxy)-4-(piperazin-1-yl)-6-(trifluoromethyl)quinazolin-7-yl)benzo[d]thiazol-2-amine: To a solution of tert-butyl 4-(7-(2-((tert-butoxycarbonyl)amino)-7-fluorobenzo[d]thiazol-4-yl)-8-fluoro-2-(((S)-1-methylpyrrolidin-2-yl)methoxy)-6-(trifluoromethyl)quinazolin-4-yl)piperazine-1-carboxylate (0.040 g, 0.051 mmol) in DCM was added excess TFA and the reaction was stirred for 2 hours at room temperature. The solvent was evaporated under reduced pressure to provide 7-fluoro-4-(8-fluoro-2-(((S)-1-methylpyrrolidin-2-yl)methoxy)-4-(piperazin-1-yl)-6-(trifluoromethyl)quinazolin-7-yl)benzo[d]thiazol-2-amine (0.040 g, 100%). LCMS ESI (+) m/z 580.2 (M+H). $^1H$ NMR (300 MHz, $CD_4OD$) δ 8.20 (s, 1H), 7.25 (m, 1H), 7.05 (m, 1H), 4.96 (m, 1H), 4.74 (m, 1H), 4.22 (m, 4H), 3.93 (m, 1H), 3.76 (m, 1H), 3.51 m, 4H), 3.28 (m, 1H), 3.11 (s, 3H), 2.44 (m, 1H), 2.17 (m, 3H).

Step I: Preparation of 1-(4-(7-(2-amino-7-fluorobenzo[d]thiazol-4-yl)-8-fluoro-2-(((S)-1-methylpyrrolidin-2-yl)methoxy)-6-(trifluoromethyl)quinazolin-4-yl)piperazin-1-yl)prop-2-en-1-one: To a mixture of 7-fluoro-4-(8-fluoro-2-(((S)-1-methylpyrrolidin-2-yl)methoxy)-4-(piperazin-1-yl)-6-(trifluoromethyl)quinazolin-7-yl)benzo[d]thiazol-2-amine (0.018 g, 0.022 mmol) in 2-Methyl-THF (0.22 mL) and water (0.22 mL) was added a 0.5 M solution of prop-2-enoyl chloride (0.012 g, 0.086 mmol) in 2-methyl-THF (0.049 mL) at −5° C. and stirred at −5° C. for 30 minutes. Water and ethyl acetate were added. The organic layer was separated, dried over sodium sulfate, filtered, and concentrated under reduced pressure. The residue was purified by flash chromatography on silica gel eluting with DCM to 30% MeOH in DCM to provide 1-(4-(7-(2-amino-7-fluorobenzo[d]thiazol-4-yl)-8-fluoro-2-(((S)-1-methylpyrrolidin-2-yl)methoxy)-6-(trifluoromethyl)quinazolin-4-yl)piperazin-1-yl)prop-2-en-1-one (0.005 g, 35%). LCMS ESI (+) m/z 634.2 (M+H). $^1H$ NMR (300 MHz, CD3OD) δ $^1HNMR$ (300 MHz, $CD_3OD$) δ 8.22 (s, 1H), 7.39-7.09 (m, 1H), 6.98 (t, J=8.8 Hz, 1H), 6.84 (dd, J=16.6, 10.5 Hz, 1H), 6.30 (d, J=16.6 Hz, 1H), 5.83 (d, J=10.6 Hz, 1H), 4.55 (s, 2H), 4.11 (s, 4H), 3.95 (s, 4H), 3.20 (m, 1H), 2.98 (m, 1H), 2.59 (s, 3H), 2.55-2.32 (m, 1H), 2.18 (m, 1H), 2.05-1.65 (m, 3H).

Synthetic Example 18: Synthesis of 1-(4-(7-(2-amino-7-fluorobenzo[d]thiazol-4-yl)-8-fluoro-2-((tetrahydro-1H-pyrrolizin-7a(5H)-yl)methoxy)-6-(trifluoromethyl)quinazolin-4-yl)piperazin-1-yl)prop-2-en-1-one (Compound 80)

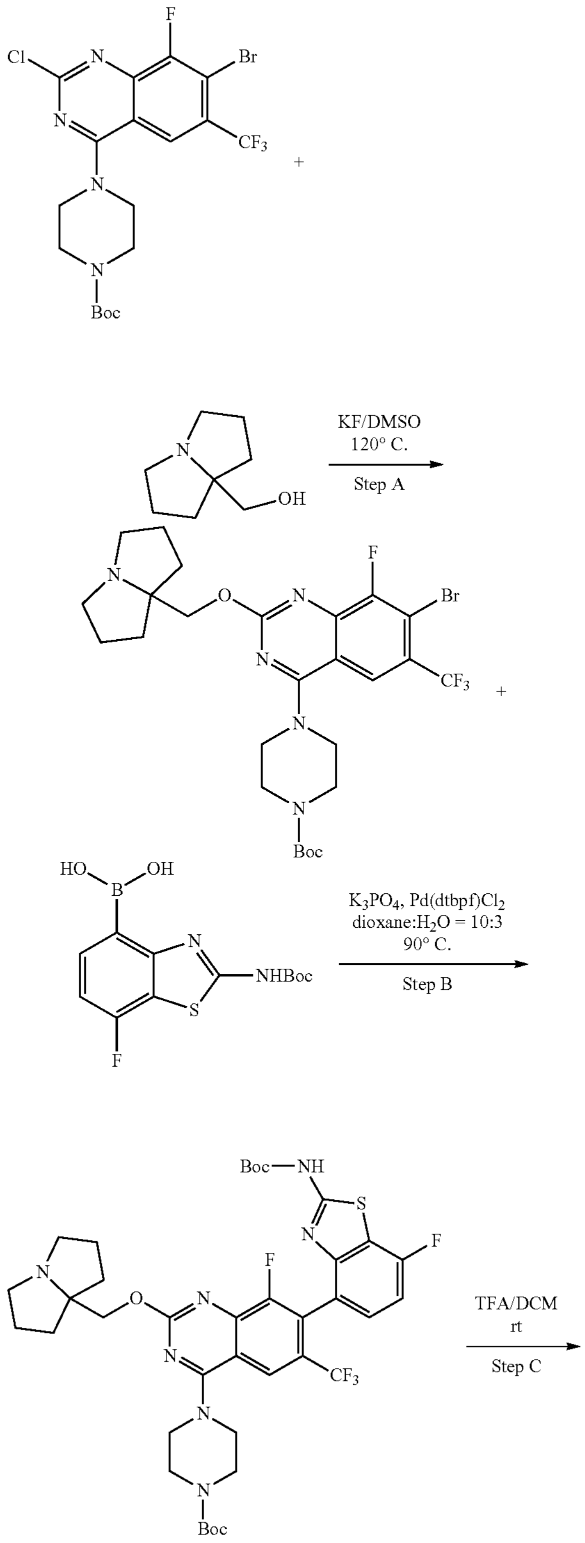

-continued

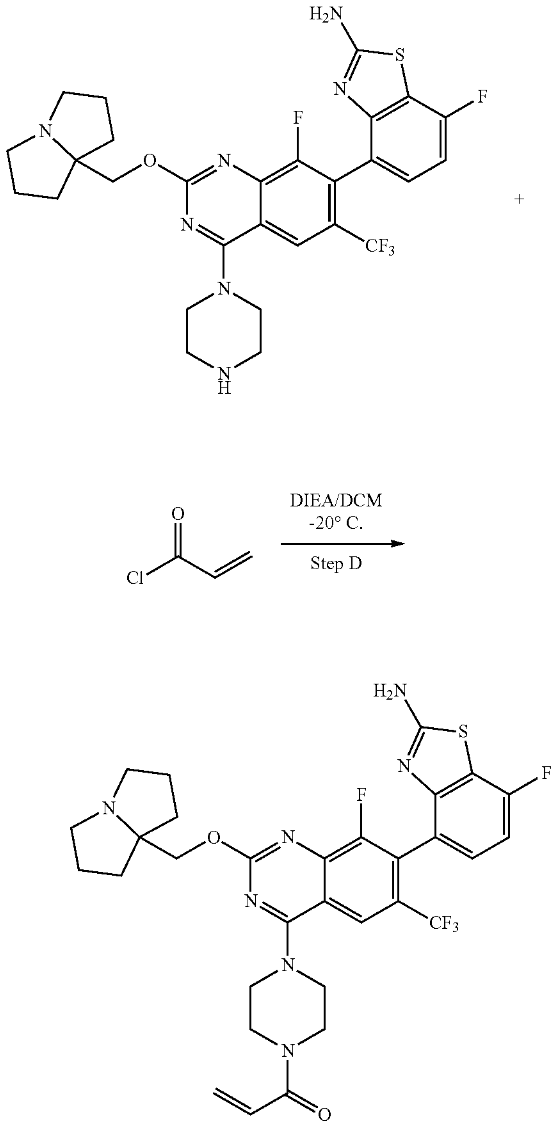

Compound 80

Step A: Preparation of 4-[7-bromo-8-fluoro-2-(1,2,3,5,6,7-hexahydropyrrolizin-8-ylmethoxy)-6-(trifluoromethyl) quinazolin-4-yl]piperazine-1-carboxylate: To a solution of 1,2,3,5,6,7-hexahydropyrrolizin-8-ylmethanol (181 mg, 1.28 mmol) in DMSO (9 mL) was added tert-butyl 4-[7-bromo-2-chloro-8-fluoro-6-(trifluoromethyl)quinazolin-4-yl]piperazine-1-carboxylate (220 mg, 0.43 mmol) and KF (199 mg, 3.43 mmol) at ambient temperature. The mixture was sealed and the stirred at 120° C. for 2 hours. Once cooled to ambient temperature, water and ethyl acetate were added. The organic layer was separated, washed with Brine, dried (sodium sulfate), filtered, and concentrated under reduced pressure. The residue was purified by preparative TLC (DCM/MeOH=10/1) to give tert-butyl 4-[7-bromo-8-fluoro-2-(1,2,3,5,6,7-hexahydropyrrolizin-8-ylmethoxy)-6-(trifluoromethyl)quinazolin-4-yl]piperazine-1-carboxylate (78 mg, 29%). LCMS ESI (+) m/z 618.3 (M+H).

Step B: Preparation of tert-butyl 4-[7-[2-(tert-butoxycarbonylamino)-7-fluoro-1,3-benzothiazol-4-yl]-8-fluoro-2-(1,2,3,5,6,7-hexahydropyrrolizin-8-ylmethoxy)-6-(trifluoromethyl)quinazolin-4-yl]piperazine-1-carboxylate: To a solution of [2-(tert-butoxycarbonylamino)-7-fluoro-1,3-benzothiazol-4-yl]boronic acid (51 mg, 0.164 mmol) in 1,4-dioxane (7 mL)/water (2.3 mL) was added tert-butyl 4-[7-bromo-8-fluoro-2-(1,2,3,5,6,7-hexahydropyrrolizin-8-ylmethoxy)-6-(trifluoromethyl)quinazolin-4-yl]piperazine-1-carboxylate (78 mg, 0.13 mmol), Pd(dtbpf)$Cl_2$ (6.6 mg, 0.010 mmol) and $K_3PO_4$ (80 mg, 0.38 mmol). The mixture was bubbled with argon for 2 minutes and then the mixture was stirred warmed to 90° C. and stirred at 90° C. for 1 hour. Once cooled to ambient temperature, water and ethyl acetate were added. The organic layer was separated and concentrated under reduced pressure. The residue was purified by preparative TLC (DCM/MeOH=10/1) to give tert-butyl 4-[7-[2-(tert-butoxycarbonylamino)-7-fluoro-1,3-benzothiazol-4-yl]-8-fluoro-2-(1,2,3,5,6,7-hexahydropyrrolizin-8-ylmethoxy)-6-(trifluoromethyl)quinazolin-4-yl]piperazine-1-carboxylate (48 mg, 42%). LCMS ESI (+) m/z 806.5 (M+H).

Step C: Preparation of 7-fluoro-4-[8-fluoro-2-(1,2,3,5,6,7-hexahydropyrrolizin-8-ylmethoxy)-4-piperazin-1-yl-6-(trifluoromethyl)quinazolin-7-yl]-1,3-benzothiazol-2-amine: tert-butyl 4-[7-[2-(tert-butoxycarbonylamino)-1,3-benzothiazol-4-yl]-8-fluoro-2-(1,2,3,5,6,7-hexahydropyrrolizin-8-ylmethoxy)-6-(trifluoromethyl) quinazolin-4-yl]piperazine-1-carboxylate (48 mg, 0.061 mmol) in DCM (4 mL) was added trifluoroacetic acid (2.0 mL, 26.0 mmol) at ambient temperature. The mixture was stirred at ambient temperature for 2 hours. The mixture was concentrated to dryness under reduced pressure. The residue was purified by preparative HPLC to give 7-fluoro-4-[8-fluoro-2-(1,2,3,5,6,7-hexahydropyrrolizin-8-ylmethoxy)-4-piperazin-1-yl-6-(trifluoromethyl)quinazolin-7-yl]-1,3-benzothiazol-2-amine (26 mg, 70%) as TFA salts. LCMS ESI (+) m/z 606.3 (M+H). $^1$H NMR (400 MHz, $CD_3OD$) δ 8.20 (s, 1H), 7.21 (dd, J=8.1, 5.4 Hz, 1H), 7.00 (t, J=8.8 Hz, 1H), 4.69 (s, 2H), 4.13-4.27 (m, 4H), 3.68 (m, 2H), 3.45-3.54 (m, 4H), 3.27-3.33 (m, 1H), 2.06-2.39 (m, 8H).

Step D: Preparation of 1-[3-[[7-(2-amino-7-fluoro-1,3-benzothiazol-4-yl)-8-fluoro-2-[[(2S,4R)-4-fluoro-1-methyl-pyrrolidin-2-yl]methoxy]-6-(trifluoromethyl)quinazolin-4-yl]amino]azetidin-1-yl]prop-2-en-1-one: To a solution of 4-[4-(azetidin-3-ylamino)-8-fluoro-2-[[(2S,4R)-4-fluoro-1-methyl-pyrrolidin-2-yl]methoxy]-6-(trifluoromethyl)quinazolin-7-yl]-7-fluoro-1,3-benzothiazol-2-amine (18 mg, 0.031 mmol) and DIEA (0.027 mL, 0.15 mmol) in DCM (4 mL) was added a solution of prop-2-enoyl prop-2-enoate (2.3 mg, 0.019 mmol) in DCM at −20° C. and stirred at −20° C. for 15 minutes. Water and ethyl acetate were added. The organic layer was separated, washed with brine, dried (sodium sulfate), filtered, and concentrated under reduced pressure. The residue was purified by preparative RP-HPLC to give 1-[3-[[7-(2-amino-7-fluoro-1,3-benzothiazol-4-yl)-8-fluoro-2-[[(2S,4R)-4-fluoro-1-methyl-pyrrolidin-2-yl] methoxy]-6-(trifluoromethyl)quinazolin-4-yl]amino]azetidin-1-yl]prop-2-en-1-one (10 mg, 51%) as TFA salt. LCMS ESI (+) m/z 660.4 (M+H). $^1$H NMR (400 MHz, $CD_3OD$) δ 8.27 (s, 1H), 7.24 (dd, J=8.1, 5.6 Hz, 1H), 7.02 (t, J=8.8 Hz, 1H), 6.81 (dd, J=16.8, 10.4 Hz, 1H), 6.30 (dd, J=16.8, 1.6 Hz, 1H), 5.82 (dd, J=10.6, 1.6 Hz, 1H), 4.68 (s, 2H), 4.11-4.31 (m, 4H), 3.84-4.10 (m, 4H), 3.68-3.70 (m, 2H), 3.26-3.31 (m, 1H), 2.09-2.35 (m, 8H).

Synthetic Example 19: 1-(3-((7-(2-amino-7-fluorobenzo[d]thiazol-4-yl)-6-chloro-8-fluoro-2-((tetrahydro-1H-pyrrolizin-7a(5H)-yl)methoxy)quinazolin-4-yl)(methyl)amino)azetidin-1-yl)prop-2-en-1-one (Compound 84)

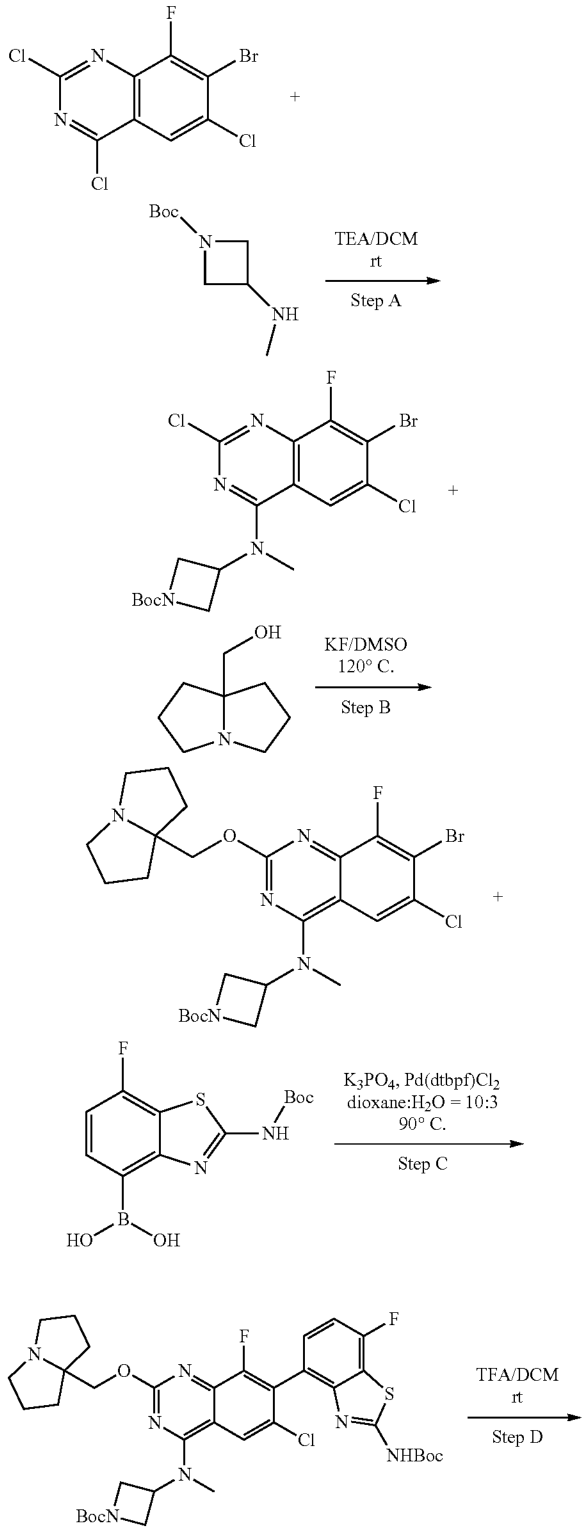

-continued

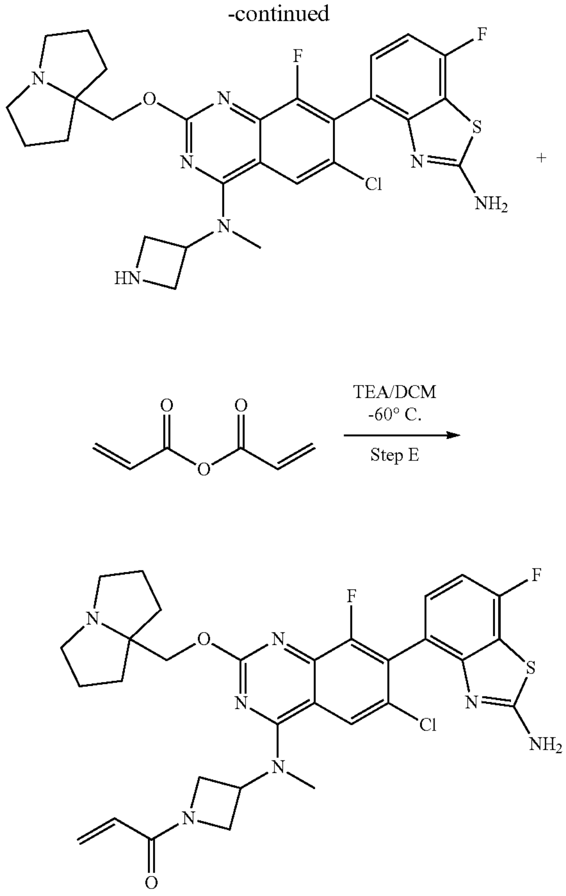

Compound 84

Step A: Preparation of tert-butyl-3-((7-bromo-2,6-dichloro-8-fluoroquinazolin-4-yl)(methyl)-amino) azetidine-1-carboxylate: To a solution of 7-bromo-2,4,6-trichloro-8-fluoroquinazoline (346 mg, 1.05 mmol) and tert-butyl 3-(methylamino)azetidine-1-carboxylate (216 mg, 1.16 mmol) in DCM (10 mL) was added DIEA (406 mg, 3.15 mmol) at ambient temperature and stirred at ambient temperature for 2 hours. The mixture was diluted with water (20 mL) and was extracted with DCM (30 mL). The organic phase was dried over anhydrous $Na_2SO_4$, filtered, and concentrated to give the crude product. The residue was purified by flash column chromatography on silica gel (PE:EA=3/1) to give tert-butyl-3-((7-bromo-2,6-dichloro-8-fluoroquinazolin-4-yl)(methyl)-amino) azetidine-1-carboxylate (360 mg, 72%).

Step B: Preparation of tert-butyl 3-((7-bromo-6-chloro-8-fluoro-2-((tetrahydro-1H-pyrrolizin-7a(5H)-yl)methoxy) quinazolin-4-yl)(methyl)amino)azetidine-1-carboxylate: A solution of tert-butyl 3-((7-bromo-2,6-dichloro-8-fluoroquinazolin-4-yl)(methyl) amino)azetidine-1-carboxylate (320 mg, 0.67 mmol), (tetrahydro-1H-pyrrolizin-7a (5H)-yl) methanol (282 mg, 2.00 mmol) and KF (310 mg, 5.36 mmol) in DMSO (3 mL) was stirred at 120° C. for 2 hours. Once cooled to ambient temperature, the mixture was diluted with water (10 mL) and was extracted with ethyl acetate (10 mL). The organic phase was dried over anhydrous $Na_2SO_4$, filtered and concentrated to give the crude product. The residue was purified by flash column chromatography on silica gel (DCM/MeOH=10/1) to give tert-butyl 3-((7-bromo-6-chloro-8-fluoro-2-((tetrahydro-1H-pyrrolizin-7a (5H)-yl)methoxy)quinazolin-4-yl)(methyl)amino)azetidine-1-carboxylate (200 mg, 51%). LCMS ESI (+) m/z 583.9 (M+H).

Step C: Preparation of tert-butyl 3-((7-(2-((tert-butoxycarbonyl)amino)-7-fluorobenzo[d]thiazol-4-yl)-6-chloro-8-fluoro-2-((tetrahydro-1H-pyrrolizin-7a(5H)-yl)methoxy) quinazolin-4-yl)(methyl)amino)azetidine-1-carboxylate: A suspension of tert-butyl 3-((7-bromo-6-chloro-8-fluoro-2-((tetrahydro-1H-pyrrolizin-7a(5H)-yl)methoxy)quinazolin-4-yl)(methyl)amino)azetidine-1-carboxylate (100 mg, 0.17 mmol), (2-((tert-butoxycarbonyl)amino)-7-fluorobenzo[d] thiazol-4-yl) boronic acid (68.7 mg, 0.22 mmol), $K_3PO_4$ (108.2 mg, 0.51 mmol) and Pd(dtbpf)$Cl_2$ (11.1 mg, 0.017 mmol) in dioxane/$H_2O$ (5 mL/1.5 mL) was stirred at 95° C. for 3 hours under Argon. Once cooled to ambient temperature, the mixture was diluted with $H_2O$ (10 mL) and was extracted with EA (10 mL). The organic phase was dried over anhydrous $Na_2SO_4$, filtered, and concentrated to give the crude product. The residue was purified by flash column chromatography on silica gel (DCM/MeOH=10/1) to give tert-butyl 3-((7-(2-((tert-butoxycarbonyl)amino)-7-fluorobenzo[d]thiazol-4-yl)-6-chloro-8-fluoro-2-((tetrahydro-1H-pyrrolizin-7a(5H)-yl)methoxy)quinazolin-4-yl)(methyl) amino)azetidine-1-carboxylate (50 mg, 38%). LCMS ESI (+) m/z 772.4 (M+H).

Step D: Preparation of 4-(4-(azetidin-3-yl(methyl) amino)-6-chloro-8-fluoro-2-((tetrahydro-1H-pyrrolizin-7a (5H)-yl)methoxy)quinazolin-7-yl)-7-fluorobenzo[d]thiazol-2-amine: To a solution of tert-butyl 3-((7-(2-((tert-butoxycarbonyl)amino)-7-fluorobenzo[d]thiazol-4-yl)-6-chloro-8-fluoro-2-((tetrahydro-1H-pyrrolizin-7a(5H)-yl) methoxy)quinazolin-4-yl)(methyl)amino)azetidine-1-carboxylate (40 mg, 0.05 mmol) in DCM (4 mL) was added TFA (1 mL) at ambient temperature, and the resulting mixture was stirred at ambient temperature for 4 hours. The mixture was concentrated in vacuo to give 4-(4-(azetidin-3-yl(methyl)amino)-6-chloro-8-fluoro-2-((tetrahydro-1H-pyrrolizin-7a(5H)-yl)methoxy)quinazolin-7-yl)-7-fluorobenzo[d]thiazol-2-amine, which was used directly for next step without further purification. LCMS ESI (+) m/z 572.3 (M+H).

Step E: Preparation of 1-(3-((7-(2-amino-7-fluorobenzo [d]thiazol-4-yl)-6-chloro-8-fluoro-2-((tetrahydro-1H-pyrrolizin-7a(5H)-yl)methoxy)quinazolin-4-yl)(methyl)amino) azetidin-1-yl)prop-2-en-1-one (84): To a solution of 4-[4-[azetidin-3-yl(methyl)amino]-6-chloro-8-fluoro-2-(1,2,3,5,6,7-hexahydropyrrolizin-8-ylmethoxy)quinazolin-7-yl]-7-fluoro-1,3-benzothiazol-2-amine from previous step and N,N-Diisopropylethylamine (0.20 mL, 1.15 mmol) in DCM (4 mL) was added acrylic anhydride (4.1 mg, 0.033 mmol) at −40° C. After addition, the mixture was warmed to 0° C. and stirred at 0° C. for 1 hour. The mixture was diluted with saturated sodium bicarbonate solution and extracted with DCM (10 mL). The organic phase was dried over anhydrous sodium sulfate, filtered, and concentrated in vacuo to give the crude product. The crude product was purified by preparative RP-HPLC to give 1-(3-((7-(2-amino-7-fluorobenzo[d]thiazol-4-yl)-6-chloro-8-fluoro-2-((tetrahydro-1H-pyrrolizin-7a(5H)-yl)methoxy)quinazolin-4-yl)(methyl) amino)azetidin-1-yl)prop-2-en-1-one (4.84 mg). LCMS ESI (+) m/z 626.3 (M+H). $^1$HNMR (400 MHz, $CD_3OD$) δ 8.11 (s, 1H), 7.25 (dd, J=8.3, 5.4 Hz, 1H), 7.03 (t, J=8.8 Hz, 1H), 6.42 (m, 1H), 6.27-6.33 (m, 1H), 5.79 (d, J=10.6 Hz, 1H), 4.85-4.97 (m, 3H), 4.42-4.73 (m, 5H), 4.14-4.30 (m, 1H), 3.62-3.73 (m, 2H), 3.52 (s, 3H), 2.02-2.37 (m, 8H)

Synthetic Example 20: Synthesis of 2-(4-((1-acryloylazetidin-3-yl)amino)-7-(2-amino-7-fluorobenzo [d]thiazol-4-yl)-8-fluoro-2-((tetrahydro-1H-pyrrolizin-7a(5H)-yl)methoxy)quinazolin-6-yl) acetonitrile (Compound 91)

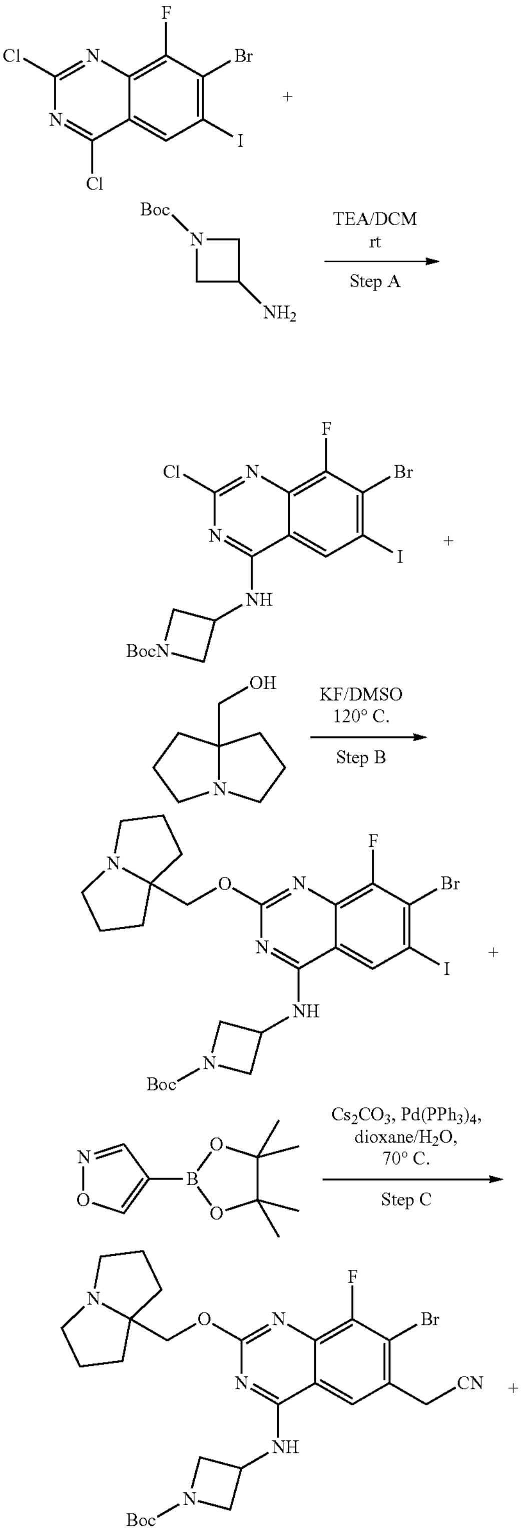

-continued

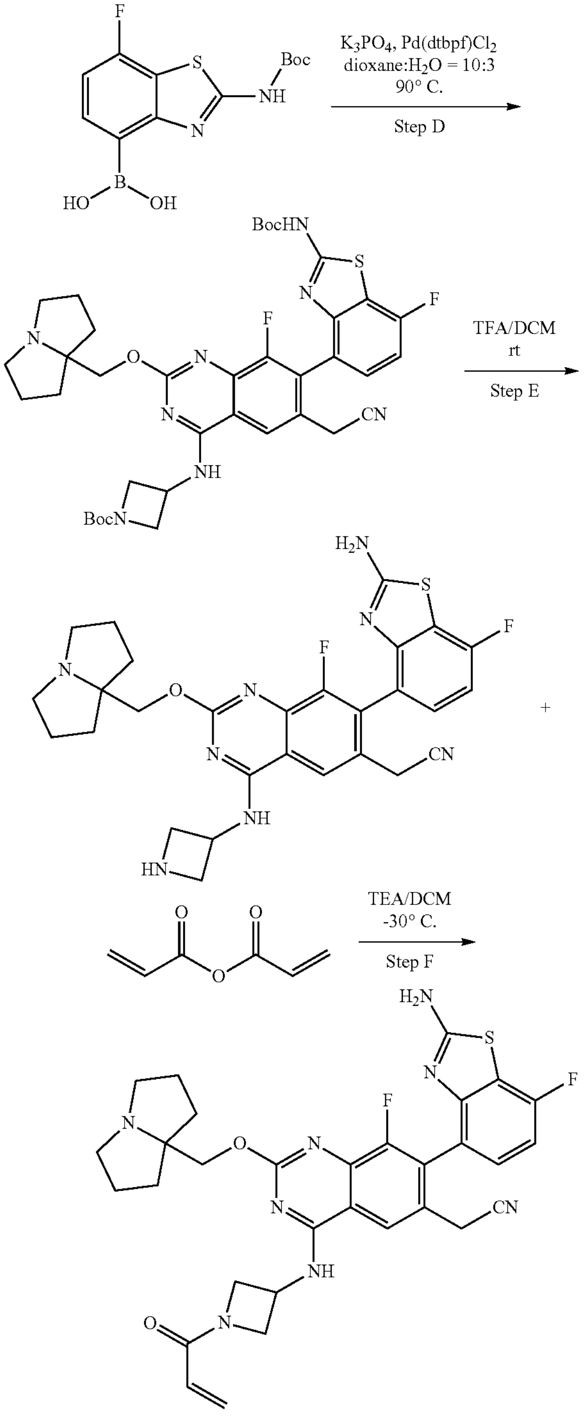

Compound 91

Step A: Preparation of tert-butyl 3-[(7-bromo-2-chloro-8-fluoro-6-iodo-quinazolin-4-yl)amino]azetidine-1-carboxylate: To a solution of 7-bromo-2,4,8-trichloro-6-iodo-quinazoline (1.10 g, 2.51 mmol) in DCM (10 mL) was added tert-butyl 3-aminoazetidine-1-carboxylate (519 mg, 3.01 mmol) and TEA (1.0 mL, 7.53 mmol) at ambient temperature and stirred at ambient temperature for 2 hours. Solvent was removed under reduced pressure, the residue was purified by flash chromatography on silica gel, eluting with 25% EtOAc in petroleum ether to give tert-butyl 3-[(7-bromo-2-chloro-8-fluoro-6-iodo-quinazolin-4-yl)amino]azetidine-1-carboxylate (1.00 g, 71%).

Step B: Preparation of tert-butyl 3-[[7-bromo-8-fluoro-2-(1,2,3,5,6,7-hexahydropyrrolizin-8-ylmethoxy)-6-iodo-quinazolin-4-yl]amino]azetidine-1-carboxylate: To a solution of tert-butyl 3-[(7-bromo-2-chloro-8-fluoro-6-iodo-quinazolin-4-yl)amino]azetidine-1-carboxylate (300 mg, 0.54 mmol) in DMSO (2 mL) was added 1,2,3,5,6,7-hexahydropyrrolizin-8-ylmethanol (228 mg, 1.61 mmol) and KF (250 mg, 4.30 mmol) at ambient temperature. The mixture was stirred at 120° C. for 2 hours. Once cooled to ambient temperature, water and ethyl acetate were added. The organic layer was separated, washed with brine, dried over sodium sulfate, filtered, and concentrated under reduced pressure. The crude product was purified by preparative TLC (DCM:MeOH=20:1) to give tert-butyl 3-[[7-bromo-8-fluoro-2-(1,2,3,5,6,7-hexahydropyrrolizin-8-ylmethoxy)-6-iodo-quinazolin-4-yl]amino]azetidine-1-carboxylate (200 mg, 56%).

Step C: Preparation of tert-butyl 3-[[7-bromo-6-(cyanomethyl)-8-fluoro-2-(1,2,3,5,6,7-hexahydropyrrolizin-8-ylmethoxy)quinazolin-4-yl]amino]azetidine-1-carboxylate: To a solution of tert-butyl 3-[[7-bromo-8-fluoro-2-(1,2,3,5,6,7-hexahydropyrrolizin-8-ylmethoxy)-6-iodo-quinazolin-4-yl]amino]azetidine-1-carboxylate (200 mg, 0.30 mmol), 4-(4,4,5,5-tetramethyl-1,3,2-dioxaborolan-2-yl)isoxazole (88 mg, 0.45 mmol), $Cs_2CO_3$ (197 mg, 0.60 mmol) in 1,4-dioxane (2.5 mL) and water (0.50 mL) was added $Pd(PPh_3)_4$ (35 mg, 0.030 mmol) under Ar at ambient temperature. The mixture was stirred at 70° C. overnight. Once cooled to ambient temperature, water, and ethyl acetate were added. The organics layer was separated, washed with brine, dried (sodium sulfate), filtered, and concentrated under reduced pressure. The crude product was purified by preparative TLC (DCM:MeOH=10:1) to give tert-butyl 3-[[7-bromo-6-(cyanomethyl)-8-fluoro-2-(1,2,3,5,6,7-hexahydropyrrolizin-8-ylmethoxy)quinazolin-4-yl]amino]azetidine-1-carboxylate (115 mg, 66%).

Step D: Preparation of tert-butyl 3-[[7-[2-(tert-butoxycarbonylamino)-7-fluoro-1,3-benzothiazol-4-yl]-6-(cyanomethyl)-8-fluoro-2-(1,2,3,5,6,7-hexahydropyrrolizin-8-ylmethoxy)quinazolin-4-yl]amino]azetidine-1-carboxylate: To a suspension of tert-butyl 3-[[7-bromo-6-(cyanomethyl)-8-fluoro-2-(1,2,3,5,6,7-hexahydropyrrolizin-8-ylmethoxy) quinazolin-4-yl]amino]azetidine-1-carboxylate (130 mg, 0.23 mmol), (2-tert-butoxycarbonyl-7-fluoro-1,3-benzothiazol-4-yl)boronic acid (87 mg, 0.29 mmol) and $K_3PO_4$ (96 mg, 0.45 mmol) was added 1,1'-Bis(di-t-butylphosphino) ferrocene palladium dichloride (15 mg, 0.023 mmol) at ambient temperature. The mixture was stirred at 90° C. for 1 hour under Ar. Once cooled to ambient temperature, the mixture was diluted with water and the product was extracted with ethyl acetate. The organics were washed with saturated brine solution and dried over sodium sulfate, filtered, and concentrated under reduced pressure. The crude product was purified by preparative TLC (DCM: MeOH=10:1) to give tert-butyl 3-[[7-[2-(tert-butoxycarbonylamino)-7-fluoro-1,3-benzothiazol-4-yl]-6-(cyanomethyl)-8-fluoro-2-(1,2,3,5,6,7-hexahydropyrrolizin-8-ylmethoxy)quinazolin-4-yl]amino]azetidine-1-carboxylate (94 mg, 54%).

Step E: Preparation of 2-[7-(2-amino-7-fluoro-1,3-benzothiazol-4-yl)-4-(azetidin-3-ylamino)-8-fluoro-2-(1,2,3,5,6,7-hexahydropyrrolizin-8-ylmethoxy)quinazolin-6-yl]acetonitrile: To a solution of tert-butyl 3-[[7-[2-(tert-butoxycarbonylamino)-7-fluoro-1,3-benzothiazol-4-yl]-6-(cyanomethyl)-8-fluoro-2-(1,2,3,5,6,7-hexahydropyrrolizin-8-ylmethoxy)quinazolin-4-yl]amino] azetidine-1-carboxylate (25 mg, 0.033 mmol) in DCM (1.5 mL) was added trifluoroacetic acid (0.83 mL, 10.8 mmol) at ambient temperature and stirred at ambient temperature for 2 hours. The solvent was removed under vacuum to give 2-[7-(2-amino-7-fluoro-1,3-benzothiazol-4-yl)-4-(azetidin-3-ylamino)-8-fluoro-2-(1,2,3,5,6,7-hexahydropyrrolizin-8-ylmethoxy)quinazolin-6-yl]acetonitrile (20 mg, 100%). LCMS ESI (+) m/z 563.4 (M+H). $^1$H NMR (400 MHz, $CD_3OD$) δ 8.18 (s, 1H), 7.28 (dd, J=8.4, 5.4 Hz, 1H), 7.05 (t, J=8.8 Hz, 1H), 5.21-5.31 (m, 1H), 4.63-4.73 (m, 2H), 4.47-4.56 (m, 2H), 4.36-4.45 (m, 2H), 3.75-3.88 (m, 2H), 3.64-3.74 (m, 2H), 3.24-3.29 (m, 2H), 2.27-2.40 (m, 2H), 2.17-2.26 (m, 2H), 2.06-2.17 (m, 4H).

Step F: Preparation of 2-[7-(2-amino-7-fluoro-1,3-benzothiazol-4-yl)-8-fluoro-2-(1,2,3,5,6,7-hexahydropyrrolizin-8-ylmethoxy)-4-[(1-prop-2-enoylazetidin-3-yl)amino]quinazolin-6-yl]acetonitrile: To a solution of 2-[7-(2-amino-7-fluoro-1,3-benzothiazol-4-yl)-4-(azetidin-3-ylamino)-8-fluoro-2-(1,2,3,5,6,7-hexahydropyrrolizin-8-ylmethoxy) quinazolin-6-yl]acetonitrile (20 mg, 0.036 mmol) and TEA (0.025 mL, 0.18 mmol) in DCM (2 mL) was added prop-2-enoyl prop-2-enoate (3.6 mg, 0.028 mmol) at −30° C. and stirred at −30° C. for 1 hour. The mixture was quenched with water and extracted with DCM. The combined organic layer was washed with brine, dried over sodium sulfate, filtered and concentrated under reduced pressure. The residue was purified by preparative RP-HPLC to afford 2-[7-(2-amino-7-fluoro-1,3-benzothiazol-4-yl)-8-fluoro-2-(1,2,3,5,6,7-hexahydropyrrolizin-8-ylmethoxy)-4-[(1-prop-2-enoylazetidin-3-yl)amino]quinazolin-6-yl]acetonitrile (17 mg, 77%). LCMS ESI (+) m/z 617.3 (M+H). $^1$HNMR (400 MHz, $CD_3OD$) δ 8.21 (s, 1H), 7.27 (dd, J=8.3, 5.5 Hz, 1H), 7.04 (t, J=8.8 Hz, 1H), 6.42 (dd, J=16.9, 10.2 Hz, 1H), 6.26-6.36 (m, 1H), 5.76-5.83 (m, 1H), 5.05-5.16 (m, 1H), 4.77-4.83 (m, 1H), 4.62-4.72 (m, 2H), 4.49-4.57 (m, 2H), 4.28-4.37 (m, 1H), 3.75-3.86 (m, 2H), 3.65-3.74 (m, 2H), 3.26-3.29 (m, 2H), 2.29-2.39 (m, 2H), 2.18-2.27 (m, 2H), 2.05-2.18 (m, 4H).

Synthetic Example 21: Synthesis of 1-[3-[[7-(2-amino-7-fluoro-1,3-benzothiazol-4-yl)-6-chloro-8-fluoro-2-[[(2S)-1-methylpyrrolidin-2-yl]methoxy] quinazolin-4-yl]amino]azetidin-1-yl]but-2-yn-1-one (Compound 92)

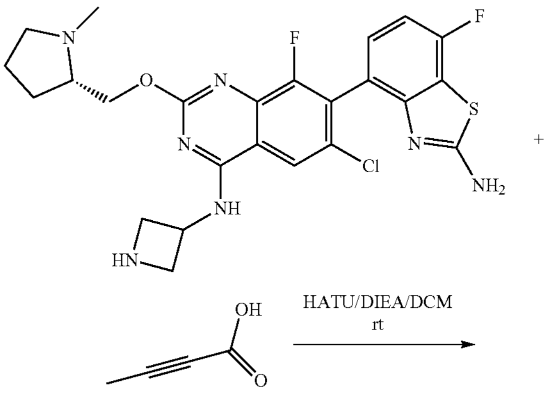

-continued

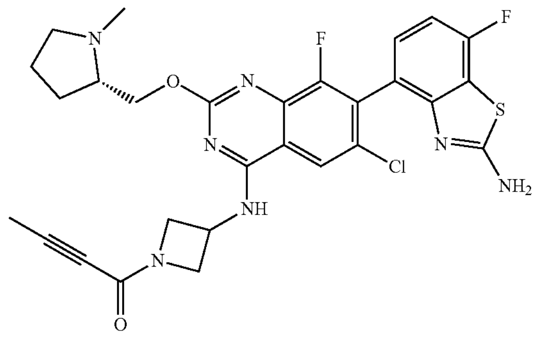

Compound 92

Preparation of 1-[3-[[7-(2-amino-7-fluoro-1,3-benzothiazol-4-yl)-6-chloro-8-fluoro-2-[[(2S)-1-methylpyrrolidin-2-yl]methoxy]quinazolin-4-yl]amino]azetidin-1-yl]but-2-yn-1-one: To a solution of but-2-ynoic acid (10 mg, 0.12 mmol) in DCM (2 mL) were added 2-(3H-[1,2,3]triazolo[4,5-b] pyridin-3-yl)-1,1,3,3-tetramethyluronium hexafluorophosphate(V) (75 mg, 0.20 mmol) and N,N-Diisopropylethylamine (0.063 mL, 0.36 mmol) and the mixture was stirred at ambient temperature for 10 minutes, then 4-[4-(azetidin-3-ylamino)-6-chloro-8-fluoro-2-[[(2S)-1-methyl pyrrolidin-2-yl]methoxy]quinazolin-7-yl]-7-fluoro-1,3-benzothiazol-2-amine (65 mg, 0.12 mmol) in DCM was added. The reaction mixture was stirred at ambient temperature for 1 hour. The reaction was quenched with water and extracted with ethyl acetate. The organic layer was washed with water and brine, dried over sodium sulfate, filtered, and concentrated under reduced pressure. The product was purified by preparative RP-HPLC to afford 1-[3-[[7-(2-amino-7-fluoro-1,3-benzothiazol-4-yl)-6-chloro-8-fluoro-2-[[(2S)-1-methylpyrrolidin-2-yl]methoxy]quinazolin-4-yl]amino]azetidin-1-yl]but-2-yn-1-one (11 mg, 15%). LCMS ESI (+) m/z 598.3 (M+H). $^1$HNMR(400 MHz, $CD_3OD$): 8.27 (s, 1H), 7.23 (t, J=2.8, Hz, 1H), 7.0-7.05 (m, 1H), 5.03-5.15 (m, 1H), 4.61-4.85 (m, 2H), 4.35-4.42 (m, 2H), 4.16-4.22 (m, 1H), 3.70-3.88 (m, 2H), 3.30-3.40 (m, 2H), 3.15 (s, 3H), 2.20-2.45 (m, 4H), 2.04 (s, 3H).

Synthetic Example 22: Synthesis of 1-(4-(7-(2-amino-7-fluorobenzo[d]oxazol-4-yl)-8-fluoro-2-((tetrahydro-1H-pyrrolizin-7a(5H)-yl)methoxy)-6-(trifluoromethyl)quinazolin-4-yl)piperazin-1-yl) prop-2-en-1-one (Compound 162)

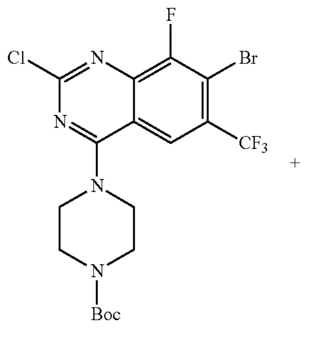

-continued

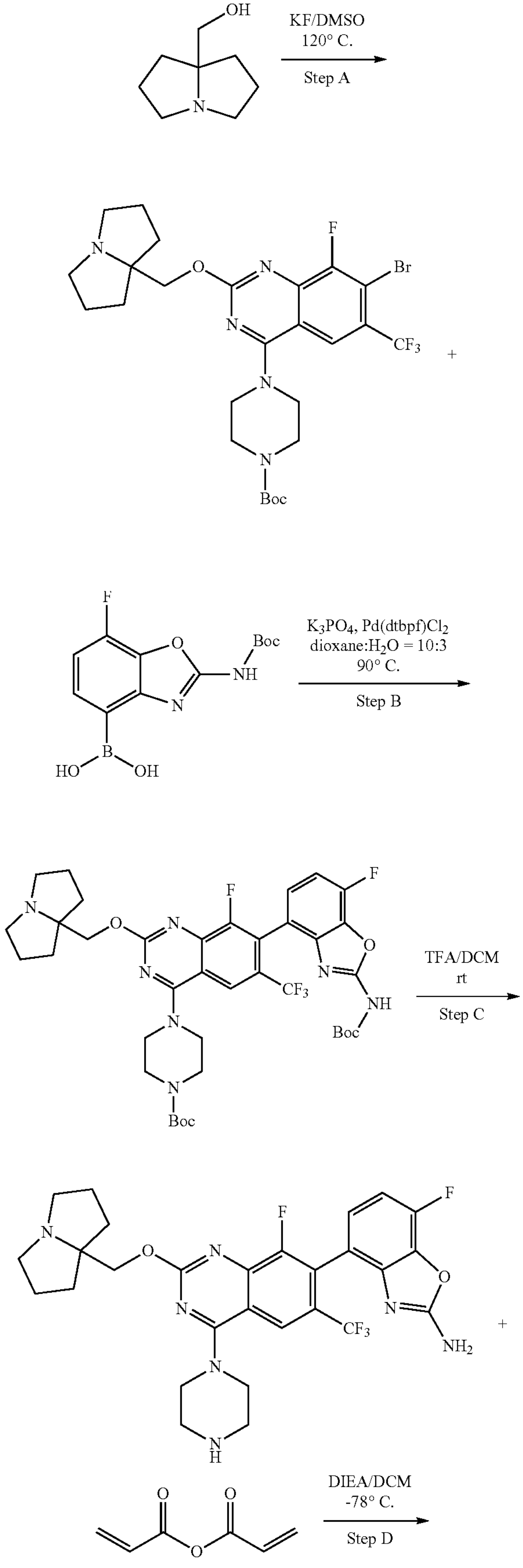

-continued

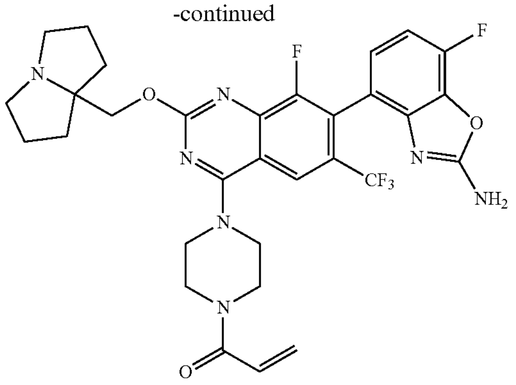

Compound 162

Step A: Preparation of tert-butyl 4-[7-bromo-8-fluoro-2-(1,2,3,5,6,7-hexahydropyrrolizin-8-ylmethoxy)-6-(trifluoromethyl)quinazolin-4-yl]piperazine-1-carboxylate: To a solution of tert-butyl 4-[7-bromo-2-chloro-8-fluoro-6-(trifluoromethyl)quinazolin-4-yl]piperazine-1-carboxylate (230 mg, 0.45 mmol) and 1,2,3,5,6,7-hexahydropyrrolizin-8-ylmethanol (158 mg, 1.12 mmol) in DMSO (3 mL) was added potassium fluoride (208 mg, 3.58 mmol) at ambient temperature. The reaction mixture was stirred at 90° C. for 3 hours. Once cooled to ambient temperature, the reaction was taken up in EtOAc (20 mL) and the organics washed with water then saturated brine solution. The organics were then separated, dried ($MgSO_4$), filtered, and concentrated under reduced pressure. The crude was then purified by preparative-TLC (DCM/MeOH=20:1) to tert-butyl 4-[7-bromo-8-fluoro-2-(1,2,3,5,6,7-hexahydropyrrolizin-8-ylmethoxy)-6-(trifluoromethyl)quinazolin-4-yl]piperazine-1-carboxylate (170 mg, 55%). LCMS ESI (+) m/z 617.2 (M+H).

Step B: Preparation of tert-butyl 4-[7-(2-amino-7-fluoro-1,3-benzoxazol-4-yl)-8-fluoro-2-(1,2,3,5,6,7-hexahydropyrrolizin-8-ylmethoxy)-6-(trifluoromethyl)quinazolin-4-yl]piperazine-1-carboxylate: To a solution of tert-butyl 4-[7-bromo-8-fluoro-2-(1,2,3,5,6,7-hexahydropyrrolizin-8-ylmethoxy)-6-(trifluoromethyl)quinazolin-4-yl]piperazine-1-carboxylate (60 mg, 0.097 mmol), (2-amino-7-fluoro-1,3-benzoxazol-4-yl)boronic acid (23 mg, 0.12 mmol), potassium phosphate (41 mg, 0.19 mmol) in 1,4-dioxane (3 mL) and water (0.9 mL) was added Pd(dtbpf)$Cl_2$ (6.3 mg, 0.0097 mmol) at ambient temperature. After bubbling with nitrogen for 2 minutes, the reaction was stirred at 90° C. for 1 hour. Once cooled to ambient temperature, the reaction was diluted with EtOAc (30 mL) and the organics washed with water and saturated brine solution. The organics were then separated, dried ($MgSO_4$), filtered, and concentrated under reduced pressure. The crude was then purified by preparative-TLC (DCM/MeOH=20:1) to afford tert-butyl 4-[7-(2-amino-7-fluoro-1,3-benzoxazol-4-yl)-8-fluoro-2-(1,2,3,5,6,7-hexahydropyrrolizin-8-ylmethoxy)-6-(trifluoromethyl)quinazolin-4-yl]piperazine-1-carboxylate (40 mg, 53%). LCMS ESI (+) m/z 690.3 (M+H).

Step C: Preparation of (7-fluoro-4-[8-fluoro-2-(1,2,3,5,6,7-hexahydropyrrolizin-8-ylmethoxy)-4-piperazin-1-yl-6-(trifluoromethyl)quinazolin-7-yl]-1,3-benzoxazol-2-amine: To a solution of tert-butyl 4-[7-(2-amino-7-fluoro-1,3-benzoxazol-4-yl)-8-fluoro-2-(1,2,3,5,6,7-hexahydropyrrolizin-8-ylmethoxy)-6-(trifluoromethyl)quinazolin-4-yl]piperazine-1-carboxylate (40 mg, 0.058 mmol) in DCM (3 mL) was added Trifluoroacetic acid (1.0 mL, 13.0 mmol) at ambient temperature and stirred at ambient temperature for 2 hours. The reaction solution was concentrated in vacuum to afford (7-fluoro-4-[8-fluoro-2-(1,2,3,5,6,7-hexahydropyrrolizin-8-ylmethoxy)-4-piperazin-1-yl-6-(trifluoromethyl) quinazolin-7-yl]-1,3-benzoxazol-2-amine (12.3 mg, 34%) which was used directly in the next step. LCMS ESI (+) m/z 590.2 (M+H). $^1$HNMR (400 MHz, $CD_3OD$) δ 8.20 (s, 1H), 7.06-7.11 (m, 1H), 6.99 (t, J=9.9, 2.4 Hz, 1H), 4.69 (s, 2H), 4.21 (t, J=4.88 Hz, 4H), 3.65-3.75 (m, 2H), 3.49 (t, J=5.12 Hz, 4H), 3.26-3.35 (m, 2H), 2.29-2.40 (m, 2H), 2.08-2.27 (m, 6H).

Step D: Preparation of 1-[4-[7-(2-amino-7-fluoro-1,3-benzoxazol-4-yl)-8-fluoro-2-(1,2,3,5,6,7-hexahydropyrrolizin-8-ylmethoxy)-6-(trifluoromethyl)quinazolin-4-yl] piperazin-1-yl]prop-2-en-1-one: To a solution of 7-fluoro-4-[8-fluoro-2-(1,2,3,5,6,7-hexahydropyrrolizin-8-ylmethoxy)-4-piperazin-1-yl-6-(trifluoromethyl)quinazolin-7-yl]-1,3-benzoxazol-2-amine (9.0 mg, 0.015 mmol) and DIEA (0.0081 mL, 0.046 mmol) in DCM (2 mL) was added prop-2-enoyl prop-2-enoate (1.71 mg, 0.014 mmol) in DCM at −78° C. The reaction was stirred at −78° C. for 15 minutes. The reaction was quenched with $H_2O$ (10 mL) and extracted with ethyl acetate. The organics were then separated, dried ($MgSO_4$), filtered, and concentrated under reduced pressure. The crude was then purified by preparative RP-HPLC to afford 1-[4-[7-(2-amino-7-fluoro-1,3-benzoxazol-4-yl)-8-fluoro-2-(1,2,3,5,6,7-hexahydropyrrolizin-8-ylmethoxy)-6-(trifluoromethyl)quinazolin-4-yl]piperazin-1-yl]prop-2-en-1-one (3.3 mg, 33%). LCMS ESI (+) m/z 643.2 (M+H). $^1$HNMR (400 MHz, $CD_3OD$): δ 8.26 (s, 1H), 7.02-7.10 (m, 1H), 6.98 (t, J=9.6 Hz, 1H), 6.81 (dd, J=16.8, 10.7 Hz, 1H), 6.29 (d, J=16.8 Hz, 1H), 5.82 (d, J=10.4 Hz, 1H), 4.67 (s, 2H), 4.10-4.21 (m, 4H), 3.89-4.01 (m, 4H), 3.64-3.73 (m, 2H), 3.24-3.29 (m, 2H), 2.26-2.37 (m, 2H), 2.05-2.25 (m, 6H).

Synthetic Example 23: Synthesis of 1-(4-(7-(2-amino-7-fluorobenzo[d]thiazol-4-yl)-2-((2,2-dimethyltetrahydro-1H-pyrrolizin-7a(5H)-yl)methoxy)-8-fluoro-6-(trifluoromethyl)quinazolin-4-yl)piperazin-1-yl)prop-2-en-1-one (Compound 171)

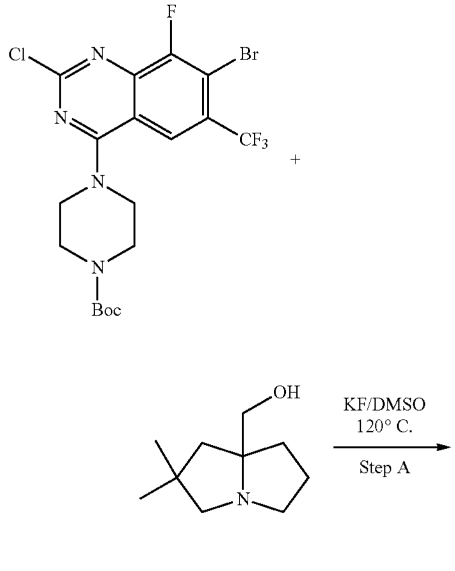

-continued

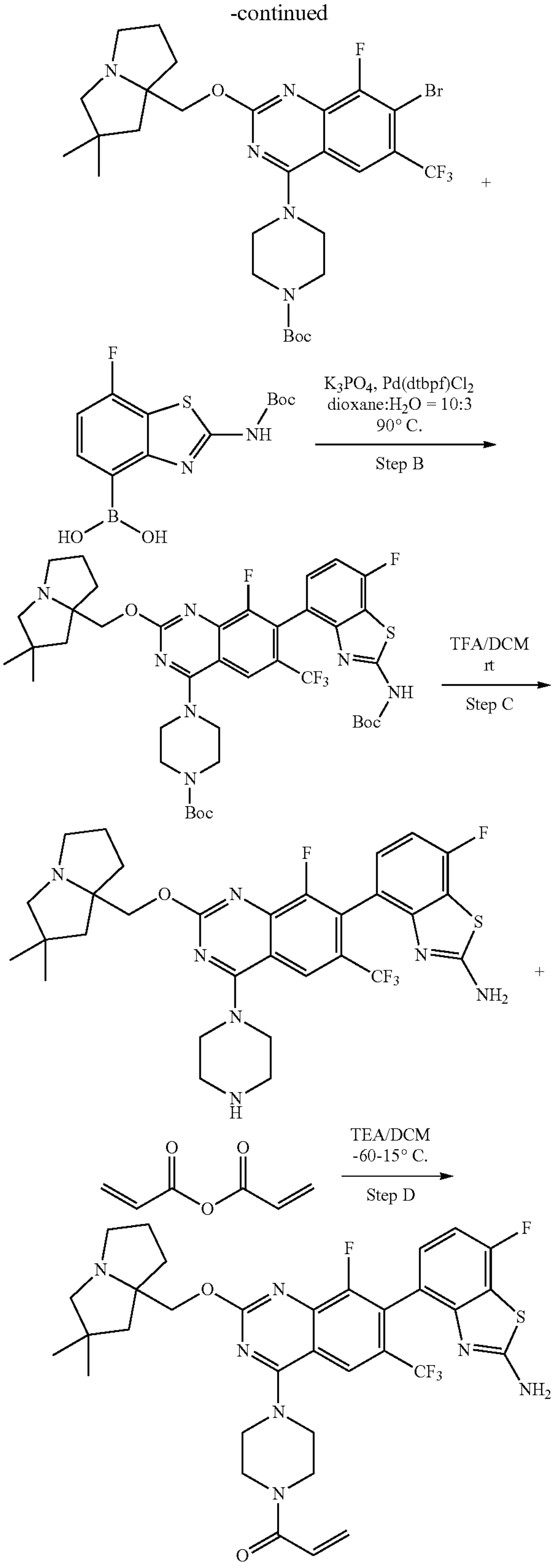

Compound 171

Step A: Preparation of 4-(7-bromo-2-((2,2-dimethyltetrahydro-1H-pyrrolizin-7a(5H)-yl)methoxy)-8-fluoro-6-(trifluoromethyl)quinazolin-4-yl)piperazine-1-carboxylate: To a solution of tert-butyl 4-(7-bromo-2-chloro-8-fluoro-6-(trifluoromethyl) quinazolin-4-yl)piperazine-1-carboxylate (300 mg, 0.58 mmol), (2,2-dimethyltetrahydro-1H-pyrrolizin-7a(5H)-yl)methanol (296.5 mg, 1.75 mmol) in DMSO (3 mL) was added potassium fluoride (271.4 mg, 4.67 mmol) at ambient temperature. The reaction mixture was stirred at 90° C. for 2 hours. Once cooled to ambient temperature, the reaction was taken up in EtOAc (20 mL) and the organics washed with 2×10 mL water then 1×10 mL saturated brine solution. The organics were then separated and dried ($MgSO_4$), filtered, and concentrated under reduced pressure. The crude was then purified by preparative-TLC (DCM/MeOH=20:1) to afford tert-butyl 4-(7-bromo-2-((2,2-dimethyltetrahydro-1H-pyrrolizin-7a(5H)-yl)methoxy)-8-fluoro-6-(trifluoromethyl)quinazolin-4-yl)piperazine-1-carboxylate (200 mg, 53%). LCMS ESI (+) m/z 646.2 (M+H).

Step B: Preparation of tert-butyl 4-(7-(2-((tert-butoxycarbonyl)amino)-7-fluorobenzo[d]thiazol-4-yl)-2-((2,2-dimethyltetrahydro-1H-pyrrolizin-7a(5H)-yl)methoxy)-8-fluoro-6-(trifluoromethyl)quinazolin-4-yl)piperazine-1-carboxylate: To a solution of tert-butyl 4-(7-bromo-2-((2,2-dimethyltetrahydro-1H-pyrrolizin-7a(5H)-yl)methoxy)-8-fluoro-6-(trifluoromethyl)quinazolin-4-yl)piperazine-1-carboxylate (200 mg, 0.31 mmol), (2-amino-7-fluoro-1,3-benzothiazol-4-yl)boronic acid (115.8 mg, 0.37 mmol), potassium phosphate (131.3 mg, 0.62 mmol) in 1,4-dioxane (5 mL) and water (1.60 mL) was added Pd(dtbpf)$Cl_2$ (20.1 mg, 0.031 mmol) at ambient temperature. After bubbling with nitrogen for 2 minutes, the reaction was stirred at 90° C. for 2 hours. Once cooled to ambient temperature, the reaction was diluted with EtOAc (30 mL) and the organics washed with 2×10 mL water then 1×10 mL saturated brine solution. The organics were then separated, dried ($MgSO_4$), and concentrated under reduced pressure. The crude was then purified by preparative-TLC (DCM:MeOH=20:1) to afford tert-butyl 4-(7-(2-((tert-butoxycarbonyl)amino)-7-fluorobenzo[d]thiazol-4-yl)-2-((2,2-dimethyltetrahydro-1H-pyrrolizin-7a(5H)-yl)methoxy)-8-fluoro-6-(trifluoromethyl) quinazolin-4-yl)piperazine-1-carboxylate (100 mg, 39%). LCMS ESI (+) m/z 834.3 (M+H).

Step C: Preparation of 4-(2-((2,2-dimethyltetrahydro-1H-pyrrolizin-7a(5H)-yl)methoxy)-8-fluoro-4-(piperazin-1-yl)-6-(trifluoromethyl)quinazolin-7-yl)-7-fluorobenzo[d]thiazol-2-amine: To a solution of tert-butyl 4-(7-(2-((tert-butoxycarbonyl)amino)-7-fluorobenzo[d]thiazol-4-yl)-2-((2,2-dimethyltetrahydro-1H-pyrrolizin-7a(5H)-yl) methoxy)-8-fluoro-6-(trifluoromethyl)quinazolin-4-yl)piperazine-1-carboxylate (100 mg, 0.12 mmol) in DCM (4 mL) was added trifluoroacetic acid (1.0 mL, 13.0 mmol) at ambient temperature and stirred at ambient temperature for 1 hour. The reaction solution was concentrated in vacuum to afford 4-(2-((2,2-dimethyltetrahydro-1H-pyrrolizin-7a(5H)-yl)methoxy)-8-fluoro-4-(piperazin-1-yl)-6-(trifluoromethyl) quinazolin-7-yl)-7-fluorobenzo[d]thiazol-2-amine (70 mg, 92%) which was used directly in the next step. LCMS ESI (+) m/z 634.1 (M+H).

Step D: Preparation of 1-(3-((7-(2-amino-7-fluorobenzo [d]thiazol-4-yl)-8-fluoro-2-(((2R)-2-fluorohexahydro-1H-pyrrolizin-7a-yl)methoxy)-6-(trifluoromethyl)quinazolin-4-yl)(cyclopropyl)amino)azetidin-1-yl)prop-2-en-1-one: To a solution of 4-(2-((2,2-dimethyltetrahydro-1H-pyrrolizin-7a(5H)-yl)methoxy)-8-fluoro-4-(piperazin-1-yl)-6-(trifluoromethyl)quinazolin-7-yl)-7-fluorobenzo[d]thiazol-2-amine (20 mg, 0.032 mmol), Triethyl amine (31.9 mg, 0.32 mmol) in DCM (2 mL) was added prop-2-enoyl prop-2-enoate (4.0 mg, 0.032 mmol) in DCM at −60° C. After addition, the reaction was warmed to ambient temperature and stirred at ambient temperature for 1 hour. The reaction was diluted with DCM (10 mL) and the organics washed with 2×10 mL water then 1×10 mL saturated brine solution. The organics were then separated, dried ($MgSO_4$), and concentrated under reduced pressure. The crude was then purified by preparative RP-HPLC to afford 1-(4-(7-(2-amino-7-fluorobenzo[d]thiazol-4-yl)-2-((2,2-dimethyltetrahydro-1H-pyrrolizin-7a (5H)-yl)methoxy)-8-fluoro-6-(trifluoromethyl) quinazolin-4-yl)piperazin-1-yl)prop-2-en-1-one (2.4 mg, 11%). LCMS ESI (+) m/z 688.2 (M+H). $^1$HNMR (400 MHz, $CD_3OD$) δ 8.26 (s, 1H), 7.21-7.25 (m, 1H), 7.02 (t, J=9.2 Hz, 1H), 6.77-6.84 (m, 1H), 6.29 (dd, J=16.8, 1.6 Hz, 1H), 5.81 (dd, J=10.6, 1.6 Hz, 1H), 4.68-4.78 (m, 2H), 4.14-4.19 (m, 4H), 3.91-3.97 (m, 4H), 3.61-3.65 (m, 1H), 3.48-3.51 (m, 1H), 3.40-3.43 (m, 1H), 3.10-3.12 (m, 1H), 2.08-2.43 (m, 6H), 1.28 (s, 3H), 1.27 (s, 3H).

Synthetic Example 24: Synthesis of 1-(3-((7-(2-amino-7-fluorobenzo[d]thiazol-4-yl)-8-fluoro-2-(((2R,7aR)-2-fluorotetrahydro-1H-pyrrolizin-7a (5H)-yl)methoxy)-6-(trifluoromethyl)quinazolin-4-yl)(cyclopropyl)amino)azetidin-1-yl)prop-2-en-1-one (Compound 178)

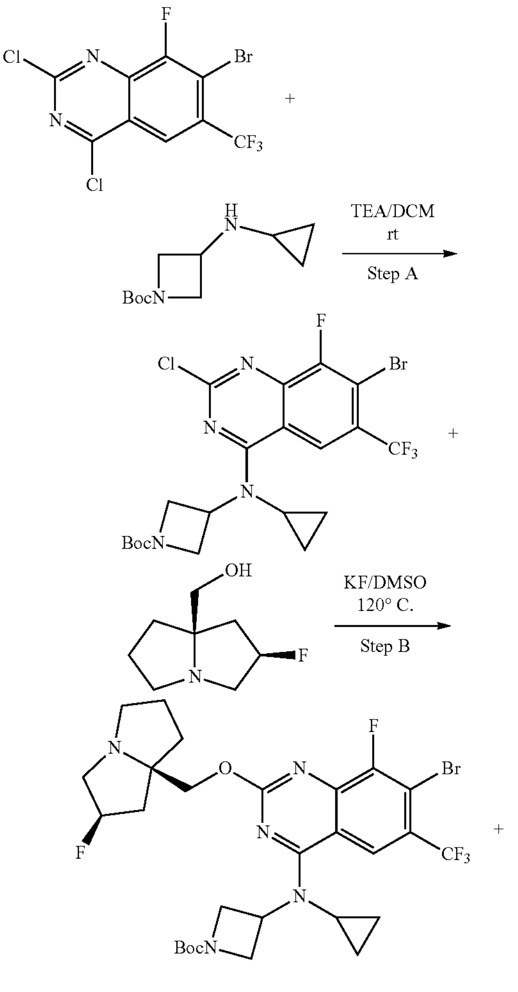

-continued

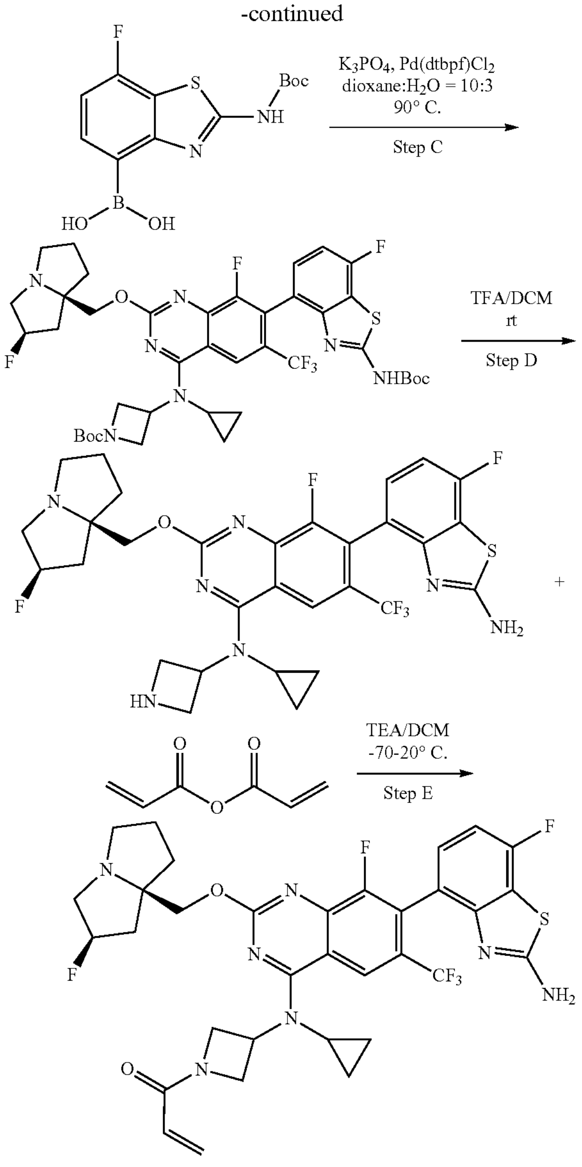

Compound 178

Step A: Preparation of tert-butyl 3-((7-bromo-2-chloro-8-fluoro-6-(trifluoromethyl)quinazolin-4-yl)(cyclopropyl)amino)azetidine-1-carboxylate: To a solution of 7-bromo-2,4-dichloro-8-fluoro-6-(trifluoromethyl)quinazoline (200 mg, 0.55 mmol), triethylamine (0.23 mL, 1.65 mmol) in DCM (5 mL) was added tert-butyl 3-(cyclopropylamino)azetidine-1-carboxylate (117 mg, 0.55 mmol) at ambient temperature. The reaction was stirred at ambient temperature for 2 hours. The reaction was concentrated to dryness and then purified by preparative-TLC (20% EtOAc in petroleum ether) to afford tert-butyl 3-[[7-bromo-2-chloro-8-fluoro-6-(trifluoromethyl)quinazolin-4-yl]-cyclopropyl-amino]azetidine-1-carboxylate (151 mg, 51%). LCMS ESI (+) m/z 539.0 (M+H).

Step B: Preparation of tert-butyl 3-((7-bromo-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidine-1-carboxylate: To a solution of tert-butyl 3-[[7-bromo-2-chloro-8-fluoro-6-(trifluoromethyl)quinazolin-4-yl]-cyclopropyl-amino]azetidine-1-carboxylate (151 mg, 0.28 mmol), ((2R,7aR)-2-fluorotetrahydro-1H-pyrrolizin-7a(5H)-yl)methanol (130 mg, 0.84 mmol) in DMSO (2 mL) was added potassium fluoride (130 mg, 2.24 mmol) at ambient temperature. The reaction was stirred at 90° C. for 2 hours. Once cooled to ambient temperature, the reaction was taken up in EtOAc (20 mL) and the organics washed with 2×10 mL water then 1×10 mL saturated brine solution. The organics were then separated, dried ($MgSO_4$) and concentrated under reduced pressure. The crude was then purified by preparative-TLC (DCM/MeOH=20:1) to afford tert-butyl 3-((7-bromo-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidine-1-carboxylate (59 mg, 31%). LCMS ESI (+) m/z 662.2 (M+H).

Step C: Preparation of tert-butyl 3-((7-(2-((tert-butoxycarbonyl)amino)-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidine-1-carboxylate: To a solution of tert-butyl 3-((7-bromo-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidine-1-carboxylate (59 mg, 0.089 mmol), (2-amino-7-fluoro-1,3-benzothiazol-4-yl)boronic acid (19 mg, 0.089 mmol), potassium phosphate (28 mg, 0.13 mmol) in 1,4-dioxane (2 mL) and water (0.60 mL) was added Pd(dtbpf)$Cl_2$ (5.8 mg, 0.0089 mmol) at ambient temperature. After bubbling with nitrogen for 2 minutes, the reaction was stirred at 90° C. for 2 hours. Once cooled to ambient temperature, reaction was diluted with EtOAc (10 mL) and the organics washed with water then with saturated brine solution. The organics were then separated, dried ($MgSO_4$) and concentrated under reduced pressure. The crude was then purified by preparative-TLC (DCM:MeOH=20:1) to afford tert-butyl 3-((7-(2-((tert-butoxycarbonyl)amino)-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidine-1-carboxylate (37 mg, 49%). LCMS ESI (+) m/z 850.3 (M+H).

Step D: Preparation of 4-(4-(azetidin-3-yl(cyclopropyl)amino)-8-fluoro-2-(((2R,7aR)-2-fluorotetrahydro-1H-pyrrolizin-7a(5H)-yl)methoxy)-6-(trifluoromethyl)quinazolin-7-yl)-7-fluorobenzo[d]thiazol-2-amine: To a solution of tert-butyl 3-((7-(2-((tert-butoxycarbonyl)amino)-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidine-1-carboxylate (37 mg, 0.044 mmol) in DCM (4 mL) was added Trifluoroacetic acid (1.0 mL, 13.0 mmol) at ambient temperature and stirred at ambient temperature for 1 hour. The reaction solution was concentrated under reduced pressure to afford 4-(4-(azetidin-3-yl(cyclopropyl)amino)-8-fluoro-2-(((2R,7aR)-2-fluorotetrahydro-1H-pyrrolizin-7a(5H)-yl)methoxy)-6-(trifluoromethyl)quinazolin-7-yl)-7-fluorobenzo[d]thiazol-2-amine (20 mg, 71%) which was used directly in the next step. LCMS ESI (+) m/z 650.2 (M+H).

Step E: Preparation of 1-(3-((7-(2-amino-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidin-1-yl)prop-2-en-1-one: To a solution of 4-(4-(azetidin-3-yl(cyclopropyl)amino)-8-fluoro-2-(((2R,7aR)-2-fluorotetrahydro-1H-pyrrolizin-7a(5H)-yl)methoxy)-6-(trifluoromethyl)quinazolin-7-yl)-7-fluorobenzo[d]thiazol-2-amine (20 mg, 0.031 mmol), Triethyl amine (0.043 mL, 0.31 mmol) in DCM (2 mL) was added prop-2-enoyl prop-2-enoate (4.7 mg, 0.037 mmol) in DCM dropwise at −60° C. under Ar.

After addition, the reaction mixture was warmed to ambient temperature and stirred at ambient temperature for 1 hour. The reaction mixture was diluted with DCM (10 mL) and the organics washed with water and brine. The organics were then separated, dried ($MgSO_4$) before concentration to dryness. The crude was then purified by preparative RP-HPLC to afford 1-(3-((7-(2-amino-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)(cyclopropyl)amino)azetidin-1-yl)prop-2-en-1-one (1.5 mg, 7%). LCMS ESI (+) m/z 704.2 (M+H). $^1$HNMR (400 MHz, $CD_3OD$): δ 8.85 (s, 1H), 7.17-7.23 (m, 1H), 6.99 (t, J=8.79 Hz, 1H), 6.37-6.46 (m, 1H), 6.29 (d, J=16.77 Hz, 1H), 5.78 (d, J=10.38 Hz, 1H), 5.50 (d, J=25.96 Hz, 1H), 4.70-4.76 (m, 4H), 4.48-4.52 (m, 1H), 4.27-4.38 (m, 1H), 3.99-4.04 (m, 1H), 3.41-3.55 (m, 2H), 2.65-2.75 (m, 1H), 2.12-2.51 (m, 5H), 1.34-1.41 (m, 2H), 1.08 (d, J=6.19 Hz, 2H), 0.72-0.76 (m, 2H).

Synthetic Example 25: Synthesis of 1-((3R)-3-((7-(2-amino-7-fluorobenzo[d]thiazol-4-yl)-6-chloro-8-fluoro-2-(((2R,7aS)-2-fluorotetrahydro-1H-pyrrolizin-7a(5H)-yl)methoxy)quinazolin-4-yl)(methyl)amino)pyrrolidin-1-yl)prop-2-en-1-one (Compound 195)

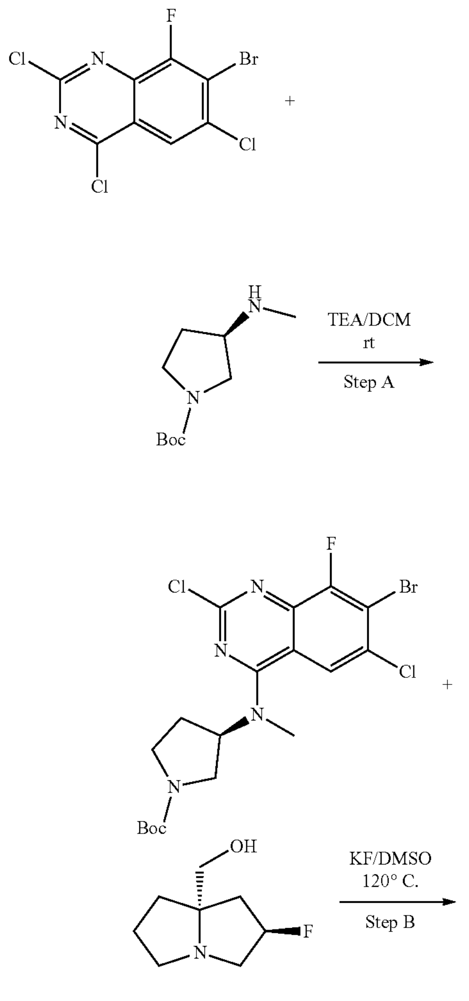

-continued

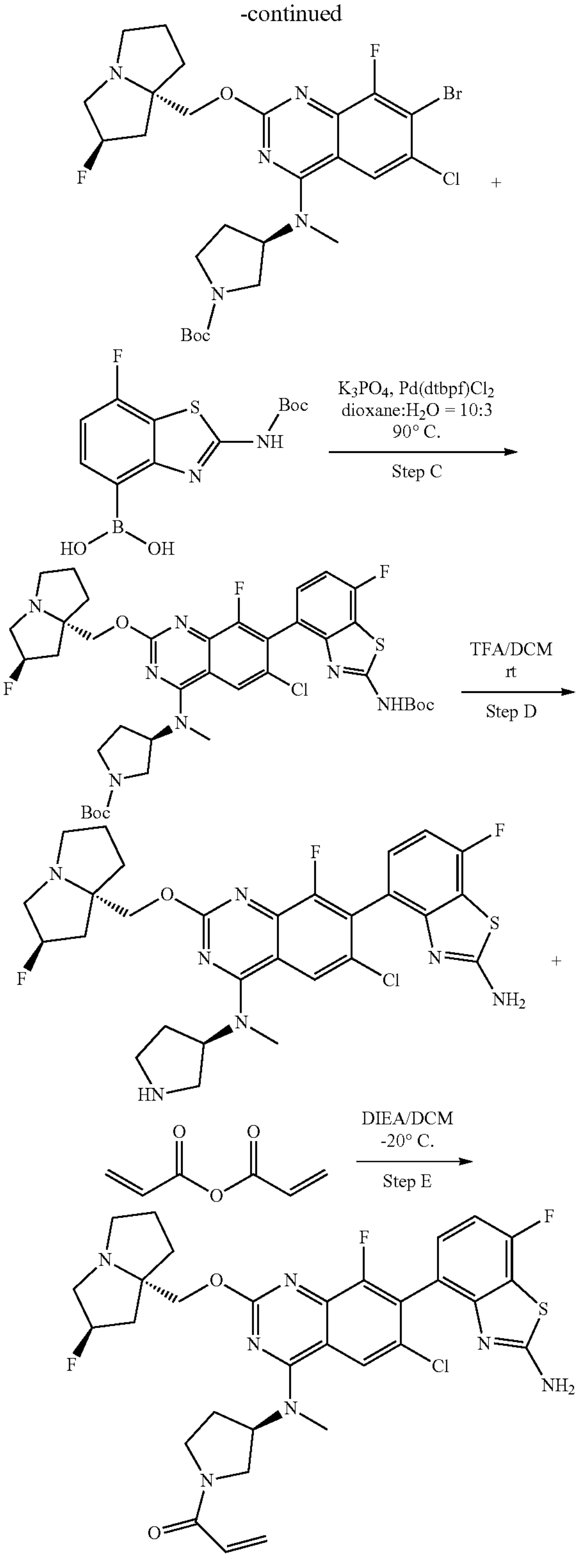

Compound 195

Step A: Preparation of tert-butyl (R)-3-((7-bromo-2,6-dichloro-8-fluoroquinazolin-4-yl)(methyl)amino)pyrrolidine-1-carboxylate: To a solution of 7-bromo-2,4,6-trichloro-8-fluoro-quinazoline (200 mg, 0.61 mmol) and triethyl amine (0.84 mL, 6.05 mmol) in DCM (8 mL) was added tert-butyl (R)-3-(methylamino)pyrrolidine-1-carboxylate (133 mg, 0.67 mmol) at ambient temperature. The reaction was stirred at ambient temperature for 12 hours. The mixture was concentrated to dryness under vacuum and the residue was purified directly on silica gel column, eluting with 30% EtOAc in petroleum ether to give tert-butyl (R)-3-((7-bromo-2,6-dichloro-8-fluoroquinazolin-4-yl)(methyl)amino)pyrrolidine-1-carboxylate (250 mg, 84%). LCMS ESI (+) m/z 493.0 (M+H).

Step B: Preparation of tert-butyl (R)-3-((7-bromo-6-chloro-8-fluoro-2-(((2R,7aS)-2-fluorotetrahydro-1H-pyrrolizin-7a(5H)-yl)methoxy)quinazolin-4-yl)(methyl)amino)pyrrolidine-1-carboxylate: To a solution of tert-butyl (R)-3-((7-bromo-2,6-dichloro-8-fluoroquinazolin-4-yl)(methyl)amino)pyrrolidine-1-carboxylate (100 mg, 0.20 mmol), ((2R,7aS)-2-fluorotetrahydro-1H-pyrrolizin-7a(5H)-yl)methanol (64 mg, 0.41 mmol) in DMSO (2 mL) was added potassium fluoride (94 mg, 1.62 mmol) at ambient temperature. The reaction was stirred at 90° C. for 2 hours. Once cooled to ambient temperature, the reaction was taken up in EtOAc (20 mL) and the organics washed with water and saturated brine solution. The organics were then separated, dried ($MgSO_4$), filtered and concentrated under reduced pressure. The crude was then purified by preparative-TLC (70% EtOAc in petroleum ether) to afford tert-butyl (R)-3-((7-bromo-6-chloro-8-fluoro-2-(((2R,7aS)-2-fluorotetrahydro-1H-pyrrolizin-7a(5H)-yl)methoxy)quinazolin-4-yl)(methyl)amino)pyrrolidine-1-carboxylate (40 mg, 32%). LCMS ESI (+) m/z 616.1 (M+H).

Step C: Preparation of tert-butyl (3R)-3-((7-(2-((tert-butoxycarbonyl)amino)-7-fluorobenzo[d]thiazol-4-yl)-6-chloro-8-fluoro-2-(((2R,7aS)-2-fluorotetrahydro-1H-pyrrolizin-7a(5H)-yl)methoxy)quinazolin-4-yl)(methyl)amino)pyrrolidine-1-carboxylate: To a solution of tert-butyl (R)-3-((7-bromo-6-chloro-8-fluoro-2-(((2R,7aS)-2-fluorotetrahydro-1H-pyrrolizin-7a(5H)-yl)methoxy)quinazolin-4-yl)(methyl)amino)pyrrolidine-1-carboxylate (40 mg, 0.065 mmol), [2-(tert-butoxycarbonylamino)-7-fluoro-1,3-benzothiazol-4-yl]boronic acid (22 mg, 0.071 mmol) in 1,4-dioxane (1 mL)/water (0.30 mL) was added Pd(dtbpf)$Cl_2$ (3.4 mg, 0.0052 mmol) and potassium phosphate (41 mg, 0.20 mmol) at ambient temperature. After bubbling with Argon for 2 minutes, the reaction was stirred at 90° C. for 1 hour. Once cooled to ambient temperature, the reaction was diluted with ethyl acetate (10 mL) and the organics washed with water then with saturated brine solution. The organics were then separated, dried ($MgSO_4$) and concentrated under reduced pressure. The crude was then purified by preparative-TLC (DCM:MeOH=10:1) to give tert-butyl (3R)-3-((7-(2-((tert-butoxycarbonyl)amino)-7-fluorobenzo[d]thiazol-4-yl)-6-chloro-8-fluoro-2-(((2R,7aS)-2-fluorotetrahydro-1H-pyrrolizin-7a(5H)-yl)methoxy)quinazolin-4-yl)(methyl)amino)pyrrolidine-1-carboxylate (25 mg, 48%). LCMS ESI (+) m/z 804.2 (M+H).

Step D: Preparation of 4-(6-chloro-8-fluoro-2-(((2R,7aS)-2-fluorotetrahydro-1H-pyrrolizin-7a(5H)-yl)methoxy)-4-(methyl((R)-pyrrolidin-3-yl)amino)quinazolin-7-yl)-7-fluorobenzo[d]thiazol-2-amine: To a solution of tert-butyl (3R)-3-((7-(2-((tert-butoxycarbonyl)amino)-7-fluorobenzo[d]thiazol-4-yl)-6-chloro-8-fluoro-2-(((2R,7aS)-2-fluorotetrahydro-1H-pyrrolizin-7a(5H)-yl)methoxy)quinazolin-4-yl)(methyl)amino)pyrrolidine-1-carboxylate (30 mg, 0.037 mmol) in DCM (3 mL) was added trifluoroacetic acid (0.23 mL, 2.93 mmol). The reaction was stirred at ambient temperature for 4 hours. The reaction solution was concentrated under reduced pressure to afford 4-(6-chloro-8-fluoro-2-(((2R,7aS)-2-fluorotetrahydro-1H-pyrrolizin-7a(5H)-yl)methoxy)-4-(methyl((R)-pyrrolidin-3-yl)amino)quinazolin-7-yl)-7-fluorobenzo[d]thiazol-2-amine which was used directly in the next step. LCMS ESI (+) m/z 604.2 (M+H).

Step E: Preparation of 1-((3R)-3-((7-(2-amino-7-fluorobenzo[d]thiazol-4-yl)-6-chloro-8-fluoro-2-(((2R,7aS)-2-fluorotetrahydro-1H-pyrrolizin-7a(5H)-yl)methoxy)quinazolin-4-yl)(methyl)amino)pyrrolidin-1-yl)prop-2-en-1-one: To a solution of 4-(6-chloro-8-fluoro-2-(((2R,7aS)-2-fluorotetrahydro-1H-pyrrolizin-7a(5H)-yl)methoxy)-4-(methyl((R)-pyrrolidin-3-yl)amino)quinazolin-7-yl)-7-fluorobenzo[d]thiazol-2-amine (35 mg, 0.043 mmol) and DIEA (0.038 mL, 0.22 mmol) in DCM (3 mL) was added prop-2-enoyl prop-2-enoate (4.4 mg, 0.035 mmol) in DCM dropwise at −20° C. under Ar and stirred at −20° C. for 1 hour. The reaction was quenched with water (20 mL) and extracted with EtOAc. The organics were then separated, dried ($MgSO_4$), filtered, and concentrated to dryness. The crude was then purified by preparative RPHPLC to afford 1-((3R)-3-((7-(2-amino-7-fluorobenzo[d]thiazol-4-yl)-6-chloro-8-fluoro-2-(((2R,7aS)-2-fluorotetrahydro-1H-pyrrolizin-7a(5H)-yl)methoxy)quinazolin-4-yl)(methyl)amino)pyrrolidin-1-yl)prop-2-en-1-one (5.1 mg, 20%). LCMS ESI (+) m/z 658.2 (M+H). $^1$HNMR (400 MHz, $CD_3OD$): δ 8.15 (s, 1H), 7.26 (dd, J=7.6, 5.6 Hz, 1H), 7.04 (t, J=8.8 Hz, 1H), 6.61-6.69 (m, 1H), 6.32 (d, J=16.8 Hz, 1H), 5.75-5.81 (m, 1H), 5.56 (d, J=51.6 Hz, 1H), 4.69-4.75 (m, 2H), 4.01-4.30 (m, 2H), 3.85-3.99 (m, 4H), 3.40-3.65 (m, 5H), 2.47-2.75 (m, 3H), 2.28-2.47 (m, 4H), 2.10-2.22 (m, 1H).

Synthetic Example 26: Synthesis of 1-((2R,5S)-4-(7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (Compound 202)

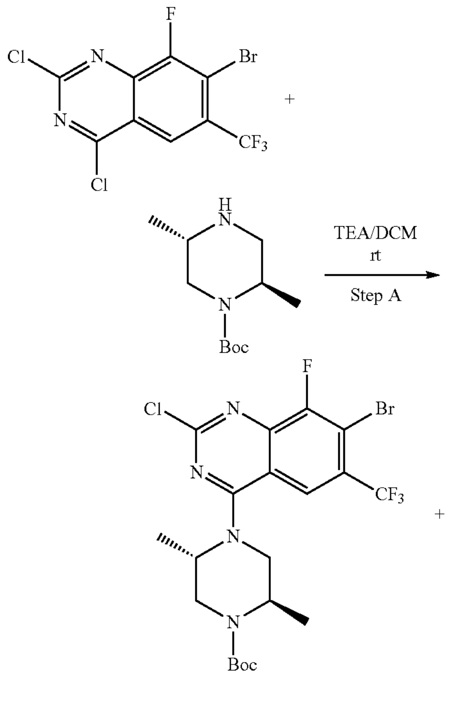

-continued

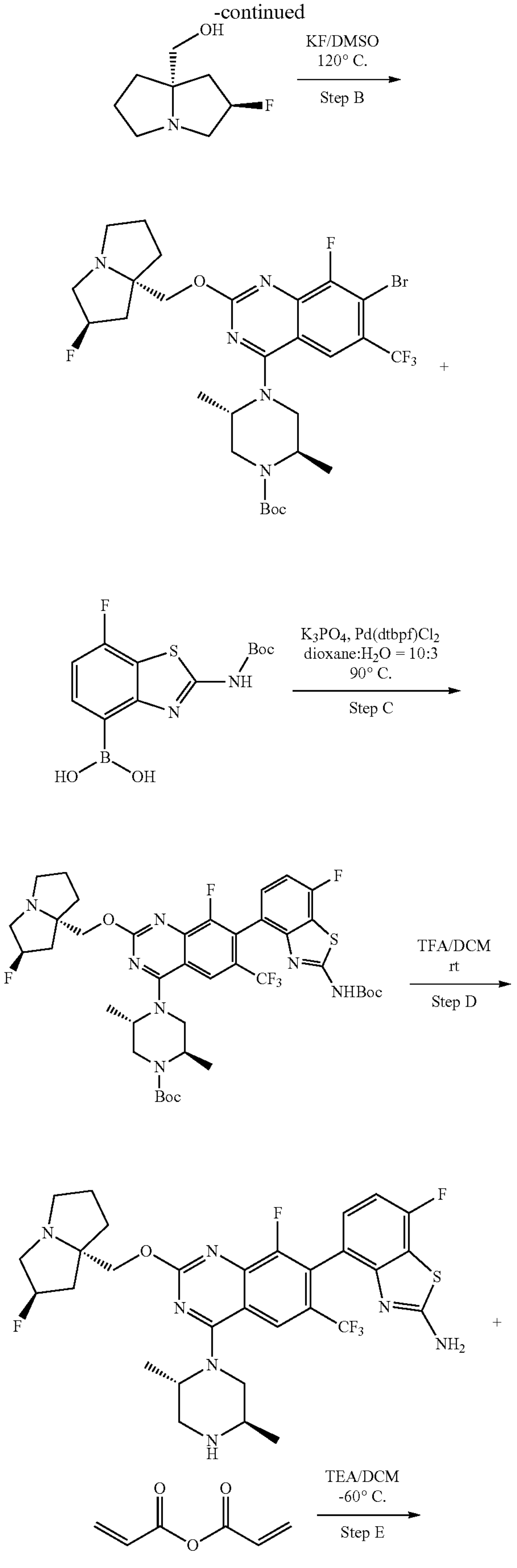

-continued

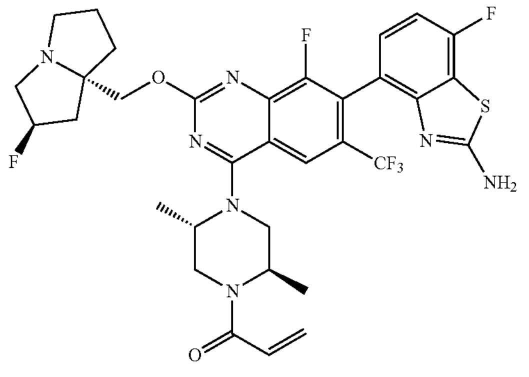

Compound 202

Step A: Preparation of tert-butyl (2R,5S)-4-(7-bromo-2-chloro-8-fluoro-6-(trifluoromethyl)quinazolin-4-yl)-2,5-dimethylpiperazine-1-carboxylate: To a solution of 7-bromo-2,4-dichloro-8-fluoro-6-(trifluoromethyl)quinazoline (300 mg, 0.83 mmol) and triethylamine (251 mg, 2.49 mmol) in DCM (5 mL) was added tert-butyl (2R,5S)-2,5-dimethylpiperazine-1-carboxylate (210 mg, 0.99 mmol) at ambient temperature. The reaction was stirred at ambient temperature for 2 hours. The mixture was concentrated to dry under vacuum and the residue was purified preparative-TLC (20% EtOAc in petroleum ether) to give tert-butyl (2R,5S)-4-(7-bromo-2-chloro-8-fluoro-6-(trifluoromethyl)quinazolin-4-yl)-2,5-dimethylpiperazine-1-carboxylate (270 mg, 60%). LCMS ESI (+) m/z 541.1 (M+H).

Step B: Preparation of tert-butyl (2R,5S)-4-(7-bromo-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-(7-bromo-2-chloro-8-fluoro-6-(trifluoromethyl)quinazolin-4-yl)-2,5-dimethylpiperazine-1-carboxylate (270 mg, 0.50 mmol) and ((2R,7aS)-2-fluorotetrahydro-1H-pyrrolizin-7a(5H)-yl)methanol (95.4 mg, 0.60 mmol) in DMSO (3 mL) was added potassium fluoride (232 mg, 4.0 mmol) at ambient temperature. The reaction was stirred at 90° C. for 2 hours. Once cooled to ambient temperature, the reaction was taken up in EtOAc (20 mL) and the organic layers washed with water and saturated brine solution. The organic layers were then separated, dried ($MgSO_4$), filtered and concentrated under reduced pressure. The crude was then purified by preparative-TLC (DCM:MeOH=20:1) to afford tert-butyl (2R,5S)-4-(7-bromo-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (140 mg, 41%). LCMS ESI (+) m/z 664.2 (M+H).

Step C: Preparation of tert-butyl (2R,5S)-4-(7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-(7-bromo-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (140 mg, 0.211 mmol) and [2-(tert-butoxycarbonylamino)-7-fluoro-1,3-benzothiazol-4-yl]boronic acid (79 mg, 0.253 mmol) in water (0.80 mL) and 1,4-dioxane (3 mL) was added Pd(dtbpf)$Cl_2$ (11.0 mg, 0.017 mmol) and potassium phosphate (89 mg, 0.42 mmol) at ambient temperature. After bubbling with argon for 2 minutes, the reaction mixture was stirred at 90° C. for 1 hour. Once cooled to ambient temperature, the reaction mixture was diluted with ethyl acetate (10 mL) and the organic layers washed with water then with saturated brine solution. The organic layers were then separated, dried ($MgSO_4$) and concentrated under reduced pressure. The crude was then purified by flash chromatography on silica gel to give tert-butyl (2R,5S)-4-(7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (110 mg, 62%). LCMS ESI (+) m/z 852.3 (M+H).

Step D: Preparation of 4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine: To a solution of tert-butyl (2R,5S)-4-(7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (80 mg, 0.094 mmol) in DCM (4 mL) was added trifluoroacetic acid (1.0 mL, 13.0 mmol) at ambient temperature and stirred at ambient temperature for 1 hour. The reaction solution was concentrated under reduced pressure to afford 4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine which was used directly in the next step. LCMS ESI (+) m/z 652.2 (M+H).

Step E: Preparation of 1-((2R,5S)-4-(7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one: To a solution of 4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine (35 mg, 0.043 mmol) and N,N-diisopropylethylamine (0.024 mL, 0.14 mmol) in DCM (3 mL) was added prop-2-enoyl prop-2-enoate (7.0 mg, 0.055 mmol) in DCM dropwise at −70° C. under Ar. The reaction mixture was stirred at −70° C. for 3 hours. The reaction was quenched with aqueous sodium bicarbonate solution and extracted with DCM. The organic layers were then separated, dried ($MgSO_4$), filtered, and concentrated to dryness. The crude was then purified by preparative RP-HPLC to afford 1-((2R,5S)-4-(7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (8.4 mg, 26%). LCMS ESI (+) m/z 706.2 (M+H). $^1$HNMR (400 MHz, $CD_3OD$): δ 8.20 (s, 1H), 7.21-7.25 (m, 1H), 6.99-7.04 (m, 1H), 6.76-6.89 (m, 1H), 6.27-6.33 (m, 1H), 5.81-5.85 (m, 1H), 5.49-5.63 (m, 1H), 4.92-5.02 (m, 3H), 4.69 (s, 2H), 4.30-4.41 (m, 1H), 3.83-4.05 (m, 5H), 3.43-3.51 (m, 1H), 2.16-2.75 (m, 6H), 1.24-1.53 (m, 6H).

Synthetic Example 27: Synthesis of 1-((2R,5S)-4-(7-(2-amino-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (Compound 204)

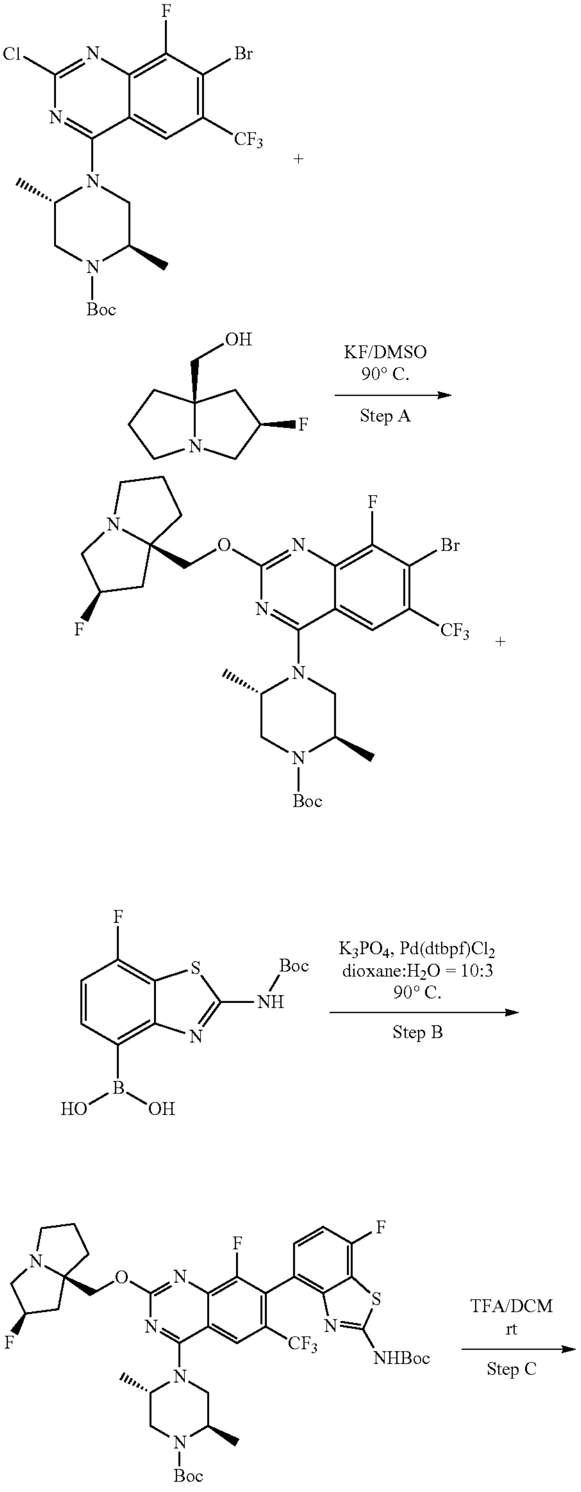

-continued

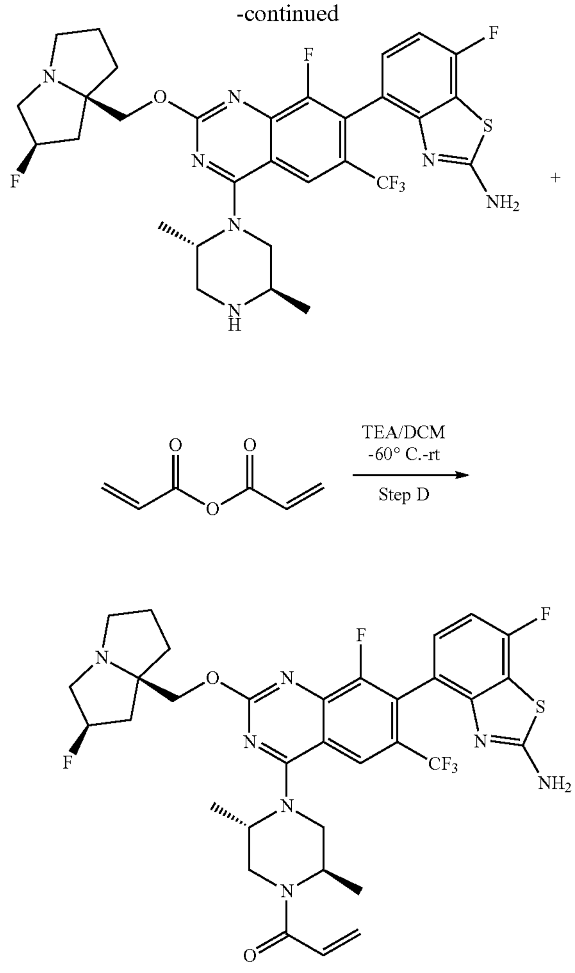

Compound 204

Step A: Preparation of tert-butyl (2R,5S)-4-(7-bromo-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-(7-bromo-2-chloro-8-fluoro-6-(trifluoromethyl)quinazolin-4-yl)-2,5-dimethylpiperazine-1-carboxylate (240 mg, 0.43 mmol), ((2R,7aR)-2-fluorotetrahydro-1H-pyrrolizin-7a(5H)-yl)methanol (211.6 mg, 1.33 mmol) in DMSO (2.5 mL) was added potassium fluoride (205.9 mg, 3.54 mmol) at ambient temperature. The reaction was stirred at 90° C. for 2 hours. Once cooled to ambient temperature, the reaction was taken up in EtOAc (20 mL) and the organics washed with water and saturated brine solution. The organics were then separated, dried ($MgSO_4$), filtered and concentrated under reduced pressure. The crude was then purified by flash chromatography on silica gel (70% EtOAc in petroleum ether) to afford tert-butyl (2R,5S)-4-(7-bromo-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazine-1-carboxylate (120 mg, 41%). LCMS ESI (+) m/z 664.2 (M+H).

Step B: Preparation of tert-butyl (2R,5S)-4-(7-(2-((tert-butoxycarbonyl)amino)-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of (2R,5S)-4-(7-bromo-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazine-1-carboxylate (120 mg, 0.18 mmol), [2-(tert-butoxycarbonylamino)-7-fluoro-1,3-benzothiazol-4-yl]boronic acid (1.10 eq, 40 mg, 0.128 mmol) (56.4 mg, 0.18 mmol), potassium phosphate (76.7 mg, 0.36 mmol) in 1,4-dioxane (5 mL) and water (1.60 mL) was added Pd(dtbpf)$Cl_2$ (11.8 mg, 0.018 mmol) at ambient temperature. After bubbling with argon for 2 minutes, the reaction was stirred at 90° C. for 2 hours. Once cooled to ambient temperature, reaction was diluted with ethyl acetate (10 mL) and the organics washed with water then with saturated brine solution. The organics were then separated, dried ($MgSO_4$), and concentrated under reduced pressure. The crude was then purified by preparative-TLC (70% EtOAc in petroleum ether) to afford tert-butyl (2R,5S)-4-(7-(2-((tert-butoxycarbonyl)amino)-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazine-1-carboxylate (100 mg, 65%). LCMS ESI (+) m/z 852.3 (M+H).

Step C: Preparation of 4-(4-((2S,5R)-2,5-dimethylpiperazin-1-yl)-8-fluoro-2-(((2R,7aR)-2-fluorotetrahydro-1H-pyrrolizin-7a(5H)-yl)methoxy)-6-(trifluoromethyl)quinazolin-7-yl)-7-fluorobenzo[d]thiazol-2-amine: To a solution of (2R,5S)-4-(7-(2-((tert-butoxycarbonyl)amino)-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazine-1-carboxylate (100 mg, 0.12 mmol) in DCM (4 mL) was added trifluoroacetic acid (1.0 mL, 13.0 mmol) at ambient temperature and stirred at ambient temperature for 1 hour. The reaction solution was concentrated under reduced pressure to afford 4-(4-((2S,5R)-2,5-dimethylpiperazin-1-yl)-8-fluoro-2-(((2R,7aR)-2-fluorotetrahydro-1H-pyrrolizin-7a(5H)-yl)methoxy)-6-(trifluoromethyl)quinazolin-7-yl)-7-fluorobenzo[d]thiazol-2-amine (70 mg, 98%) which was used directly in the next step. LCMS ESI (+) m/z 652.2 (M+H).

Step D: Preparation of 1-((2R,5S)-4-(7-(2-amino-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one: To a solution of 4-(4-((2S,5R)-2,5-dimethylpiperazin-1-yl)-8-fluoro-2-(((2R,7aR)-2-fluorotetrahydro-1H-pyrrolizin-7a(5H)-yl)methoxy)-6-(trifluoromethyl)quinazolin-7-yl)-7-fluorobenzo[d]thiazol-2-amine (30 mg, 0.047 mmol), triethylamine (61.2 mg, 0.47 mmol) in DCM (3 mL) was added prop-2-enoyl prop-2-enoate (5.97 mg, 0.047 mmol) in DCM dropwise at −60° C. under Ar. After addition, the mixture was warmed to ambient temperature and stirred at ambient temperature for 1 hour. The reaction was diluted with DCM. The organics were washed with water, brine, dried ($MgSO_4$), filtered and concentrated to dryness. The crude was then purified by preparative RP-HPLC to afford 1-((2R,5S)-4-(7-(2-amino-7-fluorobenzo[d]thiazol-4-yl)-8-fluoro-2-(((2R,7aR)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (4.87 mg, 15%). LCMS ESI (+) m/z 706.2 (M+H). $^1$HNMR (400 MHz, $CD_3OD$): δ 8.20 (s, 1H), 7.24-7.29 (m, 1H), 7.05 (t, J=9.08 Hz, 1H), 6.75-6.86 (m, 1H), 6.26-6.32 (m, 1H), 5.80-5.84 (m, 1H), 5.44-5.57 (m, 1H), 4.69-4.81 (m, 3H), 4.30-4.54 (m, 2H), 3.86-4.07 (m, 4H), 3.43-3.69 (m, 4H), 2.13-2.75 (m, 7H), 1.48-1.53 (m, 3H), 1.28-1.37 (m, 3H).

Synthetic Example 28: Synthesis of 1-((2R,5S)-4-(7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)-2,5-dimethylpiperazin-1-yl)prop-2-en-1-one (Compound 235)

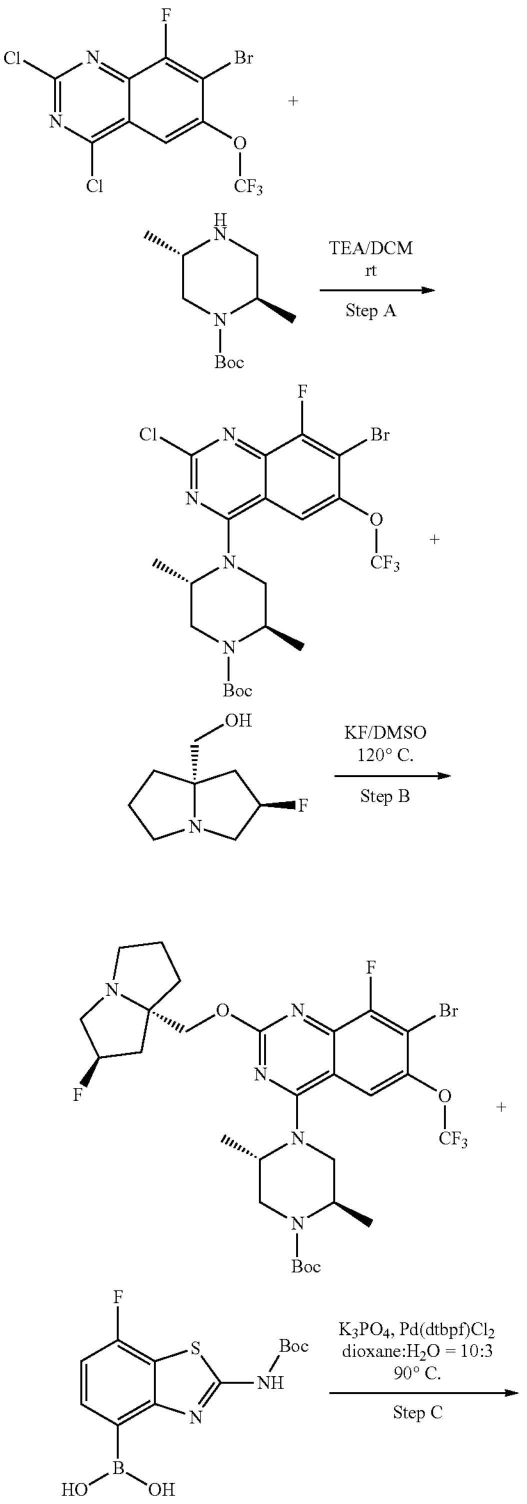

-continued

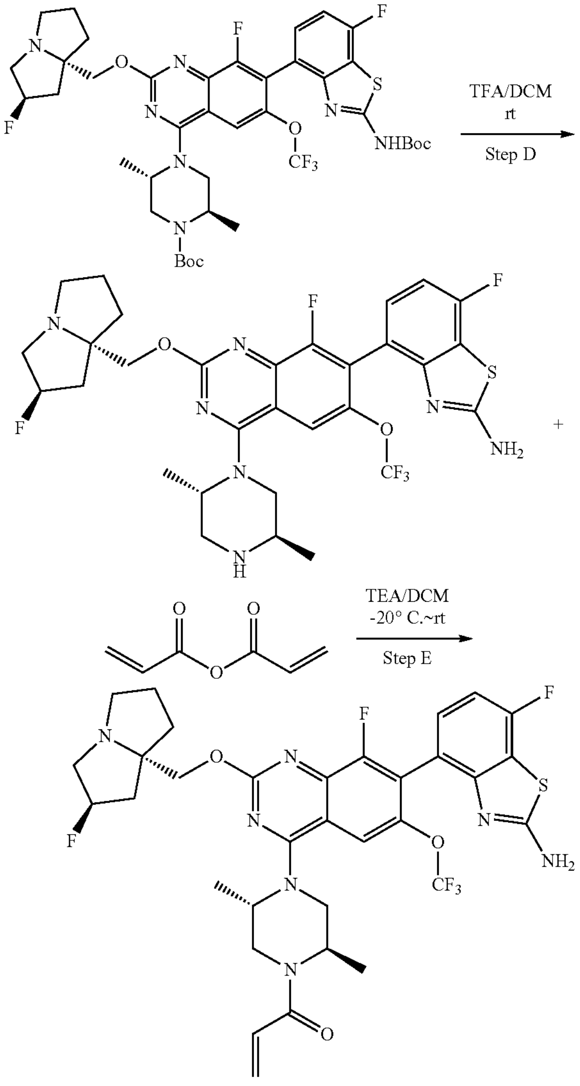

Compound 235

Step A: Preparation of tert-butyl (2R,5S)-4-[7-bromo-2-chloro-8-fluoro-6-(trifluoromethoxy)quinazolin-4-yl]-2,5-dimethyl-piperazine-1-carboxylate: To a solution of 7-bromo-2,4-dichloro-8-fluoro-6-(trifluoromethoxy)quinazoline (200 mg, 0.53 mmol) and triethyl amine (0.22 mL, 1.59 mmol) in DCM (5 mL) was added tert-butyl (2R,5S)-2,5-dimethylpiperazine-1-carboxylate (136 mg, 0.63 mmol) at ambient temperature. The reaction was stirred at ambient temperature for 2 hours. The mixture was concentrated to dry under vacuum and the residue was purified preparative-TLC (10% EtOAc in petroleum ether) to give tert-butyl (2R,5S)-4-[7-bromo-2-chloro-8-fluoro-6-(trifluoromethoxy)quinazolin-4-yl]-2,5-dimethyl-piperazine-1-carboxylate (150 mg, 51%). LCMS ESI (+) m/z 557.0 (M+H).

Step B: Preparation of tert-butyl (2R,5S)-4-(7-bromo-8-fluoro-2-(((2R,7aS)-2-fluorotetrahydro-1H-pyrrolizin-7a(5H)-yl)methoxy)-6-(trifluoromethoxy)quinazolin-4-yl)-2,5-dimethylpiperazine-1-carboxylate: To a solution of tert-butyl (2R,5S)-4-[7-bromo-2-chloro-8-fluoro-6-(trifluoromethoxy)quinazolin-4-yl]-2,5-dimethyl-piperazine-1-carboxylate (150 mg, 0.27 mmol) and ((2R,7aS)-2-fluorotetrahydro-1H-pyrrolizin-7a(5H)-yl)methanol (51 mg, 0.32 mmol) in DMSO (1 mL) was added potassium fluoride (94 mg, 1.62 mmol) at ambient temperature. The reaction was stirred at 120° C. for 6 hours. Once cooled to ambient temperature, the reaction was taken up in EtOAc (20 mL) and the organics were washed with water and saturated brine solution. The organics were then separated, dried ($MgSO_4$), filtered and concentrated under reduced pressure. The crude was then purified by preparative-TLC (DCM/MeOH=30/1) to afford tert-butyl (2R,5S)-4-(7-bromo-8-fluoro-2-(((2R,7aS)-2-fluorotetrahydro-1H-pyrrolizin-7a(5H)-yl)methoxy)-6-(trifluoromethoxy)quinazolin-4-yl)-2,5-dimethylpiperazine-1-carboxylate (75 mg, 41%). LCMS ESI (+) m/z 680.1 (M+H).

Step C: Preparation of tert-butyl (2R,5S)-4-(7-(2-((tert-butoxycarbonyl)-12-azaneyl)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy) quinazolin-4-yl)-2,5-dimethylpiperazine-1-carboxylate: To a solution of tert-butyl (2R,5S)-4-(7-bromo-8-fluoro-2-(((2R,7aS)-2-fluorotetrahydro-1H-pyrrolizin-7a(5H)-yl) methoxy)-6-(trifluoromethoxy)quinazolin-4-yl)-2,5-dimethylpiperazine-1-carboxylate (79 mg, 0.12 mmol), [2-(tert-butoxycarbonylamino)-7-fluoro-1,3-benzothiazol-4-yl] boronic acid (40 mg, 0.13 mmol), potassium phosphate (74 mg, 0.35 mmol) in 1,4-dioxane (1 mL) and water (0.30 mL) was added Pd(dtbpf)$Cl_2$ (6.1 mg, 0.0093 mmol) at ambient temperature. After bubbling with argon for 2 minutes, the reaction was stirred at 90° C. for 1 hour. Once cooled to ambient temperature, reaction was diluted with ethyl acetate (10 mL) and the organics washed with water then with saturated brine solution. The organics were then separated, dried ($MgSO_4$), and concentrated under reduced pressure. The crude was then purified by preparative-TLC (DCM/MeOH=10/1) to afford tert-butyl (2R,5S)-4-(7-(2-((tert-butoxycarbonyl)-12-azaneyl)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)-2,5-dimethylpiperazine-1-carboxylate (60 mg, 67%). LCMS ESI (+) m/z 868.4 (M+H).

Step D: Preparation of 4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethoxy)quinazolin-7-yl)-7-fluorobenzo[d]thiazol-2-amine: To a solution of tert-butyl (2R,5S)-4-(7-(2-((tert-butoxycarbonyl)-12-azaneyl)-7-fluorobenzo[d]thiazol-4-yl)-8-fluoro-2-(((2R,7aS)-2-fluorotetrahydro-1H-pyrrolizin-7a(5H)-yl) methoxy)-6-(trifluoromethoxy)quinazolin-4-yl)-2,5-dimethylpiperazine-1-carboxylate (42 mg, 0.048 mmol) in DCM (3 mL) was added trifluoroacetic acid (1.0 mL, 13.0 mmol) at ambient temperature and stirred at ambient temperature for 4 hours. The reaction solution was concentrated under reduced pressure to afford 4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethoxy) quinazolin-7-yl)-7-fluorobenzo[d]thiazol-2-amine which was used directly in the next step. LCMS ESI (+) m/z 668.3 (M+H).

Step E: Preparation of 1-((2R,5S)-4-(7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)-2,5-dimethylpiperazin-1-yl) prop-2-en-1-one: To a solution of 4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethoxy)quinazolin-7-yl)-7-fluorobenzo[d] thiazol-2-amine (40 mg, 0.060 mmol), triethylamine (0.025 mL, 0.18 mmol) in DCM (3 mL) was added prop-2-enoyl prop-2-enoate (7.6 mg, 0.060 mmol) in DCM dropwise at −20° C. under Ar and stirred −20° C. for 15 minutes. The reaction was quenched with $H_2O$ (10 mL) and extracted with EtOAc. The organics were washed with water, brine, dried ($MgSO_4$), filtered, and concentrated to dryness. The crude was then purified by preparative RP-HPLC to afford 1-((2R, 5S)-4-(7-(2-amino-7-fluorobenzo[d]thiazol-4-yl)-8-fluoro-2-(((2R,7aS)-2-fluorotetrahydro-1H-pyrrolizin-7a(5H)-yl) methoxy)-6-(trifluoromethoxy)quinazolin-4-yl)-2,5-dimethylpiperazin-1-yl)prop-2-en-1-one (11 mg, 27%). LCMS ESI (+) m/z 722.2 (M+H). $^1$HNMR (400 MHz, $CD_3OD$): δ 7.78 (s, 1H), 7.21-7.35 (m, 1H), 7.02 (t, J=8.8 Hz, 1H), 6.67-6.86 (m, 1H), 6.24-6.35 (m, 1H), 5.71-5.80 (m, 1H), 5.58 (d, J=60 Hz, 1H), 4.67-4.85 (m, 2H), 4.25-4.31 (m, 1H), 3.88-4.10 (m, 5H), 3.31-3.49 (m, 3H), 2.62-2.81 (m, 2H), 2.30-2.58 (m, 3H), 2.05-2.15 (m, 1H), 1.39-1.51 (m, 3H), 1.26-1.45 (m, 4H).

Synthetic Example 29: Synthesis of 1-((R)-3-(((S)-7-(2-amino-7-fluorobenzo[d]thiazol-4-yl)-8-fluoro-2-(((2R,7aS)-2-fluorotetrahydro-1H-pyrrolizin-7a (5H)-yl)methoxy)-6-(trifluoromethyl)quinazolin-4-yl)(cyclopropyl)amino)pyrrolidin-1-yl)prop-2-en-1-one (236) and 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl) amino)pyrrolidin-1-yl)prop-2-en-1-one (237)

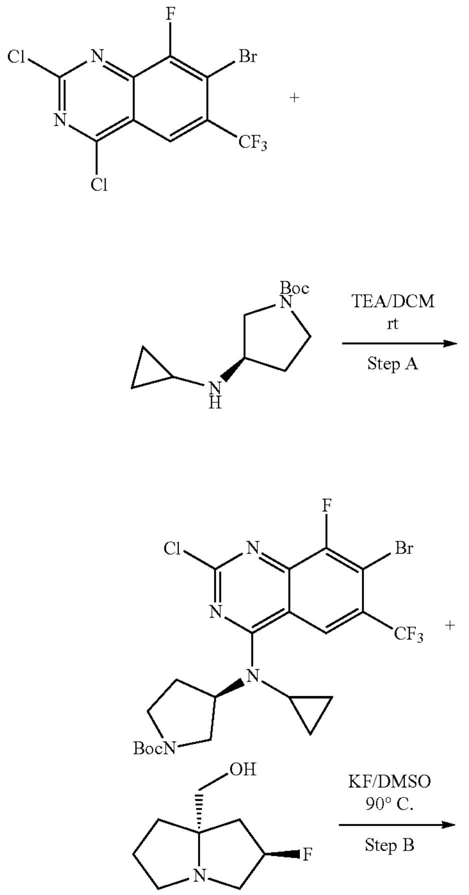

-continued

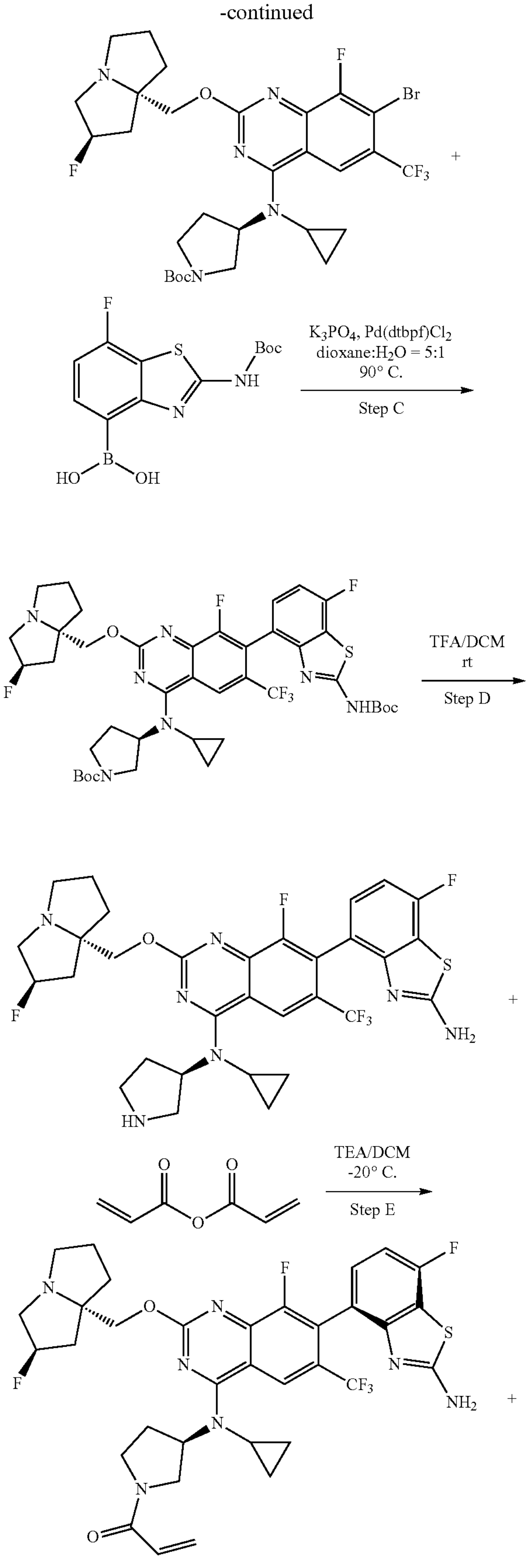

Compound 236

-continued

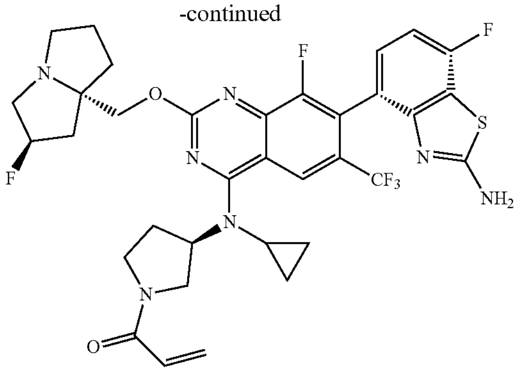

Compound 237

Step A: Preparation of tert-butyl (R)-3-((7-bromo-2-chloro-8-fluoro-6-(trifluoromethyl)quinazolin-4-yl)(cyclopropyl)amino)pyrrolidine-1-carboxylate: To a solution of 7-bromo-2,4-dichloro-8-fluoro-6-(trifluoromethoxy)quinazoline (500 mg, 1.37 mmol) and triethylamine (417.1 mg, 4.12 mmol) in DCM (5 mL) was added tert-butyl (R)-3-(cyclopropylamino)pyrrolidine-1-carboxylate (373 mg, 1.64 mmol) at ambient temperature. The reaction was stirred at ambient temperature for 3 hours. The mixture was concentrated to dry under vacuum and the residue was purified directly on silica gel column, eluting with 30% ethyl acetate in petroleum ether to give tert-butyl (R)-3-((7-bromo-2-chloro-8-fluoro-6-(trifluoromethyl)quinazolin-4-yl)(cyclopropyl)amino)pyrrolidine-1-carboxylate (200 mg, 26%). LCMS ESI (+) m/z 553.1 (M+H).

Step B: Preparation of tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate: To a solution of tert-butyl (R)-3-((7-bromo-2-chloro-8-fluoro-6-(trifluoromethyl)quinazolin-4-yl)(cyclopropyl)amino)pyrrolidine-1-carboxylate (100 mg, 0.18 mmol) and ((2R,7aS)-2-fluorotetrahydro-1H-pyrrolizin-7a(5H)-yl)methanol (43.1 mg, 0.27 mmol) in DMSO (2 mL) was added potassium fluoride (83.5 mg, 1.44 mmol) at ambient temperature. The reaction was stirred at 90° C. for 8 hours. Once cooled to ambient temperature, the reaction was taken up in EtOAc (20 mL) and the organics were washed with saturated brine solution. The organics were then separated, dried ($MgSO_4$), filtered, and concentrated under reduced pressure. The crude was then purified by preparative-TL C (DCM/MeOH=20/1) to afford tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate (42 mg, 350) LCMS ESI (+) m/z 676.2 (M+H).

Step C: Preparation of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate: To a solution of tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate (42 mg, 0.062 mmol), [2-(tert-butoxycarbonylamino)-7-fluoro-1,3-benzothiazol-4-yl]boronic acid (29.1 mg, 0.093 mmol), potassium phosphate (42.2 mg, 0.16 mmol) in 1,4-dioxane (2 mL) and water (0.60 mL) was added Pd(dtbpf)$Cl_2$ (4 mg, 0.0062 mmol) at ambient temperature. After bubbling with argon for 2 minutes, the reaction was stirred at 90° C. for 1 hour. Once cooled to ambient temperature, reaction was diluted with ethyl acetate (10 mL) and the organics washed with water then with saturated brine solution. The organics were then separated, dried ($MgSO_4$) and concentrated under reduced pressure. The crude was then purified by preparative-TLC (DCM/MeOH=20/1) to afford tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate (40 mg, 75%). LCMS ESI (+) m/z 864.4 (M+H).

Step D: Preparation of 4-(4-(cyclopropyl((R)-pyrrolidin-3-yl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine: To a solution of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate (40 mg, 0.046 mmol) in DCM (3 mL) was added trifluoroacetic acid (1.0 mL, 13.0 mmol) at ambient temperature and stirred at ambient temperature for 2 hours. The reaction solution was concentrated under reduced pressure to afford 4-(4-(cyclopropyl((R)-pyrrolidin-3-yl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine which was used directly in the next step. LCMS ESI (+) m/z 664.3 (M+H).

Step E: Preparation of 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidin-1-yl)prop-2-en-1-one (236, one atropisomer) and 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidin-1-yl)prop-2-en-1-one (237, the other atropisomer): To a solution of 4-(4-(cyclopropyl((R)-pyrrolidin-3-yl)amino)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine (40 mg, 0.063 mmol), Triethyl amine (0.044 mL, 0.31 mmol) in DCM (3 mL) was added prop-2-enoyl prop-2-enoate (9.5 mg, 0.076 mmol) in DCM dropwise at −20° C. under Ar and stirred −20° C. for 15 minutes. The reaction was quenched with $H_2O$ (10 mL) and extracted with EtOAc. The organics were washed with brine, dried ($MgSO_4$), filtered, and concentrated to dryness to give a mixture of 2 atropisomers. The crude was then purified by preparative RP-HPLC. The first compound off the column was identified as one atropisomer, 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidin-1-yl)prop-2-en-1-one (236) (6.6 mg, 12%). LCMS ESI (+) m/z 718.3 (M+H). $^1$HNMR (400 MHz, $CD_3OD$) δ 8.78 (d, J=5.6 Hz, 1H), 7.20-7.21 (m, 1H), 6.98-7.00 (m, 1H), 6.67-6.98 (m, 1H), 6.30-6.34 (m, 1H), 5.80-5.90 (m, 1H), 5.48-5.69 (m, 1H), 4.85-5.05 (m, 1H), 4.59-4.65 (m, 2H), 4.23-4.37 (m, 1H), 3.85-4.10 (m, 4H), 3.72-3.75 (m, 1H), 3.57-3.61 (m, 1H), 3.31-3.45 (m, 1H), 2.79-3.05 (m, 1H), 2.56-2.68 (m, 3H), 2.25-2.41 (m, 3H), 1.64 (m, 4H), 1.11-1.29 (m, 2H). The second compound off the column was identified as the other atropisomer, 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidin-1-yl)prop-2-en-1-one (237) (6.0 mg, 11%). LCMS ESI (+) m/z 718.3 (M+H). $^1$HNMR (400 MHz, $CD_3OD$) δ 8.79 (d, J=5.6 Hz, 1H), 7.20-7.24 (m, 1H), 6.98-7.00 (m, 1H), 6.67-6.98 (m, 1H), 6.30-6.34 (m, 1H), 5.80-5.90 (m, 1H), 5.48-5.69 (m, 1H), 4.84-4.98 (m, 1H), 4.59-4.65 (m, 2H), 4.23-4.37 (m, 1H), 3.85-4.10 (m, 4H), 3.72-3.75 (m, 1H), 3.57-3.61 (m, 1H), 3.31-3.45 (m, 1H), 2.79-3.05 (m, 1H), 2.56-2.68 (m, 3H), 2.25-2.41 (m, 3H), 2.13-2.21 (m, 1H), 1.64 (m, 4H), 1.11-1.29 (m, 2H).

Synthetic Example 30: Synthesis of 1-((3R)-3-((7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidin-1-yl)prop-2-en-1-one (Compound 238)

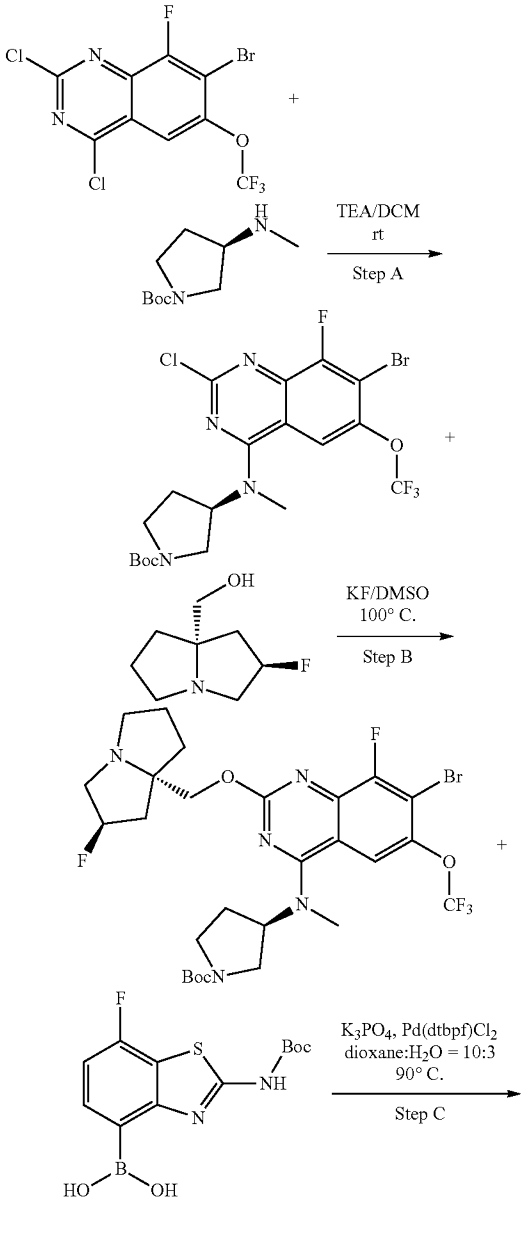

-continued

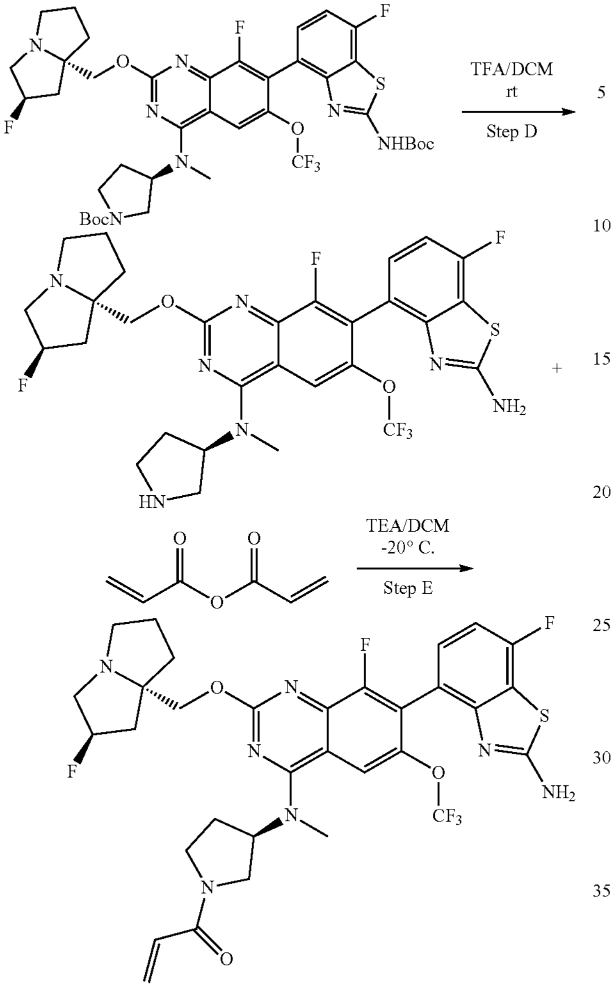

Compound 238

Step A: Preparation of tert-butyl (R)-3-((7-bromo-2-chloro-8-fluoro-6-(trifluoromethoxy)quinazolin-4-yl)(methyl)amino)pyrrolidine-1-carboxylate: To a solution of 7-bromo-2,4-dichloro-8-fluoro-6-(trifluoromethoxy)quinazoline (150 mg, 0.39 mmol) and triethylamine (118.4 mg, 1.17 mmol) in DCM (5 mL) was added (R)-tert-butyl 3-(methylamino)pyrrolidine-1-carboxylate (94.9 mg, 0.47 mmol) at ambient temperature. The reaction was stirred at ambient temperature for 3 hours. The mixture was concentrated to dry under vacuum and the residue was purified directly on silica gel column, eluting with 30% EA in petroleum ether to tert-butyl (R)-3-((7-bromo-2-chloro-8-fluoro-6-(trifluoromethoxy)quinazolin-4-yl)(methyl)amino)pyrrolidine-1-carboxylate (210 mg, 99%). LCMS ESI (+) m/z 543.0 (M+H).

Step B: Preparation of tert-butyl (R)-3-((7-bromo-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidine-1-carboxylate: To a solution of tert-butyl (R)-3-((7-bromo-2-chloro-8-fluoro-6-(trifluoromethoxy)quinazolin-4-yl)(methyl)amino)pyrrolidine-1-carboxylate (210 mg, 0.38 mmol) and ((2R,7aS)-2-fluorotetrahydro-1H-pyrrolizin-7a(5H)-yl)methanol (90.7 mg, 0.57 mmol) in DMSO (2 mL) was added potassium fluoride (176.3 mg, 3.04 mmol) at ambient temperature. The reaction was stirred at 100° C. for 8 hours. Once cooled to ambient temperature, the reaction was taken up in EtOAc (20 mL) and the organics were washed with water and saturated brine solution. The organics were then separated, dried ($MgSO_4$), filtered and concentrated under reduced pressure. The crude was then purified by preparative-TLC (DCM/MeOH=20/1) to afford tert-butyl (R)-3-((7-bromo-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidine-1-carboxylate (120 mg, 47%). LCMS ESI (+) m/z 666.2 (M+H).

Step C: Preparation of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidine-1-carboxylate: To a solution of tert-butyl (R)-3-((7-bromo-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidine-1-carboxylate (120 mg, 0.18 mmol), [2-(tert-butoxycarbonylamino)-7-fluoro-1,3-benzothiazol-4-yl]boronic acid (84.3 mg, 0.27 mmol), nd potassium phosphate (95.4 mg, 0.45 mmol) in 1,4-dioxane (7 mL) and water (2.30 mL) was added $Pd(dtbpf)Cl_2$ (5.9 mg, 0.09 mmol) at ambient temperature. After bubbling with argon for 2 minutes, the reaction was stirred at 90° C. for 1 hour. Once cooled to ambient temperature, reaction was diluted with EtOAc (10 mL) and the organics washed with water then with saturated brine solution. The organics were then separated, dried ($MgSO_4$) and concentrated under reduced pressure. The crude was then purified by preparative-TLC (DCM/MeOH=20/1) to afford tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidine-1-carboxylate (110 mg, 71%). LCMS ESI (+) m/z 854.3 (M+H).

Step D: Preparation of 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethoxy)quinazolin-7-yl)benzo[d]thiazol-2-amine: To a solution of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidine-1-carboxylate (110 mg 0.048 mmol) in DCM (3 mL) was added trifluoroacetic acid (1.0 mL, 13.0 mmol) at 0° C. The reaction was warmed to ambient temperature and stirred at ambient temperature for 2 hours. The reaction solution was concentrated under reduced pressure to afford 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethoxy)quinazolin-7-yl)benzo[d]thiazol-2-amine which was used directly in the next step. LCMS ESI (+) m/z 654.2 (M+H).

Step E: Preparation of 1-((3R)-3-((7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidin-1-yl)prop-2-en-1-one: To a solution of 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethoxy)quinazolin-7-yl)benzo[d]thiazol-2-amine (55 mg, 0.084 mmol), triethylamine (0.059 mL, 0.42 mmol) in DCM (3 mL) was added prop-2-enoyl prop-2-enoate (12.7 mg, 0.1 mmol) in DCM dropwise at −20° C. under Ar and stirred −20° C. for 15 minutes. The reaction was quenched with $H_2O$ (10 mL) and extracted with EtOAc. The organics were washed with water, brine, dried ($MgSO_4$), filtered, and concentrated to dryness. The crude was then purified by preparative RP-HPLC to afford 1-((3R)-3-((7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethoxy)quinazolin-4-yl)(methyl)amino)pyrrolidin-1-yl)prop-2-en-1-one (26 mg, 27%). LCMS ESI (+) m/z 708.3 (M+H). $^1$HNMR (400 MHz, $CD_3OD$) δ 7.98 (s, 1H), 7.27-7.30 (m, 1H), 7.01-7.05 (m, 1H), 6.64-6.68 (m, 1H), 6.30-6.34 (m, 1H), 5.79-5.81 (m, 1H), 5.49-5.63 (m, 1H), 5.19-5.38 (m, 1H), 4.66-4.74 (m, 2H), 3.82-4.02 (m, 6H), 3.47-3.79 (m, 5H), 2.30-2.63 (m, 7H), 2.03-2.28 (m, 1H).

Synthetic Example 31: Synthesis of 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (239) and 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (240)

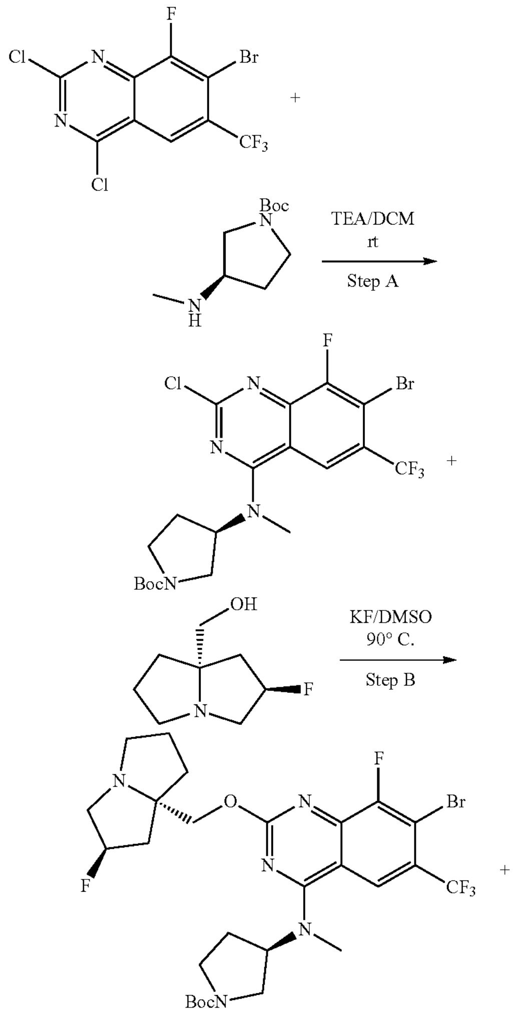

-continued

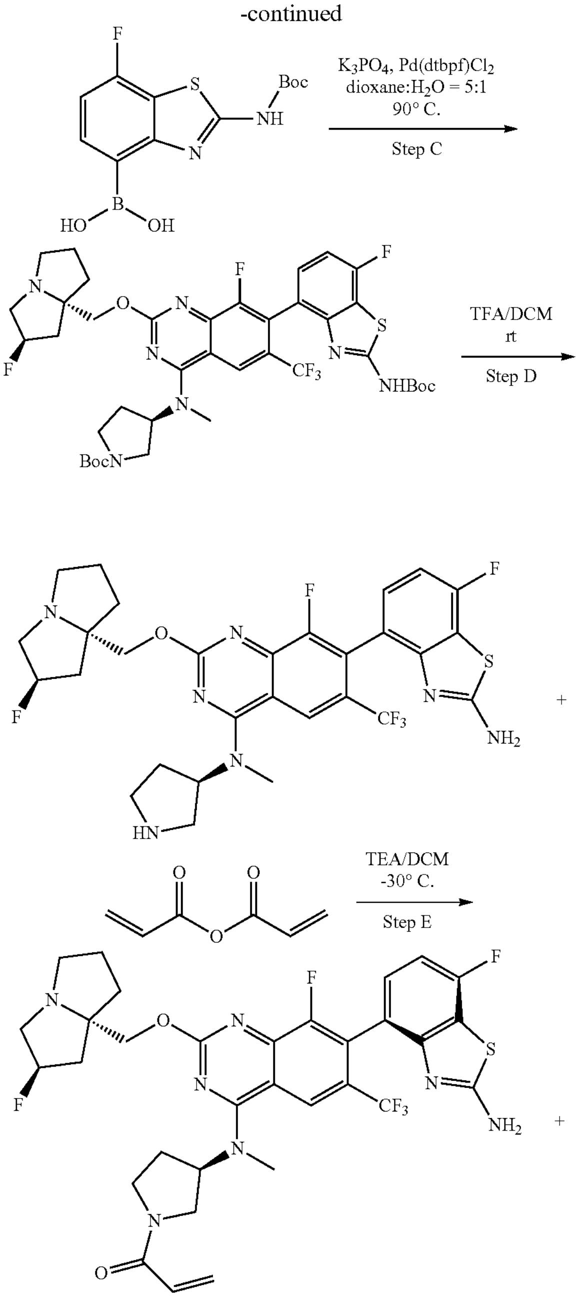

Compound 239

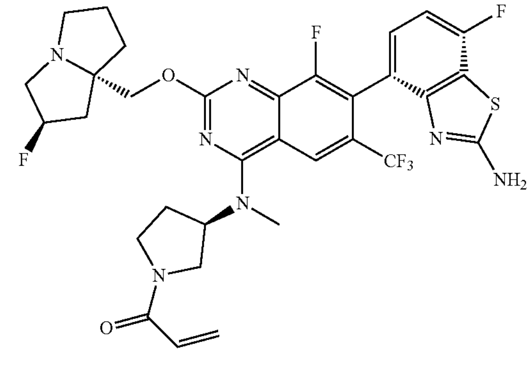

Compound 240

Step A: Preparation of tert-butyl (3R)-3-[[7-bromo-2-chloro-8-fluoro-6-(trifluoromethyl)quinazolin-4-yl]-methyl-amino]pyrrolidine-1-carboxylate: To a solution of 7-bromo-2,4-dichloro-8-fluoro-6-(trifluoromethoxy)quinazoline (200 mg, 0.43 mmol) and triethylamine (130 mg, 1.29 mmol) in DCM (5 mL) was added tert-butyl (R)-3-(methylamino)pyrrolidine-1-carboxylate (103 mg, 0.51 mmol) at ambient temperature. The reaction was stirred at ambient temperature for 30 minutes. The mixture was concentrated to dry under vacuum and the residue was purified directly on silica gel column, eluting with 10% EtOAc in petroleum ether to give tert-butyl (3R)-3-[[7-bromo-2-chloro-8-fluoro-6-(trifluoromethyl)quinazolin-4-yl]-methyl-amino]pyrrolidine-1-carboxylate (145 mg, 61%). LCMS ESI (+) m/z 527.1 (M+H).

Step B: Preparation of tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidine-1-carboxylate: To a solution of tert-butyl (R)-3-((7-bromo-2-chloro-8-fluoro-6-(trifluoromethyl)quinazolin-4-yl)(methyl)amino)pyrrolidine-1-carboxylate (145 mg, 0.28 mmol) and ((2R,7aS)-2-fluorotetrahydro-1H-pyrrolizin-7a(5H)-yl)methanol (66 mg, 0.41 mmol) in DMSO (2 mL) was added potassium fluoride (128 mg, 2.2 mmol) at ambient temperature. The reaction was stirred at 90° C. for 2 hours. Once cooled to ambient temperature, the reaction was taken up in EtOAc (20 mL) and the organic layers were washed with saturated brine solution. The organic layers were then separated, dried ($MgSO_4$), filtered, and concentrated under reduced pressure. The crude was then purified by preparative-TLC (50% EtOAc in petroleum ether) to afford tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidine-1-carboxylate (110 mg, 62%). LCMS ESI (+) m/z 650.1 (M+H).

Step C: Preparation of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidine-1-carboxylate: To a solution of tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidine-1-carboxylate (54 mg, 0.083 mmol), [2-(tert-butoxycarbonylamino)-7-fluoro-1,3-benzothiazol-4-yl]boronic acid (31 mg, 0.099 mmol), and potassium phosphate (53 mg, 0.25 mmol) in 1,4-dioxane (2 mL) and water (0.40 mL) was added Pd(dtbpf)$Cl_2$ (5.4 mg, 0.0083 mmol) at ambient temperature. After bubbling with argon for 2 minutes, the reaction was stirred at 90° C. for 1 hour. Once cooled to ambient temperature, reaction was diluted with ethyl acetate (10 mL) and the organics washed with water then with saturated brine solution. The organic layers were then separated, dried ($MgSO_4$), and concentrated under reduced pressure. The crude was then purified by preparative-TLC (50% EtOAc in petroleum ether) to afford tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidine-1-carboxylate (47 mg, 68%). LCMS ESI (+) m/z 838.2 (M+H).

Step D: Preparation of 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethyl)quinazolin-7-yl)benzo[d]thiazol-2-amine: To a solution of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(cyclopropyl)amino)pyrrolidine-1-carboxylate (47 mg, 0.056 mmol) in DCM (2 mL) was added trifluoroacetic acid (1.0 mL, 13.0 mmol) at ambient temperature. The reaction was stirred at ambient temperature for 1 hour. The reaction solution was concentrated under reduced pressure to afford 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethyl)quinazolin-7-yl)benzo[d]thiazol-2-amine which was used directly in the next step. LCMS ESI (+) m/z 638.2 (M+H).

Step E: Preparation of 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (239, one atropisomer) and 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (240, the other atropisomer): To a solution of 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethyl)quinazolin-7-yl)benzo[d]thiazol-2-amine (55 mg, 0.086 mmol), triethyl amine (0.060 mL, 0.43 mmol) in DCM (3 mL) was added prop-2-enoyl prop-2-enoate (7.6 mg, 0.060 mmol) in DCM dropwise at −40° C. under Ar and stirred −40° C. for 30 minutes. The reaction was quenched with $H_2O$ (10 mL) and extracted with EtOAc. The organic layers were washed with brine, dried ($MgSO_4$), filtered, and concentrated to dryness to give a mixture of 2 atropisomers. The crude was then purified by preparative RP-HPLC. The first compound off the column was identified as one atropisomer, 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (239) (10 mg, 17%). LCMS ESI (+) m/z 692.3 (M+H). $^1$HNMR (400 MHz, $CD_3OD$) δ 8.38 (s, 1H), 7.19-7.21 (m, 1H), 6.99 (t, J=9.2 Hz, 1H), 6.61-6.72 (m, 1H), 6.32 (d, J=16.8 Hz, 1H), 5.75-5.85 (m, 1H), 5.55 (d, J=51.6 Hz, 1H), 5.28-5.41 (m, 1H), 4.62-4.73 (m, 2H), 4.08-4.21 (m, 1H), 3.69-4.08 (m, 6H), 3.45-3.65 (m, 6H), 2.51-2.75 (m, 3H), 2.28-2.45 (m, 4H), 2.08-2.21 (m, 1H). The second compound off the column was identified as the other atropisomer, 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (240) (12 mg, 20%). LCMS ESI (+) m/z 692.3 (M+H). $^1$HNMR (400 MHz, $CD_3OD$) δ 8.38 (s, 1H), 7.19-7.22 (m, 1H), 6.99 (t, J=8.8 Hz, 1H), 6.61-6.72 (m, 1H), 6.33 (d, J=16.8 Hz, 1H), 5.75-5.85 (m, 1H), 5.53 (d, J=51.2 Hz, 1H), 5.28-5.41 (m, 1H), 4.62-4.73 (m, 2H), 4.08-4.21 (m, 1H), 3.69-4.08 (m, 6H), 3.45-3.65 (m, 6H), 2.51-2.75 (m, 3H), 2.28-2.45 (m, 4H), 2.08-2.21 (m, 1H).

Synthetic Example 32: Synthesis of (3-((7-(2-amino-7-fluorobenzo[d]thiazol-4-yl)-8-fluoro-2-((tetrahydro-1H-pyrrolizin-7a(5H)-yl)methoxy)-6-(trifluoromethyl)quinazolin-4-yl)amino)azetidin-1-yl)(aziridin-2-yl)methanone (Compound 243)

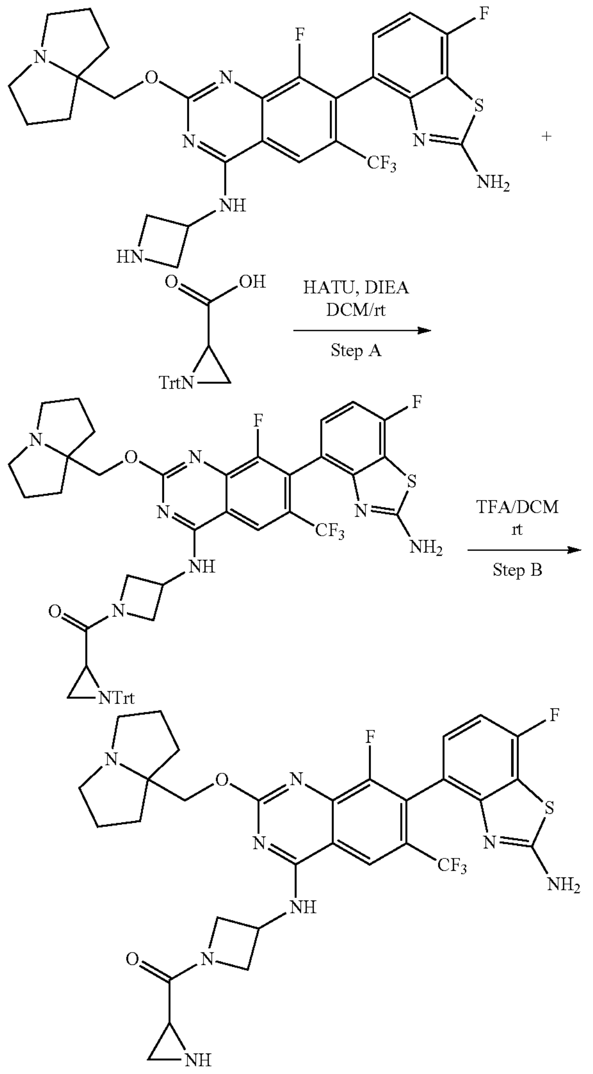

Compound 243

Step A: Preparation of tert-butyl (3-((7-(2-amino-7-fluorobenzo[d]thiazol-4-yl)-8-fluoro-2-((tetrahydro-1H-pyrrolizin-7a(5H)-yl)methoxy)-6-(trifluoromethyl)quinazolin-4-yl)amino)azetidin-1-yl)(1-tritylaziridin-2-yl)methanone: To a solution of 1-tritylaziridine-2-carboxylic acid (53 mg, 0.16 mmol) in in DCM (2 mL) was added HATU (77 mg, 0.20 mmol) and DIEA (0.072 mL, 0.41 mmol) at ambient temperature and stirred at ambient temperature for 1 hour. Then a solution of 4-[4-(azetidin-3-ylamino)-8-fluoro-2-(1,2,3,5,6,7-hexahydropyrrolizin-8-ylmethoxy)-6-(trifluoromethyl)quinazolin-7-yl]-7-fluoro-1,3-benzothiazol-2-amine (80 mg, 0.14 mmol) and DIEA (0.072 mL, 0.41 mmol) in DCM (1 mL) to was added at ambient temperature and stirred at ambient temperature for 30 minutes. The reaction mixture was diluted with DCM, washed with water and brine. The organic layer was separated, dried ($MgSO_4$), filtered and concentrated under reduced pressure. The residue was purified by preparative-TLC (DCM/MeOH=10/1) to give [3-[[7-(2-amino-7-fluoro-1,3-benzothiazol-4-yl)-8-fluoro-2-(1,2,3,5,6,7-hexahydropyrrolizin-8-ylmethoxy)-6-(trifluoromethyl)quinazolin-4-yl]amino]azetidin-1-yl]-(1-tritylaziridin-2-yl)methanone (27 mg, 22%). LCMS ESI (+) m/z 903.2 (M+H).

Step B: Preparation of (3-((7-(2-amino-7-fluorobenzo[d]thiazol-4-yl)-8-fluoro-2-((tetrahydro-1H-pyrrolizin-7a(5H)-yl)methoxy)-6-(trifluoromethyl)quinazolin-4-yl)amino)azetidin-1-yl)(aziridin-2-yl)methanone: To a stirred solution of [3-[[7-(2-amino-7-fluoro-1,3-benzothiazol-4-yl)-8-fluoro-2-(1,2,3,5,6,7-hexahydropyrrolizin-8-ylmethoxy)-6-(trifluoromethyl)quinazolin-4-yl]amino]azetidin-1-yl]-(1-tritylaziridin-2-yl)methanone (27 mg, 0.030 mmol) in DCM (2 mL) was added triethyl silane (0.024 mL, 0.15 mmol) and trifluoroacetic acid (0.012 mL, 0.15 mmol) at 0° C. After 30 minutes the reaction mixture was basified to pH-8 with DIEA and concentrated under reduced pressure. The crude product was purified by preparative RP-HPLC to afford [3-[[7-(2-amino-7-fluoro-1,3-benzothiazol-4-yl)-8-fluoro-2-(1,2,3,5,6,7-hexahydropyrrolizin-8-ylmethoxy)-6-(trifluoromethyl)quinazolin-4-yl]amino]azetidin-1-yl]-(aziridin-2-yl)methanone (2.2 mg, 10%). LCMS ESI (+) m/z 661.2 (M+H). $^1$HNMR (400 MHz, $CD_3OD$) δ 8.61 (s, 1H), 7.16-7.25 (m, 1H), 6.98 (t, J=8.8 Hz, 1H), 4.96-5.21 (m, 2H), 4.66 (s, 2H), 4.46-4.61 (m, 2H), 4.15-4.34 (m, 1H), 3.76-3.98 (m, 1H), 3.64-3.74 (m, 2H), 3.34-3.39 (m, 2H), 3.20-3.29 (m, 2H), 2.46-2.60 (m, 1H), 2.28-2.38 (m, 2H), 2.19-2.25 (m, 2H), 2.08-2.18 (m, 4H).

Synthetic Example 33: Synthesis of 4-(4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 252), 4-((S)-4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 313) and 4-((R)-4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 314)

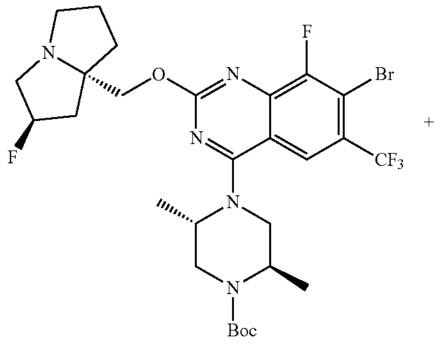

-continued

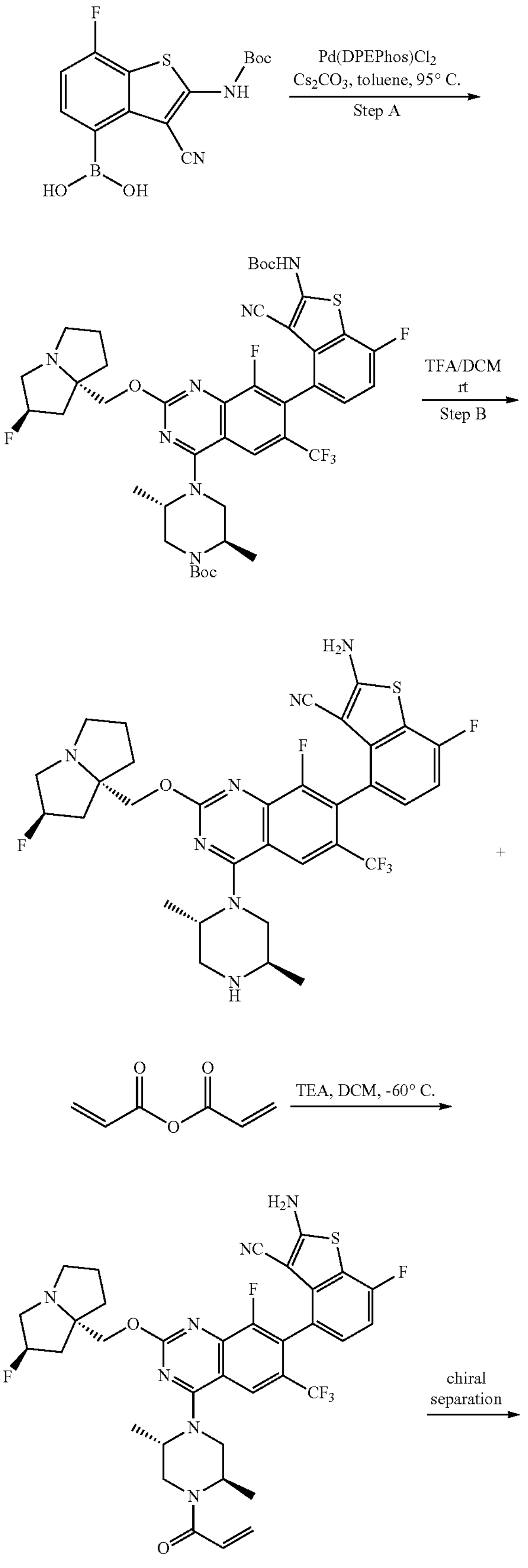

Compound 252

-continued

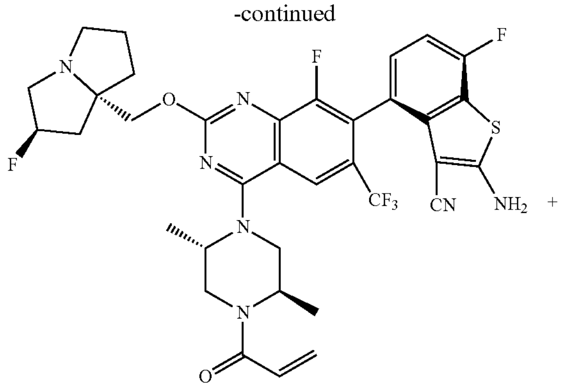

Compound 313

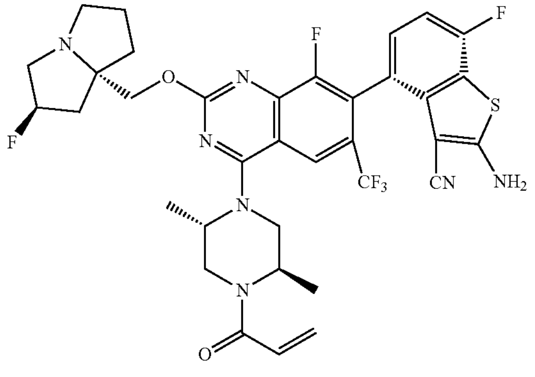

Compound 314

Step A: Preparation of tert-butyl (2R,5S)-4-(7-(2-((tert-butoxycarbonyl)amino)-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a mixture of tert-butyl (2R,5S)-4-[7-bromo-8-fluoro-2-[[(2R,8S)-2-fluoro-1,2,3,5,6,7-hexahydropyrrolizin-8-yl]methoxy]-6-(trifluoromethyl)quinazolin-4-yl]-2,5-dimethyl-piperazine-1-carboxylate (100 mg, 0.15 mmol), tert-butyl N-[3-cyano-4-(5,5-dimethyl-1,3,2-dioxaborinan-2-yl)-7-fluoro-benzothiophen-2-yl]carbamate (91 mg, 0.23 mmol), and $Cs_2CO_3$ (147 mg, 0.45 mmol) in toluene (2 mL) was added $DPEPhosPdCl_2$ (16 mg, 0.023 mmol) at ambient temperature. After bubbling with nitrogen for 2 minutes, the reaction mixture was stirred at 95° C. for 6 hours. After cooling to ambient temperature, reaction mixture was diluted with ethyl acetate and the organic layers washed with water, then with saturated brine solution. The organic layers were then separated, dried ($Na_2SO_4$) and concentrated under reduced pressure. The crude was then purified by preparative-TLC (20% MeOH in DCM) to afford tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidine-1-carboxylate (33 mg, 20%). LCMS ESI (+) m/z 876.3 (M+H).

Step B: Preparation of 2-amino-4-(4-((2S,5R)-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-7-fluorobenzo[b]thiophene-3-carbonitrile: To a solution of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)

(methyl)amino)pyrrolidine-1-carboxylate (33.0 mg, 0.038 mmol) in DCM (1 mL) was added trifluoroacetic acid (0.5 mL) at ambient temperature. The reaction was stirred at ambient temperature for 1 hour. The reaction solution was concentrated under reduced pressure to afford 7-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)-6-(trifluoromethyl)quinazolin-7-yl)benzo[d]thiazol-2-amine, which was used directly in the next step. LCMS ESI (+) m/z 675.22 (M+H).

Step C: Preparation of 4-(4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 252), 4-((S)-4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 313) and 4-((R)-4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 314): To a solution of 2-amino-4-[4-[(2S,5R)-2,5-dimethylpiperazin-1-yl]-8-fluoro-2-[[(2R,8S)-2-fluoro-1,2,3,5,6,7-hexahydropyrrolizin-8-yl]methoxy]-6-(trifluoromethyl)quinazolin-7-yl]-7-fluoro-benzothiophene-3-carbonitrile (30 mg, 0.044 mmol) and TEA (0.019 mL, 0.13 mmol) in DCM (3 mL) was added prop-2-enoyl prop-2-enoate (4.4 mg, 0.0399 mmol) at −78° C. The mixture was stirred at −78° C. for 40 minutes. The reaction was quenched with $H_2O$ (10 mL) and extracted with EtOAc. The organic layers were washed with brine, dried ($MgSO_4$), filtered and concentrated to dryness. The crude was purified by preparative RP-HPLC to give 4-(4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 252) (2.2 mg, 6%) as a white solid. LCMS ESI (+) m/z 730.4 (M+H). $^1$HNMR (400 MHz, $CD_3OD$) δ 8.18 (s, 1H), 7.21-7.28 (m, 1H), 7.01-7.07 (m, 1H), 6.73-6.92 (m, 1H), 6.26-6.37 (m, 1H), 5.78-5.86 (m, 1H), 5.57 (d, J=52.4 Hz, 1H), 4.27-4.74 (m, 4H), 3.81-4.10 (m, 5H), 3.42-3.59 (m, 1H), 2.52-2.79 (m, 2H), 2.11-2.49 (m, 5H), 1.62-1.64 (m, 1H), 1.41-1.56 (m, 3H), 1.21-1.38 (m, 3H).

The single diastereomers of 4-(4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 252) (134.4 mg) were separated with chiral chromatography condition [ChiralPak IH 3 cm×25 cm, 5 μm, $CO_2$:MeOH (0.2% 2 mM ammonium in methanol)=70:30], 80 mL/min]. The first compound off the column was identified as one atropisomer, 44-((S)-4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 313) (40.1 mg, 99.88% de); LCMS ESI (+) m/z 730.3 (M+H). $^1$HNMR (400 MHz, $CD_3OD$) δ 8.13 (s, 1H), 7.17-7.28 (m, 1H), 7.02 (t, J=8.8 Hz, 1H), 6.91-6.73 (m, 1H), 6.22-6.35 (m, 1H), 5.81 (dd, J=10.8, 4.0 Hz, 1H), 5.33 (d, J=53.6 Hz, 1H), 4.93-5.01 (m, 1H), 4.56-4.67 (m, 1H), 4.25-4.39 (m, 4H), 3.83-4.06 (m, 2H), 3.36-3.59 (m, 2H), 3.22-3.28 (m, 1H), 3.03-3.14 (m, 1H), 1.82-2.46 (m, 6H), 1.48 (t, J=6.0 Hz, 3H), 1.28 (dd, J=24.4, 6.8 Hz, 3H). The second compound off the column was identified as the other atropisomer, 4-((R)-4-((2S,5R)-4-acryloyl-2,5-dimethylpiperazin-1-yl)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 314) (53.3 mg, 99.48% de). LCMS ESI (+) m/z 730.3 (M+H). $^1$HNMR (400 MHz, $CD_3OD$) δ 8.15 (s, 1H), 7.17-7.28 (m, 1H), 7.02 (t, J=8.8 Hz, 1H), 6.91-6.73 (m, 1H), 6.22-6.35 (m, 1H), 5.78-5.92 (m, 1H), 5.33 (d, J=53.6 Hz, 1H), 4.93-5.01 (m, 1H), 4.20-4.61 (m, 4H), 3.83-4.06 (m, 2H), 3.48-3.59 (m, 1H), 3.12-3.28 (m, 3H), 3.03-3.14 (m, 1H), 1.82-2.46 (m, 6H), 1.48 (t, J=6.0 Hz, 3H), 1.28 (dd, J=24.4, 6.8 Hz, 3H).

Synthetic Example 34: Synthesis of 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidin-1-yl)prop-2-en-1-one (Compound 271) and 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidin-1-yl)prop-2-en-1-one (Compound 272)

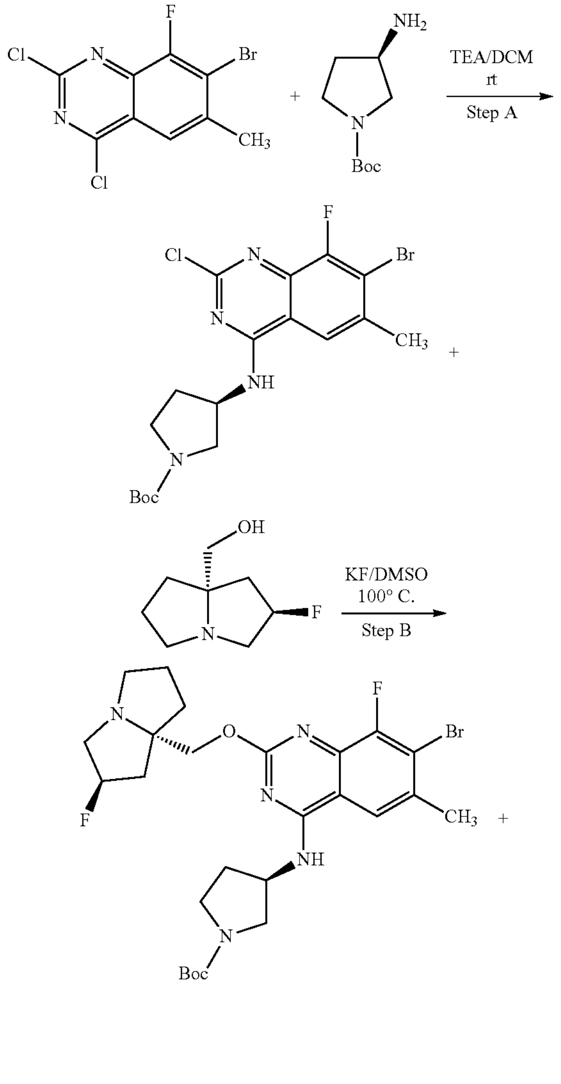

-continued

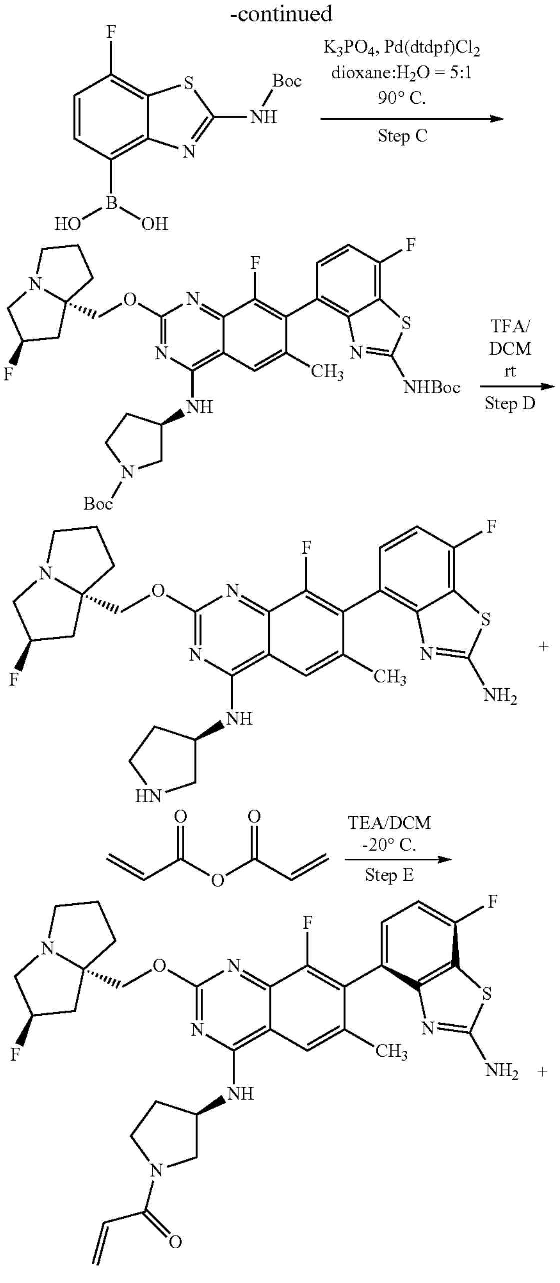

Compound 271

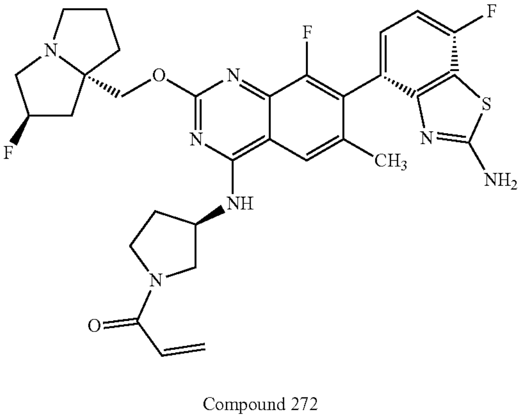

Compound 272

Step A: Preparation of tert-butyl (R)-3-((7-bromo-2-chloro-8-fluoro-6-(trifluoromethyl)quinazolin-4-yl)amino) pyrrolidine-1-carboxylate: To a solution of 7-bromo-2,4-dichloro-8-fluoro-6-(trifluoromethoxy)quinazoline (300 mg, 0.82 mmol) and triethylamine (0.23 mL, 1.65 mmol) in DCM (3 mL) was added tert-butyl 3-aminopyrrolidine-1-carboxylate (154 mg, 0.82 mmol) at ambient temperature. The reaction was stirred at ambient temperature for 1 hour. The mixture was concentrated to dry under vacuum and the residue was purified directly by flash chromatography on silica gel, eluting with 25% Ethyl acetate in petroleum ether to give tert-butyl (R)-3-((7-bromo-2-chloro-8-fluoro-6-(trifluoromethyl)quinazolin-4-yl)amino)pyrrolidine-1-carboxylate (240 mg, 56%). LCMS ESI (+) m/z 513.0 (M+H).

Step B: Preparation of tert-butyl (R)-3-((7-bromo-8-fluoro-2-(((2R,7aS)-2-fluorotetrahydro-1H-pyrrolizin-7a (5H)-yl)methoxy)-6-(trifluoromethyl)quinazolin-4-yl) amino)pyrrolidine-1-carboxylate: To a solution of tert-butyl (R)-3-((7-bromo-2-chloro-8-fluoro-6-(trifluoromethyl)quinazolin-4-yl)amino)pyrrolidine-1-carboxylate (230 mg, 0.45 mmol) and ((2R,7aS)-2-fluorotetrahydro-1H-pyrrolizin-7a(5H)-yl)methanol (214 mg, 1.34 mmol) in DMSO (1.5 mL) was added potassium fluoride (209.1 mg, 3.6 mmol) at ambient temperature. The reaction was stirred at 90° C. for 8 hours. After cooled to ambient temperature, the reaction was taken up in EtOAc (20 mL) and the organics were washed with saturated brine solution. The organics were then separated, dried ($MgSO_4$), filtered and concentrated under reduced pressure. The crude was then purified by Preparative-TLC (DCM/MeOH=20/1) to afford tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidine-1-carboxylate (185 mg, 45%). LCMS ESI (+) m/z 636.2 (M+H).

Step C: Preparation of tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a (5H)-yl)methoxy)-6-(trifluoromethyl)quinazolin-4-yl) amino)pyrrolidine-1-carboxylate: To a solution of tert-butyl (R)-3-((7-bromo-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidine-1-carboxylate (185 mg, 0.29 mmol), [2-(tert-butoxycarbonylamino)-7-fluoro-1,3-benzothiazol-4-yl]boronic acid (109 mg, 0.35 mmol), Potassium phosphate (123 mg, 0.58 mmol) in 1, 4-Dioxane (5 mL) and Water (1 mL) was added Pd(dtbpf)$Cl_2$ (19 mg, 0.029 mmol) at ambient temperature. After bubbled with Argon for 2 minutes, the reaction was stirred at 90° C. for 4 hours. After cooled to ambient temperature, reaction was diluted with ethyl acetate (10 mL) and the organics washed with water then with saturated brine solution. The organics were then separated, dried ($MgSO_4$) and concentrated under reduced pressure. The crude was then purified by Preparative-TLC (petroleum ether/ethyl acetate=1:1) to afford tert-butyl (3R)-3-((7-(2-((tert-butoxycarbonyl)amino)-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidine-1-carboxylate (90 mg, 37%). LCMS ESI (+) m/z 824 (M+H).

Step D: Preparation of 7-fluoro-4-(8-fluoro-2-(((2R,7aS)-2-fluorotetrahydro-1H-pyrrolizin-7a(5H)-yl)methoxy)-4-(((R)-pyrrolidin-3-yl)amino)-6-(trifluoromethyl)quinazolin-7-yl)benzo[d]thiazol-2-amine: To a solution of tert-butyl 3-[[7-[2-(tert-butoxycarbonylamino)-7-fluoro-1,3-benzothiazol-4-yl]-8-fluoro-2-[[(2R,8S)-2-fluoro-1,2,3,5,6,7-hexahydropyrrolizin-8-yl]methoxy]-6-(trifluoromethyl)quinazolin-4-yl]amino]pyrrolidine-1-carboxylate (23 mg, 0.028 mmol) in DCM (2 mL) was added Trifluoroacetic acid (0.6 mL, 7.79 mmol) at ambient temperature and stirred at ambient temperature for 1 hour. The mixture was concentrated under reduced pressure to afford 7-fluoro-4-(8-fluoro-2-(((2R,7aS)-2-fluorotetrahydro-1H-pyrrolizin-7a(5H)-yl)methoxy)-4-(((R)-pyrrolidin-3-yl)amino)-6-(trifluoromethyl)quinazolin-7-yl)benzo[d]thiazol-2-amine which was used directly in the next step. LCMS ESI (+) m/z 624.2 (M+H).

Step E: Preparation of 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidin-1-yl)prop-2-en-1-one (Compound 271) and 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidin-1-yl)prop-2-en-1-one (Compound 272): To a solution of 7-fluoro-4-[8-fluoro-2-[[(2R,8S)-2-fluoro-1,2,3,5,6,7-hexahydropyrrolizin-8-yl]methoxy]-4-[[(3R)-pyrrolidin-3-yl]amino]-6-(trifluoromethyl)quinazolin-7-yl]-1,3-benzothiazol-2-amine (43 mg, 0.069 mmol) and TEA (48 μL, 0.35 mmol) in DCM (3 mL) was added prop-2-enoyl prop-2-enoate (7.8 mg, 0.062 mmol) in DCM dropwise at −20° C. and stirred −20° C. for 1 hour. The reaction was quenched with $H_2O$ (10 mL) and extracted with DCM. The organics were washed with brine, dried ($MgSO_4$), filtered and concentrated to dryness. The crude was then purified by preparative RP-HPLC. The first compound off the column was identified as one atropisomer, 1-((R)-3-(((S)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidin-1-yl)prop-2-en-1-one (Compound 271) (6.8 mg, 14%). LCMS ESI (+) m/z 678.2 (M+H). $^1$HNMR (400 MHz, $CD_3OD$) δ 8.67 (s, 1H), 7.20 (s, 1H) 6.97-7.01 (m, 1H), 6.65 (t, J=10.4 Hz, 1H), 6.30 (d, J=2 Hz, 1H), 5.80 (d, J=10.8 Hz, 1H), 5.55 (d, J=52 Hz, 1H), 4.65-4.95 (m, 3H), 3.66-4.04 (m, 8H, 2.31-2.44 (m, 8H). The second compound off the column was identified as the other atropisomer, 1-((R)-3-(((R)-7-(2-amino-7-fluorobenzo[d]thiazol-4-yl)-8-fluoro-2-(((2R,7aS)-2-fluorotetrahydro-1H-pyrrolizin-7a(5H)-yl)methoxy)-6-(trifluoromethyl)quinazolin-4-yl)amino)pyrrolidin-1-yl)prop-2-en-1-one (Compound 272) (6.2 mg, 13%). LCMS ESI (+) m/z 678.2 (M+H). $^1$HNMR (400 MHz, $CD_3OD$) δ 8.67 (s, 1H), 7.18-7.22 (m, 1H), 6.99 (d, J=8.8 Hz, 1H), 6.60-6.81 (m, 1H), 6.28-6.36 (m, 1H), 5.77-5.83 (m, 1H), 5.55 (d, J=52 Hz, 1H), 4.65-4.95 (m, 3H), 3.66-4.04 (m, 8H), 2.31-2.44 (m, 8H).

Synthetic Example 35: Synthesis of 1-((2R,5S)-4-(7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (Compound 295)

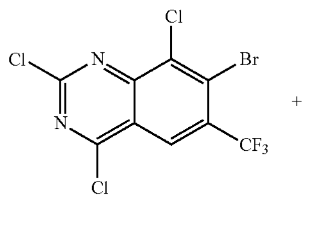

-continued

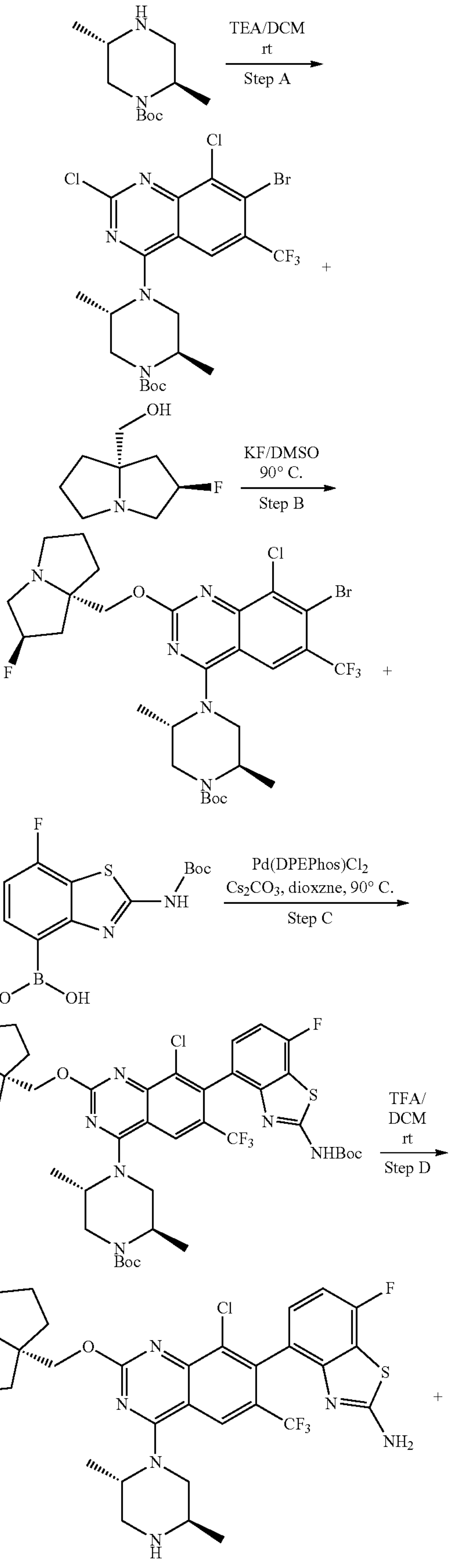

-continued

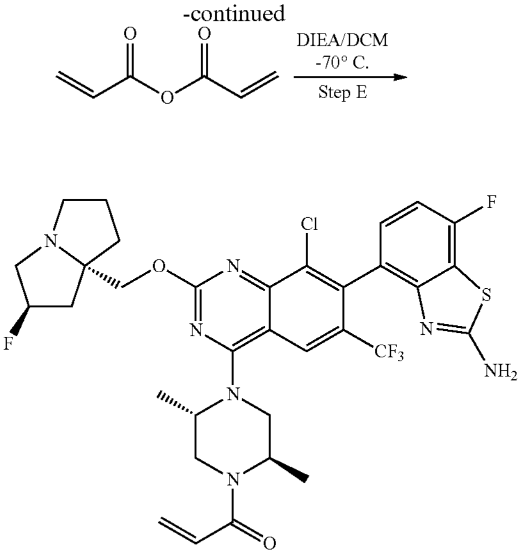

Compound 295

Step A: Preparation of tert-butyl (2R,5S)-4-(7-bromo-2,8-dichloro-6-(trifluoromethyl)quinazolin-4-yl)-2,5-dimethylpiperazine-1-carboxylate: To a solution of 7-bromo-2,4,8-trichloro-6-(trifluoromethoxy)quinazoline (150 mg, 0.39 mmol) and Triethyl amine (150 mg, 1.17 mmol) in DCM (5 mL) was added tert-butyl (2R,5S)-2,5-dimethylpiperazine-1-carboxylate (100.7 mg, 0.47 mmol) at ambient temperature. The reaction was stirred at ambient temperature for 4 hours. The mixture was concentrated to dryness under vacuum and the residue was purified directly by flash chromatography on silica gel to give tert-butyl (2R,5S)-4-(7-bromo-2,8-dichloro-6-(trifluoromethyl)quinazolin-4-yl)-2,5-dimethylpiperazine-1-carboxylate (76 mg, 36%).

Step B: Preparation of tert-butyl (2R,5S)-4-(7-bromo-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-(7-bromo-2,8-dichloro-6-(trifluoromethyl)quinazolin-4-yl)-2,5-dimethylpiperazine-1-carboxylate (76 mg, 0.14 mmol) and ((2R,7aS)-2-fluorotetrahydro-1H-pyrrolizin-7a(5H)-yl)methanol (66.8 mg, 0.42 mmol) in DMSO (2 mL) was added potassium fluoride (65 mg, 1.12 mmol) at ambient temperature. The reaction was stirred at 90° C. for 4 hours. After cooled to ambient temperature, the reaction was taken up in EtOAc (20 mL) and the organics were washed with saturated brine solution. The organics were then separated, dried ($MgSO_4$), filtered and concentrated under reduced pressure. The crude was then purified by preparative-TLC to afford tert-butyl (2R,5S)-4-(7-bromo-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (47 mg, 50%). LCMS ESI (+) m/z 680.2 (M+H).

Step C: Preparation of tert-butyl (2R,5S)-4-(7-(2-((tert-butoxycarbonyl)amino)-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-(7-bromo-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (47 mg, 0.07 mmol), [2-(tert-butoxycarbonylamino)-7-fluoro-1,3-benzothiazol-4-yl]boronic acid (43.7 mg, 0.14 mmol), cesium carbonate (45.6 mg, 0.14 mmol) and Pd(DPEPhos)$Cl_2$ (10 mg, 0.014 mmol) in 1, 4-Dioxane (2 mL) was bubbled with Argon for 2 minutes, the reaction was stirred at 90° C. for 16 hours. After cooled to ambient temperature, reaction was diluted with ethyl acetate (10 mL) and the organics washed with water then with saturated brine solution. The organics were then separated, dried ($MgSO_4$) and concentrated under reduced pressure. The crude was then purified by flash chromatography on silica gel to give tert-butyl (2R,5S)-4-(7-(2-((tert-butoxycarbonyl)amino)-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (33 mg, 54%). LCMS ESI (+) m/z 868.2 (M+H).

Step D: Preparation of 4-(8-chloro-4-((2S,5R)-2,5-dimethylpiperazin-1-yl)-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine: To a solution of tert-butyl (2R,5S)-4-(7-(2-((tert-butoxycarbonyl)amino)-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate (33 mg, 0.050 mmol) in DCM (1.5 mL) was added Trifluoroacetic acid (0.5 mL) at ambient temperature and stirred at ambient temperature for 2 hour. The mixture was concentrated under reduced pressure to afford 4-(8-chloro-4-((2S,5R)-2,5-dimethylpiperazin-1-yl)-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine which was used directly in the next step. LCMS ESI (+) m/z 668.2 (M+H).

Step E: Preparation of 1-((2R,5S)-4-(7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one: To a solution of 4-(8-chloro-4-((2S,5R)-2,5-dimethylpiperazin-1-yl)-2-(((2R,7aS)-2-fluorotetrahydro-1H-pyrrolizin-7a(5H)-yl)methoxy)-6-(trifluoromethyl)quinazolin-7-yl)-7-fluorobenzo[d]thiazol-2-amine (35 mg, 0.05 mmol) and DIEA (25.8 mg, 0.2 mmol) in DCM (3 mL) was added prop-2-enoyl prop-2-enoate (75.7 mg, 0.045 mmol) in DCM dropwise at −70° C. and stirred −70° C. for 1 hour. The reaction was quenched with $H_2O$ (10 mL) and extracted with DCM. The organics were washed with brine, dried ($MgSO_4$), filtered and concentrated to dryness. The crude was then purified by preparative RP-HPLC to give 1-((2R,5S)-4-(7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (8.2 mg, 22%). LCMS ESI (+) m/z 722.3 (M+H). $^1$HNMR (400 MHz, $CD_3OD$) δ 8.32 (s, 1H), 7.12-7.14 (m, 1H), 6.99 (t, J=8.8 Hz, 1H), 6.75-6.88 (m, 1H), 6.27-6.32 (m, 1H), 5.80-5.84 (m, 1H), 5.49-5.62 (d, J=51.58 Hz, 1H), 4.94-5.01 (m, 1H), 4.70-4.73 (m, 2H), 4.30-4.55 (m, 2H), 3.83-4.05 (m, 5H), 3.43-3.54 (m, 2H), 2.12-2.75 (m, 6H), 1.46-1.53 (m, 3H), 1.28-1.32 (m, 3H).

Synthetic Example 36: Synthesis of 1-((2R,5S)-4-(7-(2-amino-5,7-difluorobenzo[d]thiazol-4-yl)-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one (Compound 298)

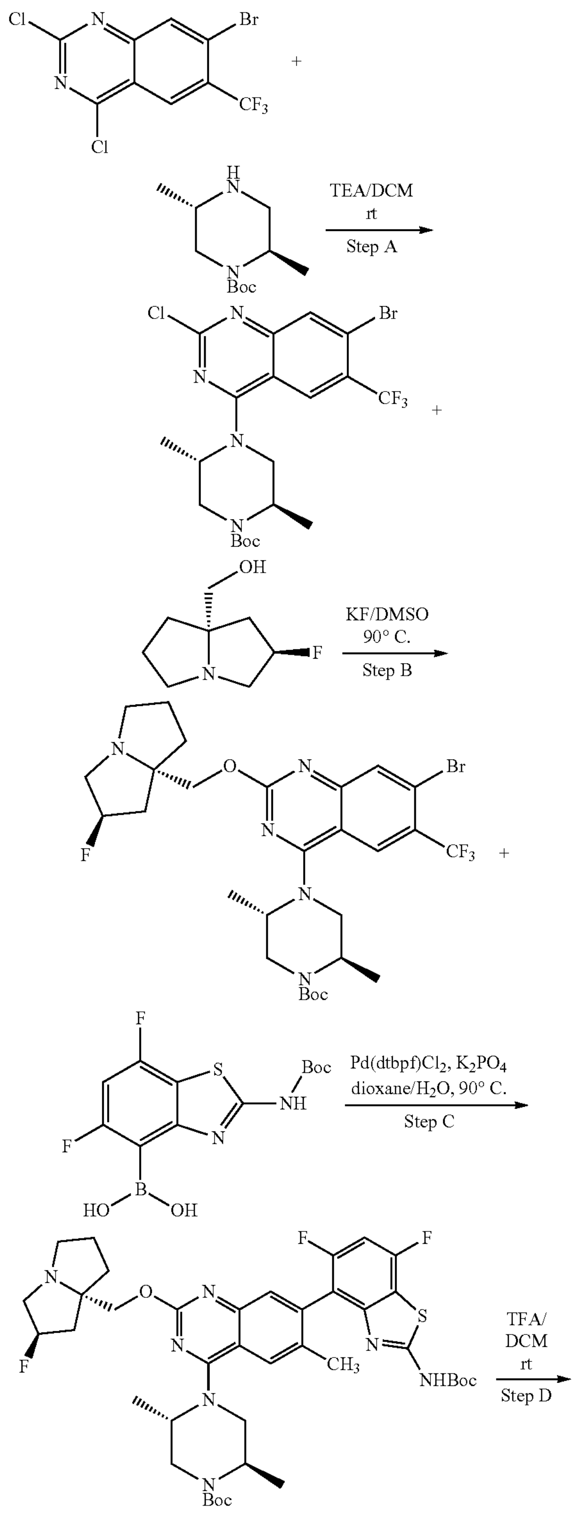

-continued

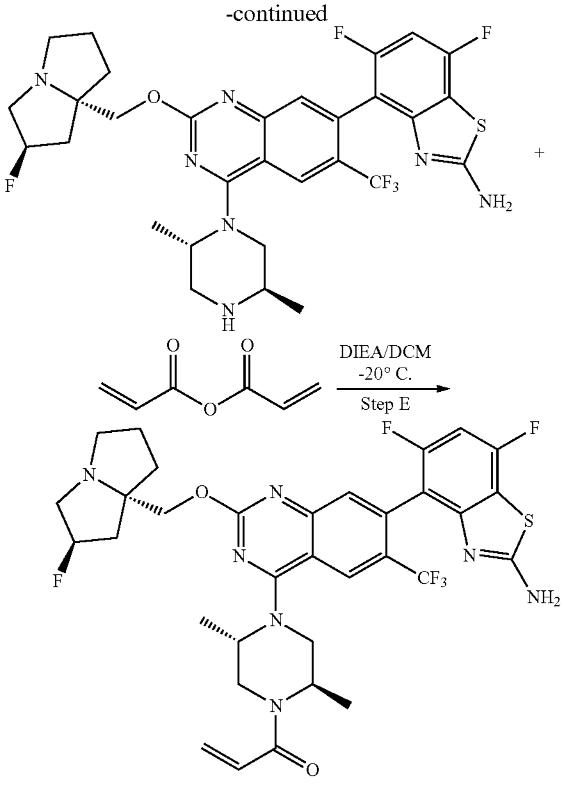

Compound 298

Step A: Preparation of tert-butyl (2R,5S)-4-[7-bromo-2-chloro-6-(trifluoromethyl)quinazolin-4-yl]-2,5-dimethyl-piperazine-1-carboxylate: To a solution of 7-bromo-2,4-dichloro-6-(trifluoromethyl)quinazoline (500 mg, 1.45 mmol) in DCM (10 mL) were added tert-butyl (2R,5S)-2,5-dimethylpiperazine-1-carboxylate (372 mg, 1.73 mmol) and DIEA (0.51 mL, 2.89 mmol) at ambient temperature. The reaction was stirred at ambient temperature for 2 hours. The mixture was concentrated to dry under vacuum and the residue was purified directly by flash chromatography on silica gel (ethyl acetate/petroleum ether=1:4) to give tert-butyl (2R,5S)-4-[7-bromo-2-chloro-6-(trifluoromethyl)quinazolin-4-yl]-2,5-dimethyl-piperazine-1-carboxylate (430 mg, 56%). LCMS ESI (+) m/z 525.1 (M+H).

Step B: Preparation of tert-butyl (2R,5S)-4-(7-bromo-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-[7-bromo-2-chloro-6-(trifluoromethyl) quinazolin-4-yl]-2,5-dimethyl-piperazine-1-carboxylate (330 mg, 0.63 mmol) in DMSO (2 mL) was added [(2R,8S)-2-fluoro-1,2,3,5,6,7-hexahydro pyrrolizin-8-yl]methanol (201 mg, 1.26 mmol) and KF (293 mg, 5.04 mmol) at ambient temperature. The reaction was stirred at 90° C. overnight. After cooled to ambient temperature, the reaction was taken up in EtOAc (50 mL) and the organics were washed with saturated brine solution. The organics were then separated, dried ($MgSO_4$), filtered and concentrated under reduced pressure. The crude was then purified by preparative-TLC to afford tert-butyl (2R,5S)-4-(7-bromo-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate(86 mg, 21%). LCMS ESI (+) m/z 646.3 (M+H).

Step C: Preparation of tert-butyl (2R,5S)-4-(7-(2-((tert-butoxycarbonyl)amino)-5,7-difluorobenzo[d]thiazol-4-yl)-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate: To a solution of tert-butyl (2R,5S)-4-(7-bromo-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate(60 mg, 0.093 mmol) in 1,4-dioxane (3 mL) and water (1 mL) were added [2-(tert-butoxycarbonylamino)-5,7-difluoro-1,-3-benzothiazol-4-yl]boronic acid (37 mg, 0.11 mmol), Pd(dtbpf)$Cl_2$(6.0 mg, 0.0093 mmol) and $K_3PO_4$ (39 mg, 0.19 mmol) at ambient temperature. The reaction was stirred at 90° C. for 1 hour. After cooled to ambient temperature, reaction was diluted with ethyl acetate (20 mL) and the organics washed with water then with saturated brine solution. The organics were then separated, dried ($MgSO_4$) and concentrated under reduced pressure. The crude was then purified by preparative TLC (MeOH/DCM=1:20) to give tert-butyl (2R,5S)-4-(7-(2-((tert-butoxycarbonyl)amino)-5,7-difluorobenzo[d]thiazol-4-yl)-2-(((2R,7aS)-2-fluorotetrahydro-1H-pyrrolizin-7a(5H)-yl)methoxy)-6-(trifluoromethyl)quinazolin-4-yl)-2,5-dimethylpiperazine-1-carboxylate(70 mg, 88%). LCMS ESI (+) m/z 852.2 (M+H).

Step D: Preparation of 4-(4-((2S,5R)-2,5-dimethylpiperazin-1-yl)-2-(((2R,7aS)-2-fluorotetrahydro-1H-pyrrolizin-7a(5H)-yl)methoxy)-6-(trifluoromethyl)quinazolin-7-yl)-5,7-difluorobenzo[d]thiazol-2-amine: To a solution of tert-butyl (2R,5S)-4-[7-[2-(tert-butoxycarbonylamino)-5,7-difluoro-1,3-benzothiazol-4-yl]-2-[[(2R,8S)-2-fluoro-1,2,3,5,6,7-hexahydropyrrolizin-8-yl]methoxy]-6-(trifluoromethyl)quinazolin-4-yl]-2,5-dimethyl-piperazine-1-carboxylate (45 mg, 0.053 mmol) in DCM (2 mL) was added TFA (0.50 mL) at ambient temperature and stirred at ambient temperature for 4 hour. The mixture was concentrated under reduced pressure to afford 4-(4-((2S,5R)-2,5-dimethylpiperazin-1-yl)-2-(((2R,7aS)-2-fluorotetrahydro-1H-pyrrolizin-7a(5H)-yl)methoxy)-6-(trifluoromethyl)quinazolin-7-yl)-5,7-difluorobenzo[d]thiazol-2-amine which was used directly in the next step. LCMS ESI (+) m/z 652.2 (M+H).

Step E: Preparation of 1-((2R,5S)-4-(7-(2-amino-5,7-difluorobenzo[d]thiazol-4-yl)-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one: To a solution of 4-[4-[(2S,5R)-2,5-dimethylpiperazin-1-yl]-2-[[(2R,8S)-2-fluoro-1,2,3,5,6,7-hexahydropyrrolizin-8-yl]methoxy]-6-(trifluoromethyl)quinazolin-7-yl]-5,7-difluoro-1,3-benzothiazol-2-amine (40 mg, 0.049 mmol) in DCM (3 mL) was added DIEA (0.087 mL, 0.49 mmol). The mixture was cooled to −20° C. and prop-2-enoyl prop-2-enoate (7.4 mg, 0.059 mmol) was added slowly. Then the mixture was warmed to room temperature and kept at this temperature for 30 minutes. The reaction was quenched with $H_2O$ (10 mL) and extracted with DCM. The organics were washed with brine, dried ($MgSO_4$), filtered and concentrated to dryness. The crude was then purified by preparative RP-HPLC to give 1-[(2R,5S)-4-[7-(2-amino-5,7-difluoro-1,3-benzothiazol-4-yl)-2-[[(2R,8S)-2-fluoro-1,2,3,5,6,7-hexahydropyrrolizin-8-yl]methoxy]-6-(trifluoromethyl)quinazolin-4-yl]-2,5-dimethyl-piperazin-1-yl]prop-2-en-1-one (814 mg, 39%). LCMS ESI (+) m/z 706.3 (M+H). $^1$HNMR (400 MHz, $CD_3OD$) δ 8.42 (s, 1H), 7.62 (s, J=2.44 Hz, 1H), 6.76-6.92 (m, 2H), 6.28-6.33 (m, 1H), 5.84 (t, J=7.92 Hz, 1H), 5.60 (d, J=51.2 Hz, 1H), 4.97-5.05 (m, 2H), 4.68-4.78 (m, 2H), 4.33-4.57 (m, 2H), 3.83-4.09 (m, 5H), 3.45-3.54 (m, 1H), 2.20-2.78 (m, 6H), 1.28-1.57 (m, 6H).

Synthetic Example 37: Synthesis of 1-((R)-3-(((S)-7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (Compound 302) and 1-((R)-3-(((R)-7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (Compound 303)

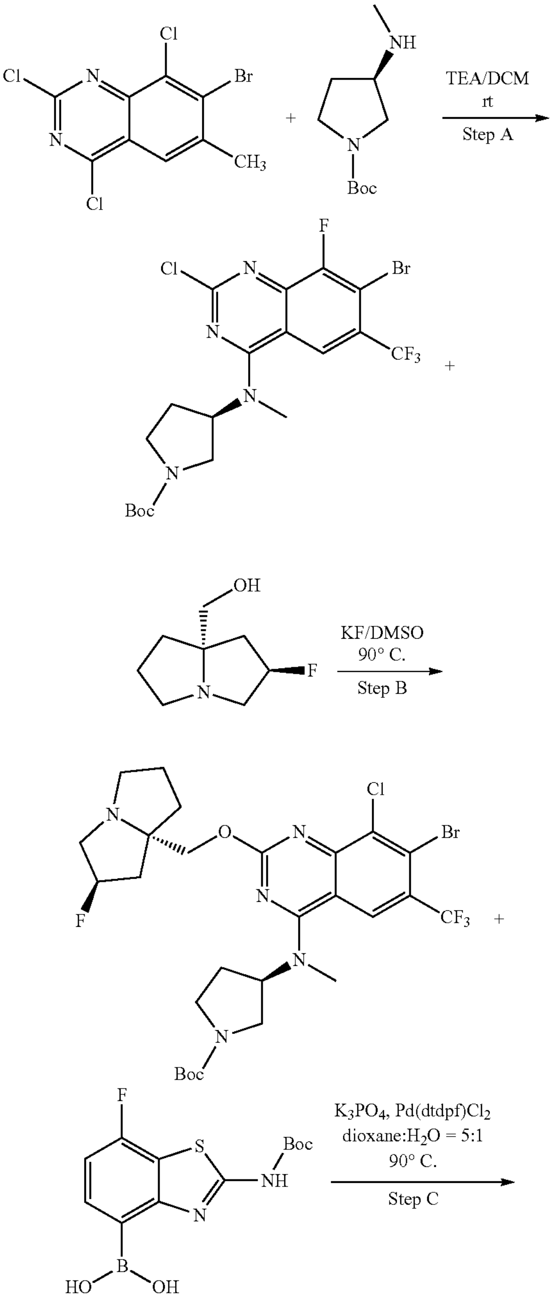

-continued

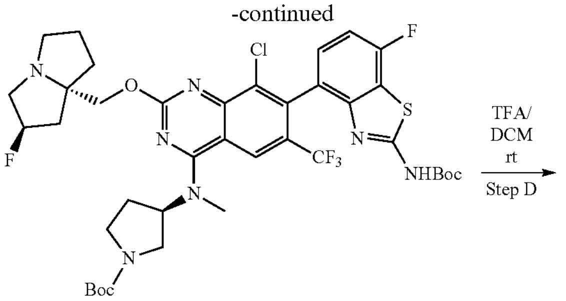

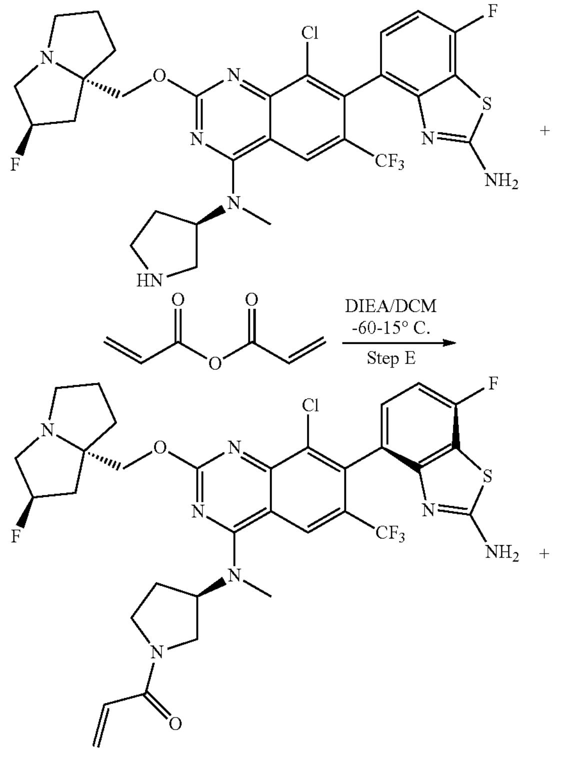

Compound 302

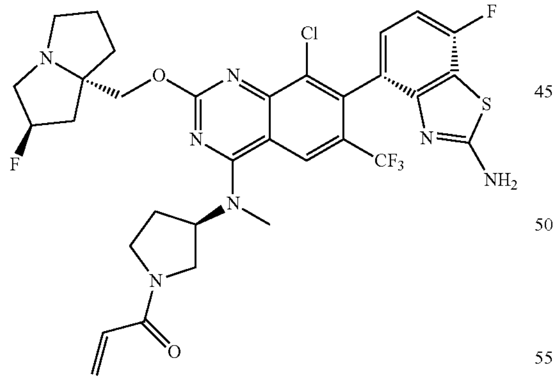

Compound 303

Step A: Preparation of tert-butyl (3R)-3-[[7-bromo-2,8-dichloro-6-(trifluoromethyl)quinazolin-4-yl]-methyl-amino]pyrrolidine-1-carboxylate: To a solution of 7-bromo-2,4,8-trichloro-6-(trifluoromethyl)quinazoline (150 mg, 0.39 mmol) and tert-butyl (3R)-3-(methylamino)pyrrolidine-1-carboxylate (79 mg, 0.39 mmol) in DCM (10 mL) was added DIEA (0.21 mL, 1.18 mmol) at ambient temperature. The reaction was stirred at ambient temperature for 2 hours. The mixture was diluted with water (10 mL) and extracted with DCM (10 mL). The organic phase was dried over anhydrous $Na_2SO_4$, filtered and concentrated to give the crude product. It was purified by preparative TLC to give tert-butyl (3R)-3-[[7-bromo-2,8-dichloro-6-(trifluoromethyl)quinazolin-4-yl]-methyl-amino]pyrrolidine-1-carboxylate (70 mg, 32%). LCMS ESI (+) m/z 543.0 (M+H).

Step B: Preparation of tert-butyl (3R)-3-[[7-bromo-8-chloro-2-[[(2R,8S)-2-fluoro-1,2,3,5,6,7-hexahydropyrrolizin-8-yl]methoxy]-6-(trifluoromethyl)quinazolin-4-yl]-methyl-amino]pyrrolidine-1-carboxylate: To a solution of tert-butyl (3R)-3-[[7-bromo-2,8-dichloro-6-(trifluoromethyl)quinazolin-4-yl]-methyl-amino]pyrrolidine-1-carboxylate (100 mg, 0.18 mmol) and [(2R,8S)-2-fluoro-1,2,3,5,6,7-hexahydropyrrolizin-8-yl]methanol (44 mg, 0.28 mmol) in DMSO (0.70 mL) was added KF (85 mg, 1.47 mmol) at ambient temperature. The reaction was stirred at 90° C. for 2 hours. After cooled to ambient temperature, the reaction was taken up in EtOAc (20 mL) and the organics were washed with saturated brine solution. The organics were then separated, dried ($MgSO_4$), filtered and concentrated under reduced pressure. The crude was then purified by Preparative-TLC to afford tert-butyl (3R)-3-[[7-bromo-8-chloro-2-[[(2R,8S)-2-fluoro-1,2,3,5,6,7-hexahydropyrrolizin-8-yl]methoxy]-6-(trifluoromethyl)quinazolin-4-yl]-methyl-amino]pyrrolidine-1-carboxylate (75 mg, 61%). LCMS ESI (+) m/z 666.1 (M+H).

Step C: Preparation of tert-butyl (3R)-3-[[7-[2-(tert-butoxycarbonylamino)-7-fluoro-1,3-benzothiazol-4-yl]-8-chloro-2-[[(2R,8S)-2-fluoro-1,2,3,5,6,7-hexahydropyrrolizin-8-yl]methoxy]-6-(trifluoromethyl)quinazolin-4-yl]-methyl-amino]pyrrolidine-1-carboxylate: To a solution of tert-butyl (3R)-3-[[7-bromo-8-chloro-2-[[(2R,8S)-2-fluoro-1,2,3,5,6,7-hexahydropyrrolizin-8-yl]methoxy]-6-(trifluoromethyl)quinazolin-4-yl]-methyl-amino]pyrrolidine-1-carboxylate (50 mg, 0.075 mmol), [2-(tert-butoxycarbonylamino)-7-fluoro-1,3-benzothiazol-4-yl] boronic acid (30 mg, 0.098 mmol) and $K_3PO_4$ (48 mg, 0.23 mmol) in 1,4-dioxane (2 mL) and water (0.40 mL) was added Pd(dtbpf)$Cl_2$ (4.9 mg, 0.0075 mmol) under nitrogen at ambient temperature. The reaction was stirred at 90° C. for 2 hours. After cooled to ambient temperature, reaction was diluted with ethyl acetate (10 mL) and the organics washed with water then with saturated brine solution. The organics were then separated, dried ($MgSO_4$) and concentrated under reduced pressure. The crude was then purified by preparative-TLC to afford tert-butyl (3R)-3-[[7-[2-(tert-butoxycarbonylamino)-7-fluoro-1,3-benzothiazol-4-yl]-8-chloro-2-[[(2R,8S)-2-fluoro-1,2,3,5,6,7-hexahydropyrrolizin-8-yl]methoxy]-6-(trifluoromethyl)quinazolin-4-yl]-methyl-amino]pyrrolidine-1-carboxylate (35 mg, 54%). LCMS ESI (+) m/z 854.3 (M+H).

Step D: Preparation of -[8-chloro-2-[[(2R,8S)-2-fluoro-1,2,3,5,6,7-hexahydropyrrolizin-8-yl]methoxy]-4-[methyl-[(3R)-pyrrolidin-3-yl]amino]-6-(trifluoromethyl)quinazolin-7-yl]-7-fluoro-1,3-benzothiazol-2-amine: To a solution of tert-butyl (3R)-3-[[7-[2-(tert-butoxycarbonylamino)-7-fluoro-1,3-benzothiazol-4-yl]-8-chloro-2-[[(2R,8S)-2-fluoro-1,2,3,5,6,7-hexahydropyrrolizin-8-yl]methoxy]-6-(trifluoromethyl)quinazolin-4-yl]-methyl-amino] pyrrolidine-1-carboxylate (20 mg, 0.023 mmol) in DCM (5 mL) was added TFA (0.50 mL) at ambient temperature and stirred at ambient temperature for 2 hours. The mixture was concentrated under reduced pressure and purified by preparative RP-HPLC to give 4-[8-chloro-2-[[(2R,8S)-2-fluoro-1,2,3,5,6,7-hexahydropyrrolizin-8-yl]methoxy]-4-[methyl-[(3R)-pyrrolidin-3-yl]amino]-6-(trifluoromethyl)

quinazolin-7-yl]-7-fluoro-1,3-benzothiazol-2-amine (4.5 mg, 29% yield). LCMS ESI (+) m/z 654.3 (M+H).

Step E: Preparation of 1-((R)-3-(((S)-7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (Compound 302) and 1-((R)-3-(((R)-7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (Compound 303): To a solution of 4-[8-chloro-2-[[(2R,8S)-2-fluoro-1,2,3,5,6,7-hexahydropyrrolizin-8-yl]methoxy]-4-[methyl-[(3R)-pyrrolidin-3-yl]amino]-6-(trifluoromethyl)quinazolin-7-yl]-7-fluoro-1,3-benzothiazol-2-amine (30 mg, 0.046 mmol) and DIEA (0.024 mL, 0.14 mmol) in DCM (5 mL) was added prop-2-enoyl prop-2-enoate (5.8 mg, 0.046 mmol) at −60° C. After addition, the mixture was warmed to ambient temperature and stirred at ambient temperature for 1 hour. The reaction was quenched with $H_2O$ (10 mL) and extracted with DCM. The organics were washed with brine, dried ($MgSO_4$), filtered and concentrated to dryness. The crude was then purified by preparative RP-HPLC. The first compound off the column was identified as one atropisomer, 1-((R)-3-(((S)-7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (Compound 302) (4.5 mg, 13%). LCMS ESI (+) m/z 708.3 (M+H). $^1$HNMR (400 MHz, $CD_3OD$) δ 8.50 (s, 1H), 7.13-7.16 (m, 1H), 7.00-7.03 (m, 1H), 6.62-6.71 (m, 1H), 6.32 (d, J=16.7 Hz, 1H), 5.78-5.82 (m, 1H), 5.55 (d, J=51.4 Hz, 1H), 5.22-5.36 (m, 1H), 4.66-4.76 (m, 2H), 4.04-4.21 (m, 1H), 3.90-4.04 (m, 1H), 3.72-3.90 (m, 3H), 3.50-3.63 (m, 1H), 3.41-3.50 (m, 5H), 2.32-2.80 (m, 7H), 2.11-2.12 (m, 1H). The second compound off the column was identified as the other atropisomer, 1-((R)-3-(((R)-7-(2-amino-7-fluorobenzo[d]thiazol-4-yl)-8-chloro-2-(((2R,7aS)-2-fluorotetrahydro-1H-pyrrolizin-7a(5H)-yl)methoxy)-6-(trifluoromethyl)quinazolin-4-yl)(methyl)amino)pyrrolidin-1-yl)prop-2-en-1-one (Compound 303) (2.2 mg, 6%). LCMS ESI (+) m/z 708.3 (M+H). $^1$HNMR (400 MHz, $CD_3OD$) δ 8.50 (s, 1H), 7.12-7.16 (m, 1H), 7.01 (t, J=8.8 Hz, 1H), 6.61-6.71 (m, 1H), 6.32 (d, J=16.8 Hz, 1H), 5.77-5.82 (m, 1H), 5.55 (d, J=51.6 Hz, 1H), 5.24-5.36 (m, 1H), 4.64-4.78 (m, 2H), 3.46-4.19 (m, 12H), 2.10-2.72 (m, 8H).

Synthetic Example 38: Synthesis of 4-(4-(((3S,4R)-1-acryloyl-4-fluoropyrrolidin-3-yl)(methyl)amino)-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 315)

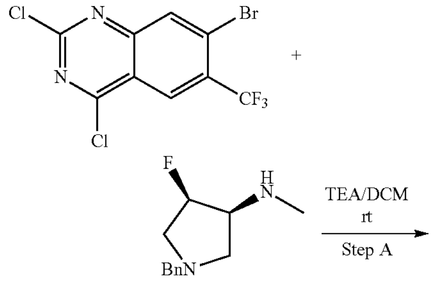

-continued

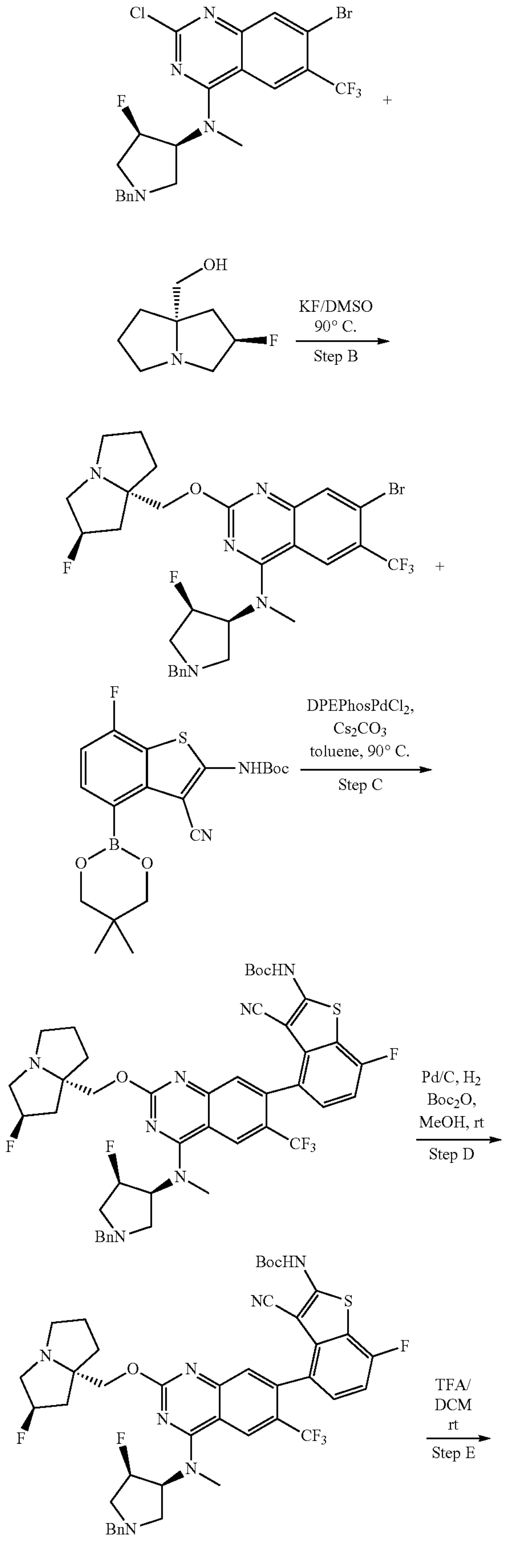

-continued

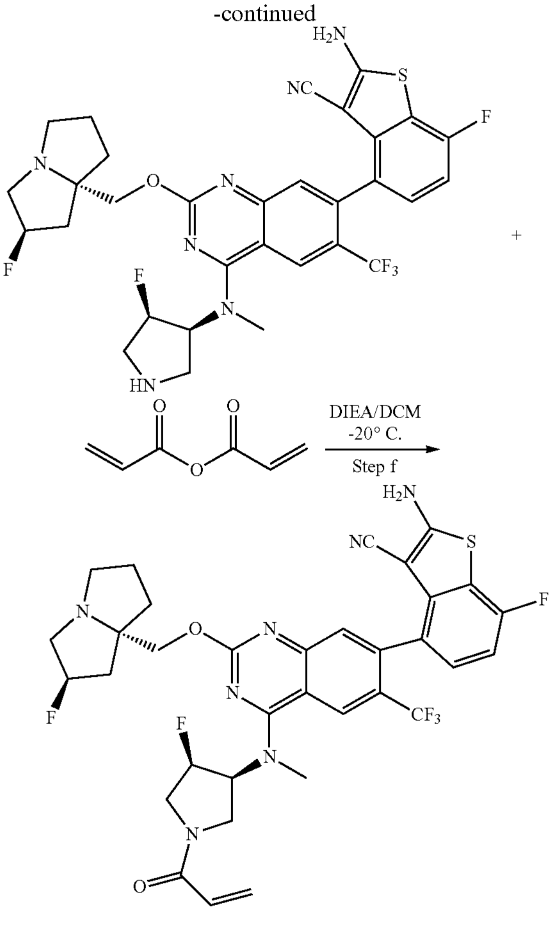

Compound 315

Step A: Preparation of N-[(3S,4R)-1-benzyl-4-fluoro-pyrrolidin-3-yl]-7-bromo-2-chloro-N-methyl-6-(trifluoromethyl)quinazolin-4-amine: To a solution of 7-bromo-2,4-dichloro-6-(trifluoromethyl)quinazoline (138 mg, 0.40 mmol) in DCM (5 mL) was added (3S,4R)-1-benzyl-4-fluoro-N-methyl-pyrrolidin-3-amine (99 mg, 0.48 mmol) and TEA (0.17 mL, 1.19 mmol) at room temperature and stirred for 2 hours at ambient temperature. The reaction was concentrated to dry and the residue was taken up in EtOAc (40 mL) and the organic layers washed with 2×40 mL water, then 1×40 mL saturated brine solution. The organic layers were then separated and dried ($Na_2SO_4$) before concentration to dryness. The crude was then purified by flash column chromatography on silica gel eluting with 25% EtOAc in petroleum ether to give N-[(3S,4R)-1-benzyl-4-fluoro-pyrrolidin-3-yl]-7-bromo-2-chloro-N-methyl-6-(trifluoromethyl)quinazolin-4-amine (127 mg, 61% yield). LCMS ESI (+) m/z 517 (M+H).

Step B: Preparation of N-[(3S,4R)-1-benzyl-4-fluoro-pyrrolidin-3-yl]-7-bromo-2-[[(2R,8S)-2-fluoro-1,2,3,5,6,7-hexahydropyrrolizin-8-yl]methoxy]-N-methyl-6-(trifluoromethyl)quinazolin-4-amine: To a solution of [(2R,8S)-2-fluoro-1,2,3,5,6,7-hexahydropyrrolizin-8-yl]methanol (97 mg, 0.61 mmol) in DMSO (0.20 mL) was added N-[(3S,4R)-1-benzyl-4-fluoro-pyrrolidin-3-yl]-7-bromo-2-chloro-N-methyl-6-(trifluoromethyl)quinazolin-4-amine (105 mg, 0.20 mmol) and potassium fluoride (94 mg, 1.62 mmol) at ambient temperature. The reaction was stirred at 90° C. for 8 hours. After cooled to ambient temperature, the reaction was taken up in EtOAc (50 mL) and the organic layers were washed with saturated brine solution. The organic layers were then separated, dried ($MgSO_4$), filtered and concentrated under reduced pressure. The crude was then purified by preparative-TLC (DCM/MeOH=20:1) to give N-[(3S,4R)-1-benzyl-4-fluoro-pyrrolidin-3-yl]-7-bromo-2-[[(2R,8S)-2-fluoro-1,2,3,5,6,7-hexahydropyrrolizin-8-yl]methoxy]-N-methyl-6-(trifluoromethyl)quinazolin-4-amine (90 mg, 69%). LCMS ESI (+) m/z 640 (M+H).

Step C: Preparation of tert-butyl N-[4-[4-[[(4R)-1-benzyl-4-fluoro-pyrrolidin-3-yl]-methyl-amino]-2-[[(2R,8S)-2-fluoro-1,2,3,5,6,7-hexahydropyrrolizin-8-yl]methoxy]-6-(trifluoromethyl)quinazolin-7-yl]-3-cyano-7-fluoro-benzothiophen-2-yl]carbamate: To a solution of tert-butyl N-[3-cyano-4-(5,5-dimethyl-1,3,2-dioxaborinan-2-yl)-7-fluoro-benzothiophen-2-yl]carbamate (95 mg, 0.23 mmol) in 1,4-dioxane (1.5 mL) was added N-[(4R)-1-benzyl-4-fluoro-pyrrolidin-3-yl]-7-bromo-2-[[(2R,8S)-2-fluoro-1,2,3,5,6,7-hexahydropyrrolizin-8-yl]methoxy]-N-methyl-6-(trifluoromethyl)quinazolin-4-amine (50 mg, 0.078 mmol) and cesium carbonate (76 mg, 0.23 mmol) at room temperature. The mixture was stirred at 95° C. for 8 hours. After cooled to ambient temperature, reaction mixture was diluted with ethyl acetate (20 mL) and the organic layers washed with water, then with saturated brine solution. The organic layers were then separated, dried ($MgSO_4$) and concentrated under reduced pressure. The crude was then purified by preparative TLC (MeOH/DCM=1:20) to give tert-butyl N-[4-[4-[[(4R)-1-benzyl-4-fluoro-pyrrolidin-3-yl]-methyl-amino]-2-[[(2R,8S)-2-fluoro-1,2,3,5,6,7-hexahydropyrrolizin-8-yl]methoxy]-6-(trifluoromethyl)quinazolin-7-yl]-3-cyano-7-fluoro-benzothiophen-2-yl]carbamate (50 mg, 75%). LCMS ESI (+) m/z 852 (M+H).

Step D: Preparation of 4-(4-((2S,5R)-2,5-dimethylpiperazin-1-yl)-2-(((2R,7aS)-2-fluorotetrahydro-1H-pyrrolizin-7a(5H)-yl)methoxy)-6-(trifluoromethyl)quinazolin-7-yl)-5,7-difluorobenzo[d]thiazol-2-amine: A suspension of tert-butyl N-[4-[4-[[(3S,4R)-1-benzyl-4-fluoro-pyrrolidin-3-yl]-methyl-amino]-2-[[(2R,8S)-2-fluoro-1,2,3,5,6,7-hexahydropyrrolizin-8-yl]methoxy]-6-(trifluoromethyl)quinazolin-7-yl]-3-cyano-7-fluoro-benzothiophen-2-yl]carbamate (30 mg, 0.035 mmol), di-tert-butyl decarbonate (0.032 mL, 0.14 mmol) and 10% Pd/C (59 mg, 0.56 mmol) in methanol (5 mL) was stirred at 1 atmosphere of hydrogen for 4 hours at ambient temperature. After filtered on Celite® and concentrated to dry, the crude was purified by preparative-TLC to give tert-butyl (3S,4R)-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]-6-(trifluoromethyl)quinazolin-4-yl]-methyl-amino]-4-fluoro-pyrrolidine-1-carboxylate (30 mg, 98%). LCMS ESI (+) m/z 862 (M+H).

Step E: Preparation of 2-amino-7-fluoro-4-[2-[[(2R,8S)-2-fluoro-1,2,3,5,6,7-hexahydropyrrolizin-8-yl]methoxy]-4-[[(3S,4R)-4-fluoropyrrolidin-3-yl]-methyl-amino]-6-(trifluoromethyl)quinazolin-7-yl]benzothiophene-3-carbonitrile: To a solution of tert-butyl (3S,4R)-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]-6-(trifluoromethyl)quinazolin-4-yl]-methyl-amino]-4-fluoro-pyrrolidine-1-carboxylate (20 mg, 0.023 mmol) in DCM (2 mL) was added TFA (0.60 mL, 7.79 mmol) at ambient temperature and stirred at ambient temperature for 1 hour. The mixture was concentrated under reduced pressure and purified by preparative RP-HPLC to give 2-amino-7-fluoro-4-[2-[[(2R,8S)-2-fluoro-1,2,3,5,6,7-hexahydropyrrolizin-8-yl]

methoxy]-4-[[(3S,4R)-4-fluoropyrrolidin-3-yl]-methyl-amino]-6-(trifluoromethyl)quinazolin-7-yl]benzothiophene-3-carbonitrile (9.7 mg, 60%). LCMS ESI (+) m/z 662.3 (M+H).

Step F: Preparation of 1-((2R,5S)-4-(7-(2-amino-5,7-difluorobenzo[d]thiazol-4-yl)-2-(((2R,7aS)-2-fluorotetrahydro-1H-pyrrolizin-7a(5H)-yl)methoxy)-6-(trifluoromethyl)quinazolin-4-yl)-2,5-dimethylpiperazin-1-yl)prop-2-en-1-one: To a solution of 2-amino-7-fluoro-4-[2-[[(2R,8S)-2-fluoro-1,2,3,5,6,7-hexahydropyrrolizin-8-yl]methoxy]-4-[[(3S,4R)-4-fluoropyrrolidin-3-yl]-methyl-amino]-6-(trifluoromethyl)quinazolin-7-yl]benzothiophene-3-carbonitrile (42 mg, 0.063 mmol) and DIEA (0.034 mL, 0.49 mmol) in DCM (3 mL) was added prop-2-enoyl prop-2-enoate (7.4 mg, 0.059 mmol) at 0° C. Then the mixture was warmed to room temperature and kept at this temperature for 1 hour. The reaction was quenched with $H_2O$ (10 mL) and extracted with DCM. The organic layers were washed with brine, dried ($MgSO_4$), filtered and concentrated to dryness. The crude was then purified by preparative RP-HPLC to give 4-(4-(((3S,4R)-1-acryloyl-4-fluoropyrrolidin-3-yl)(methyl)amino)-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (16 mg, 35%). LCMS ESI (+) m/z 716.3 (M+H). $^1$HNMR (400 MHz, $CD_3OD$) δ 8.64-8.65 (m, 1H), 7.60-7.61 (m, 1H), 7.22 (t, J=8.8 Hz, 1H), 7.00-7.02 (m, 1H), 6.64-6.80 (m, 1H), 6.37 (d, J=16.8 Hz, 1H), 5.58-5.85 (m, 4H), 4.70-4.79 (m, 2H), 3.76-4.35 (m, 10H), 3.47-3.48 (m, 1H), 2.23-2.68 (m, 6H).

Synthetic Example 39: Synthesis of 4-((2S,5R)-4-acryloyl-2,5-dimethylpiperazin-1-yl)-7-(2-amino-3-cyano-7-fluorobenzo[b]thiophen-4-yl)-8-fluoro-2-(((2R,7aS)-2-fluorotetrahydro-1H-pyrrolizin-7a(5H)-yl)methoxy)quinazoline-6-carbonitrile (Compound 324)

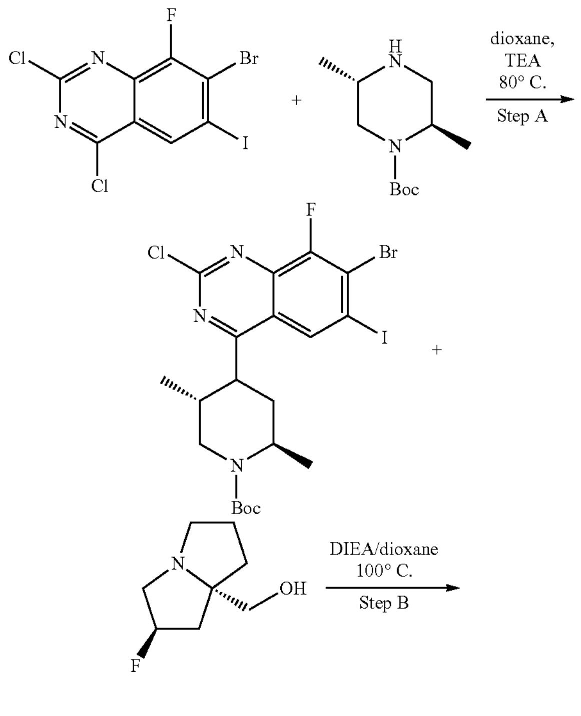

-continued

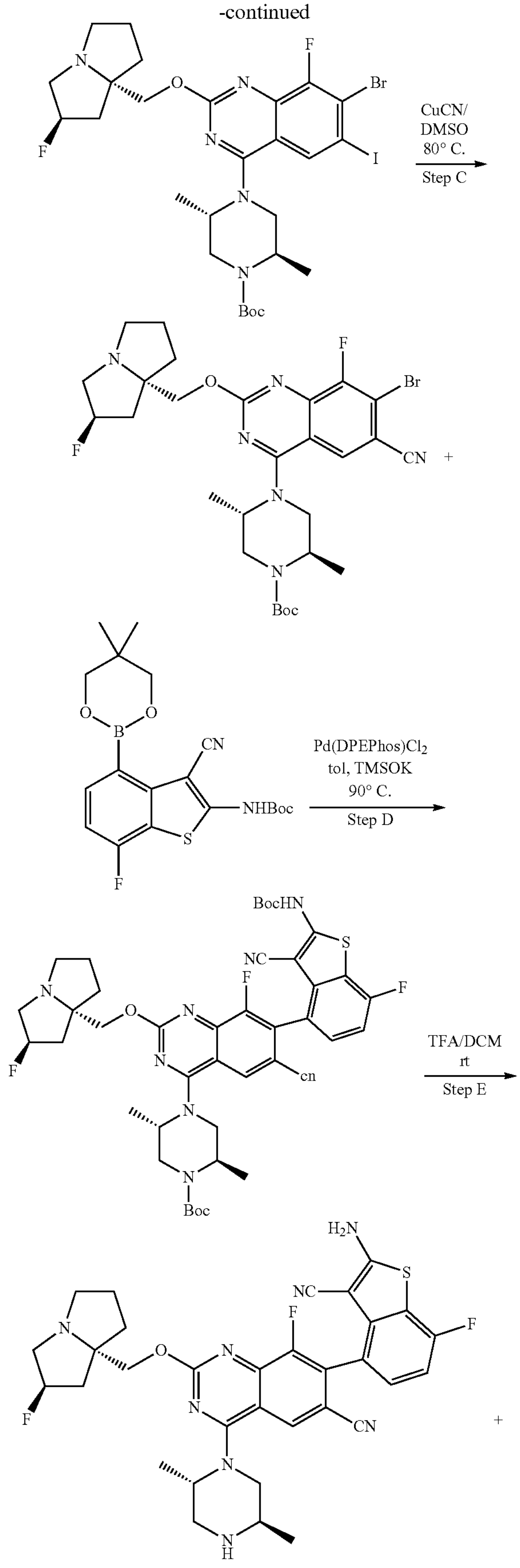

-continued

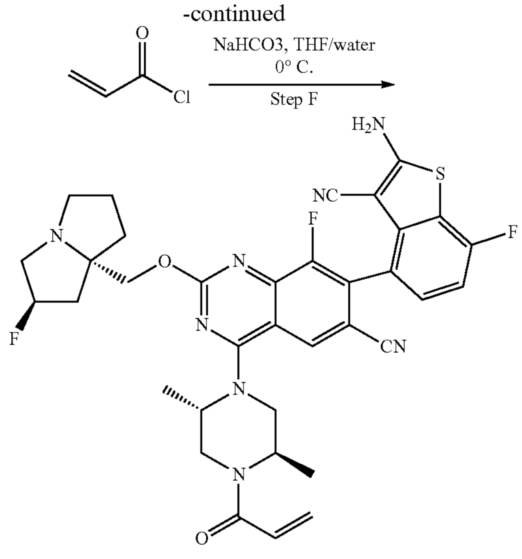

Compound 324

Step A: Preparation of tert-butyl (2R,5S)-4-(7-bromo-2-chloro-8-fluoro-6-iodo-quinazolin-4-yl)-2,5-dimethyl-piperazine-1-carboxylate: To a solution of 7-bromo-2,4-dichloro-8-fluoro-6-iodo-quinazoline (10.00 g, 4.74 mmol, 20% purity) in dioxane (5 mL) was added TEA (2.0 mL, 14.2 mmol) and tert-butyl (2R,5S)-2,5-dimethylpiperazine-1-carboxylate (1.32 g, 6.16 mmol) at ambient temperature. After addition, the reaction mixture was stirred at 80° C. overnight. The solvent was removed and the residue was dissolved in EA (50 mL), washed with water and brine, dried over $Na_2SO_4$, concentrated. The residue was purified by flash chromatography on silica gel (Petroleum ether/ethyl acetate=5/1) to give tert-butyl (2R,5S)-4-(7-bromo-2-chloro-8-fluoro-6-iodo-quinazolin-4-yl)-2,5-dimethyl-piperazine-1-carboxylate (1.30 g, 35%). LCMS ESI (+) m/z 598.9 (M+H).

Step B: Preparation of tert-butyl (2R,5S)-4-[7-bromo-8-fluoro-2-[[(2R,8S)-2-fluoro-1,2,3,5,6,7-hexahydropyrrolizin-8-yl]methoxy]-6-iodo-quinazolin-4-yl]-2,5-dimethyl-piperazine-1-carboxylate: To a solution of tert-butyl (2R,5S)-4-(7-bromo-2-chloro-8-fluoro-6-iodo-quinazolin-4-yl)-2,5-dimethyl-piperazine-1-carboxylate (1.50 g, 2.50 mmol) in 1,4-Dioxane (5 mL) was added [(2R,8S)-2-fluoro-1,2,3,5,6,7-hexahydropyrrolizin-8-yl]methanol (0.64 g, 4.00 mmol) and DIEA (2.2 mL, 12.5 mmol). After addition, the reaction mixture was stirred at 100° C. for 48 hours. The solvent was removed and the residue was dissolved in EA (50 mL), washed with water and brie, dried over $Na_2SO_4$, concentrated. The residue was purified by preparative-TLC to give tert-butyl (2R,5S)-4-[7-bromo-8-fluoro-2-[[(2R,8S)-2-fluoro-1,2,3,5,6,7-hexahydropyrrolizin-8-yl]methoxy]-6-iodo-quinazolin-4-yl]-2,5-dimethyl-piperazine-1-carboxylate (800 mg, 36%). LCMS ESI (+) m/z 722.0 (M+H).

Step C: Preparation of give tert-butyl (2R,5S)-4-[7-bromo-6-cyano-8-fluoro-2-[[(2R,8S)-2-fluoro-1,2,3,5,6,7-hexahydropyrrolizin-8-yl]methoxy]quinazolin-4-yl]-2,5-dimethyl-piperazine-1-carboxylate: To a solution of tert-butyl (2R,5S)-4-[7-bromo-8-fluoro-2-[[(2R,8S)-2-fluoro-1,2,3,5,6,7-hexahydropyrrolizin-8-yl]methoxy]-6-iodo-quinazolin-4-yl]-2,5-dimethyl-piperazine-1-carboxylate (500 mg, 0.69 mmol) in DMSO (10 mL) was added CuCN (155 mg, 1.73 mmol) at ambient temperature. After addition, the reaction mixture was stirred at 80° C. for 16 hours. The reaction mixture was poured into ice water, extracted with EA (3×10 mL), the combined organic phase was washed with water and brine, dried over $Na_2SO_4$, concentrated. The residue was purified by flash chromatography on silica gel (DCM/MeOH=20/1) to give tert-butyl (2R,5S)-4-[7-bromo-6-cyano-8-fluoro-2-[[(2R,8S)-2-fluoro-1,2,3,5,6,7-hexahydropyrrolizin-8-yl]methoxy]quinazolin-4-yl]-2,5-dimethyl-piperazine-1-carboxylate (340 mg, purity: 27%, 21%). LCMS ESI (+) m/z 621.1 (M+H).

Step D: Preparation of tert-butyl (2R,5S)-4-[7-[2-(tert-butoxycarbonylamino)-3-cyano-7-fluoro-benzothiophen-4-yl]-6-cyano-8-fluoro-2-[[(2R,8S)-2-fluoro-1,2,3,5,6,7-hexahydropyrrolizin-8-yl]methoxy]quinazolin-4-yl]-2,5-dimethyl-piperazine-1-carboxylate: To a solution of tert-butyl (2R,5S)-4-[7-bromo-6-cyano-8-fluoro-2-[[(2R,8S)-2-fluoro-1,2,3,5,6,7-hexahydropyrrolizin-8-yl]methoxy]quinazolin-4-yl]-2,5-dimethyl-piperazine-1-carboxylate (150 mg, 0.24 mmol) in toluene (2 mL) was added tert-butyl N-[3-cyano-4-(5,5-dimethyl-1,3,2-dioxaborinan-2-yl)-7-fluoro-benzothiophen-2-yl]carbamate (195 mg, 0.48 mmol), TMSOK (93 mg, 0.72 mmol) and Pd(DPEPhos)$Cl_2$ (35 mg, 0.048 mmol) at ambient temperature. After addition, the reaction mixture was stirred at 90° C. for 8 hours. After cooled to ambient temperature, 50 mL of EA was added, and then the reaction mixture was washed with water and brine, dried over $Na_2SO_4$, concentrated. The residue was purified with preparative RP-HPLC to give tert-butyl (2R,5S)-4-[7-[2-(tert-butoxycarbonylamino)-3-cyano-7-fluoro-benzothiophen-4-yl]-6-cyano-8-fluoro-2-[[(2R,8S)-2-fluoro-1,2,3,5,6,7-hexahydropyrrolizin-8-yl]methoxy]quinazolin-4-yl]-2,5-dimethyl-piperazine-1-carboxylate (30 mg, 12%). LCMS ESI (+) m/z 833.1 (M+H).

Step E: Preparation of 7-(2-amino-3-cyano-7-fluoro-benzothiophen-4-yl)-4-[(2S,5R)-2,5-dimethylpiperazin-1-yl]-8-fluoro-2-[[(2R,8S)-2-fluoro-1,2,3,5,6,7-hexahydropyrrolizin-8-yl]methoxy]quinazoline-6-carbonitrile: To a solution of tert-butyl (2R,5S)-4-[7-[2-(tert-butoxycarbonylamino)-3-cyano-7-fluoro-benzothiophen-4-yl]-6-cyano-8-fluoro-2-[[(2R,8S)-2-fluoro-1,2,3,5,6,7-hexahydropyrrolizin-8-yl]methoxy]quinazolin-4-yl]-2,5-dimethyl-piperazine-1-carboxylate (25 mg, 0.030 mmol) in DCM (2 mL) was added TFA (0.50 mL, 6.71 mmol) at ambient temperature. The reaction mixture was stirred at ambient temperature for 16 hours. The solvent was removed to give 7-(2-amino-3-cyano-7-fluoro-benzothiophen-4-yl)-4-[(2S,5R)-2,5-dimethylpiperazin-1-yl]-8-fluoro-2-[[(2R,8S)-2-fluoro-1,2,3,5,6,7-hexahydropyrrolizin-8-yl]methoxy]quinazoline-6-carbonitrile (26 mg, 100%), which was used in next step directly without further purification. LCMS ESI (+) m/z 633.2 (M+H).

Step F: Preparation of 4-((2S,5R)-4-acryloyl-2,5-dimethylpiperazin-1-yl)-7-(2-amino-3-cyano-7-fluorobenzo[b]thiophen-4-yl)-8-fluoro-2-(((2R,7aS)-2-fluorotetrahydro-1H-pyrrolizin-7a(5H)-yl)methoxy)quinazoline-6-carbonitrile: To a solution of 7-(2-amino-3-cyano-7-fluoro-benzothiophen-4-yl)-4-[(2S,5R)-2,5-dimethylpiperazin-1-yl]-8-fluoro-2-[[(2R,8S)-2-fluoro-1,2,3,5,6,7-hexahydropyrrolizin-8-yl]methoxy]quinazoline-6-carbonitrile (26 mg, 0.033 mmol) in THF (5 mL) and water (5 mL) was added sodium biocarbonate (14 mg, 0.16 mmol) at 0° C., then Acrylyl chloride (3.0 mg, 0.033 mmol) in 1 mL of THF was added dropwise, after addition the reaction mixture was stirred at 0° C. for 10 minutes. The reaction mixture was extracted with EA (3×5 mL), the combined organic phase was washed with brine, dried over $Na_2SO_4$, concentrated. The residue was purified by preparative-TLC to give 7-(2-amino-3-cyano-7-fluoro-benzothiophen-4-yl)-

4-[(2S,5R)-2,5-dimethyl-4-prop-2-enoyl-piperazin-1-yl]-8-fluoro-2-[[(2R,8S)-2-fluoro-1,2,3,5,6,7-hexahydropyrrolizin-8-yl]methoxy]quinazoline-6-carbonitrile (14 mg, 56%). LCMS ESI (+) m/z 687.1 (M+H). $^{1}$HNMR (400 MHz, $CDCl_3$) δ 8.05-8.00 (m, 1H), 7.34-7.31 (m, 1H), 7.06 (t, 1H), 6.64-6.52 (m, 1H), 6.40 (t, 1H), 5.80 (d, 1H), 5.71 (s, 1H), 5.59 (s, 1H), 5.38 (s, 0.5H), 5.24 (s, 0.5H), 5.05-4.73 (m, 2H), 4.42-4.08 (m, 4H), 3.95-3.83 (m, 2H), 3.71 (d, 1H), 3.52-3.44 (m, 1H), 3.27-3.20 (m, 2H), 3.08-2.94 (m, 1H), 2.30-2.15 (m, 3H), 1.96-1.80 (m, 2H), 1.43-1.37 (m, 3H), 1.27-1.17 (m, 3H).

Synthetic Example 40: Synthesis of 4-(2-(3-(5-azaspiro[2.3]hexan-5-yl)azetidin-1-yl)-4-((2S,5R)-4-acryloyl-2,5-dimethylpiperazin-1-yl)-8-fluoro-6-(trifluoromethyl)quinazolin-7-yl)-2-amino-7-fluorobenzo[b]thiophene-3-carbonitrile (Compound 338)

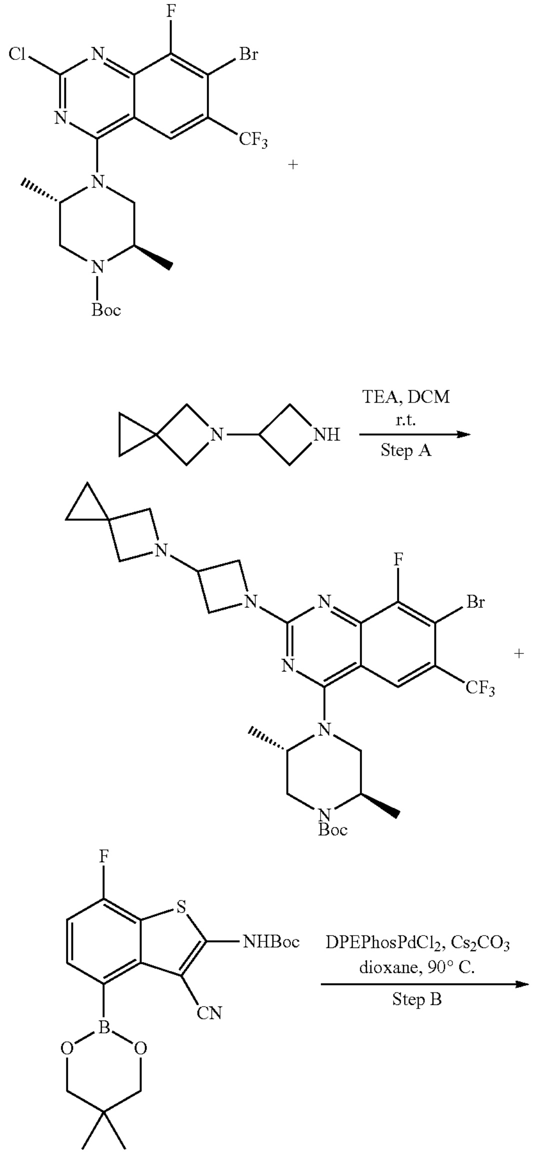

-continued

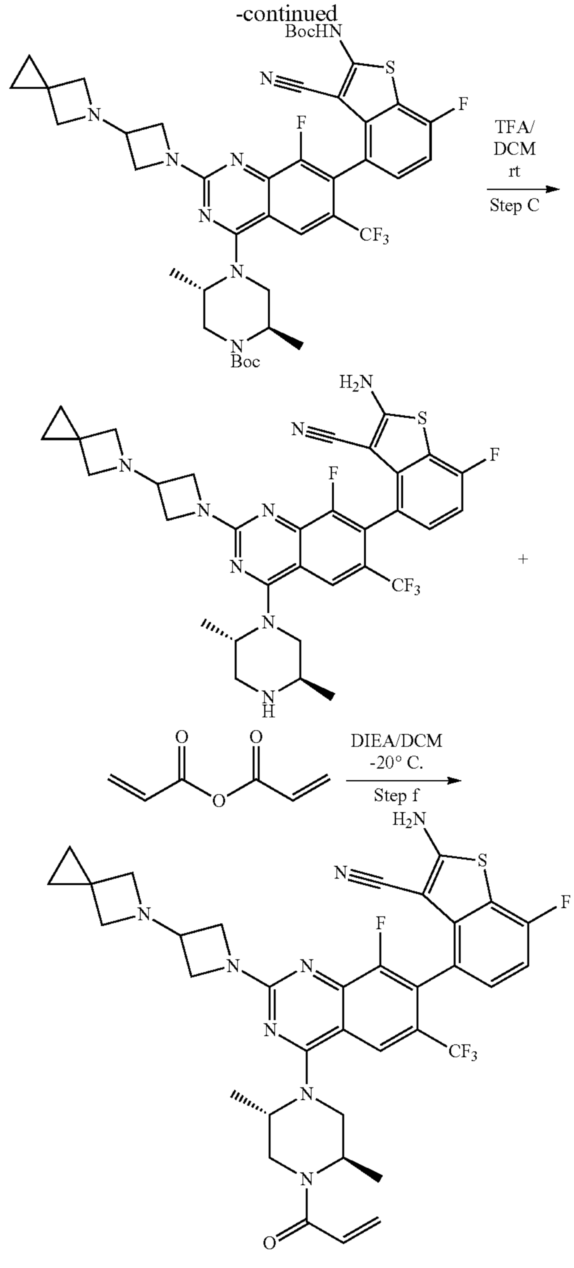

Compound 338

Step A: Preparation of tert-butyl-(2R,5S)-4-[2-[3-(5-azaspiro[2.3]hexan-5-yl)azetidin-1-yl]-7-bromo-8-fluoro-6-(trifluoromethyl)quinazolin-4-yl]-2,5-dimethyl-piperazine-1-carboxylate: To a solution of tert-butyl (2R,5S)-4-[7-bromo-2-chloro-8-fluoro-6-(trifluoromethyl)quinazolin-4-yl]-2,5-dimethyl-piperazine-1-carboxylate (194 mg, 0.36 mmol) in DCM (2 mL) was added DIEA (290 mg, 1.63 mmol) and 5-(azetidin-3-yl)-5-azaspiro[2.3]hexane (45 mg, 0.326 mmol) at ambient temperature and stirred for 2 hours at ambient temperature. The reaction was concentrated to dry and the residue was directly purified by flash column chromatography on silica gel eluting with 50% EtOAc in Petroleum ether to give tert-butyl-(2R,5S)-4-[2-[3-(5-azaspiro[2.3]hexan-5-yl)azetidin-1-yl]-7-bromo-8-fluoro-6-(trifluoromethyl)quinazolin-4-yl]-2,5-dimethyl-piperazine-1-carboxylate (160 mg, 76%). LCMS ESI (+) m/z 643.3 (M+H).

Step B: Preparation of tert-butyl-(2R,5S)-4-[2-[3-(5-azaspiro[2.3]hexan-5-yl)azetidin-1-yl]-7-[2-(tert-butoxycarbonylamino)-3-cyano-7-fluoro-benzothiophen-4-yl]-8-fluoro-6-(trifluoromethyl)quinazolin-4-yl]-2,5-dimethyl-piperazine-1-carboxylate: To a solution of tert-butyl-(2R,5S)-4-[2-[3-(5-azaspiro[2.3]hexan-5-yl)azetidin-1-yl]-7-bromo-8-fluoro-6-(trifluoromethyl)quinazolin-4-yl]-2,5-dimethyl-piperazine-1-carboxylate (170 mg, 0.26 mmol) in 1,4-Dioxane (10 mL) was added tert-butyl N-[3-cyano-4-(5,5-dimethyl-1,3,2-dioxaborinan-2-yl)-7-fluoro-benzothiophen-2-yl]carbamate (320 mg, 0.79 mmol), $Cs_2CO_3$ (215 mg, 0.66 mmol) and Pd(DPEPhos)$Cl_2$ (56 mg, 0.079 mmol) at ambient temperature. The mixture was bubbled with Ar for 1-2 min and then sealed. The mixture was stirred at 90° C. for 8 hours. After cooled to ambient temperature, reaction was diluted with ethyl acetate (20 mL) and the organics washed with water then with saturated brine solution. The organics were then separated, dried ($MgSO_4$) and concentrated under reduced pressure. The crude was then purified by Preparative TLC (MeOH/DCM=1:20) to give tert-butyl-(2R,5S)-4-[2-[3-(5-azaspiro[2.3]hexan-5-yl)azetidin-1-yl]-7-[2-(tert-butoxycarbonylamino)-3-cyano-7-fluoro-benzothiophen-4-yl]-8-fluoro-6-(trifluoromethyl)quinazolin-4-yl]-2,5-dimethyl-piperazine-1-carboxylate (80 mg, 35%). LCMS ESI (+) m/z 855.5 (M+H).

Step C: Preparation of 2-amino-4-[2-[3-(5-azaspiro[2.3]hexan-5-yl)azetidin-1-yl]-8-fluoro-4-[rac-(2S,5R)-2,5-dimethylpiperazin-1-yl]-6-(trifluoromethyl)quinazolin-7-yl]-7-fluoro-benzothiophene-3-carbonitrile: To a solution of tert-butyl rac-(2R,5S)-4-[2-[3-(5-azaspiro[2.3]hexan-5-yl)azetidin-1-yl]-7-[2-(tert-butoxycarbonylamino)-3-cyano-7-fluoro-benzothiophen-4-yl]-8-fluoro-6-(trifluoromethyl)quinazolin-4-yl]-2,5-dimethyl-piperazine-1-carboxylate (50 mg, 0.059 mmol) in DCM (2 mL) was added TFA (1.0 mL, 4.78 mmol) at ambient temperature and stirred at ambient temperature for 2 hour. The mixture was concentrated under reduced pressure. The residue obtained was suspended in saturated sodium bicarbonate and DCM. The organic layer was separated, dried (sodium sulfate), filtered and concentrated under reduced pressure to give 2-amino-4-[2-[3-(5-azaspiro[2.3]hexan-5-yl)azetidin-1-yl]-8-fluoro-4-[rac-(2S,5R)-2,5-dimethylpiperazin-1-yl]-6-(trifluoromethyl)quinazolin-7-yl]-7-fluoro-benzothiophene-3-carbonitrile (35 mg, 91%). LCMS ESI (+) m/z 655.3 (M+H).

Step D: Preparation of 4-(2-(3-(5-azaspiro[2.3]hexan-5-yl)azetidin-1-yl)-4-((2S,5R)-4-acryloyl-2,5-dimethylpiperazin-1-yl)-8-fluoro-6-(trifluoromethyl)quinazolin-7-yl)-2-amino-7-fluorobenzo[b]thiophene-3-carbonitrile: To a solution of 2-amino-4-[2-[3-(5-azaspiro[2.3]hexan-5-yl)azetidin-1-yl]-8-fluoro-4-[(2S,5R)-2,5-dimethylpiperazin-1-yl]-6-(trifluoromethyl)quinazolin-7-yl]-7-fluoro-benzothiophene-3-carbonitrile (40 mg, 0.061 mmol) in DCM (2 mL) was added DIEA (39 mg, 0.31 mmol) and the mixture was stirred at −78° C. for 10 minutes. A solution of prop-2-enoyl prop-2-enoate (6.2 mg, 0.049 mmol) in DCM (1 mL) was added at −78° C. and stirred at this temperature for 15 minutes. The reaction was quenched with $H_2O$ (10 mL) and extracted with DCM. The organics were washed with brine, dried ($MgSO_4$), filtered and concentrated to dryness. The crude was then purified by preparative RP-HPLC to give 4-(4-(((3S,4R)-1-acryloyl-4-fluoropyrrolidin-3-yl)(methyl)amino)-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (19 mg, 44%). LCMS ESI (+) m/z 709.4 (M+H). $^1$HNMR (400 MHz, $CD_3OD$) δ 8.08 (s, 1H), 7.22 (t, J=7.80 Hz, 1H), 7.03 (t, J=9.0 Hz, 1H), 6.74-6.89 (m, 1H), 6.29 (dd, J=16.6, 6.4 Hz, 1H), 5.82 (t, J=7.8 Hz, 1H), 4.95-5.0 (m, 1H), 4.57-4.66 (m, 4H), 4.25-4.35 (s, 7H), 3.79-4.03 (m, 2H), 3.45-3.57 (m, 1H), 1.42-1.54 (m, 3H), 1.25-1.39 (m, 3H), 0.86 (s, 4H).

Synthetic Example 41: Synthesis of 4-(4-(((R)-1-acryloylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 348)

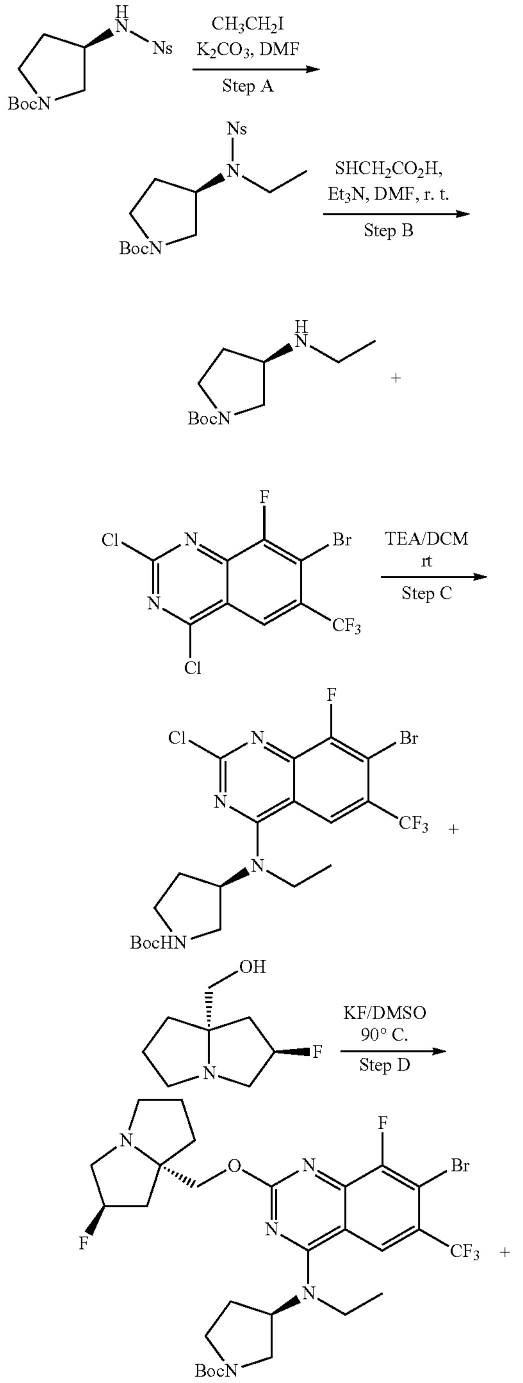

-continued

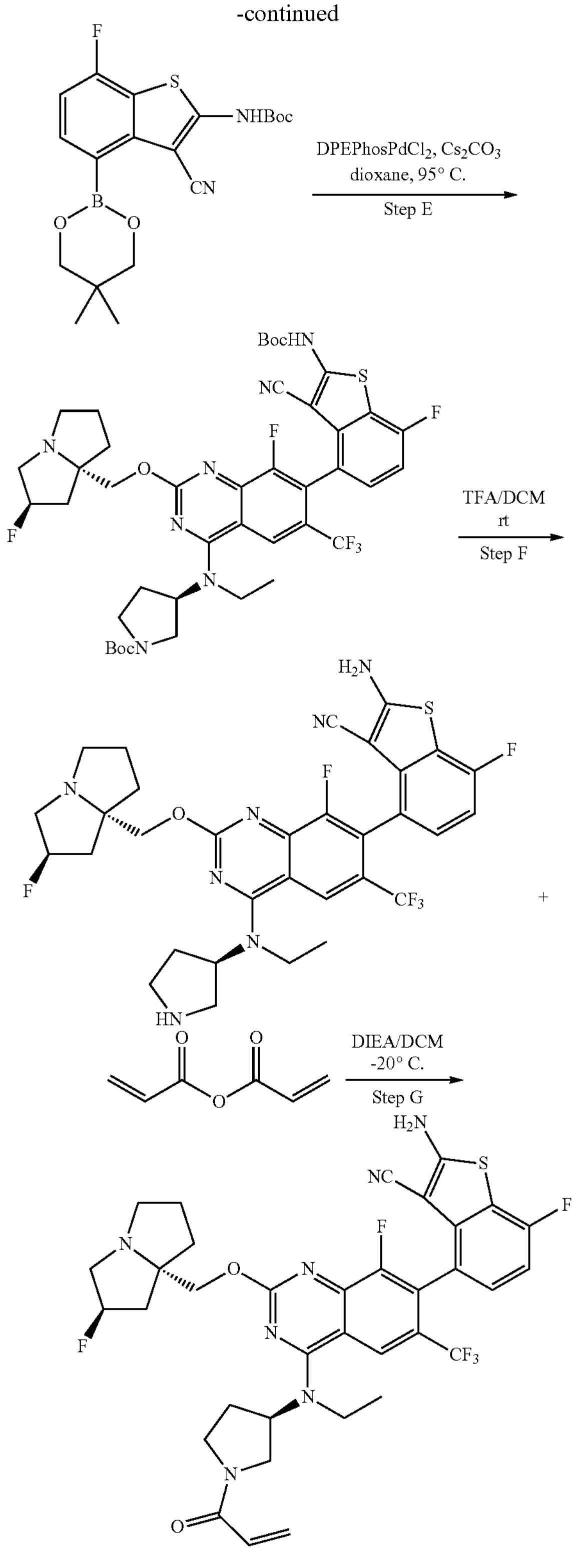

Compound 348

Step A: Preparation of tert-butyl-(3R)-3-[ethyl-(4-nitrophenyl)sulfonyl-amino]pyrrolidine-1-carboxylate: To a solution of tert-butyl (3R)-3-[(4-nitrophenyl)sulfonylamino]pyrrolidine-1-carboxylate (500 mg, 1.35 mmol) and $K_2CO_3$ (97 mg, 4.04 mmol) in DMF (5 mL) was added Iodoethane (0.54 mL, 6.73 mmol) at ambient temperature and stirred at ambient temperature for 3 hours. The reaction was quenched with water and extracted with ethyl acetate. The combined organic layers were washed with an aqueous solution of NaCl, dried over $Na_2SO_4$ and concentrated under reduced pressure. The crude product was purified by column chromatography on silica gel eluted with (petroleum ether/ethyl acetate 20:1 to 5:1) to give tert-butyl-(3R)-3-[ethyl-(4-nitrophenyl)sulfonyl-amino]pyrrolidine-1-carboxylate (490 mg, 77%). LCMS ESI (+) m/z 344.3 (M+H).

Step B: Preparation of tert-butyl (3R)-3-(ethylamino)pyrrolidine-1-carboxylate: To a solution of tert-butyl (3R)-3-[ethyl-(4-nitrophenyl)sulfonyl-amino]pyrrolidine-1-carboxylate (490 mg, 1.04 mmol) and TEA (1.7 mL, 12.2 mmol) in DMF (5 mL) was added 2-sulfanylacetic acid (1.13 g, 12.2 mmol) at ambient temperature and stirred at this temperature for 10 hours. The reaction was quenched with water and extracted with ethyl acetate. The combined organic layers were washed with an aqueous solution of $NaHCO_3$, brine dried over sodium sulfate, filtered and evaporated to dryness. The crude product tert-butyl (3R)-3-(ethylamino)pyrrolidine-1-carboxylate (250 mg, 85%) was used directly for the next step. LCMS ESI (+) m/z 215.2 (M+H).

Step C: Preparation of tert-butyl-(3R)-3-[[7-bromo-2-chloro-8-fluoro-6-(trifluoromethyl)quinazolin-4-yl]-ethyl-amino]pyrrolidine-1-carboxylate: To a solution of -bromo-2,4-dichloro-8-fluoro-6-(trifluoromethyl)quinazoline (374 mg, 1.02 mmol) and DIEA (0.39 mL, 2.8 mmol) in DCM (5 mL) was added tert-butyl (3R)-3-(ethylamino)pyrrolidine-1-carboxylate (200 mg, 0.93 mmol) at ambient temperature and stirred at this temperature for 1 hour. The reaction was concentrated to dry and the residue was taken up in EtOAc and the organics washed with water then saturated brine solution. The organics were then separated and dried ($Na_2SO_4$) before concentration to dryness. The crude was then purified by preparative TLC (eluting with 30% EtOAc in petroleum ether) to give tert-butyl-(3R)-3-[[7-bromo-2-chloro-8-fluoro-6-(trifluoromethyl)quinazolin-4-yl]-ethyl-amino]pyrrolidine-1-carboxylate (170 mg, 33%). LCMS ESI (+) m/z 541.2 (M+H).

Step D: Preparation of tert-butyl (3R)-3-[[7-bromo-8-fluoro-2-[[(2R,8S)-2-fluoro-1,2,3,5,6,7-hexahydropyrrolizin-8-yl]methoxy]-6-(trifluoromethyl)quinazolin-4-yl]-ethyl-amino]pyrrolidine-1-carboxylate: To a solution of tert-butyl (3R)-3-[[7-bromo-2-chloro-8-fluoro-6-(trifluoromethyl)quinazolin-4-yl]-ethyl-amino]pyrrolidine-1-carboxylate (160 mg, 0.30 mmol) and KF (137 mg, 2.36 mmol) in DMSO (4 mL) was added [(2R,8S)-2-fluoro-1,2,3,5,6,7-hexahydropyrrolizin-8-yl]methanol (71 mg, 0.44 mmol) at ambient temperature. The reaction was stirred at 90° C. for 4 hours. After cooled to ambient temperature, the reaction was taken up in EtOAc (50 mL) and the organics were washed with saturated brine solution. The organics were then separated, dried ($MgSO_4$), filtered and concentrated under reduced pressure. The crude was then purified by preparative-TLC eluting with 50% EtOAc in petroleum ether to give tert-butyl (3R)-3-[[7-bromo-8-fluoro-2-[[(2R,8S)-2-fluoro-1,2,3,5,6,7-hexahydropyrrolizin-8-yl]methoxy]-6-(trifluoromethyl)quinazolin-4-yl]-ethyl-amino]pyrrolidine-1-carboxylate (100 mg, 45%). LCMS ESI (+) m/z 664.2 (M+H).

Step E: Preparation of tert-butyl (3R)-3-((7-(2-((tert-butoxycarbonyl)-12-azaneyl)-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-(trifluoromethyl)quinazolin-4-yl)(ethyl)amino)pyrrolidine-1-carboxylate: To a solution of tert-butyl (3R)-3-[[7-bromo-8-fluoro-2-[[(2R,8S)-2-fluoro-1,2,3,5,6,7-hexahydropyrrolizin-8-yl]methoxy]-6-(trifluoromethyl)quinazolin-4-yl]-ethyl-amino]pyrrolidine-1-carboxylate (60 mg, 0.090 mmol), tert-butyl N-[3-cyano-4-(5,5-dimethyl-1,3,2-dioxaborinan-2-yl)-7-fluoro-benzothiophen-2-yl]carbamate (91 mg, 0.23 mmol) and $Cs_2CO_3$ (74 mg, 0.23 mmol) in 1,4-Dioxane (2 mL) was added $DPEPhosPdCl_2$ (6.5 mg, 0.0090 mmol) at ambient temperature. The mixture was stirred at 95° C. for 8 hours. After cooled to ambient temperature, reaction was diluted with ethyl acetate (20 mL) and the organics washed with water then with saturated brine solution. The organics were then separated, dried ($MgSO_4$) and concentrated under reduced pressure. The crude was then purified by preparative TLC eluting with 20% MeOH in DCM to give tert-butyl (3R)-3-((7-(2-((tert-butoxycarbonyl)-12-azaneyl)-3-cyano-7-fluorobenzo[b]thiophen-4-yl)-8-fluoro-2-(((2R,7aS)-2-fluorotetrahydro-1H-pyrrolizin-7a(5H)-yl)methoxy)-6-(trifluoromethyl)quinazolin-4-yl)(ethyl)amino)pyrrolidine-1-carboxylate (38 mg, 31%). LCMS ESI (+) m/z 876.3 (M+H).

Step F: Preparation of 2-amino-4-[4-[ethyl-[(3R)-pyrrolidin-3-yl]amino]-8-fluoro-2-[[(2R,8S)-2-fluoro-1,2,3,5,6,7-hexahydropyrrolizin-8-yl]methoxy]-6-(trifluoromethyl)quinazolin-7-yl]-7-fluoro-benzothiophene-3-carbonitrile: To a solution of tert-butyl (3R)-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl]methoxy]-6-(trifluoromethyl)quinazolin-4-yl]-ethyl-amino]pyrrolidine-1-carboxylate (38 mg, 0.043 mmol) in DCM (mL) was added TFA (0.86 mL, 11.2 mmol) at ambient temperature and stirred at ambient temperature for 5 hours. The mixture was concentrated under reduced pressure to give 2-amino-4-[4-[ethyl-[(3R)-pyrrolidin-3-yl]amino]-8-fluoro-2-[[(2R,8S)-2-fluoro-1,2,3,5,6,7-hexahydropyrrolizin-8-yl]methoxy]-6-(trifluoromethyl)quinazolin-7-yl]-7-fluoro-benzothiophene-3-carbonitrile (40 mg, 95%) was used directly for the next step. LCMS ESI (+) m/z 676.2 (M+H).

Step G: Preparation of 4-(4-(((R)-1-acryloylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile: To a solution of 2-amino-4-[4-[ethyl-[(3R)-pyrrolidin-3-yl]amino]-8-fluoro-2-[[(2R,8S)-2-fluoro-1,2,3,5,6,7-hexahydropyrrolizin-8-yl]methoxy]-6-(trifluoromethyl)quinazolin-7-yl]-7-fluoro-benzothiophene-3-carbonitrile (30 mg, 0.044 mmol) and DIEA (0.024 mL, 0.13 mmol) in DCM (mL) was added prop-2-enoyl prop-2-enoate (5.6 mg, 0.0444 mmol) at–78° C. The mixture was stirring for 1 hour at –78° C. The reaction was quenched with $H_2O$ (10 mL) and extracted with DCM. The organics were washed with brine, dried ($MgSO_4$), filtered and concentrated to dryness. The crude was then purified by preparative RP-HPLC to give 4-(4-(((R)-1-acryloylpyrrolidin-3-yl)(ethyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (6.2 mg, 18%). LCMS ESI (+) m/z 730.2 (M+H). $^1$HNMR (400 MHz, $CD_3OD$) δ. 8.27-8.32 (m, 1H), 7.20-7.27 (m, 1H), 6.99-7.07 (m, 1H), 6.57-6.74 (m, 1H), 6.28-6.37 (m, 1H), 5.75-5.84 (m, 1H), 5.55 (d, J=57.6 Hz, 1H), 4.97-5.07 (m, 1H), 4.52-4.74 (m, 2H), 3.39-4.18 (m, 10H), 2.04-2.76 (m, 8H), 1.45-1.58 (m, 3H).

Synthetic Example 42: Synthesis of 4-(4-(((2R,3R)-1-acryloyl-2-methylpyrrolidin-3-yl)(methyl)amino)-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 354)

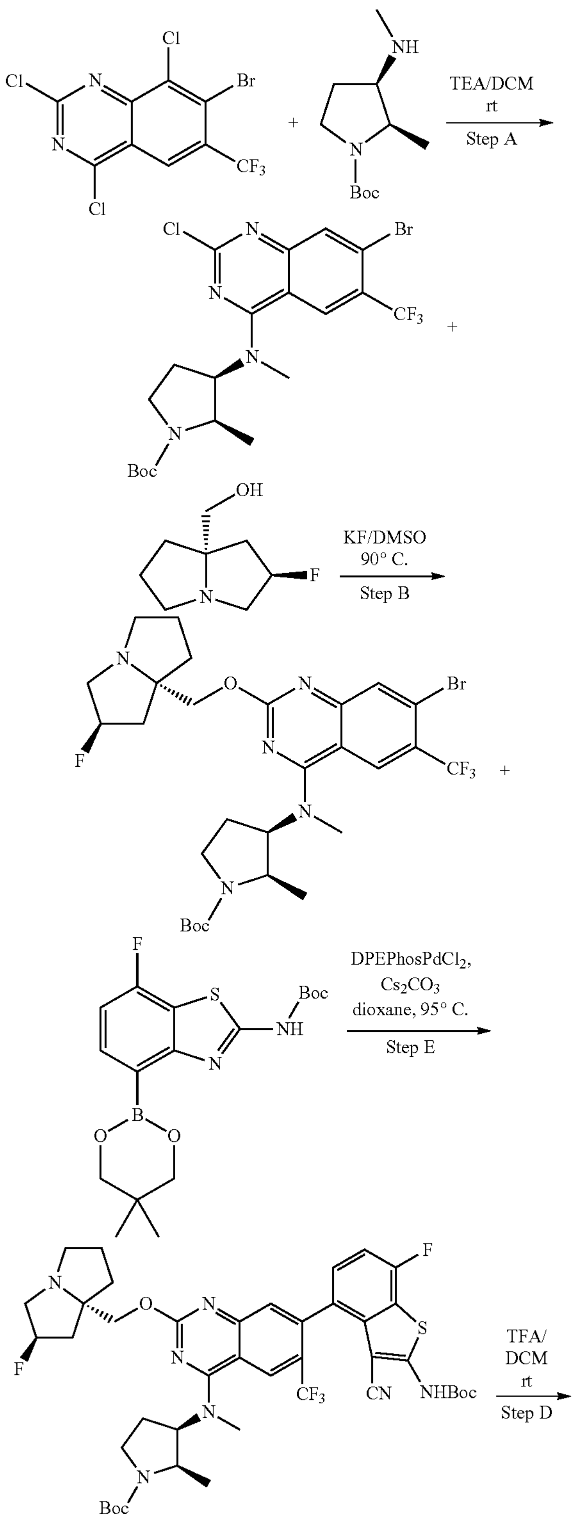

-continued

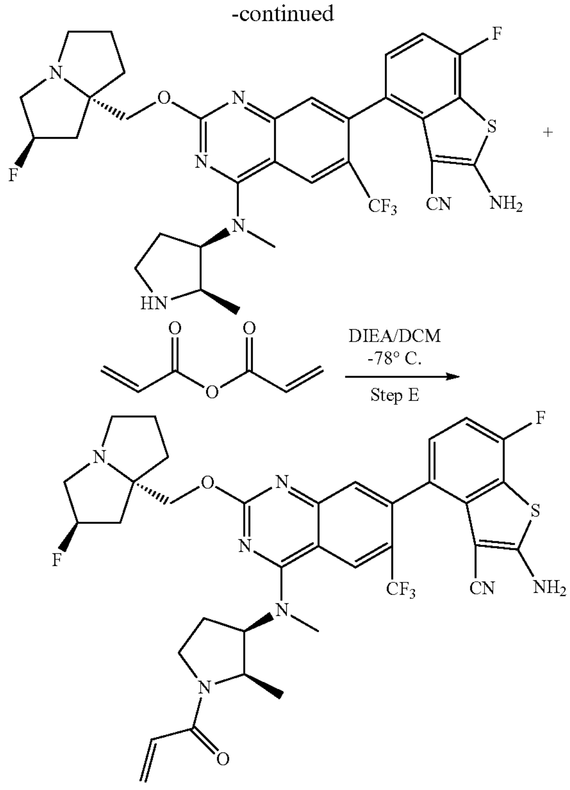

Compound 354

Step A: Preparation of give tert-butyl-(2R,3R)-3-[[7-bromo-2-chloro-6-(trifluoromethyl)quinazolin-4-yl]-methyl-amino]-2-methyl-pyrrolidine-1-carboxylate: To a solution of 7-bromo-2,4-dichloro-6-(trifluoromethyl)quinazoline (135 mg, 0.39 mmol) and DIEA (0.16 mL, 0.98 mmol) in DCM (4 mL) was added tert-butyl (2R,3R)-2-methyl-3-(methylamino)pyrrolidine-1-carboxylate (70 mg, 0.33 mmol) at ambient temperature and stirred at ambient temperature for 1 hour. The reaction was evaporated to dryness and it was purified by preparative TLC eluting with 20% EtOAc in petroleum ether to give tert-butyl-(2R,3R)-3-[[7-bromo-2-chloro-6-(trifluoromethyl)quinazolin-4-yl]-methyl-amino]-2-methyl-pyrrolidine-1-carboxylate (110 mg, 64%). LCMS ESI (+) m/z 523.2 (M+H).

Step B: Preparation of tert-butyl (2R,3R)-3-[[7-bromo-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate: To a solution of tert-butyl (2R,3R)-3-[[7-bromo-2-chloro-6-(trifluoromethyl)quinazolin-4-yl]-methyl-amino]-2-methyl-pyrrolidine-1-carboxylate (110 mg, 0.21 mmol) and KF (97.4 mg, 1.68 mmol) in DMSO (2 mL) was added [(2R,8S)-2-fluoro-1,2,3,5,6,7-hexahydropyrrolizin-8-yl]methanol (67.2 mg, 0.42 mmol) at ambient temperature. The reaction was stirred at 90° C. for 5 hours. After cooled to ambient temperature, the reaction was taken up in EtOAc (20 mL) and the organics were washed with saturated brine solution. The organics were then separated, dried ($MgSO_4$), filtered and concentrated under reduced pressure. The crude was then purified by preparative-TLC eluting with 50% EtOAc in petroleum ether to afford tert-butyl (2R,3R)-3-[[7-bromo-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate (85 mg, 63%). LCMS ESI (+) m/z 646.2 (M+H).

Step C: Preparation of tert-butyl-(2R,3R)-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate: To a solution of tert-butyl (2R,3R)-3-[[7-bromo-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate (50 mg, 0.077 mmol), tert-butyl N-[3-cyano-4-(5,5-dimethyl-1,3,2-dioxaborinan-2-yl)-7-fluoro-benzothiophen-2-yl]carbamate (94 mg, 0.23 mmol) and $Cs_2CO_3$ (63 mg, 0.19 mmol) in 1,4-Dioxane (2.5 mL) was added DPEPhosPd$Cl_2$ (8.3 mg, 0.012 mmol) under nitrogen at ambient temperature. The reaction was stirred at 95° C. for 4 hours. After cooled to ambient temperature, reaction was diluted with ethyl acetate (10 mL) and the organics washed with water then with saturated brine solution. The organics were then separated, dried ($MgSO_4$) and concentrated under reduced pressure. The crude was then purified by preparative-TLC eluting with 20% MeOH in DCM to afford tert-butyl-(2R,3R)-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate (50 mg, 65%). LCMS ESI (+) m/z 858.3 (M+H).

Step D: Preparation of 2-amino-7-fluoro-4-[2-[[(2R,8S)-2-fluoro-1,2,3,5,6,7-hexahydropyrrolizin-8-yl]methoxy]-4-[methyl-[(2R,3R)-2-methylpyrrolidin-3-yl]amino]-6-(trifluoromethyl)quinazolin-7-yl]benzothiophene-3-carbonitrile: To a solution of tert-butyl (2R,3R)-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate (50 mg, 0.051 mmol) in DCM (2 mL) was added TFA (1.0 mL, 13.0 mmol) at ambient temperature and stirred at ambient temperature for 3 hours. The mixture was concentrated under reduced pressure to give 2-amino-7-fluoro-4-[2-[[(2R,8S)-2-fluoro-1,2,3,5,6,7-hexahydropyrrolizin-8-yl]methoxy]-4-[methyl-[(2R,3R)-2-methylpyrrolidin-3-yl]amino]-6-(trifluoromethyl)quinazolin-7-yl]benzothiophene-3-carbonitrile (35 mg, 92%) which was used directly for the next step. LCMS ESI (+) m/z 658.2 (M+H).

Step E: Preparation of 4-(4-(((2R,3R)-1-acryloyl-2-methylpyrrolidin-3-yl)(methyl)amino)-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile: To a solution of 2-amino-7-fluoro-4-[2-[[(2R,8S)-2-fluoro-1,2,3,5,6,7-hexahydropyrrolizin-8-yl]methoxy]-4-[methyl-[(2R,3R)-2-methylpyrrolidin-3-yl]amino]-6-(trifluoromethyl)quinazolin-7-yl]benzothiophene-3-carbonitrile (35 mg, 0.053 mmol) and DIEA (20.5 mg, 0.16 mmol) in DCM (5 mL) was added prop-2-enoyl prop-2-enoate (6.7 mg, 0.053 mmol) at −78° C. The mixture was stirring at −78° C. for 40 minutes. The reaction was quenched with $H_2O$ (10 mL) and extracted with DCM. The organics were washed with brine, dried ($MgSO_4$), filtered and concentrated to dryness. The crude was then purified by preparative RP-HPLC to give 4-(4-(((2R,3R)-1-acryloyl-2-methylpyrrolidin-3-yl)(methyl)amino)-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (29 mg, 78%). LCMS ESI (+) m/z 712.2 (M+H). $^1$HNMR (400 MHz, $CD_3OD$) δ 8.58-8.62 (m, 1H), 7.55-7.58 (m, 1H), 7.18-7.24 (m, 1H), 7.00 (t, J=8.8 Hz, 1H), 6.62-6.74 (m, 1H), 6.29-6.40 (m, 1H), 5.80 (d, J=10.4 Hz, 1H), 5.58 (d, J=52.4 Hz, 1H), 4.90-5.13 (m, 2H), 4.63-4.77 (m, 2H), 3.85-4.04 (m, 4H), 3.55-3.84 (m, 4H), 3.44-3.53 (m, 1H), 2.11-2.81 (m, 8H), 1.09-1.22 (m, 3H).

Synthetic Example 43: Synthesis of 4-(4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (Compound 358)

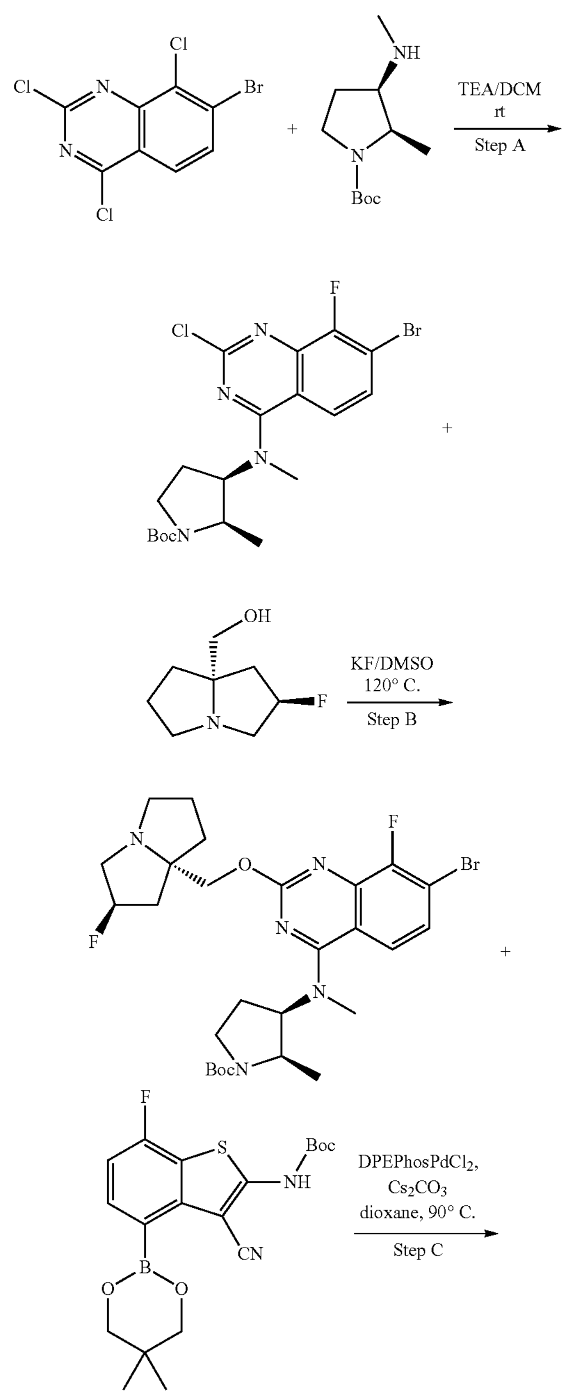

-continued

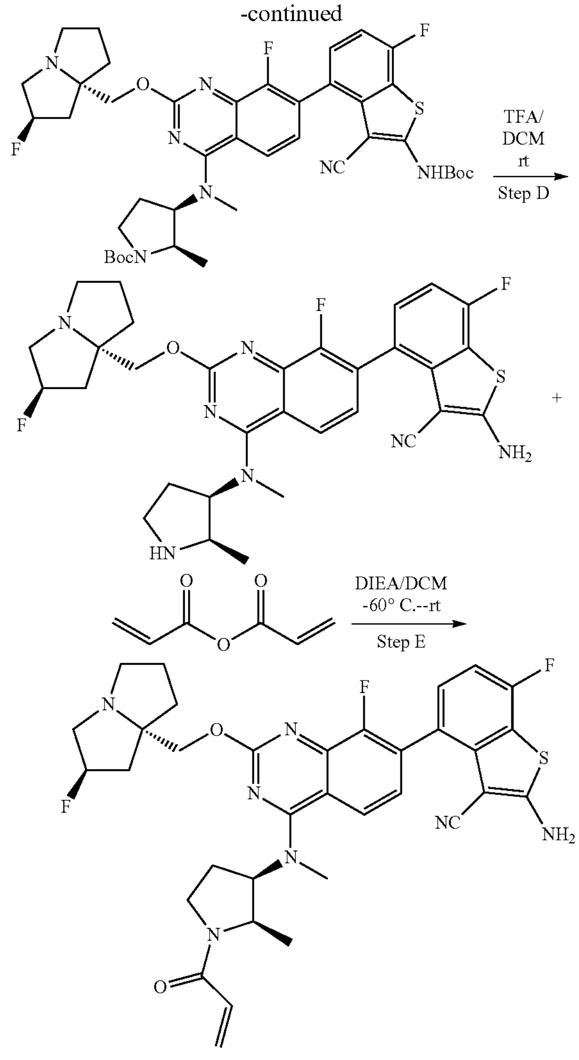

Compound 358

Step A: Preparation of give tert-butyl-(2R,3R)-3-[(7-bromo-2-chloro-8-fluoro-quinazolin-4-yl)-methyl-amino]-2-methyl-pyrrolidine-1-carboxylate: To a solution of 7-bromo-2,4-dichloro-8-fluoro-quinazoline (107 mg, 0.36 mmol) and DIEA (0.15 mL, 1.08 mmol) in DCM (2 mL) was added tert-butyl (2R,3R)-2-methyl-3-(methylamino)pyrrolidine-1-carboxylate (70 mg, 0.33 mmol) at ambient temperature and stirred at ambient temperature for 1 hour. The reaction was evaporated to dryness and it was purified by column chromatography on silica gel eluting with 25% EtOAc in petroleum ether to give tert-butyl (2R,3R)-3-[(7-bromo-2-chloro-8-fluoro-quinazolin-4-yl)-methyl-amino]-2-methyl-pyrrolidine-1-carboxylate (88 mg, 51%).

Step B: Preparation of tert-butyl (2R,3R)-3-[[7-bromo-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of tert-butyl-(2R,3R)-3-[(7-bromo-2-chloro-8-fluoro-quinazolin-4-yl)-methyl-amino]-2-methyl-pyrrolidine-1-carboxylate (88 mg, 0.19 mmol) in DMSO (0.90 mL) was added [(2R,8S)-2-fluoro-1,2,3,5,6,7-hexahydropyrrolizin-8-yl]methanol (35 mg, 0.22 mmol) and KF (86 mg, 1.49 mmol) at ambient temperature. The reaction was stirred at 120° C. for 3 hours. After cooled to ambient temperature, the reaction was taken up in EtOAc (20 mL) and the organics were washed with saturated brine solution. The organics were then separated, dried ($MgSO_4$), filtered and concentrated under reduced pressure. The crude was then purified by column chromatography on silica gel eluting with 50% EtOAc in petroleum ether to afford tert-butyl (2R,3R)-3-[[7-bromo-8-fluoro-2-[[(2R,8S)-2-fluoro-1,2,3,5,6,7-hexahydropyrrolizin-8-yl] methoxy]quinazolin-4-yl]-methyl-amino]-2-methyl-pyrrolidine-1-carboxylate (48 mg, 43%). LCMS ESI (+) m/z 596.0 (M+H).

Step C: Preparation of tert-butyl (2R,3R)-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: A solution of tert-butyl (2R,3R)-3-[[7-bromo-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (40 mg, 0.067 mmol), tert-butyl N-[3-cyano-4-(5,5-dimethyl-1,3,2-dioxaborinan-2-yl)-7-fluoro-benzothiophen-2-yl]carbamate (9.3 mg, 0.023 mmol), $Cs_2CO_3$ (10 mg, 0.031 mmol), $DPEPhosePdCl_2$ (1.1 mg, 0.0015 mmol) in 1,4-Dioxane (1.2 mL) was stirred at 95° C. for 3 hours. After cooled to ambient temperature, reaction was diluted with ethyl acetate (10 mL) and the organics washed with water then with saturated brine solution. The organics were then separated, dried ($MgSO_4$) and concentrated under reduced pressure. The crude was then purified by preparative-TLC eluting with 100% ethyl acetate to afford tert-butyl (2R,3R)-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (50 mg, 92%). LCMS ESI (+) m/z 808.0 (M+H).

Step D: Preparation of 2-amino-7-fluoro-4-[8-fluoro-2-[[(2R,8S)-2-fluoro-1,2,3,5,6,7-hexahydropyrrolizin-8-yl] methoxy]-4-[methyl-[(2R,3R)-2-methylpyrrolidin-3-yl] amino]quinazolin-7-yl]benzothiophene-3-carbonitrile: To a solution of tert-butyl (2R,3R)-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl] methoxy]quinazolin-4-yl]-methyl-amino]-2-methyl-pyrrolidine-1-carboxylate (50 mg, 0.062 mmol) in DCM (3 mL) was added TFA (1.5 mL) at ambient temperature and stirred at ambient temperature for 1.5 hours. The mixture was concentrated under reduced pressure to give 2-amino-7-fluoro-4-[8-fluoro-2-[[(2R,8S)-2-fluoro-1,2,3,5,6,7-hexahydropyrrolizin-8-yl]methoxy]-4-[methyl-[(2R,3R)-2-methylpyrrolidin-3-yl]amino]quinazolin-7-yl] benzothiophene-3-carbonitrile (40 mg, 100%) which was used directly for the next step. LCMS ESI (+) m/z 608.3 (M+H).

Step E: Preparation of 4-(4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile: To a solution of 22-amino-7-fluoro-4-[8-fluoro-2-[[(2R,8S)-2-fluoro-1,2,3,5,6,7-hexahydropyrrolizin-8-yl] methoxy]-4-[methyl-[(3R)-pyrrolidin-3-yl]amino]pyrido[4,3-d]pyrimidin-7-yl]benzothiophene-3-carbonitrile (30 mg, 0.017 mmol) in DCM (1 mL) was added prop-2-enoyl prop-2-enoate (2.1 mg, 0.017 mmol) at −30° C., followed by TEA (5.1 mg, 0.050 mmol). The mixture was stirred at −30° C. for 0.5 hr. The reaction was quenched with $H_2O$ (10 mL) and extracted with DCM. The organics were washed with brine, dried ($MgSO_4$), filtered and concentrated to dryness. The crude was then purified by preparative-TLC (DCM: MeOH=15:1) to give 4-(4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy) quinazolin-7-yl)-2-amino-7-fluorobenzo[b]thiophene-3-carbonitrile (17 mg, 52%). LCMS ESI (+) m/z 662.24 (M+H). $^1$HNMR (400 MHz, $CD_3OD$) δ 8.10-8.20 (m, 1H), 7.35-7.46 (m, 1H), 7.29 (dd, J=8.1, 5.3 Hz, 1H), 7.05 (t, J=8.9 Hz, 1H), 6.60-6.71 (m, 1H), 6.34 (t, J=16.5 Hz, 1H), 5.79 (dd, J=10.4, 1.6 Hz, 1H), 5.55 (d, J=52.8 Hz, 1H), 4.90-5.12 (m, 2H), 4.59-4.87 (m, 3H), 3.78-4.10 (m, 4H), 3.64-3.73 (m, 3H), 3.42-3.54 (m, 1H), 2.55-2.78 (m, 3H), 2.27-2.54 (m, 4H), 2.05-2.22 (m, 1H), 1.05-1.22 (m, 3H).

Synthetic Example 44: Synthesis of 4-(4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b] thiophene-3-carbonitrile (Compound 363), 4-((R)-4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 457) and 4-((S)-4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 458)

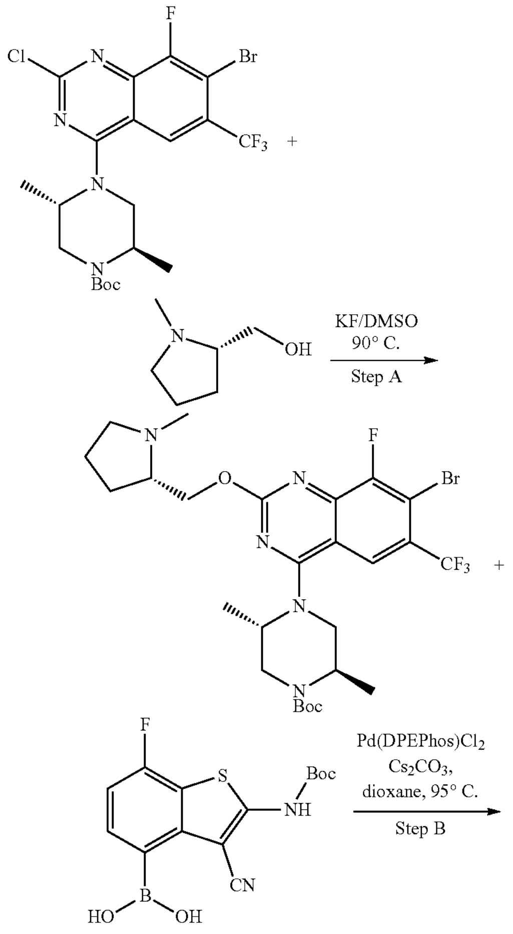

-continued

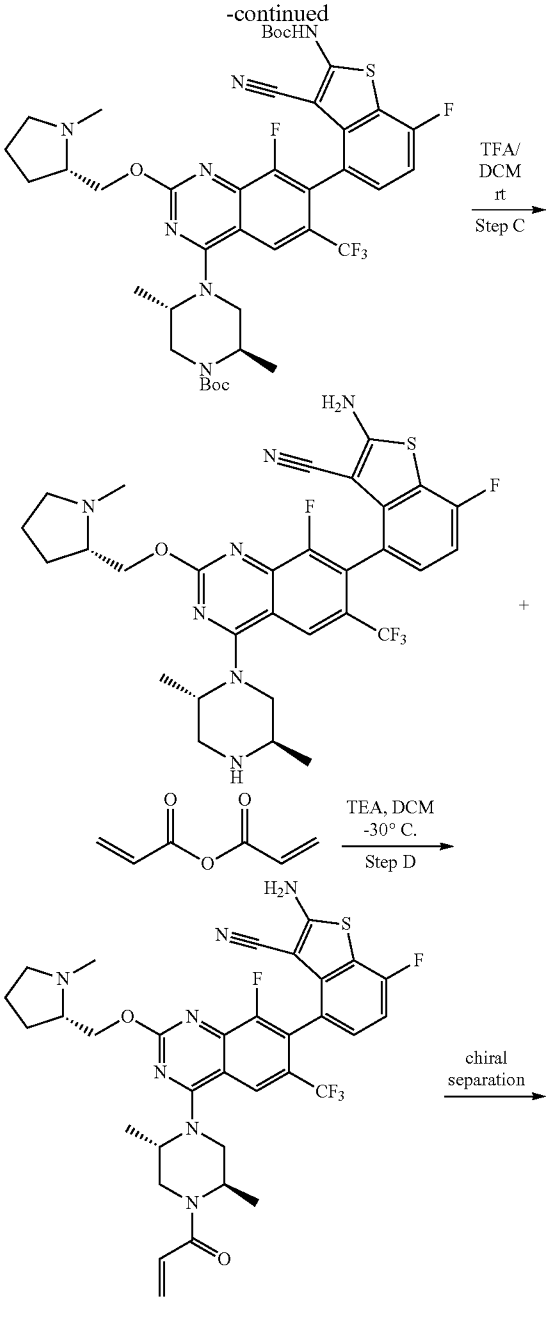

Compound 363

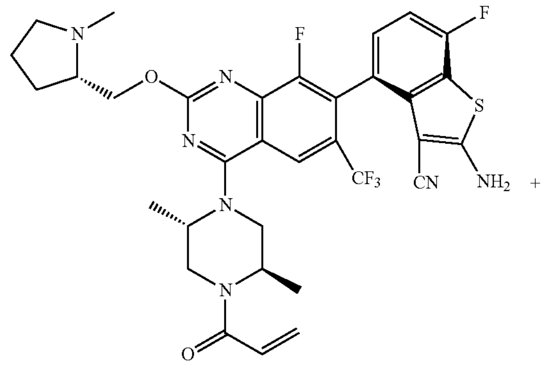

Compound 458

-continued

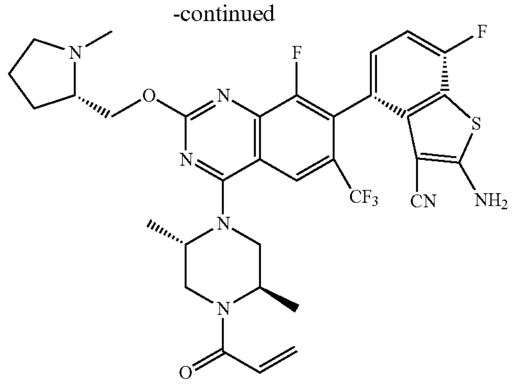

Compound 457

Step A: Preparation of tert-butyl (2R,5S)-4-(7-bromo-8-fluoro-2-(((S)-1-methylpyrrolidin-2-yl)methoxy)-6-(trifluoromethyl)quinazolin-4-yl)-2,5-dimethylpiperazine-1-carboxylate: A mixture of [(2S)-1-methylpyrrolidin-2-yl] methanol (128 mg, 1.11 mmol), tert-butyl-(2R,5S)-4-[7-bromo-2-chloro-8-fluoro-6-(trifluoromethyl)quinazolin-4-yl]-2,5-dimethyl-piperazine-1-carboxylate (300 mg, 0.55 mmol), KF (257 mg, 4.43 mmol) in DMSO (5 mL) was stirred at 90° C. under Ar for 2 hours. After cooled to ambient temperature, the reaction was quenched with water and extracted with EtOAc (30 mL×3). The organic layers were isolated, washed with water, brine, dried ($MgSO_4$), filtered and concentrated under reduced pressure. The crude was then purified by preparative-TLC (100% EtOAc) to give tert-butyl (2R,5S)-4-[7-bromo-8-fluoro-2-[[(2S)-1-methylpyrrolidin-2-yl]methoxy]-6-(trifluoromethyl)quinazolin-4-yl]-2,5-dimethyl-piperazine-1-carboxylate (210 mg, 61%) as solid. LCMS ESI (+) m/z 620.0 (M+H).

Step B: Preparation of tert-butyl (2R,5S)-4-[7-[2-(tert-butoxycarbonylamino)-3-cyano-7-fluoro-benzothiophen-4-yl]-8-fluoro-2-[[(2S)-1-methylpyrrolidin-2-yl]methoxy]-6-(trifluoromethyl)quinazolin-4-yl]-2,5-dimethyl-piperazine-1-carboxylate: To a mixture of tert-butyl (2R,5S)-4-[7-bromo-8-fluoro-2-[[(2S)-1-methylpyrrolidin-2-yl] methoxy]-6-(trifluoromethyl)quinazolin-4-yl]-2,5-dimethyl-piperazine-1-carboxylate (190 mg, 0.31 mmol) in 1,4-dioxane (4.0 mL) were added tert-butyl N-[3-cyano-4-(5,5-dimethyl-1,3,2-dioxaborinan-2-yl)-7-fluoro-benzothiophen-2-yl]carbamate (371 mg, 0.92 mmol), cesium carbonate (249 mg, 0.77 mmol) and $DPEPhosPdCl_2$ (22 mg, 0.031 mmol) at ambient temperature. After bubbled with nitrogen for 2 minutes, the reaction was stirred at 95° C. for 8 hours. After cooled to ambient temperature, reaction was diluted with ethyl acetate and the organic layers washed with water, then with saturated brine solution. The organic layers were then separated, dried ($Na_2SO_4$) and concentrated under reduced pressure. The crude was then purified by Preparative-TLC (EtOAc/PE=1:1) to afford tert-butyl (2R,5S)-4-[7-[2-(tert-butoxycarbonylamino)-3-cyano-7-fluoro-benzothiophen-4-yl]-8-fluoro-2-[[(2S)-1-methylpyrrolidin-2-yl] methoxy]-6-(trifluoromethyl)quinazolin-4-yl]-2,5-dimethyl-piperazine-1-carboxylate (85 mg, 33%). LCMS ESI (+) m/z 832.3 (M+H).

Step C: Preparation of 2-amino-4-[4-[(2S,5R)-2,5-dimethylpiperazin-1-yl]-8-fluoro-2-[[(2S)-1-methylpyrrolidin-2-yl]methoxy]-6-(trifluoromethyl)quinazolin-7-yl]-7-fluoro-benzothiophene-3-carbonitrile: To a solution of tert-butyl (2R,5S)-4-[7-[2-(tert-butoxycarbonylamino)-3-cyano-7-fluoro-benzothiophen-4-yl]-8-fluoro-2-[[(2S)-1-methylpyrrolidin-2-yl]methoxy]-6-(trifluoromethyl)quinazolin-4-yl]-2,5-dimethyl-piperazine-1-carboxylate (85 mg, 0.10 mmol) in DCM (3 mL) was added trifluoroacetic acid (3.5 mL, 45.9 mmol) at ambient temperature. The reaction was stirred at ambient temperature for 2 hours. The reaction solution was concentrated under reduced pressure. The residue was dissolved in EtOAc (20 mL) and then to this was added water (20 mL). The mixture was stirred for 5 minutes and pH adjusted to ~8-9 with saturated $NaHCO_3$ solution. After extracting with EtOAc (20 mL×3), the combined organic layers were washed with brine and dried over $Na_2SO_4$, filtered and concentrated under reduced pressure to give 2-amino-4-[4-[(2S,5R)-2,5-dimethylpiperazin-1-yl]-8-fluoro-2-[[(2S)-1-methylpyrrolidin-2-yl]methoxy]-6-(trifluoromethyl)quinazolin-7-yl]-7-fluoro-benzothiophene-3-carbonitrile (50 mg, 77%). LCMS ESI (+) m/z 632.3 (M+H).

Step D: Preparation of 4-(4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 363), 4-((R)-4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 457) and 4-((S)-4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 458): To a solution of 2-amino-4-[4-[(2S,5R)-2,5-dimethylpiperazin-1-yl]-8-fluoro-2-[[(2S)-1-methyl pyrrolidin-2-yl]methoxy]-6-(trifluoromethyl)quinazolin-7-yl]-7-fluoro-benzothiophene-3-carbonitrile (50 mg, 0.079 mmol) in DCM (1 mL) was added prop-2-enoyl prop-2-enoate (8.0 mg, 0.063 mmol). The mixture was cooled to −30° C. and to this was added $Et_3N$ (5.1 mg, 0.40 mmol) dropwise at −30° C. under Ar. The mixture was stirred for 1 hr at −30° C. and the mixture was quenched with water. After extracted with $CH_2Cl_2$, the combined organic layers were washed with brine and dried over anhydrous $Na_2SO_4$, filtered and concentrated to dryness under vacuum, and the residue was purified by preparative RP-HPLC to afford 4-(4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 363) (24 mg, 44%). LCMS ESI (+) m/z 686.3 (M+H). $^1$HNMR (400 MHz, $CD_3OD$) δ 8.18 (s, 1H), 7.22-7.25 (m, 1H), 7.03 (t, J=8.0 Hz, 1H), 6.73-6.90 (m, 1H), 6.26-6.32 (m, 1H), 5.80-5.82 (m, 1H), 4.89-4.97 (m, 2H), 4.29-4.69 (m, 3H), 3.84-4.07 (m, 3H), 3.51-3.73 (m, 3H), 3.09-3.26 (m, 3H), 2.09-2.40 (m, 4H), 1.48-1.51 (m, 3H), 1.26-1.33 (m, 3H).

The single diasteremers of 4-(4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 363) (120 mg) were separated with chiral chromatography condition [ChiralPak AD-H 2 cm×25 cm, 5 μm, Hexane (0.2% ammonium in methanol):EtOH 70:30], 20 mL/min]. The first compound off the column was identified as one atropisomer, 4-((R)-4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 457) (47.1 mg, 99.99% de); LCMS ESI (+) m/z 686.1 (M+H). $^1$HNMR (400 MHz, $CD_3OD$) δ 8.14 (s, 1H), 7.20-7.25 (m, 1H), 6.99-7.04 (m, 1H), 6.75-6.87 (m, 1H), 6.25-6.32 (m, 1H), 5.78-5.84 (m, 1H), 4.89-4.94 (m, 1H), 4.49 (d, 2H), 4.25-4.45 (m, 2H), 3.86-3.97 (m, 2H), 3.43-3.58 (m, 1H), 3.06-3.13 (m, 1H), 2.77-2.83 (m, 1H), 2.52 (s, 3H), 2.32-2.39 (m, 1H), 2.08-2.16 (m, 1H), 1.72-1.86 (m, 3H), 1.46-1.53 (m, 3H), 1.40 (d, 1H), 1.27-1.35 (m, 2H). The second compound off the column was identified as the other atropisomer, 4-((S)-4-((2S,5R)-4-acryloyl-2,5-dimethylpiperazin-1-yl)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 458) (44.1 mg, 99.99% de). LCMS ESI (+) m/z 686.1 (M+H). $^1$HNMR (400 MHz, $CD_3OD$) δ 8.13 (s, 1H), 7.19-7.25 (m, 1H), 6.98-7.04 (m, 1H), 6.76-6.87 (m, 1H), 6.24-6.32 (m, 1H), 5.77-5.84 (m, 1H), 4.90-4.96 (m, 1H), 4.46-4.53 (m, 2H), 4.14-4.40 (m, 2H), 3.88-4.06 (m, 2H), 3.48-3.65 (m, 1H), 3.09-3.16 (m, 1H), 2.81-2.90 (m, 2H), 2.55 (s, 3H), 2.35-2.45 (m, 1H), 2.09-2.18 (m, 1H), 1.73-1.91 (m, 3H), 1.475 (t, 3H), 1.22-1.32 (m, 3H).

Synthetic Example 45: Synthesis of 4-(4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 381), 4-((S)-4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 434), 4-((R)-4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 435), 4-((S)-4-(((2S,3S)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 472) and 4-((R)-4-(((2S,3S)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 473)

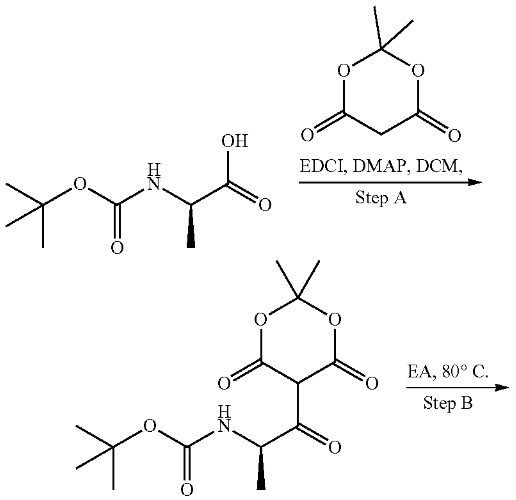

-continued
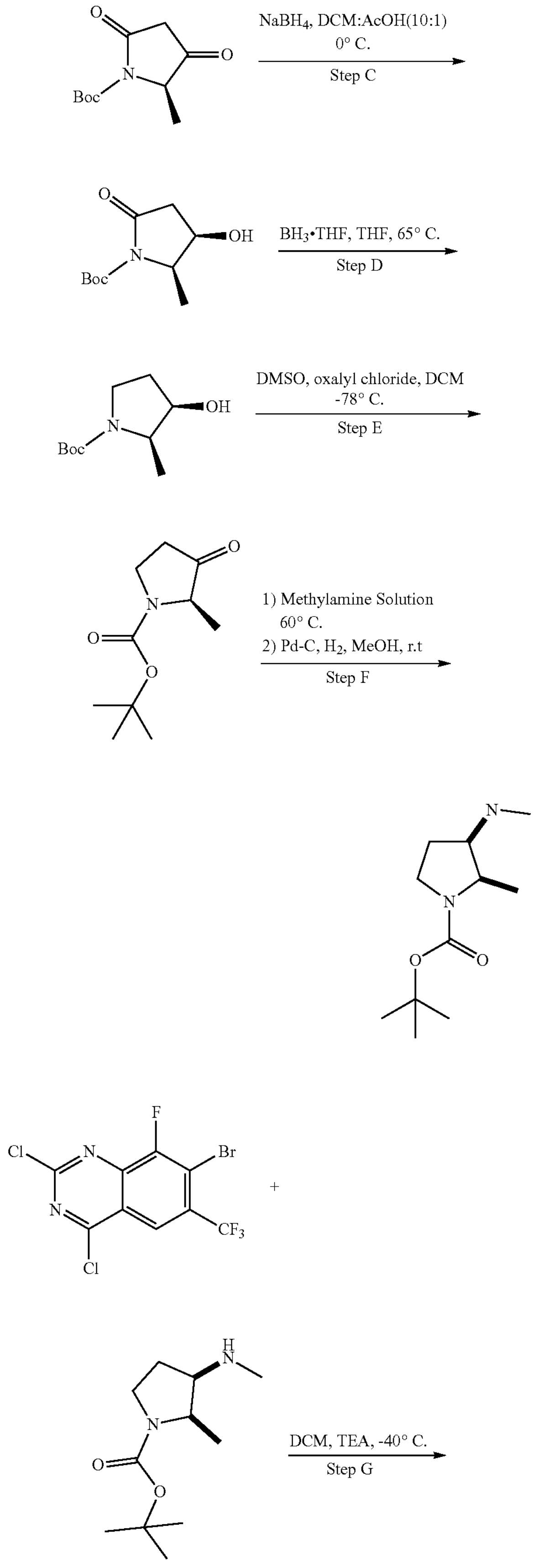
-continued
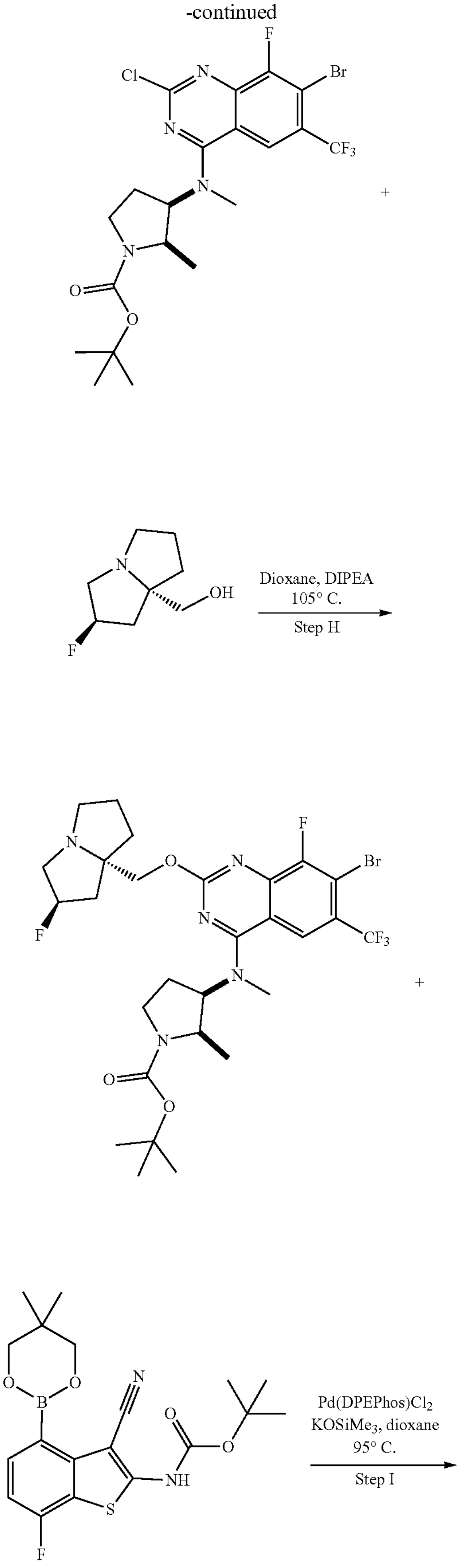

-continued
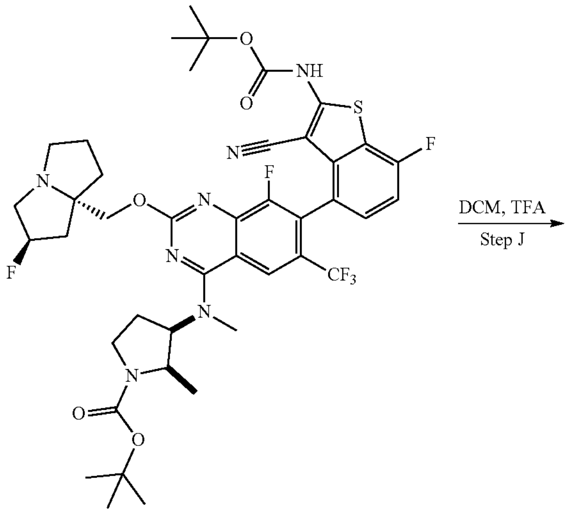
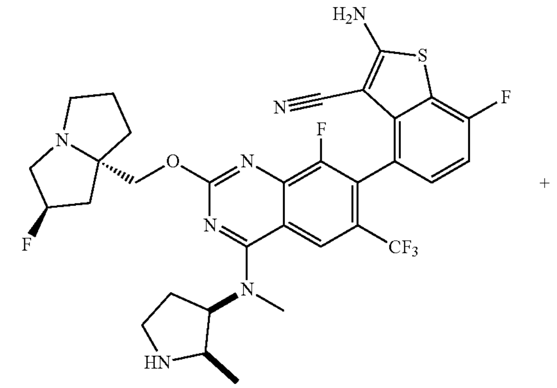
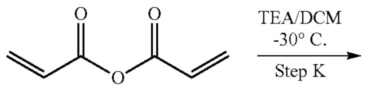
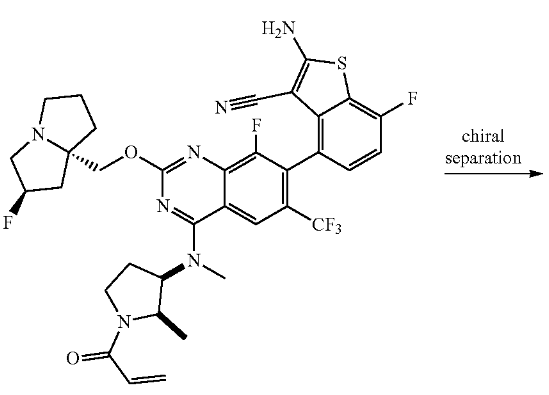
Compound 381
-continued
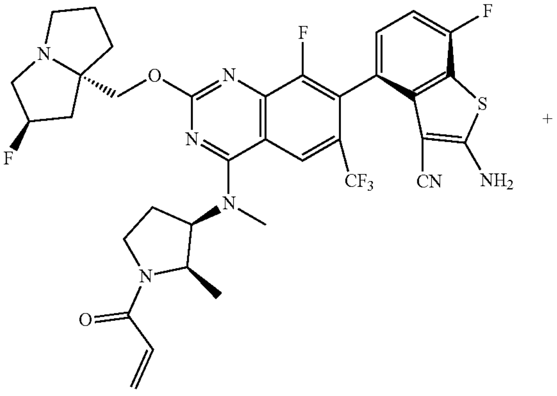
Compound 434
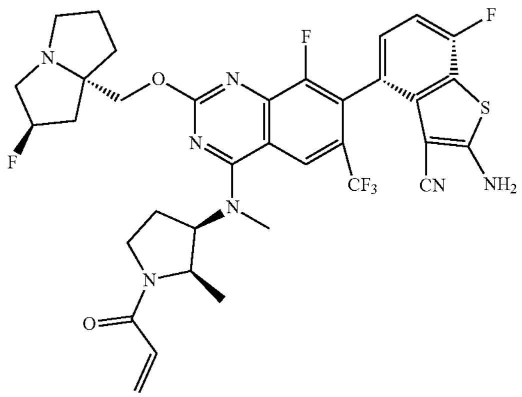
Compound 435
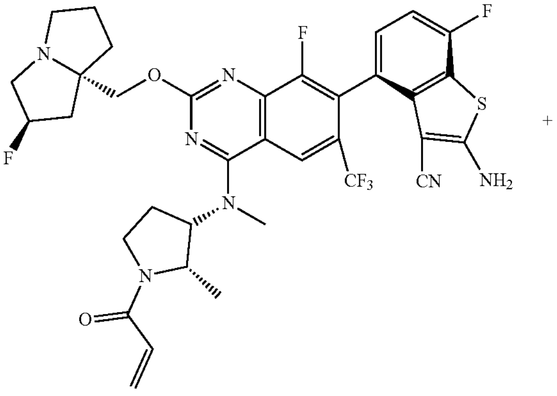
Compound 472

-continued

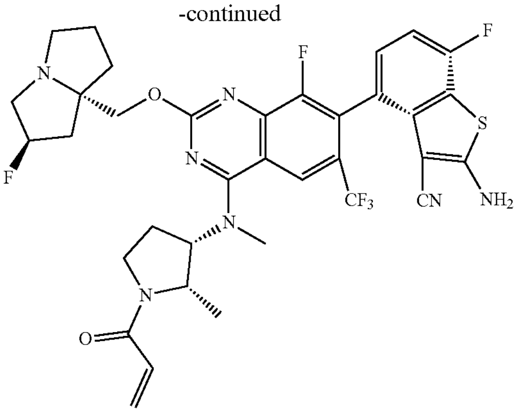

Compound 473

Step A: Preparation of tert-butyl (R)-(1-(2,2-dimethyl-4,6-dioxo-1,3-dioxan-5-yl)-1-oxopropan-2-yl)carbamate: To a solution of 2,2-dimethyl-1,3-dioxane-4,6-dione (1.10 eq, 37.71 g, 262 mmol) in DCM (1000 mL) was added (2R)-2-(tert-butoxycarbonylamino)propanoic acid (1.00 eq, 45.00 g, 238 mmol) and DMAP (1.50 eq, 43.52 g, 357 mmol), then EDCI (2.40 eq, 109.59 g, 571 mmol) was added at 0° C. After addition, the reaction mixture was stirred at 25° C. for 16 hours. LC-MS showed the reaction was completed. The solvent was removed and the residue was dissolved in EA (1000 mL), washed with 5% $NaHSO_4$ (5×200 mL) and brine (200 mL), dried over $Na_2SO_4$ to give a solution of tert-butyl N-[(1R)-2-(2,2-dimethyl-4,6-dioxo-1,3-dioxan-5-yl)-1-methyl-2-oxo-ethyl]carbamate (75.0 g, 80%) in ethyl acetate, which was used next step directly without further purification. LCMS ESI (+) m/z 338.2 (M+23)

Step B: Preparation of tert-butyl (R)-2-methyl-3,5-dioxopyrrolidine-1-carboxylate: A mixture of tert-butyl N-[(1R)-2-(2,2-dimethyl-4,6-dioxo-1,3-dioxan-5-yl)-1-methyl-2-oxo-ethyl]carbamate (1.00 eq, 75.00 g, 190 mmol) in ethyl acetate (1000 mL) was stirred at 80° C. for 3 hours. The solvent was removed to give crude of tert-butyl (2R)-2-methyl-3,5-dioxo-pyrrolidine-1-carboxylate (40.0 g, 87%) as a solid, which was used in next step directly without further purification. LCMS ESI (+) m/z 158.1 (M+H−56)

Step C: Preparation of tert-butyl (2R,3R)-3-hydroxy-2-methyl-5-oxopyrrolidine-1-carboxylate: To a solution of tert-butyl (2R)-2-methyl-3,5-dioxo-pyrrolidine-1-carboxylate (1.00 eq, 43.00 g, 202 mmol) in DCM (1000 mL) was added acetic acid (100 mL), then $NaBH_4$ (2.00 eq, 15.33 g, 403 mmol) was added slowly in portions at 0° C. under $N_2$. After addition, the reaction mixture was stirred at 0° C. for 3 hours. The reaction mixture was adjusted pH=8 with sat. $NaHCO_3$. The resulting mixture was extracted with EA (3×300 mL), the combined organic phase was washed with brine, dried over $Na_2SO_4$, and concentrated. The residue was purified by colum chromatography on silica gel (PE/EA=1/1) to give tert-butyl (2R,3R)-3-hydroxy-2-methyl-5-oxo-pyrrolidine-1-carboxylate (20.0 g, 43%) as a solid. $^1$H NMR (400 MHz, $CDCl_3$) δ 4.52-4.47 (m, 1H), 4.29-4.23 (m, 1H), 2.61-2.55 (m, 2H), 2.23 (d, 1H), 1.53 (s, 9H), 1.33 (d, 3H).

Step D: Preparation of tert-butyl (2R,3R)-3-hydroxy-2-methylpyrrolidine-1-carboxylate: To a solution of tert-butyl (2R,3R)-3-hydroxy-2-methyl-5-oxo-pyrrolidine-1-carboxylate (1.00 eq, 20.00 g, 92.9 mmol) in THF (200 mL) was added 1M $BH_3$/THF (3.00 eq, 280 mL, 279 mmol) at 0° C. After addition, the reaction mixture was stirred at 65° C. for 16 hours. After cooled to ambient temperature, the reaction mixture was quenched with saturated $NH_4Cl$ solution, extracted with EA (3×100 mL), the combined organic phase was washed with brine, dried over $Na_2SO_4$, and concentrated. The residue was purified by flash chromatography on silica gel (PE/EA=2/1) to give tert-butyl (2R,3R)-3-hydroxy-2-methyl-pyrrolidine-1-carboxylate (15.00 g, 76%) as a solid. LCMS ESI (+) m/z 146.1 (M+H−56). $^1$HNMR (400 MHz, $CDCl_3$) δ 4.33-4.30 (m, 1H), 3.86 (s, 1H), 3.41-3.35 (m, 2H), 2.05-2.02 (m, 1H), 1.87-1.82 (m, 1H), 1.67 (d, 1H), 1.49 (s, 9H), 1.20 (d, 3H).

Step E: Preparation of tert-butyl (R)-2-methyl-3-oxopyrrolidine-1-carboxylate: To a solution of DMSO (3.00 eq, 11.63 g, 149 mmol) in DCM (50 mL) was added oxalyl chloride (2.00 eq, 12.62 g, 99.4 mmol) at −78° C. under $N_2$. The mixture was stirred at −78° C. for 1 h, then a solution of tert-butyl (2R,3R)-3-hydroxy-2-methyl-pyrrolidine-1-carboxylate (1.00 eq, 10.00 g, 49.7 mmol) in DCM (50 mL) was added and stirred at −78° C. for 1 h. TEA (6.00 eq, 30.17 g, 298 mmol) was added and stirred at −78° C. for 1 hour. The mixture was then diluted with water and extracted with DCM (3×100 mL). The combined extracts were washed with brine, dried over sodium sulfate, filtered and concentrated. The residue was purified by column chromatography on silica gel to give tert-butyl (R)-2-methyl-3-oxopyrrolidine-1-carboxylate (8.0 g, 72%) as an oil. $^1$H NMR (400 MHz, $CDCl_3$) δ 3.91 (t, 2H), 3.61-3.54 (m, 1H), 2.65-2.49 (m, 2H), 1.49 (s, 9H), 1.32 (d, 3H).

Step F: Preparation of tert-butyl 2-methyl-3-(methylamino)pyrrolidine-1-carboxylate: A solution of tert-butyl (2R)-2-methyl-3-oxo-pyrrolidine-1-carboxylate (1.00 eq, 5.00 g, 25.1 mmol) in methylamine ethanol solution (30.9 eq, 100 mL, 774 mmol) was stirred at 25° C. for 16 hours. The solvent was removed under vacuum, the residue was dissolved in methanol, Pd/C (1.00 eq, 2671 mg, 25.1 mmol) was added and stirred at 15° C. under 1 atmosphere of hydrogen for 16 hours, filtered and concentrated. The residue was purified by column chromatography on silica gel to give tert-butyl-2-methyl-3-(methylamino)pyrrolidine-1-carboxylate (3.30 g, 55%) as an oil. LCMS ESI (+) m/z 215 (M+H). $^1$H NMR (400 MHz, $CDCl_3$) δ 4.06-3.93 (m, 1H), 3.39-3.13 (m, 3H), 2.44 (d, 3H), 2.07-2.04 (m, 1H), 1.62-1.52 (m, 1H), 1.46 (s, 9H), 1.02 (d, 3H).

Step G: Preparation of tert-butyl-3-[[7-bromo-2-chloro-8-fluoro-6-(trifluoromethyl) quinazolin-4-yl]-methyl-amino]-2-methyl-pyrrolidine-1-carboxylate: To a solution of 7-bromo-2,4-dichloro-8-fluoro-6-(trifluoromethyl)quinazoline (1.00 eq, 155 mg, 0.426 mmol) in DCM (2 mL) was added TEA (3.00 eq, 129 mg, 1.28 mmol), then tert-butyl-2-methyl-3-(methylamino)pyrrolidine-1-carboxylate (1.00 eq, 91 mg, 0.426 mmol) in DCM (2 mL) at −40° C. After addition, the reaction mixture was warmed to ambient temperature and stirred at ambient temperature for 16 hours. The reaction was quenched with ice-water, extracted with DCM (3×20 mL), the combined organic phase was washed with brine, dried over $Na_2SO_4$, concentrated. The residue was purified by preparative-TLC to afford tert-butyl-3-[[7-bromo-2-chloro-8-fluoro-6-(trifluoromethyl) quinazolin-4-yl]-methyl-amino]-2-methyl-pyrrolidine-1-carboxylate (226 mg, 93%) as a solid. LCMS ESI (+) m/z 541 (M+H).

Step H: Preparation of tert-butyl-3-[[7-bromo-8-fluoro-2-[[(2R,8S)-2-fluoro-1,2,3,5,6,7-hexahydropyrrolizin-8-yl] methoxy]-6-(trifluoromethyl)quinazolin-4-yl]-methyl-amino]-2-methyl-pyrrolidine-1-carboxylate: A solution of tert-butyl-3-[[7-bromo-2-chloro-8-fluoro-6-(trifluoromethyl)quinazolin-4-yl]-methyl-amino]-2-methyl-pyrrolidine-1-carboxylate (1.00 eq, 206 mg, 0.380 mmol), [(2R,8S)-2-fluoro-1,2,3,5,6,7-hexahydropyrrolizin-8-yl]

methanol (2.00 eq, 121 mg, 0.76 mmol) and DIEA (30.0 eq, 2.0 mL, 11.4 mmol) was stirred at 100° C. for 16 hours. After cooled to ambient temperature, the reaction was quenched with water and extracted with EA (4×50 mL). The combined organic phase was washed with brine, dried over sodium sulfate and concentrated. The residue was purified by prep-TLC to give tert-butyl-3-[[7-bromo-8-fluoro-2-[[(2R,8S)-2-fluoro-1,2,3,5,6,7-hexahydropyrrolizin-8-yl]methoxy]-6-(trifluoromethyl) quinazolin-4-yl]-methyl-amino]-2-methyl-pyrrolidine-1-carboxylate (169 mg, 61%) as a solid. LCMS ESI (+) m/z 664 (M+H).

Step I: Preparation of tert-butyl-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl]methoxy]-6-(trifluoromethyl) quinazolin-4-yl]-methyl-amino]-2-methyl-pyrrolidine-1-carboxylate: To a mixture of tert-butyl-3-[[7-bromo-8-fluoro-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate (1.00 eq, 149 mg, 0.22 mmol) in 1,4-dioxane (5 mL) was added tert-butyl N-[3-cyano-4-(5,5-dimethyl-1,3,2-dioxaborinan-2-yl)-7-fluoro-benzothiophen-2-yl]carbamate (1.50 eq, 136 mg, 0.34 mmol), potassium trimethylsilanolate (3.00 eq, 0.14 mL, 0.67 mmol) and Pd(DPEPhos)$Cl_2$ (0.400 eq, 64.2 mg, 0.090 mmol); after addition, the reaction mixture was stirred at 95° C. for 16 hours under $N_2$. After cooled to ambient temperature, the reaction was quenched by water and extracted by EA (3×30 mL). The combined organic phase was washed with brine, dried over sodium sulfate and concentrated. The residue was purified by preparative-TLC to give tert-butyl-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl]methoxy]-6-(trifluoromethyl)quinazolin-4-yl]-methyl-amino]-2-methyl-pyrrolidine-1-carboxylate (97 mg, 24%) as a solid. LCMS ESI (+) m/z 876 (M+H).

Step J: Preparation of 2-amino-7-fluoro-4-[8-fluoro-2-[[(2R,8S)-2-fluoro-1,2,3,5,6,7-hexahydropyrrolizin-8-yl]methoxy]-4-[methyl-[2-methylpyrrolidin-3-yl]amino]-6-(trifluoromethyl) quinazolin-7-yl]benzothiophene-3-carbonitrile: A solution of tert-butyl-3-[[7-[2-(tert-butoxycarbonylamino)-3-cyano-7-fluoro-benzothiophen-4-yl]-8-fluoro-2-[[(2R,8S)-2-fluoro-1,2,3,5,6,7-hexahydropyrrolizin-8-yl]methoxy]-6-(trifluoromethyl) quinazolin-4-yl]-methyl-amino]-2-methyl-pyrrolidine-1-carboxylate (1.00 eq, 87 mg, 0.099 mmol) and TFA (65.3 eq, 0.50 mL, 6.49 mmol) in DCM (2 mL) was stirred at 25° C. for 4 hours. The mixture was concentrated and dried in vacuum. The residue was purified by preparative RP-HPLC to give 2-amino-7-fluoro-4-[8-fluoro-2-[[(2R,8S)-2-fluoro-1,2,3,5,6,7-hexahydropyrrolizin-8-yl]methoxy]-4-[methyl-[2-methylpyrrolidin-3-yl]amino]-6-(trifluoromethyl) quinazolin-7-yl]benzothiophene-3-carbonitrile (33 mg, 46%) as a solid. LCMS ESI (+) m/z 676 (M+H).

Step K: Preparation of 4-(4-(((1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 381), 4-((S)-4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 434), 4-((R)-4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 435), 4-((S)-4-(((2S,3S)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 472) and 4-((R)-4-(((2S,3S)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 473): To a solution of 2-amino-7-fluoro-4-[8-fluoro-2-[[(2R,8S)-2-fluoro-1,2,3,5,6,7-hexahydropyrrolizin-8-yl]methoxy]-4-[methyl-[2-methylpyrrolidin-3-yl]amino]-6-(trifluoromethyl)quinazolin-7-yl]benzothiophene-3-carbonitrile (1.00 eq, 23 mg, 0.034 mmol) in DCM (1 mL) was added TEA (3.00 eq, 10 mg, 0.102 mmol) at −30° C. under $N_2$, then a solution of prop-2-enoyl prop-2-enoate (0.800 eq, 3.4 mg, 0.0272 mmol) in DCM (0.5 mL) was added dropwise at −30° C. After addition, the reaction mixture was stirred at −30° C. for 1 hour. The reaction was quenched by MeOH and water, extracted with DCM (3×5 mL). The combined organic phase was washed with brine, dried over sodium sulfate and concentrated. The residue was purified by preparative-TLC to give 4-(4-(((1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (2.2 mg, 5%) as a solid. LCMS ESI (+) m/z 730.2 (M+H). $^1$HNMR (400 MHz, $CD_3OD$) 8.37 (s, 1H), 7.22 (t, 1H), 7.01 (t, 1H), 6.68-6.61 (m, 1H), 6.32 (t, 1H), 5.78 (d, 1H), 5.50-5.31 (m, 1H), 5.06-5.04 (m, 1H), 4.56-4.39 (m, 2H), 3.8-3.67 (m, 1H), 3.63 (s, 4H), 3.58 (t, 2H), 3.44 (t, 1H), 2.46-2.09 (m, 8H), 1.28 (s, 1H), 1.16-1.09 (m, 4H).

The single diastereomers of 4-(4-(((1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 381) (2081 mg) were separated with chiral chromatography condition [Chiral ART Cellulose-SC 3 cm×25 cm, 5 μm, $CO_2$:[EtOH: DCM=2:1(0.2% 2 mM $NH_3$-MeOH)]=60:40, 80 mL/min]. The first compound off the column was identified as one atropisomer, 4-((S)-4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 434) (600.5 mg, 99.49% de); LCMS ESI (+) m/z 730.0 (M+H). $^1$HNMR (400 MHz, $CD_3OD$) δ 8.34 (s, 1H), 7.19-7.27 (m, 1H), 6.99-7.05 (m, 1H), 6.62-6.70 (m, 1H), 6.28-6.39 (m, 1H), 5.77 (d, J=10.5 Hz, 1H), 5.29 (d, J=52.2 Hz, 1H), 5.02-5.09 (m, 1H), 4.87-4.92 (m, 1H), 4.20-4.36 (m, 2H), 3.55-4.05 (m, 5H), 3.11-3.26 (m, 3H), 2.94-3.04 (m, 1H), 1.80-2.80 (m, 8H), 1.11 (dd, J=10.0, 6.7 Hz, 3H). The second compound off the column was identified as another atropisomer, 4-((R)-4-(((2S,3S)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 473) (296.5 mg, 99.99% de). LCMS ESI (+) m/z 730.0 (M+H). $^1$HNMR (400 MHz, $CD_3OD$) δ 8.35 (s, 1H), 7.20-7.27 (m, 1H), 6.98-7.06 (m, 1H), 6.59-6.73 (m, 1H), 6.26-6.40 (m, 1H), 5.73-5.81 (m, 1H), 5.32 (d, J=53.2 Hz, 1H), 5.01-5.12 (m, 1H), 4.87-4.94 (m, 1H), 4.19-4.36 (m, 3H), 3.54-4.01 (m, 5H), 3.19-3.28 (m, 3H), 2.98-3.10 (m, 1H), 1.93-2.67 (m, 8H), 1.06-1.18 (m, 3H). The third compound off the column was identified as another atropisomer, 4-((S)-4-(((2S,3S)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 472) (190.7 mg, 81.8% de). LCMS ESI (+) m/z 730.0 (M+H). $^1$HNMR (400 MHz, $CD_3OD$) δ8.35 (s, 1H), 7.18-7.26 (m, 1H), 7.01 (t, J=9.0 Hz, 1H), 6.61-6.74 (m, 1H), 6.26-6.39 (m, 1H), 5.77 (d, J=10.7 Hz, 1H), 5.31 (d, J=54.6 Hz, 1H), 4.98-5.10 (m, 1H), 4.87-4.94 (m, 1H), 4.21-4.37 (m, 2H), 3.55-3.97 (m, 5H), 3.14-3.29 (m, 3H), 2.96-3.06 (m, 1H), 2.57-2.75 (m, 1H), 1.87-2.48 (m, 7H), 1.07-1.18 (m, 3H). The fourth compound off the column was identified as another atropisomer, 4-((R)-4-(((2R,3R)-1-acryloyl-2-methylpyrrolidin-3-yl)(methyl)amino)-8-fluoro-2-(((2R,7aS)-2-fluorotetrahydro-1H-pyrrolizin-7a(5H)-yl)methoxy)-6-(trifluoromethyl)quinazolin-7-yl)-2-amino-7-fluorobenzo[b]thiophene-3-carbonitrile (Compound 435) (462.4 mg, 99.99% de). LCMS ESI (+) m/z 730.0 (M+H). $^1$HNMR (400 MHz, $CD_3OD$) δ 8.35 (s, 1H), 7.19-7.25 (m, 1H), 7.01 (t, J=8.9 Hz, 1H), 6.61-6.71 (m, 1H), 6.30-6.41 (m, 1H), 5.78 (d, J=12.2 Hz, 1H), 5.30 (d, J=53.4 Hz, 1H), 5.01-5.07 (m, 1H), 4.87-4.94 (m, 1H), 4.21-4.36 (m, 2H), 3.55-4.05 (m, 5H), 3.13-3.27 (m, 3H), 2.97-3.06 (m, 1H), 1.80-2.80 (m, 8H), 1.14 (t, J=7.1 Hz, 3H).

Synthetic Example 46: Synthesis of 4-(4-(((R)-1-acryloylpyrrolidin-3-yl)(methyl)amino)-8-fluoro-6-(trifluoromethyl)quinazolin-7-yl)-2-amino-7-fluorobenzo[b]thiophene-3-carbonitrile (Compound 383)

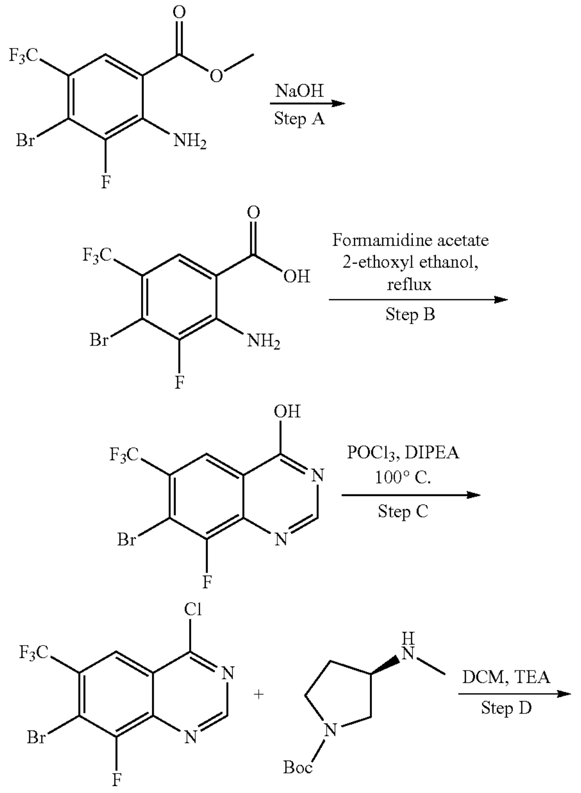

-continued

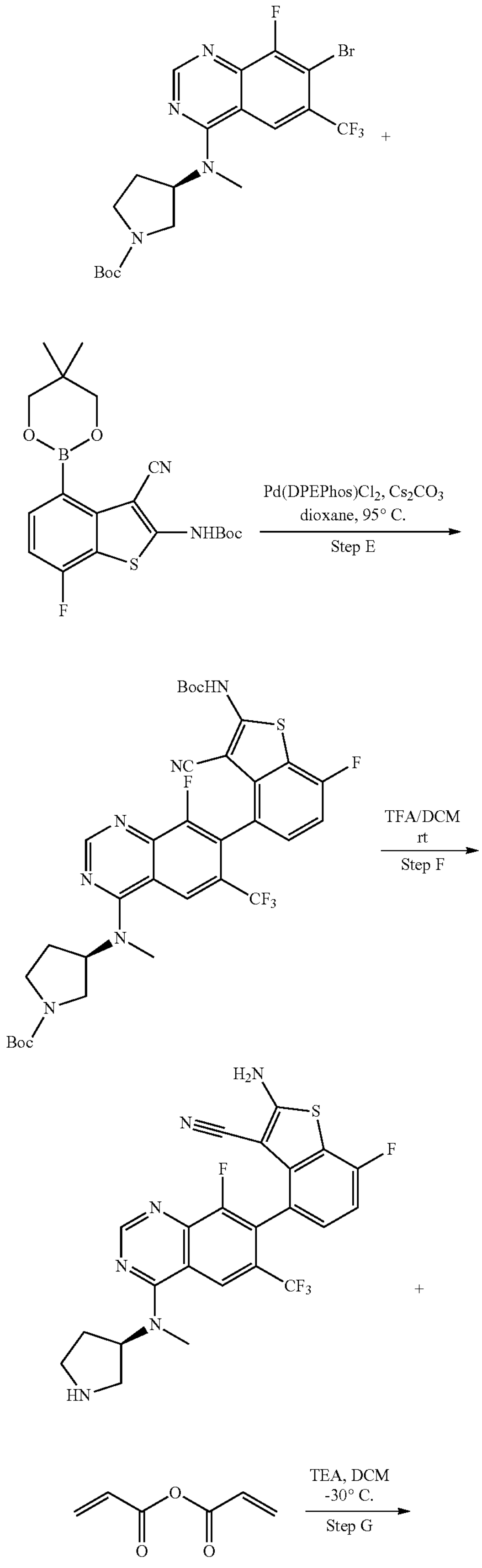

-continued

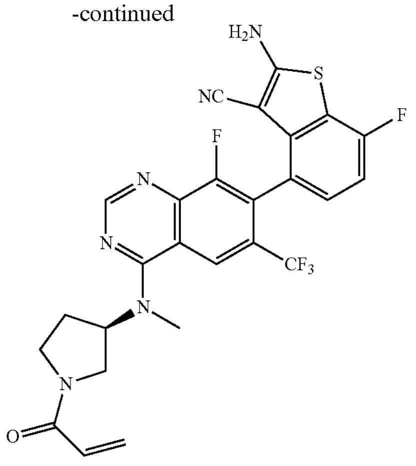

Compound 383

Step A: Preparation of 2-amino-4-bromo-3-fluoro-5-(trifluoromethyl)benzoic acid: To a solution of methyl 2-amino-4-bromo-3-fluoro-5-(trifluoromethyl)benzoate (1.00 eq, 5.00 g, 15.8 mmol) in THF (40 mL) and water (10 mL) was added NaOH (1.50 eq, 949 mg, 23.7 mmol) at 0° C.; after addition, the resulting solution was stirred at 25° C. for 2 hours. The THF was removed and the pH of residue was adjusted with AcOH solution until pH=5, extracted with EA (3×50 mL), the combined organic phase was washed with brine, dried over $Na_2SO_4$, concentrated to give 2-amino-4-bromo-3-fluoro-5-(trifluoromethyl)benzoic acid (4.20 g, 77%) as a solid. LCMS ESI (+) m/z 302 (M+H).

Step B: Preparation of 7-bromo-8-fluoro-6-(trifluoromethyl)quinazolin-4-ol: To a solution of 2-amino-4-bromo-3-fluoro-5-(trifluoromethyl)benzoic acid (1.00 eq, 1.00 g, 3.31 mmol) in 2-ethoxyethanol (15 mL) was added formamidine acetate (4.00 eq, 1.38 g, 13.2 mmol) at 25° C.; after addition, the reaction mixture was stirred at 140° C. for 16 hours. After cooled to ambient temperature, the mixture was concentrated to give under reduced pressure, 20 mL of water was added and extracted with EA (3×20 mL), the combined organic phase was washed with brine, dried over $Na_2SO_4$, and concentrated. The residue was purified by flash chromatography on silica gel (PE-PE/EA=1/1) to give 7-bromo-8-fluoro-6-(trifluoromethyl)quinazolin-4-ol (420 mg, 35%) as a solid. LCMS ESI (+) m/z 311 (M+H).

Step C: Preparation of 7-bromo-4-chloro-8-fluoro-6-(trifluoromethyl)quinazoline: To a solution of 7-bromo-8-fluoro-6-(trifluoromethyl)quinazolin-4-ol (1.00 eq, 420 mg, 1.35 mmol) in $POCl_3$ (1.00 eq, 0.13 mL, 1.35 mmol) was added DIEA (5.00 eq, 1.2 mL, 6.75 mmol) at 25° C., after addition the reaction mixture was stirred at 100° C. for 2 hours. After cooled to ambient temperature, the mixture was concentrated to give the crude product. The residue was purified by flash chromatography on silica gel (PE-PE/EA=10/1) to give 7-bromo-4-chloro-8-fluoro-6-(trifluoromethyl)quinazoline (300 mg, 45%) as a solid. LCMS ESI (+) m/z 329 (M+H).

Step D: Preparation of tert-butyl (3R)-3-[[7-bromo-8-fluoro-6-(trifluoromethyl)quinazolin-4-yl]-methyl-amino]pyrrolidine-1-carboxylate: To a solution of 7-bromo-4-chloro-8-fluoro-6-(trifluoromethyl)quinazoline (1.00 eq, 300 mg, 0.91 mmol), DIEA (3.00 eq, 0.49 mL, 2.73 mmol) in DCM (10 mL) was added tert-butyl (3R)-3-(methylamino)pyrrolidine-1-carboxylate (1.00 eq, 182 mg, 0.91 mmol) at 0° C.; after addition, the reaction mixture was stirred at 25° C. for 16 hours. 20 mL of water was added the mixture, extracted with DCM (3×20 mL), the combined organic phase was washed with brine, dried over $Na_2SO_4$, and concentrated. The residue was purified by flash chromatography on silica gel (PE-PE/EA=5/1) to give tert-butyl (3R)-3-[[7-bromo-8-fluoro-6-(trifluoromethyl)quinazolin-4-yl]-methyl-amino]pyrrolidine-1-carboxylate (240 mg, 44%) as a solid. LCMS ESI (+) m/z 492 (M+H).

Step E: Preparation of tert-butyl (3R)-3-[[7-[2-(tert-butoxycarbonylamino)-3-cyano-7-fluoro-benzothiophen-4-yl]-8-fluoro-6-(trifluoromethyl)quinazolin-4-yl]-methyl-amino]pyrrolidine-1-carboxylate: To a solution of tert-butyl (3R)-3-[[7-bromo-8-fluoro-6-(trifluoromethyl)quinazolin-4-yl]-methyl-amino]pyrrolidine-1-carboxylate (1.00 eq, 220 mg, 0.45 mmol) in 1,4-dioxane (6 mL) was added tert-butyl N-[3-cyano-4-(5,5-dimethyl-1,3,2-dioxaborinan-2-yl)-7-fluoro-benzothiophen-2-yl]carbamate (1.50 eq, 270 mg, 0.67 mmol), $Cs_2CO_3$ (3.00 eq, 436 mg, 1.34 mmol) and Pd(DPEPhos)$Cl_2$ (0.20 eq, 0.088 mL, 0.089 mmol); after addition, the resulting solution was stirred at 95° C. for 16 hours under $N_2$. After cooled to ambient temperature, the reaction was quenched by water and extracted by EtOAc (30 mL×3). The combined organic phase was washed with brine, dried over sodium sulfate and concentrated. The residue was purified by column chromatography on silica gel eluted with (PE/EA=1:1) to afford tert-butyl (3R)-3-[[7-[2-(tert-butoxycarbonylamino)-3-cyano-7-fluoro-benzothiophen-4-yl]-8-fluoro-6-(trifluoromethyl)quinazolin-4-yl]-methyl-amino]pyrrolidine-1-carboxylate (70 mg, 19% yield) as a solid. LCMS ESI (+) m/z 705 (M+H).

Step F: Preparation of 2-amino-7-fluoro-4-[8-fluoro-4-[methyl-[(3R)-pyrrolidin-3-yl]amino]-6-(trifluoromethyl)quinazolin-7-yl]benzothiophene-3-carbonitrile: To a solution of tert-butyl (3R)-3-[[7-[2-(tert-butoxycarbonylamino)-3-cyano-7-fluoro-benzothiophen-4-yl]-8-fluoro-6-(trifluoromethyl)quinazolin-4-yl]-methyl-amino]pyrrolidine-1-carboxylate (1.00 eq, 60 mg, 0.0851 mmol) in DCM (3 mL) was added TFA (152 eq, 1.0 mL, 13.0 mmol) at 25° C.; after addition, the reaction mixture was stirred at 25° C. for 16 hours. The mixture was concentrated under reduced pressure to give the crude product. The crude product was purified by preparative RP-HPLC to give 2-amino-7-fluoro-4-[8-fluoro-4-[methyl-[(3R)-pyrrolidin-3-yl]amino]-6-(trifluoromethyl)quinazolin-7-yl]benzothiophene-3-carbonitrile (25 mg, 57%) as a solid. LCMS ESI (+) m/z 505 (M+H).

Step G: Preparation of 2-amino-7-fluoro-4-[8-fluoro-4-[methyl-[(3R)-1-prop-2-enoylpyrrolidin-3-yl]amino]-6-(trifluoromethyl)quinazolin-7-yl]benzothiophene-3-carbonitrile: To a solution of 2-amino-7-fluoro-4-[8-fluoro-4-[methyl-[(3R)-pyrrolidin-3-yl]amino]-6-(trifluoromethyl)quinazolin-7-yl]benzothiophene-3-carbonitrile (1.00 eq, 15 mg, 0.030 mmol) and TEA (3.00 eq, 9.0 mg, 0.0892 mmol) in DCM (2 mL) was added prop-2-enoyl prop-2-enoate (0, 3.0 mg, 0.024 mmol) at −30° C.; after addition, the reaction mixture was stirred at −30° C. for 1 hours. 3 mL of water was added the mixture, extracted with DCM (3×5 mL), the combined organic phase was washed with brine, dried over $Na_2SO_4$, and concentrated. The residue was purified by preparative-TLC (DCM:MeOH=10/1) to give 2-amino-7-fluoro-4-[8-fluoro-4-[methyl-[(3R)-1-prop-2-enoylpyrrolidin-3-yl]amino]-6-(trifluoromethyl)quinazolin-7-yl]benzothiophene-3-carbonitrile (8.7 mg, 51%) as a solid. LCMS ESI (+) m/z 559 (M+H). $^1H$ NMR (400 MHz, $CD_3OD$) δ 8.73 (s, 1H), 8.42 (s, 1H), 7.28 (t, 1H), 7.06 (t, 1H), 6.63-6.77 (m, 1H), 6.34 (d, 1H), 5.76-5.88 (m, 1H), 5.34-

5.54 (m, 1H), 3.89-4.35 (m, 2H), 3.53-3.88 (m, 2H), 3.48-3.54 (m, 3H), 2.36-2.65 (m, 2H).
Synthetic Example 47: Synthesis of 4-((1-acryloyl-2-methylpyrrolidin-3-yl)(methyl)amino)-7-(2-amino-3-cyano-7-fluorobenzo[b]thiophen-4-yl)-2-(((2R,7aS)-2-fluorotetrahydro-1H-pyrrolizin-7a(5H)-yl)methoxy)quinazoline-6-carbonitrile (Compound 387)
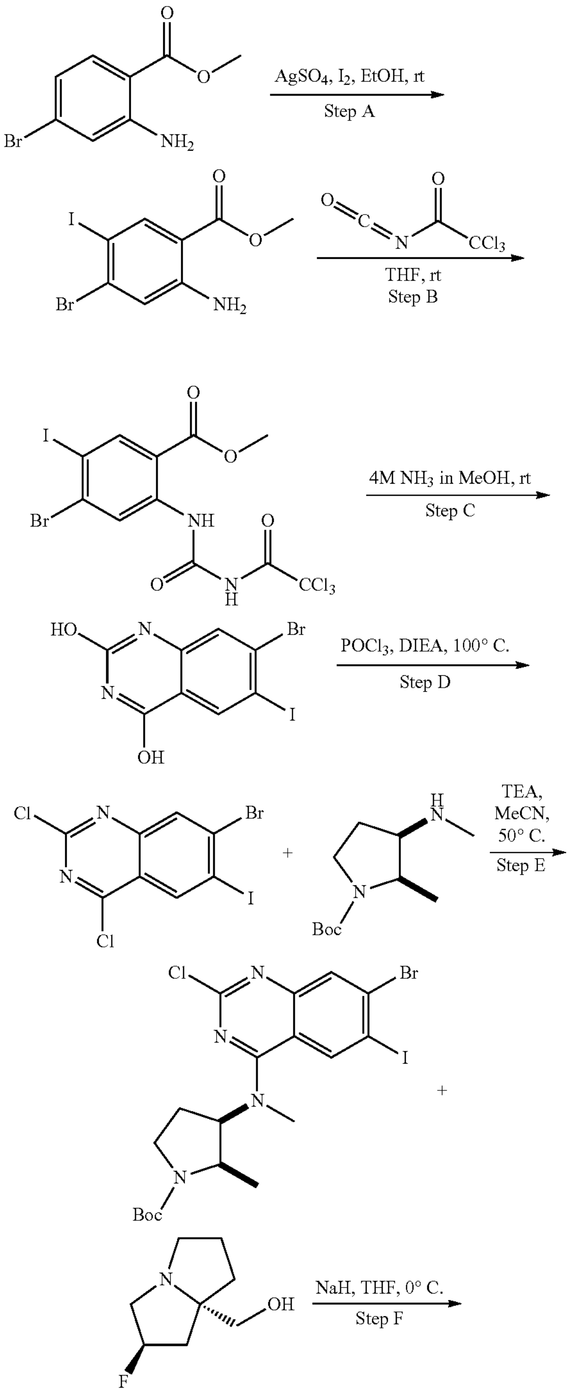
-continued
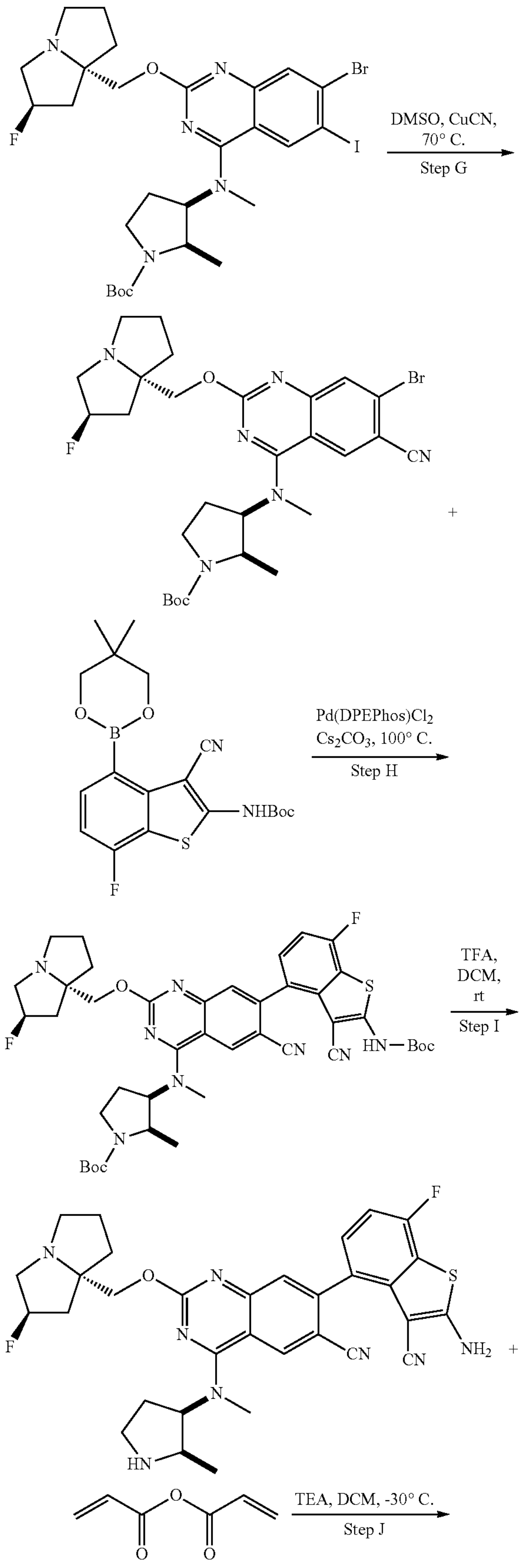

-continued

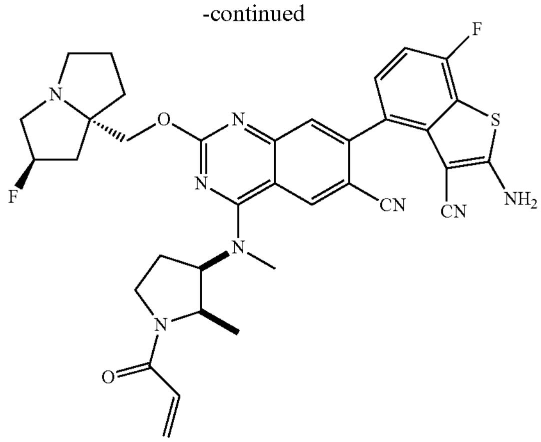

Compound 387

Step A: Preparation of methyl 2-amino-4-bromo-5-iodo-benzoate: To a mixture of $I_2$ (1.00 eq, 22.08 g, 86.9 mmol), $AgSO_4$ (1.00 eq, 17.73 g, 86.9 mmol) in ethanol (1000 mL) was added methyl 2-amino-4-bromo-benzoate (1.00 eq, 20.00 g, 86.9 mmol). The mixture was stirred for 1 hour at 25° C. The reaction mixture was filtered. The filtrate was concentrated under reduced pressure and the residue obtained was dissolved in ethyl acetate (1000 mL), washed with $NaHCO_3$ aqueous solution (1000 mL×3), dried over $Na_2SO_4$ and concentrated to give a residue. The residue was recrystallized with DCM/PE=1:10 to give methyl 2-amino-4-bromo-5-iodobenzoate (18.0 g, 57) as a solid. LCMS ESI (+) m/z 357.8 (M+H).

Step B: Preparation of methyl 4-bromo-5-iodo-2-[(2,2,2-trichloroacetyl)carbamoylamino]benzoate: To a solution of methyl 2-amino-4-bromo-5-iodo-benzoate (1.00 eq, 18 g, 50.3 mmol) in THF (180 mL) was added 2,2,2-trichloro-acetyl isocyanate (1.50 eq, 14.2 g, 75.4 mmol). The mixture was stirred for 12 hours at 25° C. The mixture was quenched with water (500 mL) and extracted with DCM (500 mL×3). The organic layer was dried over $Na_2SO_4$ and concentrated to give a residue. The residue was recrystallized with DCM/PE=1:5 to give methyl 4-bromo-5-iodo-2-[(2,2,2-trichloroacetyl)carbamoylamino]benzoate (30.0 g, 90% yield) as a solid. LCMS ESI (+) m/z 544 (M+H).

Step C: Preparation of 7-bromo-6-iodo-quinazoline-2,4-diol: To a solution of methyl 4-bromo-5-iodo-2-[(2,2,2-trichloroacetyl)carbamoylamino]benzoate (1.00 eq, 20.00 g, 36.7 mmol) in methanol (100 mL) was added 4M $NH_3$/MeOH (200 mL). The mixture was stirred for 3 hours at 25° C. The mixture was concentrated to give a residue. The residue was recrystallized with DCM/PE=1:5 to give 7-bromo-6-iodo-quinazoline-2,4-diol (20.0 g, 96% yield) as a solid. LCMS ESI (+) m/z 367 (M+H).

Step D: Preparation of 7-bromo-2,4-dichloro-6-iodo-quinazoline: To a solution of 7-bromo-6-iodo-quinazoline-2,4-diol (1.00 eq, 10.00 g, 27.3 mmol) in $POCl_3$ (100 mL) was added DIEA (5.00 eq, 24 mL, 136 mmol). The mixture was stirred for 3 hours at 100° C. After cooled to ambient temperature, the mixture was concentrated to give a residue. The residue was purified by column chromatography on silica gel with EA/PE=1:20-1:5 to give 7-bromo-2,4-dichloro-6-iodo-quinazoline (8.0 g, 72% yield) as a solid. LCMS ESI (+) m/z 404 (M+H).

Step E: Preparation of tert-butyl-3-[(7-bromo-2-chloro-6-iodo-quinazolin-4-yl)-methyl-amino]-2-methyl-pyrrolidine-1-carboxylate: To a solution of 7-bromo-2,4-dichloro-6-iodo-quinazoline (1.00 eq, 11.3 g, 28.0 mmol) in acetonitrile (200 mL) was added TEA (3.00 eq, 8.49 g, 83.9 mmol) and tert-butyl-2-methyl-3-(methylamino)pyrrolidine-1-carboxylate (1.00 eq, 6.00 g, 28.0 mmol). The mixture was stirred for 5 hours at 50° C. After cooled to ambient temperature, the mixture was quenched with water (500 mL) and extracted with EA (500 mL×3). The organic layer was dried over $Na_2SO_4$ and concentrated to give a residue. The residue was purified by column chromatography on silica gel with EA/PE=1:8 to give tert-butyl-3-[(7-bromo-2-chloro-6-iodo-quinazolin-4-yl)-methyl-amino]-2-methyl-pyrrolidine-1-carboxylate (8.9 g, 49% yield) as a solid. LCMS ESI (+) m/z 582 (M+H).

Step F: Preparation of tert-butyl-3-[[7-bromo-2-[[(2R,8S)-2-fluoro-1,2,3,5,6,7-hexahydropyrrolizin-8-yl]methoxy]-6-iodo-quinazolin-4-yl]-methyl-amino]-2-methyl-pyrrolidine-1-carboxylate: To a solution of [(2R,8S)-2-fluoro-1,2,3,5,6,7-hexahydropyrrolizin-8-yl]methanol (2.00 eq, 4.38 g, 27.5 mmol) in THF (100 mL) was added NaH (5.00 eq, 2.75 g, 68.8 mmol) at 0° C. The mixture was stirred for 1 hour at 0° C. and tert-butyl-3-[(7-bromo-2-chloro-6-iodo-quinazolin-4-yl)-methyl-amino]-2-methyl-pyrrolidine-1-carboxylate (1.00 eq, 8.00 g, 13.8 mmol) was added. The mixture was stirred for 4 hours at 0° C. The mixture was quenched with water (500 mL) and extracted with EA (500 mL×3). The organic layer was dried over $Na_2SO_4$ and concentrated to give a residue. The residue was purified by column chromatography on silica gel with EA/PE=1:5 to give tert-butyl-3-[[7-bromo-2-[[(2R,8S)-2-fluoro-1,2,3,5,6,7-hexahydropyrrolizin-8-yl]methoxy]-6-iodo-quinazolin-4-yl]-methyl-amino]-2-methyl-pyrrolidine-1-carboxylate (9.16 g, 85% yield) as a solid. LCMS ESI (+) m/z 704 (M+H).

Step G: Preparation of tert-butyl-3-[[7-bromo-6-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of tert-butyl-3-[[7-bromo-2-[[(2R,8S)-2-fluoro-1,2,3,5,6,7-hexahydropyrrolizin-8-yl]methoxy]-6-iodo-quinazolin-4-yl]-methyl-amino]-2-methyl-pyrrolidine-1-carboxylate (1.00 eq, 9.00 g, 12.8 mmol) in DMSO (400 mL) was added CuCN (10.0 eq, 11.5 g, 128 mmol). The mixture was stirred for 9 hours at 70° C. After cooled to ambient temperature, the mixture was quenched with water (2500 mL) and extracted with DCM (1000 mL×3). The organic layer was dried over $Na_2SO_4$ and concentrated to give a residue. The residue was purified by column chromatography on silica gel with DCM/MeOH=20:1 to give tert-butyl-3-[[7-bromo-6-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (3.3 g, 38% yield) as a yellow solid. LCMS ESI (+) m/z 604 (M+H).

Step H: Preparation of tert-butyl-3-[[7-[2-(tert-butoxycarbonylamino)-3-cyano-7-fluoro-benzothiophen-4-yl]-6-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of tert-butyl-3-[[7-bromo-6-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 320 mg, 0.53 mmol) in 1,4-dioxane (16 mL) was added tert-butyl N-[3-cyano-4-(5,5-dimethyl-1,3,2-dioxaborinan-2-yl)-7-fluoro-benzothiophen-2-yl]carbamate (1.50 eq, 322 mg, 0.80 mmol), $Cs_2CO_3$ (3.00 eq, 518 mg, 1.59 mmol) and $Pd(DPEphos)Cl_2$ (0.200 eq, 75.9 mg, 0.106 mmol) under $N_2$. The mixture was stirred for 3 hours at 100° C. After cooled to ambient temperature, the mixture was quenched with water (50 mL) and extracted with EA (50 mL×3). The organic layer was dried over $Na_2SO_4$ and concentrated to give a residue. The residue was purified by preparative-TLC with DCM/MeOH=20:1 to give tert-butyl-3-[[7-[2-(tert-butoxycarbonylamino)-3-cyano-7-fluoro-benzothiophen-4-yl]-6-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (227 mg, 48.3% yield) as a yellow solid. LCMS ESI (+) m/z 815 (M+H).

Step I: Preparation of 7-(2-amino-3-cyano-7-fluoro-benzothiophen-4-yl)-2-[[(2R,8S)-2-fluoro-1,2,3,5,6,7-hexahydropyrrolizin-8-yl]methoxy]-4-[methyl-[2-methylpyrrolidin-3-yl]amino]quinazoline-6-carbonitrile: To a solution of tert-butyl-3-[[7-[2-(tert-butoxycarbonylamino)-3-cyano-7-fluoro-benzothiophen-4-yl]-6-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 220 mg, 0.270 mmol) in DCM (5 mL) was added TFA (240 eq, 5.0 mL, 64.9 mmol). The mixture was stirred for 1 hour at 25° C. The mixture was concentrated to give 7-(2-amino-3-cyano-7-fluoro-benzothiophen-4-yl)-2-[[(2R,8S)-2-fluoro-1,2,3,5,6,7-hexahydropyrrolizin-8-yl]methoxy]-4-[methyl-[(2R,3R)-2-methylpyrrolidin-3-yl]amino]quinazoline-6-carbonitrile (310 mg, 100% yield) as a solid. LCMS ESI (+) m/z 615 (M+H).

Step J: Preparation of 7-(2-amino-3-cyano-7-fluoro-benzothiophen-4-yl)-2-[[(2R,8S)-2-fluoro-1,2,3,5,6,7-hexahydropyrrolizin-8-yl]methoxy]-4-[methyl-[2-methyl-1-prop-2-enoyl-pyrrolidin-3-yl]amino]quinazoline-6-carbonitrile: To a solution of 7-(2-amino-3-cyano-7-fluoro-benzothiophen-4-yl)-2-[[(2R,8S)-2-fluoro-1,2,3,5,6,7-hexahydropyrrolizin-8-yl]methoxy]-4-[methyl-[2-methylpyrrolidin-3-yl]amino]quinazoline-6-carbonitrile (1.00 eq, 35 mg, 0.057 mmol) in DCM (1 mL) was added TEA (4.00 eq, 23 mg, 0.228 mmol) and prop-2-enoyl prop-2-enoate (1.20 eq, 8.6 mg, 0.0683 mmol) at −30° C. The mixture was stirred for 0.5 hours at −30° C. The mixture was quenched with MeOH (0.5 mL)/water and extracted with DCM (10 mL×3). The organic layer was dried over $Na_2SO_4$ and concentrated to give a residue. The residue was purified by preparative-TLC with DCM/MeOH=15:1 to give 7-(2-amino-3-cyano-7-fluoro-benzothiophen-4-yl)-2-[[(2R,8S)-2-fluoro-1,2,3,5,6,7-hexahydropyrrolizin-8-yl]methoxy]-4-[methyl-[2-methyl-1-prop-2-enoyl-pyrrolidin-3-yl]amino]quinazoline-6-carbonitrile (16.1 mg, 41% yield) as a solid. LCMS ESI (+) m/z 669 (M+H). $^1H$ NMR (400 MHz, $CD_3OD$) δ 8.64-8.63 (m, 1H), 7.60-7.58 (m, 1H), 7.30-7.27 (m, 1H), 7.06-7.01 (m, 1H), 6.71-6.62 (m, 1H), 6.37-6.28 (m, 1H), 5.79-5.76 (m, 1H), 5.37-5.24 (m, 1H), 5.03-5.01 (m, 1H), 4.31-4.20 (m, 2H), 3.98-3.54 (m, 5H), 3.25-3.17 (m, 2H), 3.01-3.00 (m, 1H), 2.69-1.89 (m, 9H), 1.28 (s, 1H), 1.12-1.07 (m, 3H).

Synthetic Example 48: Synthesis of 4-((1-acryloyl-2-methylpyrrolidin-3-yl)(methyl)amino)-7-(2-amino-3-cyano-7-fluorobenzo[b]thiophen-4-yl)-6-chloro-2-(((2R,7aS)-2-fluorotetrahydro-1H-pyrrolizin-7a(5H)-yl)methoxy)quinazoline-8-carbonitrile (Compound 388)

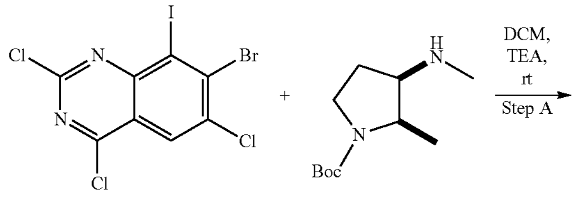

-continued

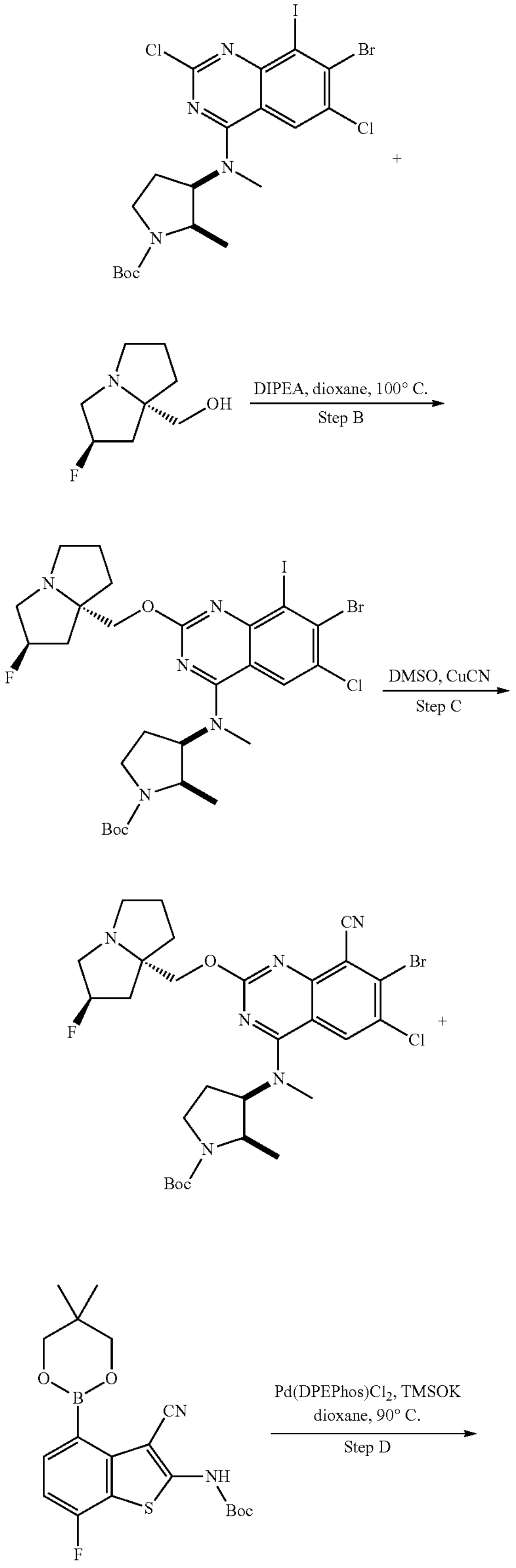

-continued

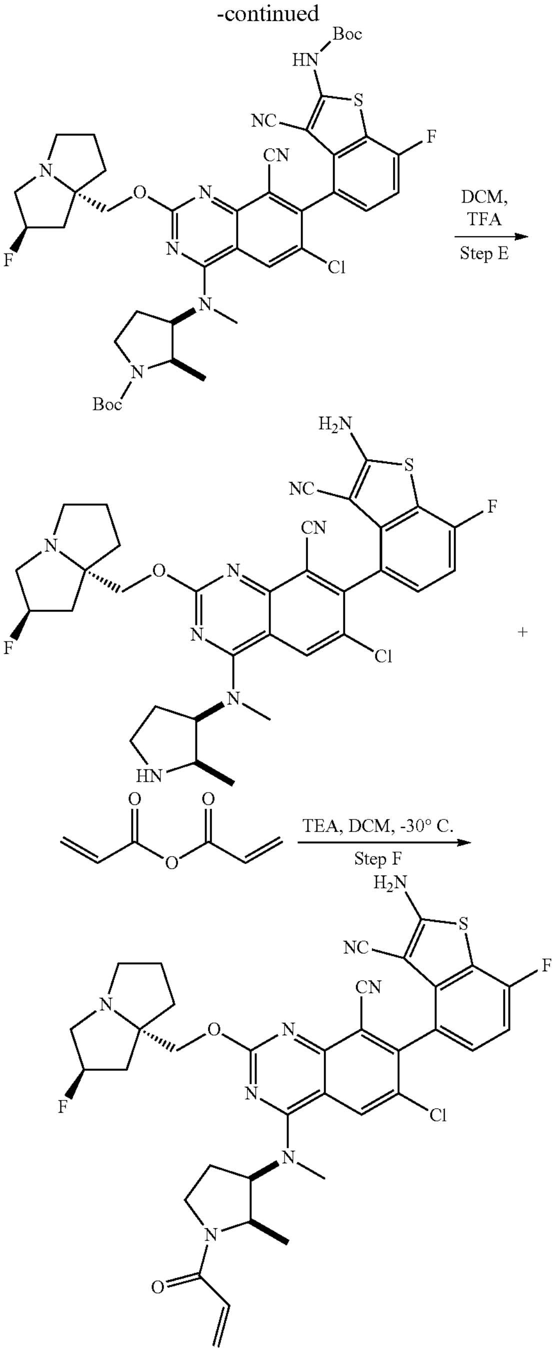

Compound 388

Step A: Preparation of tert-butyl-3-((7-bromo-2,6-dichloro-8-iodoquinazolin-4-yl)(methyl)amino)-2-methylpyrrolidine-1-carboxylate: To a solution of 7-bromo-2,4,6-trichloro-8-iodo-quinazoline (1.00 eq, 250 mg, 0.570 mmol) and DIEA (3.00 eq, 0.30 mL, 1.71 mmol) in DCM (3 mL) was added tert-butyl-2-methyl-3-(methylamino)pyrrolidine-1-carboxylate (1.00 eq, 122 mg, 0.570 mmol) at−40° C. under $N_2$; after addition, the reaction mixture was stirred at 25° C. for 16 hours. The reaction was quenched with ice-water, extracted with DCM (3x20 mL), the combined organic phase was washed with brine, dried over $Na_2SO_4$, and concentrated. The residue was purified by preparative-TLC to afford tert-butyl-3-[(7-bromo-2,6-dichloro-8-iodo-quinazolin-4-yl)-methyl-amino]-2-methyl-pyrrolidine-1-carboxylate (370 mg, 95% yield) as a solid. LCMS ESI (+) m/z 614.8 (M+H).

Step B: Preparation of tert-butyl-3-((7-bromo-6-chloro-2-(((2R,7aS)-2-fluorotetrahydro-1H-pyrrolizin-7a(5H)-yl)methoxy)-8-iodoquinazolin-4-yl)(methyl)amino)-2-methylpyrrolidine-1-carboxylate: A solution of tert-butyl-3-[(7-bromo-2,6-dichloro-8-iodo-quinazolin-4-yl)-methyl-amino]-2-methyl-pyrrolidine-1-carboxylate (1.00 eq, 200 mg, 0.325 mmol) and [(2R,8S)-2-fluoro-1,2,3,5,6,7-hexahydropyrrolizin-8-yl]methanol (3.00 eq, 155 mg, 0.973 mmol) in DIEA (69.2 eq, 4.0 mL, 22.5 mmol) was stirred at 100° C. for 16 hours. After cooled to ambient temperature, the reaction was quenched with water and extracted with EA (4x50 mL). The combined organic phase was washed with brine, dried over sodium sulfate and concentrated. The residue was purified by preparative-TLC to give tert-butyl-3-[[7-bromo-6-chloro-2-[[(2R,8 S)-2-fluoro-1,2,3,5,6,7-hexahydropyrrolizin-8-yl]methoxy]-8-iodo-quinazolin-4-yl]-methyl-amino]-2-methyl-pyrrolidine-1-carboxylate (90 mg, 35% yield) as a solid. LCMS ESI (+) m/z 738.2 (M+H).

Step C: Preparation of tert-butyl-3-((7-bromo-6-chloro-8-cyano-2-(((2R,7aS)-2-fluorotetrahydro-1H-pyrrolizin-7a(5H)-yl)methoxy)quinazolin-4-yl)(methyl)amino)-2-methylpyrrolidine-1-carboxylate: A solution of tert-butyl-3-[[7-bromo-6-chloro-2-[[(2R,8S)-2-fluoro-1,2,3,5,6,7-hexahydropyrrolizin-8-yl]methoxy]-8-iodo-quinazolin-4-yl]-methyl-amino]-2-methyl-pyrrolidine-1-carboxylate (1.00 eq, 80 mg, 0.108 mmol) and CuCN (5.00 eq, 48 mg, 0.541 mmol) in DMSO (5 mL) was stirred at 60° C. for 16 hours. After cooled to ambient temperature, the mixture was then diluted with water and extracted with EA (3x20 mL). The combined extracts were washed with brine, dried over sodium sulfate, filtered and concentrated, the residue was purified by preparative-TLC to give tert-butyl-3-[[7-bromo-6-chloro-8-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (60 mg, 68% yield) as a solid. LCMS ESI (+) m/z 637.0 (M+H).

Step D: Preparation of tert-butyl-3-((7-(2-((tert-butoxycarbonyl)amino)-3-cyano-7-fluorobenzo[b]thiophen-4-yl)-6-chloro-8-cyano-2-(((2R,7aS)-2-fluorotetrahydro-1H-pyrrolizin-7a(5H)-yl)methoxy)quinazolin-4-yl)(methyl)amino)-2-methylpyrrolidine-1-carboxylate: A solution of tert-butyl-3-[[7-bromo-6-chloro-8-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 20 mg, 0.031 mmol), tert-butyl N-[3-cyano-4-(5,5-dimethyl-1,3,2-dioxaborinan-2-yl)-7-fluoro-benzothiophen-2-yl]carbamate (1.50 eq, 19 mg, 0.0470 mmol), $Cs_2CO_3$ (2.50 eq, 26 mg, 0.078 mmol) and Pd(DPEPhos)$Cl_2$ (0.40 eq, 0.012 mL, 0.013 mmol) in 1,4-dioxane (1 mL) was stirred at 95° C. for 16 hours under $N_2$. After cooled to ambient temperature, the mixture was then diluted with water and extracted with EA (3x20 mL). The combined extracts were washed with brine, dried over sodium sulfate, filtered and concentrated, the residue was purified by preparative-TLC to give tert-butyl-3-[[7-[2-(tert-butoxycarbonylamino)-3-cyano-7-fluoro-benzothiophen-4-yl]-6-chloro-8-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (30 mg, 57% yield) as a yellow solid. LCMS ESI (+) m/z 849.3 (M+H).

Step E: Preparation of 7-(2-amino-3-cyano-7-fluorobenzo[b]thiophen-4-yl)-6-chloro-2-(((2R,7aS)-2-fluorotetrahydro-1H-pyrrolizin-7a(5H)-yl)methoxy)-4-(methyl(2-methylpyrrolidin-3-yl)amino)quinazoline-8-carbonitrile: A solution of tert-butyl-3-[[7-[2-(tert-butoxycarbonylamino)-3-cyano-7-fluoro-benzothiophen-4-yl]-6-chloro-8-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 20 mg, 0.0235 mmol) and TFA (276 eq, 0.50 mL, 6.49 mmol) in DCM (2 mL) was stirred at 15° C. for 5 hours. The solvent was removed under vacuum, the residue was purified by preparative RP-HPLC to give 7-(2-amino-3-cyano-7-fluoro-benzothiophen-4-yl)-6-chloro-2-[[(2R,8S)-2-fluoro-1,2,3,5,6,7-hexahydropyrrolizin-8-yl]methoxy]-4-[methyl-[2-methylpyrrolidin-3-yl]amino]quinazoline-8-carbonitrile (12 mg, 75% yield) as a solid. LCMS ESI (+) m/z 649.1 (M+H).

Step F: Preparation of 4-((1-acryloyl-2-methylpyrrolidin-3-yl)(methyl)amino)-7-(2-amino-3-cyano-7-fluorobenzo[b]thiophen-4-yl)-6-chloro-2-(((2R,7aS)-2-fluorotetrahydro-1H-pyrrolizin-7a(5H)-yl)methoxy)quinazoline-8-carbonitrile: To a solution of 7-(2-amino-3-cyano-7-fluoro-benzothiophen-4-yl)-6-chloro-2-[[(2R,8S)-2-fluoro-1,2,3,5,6,7-hexahydropyrrolizin-8-yl]methoxy]-4-[methyl-[2-methylpyrrolidin-3-yl]amino]quinazoline-8-carbonitrile (1.00 eq, 10 mg, 0.015 mmol) in DCM (1 mL) was added TEA (1.00 eq, 1.6 mg, 0.015 mmol) at −30° C. under $N_2$, then a solution of prop-2-enoyl prop-2-enoate (0.80 eq, 1.6 mg, 0.012 mmol) in DCM (0.5 mL) was added dropwise at −30° C.; after addition, the reaction mixture was stirred at −30° C. for 1 hour. The reaction was quenched by MeOH and water, extracted with DCM (3×5 mL). The combined organic phase was washed with brine, dried over sodium sulfate and concentrated. The residue was purified by preparative-TLC to give 7-(2-amino-3-cyano-7-fluoro-benzothiophen-4-yl)-6-chloro-2-[[(2R,8S)-2-fluoro-1,2,3,5,6,7-hexahydropyrrolizin-8-yl]methoxy]-4-[methyl-[2-methyl-1-prop-2-enoyl-pyrrolidin-3-yl]amino]quinazoline-8-carbonitrile (1.9 mg, 17% yield) as a solid. LCMS ESI (+) m/z 703.3 (M+H). $^1H$ NMR (400 MHz, $CD_3OD$) δ 8.35 (s, 1H), 8.17 (d, 1H), 7.87 (s, 1H), 7.29-7.25 (m, 1H), 7.10-7.06 (t, 1H), 6.68-6.61 (m, 1H), 6.58 (s, 1H), 6.37-6.29 (m, 1H), 5.79 (d, 1H), 5.52 (d, 0.5H), 5.38 (d, 0.5H), 5.06-5.01 (m, 1H), 4.66-4.45 (m, 2H), 3.95-3.53 (m, 7H), 2.92-2.85 (m, 1H), 2.69-2.03 (m, 8H), 1.37-1.29 (m, 3H).

Synthetic Example 49: Synthesis of 4-(4-((1-acryloyl-2-(methoxymethyl)pyrrolidin-3-yl)(methyl)amino)-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (Compound 389)

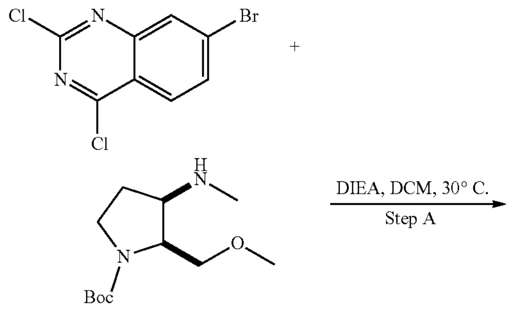

-continued

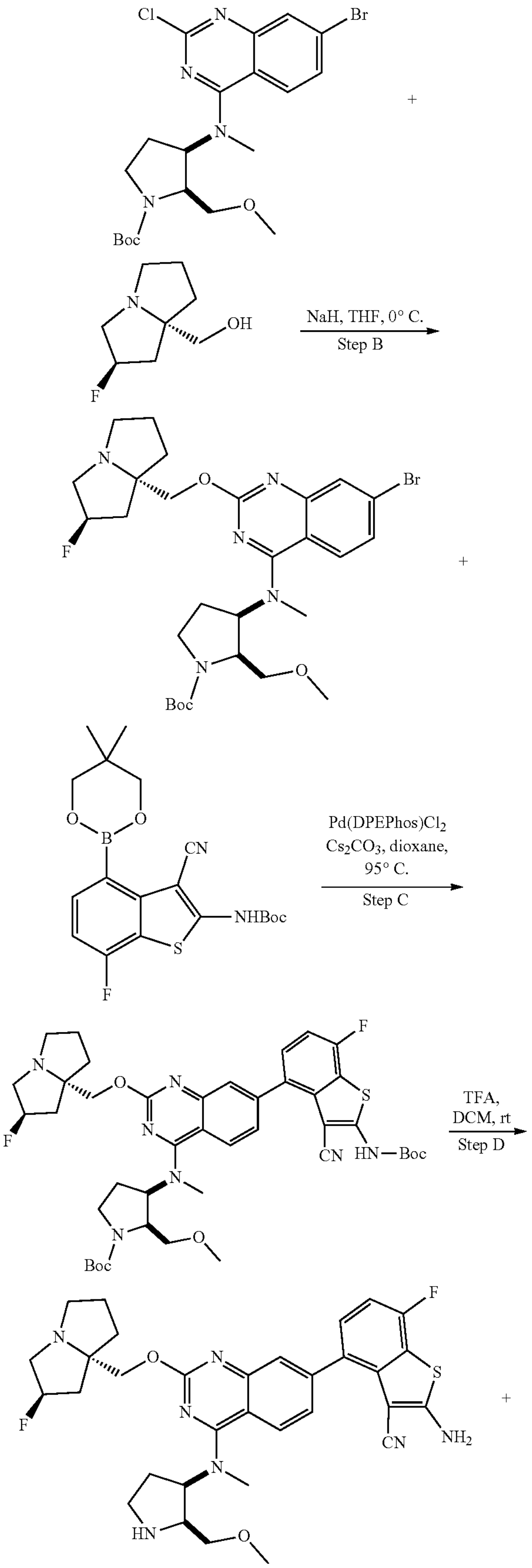

-continued

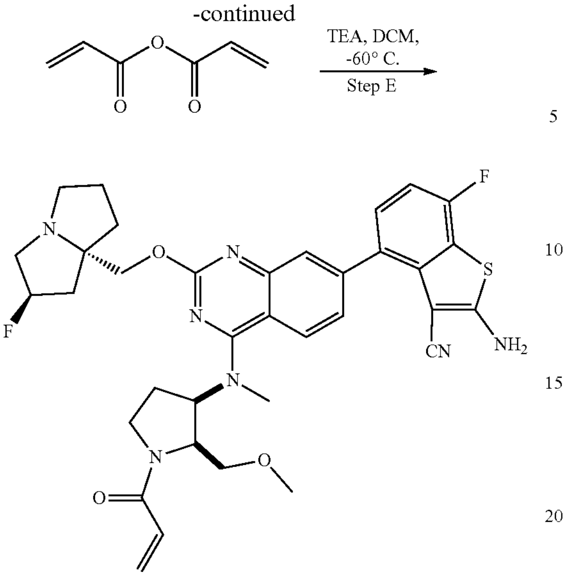

Compound 389

Step A: Preparation of tert-butyl-3-[(7-bromo-2-chloro-quinazolin-4-yl)-methyl-amino]-2-(methoxymethyl)pyrrolidine-1-carboxylate: To a solution of 7-bromo-2,4-dichloro-quinazoline (1.00 eq, 200 mg, 0.720 mmol) in DIEA (3.00 eq, 0.38 mL, 2.16 mmol) was added tert-butyl rac-(2S,3R)-2-(methoxymethyl)-3-(methylamino) pyrrolidine-1-carboxylate (1.00 eq, 176 mg, 0.720 mmol) at ambient temperature. The reaction was stirred at ambient temperature for 3 hours. The reaction was diluted with DCM and the organic layers were washed with water and brine. The organic layers were then separated and dried ($MgSO_4$) before concentration to dryness. The crude was then purified by preparative-TLC (PE:EA=1:1) to afford tert-butyl-3-[(7-bromo-2-chloro-quinazolin-4-yl)-methyl-amino]-2-(methoxymethyl) pyrrolidine-1-carboxylate (120 mg, 0.247 mmol, 34% yield). LCMS ESI (+) m/z 484.9 (M+H).

Step B: Preparation of tert-butyl-3-[[7-bromo-2-[[rac-(2R,8S)-2-fluoro-1,2,3,5,6,7-hexahydropyrrolizin-8-yl] methoxy]quinazolin-4-yl]-methyl-amino]-2-(methoxymethyl)pyrrolidine-1-carboxylate: To a solution of [(2R,8S)-2-fluoro-1,2,3,5,6,7-hexahydropyrrolizin-8-yl]methanol (39 mg, 0.24 mmol) in THF (3.0 mL) was added NaH (10 mg, 0.25 mmol) under Ar. The mixture was stirred at 0° C. for 0.5 hr under Ar, then tert-butyl-3-[(7-bromo-2-chloro-quinazolin-4-yl)-methyl-amino]-2-(methoxymethyl)pyrrolidine-1-carboxylate (80 mg, 0.17 mmol) was added at 0° C. The temperature was allowed to warm to rt and stirred at rt for 2 hours. The reaction was taken up in EtOAc (10 mL) and the organic layers washed with water and brine solution. The organic layers were then separated and dried ($MgSO_4$) before concentration to dryness. The crude was then purified by preparative-TLC (DCM:MeOH=20:1) to afford tert-butyl-3-[[7-bromo-2-[[(2R,8S)-2-fluoro-1,2,3,5,6,7-hexahydropyrrolizin-8-yl]methoxy]quinazolin-4-yl]-methyl-amino]-2-(methoxymethyl)pyrrolidine-1-carboxylate (50 mg, 50% yield) as solid. LCMS ESI (+) m/z 608.2 (M+H).

Step C: Preparation of tert-butyl-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl] methoxy]quinazolin-4-yl]-methyl-amino]-2-(methoxymethyl)pyrrolidine-1-carboxylate: To a solution of tert-butyl-3-[[7-bromo-2-[[(2R,8S)-2-fluoro-1,2,3,5,6,7-hexahydropyrrolizin-8-yl]methoxy]quinazolin-4-yl]-methyl-amino]-2-(methoxymethyl)pyrrolidine-1-carboxylate (1.00 eq, 60 mg, 0.0986 mmol), tert-butyl N-[3-cyano-4-(5,5-dimethyl-1,3,2-dioxaborinan-2-yl)-7-fluoro-benzothiophen-2-yl]carbamate (2.50 eq, 100 mg, 0.246 mmol), and $Cs_2CO_3$ (2.00 eq, 64 mg, 0.197 mmol) in 1,4-dioxane (5 mL) was added $DPEPhosPdCl_2$ (0.200 eq, 14 mg, 0.0197 mmol). After nitrogen protection, the reaction was stirred at 95° C. for 2 hours. The reaction was diluted with EA (10 mL) and the organic layers washed with water and brine. The organic layers were then separated and dried ($MgSO_4$) before concentration to dryness. The crude was then purified by preparative-TLC (PE:EA=1:3) to afford tert-butyl-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]quinazolin-4-yl]-methyl-amino]-2-(methoxymethyl)pyrrolidine-1-carboxylate (40 mg, 49% yield). LCMS ESI (+) m/z 820.1 (M+H).

Step D: Preparation of 2-amino-7-fluoro-4-[4-[methyl-[2-(methoxymethyl)pyrrolidin-3-yl]amino]-2-[[(2R,8S)-2-fluoro-1,2,3,5,6,7-hexahydropyrrolizin-8-yl]methoxy]quinazolin-7-yl]benzothiophene-3-carbonitrile: To a solution of tert-butyl-3-[[7-[2-(tert-butoxycarbonylamino)-3-cyano-7-fluoro-benzothiophen-4-yl]-2-[[(2R,8S)-2-fluoro-1,2,3,5,6,7-hexahydropyrrolizin-8-yl]methoxy]quinazolin-4-yl]-methyl-amino]-2-(methoxymethyl)pyrrolidine-1-carboxylate (1.00 eq, 65 mg, 0.079 mmol) in DCM (3 mL) was added TFA (164 eq, 1.0 mL, 13.0 mmol) at ambient temperature and stirred at ambient temperature for 1 hour. The reaction mixture was concentrated in vacuum to afford 2-amino-7-fluoro-4-[4-[methyl-[2-(methoxymethyl)pyrrolidin-3-yl]amino]-2-[[(2R,8S)-2-fluoro-1,2,3,5,6,7-hexahydropyrrolizin-8-yl]methoxy]quinazolin-7-yl]benzothiophene-3-carbonitrile (100 mg, 100% yield). LCMS ESI (+) m/z 620.1 (M+H).

Step E: Preparation of 4-(4-((1-acryloyl-2-(methoxymethyl)pyrrolidin-3-yl)(methyl)amino)-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile: To a solution of 2-amino-7-fluoro-4-[4-[methyl-[2-(methoxymethyl)pyrrolidin-3-yl]amino]-2-[[(2R,8S)-2-fluoro-1,2,3,5,6,7-hexahydropyrrolizin-8-yl]methoxy]quinazolin-7-yl] benzothiophene-3-carbonitrile (1.00 eq, 100 mg, 0.161 mmol) and TEA (10.0 eq, 0.22 mL, 1.61 mmol) in DCM (5 mL) was added prop-2-enoyl prop-2-enoate (1.00 eq, 20 mg, 0.161 mmol) at −60° C. The reaction was warmed to ambient temperature and stirred at ambient temperature for 1 hour. The reaction was diluted with DCM (10 mL) and the organic layers were washed with water and brine. The organic layers were then separated and dried ($MgSO_4$) before concentration to dryness. The crude was then purified by preparative RP-HPLC to afford 2-amino-7-fluoro-4-[4-[methyl-[2-(methoxymethyl)-1-prop-2-enoyl-pyrrolidin-3-yl]amino]-2-[[(2R,8S)-2-fluoro-1,2,3,5,6,7-hexahydropyrrolizin-8-yl]methoxy]quinazolin-7-yl]benzothiophene-3-carbonitrile (29 mg, 0.0433 mmol, 27% yield). LCMS ESI (+) m/z 674.2 (M+H). $^1H$ NMR (400 MHz, $CD_3OD$): δ 8.46 (d, J=8.74 Hz, 1H), 7.63-7.67 (m, 2H), 7.30-7.33 (m, 1H), 7.06 (t, J=9.00 Hz, 1H), 6.68-6.83 (m, 1H), 6.35-6.39 (m, 1H), 5.81-5.86 (m, 1H), 5.62 (d, J=50.30 Hz, 1H), 5.14-5.26 (m, 1H), 4.95-5.00 (m, 1H), 3.91-4.03 (m, 4H), 3.36-3.84 (m, 8H), 3.27-3.29 (m, 4H), 2.25-2.95 (m, 8H).

Synthetic Example 50: Synthesis of 4-(4-((1-acryloyl-2-methylpyrrolidin-3-yl)(methyl)amino)-6-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (Compound 390)

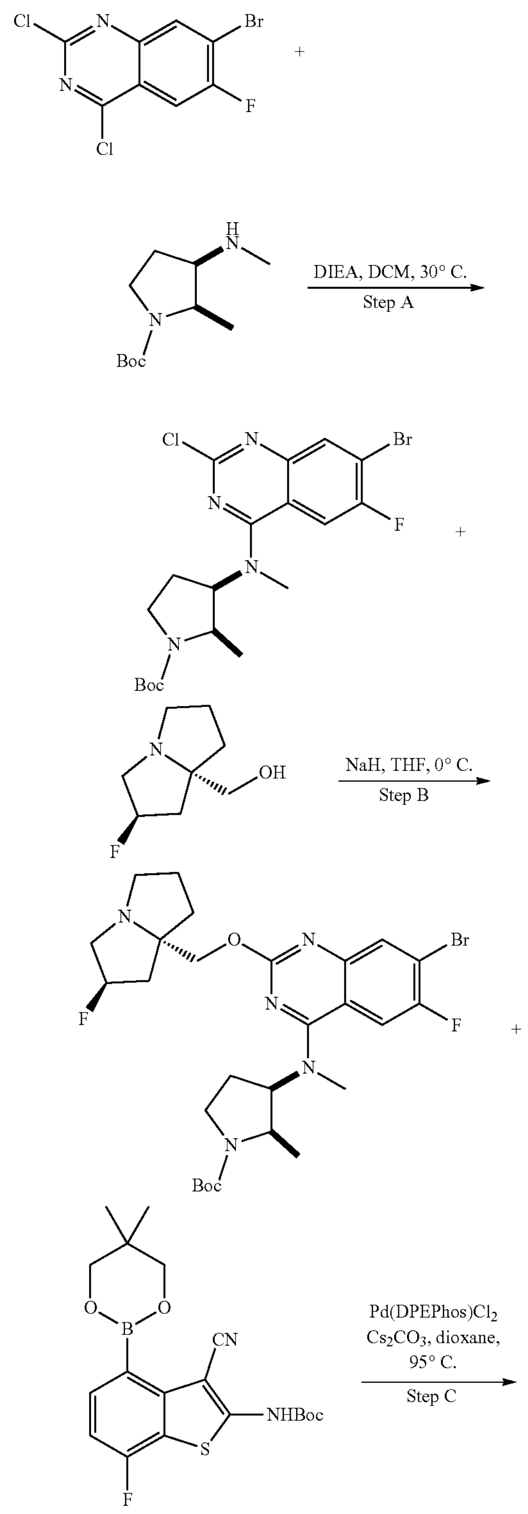

-continued

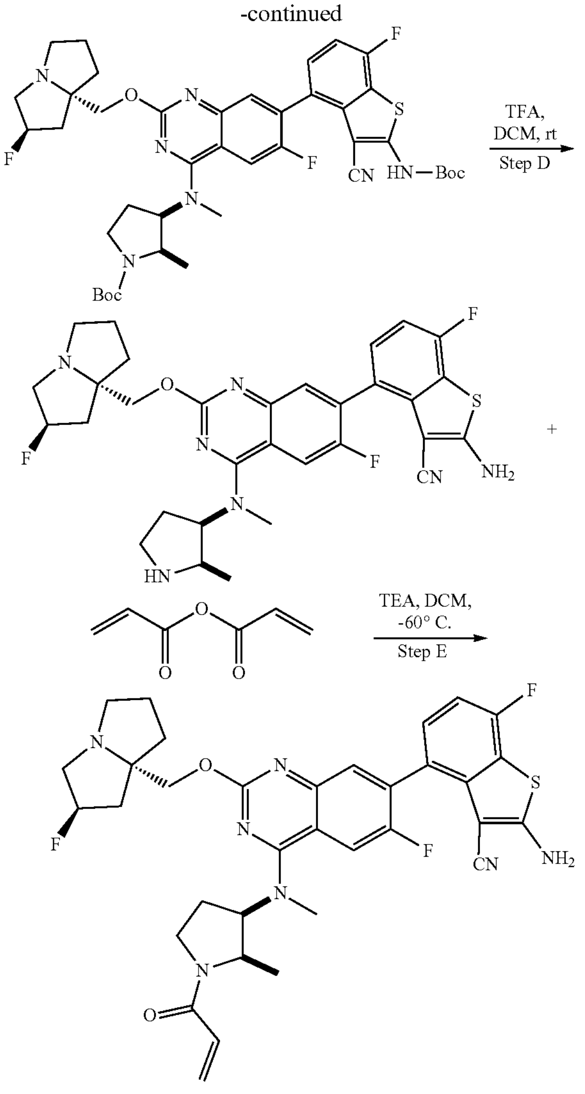

Compound 390

Step A: Preparation of tert-butyl-3-[(7-bromo-2-chloro-6-fluoro-quinazolin-4-yl)-methyl-amino]-2-methyl-pyrrolidine-1-carboxylate: To a solution of 7-bromo-2,4-dichloro-6-fluoro-quinazoline (1.00 eq, 150 mg, 0.51 mmol) and DIEA (3.00 eq, 0.26 mL, 1.52 mmol) in DCM (5 mL) was added tert-butyl-2-methyl-3-(methylamino)pyrrolidine-1-carboxylate (1.50 eq, 163 mg, 0.76 mmol) at 0° C. After addition, the mixture was warmed to ambient temperature and stirred for 3 hours. The reaction mixture was diluted with DCM (10 mL) and the organic layer was separated and washed with water and brine, and dried ($MgSO_4$) before concentration to dryness. The crude was then purified by preparative-TLC (30% EtOAc in hexanes) to afford tert-butyl-3-[(7-bromo-2-chloro-6-fluoro-quinazolin-4-yl)-methyl-amino]-2-methyl-pyrrolidine-1-carboxylate (80 mg, 33% yield). LCMS ESI (+) m/z 475.1 (M+H).

Step B: Preparation of tert-butyl-3-[[7-bromo-6-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of (2R,8S)-2-fluoro-1,2,3,5,6,7-hexahydropyrrolizin-8-yl]methanol (1.50 eq, 30 mg, 0.190 mmol) in THF (3.0 mL) was added NaH (1.50 eq, 7.6 mg, 0.19 mmol) under Ar at 0° C. The mixture was stirred at 0° C. for 0.5 hr under Ar, then tert-butyl-3-[(7-bromo-2-chloro-6-fluoro-quinazolin-4-yl)-methyl-amino]-2-methyl-pyrrolidine-1-carboxylate (1.00 eq, 60 mg, 0.127 mmol was added at 0° C. The temperature was allowed to warm to rt and stirred at rt for 2 hours. The reaction was taken up in EtOAc (10 mL) and the organic layers washed with water and brine solution. The organic layers were then separated and dried ($MgSO_4$) before concentration to dryness. The crude was then purified by preparative-TLC (DCM:MeOH=20:1) to afford tert-butyl-3-[[7-bromo-6-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (45 mg, 60% yield) as solid. LCMS ESI (+) m/z 596.2 (M+H).

Step C: Preparation of tert-butyl-3-[[7-[2-(tert-butoxycarbonylamino)-3-cyano-7-fluoro-benzothiophen-4-yl]-6-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of tert-butyl-3-[[7-bromo-6-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 60 mg, 0.10 mmol), tert-butyl N-[3-cyano-4-(5,5-dimethyl-1,3,2-dioxaborinan-2-yl)-7-fluoro-benzothiophen-2-yl]carbamate (2.50 eq, 102 mg, 0.25 mmol), and $Cs_2CO_3$ (2.00 eq, 66 mg, 0.20 mmol) in 1,4-dioxane (5 mL) was added DPEPhosPd$Cl_2$ (0.200 eq, 14 mg, 0.020 mmol). After nitrogen protection, the reaction was stirred at 95° C. for 2 hours. After cooled to ambient temperature, the reaction was diluted with EA (10 mL) and the organic layers washed with water and brine. The organic layers were then separated and dried ($MgSO_4$) before concentration to dryness. The crude was then purified by preparative-TLC (PE:EA=1:3) to afford tert-butyl-3-[[7-[2-(tert-butoxycarbonylamino)-3-cyano-7-fluoro-benzothiophen-4-yl]-6-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (50 mg, 62% yield). LCMS ESI (+) m/z 808.0 (M+H).

Step D: Preparation of 2-amino-7-fluoro-4-[6-fluoro-4-[methyl-[2-methylpyrrolidin-3-yl]amino]-2-[[(2R,8S)-2-fluoro-1,2,3,5,6,7-hexahydropyrrolizin-8-yl]methoxy]quinazolin-7-yl]benzothiophene-3-carbonitrile: To a solution of tert-butyl-3-[[7-[2-(tert-butoxycarbonylamino)-3-cyano-7-fluoro-benzothiophen-4-yl]-6-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 55 mg, 0.0681 mmol) in DCM (3 mL) was added TFA (191 eq, 1.0 mL, 13.0 mmol) at ambient temperature and stirred at ambient temperature for 2 hours. The reaction mixture was concentrated in vacuum to afford-amino-7-fluoro-4-[6-fluoro-4-[methyl-[2-methylpyrrolidin-3-yl]amino]-2-[[(2R,8S)-2-fluoro-1,2,3,5,6,7-hexahydropyrrolizin-8-yl]methoxy]quinazolin-7-yl]benzothiophene-3-carbonitrile (100 mg, 100% yield). LCMS ESI (+) m/z 608.0 (M+H).

Step E: Preparation of 4-(4-((1-acryloyl-2-methylpyrrolidin-3-yl)(methyl)amino)-6-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile: To a solution of 2-amino-7-fluoro-4-[6-fluoro-4-[methyl-[2-methylpyrrolidin-3-yl]amino]-2-[[(2R,8S)-2-fluoro-1,2,3,5,6,7-hexahydropyrrolizin-8-yl]methoxy]quinazolin-7-yl]benzothiophene-3-carbonitrile (1.00 eq, 100 mg, 0.17 mmol) and TEA (10.0 eq, 0.23 mL, 1.65 mmol) in DCM (5 mL) was added prop-2-enoyl prop-2-enoate (1.00 eq, 21 mg, 0.17 mmol) at −60° C. The reaction was warmed to ambient temperature and stirred at ambient temperature for 1 hour. The reaction was diluted with DCM (10 mL) and the organic layers were washed with water and brine. The organic layers were then separated and dried ($MgSO_4$) before concentration to dryness. The crude was then purified by preparative RP-HPLC to afford 4-(4-((1-acryloyl-2-methylpyrrolidin-3-yl)(methyl)amino)-6-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (31 mg, 28% yield). LCMS ESI (+) m/z 662.2 (M+H). $^1$H NMR (400 MHz, $CD_3OD$): δ 8.09 (t, J=9.54 Hz, 1H), 7.66-7.68 (m, 1H), 7.28-7.32 (m, 1H), 7.06 (t, J=9.04 Hz, 1H), 6.64-6.73 (m, 1H), 6.32-6.40 (m, 1H), 5.80-5.83 (m, 1H), 5.61 (d, J=51.60 Hz, 1H), 4.98-5.09 (m, 1H), 4.71-4.78 (m, 2H), 3.90-4.00 (m, 4H), 3.61-3.75 (m, 4H), 3.47-3.54 (m, 1H), 2.21-2.99 (m, 8H), 1.10-1.19 (m, 3H).

Synthetic Example 51: Synthesis of 4-(4-((1-acryloyl-2-methylpyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile (Compound 395)

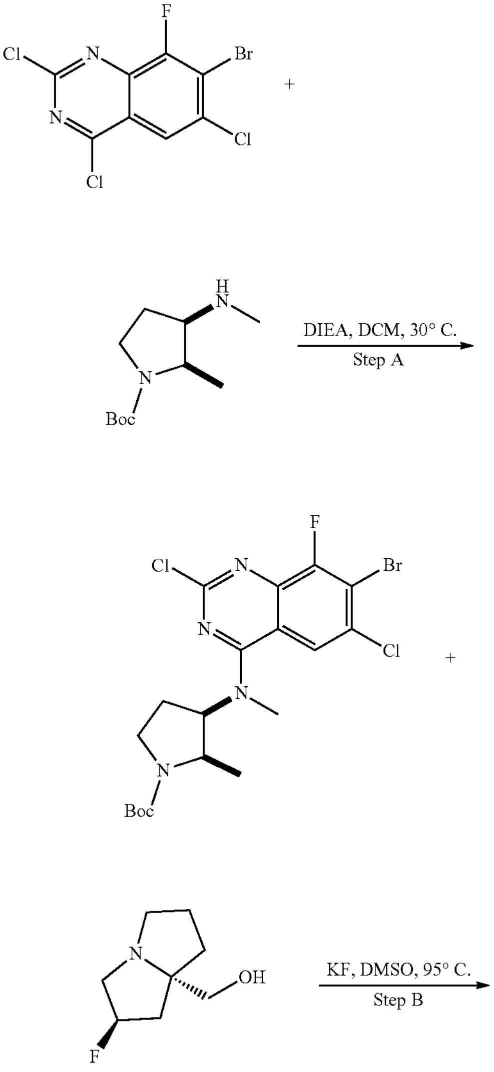

-continued

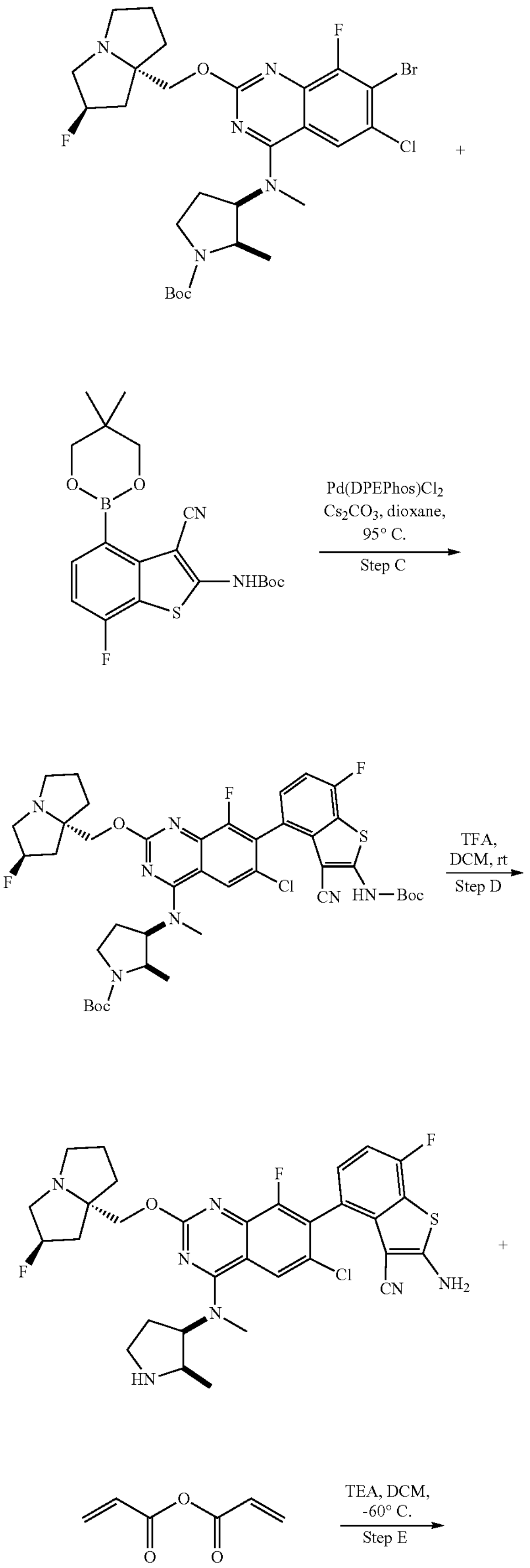

-continued

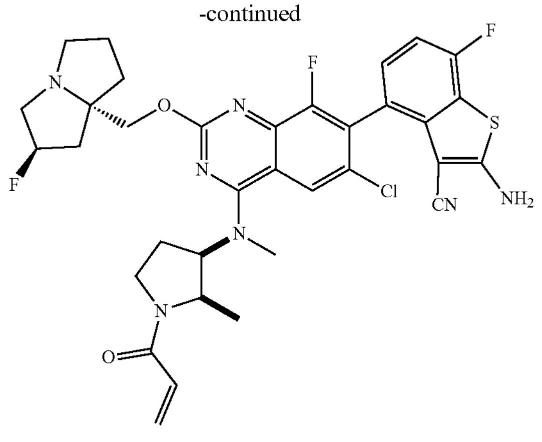

Compound 395

Step A: Preparation of tert-butyl-3-[(7-bromo-2,6-dichloro-8-fluoro-quinazolin-4-yl)-methyl-amino]-2-methyl-pyrrolidine-1-carboxylate: To a solution of 7-bromo-2,4,6-trichloro-8-fluoro-quinazoline (1.00 eq, 150 mg, 0.45 mmol) and N,N-diisopropylethylamine (3.00 eq, 0.24 mL, 1.36 mmol) in DCM (10 mL) was added tert-butyl-2-methyl-3-(methylamino)pyrrolidine-1-carboxylate (1.30 eq, 126 mg, 0.59 mmol) at 0° C. After addition, the mixture was warmed to ambient temperature and stirred for 3 hours. The reaction was diluted with DCM (10 mL) and the organic layer was separated and washed with water and brine, and dried ($MgSO_4$) before concentration to dryness. The crude was then purified by preparative-TLC (30% EtOAc in hexanes) to afford tert-butyl-3-[(7-bromo-2,6-dichloro-8-fluoro-quinazolin-4-yl)-methyl-amino]-2-methyl-pyrrolidine-1-carboxylate (130 mg, 56% yield). LCMS ESI (+) m/z 507.0 (M+H).

Step B: Preparation of tert-butyl-3-[[7-bromo-6-chloro-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of tert-butyl-3-[(7-bromo-2,6-dichloro-8-fluoro-quinazolin-4-yl)-methyl-amino]-2-methyl-pyrrolidine-1-carboxylate (1.00 eq, 100 mg, 0.20 mmol) and [(2R,8S)-2-fluoro-1,2,3,5,6,7-hexahydropyrrolizin-8-yl]methanol (3.00 eq, 94 mg, 0.59 mmol) in DMSO (1 mL) was added KF (8.00 eq, 91 mg, 1.57 mmol) at ambient temperature. The reaction was stirred at 95° C. for 16 hours. After cooled to ambient temperature, the reaction was taken up in EtOAc (10 mL) and the organic layers washed with water and brine solution. The organic layers were then separated and dried ($MgSO_4$) before concentration to dryness. The crude was then purified by preparative-TLC (DCM:MeOH=20:1) to afford tert-butyl-3-[[7-bromo-6-chloro-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (75 mg, 60% yield) as solid. LCMS ESI (+) m/z 630.2 (M+H).

Step C: Preparation of tert-butyl-3-[[7-[2-(tert-butoxycarbonylamino)-3-cyano-7-fluoro-benzothiophen-4-yl]-6-chloro-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate: To a solution of tert-butyl-3-[[7-bromo-6-chloro-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 75 mg, 0.12 mmol), tert-butyl N-[3-cyano-4-(5,5-dimethyl-1,3,2-dioxaborinan-2-yl)-7-fluoro-benzothiophen-2-yl]carbamate (2.50 eq, 120 mg, 0.30 mmol), and $Cs_2CO_3$ (2.00 eq, 77 mg, 0.24 mmol) in 1,4-dioxane (5 mL) was added $DPEPhosPdCl_2$ (0.20 eq, 17 mg, 0.024 mmol). After nitrogen protection, the reaction was stirred at 95° C. for 4 hours. After cooled to ambient temperature, the reaction was diluted with EA (10 mL) and the organic layers washed with water and brine. The organic layers were then separated and dried ($MgSO_4$) before concentration to dryness. The crude was then purified by preparative-TLC (PE:EA=1:3) to afford tert-butyl-3-[[7-[2-(tert-butoxycarbonylamino)-3-cyano-7-fluoro-benzothiophen-4-yl]-6-chloro-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (50 mg, 50%) as solid. LCMS ESI (+) m/z 842.3 (M+H).

Step D: Preparation of 2-amino-4-[6-chloro-8-fluoro-4-[methyl-[2-methylpyrrolidin-3-yl]amino]-2-[[(2R,8S)-2-fluoro-1,2,3,5,6,7-hexahydropyrrolizin-8-yl]methoxy]quinazolin-7-yl]-7-fluoro-benzothiophene-3-carbonitrile: To a solution of tert-butyl-3-[[7-[2-(tert-butoxycarbonylamino)-3-cyano-7-fluoro-benzothiophen-4-yl]-6-chloro-8-fluoro-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (1.00 eq, 65 mg, 0.077 mmol) in DCM (3 mL) was added TFA (168 eq, 1.0 mL, 13.0 mmol) at ambient temperature and stirred at ambient temperature for 2 hours. The reaction mixture was concentrated in vacuum to afford 2-amino-4-[6-chloro-8-fluoro-4-[methyl-[2-methylpyrrolidin-3-yl]amino]-2-[[(2R,8S)-2-fluoro-1,2,3,5,6,7-hexahydropyrrolizin-8-yl]methoxy]quinazolin-7-yl]-7-fluoro-benzothiophene-3-carbonitrile (14 mg, 28% yield). LCMS ESI (+) m/z 642.9 (M+H).

Step E: Preparation of 4-(4-((1-acryloyl-2-methylpyrrolidin-3-yl)(methyl)amino)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile: To a solution of 2-amino-4-[6-chloro-8-fluoro-4-[methyl-[2-methylpyrrolidin-3-yl]amino]-2-[[(2R,8S)-2-fluoro-1,2,3,5,6,7-hexahydropyrrolizin-8-yl]methoxy]quinazolin-7-yl]-7-fluoro-benzothiophene-3-carbonitrile (1.00 eq, 50 mg, 0.078 mmol) and TEA (10.0 eq, 0.11 mL, 0.78 mmol) in DCM (5 mL) was added prop-2-enoyl prop-2-enoate (1.00 eq, 9.8 mg, 0.078 mmol) at −60° C. The reaction was warmed to ambient temperature and stirred at ambient temperature for 1 hour. The reaction was diluted with DCM (10 mL) and the organic layers were washed with water and brine. The organic layers were then separated and dried ($MgSO_4$) before concentration to dryness. The crude was then purified by preparative RP-HPLC to afford 2-amino-4-[6-chloro-8-fluoro-4-[methyl-[2-methyl-1-prop-2-enoyl-pyrrolidin-3-yl]amino]-2-[[(2R,8S)-2-fluoro-1,2,3,5,6,7-hexahydropyrrolizin-8-yl]methoxy]quinazolin-7-yl]-7-fluoro-benzothiophene-3-carbonitrile (25 mg, 0.036 mmol, 46% yield). LCMS ESI (+) m/z 696.0 (M+H). $^1H$ NMR (400 MHz, $CD_3OD$): δ 8.19 (s, 1H), 7.23-7.27 (m, 1H), 7.08 (t, J=8.8 Hz, 1H), 6.64-6.71 (m, 1H), 6.31-6.40 (m, 1H), 5.81 (d, J=12.0 Hz, 1H), 5.58 (d, J=52.4 Hz, 1H), 4.98-5.09 (m, 1H), 4.60-4.79 (m, 3H), 3.46-4.04 (m, 9H), 2.16-2.71 (m, 8H), 1.16-1.19 (m, 3H).

Synthetic Example 52: Synthesis of 4-(4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410), 4-((S)-4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410a) and 4-((R)-4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410b)

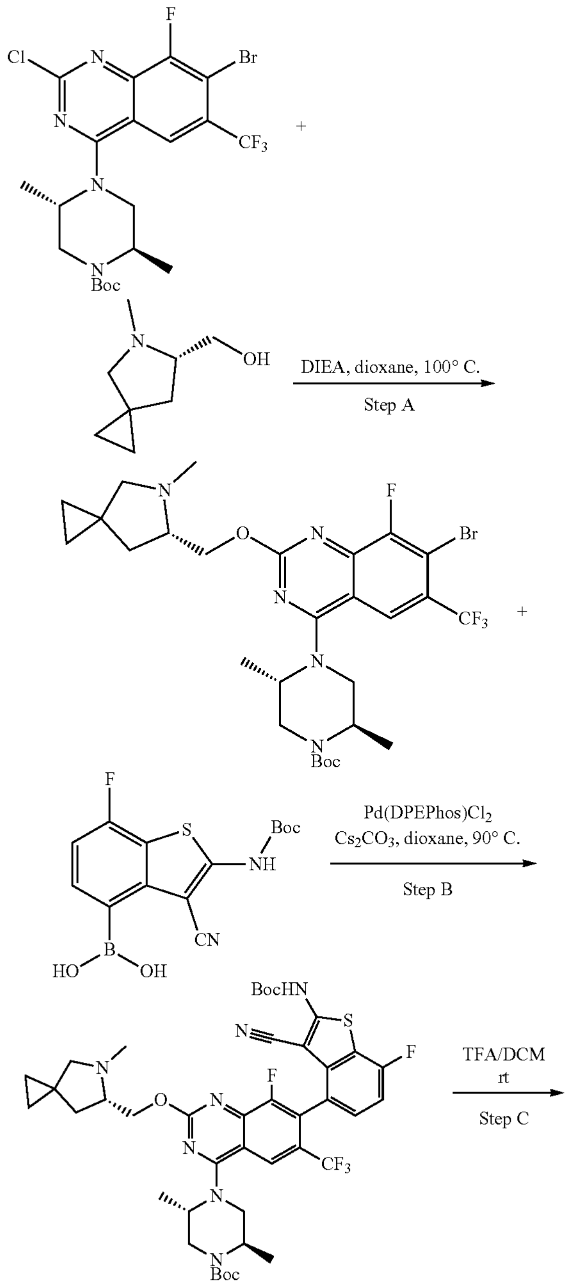

-continued

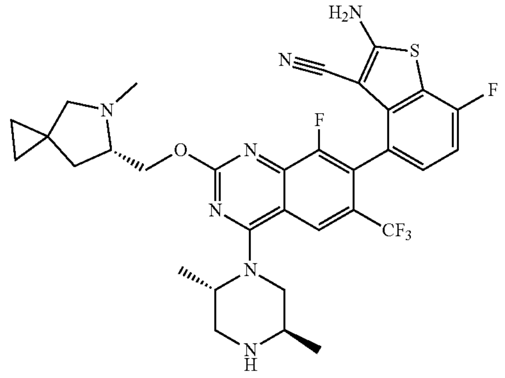

+

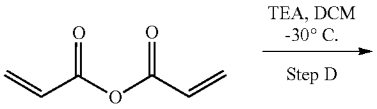

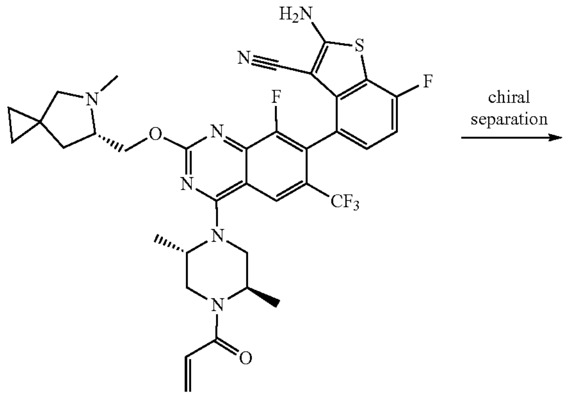

Compound 410

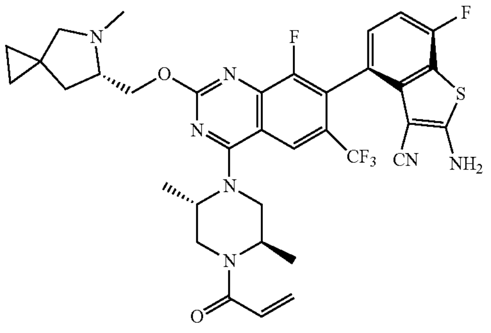

+

Compound 410a

-continued

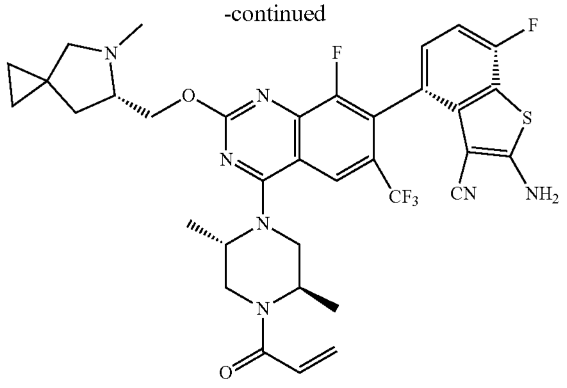

Compound 410b

Step A: Preparation of tert-butyl (2R,5S)-4-[7-bromo-8-fluoro-2-[[(6S)-5-methyl-5-azaspiro [2.4]heptan-6-yl] methoxy]-6-(trifluoromethyl) quinazolin-4-yl]-2,5-dimethyl-piperazine-1-carboxylate: A solution of tert-butyl (2R,5S)-4-[7-bromo-2-chloro-8-fluoro-6-(trifluoromethyl) quinazolin-4-yl]-2,5-dimethyl-piperazine-1-carboxylate (1.00 eq, 500 mg, 0.923 mmol), [(6S)-5-methyl-5-azaspiro [2.4]heptan-6-yl]methanol (2.00 eq, 261 mg, 1.85 mmol) and DIPEA (42.6 eq, 7.0 mL, 39.3 mmol) was stirred at 100° C. for 16 hours. The reaction was quenched by water and extracted by EA (50 mL×4). The organic phase was washed with brine, dried over sodium sulfate and concentrated. The residue was purified by column chromatography on silica gel eluted with (PE/EA 20:1, 10:1, 5:1, 1:1, EA) to afford tert-butyl (2R,5S)-4-[7-bromo-8-fluoro-2-[[(6S)-5-methyl-5-azaspiro[2.4]heptan-6-yl]methoxy]-6-(trifluoromethyl) quinazolin-4-yl]-2,5-dimethyl-piperazine-1-carboxylate (253 mg, 33% yield) as a solid. LCMS ESI (+) m/z 646.2 (M+H).

Step B: Preparation of tert-butyl (2R,5S)-4-[7-[2-(tert-butoxycarbonylamino)-3-cyano-7-fluoro-benzothiophen-4-yl]-8-fluoro-2-[[(6S)-5-methyl-5-azaspiro[2.4]heptan-6-yl] methoxy]-6-(trifluoromethyl) quinazolin-4-yl]-2,5-dimethyl-piperazine-1-carboxylate: A mixture of tert-butyl (2R,5S)-4-[7-bromo-8-fluoro-2-[[(6S)-5-methyl-5-azaspiro [2.4]heptan-6-yl]methoxy]-6-(trifluoromethyl)quinazolin-4-yl]-2,5-dimethyl-piperazine-1-carboxylate (1.00 eq, 253 mg, 0.39 mmol), tert-butyl N-[3-cyano-4-(5,5-dimethyl-1,3,2-dioxaborinan-2-yl)-7-fluoro-benzothiophen-2-yl]carbamate (1.50 eq, 237 mg, 0.59 mmol), $Cs_2CO_3$ (3.00 eq, 383 mg, 1.17 mmol) and $Pd(DPEPhos)Cl_2$ (0.40 eq, 112 mg, 0.16 mmol) in 1,4-dioxane (1 mL) was stirred at 90° C. for 16 hours under $N_2$. After cooled to ambient temperature, the reaction was quenched with water and extracted with EA (20 mL×4). The combined organic phase was washed with brine, dried over sodium sulfate and concentrated. The residue was purified by preparative RP-HPLC to give tert-butyl (2R,5S)-4-[7-[2-(tert-butoxycarbonylamino)-3-cyano-7-fluoro-benzothiophen-4-yl]-8-fluoro-2-[[(6S)-5-methyl-5-azaspiro [2.4]heptan-6-yl]methoxy]-6-(trifluoromethyl) quinazolin-4-yl]-2,5-dimethyl-piperazine-1-carboxylate (50 mg, 14% yield) as a solid. LCMS ESI (+) m/z 858.3 (M+H).

Step C: Preparation of 2-amino-4-[4-[(2S,5R)-2,5-dimethylpiperazin-1-yl]-8-fluoro-2-[[(6S)-5-methyl-5-azaspiro [2.4]heptan-6-yl]methoxy]-6-(trifluoromethyl)quinazolin-7-yl]-7-fluoro-benzothiophene-3-carbonitrile: To a solution of tert-butyl (2R,5S)-4-[7-[2-(tert-butoxycarbonylamino)-3-cyano-7-fluoro-benzothiophen-4-yl]-8-fluoro-2-[[(6S)-5-methyl-5-azaspiro[2.4]heptan-6-yl]methoxy]-6-(trifluoromethyl)quinazolin-4-yl]-2,5-dimethyl-piperazine-1-carboxylate (1.00 eq, 50 mg, 0.058 mmol) in DCM (4 mL) was added TFA (1.0 mL, 1.00 mmol) at ambient temperature and stirred at ambient temperature for 2 hours. The solvent was removed in vacuum. The residue was purified by preparative RP-HPLC to afford 2-amino-4-[4-[(2S,5R)-2,5-dimethylpiperazin-1-yl]-8-fluoro-2-[[(6S)-5-methyl-5-azaspiro [2.4]heptan-6-yl]methoxy]-6-(trifluoromethyl) quinazolin-7-yl]-7-fluoro-benzothiophene-3-carbonitrile (28 mg, 69% yield) as a solid. LCMS ESI (+) m/z 658.1 (M+H).

Step D: Preparation of 4-(4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410), 4-((S)-4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410a) and 4-((R)-4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410b): To a solution of 2-amino-4-[4-[(2S,5R)-2,5-dimethylpiperazin-1-yl]-8-fluoro-2-[[(6S)-5-methyl-5-azaspiro[2.4]heptan-6-yl]methoxy]-6-(trifluoromethyl)quinazolin-7-yl]-7-fluoro-benzothiophene-3-carbonitrile (1.00 eq, 27 mg, 0.0407 mmol) in DCM (2 mL) was added TEA (3.00 eq, 12 mg, 0.122 mmol) at −30° C. under $N_2$, then a solution of prop-2-enoyl prop-2-enoate (0.80 eq, 4.1 mg, 0.033 mmol) in DCM (1 mL) was added dropwise at−30° C. and stirred at −30° C. for 1 hour. The reaction was quenched with MeOH and water, extracted with DCM (10 mL×3). The combined organic phase was washed with brine, dried over sodium sulfate and concentrated. The residue was purified by preparative-TLC to give 4-(4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (11 mg, 36% yield) as a solid. LCMS ESI (+) m/z 712.2 (M+H). $^1$H NMR (400 MHz, $CD_3OD$) δ 8.13 (d, 1H), 7.24-7.21 (m, 1H), 7.01 (t, 1H), 6.85-6.75 (m, 1H), 6.31-6.25 (m, 1H), 5.83-5.78 (m, 1H), 4.58 (d, 3H), 4.27 (d, 1H), 4.01-3.88 (m, 2H), 2.82 (d, 1H), 2.71 (d, 1H), 2.60 (d, 3H), 2.21-2.16 (m, 1H), 1.79-1.74 (m, 1H), 1.52-1.46 (m, 3H), 1.32-1.28 (m, 6H), 0.67-0.56 (m, 4H).

The single diastereomers of 4-(4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410) (463.7 mg) were separated with chiral chromatography condition [(R, R)-WHELK-01-Kromasil 3 cm×25 cm, 5 μm, $CO_2$:[MeOH:DCM=2:1 (0.2% 2 mM NH3-MeOH)]=55:45, 80 mL/min]. The first compound off the column was identified as one atropisomer, 4-((S)-4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410a) (198.4 mg, 99.61% de); LCMS ESI (+) m/z 712.4 (M+H). $^1$HNMR (400 MHz, $CD_3OD$) δ 8.16 (s, 1H), 7.22-7.27 (m, 1H), 7.01-7.07 (m, 1H), 6.72-6.95 (m, 1H), 6.27-6.34 (m, 1H), 5.81-5.84 (m, 1H), 4.90 (m, 1H), 4.60 (d, 3H), 4.27-4.42 (m, 1H), 3.88-3.97 (m, 2H), 2.83 (d, 1H), 2.74 (d, 1H), 2.62 (s, 3H), 2.17-2.24 (m, 1H), 1.75-1.82 (m, 1H), 1.50-1.54 (m, 3H), 1.32-1.42 (m, 5H), 0.68-0.70 (m, 4H). The second compound off the column was identified as the other atropisomer, 4-((R)-4-((2S,5R)-4-acryloyl-2,5-dimethylpiperazin-1-yl)-8-fluoro-2-(((S)-5-methyl-5-azaspiro[2.4]heptan-6-yl)methoxy)-6-(trifluoromethyl)quinazolin-7-yl)-2-amino-7-fluorobenzo[b]thiophene-3-carbonitrile (Compound 410b) (167.2 mg, 98.5% de). LCMS ESI (+) m/z 712.4 (M+H). $^1$HNMR (400 MHz, $CD_3OD$) δ 8.15 (s, 1H), 7.23-7.27 (m, 1H), 7.00-7.06 (m, 1H), 6.77-6.93 (m, 1H), 6.27-6.34 (m, 1H), 5.81-5.84 (m, 1H), 4.97 (m, 1H), 4.22-4.63 (m, 4H), (m, 1H), 3.90-4.12 (m, 2H), 3.10 (m, 1H), 2.77 (d, 1H), 2.66 (d, 1H), 2.55 (s, 3H), 2.14-2.21 (m, 1H), 1.73-1.80 (m, 1H), 1.49 (m, 3H), 1.25-1.34 (m, 5H), 0.55-0.69 (m, 4H).

Synthetic Example 53: Synthesis of 4-((1-acryloyl-2-methylpyrrolidin-3-yl)(ethyl)amino)-7-(2-amino-3-cyano-7-fluorobenzo[b]thiophen-4-yl)-2-(((2R,7aS)-2-fluorotetrahydro-1H-pyrrolizin-7a(5H)-yl)methoxy)quinazoline-8-carbonitrile (Compound 415)

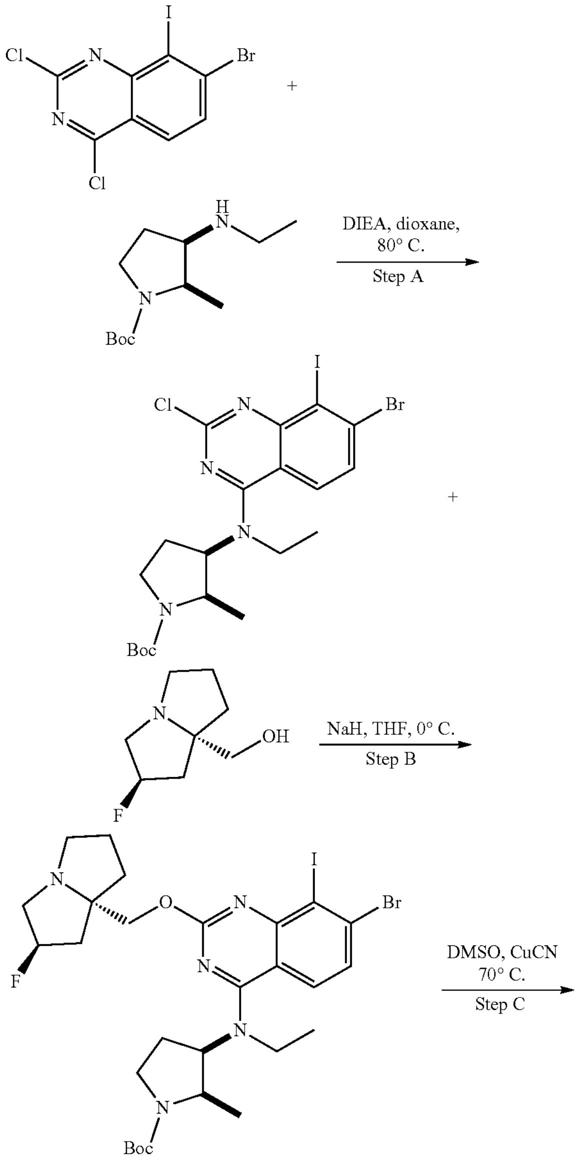

-continued

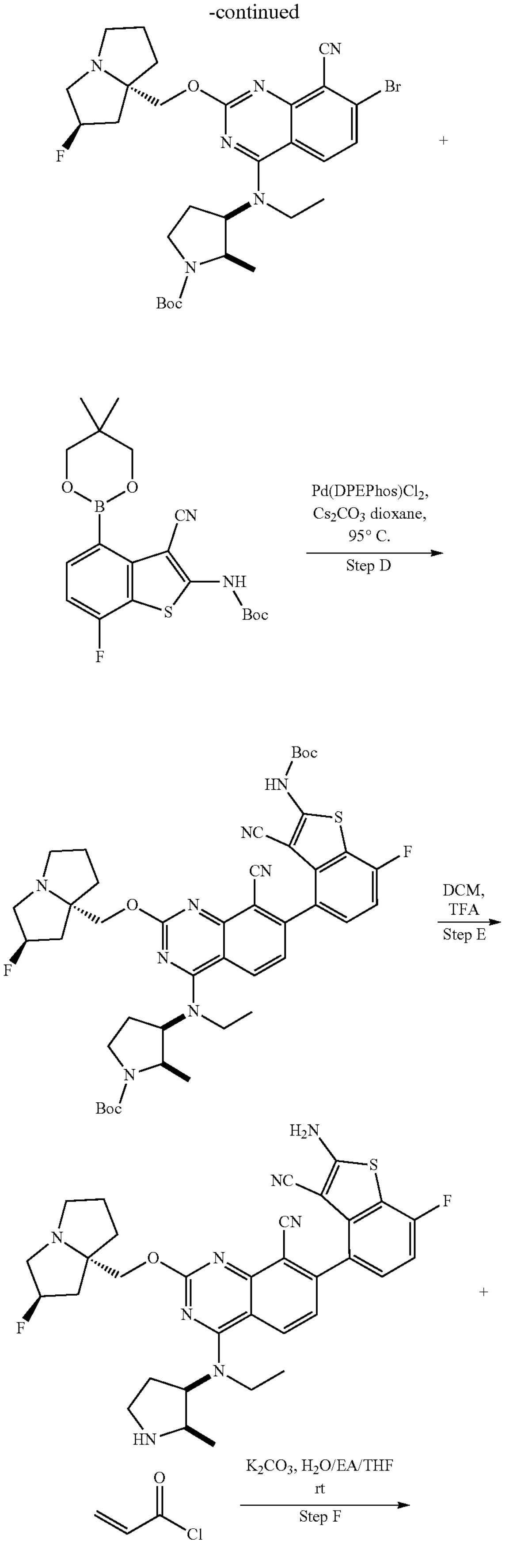

-continued

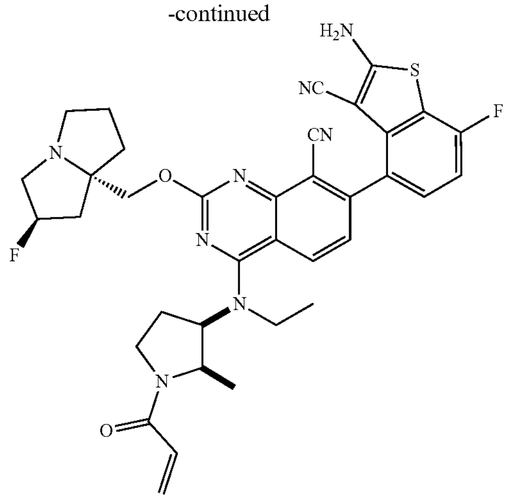

Compound 415

Step A: Preparation of tert-butyl 3-[(7-bromo-2-chloro-8-iodo-quinazolin-4-yl)-ethyl-amino]-2-methyl-pyrrolidine-1-carboxylate: To a solution of 7-bromo-2,4-dichloro-8-iodo-quinazoline (1.00 eq, 200 mg, 0.495 mmol) in 1,4-dioxane (3 mL) was added DIEA (3.00 eq, 0.26 mL, 1.49 mmol) and tert-butyl-3-(ethylamino)-2-methyl-pyrrolidine-1-carboxylate (1.20 eq, 136 mg, 0.594 mmol) at ambient temperature. The residue was purified by column chromatography on silica gel eluting with 25% ethyl acetate in petroleum ether to afford tert-butyl-3-[(7-bromo-2,6-dichloro-8-iodo-quinazolin-4-yl)-methyl-amino]-2-methyl-pyrrolidine-1-carboxylate (118 mg, 40% yield) as a solid. LCMS ESI (+) m/z 594.7 (M+H).

Step B: Preparation of tert-butyl-3-[[7-bromo-2-[[(2R,8S)-2-fluoro-1,2,3,5,6,7-hexahydropyrrolizin-8-yl]methoxy]-8-iodo-quinazolin-4-yl]-ethyl-amino]-2-methyl-pyrrolidine-1-carboxylate: To a solution of [(2R,8S)-2-fluoro-1,2,3,5,6,7-hexahydropyrrolizin-8-yl]methanol (1.50 eq, 47 mg, 0.297 mmol) in THF (5.0 mL) was added NaH (1.50 eq, 0.012 mL, 0.297 mmol) at 0° C. The mixture was sealed and the stirred for 30 minutes at 0° C. Then tert-butyl-3-[(7-bromo-2-chloro-8-iodo-quinazolin-4-yl)-ethyl-amino]-2-methyl-pyrrolidine-1-carboxylate (1.00 eq, 118 mg, 0.198 mmol) was added. The mixture was warmed to room temperature and stirred for 2 hours at room temperature. Ice water was added and the mixture was extracted with EtOAc and the combined organic layers were concentrated to dry under vacuum. The residue was purified by preparative-TLC (PE: EtOAc=1:1) to give tert-butyl-3-[[7-bromo-2-[[(2R,8S)-2-fluoro-1,2,3,5,6,7-hexahydropyrrolizin-8-yl]methoxy]-8-iodo-quinazolin-4-yl]-ethyl-amino]-2-methyl-pyrrolidine-1-carboxylate (82 mg, 58% yield) as solid. LCMS ESI (+) m/z 717.9 (M+H).

Step C: Preparation of tert-butyl-3-((7-bromo-6-chloro-8-cyano-2-(((2R,7aS)-2-fluorotetrahydro-1H-pyrrolizin-7a(5H)-yl)methoxy)quinazolin-4-yl)(methyl)amino)-2-methylpyrrolidine-1-carboxylate: To a solution of tert-butyl-3-[[7-bromo-2-[[(2R,8S)-2-fluoro-1,2,3,5,6,7-hexahydropyrrolizin-8-yl]methoxy]-8-iodo-quinazolin-4-yl]-methyl-amino]-2-methyl-pyrrolidine-1-carboxylate (1.00 eq, 72 mg, 0.10 mmol) in DMSO (1 mL) was added CuCN (1.10 eq, 10 mg, 0.11 mmol). The resulting reaction mixture was stirred for 24 hrs at 70° C. After cooled to ambient temperature, water was added and the mixture was extracted with EtOAc. The combined organic layers were washed with brine, dried (sodium sulfate), filtered and concentrated under reduced pressure. The residue was purified by preparative-TLC (PE/EtOAc=1/1) to give tert-butyl-3-[[7-bromo-8-cyano-2-[[(2R,8S)-2-fluoro-1,2,3,5,6,7-hexahydropyrrolizin-8-yl]methoxy]quinazolin-4-yl]-methyl-amino]-2-methyl-pyrrolidine-1-carboxylate (54 mg, 88% yield). LCMS ESI (+) m/z 617.0 (M+H).

Step D: Preparation of tert-butyl-3-[[7-[2-(tert-butoxycarbonylamino)-3-cyano-7-fluoro-benzothiophen-4-yl]-8-cyano-2-[[(2R,8S)-2-fluoro-1,2,3,5,6,7-hexahydropyrrolizin-8-yl]methoxy]quinazolin-4-yl]-ethyl-amino]-2-methyl-pyrrolidine-1-carboxylate: To a solution of tert-butyl-3-[[7-bromo-8-cyano-2-[[(2R,8S)-2-fluoro-1,2,3,5,6,7-hexahydropyrrolizin-8-yl]methoxy]quinazolin-4-yl]-ethyl-amino]-2-methyl-pyrrolidine-1-carboxylate (1.00 eq, 54 mg, 0.087 mmol), tert-butyl N-[3-cyano-4-(5,5-dimethyl-1,3,2-dioxaborinan-2-yl)-7-fluoro-benzothiophen-2-yl]carbamate (2.50 eq, 88 mg, 0.22 mmol), and $Cs_2CO_3$ (2.00 eq, 57 mg, 0.18 mmol) in 1,4-dioxane (1.5 mL) was added DPEPhosPd$Cl_2$ (0.30 eq, 19 mg, 0.026 mmol). After nitrogen protection, the reaction was stirred at 95° C. for 16 hours. After cooled to ambient temperature, the reaction was diluted with EA (20 mL) and the organic layers washed with water and saturated brine solution. The organic layers were then separated and dried ($MgSO_4$) before concentration to dryness. The crude was then purified by preparative-TLC (PE:EA=1:3) to afford tert-butyl-3-[[7-[2-(tert-butoxycarbonylamino)-3-cyano-7-fluoro-benzothiophen-4-yl]-8-cyano-2-[[(2R,8S)-2-fluoro-1,2,3,5,6,7-hexahydropyrrolizin-8-yl]methoxy]quinazolin-4-yl]-ethyl-amino]-2-methyl-pyrrolidine-1-carboxylate (59 mg, 81% yield). LCMS ESI (+) m/z 829.0 (M+H).

Step E: Preparation of 7-(2-amino-3-cyano-7-fluoro-benzothiophen-4-yl)-4-[ethyl-[2-methylpyrrolidin-3-yl]amino]-2-[[(2R,8S)-2-fluoro-1,2,3,5,6,7-hexahydropyrrolizin-8-yl]methoxy]quinazoline-8-carbonitrile: A solution of tert-butyl-3-[[7-[2-(tert-butoxycarbonylamino)-3-cyano-7-fluoro-benzothiophen-4-yl]-8-cyano-2-[[(2R,8S)-2-fluoro-1,2,3,5,6,7-hexahydropyrrolizin-8-yl]methoxy]quinazolin-4-yl]-ethyl-amino]-2-methyl-pyrrolidine-1-carboxylate (1.00 eq, 59 mg, 0.0712 mmol) in DCM (2 mL) was added TFA (182 eq, 1.0 mL, 13.0 mmol). The mixture was stirred for 2 hours at room temperature. The solvent was removed under vacuum to give 7-(2-amino-3-cyano-7-fluoro-benzothiophen-4-yl)-4-[ethyl-[2-methylpyrrolidin-3-yl]amino]-2-[[(2R,8S)-2-fluoro-1,2,3,5,6,7-hexahydropyrrolizin-8-yl]methoxy]quinazoline-8-carbonitrile (45 mg, 100% yield). LCMS ESI (+) m/z 629.0 (M+H).

Step F: Preparation of 4-((1-acryloyl-2-methylpyrrolidin-3-yl)(ethyl)amino)-7-(2-amino-3-cyano-7-fluorobenzo[b]thiophen-4-yl)-2-(((2R,7aS)-2-fluorotetrahydro-1H-pyrrolizin-7a(5H)-yl)methoxy)quinazoline-8-carbonitrile: A solution of 7-(2-amino-3-cyano-7-fluoro-benzothiophen-4-yl)-4-[ethyl-[2-methylpyrrolidin-3-yl]amino]-2-[[(2R,8S)-2-fluoro-1,2,3,5,6,7-hexahydropyrrolizin-8-yl]methoxy]quinazoline-8-carbonitrile (1.00 eq, 45 mg, 0.072 mmol) in THF (1 mL) was added dropwise to a solution of $K_2CO_3$ (5.00 eq, 49 mg, 0.36 mmol) in water (1 mL) and ethyl acetate (1 mL). The reaction mixture was stirred at rt for 30 minutes and cooled to 0° C. A solution of acryloyl chloride (1.00 eq, 0.0058 mL, 0.072 mmol) in DCM (0.2 mL) was added to the mixture dropwise at 0° C., and stirred at 0° C. for 30 minutes. The reaction mixture was extracted with EtOAc (20 mM). The organic layers were then separated and dried ($Na_2SO_4$) before concentration to dryness. The residue was purified by preparative RP-HPLC to give 7-(2-amino-3-cyano-7-fluoro-benzothiophen-4-yl)-4-[ethyl-[2-methyl-1-prop-2-enoyl-pyrrolidin-3-yl]amino]-2-[[(2R,8S)-2-fluoro-1,2,3,5,6,7-hexahydropyrrolizin-8-yl]methoxy]quinazoline-8-carbonitrile (23 mg, 0.0336 mmol, 47% yield) as solid. LCMS ESI (+) m/z 683.0 (M+H). $^1H$ NMR (400 MHz, $CD_3OD$): δ 8.46-8.51 (m, 1H), 7.50-7.60 (m, 1H), 7.30-7.39 (m, 1H), 7.06-7.15 (m, 1H), 6.61-6.74 (m, 1H), 6.28-6.40 (m, 1H), 5.77-5.86 (m, 1H), 5.59 (d, J=52.1 Hz, 1H), 4.98-5.14 (m, 1H), 4.58-4.81 (m, 3H), 4.10-4.22 (m, 1H), 3.91-4.04 (m, 4H), 3.45-3.78 (m, 3H), 2.46-2.73 (m, 5H), 2.32-2.41 (m, 2H), 2.11-2.24 (m, 1H), 1.34-1.43 (m, 3H), 0.98-1.15 (m, 3H).

Synthetic Example 54: Synthesis of 4-(4-((1-acryloyl-2-(methoxymethyl)pyrrolidin-3-yl)(methyl)amino)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile (Compound 426)

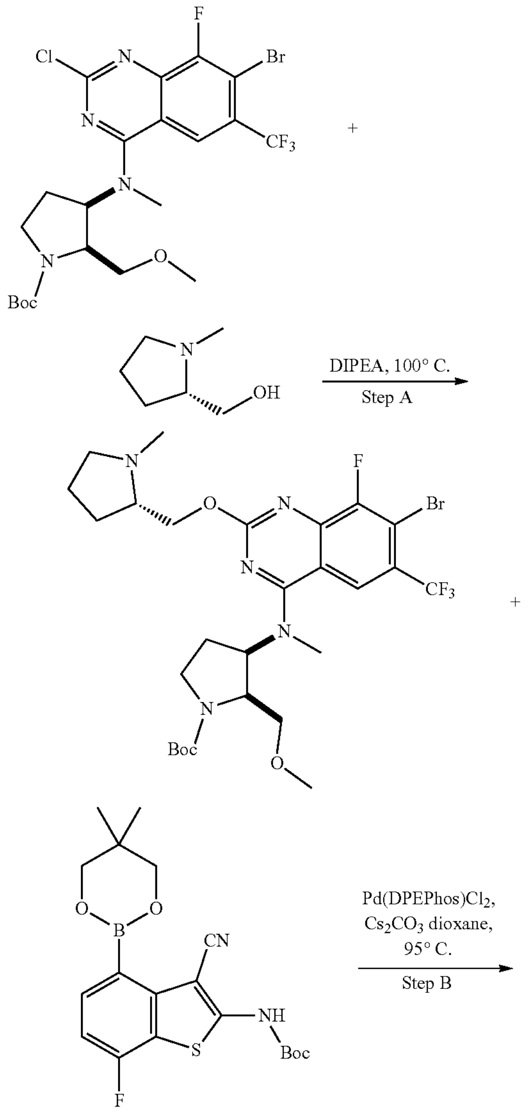

-continued

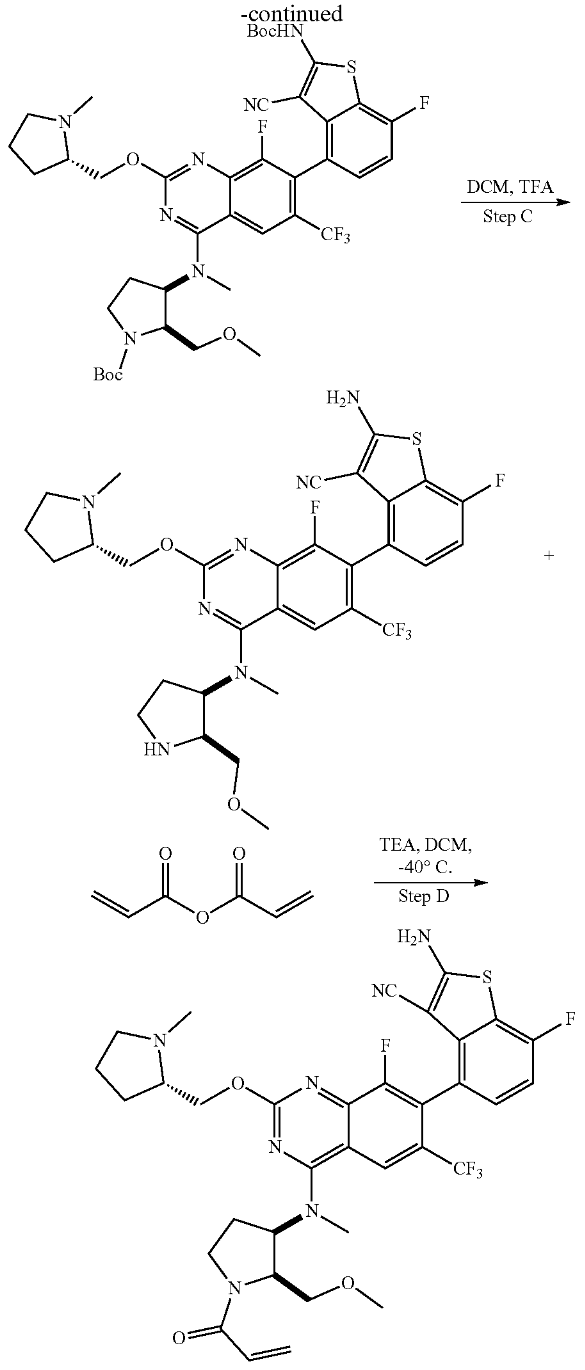

Compound 426

Step A: Preparation of tert-butyl (2S,3R)-3-((7-bromo-8-fluoro-2-(((S)-1-methylpyrrolidin-2-yl) methoxy)-6-(trifluoromethyl)quinazolin-4-yl)(methyl)amino)-2-(methoxymethyl)pyrrolidine-1-carboxylate: A solution of tert-butyl-3-[[7-bromo-2-chloro-8-fluoro-6-(trifluoromethyl)quinazolin-4-yl]-methyl-amino]-2-(methoxymethyl) pyrrolidine-1-carboxylate (1.00 eq, 600 mg, 1.05 mmol) and [(2S)-1-methylpyrrolidin-2-yl]methanol (2.00 eq, 242 mg, 2.10 mmol) in DIEA (30.0 eq, 5.6 mL, 31.5 mmol) was stirred at 100° C. for 16 hours. After cooled to ambient temperature, the mixture was diluted with water and extracted with EA (3×10 mL). The combined extracts were washed with brine, dried over sodium sulfate, filtered and concentrated the residue was purified by preparative-TLC to give tert-butyl-3-[[7-bromo-8-fluoro-2-[[(2S)-1-methylpyrrolidin-2-yl]methoxy]-6-(trifluoromethyl) quinazolin-4-yl]-methyl-amino]-2-(methoxymethyl) pyrrolidine-1-carboxylate (440 mg, 59% yield) as a solid. LCMS ESI (+) m/z 650.1 (M+H).

Step B: Preparation of tert-butyl-3-((7-(2-((tert-butoxycarbonyl) amino)-3-cyano-7-fluorobenzo [b]thiophen-4-yl)-8-fluoro-2-(((S)-1-methylpyrrolidin-2-yl) methoxy)-6-(trifluoromethyl) quinazolin-4-yl) (methyl)amino)-2-(methoxymethyl)pyrrolidine-1-carboxylate: A solution of tert-butyl-3-[[7-bromo-8-fluoro-2-[[(2S)-1-methylpyrrolidin-2-yl]methoxy]-6-(trifluoromethyl)quinazolin-4-yl]-methyl-amino]-2-(methoxymethyl)pyrrolidine-1-carboxylate (1.00 eq, 440 mg, 0.62 mmol), tert-butyl N-[3-cyano-4-(5,5-dimethyl-1,3,2-dioxaborinan-2-yl)-7-fluoro-benzothiophen-2-yl]carbamate (1.50 eq, 392 mg, 0.97 mmol), $Cs_2CO_3$ (3.00 eq, 606 mg, 1.86 mmol) and DPEPhosPdC$l_2$ (0.40 eq, 185 mg, 0.26 mmol) in 1,4-dioxane (20 mL) was stirred at 95° C. under argon for 16 hours. After cooled to ambient temperature, the mixture was diluted with water and extracted with EA (3×10 mL). The combined extracts were washed with brine, dried over sodium sulfate, filtered and concentrated, the residue was purified by preparative RP-HPLC to give tert-butyl-3-[[7-[2-(tert-butoxycarbonylamino)-3-cyano-7-fluoro-benzothiophen-4-yl]-8-fluoro-2-[[(2S)-1-methylpyrrolidin-2-yl] methoxy]-6-(trifluoromethyl)quinazolin-4-yl]-methyl-amino]-2-(methoxymethyl)pyrrolidine-1-carboxylate (150 mg, 25% yield) as a solid. LCMS ESI (+) m/z 862.3 (M+H).

Step C: Preparation of 2-amino-7-fluoro-4-(8-fluoro-4-((2-(methoxymethyl)pyrrolidin-3-yl) (methyl)amino)-2-(((S)-1-methylpyrrolidin-2-yl)methoxy)-6-(trifluoromethyl) quinazolin-7-yl)benzo[b]thiophene-3-carbonitrile: A solution of tert-butyl-3-[[7-[2-(tert-butoxycarbonylamino)-3-cyano-7-fluoro-benzothiophen-4-yl]-8-fluoro-2-[[(2S)-1-methylpyrrolidin-2-yl]methoxy]-6-(trifluoromethyl)quinazolin-4-yl]-methyl-amino]-2-(methoxymethyl) pyrrolidine-1-carboxylate (1.00 eq, 150 mg, 0.167 mmol) and TFA (224 eq, 3.0 mL, 38.9 mmol) in DCM (8 mL) was stirred at 25° C. for 4 hours. The reaction mixture was concentrated to dryness to obtain 2-amino-7-fluoro-4-[8-fluoro-4-[[2-(methoxymethyl)pyrrolidin-3-yl]-methyl-amino]-2-[[(2S)-1-methylpyrrolidin-2-yl]methoxy]-6-(trifluoromethyl)quinazolin-7-yl]benzothiophene-3-carbonitrile (180 mg, 100% yield), which was used directly in the next step without further purification. LCMS ESI (+) m/z 662.2 (M+H).

Step D: Preparation of 4-(4-((1-acryloyl-2-(methoxymethyl)pyrrolidin-3-yl)(methyl)amino)-8-fluoro-2-(((S)-1-methylpyrrolidin-2-yl)methoxy)-6-(trifluoromethyl)quinazolin-7-yl)-2-amino-7-fluorobenzo[b]thiophene-3-carbonitrile: To a solution of 2-amino-7-fluoro-4-[8-fluoro-4-[[(2S,3R)-2-(methoxymethyl)pyrrolidin-3-yl]-methyl-amino]-2-[[(2S)-1-methylpyrrolidin-2-yl]methoxy]-6-(trifluoromethyl)quinazolin-7-yl]benzothiophene-3-carbonitrile (1.00 eq, 180 mg, 0.18 mmol) in DCM (3 mL) was added TEA (5.00 eq, 84 mg, 0.83 mmol) until pH=7, then prop-2-enoyl prop-2-enoate (0.80 eq, 17 mg, 0.13 mmol) in DCM (0.5 mL) was added at −40° C. under $N_2$; after addition, the reaction mixture was stirred at −40° C. for 0.5 hour. The mixture was quenched with methanol, then diluted with water and extracted with DCM (4×10 mL). The combined extracts were washed with brine, dried over sodium sulfate, filtered and concentrated the residue was purified by preparative-TLC to give 4-(4-((1-acryloyl-2-(methoxymethyl)pyrrolidin-3-yl)(methyl)amino)-8-fluoro- 2-(((S)-1-methylpyrrolidin-2-yl)methoxy)-6-(trifluoromethyl)quinazolin-7-yl)-2-amino-7-fluorobenzo[b]thiophene-3-carbonitrile (39 mg, 32% yield) as a solid. LCMS ESI (+) m/z 716 (M+H). $^1H$ NMR (400 MHz, $CD_3OD$) δ 8.39 (s, 1H), 7.22 (t, 1H), 7.01 (t, 1H), 6.65-6.77 (m, 1H), 6.29-6.36 (m, 1H), 5.75-5.80 (m, 1H), 4.95-5.05 (m, 2H), 4.42-4.54 (m, 2H), 3.69-3.95 (m, 2H), 3.56-3.67 (m, 4H), 3.06-3.27 (m, 5H), 2.88-2.96 (m, 1H), 2.66-2.84 (m, 1H), 2.54-2.58 (m, 3H), 2.37-2.50 (m, 2H), 2.07-2.16 (m, 1H), 1.68-1.89 (m, 3H).

Synthetic Example 55: Synthesis of 4-(4-((2S,5R)-4-acryloyl-2,5-dimethylpiperazin-1-yl)-2-(((S)-1,2-dimethylpyrrolidin-2-yl)methoxy)-8-fluoro-6-(trifluoromethyl)quinazolin-7-yl)-2-amino-7-fluorobenzo[b]thiophene-3-carbonitrile (Compound 447)

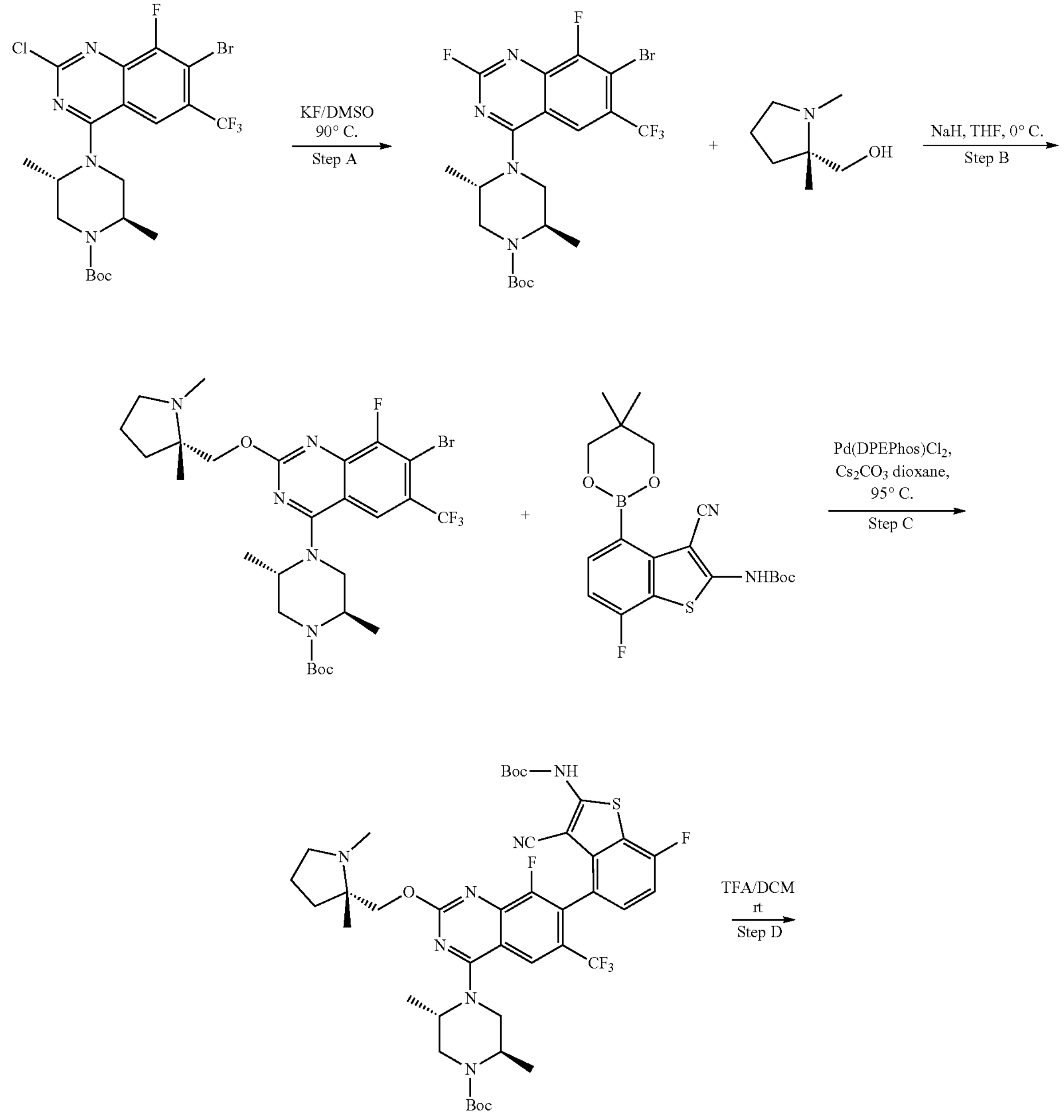

-continued

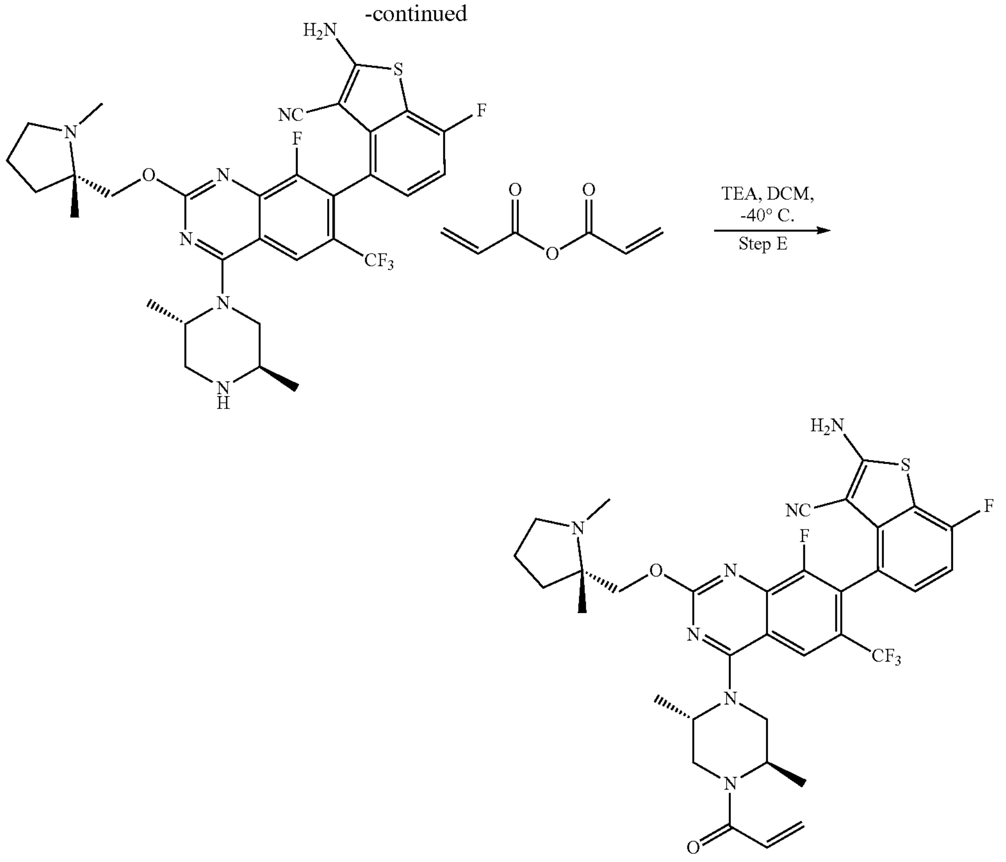

Compound 447

Step A: Preparation of tert-butyl (2R,5S)-4-[7-bromo-2,8-difluoro-6-(trifluoromethyl) quinazolin-4-yl]-2,5-dimethyl-piperazine-1-carboxylate: To a mixture of tert-butyl (2R,5S)-4-[7-bromo-2-chloro-8-fluoro-6-(trifluoromethyl) quinazolin-4-yl]-2,5-dimethyl-piperazine-1-carboxylate (1.00 eq, 800 mg, 1.48 mmol) in DMSO (8 mL) was added KF (8.00 eq, 687 mg, 11.8 mmol). The reaction mixture was stirred at 90° C. for 2 hours. After cooled to ambient temperature, the resulting mixture was added water and extracted with EA, the organic layer was concentrated under reduced pressure, the crude product was purified by preparative-TLC (PE:EA=5:1) to give tert-butyl (2R,5S)-4-[7-bromo-2,8-difluoro-6-(trifluoromethyl) quinazolin-4-yl]-2,5-dimethyl-piperazine-1-carboxylate (694 mg, 71% yield) as a solid. LCMS ESI (+) m/z 525.0 (M+H).

Step B: Preparation of tert-butyl (2R,5S)-4-[7-bromo-2-[[(2S)-1,2-dimethylpyrrolidin-2-yl]methoxy]-8-fluoro-6-(trifluoromethyl)quinazolin-4-yl]-2,5-dimethyl-piperazine-1-carboxylate: To a solution of [(2S)-1,2-dimethylpyrrolidin-2-yl]methanol (1.10 eq, 135 mg, 1.05 mmol) in THF (6 mL) was added NaH (4.42 eq, 101 mg, 4.21 mmol) at 0° C. under $N_2$. The mixture was stirred for 30 minutes followed by addition of a solution of tert-butyl (2R,5S)-4-[7-bromo-2,8-difluoro-6-(trifluoromethyl)quinazolin-4-yl]-2,5-dimethyl-piperazine-1-carboxylate (1.00 eq, 500 mg, 0.95 mmol) in THF (6 mL). After addition, the reaction mixture was warmed to ambient temperature and stirred for 3 hours. The resulting solution was quenched with water, extracted with EA (3*15 mL), the combined organic phase was washed with brine, dried over $Na_2SO_4$ and concentrated. The residue was purified by preparative-TLC (DCM: MeOH=20:1) to give tert-butyl (2R,5S)-4-[7-bromo-2-[[(2S)-1,2-dimethylpyrrolidin-2-yl]methoxy]-8-fluoro-6-(trifluoromethyl)quinazolin-4-yl]-2,5-dimethyl-piperazine-1-carboxylate (110 mg, 0.156 mmol, 16.39% yield) as a yellow solid. LCMS ESI (+) m/z 634.2 (M+H).

Step C: Preparation of tert-butyl (2R,5S)-4-[7-[2-(tert-butoxycarbonylamino)-3-cyano-7-fluoro-benzothiophen-4-yl]-2-[[(2S)-1,2-dimethylpyrrolidin-2-yl]methoxy]-8-fluoro-6-(trifluoromethyl) quinazolin-4-yl]-2,5-dimethyl-piperazine-1-carboxylate: To a solution of tert-butyl (2R,5S)-4-[7-bromo-2-[[(2S)-1,2-dimethylpyrrolidin-2-yl]methoxy]-8-fluoro-6-(trifluoromethyl)quinazolin-4-yl]-2,5-dimethyl-piperazine-1-carboxylate (1.00 eq, 120 mg, 0.19 mmol) in 1,4-dioxane (3 mL) was added tert-butyl N-[3-cyano-4-(5,5-dimethyl-1,3,2-dioxaborinan-2-yl)-7-fluoro-benzothiophen-2-yl]carbamate (1.50 eq, 115 mg, 0.28 mmol), $Cs_2CO_3$ (3.00 eq, 185 mg, 0.57 mmol) and Pd(DPEPhos)$Cl_2$ (0.40 eq, 54 mg, 0.076 mmol). The reaction mixture was stirred at 95° C. for 3 hours under nitrogen environment. After cooled to ambient temperature, the resulting mixture was added water and extracted with EA, the combined organic phase was washed with brine, dried over $Na_2SO_4$, concentrated. The crude product was purified by preparative-TLC to give tert-butyl (2R,5S)-4-[7-[2-(tert-butoxycarbonylamino)-3-cyano-7-fluoro-benzothiophen-4-yl]-2-[[(2S)-1,2-dimethylpyrrolidin-2-yl]methoxy]-8-fluoro-6-(trifluoromethyl)quinazolin-4-yl]-2,5-dimethyl-piperazine-1-carboxylate (180 mg, 56% yield) as a solid. LCMS ESI (+) m/z 846.4 (M+H).

Step D: Preparation of 2-amino-4-[4-[(2S,5R)-2,5-dimethylpiperazin-1-yl]-2-[[(2S)-1,2-dimethylpyrrolidin-2-yl]methoxy]-8-fluoro-6-(trifluoromethyl)quinazolin-7-yl]-7-fluoro-benzothiophene-3-carbonitrile: To a solution of tert-butyl (2R,5S)-4-[7-[2-(tert-butoxycarbonylamino)-3-cyano-7-fluoro-benzothiophen-4-yl]-2-[[(2S)-1,2-dimethylpyrrolidin-2-yl]methoxy]-8-fluoro-6-(trifluoromethyl)quinazolin-4-yl]-2,5-dimethyl-piperazine-1-carboxylate (1.00 eq, 140 mg, 0.17 mmol) in DCM (4 mL) was added TFA (78.4 eq, 1.0 mL, 13.0 mmol). The reaction mixture was stirred at 25° C. for 5 hours. The mixture solution was concentrated under reduced pressure to obtain 2-amino-4-[4-[(2S,5R)-2,5-dimethylpiperazin-1-yl]-2-[[(2S)-1,2-dimethylpyrrolidin-2-yl]methoxy]-8-fluoro-6-(trifluoromethyl)quinazolin-7-yl]-7-fluoro-benzothiophene-3-carbonitrile (140 mg, 91% yield) as an oil, which was used directly next step without further purification. LCMS ESI (+) m/z 646.2 (M+H).

Step E: Preparation of 4-(4-((2S,5R)-4-acryloyl-2,5-dimethylpiperazin-1-yl)-2-(((S)-1,2-dimethylpyrrolidin-2-yl)methoxy)-8-fluoro-6-(trifluoromethyl)quinazolin-7-yl)-2-amino-7-fluorobenzo[b]thiophene-3-carbonitrile: To a solution of 2-amino-4-[4-[(2S,5R)-2,5-dimethylpiperazin-1-yl]-2-[[(2S)-1,2-dimethylpyrrolidin-2-yl]methoxy]-8-fluoro-6-(trifluoromethyl)quinazolin-7-yl]-7-fluoro-benzothiophene-3-carbonitrile (1.00 eq, 140 mg, 0.22 mmol) in DCM (2 mL) was added TEA (10.0 eq, 219 mg, 2.17 mmol) and prop-2-enoyl prop-2-enoate (1.00 eq, 27 mg, 0.22 mmol) at −40° C. The reaction mixture was stirred at −40° C. for 1 hour. The resulting mixture was quenched with MeOH and water, extracted with DCM, the combined organic phase was washed with brine, dried over $Na_2SO_4$, concentrated. The crude product was purified by preparative-TLC (DCM/MeOH=10:1) to afford 2-amino-4-[4-[(2S,5R)-2,5-dimethyl-4-prop-2-enoyl-piperazin-1-yl]-2-[[(2S)-1,2-dimethylpyrrolidin-2-yl]methoxy]-8-fluoro-6-(trifluoromethyl)quinazolin-7-yl]-7-fluoro-benzothiophene-3-carbonitrile (11 mg, 6% yield) as a solid. LCMS ESI (+) m/z 700.1 (M+H). $^1$H NMR (400 MHz, $CD_3OD$) δ 8.14 (s, 1H), 7.20-7.25 (m, 1H), 6.99-7.04 (m, 1H), 6.77-6.87 (m, 1H), 6.25-6.32 (m, 1H), 5.78-5.84 (m, 1H), 4.90-4.96 (m, 1H), 4.25-4.58 (m, 4H), 3.83-4.02 (m, 2H), 3.39-3.61 (m, 1H), 3.16-3.23 (m, 1H), 2.91-2.99 (m, 1H), 2.64 (s, 3H), 2.11-2.19 (m, 1H), 1.81-1.99 (m, 3H), 1.43-1.56 (m, 3H), 1.27-1.31 (m, 6H).

A compound of present disclosure, such as a compound of a formula included in any one of Tables 2-5, may be synthesized according to one of the general routes outlined in Synthetic Examples 1-59 or by various other methods generally known in the art.

Tables 2-5 include selected compounds of the present disclosure.

TABLE 2

Selected compounds of the present disclosure.

| Compound No. | Structure | Analytical data |
|---|---|---|
| 1 | 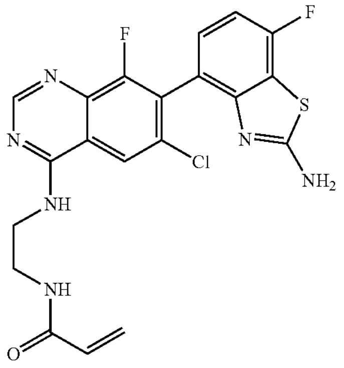 [SMILES: C=CC(=O)NCCNc1ncnc2c(F)c(-c3ccc(F)c4sc(N)nc34)c(Cl)cc12] | LCMS m/z [M + 1]: 461.1<br>1HNMR (400 MHz, CD3OD): δ 8.77 (s, 1H), 8.36 (s, 1H), 7.28 (dd, J = 8.4, 5.2 Hz, 1H), 7.03 (t, J = 9.2 Hz, 1H), 6.22 (t, J = 1.6 Hz, 1H), 5.67 (dd, J = 6.8, 5.2 Hz, 2H), 3.91-4.10 (m, 2H), 3.62-3.80 (m, 2H). |
| 2 | 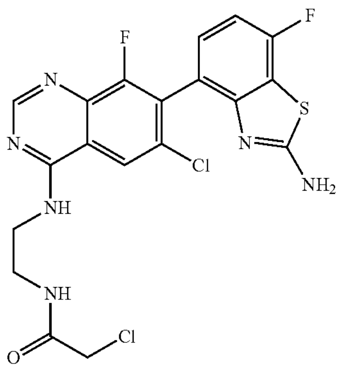 [SMILES: Nc1nc2c(-c3c(Cl)cc4c(NCCNC(=O)CCl)ncnc4c3F)ccc(F)c2s1] | LCMS m/z [M + 1]: 483.1<br>$^1$HNMR (400 MHz, $CD_3OD$): δ 8.78 (s, 1H), 8.35 (s, 1H), 7.28 (dd, J = 8.0, 5.2 Hz, 1H), 7.04 (t, J = 8.8 Hz, 1H), 4.08 (s, 2H), 3.95-4.05 (m, 2H), 3.60-3.71 (m, 2H). |

TABLE 2-continued

Selected compounds of the present disclosure.

| Compound No. | Structure | Analytical data |
| --- | --- | --- |
| 3 | 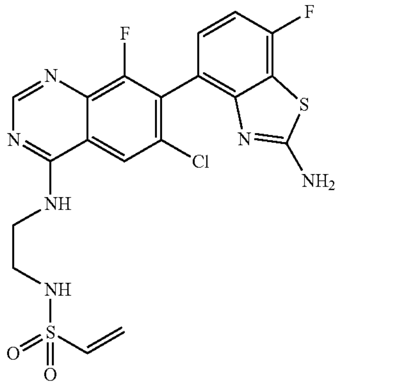 [SMILES: C=CS(=O)(=O)NCCNc1ncnc2c(F)c(-c3ccc(F)c4sc(N)nc34)c(Cl)cc12] | LCMS m/z [M + 1]: 497.1 $^{1}$HNMR (400 MHz, $CD_3OD$): δ 8.79 (s, 1H), 8.44 (s, 1H), 7.30 (dd, J = 8.0, 5.6 Hz, 1H), 7.04 (t, J = 9.2 Hz, 1H), 6.66 (dd, J = 16.8, 10.4 Hz, 1H), 6.14 (d, J = 16.4 Hz, 1H), 5.97 (d, J = 10 Hz, 1H), 3.98 (t, J = 5.6 Hz, 2H), 3.38 (t, J = 5.6 Hz, 2H). |
| 4 | 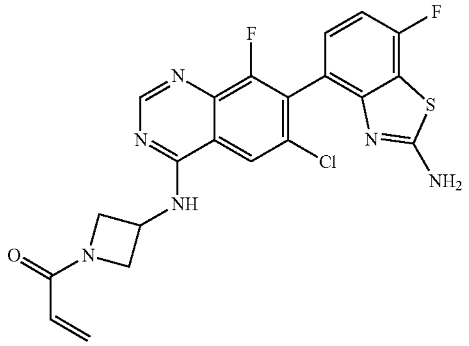 [SMILES: C=CC(=O)N1CC(Nc2ncnc3c(F)c(-c4ccc(F)c5sc(N)nc45)c(Cl)cc23)C1] | LCMS m/z [M + 1]: 473.1 $^{1}$HNMR (400 MHz, $CD_3OD$): 8.57 (s, 1H), 8.33 (s, 1H), 7.26 (t, J = 6.8 Hz, 1H), 7.02 (t, J = 9.2 Hz, 1H), 6.28-6.48 (m, 2H), 5.79 (d, J = 10.4 Hz, 1H), 4.51-4.60 (m, 3H), 4.37-4.41 (m, 1H), 4.21-4.25 (m, 1H). |
| 5 | 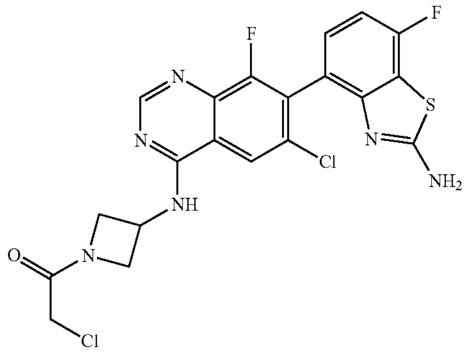 [SMILES: Nc1nc2c(-c3c(Cl)cc4c(NC5CN(C(=O)CCl)C5)ncnc4c3F)ccc(F)c2s1] | LCMS m/z [M + 1]: 495.1 $^{1}$HNMR (400 MHz, $CD_3OD$): 8.80 (s, 1H), 8.52 (s, 1H), 7.29 (dd, J = 8.8, 5.6 Hz, 1H), 7.04 (t, J = 8.4 Hz, 1H), 5.12-5.27 (m, 1H), 4.80-4.87 (m, 1H), 4.41-4.56 (m, 2H), 4.24-4.28 (m, 1H), 4.10-4.19 (m, 2H). |
| 6 | 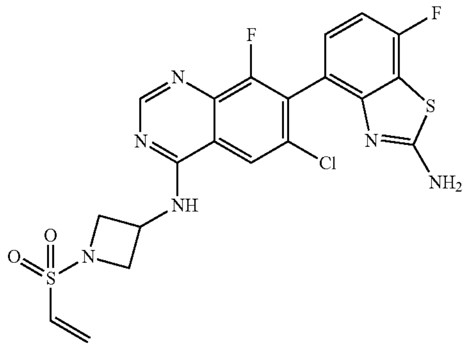 [SMILES: C=CS(=O)(=O)N1CC(Nc2ncnc3c(F)c(-c4ccc(F)c5sc(N)nc45)c(Cl)cc23)C1] | LCMS m/z [M + 1]: 509.1 $^{1}$HNMR (400 MHz, $CD_3OD$): 8.25 (s, 1H), 8.05 (s, 1H), 7.22 (dd, J = 8.0, 5.6 Hz, 1H), 6.99 (t, J = 8.4 Hz, 1H), 6.66-6.73 (m, 1H), 6.18 (d, J = 16.8 Hz, 1H), 6.0 (d, J = 10 Hz, 1H), 4.58-4.62 (m, 3H), 4.45-4.51 (m, 1H), 4.32-4.37 (m, 1H). |

TABLE 2-continued

| Selected compounds of the present disclosure. | | |
|---|---|---|
| Compound No. | Structure | Analytical data |
| 9 | 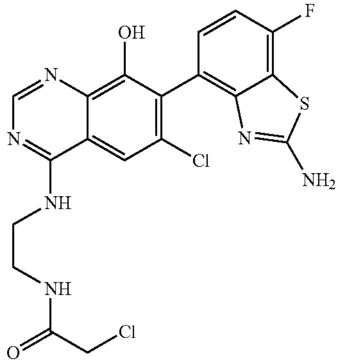 [SMILES: Nc1nc2c(-c3c(Cl)cc4c(NCCNC(=O)CCl)ncnc4c3O)ccc(F)c2s1] | LCMS m/z [M + 1]: 481.0<br>$^1$HNMR (400 MHz, $CD_3OD$): δ:8.66 (s, 1H),7.99 (s, 1H), 7.20-7.24 (m, 1H), 7.03 (t, J = 8.4 Hz, 1H), 4.04 (s, 2H), 3.99-4.02 (m, 2H), 3.64-3.67 (m, 2H). |
| 10 | 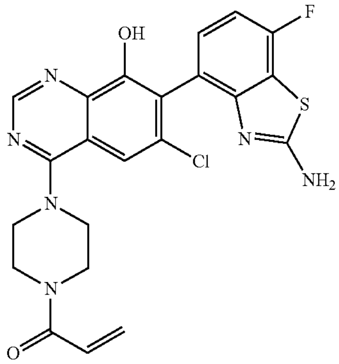 | LCMS m/z [M + 1]: 485.1<br>$^1$HNMR (400 MHz, $CD_3OD$): δ 8.65 (s, 1H), 7.91 (s, 1H), 7.25 (dd, J = 8.4, 5.6 Hz, 1H), 7.05 (t, J = 8.8 Hz, 1H) , 6.80 (dd, J = 8.4, 5.6 Hz, 1H), 6.31 (d, J = 16.8 Hz, 1H), 5.83 (d, J = 10.8 Hz, 1H), 4.30-4.43 (m, 4H), 3.90-4.0 (m, 4H). |
| 14 | 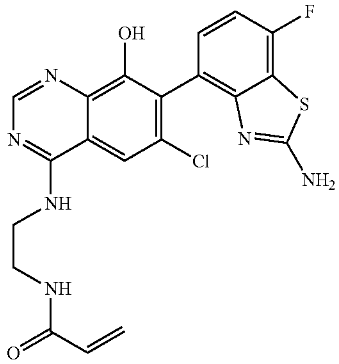 [SMILES: C=CC(=O)NCCNc1ncnc2c(O)c(-c3ccc(F)c4sc(N)nc34)c(Cl)cc12] | LCMS m/z [M + 1]: 459.1<br>$^1$HNMR (400 MHz, $CD_3OD$): δ 8.62 (s, 1H), 7.95 (s, 1H), 7.19-7.23 (m, 1H), 7.01 (t, J = 8.6 Hz, 1H), 6.22 (d, J = 5.6 Hz, 2H), 5.67 (t, J = 5.6 Hz, 1H), 3.84-4.06 (m, 2H), 3.62-3.77 (m, 2H). |
| 15 | 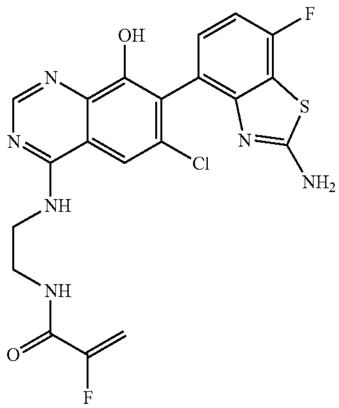 [SMILES: C=C(F)C(=O)NCCNc1ncnc2c(O)c(-c3ccc(F)c4sc(N)nc34)c(Cl)cc12] | LCMS m/z [M + 1]: 477.1<br>$^1$HNMR (400 MHz, $CD_3OD$): δ 8.66 (s, 1H), 7.99 (s, 1H), 7.22-7.25 (m, 1H), 7.02-7.07 (m, 1H), 5.63 (dd, J = 47.2 Hz, J = 3.2 Hz, 1H), 5.11-5.21 (m, 1H), 3.95-4.10 (m, 2H), 3.60-3.76 (m, 2H). |

TABLE 2-continued

| Compound No. | Structure | Analytical data |
|---|---|---|
| 16 | 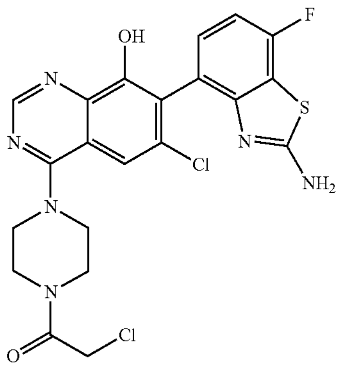 [SMILES: Nc1nc2c(-c3c(Cl)cc4c(N5CCN(C(=O)CCl)CC5)ncnc4c3O)ccc(F)c2s1] | LCMS m/z [M + 1]: 507.1 $^{1}$HNMR (400 MHz, $CD_3OD$): δ 8.56 (s, 1H), 7.79 (s, 1H), 7.14 (dd, J = 8.4, 5.6 Hz, 1H), 6.94 (t, J = 8.8 Hz, 1H), 4.29 (dd, J = 12.8, 2 Hz, 4H), 4.24 (s, 2H), 3.75-3.90 (m, 4H). |
| 18 | 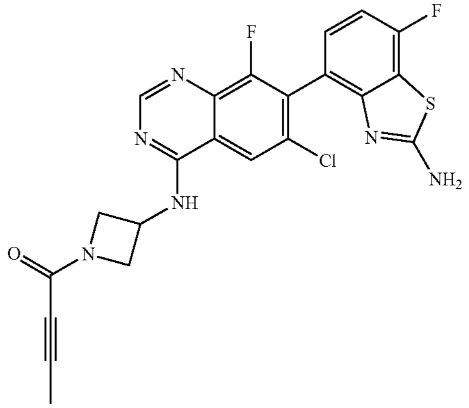 [SMILES: CC#CC(=O)N1CC(Nc2ncnc3c(F)c(-c4ccc(F)c5sc(N)nc45)c(Cl)cc23)C1] | LCMS m/z [M + 1]: 485.1 $^{1}$HNMR (400 MHz, $CD_3OD$) δ 8.55 (s, 1H), 8.30 (d, J = 1.4 Hz, 1H), 7.24 (dd, J = 8.3, 5.7 Hz, 1H), 7.00 (t, J = 8.8 Hz, 1H), 5.02-5.07 (m, 1H), 4.65-4.74 (m, 1H), 4.44-4.51 (m, 1H), 4.27-4.34 (m, 1H), 4.09-4.17 (m, 1H), 2.04 (s, 3H). |
| 19 | 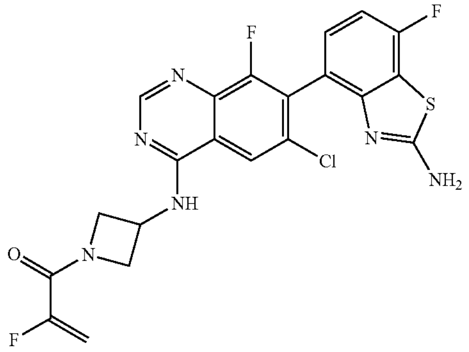 [SMILES: C=C(F)C(=O)N1CC(Nc2ncnc3c(F)c(-c4ccc(F)c5sc(N)nc45)c(Cl)cc23)C1] | LCMS m/z [M + 1]: 491.1 $^{1}$HNMR (400 MHz, $CD_3OD$): 8.81 (s, 1H), 8.53 (s, 1H), 7.29 (dd, J = 8.4, 5.2 Hz, 1H), 7.04 (t, J = 8.8 Hz, 1H), 5.60 (dd, J = 47.2, 3.6 Hz, 1H), 5.23-5.28 (m, 2H), 4.90-4.95 (m, 1H), 4.56-4.64 (m, 2H), 4.28-4.32 (m, 1H). |
| 20 | 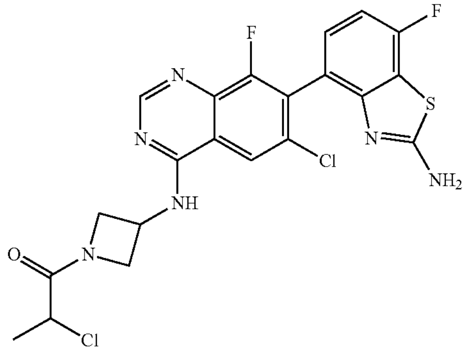 [SMILES: CC(Cl)C(=O)N1CC(Nc2ncnc3c(F)c(-c4ccc(F)c5sc(N)nc45)c(Cl)cc23)C1] | LCMS m/z [M + 1]: 509.1 $^{1}$HNMR (400 MHz, $CD_3OD$): 8.82 (s, 1H), 8.54 (d, J = 12 Hz, 1H), 7.31 (dd, J = 8.4, 5.2 Hz, 1H), 7.06 (t, J = 8.8 Hz, 1H), 5.25-5.29 (m, 1H), 4.80-4.85 (m, 1H), 4.53-4.64 (m, 3H), 4.25-4.31 (m, 1H), 1.63 (d, J = 6.8 Hz, 3H). |

Selected compounds of the present disclosure.

TABLE 2-continued
Selected compounds of the present disclosure.
| Compound No. | Structure | Analytical data |
|---|---|---|
| 21 | 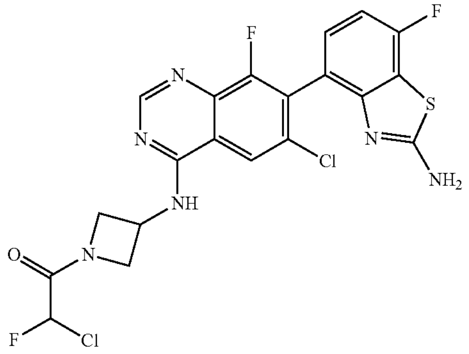 [SMILES: Nc1nc2c(-c3c(Cl)cc4c(NC5CN(C(=O)C(F)Cl)C5)ncnc4c3F)ccc(F)c2s1] | LCMS m/z [M + 1]: 513.1<br>$^1$HNMR (400 MHz, $CD_3OD$) δ 8.67 (s, 1H), 8.22 (d, J = 1.2 Hz, 1H), 7.26 (ddd, J = 8.4, 5.4, 1.3 Hz, 1H), 7.04 (td, J = 8.8, 2.0 Hz, 1H), 6.56 (dd, J = 49.6, 2.0 Hz, 1H), 4.91-4.95 (m, 2H), 4.69-4.73 (m, 1H), 3.71-3.82 (m, 2H). |
| 22 | 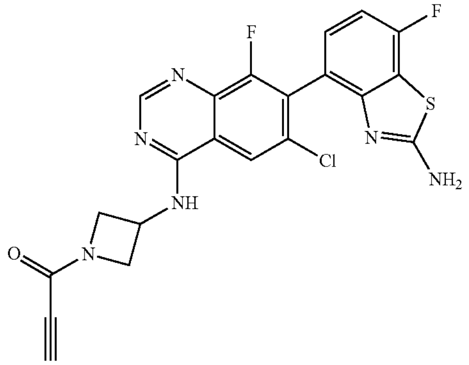 [SMILES: C#CC(=O)N1CC(Nc2ncnc3c(F)c(-c4ccc(F)c5sc(N)nc45)c(Cl)cc23)C1] | LCMS m/z [M + 1]: 471.0<br>$^1$HNMR (400 MHz, $CDCl_3$): δ 7.96 (d, J = 4.8 Hz, 1H), 7.80 (s, 1H), 7.21 (m, 1H), 6.99 (t, J = 9.2 Hz, 1H), 5.41 (br, 2H), 4.52-4.58 (m, 1H), 4.25 (t, J = 10.8 Hz,1H), 3.91-3.97 (m, 1H), 3.67 (m, 2H), 2.83 (d, J = 6.0 Hz, 1H). |
| 23 | 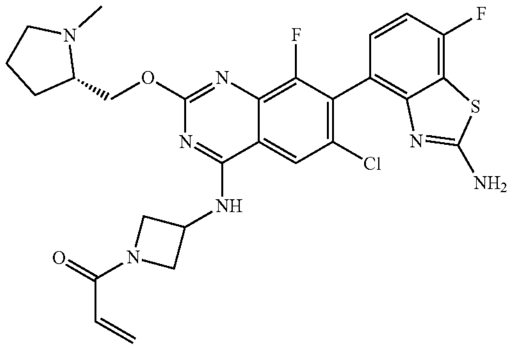 [SMILES: C=CC(=O)N1CC(Nc2nc(OC[C@@H]3CCCN3C)nc3c(F)c(-c4ccc(F)c5sc(N)nc45)c(Cl)cc23)C1] | LCMS m/z [M + 1]: 586.2<br>$^1$HNMR (400 MHz, $CD_3OD$): δ 8.22 (s, 1H), 7.20-7.23 (m, 1H), 6.99 (t, J = 8.8 Hz, 1H), 6.37-6.43 (m, 1H), 6.26-6.31 (m, 1H), 5.76-5.79 (dd, J = 10.0, 1.2 Hz, 1H), 4.99-5.05 (m, 1H), 4.76 (t, J = 8.8 Hz, 1H), 4.66-4.69 (m, 1H), 4.49-4.56 (m, 2H), 4.41-4.44 (m, 1H), 4.21-4.25 (m, 1H), 3.34-3.50 (m, 2H), 2.85-2.92 (m, 4H), 2.23-2.32 (m, 1H), 1.91-2.06 (m, 3H). |
| 23a | 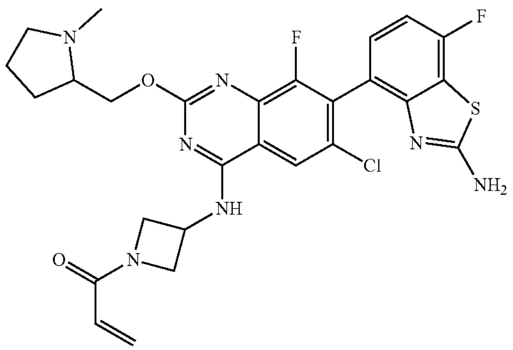 [SMILES: C=CC(=O)N1CC(Nc2nc(OCC3CCCN3C)nc3c(F)c(-c4ccc(F)c5sc(N)nc45)c(Cl)cc23)C1] | |

TABLE 2-continued
| Selected compounds of the present disclosure. | | |
|---|---|---|
| Compound No. | Structure | Analytical data |
| 24 | 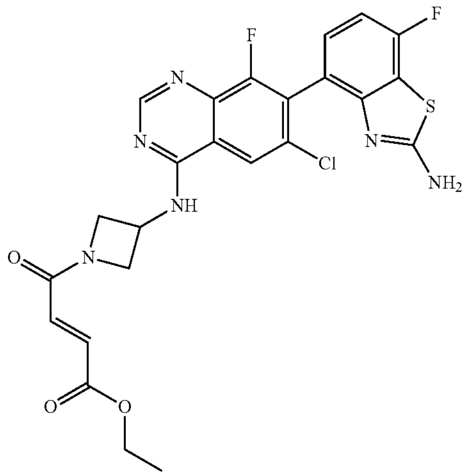 [SMILES: CCOC(=O)/C=C/C(=O)N1CC(Nc2ncnc3c(F)c(-c4ccc(F)c5sc(N)nc45)c(Cl)cc23)C1] | LCMS m/z [M + 1]: 545.1<br>$^1$HNMR (700 MHz, CD3CN) δ 8.76 (s, 1H), 8.68 (s, 1H), 8.30 (s, 1H), 7.55-7.47 (m, 2H), 7.43-7.38 (m, 1H), 7.21-7.13 (m, 1H), 7.04 (dd, J = 15.4, 3.0 Hz, 1H), 6.71 (dd, J = 15.5, 3.3 Hz, 1H), 5.14 (s, 1H), 4.82-4.75 (m, 1H), 4.51-4.39 (m, 2H), 4.27-4.17 (m, 3H), 1.30 (t, J = 7.1 Hz, 3H). |
| 25 | 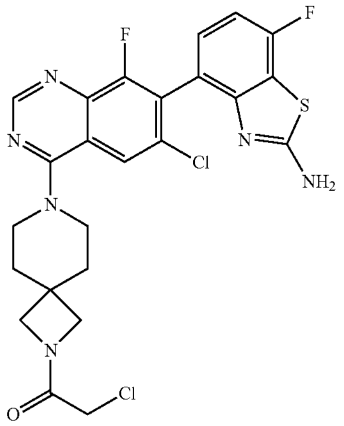 [SMILES: Nc1nc2c(-c3c(Cl)cc4c(N5CCC6(CC5)CN(C(=O)CCl)C6)ncnc4c3F)ccc(F)c2s1] | LCMS m/z [M + 1]: 549.1<br>$^1$HNMR (700 MHz, $CD_3OD$) δ 8.62 (s, 1H), 7.97 (d, J = 1.4 Hz, 1H), 7.25 (dd, J = 8.4, 5.4 Hz, 1H), 7.01 (dd, J = 9.2, 8.4 Hz, 1H), 4.14 (s, 2H), 4.08 (s, 2H), 3.98-3.91 (m, 4H), 3.89 (s, 2H), 2.09-2.00 (m, 4H). |
| 26 | 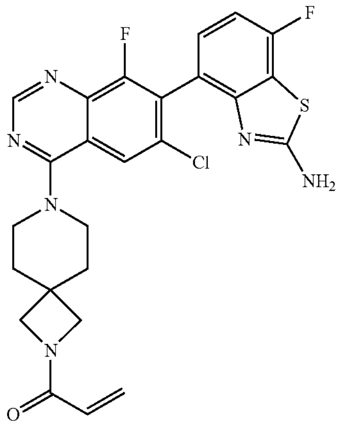 [SMILES: C=CC(=O)N1CC2(CCN(c3ncnc4c(F)c(-c5ccc(F)c6sc(N)nc56)c(Cl)cc34)CC2)C1] | LCMS m/z [M + 1]: 527.1<br>$^1$HNMR (700 MHz, $CD_3S(O)CD_3$) δ 8.67 (s, 1H), 7.94 (s, 2H), 7.90 (d, J = 1.3 Hz, 1H), 7.27 (dd, J = 8.4, 5.6 Hz, 1H), 7.07 (dd, J = 9.2, 8.4 Hz, 1H), 6.34 (dd, J = 17.0, 10.3 Hz, 1H), 6.12 (dd, J = 17.0, 2.3 Hz, 1H), 5.68 (dd, J = 10.3, 2.3 Hz, 1H), 4.02 (s, 2H), 3.77 (q, J = 3.5 Hz, 4H), 3.74 (s, 2H), 1.93 (t, J = 5.6 Hz, 4H). |

TABLE 2-continued

| Selected compounds of the present disclosure. | | |
|---|---|---|
| Compound No. | Structure | Analytical data |
| 27 | 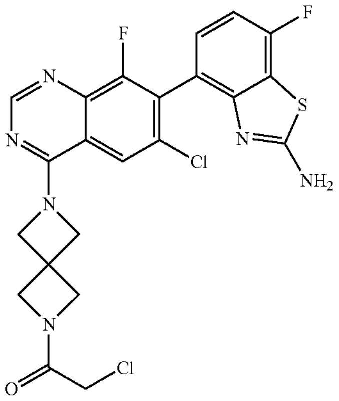 [SMILES: Nc1nc2c(-c3c(Cl)cc4c(N5CC6(CN(C(=O)CCl)C6)C5)ncnc4c3F)ccc(F)c2s1] | LCMS m/z [M + 1]: 521<br>$^1$HNMR (700 MHz, $CD_3S(O)CD_3$) δ 8.54 (s, 1H), 7.95 (s, 2H), 7.82 (d, J = 1.3 Hz, 1H), 7.25 (dd, J = 8.4, 5.6 Hz, 1H), 7.07 (t, J = 8.8 Hz, 1H), 4.46 (s, 2H), 4.19 (s, 2H), 4.14 (s, 2H), 2.50 (s, 2H), 2.50 (s, 2H). |
| 28 | 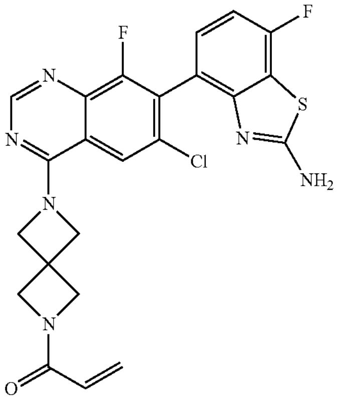 [SMILES: C=CC(=O)N1CC2(C1)CN(c1ncnc3c(F)c(-c4ccc(F)c5sc(N)nc45)c(Cl)cc13)C2] | LCMS m/z [M + 1]: 499<br>$^1$HNMR (700 MHz, $CD_3S(O)CD_3$) δ 8.54 (s, 1H), 7.95 (s, 2H), 7.82 (d, J = 1.3 Hz, 1H), 7.25 (dd, J = 8.4, 5.6 Hz, 1H), 7.09-7.04 (m, 1H), 6.32 (dd, J = 16.9, 10.3 Hz, 1H), 6.11 (dd, J = 17.0, 2.3 Hz, 1H), 5.69 (dd, J = 10.3, 2.3 Hz, 1H), 4.48 (s, 2H), 4.20 (s, 2H), 2.50 (s, 2H), 2.50 (s, 2H). |
| 29 | 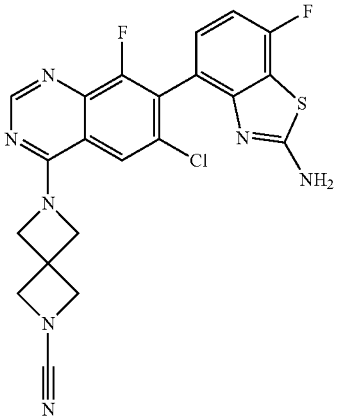 [SMILES: N#CN1CC2(C1)CN(c1ncnc3c(F)c(-c4ccc(F)c5sc(N)nc45)c(Cl)cc13)C2] | LCMS m/z [M + 1]: 498.1<br>$^1$HNMR (700 MHz, $CD_3S(O)CD_3$) δ 8.66 (s, 1H), 7.94 (s, 2H), 7.88 (d, J = 1.2 Hz, 1H), 7.26 (dd, J = 8.4, 5.6 Hz, 1H), 7.07 (dd, J = 9.2, 8.4 Hz, 1H), 3.99 (s, 4H), 3.76-3.68 (m, 4H), 1.95 (t, J = 5.5 Hz, 4H). |
| 30 | 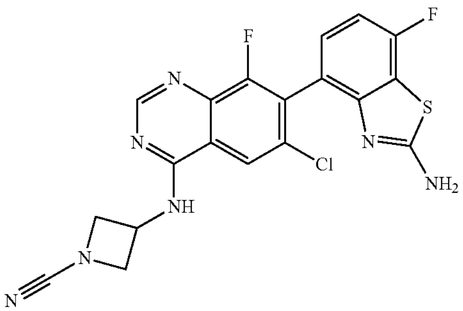 [SMILES: N#CN1CC(Nc2ncnc3c(F)c(-c4ccc(F)c5sc(N)nc45)c(Cl)cc23)C1] | LCMS m/z [M + 1]: 440.0<br>$^1$HNMR (700 MHz, $CD_3S(O)CD_3$) δ 8.98 (d, J = 6.0 Hz, 1H), 8.56 (s, 1H), 8.43 (s, 1H), 7.94 (s, 2H), 7.27 (dd, J = 8.4, 5.6 Hz, 1H), 7.07 (dd, J = 9.2, 8.4 Hz, 1H), 5.05-4.97 (m, 1H), 4.55 (t, J = 8.0 Hz, 2H), 4.34-4.24 (m, 2H). |

TABLE 2-continued
| Compound No. | Structure | Analytical data |
|---|---|---|
| 31 | 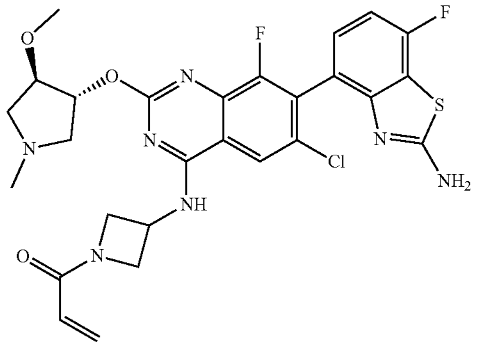 [SMILES: C=CC(=O)N1CC(Nc2nc(O[C@@H]3CN(C)C[C@H]3OC)nc3c(F)c(-c4ccc(F)c5sc(N)nc45)c(Cl)cc23)C1] | LCMS m/z [M + 1]: 602.2<br>$^1$HNMR (400 MHz, $CD_3OD$): δ 8.49 (s, 1H), 8.21 (s, 1H), 7.20 (dd, J = 4.4, 5.6 Hz, 1H), 6.99 (t, J = 8.8 Hz, 1H), 6.30-6.38 (m, 2H), 5.77 (d, J = 10 Hz, 1H), 4.90-5.05 (m, 2H), 4.76-4.78 (m, 2H), 4.48-4.50 (m, 1H), 4.38-4.40 (m, 1H), 4.12-4.28 (m, 2H), 3.50-3.73 (m, 1H), 3.49 (s, 3H), 3.09-3.22 (m, 2H), 2.69 (s, 3H). |
| 31a | 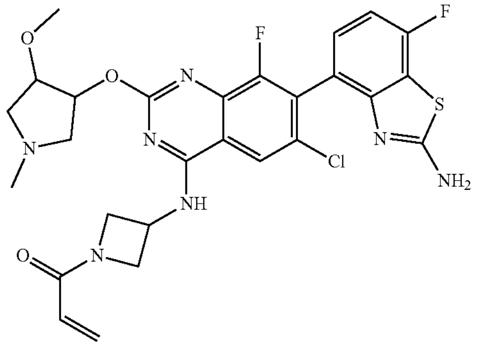 [SMILES: C=CC(=O)N1CC(Nc2nc(OC3CN(C)CC3OC)nc3c(F)c(-c4ccc(F)c5sc(N)nc45)c(Cl)cc23)C1] | |
| 32 | 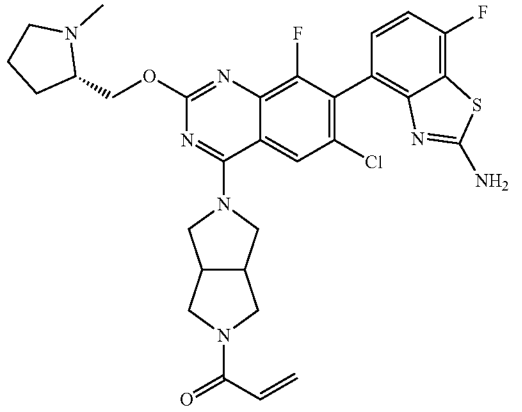 [SMILES: C=CC(=O)N1CC2CN(c3nc(OC[C@@H]4CCCN4C)nc4c(F)c(-c5ccc(F)c6sc(N)nc56)c(Cl)cc34)CC2C1] | LCMS m/z [M + 1]: 626.2<br>$^1$HNMR (400 MHz, $CD_3OD$) δ 8.20 (s, 1H), 7.18-7.25 (m, 1H), 6.99 (t, J = 8.8 Hz, 1H), 6.62 (dd, J = 16.8, 10.4 Hz, 1H), 6.29 (dd, J = 16.8, 1.7 Hz, 1H), 5.76 (dd, J = 10.5, 1.6 Hz, 1H), 4.51-4.63 (m, 2H), 4.28-4.39 (m, 2H), 3.92-4.07 (m, 3H), 3.86 (dd, J = 12.6, 7.1 Hz, 1H), 3.71 (dd, J = 10.7, 4.6 Hz, 1H), 3.53-3.62 (m, 1H), 3.11-3.28 (m, 4H), 2.67-2.82 (m, 4H), 2.21 (d, J = 6.0 Hz, 1H), 1.81-2.02 (m, 3H). |
| 32a | 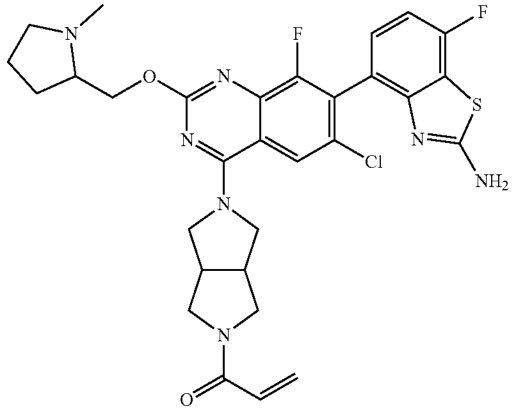 [SMILES: C=CC(=O)N1CC2CN(c3nc(OCC4CCCN4C)nc4c(F)c(-c5ccc(F)c6sc(N)nc56)c(Cl)cc34)CC2C1] | |
Selected compounds of the present disclosure.

TABLE 2-continued
Selected compounds of the present disclosure.
| Compound No. | Structure | Analytical data |
|---|---|---|
| 34 | 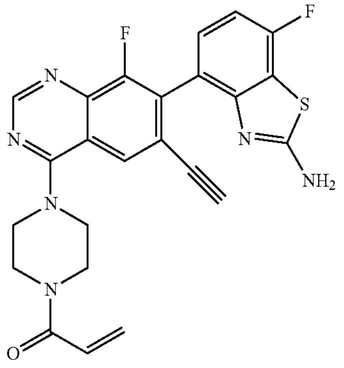 [SMILES: C#Cc1cc2c(N3CCN(C(=O)C=C)CC3)ncnc2c(F)c1-c1ccc(F)c2sc(N)nc12] | LCMS m/z [M + 1]: 477.1 $^1$HNMR (300 MHz, $CD_3OD$) δ 8.65 (s, 1H), 8.10 (d, J = 1.2 Hz, 1H), 7.30 (dd, J = 8.5, 5.5 Hz, 1H), 7.04-6.94 (m, 1H), 6.82 (dd, J = 16.8, 10.6 Hz, 1H), 6.28 (dd, J = 16.8, 1.9 Hz, 1H), 5.81 (dd, J = 10.6, 1.9 Hz, 1H), 4.14-3.99 (m, 4H), 3.97-3.85 (m, 4H), 3.51 (s, 1H). |
| 35 | 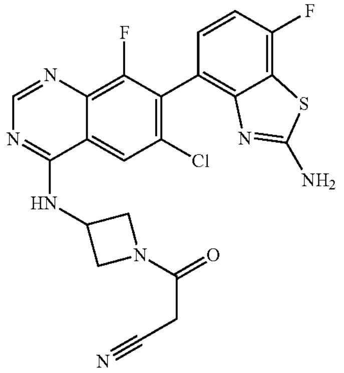 [SMILES: N#CCC(=O)N1CC(Nc2ncnc3c(F)c(-c4ccc(F)c5sc(N)nc45)c(Cl)cc23)C1] | LCMS m/z [M + 1]: 486.1 $^1$HNMR (700 MHz, $CD_3CN$) δ 8.55 (s, 1H), 8.07 (dd, J = 4.9, 1.4 Hz, 1H), 7.42 (d, J = 5.7 Hz, 1H), 7.29 (dd, J = 8.4, 5.5 Hz, 1H), 7.04 (t, J = 8.8 Hz, 1H), 6.23 (s, 2H), 4.96-4.90 (m, 1H), 4.58-4.53 (m, 1H), 4.39-4.33 (m, 1H), 4.20 (dd, J = 9.4, 5.2 Hz, 1H), 4.08-4.03 (m, 1H), 3.42 (s, 2H). |
| 36 | 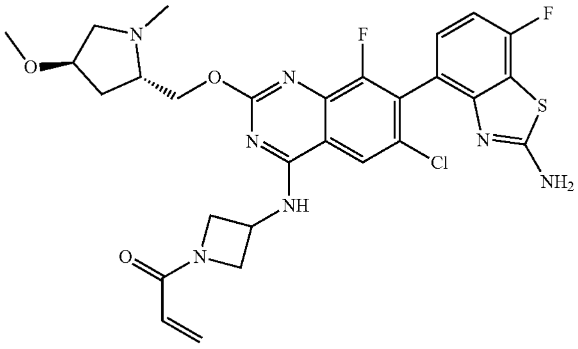 [SMILES: C=CC(=O)N1CC(Nc2nc(OC[C@@H]3C[C@@H](OC)CN3C)nc3c(F)c(-c4ccc(F)c5sc(N)nc45)c(Cl)cc23)C1] | LCMS m/z [M + 1]: 616.2 $^1$HNMR (400 MHz, $CD_3OD$): δ 8.30 (s, 1H), 7.25 (t, J = 3.6 Hz, 1H), 7.00-7.06 (m, 1H), 6.31-6.39 (m, 2H), 5.79 (d, J = 10 Hz, 1H), 4.75-5.10 (m, 3H), 4.64-4.67 (m, 1H), 4.44-4.54 (m, 2H), 4.09-4.27 (m, 3H), 3.71-3.90 (m, 1H), 3.39 (s, 3H), 3.12 (s, 3H), 2.49-2.54 (m, 1H), 2.05-2.28 (m, 1H). |
| 36a | 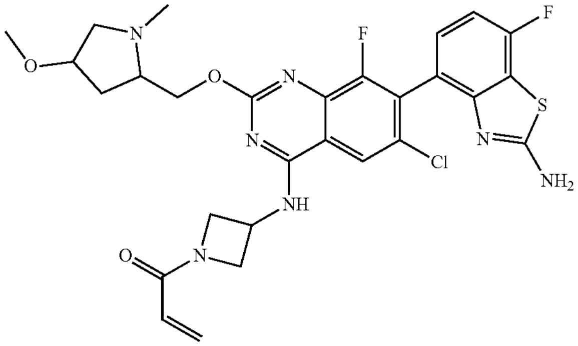 [SMILES: C=CC(=O)N1CC(Nc2nc(OCC3CC(OC)CN3C)nc3c(F)c(-c4ccc(F)c5sc(N)nc45)c(Cl)cc23)C1] | |

TABLE 2-continued
| Selected compounds of the present disclosure. | | |
|---|---|---|
| Compound No. | Structure | Analytical data |
| 37 | 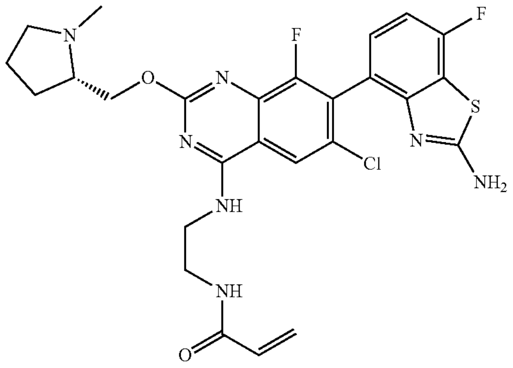 [SMILES: C=CC(=O)NCCNc1nc(OC[C@@H]2CCCN2C)nc2c(F)c(-c3ccc(F)c4sc(N)nc34)c(Cl)cc12] | LCMS m/z [M + 1]: 574.1<br>$^{1}$HNMR (400 MHz, $CD_3OD$) δ 8.12 (s, 1H), 7.16-7.23 (m, 1H), 7.00 (t, J = 8.8 Hz, 1H), 6.14-6.33 (m, 2H), 5.62-5.74 (m, 1H), 4.61-4.68 (m, 1H), 3.50-3.94 (m, 6H), 3.08 (s, 3H), 2.32-2.45 (m, 1H), 2.01-2.29 (m, 4H). |
| 37a | 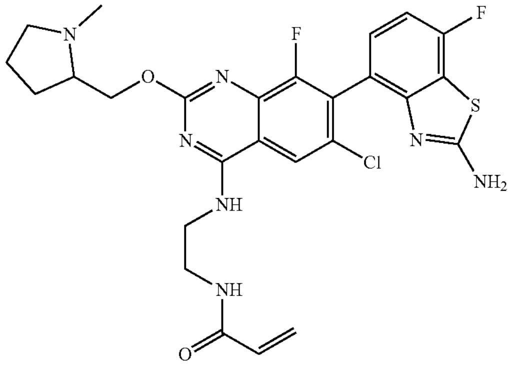 [SMILES: C=CC(=O)NCCNc1nc(OCC2CCCN2C)nc2c(F)c(-c3ccc(F)c4sc(N)nc34)c(Cl)cc12] | |
| 38 | 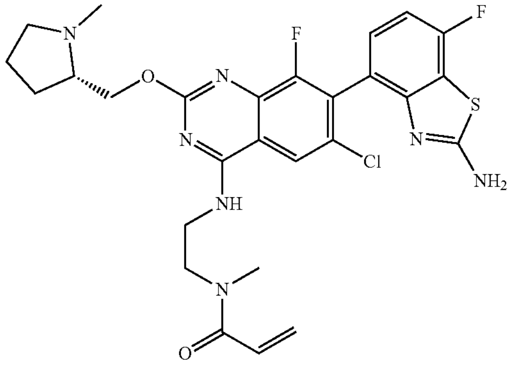 [SMILES: C=CC(=O)N(C)CCNc1nc(OC[C@@H]2CCCN2C)nc2c(F)c(-c3ccc(F)c4sc(N)nc34)c(Cl)cc12] | LCMS m/z [M + 1]: 588.2<br>$^{1}$HNMR (400 MHz, $CD_3OD$) δ 8.06-8.15 (m, 1H), 7.25 (dd, J = 8.1, 5.0 Hz, 1H), 7.03 (t, J = 8.7 Hz, 1H), 6.70-6.84 (m, 1H), 6.05-6.23 (m, 1H), 5.55-5.78 (m, 1H), 4.92-5.03 (m, 2H), 4.60-4.82 (m, 1H), 3.70-3.96 (m, 6H), 3.05-3.25 (m, 6H), 2.35-2.47 (m, 1H), 2.05-2.25 (m, 3H). |
| 38a | 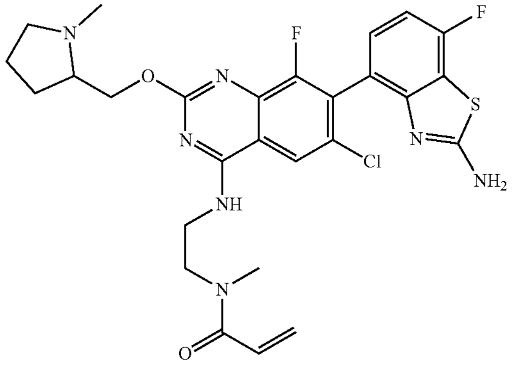 [SMILES: C=CC(=O)N(C)CCNc1nc(OCC2CCCN2C)nc2c(F)c(-c3ccc(F)c4sc(N)nc34)c(Cl)cc12] | |

TABLE 2-continued
Selected compounds of the present disclosure.
| Compound No. | Structure | Analytical data |
|---|---|---|
| 39 | 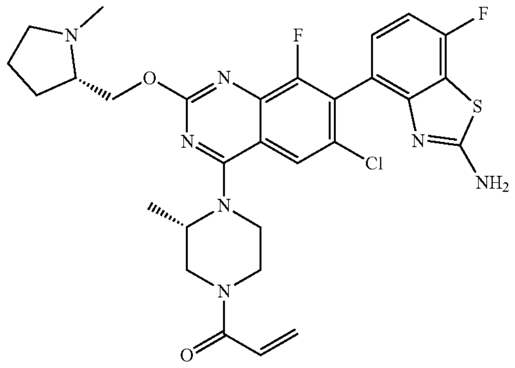 [SMILES: C=CC(=O)N1CCN(c2nc(OC[C@@H]3CCCN3C)nc3c(F)c(-c4ccc(F)c5sc(N)nc45)c(Cl)cc23)[C@@H](C)C1] | LCMS m/z [M + 1]: 614.2<br>$^1$HNMR (400 MHz, $CD_3OD$) δ 7.94 (s, 1H), 7.22-7.25 (m, 1H), 7.02 (t, J = 8.8 Hz, 1H), 6.73-6.90 (m, 1H), 6.30 (d, J = 15.8 Hz, 1H), 5.83 (d, J = 10.4 Hz, 1H), 4.61-4.70 (m, 1H), 4.31-4.60 (m, 2H), 4.01-4.29 (m, 1H), 3.48-3.96 (m, 8H), 3.08 (s, 3H), 2.02-2.48 (m, 4H), 1.45 (s, 3H). |
| 39a | 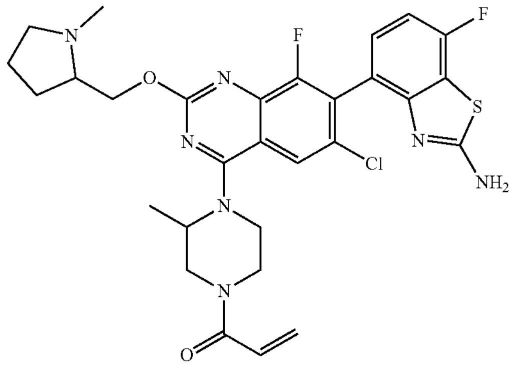 [SMILES: C=CC(=O)N1CCN(c2nc(OCC3CCCN3C)nc3c(F)c(-c4ccc(F)c5sc(N)nc45)c(Cl)cc23)C(C)C1] | |
| 40 | 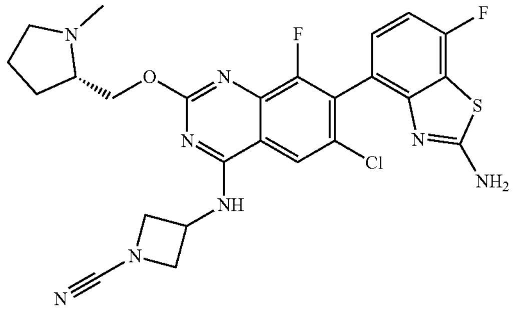 [SMILES: CN1CCC[C@H]1COc1nc(NC2CN(C#N)C2)c2cc(Cl)c(-c3ccc(F)c4sc(N)nc34)c(F)c2n1] | LCMS m/z [M + 1]: 557.3<br>$^1$HNMR (400 MHz, $CD_3OD$): δ 8.23 (s, 1H), 7.19-7.23 (m, 1H), 6.99 (t, J = 8.8 Hz, 1H), 5.03-5.13 (m, 1H), 4.74 (dt, J = 12.9, 3.4 Hz, 1H), 4.49-4.68 (m, 3H), 4.39 (dd, J = 8.1, 6.0 Hz, 2H), 3.50-3.68 (m, 2H), 2.95-3.08 (m, 1H), 2.93 (s, 3H), 2.22-2.33 (m, 1H), 1.94-2.15 (m, 3H). |
| 40a | 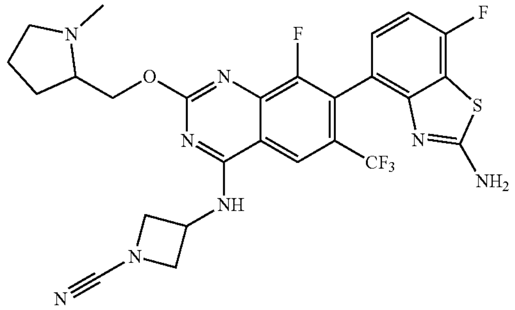 [SMILES: CN1CCCC1COc1nc(NC2CN(C#N)C2)c2cc(C(F)(F)F)c(-c3ccc(F)c4sc(N)nc34)c(F)c2n1] | |

TABLE 2-continued
| Selected compounds of the present disclosure. | | |
|---|---|---|
| Compound No. | Structure | Analytical data |
| 41 | 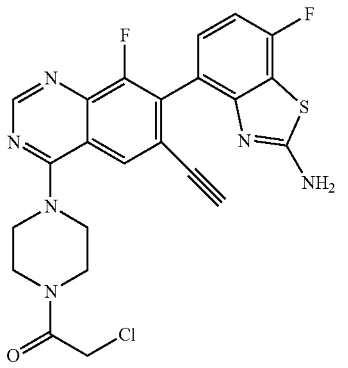 [SMILES: C#Cc1cc2c(N3CCN(C(=O)CCl)CC3)ncnc2c(F)c1-c1ccc(F)c2sc(N)nc12] | LCMS m/z [M + 1]: 499.18 $^1$HNMR (300 MHz, $CD_3OD$) δ 8.66 (s, 1H), 8.10 (s, 1H), 7.30 (dd, J = 8.6, 5.5 Hz, 1H), 6.98 (t, J = 8.9 Hz, 1H), 4.35 (s, 2H), 4.12-3.98 (m, 4H), 3.92-3.78 (m, 4H), 3.52 (s, 1H). |
| 42 | 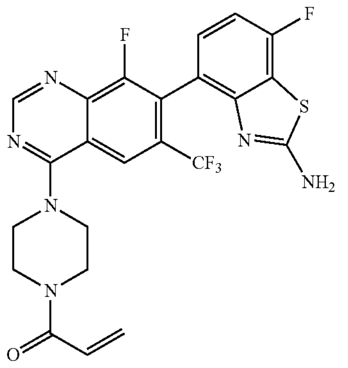 [SMILES: C=CC(=O)N1CCN(c2ncnc3c(F)c(-c4ccc(F)c5sc(N)nc45)c(C(F)(F)F)cc23)CC1] | LCMS m/z [M + 1]: 521.06 $^1$HNMR (300 MHz, $CD_3OD$) δ 8.74 (s, 1H), 8.30 (s, 1H), 7.28-7.18 (m, 1H), 7.04-6.95 (m, 1H), 6.84 (dd, J = 16.8, 10.6 Hz, 1H), 6.30 (dd, J = 16.8, 1.9 Hz, 1H), 5.83 (dd, J = 10.6, 1.9 Hz, 1H), 4.13 (dd, J = 9.2, 5.0 Hz, 4H), 3.95 (s, 4H). |
| 44 | 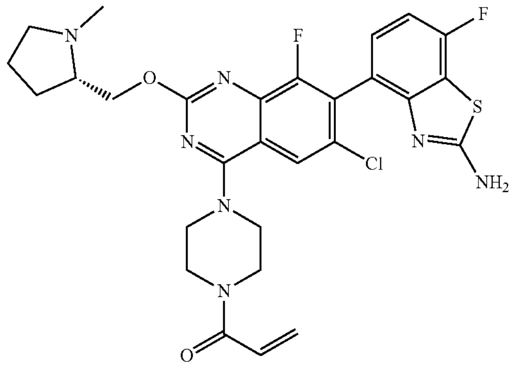 [SMILES: C=CC(=O)N1CCN(c2nc(OC[C@@H]3CCCN3C)nc3c(F)c(-c4ccc(F)c5sc(N)nc45)c(Cl)cc23)CC1] | LCMS m/z [M + 1]: 600.2 $^1$H NMR (400 MHz, $CD_3OD$) δ 8.02 (s, 1H), 7.20-7.27 (m, 1H), 7.01 (t, J = 8.8 Hz, 1H), 6.81 (dd, J = 16.8, 10.7 Hz, 1H), 6.29 (dd, J = 16.8, 1.8 Hz, 1H), 5.82 (dd, J = 10.6, 1.8 Hz, 1H), 4.71 (d, J=2.8 Hz, 1H), 4.59 (dd, J = 12.6, 6.1 Hz, 1H), 3.81-4.03 (m, 4H), 3.92 (m, 4H), 3.67-3.78 (m, 2H), 2.98 (m 1H), 2.88 (s, 3H), 2.15-2.26 (m, 1H), 1.92-2.14 (m, 3H). |
| 44a | 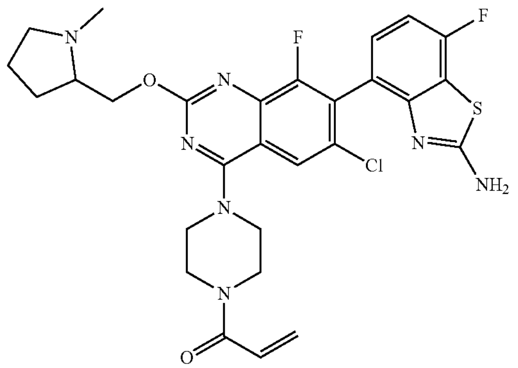 | |

TABLE 2-continued
Selected compounds of the present disclosure.
| Compound No. | Structure | Analytical data |
| --- | --- | --- |
| 45 | 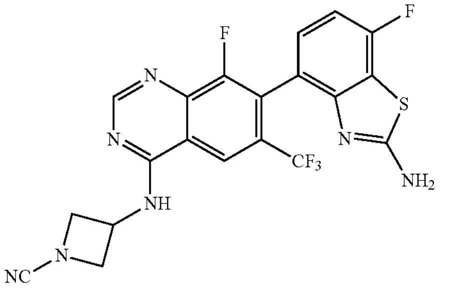 [SMILES: N#CN1CC(Nc2ncnc3c(F)c(-c4ccc(F)c5sc(N)nc45)c(C(F)(F)F)cc23)C1] | LCMS m/z [M + 1]: 477.90<br>$^1H$ NMR (300 MHz, $CD_3OD$) δ 8.65 (d, J = 7.1 Hz, 2H), 7.30-7.16 (m, 1H), 6.99 (t, J = 8.9 Hz, 1H), 5.22-5.10 (m, 1H), 4.64 (t, J = 7.8 Hz, 2H), 4.44-4.34 (m, 2H). |
| 46 | 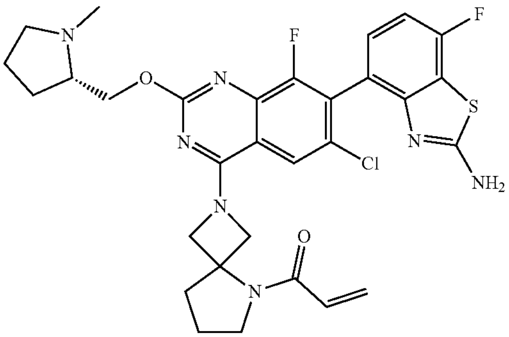 [SMILES: C=CC(=O)N1CCCC12CN(c1nc(OC[C@@H]3CCCN3C)nc3c(F)c(-c4ccc(F)c5sc(N)nc45)c(Cl)cc13)C2] | LCMS m/z [M + 1]: 626.2<br>$^1H$ NMR (400 MHz, $CD_3OD$) δ 7.90 (s, 1H), 7.19-7.31 (m, 1H), 7.02 (t, J = 8.8 Hz, 1H), 6.67 (dd, J = 16.8, 10.5 Hz, 1H), 6.26 (d, J = 16.9 Hz, 1H), 5.73-5.83 (m, 1H), 5.41-5.50 (m, 1H), 5.05-5.20 (m, 1H), 4.95 (m, 3H), 4.60-4.68 (m, 1H), 4.30-4.45 (m, 1H), 3.80-4.00 (m, 1H), 3.74 (t, J = 6.6 Hz, 3H), 3.08 (s, 3H), 2.31-2.60 (m, 3H), 1.91-2.24 (m, 5H). |
| 46a | 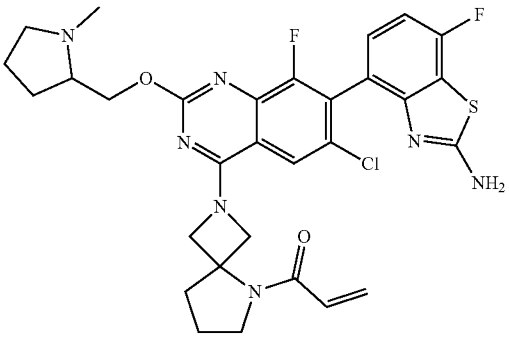 [SMILES: C=CC(=O)N1CCCC12CN(c1nc(OCC3CCCN3C)nc3c(F)c(-c4ccc(F)c5sc(N)nc45)c(Cl)cc13)C2] | |
| 47 | 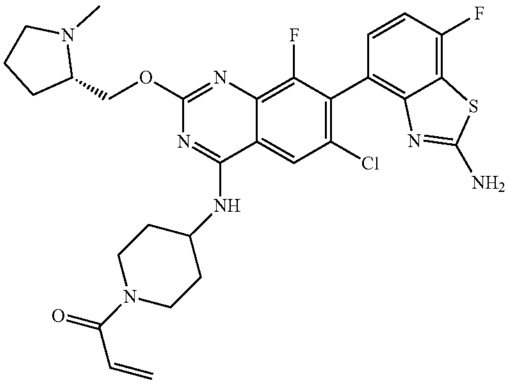 [SMILES: C=CC(=O)N1CCC(Nc2nc(OC[C@@H]3CCCN3C)nc3c(F)c(-c4ccc(F)c5sc(N)nc45)c(Cl)cc23)CC1] | LCMS m/z [M + 1]: 614.4<br>$^1HNMR$ (400 MHz, $CD_3OD$): δ 8.22 (s, 1H), 7.20-7.28 (m, 1H), 6.91-7.01 (m, 1H), 6.79-6.88 (m, 1H), 6.23 (dd, J = 16.8, 2 Hz, 1H), 5.77 (dd, J = 10.4, 1.6 Hz, 1H), 4.55-4.83 (m, 4H), 4.23 (d, J = 14 Hz, 1H), 3.50-3.61 (m, 2H), 2.86-2.98 (m, 2H), 2.85 (s, 3H), 1.95-2.31 (m, 6H), 1.52-1.67 (m, 2H). |

TABLE 2-continued
Selected compounds of the present disclosure.
| Compound No. | Structure | Analytical data |
|---|---|---|
| 47a | 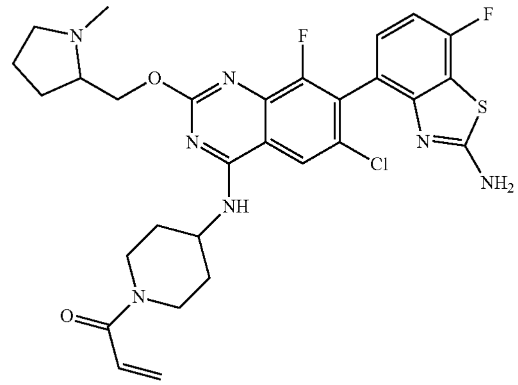 [SMILES: C=CC(=O)N1CCC(Nc2nc(OCC3CCCN3C)nc3c(F)c(-c4ccc(F)c5sc(N)nc45)c(Cl)cc23)CC1] | |
| 49 | 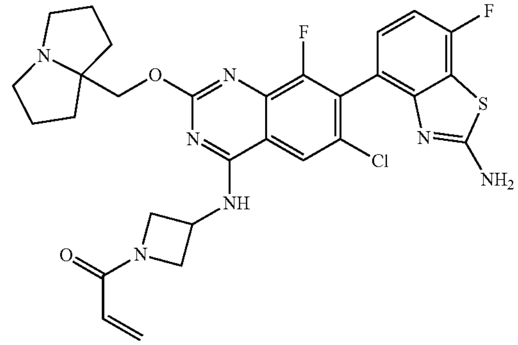 [SMILES: C=CC(=O)N1CC(Nc2nc(OCC34CCCN3CCC4)nc3c(F)c(-c4ccc(F)c5sc(N)nc45)c(Cl)cc23)C1] | LCMS m/z [M + 1]: 612.3<br>$^1$HNMR (400 MHz, $CD_3OD$) δ 8.28 (s, 1H), 7.24 (dd, J = 8.4, 5.4 Hz, 1H), 7.02 (t, J = 8.8 Hz, 1H), 6.41 (dd, J = 16.9, 10.2 Hz, 1H), 6.29 (dd, J = 17.0, 1.5 Hz, 1H), 5.79 (dd, J = 10.1 and 1.5 Hz, 1H), 5.00-5.08 (m, 1H), 4.77 (t, J = 8.4 Hz, 1H), 4.58-4.68 (m, 2H), 4.45-4.56 (m, 2H), 4.21-4.32 (m, 3H), 3.64-3.74 (m, 2H), 1.98-2.40 (m, 8H). |
| 50 | 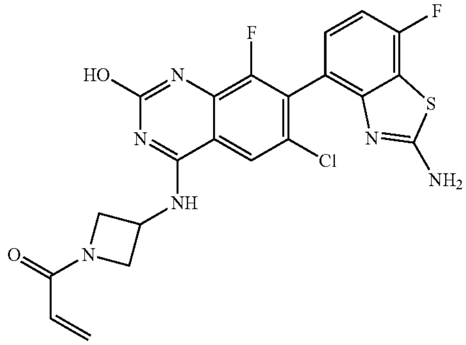 [SMILES: C=CC(=O)N1CC(Nc2nc(O)nc3c(F)c(-c4ccc(F)c5sc(N)nc45)c(Cl)cc23)C1] | LCMS m/z [M + 1]: 489.2<br>$^1$HNMR (400 MHz, $CD_3OD$) δ 8.20 (s, 1H), 7.24 (dd, J = 8.5, 5.3 Hz, 1H), 7.01 (t, J = 8.8 Hz, 1H), 6.23-6.46 (m, 2H), 5.77 (dd, J = 10.2, 2.1 Hz, 1H), 4.97-5.08 (m, 1H), 4.76 (t, J = 8.7 Hz, 1H), 4.45-4.55 (m, 1H), 4.30-4.39 (m, 1H), 4.20 (dd, J = 11.2, 5.3 Hz, 1H). |
| 51 | 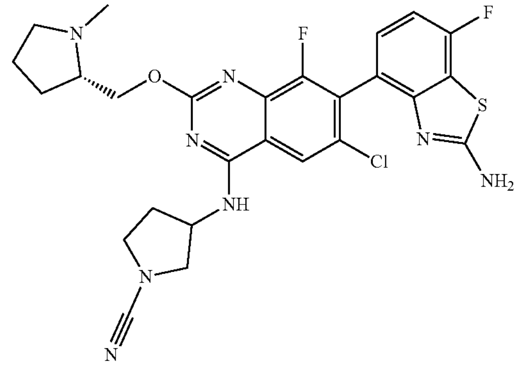 [SMILES: CN1CCC[C@H]1COc1nc(NC2CCN(C#N)C2)c2cc(Cl)c(-c3ccc(F)c4sc(N)nc34)c(F)c2n1] | LCMS m/z [M + 1]: 571.1<br>$^1$HNMR (400 MHz, $CD_3OD$) δ 8.29 (s, 1H), 7.14-7.28 (m, 1H), 6.99 (t, J = 8.8 Hz, 1H), 4.65-4.75 (m, 1H), 4.51-4.62 (m, 4H), 3.88 (dd, J = 10.1, 6.4 Hz, 1H), 3.36-3.71 (m, 4H), 2.71-2.90 (m, 5H), 2.12-2.49 (m, 2H), 1.94-2.07 (m, 2H). |

TABLE 2-continued
Selected compounds of the present disclosure.
| Compound No. | Structure | Analytical data |
|---|---|---|
| 51a | 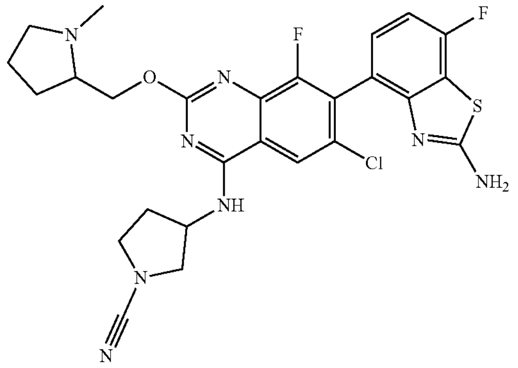 [SMILES: CN1CCCC1COc1nc(NC2CCN(C#N)C2)c2cc(Cl)c(-c3ccc(F)c4sc(N)nc34)c(F)c2n1] | |
| 52 | 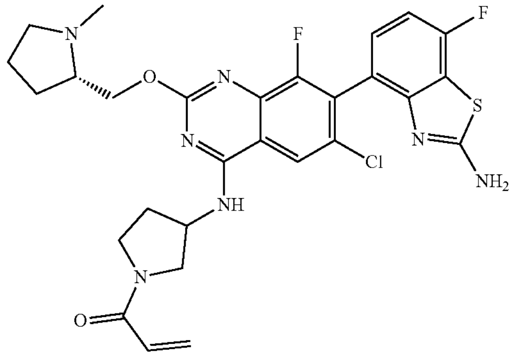 [SMILES: C=CC(=O)N1CCC(Nc2nc(OC[C@@H]3CCCN3C)nc3c(F)c(-c4ccc(F)c5sc(N)nc45)c(Cl)cc23)C1] | LCMS m/z [M + 1]: 600.2<br>$^1$HNMR (400 MHz, $CD_3OD$) δ 8.29 (s, 1H), 7.20 (d, J = 5.7 Hz, 1H), 6.99 (t, J = 8.8 Hz, 1H), 6.58-6.68 (m, 1H), 6.31 (d, J = 17.0 Hz, 1H), 5.78 (dd, J = 16.1, 5.7 Hz, 1H), 4.64-4.82 (m, 1H), 4.51-4.64 (m, 2H), 3.40-4.19 (m, 6H), 2.82-3.03 (m, 5H), 2.15-2.52 (m, 2H), 1.91-2.11 (m, 2H). |
| 52a | 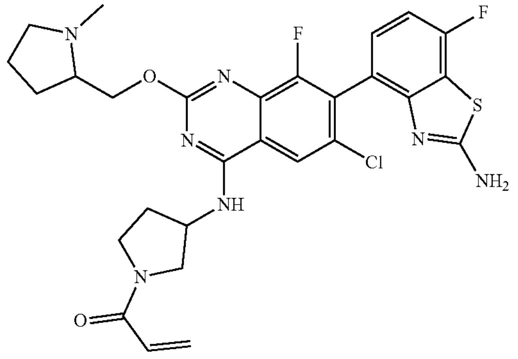 [SMILES: C=CC(=O)N1CCC(Nc2nc(OCC3CCCN3C)nc3c(F)c(-c4ccc(F)c5sc(N)nc45)c(Cl)cc23)C1] | |
| 53 | 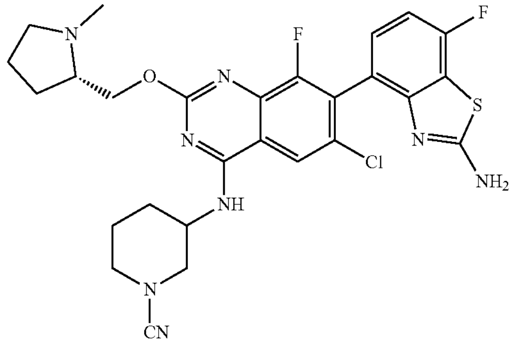 [SMILES: CN1CCC[C@H]1COc1nc(NC2CCCN(C#N)C2)c2cc(Cl)c(-c3ccc(F)c4sc(N)nc34)c(F)c2n1] | LCMS m/z [M + 1]: 585.2<br>$^1$HNMR (400 MHz, $CD_3OD$): δ 8.24 (s, 1H), 7.18-7.22 (m, 1H), 6.98 (t, J = 8.4 Hz, 1H), 4.55-4.65 (m, 1H), 4.44-4.54 (m, 1H), 3.65-3.85 (m, 2H), 3.54-3.63 (m, 1H), 3.42-3.46 (m, 2H), 3.10-3.16 (m, 2H), 3.02 (s, 3H), 2.34-2.38 (m, 1H), 1.76-2.15 (m, 8H). |

TABLE 2-continued
| Selected compounds of the present disclosure. | | |
|---|---|---|
| Compound No. | Structure | Analytical data |
| 53a | 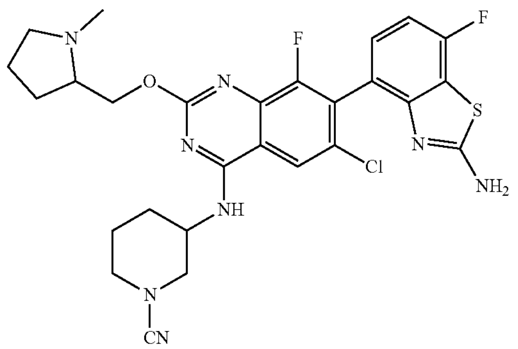 [SMILES: CN1CCCC1COc1nc(NC2CCCN(C#N)C2)c2cc(Cl)c(-c3ccc(F)c4sc(N)nc34)c(F)c2n1] | |
| 54 | 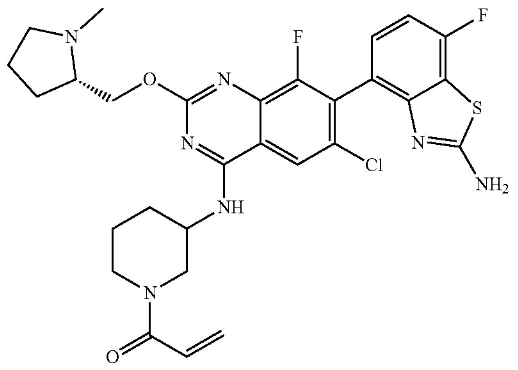 [SMILES: C=CC(=O)N1CCCC(Nc2nc(OC[C@@H]3CCCN3C)nc3c(F)c(-c4ccc(F)c5sc(N)nc45)c(Cl)cc23)C1] | LCMS m/z [M + 1]: 614.2 $^1$HNMR (400 MHz, $CD_3OD$): δ 8.31-8.35 (m, 1H), 7.22-7.28 (m, 1H), 7.01-7.08 (m, 1H), 6.81-6.88 (m, 1H), 6.23 (d, J = 15.58 Hz, 1H), 5.71-5.81 (m, 1H), 5.00-5.14 (m, 2H), 4.61-4.68 (m, 1H), 4.13-4.44 (m, 2H), 3.75-3.95 (m, 2H), 3.19-3.29 (m, 2H), 3.01-3.12 (m, 3H), 2.68-2.79 (m, 1H), 2.36-2.40 (m, 1H), 1.89-2.21 (m, 6H), 1.52-1.70 (m, 1H). |
| 54a | 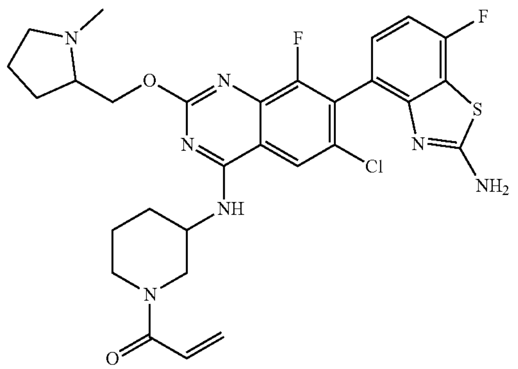 [SMILES: C=CC(=O)N1CCCC(Nc2nc(OCC3CCCN3C)nc3c(F)c(-c4ccc(F)c5sc(N)nc45)c(Cl)cc23)C1] | |
| 55 | 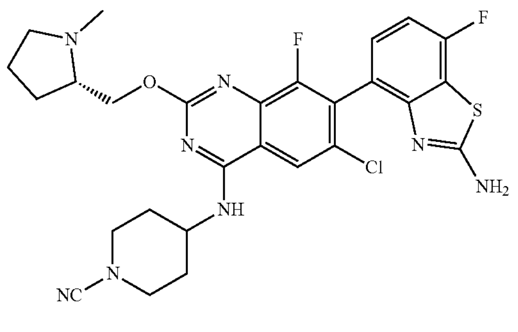 [SMILES: CN1CCC[C@H]1COc1nc(NC2CCN(C#N)CC2)c2cc(Cl)c(-c3ccc(F)c4sc(N)nc34)c(F)c2n1] | LCMS m/z [M + 1]: 585.3 $^1$HNMR (400 MHz, $CD_3OD$): δ 8.29 (s, 1H), 7.22-7.25 (m, 1H), 6.90-7.05 (m, 1H), 4.90-4.94 (m, 1H), 4.64 (dd, J = 11.2, 5.2 Hz, 1H), 4.39-4.49 (m, 1H), 3.80-3.89 (m, 1H), 3.65-3.75 (m, 1H), 3.50-3.61 (m, 2H), 3.15-3.25 (m, 2H), 3.08 (s, 3H), 2.30-2.39 (m, 1H), 2.03-2.18 (m, 6H), 1.85-1.94 (m, 1H). |

TABLE 2-continued
Selected compounds of the present disclosure.
| Compound No. | Structure | Analytical data |
|---|---|---|
| 55a | 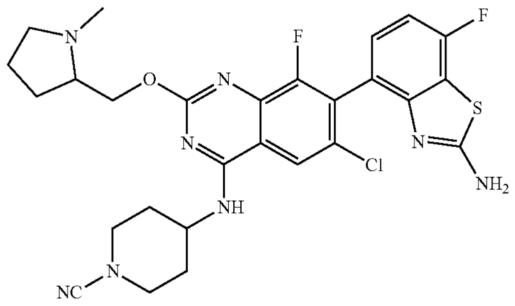 [SMILES: CN1CCCC1COc1nc(NC2CCN(C#N)CC2)c2cc(Cl)c(-c3ccc(F)c4sc(N)nc34)c(F)c2n1] | |
| 56 | 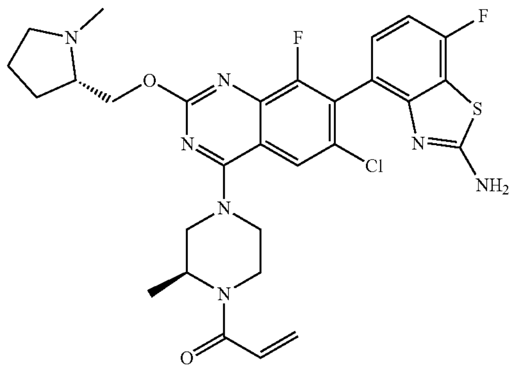 [SMILES: C=CC(=O)N1CCN(c2nc(OC[C@@H]3CCCN3C)nc3c(F)c(-c4ccc(F)c5sc(N)nc45)c(Cl)cc23)C[C@@H]1C] | LCMS m/z [M + 1]: 614.4 $^1H$ NMR (400 MHz, $CD_3OD$): δ 8.12 (s, 1H), 7.26 (dd, J = 8, 5.6 Hz, 1H), 7.04 (t, J = 9.2 Hz, 1H), 6.79 (dd, J = 16.4, 10.8 Hz, 1H), 6.27 (d, J = 16 Hz, 1H), 5.80 (d, J = 10.4 Hz, 1H), 4.66-4.71 (m, 1H), 4.30-4.48 (m, 3H), 3.73-4.02 (m, 6H), 3.08 (s, 3H), 2.03-2.41 (m, 5H), 1.34-1.45 (m, 3H). |
| 56a | 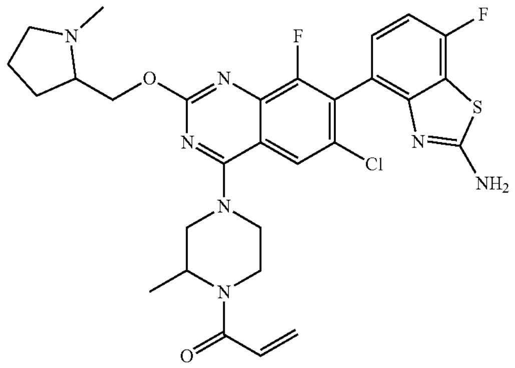 [SMILES: C=CC(=O)N1CCN(c2nc(OCC3CCCN3C)nc3c(F)c(-c4ccc(F)c5sc(N)nc45)c(Cl)cc23)CC1C] | |
| 57 | 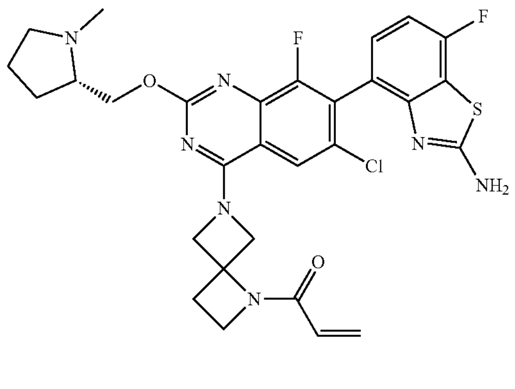 [SMILES: C=CC(=O)N1CCC12CN(c1nc(OC[C@@H]3CCCN3C)nc3c(F)c(-c4ccc(F)c5sc(N)nc45)c(Cl)cc13)C2] | LCMS m/z [M + 1]: 612.2 $^1$HNMR (400 MHz, $CD_3OD$): δ 7.90 (s, 1H), 7.23-7.26 (m, 1H), 7.03 (t, J = 8.8 Hz, 1H), 6.26-6.39 (m, 2H), 5.78-5.81 (dd, J = 2.4, 9.6 Hz, 1H), 5.43-5.54 (m, 1H), 5.07-5.19 (m, 2H), 4.92-4.96 (m, 2H), 4.64-4.70 (m, 1H), 4.25 (t, J = 8.0 Hz, 2H), 3.90 (s, 1H), 3.72 (s, 1H), 3.24-3.28 (m, 1H), 3.08 (s, 3H), 2.72 (t, J = 8.0 Hz, 2H), 2.36-2.43 (m, 1H), 2.04-2.24 (m, 3H). |

TABLE 2-continued
| Selected compounds of the present disclosure. | | |
|---|---|---|
| Compound No. | Structure | Analytical data |
| 57a | 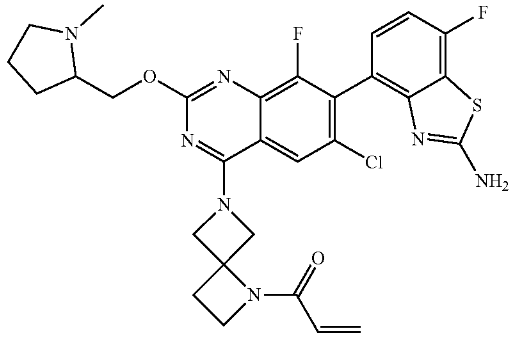 [SMILES: C=CC(=O)N1CCC12CN(c1nc(OCC3CCCN3C)nc3c(F)c(-c4ccc(F)c5sc(N)nc45)c(Cl)cc13)C2] | |
| 58 | 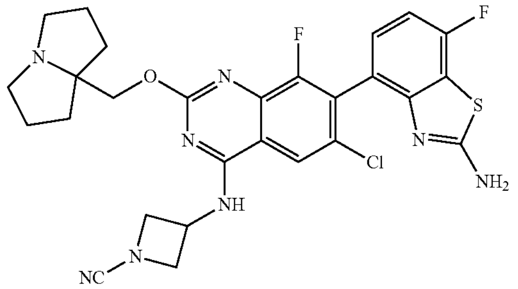 [SMILES: N#CN1CC(Nc2nc(OCC34CCCN3CCC4)nc3c(F)c(-c4ccc(F)c5sc(N)nc45)c(Cl)cc23)C1] | LCMS m/z [M + 1]: 583.3 $^1$HNMR (400 MHz, $CD_3OD$) δ 8.24 (s, 1H), 7.21 (dd, J = 8.4, 5.4 Hz, 1H), 7.00 (t, J = 8.8 Hz, 1H), 5.03-5.11 (m, 1H), 4.62-4.58 (m, 4H), 4.42 (dd, J = 6.4, 7.6 Hz, 2H), 3.59-3.65 (m, 2H), 3.25-3.12 (m, 2H), 2.26-2.36 (m, 2H), 2.15-2.25 (m, 2H), 2.06-2.23 (m, 4H). |
| 59 | 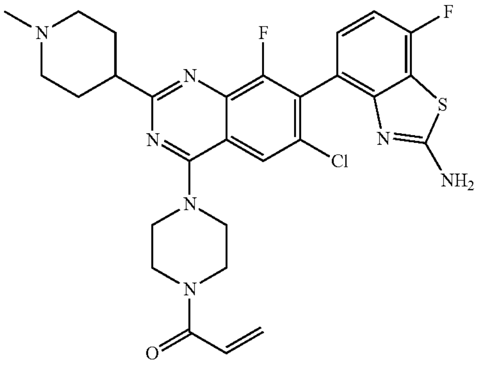 [SMILES: C=CC(=O)N1CCN(c2nc(C3CCN(C)CC3)nc3c(F)c(-c4ccc(F)c5sc(N)nc45)c(Cl)cc23)CC1] | LCMS m/z [M + 1]: 584.2 $^1$HNMR (400 MHz, $CD_3OD$) δ 8.00 (s, 1H), 7.23 (dd, J = 8.4, 5.5 Hz, 1H), 7.00 (t, J = 8.8 Hz, 1H), 6.76-6.89 (m, 1H), 6.28 (d, J = 16.8 Hz, 1H), 5.81 (d, J = 12.1 Hz, 1H), 3.81-4.10 (m, 8H), 3.31-3.50 (m, 3H), 3.01-3.16 (m, 1H), 2.86-3.00 (m, 1H), 2.74 (s, 3H), 2.10-2.33 (m, 4H). |
| 60 | 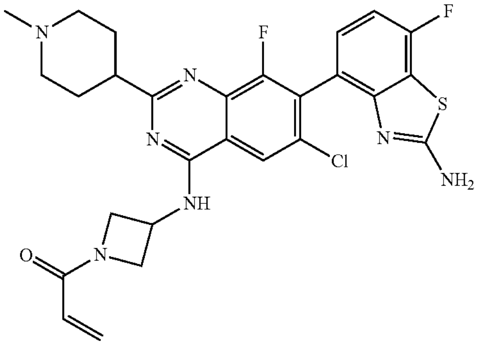 [SMILES: C=CC(=O)N1CC(Nc2nc(C3CCN(C)CC3)nc3c(F)c(-c4ccc(F)c5sc(N)nc45)c(Cl)cc23)C1] | LCMS m/z [M + 1]: 570.2 $^1$HNMR (400 MHz, $CD_3OD$): δ 8.23 (s, 1H), 7.20-7.24 (m, 1H), 6.99 (t, J = 8.8 Hz, 1H), 6.38-6.45 (m, 1H), 6.26-6.31 (m, 1H), 5.76-5.79 (dd, J = 10.4, 1.2 Hz, 1H), 4.98-5.05 (m, 1H), 4.80-4.84 (m, 1H), 4.51-4.55 (m, 1H), 4.34-4.37 (m, 1H), 4.19-4.22 (m, 1H), 3.02-3.06 (m, 2H), 2.77-2.84 (m, 1H), 2.37 (s, 3H), 2.21-2.23 (m, 2H), 2.06-2.14 (m, 2H), 1.89-1.97 (m, 2H). |

TABLE 2-continued
| Selected compounds of the present disclosure. | | |
|---|---|---|
| Compound No. | Structure | Analytical data |
| 61 | 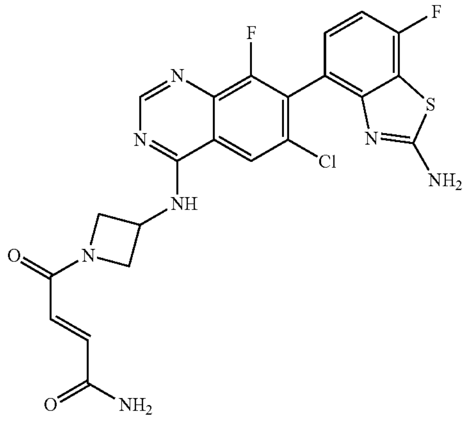 [SMILES: NC(=O)/C=C/C(=O)N1CC(Nc2ncnc3c(F)c(-c4ccc(F)c5sc(N)nc45)c(Cl)cc23)C1] | LCMS m/z [M + 1]: 516.0 $^1$HNMR (700 MHz, $CD_3CN$) δ 8.77 (s, 1H), 8.71 (s, 1H), 8.31 (s, 1H), 7.51 (s, 2H), 7.43 (dd, J = 8.5, 5.2 Hz, 1H), 7.19 (t, J = 8.8 Hz, 1H), 6.94-6.84 (m, 2H), 6.59 (s, 1H), 6.08 (s, 1H), 5.20-5.14 (m, 1H), 4.79 (t, J = 8.7 Hz, 1H), 4.52-4.42 (m, 2H), 4.26-4.17 (m, 1H). |
| 62 | 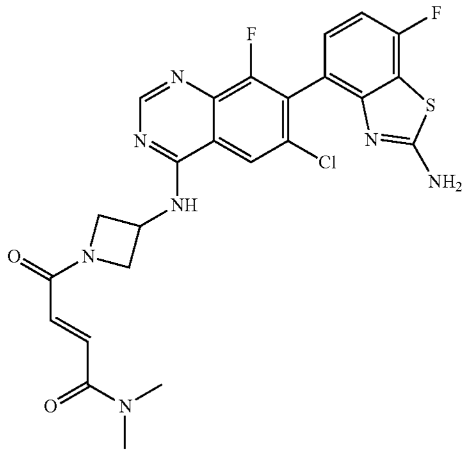 [SMILES: CN(C)C(=O)/C=C/C(=O)N1CC(Nc2ncnc3c(F)c(-c4ccc(F)c5sc(N)nc45)c(Cl)cc23)C1] | LCMS m/z [M + 1]: 544.1 $^1$HNMR (700 MHz, $CD_3S(O)CD_3$) δ 8.96 (d, J = 6.1 Hz, 1H), 8.58 (s, 1H), 8.45 (s, 1H), 7.94 (d, J = 3.8 Hz, 2H), 7.30-7.25 (m, 2H), 7.10-7.05 (m, 1H), 6.81 (dd, J = 15.0, 6.3 Hz, 1H), 5.05-4.97 (m, 1H), 4.74 (t, J = 8.5 Hz, 1H), 4.41-4.36 (m, 1H), 4.36-4.29 (m, 1H), 4.15-4.08 (m, 1H), 3.08 (d, J = 1.5 Hz, 3H), 2.92 (d, J = 1.4 Hz, 3H). |
| 63 | 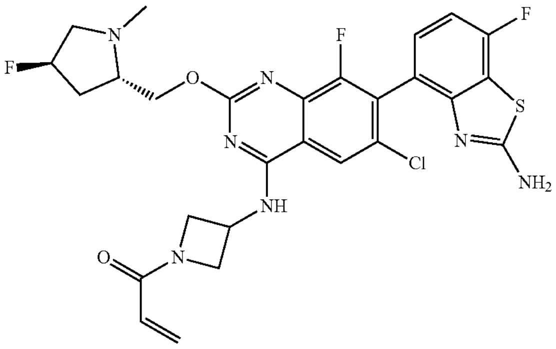 [SMILES: C=CC(=O)N1CC(Nc2nc(OC[C@@H]3C[C@@H](F)CN3C)nc3c(F)c(-c4ccc(F)c5sc(N)nc45)c(Cl)cc23)C1] | LCMS m/z [M + 1]: 604.1 $^1$HNMR (400 MHz, $CD_3OD$): δ: 8.29 (s, 1H), 7.23-7.27 (m, 1H), 7.01-7.06 (m, 1H), 6.27-6.43 (m, 2H), 5.80 (dd, J = 10.4 Hz, 1.6 Hz, 1H), 5.40-5.53 (m, 1H), 4.96-5.04 (m, 2H), 4.67-4.80 (m, 2H), 4.43-4.54 (m, 2H), 4.23-4.24 (m, 2H), 3.98-4.09 (m, 2H), 3.61-3.70 (m, 1H), 3.17 (s, 3H), 2.62-2.71 (m, 1H), 2.32-2.45 (m, 1H) |

TABLE 2-continued
| Selected compounds of the present disclosure. | | |
|---|---|---|
| Compound No. | Structure | Analytical data |
| 63a | 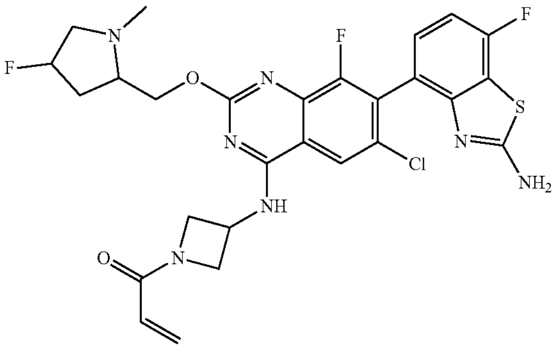 [SMILES: C=CC(=O)N1CC(Nc2nc(OCC3CC(F)CN3C)nc3c(F)c(-c4ccc(F)c5sc(N)nc45)c(Cl)cc23)C1] | |
| 64 | 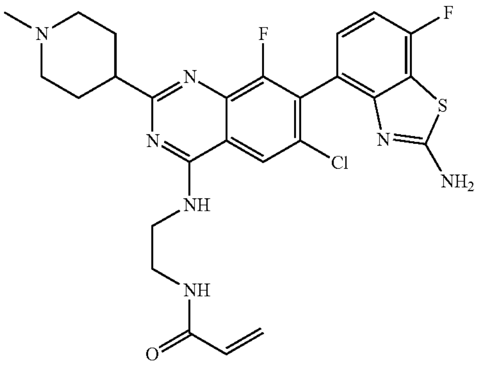 [SMILES: C=CC(=O)NCCNc1nc(C2CCN(C)CC2)nc2c(F)c(-c3ccc(F)c4sc(N)nc34)c(Cl)cc12] | LCMS m/z [M + 1]: 558.3<br>$^1$HNMR (400 MHz, $CD_3OD$): δ 8.11 (s, 1H), 7.21 (dd, J = 8.4 Hz, 5.2 Hz , 1H), 6.99 (t, J = 8.8 Hz, 1H), 6.22-6.24 (m, 2H), 5.67 (dd, J = 6.8, 4.8, 1H), 3.80-3.84 (m, 2H), 3.60-3.64 (m, 2H), 3.44-3.47 (m, 3H), 2.98-3.10 (m, 3H), 2.78 (s, 3H), 2.15-2.28 (m, 4H). |
| 65 | 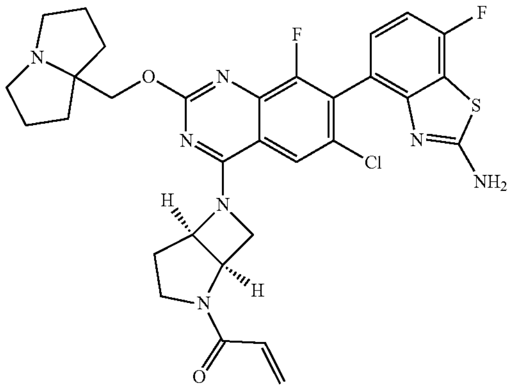 [SMILES: C=CC(=O)N1CC[C@@H]2[C@H]1CN2c1nc(OCC23CCCN2CCC3)nc2c(F)c(-c3ccc(F)c4sc(N)nc34)c(Cl)cc12] | LCMS m/z [M + 1]: 638.3<br>$^1$HNMR (400 MHz, $CD_3OD$): δ 7.86 (s, 1H), 7.20-7.23 (m, 1H), 7.00-7.03 (m, 1H), 6.60-6.78 (m, 1H), 6.33-6.38 (m, 1H), 5.85 (dd, J = 10.4 Hz, 1.6Hz, 1H), 4.86-5.08 (m, 2H), 4.52-4.68 (m, 4H), 4.23-4.35 (m, 2H), 3.64-3.98 (m, 4H), 2.55-2.67 (m, 2H), 2.07-2.33 (m, 8H). |
| 65a | 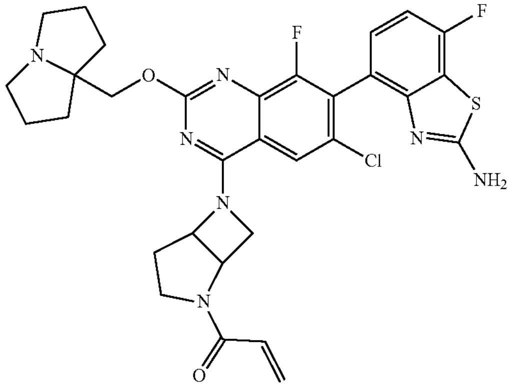 [SMILES: C=CC(=O)N1CCC2C1CN2c1nc(OCC23CCCN2CCC3)nc2c(F)c(-c3ccc(F)c4sc(N)nc34)c(Cl)cc12] | |

TABLE 2-continued
Selected compounds of the present disclosure.
| Compound No. | Structure | Analytical data |
|---|---|---|
| 66 | 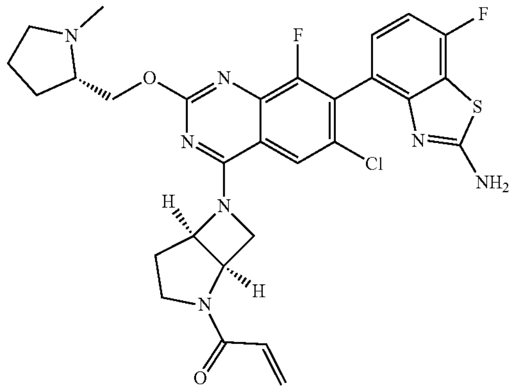 [SMILES: C=CC(=O)N1CC[C@@H]2[C@H]1CN2c1nc(OC[C@@H]2CCCN2C)nc2c(F)c(-c3ccc(F)c4sc(N)nc34)c(Cl)cc12] | LCMS m/z [M + 1]: 612.3<br>$^1$HNMR (400 MHz, $CD_3OD$): δ: 7.81 (s, 1H), 7.18-7.21 (m, 1H), 6.96-7.00 (m, 1H), 6.71-6.96 (m, 1H), 6.32-6.37 (m, 1H), 5.80 (d, J = 14.4 Hz, 1H), 5.45-5.70 (m, 1H), 5.00-5.04 (m, 1H), 4.49-4.63 (m, 3H), 4.21-4.34 (m, 1H), 3.69-3.97 (m, 2H), 3.37-3.39 (m, 2H), 2.79 (s, 4H), 2.54-2.65 (m, 1H), 2.17-2.27 (m, 2H), 1.89-2.02 (m, 3H). |
| 66a | 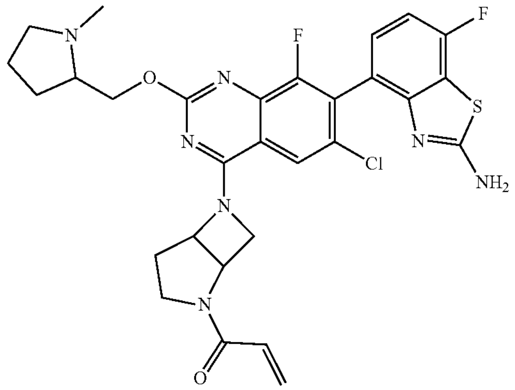 [SMILES: C=CC(=O)N1CCC2C1CN2c1nc(OCC2CCCN2C)nc2c(F)c(-c3ccc(F)c4sc(N)nc34)c(Cl)cc12] | |
| 67 | 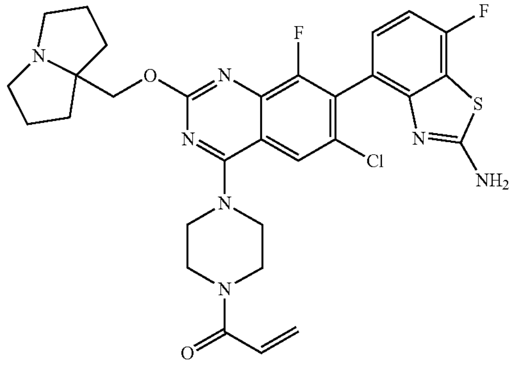 [SMILES: C=CC(=O)N1CCN(c2nc(OCC34CCCN3CCC4)nc3c(F)c(-c4ccc(F)c5sc(N)nc45)c(Cl)cc23)CC1] | LCMS m/z [M + 1]: 626.3<br>$^1$HNMR (400 MHz, $CD_3OD$): δ 8.01 (s, 1H), 7.23-7.27 (m, 1H), 7.03 (t, J = 8.8 Hz, 1H), 6.81-6.88 (m, 1H), 6.29-6.34 (m, 1H), 5.83-5.86 (dd, J = 1.6,10.4 Hz, 1H), 4.49 (s, 2H), 4.07 (s, 4H), 3.95 (s, 4H), 3.39-3.44 (m, 2H), 3.00-3.06 (m, 2H), 2.19-2.25 (m, 2H), 1.92-2.14 (m, 6H). |
| 68 | 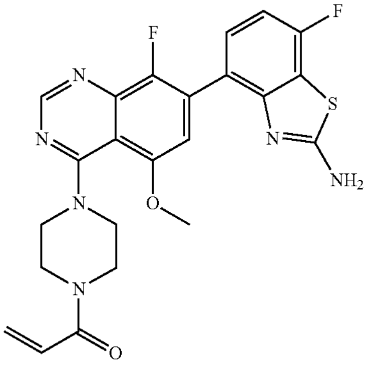 [SMILES: C=CC(=O)N1CCN(c2ncnc3c(F)c(-c4ccc(F)c5sc(N)nc45)cc(OC)c23)CC1] | LCMS m/z [M + 1]: 483.3<br>$^1$HNMR (400 MHz, $CD_3OD$): δ 8.58 (s, 1H), 7.46-4.79 (m, 2H), 7.03 (t, J = 8.8 Hz, 1H), 6.82 (dd, J = 16.8, 10.74 Hz, 1H), 6.31 (d, J = 16.8 Hz, 1H), 5.82(d, J = 12 Hz, 1H), 4.01-4.31 (m, 7H), 3.81-4.00 (m, 4H). |

TABLE 2-continued

Selected compounds of the present disclosure.

| Compound No. | Structure | Analytical data |
| --- | --- | --- |
| 69 | 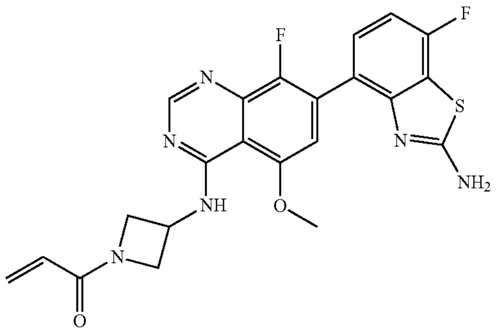 [SMILES: C=CC(=O)N1CC(Nc2ncnc3c(F)c(-c4ccc(F)c5sc(N)nc45)cc(OC)c23)C1] | LCMS m/z [M + 1]: 469.0<br>$^1$HNMR (400 MHz, $CD_3OD$): δ 8.75 (s, 1H), 7.53 (d, J = 5.2 Hz, 1H), 7.46 (t, J = 6.4 Hz, 1H), 7.03 (t, J = 8.8 Hz, 1H), 6.26-6.42 (m, 2H), 5.78 (dd, J = 10 and 2 Hz, 1H), 5.23 (m, 1H), 4.76-4.80 (m, 1H), 4.51-4.55 (m, 2H), 4.27 (dd, J = 10.8 and 4.8 Hz, 1H), 4.19 (s, 3H). |
| 70 | 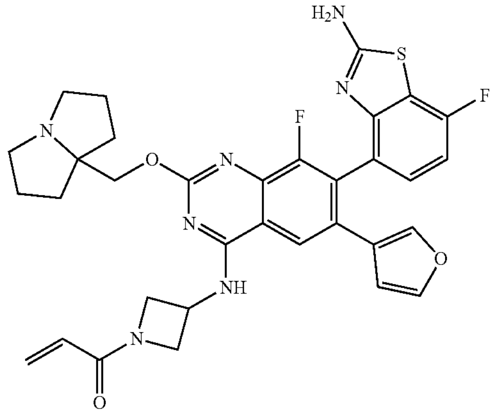 [SMILES: C=CC(=O)N1CC(Nc2nc(OCC34CCCN3CCC4)nc3c(F)c(-c4ccc(F)c5sc(N)nc45)c(-c4ccoc4)cc23)C1] | LCMS m/z [M + 1]: 644.4<br>$^1$HNMR (400 MHz, $CD_3OD$) δ 8.28 (s, 1H), 7.35 (s, 1H), 7.13 (dd, J = 8.4, 5.2 Hz, 1H), 7.05 (s, 1H), 6.98 (t, J = 8.9 Hz, 1H), 6.39-6.45 (m, 1H), 6.28-6.32 (m, 1H), 6.26 (s, 1H), 5.79 (dd, J = 10.2 and 1.84 Hz, 1H), 5.08-5.15 (m, 1H), 4.72-4.80 (m, 2H), 4.65-4.73 (m, 3H), 4.50-4.56 (m, 2H), 4.32 (dd, J = 10.9, 5.4 Hz, 1H), 3.67-3.72 (m, 2H), 2.08-2.38 (m, 8H). |
| 71 | 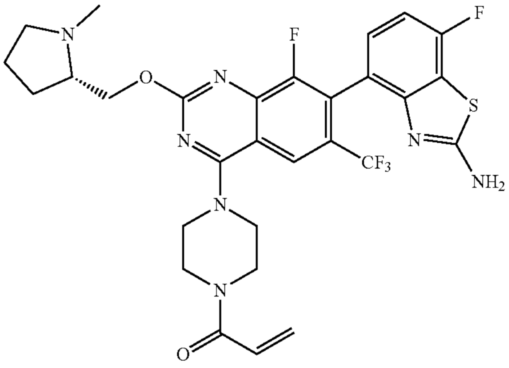 [SMILES: C=CC(=O)N1CCN(c2nc(OC[C@@H]3CCCN3C)nc3c(F)c(-c4ccc(F)c5sc(N)nc45)c(C(F)(F)F)cc23)CC1] | LCMS m/z [M + 1]: 634.2<br>$^1$HNMR (300 MHz, $CD_3OD$) δ 8.22 (s, 1H), 7.39-7.09 (m, 1H), 6.98 (t, J = 8.8 Hz, 1H), 6.84 (dd, J = 16.6, 10.5 Hz, 1H), 6.30 (d, J = 16.6 Hz, 1H), 5.83 (d, J = 10.6 Hz, 1H), 4.55 (s, 2H), 4.11 (s, 4H), 3.95 (s, 4H), 3.20 (m, 1H), 2.98 (m, 1H), 2.59 (s, 3H), 2.55-2.32 (m, 1H), 2.18 (m, 1H), 2.05-1.65 (m, 3H). |
| 71a | 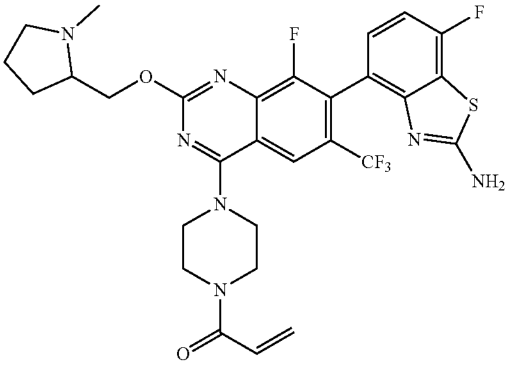 [SMILES: C=CC(=O)N1CCN(c2nc(OCC3CCCN3C)nc3c(F)c(-c4ccc(F)c5sc(N)nc45)c(C(F)(F)F)cc23)CC1] | |

TABLE 2-continued
| Selected compounds of the present disclosure. | | |
|---|---|---|
| Compound No. | Structure | Analytical data |
| 72 | 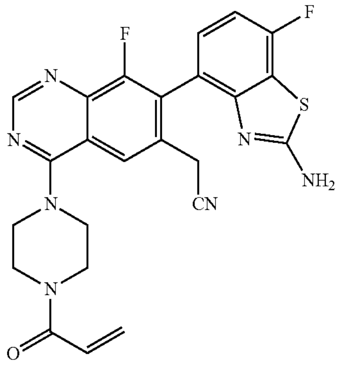 [SMILES: C=CC(=O)N1CCN(c2ncnc3c(F)c(-c4ccc(F)c5sc(N)nc45)c(CC#N)cc23)CC1] | LCMS m/z [M + 1]: 492.0 $^1$HNMR (300 MHz, $CDCl_3$) δ 8.83 (s, 1H), 7.98 (s, 1H), 7.30-7.26 (m, 1H) 7.05 (t, J = 8.6 Hz, 1H), 6.62 (dd, J = 16.7, 10.5 Hz, 1H), 6.38 (dd, J = 16.7, 1.8 Hz, 1H), 5.79 (dd, J = 10.5, 1.9 Hz, 1H), 5.34 (s, 2H), 4.00-3.81 (m, 9H), 3.53 (d, J = 19.5 Hz, 1H). |
| 73 | 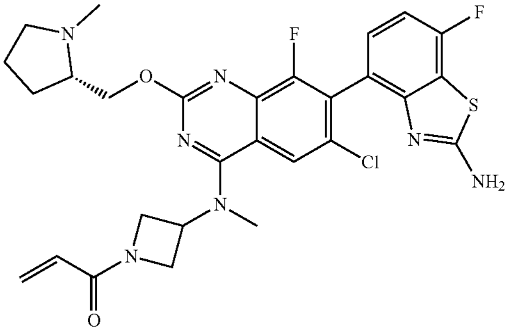 | LCMS m/z [M + 1]: 600.3 $^1$HNMR (400 MHz, $CD_3OD$): δ 8.13 (s, 1H), 7.23 (m, 1H), 7.02 (m, 1H), 6.41 (m, 1H), 6.29 (d, J = 16.8 Hz, 1H), 5.78 (d, J = 10.0 Hz, 1H), 7.73 (m, 2H), 4.70 (m, 1H), 4.63 (m, 1H), 4.46 (m, 2H), 4.24 (m, 1H), 3.88 (m, 1H), 3.73 (m 1H), 3.52 (s, 3H), 3.10 (m, 1H), 3.05 (s, 3H), 2.40 (m, 1H), 2.08-2.37 (m, 3H). |
| 73a | 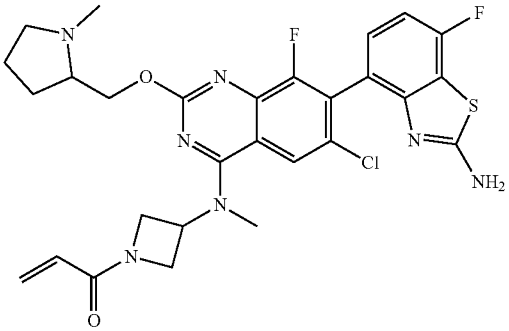 [SMILES: C=CC(=O)N1CC(N(C)c2nc(OC[C@@H]3CCCN3C)nc3c(F)c(-c4ccc(F)c5sc(N)nc45)c(Cl)cc23)C1] | |
| 74 | 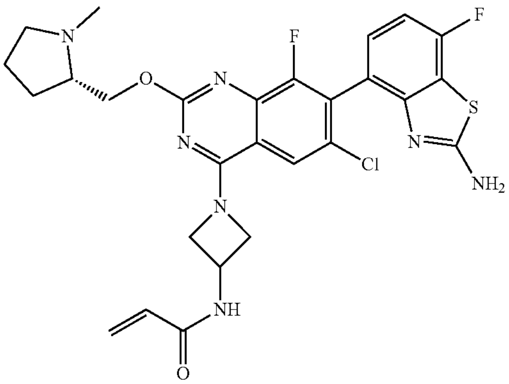 [SMILES: C=CC(=O)NC1CN(c2nc(OC[C@@H]3CCCN3C)nc3c(F)c(-c4ccc(F)c5sc(N)nc45)c(Cl)cc23)C1] | LCMS m/z [M + 1]: 586.3 $^1$HNMR (400 MHz, $CD_3OD$): δ 7.87 (s, 1H), 7.22-7.25 (m, 1H), 7.00-7.04 (m, 1H), 6.31 (d, J = 6.0 Hz, 2H), 5.75 (t, J = 6.0 Hz, 1H), 4.72-5.2 (m, 4 H) 4.63-4.69 (m, 2H), 3.89 (m, 1H), 3.66-3.81 (m, 1H), 3.21-3.32 (m, 2H), 3.07 (s, 3H), 2.36-2.42 (m, 1H), 2.03-2.21 (m, 3H). |

TABLE 2-continued
| Compound No. | Structure | Analytical data |
|---|---|---|
| | Selected compounds of the present disclosure. | |
| 74a | 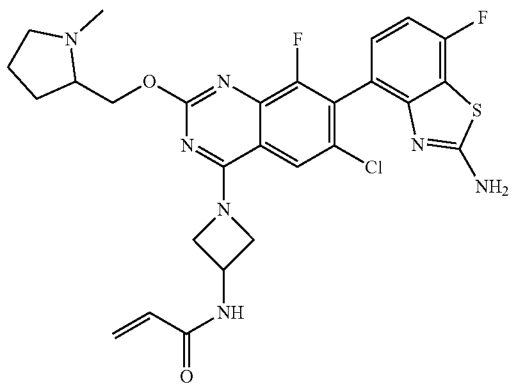 [SMILES: C=CC(=O)NC1CN(c2nc(OCC3CCCN3C)nc3c(F)c(-c4ccc(F)c5sc(N)nc45)c(Cl)cc23)C1] | |
| 75 | 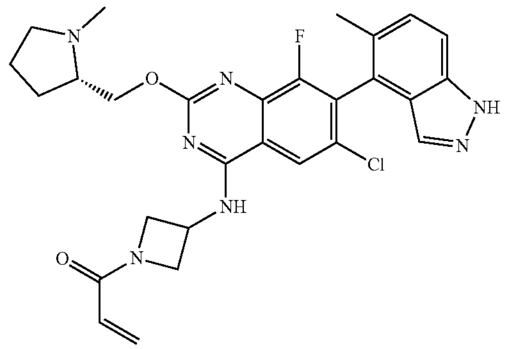 [SMILES: C=CC(=O)N1CC(Nc2nc(OC[C@@H]3CCCN3C)nc3c(F)c(-c4c(C)ccc5[nH]ncc45)c(Cl)cc23)C1] | LCMS m/z [M + 1]: 550.3 $^1$HNMR (400 MHz, $CD_3OD$): δ 8.36 (s, 1H), 7.59 (d, J = 8.8 Hz, 1H), 7.49 (s, 1H), 7.43 (d, J = 8.8 Hz, 1H), 6.27-6.42 (m, 2H), 5.79 (d, J = 8.4 Hz, 1H), 5.00-5.10 (m, 1H), 4.72-4.82 (m, 2H), 4.45-4.65 (m, 3H), 4.20-4.30 (m, 1H), 3.85-3.95 (m, 1H), 3.70-3.80 (m, 1H), 3.25-3.30 (m, 1H), 3.08 (s, 3H), 2.35-2.45 (m, 1H), 2.22 (s, 3H), 2.05-2.25 (m, 3H). |
| 75a | 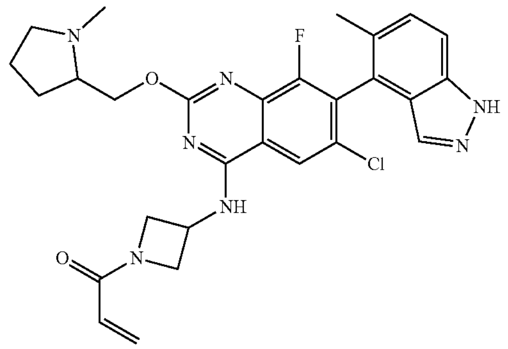 [SMILES: C=CC(=O)N1CC(Nc2nc(OCC3CCCN3C)nc3c(F)c(-c4c(C)ccc5[nH]ncc45)c(Cl)cc23)C1] | |
| 76 | 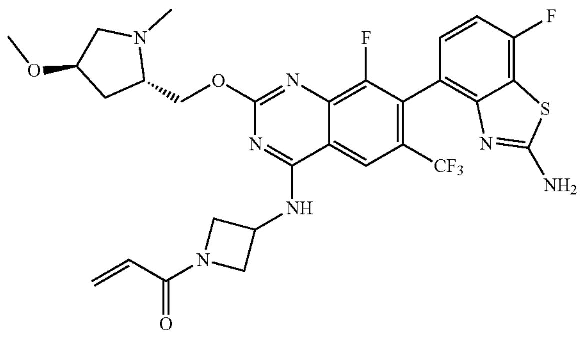 [SMILES: C=CC(=O)N1CC(Nc2nc(OC[C@@H]3C[C@@H](OC)CN3C)nc3c(F)c(-c4ccc(F)c5sc(N)nc45)c(C(F)(F)F)cc23)C1] | LCMS m/z [M + 1]: 650.2 $^1$HNMR (400 MHz, $CD_3OD$) δ 8.62 (s, 1H), 7.20-7.28 (m, 1H), 7.00 (t, J = 8.8 Hz, 1H), 6.35-6.44 (m, 1H), 6.25-6.33 (m, 1H), 5.79 (d, J = 11.9 Hz, 1H), 5.00-5.17 (m, 1H), 4.75-4.84 (m, 2H), 4.42-4.70 (m, 3H), 3.96-4.41 (m, 3H), 3.71-3.90 (m, 1H), 3.39 (s, 3H), 3.13 (s, 3H), 2.46-2.56 (m, 1H), 2.02-2.25 (m, 2H). |

TABLE 2-continued
| Selected compounds of the present disclosure. | | |
|---|---|---|
| Compound No. | Structure | Analytical data |
| 76a | 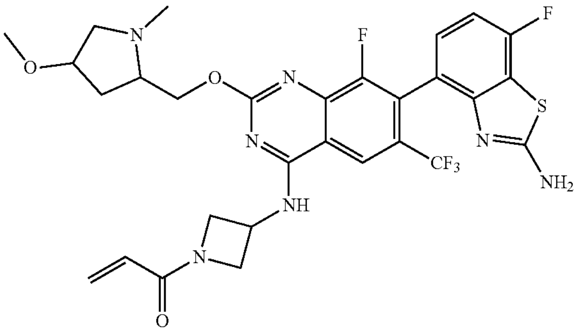 [SMILES: C=CC(=O)N1CC(Nc2nc(OCC3CC(OC)CN3C)nc3c(F)c(-c4ccc(F)c5sc(N)nc45)c(C(F)(F)F)cc23)C1] | |
| 77 | 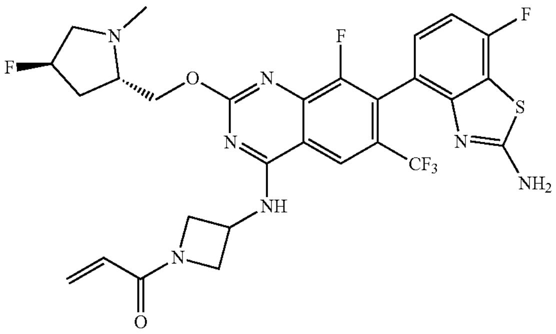 [SMILES: C=CC(=O)N1CC(Nc2nc(OC[C@@H]3C[C@@H](F)CN3C)nc3c(F)c(-c4ccc(F)c5sc(N)nc45)c(C(F)(F)F)cc23)C1] | LCMS m/z [M + 1]: 638.4 $^1$HNMR (400 MHz, $CD_3OD$) δ 8.62 (s, 1H), 7.19-7.26 (m, 1H), 6.99-7.03 (m, 1H), 6.37-6.44 (m, 1H), 6.29 (d, J = 19.2 Hz, 1H), 5.79 (d, J = 10.1 Hz, 1H), 5.46 (d, J = 52.4 Hz, 1H), 4.96-5.06 (m, 2H), 4.68-4.81(m, 2H), 4.47-4.55 (m, 2H), 4.20-4.30 (m, 2H), 3.95-4.12 (m, 1H), 3.59-3.70 (m, 1H), 3.17 (s, 3H), 2.58-2.75 (m, 1H), 2.25-2.46 (m, 1H). |
| 77a | 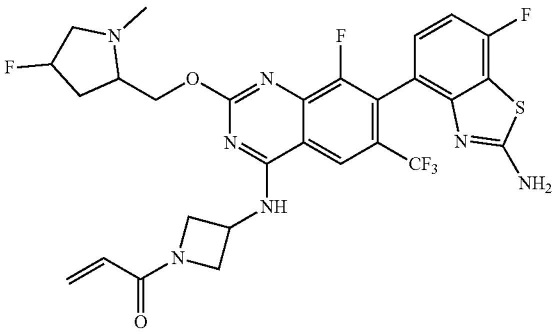 [SMILES: C=CC(=O)N1CC(Nc2nc(OCC3CC(F)CN3C)nc3c(F)c(-c4ccc(F)c5sc(N)nc45)c(C(F)(F)F)cc23)C1] | |
| 78 | 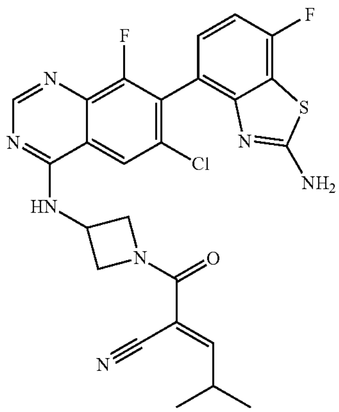 [SMILES: CC(C)/C=C(\C#N)C(=O)N1CC(Nc2ncnc3c(F)c(-c4ccc(F)c5sc(N)nc45)c(Cl)cc23)C1] | LCMS m/z [M + 1]: 540.1 $^1$HNMR (700 MHz, $CD_3S(O)CD_3$) δ 8.95 (d, J = 5.6 Hz, 1H), 8.58 (s, 1H), 8.45 (s, 1H), 7.95 (s, 2H), 7.33-7.24 (m, 2H), 7.08 (t, J = 8.7 Hz, 1H), 4.95 (s, 1H), 4.85 (t, J = 8.4 Hz, 1H), 4.51-4.39 (m, 2H), 4.19-4.08 (m, 1H), 2.82 (s, 1H), 1.13-1.08 (m, 6H). |

TABLE 2-continued
| Selected compounds of the present disclosure. | | |
|---|---|---|
| Compound No. | Structure | Analytical data |
| 79 | 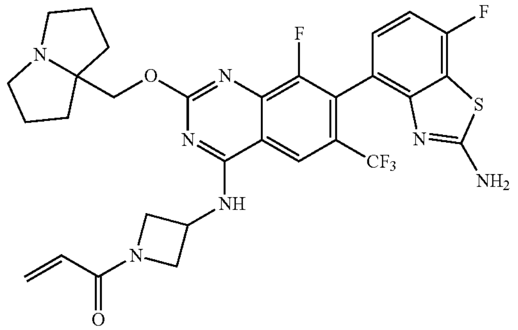 [SMILES: C=CC(=O)N1CC(Nc2nc(OCC34CCCN3CCC4)nc3c(F)c(-c4ccc(F)c5sc(N)nc45)c(C(F)(F)F)cc23)C1] | LCMS m/z [M + 1]: 646.4<br>$^1$HNMR (400 MHz, $CD_3OD$) δ 8.60 (s, 1H), 7.21 (dd, J = 8.1, 5.5 Hz, 1H), 7.00 (t, J = 8.8 Hz, 1H), 6.38-6.45 (m, 1H), 6.27-6.32 (m, 1H), 5.79 (dd, J = 10.2, 1.8 Hz, 1H), 5.03-5.10 (m, 1H), 4.76-4.80 (m, 3H), 4.64 (s, 2H), 4.48-4.55 (m, 2H), 4.29 (dd, J = 10.7, 5.4 Hz, 1H), 3.65-3.72 (m, 2H), 2.06-2.47 (m, 8H). |
| 80 | 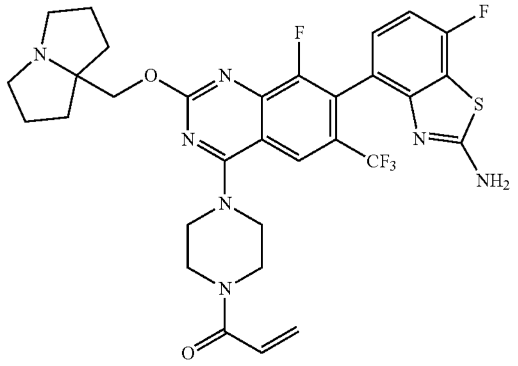 | LCMS m/z [M + 1]: 660.4<br>$^1$HNMR (400 MHz, $CD_3OD$) δ 8.27 (s, 1H), 7.24 (dd, J = 8.1, 5.6 Hz, 1H), 7.02 (t, J = 8.8 Hz, 1H), 6.81 (dd, J = 16.8, 10.4 Hz, 1H), 6.30 (dd, J = 16.8, 1.6 Hz, 1H), 5.82 (dd, J = 10.6, 1.6 Hz, 1H), 4.68 (s, 2H), 4.11-4.31 (m, 4H), 3.84-4.10 (m, 4H), 3.68-3.70 (m, 2H), 3.26-3.31 (m, 2H), 2.09-2.35 (m, 8H) |
| 81 | 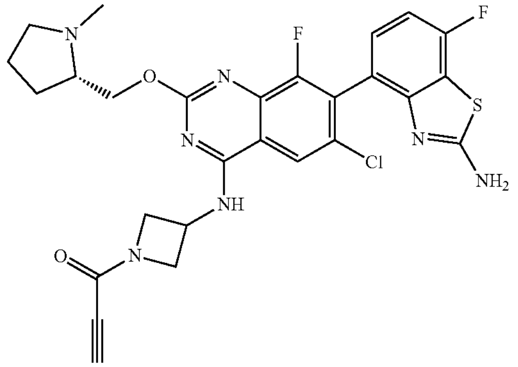 [SMILES: C#CC(=O)N1CC(Nc2nc(OCC3CCCN3C)nc3c(F)c(-c4ccc(F)c5sc(N)nc45)c(Cl)cc23)C1] | LCMS m/z [M + 1]: 584.2<br>$^1$HNMR (400 MHz, $CD_3OD$): 8.30 (s, 1H), 7.25 (t, J = 5.6, Hz, 1H), 7.03 (t, J = 8.8, Hz, 1H), 5.03-5.22 (m, 2H), 4.61-4.86 (m, 3H), 4.45-4.58 (m, 2H), 4.21-4.30 (m, 1H), 3.98 (s, 1H), 3.87-3.95 (m, 2H), 3.09 (s, 3H), 2.21-2.42 (m, 1H), 2.02-2.30 (m, 3H). |
| 81a | 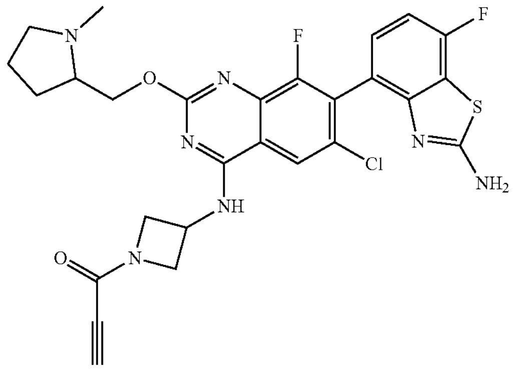 | |

TABLE 2-continued

| Selected compounds of the present disclosure. | | |
|---|---|---|
| Compound No. | Structure | Analytical data |
| 82 | 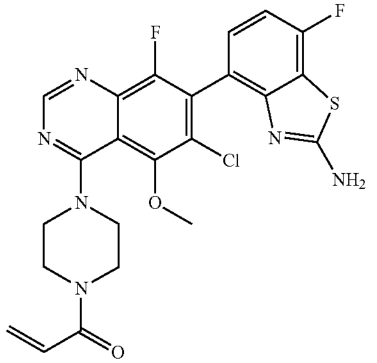 [SMILES: C=CC(=O)N1CCN(c2ncnc3c(F)c(-c4ccc(F)c5sc(N)nc45)c(Cl)c(OC)c23)CC1] | LCMS m/z [M + 1]: 517.3<br>$^1$HNMR (400 MHz, $CD_3OD$): δ 8.60 (s, 1 H), 7.23-7.26 (m, 1 H), 6.99-7.03 (m, 1 H), 6.80-6.87 (m, 1H), 6.24-6.28 (m, 1H), 5.78-5.81 (m, 1H), 3.77-3.88 (m, 11H). |
| 83 | 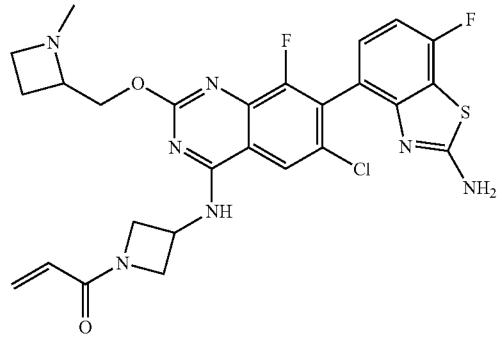 [SMILES: C=CC(=O)N1CC(Nc2nc(OCC3CCN3C)nc3c(F)c(-c4ccc(F)c5sc(N)nc45)c(Cl)cc23)C1] | LCMS m/z [M + 1]: 572.3<br>$^1$HNMR (400 MHz, $CD_3OD$) δ 8.35 (s, 1H), 7.18-7.30 (m, 1H), 6.96-7.05 (m, 1H), 6.24-6.45 (m, 2H), 5.79 (dd, J = 10.1, 2.1 Hz, 1H), 4.98-5.12 (m, 1H), 4.73-4.83 (m, 1H), 4.38-4.67 (m, 4H), 4.20-4.33 (m, 1H), 3.74-3.96 (m, 3H), 3.46 (s, 3H), 2.16-2.41 (m, 2H). |
| 84 | 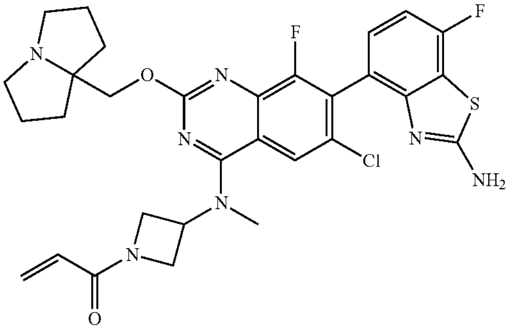 [SMILES: C=CC(=O)N1CC(N(C)c2nc(OCC34CCCN3CCC4)nc3c(F)c(-c4ccc(F)c5sc(N)nc45)c(Cl)cc23)C1] | LCMS m/z [M + 1]: 626.3<br>$^1$HNMR (400 MHz, $CD_3OD$) δ 8.11 (s, 1H), 7.25 (dd, J = 8.3, 5.4 Hz, 1H), 7.03 (t, J = 8.8 Hz, 1H), 6.42 (m, 1H), 6.27-6.33 (m, 1H), 5.79 (d, J = 10.6 Hz, 1H), 4.85-4.97 (m, 3H), 4.42-4.73 (m, 5H), 4.14-4.30 (m, 1H), 3.62-3.73 (m, 2H), 3.52 (s, 3H), 2.02-2.37 (m, 8H) |
| 85 | 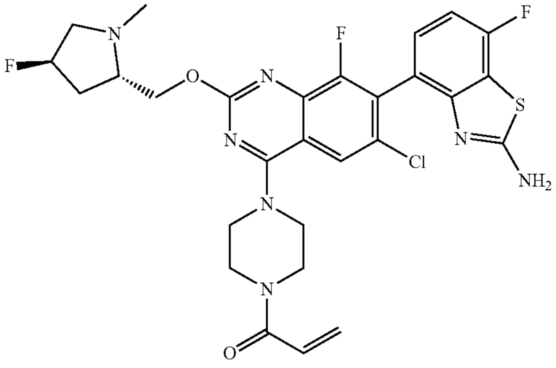 [SMILES: C=CC(=O)N1CCN(c2nc(OC[C@@H]3C[C@@H](F)CN3C)nc3c(F)c(-c4ccc(F)c5sc(N)nc45)c(Cl)cc23)CC1] | LCMS m/z [M + 1]: 618.0<br>$^1$HNMR (400 MHz, $CD_3OD$) δ 8.05 (s, 1H), 7.20-7.35 (m, 1H), 7.04 (td, J = 9.1, 1.8 Hz, 1H), 6.81 (dd, J = 16.8, 10.6 Hz, 1H), 6.29 (dd, J = 16.8, 1.6 Hz, 1H), 5.82 (dd, J = 10.7, 1.6 Hz, 1H), 5.47 (d, J = 51.9 Hz, 1H), 4.95-5.03 (m, 1H), 4.69-4.78 (m, 1H), 4.25 (s, 1H), 3.88-4.41 (m, 9H), 3.60-3.72 (m, 1H), 3.18 (s, 3H), 2.52-2.70 (m, 1H), 2.30-2.49 (m, 1H). |

TABLE 2-continued
| Compound No. | Structure | Analytical data |
|---|---|---|
| | Selected compounds of the present disclosure. | |
| 85a | 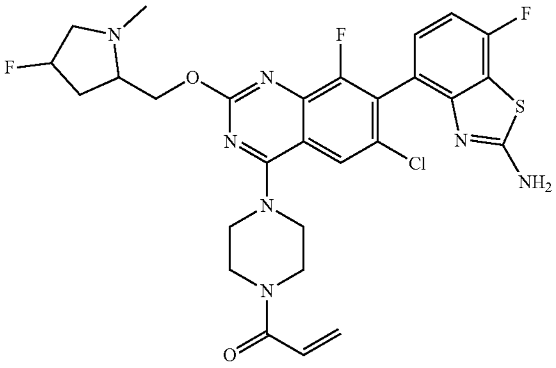 [SMILES: C=CC(=O)N1CCN(c2nc(OCC3CC(F)CN3C)nc3c(F)c(-c4ccc(F)c5sc(N)nc45)c(Cl)cc23)CC1] | |
| 86 | 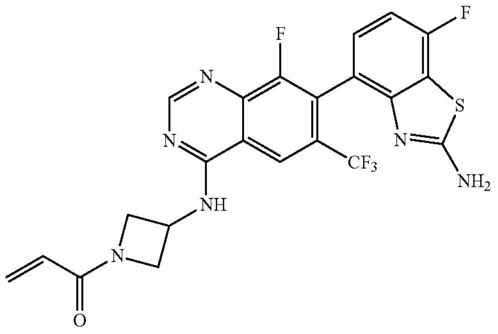 [SMILES: C=CC(=O)N1CC(Nc2ncnc3c(F)c(-c4ccc(F)c5sc(N)nc45)c(C(F)(F)F)cc23)C1] | LCMS m/z [M + 1]: 506.99 $^1$HNMR (300 MHz, $CD_3OD$) δ 8.65 (s, 1H), 8.63 (s, 1H), 7.26-7.17 (m, 1H), 6.98 (t, J = 8.9 Hz, 1H), 6.40 (dd, J = 17.0, 10.1 Hz, 1H), 6.28 (dd, J = 16.8, 2.4 Hz, 1H), 5.77 (dd, J = 10.4, 2.1 Hz, 1H), 5.15-5.04 (m, 1H), 4.79 (t, J = 9.2 Hz, 1H), 4.53 (dd, J = 10.5, 9.2 Hz, 1H), 4.39 (dd, J = 9.7, 5.2 Hz, 1H), 4.24 (dd, J = 11.2, 5.2 Hz, 1H). |
| 87 | 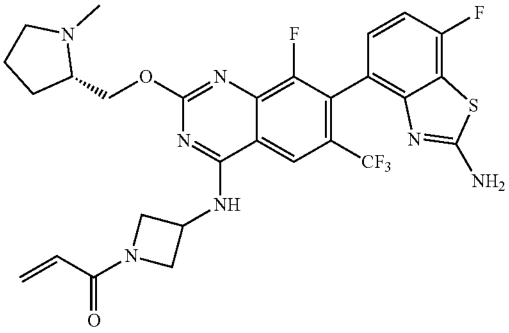 [SMILES: C=CC(=O)N1CC(Nc2nc(OC[C@@H]3CCCN3C)nc3c(F)c(-c4ccc(F)c5sc(N)nc45)c(C(F)(F)F)cc23)C1] | LCMS m/z [M + 1]: 620.26 $^1$HNMR (300 MHz, $CD_3OD$) δ 8.55 (s, 1H), 7.35-7.09 (m, 1H), 6.97 (t, J = 8.8 Hz, 1H), 6.49-6.11 (m, 2H), 5.79 (dd, J = 10.0, 2.1 Hz, 1H), 5.07 (dd, J = 12.0, 6.5 Hz, 1H), 4.81 (t, J = 8.6 Hz, 1H), 4.49 (m, 4H), 4.28 (m, 1H), 3.20-3.00 (m, 1H), 2.97-2.67 (m, 1H), 2.54 (s, 3H), 2.38 (q, J = 8.7 Hz, 1H), 2.26-2.01 (m, 1H), 1.81 (m, 3H). |
| 87a | 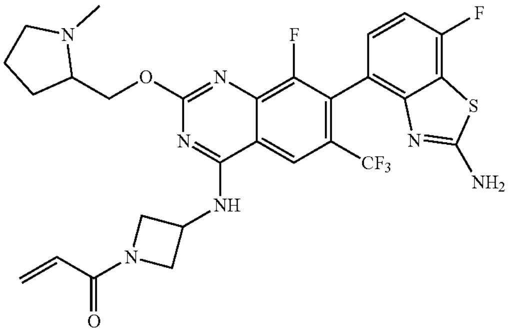 [SMILES: C=CC(=O)N1CC(Nc2nc(OCC3CCCN3C)nc3c(F)c(-c4ccc(F)c5sc(N)nc45)c(C(F)(F)F)cc23)C1] | |

TABLE 2-continued
| Selected compounds of the present disclosure. | | |
|---|---|---|
| Compound No. | Structure | Analytical data |
| 88 | 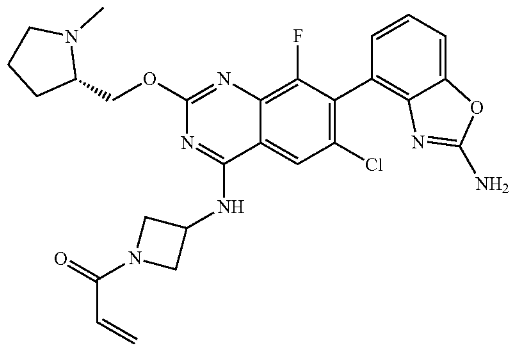 | LCMS m/z [M + 1]: 552.3<br>$^{1}$HNMR (400 MHz, $CD_3OD$): δ 8.28 (s, 1H), 7.44 (d, J = 7.6 Hz, 1H), 7.17-7.22 (m, 2H), 6.26-6.39 (m, 2H), 5.77-5.80 (m, 1H), 5.00-5.10 (m, 1H), 4.76-4.80 (m, 2H), 4.60-4.68 (m, 1H), 4.46-4.53 (m, 2H), 4.21-4.25 (m, 1H), 3.65-3.86 (m, 2H), 3.08(s, 3H), 2.36-2.40 (m, 1H), 2.07-2.20 (m, 3H). |
| 88a | 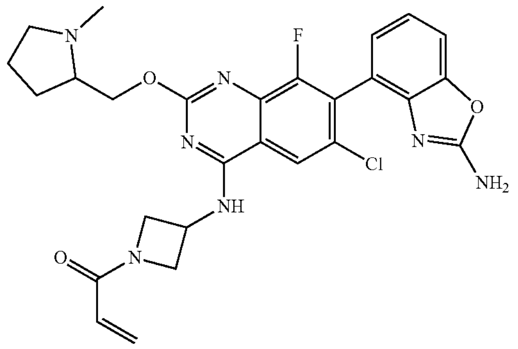 [SMILES: C=CC(=O)N1CC(Nc2nc(OC[C@@H]3CCCN3C)nc3c(F)c(-c4cccc5oc(N)nc45)c(Cl)cc23)C1] | |
| 89 | 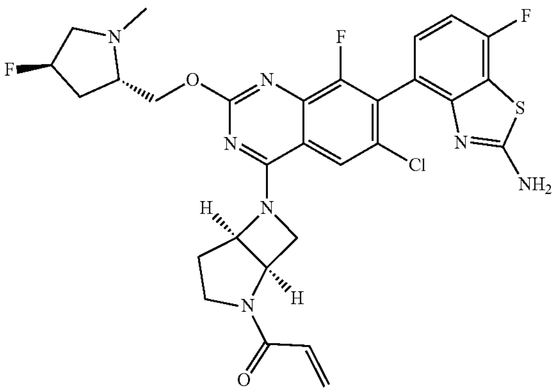 | LCMS m/z [M + 1]: 630.2<br>$^{1}$HNMR (400 MHz, $CD_3OD$): δ 7.86 (s, 1H), 7.16-7.28 (m, 1H), 6.98-7.02 (m, 1H), 6.60-6.79 (m, 1H), 6.33-6.38 (m, 1H), 5.78-5.90 (m, 1H), 4.93-5.07 (m, 4H), 4.67-4.72 (m, 1H), 4.52-4.56 (m, 1H), 4.24-4.43 (m, 2H), 3.91-4.10 (m, 2H), 3.60-3.80 (m, 2H), 3.16 (s, 3H), 2.56-2.70 (m, 2H), 2.16-2.44 (m, 2H). |
| 89a | 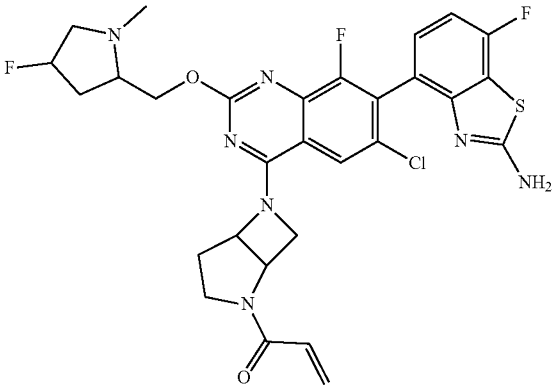 | |

TABLE 2-continued
Selected compounds of the present disclosure.
| Compound No. | Structure | Analytical data |
|---|---|---|
| 90 | 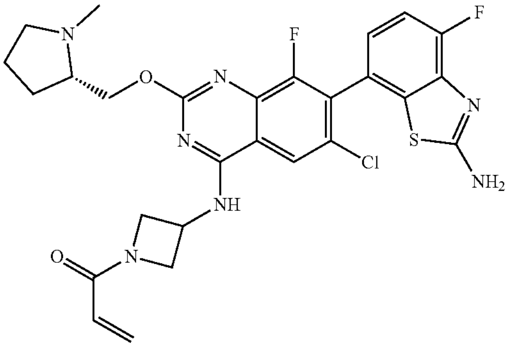 [SMILES: C=CC(=O)N1CC(Nc2nc(OC[C@@H]3CCCN3C)nc3c(F)c(-c4ccc(F)c5nc(N)sc45)c(Cl)cc23)C1] | LCMS m/z [M + 1]: 586.3<br>$^1$HNMR (400 MHz, $CD_3OD$): δ 8.31 (s, 1H), 7.20-7.24 (m, 1H), 7.03-7.05 (m, 1H), 6.37-6.44 (m, 2H), 5.80 (d, J = 9.6 Hz, 1H), 5.01-5.03 (m, 1H), 4.75-4.79 (m, 2H), 4.62-4.64 (m, 1H), 4.45-4.54 (m, 2H), 4.25-4.26 (m, 1H), 3.72-3.89 (m, 2H), 3.11-3.13 (m, 1H), 3.09 (s, 3H), 2.08-2.41 (m, 4H). |
| 90a | 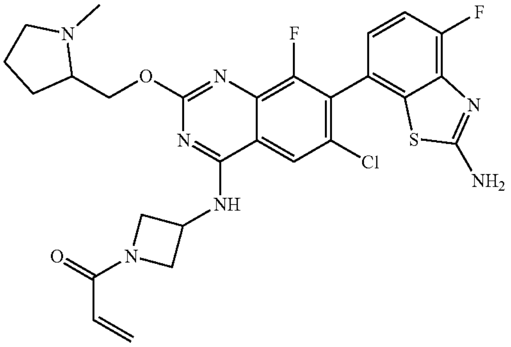 | |
| 91 | 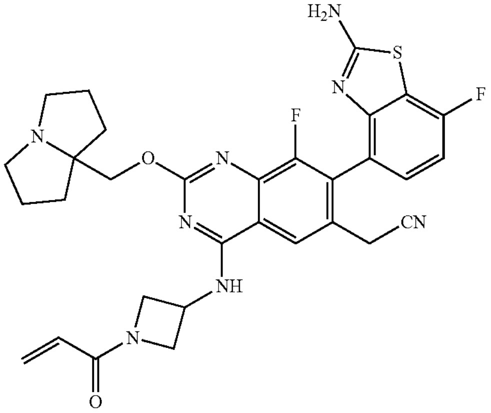 [SMILES: C=CC(=O)N1CC(Nc2nc(OCC34CCCN3CCC4)nc3c(F)c(-c4ccc(F)c5sc(N)nc45)c(CC#N)cc23)C1] | LCMS m/z [M + 1]: 617.3<br>$^1$HNMR (400 MHz, $CD_3OD$) δ 8.21 (s, 1H), 7.27 (dd, J = 8.3, 5.5 Hz, 1H), 7.04 (t, J = 8.8 Hz, 1H), 6.42 (dd, J = 16.9, 10.2 Hz, 1H), 6.26-6.36 (m, 1H), 5.76-5.83 (m, 1H), 5.05-5.16 (m, 1H), 4.77-4.83 (m, 1H), 4.62-4.72 (m, 2H), 4.49-4.57 (m, 2H), 4.28-4.37 (m, 1H), 3.75-3.86 (m, 2H), 3.65-3.74 (m, 2H), 3.26-3.29 (m, 2H), 2.29-2.39 (m, 2H), 2.18-2.27 (m, 2H), 2.05-2.18 (m, 4H). |
| 92 | 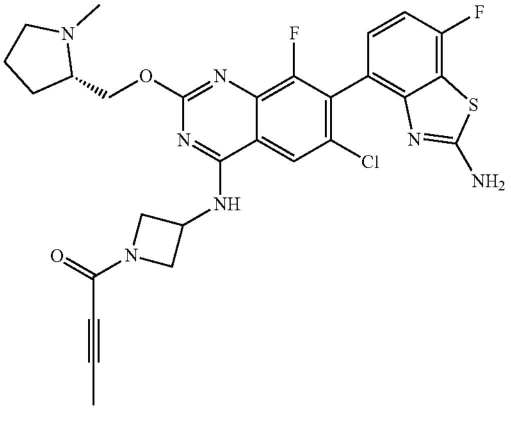 [SMILES: CC#CC(=O)N1CC(Nc2nc(OC[C@@H]3CCCN3C)nc3c(F)c(-c4ccc(F)c5sc(N)nc45)c(Cl)cc23)C1] | LCMS m/z [M + 1]: 598.3<br>$^1$HNMR (400 MHz, $CD_3OD$): 8.27 (s, 1H), 7.23 (t, J = 2.8, Hz, 1H), 7.0-7.05 (m, 1H), 5.03-5.15 (m, 1H), 4.61-4.85 (m, 2H), 4.35-4.42 (m, 2H), 4.16-4.22 (m, 1H), 3.70-3.88 (m, 2H), 3.30-3.40 (m, 2H), 3.15 (s, 3H), 2.20-2.45 (m, 4H), 2.04 (s, 3H). |

TABLE 2-continued
| Selected compounds of the present disclosure. | | |
|---|---|---|
| Compound No. | Structure | Analytical data |
| 92a | 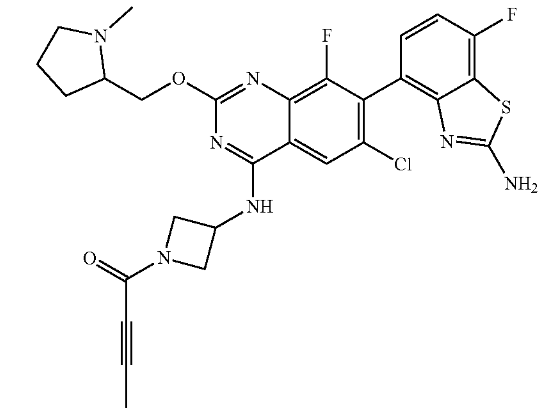 [SMILES: CC#CC(=O)N1CC(Nc2nc(OCC3CCCN3C)nc3c(F)c(-c4ccc(F)c5sc(N)nc45)c(Cl)cc23)C1] | |
| 93 | 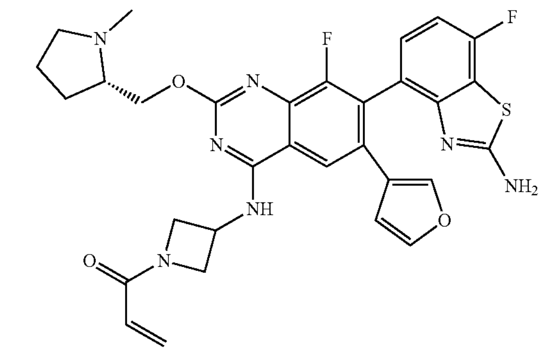 [SMILES: C=CC(=O)N1CC(Nc2nc(OCC3CCCN3C)nc3c(F)c(-c4ccc(F)c5sc(N)nc45)c(-c4ccoc4)cc23)C1] | LCMS m/z [M + 1]: 618.2 $^1H$ NMR (400 MHz, $CD_3OD$) δ 8.26 (s, 1H), 7.35 (s, 1H), 7.07-7.14 (m, 1H), 7.03 (s, 1H), 6.96 (t, J = 8.7 Hz, 1H), 6.37-6.46 (m, 1H), 6.32 (d, J = 1.5 Hz, 1H), 6.23-6.30 (m, 1H), 5.79 (dd, J = 10.0, 1.5 Hz, 1H), 5.10 (dt, J = 16.7, 6.3 Hz, 2H), 4.75-4.85 (m, 3H), 4.61-4.70 (m, 1H), 4.45-4.58 (m, 2H), 4.23-4.33 (m, 1H), 3.89-3.92 (m, 1H), 3.67-3.77 (m, 1H), 3.10 (s, 3H), 2.44-2.38 (m, 2H), 2.19-2.22 (m, 2H), 2.01-2.15 (m, 3H). |
| 93a | 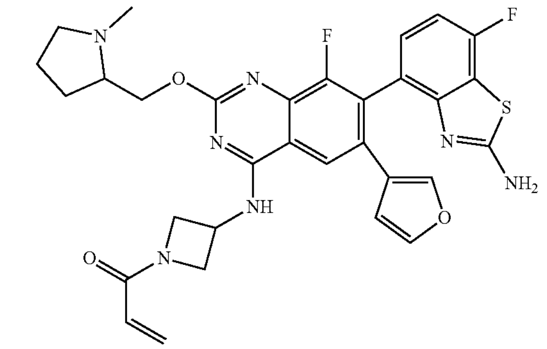 | |
| 94 | 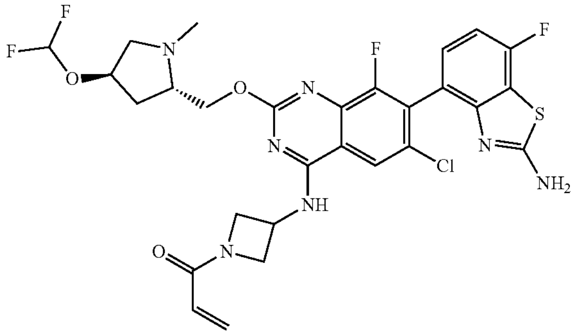 [SMILES: C=CC(=O)N1CC(Nc2nc(OC[C@@H]3C[C@@H](OC(F)F)CN3C)nc3c(F)c(-c4ccc(F)c5sc(N)nc45)c(Cl)cc23)C1] | LCMS m/z [M + 1]: 652.3 $^1$HNMR (400 MHz, $CD_3OD$): δ 8.29 (s, 1H), 7.20-7.35 (m, 1H), 7.03 (t, J = 8.8 Hz, 1H), 6.27-6.75 (m , 4H), 5.79 (d, J = 10 Hz, 1H), 4.75-4.80 (m, 2H), 4.66-4.69 (m, 2H), 4.45-4.54 (m, 2H), 4.01-4.25 (m, 2H), 3.50-3.73 (m, 1H), 3.17 (s , 3H), 2.41-2.54 (m, 2H). |

TABLE 2-continued
Selected compounds of the present disclosure.
| Compound No. | Structure | Analytical data |
|---|---|---|
| 94a | 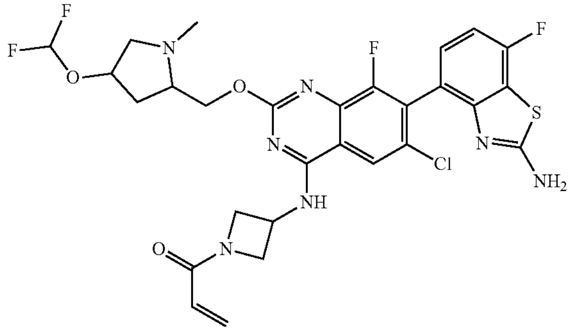 [SMILES: C=CC(=O)N1CC(Nc2nc(OCC3CC(OC(F)F)CN3C)nc3c(F)c(-c4ccc(F)c5sc(N)nc45)c(Cl)cc23)C1] | |
| 95 | 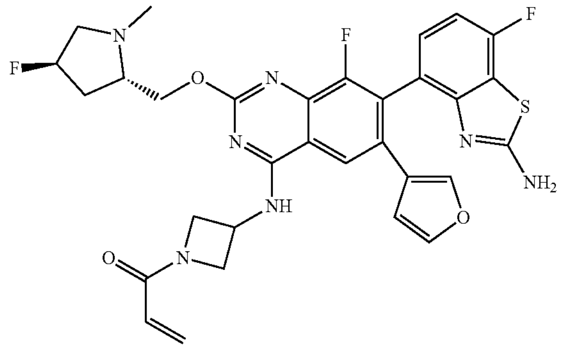 [SMILES: C=CC(=O)N1CC(Nc2nc(OC[C@@H]3C[C@@H](F)CN3C)nc3c(F)c(-c4ccc(F)c5sc(N)nc45)c(-c4ccoc4)cc23)C1] | LCMS m/z [M + 1]: 636.4 $^{1}$HNMR (400 MHz, $CD_3OD$): δ 8.29 (s, 1H), 7.35 (s, 1H), 6.96-7.15 (m, 3H), 6.27-6.44 (m, 3H), 5.79 (d, J = 10.4 Hz, 1H), 5.44 (d, J = 51.4 Hz, 1H), 4.97-5.23 (m, 2H), 4.75-4.81 (m, 2H), 4.46-4.57 (m, 2H), 4.20-4.27 (m, 2H), 4.01-4.18 (m, 1H), 3.65-3.70 (m, 1H), 3.20 (s, 3H), 2.60-2.75 (m, 1H), 2.31-2.48 (m, 1H). |
| 95a | 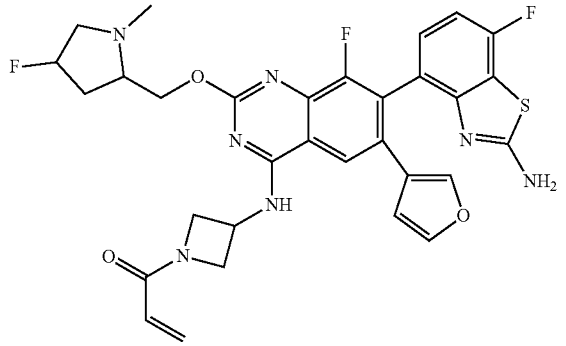 [SMILES: C=CC(=O)N1CC(Nc2nc(OCC3CC(F)CN3C)nc3c(F)c(-c4ccc(F)c5sc(N)nc45)c(-c4ccoc4)cc23)C1] | |
| 96 | 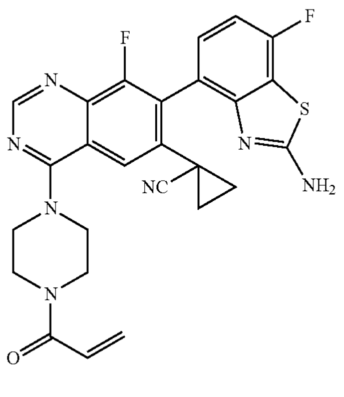 [SMILES: C=CC(=O)N1CCN(c2ncnc3c(F)c(-c4ccc(F)c5sc(N)nc45)c(C4(C#N)CC4)cc23)CC1] | LCMS m/z [M + 1]: 518.26 $^{1}$HNMR (300 MHz, $CDCl_3$) δ 8.82 (s, 1H), 7.80 (s, 1H), 7.40 (dd, J = 8.4, 5.3 Hz, 1H), 7.06 (t, J = 8.6 Hz, 1H), 6.62 (dd, J = 16.7, 10.4 Hz, 1H), 6.39 (d, J = 16.6 Hz, 1H), 5.80 (d, J = 10.3 Hz, 1H), 5.56 (s, 2H), 4.05-3.75 (m, 8H), 1.42-1.39 (m, 1H), 1.27-1.12 (m, 2H), 1.08-0.95 (m, 1H). |

TABLE 2-continued
Selected compounds of the present disclosure.
| Compound No. | Structure | Analytical data |
|---|---|---|
| 97 | 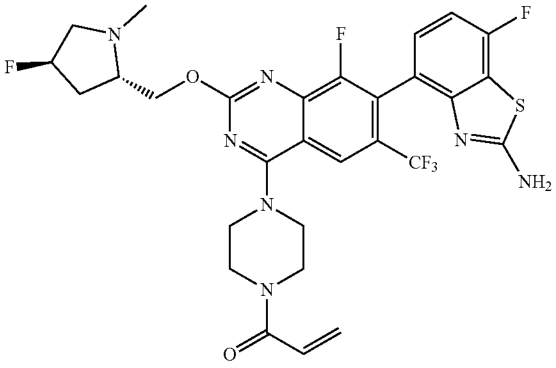 [SMILES: C=CC(=O)N1CCN(c2nc(OC[C@@H]3C[C@@H](F)CN3C)nc3c(F)c(-c4ccc(F)c5sc(N)nc45)c(C(F)(F)F)cc23)CC1] | LCMS m/z [M + 1]: 652.1 $^{1}$HNMR (400 MHz, $CD_3OD$) δ 8.27 (s, 1H), 7.23-7.30 (m, 1H), 7.06 (td, J = 8.96, 2.6Hz, 1H), 6.81 (dd, J = 16.8, 10.6 Hz, 1H), 6.30 (dd, J = 16.8, 1.68 Hz, 1H), 5.82 (dd, J = 10.6, 1.68 Hz, 1H), 5.47 (d, J= 52 Hz, 1H), 4.96-5.05 (m, 1H), 4.71-4.78 (m, 1H), 4.14-4.32 (m, 5H), 3.88-4.14 (m, 5H), 3.58-3.74 (m, 1H), 3.18 (s, 3H), 2.62-2.74 (m, 1H), 2.29-2.49 (m, 1H). |
| 97a | 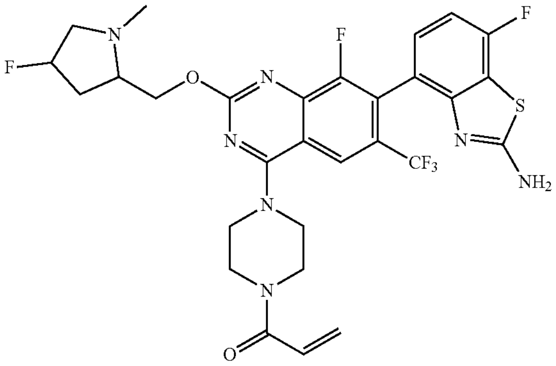 | |
| 98 | 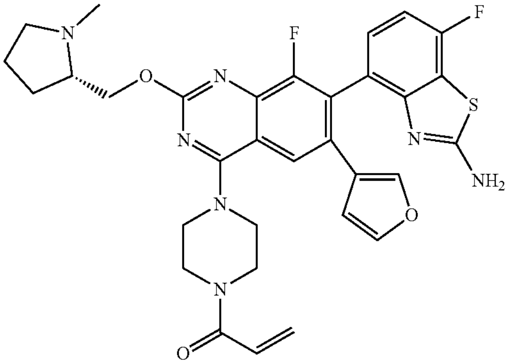 [SMILES: C=CC(=O)N1CCN(c2nc(OC[C@@H]3CCCN3C)nc3c(F)c(-c4ccc(F)c5sc(N)nc45)c(-c4ccoc4)cc23)CC1] | LCMS m/z [M + 1]: 632.1 $^{1}$HNMR (400 MHz, $CD_3OD$) δ 7.99 (s, 1H), 7.33 (s, 1H), 7.18 (s, 1H), 7.12 (dd, J = 8.1, 5.6 Hz, 1H), 6.95-6.99 (m, 1H), 6.81 (dd, J = 16.8, 10.6 Hz, 1H), 6.30 (d, J = 16.8 Hz, 1H), 6.15 (s, 1H), 5.83 (d, J = 10.6 Hz, 1H), 4.94-5.05 (m, 2H), 4.69-4.79 (m, 1H), 4.18-4.25 (m, 4H), 3.88-4.03 (m, 5H), 3.67-3.80 (m, 1H), 3.10 (s, 3H), 2.36-2.47 (m, 1H), 2.17-2.27 (m, 1H), 2.06-2.17 (m, 2H). |
| 98a | 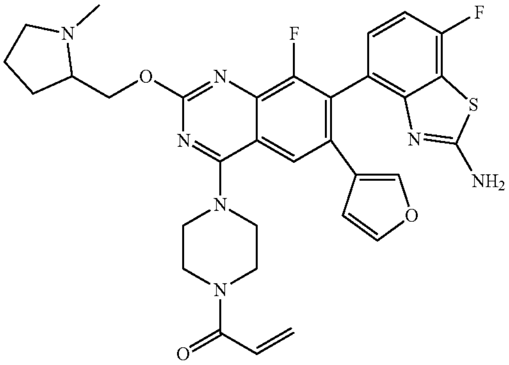 [SMILES: C=CC(=O)N1CCN(c2nc(OCC3CCCN3C)nc3c(F)c(-c4ccc(F)c5sc(N)nc45)c(-c4ccoc4)cc23)CC1] | |

TABLE 2-continued

Selected compounds of the present disclosure.

| Compound No. | Structure | Analytical data |
|---|---|---|
| 99 | 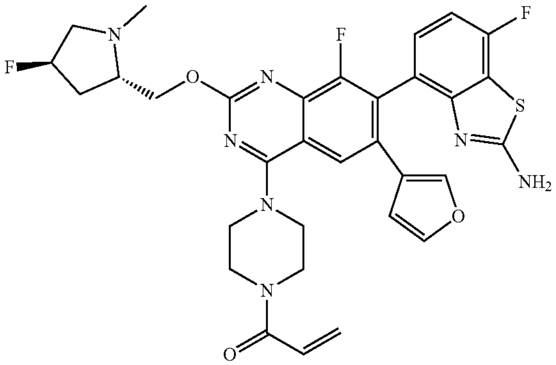 [SMILES: C=CC(=O)N1CCN(c2nc(OC[C@@H]3C[C@@H](F)CN3C)nc3c(F)c(-c4ccc(F)c5sc(N)nc45)c(-c4ccoc4)cc23)CC1] | LCMS m/z [M + 1]: 650.1 $^1$HNMR (400 MHz, $CD_3OD$) δ 7.98 (s, 1H), 7.33 (s, 1H), 7.18 (s, 1H), 7.09-7.13 (m, 1H), 6.94-6.98 (m, 1H), 6.81 (dd, J = 16.8, 10.6 Hz, 1H), 6.29 (dd, J = 16.8, 1.6 Hz, 1H), 6.15 (s, 1H), 5.82 (dd, J = 10.6, 1.7 Hz, 1H), 5.47 (d, J = 52.0 Hz, 1H), 4.98-5.15 (m, 2H), 4.72-4.79 (m, 1H), 4.24-4.34 (m, 1H), 4.15-4.23 (m, 4H), 3.90-4.04 (m, 4H), 3.58-3.73 (m, 1H), 3.19 (s, 3H), 2.62-2.79 (m, 1H), 2.28-2.51 (m, 1H). |
| 99a | 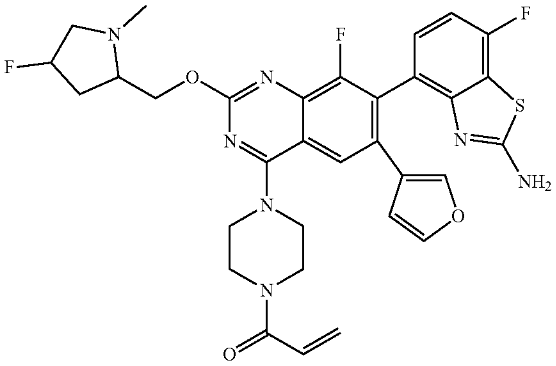 [SMILES: C=CC(=O)N1CCN(c2nc(OCC3CC(F)CN3C)nc3c(F)c(-c4ccc(F)c5sc(N)nc45)c(-c4ccoc4)cc23)CC1] | |
| 100 | 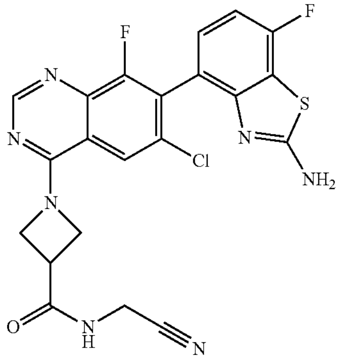 [SMILES: N#CCNC(=O)C1CN(c2ncnc3c(F)c(-c4ccc(F)c5sc(N)nc45)c(Cl)cc23)C1] | LCMS m/z [M + 1]: 486.0 $^1$HNMR (700 MHz, $CD_3OD$) δ 8.58 (s, 1H), 7.96 (d, J = 1.4 Hz, 1H), 7.26 (dd, J = 8.4, 5.4 Hz, 1H), 7.02 (dd, J = 9.1, 8.4 Hz, 1H), 5.16-4.96 (m, 2H), 4.26 (s, 2H), 3.77 (tt, J = 8.9, 5.7 Hz, 1H), 3.34 (s, 2H), 2.66 (s, 1H). |
| 101 | 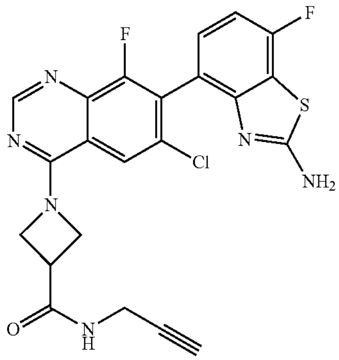 [SMILES: C#CCNC(=O)C1CN(c2ncnc3c(F)c(-c4ccc(F)c5sc(N)nc45)c(Cl)cc23)C1] | LCMS m/z [M + 1]: 485.0 $^1$H NMR (700 MHz, $CD_3OD$) δ 8.47 (s, 1H), 7.90 (d, J = 1.5 Hz, 1H), 7.69-7.62 (m, 3H), 7.56 (tdd, J = 7.3, 4.1, 2.4 Hz, 2H), 7.23 (dd, J = 8.4, 5.4 Hz, 1H), 7.00 (dd, J = 9.2, 8.4 Hz, 1H), 4.05 (d, J = 2.5 Hz, 2H), 3.69 (tt, J = 8.8, 5.7 Hz, 1H), 3.34 (s, 2H), 2.67-2.62 (m, 1H). |

TABLE 2-continued

| Compound No. | Structure | Analytical data |
| --- | --- | --- |
| Selected compounds of the present disclosure. | | |
| 102 | 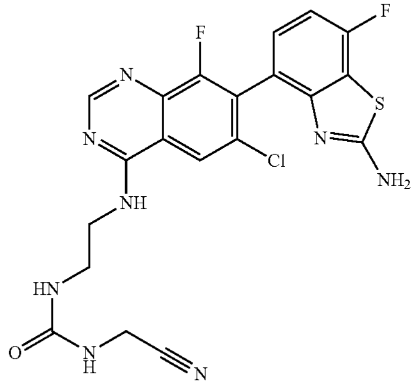 [SMILES: N#CCNC(=O)NCCNc1ncnc2c(F)c(-c3ccc(F)c4sc(N)nc34)c(Cl)cc12] | LCMS m/z [M + 1]: 474.0 $^1$HNMR (700 MHz, $CD_3OD$) δ 8.53 (s, 1H), 8.16 (d, J = 1.4 Hz, 1H), 7.23 (dd, J = 8.4, 5.4 Hz, 1H), 7.00 (dd, J = 9.2, 8.4 Hz, 1H), 4.16 (d, J = 0.8 Hz, 2H), 3.98-3.88 (m, 2H), 2.72 (td, J = 6.8, 1.5 Hz, 3H). |
| 103 | 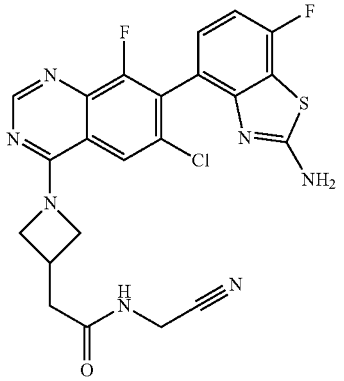 [SMILES: N#CCNC(=O)CC1CN(c2ncnc3c(F)c(-c4ccc(F)c5sc(N)nc45)c(Cl)cc23)C1] | LCMS m/z [M + 1]: 500.0 $^1$HNMR (700 MHz, $CD_3OD$) δ 8.42 (s, 1H), 7.85 (d, J = 1.4 Hz, 1H), 7.23 (dd, J = 8.4, 5.4 Hz, 1H), 6.99 (dd, J = 9.1, 8.3 Hz, 1H), 4.79-4.76 (m, 3H), 4.36-4.33 (m, 1H), 4.17 (s, 2H), 3.30-3.19 (m, 1H), 2.75 (d, J = 7.8 Hz, 2H). |
| 104 | 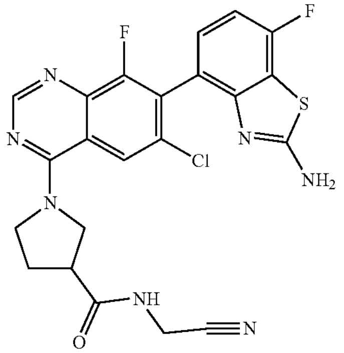 [SMILES: N#CCNC(=O)C1CCN(c2ncnc3c(F)c(-c4ccc(F)c5sc(N)nc45)c(Cl)cc23)C1] | LCMS m/z [M + 1]: 500.1 $^1$HNMR (700 MHz, $CD_3OD$) δ 8.47 (d, J = 5.0 Hz, 1H), 8.20 (td, J = 4.0, 1.6 Hz, 1H), 7.23 (dq, J = 10.0, 5.1 Hz, 1H), 7.02-6.96 (m, 1H), 4.25-4.10 (m, 7H), 4.08-4.01 (m, 2H), 3.25 (h, J = 7.1 Hz, 1H), 2.37 (qt, J = 6.9, 4.0 Hz, 1H), 2.29 (dt, J = 13.9, 4.5 Hz, 1H). |
| 105 | 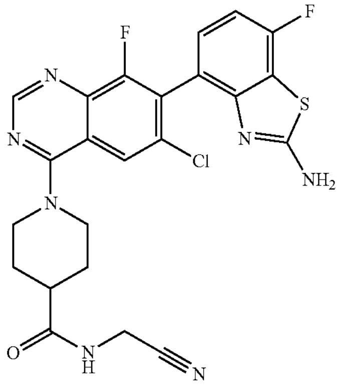 [SMILES: N#CCNC(=O)C1CCN(c2ncnc3c(F)c(-c4ccc(F)c5sc(N)nc45)c(Cl)cc23)CC1] | LCMS m/z [M + 1]: 514.0 $^1$HNMR (700 MHz, $CD_3OD$) δ 8.61 (s, 1H), 7.92 (d, J = 1.4 Hz, 1H), 7.24 (dd, J = 8.4, 5.4 Hz, 1H), 6.99 (dd, J = 9.2, 8.4 Hz, 1H), 4.56-4.48 (m, 2H), 4.17 (s, 2H), 3.42-3.33 (m, 2H), 2.67 (tt, J = 11.2, 4.3 Hz, 1H), 2.02-1.87 (m, 5H). |

TABLE 2-continued

Selected compounds of the present disclosure.

| Compound No. | Structure | Analytical data |
|---|---|---|
| 106 | 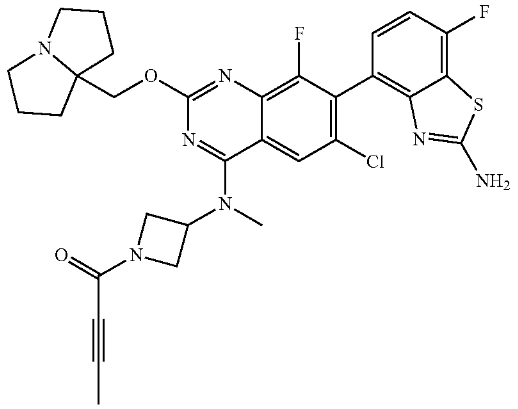 [SMILES: CC#CC(=O)N1CC(N(C)c2nc(OCC34CCCN3CCC4)nc3c(F)c(-c4ccc(F)c5sc(N)nc45)c(Cl)cc23)C1] | LCMS m/z [M + 1]: 638.1<br>$^1$HNMR (400 MHz, $CD_3OD$) δ 8.11 (s, 1H), 7.22-7.26 (m, 1H), 7.00-7.05 (m, 1H), 4.93-4.99 (m, 2H), 4.56-4.68 (m, 3H), 4.40-4.52 (m, 2H), 4.17-4.24 (m, 2H), 3.65-3.71 (m, 2H), 3.51 (s, 3H), 2.06-2.40 (m, 8H), 2.04 (s, 3H). |
| 109 | 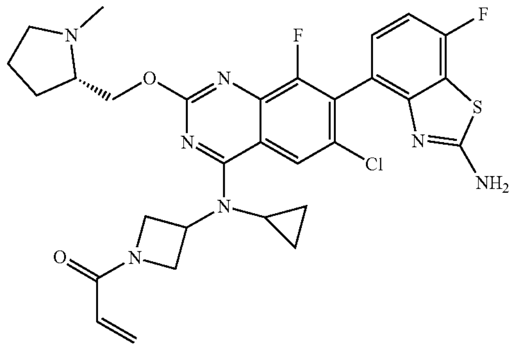 [SMILES: C=CC(=O)N1CC(N(c2nc(OC[C@@H]3CCCN3C)nc3c(F)c(-c4ccc(F)c5sc(N)nc45)c(Cl)cc23)C2CC2)C1] | LCMS m/z [M + 1]: 626.1<br>$^1$HNMR (400 MHz, $CD_3OD$): δ 8.30 (s, 1H), 7.24 (t, J = 6.8 Hz, 1H), 7.00-7.13 (m, 2H), 6.28 (d, J = 16.8 Hz, 1H), 5.81(d, J = 11.2 Hz, 1H), 5.07-5.21 (m, 3H), 4.65-4.67 (m, 1H), 4.53 (m, 1H), 4.35 (m, 1H), 3.94-3.96 (m, 2H), 3.78 (m, 1H), 3.12 (m, 1H), 3.10 (s, 3H) 3.02 (m, 1H), 2.43-2.45 (m, 1H), 2.03-2.21 (m, 3H), 1.08-1.09 (m, 2H), 0.88-1.0 (m, 2H). |
| 109a | 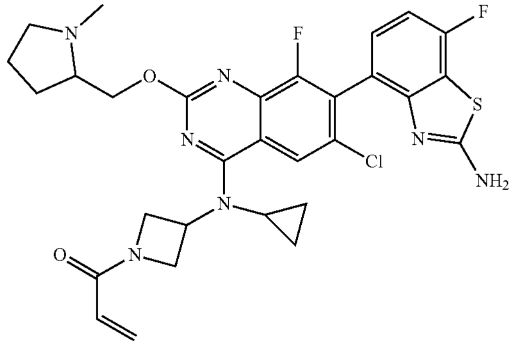 [SMILES: C=CC(=O)N1CC(N(c2nc(OCC3CCCN3C)nc3c(F)c(-c4ccc(F)c5sc(N)nc45)c(Cl)cc23)C2CC2)C1] | |
| 114 | 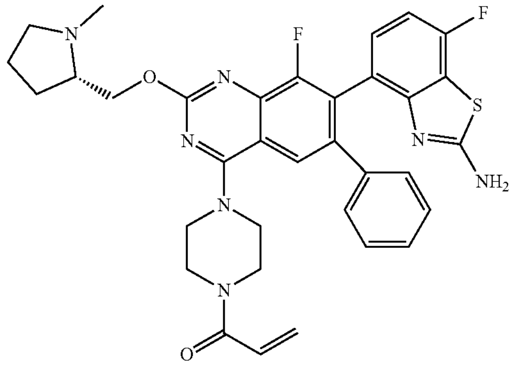 [SMILES: C=CC(=O)N1CCN(c2nc(OC[C@@H]3CCCN3C)nc3c(F)c(-c4ccc(F)c5sc(N)nc45)c(-c4ccccc4)cc23)CC1] | LCMS m/z [M + 1]: 642.5<br>$^1$H NMR (300 MHz, $CDCl_3$) δ 8.27 (s, 1H), 7.69 (s, 1H), 7.18 (d, J = 4.0 Hz, 2H), 7.10-7.05(m, 2H), 6.93-6.84 (m, 1H), 6.75 (td, J = 9.0, 3.1 Hz, 1H), 6.62 (dd, J = 16.6, 10.3 Hz, 1H), 6.38 (dd, J = 17.8, 2.6 Hz, 1H), 5.79 (d, J = 10.6 Hz, 1H), 4.99-4.90 (m, 1H), 4.81-4.71 (m, 1H), 4.02-3.70 (m, 7H), 3.66-3.56 (m, 1H), 2.98 (d, J = 8.4 Hz, 2H), 2.93-2.85 (m, 1H), 2.64 (s, 3H), 2.41-2.03 (m, 4H). |

TABLE 2-continued
| Selected compounds of the present disclosure. | | |
|---|---|---|
| Compound No. | Structure | Analytical data |
| 114a | 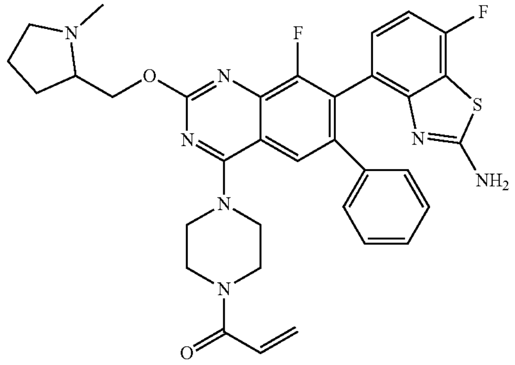 [SMILES: C=CC(=O)N1CCN(c2nc(OCC3CCCN3C)nc3c(F)c(-c4ccc(F)c5sc(N)nc45)c(-c4ccccc4)cc23)CC1] | |
| 118 | 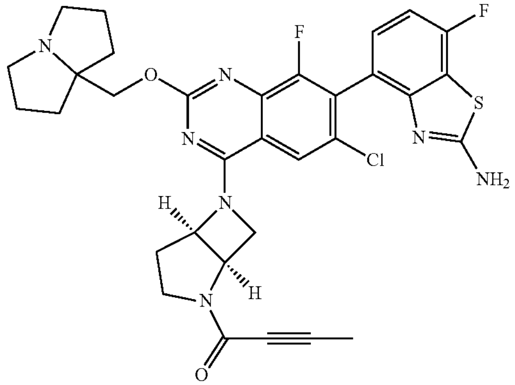 [SMILES: CC#CC(=O)N1CC[C@@H]2[C@H]1CN2c1nc(OCC23CCCN2CCC3)nc2c(F)c(-c3ccc(F)c4sc(N)nc34)c(Cl)cc12] | LCMS m/z [M + 1]: 650.0<br>$^{1}$HNMR (400 MHz, $CD_3OD$) δ 7.80-7.82 (m, 1H), 7.18-7.20 (m, 1H), 6.96-7.00 (m, 1H), 5.56-5.60 (m, 1H), 5.10 (m, 1H), 4.60 (m, 1H), 4.49 (m, 1H), 4.32-4.40 (m, 3H), 4.23-4.27 (m, 1H), 3.98 (m, 1H), 3.64 (m, 1H), 3.12 (m, 1H), 2.90 (m, 2H), 2.58 (m, 1H), 1.84-2.14 (m, 8H), 1.30 (m 3H). |
| 118a | 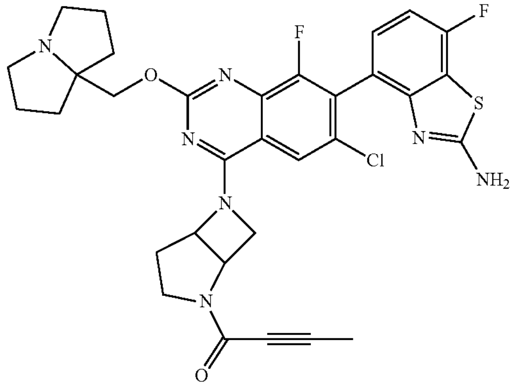 [SMILES: CC#CC(=O)N1CCC2C1CN2c1nc(OCC23CCCN2CCC3)nc2c(F)c(-c3ccc(F)c4sc(N)nc34)c(Cl)cc12] | |
| 119 | 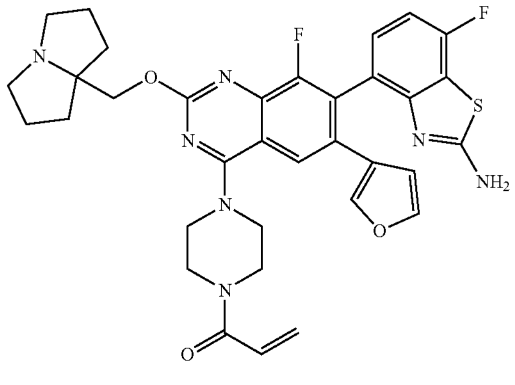 [SMILES: C=CC(=O)N1CCN(c2nc(OCC34CCCN3CCC4)nc3c(F)c(-c4ccc(F)c5sc(N)nc45)c(-c4ccoc4)cc23)CC1] | LCMS m/z [M + 1]: 658.2<br>$^{1}$HNMR (400 MHz, $CD_3OD$) δ 7.99 (s, 1H), 7.33 (s, 1H), 7.18 (s, 1H), 7.06-7.16 (m, 1H), 6.96 (t, J = 8.8 Hz, 1H), 6.81 (dd, J = 16.8, 10.6 Hz, 1H), 6.28-6.32 (m, 1H), 6.16 (s, 1H), 5.83 (d, J = 10.8 Hz, 1H), 4.92 (m, 2H), 4.72 (m, 2H), 4.18-4.25 (m, 4H), 3.85-4.05 (m, 4H), 3.62-3.69 (m, 2H), 2.06-2.45 (m, 8H). |

TABLE 2-continued
| Selected compounds of the present disclosure. | | |
|---|---|---|
| Compound No. | Structure | Analytical data |
| 120 | 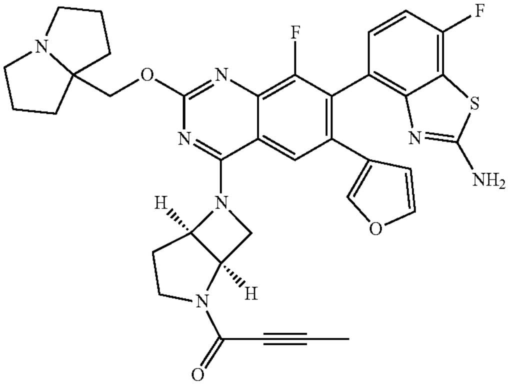 [SMILES: CC#CC(=O)N1CC[C@@H]2[C@H]1CN2c1nc(OCC23CCCN2CCC3)nc2c(F)c(-c3ccc(F)c4sc(N)nc34)c(-c3ccoc3)cc12] | LCMS m/z [M + 1]: 682.1 $^1$HNMR (400 MHz, $CD_3OD$) δ 7.84 (s, 1H), 7.33 (s, 1H), 7.16 (d, J = 11.4 Hz, 1H), 7.07-7.14 (m, 1H), 6.93-6.96 (m, 1H), 6.14 (s, 1H), 5.60-5.78 (m, 1H), 5.02-5.23 (m, 3H), 4.65-4.78 (m, 2H), 4.24-4.41 (m, 1H), 3.95-4.05 (m, 1H), 3.60-3.75 (m, 2H), 3.24-3.29 (m, 1H), 2.61-2.71 (m, 1H), 2.27-2.39 (m, 2H), 2.19-2.27 (m, 4H), 2.09-2.19 (m, 4H), 2.07 (s, 3H). |
| 120a | 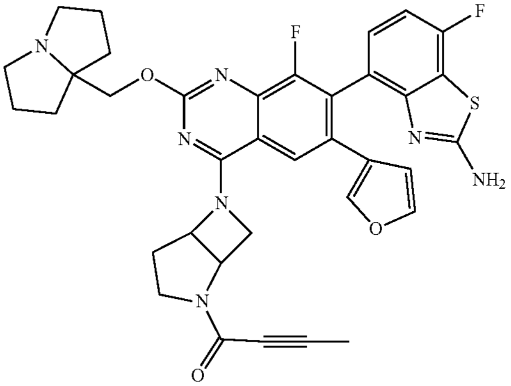 [SMILES: CC#CC(=O)N1CCC2C1CN2c1nc(OCC23CCCN2CCC3)nc2c(F)c(-c3ccc(F)c4sc(N)nc34)c(-c3ccoc3)cc12] | |
| 121 | 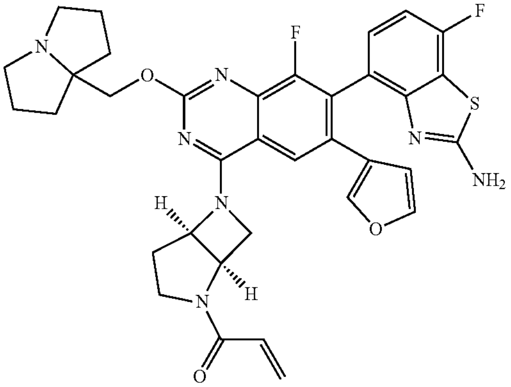 [SMILES: C=CC(=O)N1CC[C@@H]2[C@H]1CN2c1nc(OCC23CCCN2CCC3)nc2c(F)c(-c3ccc(F)c4sc(N)nc34)c(-c3ccoc3)cc12] | LCMS m/z [M + 1]: 670.1 $^1$HNMR (400 MHz, $CD_3OD$) δ 7.84 (s, 1H), 7.32 (s, 1H), 7.05-7.20 (m, 2H), 6.95 (t, J = 8.8 Hz, 1H), 6.60-6.81 (m, 1H), 6.31-6.41 (m, 1H), 6.14 (s, 1H), 5.84 (d, J = 10.8 Hz, 1H), 5.55-5.74 (m, 1H), 5.05-5.29 (m, 2H), 4.64-4.76 (m, 4H), 4.24-4.39 (m, 1H), 3.92-4.01 (m, 1H), 3.65-3.78 (m, 2H), 2.60-2.76 (m, 1H), 2.10-2.35 (m, 10H). |

TABLE 2-continued
Selected compounds of the present disclosure.
| Compound No. | Structure | Analytical data |
|---|---|---|
| 121a | 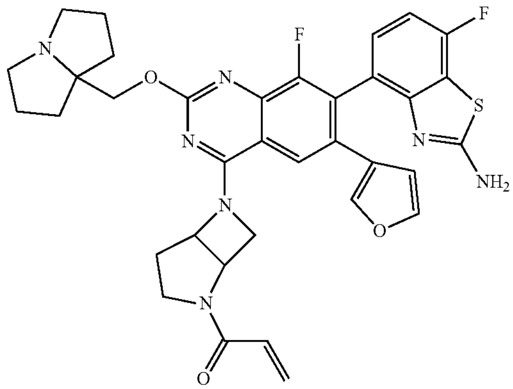 [SMILES: C=CC(=O)N1CCC2C1CN2c1nc(OCC23CCCN2CCC3)nc2c(F)c(-c3ccc(F)c4sc(N)nc34)c(-c3ccoc3)cc12] | |
| 122 | 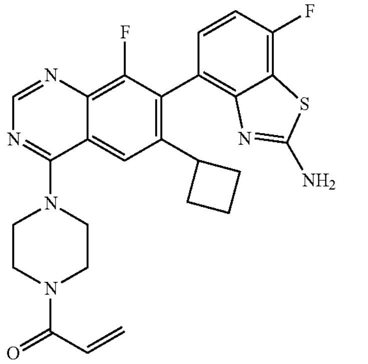 [SMILES: C=CC(=O)N1CCN(c2ncnc3c(F)c(-c4ccc(F)c5sc(N)nc45)c(C4CCC4)cc23)CC1] | LCMS m/z [M + 1]: 507.3<br>$^{1}$H NMR (300 MHz, $CDCl_3$) δ 8.82 (s, 1H), 7.62 (s, 1H), 7.16 (dd, J = 8.4, 5.6 Hz, 1H), 6.99 (t, J = 8.6 Hz, 1H), 6.66 (dd, J = 16.8, 10.5 Hz, 1H), 6.53-6.27 (m, 1H), 5.92-5.69 (m, 1H), 5.41 (m, 2H), 3.92 (m, 8H), 3.56 (m, 1H), 1.88 (m, 4H), 1.71 (m, 2H). |
| 126 | 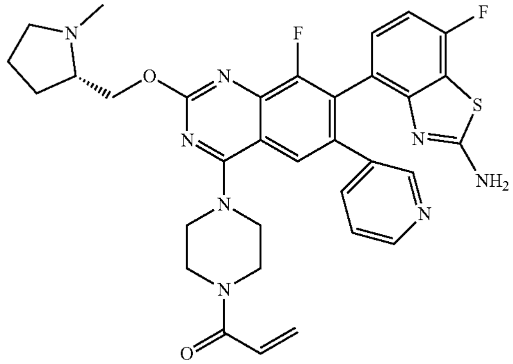 [SMILES: C=CC(=O)N1CCN(c2nc(OCC3CCCN3C)nc3c(F)c(-c4ccc(F)c5sc(N)nc45)c(-c4cccnc4)cc23)CC1] | LCMS m/z [M + 1]: 643.4<br>$^{1}$H NMR (300 MHz, $CD_3OD$) δ 7.88 (d, J = 10.6 Hz, 2H), 7.67 (d, J = 1.5 Hz, 2H), 7.08 (dd, J = 9.2, 7.6 Hz, 1H), 6.89-6.75 (m, 3H), 6.29 (dd, J = 16.7, 2.0 Hz, 1H), 5.82 (dd, J = 10.7, 1.6 Hz, 1H), 4.64 (m, 1H), 4.17-4.05 (m, 4H), 3.98-3.88 (m, 4H), 3.55 (s, 1H), 3.43 (s, 1H), 2.98 (s, 2H), 2.67 (s, 3H), 2.39-2.27 (m, 1H), 2.16-2.00 (m, 3H). |
| 126a | 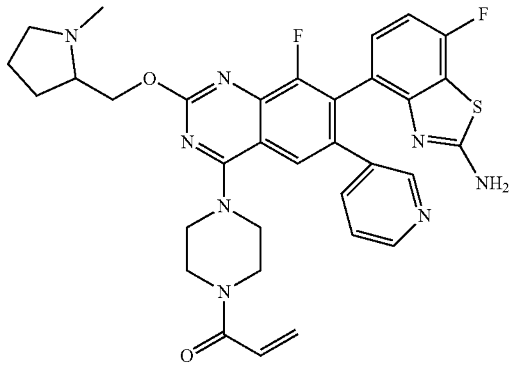 | |

TABLE 2-continued
| Selected compounds of the present disclosure. | | |
|---|---|---|
| Compound No. | Structure | Analytical data |
| 127 | 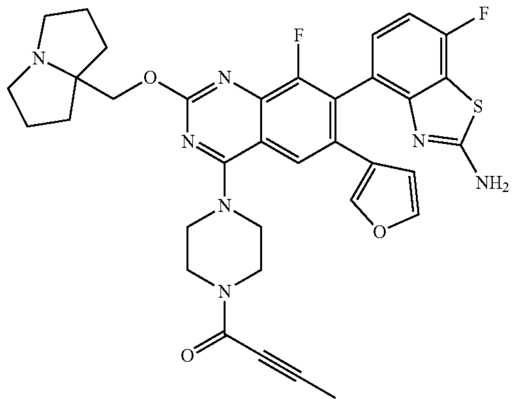 [SMILES: CC#CC(=O)N1CCN(c2nc(OCC34CCCN3CCC4)nc3c(F)c(-c4ccc(F)c5sc(N)nc45)c(-c4ccoc4)cc23)CC1] | LCMS m/z [M + 1]: 670.2 $^{1}$HNMR (400 MHz, $CD_3OD$) δ 7.97 (s, 1H), 7.33 (s, 1H), 7.19 (s, 1H), 7.08-7.17 (m, 1H), 6.97 (t, J = 8.7 Hz, 1H), 6.16 (s, 1H), 4.72 (m, 4H), 4.02-4.29 (m, 6H), 3.79-3.88 (m, 2H), 3.65-3.72 (m, 2H), 1.95-2.41 (m, 11H). |
| 128 | 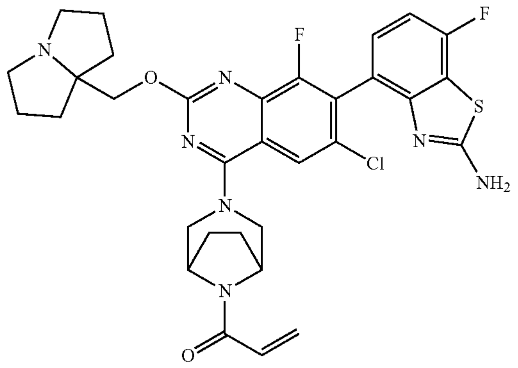 [SMILES: C=CC(=O)N1C2CCC1CN(c1nc(OCC34CCCN3CCC4)nc3c(F)c(-c4ccc(F)c5sc(N)nc45)c(Cl)cc13)C2] | LCMS m/z [M + 1]: 652.2 $^{1}$HNMR (400 MHz, $CD_3OD$): δ 7.96 (s, 1H), 7.23 (dd, J = 8.36, 5.64 Hz, 1H), 7.01 (t, J = 8.8 Hz, 1H), 6.80 (dd, J = 16.72, 10.36 Hz, 1H), 6.38 (d, J = 16.8, 1H), 5.85 (d, J = 10.84, 1H), 4.67-4.73 (m, 2H), 4.63-4.67 (m, 2H), 4.57-4.63 (m, 1H), 3.64-3.76 (m, 5H), 3.24-3.39 (m, 2H), 2.28-2.36 (m, 2H), 2.19-2.26 (m, 2H) 2.03-2.19 (m, 6H), 1.87-1.93 (m, 2H). |
| 129 | 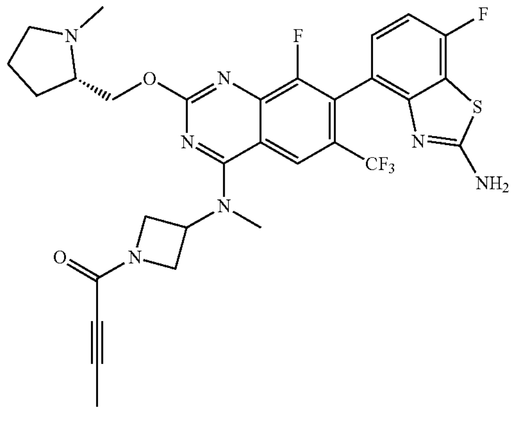 | LCMS m/z [M + 1]: 646.2 $^{1}$HNMR (400 MHz, $CD_3OD$): δ 8.35 (s, 1H), 7.23-7.29 (m, 1H), 7.01-7.06 (m, 1H), 5.01-5.12 (m, 2H), 4.59-4.72 (m, 2H), 4.48-4.56 (m, 1H), 4.42-4.48 (m, 1H), 4.21-4.28 (m, 1H), 3.86-3.94 (m, 1H), 3.68-3.79 (m, 1H), 3.57 (s, 3H), 3.21-3.29 (m, 1H), 3.09 (s, 3H), 2.36-2.48 (m, 1H), 2.16-2.27 (m, 1H), 2.06-2.15 (m, 2H), 2.04 (s, 3H). |

TABLE 2-continued
| Selected compounds of the present disclosure. | | |
|---|---|---|
| Compound No. | Structure | Analytical data |
| 129a | 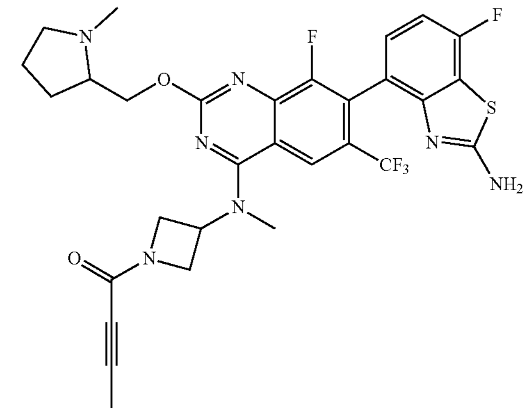 [SMILES: CC#CC(=O)N1CC(N(C)c2nc(OCC3CCCN3C)nc3c(F)c(-c4ccc(F)c5sc(N)nc45)c(C(F)(F)F)cc23)C1] | |
| 131 | 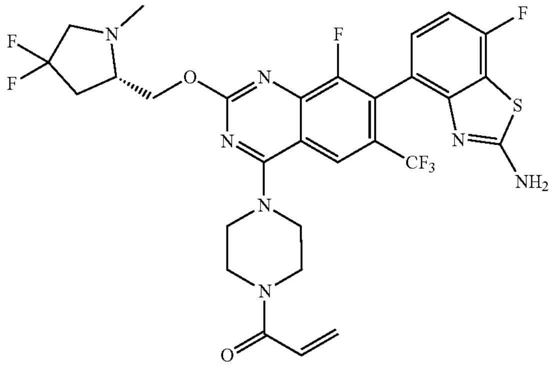 [SMILES: C=CC(=O)N1CCN(c2nc(OC[C@@H]3CC(F)(F)CN3C)nc3c(F)c(-c4ccc(F)c5sc(N)nc45)c(C(F)(F)F)cc23)CC1] | LCMS m/z [M + 1]: 670.0 $^{1}$HNMR (400 MHz, $CD_3OD$) δ 8.25 (s, 1H), 7.19-7.22 (m, 1H), 6.99 (t, J = 8.75 Hz, 1H), 6.76-6.83 (m, 1H), 6.28 (d, J = 16.61 Hz, 1H), 5.81 (d, J = 10.67 Hz, 1H), 4.96-5.01 (m, 1H), 4.72-4.76 (m, 1H), 4.24-4.26 (m, 1H), 4.10-4.15 (m, 5H), 3.93 (m, 4H), 3.75-3.85 (m, 1H), 3.14 (s, 3H), 2.91-2.98 (m, 1H), 2.68-2.74 (m, 1H). |
| 131a | 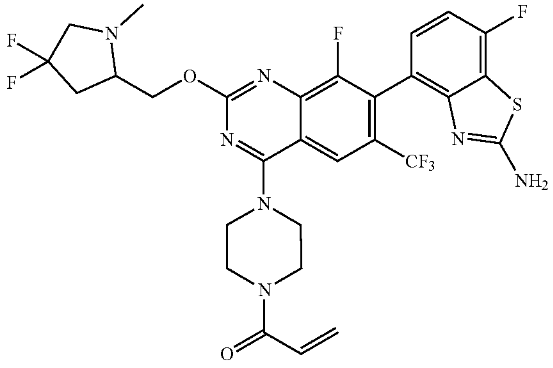 [SMILES: C=CC(=O)N1CCN(c2nc(OCC3CC(F)(F)CN3C)nc3c(F)c(-c4ccc(F)c5sc(N)nc45)c(C(F)(F)F)cc23)CC1] | |
| 132 | 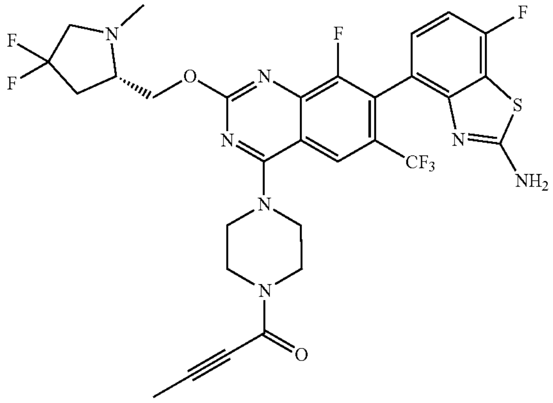 [SMILES: CC#CC(=O)N1CCN(c2nc(OC[C@@H]3CC(F)(F)CN3C)nc3c(F)c(-c4ccc(F)c5sc(N)nc45)c(C(F)(F)F)cc23)CC1] | LCMS m/z [M + 1]: 682.0 $^{1}$HNMR (400 MHz, $CD_3OD$) δ 8.24 (s, 1H), 7.20-7.23 (m, 1H), 7.00 (t, J = 8.86 Hz, 1H), 4.97-5.02 (m, 1H), 4.73-4.77 (m, 1H), 4.24-4.30 (m, 1H), 4.07-4.14 (m, 6H), 3.77-3.85 (m, 4H), 3.15 (s, 3H), 2.94-2.98 (m, 1H), 2.70-2.76 (m, 1H). 2.07 (s, 3H). |

TABLE 2-continued
| Selected compounds of the present disclosure. | | |
|---|---|---|
| Compound No. | Structure | Analytical data |
| 132a | 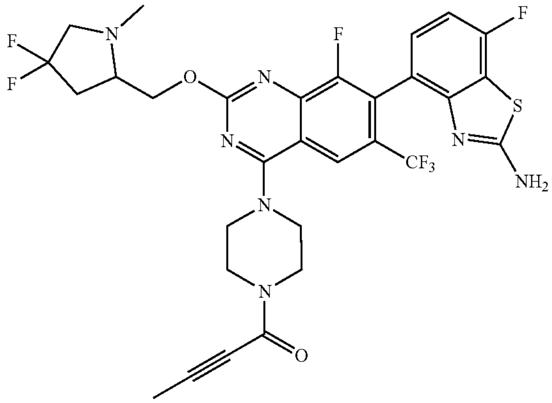 [SMILES: CC#CC(=O)N1CCN(c2nc(OCC3CC(F)(F)CN3C)nc3c(F)c(-c4ccc(F)c5sc(N)nc45)c(C(F)(F)F)cc23)CC1] | |
| 133 | 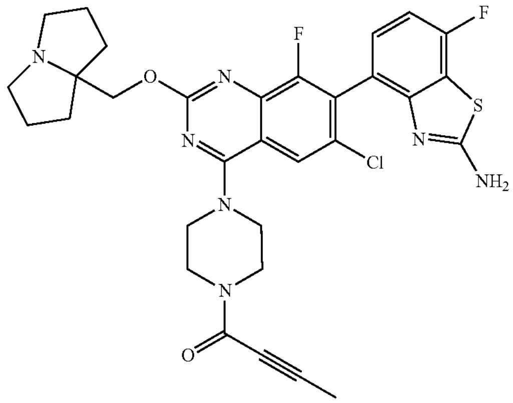 [SMILES: CC#CC(=O)N1CCN(c2nc(OCC34CCCN3CCC4)nc3c(F)c(-c4ccc(F)c5sc(N)nc45)c(Cl)cc23)CC1] | LCMS m/z [M + 1]: 638.1<br>$^1$HNMR (400 MHz, $CD_3OD$): δ 8.03 (s, 1H), 7.22-7.27 (m, 1H), 7.02-7.06 (m, 1H), 4.67 (s, 2H), 4.05-4.09 (m, 6H), 3.81-3.89 (m, 2H), 3.65-3.72 (m, 2H), 3.21-3.30 (m, 2H), 2.21-2.35 (m, 8H), 2.07 (s, 3H). |
| 134 | 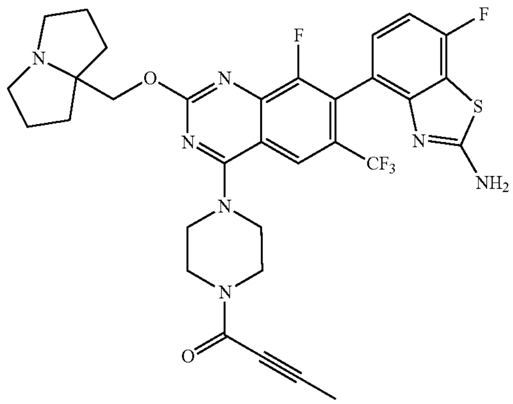 [SMILES: CC#CC(=O)N1CCN(c2nc(OCC34CCCN3CCC4)nc3c(F)c(-c4ccc(F)c5sc(N)nc45)c(C(F)(F)F)cc23)CC1] | LCMS m/z [M + 1]: 672.2<br>$^1$HNMR (400 MHz, $CD_3OD$): δ 8.24 (s, 1H), 7.20-7.24 (m, 1H), 7.01 (t, J = 8.8 Hz, 1H), 4.67 (s, 2H), 4.12-4.18 (m, 2H), 4.04-4.11 (m, 4H), 3.82-3.88 (m, 2H), 3.64-3.74 (m, 2H), 3.25-3.29 (m, 2H), 2.11-2.37 (m, 8H), 2.07 (s, 3H). |

TABLE 2-continued
| Selected compounds of the present disclosure. | | |
|---|---|---|
| Compound No. | Structure | Analytical data |
| 138 | 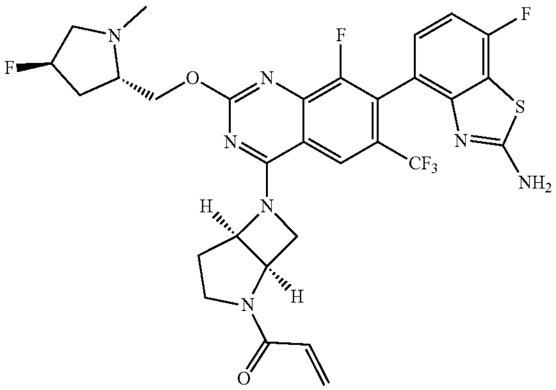 [SMILES: C=CC(=O)N1CC[C@@H]2[C@H]1CN2c1nc(OC[C@@H]2C[C@@H](F)CN2C)nc2c(F)c(-c3ccc(F)c4sc(N)nc34)c(C(F)(F)F)cc12] | LCMS m/z [M + 1]: 664.1<br>$^1$HNMR (400 MHz, $CD_3OD$): δ 8.09-8.11 (m, 1H), 7.09-7.25 (m, 1H), 6.97-7.02 (m, 1H), 6.61-6.79 (m, 1H), 6.34-6.39 (m, 1H), 5.82-5.85 (m, 1H), 5.40-5.61 (m, 2H), 4.94-5.02 (m, 3H), 4.69-4.74 (m, 1H), 4.24-4.34 (m, 3H), 3.60-4.60 (m, 3H), 3.16 (m, 3H), 2.61-2.71 (m, 2H), 2.20-2.42 (m, 2H). |
| 138a | 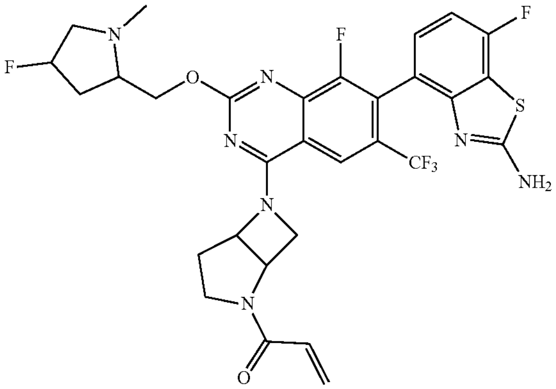 [SMILES: C=CC(=O)N1CCC2C1CN2c1nc(OCC2CC(F)CN2C)nc2c(F)c(-c3ccc(F)c4sc(N)nc34)c(C(F)(F)F)cc12] | |
| 141 | 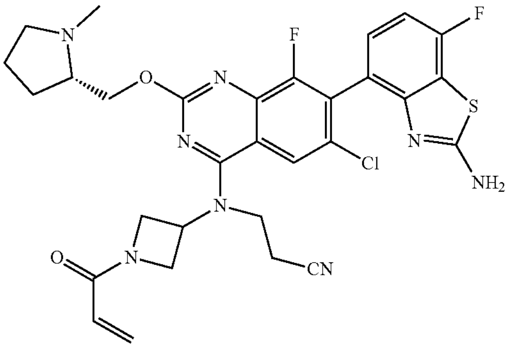 [SMILES: C=CC(=O)N1CC(N(CCC#N)c2nc(OC[C@@H]3CCCN3C)nc3c(F)c(-c4ccc(F)c5sc(N)nc45)c(Cl)cc23)C1] | LCMS m/z [M + 1]: 639.1<br>$^1$HNMR (400 MHz, $CD_3OD$) δ 7.98 (s, 1H), 7.25 (t, J = 8.4 Hz, 1H), 7.03 (t, J = 8.8 Hz, 1H), 6.37-6.41 (m, 1H), 6.28 (d, J = 20 Hz, 1H), 5.78 (d, J = 9.6 Hz, 1H), 5.05-5.07 (m, 1H), 4.47-4.87 (m, 3H), 4.25-4.35 (m, 3H), 3.71-3.92 (m, 2H), 3.25-3.30 (m, 2H), 3.08 (s, 3H), 2.85 (t, J = 12.4 Hz, 2H), 2.39-2.41 (m, 1H), 2.03-2.24 (m, 4H). |
| 141a | 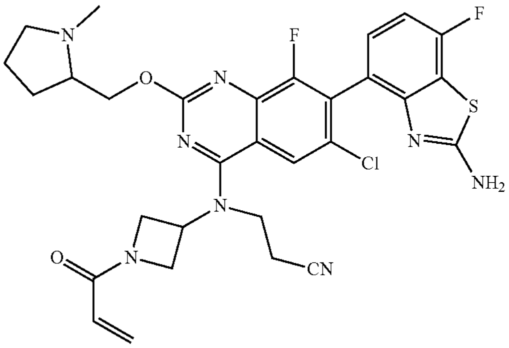 [SMILES: C=CC(=O)N1CC(N(CCC#N)c2nc(OCC3CCCN3C)nc3c(F)c(-c4ccc(F)c5sc(N)nc45)c(Cl)cc23)C1] | |

TABLE 2-continued
| Selected compounds of the present disclosure. | | |
|---|---|---|
| Compound No. | Structure | Analytical data |
| 142 | 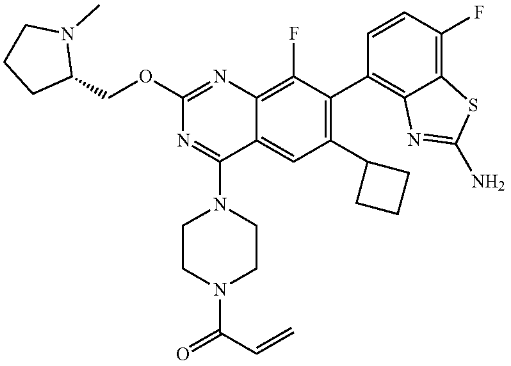 | LCMS m/z [M + 1]: 620.4 |
| 142a | 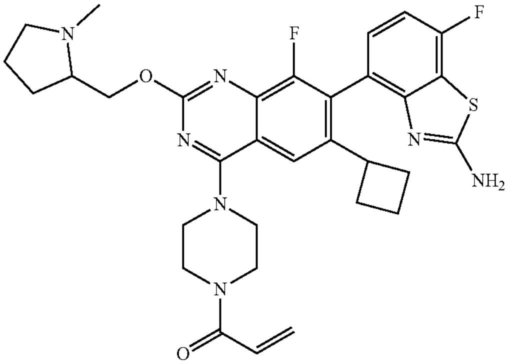 [SMILES: C=CC(=O)N1CCN(c2nc(OCC3CCCN3C)nc3c(F)c(-c4ccc(F)c5sc(N)nc45)c(C4CCC4)cc23)CC1] | |
| 143 | 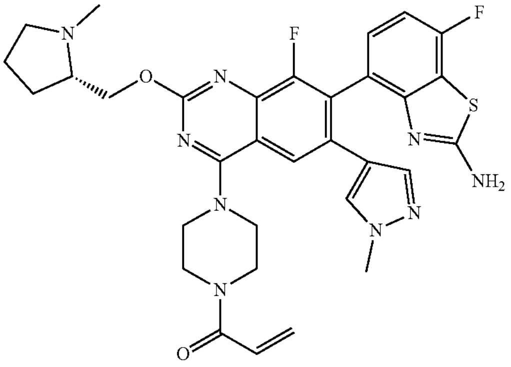 [SMILES: C=CC(=O)N1CCN(c2nc(OC[C@@H]3CCCN3C)nc3c(F)c(-c4ccc(F)c5sc(N)nc45)c(-c4cnn(C)c4)cc23)CC1] | LCMS m/z [M + 1]: 646.2 $^{1}$HNMR (300 MHz, Methanol-$d_4$) δ 7.84 (d, J = 1.4 Hz, 1H), 7.28 (s, 1H), 7.07 (ddd, J = 8.5, 5.5, 1.3 Hz, 1H), 7.00 (d, J = 0.8 Hz, 1H), 6.92 (t, J = 8.8 Hz, 1H), 6.81 (dd, J = 16.8, 10.6 Hz, 1H), 6.27 (dd, J = 16.8, 2.0 Hz, 1H), 5.80 (dd, J = 10.6, 2.0 Hz, 1H), 4.51 (ddd, J = 11.1, 5.8, 2.6 Hz, 1H), 4.41 (ddd, J = 10.8, 5.7, 4.1 Hz, 1H), 4.06-3.98 (m, 4H), 3.92-3.88 (s, 4H), 3.72 (s, 3H), 3.08 (dt, J = 9.3, 4.5 Hz, 1H), 2.78 (p, J = 6.3 Hz, 1H), 2.35 (q, J = 8.9 Hz, 1H), 2.21-2.03 (m, 1H), 1.93-1.66 (m, 3H). |
| 143a | 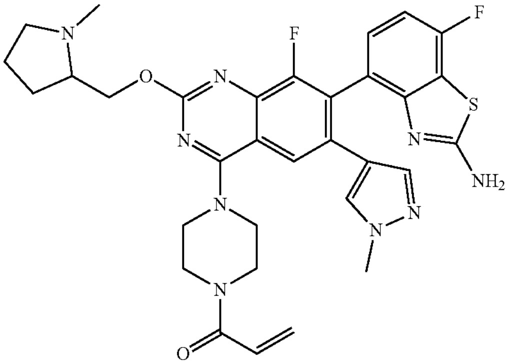 | |

TABLE 2-continued
Selected compounds of the present disclosure.
| Compound No. | Structure | Analytical data |
|---|---|---|
| 144 | 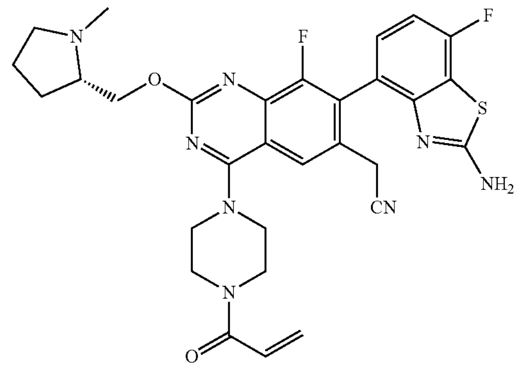 [SMILES: C=CC(=O)N1CCN(c2nc(OC[C@@H]3CCCN3C)nc3c(F)c(-c4ccc(F)c5sc(N)nc45)c(CC#N)cc23)CC1] | LCMS m/z [M + 1]: 605.3 $^1$HNMR (300 MHz, Methanol-$d_4$) δ 7.96 (s, 1H), 7.26 (dd, J = 8.5, 5.5 Hz, 1H), 7.01 (t, J = 8.8 Hz, 1H), 6.82 (dd, J = 16.8, 10.6 Hz, 1H), 6.28 (dd, J = 16.8, 2.0 Hz, 1H), 5.81 (dd, J = 10.5, 2.0 Hz, 1H), 4.60-4.37 (m, 2H), 4.08-3.89 (m, 8H), 3.92-3.60 (m, 2H), 3.15-3.08 (m, 1H), 2.89-2.80 (m, 1H), 2.54 (s, 3H), 2.40 (q, J = 8.9 Hz, 1H), 2.20-2.04 (m, 1H), 1.92-1.69 (m, 3H). |
| 144a | 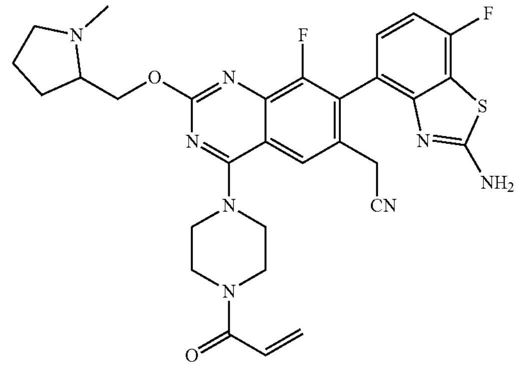 [SMILES: C=CC(=O)N1CCN(c2nc(OCC3CCCN3C)nc3c(F)c(-c4ccc(F)c5sc(N)nc45)c(CC#N)cc23)CC1] | |
| 145 | 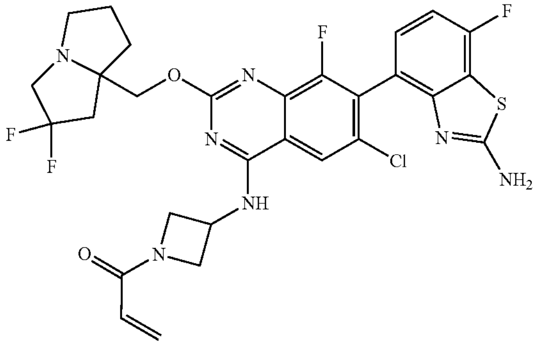 [SMILES: C=CC(=O)N1CC(Nc2nc(OCC34CCCN3CC(F)(F)C4)nc3c(F)c(-c4ccc(F)c5sc(N)nc45)c(Cl)cc23)C1] | LCMS m/z [M + 1]: |
| 146 | 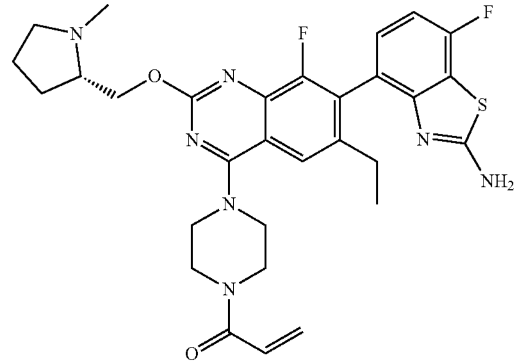 | LCMS m/z [M + 1]: 594.3 $^1$HNMR (300 MHz, $CD_3OD$) δ 7.72 (s, 1H), 7.19 (dd, J = 8.5, 5.5 Hz, 1H), 7.01 (t, J = 8.8 Hz, 1H), 6.85 (dd, J = 16.8, 10.5 Hz, 1H), 6.30 (dd, J = 16.8, 1.9 Hz, 1H), 5.83 (dd, J = 10.6, 1.9 Hz, 1H), 4.63 (ddd, J = 18.3, 12.3, 7.2 Hz, 2H), 4.04 (m, 4H), 3.94 (m, 4H), 3.38 (m, 2H), 2.83 (s, 4H), 2.56 (ddt, J = 22.3, 14.8, 7.3 Hz, 2H), 2.29 (m, 1H), 1.98 (m, 3H), 1.07 (t, J = 7.5 Hz, 3H). |

TABLE 2-continued
| Selected compounds of the present disclosure. | | |
|---|---|---|
| Compound No. | Structure | Analytical data |
| 146a | 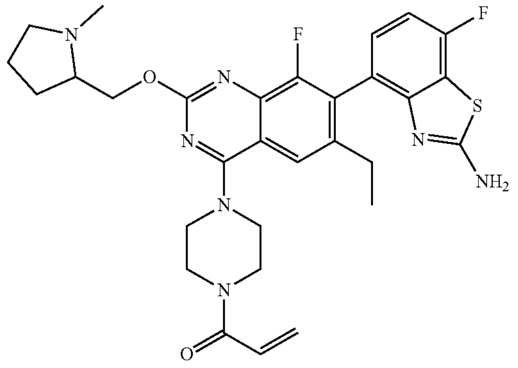 [SMILES: C=CC(=O)N1CCN(c2nc(OCC3CCCN3C)nc3c(F)c(-c4ccc(F)c5sc(N)nc45)c(CC)cc23)CC1] | |
| 149 | 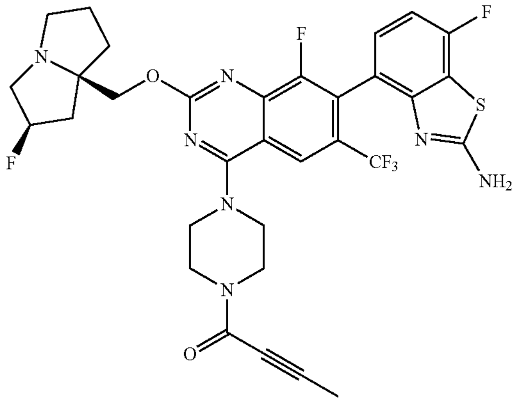 [SMILES: CC#CC(=O)N1CCN(c2nc(OC[C@]34CCCN3C[C@H](F)C4)nc3c(F)c(-c4ccc(F)c5sc(N)nc45)c(C(F)(F)F)cc23)CC1] | LCMS m/z [M + 1]: 690.0 $^1$HNMR (400 MHz, $CD_3OD$): δ 8.18 (s, 1H), 7.18-7.21 (m, 1H), 6.95-6.99 (m, 1H), 5.37 (d, J = 52.8 Hz, 1H), 4.42-4.53 (m, 2H), 4.02-4.08 (m, 6H), 3.82-3.85 (m, 2H), 3.50-3.58 (m, 1H), 3.21-3.30 (m, 1H), 2.90-3.11 (m, 2H), 2.50-2.55 (m, 1H), 1.90-2.18 (m, 8H). |
| 149a | 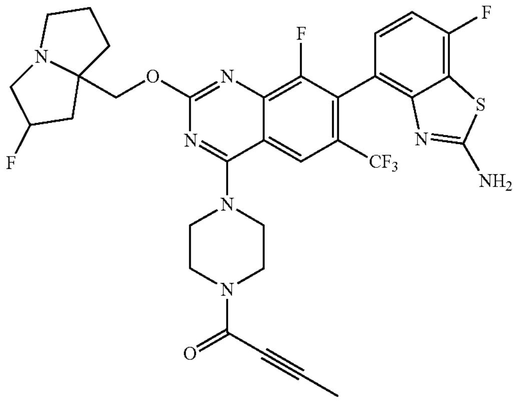 [SMILES: CC#CC(=O)N1CCN(c2nc(OCC34CCCN3CC(F)C4)nc3c(F)c(-c4ccc(F)c5sc(N)nc45)c(C(F)(F)F)cc23)CC1] | |
| 150 | 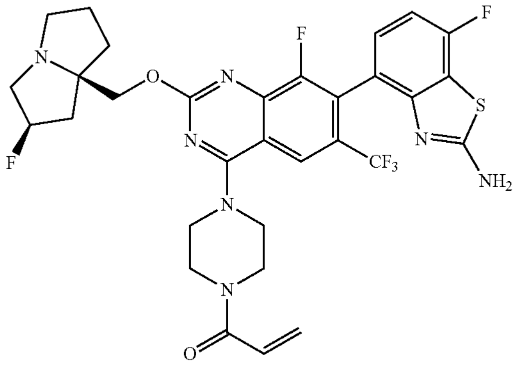 [SMILES: C=CC(=O)N1CCN(c2nc(OC[C@]34CCCN3C[C@H](F)C4)nc3c(F)c(-c4ccc(F)c5sc(N)nc45)c(C(F)(F)F)cc23)CC1] | LCMS m/z [M + 1]: 678.0 $^1$HNMR (400 MHz, $CD_3OD$): δ 8.27 (s, 1H), 7.20-7.25 (m, 1H), 7.01-7.08 (m, 1H), 6.82 (dd, J = 10.4, 16.4 Hz, 1H), 6.31 (d, J = 16.8 Hz, 1H), 5.84 (d, J = 10.8 Hz, 1H), 5.50 (d, J = 52 Hz, 1H), 4.72-4.82 (m, 2H), 4.10-4.15 (m, 4H), 3.94-4.03 (m, 5H), 3.63-3.70 (m, 1H), 3.43-3.48 (m, 2H), 2.70-2.80 (m, 1H), 2.35-2.55 (m, 2H), 2.15-2.32 (m, 3H). |

TABLE 2-continued

Selected compounds of the present disclosure.

| Compound No. | Structure | Analytical data |
| --- | --- | --- |
| 150a | 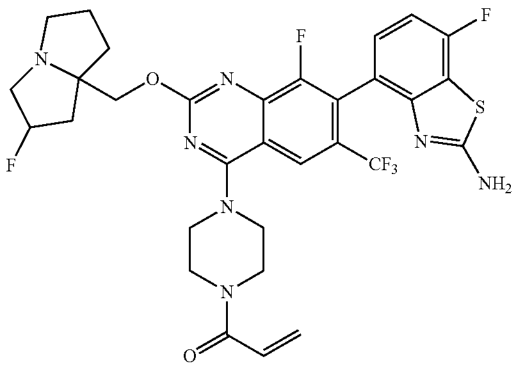 [SMILES: C=CC(=O)N1CCN(c2nc(OCC34CCCN3CC(F)C4)nc3c(F)c(-c4ccc(F)c5sc(N)nc45)c(C(F)(F)F)cc23)CC1] | |
| 151 | 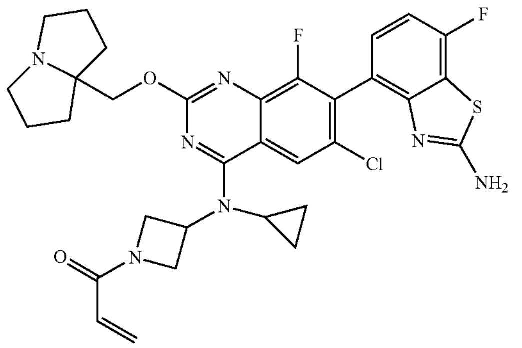 | LCMS m/z [M + 1]: 652.1<br>$^{1}$HNMR (400 MHz, $CD_3OD$) δ 8.54 (s, 1H), 7.22-7.25 (m, 1H), 7.01 (t, J = 8.77 Hz, 1H), 6.39-6.46 (m, 1H), 6.26-6.31 (m, 1H), 5.77-5.79 (m, 1H), 4.77-4.82 (m, 2H), 4.67-4.74 (m, 1H), 4.62-4.66 (m, 1H), 4.57-4.59 (m, 2H), 4.46-4.51 (m, 1H), 4.26-4.32 (m, 1H), 3.66-3.71 (m, 3H), 3.26 (m, 1H), 2.17-2.32 (m, 4H), 2.05-2.16 (m, 4H), 1.07-1.08 (m, 2H), 0.69-0.75 (m, 2H). |
| 152 | 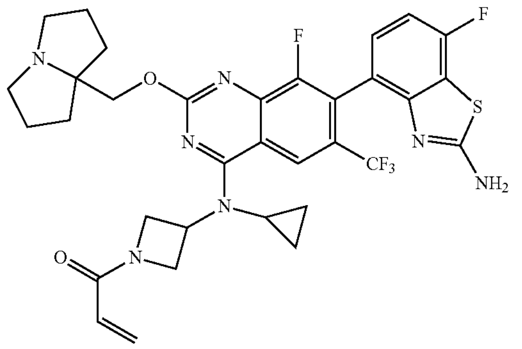 [SMILES: C=CC(=O)N1CC(N(c2nc(OCC34CCCN3CCC4)nc3c(F)c(-c4ccc(F)c5sc(N)nc45)c(Cl)cc23)C2CC2)C1] | LCMS m/z [M + 1]: 686.1<br>$^{1}$HNMR (400 MHz, $CD_3OD$) δ 8.85 (s, 1H), 7.23-7.26 (m, 1H), 7.02 (t, J = 8.86 Hz, 1H), 6.39-6.47 (m, 1H), 6.27-6.31 (m, 1H), 5.77-5.80 (m, 1H), 4.82-4.85 (m, 2H), 4.67-4.76 (m, 2H), 4.56-4.64 (m, 2H), 4.48-4.53 (m, 1H), 4.30-4.37 (m, 1H), 3.76-3.77 (m, 1H), 3.66-3.70 (m, 2H), 3.25-3.28 (m, 1H), 2.27-2.33 (m, 2H), 2.18-2.25 (m, 2H), 2.06-2.16 (m, 4H), 1.07-1.09 (m, 2H), 0.73-0.78 (m, 2H). |
| 153 | 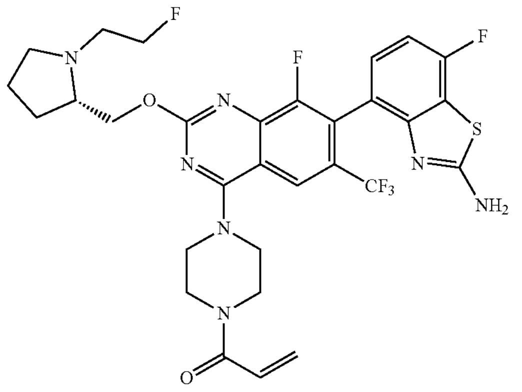 [SMILES: C=CC(=O)N1CCN(c2nc(OC[C@@H]3CCCN3CCF)nc3c(F)c(-c4ccc(F)c5sc(N)nc45)c(C(F)(F)F)cc23)CC1] | LCMS m/z [M + 1]: 666.0<br>$^{1}$HNMR (400 MHz, $CD_3OD$) δ 8.25 (s, 1H), 7.10-7.39 (m, 1H), 6.99-7.02 (m, 1H), 6.81 (dd, J = 10.6, 16.8 Hz, 1H), 6.29 (d, J = 16.7 Hz, 1H), 5.82 (d, J = 10.6 Hz, 1H), 4.85-4.91 (m, 1H), 4.75-4.81 (m, 2H), 4.65-4.72 (m, 1H), 4.05-4.19 (m, 5H), 3.89-3.99 (m, 5H), 3.78-3.88 (m, 1H), 3.52-3.69 (m, 1H), 3.31-3.45 (m, 1H), 2.35-2.46 (m, 1H), 2.01-2.29 (m, 3H). |

TABLE 2-continued
| Selected compounds of the present disclosure. | | |
|---|---|---|
| Compound No. | Structure | Analytical data |
| 153a | 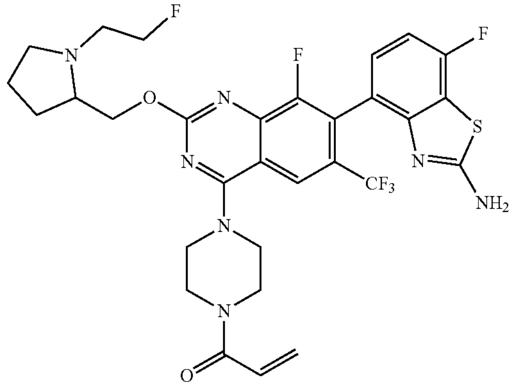 [SMILES: C=CC(=O)N1CCN(c2nc(OCC3CCCN3CCF)nc3c(F)c(-c4ccc(F)c5sc(N)nc45)c(C(F)(F)F)cc23)CC1] | |
| 154 | 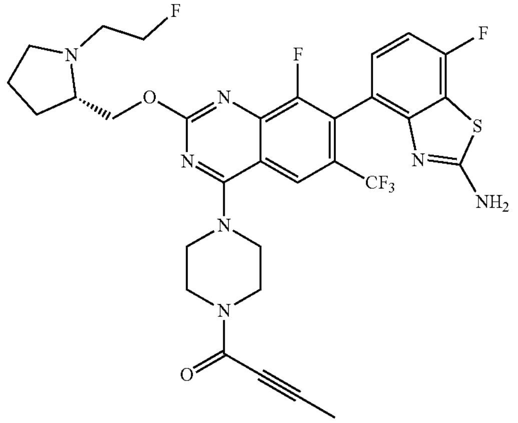 [SMILES: CC#CC(=O)N1CCN(c2nc(OC[C@@H]3CCCN3CCF)nc3c(F)c(-c4ccc(F)c5sc(N)nc45)c(C(F)(F)F)cc23)CC1] | LCMS m/z [M + 1]: 678.2 $^1$HNMR (400 MHz, $CD_3OD$) δ 8.23 (s, 1H), 7.19-7.22 (m, 1H), 6.97-7.01 (m, 1H), 4.85-4.91 (m, 1H), 4.75-4.80 (m, 2H), 4.68-4.75 (m, 1H), 3.95-4.19 (m, 8H), 3.79-3.89 (m, 3H), 3.53-3.69 (m, 2H), 2.35-2.47 (m, 1H), 2.18-2.31 (m, 1H), 2.03-2.18 (m, 2H), 2.03 (s, 3H). |
| 154a | 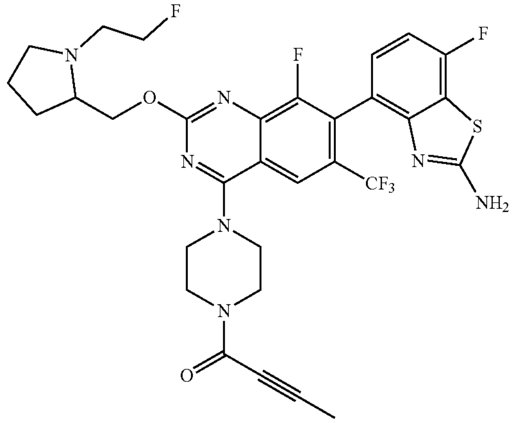 [SMILES: CC#CC(=O)N1CCN(c2nc(OCC3CCCN3CCF)nc3c(F)c(-c4ccc(F)c5sc(N)nc45)c(C(F)(F)F)cc23)CC1] | |

TABLE 2-continued
| Selected compounds of the present disclosure. | | |
|---|---|---|
| Compound No. | Structure | Analytical data |
| 156 | 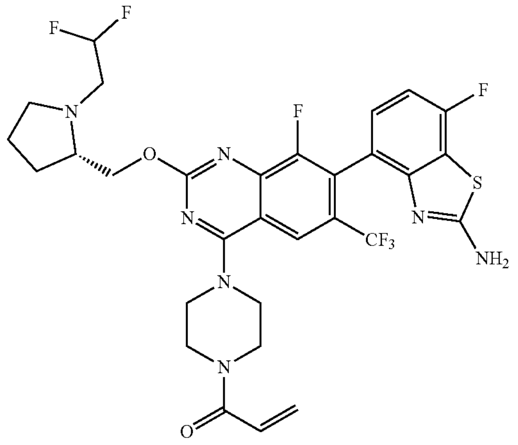 | LCMS m/z [M + 1]: 684.2 $^1$HNMR (400 MHz, $CD_3OD$) δ 8.27 (s, 1H), 7.19-7.29 (m, 1H), 7.03 (t, J = 8.8 Hz, 1H), 6.81 (dd, J = 16.8, 10.6 Hz, 1H), 6.25-6.58 (m, 2H), 5.75-5.85 (m, 1H), 4.83-4.95 (m, 1H), 4.65-4.75 (m, 1H), 4.05-4.25 (m, 6H), 3.70-4.01 (m, 6H), 3.35-3.45 (m, 1H), 2.50-2.35 (m, 1H), 2.32-2.03 (m, 3H). |
| 156a | 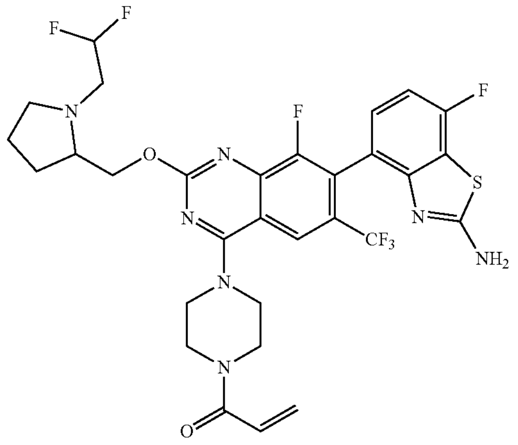 [SMILES: C=CC(=O)N1CCN(c2nc(OC[C@@H]3CCCN3CC(F)F)nc3c(F)c(-c4ccc(F)c5sc(N)nc45)c(C(F)(F)F)cc23)CC1] | |
| 158 | 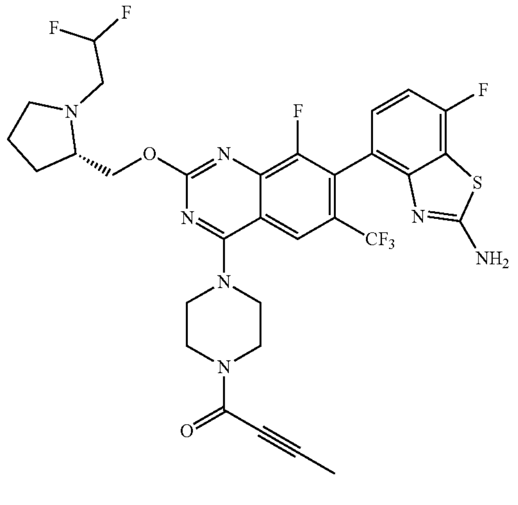 [SMILES: CC#CC(=O)N1CCN(c2nc(OC[C@@H]3CCCN3CC(F)F)nc3c(F)c(-c4ccc(F)c5sc(N)nc45)c(C(F)(F)F)cc23)CC1] | LCMS m/z [M + 1]: 696.0 $^1$HNMR (400 MHz, $CD_3OD$) δ 8.24 (s, 1H), 7.18-7.27 (m, 1H), 6.92-7.10 (m, 1H), 6.41 (t, J = 53.3 Hz, 1H), 4.69-4.80 (m, 1H), 4.01-4.38 (m, 9H), 3.65-3.90 (m, 4H), 3.38-3.51 (m, 1H), 2.08-2.42 (m, 7H). |

TABLE 2-continued
| Selected compounds of the present disclosure. | | |
|---|---|---|
| Compound No. | Structure | Analytical data |
| 158a | 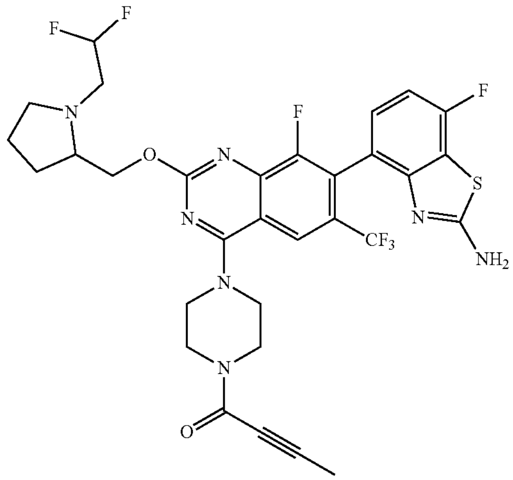 [SMILES: CC#CC(=O)N1CCN(c2nc(OCC3CCCN3CC(F)F)nc3c(F)c(-c4ccc(F)c5sc(N)nc45)c(C(F)(F)F)cc23)CC1] | |
| 159 | 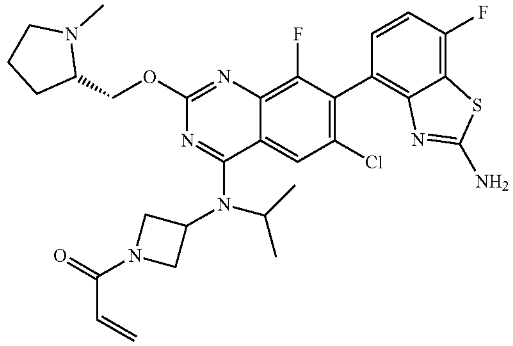 | LCMS m/z [M + 1]: 628.1 $^1$HNMR (400 MHz, $CD_3OD$): δ 8.30 (m, 1H), 7.22-7.25 (m, 1H), 7.02 (t, J = 8.0 Hz, 1H), 6.79-6.85 (m, 1H), 6.19-6.23 (m, 1H), 5.77-5.80 (m, 1H), 5.07-5.30 (m, 2H), 3.75-4.61 (m, 6H), 3.09-3.15 (m, 3H), 2.03-2.44 (m, 4H), 1.31-1.38 (m, 6H). |
| 159a | 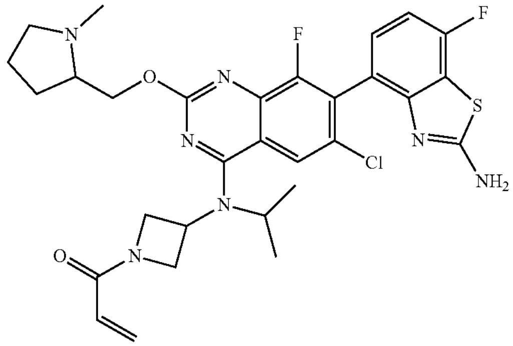 [SMILES: C=CC(=O)N1CC(N(c2nc(OCC3CCCN3C)nc3c(F)c(-c4ccc(F)c5sc(N)nc45)c(Cl)cc23)C(C)C)C1] | |
| 160 | 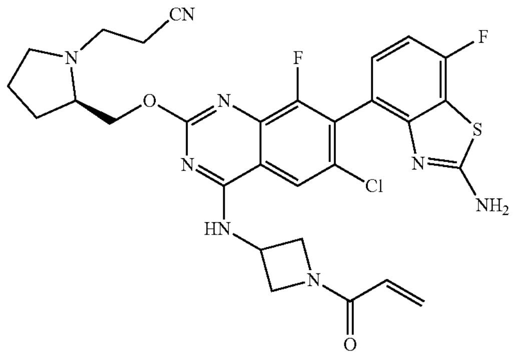 [SMILES: C=CC(=O)N1CC(Nc2nc(OC[C@H]3CCCN3CCC#N)nc3c(F)c(-c4ccc(F)c5sc(N)nc45)c(Cl)cc23)C1] | |

TABLE 2-continued
Selected compounds of the present disclosure.
| Compound No. | Structure | Analytical data |
|---|---|---|
| 160a | 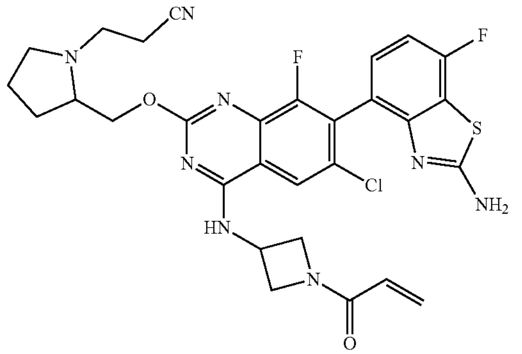 [SMILES: C=CC(=O)N1CC(Nc2nc(OCC3CCCN3CCC#N)nc3c(F)c(-c4ccc(F)c5sc(N)nc45)c(Cl)cc23)C1] | |
| 161 | 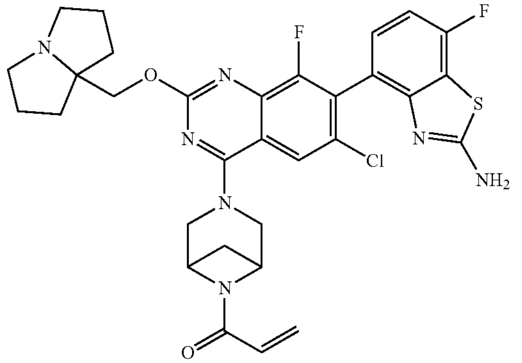 [SMILES: C=CC(=O)N1C2CC1CN(c1nc(OCC34CCCN3CCC4)nc3c(F)c(-c4ccc(F)c5sc(N)nc45)c(Cl)cc13)C2] | LCMS m/z [M + 1]: 638.0<br>$^1$HNMR (400 MHz, $CD_3OD$) δ 8.41 (s, 1H), 7.24-7.27 (m, 1H), 7.03 (t, J = 8.79 Hz, 1H), 6.47-6.54 (m, 1H), 6.27-6.31 (m, 1H), 5.77-5.80 (m, 1H), 4.60-4.72 (m, 4H), 4.40-4.55 (m, 3H), 3.66-3.72 (m, 2H), 3.21-3.28 (m, 2H), 2.88-2.93 (m, 1H), 2.07-2.34 (m, 10H). |
| 162 | 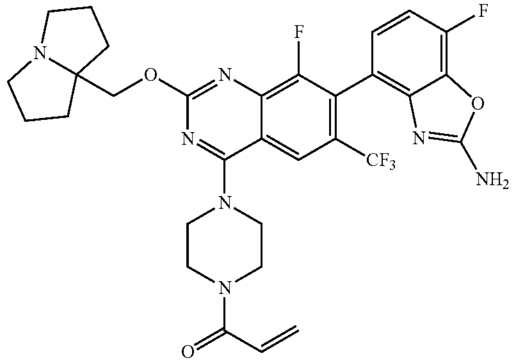 [SMILES: C=CC(=O)N1CCN(c2nc(OCC34CCCN3CCC4)nc3c(F)c(-c4ccc(F)c5oc(N)nc45)c(C(F)(F)F)cc23)CC1] | LCMS m/z [M + 1]: 644.2<br>$^1$HNMR (400 MHz, $CD_3OD$): δ 8.26 (s, 1H), 7.02-7.10 (m, 1H), 6.98 (t, J = 9.76, 1H), 6.81 (dd, J = 16.8, 10.6 Hz, 1H), 6.29 (d, J = 16.8 Hz, 1H), 5.82 (d, J = 10.4 Hz, 1H), 4.67 (s, 2H), 4.08-4.23 (m, 4H), 3.85-4.01 (m, 4H), 3.64-3.73 (m, 2H), 3.24-3.29 (m, 2H), 2.26-2.37 (m, 2H), 2.05-2.25 (m, 6H). |
| 163 | 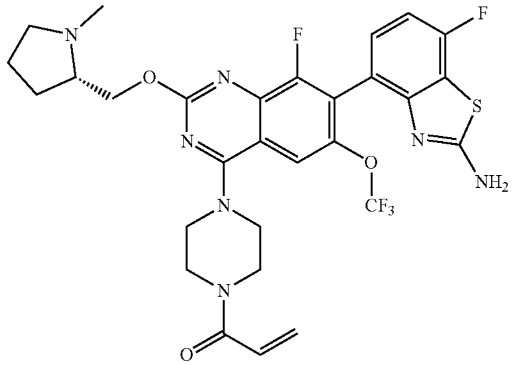 [SMILES: C=CC(=O)N1CCN(c2nc(OC[C@@H]3CCCN3C)nc3c(F)c(-c4ccc(F)c5sc(N)nc45)c(OC(F)(F)F)cc23)CC1] | LCMS m/z [M + 1]: 650.3<br>$^1$HNMR (300 MHz, $CD_3OD$) δ 7.79 (s, 1H), 7.27 (dd, J = 8.4, 5.4 Hz, 1H), 7.01 (t, J = 8.3 Hz, 1H), 6.84 (dd, J = 16.8, 10.6 Hz, 1H), 6.29 (dd, J = 16.8, 1.9 Hz, 1H), 5.82 (dd, J = 10.6, 1.9 Hz, 1H), 4.61-4.42 (m, 2H), 4.10-3.86 (m, 8H) 3.18-3.06 (m, 1H), 2.96-2.75 (m, 1H), 2.55 (s, 3H), 2.40 (q, J = 8.7 Hz, 1H), 2.26-2.01 (m, 1H), 2.00-1.70 (m, 3H). |

TABLE 2-continued
Selected compounds of the present disclosure.
| Compound No. | Structure | Analytical data |
|---|---|---|
| 164 | 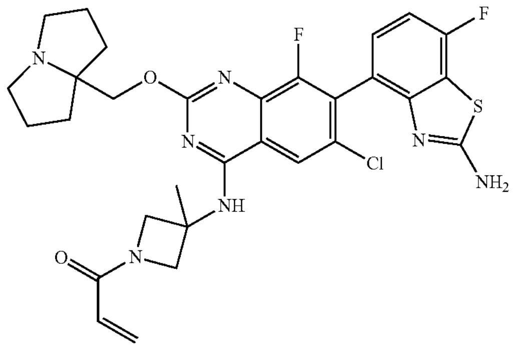 [SMILES: C=CC(=O)N1CC(C)(Nc2nc(OCC34CCCN3CCC4)nc3c(F)c(-c4ccc(F)c5sc(N)nc45)c(Cl)cc23)C1] | LCMS m/z [M + 1]: 626.2 ¹HNMR (500 MHz, $CD_3OD$) δ 8.29 (s, 1H), 7.27 (dd, J = 8.5, 5.4 Hz, 1H), 7.05 (t, J = 8.8 Hz, 1H), 6.42 (dd, J = 17.0, 10.3 Hz, 1H), 6.34-6.24 (m, 1H), 5.79 (dd, J = 10.3, 2.0 Hz, 1H), 4.78-4.73 (m, 1H), 4.67-4.58 (m, 2H), 4.58-4.52 (m, 1H), 4.43-4.38 (m, 1H), 4.17-4.11 (m, 1H), 3.75-3.66 (m, 2H), 3.37-3.24 (m, 2H), 2.38-2.29 (m, 2H), 2.29-2.19 (m, 2H), 2.19-2.14 (m, 2H), 2.13-2.06 (m, 2H), 1.85 (s, 3H). |
| 165 | 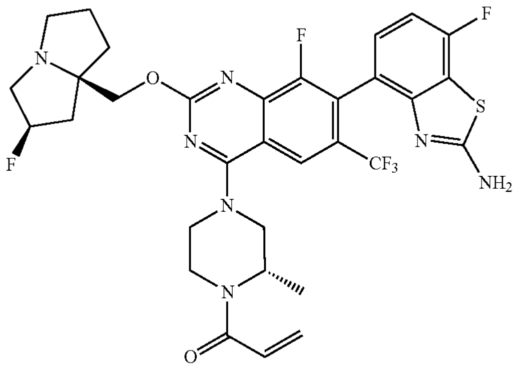 [SMILES: C=CC(=O)N1CCN(c2nc(OC[C@]34CCCN3C[C@H](F)C4)nc3c(F)c(-c4ccc(F)c5sc(N)nc45)c(C(F)(F)F)cc23)C[C@@H]1C] | LCMS m/z [M + 1]: 692.0 ¹HNMR (400 MHz, $CD_3OD$) δ 8.29 (s, 1H), 7.24-7.27 (m, 1H), 7.04 (t, J = 8.82 Hz, 1H), 6.77-6.83 (m, 1H), 6.28 (d, J = 15.72 Hz, 1H), 5.80 (d, J = 10.35 Hz, 1H), 5.51 (d, J = 51.0 Hz, 1H), 4.71-4.83 (m, 3H), 4.35-4.50 (m, 3H), 3.97-4.08 (m, 2H), 3.65-3.81 (m, 3H), 3.44-3.57 (m, 2H), 2.67-2.75 (m, 1H), 2.38-2.53 (m, 2H), 2.25-2.30 (m, 2H), 2.13-2.16 (m, 1H), 1.32-1.50 (m, 3H). |
| 165a | 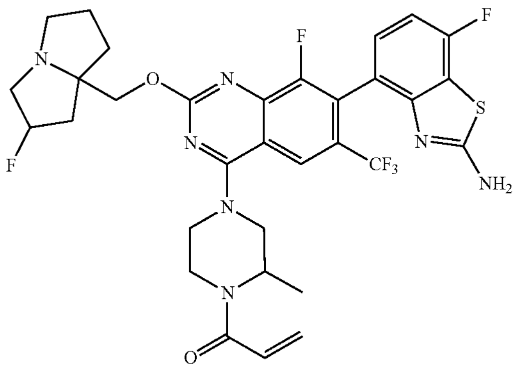 [SMILES: C=CC(=O)N1CCN(c2nc(OCC34CCCN3CC(F)C4)nc3c(F)c(-c4ccc(F)c5sc(N)nc45)c(C(F)(F)F)cc23)CC1C] | |
| 166 | 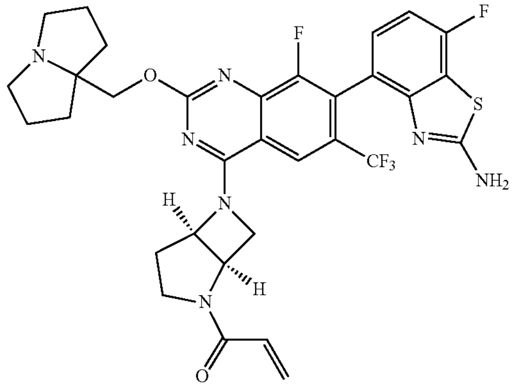 [SMILES: C=CC(=O)N1CC[C@@H]2[C@H]1CN2c1nc(OCC23CCCN2CCC3)nc2c(F)c(-c3ccc(F)c4sc(N)nc34)c(C(F)(F)F)cc12] | LCMS m/z [M + 1]: 672. ¹HNMR (400 MHz, $CD_3OD$): δ: 8.10 (s, 1H), 7.17-7.21 (m, 1H), 6.96-7.00 (m, 1H), 6.61-6.79 (m, 1H), 6.34-6.39 (m, 1H), 5.82-5.85 (m, 1H), 5.59-5.69 (m, 1H), 5.05-5.11 (m, 2H), 4.47-4.65 (m, 3H), 4.24-4.36 (m, 1H), 3.95 (m, 1H), 3.66 (m, 3H), 2.59-2.69 (m, 1H), 2.11-2.31 (m, 10H). |

TABLE 2-continued
| Selected compounds of the present disclosure. | | |
|---|---|---|
| Compound No. | Structure | Analytical data |
| 166a | 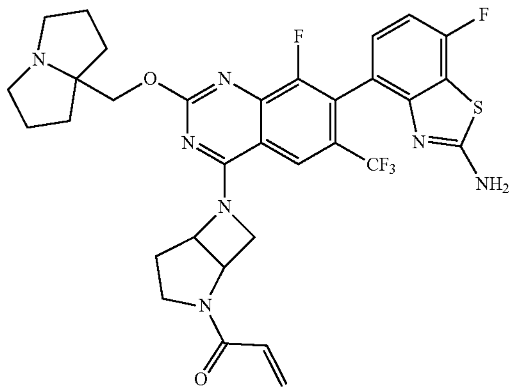 [SMILES: C=CC(=O)N1CCC2C1CN2c1nc(OCC23CCCN2CCC3)nc2c(F)c(-c3ccc(F)c4sc(N)nc34)c(C(F)(F)F)cc12] | |
| 167 | 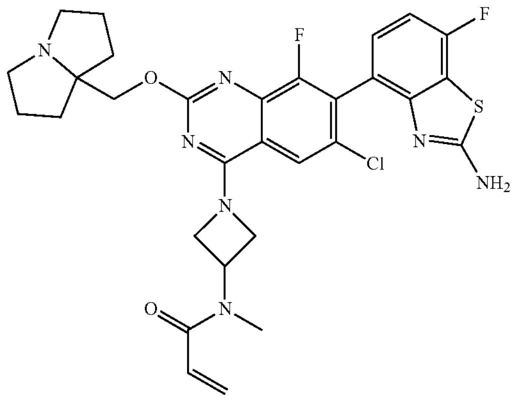 [SMILES: C=CC(=O)N(C)C1CN(c2nc(OCC34CCCN3CCC4)nc3c(F)c(-c4ccc(F)c5sc(N)nc45)c(Cl)cc23)C1] | LCMS m/z [M + 1]: 626.2 $^{1}$HNMR (400 MHz, $CD_3OD$): δ 7.92 (s, 1H), 7.23 (dd, J = 8.8, 5.6 Hz, 1H), 7.02 (t, J = 8.8 Hz, 1H), 6.79 (dd, J = 16.8, 10.6 Hz, 1H), 6.28 (d, J = 17.2 Hz, 1H), 5.81 (d, J = 10.8, 1H), 5.15-5.48 (m, 2H), 4.95-5.10 (m, 2H), 4.66 (s, 2H), 3.63-3.72 (m, 2H), 3.23-3.28 (m, 6H), 2.27-2.35 (m, 2H), 2.18-2.26 (m, 2H), 2.05-2.17 (m, 4H). |
| 169 | 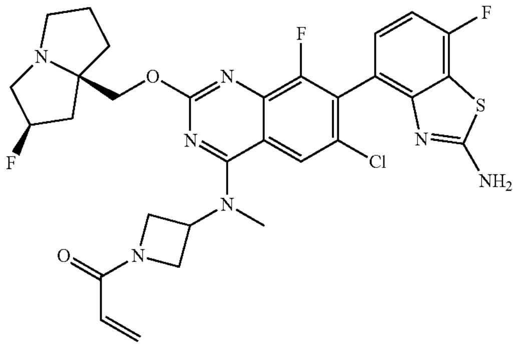 [SMILES: C=CC(=O)N1CC(N(C)c2nc(OC[C@]34CCCN3C[C@H](F)C4)nc3c(F)c(-c4ccc(F)c5sc(N)nc45)c(Cl)cc23)C1] | LCMS m/z [M + 1]: 644.2 $^{1}$HNMR (400 MHz, $CD_3OD$) δ 8.10 (s, 1H), 7.23 (t, J = 8 Hz, 1H), 6.98-7.03 (m, 1H), 6.36-6.40 (m, 1H), 6.26-6.30 (m, 1H), 5.69 (d, J = 8.0 Hz, 1H), 5.44-5.61 (m, 1H), 4.68-4.71 (m, 3H), 4.45-4.46 (m, 2H), 4.21-4.25 (m, 1H), 3.99-4.06 (m, 1H), 3.63-3.65 (m, 1H), 3.5 (s, 3H), 3.11-3.12 (m, 1H), 2.11-2.75 (m, 8 H). |
| 169a | 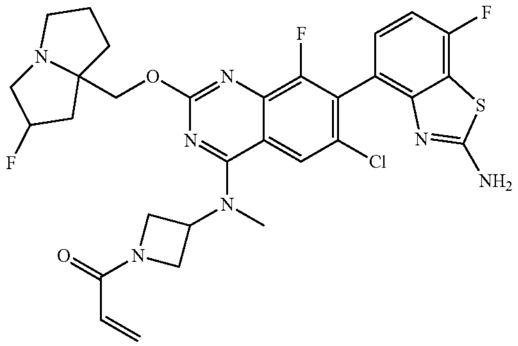 [SMILES: C=CC(=O)N1CC(N(C)c2nc(OCC34CCCN3CC(F)C4)nc3c(F)c(-c4ccc(F)c5sc(N)nc45)c(Cl)cc23)C1] | |

TABLE 2-continued
| Selected compounds of the present disclosure. | | |
|---|---|---|
| Compound No. | Structure | Analytical data |
| 170 | 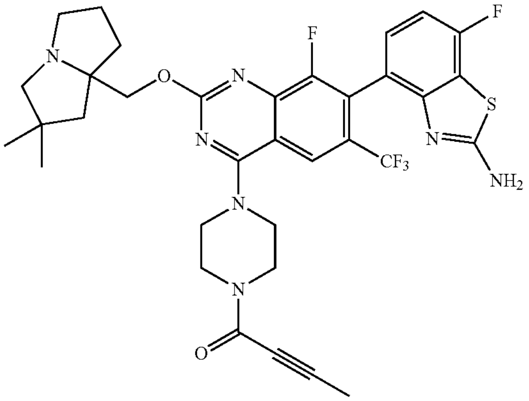 [SMILES: CC#CC(=O)N1CCN(c2nc(OCC34CCCN3CC(C)(C)C4)nc3c(F)c(-c4ccc(F)c5sc(N)nc45)c(C(F)(F)F)cc23)CC1] | LCMS m/z [M + 1]: 700.1 $^1$HNMR (400 MHz, $CD_3OD$) δ 8.23 (s, 1H), 7.18-7.22 (m, 1H), 6.98 (t, J = 8.8 Hz, 1H), 4.67-4.77 (m, 2H), 4.11-4.13 (m, 2H), 4.06-4.08 (m, 4H), 3.83-3.86 (m, 2H), 3.61-3.64 (m, 1H), 3.47-3.50 (m, 1H), 3.43-3.44 (m, 1H), 3.10-3.13 (m, 1H), 2.11-2.43 (m, 6H), 2.07 (s, 3H), 1.28 (s, 3H), 1.27 (s, 3H). |
| 171 | 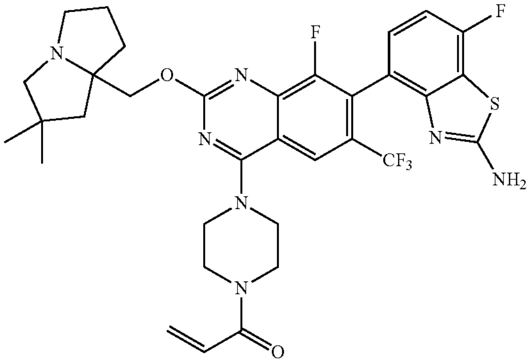 [SMILES: C=CC(=O)N1CCN(c2nc(OCC34CCCN3CC(C)(C)C4)nc3c(F)c(-c4ccc(F)c5sc(N)nc45)c(C(F)(F)F)cc23)CC1] | LCMS m/z [M + 1]: 688.2 $^1$HNMR (400 MHz, $CD_3OD$) δ 8.26 (s, 1H), 7.21-7.25 (m, 1H), 7.02 (t, J = 9.2 Hz, 1H), 6.77-6.84 (m, 1H), 6.29 (dd, J = 16.8, 1.6 Hz, 1H), 5.81 (dd, J = 10.6, 1.6 Hz, 1H), 4.68-4.78 (m, 2H), 4.14-4.19 (m, 4H), 3.91-3.97 (m, 4H), 3.61-3.65 (m, 1H), 3.48-3.51 (m, 1H), 3.40-3.43 (m, 1H), 3.10-3.12 (m, 1H), 2.08-2.43 (m, 6H), 1.28 (s, 3H), 1.27 (s, 3H). |
| 172 | 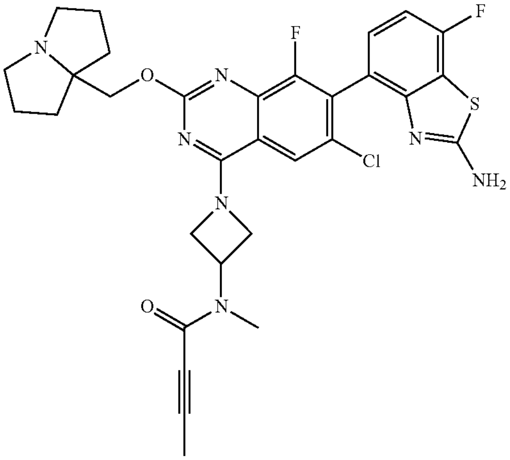 [SMILES: CC#CC(=O)N(C)C1CN(c2nc(OCC34CCCN3CCC4)nc3c(F)c(-c4ccc(F)c5sc(N)nc45)c(Cl)cc23)C1] | LCMS m/z [M + 1]: 638.2 $^1$HNMR (400 MHz, $CD_3OD$): δ 7.90 (d, J = 12 Hz, 1H), 7.23 (dd, J = 8.4, 5.6 Hz, 1H), 7.01 (t, J = 8.8 Hz, 1H), 5.72-5.82 (m, 0.5H), 5.17-5.29 (m, 0.5H), 4.89-5.13 (m, 2H), 4.71-4.86 (m, 2H), 4.63-4.68 (m, 2H), 3.62-3.73 (m, 2H), 3.39 (s, 1.5H), 3.23-3.29 (m, 2H), 3.16 (s, 1.5H), 2.25-2.35 (m, 2H), 2.16-2.25 (m, 2H), 2.05-2.15 (m, 7H). |

TABLE 2-continued
Selected compounds of the present disclosure.
| Compound No. | Structure | Analytical data |
|---|---|---|
| 176 | 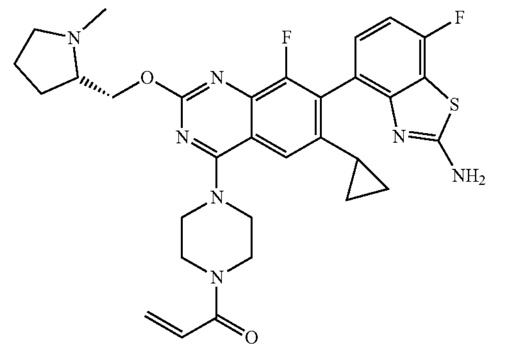 | LCMS m/z [M + Na]: 628.2 $^1$HNMR (300 MHz, $CD_3OD$) δ 7.44 (s, 1H), 7.36-7.15 (m, 1H), 7.02 (t, J = 8.8 Hz, 1H), 6.84 (dd, J = 16.9, 10.7 Hz, 1H), 6.30 (dd, J = 16.8, 1.9 Hz, 1H), 6.07-5.72 (m, 1H), 4.75 (m, 1H), 4.71-4.48 (m, 1H), 4.02 (bs, 4H), 3.94 (bs, 4H), 3.57 (m, 2H), 2.99 (m, 1H), 2.93 (s, 3H), 2.34 (m, 1H), 2.03 (m, 3H), 1.73 (m, 1H), 0.93 and 0.58 (m, 1H), 0.76 (m 3H). |
| 176a | 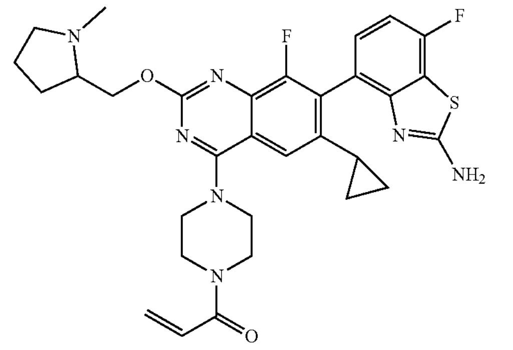 [SMILES: C=CC(=O)N1CCN(c2nc(OCC3CCCN3C)nc3c(F)c(-c4ccc(F)c5sc(N)nc45)c(C4CC4)cc23)CC1] | |
| 177 | 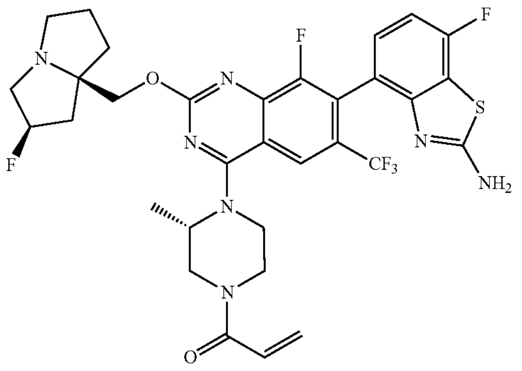 [SMILES: C=CC(=O)N1CCN(c2nc(OC[C@]34CCCN3C[C@H](F)C4)nc3c(F)c(-c4ccc(F)c5sc(N)nc45)c(C(F)(F)F)cc23)[C@@H](C)C1] | LCMS m/z [M + 1]: 692.3 $^1$HNMR (400 MHz, $CD_3OD$): δ 8.13 (s, 1H), 7.15-7.22 (m, 1H), 6.97 (t, J = 8.8 Hz, 1H), 6.73-6.92 (m, 1H), 6.24-6.35 (m, 1H), 5.81 (d, J = 11.6 Hz, 1H), 5.35 (d, J = 53.2 Hz, 1H), 4.31-4.62 (m, 4H), 4.01-4.22 (m, 1H), 3.58-3.85 (m, 2H), 3.41-3.52 (m, 1H), 3.34-3.42 (m, 1H ), 3.21-3.29 (m, 1H), 3.12-3.20 (m, 1H), 2.87-3.04 (m, 1H), 2.74-2.83 (m, 1H), 2.46-2.59 (m, 1H), 1.93-2.21 (m, 4H), 1.78-1.91 (m,1H), 1.46-1.52 (m, 3H). |
| 177a | 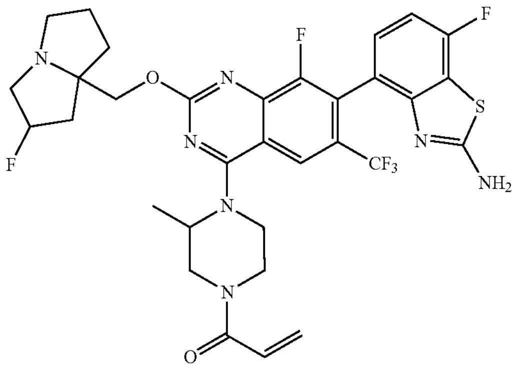 | |

TABLE 2-continued
| Selected compounds of the present disclosure. | | |
|---|---|---|
| Compound No. | Structure | Analytical data |
| 178 | 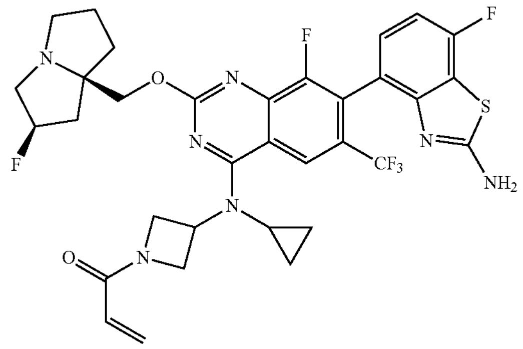 | LCMS m/z [M + 1]: 704.2<br>$^{1}$H NMR (400 MHz, $CD_3OD$): δ 8.85 (s, 1H), 7.17-7.23 (m, 1H), 6.99 (t, J = 8.79 Hz, 1H), 6.37-6.46 (m, 1H), 6.29 (d, J = 16.77 Hz), 5.78 (d, J = 10.38 Hz), 5.50 (d, J = 51.92 Hz), 4.70-4.76 (m, 4H), 4.48-4.52 (m, 1H), 4.27-4.38 (m, 1H), 3.99-4.04 (m, 1H), 3.41-3.55 (m, 2H), 2.65-2.75 (m, 1H), 2.12-2.51 (m, 5H), 1.34-1.41 (m, 2H), 1.08 (d, J = 6.19 Hz, 2H), 0.72-0.76 (m, 2H). |
| 178a | 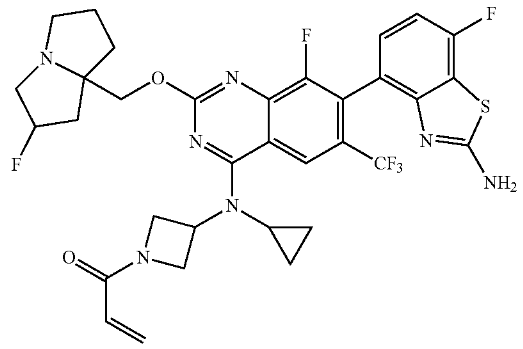 | |
| 180 | 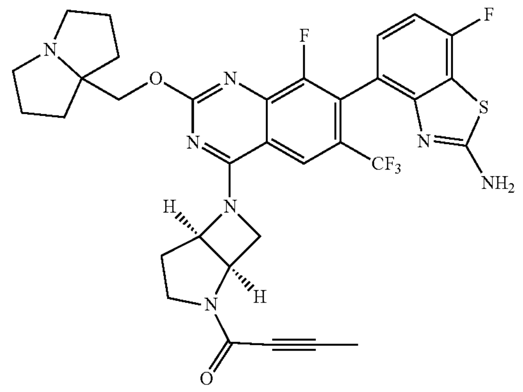 | LCMS m/z [M + 1]: 684.2<br>$^{1}$HNMR (400 MHz, $CD_3OD$) δ 8.06 (s, 1H), 7.15-7.26 (m, 1H), 6.91-7.00 (m, 1H), 5.52-5.70 (m, 1H), 4.90-5.21 (m, 2H), 4.42-4.80 (m, 1H), 4.18-4.40 (m, 3H), 3.58-4.10 (m, 1H), 3.14-3.29 (m, 2H), 2.72-2.90 (m, 2H), 2.55-2.70 (m, 1H), 1.72-2.32 (m, 13H). |
| 180a | 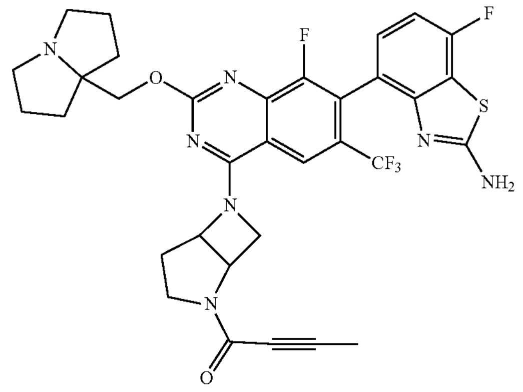 | |

TABLE 2-continued
| Selected compounds of the present disclosure. | | |
|---|---|---|
| Compound No. | Structure | Analytical data |
| 181 | 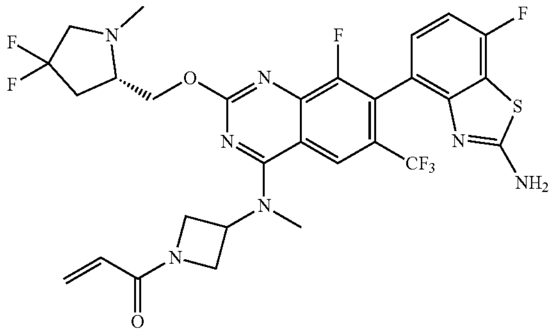 [SMILES: C=CC(=O)N1CC(N(C)c2nc(OC[C@@H]3CC(F)(F)CN3C)nc3c(F)c(-c4ccc(F)c5sc(N)nc45)c(C(F)(F)F)cc23)C1] | LCMS m/z [M + 1]: 670.2 $^{1}$H NMR (400 MHz, $CD_3OD$): δ 8.35 (s, 1H), 7.22 (t, J = 7.6 Hz, 1H), 7.0 (t, J = 8.4 Hz, 1H), 6.27-6.45 (m, 2H), 5.78 (d, J = 11.6 Hz, 1H), 4.94-5.06 (m, 2H), 4.71-4.76 (m, 2H), 4.50-4.62 (m, 2H), 4.18-4.30 (m, 3H), 3.75-3.90 (m, 1H), 3.57 ( s, 3H), 3.20 ( s, 3H), 2.90-3.03 (m, 1H), 2.68-2.85 (m, 1H). |
| 181a | 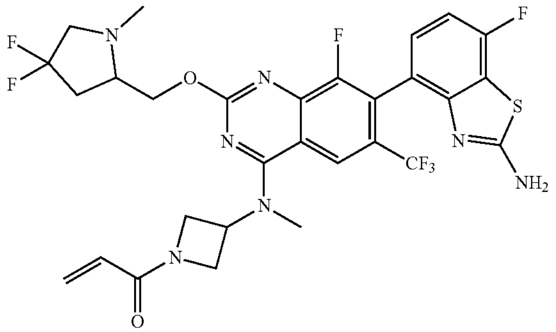 [SMILES: C=CC(=O)N1CC(N(C)c2nc(OCC3CC(F)(F)CN3C)nc3c(F)c(-c4ccc(F)c5sc(N)nc45)c(C(F)(F)F)cc23)C1] | |
| 183 | 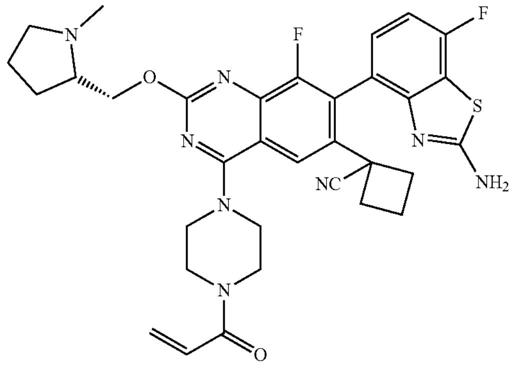 | LCMS m/z [M + Na]: 666.99 $^{1}$HNMR (300 MHz, $CD_3OD$) δ 7.66 (s, 1H), 7.32 (dd, J = 8.4, 5.4 Hz, 1H), 7.01 (t, J = 8.8 Hz, 1H), 6.83 (dd, J = 16.8, 10.6 Hz, 1H), 6.28 (dd, J = 16.8, 2.0 Hz, 1H), 5.81 (dd, J = 10.6, 2.0 Hz, 1H), 4.56-4.39 (m, 2H), 4.07-4.00 (m, 4H), 3.97-3.90 (m, 4H), 3.13-3.04 (m, 1H), 2.81-2.64 (m, 2H), 2.52 (s, 3H), 2.34 (t, J = 8.9 Hz, 1H), 2.24 (s, 1H), 2.19-1.98 (m, 2H), 1.86-1.72 (m, 4H), 1.66-1.54 (m, 2H). |
| 183a | 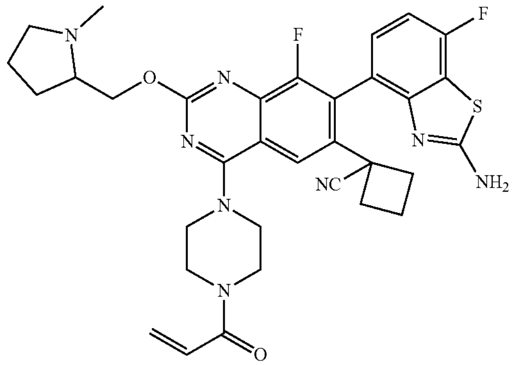 [SMILES: C=CC(=O)N1CCN(c2nc(OCC3CCCN3C)nc3c(F)c(-c4ccc(F)c5sc(N)nc45)c(C4(C#N)CCC4)cc23)CC1] | |

TABLE 2-continued
Selected compounds of the present disclosure.
| Compound No. | Structure | Analytical data |
|---|---|---|
| 184 | 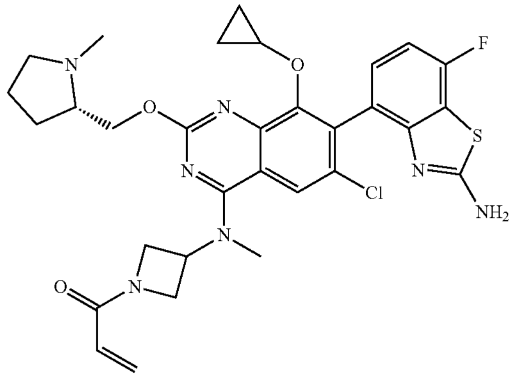 [SMILES: C=CC(=O)N1CC(N(C)c2nc(OC[C@@H]3CCCN3C)nc3c(OC4CC4)c(-c4ccc(F)c5sc(N)nc45)c(Cl)cc23)C1] | LCMS m/z [M + 1]: 638.1 $^1$HNMR (700 MHz, $CD_3OD$) δ 7.95 (s, 1H), 7.05 (ddd, J = 8.3, 5.5, 1.6 Hz, 1H), 6.92 (dd, J = 9.2, 8.3 Hz, 1H), 6.79 (d, J = 16.0 Hz, 1H), 6.27 (d, J = 16.8 Hz, 1H), 5.79 (d, J = 10.6 Hz, 1H), 4.56-4.39 (m, 1H), 4.34-4.29 (m, 1H), 4.24-4.10 (m, 1H), 4.01 (d, J = 11.2 Hz, 1H), 3.83-3.70 (m, 2H), 3.16-3.05 (m, 4H), 2.99 (s, 1H), 2.77 (d, J = 9.2 Hz, 1H), 2.46 (d, J = 1.1 Hz, 3H), 2.36 (qd, J = 9.1, 3.9 Hz, 1H), 2.07 (tdd, J = 10.4, 8.9, 5.0 Hz, 1H), 1.89-1.67 (m, 3H), 1.38-1.23 (m, 2H), 0.37-0.30 (m, 1H), 0.30-0.20 (m, 2H). |
| 184a | 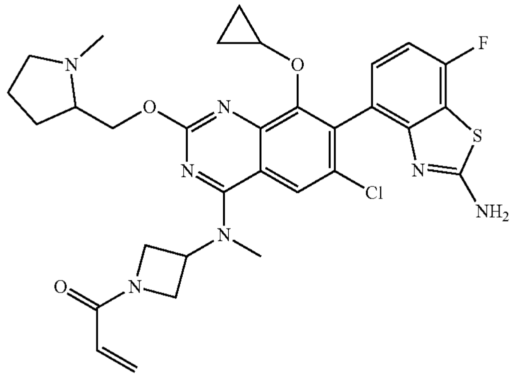 [SMILES: C=CC(=O)N1CC(N(C)c2nc(OCC3CCCN3C)nc3c(OC4CC4)c(-c4ccc(F)c5sc(N)nc45)c(Cl)cc23)C1] | |
| 185 | 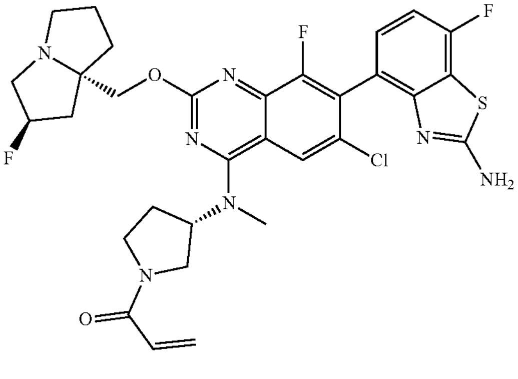 [SMILES: C=CC(=O)N1CC[C@H](N(C)c2nc(OC[C@@]34CCCN3C[C@H](F)C4)nc3c(F)c(-c4ccc(F)c5sc(N)nc45)c(Cl)cc23)C1] | LCMS m/z [M + 1]: 658.2 $^1$HNMR (400 MHz, $CD_3OD$) δ 8.14 (s, 1H), 7.23-7.26 (m, 1H), 7.02 (t, J = 8.8 Hz, 1H), 6.62-6.71 (m, 1H), 6.30-6.34 (m, 1H), 5.78-5.81 (m, 1H), 5.48-5.61 (m, 1H), 5.25-5.36 (m, 1H), 4.61-4.72 (m, 2H), 3.72-4.17 (m, 6H), 3.53-3.62 (m, 1H), 3.42-3.49 (m, 4H), 2.29-2.71 (m, 8H). |
| 185a | 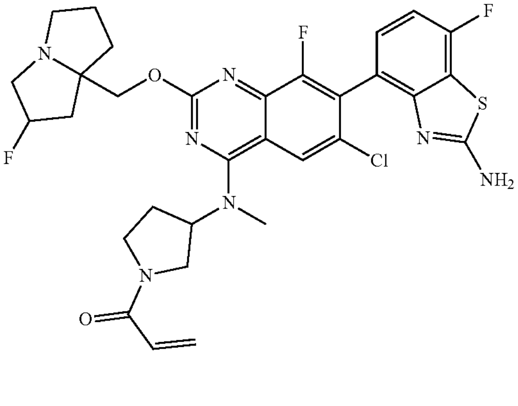 [SMILES: C=CC(=O)N1CCC(N(C)c2nc(OCC34CCCN3CC(F)C4)nc3c(F)c(-c4ccc(F)c5sc(N)nc45)c(Cl)cc23)C1] | |

TABLE 2-continued

Selected compounds of the present disclosure.

| Compound No. | Structure | Analytical data |
|---|---|---|
| 186 | 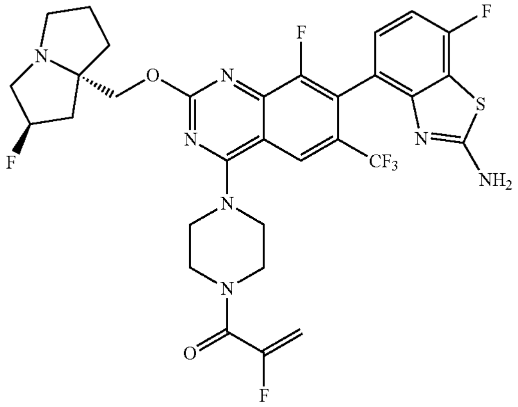 [SMILES: C=C(F)C(=O)N1CCN(c2nc(OC[C@@]34CCCN3C[C@H](F)C4)nc3c(F)c(-c4ccc(F)c5sc(N)nc45)c(C(F)(F)F)cc23)CC1] | LCMS m/z [M + 1]: 696.2<br>$^{1}$HNMR (400 MHz, $CD_3OD$) δ 8.26 (s, 1H), 7.22 (dd, J = 8.0, 5.6 Hz, 1H), 7.00 (t, J = 8.96 Hz 1H), 5.56 (d, J = 51.6 Hz, 1H), 5.38 (dd, J = 26.8, 4.0 Hz, 1H), 5.28 (dd, J = 5.6, 3.6 Hz, 1H), 4.63-4.79 (m, 2H), 4.14-4.20 (m, 4H), 3.82-4.05 (m, 6H), 3.42-3.50 (m, 1H), 3.32-3.35 (m, 1H), 2.53-2.74 (m, 2H), 2.29-2.46 (m, 3H), 2.13-2.21 (m, 1H). |
| 186a | 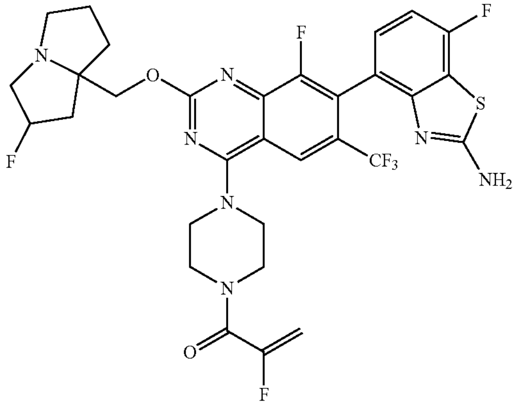 [SMILES: C=C(F)C(=O)N1CCN(c2nc(OCC34CCCN3CC(F)C4)nc3c(F)c(-c4ccc(F)c5sc(N)nc45)c(C(F)(F)F)cc23)CC1] | |
| 187 | 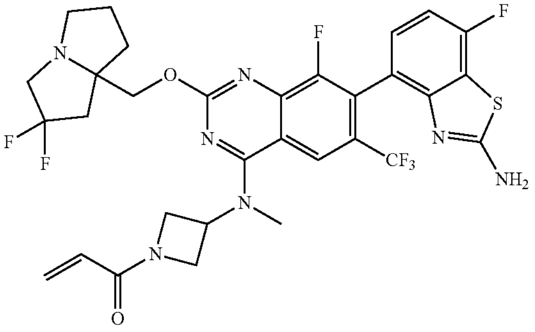 [SMILES: C=CC(=O)N1CC(N(C)c2nc(OCC34CCCN3CC(F)(F)C4)nc3c(F)c(-c4ccc(F)c5sc(N)nc45)c(C(F)(F)F)cc23)C1] | LCMS m/z [M + 1]: 696.2<br>$^{1}$HNMR (400 MHz, $CD_3OD$): δ 8.23 (s, 1H), 7.19-7.21 (m, 1H), 6.96 (t, J = 8.79 Hz, 1H), 6.38-6.45 (m, 1H), 6.26-6.30 (m, 1H), 5.77 (d, J = 10.78 Hz, 1H), 4.99-5.50 (m, 1H), 4.74 (t, J = 8.79 Hz, 1H), 4.46-4.54 (m, 2H), 4.25-4.31 (m, 3H), 3.40-3.52 (m, 4H), 3.10-3.19 (m, 2H), 2.83-2.89 (m, 1H), 2.53-2.6 (m, 1H), 2.28-2.39 (m, 1H), 2.12-2.19 (m, 1H), 1.87-2.02 (m, 3H). |
| 188 | 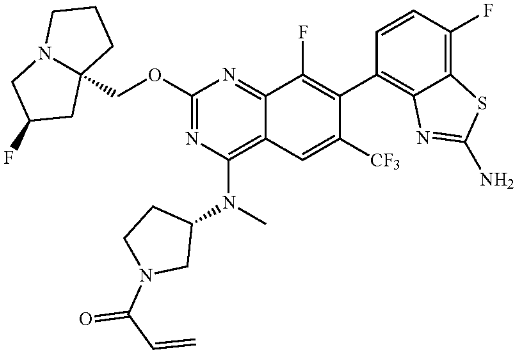 [SMILES: C=CC(=O)N1CC[C@H](N(C)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 692.2<br>$^{1}$HNMR (400 MHz, $CD_3OD$): δ 8.38 (s, 1H), 7.20-7.26 (m, 1H), 6.99 (t, J = 8.79 Hz, 1H), 6.62-6.72 (m, 1H), 6.33 (d, J = 16.77 Hz), 5.77-5.82 (m, 1H), 5.56 (d, J = 51.44 Hz, 1H), 5.28-5.43 (m, 1H), 4.62-4.76 (m, 2H), 3.70-4.19 (m, 6H), 3.42-3.63 (m, 5H), 2.15-2.68 (m, 8H). |

TABLE 2-continued
| Selected compounds of the present disclosure. | | |
|---|---|---|
| Compound No. | Structure | Analytical data |
| 188a | 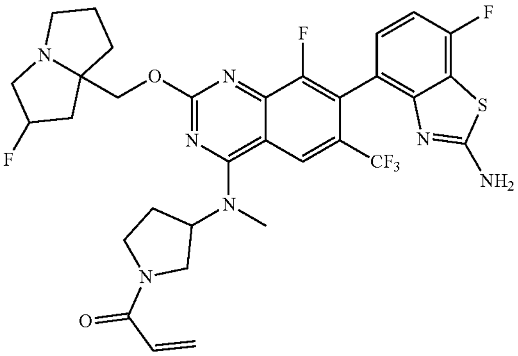 | |
| 189 | 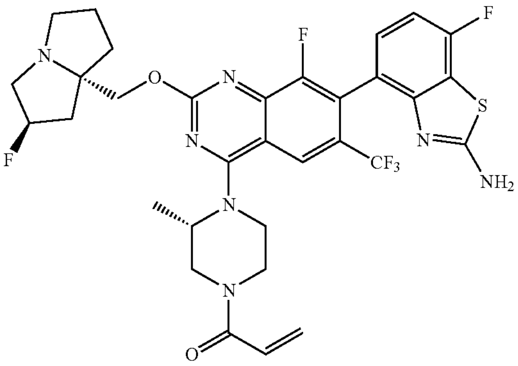 [SMILES: C=CC(=O)N1CCN(c2nc(OC[C@@]34CCCN3C[C@H](F)C4)nc3c(F)c(-c4ccc(F)c5sc(N)nc45)c(C(F)(F)F)cc23)[C@@H](C)C1] | LCMS m/z [M + 1]: 692.2 $^1$HNMR (400 MHz, $CD_3OD$) δ 8.19 (s, 1H), 7.22-7.25 (m, 1H), 7.00-7.05 (m, 1H), 6.75-6.98 (m, 1H), 6.31 (d, J = 8 Hz, 1H), 5.84 (d, J = 4 Hz, 1H), 5.51-5.64 (m, 1H), 4.70-4.74 (m, 2H), 4.68-4.69 (m, 2H), 3.93-4.03 (m, 1H), 3.83-3.91 (m, 3H), 3.58-3.63 (m, 1H), 2.59-2.64 (m, 2H), 2.32-2.37 (m, 3H), 2.18-2.32 (m, 1H), 1.48-1.59 (m, 3H). |
| 189a | 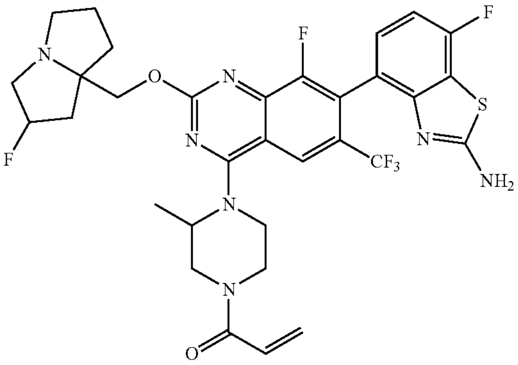 [SMILES: C=CC(=O)N1CCN(c2nc(OCC34CCCN3CC(F)C4)nc3c(F)c(-c4ccc(F)c5sc(N)nc45)c(C(F)(F)F)cc23)C(C)C1] | |
| 190 | 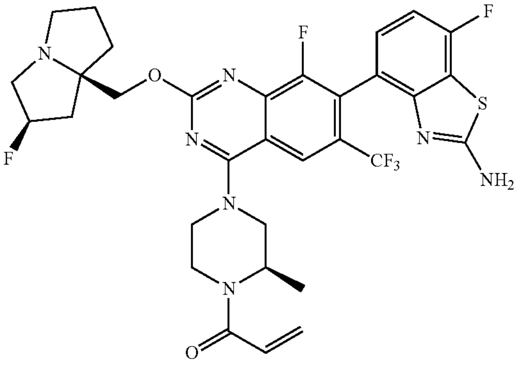 [SMILES: C=CC(=O)N1CCN(c2nc(OC[C@]34CCCN3C[C@H](F)C4)nc3c(F)c(-c4ccc(F)c5sc(N)nc45)c(C(F)(F)F)cc23)C[C@H]1C] | LCMS m/z [M + 1]: 692.2 $^1$HNMR (400 MHz, $CD_3OD$) δ 8.28 (s, 1H), 7.21-7.28 (m, 1H), 6.98-7.10 (m, 1H), 6.79 (dd, J = 16.8, 10.8 Hz, 1H), 6.29 (d, J = 12.8 Hz, 1H), 5.80 (d, J = 10.4 Hz, 1H), 5.44-5.57 (m, 1H), 4.70-4.85 (m, 3H), 4.20-4.70 (m, 3H), 3.92-4.20 (m, 3H), 3.38-3.82 (m, 5H), 2.72 (t, J = 4.8 Hz, 1H), 2.35-2.55 (m, 2H), 2.10-2.35 (m, 3H), 1.35 (br, 3H). |

TABLE 2-continued
Selected compounds of the present disclosure.
| Compound No. | Structure | Analytical data |
|---|---|---|
| 190a | 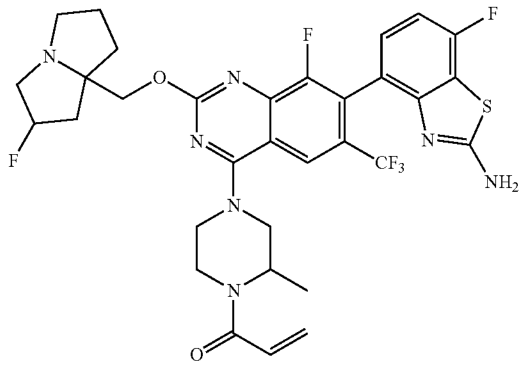 [SMILES: C=CC(=O)N1CCN(c2nc(OCC34CCCN3CC(F)C4)nc3c(F)c(-c4ccc(F)c5sc(N)nc45)c(C(F)(F)F)cc23)CC1C] | |
| 191 | 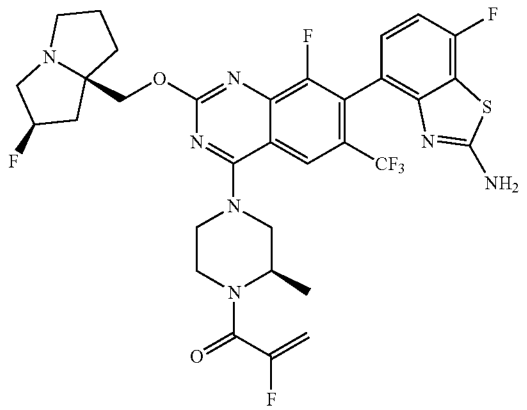 [SMILES: C=C(F)C(=O)N1CCN(c2nc(OC[C@]34CCCN3C[C@H](F)C4)nc3c(F)c(-c4ccc(F)c5sc(N)nc45)c(C(F)(F)F)cc23)C[C@H]1C] | LCMS m/z [M + 1]: 710.2 $^1$HNMR (400 MHz, $CD_3OD$) δ 8.28 (s, 1H), 7.25-7.31 (m, 1H), 7.06 (dd, J = 17.2 Hz, 8.4 Hz, 1H), 5.45-5.57 (m, 1H), 5.22-5.35 (m, 2H), 4.60-4.82 (m, 3H), 4.45-4.58 (m, 1H), 4.30-4.45 (m, 1H), 4.15-4.30 (m, 1H), 3.60-4.10 (m, 5H), 3.40-3.60 (m, 2H), 2.72 (t, J = 4.8 Hz, 1H), 2.35-2.55 (m, 2H), 2.20-2.35 (m, 2H), 2.10-2.20 (m, 1H), 1.40 (d, J = 6.4 Hz, 3H). |
| 191a | 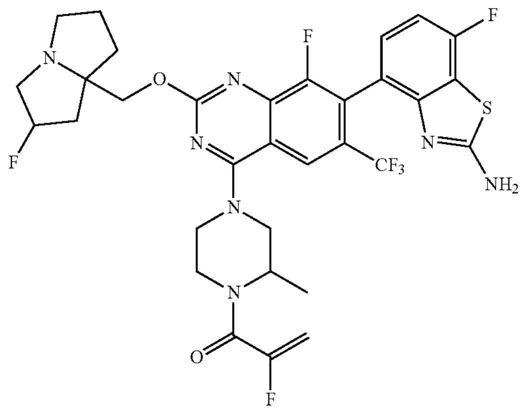 [SMILES: C=C(F)C(=O)N1CCN(c2nc(OCC34CCCN3CC(F)C4)nc3c(F)c(-c4ccc(F)c5sc(N)nc45)c(C(F)(F)F)cc23)CC1C] | |
| 192 | 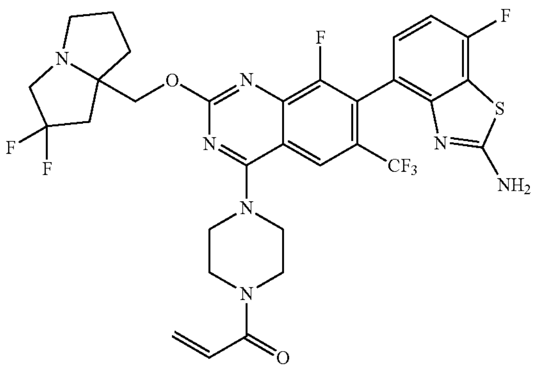 [SMILES: C=CC(=O)N1CCN(c2nc(OCC34CCCN3CC(F)(F)C4)nc3c(F)c(-c4ccc(F)c5sc(N)nc45)c(C(F)(F)F)cc23)CC1] | LCMS m/z [M + 1]: 696.2 $^1$HNMR (400 MHz, $CD_3OD$) δ 8.28 (s, 1H), 7.14-7.33 (m, 1H), 7.01 (t, J = 8.8 Hz, 1H), 6.81 (dd, J = 16.8, 10.6 Hz, 1H), 6.30 (dd, J = 16.7, 1.7 Hz, 1H), 5.82 (dd, J = 10.6, 1.7 Hz, 1H), 4.70-4.80 (m, 2H), 4.11-4.40 (m, 5H), 3.79-4.06 (m, 6H), 3.41-3.51 (m, 1H), 2.73-3.10 (m, 2H), 2.13-2.53 (m, 4H). |

TABLE 2-continued
| Selected compounds of the present disclosure. | | |
|---|---|---|
| Compound No. | Structure | Analytical data |
| 193 | 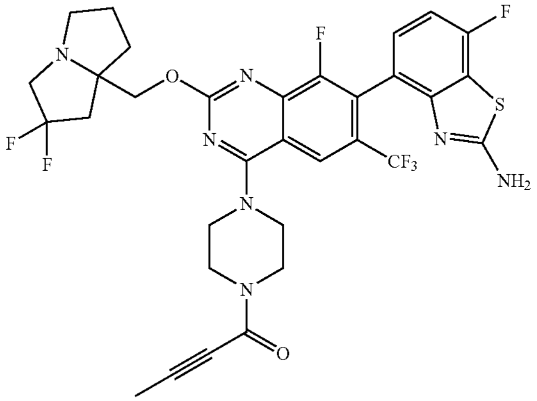 [SMILES: CC#CC(=O)N1CCN(c2nc(OCC34CCCN3CC(F)(F)C4)nc3c(F)c(-c4ccc(F)c5sc(N)nc45)c(C(F)(F)F)cc23)CC1] | LCMS m/z [M + 1]: 708.1 $^1$H NMR (400 MHz, $CD_3OD$) δ 8.25 (s, 1H), 7.18-7.23 (m, 1H), 6.99 (t, J = 8.8 Hz, 1H), 4.72-4.76 (m, 2H), 4.03-4.31 (m, 8H), 3.82-3.98 (m, 3H), 3.42-3.53 (m, 1H), 2.72-3.15 (m, 2H), 2.14-2.57 (m, 4H), 2.07 (s, 3H). |
| 194 | 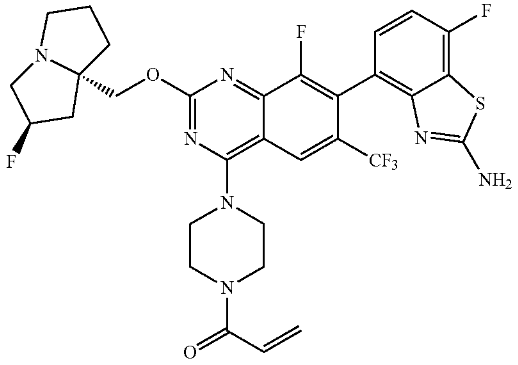 [SMILES: C=CC(=O)N1CCN(c2nc(OC[C@@]34CCCN3C[C@H](F)C4)nc3c(F)c(-c4ccc(F)c5sc(N)nc45)c(C(F)(F)F)cc23)CC1] | LCMS m/z [M + 1]: 678.2 $^1$H NMR (400 MHz, $CD_3OD$) δ 8.27 (s, 1H), 7.18-7.28 (m, 1H), 7.03 (t, J = 9.00 Hz 1H), 6.78 (dd, J = 16.8, 10.8 Hz, 1H), 6.29 (dd, J = 16.8, 1.6 Hz, 1H), 5.82 (dd, J = 10.8, 1.6 Hz, 1H), 5.56 (d, J = 51.6 Hz, 1H), 4.63-4.77 (m, 2H), 4.16-4.22 (m, 4H), 3.82-4.07 (m, 7H), 3.42-3.50 (m, 1H), 2.53-2.75 (m, 2H), 2.28-2.48 (m, 3H), 2.09-2.20 (m, 1H). |
| 194a | 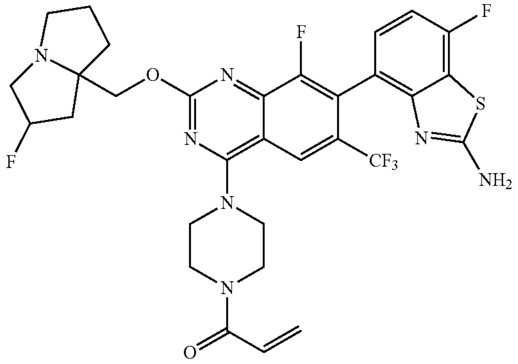 [SMILES: C=CC(=O)N1CCN(c2nc(OCC34CCCN3CC(F)C4)nc3c(F)c(-c4ccc(F)c5sc(N)nc45)c(C(F)(F)F)cc23)CC1] | |
| 195 | 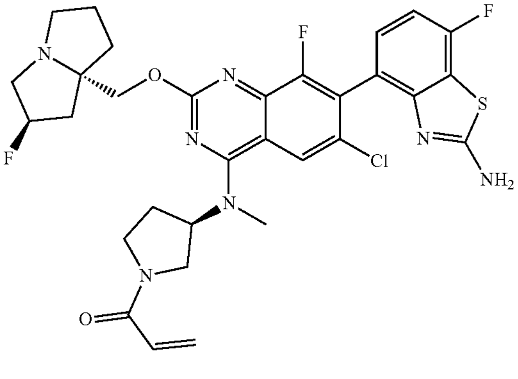 [SMILES: C=CC(=O)N1CC[C@@H](N(C)c2nc(OC[C@@]34CCCN3C[C@H](F)C4)nc3c(F)c(-c4ccc(F)c5sc(N)nc45)c(Cl)cc23)C1] | LCMS m/z [M + 1]: 658.2 $^1$H NMR (400 MHz, $CD_3OD$): δ 8.15 (s, 1H), 7.26 (dd, J = 7.6, 5.6 Hz, 1H), 7.04 (t, J = 8.8 Hz, 1H), 6.61-6.69 (m, 1H), 6.32 (d, J = 16.8 Hz, 1H), 5.75-5.81 (m, 1H), 5.56 (d, J = 51.6 Hz, 1H), 4.69-4.75 (m, 2H), 4.01-4.30 (m, 2H), 3.85-3.99 (m, 4H), 3.40-3.65 (m, 5 H), 2.47-2.75 (m, 3H), 2.28-2.47(m, 4H), 2.10-2.22 (m, 1 H). |

TABLE 2-continued
| Selected compounds of the present disclosure. | | |
|---|---|---|
| Compound No. | Structure | Analytical data |
| 195a | 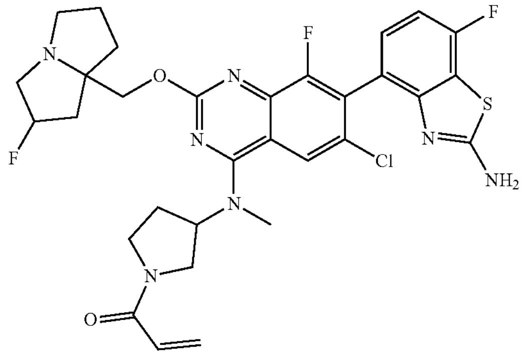 | |
| 196 | 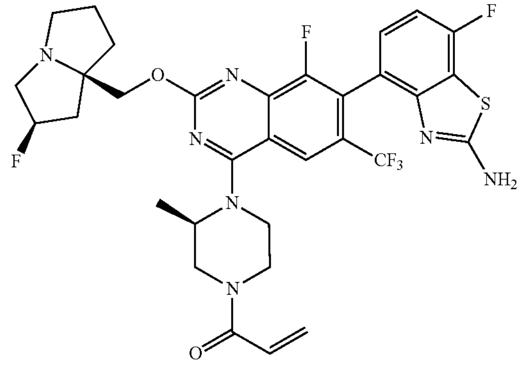 [SMILES: C=CC(=O)N1CCN(c2nc(OC[C@]34CCCN3C[C@H](F)C4)nc3c(F)c(-c4ccc(F)c5sc(N)nc45)c(C(F)(F)F)cc23)[C@H](C)C1] | LCMS m/z [M + 1]: 692.2<br>$^1$HNMR (400 MHz, $CD_3OD$) δ 8.18 (s, 1H), 7.21 (t, J = 8 Hz, 1H), 6.97-7.02 (m, 1H), 6.76-6.87 (m, 1H), 6.28-6.32 (m, 1H), 5.82 (d, J = 10.8 Hz, 1H), 5.44-5.57 (m, 1H),4.74-4.47 (m, 2H), 4.39-4.48 (m, 2H), 3.99-4.07 (m, 1H), 3.80-3.92 (m, 1H), 3.56-3.71 (m, 2H), 3.43-3.52 (m, 2H), 2.66-2.75 (m, 1H), 2.38-2.52 (m, 2H), 2.25-2.29 (m, 2H), 2.12-2.19 (m, 1H), 1.51 (s, 3H). |
| 196a | 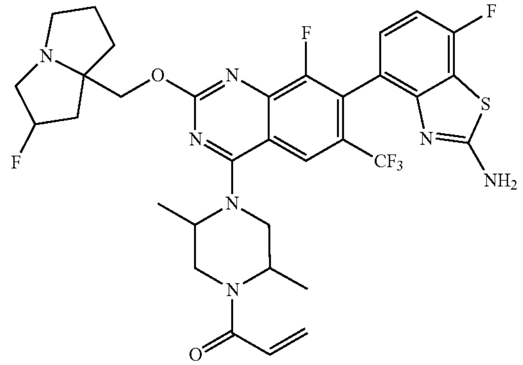 [SMILES: C=CC(=O)N1CC(C)N(c2nc(OCC34CCCN3CC(F)C4)nc3c(F)c(-c4ccc(F)c5sc(N)nc45)c(C(F)(F)F)cc23)CC1C] | |
| 197 | 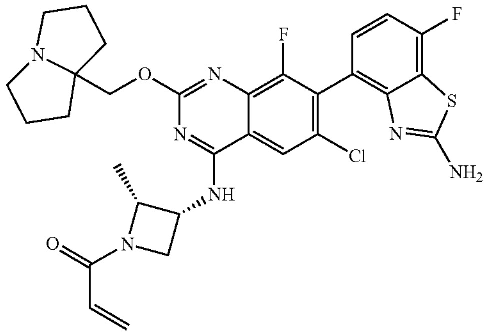 [SMILES: C=CC(=O)N1C[C@@H](Nc2nc(OCC34CCCN3CCC4)nc3c(F)c(-c4ccc(F)c5sc(N)nc45)c(Cl)cc23)[C@H]1C] | LCMS m/z [M + 1]: 626.1<br>$^1$HNMR (500 MHz, $CD_3OD$) δ 8.38 (d, J = 7.6 Hz, 1H), 7.31-7.21 (m, 1H), 7.09-7.00 (m, 1H), 6.50-6.25 (m, 2H), 5.83-5.74 (m, 1H), 5.36-5.24 (m, 1H), 5.10-5.02 (m, 1H), 4.74-4.55 (m, 3H), 4.49-4.31 (m, 1H), 3.75-3.63 (m, 2H), 2.40-2.27 (m, 3H), 2.27-2.19 (m, 2H), 2.19-2.07 (m, 4H), 1.40-1.32 (m, 3H). |

TABLE 2-continued
| Selected compounds of the present disclosure. | | |
|---|---|---|
| Compound No. | Structure | Analytical data |
| 197a | 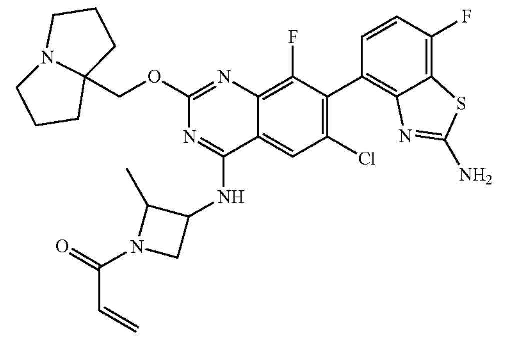 [SMILES: C=CC(=O)N1CC(Nc2nc(OCC34CCCN3CCC4)nc3c(F)c(-c4ccc(F)c5sc(N)nc45)c(Cl)cc23)C1C] | |
| 198 | 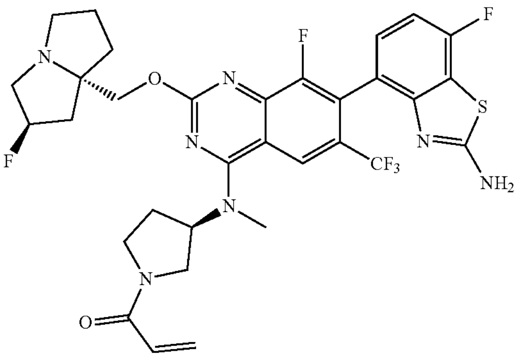 | LCMS m/z [M + 1]: 692.2<br>$^1$HNMR (400 MHz, $CD_3OD$) δ 8.40 (s, 1H), 7.27 (dd, J = 8.1, 5.5 Hz, 1H), 7.06 (t, J = 8.8 Hz, 1H), 6.61-6.73 (m, 1H), 6.33 (d, J = 16.8 Hz, 1H), 5.80 (t, J = 9.6 Hz, 1H), 5.56 (d, J = 51.8 Hz, 1H), 5.28-5.45 (m, 1H), 4.63-4.77 (m, 2H), 4.08-4.22 (m, 1H), 3.99-4.07 (m, 1H), 3.87-3.95 (m, 2H), 3.70-3.80 (m, 1H), 3.58-3.67 (m, 1H), 3.53 (s, 3H), 3.43-3.49 (m, 1H), 2.56-2.74 (m, 2H), 2.48-2.55 (m, 1H), 2.29-2.46 (m, 4H), 2.10-2.22 (m, 1H). |
| 198a | 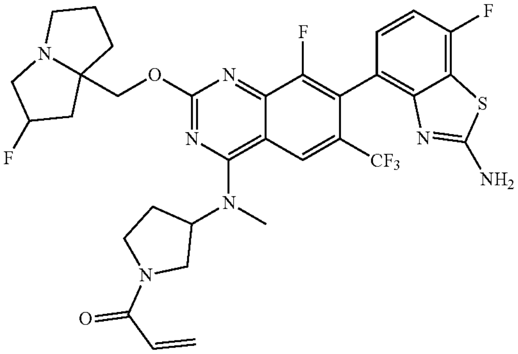 | |
| 199 | 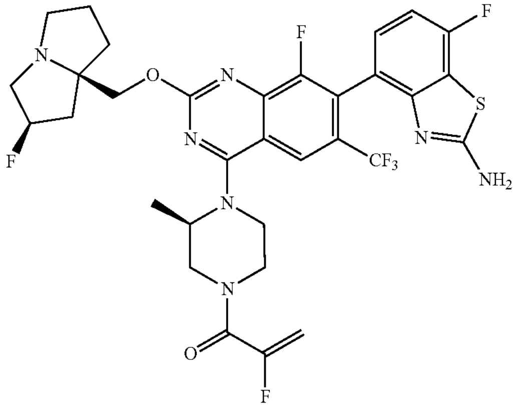 [SMILES: C=C(F)C(=O)N1CCN(c2nc(OC[C@]34CCCN3C[C@H](F)C4)nc3c(F)c(-c4ccc(F)c5sc(N)nc45)c(C(F)(F)F)cc23)[C@H](C)C1] | LCMS m/z [M + 1]: 710.2<br>$^1$HNMR (400 MHz, $CD_3OD$) δ 8.18 (s, 1H), 7.23 (t, J = 8 Hz, 1H), 7.01(t, J = 8 Hz, 1H), 5.44-5.57 (m, 1H), 5.26-5.37 (m, 2H), 4.74-4.92 (m, 2H), 4.45-4.49 (m, 1H), 4.11-4.42 (m, 2H), 4.00-4.07 (m, 2H), 3.85-3.91 (m, 1H), 3.64-3.71 (m, 2H), 3.38-3.47 (m, 3H), 2.66-2.75 (m, 1H), 2.37-2.52 (m, 2H), 2.26-2.29 (m, 2H), 2.12-2.15 (m, 1H), 1.52 (d, J = 6.4 Hz, 3H). |

TABLE 2-continued
| Compound No. | Structure | Analytical data |
|---|---|---|
| | Selected compounds of the present disclosure. | |
| 199a | 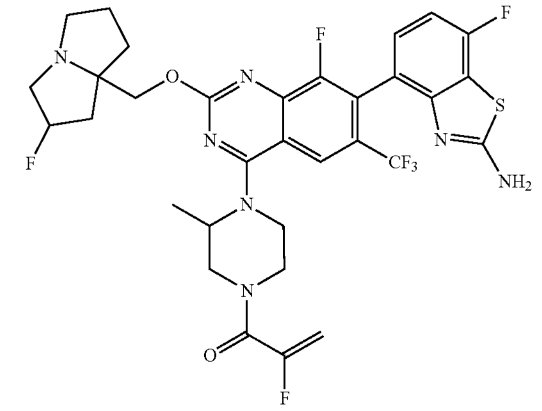 [SMILES: C=C(F)C(=O)N1CCN(c2nc(OCC34CCCN3CC(F)C4)nc3c(F)c(-c4ccc(F)c5sc(N)nc45)c(C(F)(F)F)cc23)C(C)C1] | |
| 201 | 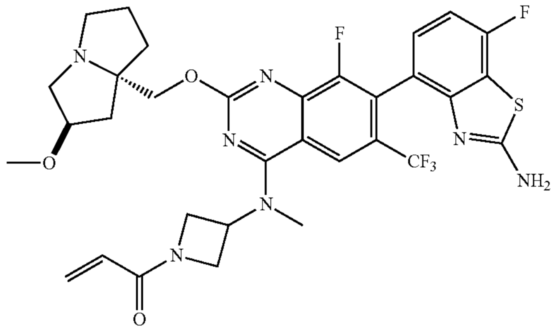 [SMILES: C=CC(=O)N1CC(N(C)c2nc(OC[C@@]34CCCN3C[C@H](OC)C4)nc3c(F)c(-c4ccc(F)c5sc(N)nc45)c(C(F)(F)F)cc23)C1] | LCMS m/z [M + 1]: 690.2<br>$^1$HNMR (400 MHz, $CD_3OD$) δ 8.35 (s, 1H), 7.19-7.22 (m, 1H), 6.99 (t, J = 8.8 Hz, 1H), 6.39-6.45 (m, 1H), 6.27-6.31 (m, 1H), 5.79 (d, J=10 Hz, 1H), 4.47-4.73 (m, 5H), 4.28 (s, 2H), 3.52-3.80 (m, 7H), 3.50 (s, 3H), 2.02-2.42 (m, 6H). |
| 201a | 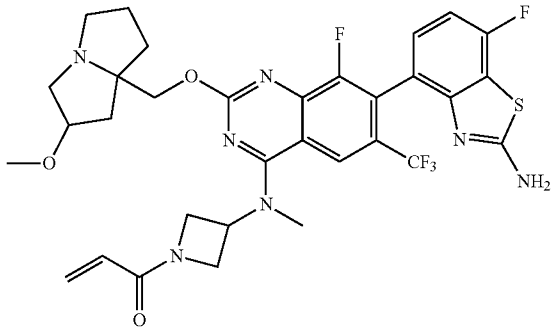 [SMILES: C=CC(=O)N1CC(N(C)c2nc(OCC34CCCN3CC(OC)C4)nc3c(F)c(-c4ccc(F)c5sc(N)nc45)c(C(F)(F)F)cc23)C1] | |
| 202 | 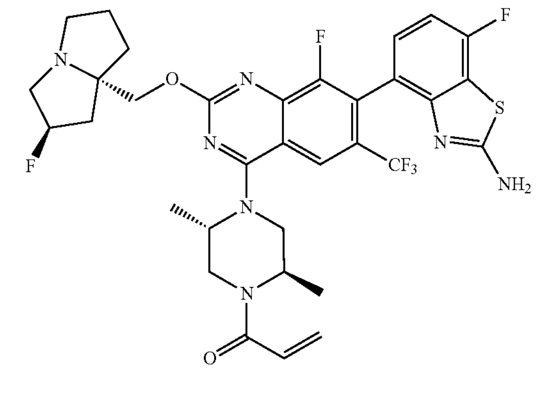 [SMILES: C=CC(=O)N1C[C@H](C)N(c2nc(OC[C@@]34CCCN3C[C@H](F)C4)nc3c(F)c(-c4ccc(F)c5sc(N)nc45)c(C(F)(F)F)cc23)C[C@H]1C] | LCMS m/z [M + 1]: 706.2<br>$^1$H NMR (400 MHz, $CD_3OD$): δ 8.20 (s, 1H), 7.21-7.25 (m, 1H), 6.99-7.04 (m, 1H), 6.76-6.89 (m, 1H), 6.27-6.33 (m, 1H), 5.81-5.85 (m, 1H), 5.49-5.63 (m, 1H), 4.92-5.02 (m, 3H), 4.69 (s, 2H), 4.30-4.41 (m, 1H), 3.83-4.05 (m, 5H), 3.43-3.51 (m, 1H), 2.16-2.75 (m, 6H), 1.24-1.53 (m, 6H). |

TABLE 2-continued
Selected compounds of the present disclosure.
| Compound No. | Structure | Analytical data |
| --- | --- | --- |
| 202a | 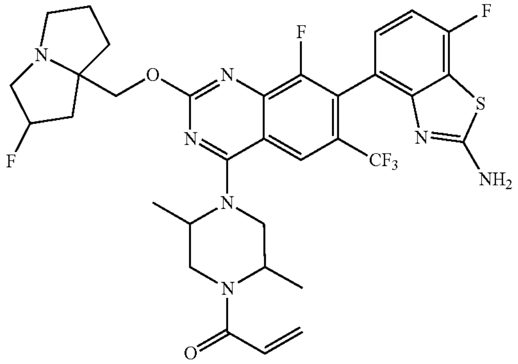 [SMILES: C=CC(=O)N1CC(C)N(c2nc(OCC34CCCN3CC(F)C4)nc3c(F)c(-c4ccc(F)c5sc(N)nc45)c(C(F)(F)F)cc23)CC1C] | |
| 203 | 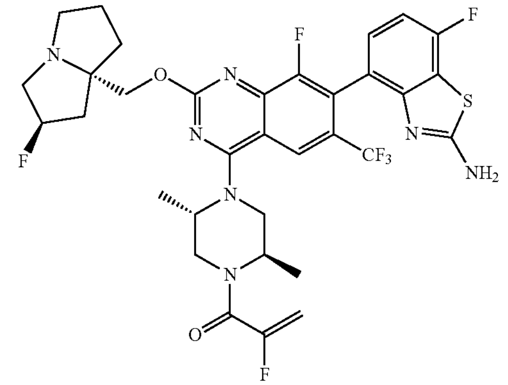 [SMILES: C=C(F)C(=O)N1C[C@H](C)N(c2nc(OC[C@@]34CCCN3C[C@H](F)C4)nc3c(F)c(-c4ccc(F)c5sc(N)nc45)c(C(F)(F)F)cc23)C[C@H]1C] | LCMS m/z [M + 1]: 724.2 $^1$HNMR (400 MHz, $CD_3OD$): δ 8.20 (s, 1H), 7.19-7.22 (m, 1H), 6.97-7.02 (m, 1H), 5.22-5.63 (m, 3H), 4.92-5.02 (m, 3H), 4.68 (s, 2H), 4.30-4.41 (m, 1H), 3.83-4.05 (m, 5H), 3.43-3.51 (m, 1H), 2.16-2.75 (m, 6H), 1.33-1.52 (m, 6H). |
| 203a | 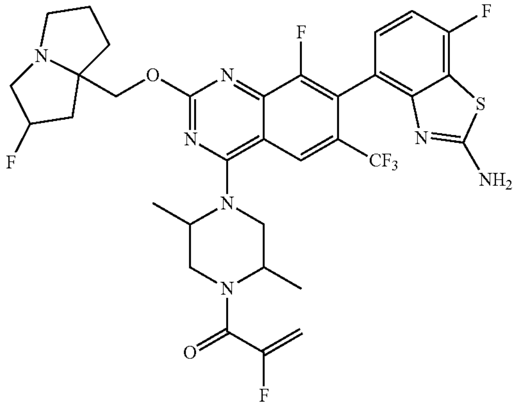 [SMILES: C=C(F)C(=O)N1CC(C)N(c2nc(OCC34CCCN3CC(F)C4)nc3c(F)c(-c4ccc(F)c5sc(N)nc45)c(C(F)(F)F)cc23)CC1C] | |
| 204 | 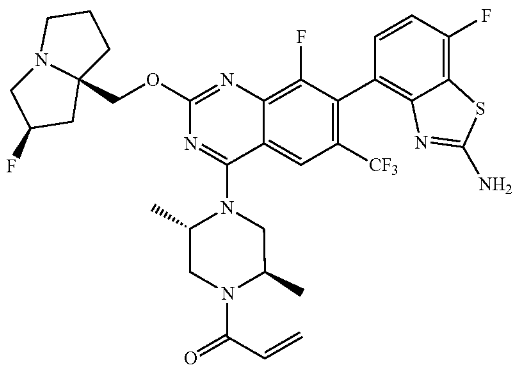 [SMILES: C=CC(=O)N1C[C@H](C)N(c2nc(OC[C@]34CCCN3C[C@H](F)C4)nc3c(F)c(-c4ccc(F)c5sc(N)nc45)c(C(F)(F)F)cc23)C[C@H]1C] | LCMS m/z [M + 1]: 706.2 $^1$HNMR (400 MHz, $CD_3OD$) δ 8.20 (s, 1H), 7.24-7.29 (m, 1H), 7.05 (t, J = 9.2 Hz, 1H), 6.75-6.86 (m, 1H), 6.26-6.32 (m, 1H), 5.80-5.84 (m, 1H), 5.44-5.57 (m, 1H), 4.69-4.81 (m, 2H), 4.30-4.54 (m, 2H), 3.86-4.07 (m, 4H), 3.43-3.69 (m, 4H), 2.13-2.75 (m, 5H), 1.48-1.53 (m, 3H), 1.28-1.37 (m, 3H). |

TABLE 2-continued
| Selected compounds of the present disclosure. | | |
|---|---|---|
| Compound No. | Structure | Analytical data |
| 204a | 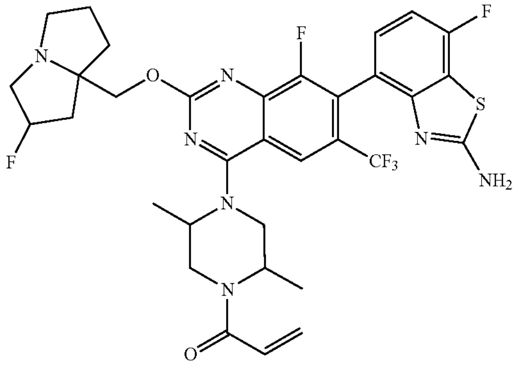 [SMILES: C=CC(=O)N1CC(C)N(c2nc(OCC34CCCN3CC(F)C4)nc3c(F)c(-c4ccc(F)c5sc(N)nc45)c(C(F)(F)F)cc23)CC1C] | |
| 205 | 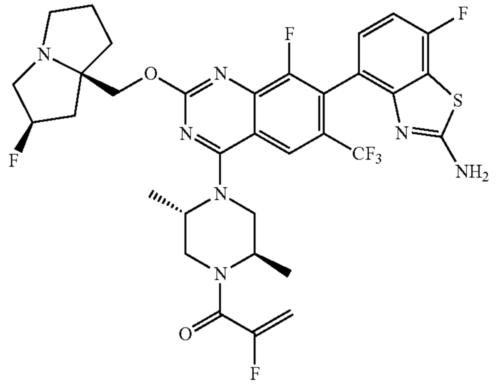 [SMILES: C=C(F)C(=O)N1C[C@H](C)N(c2nc(OC[C@]34CCCN3C[C@H](F)C4)nc3c(F)c(-c4ccc(F)c5sc(N)nc45)c(C(F)(F)F)cc23)C[C@H]1C] | LCMS m/z [M + 1]: 724.2 $^1$HNMR (400 MHz, $CD_3OD$) δ 8.19 (s, 1H), 7.20-7.26 (m, 1H), 6.98-7.03 (m, 1H), 5.43-5.56 (m, 1H), 5.22-5.33 (m, 2H), 4.70-4.80 (m, 3H), 4.38-4.47 (m, 2H), 3.87-4.03 (m, 4H), 3.64-3.71 (m, 1H), 3.52-3.55 (m, 1H), 3.43-3.47 (m, 2H), 2.12-2.72 (m, 6H), 1.51-1.53 (m, 3H), 1.32-1.37 (m, 3H). |
| 205a | 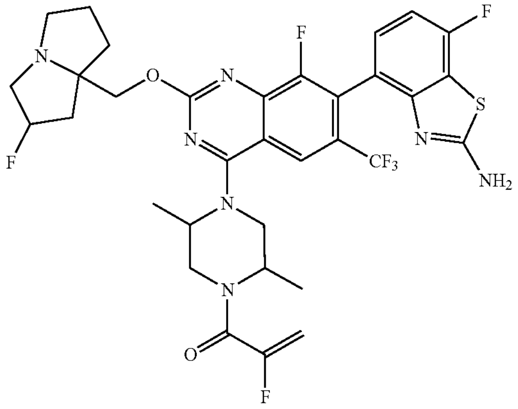 [SMILES: C=C(F)C(=O)N1CC(C)N(c2nc(OCC34CCCN3CC(F)C4)nc3c(F)c(-c4ccc(F)c5sc(N)nc45)c(C(F)(F)F)cc23)CC1C] | |
| 206 | 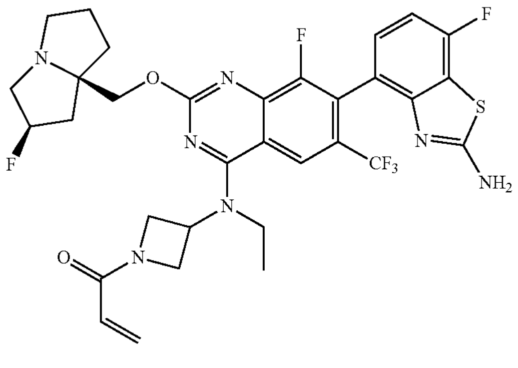 [SMILES: C=CC(=O)N1CC(N(CC)c2nc(OC[C@]34CCCN3C[C@H](F)C4)nc3c(F)c(-c4ccc(F)c5sc(N)nc45)c(C(F)(F)F)cc23)C1] | LCMS m/z [M + 1]: 692.2 $^1$HNMR (400 MHz, $CD_3OD$) δ 8.65 (s, 1H), 7.18-7.26 (m, 1H), 7.00 (t, J = 8.7 Hz, 1H), 6.75-6.85 (m, 1H), 6.34 (d, J = 16.6 Hz, 1H), 5.85 (d, J = 10.7 Hz, 1H), 5.53 (d, J = 52.2 Hz, 1H), 5.05-5.12 (m, 1H), 4.52-4.76 (m, 2H), 4.08-4.33 (m, 2H), 3.90-4.01 (m, 1H), 3.48-3.66 (m, 6H), 3.34-3.38 (m, 1H), 2.77-2.93(m, 1H), 2.44-2.64 (m, 1H), 2.23-2.40 (m, 4H), 1.32 (t, J = 6.7 Hz, 3H). |

TABLE 2-continued
| Compound No. | Structure | Analytical data |
|---|---|---|
| 206a | 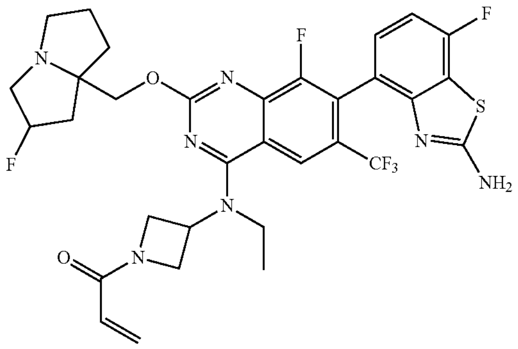 [SMILES: C=CC(=O)N1CC(N(CC)c2nc(OCC34CCCN3CC(F)C4)nc3c(F)c(-c4ccc(F)c5sc(N)nc45)c(C(F)(F)F)cc23)C1] | |
| 207 | 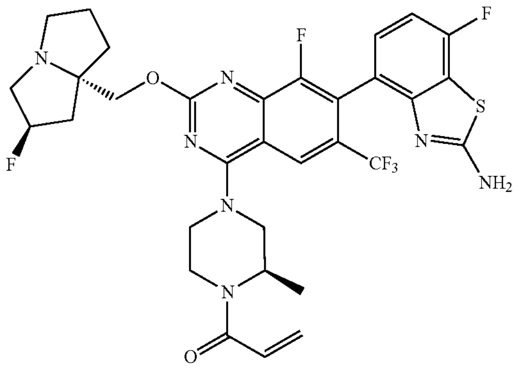 [SMILES: C=CC(=O)N1CCN(c2nc(OC[C@@]34CCCN3C[C@H](F)C4)nc3c(F)c(-c4ccc(F)c5sc(N)nc45)c(C(F)(F)F)cc23)C[C@H]1C] | LCMS m/z [M + 1]: 692.2 $^1$HNMR (400 MHz, $CD_3OD$) δ 8.29 (s, 1H), 7.25 (dd, J = 13.8, 5.6 Hz, 1H), 7.03 (td, J = 8.9, 2.1 Hz, 1H), 6.80 (dd, J = 16.7, 10.7 Hz, 1H), 6.28 (d, J = 16.7 Hz, 1 H), 5.81 (d, J = 10.4 Hz, 1H), 5.56 (d, J = 51.9 Hz, 1H), 4.65-4.75 (m, 2H), 4.46-4.56 (m, 1H), 4.27-4.40 (m, 1H), 3.96-4.06 (m, 2H), 3.74-3.96 (m, 4H), 3.41-3.52 (m, 1H), 3.31-3.34 (m, 2H), 2.52-2.73 (m, 2H), 2.28-2.47 (m, 3H), 2.12-2.24 (m, 1H), 1.32 (brs, 3H). |
| 207a | 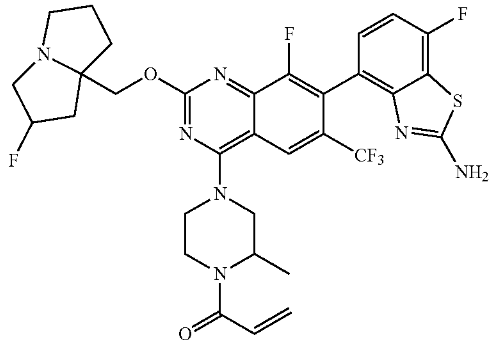 [SMILES: C=CC(=O)N1CCN(c2nc(OCC34CCCN3CC(F)C4)nc3c(F)c(-c4ccc(F)c5sc(N)nc45)c(C(F)(F)F)cc23)CC1C] | |
| 208 | 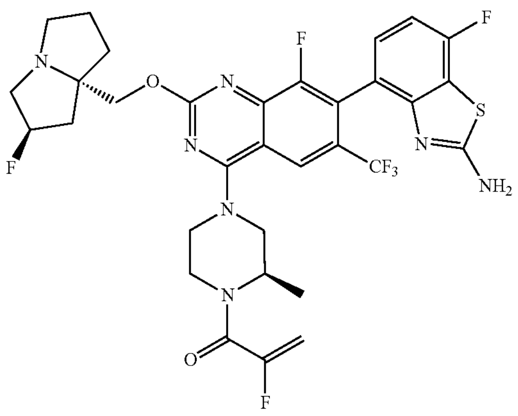 [SMILES: C=C(F)C(=O)N1CCN(c2nc(OC[C@@]34CCCN3C[C@H](F)C4)nc3c(F)c(-c4ccc(F)c5sc(N)nc45)c(C(F)(F)F)cc23)C[C@H]1C] | LCMS m/z [M + 1]: 710.2 $^1$H NMR (400 MHz, $CD_3OD$) δ 8.27 (s, 1H), 7.24 (dd, J = 13.1, 7.4 Hz, 1H), 6.97-7.08 (m, 1H), 5.56 (d, J = 51.9 Hz, 1H), 5.32 (dd, J = 21.6, 3.9 Hz, 1H), 5.24 (dd, J = 10.4, 3.9 Hz, 1H), 4.61-4.76 (m, 3H), 4.47-4.57 (m, 1H), 4.32-4.43 (m, 1H), 4.13-4.28 (m, 1H), 3.85-4.07 (m, 4H), 3.65-3.83 (m, 2H), 3.42-3.54 (m, 1H), 2.55-2.75 (m, 2H), 2.29-2.49 (m, 3H), 2.11-2.23 (m, 1H), 1.40 (d, J = 5.4 Hz, 3H). |

TABLE 2-continued
| Selected compounds of the present disclosure. | | |
|---|---|---|
| Compound No. | Structure | Analytical data |
| 208a | 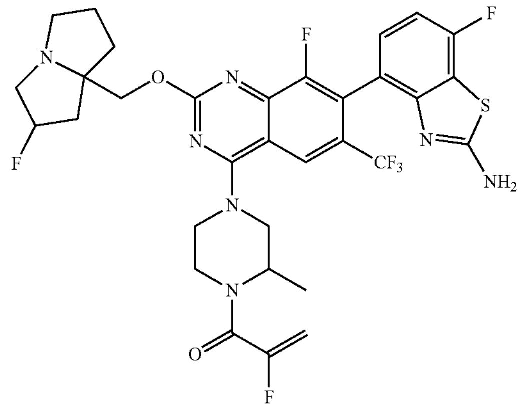 | |
| 209 | 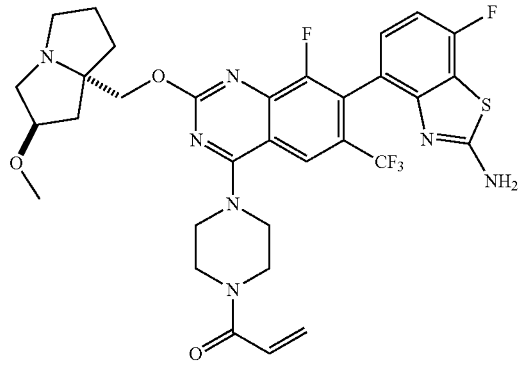 | LCMS m/z [M + 1]: 690.2 $^1$H NMR (400 MHz, $CD_3OD$): δ 8.27 (s, 1H), 7.21-7.25 (m, 1H), 7.02 (t, J = 8.79 Hz, 1H), 6.77-6.84 (m, 1H), 6.27-6.32 (m, 1H), 5.80-5.84 (m, 1H), 4.61-4.72 (m, 2H), 4.28 (br, 1H), 4.17 (br, 4H), 3.94 (br, 4H), 3.75-3.84 (m, 2H), 3.64 (d, J = 13.18 Hz, 1H), 3.48-3.56 (m, 1H), 3.39 (s, 3H), 2.10-2.58 (m, 6H). |
| 209a | 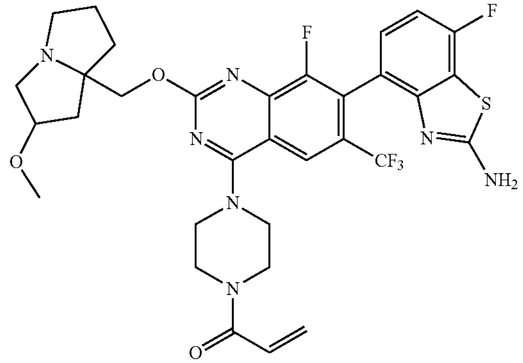 [SMILES: C=CC(=O)N1CCN(c2nc(OCC34CCCN3CC(OC)C4)nc3c(F)c(-c4ccc(F)c5sc(N)nc45)c(C(F)(F)F)cc23)CC1] | |
| 210 | 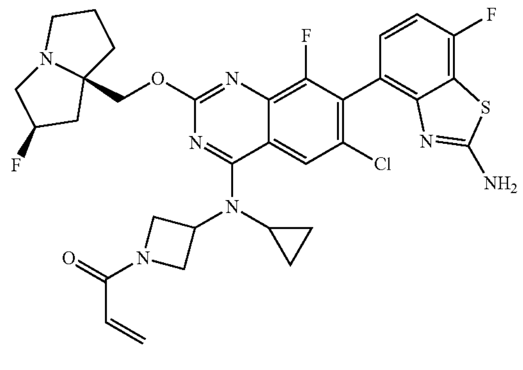 [SMILES: C=CC(=O)N1CC(N(c2nc(OC[C@]34CCCN3C[C@H](F)C4)nc3c(F)c(-c4ccc(F)c5sc(N)nc45)c(Cl)cc23)C2CC2)C1] | LCMS m/z [M + 1]: 670.2 $^1$HNMR (400 MHz, $CD_3OD$) δ 8.55 (s, 1H), 7.23-7.26 (m, 1H), 7.02 (t, J = 8.8 Hz, 1H), 6.35-6.49 (m, 1H), 6.27-6.34 (m, 1H), 5.78 (d, J = 10.4 Hz, 1H), 5.49 (d, J = 51.6 Hz, 1H), 4.68-4.75 (m, 2H), 4.45-4.52 (m, 1H), 4.25-4.35 (m, 1H), 3.98-4.08 (m, 1H), 3.63-3.76 (m, 2H), 3.42-3.58 (m, 3H), 2.55-2.79 (m, 1H), 2.37-2.53 (m, 2H), 2.22-2.31 (m, 2H), 2.09-2.17 (m, 1H), 1.28-1.41 (m, 2H), 1.02-1.18 (m, 2H), 0.56-0.78 (m, 2H). |

TABLE 2-continued
| Selected compounds of the present disclosure. | | |
|---|---|---|
| Compound No. | Structure | Analytical data |
| 210a | 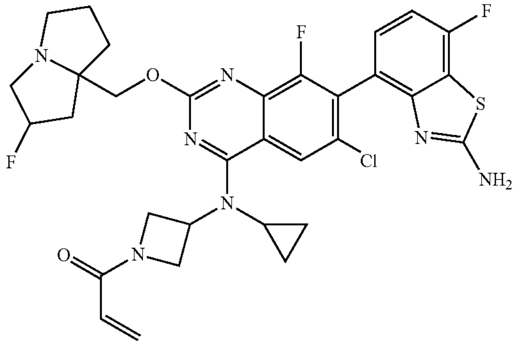 [SMILES: C=CC(=O)N1CC(N(c2nc(OCC34CCCN3CC(F)C4)nc3c(F)c(-c4ccc(F)c5sc(N)nc45)c(Cl)cc23)C2CC2)C1] | |
| 211 | 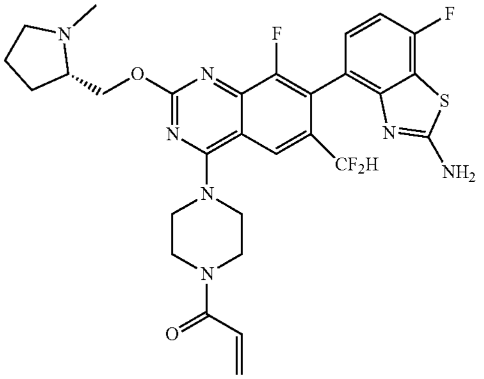 [SMILES: C=CC(=O)N1CCN(c2nc(OC[C@@H]3CCCN3C)nc3c(F)c(-c4ccc(F)c5sc(N)nc45)c(C(F)F)cc23)CC1] | LCMS m/z [M + 1]: 616.29<br>$^1$HNMR (300 MHz, $CD_3OD$) δ 8.13 (s, 1H), 7.25 (dd, J = 8.4, 5.4 Hz, 1H), 7.09-6.95 (m, 1H), 6.84 (dd, J = 16.9, 10.7 Hz, 1H), 6.57 (t, J = 55.1 Hz, 1H), 6.36-6.14 (m, 1H), 5.83 (d, J = 10.6 Hz, 1H), 4.57 (d, J = 5.5 Hz, 2H), 4.09 (s, 4H), 3.95 (s, 4H), 3.30-3.17 (m, 1H), 3.08 (s, 1H), 2.67 (s, 3H), 2.63-2.43 (m, 1H), 2.17 (m, 1H), 1.92 (m, 3H). |
| 211a | 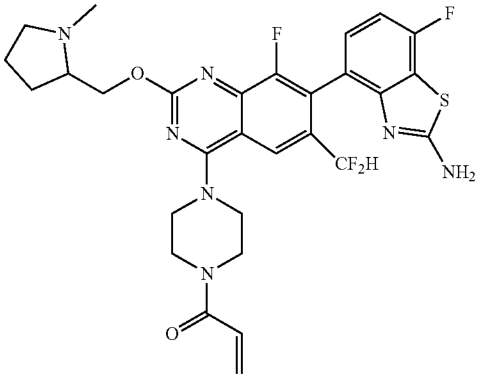 [SMILES: C=CC(=O)N1CCN(c2nc(OCC3CCCN3C)nc3c(F)c(-c4ccc(F)c5sc(N)nc45)c(C(F)F)cc23)CC1] | |
| 212 | 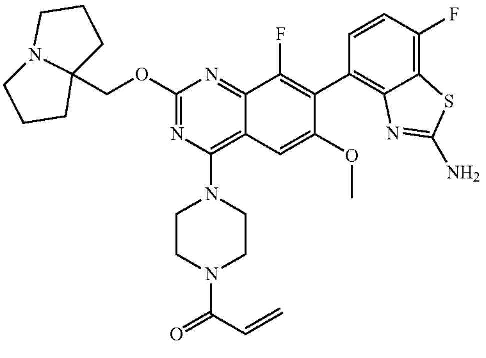 [SMILES: C=CC(=O)N1CCN(c2nc(OCC34CCCN3CCC4)nc3c(F)c(-c4ccc(F)c5sc(N)nc45)c(OC)cc23)CC1] | LCMS m/z [M + 1]: 622.44<br>$^1$HNMR (300 MHz, $CDCl_3$) δ 7.21 (dd, J = 8.5, 5.5 Hz, 1H), 6.99-6.83 (m, 2H), 6.61 (dd, J = 16.8, 10.4 Hz, 1H), 6.35 (dd, J = 16.7, 2.0 Hz, 1H), 6.24 (br s, 2H), 5.77 (dd, J = 10.4, 2.0 Hz, 1H), 4.29-4.06 (m, 2H), 3.97-3.76 (m, 8H), 3.74 (s, 3H), 3.13 (dt, J = 10.6, 5.6 Hz, 2H), 2.65 (dt, J = 10.0, 6.7 Hz, 2H), 2.14 (dt, J = 12.2, 5.8 Hz, 2H), 1.89 (p, J = 6.2, 5.5 Hz, 4H), 1.69 (dt, J = 14.3, 7.5 Hz, 2H) |

TABLE 2-continued
Selected compounds of the present disclosure.
| Compound No. | Structure | Analytical data |
| --- | --- | --- |
| 213 | 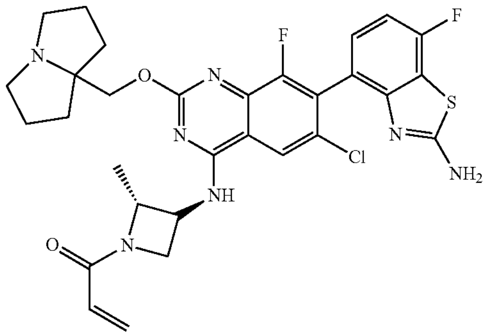 | LCMS m/z [M + 1]: $^1$HNMR (500 MHz, $CD_3OD$) δ 8.26 (s, 1H), 7.27-7.16 (m, 1H), 7.04-6.96 (m, 1H), 6.44-6.24 (m, 2H), 5.78 (d, J = 10.2 Hz, 1H), 4.77-4.69 (m, 1H), 4.69-4.60 (m, 3H), 4.58-4.40 (m, 2H), 4.38-4.14 (m, 1H), 3.72-3.62 (m, 2H), 2.35-2.27 (m, 3H), 2.26-2.18 (m, 2H), 2.17-2.04 (m, 4H), 1.74 (d, J = 6.4 Hz, 1H), 1.68 (d, J = 6.4 Hz, 2H). |
| 213a | 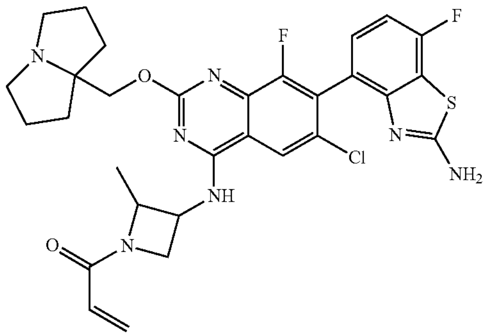 [SMILES: C=CC(=O)N1CC(Nc2nc(OCC34CCCN3CCC4)nc3c(F)c(-c4ccc(F)c5sc(N)nc45)c(Cl)cc23)C1C] | |
| 215 | 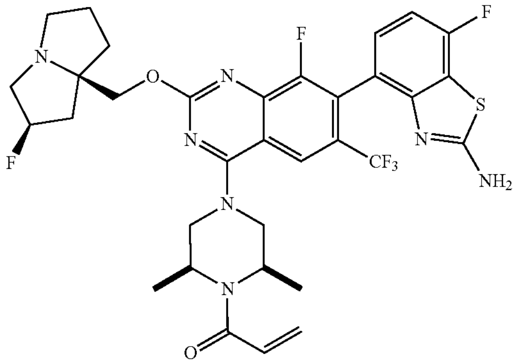 [SMILES: C=CC(=O)N1[C@H](C)CN(c2nc(OC[C@]34CCCN3C[C@H](F)C4)nc3c(F)c(-c4ccc(F)c5sc(N)nc45)c(C(F)(F)F)cc23)C[C@@H]1C] | LCMS m/z [M + 1]: 706.2 |
| 215a | 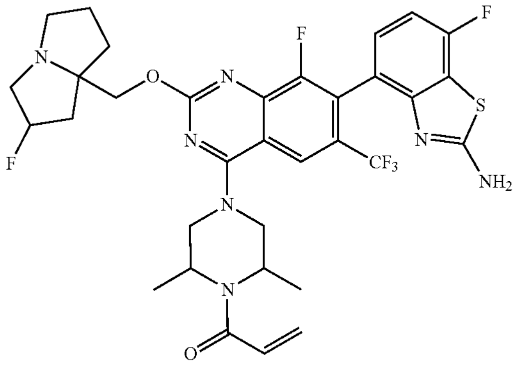 [SMILES: C=CC(=O)N1C(C)CN(c2nc(OCC34CCCN3CC(F)C4)nc3c(F)c(-c4ccc(F)c5sc(N)nc45)c(C(F)(F)F)cc23)CC1C] | |

TABLE 2-continued
| Compound No. | Structure | Analytical data |
|---|---|---|
| | Selected compounds of the present disclosure. | |
| 216 | 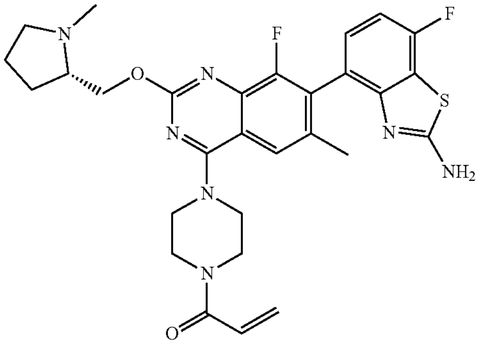 [SMILES: C=CC(=O)N1CCN(c2nc(OC[C@@H]3CCCN3C)nc3c(F)c(-c4ccc(F)c5sc(N)nc45)c(C)cc23)CC1] | LCMS m/z [M + Na]: 602.22 $^1$HNMR (300 MHz, d6-Acetone) δ 7.25 (dd, J = 8.4, 5.7 Hz, 1H), 7.14 (s, 1H), 7.04 (t, J = 8.8 Hz, 1H), 6.85 (dd, J = 16.7, 10.4 Hz, 1H), 6.25 (dd, J = 16.7, 2.4 Hz, 1H), 5.72 (dd, J = 10.5, 2.4 Hz, 1H), 4.47 (dd, J = 10.7, 4.9 Hz, 1H), 4.26 (dt, J = 10.9, 5.3 Hz, 1H), 4.02-3.84 (m, 8H), 3.23 (dd, J = 40.9, 13.3 Hz, 1H), 2.99 (d, J = 7.3 Hz, 1H), 2.66 (d, J = 5.1 Hz, 1H), 2.44 (d, J = 4.9 Hz, 3H), 2.29-2.17 (m, 3H), 1.76-1.70 (dd, J = 12.0, 6.7 Hz, 2H). |
| 216a | 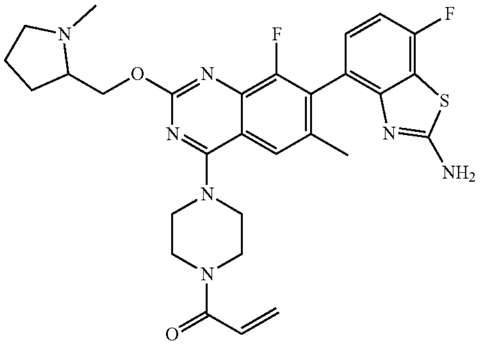 [SMILES: C=CC(=O)N1CCN(c2nc(OCC3CCCN3C)nc3c(F)c(-c4ccc(F)c5sc(N)nc45)c(C)cc23)CC1] | |
| 217 | 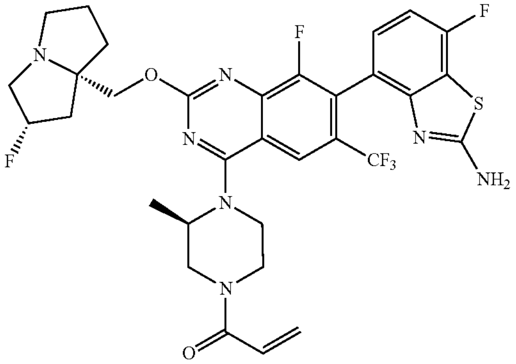 [SMILES: C=CC(=O)N1CCN(c2nc(OC[C@@]34CCCN3C[C@@H](F)C4)nc3c(F)c(-c4ccc(F)c5sc(N)nc45)c(C(F)(F)F)cc23)[C@H](C)C1] | LCMS m/z [M + 1]: 692.2 $^1$H NMR (400 MHz, $CD_3OD$) δ 8.18 (s, 1H), 7.17-7.25 (m, 1H), 6.99 (t, J = 8.72 Hz , 1H), 6.74-6.91 (m, 1H) , 6.30 (d, J = 16.8 Hz, 1H), 5.82 (d, J = 10.8 Hz, 1H), 5.49 (d, J = 51.2 Hz, 1H), 4.96-5.05 (m, 2H), 4.66-4.77 (m, 2H), 4.45-4.51 (m, 1H), 3.98-4.09 (m, 1H), 3.78-3.93 (m, 2H), 3.63-3.72 (m, 2H), 3.52-3.60 (m, 1H), 3.41-3.49 (m, 2H), 2.64-2.75 (m, 1H), 2.38-2.50 (m, 2H) 2.24-2.30 (m, 2H), 2.11-2.19 (m, 1H) 1.47-1.55 (m, 3H). |
| 217a | 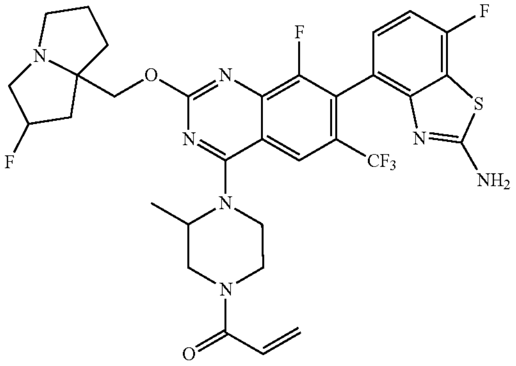 [SMILES: C=CC(=O)N1CCN(c2nc(OCC34CCCN3CC(F)C4)nc3c(F)c(-c4ccc(F)c5sc(N)nc45)c(C(F)(F)F)cc23)C(C)C1] | |

TABLE 2-continued
| Compound No. | Structure | Analytical data |
|---|---|---|
| 218 | 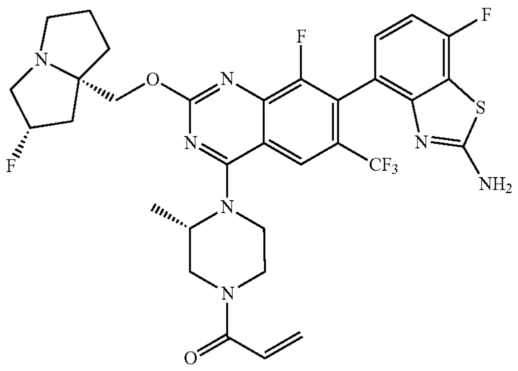 [SMILES: C=CC(=O)N1CCN(c2nc(OC[C@@]34CCCN3C[C@@H](F)C4)nc3c(F)c(-c4ccc(F)c5sc(N)nc45)c(C(F)(F)F)cc23)[C@@H](C)C1] | LCMS m/z [M + 1]: 692.2 $^1$HNMR (400 MHz, $CD_3OD$) δ 8.19 (s, 1H), 7.21-7.25 (m, 1H), 7.01-7.03 (m, 1H), 6.75-6.98 (m, 1H), 6.30 (d, J = 8 Hz, 1H), 5.82 (d, J = 4 Hz, 1H), 5.44-5.48 (m, 1H), 4.71-4.85 (m, 2H), 4.48-4.70 (m, 2H), 4.04-4.08 (m, 2H), 3.71-3.90 (m, 2H), 3.47-3.69 (m, 5H), 2.03-2.71 (m, 6H), 1.51 (s, 3H). |
| 218a | 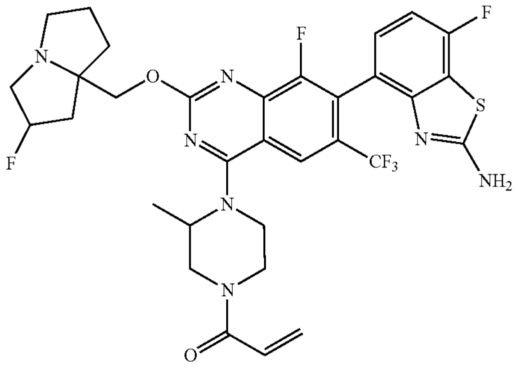 [SMILES: C=CC(=O)N1CCN(c2nc(OCC34CCCN3CC(F)C4)nc3c(F)c(-c4ccc(F)c5sc(N)nc45)c(C(F)(F)F)cc23)C(C)C1] | |
| 219 | 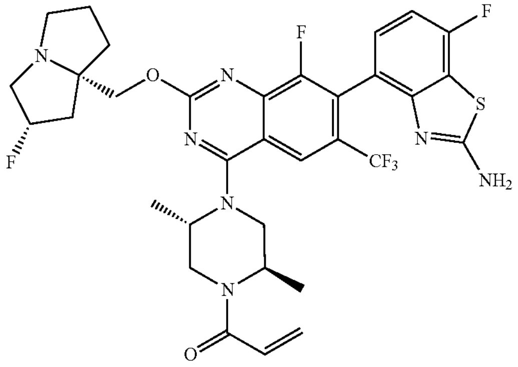 [SMILES: C=CC(=O)N1C[C@H](C)N(c2nc(OC[C@@]34CCCN3C[C@@H](F)C4)nc3c(F)c(-c4ccc(F)c5sc(N)nc45)c(C(F)(F)F)cc23)C[C@H]1C] | LCMS m/z [M + 1]: 706.2 $^1$HNMR (400 MHz, $CD_3OD$): δ 8.20 (s, 1H), 7.21-7.27 (m, 1H), 7.03 (td, J = 8.8, 2.8 Hz, 1H), 6.72-6.89 (m, 1H), 6.29 (dd, J = 16.8, 6.8 Hz, 1H), 5.78-5.86 (m, 1H), 5.51 (d, J = 50.8 Hz, 1H), 4.75-4.80 (m, 2H), 4.35-4.52 (m, 2H), 3.85-4.08 (m, 4H), 3.47-3.71 (m, 4H), 2.42-2.71 (m, 3H), 2.11-2.32 (m, 3H), 1.51-1.56 (m, 3H), 1.28-1.40 (m, 3H). |
| 219a | 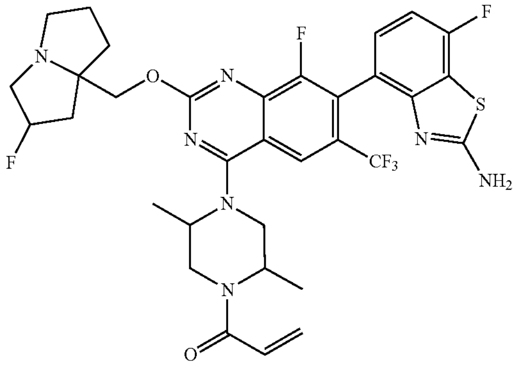 [SMILES: C=CC(=O)N1CC(C)N(c2nc(OCC34CCCN3CC(F)C4)nc3c(F)c(-c4ccc(F)c5sc(N)nc45)c(C(F)(F)F)cc23)CC1C] | |
Selected compounds of the present disclosure.

TABLE 2-continued
| Selected compounds of the present disclosure. | | |
|---|---|---|
| Compound No. | Structure | Analytical data |
| 220 | 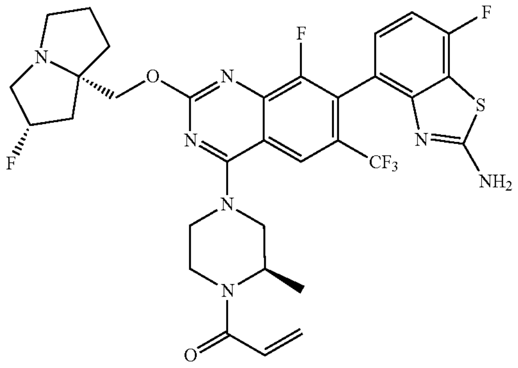 [SMILES: C=CC(=O)N1CCN(c2nc(OC[C@@]34CCCN3C[C@@H](F)C4)nc3c(F)c(-c4ccc(F)c5sc(N)nc45)c(C(F)(F)F)cc23)C[C@H]1C] | LCMS m/z [M + 1]: 692.2<br>$^1$HNMR (400 MHz, $CD_3OD$) δ 8.28 (s, 1H), 7.13-7.39 (m, 1H), 7.00 (t, J = 8.8 Hz, 1H), 6.80 (dd, J = 16.9, 10.9 Hz, 1H), 6.28 (d, J = 17.2 Hz, 1H), 5.80 (d, J = 10.9 Hz, 1H), 5.50 (d, J = 50.8 Hz, 1H), 4.64-4.80 (m, 2H), 4.31-4.52 (m, 2H), 3.95-4.12 (m, 2H), 3.51-3.93 (m, 3H), 3.40-3.49 (m, 4H), 2.98-2.75 (m, 1H), 2.32-2.54 (m, 2H), 2.11-2.25 (m, 3H), 1.23-1.52 (m, 3H). |
| 220a | 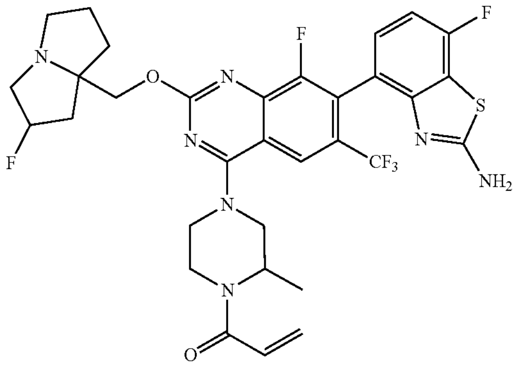 [SMILES: C=CC(=O)N1CCN(c2nc(OCC34CCCN3CC(F)C4)nc3c(F)c(-c4ccc(F)c5sc(N)nc45)c(C(F)(F)F)cc23)CC1C] | |
| 221 | 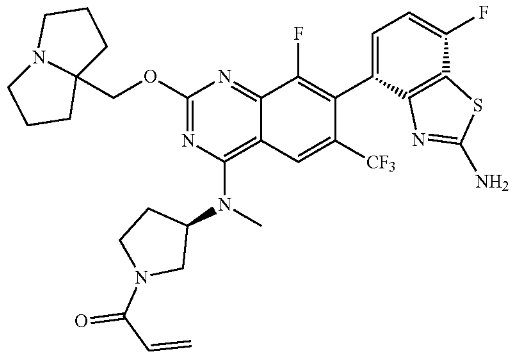 | LCMS m/z [M + 1]: 674.2<br>$^1$HNMR (400 MHz, $CD_3OD$) δ 8.38 (s, 1H), 7.17-7.26 (m, 1H), 7.00 (t, J = 8.8 Hz, 1H), 6.62-6.74 (m, 1H), 6.34 (d, J = 16.8 Hz, 1H), 5.76-5.84 (m, 1H), 5.29-5.42 (m, 1H), 4.66 (s, 2H), 4.04-4.21 (m, 2H), 3.81-3.99 (m, 2H), 3.64-3.76 (m, 4H), 3.51 (d, J = 4.4 Hz, 3H), 2.43-2.55 (m, 2H), 2.30-2.37 (m, 2H), 2.09-2.23 (m, 6H). |
| 221a | 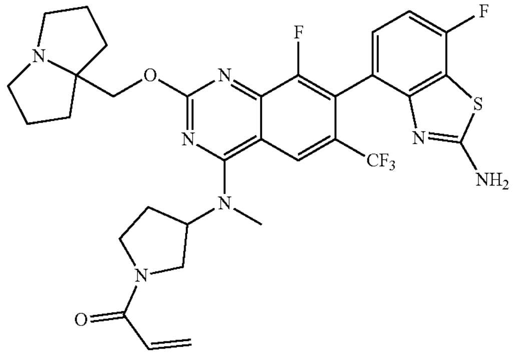 [SMILES: C=CC(=O)N1CCC(N(C)c2nc(OCC34CCCN3CCC4)nc3c(F)c(-c4ccc(F)c5sc(N)nc45)c(C(F)(F)F)cc23)C1] | |

TABLE 2-continued
Selected compounds of the present disclosure.
| Compound No. | Structure | Analytical data |
|---|---|---|
| 222 | 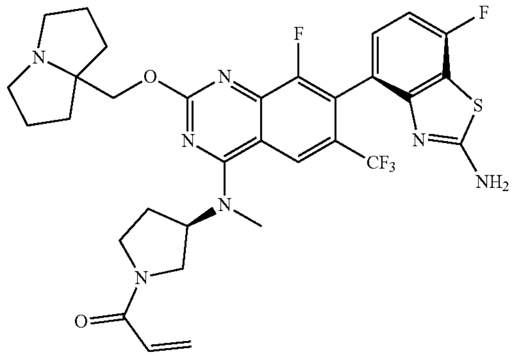 | LCMS m/z [M + 1]: 674.2 $^{1}$H NMR (400 MHz, $CD_3OD$) δ 8.38 (s, 1H), 7.17-7.26 (m, 1H), 7.00 (t, J = 8.8 Hz, 1H), 6.62-6.74 (m, 1H), 6.32 (d, J = 16.8 Hz, 1H), 5.76-5.84 (m, 1H), 5.29-5.42 (m, 1H), 4.67 (s, 2H), 4.04-4.21 (m, 2H), 3.81-3.99 (m, 2H), 3.64-3.76 (m, 4H), 3.51 (d, J = 4.4 Hz, 3H), 2.43-2.55 (m, 2H), 2.30-2.37 (m, 2H), 2.09-2.23 (m, 6H). |
| 223 | 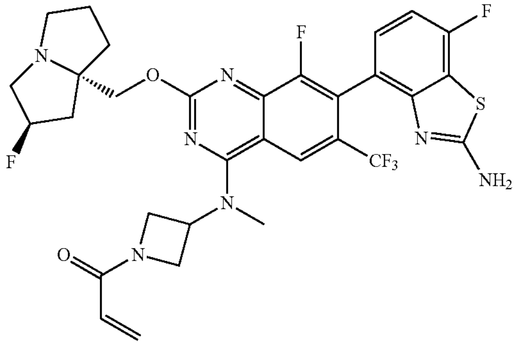 [SMILES: C=CC(=O)N1CC(N(C)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 678.2 $^{1}$HNMR (400 MHz, $CD_3OD$) δ 8.29 (s, 1H), 7.17-7.21 (m, 1H), 6.96 (t, J = 8.8 Hz, 1H), 6.38-6.45 (m, 1H), 6.28 (d, J = 16.8 Hz,1H), 5.77 (d, J = 10.4 Hz, 1H), 5.35-5.43 (m, 1H), 4.99-5.03 (m, 1H), 4.71-4.75 (m, 1H), 4.46-4.53 (m, 2H), 4.27-4.40 (m, 2H), 3.53 (s, 3H), 3.38-3.47 (m, 4H), 3.10-3.13 (m, 1H), 1.94-2.45 (m, 6H). |
| 223a | 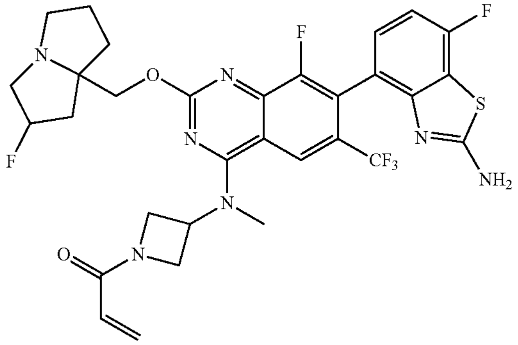 [SMILES: C=CC(=O)N1CC(N(C)c2nc(OCC34CCCN3CC(F)C4)nc3c(F)c(-c4ccc(F)c5sc(N)nc45)c(C(F)(F)F)cc23)C1] | |
| 224 | 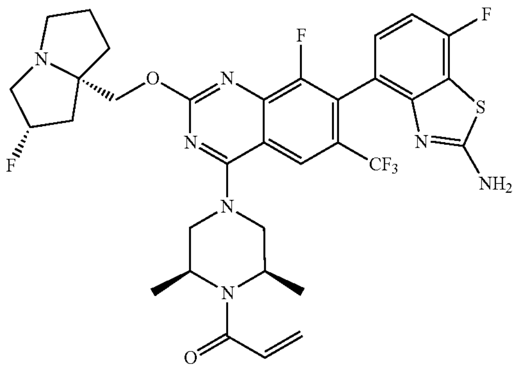 [SMILES: C=CC(=O)N1[C@H](C)CN(c2nc(OC[C@@]34CCCN3C[C@@H](F)C4)nc3c(F)c(-c4ccc(F)c5sc(N)nc45)c(C(F)(F)F)cc23)C[C@@H]1C] | LCMS m/z [M + 1]: 706.2 $^{1}$HNMR (400 MHz, $CD_3OD$) δ 8.37 (s, 1H), 7.24-7.25 (m, 1H), 7.02-7.04 (m, 1H), 6.81-6.88 (m, 1H), 6.28-6.32 (m, 1H), 5.82 (d, J = 6 Hz, 1H), 5.45-5.57 (m, 1H), 4.73-4.79 (m, 3H), 4.46-4.49 (m, 2H),3.96-4.07 (m, 1H), 3.65-3.70 (m, 3H), 3.44-3.47 (m, 2H), 2.41-2.71 (m, 4H), 2.28-2.30 (m, 2H), 1.46-1.60 (m, 6H). |

TABLE 2-continued
Selected compounds of the present disclosure.
| Compound No. | Structure | Analytical data |
|---|---|---|
| 224a | 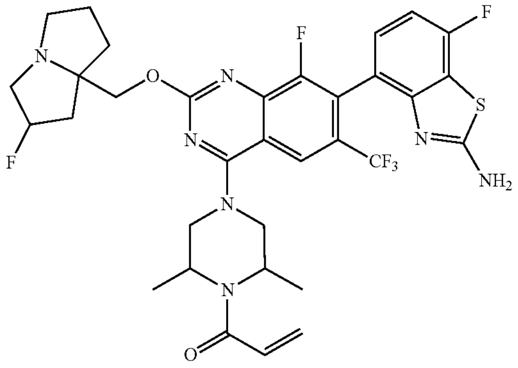 [SMILES: C=CC(=O)N1C(C)CN(c2nc(OCC34CCCN3CC(F)C4)nc3c(F)c(-c4ccc(F)c5sc(N)nc45)c(C(F)(F)F)cc23)CC1C] | |
| 225 | 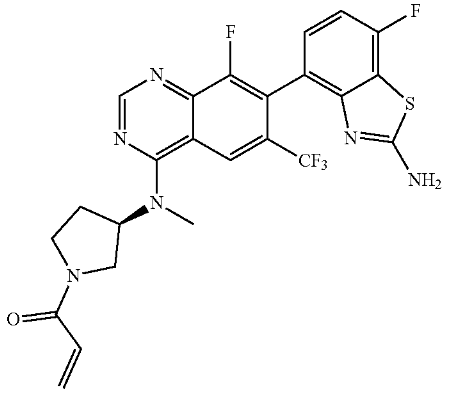 [SMILES: C=CC(=O)N1CC[C@@H](N(C)c2ncnc3c(F)c(-c4ccc(F)c5sc(N)nc45)c(C(F)(F)F)cc23)C1] | LCMS m/z [M + 1]: 535.1<br>$^1$HNMR (400 MHz, $CD_3OD$) δ 8.81 (s, 1H), 8.55 (s, 1H), 7.27-7.30 (m, 1H), 7.05 (t, J = 9.1 Hz, 1H), 6.60-6.71 (m, 1H), 6.30-6.35 (m, 1H), 5.74-5.82 (m, 2H), 3.55-4.21 (m, 4H), 3.67 (s, 3H), 2.41-2.57 (m, 2H). |
| 225a | 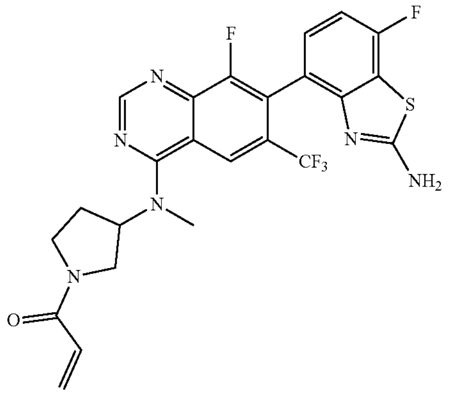 [SMILES: C=CC(=O)N1CCC(N(C)c2ncnc3c(F)c(-c4ccc(F)c5sc(N)nc45)c(C(F)(F)F)cc23)C1] | |
| 228 | 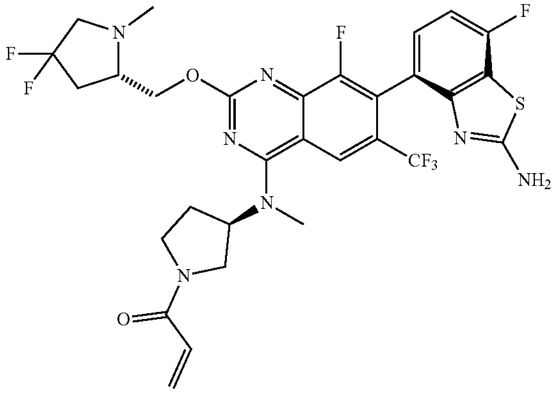 | LCMS m/z [M + 1]: 684.2<br>$^1$HNMR (400 MHz, $CD_3OD$) δ 8.32 (s, 1H), 7.19 (m, 1H), 6.94 (m, 1H), 6.67 (m, 1H), 6.32 (m, 1H), 5.78 (m, 1H), 5.30 (m, 2H), 4.57 (m, 1H), 3.87-4.22 (m, 2H), 3.42-3.75 (m, 3H), 3.53 (s, 3H), 3.22 (m, 1H), 2.84 (m, 1H), 2.26-2.63 (m, 7H). |

TABLE 2-continued
| Compound No. | Structure | Analytical data |
| --- | --- | --- |
| Selected compounds of the present disclosure. | | |
| 228a | 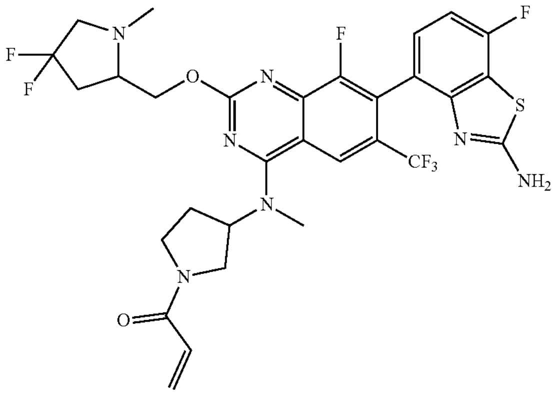 [SMILES: C=CC(=O)N1CCC(N(C)c2nc(OCC3CC(F)(F)CN3C)nc3c(F)c(-c4ccc(F)c5sc(N)nc45)c(C(F)(F)F)cc23)C1] | |
| 229 | 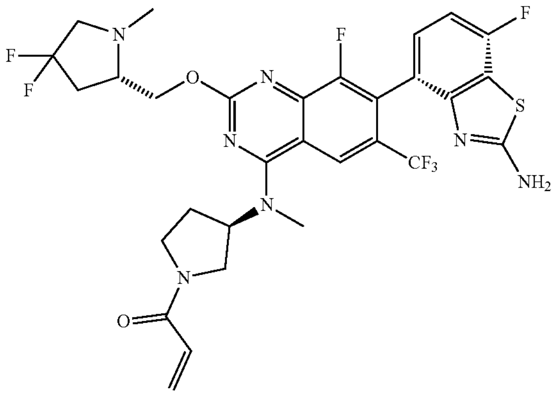 | LCMS m/z [M + 1]: 684.2 $^1$HNMR (400 MHz, $CD_3OD$) δ 8.33 (s, 1H), 7.19 (m, 1H), 6.94 (m, 1H), 6.65 (m, 1H), 6.31 (m, 1H), 5.79 (m, 1H), 5.29 (m, 1H), 4.59 (m, 1H), 4.50 (m, 1H), 3.81-4.23 (m, 2H), 3.63-3.78 (m, 3H), 3.46 (bs, 3H), 3.08 (m, 1H), 2.73 (m, 1H), 2.21-2.65 (m, 7H). |
| 230 | 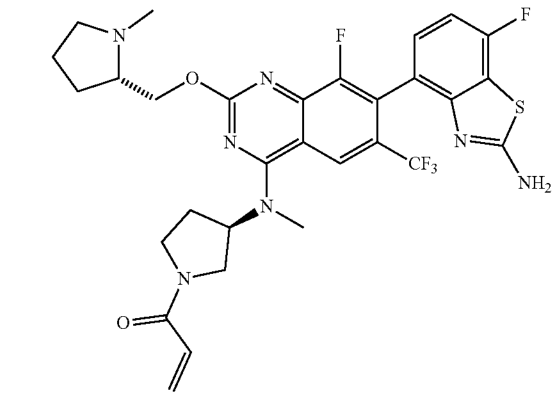 [SMILES: C=CC(=O)N1CC[C@@H](N(C)c2nc(OC[C@@H]3CCCN3C)nc3c(F)c(-c4ccc(F)c5sc(N)nc45)c(C(F)(F)F)cc23)C1] | LCMS m/z [M + 1]: 648.2 $^1$HNMR (400 MHz, $CD_3OD$) δ 8.37 (s, 1H), 7.21 (s, 1H), 6.99-7.01 (m, 1H), 6.65-6.69 (m, 1H), 6.30-6.34 (m, 1H), 5.79-5.81 (m, 1H), 5.29-5.37 (m, 2H), 3.64-4.18 (m, 6H), 3.50 (s, 3H), 3.14-3.30 (m, 1H), 3.08 (s, 3H), 2.08-2.51 (m, 6H). |

TABLE 2-continued
Selected compounds of the present disclosure.
| Compound No. | Structure | Analytical data |
|---|---|---|
| 230a | 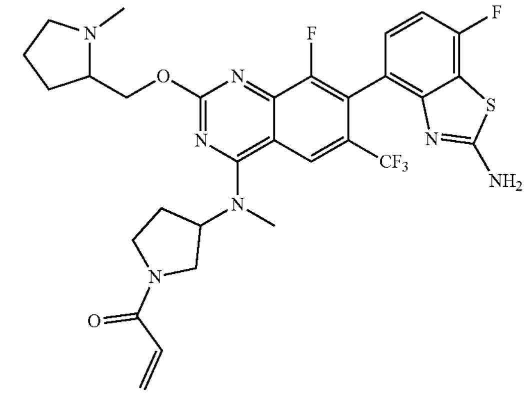 [SMILES: C=CC(=O)N1CCC(N(C)c2nc(OCC3CCCN3C)nc3c(F)c(-c4ccc(F)c5sc(N)nc45)c(C(F)(F)F)cc23)C1] | |
| 231 | 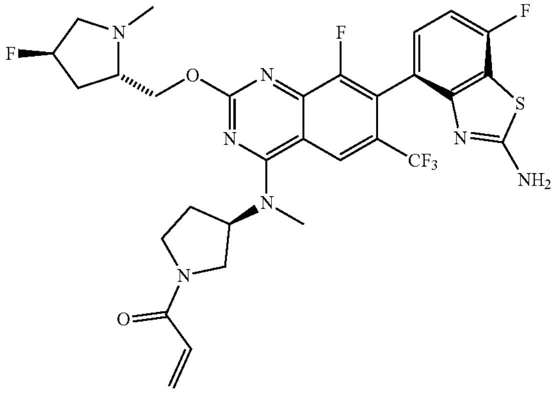 | LCMS m/z [M + 1]: 666.2<br>$^{1}$HNMR (400 MHz, $CD_3OD$) δ 8.38 (s, 1H), 7.22 (dd, J = 7.6, 5.6 Hz, 1H), 7.01 (t, J = 9.2 Hz, 1H), 6.61-6.72 (m, 1H), 6.32 (d, J = 16.8 Hz, 1H), 5.78-5.83(m, 1H), 5.58 (d, J = 51.6 Hz, 1H), 5.38-5.45 (m, 1H), 4.69-4.99 (m, 2H), 4.21-4.30 (m, 1H), 3.89-4.21 (m, 2H), 3.58-3.86 (m, 2H), 3.55-3.68 (m, 2H), 3.51 (s, 3H), 3.17 (s, 3H), 2.61-2.75 (m, 1H), 2.33-2.57 (m, 3H). |
| 231a | 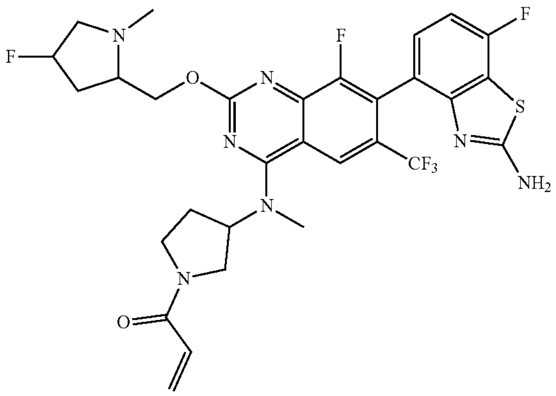 [SMILES: C=CC(=O)N1CCC(N(C)c2nc(OCC3CC(F)CN3C)nc3c(F)c(-c4ccc(F)c5sc(N)nc45)c(C(F)(F)F)cc23)C1] | |

TABLE 2-continued
Selected compounds of the present disclosure.
| Compound No. | Structure | Analytical data |
|---|---|---|
| 232 | 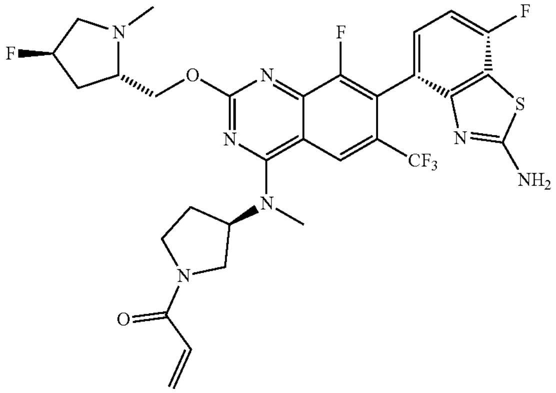 | LCMS m/z [M + 1]: 666.2 $^1$HNMR (400 MHz, $CD_3OD$) δ 8.38 (s, 1H), 7.22 (dd, J = 7.6, 5.6 Hz, 1H), 7.01 (t, J = 9.2 Hz, 1H), 6.61-6.72 (m, 1H), 6.32 (d, J = 16.8 Hz, 1H), 5.78-5.83 (m, 1H), 5.58 (d, J = 51.6 Hz, 1H), 5.38-5.45 (m, 1H), 4.69-4.99 (m, 2H), 4.21-4.30 (m, 1H), 3.89-4.21 (m, 2H), 3.58-3.86 (m, 2H), 3.55-3.68 (m, 2H), 3.51 (s, 3H), 3.17 (s, 3H), 2.61-2.75 (m, 1H), 2.33-2.57 (m, 3H). |
| 235 | 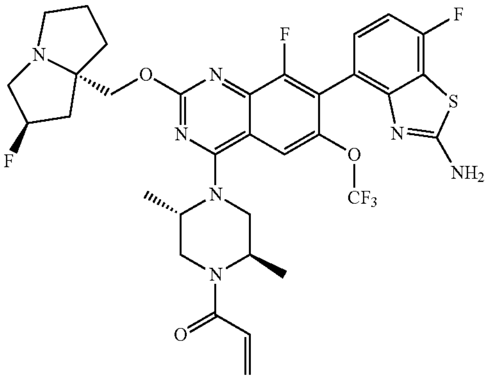 [SMILES: C=CC(=O)N1C[C@H](C)N(c2nc(OC[C@@]34CCCN3C[C@H](F)C4)nc3c(F)c(-c4ccc(F)c5sc(N)nc45)c(OC(F)(F)F)cc23)C[C@H]1C] | LCMS m/z [M + 1]: 722.3 $^1$HNMR (400 MHz, $CD_3OD$): δ 7.78 (s, 1H), 7.21-7.35 (m, 1H), 7.02 (t, J = 8.8 Hz, 1H), 6.67-6.86 (m, 1H), 6.24-6.35 (m, 1H), 5.71-5.80 (m, 1H), 5.58 (d, J = 52 Hz, 1H), 4.67-4.85 (m, 2H), 4.25-4.31 (m, 1H), 3.88-4.10 (m, 5H), 3.31-3.49 (m, 3H), 2.62-2.81 (m, 2H), 2.30-2.58 (m, 3H), 2.05-2.15 (m, 1H), 1.39-1.51 (m, 3H), 1.26-1.45 (m, 4H). |
| 235a | 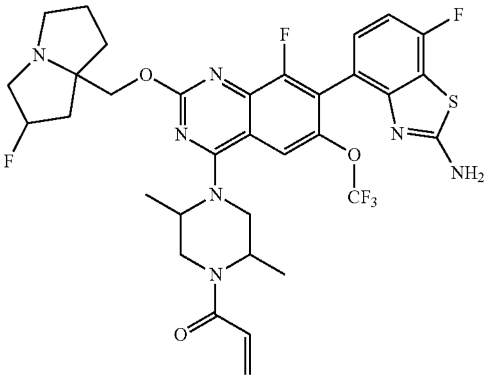 [SMILES: C=CC(=O)N1CC(C)N(c2nc(OCC34CCCN3CC(F)C4)nc3c(F)c(-c4ccc(F)c5sc(N)nc45)c(OC(F)(F)F)cc23)CC1C] | |
| 236 | 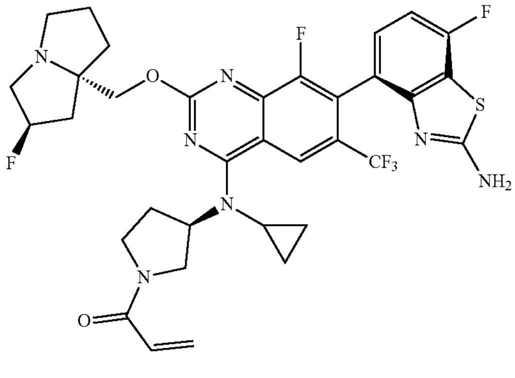 | LCMS m/z [M + 1]: 718.3 $^1$HNMR (400 MHz, $CD_3OD$) δ 8.78 (d, J = 5.6 Hz, 1H), 7.20-7.21 (m, 1H), 6.98-7.00 (m, 1H), 6.67-6.80 (m, 1H), 6.30-6.38 (m, 1H), 5.72-5.90 (m, 1H), 5.48-5.69 (m, 1H), 4.85-5.05 (m, 1H), 4.59-4.65 (m, 2H), 4.23-4.37 (m, 1H), 3.85-4.10 (m, 4H), 3.72-3.75 (m, 1H), 3.57-3.61 (m, 1H), 3.31-3.45 (m, 1H), 2.56-2.90 (m, 5H), 2.25-2.41 (m, 4H), 1.11-1.29 (m, 2H), 0.62-0.88 (m, 2H). |

TABLE 2-continued
Selected compounds of the present disclosure.
| Compound No. | Structure | Analytical data |
| --- | --- | --- |
| 236a | 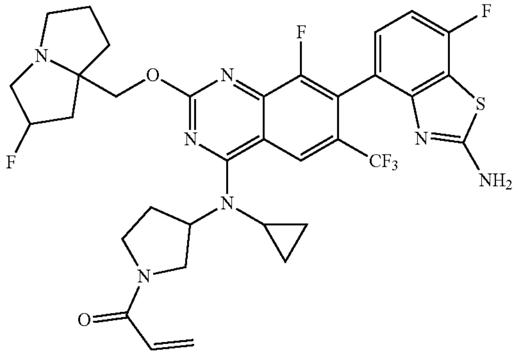 [SMILES: C=CC(=O)N1CCC(N(c2nc(OCC34CCCN3CC(F)C4)nc3c(F)c(-c4ccc(F)c5sc(N)nc45)c(C(F)(F)F)cc23)C2CC2)C1] | |
| 237 | 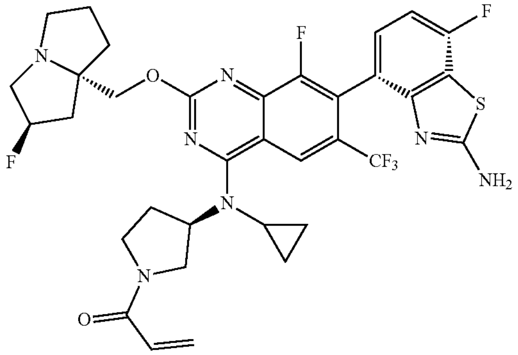 | LCMS m/z [M + 1]: 718.3<br>$^1$HNMR (400 MHz, $CD_3OD$) δ 8.79 (d, J = 5.6 Hz, 1H), 7.20-7.24 (m, 1H), 6.98-7.00 (m, 1H), 6.67-6.98 (m, 1H), 6.30-6.34 (m, 1H), 5.72-5.90 (m, 1H), 5.48-5.69 (m, 1H), 4.84-4.98 (m, 1H), 4.59-4.65 (m, 2H), 4.23-4.37 (m, 1H), 3.85-4.10 (m, 4H), 3.72-3.75 (m, 1H), 3.57-3.61 (m, 1H), 3.31-3.45 (m, 1H), 2.79-2.90 (m, 1H), 2.56-2.68 (m, 3H), 2.25-2.41 (m, 3H), 2.13-2.21 (m, 1H), 1.11-1.29 (m, 2H), 0.64-0.82 (m, 2H). |
| 238 | 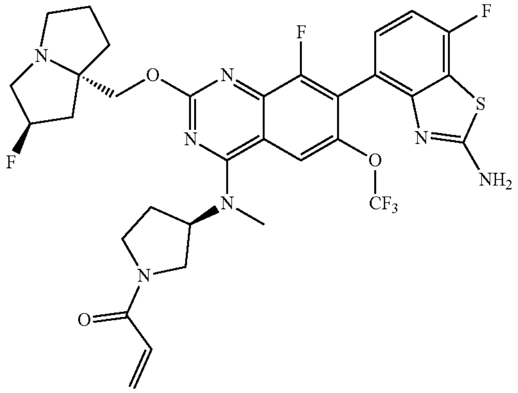 [SMILES: C=CC(=O)N1CC[C@@H](N(C)c2nc(OC[C@@]34CCCN3C[C@H](F)C4)nc3c(F)c(-c4ccc(F)c5sc(N)nc45)c(OC(F)(F)F)cc23)C1] | LCMS m/z [M + 1]: 708.3<br>$^1$HNMR (400 MHz, $CD_3OD$) δ 7.98 (s, 1H), 7.27-7.30 (m, 1H), 7.01-7.05 (m, 1H), 6.64-6.68 (m, 1H), 6.30-6.34 (m, 1H), 5.79-5.81 (m, 1H), 5.49-5.63 (m, 1H), 5.19-5.38 (m, 1H), 4.66-4.74 (m, 2H), 3.82-4.02 (m, 6H), 3.47-3.79 (m, 5H), 2.30-2.63 (m, 7H), 2.03-2.28 (m, 1H). |
| 238a | 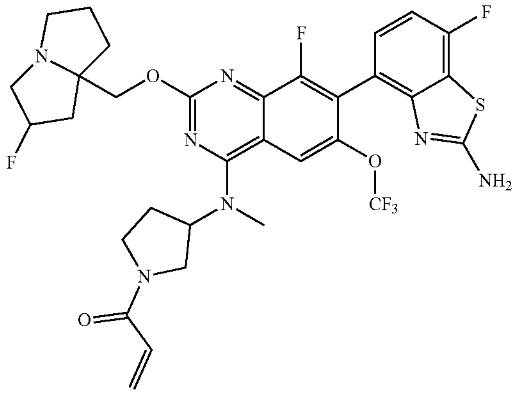 [SMILES: C=CC(=O)N1CCC(N(C)c2nc(OCC34CCCN3CC(F)C4)nc3c(F)c(-c4ccc(F)c5sc(N)nc45)c(OC(F)(F)F)cc23)C1] | |

TABLE 2-continued

| Selected compounds of the present disclosure. | | |
|---|---|---|
| Compound No. | Structure | Analytical data |
| 239 | 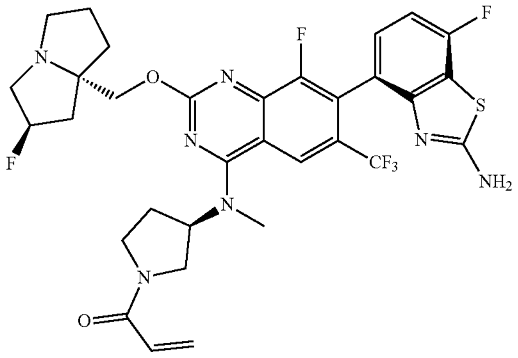 | LCMS m/z [M + 1]: 692.3 $^1$H NMR (400 MHz, $CD_3OD$) δ 8.38 (s, 1H), 7.19-7.21 (m, 1H), 6.99 (t, J = 9.2 Hz, 1H), 6.61-6.72 (m, 1H), 6.32 (d, J = 16.8 Hz, 1H), 5.75-5.85 (m, 1H), 5.30 and 5.50 (1H), 5.28-5.41 (m, 1H), 4.62-4.73 (m, 2H), 4.08-4.21 (m, 1H), 3.69-4.08 (m, 5H), 3.45-3.65 (m, 5H), 2.51-2.75 (m, 3H), 2.28-2.45 (m, 4H), 2.08-2.21 (m, 1H). |
| 239a | 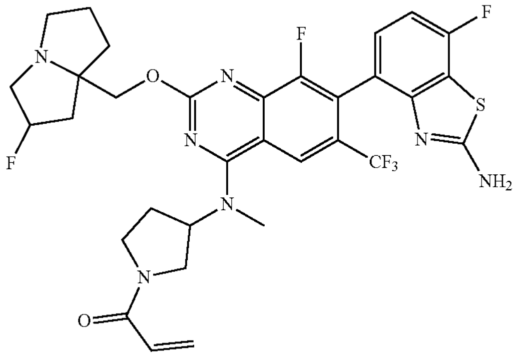 [SMILES: C=CC(=O)N1CCC(N(C)c2nc(OCC34CCCN3CC(F)C4)nc3c(F)c(-c4ccc(F)c5sc(N)nc45)c(C(F)(F)F)cc23)C1] | |
| 240 | 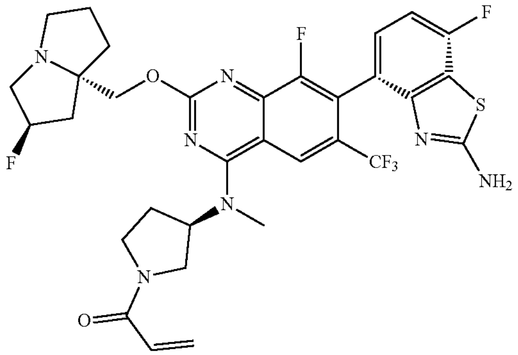 | LCMS m/z [M + 1]: 692.3 $^1$HNMR (400 MHz, $CD_3OD$) δ 8.38 (s, 1H), 7.19-7.22 (m, 1H), 6.99 (t, J = 8.8 Hz, 1H), 6.61-6.72 (m, 1H), 6.33(d, J = 16.8 Hz, 1H), 5.75-5.85 (m, 1H), 5.53(d, J = 51.2 Hz, 1H), 5.28-5.41 (m, 1H), 4.62-4.73 (m, 2H), 4.08-4.21 (m, 1H), 3.69-4.08 (m, 5H), 3.45-3.65 (m, 5H), 2.51-2.75 (m, 3H), 2.28-2.45 (m, 4H), 2.08-2.21 (m, 1H). |
| 241 | 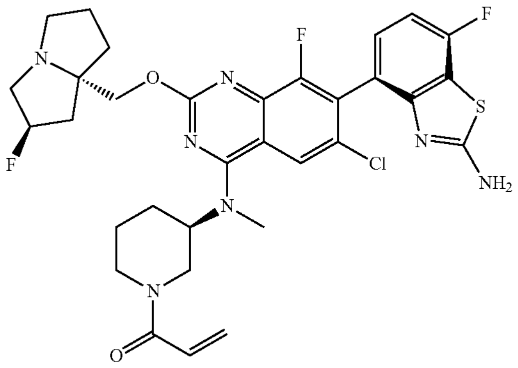 | LCMS m/z [M + 1]: 672.2 $^1$HNMR (400 MHz, $CD_3OD$) δ 8.17 (s, 1H), 7.23 (dd, J = 8.4, 5.6 Hz, 1H), 7.01 (t, J = 9.00 Hz, 1H), 6.84 (dd, J = 10.0, 6.0 Hz, 1H), 6.20 (d, J = 17.2 Hz, 1H), 5.78 (d, J = 10.8 Hz, 1H), 5.58 (d, J = 52.8 Hz, 1H), 4.95-5.05 (m, 3H), 4.55-4.68 (m, 1H), 4.46-4.49 (m, 1H), 4.08-4.22 (m, 1H), 3.85-3.95 (m, 2H), 3.54 (s, 3H), 3.42-3.51 (m, 2H), 3.11-3.21 (m, 1H), 2.87-2.94 (m, 1H), 2.59-2.71 (m, 2H), 2.46-2.55 (m, 1H), 2.29-2.37 (m, 2H), 2.16-2.22 (m, 3H), 1.97-2.01 (m, 1H). |

TABLE 2-continued

Selected compounds of the present disclosure.

| Compound No. | Structure | Analytical data |
|---|---|---|
| 241a | 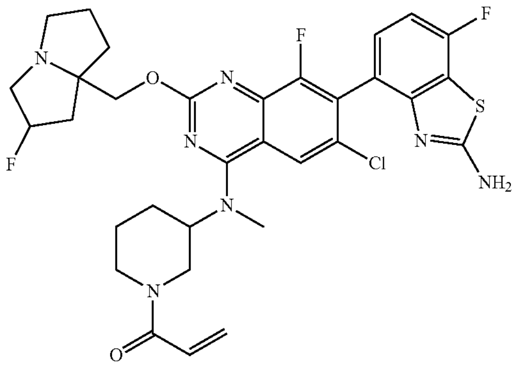 [SMILES: C=CC(=O)N1CCCC(N(C)c2nc(OCC34CCCN3CC(F)C4)nc3c(F)c(-c4ccc(F)c5sc(N)nc45)c(Cl)cc23)C1] | |
| 242 | 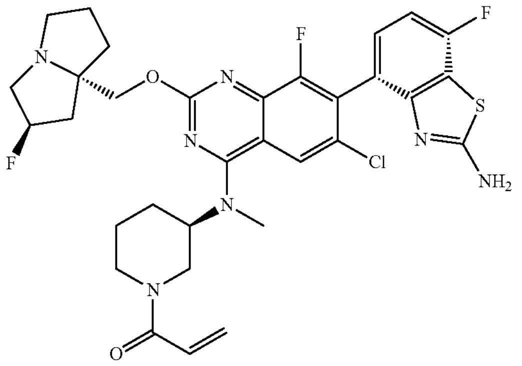 | LCMS m/z [M + 1]: 672.2 $^1$HNMR (400 MHz, $CD_3OD$) δ 8.17 (s, 1H), 7.23 (dd, J = 8.4, 5.6 Hz, 1H), 7.01 (t, J = 9.00 Hz, 1H), 6.84 (dd, J = 10.0, 6.0 Hz, 1H), 6.20 (d, J = 17.2 Hz, 1H), 5.78 (d, J = 10.8 Hz, 1H), 5.58 (d, J = 52.8 Hz, 1H), 4.95-5.05 (m, 3H), 4.55-4.68 (m, 1H), 4.46-4.49 (m, 1H), 4.08-4.22 (m, 1H), 3.85-3.95 (m, 2H), 3.54 (s, 3H), 3.42-3.51 (m, 2H), 3.11-3.21 (m, 1H), 2.87-2.94 (m, 1H), 2.59-2.71 (m, 2H), 2.46-2.55 (m, 1H), 2.29-2.37 (m, 2H), 2.16-2.22 (m, 3H), 1.97-2.01 (m, 1H). |
| 243 | 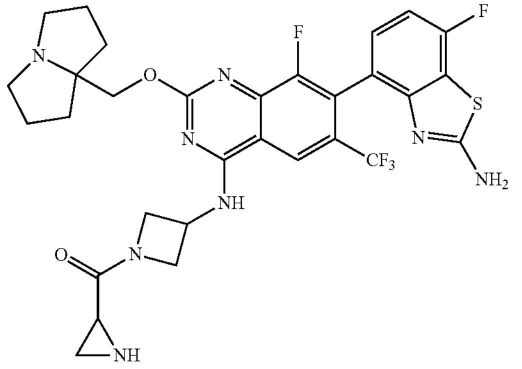 [SMILES: Nc1nc2c(-c3c(C(F)(F)F)cc4c(NC5CN(C(=O)C6CN6)C5)nc(OCC56CCCN5CCC6)nc4c3F)ccc(F)c2s1] | LCMS m/z [M + 1]: 661.2 $^1$HNMR (400 MHz, $CD_3OD$) δ 8.61 (s, 1H), 7.16-7.25 (m, 1H), 6.98 (t, J = 8.8 Hz, 1H), 4.96-5.21 (m, 2H), 4.66 (s, 2H), 4.46-4.61 (m, 2H), 4.15-4.34 (m, 1H), 3.76-3.98 (m, 1H), 3.64-3.74 (m, 2H), 3.34-3.39 (m, 2H), 3.20-3.29 (m, 2H), 2.46-2.60 (m, 1H), 2.28-2.38 (m, 2H), 2.19-2.25 (m, 2H), 2.08-2.18 (m, 4H). |
| 244 | 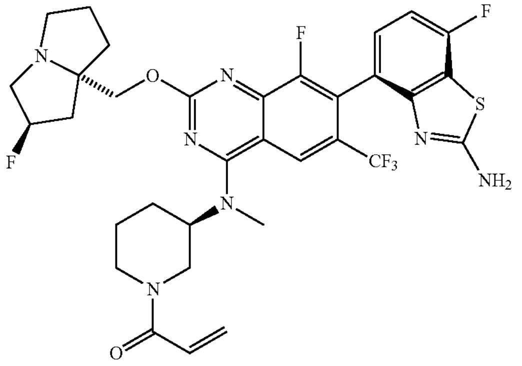 | LCMS m/z [M + 1]: 706.3 $^1$HNMR (400 MHz, $CD_3OD$) δ 8.3 (s, 1H), 7.21 (dd, J = 8.0, 6.0 Hz, 1H), 6.98 (t, J = 8.8 Hz, 1H), 6.88 (dd, J = 16.4, 6.8 Hz, 1H), 6.21 (d, J = 16.8 Hz, 1H), 5.78 (d, J = 10.4 Hz, 1H), 5.58 (d, J = 52.6 Hz, 1H), 4.98-5.05 (m, 3H), 4.60-4.66 (m, 1H), 4.43-4.49 (m, 1H), 4.08-4.22 (m, 1H), 3.85-3.95 (m, 2H), 3.55 (s, 3H), 3.42-3.51 (m, 2H), 3.11-3.21 (m, 1H), 2.87-2.94 (m, 1H), 2.47-2.73 (m, 3H), 2.29-2.37 (m, 2H), 2.16-2.22 (m, 3H), 1.97-2.01 (m, 1H). |

TABLE 2-continued

| Selected compounds of the present disclosure. | | |
|---|---|---|
| Compound No. | Structure | Analytical data |
| 244a | 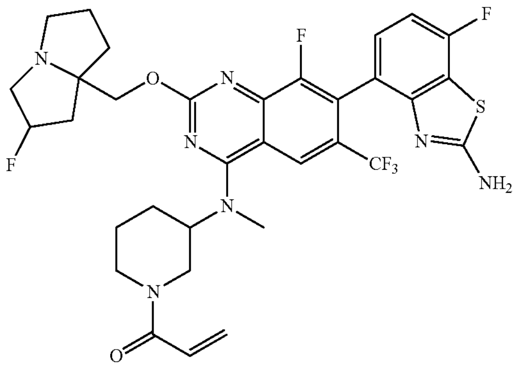 [SMILES: C=CC(=O)N1CCCC(N(C)c2nc(OCC34CCCN3CC(F)C4)nc3c(F)c(-c4ccc(F)c5sc(N)nc45)c(C(F)(F)F)cc23)C1] | |
| 245 | 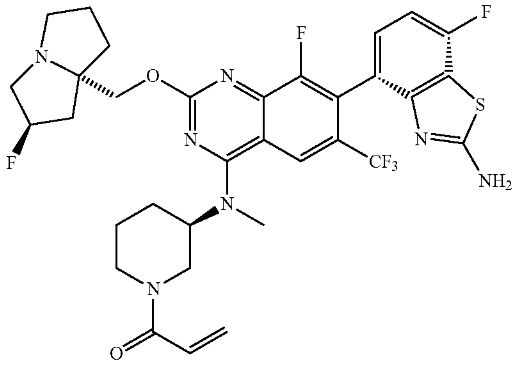 | LCMS m/z [M + 1]: 706.3<br>$^1$HNMR (400 MHz, $CD_3OD$) δ 8.38 (s, 1H), 7.21 (dd, J = 8.0, 5.6 Hz, 1H), 6.98 (t, J = 8.8 Hz, 1H), 6.88 (dd, J = 16.8, 6.8 Hz, 1H), 6.21 (d, J = 17.2 Hz, 1H), 5.78 (d, J = 10.8 Hz, 1H), 5.58 (d, J = 52.6 Hz, 1H), 4.98-5.05 (m, 3H), 4.60-4.66 (m, 1H), 4.43-4.49 (m, 1H), 4.08-4.22 (m, 1H), 3.85-3.95 (m, 2H), 3.55 (s, 3H), 3.42-3.51 (m, 2H), 3.11-3.21 (m, 1H), 2.87-2.94 (m, 1H), 2.47-2.73 (m, 3H), 2.29-2.37 (m, 2H), 2.16-2.22 (m, 3H), 1.97-2.01 (m, 1H). |
| 246 | 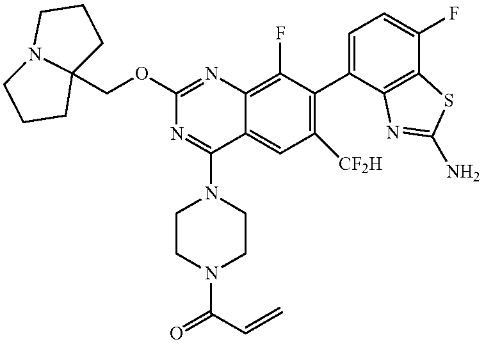 [SMILES: C=CC(=O)N1CCN(c2nc(OCC34CCCN3CCC4)nc3c(F)c(-c4ccc(F)c5sc(N)nc45)c(C(F)F)cc23)CC1] | LCMS m/z [M − 1]: 640.26<br>$^1$H NMR (300 MHz, $CD_3OD$) δ 8.11 (s, 1H), 7.25 (dd, J = 8.3, 5.5 Hz, 1H), 7.17-6.94 (m, 1H), 6.84 (dd, J = 16.8, 10.5 Hz, 1H), 6.56 (t, J = 55.3 Hz, 1H), 6.30 (dd, J = 16.8, 1.9 Hz, 1H), 5.82 (dd, J = 10.6, 2.0 Hz, 1H), 4.29 (s, 2H), 4.08 (m, 4H), 3.95 (m, 4H), 3.10 (dt, J = 11.2, 5.7 Hz, 2H), 2.79-2.56 (m, 2H), 2.19-1.99 (m, 2H), 1.91 (m, 4H), 1.82-1.56 (m, 2H). |
| 247 | 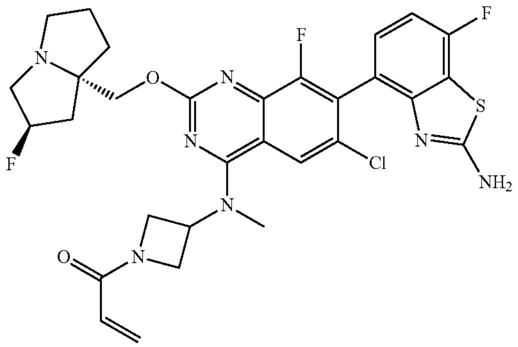 [SMILES: C=CC(=O)N1CC(N(C)c2nc(OC[C@@]34CCCN3C[C@H](F)C4)nc3c(F)c(-c4ccc(F)c5sc(N)nc45)c(Cl)cc23)C1] | LCMS m/z [M + 1]: 644.1<br>$^1$H NMR (300 MHz, $CD_3OD$) δ 8.05 (s, 1H), 7.19-7.25 (m, 1H), 6.99 (t, J = 8.8 Hz, 1H), 6.37-6.46 (m, 1H), 6.24-6.32 (m, 1H), 5.75-5.81 (m, 1H), 5.38 (d, J = 52.8 Hz, 1H), 4.90-5.08 (m, 2H), 4.68-4.75 (m, 1H), 4.20-4.59 (m, 6H), 3.40-3.51 (m, 4H), 3.12-3.21 (m, 1H), 1.91-2.50 (m, 6H). |

TABLE 2-continued
| Selected compounds of the present disclosure. | | |
|---|---|---|
| Compound No. | Structure | Analytical data |
| 247a | 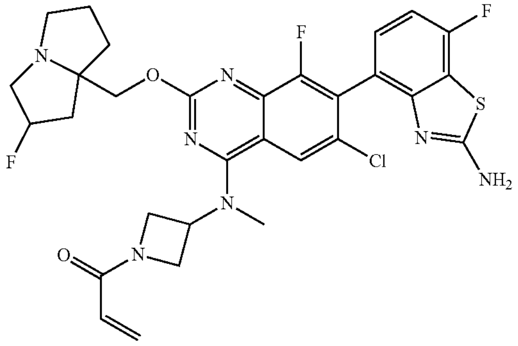 [SMILES: C=CC(=O)N1CC(N(C)c2nc(OCC34CCCN3CC(F)C4)nc3c(F)c(-c4ccc(F)c5sc(N)nc45)c(Cl)cc23)C1] | |
| 248 | 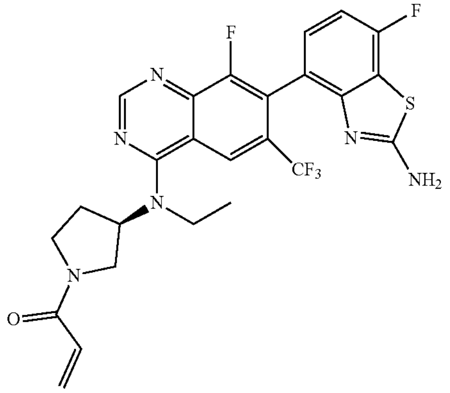 [SMILES: C=CC(=O)N1CC[C@@H](N(CC)c2ncnc3c(F)c(-c4ccc(F)c5sc(N)nc45)c(C(F)(F)F)cc23)C1] | LCMS m/z [M + 1]: 549.2<br>$^1$H NMR (300 MHz, $CD_3OD$) δ 8.79 (s, 1H), 8.40 (s, 1H), 7.24-7.27 (m, 1H), 7.01 (t, J = 8.8 Hz, 1H), 6.58-6.71 (m, 1H), 6.30-6.34 (m, 1H), 5.76-5.81 (m, 1H), 5.27-5.33 (m, 1H), 3.52-4.22 (m, 6H), 2.48-2.67 (m, 2H), 1.57 (t, J = 6.8 Hz, 3H). |
| 248a | 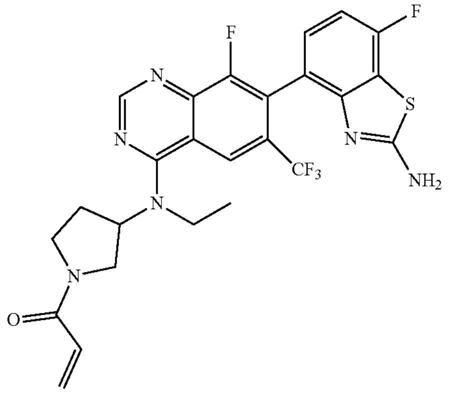 [SMILES: C=CC(=O)N1CCC(N(CC)c2ncnc3c(F)c(-c4ccc(F)c5sc(N)nc45)c(C(F)(F)F)cc23)C1] | |
| 249 | 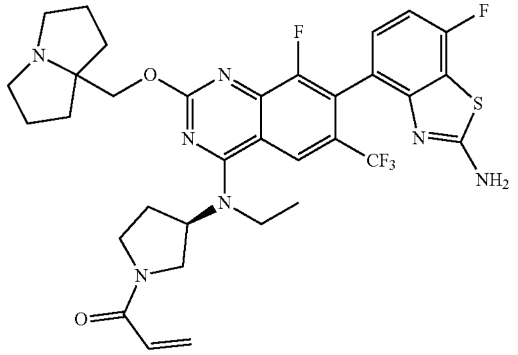 [SMILES: C=CC(=O)N1CC[C@@H](N(CC)c2nc(OCC34CCCN3CCC4)nc3c(F)c(-c4ccc(F)c5sc(N)nc45)c(C(F)(F)F)cc23)C1] | LCMS m/z [M + 1]: 688.3<br>$^1$H NMR (300 MHz, $CD_3OD$) δ 8.30 (s, 1H), 7.20-7.23 (m, 1H), 6.99 (t, J = 8.8 Hz, 1H), 6.59-6.72 (m, 1H), 6.39-6.34 (m, 1H), 5.75-5.81 (m, 1H), 4.99-5.03 (m, 1H), 4.60-4.62 (m, 2H), 3.90-4.15 (m, 5H), 3.68-3.75 (m, 4H), 2.42-2.61 (m, 2H), 2.10-2.29 (m, 9H), 1.49-1.53 (m, 3H). |

TABLE 2-continued
Selected compounds of the present disclosure.
| Compound No. | Structure | Analytical data |
|---|---|---|
| 249a | 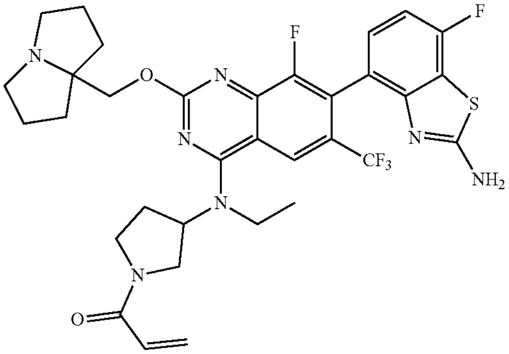 [SMILES: C=CC(=O)N1CCC(N(CC)c2nc(OCC34CCCN3CCC4)nc3c(F)c(-c4ccc(F)c5sc(N)nc45)c(C(F)(F)F)cc23)C1] | |
| 250 | 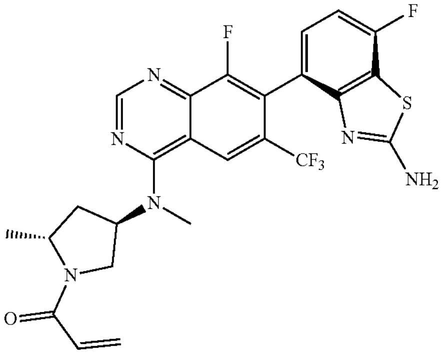 | LCMS m/z [M + 1]: 549.2<br>$^{1}$H NMR (300 MHz, $CD_3OD$) δ 8.82 (s, 1H), 8.55 (s, 1H), 7.27-7.30 (m, 1H), 7.02 (t, J = 8.78 Hz, 1H), 6.60-6.68 (m, 1H), 6.31-6.40 (m, 1H), 5.90-5.97 (m, 1H), 5.78-5.85 (m, 1H), 4.55-4.62 (m, 1H), 4.00-4.24 (m, 1H), 3.81-3.90 (m, 1H), 3.64 (s, 3H), 2.58-2.76 (m, 1H), 2.19-2.34 (m, 1H), 1.37-1.41 (m, 3H). |
| 250a | 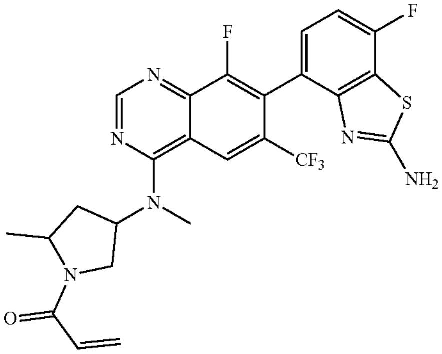 [SMILES: C=CC(=O)N1CC(N(C)c2ncnc3c(F)c(-c4ccc(F)c5sc(N)nc45)c(C(F)(F)F)cc23)CC1C] | |
| 251 | 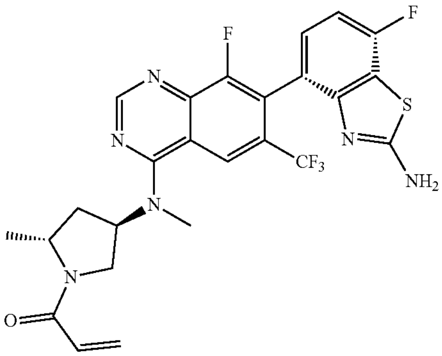 | LCMS m/z [M + 1]: 549.2<br>$^{1}$H NMR (300 MHz, $CD_3OD$) δ 8.82 (s, 1H), 8.55 (s, 1H), 7.27-7.31 (m, 1H), 7.05 (t, J = 8.78 Hz, 1H), 6.61-6.78 (m, 1H), 6.32-6.40 (m, 1H), 5.90-5.97 (m, 1H), 5.78-5.85 (m, 1H), 4.55-4.61 (m, 1H), 4.01-4.25 (m, 1H), 3.82-3.91 (m, 1H), 3.64 (s, 3H), 2.58-2.76 (m, 1H), 2.17-2.33 (m, 1H), 1.37-1.41 (m, 3H). |

TABLE 2-continued
Selected compounds of the present disclosure.
| Compound No. | Structure | Analytical data |
| --- | --- | --- |
| 252 | 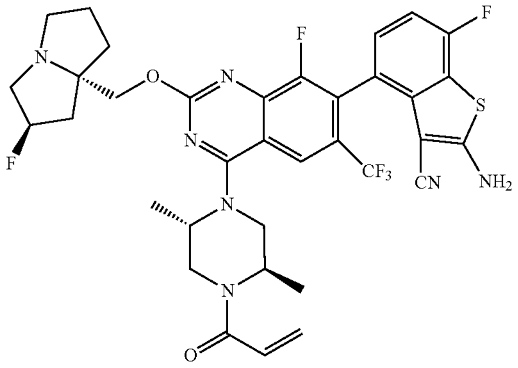 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)c(C(F)(F)F)cc23)C[C@H]1C] | LCMS m/z [M + 1]: 730.4<br>$^1$HNMR (400 MHz, $CD_3OD$) δ 8.18 (s, 1H), 7.21-7.28 (m, 1H), 7.03 (t, J = 8.8 Hz, 1H), 6.73-6.92 (m, 1H), 6.26-6.37 (m, 1H), 5.78-5.86 (m, 1H), 5.57 (d, J = 52.4 Hz, 1H), 4.27-4.74 (m, 4H), 3.81-4.10 (m, 5H), 3.42-3.59 (m, 1H), 2.52-2.79 (m, 2H), 2.11-2.49 (m, 4H), 1.62-1.64 (m, 1H), 1.41-1.56 (m, 3H), 1.21-1.38 (m, 4H). |
| 252a | 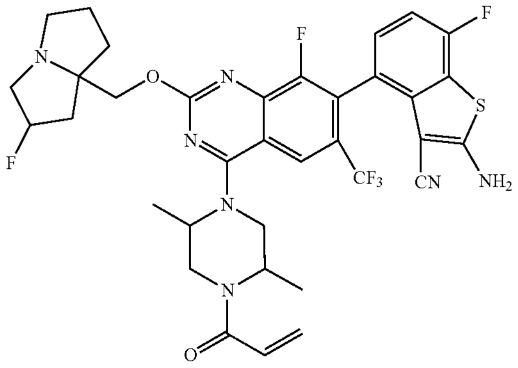 [SMILES: C=CC(=O)N1CC(C)N(c2nc(OCC34CCCN3CC(F)C4)nc3c(F)c(-c4ccc(F)c5sc(N)c(C#N)c45)c(C(F)(F)F)cc23)CC1C] | |
| 253 | 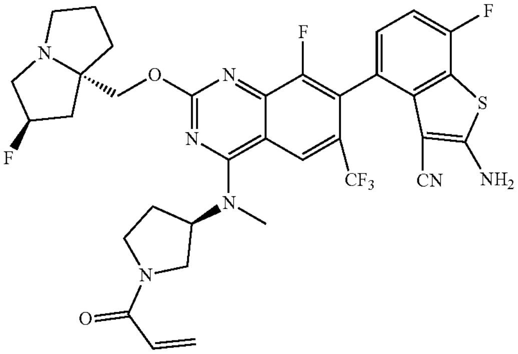 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(C(F)(F)F)cc23)C1] | LCMS m/z [M + 1]: 716.2<br>$^1$HNMR (400 MHz, $CD_3OD$) δ 8.38 (s, 1H), 7.19-7.27 (m, 1H), 7.03 (t, J = 9.2 Hz, 1H), 6.62-6.74 (m, 1H), 6.27-6.38 (m, 1H), 5.75-5.84 (m, 1H), 5.56 (d, J = 51.2 Hz, 1H), 5.25-5.44 (m, 1H), 4.58-4.77 (m, 2H), 3.68-4.21 (m, 6H), 3.41-3.65 (m, 5H), 2.26-2.75 (m, 7H), 2.05-2.24 (m, 1H). |
| 253a | 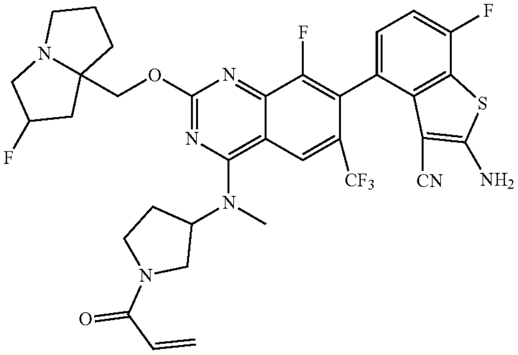 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1] | |

TABLE 2-continued
Selected compounds of the present disclosure.
| Compound No. | Structure | Analytical data |
| --- | --- | --- |
| 254 | 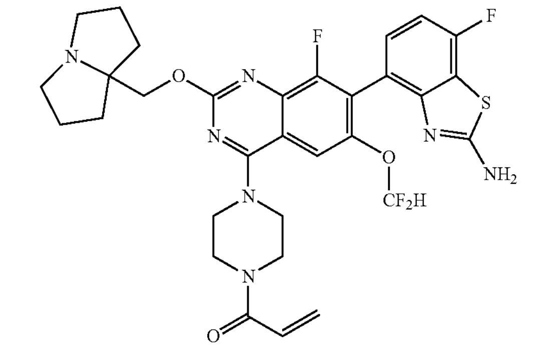 [SMILES: C=CC(=O)N1CCN(c2nc(OCC34CCCN3CCC4)nc3c(F)c(-c4ccc(F)c5sc(N)nc45)c(OC(F)F)cc23)CC1] | LCMS m/z [M + 1]: 658.46 $^1$HNMR (300 MHz, Chloroform-d) δ 7.45 (s, 1H), 7.33-7.18 (m, 1H), 6.98 (t, J = 8.7 Hz, 1H), 6.59 (dd, J = 16.8, 10.5 Hz, 1H), 6.40 (dd, J = 76.7, 70.4 Hz, 1H), 6.35 (dd, J = 17.1, 2.3 Hz, 1H) 5.78 (dd, J = 10.4, 2.0 Hz, 1H), 5.69 (br s, 2H), 4.21 (s, 2H), 3.93-3.65 (m, 8H), 3.10 (dt, J = 10.6, 5.5 Hz, 2H), 2.72-2.58 (m, 2H), 2.08 (m, 2H), 1.87 (p, J = 6.5 Hz, 4H), 1.71-1.56. |
| 255 | 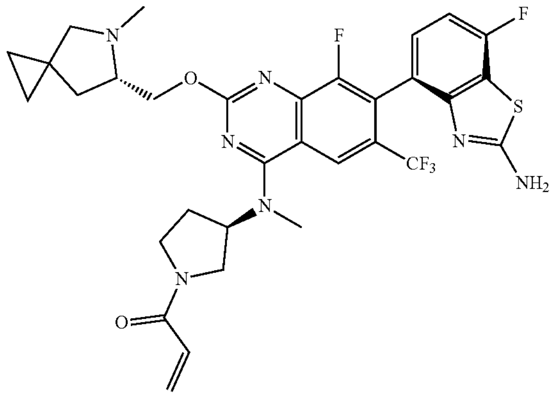 | LCMS m/z [M + 1]: 674.2 $^1$H NMR (300 MHz, $CD_3OD$) δ 8.39 (s, 1H), δ 7.19-7.23 (m, 1H), 6.98 (t, J = 8.8 Hz, 1H), 6.62-6.71 (m, 1H), 6.32 (d, J = 16.6 Hz, 1H), 5.77-5.82 (m, 1H), 5.26-5.40 (m, 1H), 4.92-4.97 (m, 1H), 4.69-4.73 (m, 2H), 3.35-4.19 (m, 9H), 3.12 (s, 3H), 1.99-2.52 (m, 4H), 0.73-0.83 (m, 4H). |
| 255a | 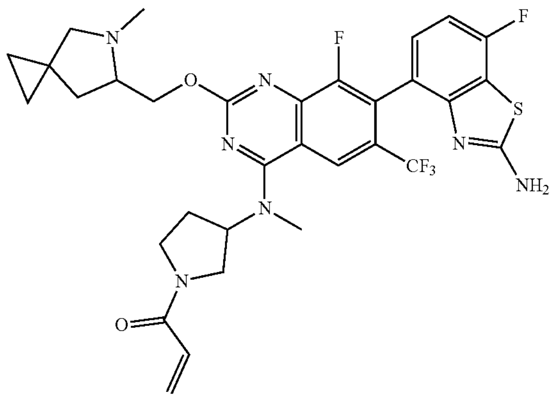 [SMILES: C=CC(=O)N1CCC(N(C)c2nc(OCC3CC4(CC4)CN3C)nc3c(F)c(-c4ccc(F)c5sc(N)nc45)c(C(F)(F)F)cc23)C1] | |
| 256 | 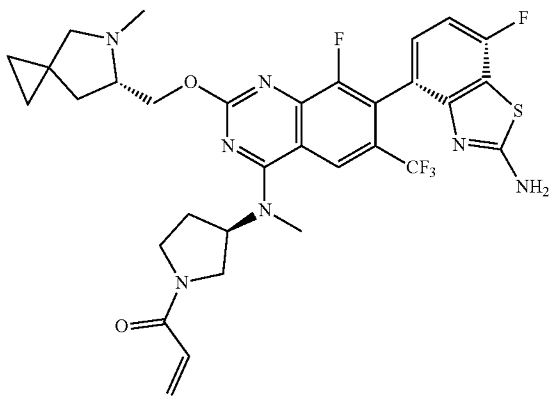 | LCMS m/z [M + 1]: 674.3 $^1$H NMR (300 MHz, $CD_3OD$) δ 8.40 (s, 1H), 7.21-7.25 (m, 1H), 7.01 (t, J = 9.00 Hz, 1H), 6.64-6.73 (m, 1H), 6.32-6.36 (m, 1H), 5.79-5.83 (m, 1H), 5.29-5.42 (m, 1H), 4.92-4.95 (m, 2H), 4.69-4.74 (m, 1H), 4.12-4.19 (m, 2H), 3.93-4.05 (m, 1H), 3.74-3.83 (m, 1H), 3.58-3.65 (m, 1H), 3.43-3.53 (m, 4H) , 3.14 (s, 3H), 2.41-2.54 (m, 3H), 1.99-2.05 (m, 1H), 0.72-0.85 (m, 4H). |

TABLE 2-continued
| Compound No. | Structure | Analytical data |
|---|---|---|
| Selected compounds of the present disclosure. | | |
| 257 | 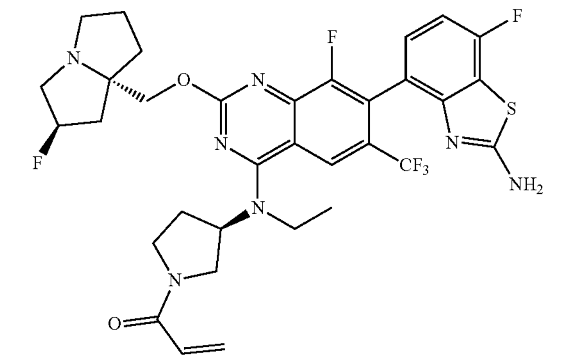 [SMILES: C=CC(=O)N1CC[C@@H](N(CC)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 706.3<br>$^{1}$H NMR (300 MHz, $CD_3OD$) δ 8.29-8.30 (m, 1H), 7.20-7.23 (m, 1H), 6.99 (t, J = 8.8 Hz, 1H), 6.59-6.72 (m, 1H), 6.29-6.34 (m, 1H), 5.76-5.82 (m, 1H), 5.55 (d, J = 50.8 Hz, 1H), 4.99-5.04 (m, 1H), 4.57-4.69 (m, 2H), 3.67-4.17 (m, 9H), 3.43-3.56 (m, 1H), 2.11-2.68 (m, 8H), 1.48-1.54 (m, 3H). |
| 257a | 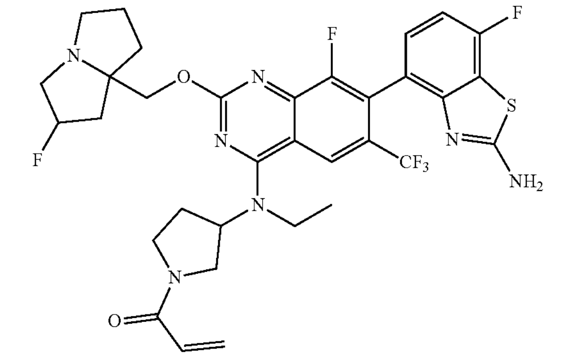 [SMILES: C=CC(=O)N1CCC(N(CC)c2nc(OCC34CCCN3CC(F)C4)nc3c(F)c(-c4ccc(F)c5sc(N)nc45)c(C(F)(F)F)cc23)C1] | |
| 258 | 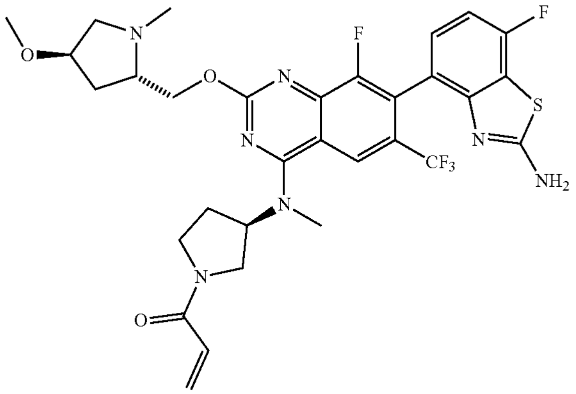 | LCMS m/z [M + 1]: 658.46<br>$^{1}$H NMR (300 MHz, $CD_3OD$) δ 8.38 (s, 1H), δ 7.23-7.26 (m, 1H), 7.00-7.05 (m, 1H), 6.62-6.71 (m, 1H), 6.32 (d, J = 16.6 Hz, 1H), 5.75-5.85 (m, 1H), 5.28-5.45 (m, 1H), 4.92-4.96 (m, 1H), 4.67-4.71 (m, 1H), 3.61-4.19 (m, 7H), 3.51-3.52 (m, 4H), 3.39 (s, 3H), 3.12 (s, 3H), 2.17-2.52 (m, 4H). |
| 258a | 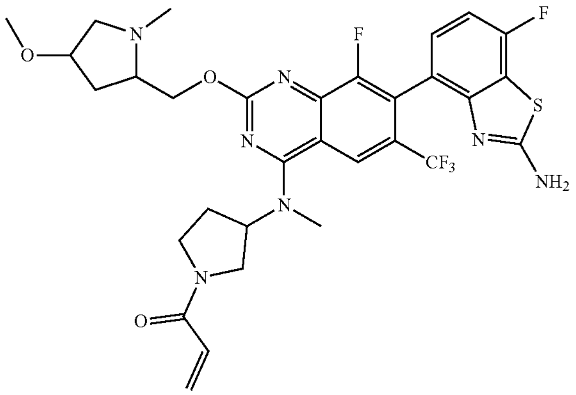 [SMILES: C=CC(=O)N1CCC(N(C)c2nc(OCC3CC(OC)CN3C)nc3c(F)c(-c4ccc(F)c5sc(N)nc45)c(C(F)(F)F)cc23)C1] | |

TABLE 3
| Selected compounds of the present disclosure. | | |
|---|---|---|
| Compound No. | Structure | Analytical data |
| 7 | 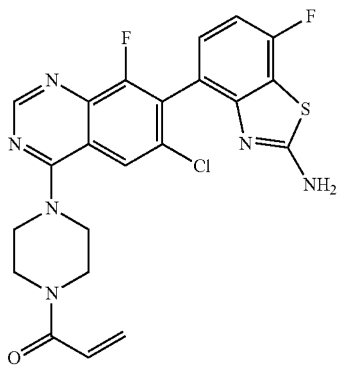 [SMILES: C=CC(=O)N1CCN(c2ncnc3c(F)c(-c4ccc(F)c5sc(N)nc45)c(Cl)cc23)CC1] | LCMS m/z [M + 1]: 487.1 $^1$HNMR (400 MHz, $CD_3OD$) δ 8.68 (s, 1H), 8.06 (s, 1H), 7.21-7.31 (m, 1H), 7.03 (t, J = 8.7 Hz, 1H), 6.84 (dd, J = 16.6, 10.6 Hz, 1H), 6.30 (d, J = 16.7 Hz, 1H), 5.83 (d, J = 10.4 Hz, 1H), 4.0-4.12 (m, 4H), 3.85-4.00 (m, 4H). |
| 8 | 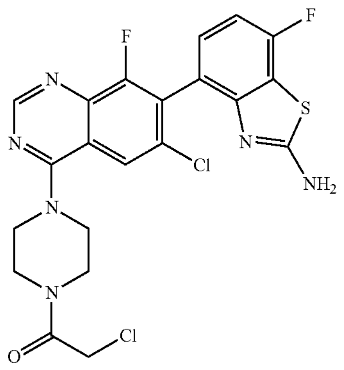 [SMILES: Nc1nc2c(-c3c(Cl)cc4c(N5CCN(C(=O)CCl)CC5)ncnc4c3F)ccc(F)c2s1] | LCMS m/z [M + 1]: 509.0 $^1$HNMR (400 MHz, $CD_3OD$) δ 8.75 (s, 1H), 8.23 (s, 1H), 7.23-7.34 (m, 1H), 7.04 (t, J = 8.5 Hz, 1H), 4.31-4.50 (m, 6H), 3.81-4.03 (m, 4H). |
| 11 | 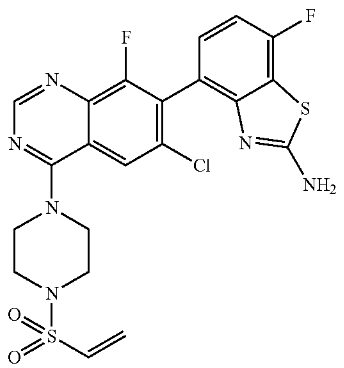 [SMILES: C=CS(=O)(=O)N1CCN(c2ncnc3c(F)c(-c4ccc(F)c5sc(N)nc45)c(Cl)cc23)CC1] | LCMS m/z [M + 1]: 523.0 $^1$HNMR (400 MHz, $CD_3OD$) δ 8.74 (s, 1H), 8.16 (s, 1H), 7.29 (dd, J = 8.4, 5.4 Hz, 1H), 7.05 (t, J = 8.8 Hz, 1H), 6.64-6.76 (m, 1H), 6.12-6.26 (m, 2H), 4.25-4.50 (m, 4H), 3.41-3.47 (m, 4H). |
| 12 | 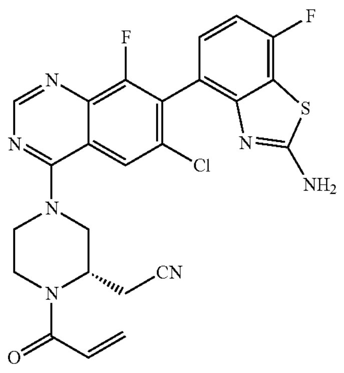 [SMILES: C=CC(=O)N1CCN(c2ncnc3c(F)c(-c4ccc(F)c5sc(N)nc45)c(Cl)cc23)C[C@@H]1CC#N] | LCMS m/z [M + 1]: 526.2 $^1$HNMR (400 MHz, $CD_3OD$) δ 8.70 (s, 1H), 8.08 (s, 1H), 7.23-7.33 (m, 1H), 7.03 (t, J = 8.8 Hz, 1H), 6.76-6.97 (m, 1H), 6.32 (d, J = 16.6 Hz, 1H), 5.86 (d, J = 9.5 Hz, 1H), 5.06-5.22 (m, 1H), 4.41-4.60 (m, 2H), 4.02-4.28 (m, 1H), 3.64-3.93 (m, 2H), 3.46-3.64 (m, 1H), 2.94-3.14 (m, 2H) |

TABLE 3-continued

| Compound No. | Structure | Analytical data |
|---|---|---|
| 13 | 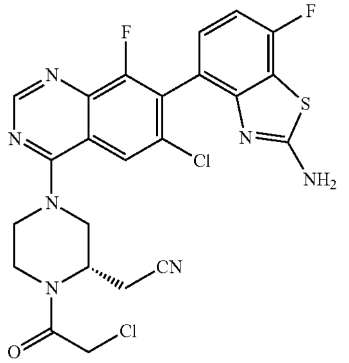 [SMILES: N#CC[C@H]1CN(c2ncnc3c(F)c(-c4ccc(F)c5sc(N)nc45)c(Cl)cc23)CCN1C(=O)CCl] | LCMS m/z [M + 1]: 548.1<br>$^1$H NMR (400 MHz, $CD_3OD$) δ 8.60 (s, 1H), 7.97 (s, 1H), 7.11-7.19 (m, 1H), 6.91 (t, J = 8.8 Hz, 1H), 4.92-4.96 (m, 1H), 4.21-4.52 (m, 6H), 3.85-3.98 (m, 1H), 3.58-3.77 (m, 2H), 2.86-2.95 (m, 1H). |
| 17 | 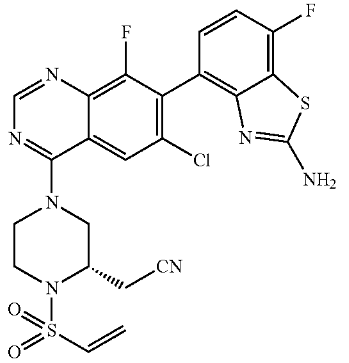 [SMILES: C=CS(=O)(=O)N1CCN(c2ncnc3c(F)c(-c4ccc(F)c5sc(N)nc45)c(Cl)cc23)C[C@@H]1CC#N] | LCMS m/z [M + 1]: 562.1<br>$^1$HNMR (400 MHz, $CD_3OD$) δ 8.58 (s, 1H), 7.94 (s, 1H), 7.15 (dd, J = 8.4, 5.5 Hz, 1H), 6.91 (t, J = 8.8 Hz, 1H), 6.59-6.71 (m, 1H), 6.17 (dd, J = 16.5, 5.0 Hz, 1H), 5.92 (t, J = 9.9 Hz, 1H), 4.36-4.45 (m, 1H), 4.18-4.34 (m, 2H), 3.63-3.80 (m, 2H), 3.48-3.61 (m, 2H), 2.89-2.97 (m, 2H). |
| 33 | 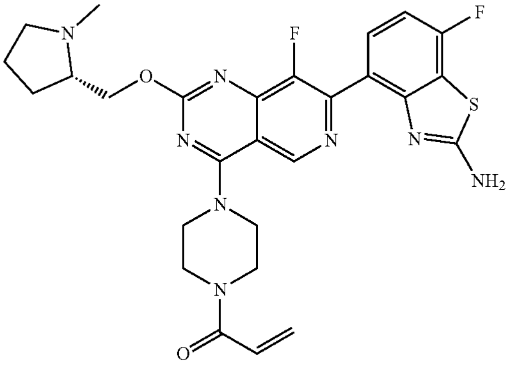 [SMILES: C=CC(=O)N1CCN(c2nc(OC[C@@H]3CCCN3C)nc3c(F)c(-c4ccc(F)c5sc(N)nc45)ncc23)CC1] | LCMS m/z [M + 1]: 567.3<br>$^1$HNMR (300 MHz, $CD_3OD$) δ 9.13 (s, 1H), 7.49 (dd, J = 8.5, 5.5 Hz, 1H), 7.03 (t, J = 8.8 Hz, 1H), 6.83 (dd, J = 16.7, 10.6 Hz, 1H), 6.30 (dd, J = 16.8, 1.9 Hz, 1H), 5.83 (dd, J = 10.6, 1.8 Hz, 1H), 4.52 (m, 2H), 4.18 (m, 4H), 4.03 (m, 4H), 3.12 (dd, J = 9.5, 4.5 Hz, 1H), 2.83 (d, J = 7.9 Hz, 1H), 2.55 (s, 3H), 2.40 (dd, J = 17.8, 8.9 Hz, 1H), 2.14 (dd, J = 11.2, 6.0 Hz, 1H), 2.01-1.44 (m, 3H). |
| 43 | 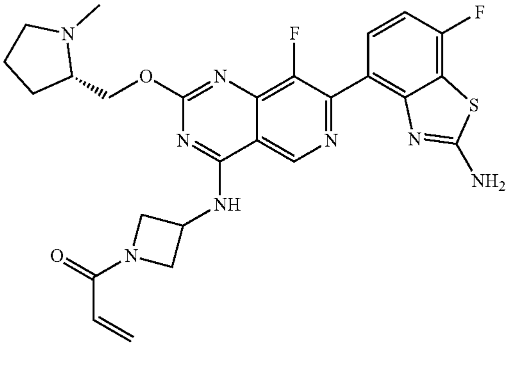 [SMILES: C=CC(=O)N1CC(Nc2nc(OC[C@@H]3CCCN3C)nc3c(F)c(-c4ccc(F)c5sc(N)nc45)ncc23)C1] | LCMS m/z [M + 1]: 553.2<br>$^1$HNMR (300 MHz, $CD_3OD$) δ 9.24 (s, 1H), 7.46 (dd, J = 8.5, 5.6 Hz, 1H), 7.03 (t, J = 8.8 Hz, 1H), 6.35 (m, 2H), 5.79 (dd, J = 10.0, 2.2 Hz, 1H), 5.08 (m, 1H), 4.79 (t, J = 8.7 Hz, 1H), 4.47 (m, 4H), 4.26 (m, 1H), 3.11 (m, 1H), 2.80 (m, 1H), 2.55 (s, 3H), 2.39 (q, J = 9.0 Hz, 1H), 2.13 (m, 1H), 1.97-1.55 (m, 3H). |

TABLE 3-continued
Selected compounds of the present disclosure.
| Compound No. | Structure | Analytical data |
|---|---|---|
| 48 | 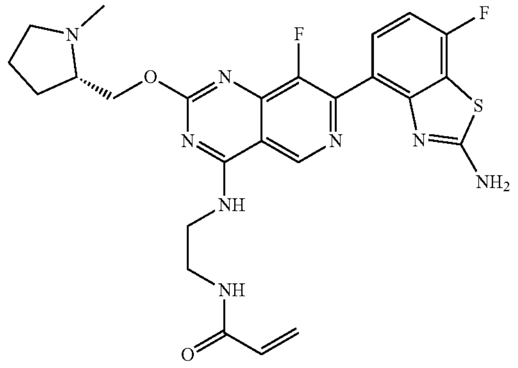 [SMILES: C=CC(=O)NCCNc1nc(OC[C@@H]2CCCN2C)nc2c(F)c(-c3ccc(F)c4sc(N)nc34)ncc12] | LCMS m/z [M + 1]: 541.23<br>$^1$HNMR (300 MHz, $CD_3OD$) δ 8.52 (s, 1H), 7.46 (dd, J = 8.5, 5.6 Hz, 1H), 7.03 (t, J = 8.8 Hz, 1H), 6.33-6.16 (m, 2H), 5.69 (dd, J = 6.8, 5.2 Hz, 1H), 4.89-4.82 (m, 1H), 4.75-4.66 (m, 1H), 3.90-3.75 (m, 3H), 3.69-3.58 (m, 3H), 3.18-3.08 (m, 1H), 3.01 (s, 3H), 2.42-2.30 (m, 1H), 2.18-2.02 (m, 3H). |
| 200 | 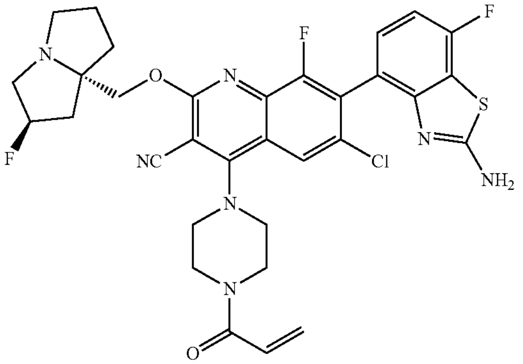 [SMILES: C=CC(=O)N1CCN(c2c(C#N)c(OC[C@@]34CCCN3C[C@H](F)C4)nc3c(F)c(-c4ccc(F)c5sc(N)nc45)c(Cl)cc23)CC1] | LCMS m/z [M + 1]: 668.2<br>$^1$HNMR (400 MHz, $CD_3OD$) δ 7.99 (s, 1H), 7.21-7.25 (m, 1H), 7.02 (t, J = 8.8 Hz, 1H), 6.82-6.89 (m, 1H), 6.29 (dd, J = 16.8, 1.6 Hz, 1H), 5.82 (dd, J = 10.6, 1.6 Hz, 1H), 5.55-5.68 (m, 1H), 4.66-4.79 (m, 2H), 3.93-4.05 (m, 7H), 3.78-3.83 (m, 4H), 3.46-3.53 (m, 1H), 2.17-2.79 (m, 6H). |
| 200a | 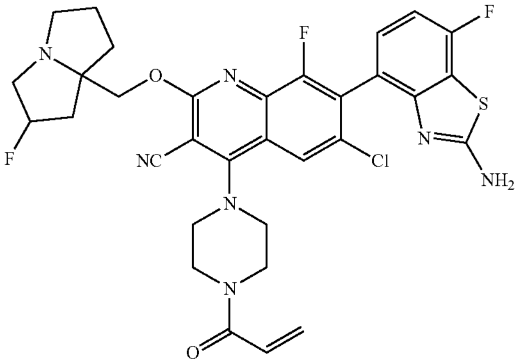 [SMILES: C=CC(=O)N1CCN(c2c(C#N)c(OCC34CCCN3CC(F)C4)nc3c(F)c(-c4ccc(F)c5sc(N)nc45)c(Cl)cc23)CC1] | |
| 214 | 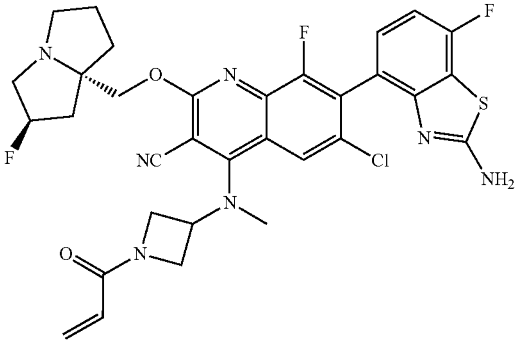 [SMILES: C=CC(=O)N1CC(N(C)c2c(C#N)c(OC[C@@]34CCCN3C[C@H](F)C4)nc3c(F)c(-c4ccc(F)c5sc(N)nc45)c(Cl)cc23)C1] | LCMS m/z [M + 1]: 668.2<br>$^1$HNMR (400 MHz, $CD_3OD$) δ 8.01 (s, 1H), 7.22-7.25 (m, 1H), 7.03 (t, J = 8.8 Hz, 1H), 6.36-6.43 (m, 1H), 6.25-6.30 (m, 1H), 5.76-5.78 (m, 1H), 5.55-5.68 (m, 1H), 4.97-4.99 (m, 2H), 4.61-4.79 (m, 2H), 4.43-4.48 (m, 1H), 4.28-4.30 (m, 2H), 3.93-4.01 (m, 3H), 3.47-3.53 (m, 1H), 3.41 (s, 3H), 2.24-2.79 (m, 6H). |

TABLE 3-continued
Selected compounds of the present disclosure.
| Compound No. | Structure | Analytical data |
|---|---|---|
| 214a | 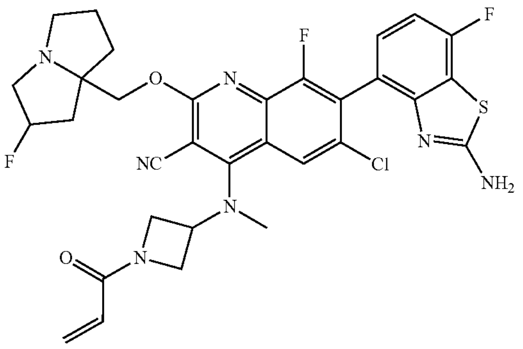 [SMILES: C=CC(=O)N1CC(N(C)c2c(C#N)c(OCC34CCCN3CC(F)C4)nc3c(F)c(-c4ccc(F)c5sc(N)nc45)c(Cl)cc23)C1] | |
| 233 | 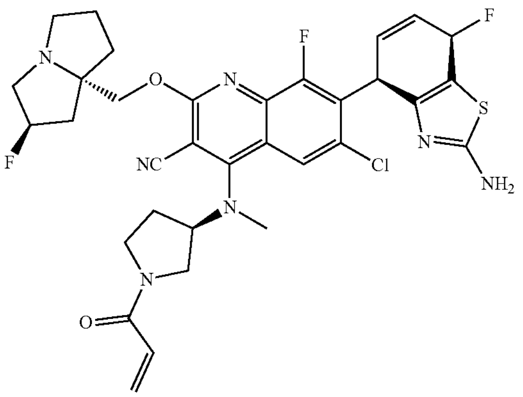 [SMILES: C=CC(=O)N1CC[C@@H](N(C)c2c(C#N)c(OC[C@@]34CCCN3C[C@H](F)C4)nc3c(F)c([C@H]4C=C[C@@H](F)c5sc(N)nc54)c(Cl)cc23)C1] | LCMS m/z [M + 1]: 682.2 $^1$HNMR (400 MHz, $CD_3OD$) δ 8.01 (s, 1H), 7.24-7.27 (m, 1H), 7.05 (t, J = 8.79 Hz, 1H), 6.58-6.66 (m, 1H), 6.25-6.30 (m, 1H), 5.74-5.78 (m, 2H), 5.63 (d, J = 51.92 Hz, 1H), 4.68-4.81 (m, 3H), 3.73-4.05 (m, 7H), 3.47-3.57 (m, 1H), 3.28 (s, 3H), 2.26-2.82 (m, 8H). |
| 233a | 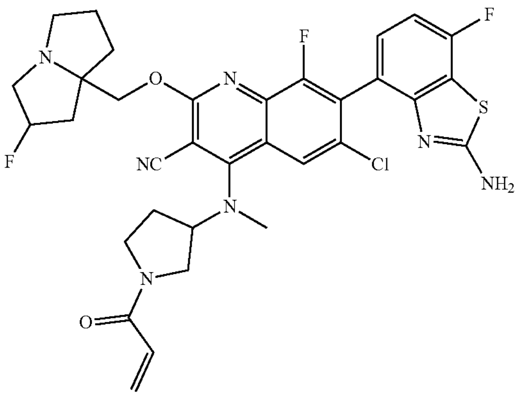 [SMILES: C=CC(=O)N1CCC(N(C)c2c(C#N)c(OCC34CCCN3CC(F)C4)nc3c(F)c(-c4ccc(F)c5sc(N)nc45)c(Cl)cc23)C1] | |
| 234 | 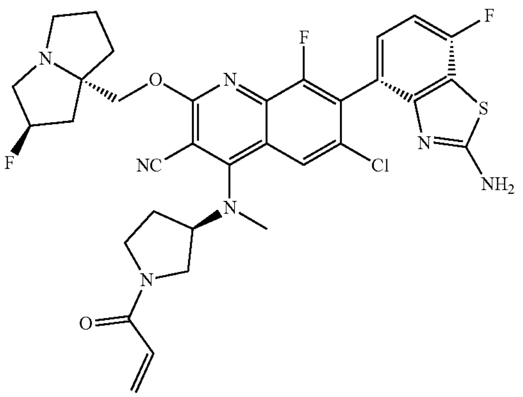 | LCMS m/z [M + 1]: 682.2 $^1$HNMR (400 MHz, $CD_3OD$) δ 8.01 (s, 1H), 7.24-7.27 (m, 1H), 7.05 (t, J = 8.79 Hz, 1H), 6.58-6.66 (m, 1H), 6.25-6.30 (m, 1H), 5.74-5.78 (m, 2H), 5.63 (d, J = 51.92 Hz, 1H), 4.68-4.81 (m, 3H), 3.73-4.05 (m, 7H), 3.47-3.57 (m, 1H), 3.28 (s, 3H), 2.26-2.82 (m, 8H). |

TABLE 3-continued
| Selected compounds of the present disclosure. | | |
|---|---|---|
| Compound No. | Structure | Analytical data |
| 234a | 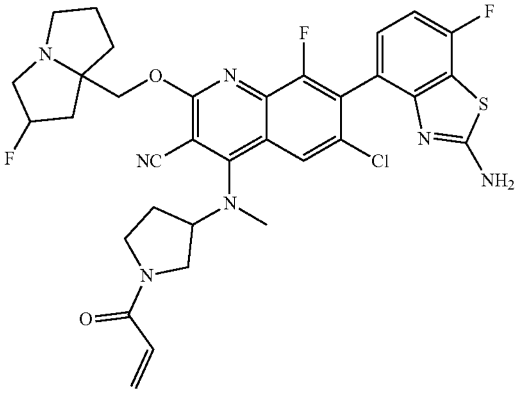 [SMILES: C=CC(=O)N1CCC(N(C)c2c(C#N)c(OCC34CCCN3CC(F)C4)nc3c(F)c(-c4ccc(F)c5sc(N)nc45)c(Cl)cc23)C1] | |
| 226 | 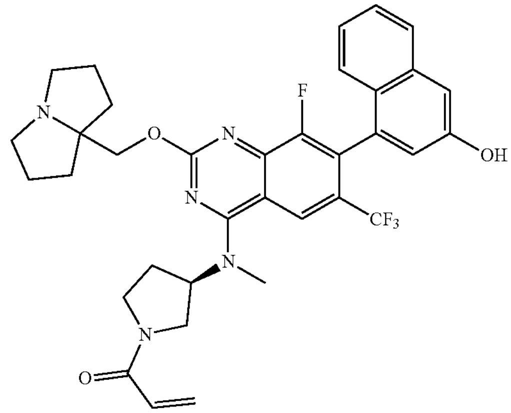 [SMILES: C=CC(=O)N1CC[C@@H](N(C)c2nc(OCC34CCCN3CCC4)nc3c(F)c(-c4cc(O)cc5ccccc45)c(C(F)(F)F)cc23)C1] | LCMS m/z [M + 1]: 650.2<br>$^1$HNMR (400 MHz, $CD_3OD$) δ 8.47 (s, 1H), 7.75 (d, J = 8.4 Hz, 1H), 7.38-7.45 (m, 1H), 7.27 (d, J = 2.2 Hz, 1H), 7.13-7.21 (m, 2H), 7.03-7.09 (m, 1H), 6.61-6.74 (m, 1H), 6.33 (d, J = 16.8 Hz, 1H), 5.75-5.85 (m, 1H), 5.31-5.45 (m, 2H), 4.74-4.77 (m, 1H), 4.67 (s, 2H), 4.08-4.24 (m, 1H), 3.73-4.06 (m, 3H), 3.61-3.71 (m, 3H), 3.48-3.56 (m, 3H), 2.40-2.56 (m, 2H), 2.25-2.34 (m, 2H), 2.04-2.21 (m, 6H). |
| 226a | 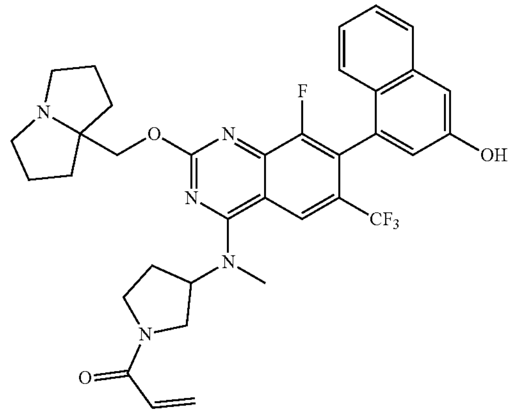 [SMILES: C=CC(=O)N1CCC(N(C)c2nc(OCC34CCCN3CCC4)nc3c(F)c(-c4cc(O)cc5ccccc45)c(C(F)(F)F)cc23)C1] | |

TABLE 3-continued
| Selected compounds of the present disclosure. | | |
|---|---|---|
| Compound No. | Structure | Analytical data |
| 227 | 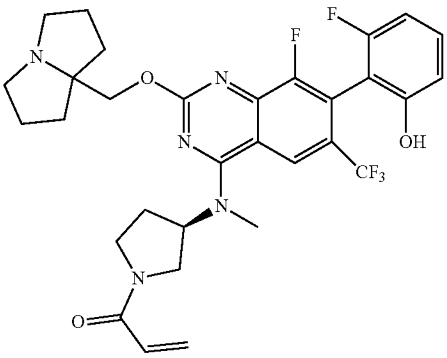 [SMILES: C=CC(=O)N1CC[C@@H](N(C)c2nc(OCC34CCCN3CCC4)nc3c(F)c(-c4c(O)cccc4F)c(C(F)(F)F)cc23)C1] | LCMS m/z [M + 1]: 618.2 $^1$HNMR (400 MHz, $CD_3OD$) δ 8.37 (s, 1H), 7.32 (dd, J = 15.1, 8.3 Hz, 1H), 6.60-6.79 (m, 3H), 6.32 (d, J = 16.8 Hz, 1H), 5.75-5.84 (m, 1H), 5.28-5.41 (m, 1H), 4.67 (s, 2H), 3.86-4.21 (m, 3H), 3.58-3.80 (m, 5H), 3.48-3.54 (m, 3H), 2.40-2.53 (m, 2H), 2.28-2.36 (m, 2H), 2.07-2.25 (m, 6H). |
| 227a | 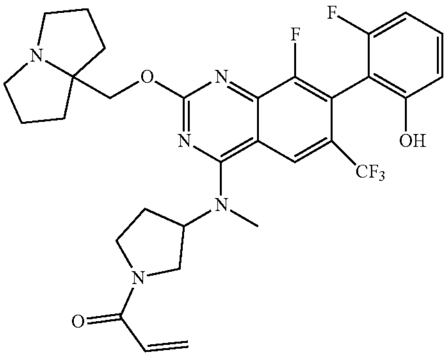 [SMILES: C=CC(=O)N1CCC(N(C)c2nc(OCC34CCCN3CCC4)nc3c(F)c(-c4c(O)cccc4F)c(C(F)(F)F)cc23)C1] | |
TABLE 4
| Selected compounds of the present disclosure. | | |
|---|---|---|
| Compound No. | Structure | Analytical data |
| 259 | 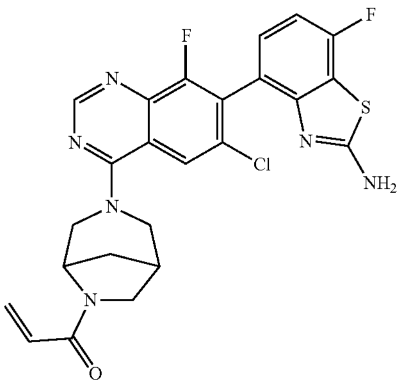 [SMILES: C=CC(=O)N1CC2CC1CN(c1ncnc3c(F)c(-c4ccc(F)c5sc(N)nc45)c(Cl)cc13)C2] | LCMS m/z [M + 1]: 513.0 $^1$HNMR (400 MHz, $CD_3OD$) δ 8.57-8.47 (m, 1H), 7.94-7.86 (m, 1H), 7.27-7.18 (m, 1H), 7.03-6.94 (m, 1H), 6.84-6.36 (m, 1H), 6.34-6.09 (m, 1H), 5.81-5.60 (m, 1H), 4.81-4.70 (m, 1H), 4.61-4.47 (m, 2H), 3.82-3.64 (m, 2H), 3.58-3.37 (m, 2H), 2.82-2.61 (m, 1H), 2.24-2.05 (m, 2H). |

TABLE 4-continued

| Selected compounds of the present disclosure. | | |
|---|---|---|
| Compound No. | Structure | Analytical data |
| 260 | 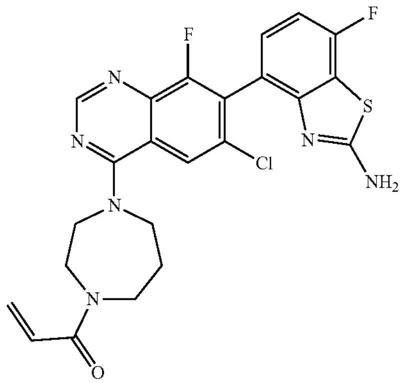 [SMILES: C=CC(=O)N1CCCN(c2ncnc3c(F)c(-c4ccc(F)c5sc(N)nc45)c(Cl)cc23)CC1] | LCMS m/z [M + 1]: 501.1 $^1$HNMR (500 MHz, $CD_3OD$) δ 8.53 (d, J = 5.8 Hz, 1H), 8.07 (dd, J = 7.1, 1.7 Hz, 1H), 7.70-7.49 (m, 1H), 7.24 (ddd, J = 8.4, 5.4, 1.0 Hz, 1H), 6.99 (td, J = 8.9, 8.3, 1.1 Hz, 1H), 6.75 (ddd, J = 16.7, 10.6, 2.9 Hz, 1H), 6.14 (ddd, J = 16.7, 6.4, 2.0 Hz, 1H), 5.70 (ddd, J = 11.3, 9.5, 2.0 Hz, 1H), 4.27-4.18 (m, 2H), 4.17-4.07 (m, 2H), 4.05-3.92 (m, 3H), 3.82-3.70 (m, 2H), 2.15 (dq, J = 14.1, 7.3, 5.8 Hz, 2H). |
| 261 | 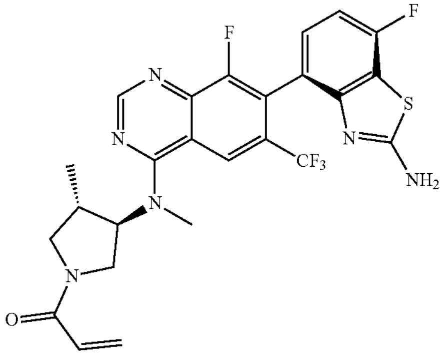 | LCMS m/z [M + 1]: 548.2 $^1$HNMR (400 MHz, $CD_3OD$) δ 8.80 (s, 1H), 8.55-8.58 (m, 1H), 7.24-7.30 (m, 1H), 7.03 (t, J = 8.8 Hz, 1H), 6.57-6.71 (m, 1H), 6.29-6.36 (m, 1H), 5.77-5.83 (m, 1H), 5.37-5.46 (m, 1H), 4.03-4.23 (m, 2H), 3.58-3.81 (m, 4H), 3.34-3.41 (m, 1H), 3.11-3.18 (m, 1H), 2.76-2.98 (m, 1H), 1.22-1.27 (m, 3H). |
| 262 | 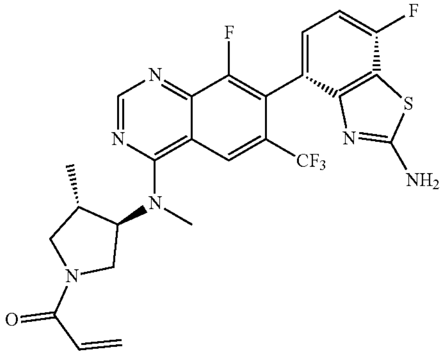 | LCMS m/z [M + 1]: 548.2 $^1$HNMR (400 MHz, $CD_3OD$) δ 8.79 (s, 1H), 8.55-8.59 (m, 1H), 7.24-7.29 (m, 1H), 7.02 (t, J = 9.2 Hz, 1H), 6.58-6.70 (m, 1H), 6.33 (d, J = 16.8 Hz, 1H), 5.77-5.82 (m, 1H), 5.34-5.44 (m, 1H), 4.02-4.26 (m, 2H), 3.60-3.84 (m, 4H), 3.34-3.40 (m, 1H), 3.09-3.18 (m, 1H), 2.77-2.97 (m, 1H), 1.20-1.25 (m, 3H). |
| 262a | 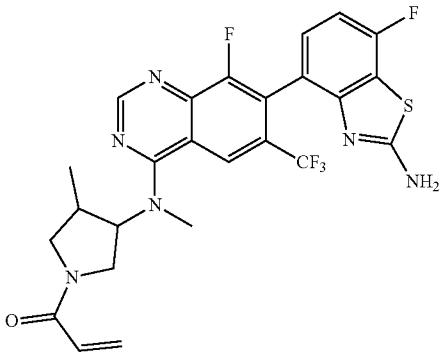 [SMILES: C=CC(=O)N1CC(C)C(N(C)c2ncnc3c(F)c(-c4ccc(F)c5sc(N)nc45)c(C(F)(F)F)cc23)C1] | |

TABLE 4-continued
| Selected compounds of the present disclosure. | | |
|---|---|---|
| Compound No. | Structure | Analytical data |
| 263 | 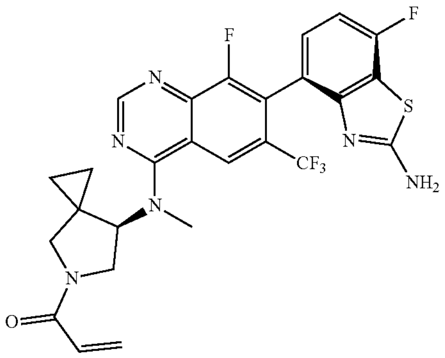 | LCMS m/z [M + 1]: 561.2 $^1$HNMR (400 MHz, $CD_3OD$) δ 8.73 (s, 1H), 8.52 (s, 1H), 7.22-7.29 (m, 1H), 7.03 (t, J = 8.8 Hz, 1H), 6.58-6.70 (m, 1H), 6.34 (dd, J = 16.8, 1.6 Hz, 1H), 5.78-5.82 (m, 1H), 5.55-5.62 (m, 1H), 4.00-4.40 (m, 3H), 3.74 (s, 3H), 3.61 (dd, J = 43.8, 10.8 Hz, 1H), 1.15-1.25 (m, 1H), 0.97-1.06 (m, 3H). |
| 264 | 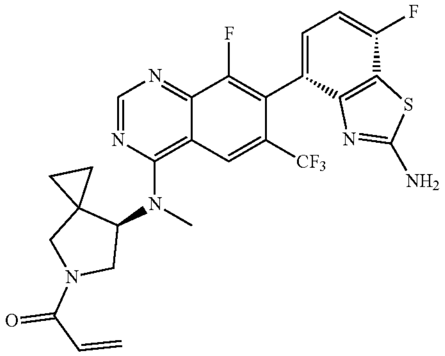 | LCMS m/z [M + 1]: 561.1 $^1$HNMR (400 MHz, $CD_3OD$) δ 8.73 (s, 1H), 8.51 (s, 1H), 7.22-7.29 (m, 1H), 7.03 (t, J = 8.8 Hz, 1H), 6.58-6.74 (m, 1H), 6.34 (dd, J = 16.4, 1.6 Hz, 1H), 5.78-5.83 (m, 1H), 5.40-5.58 (m, 1H), 4.00-4.45 (m, 3H), 3.74 (s, 3H), 3.61 (dd, J = 43.8, 11.2 Hz, 1H), 1.15-1.25 (m, 1H), 0.97-1.05 (m, 3H). |
| 264a | 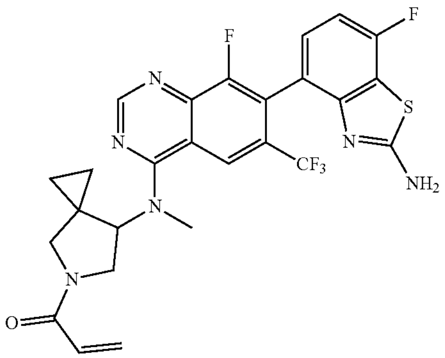 [SMILES: C=CC(=O)N1CC(N(C)c2ncnc3c(F)c(-c4ccc(F)c5sc(N)nc45)c(C(F)(F)F)cc23)C2(CC2)C1] | |
| 265 | 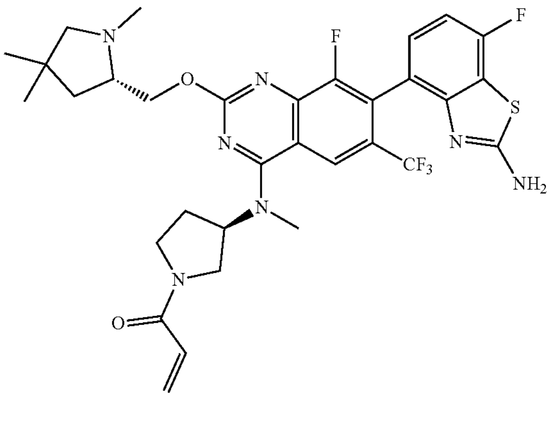 [SMILES: C=CC(=O)N1CC[C@@H](N(C)c2nc(OC[C@@H]3CC(C)(C)CN3C)nc3c(F)c(-c4ccc(F)c5sc(N)nc45)c(C(F)(F)F)cc23)C1] | LCMS m/z [M + 1]: 676.3 $^1$HNMR (400 MHz, $CD_3OD$) δ 8.37 (s, 1H), 7.21-7.24 (m, 1H), 7.00 (t, J = 8.8 Hz, 1H), 6.61-6.71 (m, 1H), 6.30-6.34 (m, 1H), 5.77-5.81 (m, 1H), 5.26-5.41 (m, 1H), 4.91-4.94 (m, 1H), 4.68-4.73 (m, 1H), 3.90-4.16 (m, 3H), 3.69-3.83 (m, 1H), 3.55-3.62 (m, 1H), 3.48-3.51 (m, 4H), 3.07-3.12 (m, 4H), 2.39-2.52 (m, 2H), 1.93-2.24 (m, 2H), 1.27 (s, 3H), 1.23 (s, 3H). |

TABLE 4-continued

| Selected compounds of the present disclosure. | | |
|---|---|---|
| Compound No. | Structure | Analytical data |
| 265a | 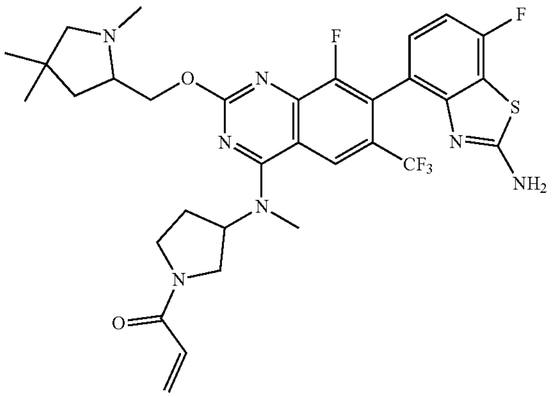 [SMILES: C=CC(=O)N1CCC(N(C)c2nc(OCC3CC(C)(C)CN3C)nc3c(F)c(-c4ccc(F)c5sc(N)nc45)c(C(F)(F)F)cc23)C1] | |
| 266 | 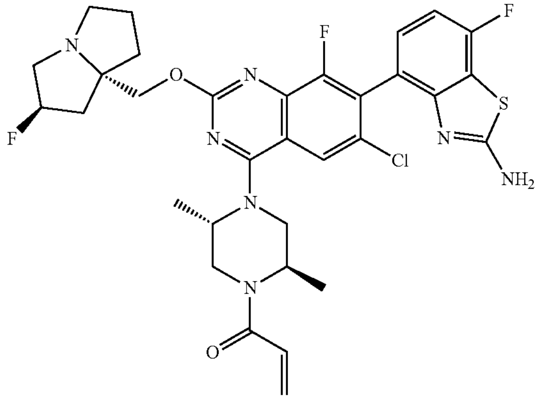 [SMILES: C=CC(=O)N1C[C@H](C)N(c2nc(OC[C@@]34CCCN3C[C@H](F)C4)nc3c(F)c(-c4ccc(F)c5sc(N)nc45)c(Cl)cc23)C[C@H]1C] | LCMS m/z [M + 1]: 672.2<br>$^1$HNMR (400 MHz, $CD_3OD$) δ 7.95 (s, 1H), 7.24-7.2 (m, 1H), 7.02 (t, J = 9.2 Hz, 1H), 6.74-6.88 (m, 1H), 6.25-6.34 (m, 1H), 5.78-5.86 (m, 1H), 5.56 (d, J = 51.6 Hz, 1H), 4.90-5.3 (m, 1H), 4.62-4.71 (m, 2H), 4.24-4.58 (m, 2H), 3.81-4.12 (m, 5H), 3.41-3.62 (m, 2H), 2.09-2.78 (m, 6H), 1.41-1.48 (m, 3H), 1.22-1.34 (m, 3H). |
| 267 | 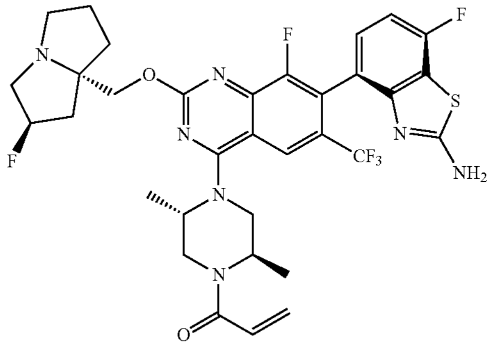 | LCMS m/z [M + 1]: 706.3<br>$^1$HNMR (400 MHz, $CD_3OD$) δ 8.15 (s, 1H), 7.17-7.25 (m, 1H), 6.97 (t, J = 8.8 Hz, 1H), 6.91-6.73 (m, 1H), 6.25-6.35 (m, 1H), 5.75-5.88 (m, 1H), 5.33 (d, J = 54.4 Hz, 1H), 4.93-5.01 (m, 1H), 4.25-4.67 (m, 5H), 3.83-4.06 (m, 2H), 3.36-3.59 (m, 3H), 3.18-3.24 (m, 1H), 1.82-2.46 (m, 6H), 1.48 (t, J = 6.8 Hz, 3H), 1.28 (dd, J = 27.2 6.4 Hz, 3H). |
| 268 | 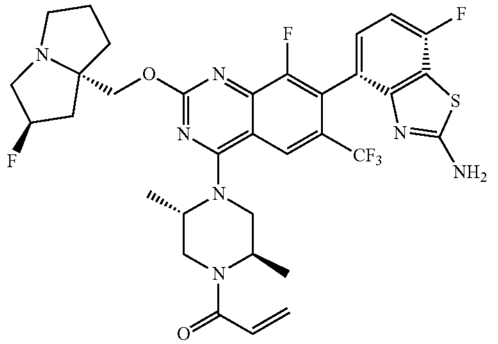 | LCMS m/z [M + 1]: 706.3<br>$^1$HNMR (400 MHz, $CD_3OD$) δ 8.17 (s, 1H), 7.18-7.27 (m, 1H), 6.99 (t, J = 9 Hz, 1H), 6.91-6.73 (m, 1H), 6.25-6.35 (m, 1H), 5.75-5.88 (m, 1H), 5.33 (d, J = 53.4 Hz, 1H), 4.93-5.01 (m, 2H), 4.25-4.67 (m, 4H), 3.83-4.06 (m, 2H), 3.36-3.59 (m, 3H), 3.18-3.24 (m, 1H), 1.82-2.46 (m, 6H), 1.48 (t, J = 6.0 Hz, 3H), 1.28 (dd, J = 21.9, 6.9 Hz, 3H). |

TABLE 4-continued
| Selected compounds of the present disclosure. | | |
|---|---|---|
| Compound No. | Structure | Analytical data |
| 268a | 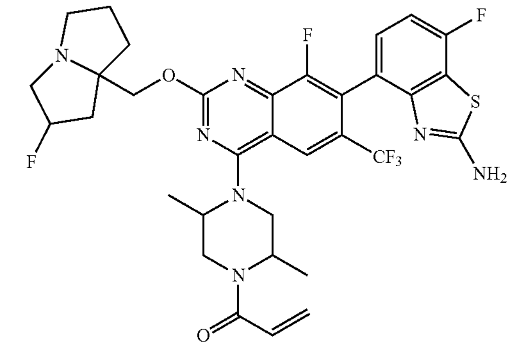 [SMILES: C=CC(=O)N1CC(C)N(c2nc(OCC34CCCN3CC(F)C4)nc3c(F)c(-c4ccc(F)c5sc(N)nc45)c(C(F)(F)F)cc23)CC1C] | |
| 269 | 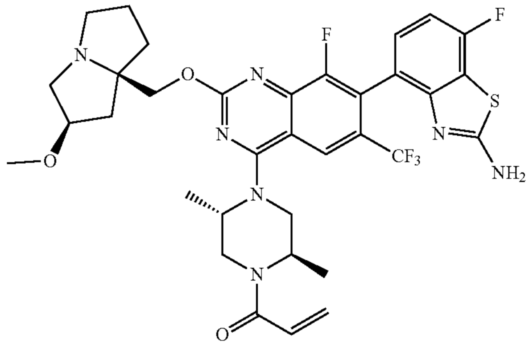 [SMILES: C=CC(=O)N1C[C@H](C)N(c2nc(OC[C@]34CCCN3C[C@H](OC)C4)nc3c(F)c(-c4ccc(F)c5sc(N)nc45)c(C(F)(F)F)cc23)C[C@H]1C] | LCMS m/z [M + 1]: 718.3 $^1$HNMR (400 MHz, $CD_3OD$) δ 8.19 (s, 1H), 7.19-7.24 (m, 1H), 7.00 (t, J = 9.2 Hz, 1H), 6.75-6.89 (m, 1H), 6.27-6.33 (m, 1H), 5.80-5.84 (m, 1H), 4.88-4.97 (m, 2H), 4.55-4.81 (m, 3H), 4.28-4.69 (m, 2H), 3.47-3.87 (m, 6H), 3.39 (s, 3H), 2.06-2.49 (m, 6H), 1.27-1.66 (m, 6H). |
| 269a | 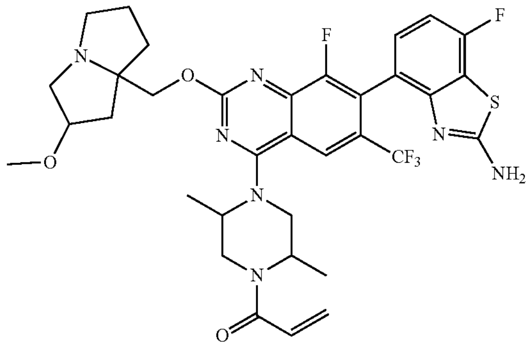 [SMILES: C=CC(=O)N1CC(C)N(c2nc(OCC34CCCN3CC(OC)C4)nc3c(F)c(-c4ccc(F)c5sc(N)nc45)c(C(F)(F)F)cc23)CC1C] | |
| 270 | 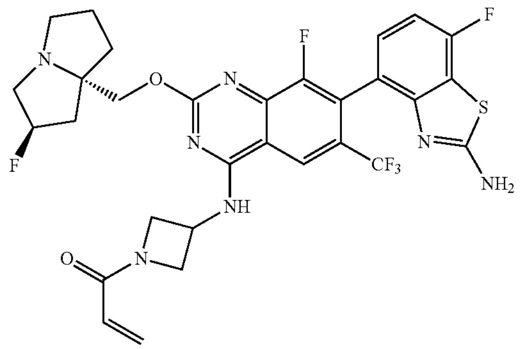 [SMILES: C=CC(=O)N1CC(Nc2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 664.2 $^1$HNMR (400 MHz, $CD_3OD$) δ 8.54 (s, 1H), 7.15-7.20 (m, 1H), 6.95 (t, J = 18.4 Hz, 1H), 6.26-6.44 (m, 1H), 6.28 (dd, J = 17.0, 1.8 Hz, 1H), 5.78 (dd, J = 10.2, 1.8 Hz, 1H), 5.45 (d, J = 53.6 Hz, 1H), 5.02-5.08 (m, 1H), 4.75-4.80 (m, 1H), 4.42-4.52 (m, 3H), 4.26-4.38 (m, 2H), 3.35-3.51 (m, 3H), 3.06-3.10 (m, 1H), 1.93-2.39 (m, 6H). |

TABLE 4-continued
| Selected compounds of the present disclosure. | | |
|---|---|---|
| Compound No. | Structure | Analytical data |
| 270a | 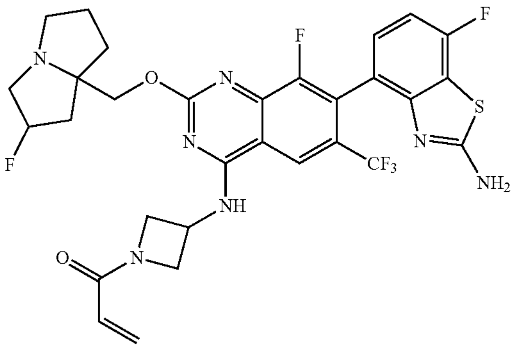 [SMILES: C=CC(=O)N1CC(Nc2nc(OCC34CCCN3CC(F)C4)nc3c(F)c(-c4ccc(F)c5sc(N)nc45)c(C(F)(F)F)cc23)C1] | |
| 271 | 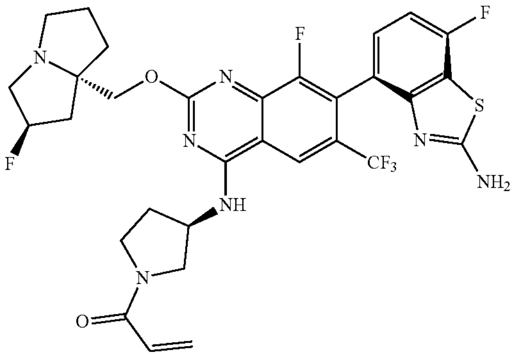 | LCMS m/z [M + 1]: 678.2<br>$^1$HNMR (400 MHz, $CD_3OD$) δ 8.67 (s, 1H), 7.18-7.22 (m, 1H), 6.99 (d, J = 8.8 Hz, 1H), 6.60-6.81 (m, 1H), 6.28-6.36 (m, 1H), 5.77-5.83 (m, 1H), 5.55 (d, J = 52 Hz, 1H), 4.65-4.95 (m, 3H), 3.66-4.04 (m, 8H), 2.31-2.44 (m, 8H). |
| 272 | 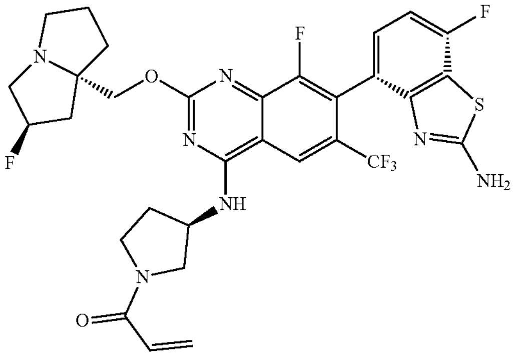 | LCMS m/z [M + 1]: 678.2<br>$^1$HNMR (400 MHz, $CD_3OD$) δ 8.67 (s, 1H), 7.18-7.22 (m, 1H), 6.99 (d, J = 8.8 Hz, 1H), 6.60-6.81 (m, 1H), 6.28-6.36 (m, 1H), 5.77-5.83 (m, 1H), 5.55 (d, J = 52 Hz, 1H), 4.65-4.95 (m, 3H), 3.66-4.04 (m, 8H), 2.31-2.44 (m, 8H). |
| 272a | 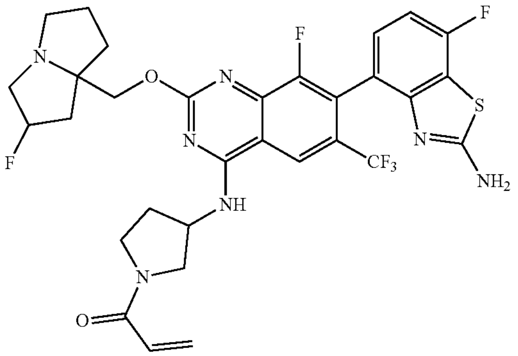 [SMILES: C=CC(=O)N1CCC(Nc2nc(OCC34CCCN3CC(F)C4)nc3c(F)c(-c4ccc(F)c5sc(N)nc45)c(C(F)(F)F)cc23)C1] | |

TABLE 4-continued
| Selected compounds of the present disclosure. | | |
|---|---|---|
| Compound No. | Structure | Analytical data |
| 273 | 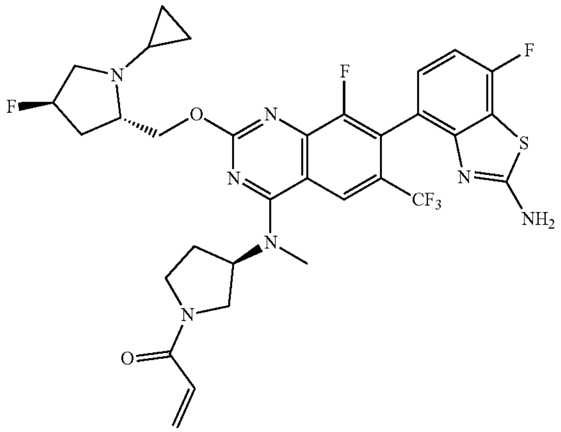 [SMILES: C=CC(=O)N1CC[C@@H](N(C)c2nc(OC[C@@H]3C[C@@H](F)CN3C3CC3)nc3c(F)c(-c4ccc(F)c5sc(N)nc45)c(C(F)(F)F)cc23)C1] | LCMS m/z [M + 1]: 692.2<br>$^1$HNMR (400 MHz, $CD_3OD$) δ 8.37 (s, 1H), 7.19-7.25 (m, 1H), 6.99 (t, J = 8.8 Hz, 1H), 6.61-6.72 (m, 1H), 6.29-6.36 (m, 1H), 5.76-5.83 (m, 1H), 5.50 (d, J = 52.4 Hz, 1H), 5.25-5.42 (m, 1H), 4.91-4.99 (m, 1H), 4.72-4.79 (m, 1H), 4.48-4.56 (m, 1H), 3.66-4.20 (m, 5H), 3.45-3.65 (m, 4H), 3.10-3.20 (m, 1H), 2.30-2.81 (m, 4H), 0.92-1.22 (m, 4H). |
| 273a | 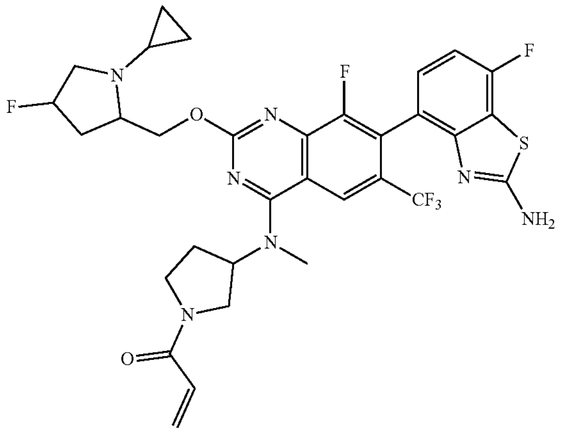 [SMILES: C=CC(=O)N1CCC(N(C)c2nc(OCC3CC(F)CN3C3CC3)nc3c(F)c(-c4ccc(F)c5sc(N)nc45)c(C(F)(F)F)cc23)C1] | |
| 274 | 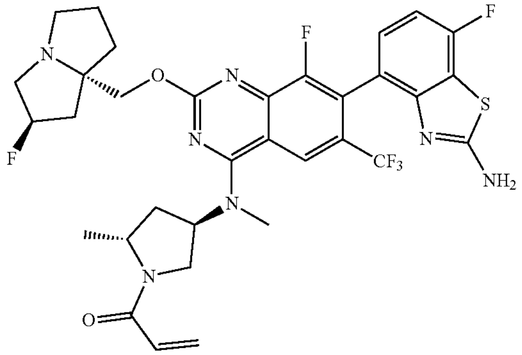 [SMILES: C=CC(=O)N1C[C@H](N(C)c2nc(OC[C@@]34CCCN3C[C@H](F)C4)nc3c(F)c(-c4ccc(F)c5sc(N)nc45)c(C(F)(F)F)cc23)C[C@H]1C] | LCMS m/z [M + 1]: 706.3<br>$^1$HNMR (400 MHz, $CD_3OD$) δ 8.37 (s, 1H), 7.18-7.29 (m, 1H), 7.01 (t, J = 8.8 Hz, 1H), 6.60-6.78 (m, 1H), 6.29-6.42 (m, 1H), 5.76-5.86 (m, 1H), 5.47-5.65 (m, 2H), 4.53-4.75 (m, 3H), 3.74-4.20 (m, 5H), 3.35-3.55 (m, 4H), 2.52-2.77 (m, 3H), 2.10-2.45 (m, 5H), 1.29-1.43 (m, 3H). |

TABLE 4-continued
Selected compounds of the present disclosure.
| Compound No. | Structure | Analytical data |
| --- | --- | --- |
| 274a | 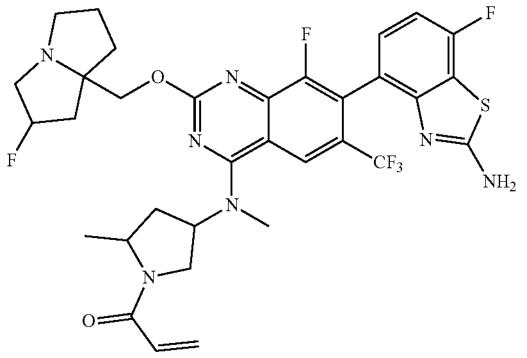 [SMILES: C=CC(=O)N1CC(N(C)c2nc(OCC34CCCN3CC(F)C4)nc3c(F)c(-c4ccc(F)c5sc(N)nc45)c(C(F)(F)F)cc23)CC1C] | |
| 275 | 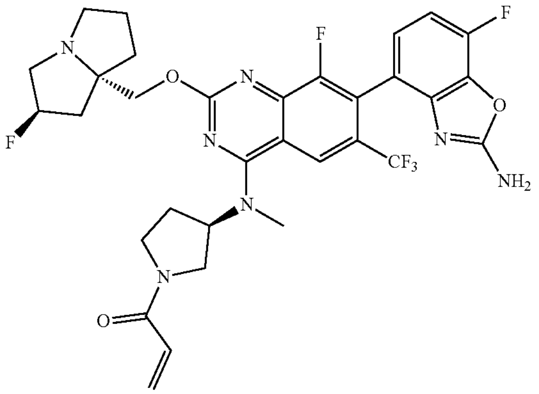 [SMILES: C=CC(=O)N1CC[C@@H](N(C)c2nc(OC[C@@]34CCCN3C[C@H](F)C4)nc3c(F)c(-c4ccc(F)c5oc(N)nc45)c(C(F)(F)F)cc23)C1] | LCMS m/z [M + 1]: 676.3 $^1$HNMR (400 MHz, $CD_3OD$) δ 8.38 (s, 1H), 7.06-7.10 (m, 1H), 6.98 (t, J = 9.6 Hz, 1H), 6.62-6.71 (m, 1H), 6.30-6.34 (m, 1H), 5.76-5.81 (m, 1H), 5.49-5.62 (d, J = 51.8 Hz, 1H), 5.28-5.41 (m, 1H), 4.61-4.72 (m, 2H), 4.08-4.19 (m, 1H), 3.56-4.04 (m, 6H), 3.50-3.52 (m, 3H), 3.42-3.48 (m, 1H), 2.13-2.69 (m, 8H), |
| 275a | 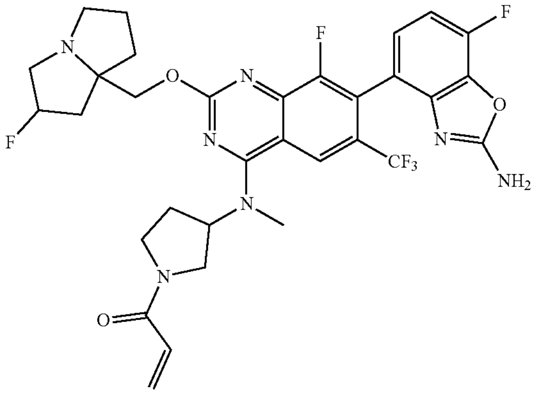 [SMILES: C=CC(=O)N1CCC(N(C)c2nc(OCC34CCCN3CC(F)C4)nc3c(F)c(-c4ccc(F)c5oc(N)nc45)c(C(F)(F)F)cc23)C1] | |
| 276 | 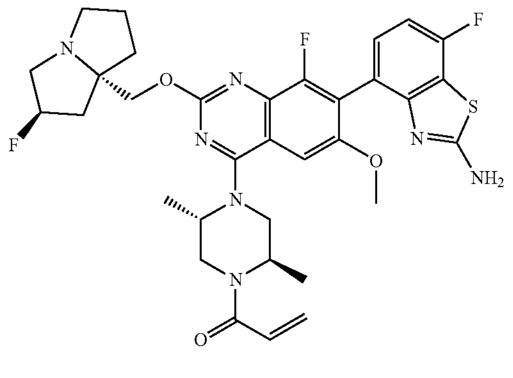 | LCMS m/z [M + 1]: 688.45 $^1$HNMR (300 MHz, $CD_3OD$) δ 7.19 (dd, J = 8.5, 5.5 Hz, 1H), 7.10 (s, 1H), 6.95 (t, J = 8.8 Hz, 1H), 6.83 (td, J = 17.0, 10.7 Hz, 1H), 6.29 (dd, J = 16.7, 5.0 Hz, 1H), 5.81 (d, J = 10.5 Hz, 1H), 5.36 (d, J = 53.4 Hz, 1H), 4.58-4.14 (m, 4H), 4.02-3.85 (m, 2H), 3.83 (s, 3H), 3.69-3.31 (m, 5H), 3.18-3.04 (m, 1H), 2.56-2.14 (m, 3H), 2.06 (dq, J = 11.7, 6.1 Hz, 2H), 1.95 (dd, J = 14.2, 7.5 Hz, 1H), 1.48-1.21 (m, 6H). |

TABLE 4-continued
| Selected compounds of the present disclosure. | | |
|---|---|---|
| Compound No. | Structure | Analytical data |
| 276a | 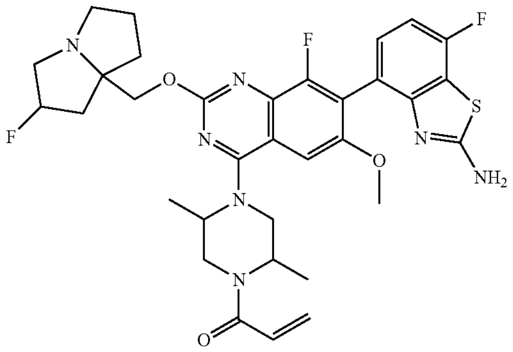 [SMILES: C=CC(=O)N1CC(C)N(c2nc(OCC34CCCN3CC(F)C4)nc3c(F)c(-c4ccc(F)c5sc(N)nc45)c(OC)cc23)CC1C] | |
| 277 | 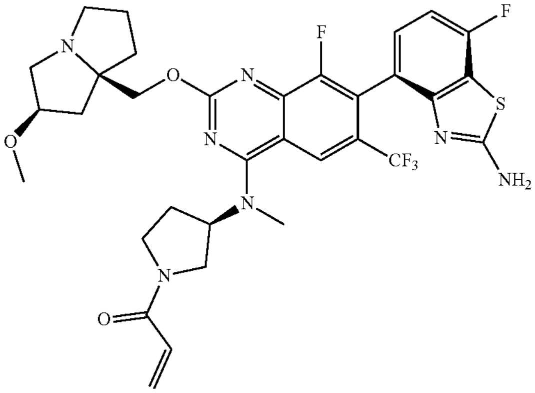 | LCMS m/z [M + 1]: 704.3 $^1$HNMR (400 MHz, $CD_3OD$) δ 8.38 (s, 1H), 7.19 7.26 (m, 1H), 7.00 (t, J = 8.8 Hz, 1H), 6.62-6.71 (m, 1H), 6.33 (d, J = 16.8 Hz, 1H), 5.75-5.84 (m, 1H), 5.28-5.42 (m, 1H), 4.57-4.70 (m, 2H), 4.27 (s, 1H), 4.09-4.21 (m, 1H), 3.90-4.05 (m, 1H), 3.71-3.84 (m, 3H), 3.55-3.65 (m, 2H), 3.46-3.55 (m, 4H), 3.38 (s, 3H), 2.28-2.56 (m, 7H), 2.05-2.15 (m, 1H). |
| 278 | 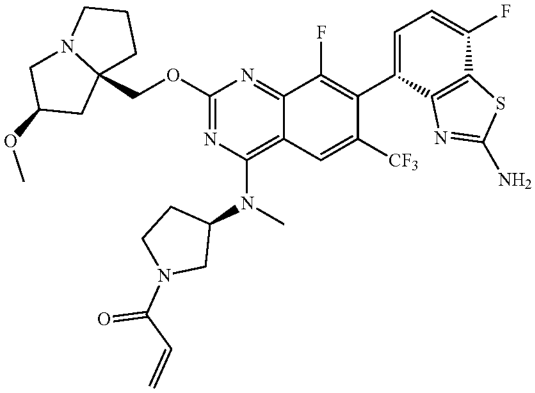 | LCMS m/z [M + 1]: 704.2 $^1$HNMR (400 MHz, $CD_3OD$) δ 8.38 (s, 1H), 7.18-7.24 (m, 1H), 6.99 (t, J = 8.8 Hz, 1H), 6.61-6.73 (m, 1H), 6.33 (d, J = 16.8 Hz, 1H), 5.76-5.84 (m, 1H), 5.28-5.40 (m, 1H), 4.64 (dd, J = 28.8, 12.4 Hz, 2H), 4.27 (s, 1H), 4.09-4.22 (m, 1H), 3.89-4.05 (m, 1H), 3.70-3.85 (m, 3H), 3.56-3.67 (m, 2H), 3.46-3.55 (m, 4H), 3.38 (s, 3H), 2.26-2.57 (m, 7H), 2.05-2.13 (m, 1H). |
| 278a | 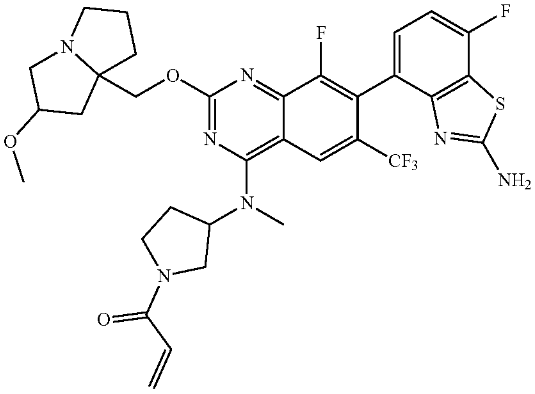 [SMILES: C=CC(=O)N1CCC(N(C)c2nc(OCC34CCCN3CC(OC)C4)nc3c(F)c(-c4ccc(F)c5sc(N)nc45)c(C(F)(F)F)cc23)C1] | |

TABLE 4-continued
| Selected compounds of the present disclosure. | | |
|---|---|---|
| Compound No. | Structure | Analytical data |
| 279 | 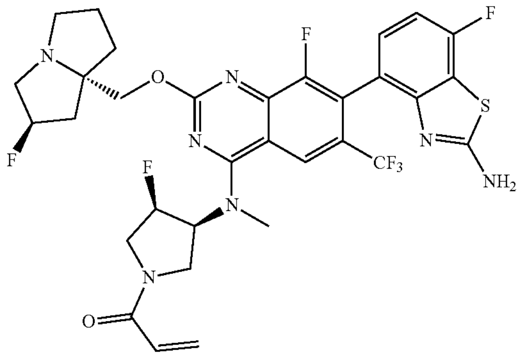 [SMILES: C=CC(=O)N1C[C@@H](F)[C@@H](N(C)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 710.2 $^1$HNMR (400 MHz, $CD_3OD$) δ 8.43 (s, 1H), 7.21-7.25 (m, 1H), 7.01 (t, J = 8.8 Hz, 1H), 6.61-6.75 (m, 1H), 6.34-6.38 (m, 1H), 5.67-5.85 (m, 2H), 5.48-5.61 (d, J = 51.8 Hz, 1H), 5.11-5.33 (m, 1H), 4.71-4.74 (m, 1H), 4.61-4.66 (m, 1H), 4.29-4.35 (m, 1H), 3.83-4.19 (m, 6H), 3.68 (d, J = 6.4 Hz, 3H), 3.42-3.49 (m, 1H), 2.14-2.71 (m, 6H), |
| 279a | 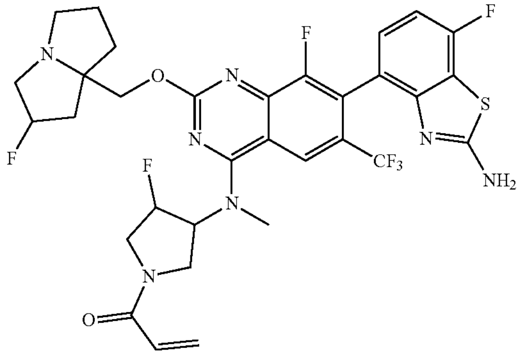 [SMILES: C=CC(=O)N1CC(F)C(N(C)c2nc(OCC34CCCN3CC(F)C4)nc3c(F)c(-c4ccc(F)c5sc(N)nc45)c(C(F)(F)F)cc23)C1] | |
| 280 | 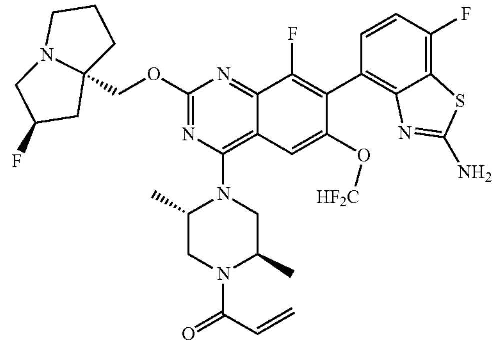 | LCMS m/z [M + 1]: 704.39 $^1$HNMR (400 MHz, $CD_3OD$) δ 7.44 (s, 1H), 7.29-7.22 (m, 1H), 6.96 (t, J = 8.7 Hz, 1H), 6.66-6.48 (m, 1H), 6.43-6.33 (m, 1H), 5.99-5.94 (m, 1H), 5.80-5.72 (m, 1H), 5.38 (s, 1H), 5.20 (s, 1H), 4.95 (s, 1H), 4.74 (s, 1H), 4.36-3.96 (m, 4H), 3.84-3.58 (m, 2H), 3.49-3.12 (m, 4H), 3.03-2.94 (m, 1H), 2.31 (s, 1H), 2.18 (dd, J = 12.4, 7.5 Hz, 2H), 2.05-2.01 (m, 2H), 1.96-1.91 (m, 1H), 1.38-1.19 (m, 6H). |
| 280a | 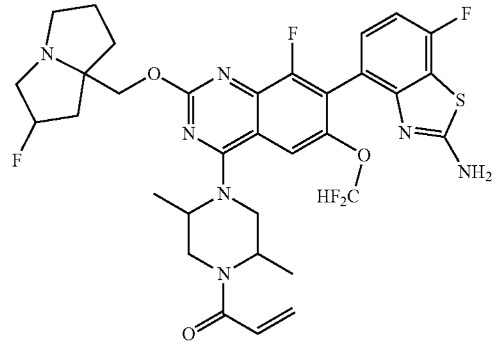 | |

TABLE 4-continued
| Selected compounds of the present disclosure. | | |
|---|---|---|
| Compound No. | Structure | Analytical data |
| 281 | 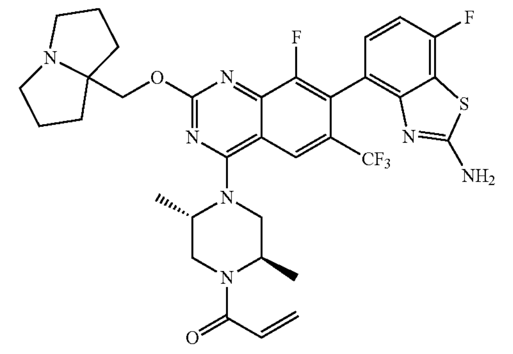 [SMILES: C=CC(=O)N1C[C@H](C)N(c2nc(OCC34CCCN3CCC4)nc3c(F)c(-c4ccc(F)c5sc(N)nc45)c(C(F)(F)F)cc23)C[C@H]1C] | LCMS m/z [M + 1]: 688.3<br>$^{1}$HNMR (400 MHz, $CD_3OD$) δ 8.19 (s, 1H), 7.18-7.26 (m, 1H), 6.99 (d, J = 8.8 Hz, 1H), 6.72-6.89 (m, 1H), 6.25-6.35 (m, 1H), 5.77-5.84 (m, 1H), 4.90-5.05 (m, 3H), 4.54-4.71 (m, 2H), 4.32-4.45 (m, 1H), 3.82-4.05 (m, 2H), 3.63-3.78 (m, 2H), 3.40-3.58 (s, 1H), 3.24-3.29 (m, 1 H), 2.03-2.35 (m, 8H), 1.25-1.55 (m, 6H). |
| 281a | 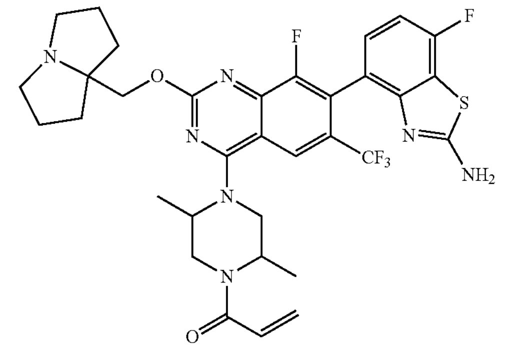 [SMILES: C=CC(=O)N1CC(C)N(c2nc(OCC34CCCN3CCC4)nc3c(F)c(-c4ccc(F)c5sc(N)nc45)c(C(F)(F)F)cc23)CC1C] | |
| 282 | 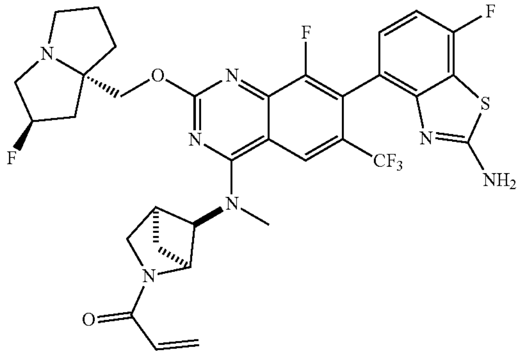 [SMILES: C=CC(=O)N1C[C@@H]2C[C@H]1[C@@H]2N(C)c1nc(OC[C@@]23CCCN2C[C@H](F)C3)nc2c(F)c(-c3ccc(F)c4sc(N)nc34)c(C(F)(F)F)cc12] | LCMS m/z [M + 1]: 704.3<br>$^{1}$HNMR (400 MHz, $CD_3OD$) δ 8.19 (d, J = 12.6 Hz, 1H), 7.17-7.27 (m, 1H), 6.96-7.07 (m, 1H), 6.37-6.51 (m, 1H), 6.03-6.23 (m, 1H), 5.49-5.71 (m, 2H), 5.11-5.28 (m, 1H), 4.63-4.76 (m, 2H), 3.82-4.15 (m, 4H), 3.56-3.67 (m, 1H), 3.31-3.50 (m, 7H), 2.56-2.78 (m, 2H), 2.29-2.49 (m, 3H), 2.09-2.24 (m, 1H), 1.90-2.03 (m, 1H), 1.47-1.61 (m, 1H). |
| 282a | 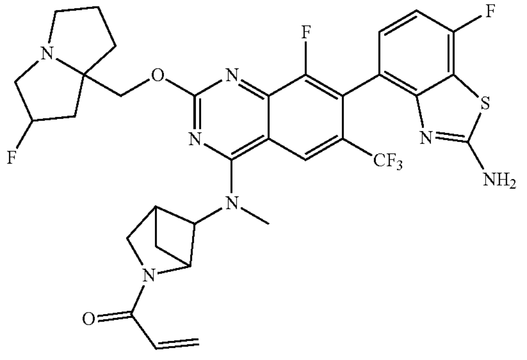 | |

TABLE 4-continued
Selected compounds of the present disclosure.
| Compound No. | Structure | Analytical data |
| --- | --- | --- |
| 283 | 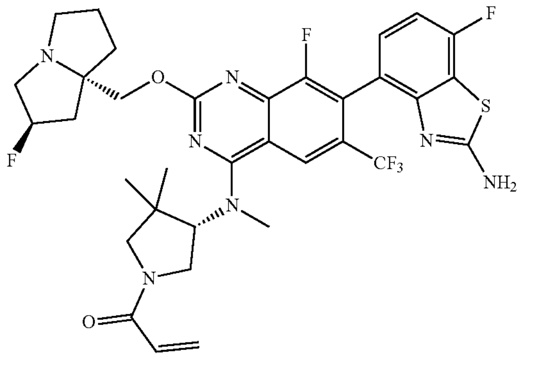 [SMILES: C=CC(=O)N1C[C@@H](N(C)c2nc(OC[C@@]34CCCN3C[C@H](F)C4)nc3c(F)c(-c4ccc(F)c5sc(N)nc45)c(C(F)(F)F)cc23)C(C)(C)C1] | LCMS m/z [M + 1]: 720.3 $^1$HNMR (400 MHz, $CD_3OD$) δ 8.45 (s, 1H), 7.21-7.30 (m, 1H), 7.02 (d, J = 8.8 Hz, 1H), 6.61-6.73 (m, 1H), 6.38 (d, J = 16.8 Hz, 1H), 5.81 (d, J = 10.4 Hz, 1H), 5.56 (d, J = 51.6 Hz, 1H), 5.32-5.49 (m, 1H), 4.68 (s, 2H), 3.42-4.30 (m, 10H), 2.50-2.78 (m, 2H), 2.28-2.42 (m, 3H), 2.04-2.19 (m, 1H), 1.35 (d, J = 6.8 Hz, 3H), 1.23 (d, J = 4.4 Hz, 3H). |
| 283a | 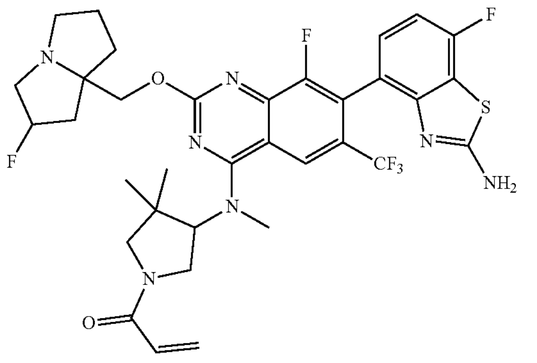 [SMILES: C=CC(=O)N1CC(N(C)c2nc(OCC34CCCN3CC(F)C4)nc3c(F)c(-c4ccc(F)c5sc(N)nc45)c(C(F)(F)F)cc23)C(C)(C)C1] | |
| 284 | 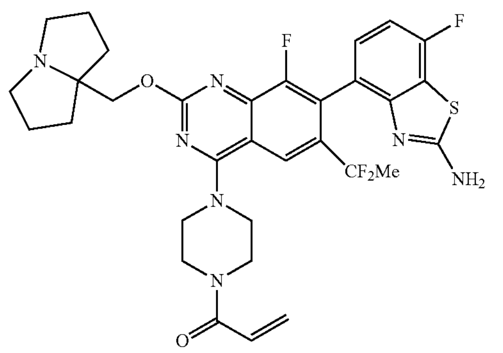 | LCMS m/z [M + 1]: 656.28 $^1$HNMR (300 MHz, $CD_3OD$) δ 8.24-8.04 (m, 1H), 7.21 (d, J = 2.8 Hz, 1H), 7.03-6.96 (m, 1H), 6.90-6.75 (m, 1H), 6.37-6.26 (m, 1H), 5.89-5.80 (m, 1H), 4.64 (s, 2H), 4.13 (s, 3H), 4.01-3.56 (m, 7H), 3.14-3.01 (m, 1H), 2.37-1.94 (m, 8H), 1.65 (dd, J = 19.3, 18.0 Hz, 3H). |
| 285 | 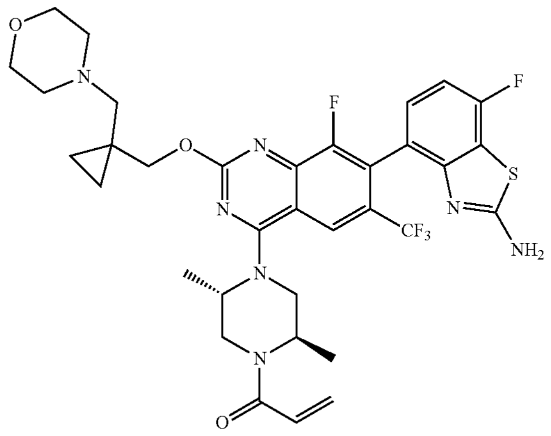 [SMILES: C=CC(=O)N1C[C@H](C)N(c2nc(OCC3(CN4CCOCC4)CC3)nc3c(F)c(-c4ccc(F)c5sc(N)nc45)c(C(F)(F)F)cc23)C[C@H]1C] | LCMS m/z [M + 1]: 718.3 $^1$HNMR (400 MHz, $CD_3OD$) δ 8.19 (s, 1H), 7.20-7.25 (m, 1H), 6.98-7.03 (m, 1H), 6.76-6.88 (m, 1H), 6.27-6.32 (m, 1H), 5.80-5.84 (m, 1H), 4.91-4.95 (m, 1H), 4.31-4.62 (m, 4H), 3.75-4.07 (m, 8H), 3.46-3.57 (m, 1H), 3.35-3.41 (m, 2H), 3.12-3.25 (m, 2H), 1.46-1.51 (m, 3H), 1.28-1.38 (m, 3H), 0.89-0.99 (m, 4H). |

TABLE 4-continued
| Selected compounds of the present disclosure. | | |
|---|---|---|
| Compound No. | Structure | Analytical data |
| 285a | 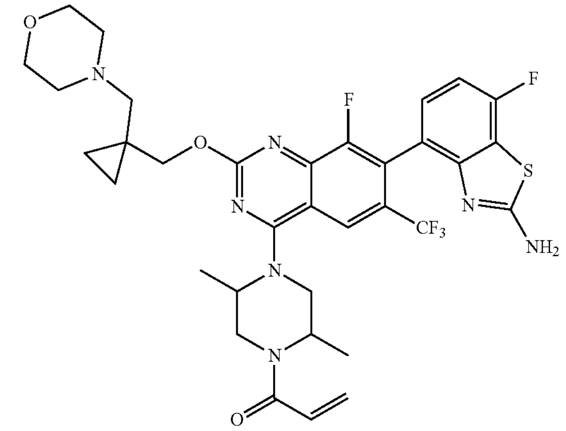 [SMILES: C=CC(=O)N1CC(C)N(c2nc(OCC3(CN4CCOCC4)CC3)nc3c(F)c(-c4ccc(F)c5sc(N)nc45)c(C(F)(F)F)cc23)CC1C] | |
| 286 | 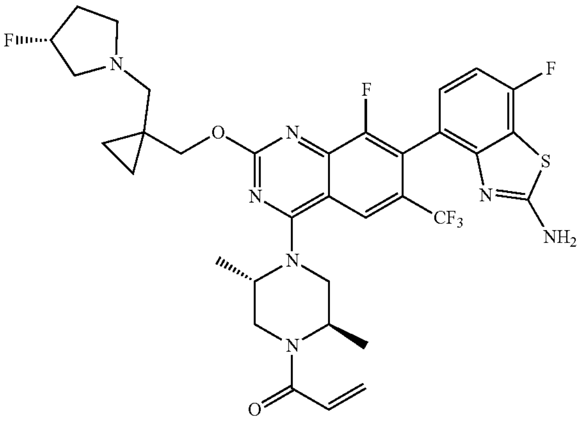 [SMILES: C=CC(=O)N1C[C@H](C)N(c2nc(OCC3(CN4CC[C@@H](F)C4)CC3)nc3c(F)c(-c4ccc(F)c5sc(N)nc45)c(C(F)(F)F)cc23)C[C@H]1C] | LCMS m/z [M + 1]: 720.3 $^1$HNMR (400 MHz, $CD_3OD$) δ 8.19 (s, 1H), 7.22-7.27 (m, 1H), 6.99-7.05 (m, 1H), 6.75-6.88 (m, 1H), 6.27-6.32 (m, 1H), 5.80-5.85 (m, 1H), 5.38-5.51 (d, J = 52 Hz, 1H), 4.91-4.98 (m, 2H), 4.30-4.64 (m, 4H), 3.47-4.04 (m, 8H), 2.32-2.45 (m, 2H), 1.48-1.52 (m, 3H), 1.28-1.37 (m, 3H), 0.89-0.98 (m, 4H). |
| 286a | 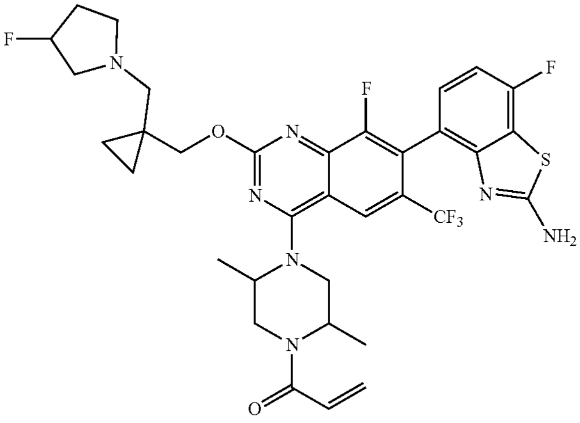 [SMILES: C=CC(=O)N1CC(C)N(c2nc(OCC3(CN4CCC(F)C4)CC3)nc3c(F)c(-c4ccc(F)c5sc(N)nc45)c(C(F)(F)F)cc23)CC1C] | |

TABLE 4-continued
| Selected compounds of the present disclosure. | | |
|---|---|---|
| Compound No. | Structure | Analytical data |
| 287 | 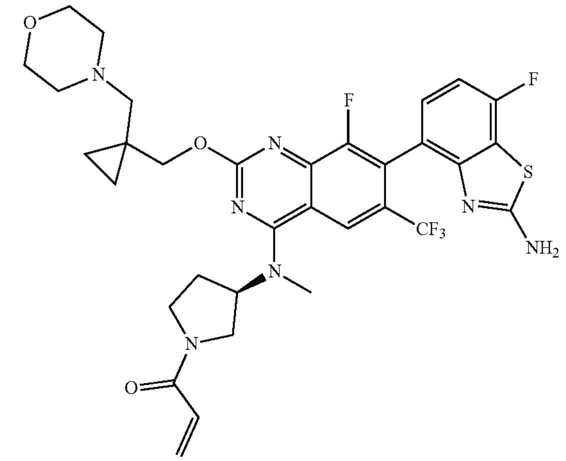 [SMILES: C=CC(=O)N1CC[C@@H](N(C)c2nc(OCC3(CN4CCOCC4)CC3)nc3c(F)c(-c4ccc(F)c5sc(N)nc45)c(C(F)(F)F)cc23)C1] | LCMS m/z [M + 1]: 704.3<br>$^1$HNMR (400 MHz, $CD_3OD$) δ 8.38 (s, 1H), 7.21-7.25 (m, 1H), 7.02 (t, J = 8.8 Hz, 1H), 6.63-6.71 (m, 1H), 6.33 (d, J = 16.8 Hz, 1H), 5.78-5.82 (m, 1H), 5.26-5.42 (m, 1H), 4.20-4.61 (m, 2H), 3.35-4.17 (m, 15H), 3.18-3.24 (m, 2H), 2.42-2.54 (m, 2H), 0.99 (s, 2H), 0.89 (s, 2H). |
| 287a | 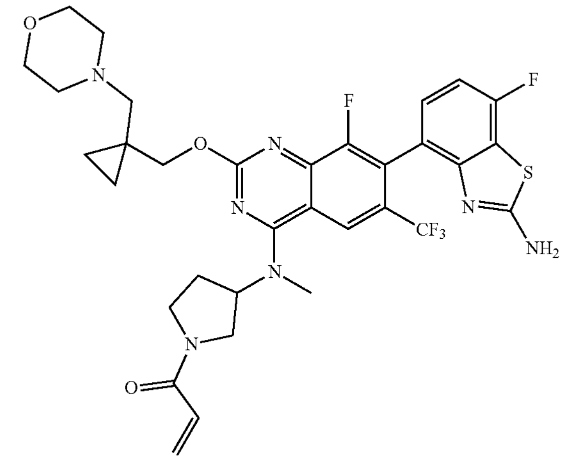 [SMILES: C=CC(=O)N1CCC(N(C)c2nc(OCC3(CN4CCOCC4)CC3)nc3c(F)c(-c4ccc(F)c5sc(N)nc45)c(C(F)(F)F)cc23)C1] | |
| 288 | 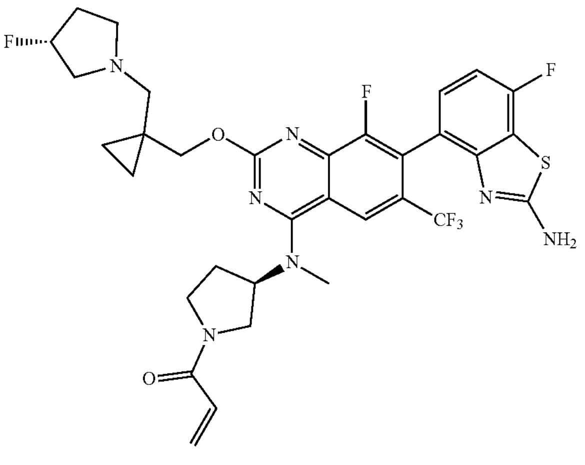 [SMILES: C=CC(=O)N1CC[C@@H](N(C)c2nc(OCC3(CN4CC[C@@H](F)C4)CC3)nc3c(F)c(-c4ccc(F)c5sc(N)nc45)c(C(F)(F)F)cc23)C1] | LCMS m/z [M + 1]: 706.3<br>$^1$HNMR (400 MHz, $CD_3OD$) δ 8.40 (s, 1H), 7.24-7.36 (m, 1H), 7.04 (t, J = 8.8 Hz, 1H), 6.62-6.71 (m, 1H), 6.33 (d, J = 16.8 Hz, 1H), 5.78-5.82 (m, 1H), 5.30-5.51 (m, 2H), 4.37-4.65 (m, 2H), 3.48-4.20 (m, 12H), 3.368-3.42 (m, 1H), 2.36-2.53 (m, 4H), 0.89-0.99 (m, 4H). |

TABLE 4-continued
| Selected compounds of the present disclosure. | | |
|---|---|---|
| Compound No. | Structure | Analytical data |
| 288a | 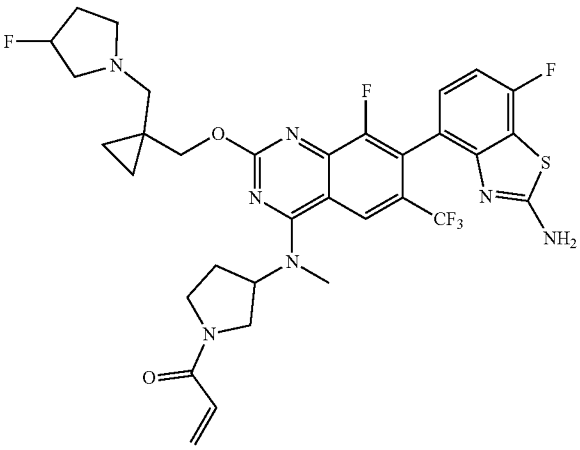 [SMILES: C=CC(=O)N1CCC(N(C)c2nc(OCC3(CN4CCC(F)C4)CC3)nc3c(F)c(-c4ccc(F)c5sc(N)nc45)c(C(F)(F)F)cc23)C1] | |
| 289 | 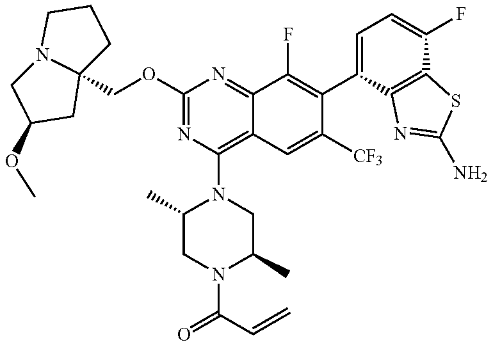 | LCMS m/z [M + 1]: 718.2<br>$^1$HNMR (400 MHz, $CD_3OD$) δ 8.20 (s, 1H), 7.21-7.27 (m, 1H), 7.03 (d, J = 8.8 Hz, 1H), 6.90 6.75 (m, 1H), 6.26-6.34 (m, 1H), 5.78-5.87 (m, 1H), 4.87-5.02 (m, 2H), 4.60-4.70 (m, 2H), 4.26-4.58 (m, 3H), 3.74-4.07 (m, 4H), 3.60-3.68 (m, 1H), 3.48-3.57 (m, 1H), 3.35-3.42 (m, 3H), 2.39-2.51 (m, 2H), 2.26-2.38 (m, 3H), 2.05-2.17 (m, 1H), 1.44-1.56 (m, 3H), 1.28-1.38 (m, 3H). |
| 289a | 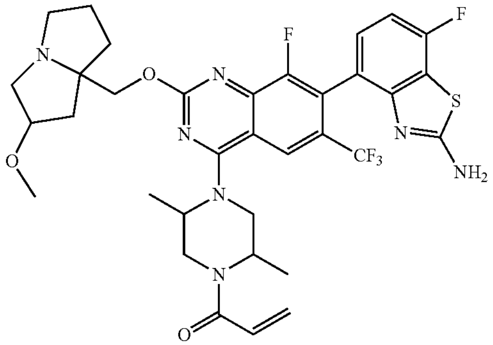 [SMILES: C=CC(=O)N1CC(C)N(c2nc(OCC34CCCN3CC(OC)C4)nc3c(F)c(-c4ccc(F)c5sc(N)nc45)c(C(F)(F)F)cc23)CC1C] | |
| 290 | 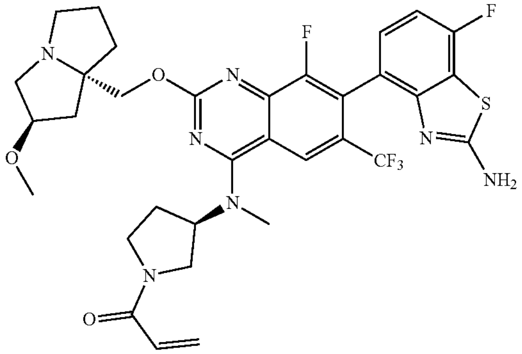 [SMILES: C=CC(=O)N1CC[C@@H](N(C)c2nc(OC[C@@]34CCCN3C[C@H](OC)C4)nc3c(F)c(-c4ccc(F)c5sc(N)nc45)c(C(F)(F)F)cc23)C1] | LCMS m/z [M + 1]: 704.2<br>$^1$HNMR (400 MHz, $CD_3OD$) δ 8.38 (s, 1H), 7.22-7.28 (m, 1H), 7.03 (t, J = 8.8 Hz, 1H), 6.61-6.73 (m, 1H), 6.29-6.36 (m, 1H), 5.75-5.84 (m, 1H), 5.28-5.45 (m, 1H), 4.58-4.72 (m, 2H), 3.89-4.32 (m, 3H), 3.59-3.85 (m, 5H), 3.45-3.57 (m, 3H), 3.38 (s, 3H), 2.01-2.57 (m, 8H), 1.28-1.34 (m, 1H). |

TABLE 4-continued
| Selected compounds of the present disclosure. | | |
|---|---|---|
| Compound No. | Structure | Analytical data |
| 290a | 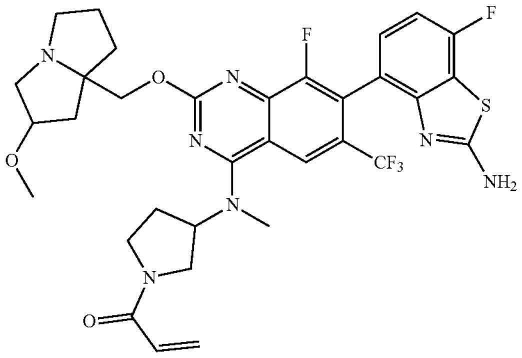 [SMILES: C=CC(=O)N1CCC(N(C)c2nc(OCC34CCCN3CC(OC)C4)nc3c(F)c(-c4ccc(F)c5sc(N)nc45)c(C(F)(F)F)cc23)C1] | |
| 291 | 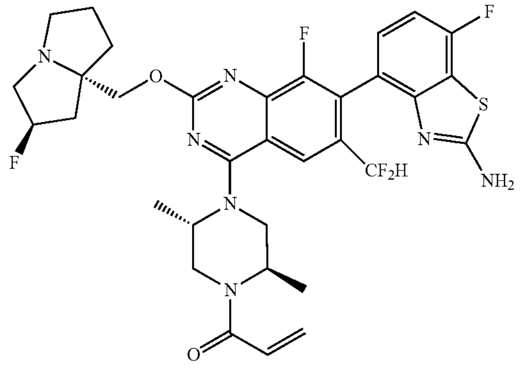 [SMILES: C=CC(=O)N1C[C@H](C)N(c2nc(OC[C@@]34CCCN3C[C@H](F)C4)nc3c(F)c(-c4ccc(F)c5sc(N)nc45)c(C(F)F)cc23)C[C@H]1C] | LCMS m/z [M + 1]: 688.38 $^{1}$HNMR (400 MHz, $CD_3OD$) δ 8.07 (s, 1H), 7.24 (ddd, J = 8.6, 5.5, 3.2 Hz, 1H), 7.07-6.95 (m, 1H), 6.90-6.76 (m, 1H), 6.56 (t, J = 55.4 Hz, 1H), 6.35-6.24 (m, 1H), 5.87-5.76 (m, 1H), 5.34 (d, J = 53.4 Hz, 1H), 4.62-4.44 (m, 1H), 4.44-4.19 (m, 4H), 4.04-3.86 (m, 2H), 3.63-3.34 (m, 2H), 3.30-3.20 (m, 2H), 3.14-3.01 (m, 1H), 2.45-2.13 (m, 3H), 2.10-1.92 (m, 3H), 1.48-1.37 (m, 3H), 1.39-1.25 (s, 3H). |
| 291a | 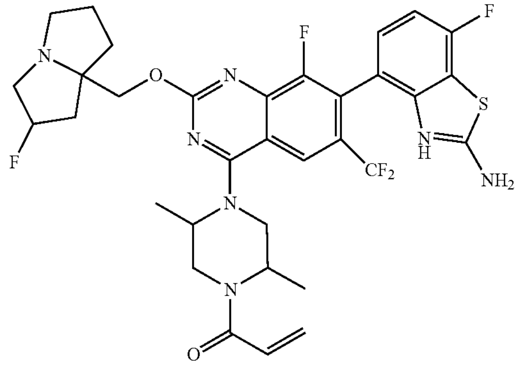 | |
| 292 | 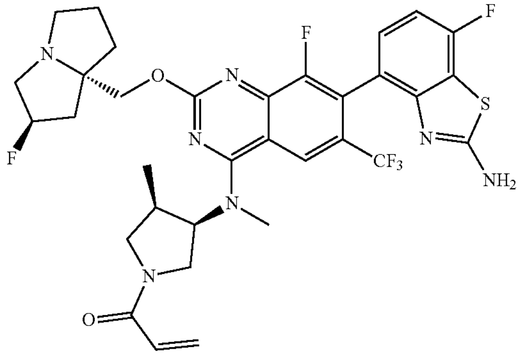 [SMILES: C=CC(=O)N1C[C@@H](C)[C@@H](N(C)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 706.2 $^{1}$HNMR (400 MHz, $CD_3OD$) δ 8.41 (s, 1H), 7.19-7.24 (m, 1H), 6.99 (t, J = 8.8 Hz, 1H), 6.62-6.73 (m, 1H), 6.31-6.39 (m, 1H), 5.79-5.84 (m, 1H), 5.40-5.64 (m, 2H), 5.24-5.39 (m, 1H), 4.66-4.79 (m, 2H), 3.84-4.08 (m, 6H), 3.42-3.62 (m, 4H), 2.10-2.73 (m, 6H), 1.09-1.25 (m, 3H). |

TABLE 4-continued
| Selected compounds of the present disclosure. | | |
|---|---|---|
| Compound No. | Structure | Analytical data |
| 292a | 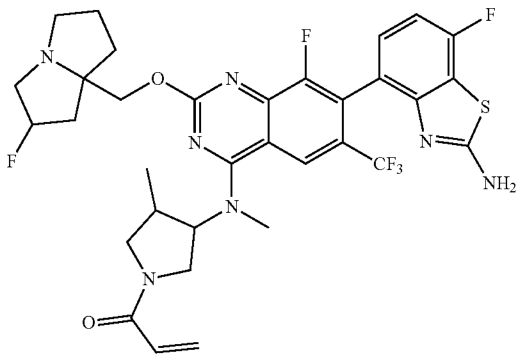 | |
| 293 | 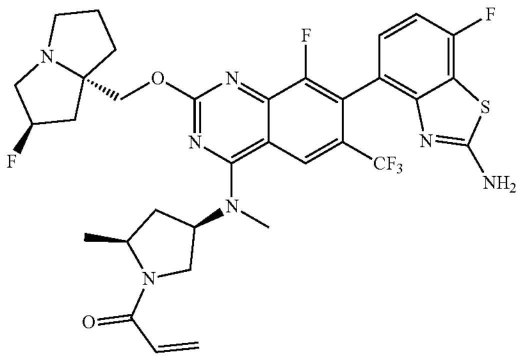 [SMILES: C=CC(=O)N1C[C@H](N(C)c2nc(OC[C@@]34CCCN3C[C@H](F)C4)nc3c(F)c(-c4ccc(F)c5sc(N)nc45)c(C(F)(F)F)cc23)C[C@@H]1C] | LCMS m/z [M + 1]: 706.4 $^1$HNMR (400 MHz, $CD_3OD$) δ 8.38 (s, 1H), 7.25 (dd, J = 8.4, 5.4 Hz, 1H), 7.04 (t, J = 8.8 Hz, 1H), 6.57-6.76 (m, 1H), 6.31 (t, J = 16.8 Hz, 1H), 5.74-5.86 (m, 1H), 5.56 (d, J = 51.6 Hz, 1H), 5.05-5.21 (m, 1H), 4.61-4.77 (m, 2H), 4.20-4.49 (m, 2H), 3.69-4.05 (m, 4H), 3.54 (s, 3H), 3.42-3.49 (m, 1H), 2.55-2.83 (m, 3H), 2.27-2.47 (m, 3H), 2.04-2.22 (m, 2H), 1.48 (d, J = 6.2 Hz, 3H). |
| 293a | 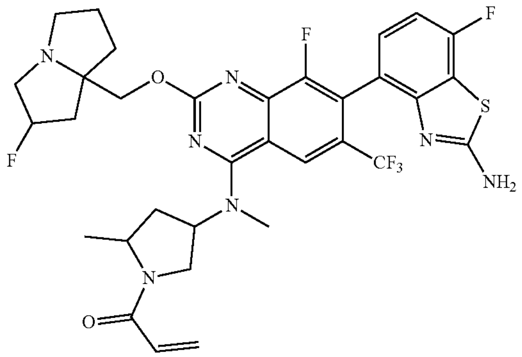 [SMILES: C=CC(=O)N1CC(N(C)c2nc(OCC34CCCN3CC(F)C4)nc3c(F)c(-c4ccc(F)c5sc(N)nc45)c(C(F)(F)F)cc23)CC1C] | |
| 294 | 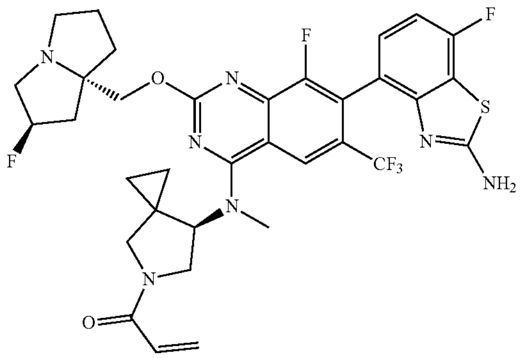 [SMILES: C=CC(=O)N1C[C@H](N(C)c2nc(OC[C@@]34CCCN3C[C@H](F)C4)nc3c(F)c(-c4ccc(F)c5sc(N)nc45)c(C(F)(F)F)cc23)C2(CC2)C1] | LCMS m/z [M + 1]: 718.4 $^1$HNMR (400 MHz, $CD_3OD$) δ 8.29-8.38 (m, 1H), 7.17-7.27 (m, 1H), 7.00 (t, J = 8.8 Hz, 1H), 6.58-6.79 (m, 1H), 6.34 (d, J = 16.8 Hz, 1H), 5.80 (d, J = 10.4 Hz, 1H), 5.56 (d, J = 52 Hz, 1H), 5.09-5.21 (m, 1H), 4.54-4.75 (m, 2H), 4.01-4.40 (m, 3H), 3.82-3.97 (m, 2H), 3.33-3.71 (m, 5H), 2.54-2.75 (m, 2H), 2.28-2.47 (m, 3H), 2.05-2.22 (m, 1H), 1.26-1.38 (m, 1H), 1.09-1.0 (m, 1H), 0.90-1.07 (m, 3H). |

TABLE 4-continued
| Selected compounds of the present disclosure. | | |
|---|---|---|
| Compound No. | Structure | Analytical data |
| 294a | 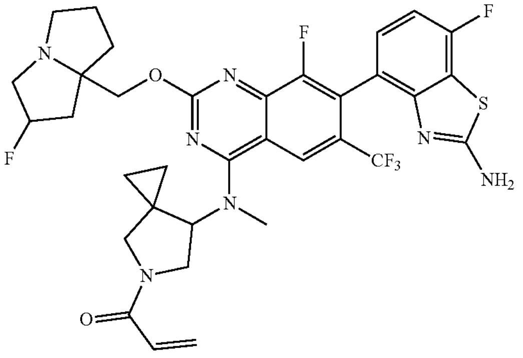 [SMILES: C=CC(=O)N1CC(N(C)c2nc(OCC34CCCN3CC(F)C4)nc3c(F)c(-c4ccc(F)c5sc(N)nc45)c(C(F)(F)F)cc23)C2(CC2)C1] | |
| 295 | 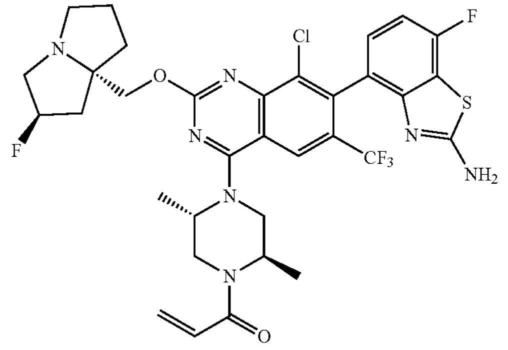 [SMILES: C=CC(=O)N1C[C@H](C)N(c2nc(OC[C@@]34CCCN3C[C@H](F)C4)nc3c(Cl)c(-c4ccc(F)c5sc(N)nc45)c(C(F)(F)F)cc23)C[C@H]1C] | LCMS m/z [M + 1]: 722.3 $^{1}$HNMR (400 MHz, $CD_3OD$) δ 8.32 (s, 1H), 7.12-7.14 (m, 1H), 6.99 (t, J = 8.8 Hz, 1H), 6.75-6.88 (m, 1H), 6.27-6.32 (m, 1H), 5.80-5.84 (m, 1H), 5.49-5.62 (d, J = 51.6 Hz, 1H), 4.94-5.01 (m, 1H), 4.70-4.73 (m, 2H), 4.30-4.55 (m, 2H), 3.83-4.05 (m, 5H), 3.43-3.54 (m, 2H), 2.12-2.75 (m, 6H), 1.46-1.53 (m, 3H), 1.28-1.32 (m, 3H). |
| 295a | 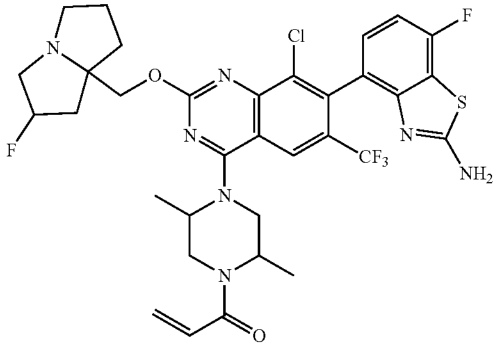 [SMILES: C=CC(=O)N1CC(C)N(c2nc(OCC34CCCN3CC(F)C4)nc3c(Cl)c(-c4ccc(F)c5sc(N)nc45)c(C(F)(F)F)cc23)CC1C] | |
| 296 | 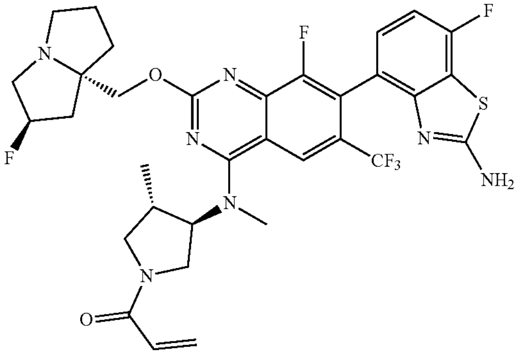 [SMILES: C=CC(=O)N1C[C@H](C)[C@@H](N(C)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 706.3 $^{1}$HNMR (400 MHz, $CD_3OD$) δ 8.41 (s, 1H), 7.24-7.26 (m, 1H), 7.04 (t, J = 8.8 Hz, 1H), 6.60-6.73 (m, 1H), 6.33 (d, J = 16.8 Hz, 1H), 5.80 (d, J = 10.4 Hz, 1H), 5.56 (d, J = 52 Hz, 1H), 4.65-5.11 (m, 3H), 3.86-4.14 (m, 5H), 3.45-3.53 (m, 5H), 2.30-3.20 (m, 8H), 1.19-1.21 (m, 3H). |

TABLE 4-continued
| Selected compounds of the present disclosure. | | |
|---|---|---|
| Compound No. | Structure | Analytical data |
| 296a | 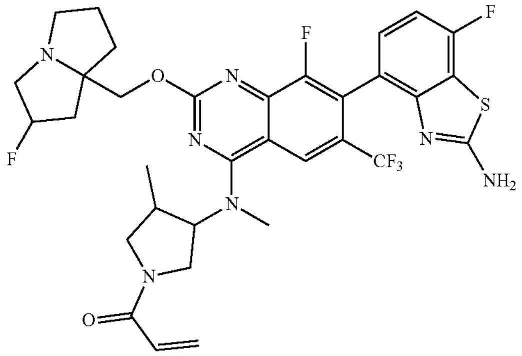 [SMILES: C=CC(=O)N1CC(C)C(N(C)c2nc(OCC34CCCN3CC(F)C4)nc3c(F)c(-c4ccc(F)c5sc(N)nc45)c(C(F)(F)F)cc23)C1] | |
| 297 | 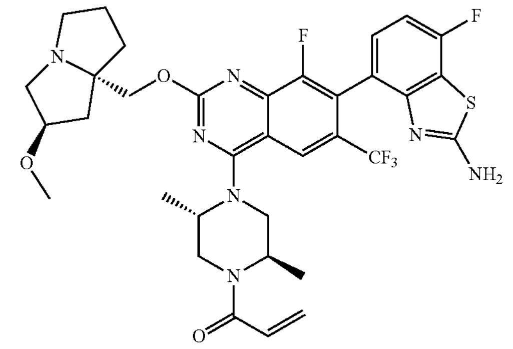 [SMILES: C=CC(=O)N1C[C@H](C)N(c2nc(OC[C@@]34CCCN3C[C@H](OC)C4)nc3c(F)c(-c4ccc(F)c5sc(N)nc45)c(C(F)(F)F)cc23)C[C@H]1C] | LCMS m/z [M + 1]: 718.3 $^1$HNMR (400 MHz, $CD_3OD$) δ 8.20 (s, 1H), 7.20-7.31 (m, 1H), 7.00-7.07 (m, 1H), 6.75-6.90 (m, 1H), 6.26-6.35 (m, 1H), 5.80-5.90 (m, 1H), 4.90-5.05 (m, 2H), 4.61-4.69 (m, 2H), 4.26-4.58 (m, 3H), 3.73-4.08 (m, 4H), 3.61-3.68 (m, 1H), 3.49-3.55 (m, 1H), 3.39 (s, 3H), 2.26-2.50 (m, 5H), 2.07-2.16 (m, 1H), 1.45-1.56 (m, 3H), 1.27-1.39 (m, 3H). |
| 297a | 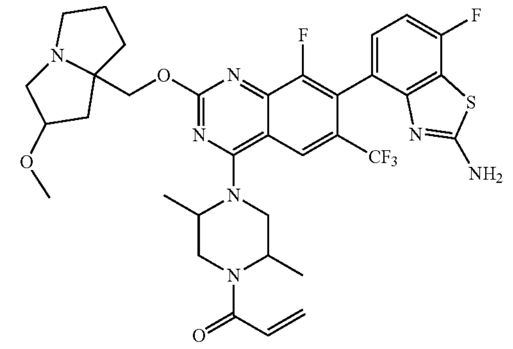 [SMILES: C=CC(=O)N1CC(C)N(c2nc(OCC34CCCN3CC(OC)C4)nc3c(F)c(-c4ccc(F)c5sc(N)nc45)c(C(F)(F)F)cc23)CC1C] | |
| 298 | 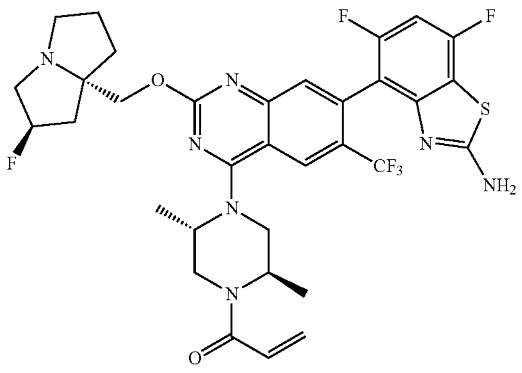 [SMILES: C=CC(=O)N1C[C@H](C)N(c2nc(OC[C@@]34CCCN3C[C@H](F)C4)nc3cc(-c4c(F)cc(F)c5sc(N)nc45)c(C(F)(F)F)cc23)C[C@H]1C] | LCMS m/z [M + 1]: 706.3 $^1$HNMR (400 MHz, $CD_3OD$) δ 8.42 (s, 1H), 7.62 (s, 1H), 6.76-6.92 (m, 2H), 6.28-6.33 (m, 1H), 5.78-5.91 (m, 1H), 5.60 (d, J = 51.2 Hz, 1H), 4.97-5.05 (m, 2H), 4.68-4.78 (m, 2H), 4.33-4.57 (m, 2H), 3.83-4.09 (m, 5H), 3.45-3.54 (m, 1H), 2.20-2.78 (m, 6H), 1.28-1.57 (m, 6H). |

TABLE 4-continued
| Selected compounds of the present disclosure. | | |
|---|---|---|
| Compound No. | Structure | Analytical data |
| 298a | 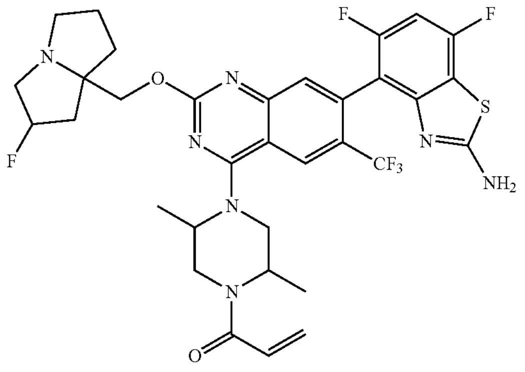 [SMILES: C=CC(=O)N1CC(C)N(c2nc(OCC34CCCN3CC(F)C4)nc3cc(-c4c(F)cc(F)c5sc(N)nc45)c(C(F)(F)F)cc23)CC1C] | |
| 299 | 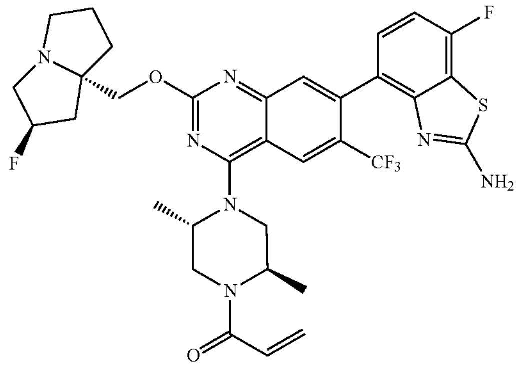 [SMILES: C=CC(=O)N1C[C@H](C)N(c2nc(OC[C@@]34CCCN3C[C@H](F)C4)nc3cc(-c4ccc(F)c5sc(N)nc45)c(C(F)(F)F)cc23)C[C@H]1C] | LCMS m/z [M + 1]: 688.4 $^1$HNMR (400 MHz, $CD_3OD$) δ 8.40 (s, 1H), 7.60 (s, 1H), 6.98 (t, J = 8.8 Hz, 1H), 6.79-6.89 (m, 1H), 6.28-6.33 (m, 1H), 5.81-5.86 (m, 1H), 5.59 (d, J = 51.6 Hz, 1H), 4.95-5.05 (m, 2H), 4.68-4.75 (m, 2H), 4.32-4.27 (m, 2H), 3.83-4.09 (m, 5H), 3.45-3.54 (m, 1H), 2.19-2.77 (m, 6H), 1.29-1.56 (m, 6H). |
| 299a | 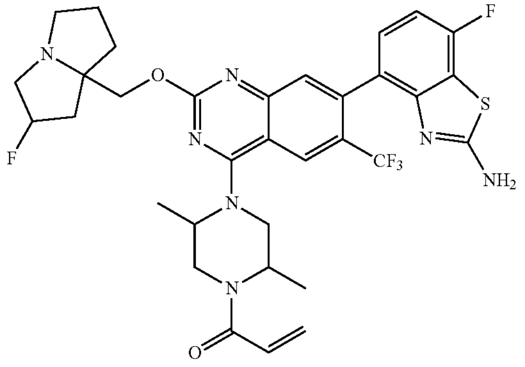 [SMILES: C=CC(=O)N1CC(C)N(c2nc(OCC34CCCN3CC(F)C4)nc3cc(-c4ccc(F)c5sc(N)nc45)c(C(F)(F)F)cc23)CC1C] | |
| 300 | 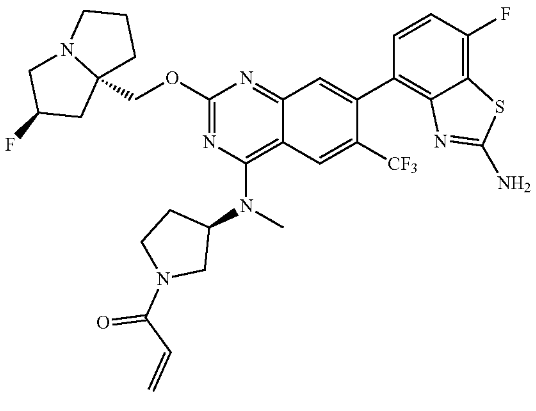 [SMILES: C=CC(=O)N1CC[C@@H](N(C)c2nc(OC[C@@]34CCCN3C[C@H](F)C4)nc3cc(-c4ccc(F)c5sc(N)nc45)c(C(F)(F)F)cc23)C1] | LCMS m/z [M + 1]: 674.3 $^1$HNMR (400 MHz, $CD_3OD$) δ 8.57 (s, 1H), 7.59 (s, 1H), 7.21 (dd, J = 8.4, 5.6 Hz, 1H), 6.97 (t, J = 8.8 Hz, 1H), 6.62-6.72 (m, 1H), 6.31-6.35 (m, 1H), 5.77-5.83 (m, 1H), 5.58 (d, J = 51.2 Hz, 1H), 5.32-5.45 (m, 1H), 4.65-4.75 (m, 2H), 3.44-4.20 (m, 12H), 2.17-2.71 (m, 8H). |

TABLE 4-continued
| Selected compounds of the present disclosure. | | |
|---|---|---|
| Compound No. | Structure | Analytical data |
| 300a | 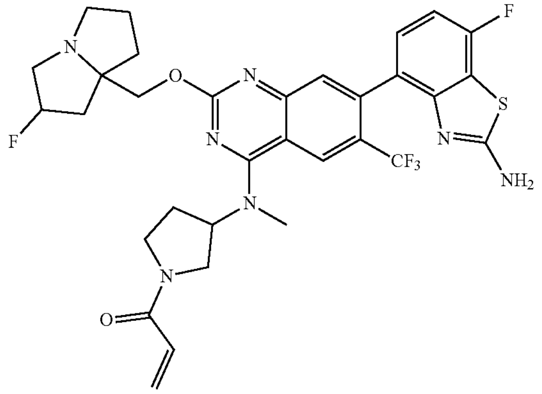 [SMILES: C=CC(=O)N1CCC(N(C)c2nc(OCC34CCCN3CC(F)C4)nc3cc(-c4ccc(F)c5sc(N)nc45)c(C(F)(F)F)cc23)C1] | |
| 301 | 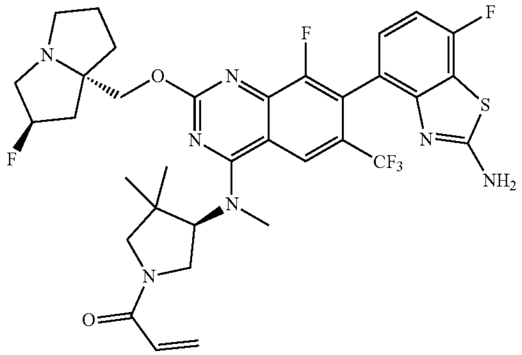 [SMILES: C=CC(=O)N1C[C@H](N(C)c2nc(OC[C@@]34CCCN3C[C@H](F)C4)nc3c(F)c(-c4ccc(F)c5sc(N)nc45)c(C(F)(F)F)cc23)C(C)(C)C1] | LCMS m/z [M + 1]: 720.4 $^{1}$HNMR (400 MHz, $CD_3OD$) δ 8.44 (s, 1H), 7.19-7.22 (m, 1H), 6.99 (t, J = 8.8 Hz, 1H), 6.61-6.72 (m, 1H), 6.32-6.36 (m, 1H), 5.79-5.82 (m, 1H), 5.56 (d, J = 51.6 Hz, 1H), 5.27-5.41 (m, 1H), 4.58-4.75 (m, 2H), 3.86-4.29 (m, 5H), 3.63-3.81 (m, 2H), 3.46-3.54 (m, 4H), 2.11-2.65 (m, 6H), 1.35 (d, J = 6.58 Hz, 3H), 1.22 (d, J = 5.40 Hz, 3H). |
| 301a | 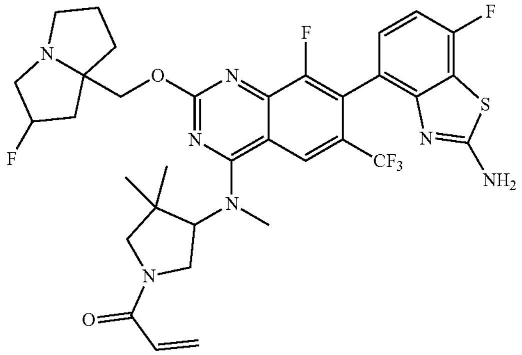 [SMILES: C=CC(=O)N1CC(N(C)c2nc(OCC34CCCN3CC(F)C4)nc3c(F)c(-c4ccc(F)c5sc(N)nc45)c(C(F)(F)F)cc23)C(C)(C)C1] | |
| 302 | 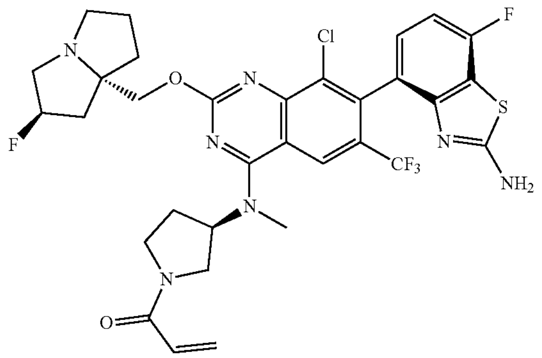 | LCMS m/z [M + 1]: 708.3 $^{1}$HNMR (400 MHz, $CD_3OD$) δ 8.50 (s, 1H), 7.13-7.16 (m, 1H), 7.01 (t, J = 8.8 Hz, 1H), 6.62-6.71 (m, 1H), 6.32 (d, J = 16.8 Hz, 1H), 5.78-5.82 (m, 1H), 5.55 (d, J = 52 Hz, 1H), 5.22-5.36 (m, 1H), 4.66-4.76 (m, 2H), 3.41-4.21 (m, 12H), 2.11-2.80 (m, 8H). |

TABLE 4-continued
| Selected compounds of the present disclosure. | | |
|---|---|---|
| Compound No. | Structure | Analytical data |
| 303 | 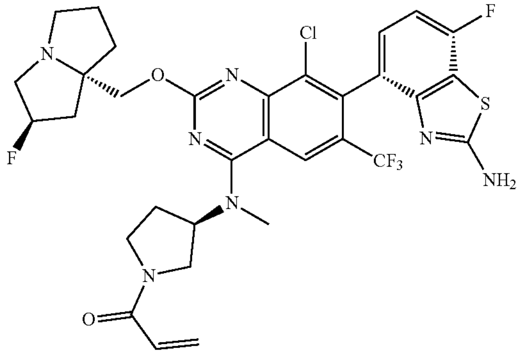 | LCMS m/z [M + 1]: 708.3 $^1$HNMR (400 MHz, $CD_3OD$) δ 8.50 (s, 1H), 7.12-7.16 (m, 1H), 7.01 (t, J = 8.8 Hz, 1H), 6.61-6.71 (m, 1H), 6.32 (d, J = 16.8 Hz, 1H), 5.77-5.82 (m, 1H), 5.55 (d, J = 51.6 Hz, 1H), 5.24-5.36 (m, 1H), 4.64-4.78 (m, 2H), 3.46-4.19 (m, 12H), 2.10-2.72 (m, 8H). |
| 303a | 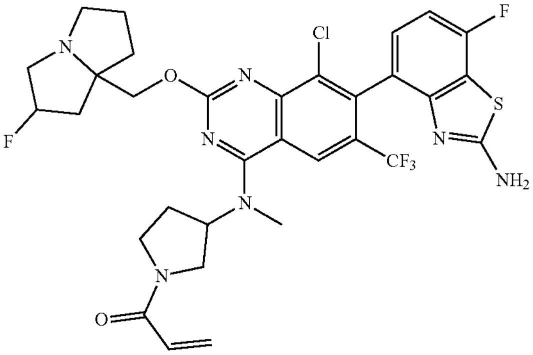 [SMILES: C=CC(=O)N1CCC(N(C)c2nc(OCC34CCCN3CC(F)C4)nc3c(Cl)c(-c4ccc(F)c5sc(N)nc45)c(C(F)(F)F)cc23)C1] | |
| 304 | 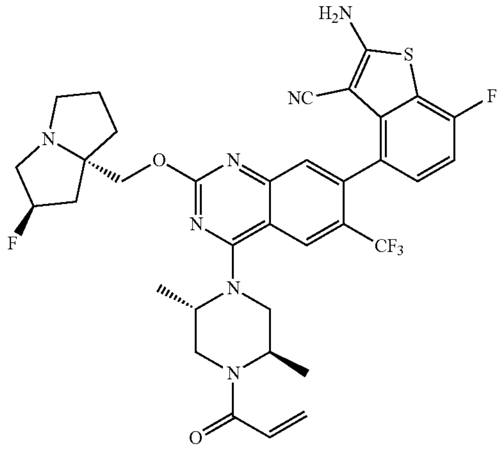 [SMILES: C=CC(=O)N1C[C@H](C)N(c2nc(OC[C@@]34CCCN3C[C@H](F)C4)nc3cc(-c4ccc(F)c5sc(N)c(C#N)c45)c(C(F)(F)F)cc23)C[C@H]1C] | LCMS m/z [M + 1]: 712.4 $^1$HNMR (400 MHz, $CD_3OD$) δ 8.39 (s, 1H), 7.59 (s, 1H), 7.20-7.24 (m, 1H), 7.00 (t, J = 8.8 Hz, 1H), 6.75-6.90 (m, 1H), 6.27-6.33 (m, 1H), 5.81-5.84 (m, 1H), 5.55 (d, J = 52 Hz, 2H), 4.97-5.14 (m, 2H), 4.68-4.79 (m, 2H), 4.31-4.59 (m, 2H), 3.88-4.16 (m, 5H), 3.45-3.51 (m, 1H), 2.21-2.77 (m, 6H), 1.24-1.59 (m, 6H). |

TABLE 4-continued
| Selected compounds of the present disclosure. | | |
|---|---|---|
| Compound No. | Structure | Analytical data |
| 304a | 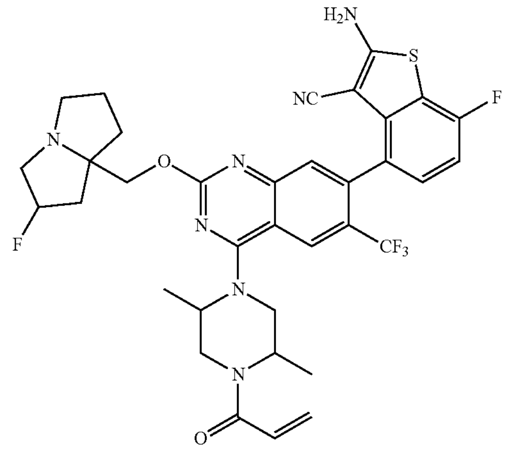 [SMILES: C=CC(=O)N1CC(C)N(c2nc(OCC34CCCN3CC(F)C4)nc3cc(-c4ccc(F)c5sc(N)c(C#N)c45)c(C(F)(F)F)cc23)CC1C] | |
| 305 | 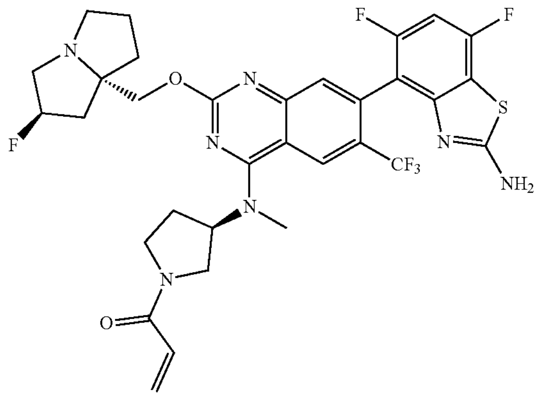 [SMILES: C=CC(=O)N1CC[C@@H](N(C)c2nc(OC[C@@]34CCCN3C[C@H](F)C4)nc3cc(-c4c(F)cc(F)c5sc(N)nc45)c(C(F)(F)F)cc23)C1] | LCMS m/z [M + 1]: 692.4<br>$^1$HNMR (400 MHz, $CD_3OD$) δ 8.55 (s, 1H), 7.56 (s, 1H), 6.86 (t, J = 9.6 Hz, 1H), 6.71-6.61 (m, 1H), 6.30-6.34 (m, 1H), 5.78-5.81 (m, 1H), 5.58 (d, J = 51.6 Hz, 1H), 5..25-5.39 (m, 1H), 3.43-4.69 (m, 12H), 2.16-2.71 (m, 8H). |
| 305a | 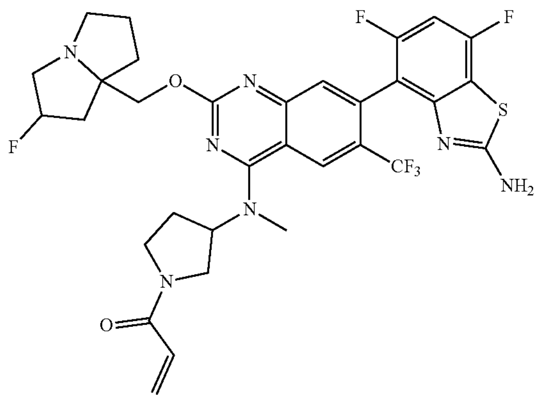 [SMILES: C=CC(=O)N1CCC(N(C)c2nc(OCC34CCCN3CC(F)C4)nc3cc(-c4c(F)cc(F)c5sc(N)nc45)c(C(F)(F)F)cc23)C1] | |

TABLE 4-continued
| Selected compounds of the present disclosure. | | |
|---|---|---|
| Compound No. | Structure | Analytical data |
| 306 | 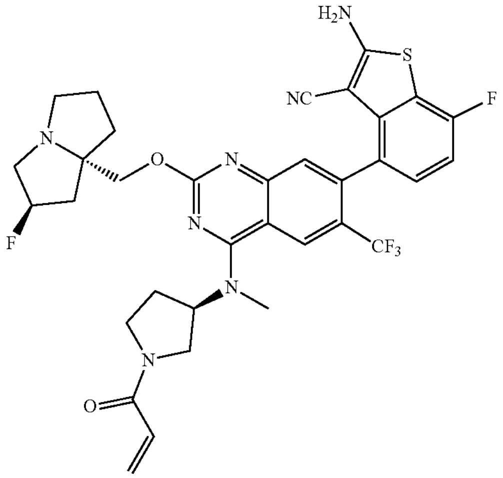 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(C(F)(F)F)cc23)C1] | LCMS m/z [M + 1]: 698.4 $^1$HNMR (400 MHz, $CD_3OD$) δ 8.52 (s, 1H), 7.54 (s, 1H), 7.15-7.22 (m, 1H), 6.99 (t, J = 9.2 Hz, 1H), 6.62-6.72 (m, 1H), 6.30-6.35 (m, 1H), 5.73-5.82 (m, 1H), 5.58 (d, J = 52 Hz, 1H), 5.23-5.41 (m, 1H), 4.58-4.73 (m, 2H), 3.43-4.16 (m, 12H), 2.16-2.76 (m, 8H). |
| 306a | 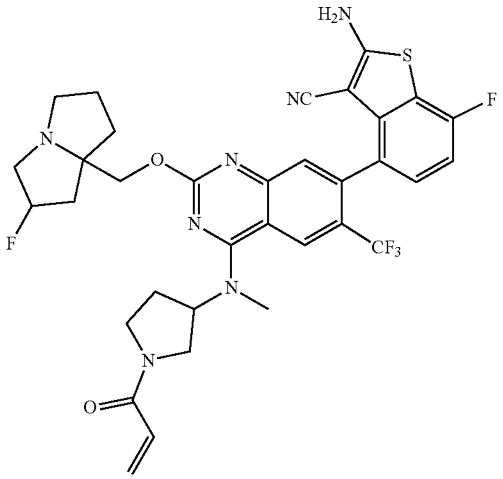 [SMILES: C=CC(=O)N1CCC(N(C)c2nc(OCC34CCCN3CC(F)C4)nc3cc(-c4ccc(F)c5sc(N)c(C#N)c45)c(C(F)(F)F)cc23)C1] | |
| 307 | 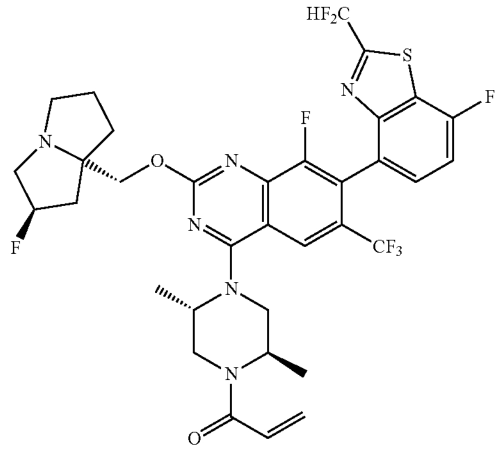 | LCMS m/z [M + 1]: 741.3 $^1$HNMR (400 MHz, $CD_3OD$) δ 8.25 (s, 1H), 7.64-7.69 (m, 1H), 7.54 (t, J = 9.2 Hz, 1H), 7.03-7.18 (m, 1H), 6.75-6.90 (m, 1H), 6.27-6.33 (m, 1H), 5.80-5.84 (m, 1H), 5.50-5.63 (d, J = 51.6 Hz, 1H), 4.94-5.01 (m, 1H), 4.68 (s, 2H), 4.30-4.55 (m, 2H), 3.83-4.05 (m, 5H), 3.43-3.54 (m, 2H), 2.15-2.75 (m, 6H), 1.49-1.53 (m, 3H), 1.28-1.38 (m, 3H), |

TABLE 4-continued
| Selected compounds of the present disclosure. | | |
|---|---|---|
| Compound No. | Structure | Analytical data |
| 307a | 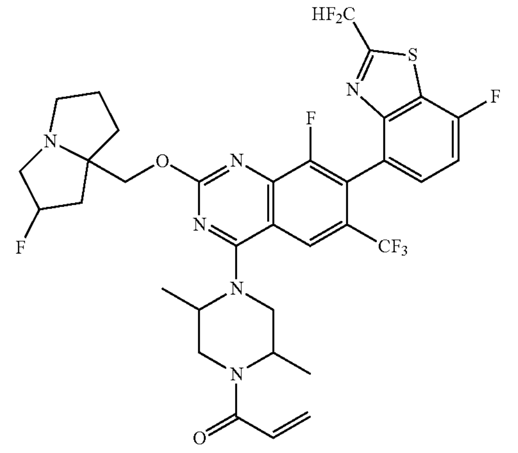 | |
| 308 | 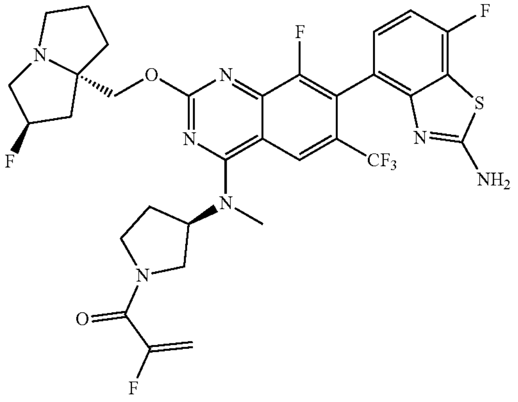 [SMILES: C=C(F)C(=O)N1CC[C@@H](N(C)c2nc(OC[C@@]34CCCN3C[C@H](F)C4)nc3c(F)c(-c4ccc(F)c5sc(N)nc45)c(C(F)(F)F)cc23)C1] | LCMS m/z [M + 1]: 710.2 $^{1}$HNMR (400 MHz, $CD_3OD$) δ 8.33 (s, 1H), 7.16-7.22 (m, 1H), 6.97 (t, J = 8.8 Hz, 1H), 5.25-5.58 (m, 4H), 4.25-4.52 (m, 3H), 4.03-4.15 (m, 1H), 3.76-3.94 (m, 2H), 3.55-3.71 (m, 1H), 3.48 (s, 3H), 3.35-3.41 (m, 2H), 3.05-3.16 (s, 1H), 1.94-2.47 (m, 8H). |
| 308a | 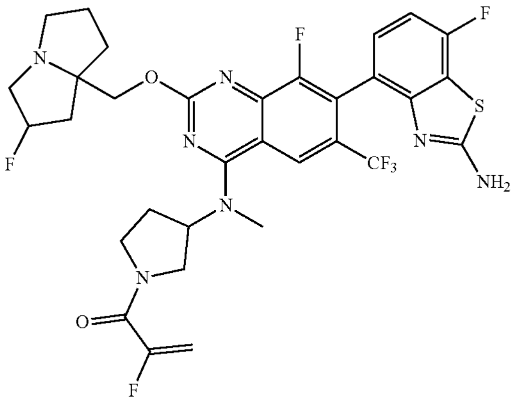 [SMILES: C=C(F)C(=O)N1CCC(N(C)c2nc(OCC34CCCN3CC(F)C4)nc3c(F)c(-c4ccc(F)c5sc(N)nc45)c(C(F)(F)F)cc23)C1] | |

TABLE 4-continued
| Selected compounds of the present disclosure. | | |
|---|---|---|
| Compound No. | Structure | Analytical data |
| 309 | 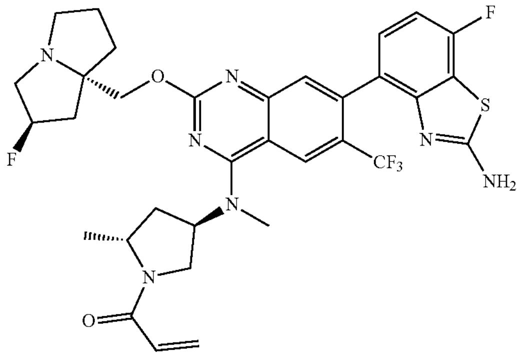 [SMILES: C=CC(=O)N1C[C@H](N(C)c2nc(OC[C@@]34CCCN3C[C@H](F)C4)nc3cc(-c4ccc(F)c5sc(N)nc45)c(C(F)(F)F)cc23)C[C@H]1C] | LCMS m/z [M + 1]: 688.3 $^1$HNMR (400 MHz, $CD_3OD$) δ 8.56 (s, 1H), 7.56 (s, 1H), 7.18-7.22 (m, 1H), 6.96 (t, J = 8.8 Hz, 1H), 6.60-6.67 (m, 1H), 6.29-6.38 (m, 1H), 5.76-5.83 (m, 1H), 5.48-5.65 (m, 2H), 4.52-4.75 (m, 3H), 3.96-4.19 (m, 1H), 3.75-3.93 (m, 4H), 3.45-3.51 (m, 4H), 2.15-2.76 (m, 8H), 1.35-1.39 (m, 3H), |
| 309a | 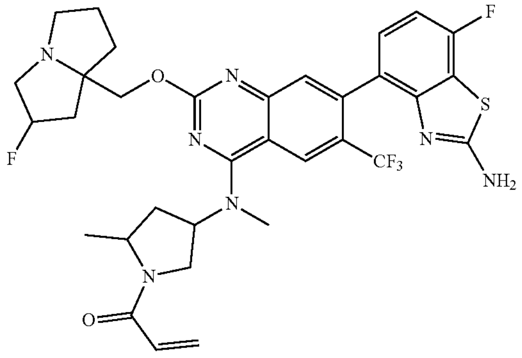 [SMILES: C=CC(=O)N1CC(N(C)c2nc(OCC34CCCN3CC(F)C4)nc3cc(-c4ccc(F)c5sc(N)nc45)c(C(F)(F)F)cc23)CC1C] | |
| 310 | 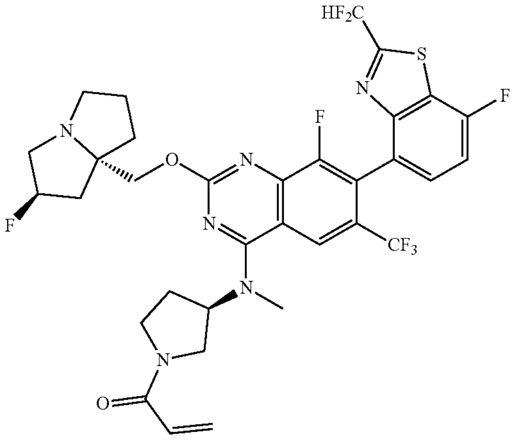 | LCMS m/z [M + 1]: 727.3 $^1$HNMR (400 MHz, $CD_3OD$) δ 8.44 (s, 1H), 7.63-7.71 (m, 1H), 7.52 (t, J = 8.8 Hz, 1H), 6.96 (d, J = 54 Hz, 1H), 6.62-6.74 (m, 1H), 6.33 (dd, J = 16.8, 2.0 Hz, 1H), 5.76-5.85 (m, 1H), 5.56 (d, J = 51.6 Hz, 1H), 5.28-5.42 (m, 1H), 4.58-4.75 (m, 2H), 3.73-4.19 (m, 6H), 3.42-3.63 (m, 5H), 2.29-2.75 (m, 7H), 2.18-2.25 (m, 1H). |

TABLE 4-continued
| Selected compounds of the present disclosure. | | |
|---|---|---|
| Compound No. | Structure | Analytical data |
| 310a | 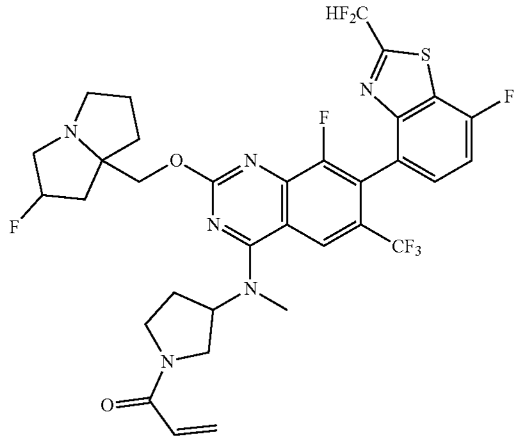 | |
| 311 | 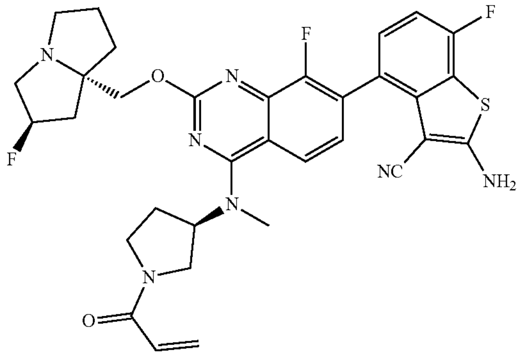 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)ccc23)C1] | LCMS m/z [M + 1]: 648.3 $^{1}$HNMR (400 MHz, $CD_3OD$) δ 8.08-8.10 (m, 1H), 7.28-7.40 (m, 2H), 7.05 (t, J = 8.8 Hz, 1H), 6.64-6.69 (m, 1H), 6.30-6.34 (m, 1H), 5.70-5.81 (m, 1H), 5.55 (d, J = 53.2 Hz, 1H), 5.29-5.47 (m, 1H), 4.62-4.75 (m, 2H), 3.72-4.09 (m, 7H), 3.41-3.68 (m, 4H), 2.34-2.63 (m, 8H). |
| 311a | 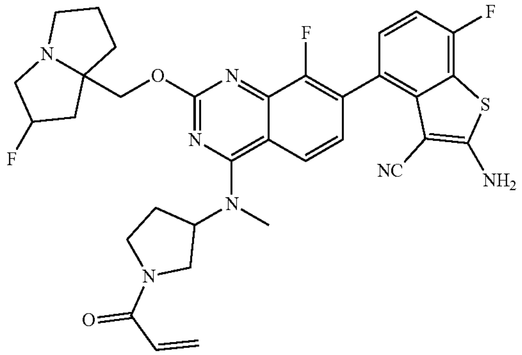 [SMILES: C=CC(=O)N1CCC(N(C)c2nc(OCC34CCCN3CC(F)C4)nc3c(F)c(-c4ccc(F)c5sc(N)c(C#N)c45)ccc23)C1] | |
| 312 | 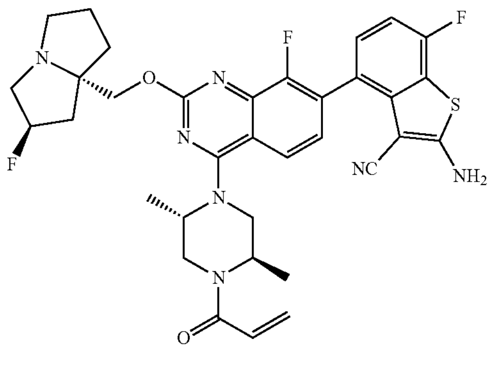 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)ccc23)C[C@H]1C] | LCMS m/z [M + 1]: 662.4 $^{1}$HNMR (400 MHz, $CD_3OD$) δ 7.88-7.95 (m, 1H), 7.36-7.46 (m, 1H), 7.25-7.36 (m, 1H), 7.06 (t, J = 8.8 Hz, 1H), 6.75-6.82 (m, 1H), 6.25-6.33 (m, 1H), 5.79-5.86 (m, 1H), 5.55 (d, J = 51.6 Hz, 1H), 5.02-5.15 (m, 2H), 4.62-4.81 (m, 2H), 4.46-4.52 (m, 2H), 3.84-4.03 (m, 4H), 3.48-3.56 (m, 2H), 2.12-2.77 (m, 6H), 1.21-1.51 (m, 6H). |

TABLE 4-continued
| Selected compounds of the present disclosure. | | |
|---|---|---|
| Compound No. | Structure | Analytical data |
| 312a | 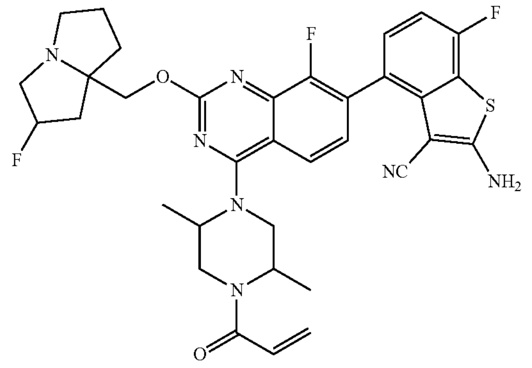 [SMILES: C=CC(=O)N1CC(C)N(c2nc(OCC34CCCN3CC(F)C4)nc3c(F)c(-c4ccc(F)c5sc(N)c(C#N)c45)ccc23)CC1C] | |
| 313 | 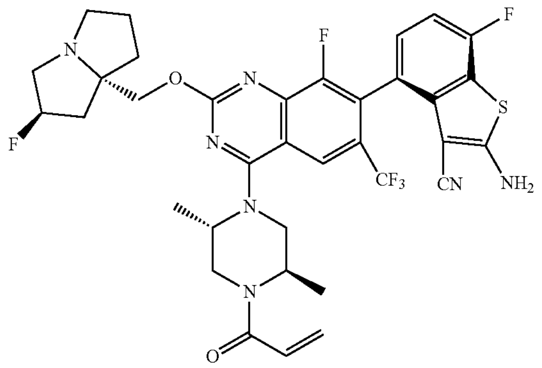 | LCMS m/z [M + 1]: 730.3 $^1$HNMR (400 MHz, $CD_3OD$) δ 8.13 (s, 1H), 7.17-7.28 (m, 1H), 7.02 (t, J = 8.8 Hz, 1H), 6.91-6.73 (m, 1H), 6.22-6.35 (m, 1H), 5.81 (dd, J = 10.8, 4.0 Hz, 1H), 5.33 (d, J = 53.6 Hz, 1H), 4.93-5.01 (m, 1H), 4.56-4.67 (m, 1H), 4.25-4.39 (m, 4H), 3.83-4.06 (m, 2H), 3.36-3.59 (m, 2H), 3.22-3.28 (m, 1H), 3.03-3.14 (m, 1H), 1.82-2.46 (m, 6H), 1.48 (t, J = 6.0 Hz, 3H), 1.28 (dd, J = 24.4, 6.8 Hz, 3H). |
| 313a | 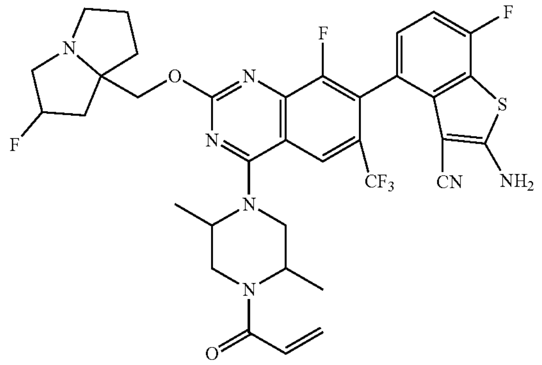 [SMILES: C=CC(=O)N1CC(C)N(c2nc(OCC34CCCN3CC(F)C4)nc3c(F)c(-c4ccc(F)c5sc(N)c(C#N)c45)c(C(F)(F)F)cc23)CC1C] | |
| 314 | 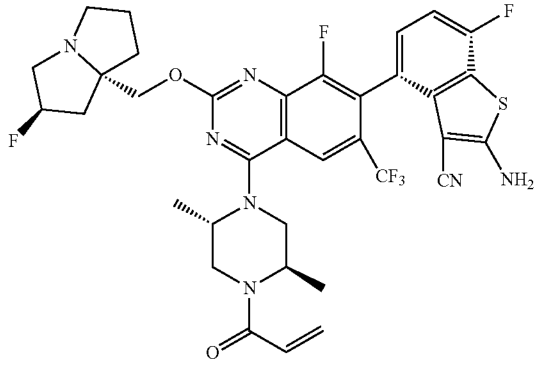 | LCMS m/z [M + 1]: 730.3 $^1$HNMR (400 MHz, $CD_3OD$) δ 8.15 (s, 1H), 7.17-7.28 (m, 1H), 7.02 (t, J = 8.8 Hz, 1H), 6.91-6.73 (m, 1H), 6.22-6.35 (m, 1H), 5.78-5.92 (m, 1H), 5.33 (d, J = 53.6 Hz, 1H), 4.93-5.01 (m, 1H), 4.20-4.61 (m, 4H), 3.83-4.06 (m, 2H), 3.48-3.59 (m, 1H), 3.12-3.28 (m, 3H), 3.03-3.14 (m, 1H), 1.82-2.46 (m, 6H), 1.48 (t, J = 6.0 Hz, 3H), 1.28 (dd, J = 24.4, 6.8 Hz, 3H). |

TABLE 4-continued
| Selected compounds of the present disclosure. | | |
|---|---|---|
| Compound No. | Structure | Analytical data |
| 314a | 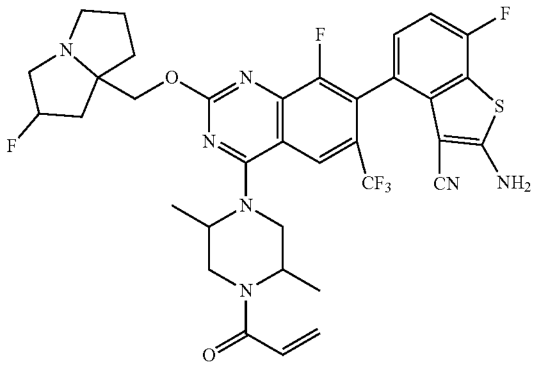 [SMILES: C=CC(=O)N1CC(C)N(c2nc(OCC34CCCN3CC(F)C4)nc3c(F)c(-c4ccc(F)c5sc(N)c(C#N)c45)c(C(F)(F)F)cc23)CC1C] | |
| 315 | 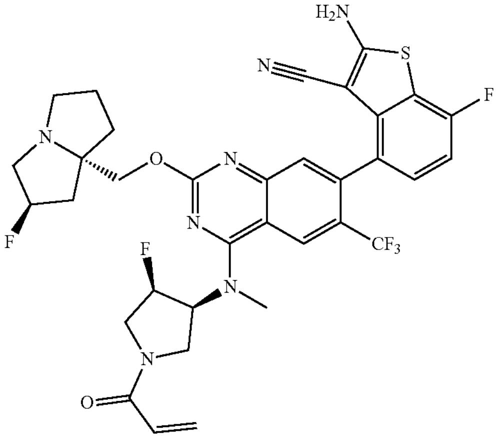 [SMILES: C=CC(=O)N1C[C@@H](F)[C@@H](N(C)c2nc(OC[C@@]34CCCN3C[C@H](F)C4)nc3cc(-c4ccc(F)c5sc(N)c(C#N)c45)c(C(F)(F)F)cc23)C1] | LCMS m/z [M + 1]: 716.3<br>$^1$HNMR (400 MHz, $CD_3OD$) δ 8.64-8.65 (m, 1H), 7.60-7.61 (m, 1H), 7.22 (t, J = 8.8 Hz, 1H), 7.00-7.02 (m, 1H), 6.64-6.80 (m, 1H), 6.37 (d, J = 16.8 Hz, 1H), 5.58-5.85 (m, 4H), 4.70-4.79 (m, 2H), 3.76-4.35 (m, 10H), 3.47-3.48 (m, 1H), 2.23-2.68 (m, 6H). |
| 315a | 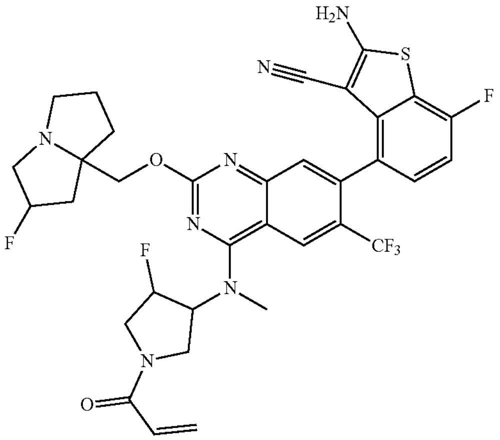 [SMILES: C=CC(=O)N1CC(F)C(N(C)c2nc(OCC34CCCN3CC(F)C4)nc3cc(-c4ccc(F)c5sc(N)c(C#N)c45)c(C(F)(F)F)cc23)C1] | |

TABLE 4-continued
| Selected compounds of the present disclosure. | | |
|---|---|---|
| Compound No. | Structure | Analytical data |
| 316 | 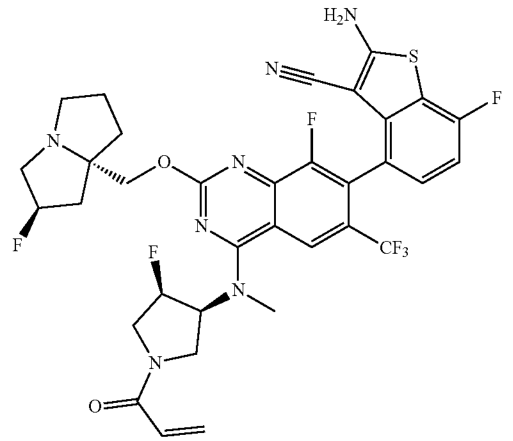 [SMILES: C=CC(=O)N1C[C@@H](F)[C@@H](N(C)c2nc(OC[C@@]34CCCN3C[C@H](F)C4)nc3c(F)c(-c4ccc(F)c5sc(N)c(C#N)c45)c(C(F)(F)F)cc23)C1] | LCMS m/z [M + 1]: 734.3<br>$^1$HNMR (400 MHz, $CD_3OD$) δ 8.42 (s, 1H), 7.23-7.24 (m, 1H), 7.03 (t, J = 8.8 Hz, 1H), 6.61-6.76 (m, 1H), 6.37 (d, J = 16.8 Hz, 1H), 5.68-5.85 (m, 2H), 5.55 (d, J = 50.4 Hz, 1H), 5.12-5.33 (m, 1H), 4.60-4.76 (m, 2H), 3.47-4.33 (m, 12H), 2.16-2.70 (m, 6H). |
| 316a | 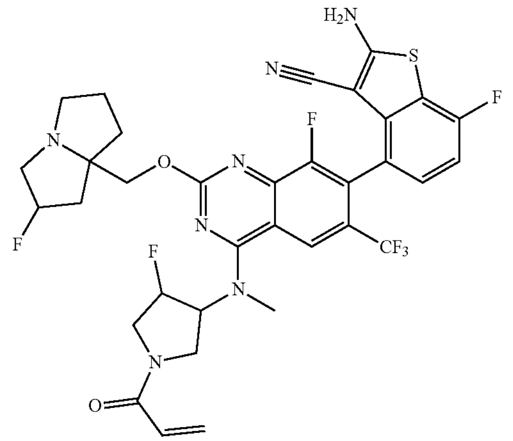 [SMILES: C=CC(=O)N1CC(F)C(N(C)c2nc(OCC34CCCN3CC(F)C4)nc3c(F)c(-c4ccc(F)c5sc(N)c(C#N)c45)c(C(F)(F)F)cc23)C1] | |
| 317 | 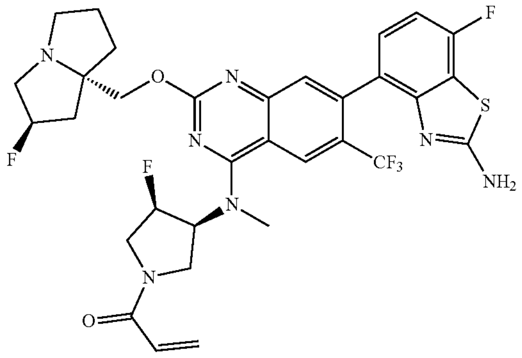 [SMILES: C=CC(=O)N1C[C@@H](F)[C@@H](N(C)c2nc(OC[C@@]34CCCN3C[C@H](F)C4)nc3cc(-c4ccc(F)c5sc(N)nc45)c(C(F)(F)F)cc23)C1] | LCMS m/z [M + 1]: 692.2<br>$^1$HNMR (400 MHz, $CD_3OD$) δ 8.62 (s, 1H), 7.61 (s, 1H), 7.19-7.29 (m, 1H), 6.94-7.05 (m, 1H), 6.61-6.77 (m, 1H), 6.37 (d, J = 16.8 Hz, 1H), 5.67-5.86 (m, 2H), 5.58 (d, J = 52.4 Hz, 1H), 5.16-5.39 (m, 1H), 4.79-4.63 (m, 2H), 4.26-4.40 (m, 1H), 4.10-4.23 (m, 1H), 3.80-4.07 (m, 5H), 3.72 (s, 3H), 3.37-3.55 (m, 1H), 2.53-2.72 (m, 2H), 2.29-2.53 (m, 3H), 2.13-2.26 (m, 1H). |

TABLE 4-continued
| Selected compounds of the present disclosure. | | |
|---|---|---|
| Compound No. | Structure | Analytical data |
| 317a | 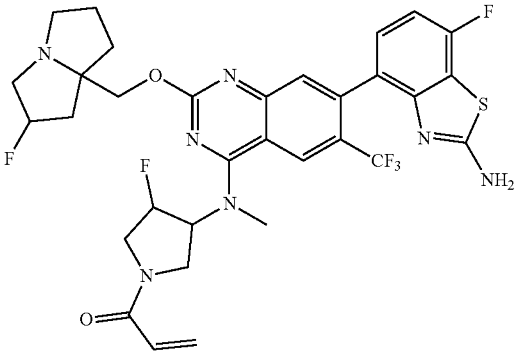 [SMILES: C=CC(=O)N1CC(F)C(N(C)c2nc(OCC34CCCN3CC(F)C4)nc3cc(-c4ccc(F)c5sc(N)nc45)c(C(F)(F)F)cc23)C1] | |
| 318 | 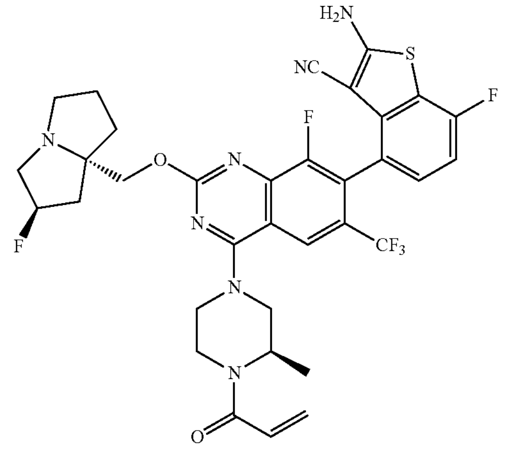 [SMILES: C=CC(=O)N1CCN(c2nc(OC[C@@]34CCCN3C[C@H](F)C4)nc3c(F)c(-c4ccc(F)c5sc(N)c(C#N)c45)c(C(F)(F)F)cc23)C[C@H]1C] | LCMS m/z [M + 1]: 716.3 $^1$HNMR (400 MHz, $CD_3OD$) δ 8.28 (s, 1H), 7.20-7.26 (m, 1H), 7.03 (t, J = 9.2 Hz, 1H), 6.74-6.88 (m, 1H), 6.21-6.36 (m, 1H), 5.80 (d, J = 10.0 Hz, 1H), 5.56 (d, J = 52.0 Hz, 1H), 4.88-4.93 (m, 1H), 4.63-4.77 (m, 2H), 4.32-4.51 (m, 2H), 3.65-4.07 (m, 6H), 3.42-3.54 (m, 1H), 2.55-2.75 (m, 2H), 2.29-2.47 (m, 3H), 2.11-2.22 (m, 1H), 1.35 (s, 3H). |
| 318a | 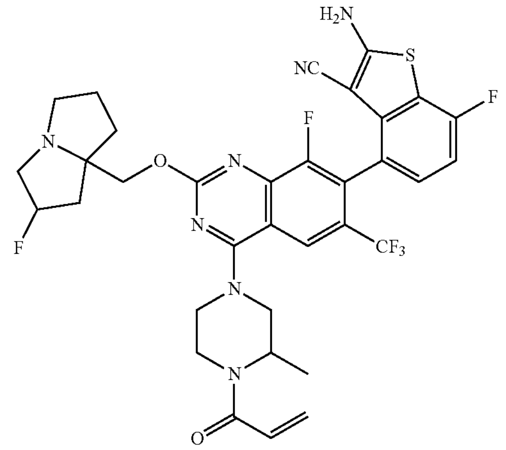 [SMILES: C=CC(=O)N1CCN(c2nc(OCC34CCCN3CC(F)C4)nc3c(F)c(-c4ccc(F)c5sc(N)c(C#N)c45)c(C(F)(F)F)cc23)CC1C] | |

TABLE 4-continued
| Selected compounds of the present disclosure. | | |
|---|---|---|
| Compound No. | Structure | Analytical data |
| 319 | 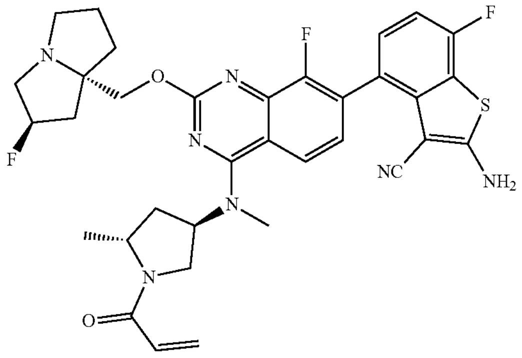 [SMILES: C=CC(=O)N1C[C@H](N(C)c2nc(OC[C@@]34CCCN3C[C@H](F)C4)nc3c(F)c(-c4ccc(F)c5sc(N)c(C#N)c45)ccc23)C[C@H]1C] | LCMS m/z [M + 1]: 662.2 $^1$HNMR (400 MHz, $CD_3OD$) δ 8.08-8.10 (m, 1H), 7.28-7.40 (m, 2H), 7.05 (t, J = 8.8 Hz, 1H), 6.64-6.69 (m, 1H), 6.30-6.34 (m, 1H), 5.70-5.81 (m, 1H), 5.42-5.65 (m, 2H), 4.48-4.88 (m, 3H), 3.72-4.09 (m, 5H), 3.40-3.55 (m, 4H), 2.34-2.633 (m, 8H), 1.34-1.39 (m, 3H). |
| 319a | 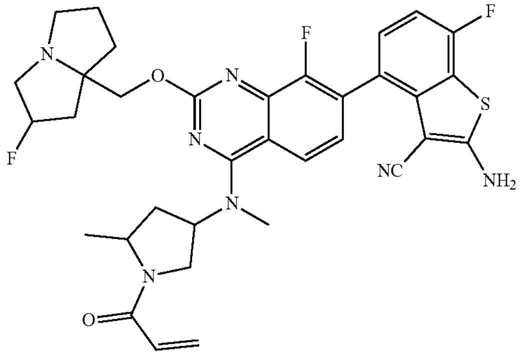 [SMILES: C=CC(=O)N1CC(N(C)c2nc(OCC34CCCN3CC(F)C4)nc3c(F)c(-c4ccc(F)c5sc(N)c(C#N)c45)ccc23)CC1C] | |
| 320 | 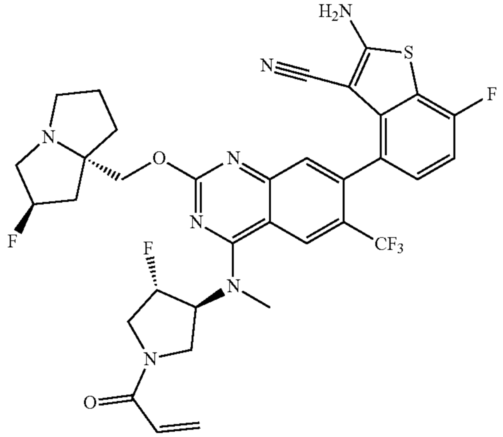 [SMILES: C=CC(=O)N1C[C@H](F)[C@@H](N(C)c2nc(OC[C@@]34CCCN3C[C@H](F)C4)nc3cc(-c4ccc(F)c5sc(N)c(C#N)c45)c(C(F)(F)F)cc23)C1] | LCMS m/z [M + 1]: 716.3 $^1$HNMR (400 MHz, $CD_3OD$) δ 8.54 (s, 1H), 7.53 (s, 1H), 7.17-7.21 (m, 1H), 6.97 (t, J = 9.2 Hz, 1H), 6.67 (dd, J = 16.8, 10.4 Hz, 1H), 6.34 (dd, J = 16.8, 4.8 Hz, 1H), 5.61-5.87 (m, 2H), 5.40 (d, J = 52.2 Hz, 1H), 5.18-5.27 (m, 1H), 4.63 (s, 1H), 4.07-4.28 (m, 4H), 3.74-4.05 (m, 2H), 3.40-3.56 (m, 5H), 3.10-3.16 (m, 1H), 2.12-2.52 (m, 2H), 1.93-2.10 (m, 4H). |

TABLE 4-continued
| Selected compounds of the present disclosure. | | |
|---|---|---|
| Compound No. | Structure | Analytical data |
| 320a | 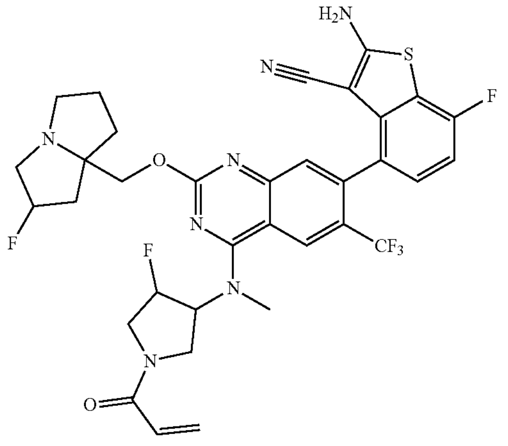 [SMILES: C=CC(=O)N1CC(F)C(N(C)c2nc(OCC34CCCN3CC(F)C4)nc3cc(-c4ccc(F)c5sc(N)c(C#N)c45)c(C(F)(F)F)cc23)C1] | |
| 321 | 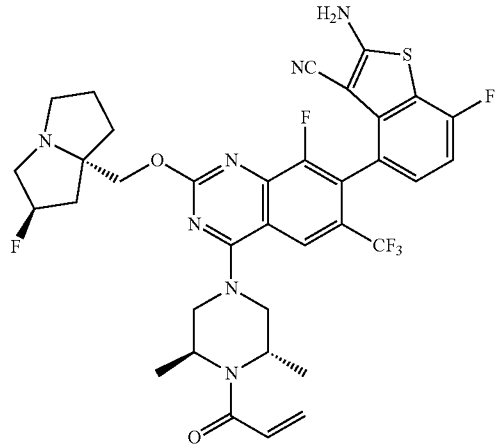 [SMILES: C=CC(=O)N1[C@@H](C)CN(c2nc(OC[C@@]34CCCN3C[C@H](F)C4)nc3c(F)c(-c4ccc(F)c5sc(N)c(C#N)c45)c(C(F)(F)F)cc23)C[C@@H]1C] | LCMS m/z [M + 1]: 730.2 $^1$HNMR (400 MHz, $CD_3OD$) δ 8.35-8.38 (m, 1H), 7.20-7.27 (m, 1H), 7.03 (t, J = 9.2 Hz, 1H), 6.77-6.87 (m, 1H), 6.38 (d, J = 16.8 Hz, 1H), 5.84 (d, J = 10.4 Hz, 1H), 5.57 (d, J = 51.6 Hz, 1H), 4.37-4.84 (m, 6H), 3.84-4.22 (m, 5H), 3.41-3.52 (m, 1H), 2.54-2.79 (m, 2H), 2.29-2.47 (m, 3H), 2.07-2.21 (m, 1H), 1.32-1.51 (m, 6H). |
| 321a | 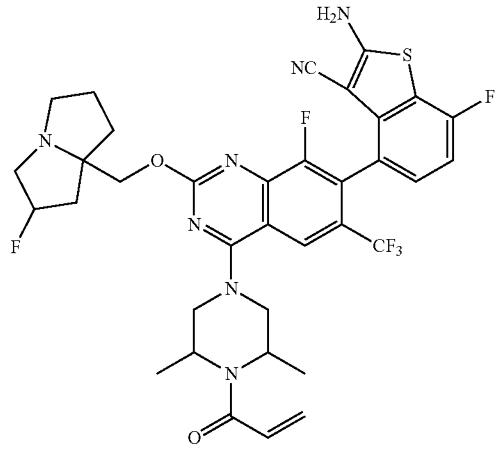 [SMILES: C=CC(=O)N1C(C)CN(c2nc(OCC34CCCN3CC(F)C4)nc3c(F)c(-c4ccc(F)c5sc(N)c(C#N)c45)c(C(F)(F)F)cc23)CC1C] | |

TABLE 4-continued
| Selected compounds of the present disclosure. | | |
|---|---|---|
| Compound No. | Structure | Analytical data |
| 322 | 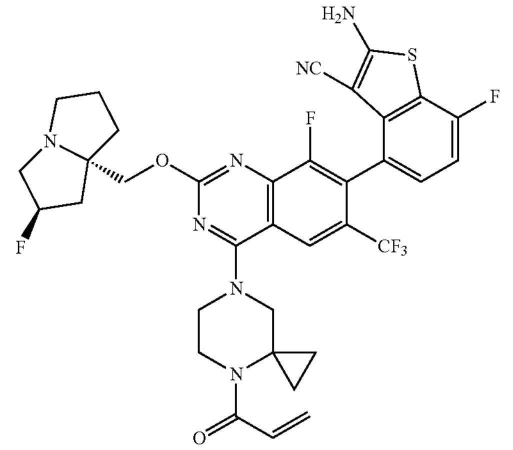 [SMILES: C=CC(=O)N1CCN(c2nc(OC[C@@]34CCCN3C[C@H](F)C4)nc3c(F)c(-c4ccc(F)c5sc(N)c(C#N)c45)c(C(F)(F)F)cc23)CC12CC2] | LCMS m/z [M + 1]: 728.3 $^1$HNMR (400 MHz, $CD_3OD$) δ 8.13 (s, 1H), 7.19-7.28 (m, 1H), 7.03 (t, J = 8.80 Hz, 1H), 6.85-7.00 (m, 1H), 6.27 (d, J = 16.4 Hz, 1H), 5.79 (d, J = 10.4 Hz, 1H), 5.57 (d, J = 52 Hz, 1H), 4.59-4.79 (m, 2H), 4.21-4.34 (m, 1H), 3.83-4.18 (m, 8H), 3.43-3.56 (m, 1H), 2.54-2.78 (m, 2H), 2.29-2.49 (m, 3H), 2.10-2.22 (m, 1H), 0.97-1.21 (m, 4H). |
| 322a | 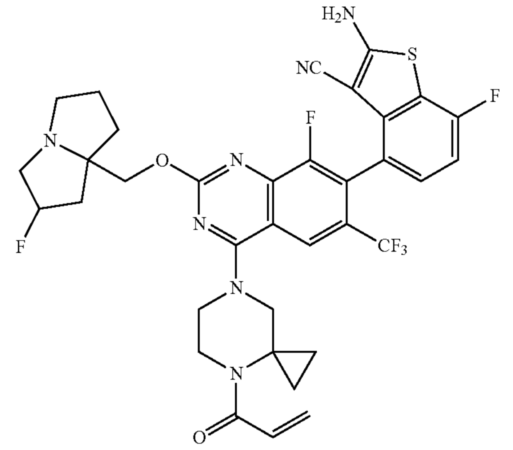 [SMILES: C=CC(=O)N1CCN(c2nc(OCC34CCCN3CC(F)C4)nc3c(F)c(-c4ccc(F)c5sc(N)c(C#N)c45)c(C(F)(F)F)cc23)CC12CC2] | |
| 323 | 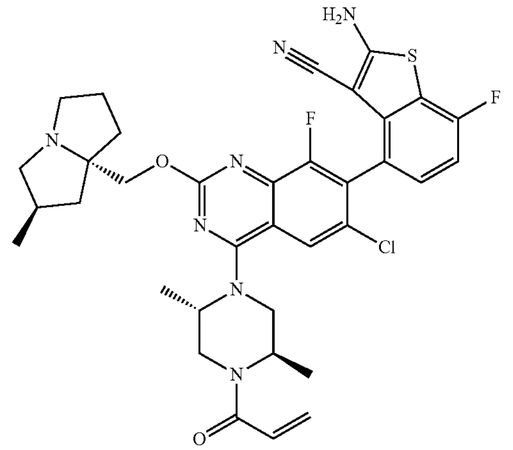 | LCMS m/z [M + 1]: 696.3 $^1$HNMR (400 MHz, $CD_3OD$) δ 7.95 (s, 1H), 7.22-7.27 (m, 1H), 7.06 (t, J = 8.8 Hz, 1H), 6.73-6.90 (m, 1H), 6.29 (dd, J = 16.0, 7.2 Hz, 1H), 5.78-5.87 (m, 1H), 5.56 (d, J = 53.6 Hz, 1H), 4.82-5.05 (m, 2H), 4.45-4.75 (m, 3H), 4.20-4.38 (m, 2H), 3.84-4.08 (m, 5H), 3.43-3.61 (m, 2H), 2.57-2.77 (m, 2H), 2.29-2.48 (m, 3H), 2.09-2.22 (m, 1H), 1.39-1.51 (m, 3H), 1.21-1.33 (m, 3H). |

TABLE 4-continued
| Selected compounds of the present disclosure. | | |
|---|---|---|
| Compound No. | Structure | Analytical data |
| 323a | 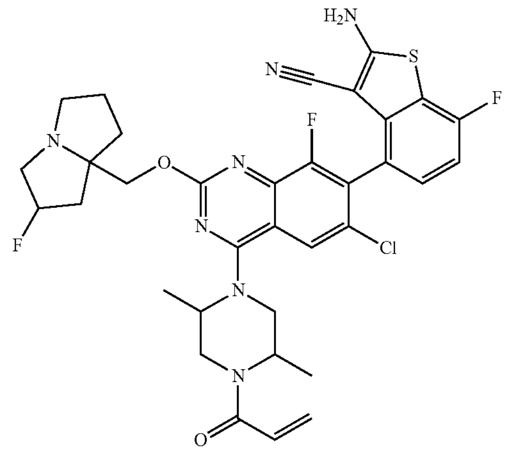 [SMILES: C=CC(=O)N1CC(C)N(c2nc(OCC34CCCN3CC(F)C4)nc3c(F)c(-c4ccc(F)c5sc(N)c(C#N)c45)c(Cl)cc23)CC1C] | |
| 324 | 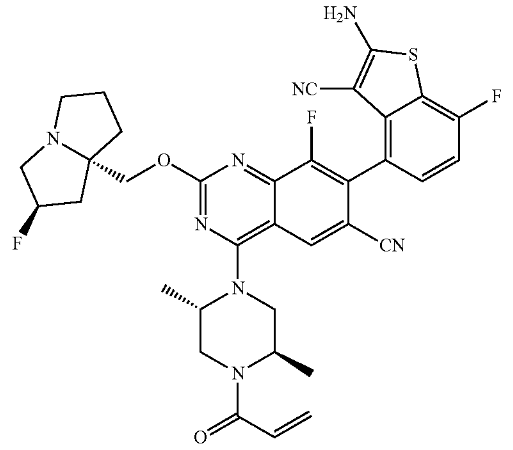 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)c(C#N)cc23)C[C@H]1C] | LCMS m/z [M + 1]: 687.1 $^{1}$HNMR (400 MHz, $CD_3OD$) δ 8.05-8.00 (m, 1H), 7.34-7.31 (m, 1H), 7.06 (t, 1H), 6.64-6.52 (m, 1H), 6.40 (t, 1H), 5.80 (d, 1H), 5.71 (s, 1H), 5.59 (s, 1H), 5.38 (s, 0.5H), 5.24 (s, 0.5H), 5.05-4.73 (m, 2H), 4.42-4.08 (m, 4H), 3.95-3.83 (m, 2H), 3.71 (d, 1H), 3.52-3.44 (m, 1H), 3.27-3.20 (m, 2H), 3.08-2.94 (m, 1H), 2.30-2.15 (m, 3H), 1.96-1.80 (m, 2H), 1.43-1.37 (m, 3H), 1.27-1.17 (m, 3H). |
| 324a | 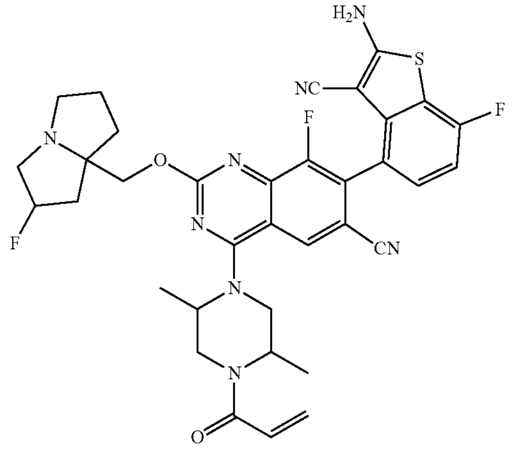 [SMILES: C=CC(=O)N1CC(C)N(c2nc(OCC34CCCN3CC(F)C4)nc3c(F)c(-c4ccc(F)c5sc(N)c(C#N)c45)c(C#N)cc23)CC1C] | |

TABLE 4-continued
| Selected compounds of the present disclosure. | | |
|---|---|---|
| Compound No. | Structure | Analytical data |
| 325 | 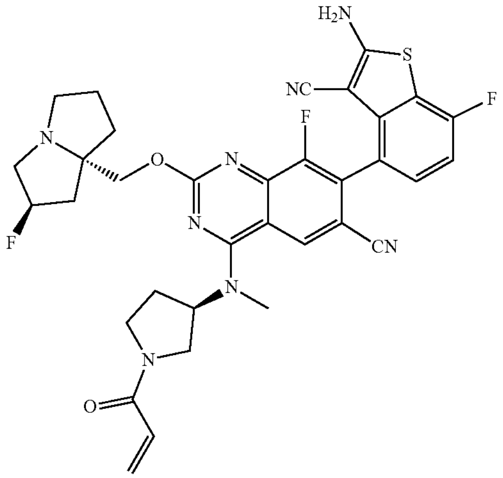 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(C#N)cc23)C1] | LCMS m/z [M + 1]: 673.1 $^1$HNMR (400 MHz, $CD_3OD$) δ $^1$HNMR (400 MHz, CD3OD) δ 8.45 (s, 1H), 7.36-7.33 (m, 1H), 7.09 (t, 1H), 6.72-6.63 (m, 1H), 6.35-6.31 (m, 1H), 5.82-5.77 (m, 1H), 5.40 (s, 0.5H), 5.39-5.33 (m, 1H), 5.27 (s, 0.5H), 4.42-3.88 (m, 4H), 3.81-3.69 (m, 1H), 3.68-3.53 (m, 1H), 3.49 (s, 3H), 3.29-3.22 (m, 2H), 2.52-2.12 (m, 5H), 2.09-1.96 (m, 2H), 1.96-1.84 (m, 1H), 1.35-1.31 (m, 1H) |
| 325a | 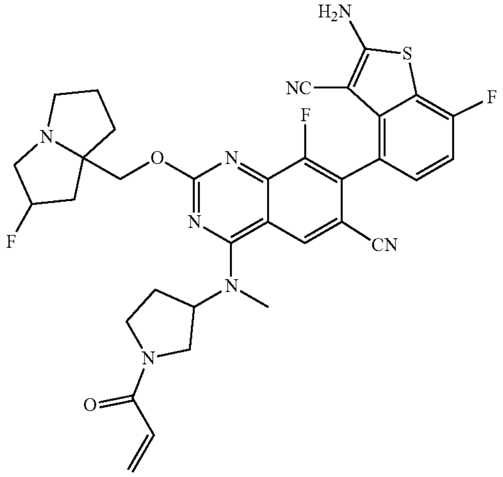 [SMILES: C=CC(=O)N1CCC(N(C)c2nc(OCC34CCCN3CC(F)C4)nc3c(F)c(-c4ccc(F)c5sc(N)c(C#N)c45)c(C#N)cc23)C1] | |
| 326 | 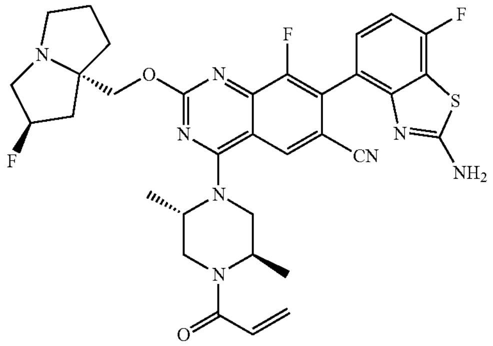 [SMILES: C=CC(=O)N1C[C@H](C)N(c2nc(OC[C@@]34CCCN3C[C@H](F)C4)nc3c(F)c(-c4ccc(F)c5sc(N)nc45)c(C#N)cc23)C[C@H]1C] | LCMS m/z [M + 1]: 663.1 $^1$HNMR (400 MHz, $CD_3OD$) δ 8.24 (d, 1H), 7.37 (q, 1H), 7.04 (t, 1H), 6.86-6.77 (m, 1H), 6.33-6.27 (m, 1H), 5.86-5.81 (m, 1H), 5.40 (s, 0.5H), 5.26 (s, 0.5H), 5.06-4.95 (m, 1H), 4.56-4.47 (m, 1H), 4.36-4.24 (m, 3H), 4.11-3.97 (m, 1H), 3.94-3.88 (m, 1H), 3.26 (d, 2H), 3.08-3.02 (m, 1H), 2.41-2.12 (m, 3H), 2.08-1.86 (m, 3H), 1.49-1.43 (m, 3H), 1.32-1.30 (m, 4H). |

TABLE 4-continued
| Compound No. | Structure | Analytical data |
|---|---|---|
| 326a | 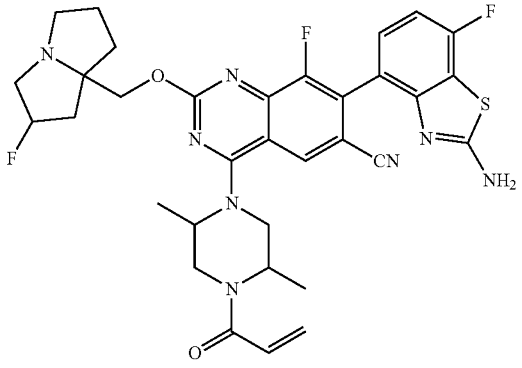 [SMILES: C=CC(=O)N1CC(C)N(c2nc(OCC34CCCN3CC(F)C4)nc3c(F)c(-c4ccc(F)c5sc(N)nc45)c(C#N)cc23)CC1C] | |
| 327 | 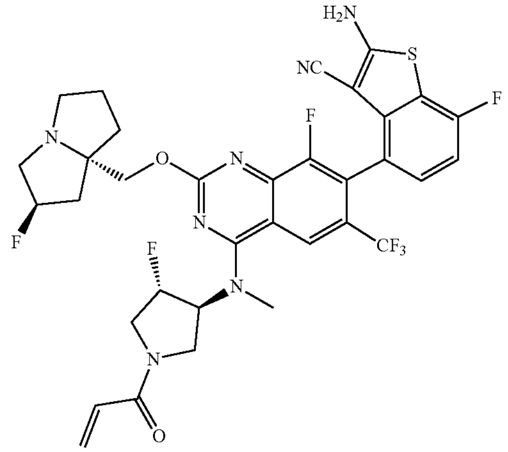 [SMILES: C=CC(=O)N1C[C@H](F)[C@@H](N(C)c2nc(OC[C@@]34CCCN3C[C@H](F)C4)nc3c(F)c(-c4ccc(F)c5sc(N)c(C#N)c45)c(C(F)(F)F)cc23)C1] | LCMS m/z [M + 1]: 734.2 $^1$HNMR (400 MHz, $CD_3OD$) δ 8.41-8.45 (m, 1H), 7.20-7.26 (m, 1H), 7.03 (t, J = 8.8 Hz, 1H), 6.62-6.72 (m, 1H), 6.32-6.4 (m, 1H), 5.73-5.88 (m, 1H), 5.47-5.72 (m, 2H), 5.15-5.38 (m, 1H), 4.57-4.78 (m, 2H), 4.18-4.39 (m, 2H), 3.80-4.10 (m, 5H), 3.58 (d, J = 20.4 Hz, 1H), 3.42-3.53 (m, 1H), 2.50-2.75 (m, 2H), 2.26-2.46 (m, 3H), 2.05-2.22 (m, 1H). |
| 327a | 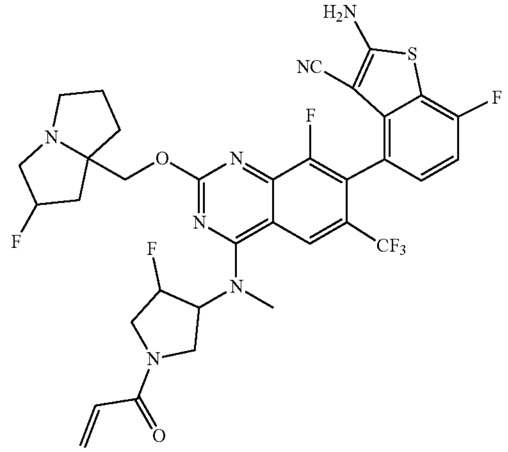 [SMILES: C=CC(=O)N1CC(F)C(N(C)c2nc(OCC34CCCN3CC(F)C4)nc3c(F)c(-c4ccc(F)c5sc(N)c(C#N)c45)c(C(F)(F)F)cc23)C1] | |
Selected compounds of the present disclosure.

TABLE 4-continued
Selected compounds of the present disclosure.
| Compound No. | Structure | Analytical data |
| --- | --- | --- |
| 328 | 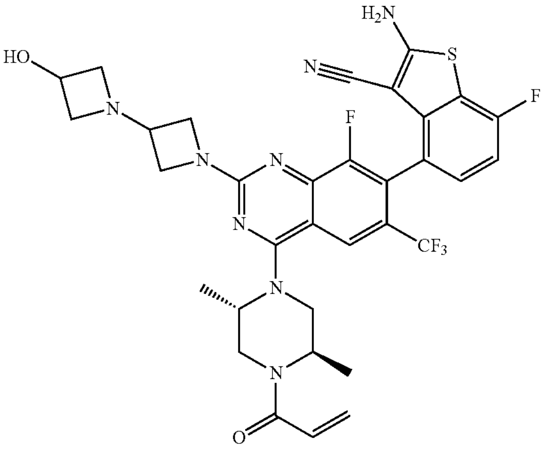 [SMILES: C=CC(=O)N1C[C@H](C)N(c2nc(N3CC(N4CC(O)C4)C3)nc3c(F)c(-c4ccc(F)c5sc(N)c(C#N)c45)c(C(F)(F)F)cc23)C[C@H]1C] | LCMS m/z [M + 1]: 699.3 $^{1}$HNMR (400 MHz, $CD_3OD$) δ 8.05 (s, 1H), 7.15-7.26 (m, 1H), 7.02 (t, J = 8.8 Hz, 1H), 6.73-6.89 (m, 1H), 6.23-6.34 (m, 1H), 5.77-5.85 (m, 1H), 4.76-4.84 (m, 1H), 4.65-4.75 (m, 1H), 4.38-4.65 (m, 6H), 4.23-4.35 (m, 3H), 4.01-4.14 (m, 2H), 3.78-3.95 (m, 2H), 3.44-3.55 (m, 1H), 1.43-1.55 (m, 3H), 1.25-1.40 (m, 3H). |
| 328a | 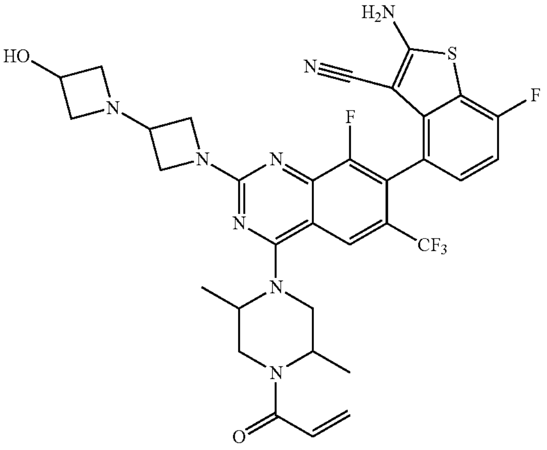 [SMILES: C=CC(=O)N1CC(C)N(c2nc(N3CC(N4CC(O)C4)C3)nc3c(F)c(-c4ccc(F)c5sc(N)c(C#N)c45)c(C(F)(F)F)cc23)CC1C] | |
| 329 | 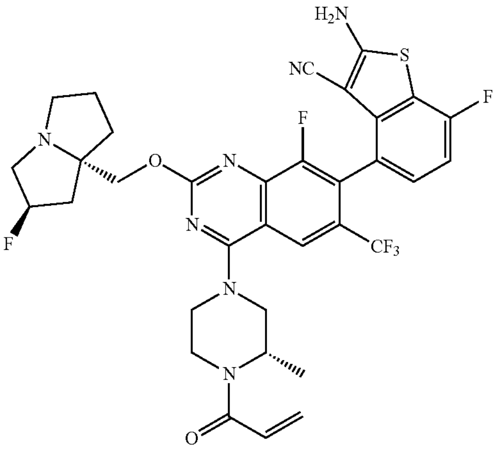 [SMILES: C=CC(=O)N1CCN(c2nc(OC[C@@]34CCCN3C[C@H](F)C4)nc3c(F)c(-c4ccc(F)c5sc(N)c(C#N)c45)c(C(F)(F)F)cc23)C[C@@H]1C] | LCMS m/z [M + 1]: 716.2 $^{1}$HNMR (400 MHz, $CD_3OD$) δ 8.28 (s, 1H), 7.22-7.25 (m, 1H), 7.03 (t, J = 8.8 Hz, 1H), 6.75-6.92 (m, 1H), 5.79-5.82 (m, 1H), 5.57 (d, J = 51.2 Hz, 1H), 4.52-4.78 (m, 3H), 4.22-4.50 (m, 3H), 3.83-4.05 (m, 5H), 3.31-3.48 (m, 2H), 2.17-2.64 (m, 6H), 1.29-1.32 (m, 3H). |

TABLE 4-continued
| Selected compounds of the present disclosure. | | |
|---|---|---|
| Compound No. | Structure | Analytical data |
| 329a | 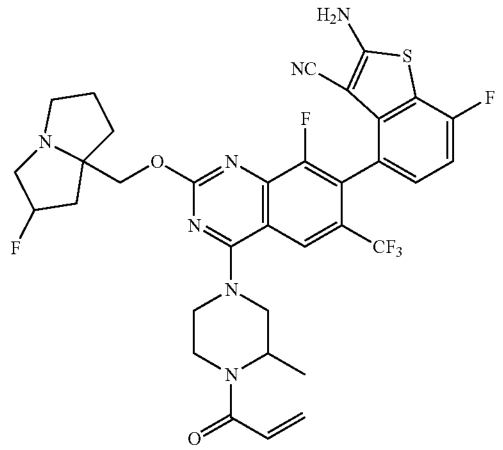 [SMILES: C=CC(=O)N1CCN(c2nc(OCC34CCCN3CC(F)C4)nc3c(F)c(-c4ccc(F)c5sc(N)c(C#N)c45)c(C(F)(F)F)cc23)CC1C] | |
| 330 | 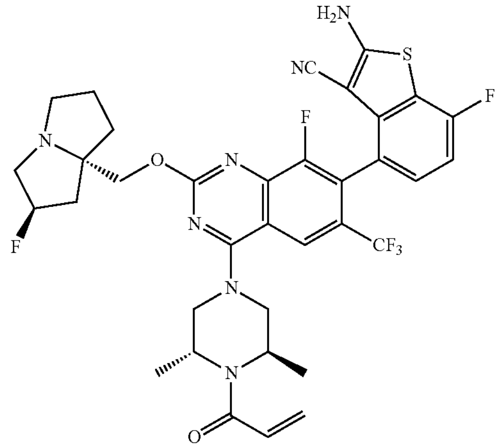 [SMILES: C=CC(=O)N1[C@H](C)CN(c2nc(OC[C@@]34CCCN3C[C@H](F)C4)nc3c(F)c(-c4ccc(F)c5sc(N)c(C#N)c45)c(C(F)(F)F)cc23)C[C@H]1C] | LCMS m/z [M + 1]: 730.4<br>$^1$HNMR (400 MHz, $CD_3OD$) δ 8.38 (s, 1H), 7.22-7.25 (m, 1H), 7.04 (t, J = 8.8 Hz, 1H), 6.75-6.92 (m, 1H), 6.38 (d, J = 16.0 Hz, 1H), 5.84 (d, J = 10.4 Hz, 1H), 5.48 (d, J = 51.2 Hz, 1H), 4.52-4.78 (m, 3H), 4.22-4.50 (m, 3H), 3.83-4.05 (m, 5H), 3.31-3.48 (m, 1H), 2.17-2.64 (m, 6H), 1.29-1.40 (m, 6H). |
| 330a | 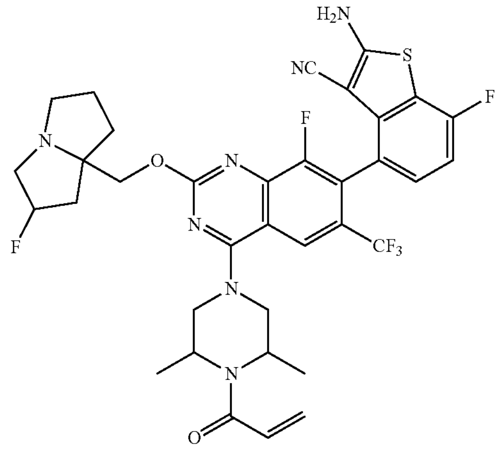 [SMILES: C=CC(=O)N1C(C)CN(c2nc(OCC34CCCN3CC(F)C4)nc3c(F)c(-c4ccc(F)c5sc(N)c(C#N)c45)c(C(F)(F)F)cc23)CC1C] | |

TABLE 4-continued
Selected compounds of the present disclosure.
| Compound No. | Structure | Analytical data |
|---|---|---|
| 331 | 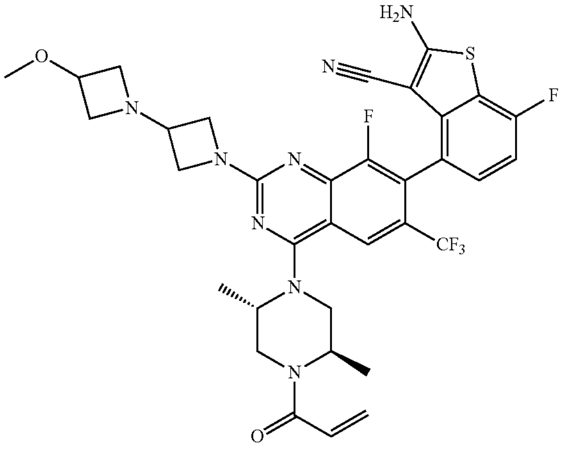 [SMILES: C=CC(=O)N1C[C@H](C)N(c2nc(N3CC(N4CC(OC)C4)C3)nc3c(F)c(-c4ccc(F)c5sc(N)c(C#N)c45)c(C(F)(F)F)cc23)C[C@H]1C] | LCMS m/z [M + 1]: 713.4 $^1$HNMR (400 MHz, $CD_3OD$) δ 8.06 (s, 1H), 7.21 (t, J = 8.56 Hz, 1H), 7.02 (t, J = 9.2 Hz, 1H), 6.74-6.89 (m, 1H), 6.29 (dd, J = 16.4, 6.2 Hz, 1H), 5.81 (t, J = 7.6 Hz, 1H), 4.95-5.0 (m, 1H), 4.45-4.63 (m, 6H), 4.17-4.34 (m, 6H), 3.75-4.02 (m, 2H), 3.46-3.54 (m, 1H), 3.37 (s, 3H), 1.47-1.53 (m, 3H), 1.12-1.39 (m, 3H). |
| 331a | 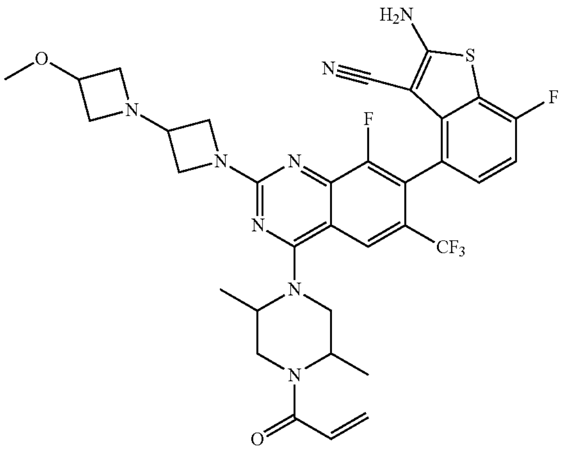 [SMILES: C=CC(=O)N1CC(C)N(c2nc(N3CC(N4CC(OC)C4)C3)nc3c(F)c(-c4ccc(F)c5sc(N)c(C#N)c45)c(C(F)(F)F)cc23)CC1C] | |
| 332 | 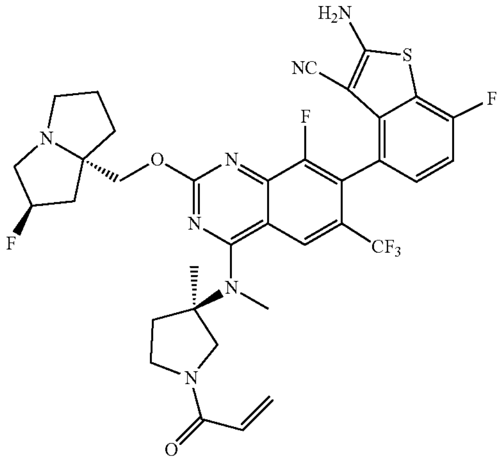 | LCMS m/z [M + 1]: 713.4 $^1$HNMR (400 MHz, $CD_3OD$) δ 8.06 (s, 1H), 7.21 (t, J = 8.56 Hz, 1H), 7.02 (t, J = 9.2 Hz, 1H), 6.74-6.89 (m, 1H), 6.29 (dd, J = 16.4, 6.2 Hz, 1H), 5.81 (t, J = 7.6 Hz, 1H), 4.95-5.0 (m, 1H), 4.45-4.63 (m, 6H), 4.17-4.34 (m, 6H), 3.75-4.02 (m, 2H), 3.46-3.54 (m, 1H), 3.37 (s, 3H), 1.47-1.53 (m, 3H), 1.12-1.39 (m, 3H). |

TABLE 4-continued
| Selected compounds of the present disclosure. | | |
|---|---|---|
| Compound No. | Structure | Analytical data |
| 332a | 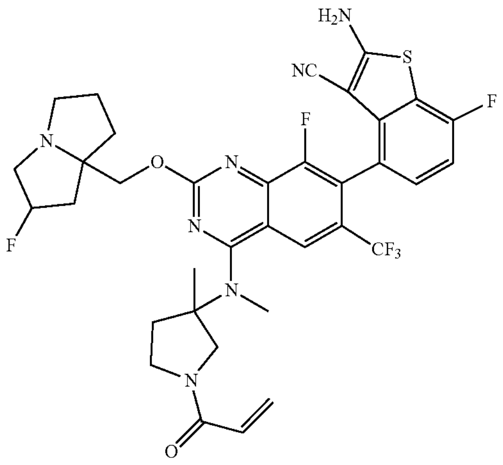 [SMILES: C=CC(=O)N1CCC(C)(N(C)c2nc(OCC34CCCN3CC(F)C4)nc3c(F)c(-c4ccc(F)c5sc(N)c(C#N)c45)c(C(F)(F)F)cc23)C1] | |
| 333 | 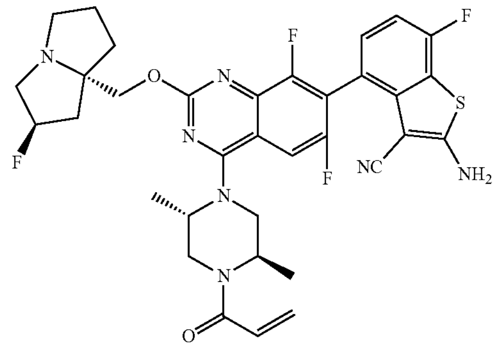 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)c(F)cc23)C[C@H]1C] | LCMS m/z [M + 1]: 680.3<br>$^1$HNMR (400 MHz, $CD_3OD$) δ 8.32 (s, 1H), 7.19-7.29 (m, 1H), 7.03 (t, J = 8.8 Hz, 1H), 6.58-6.72 (m, 1H), 6.26-6.41 (m, 1H), 5.75-5.82 (m, 1H), 5.57 (d, J = 52.0 Hz, 1H), 4.53-4.74 (m, 3H), 3.64-4.03 (m, 6H), 3.45-3.58 (m, 4H), 2.30-2.73 (m, 7H), 2.21-2.24 (m, 1H), 1.70 (s, 3H). |
| 333a | 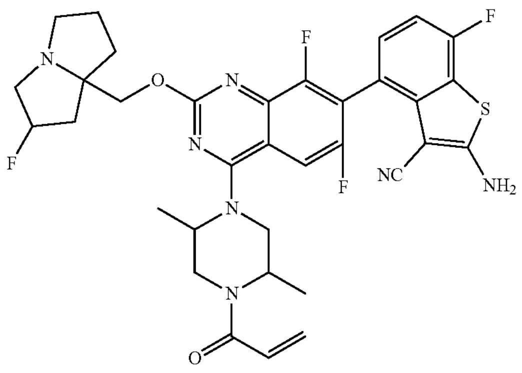 [SMILES: C=CC(=O)N1CC(C)N(c2nc(OCC34CCCN3CC(F)C4)nc3c(F)c(-c4ccc(F)c5sc(N)c(C#N)c45)c(F)cc23)CC1C] | |

TABLE 4-continued
| Selected compounds of the present disclosure. | | |
|---|---|---|
| Compound No. | Structure | Analytical data |
| 334 | 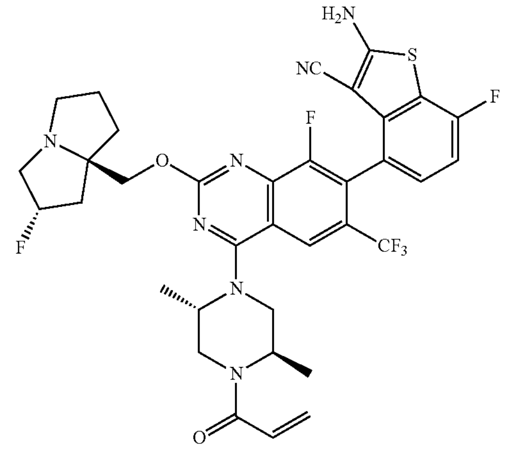 [SMILES: C=CC(=O)N1C[C@H](C)N(c2nc(OC[C@]34CCCN3C[C@@H](F)C4)nc3c(F)c(-c4ccc(F)c5sc(N)c(C#N)c45)c(C(F)(F)F)cc23)C[C@H]1C] | LCMS m/z [M + 1]: 730.3 $^1$HNMR (400 MHz, $CD_3OD$) δ 7.66 (s, 1H), 7.31-7.32 (m, 1H), 7.07 (t, J = 8.8 Hz, 1H), 6.73-6.85 (m, 1H), 6.30-6.32 (m, 1H), 5.82-5.84 (m, 1H), 5.56 (d, J = 51.6 Hz, 1H), 4.91-5.05 (m, 1H), 4.60-4.78 (m, 2H), 4.34-4.55 (m, 2H), 3.86-4.04 (m, 5H), 3.47-3.71 (m, 2H), 2.34-2.64 (m, 6H), 1.22-1.45 (m, 6H). |
| 334a | 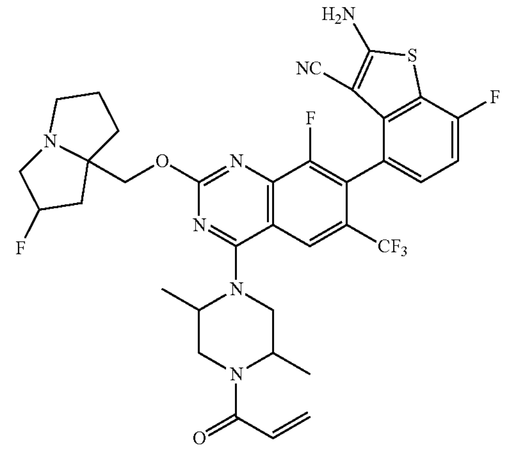 [SMILES: C=CC(=O)N1CC(C)N(c2nc(OCC34CCCN3CC(F)C4)nc3c(F)c(-c4ccc(F)c5sc(N)c(C#N)c45)c(C(F)(F)F)cc23)CC1C] | |
| 335 | 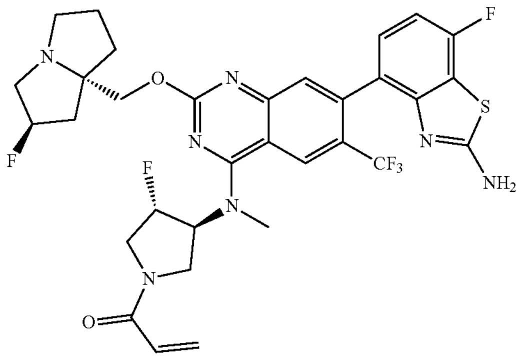 [SMILES: C=CC(=O)N1C[C@H](F)[C@@H](N(C)c2nc(OC[C@@]34CCCN3C[C@H](F)C4)nc3cc(-c4ccc(F)c5sc(N)nc45)c(C(F)(F)F)cc23)C1] | LCMS m/z [M + 1]: 692.2 $^1$HNMR (400 MHz, $CD_3OD$) δ 8.59-8.65 (d, J = 8.8 Hz, 1H), 7.59 (s, 1H), 7.17-7.25 (m, 1H), 6.98 (t, J = 8.8 Hz, 1H), 6.64-6.73 (m, 1H), 6.33-6.40 (m, 1H), 5.79-5.88 (m, 1H), 5.49-5.76 (m, 2H), 5.17-5.44 (m, 1H), 4.60-4.75 (m, 2H), 4.19-4.39 (m, 2H), 3.80-4.08 (m, 5H), 3.58-3.62 (m, 3H), 3.42-3.53 (m, 1H), 2.55-2.75 (m, 2H), 2.28-2.45 (m, 3H), 2.10-2.24 (m, 1H). |

TABLE 4-continued
| Selected compounds of the present disclosure. | | |
|---|---|---|
| Compound No. | Structure | Analytical data |
| 335a | 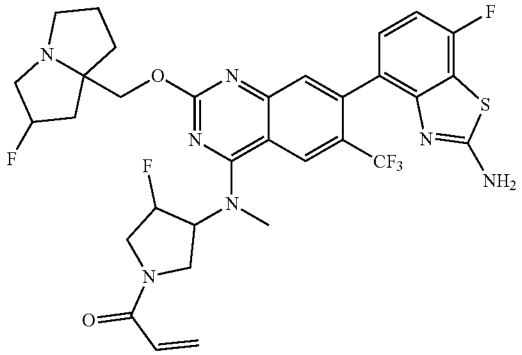 [SMILES: C=CC(=O)N1CC(F)C(N(C)c2nc(OCC34CCCN3CC(F)C4)nc3cc(-c4ccc(F)c5sc(N)nc45)c(C(F)(F)F)cc23)C1] | |
| 336 | 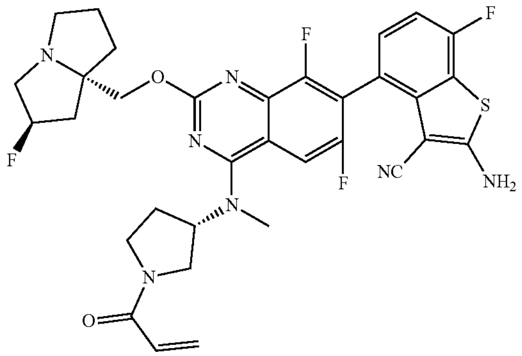 [SMILES: C=CC(=O)N1CC[C@H](N(C)c2nc(OC[C@@]34CCCN3C[C@H](F)C4)nc3c(F)c(-c4ccc(F)c5sc(N)c(C#N)c45)c(F)cc23)C1] | LCMS m/z [M + 1]: 666.3 $^1$HNMR (400 MHz, $CD_3OD$) δ 7.82-7.84 (m, 1H), 7.29-7.32 (m, 1H), 7.06 (t, J = 8.8 Hz, 1H), 6.62-6.71 (m, 1H), 6.30-6.34 (m, 1H), 5.76-5.81 (m, 1H), 5.47-5.60 (d, J = 51.6 Hz, 1H), 5.20-5.33 (m, 1H), 4.65-4.71 (m, 2H), 3.71-4.14 (m, 6H), 3.45-3.58 (m, 5H), 2.13-2.70 (m, 8H). |
| 336a | 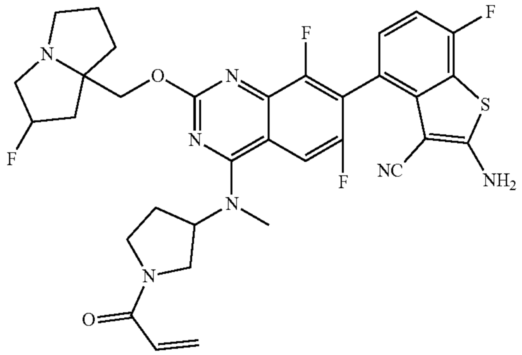 [SMILES: C=CC(=O)N1CCC(N(C)c2nc(OCC34CCCN3CC(F)C4)nc3c(F)c(-c4ccc(F)c5sc(N)c(C#N)c45)c(F)cc23)C1] | |
| 337 | 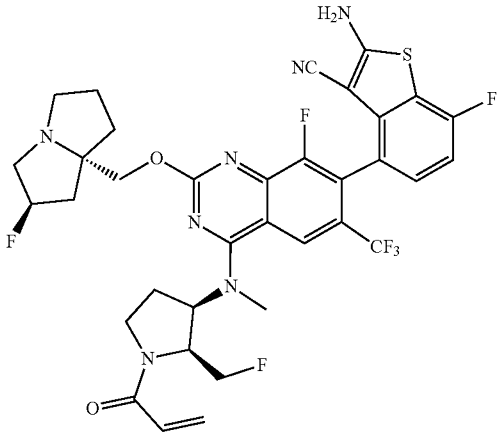 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(C(F)(F)F)cc23)[C@H]1CF] | LCMS m/z [M + 1]: 748.4 $^1$HNMR (400 MHz, $CD_3OD$) δ 8.43 (s, 1H), 7.22-7.25 (m, 1H), 7.03 (t, J = 8.8 Hz, 1H), 6.74-6.93 (m, 1H), 6.22-6.28 (m, 1H), 5.78-5.89 (m, 1H), 5.29-5.62 (m, 2H), 4.99-5.17 (m, 2H), 4.41-4.77 (m, 3H), 3.83-4.08 (m, 3H), 3.42-3.67 (m, 5H), 2.99-3.25 (m, 1H), 2.00-2.75 (m, 8H). |

TABLE 4-continued
Selected compounds of the present disclosure.
| Compound No. | Structure | Analytical data |
|---|---|---|
| 337a | 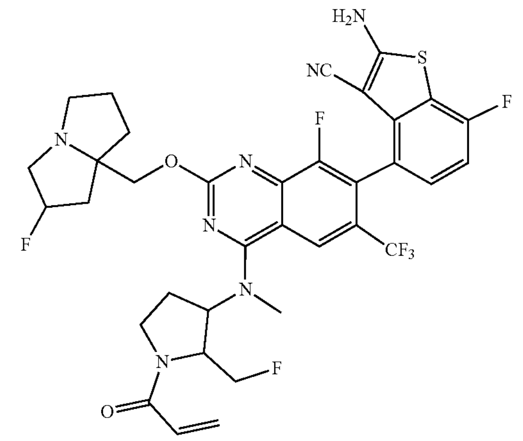 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1CF] | |
| 338 | 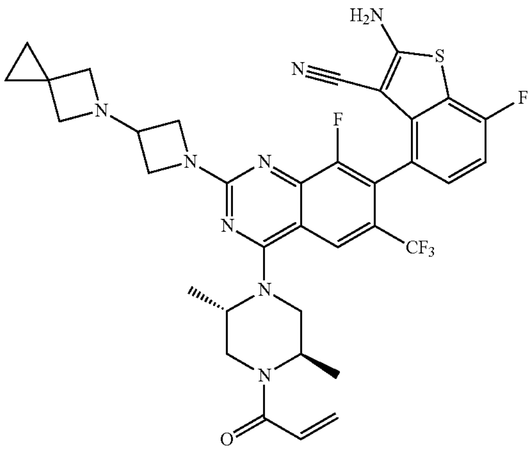 [SMILES: C=CC(=O)N1C[C@H](C)N(c2nc(N3CC(N4CC5(CC5)C4)C3)nc3c(F)c(-c4ccc(F)c5sc(N)c(C#N)c45)c(C(F)(F)F)cc23)C[C@H]1C] | LCMS m/z [M + 1]: 709.4 $^1$HNMR (400 MHz, $CD_3OD$) δ 8.08 (s, 1H), 7.22 (t, J = 7.80 Hz, 1H), 7.03 (t, J = 9.0 Hz, 1H), 6.74-6.89 (m, 1H), 6.29 (dd, J = 16.6, 6.4 Hz, 1H), 5.82 (t, J = 7.8 Hz, 1H), 4.95-5.0 (m, 1H), 4.57-4.66 (m, 4H), 4.25-4.35 (s, 7H), 3.79-4.03 (m, 2H), 3.45-3.57 (m, 1H), 1.42-1.54 (m, 3H), 1.25-1.39 (m, 3H), 0.86 (s, 4H). |
| 338a | 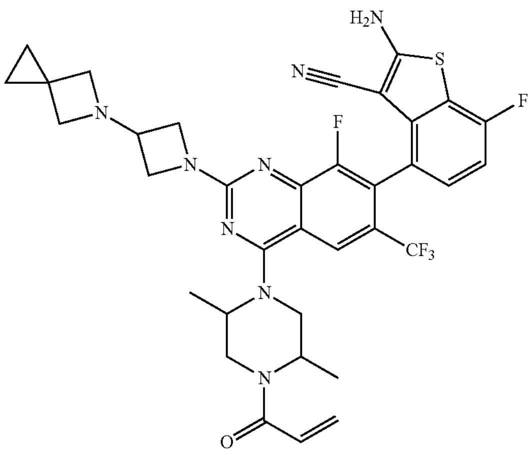 [SMILES: C=CC(=O)N1CC(C)N(c2nc(N3CC(N4CC5(CC5)C4)C3)nc3c(F)c(-c4ccc(F)c5sc(N)c(C#N)c45)c(C(F)(F)F)cc23)CC1C] | |

TABLE 4-continued
| Selected compounds of the present disclosure. | | |
|---|---|---|
| Compound No. | Structure | Analytical data |
| 339 | 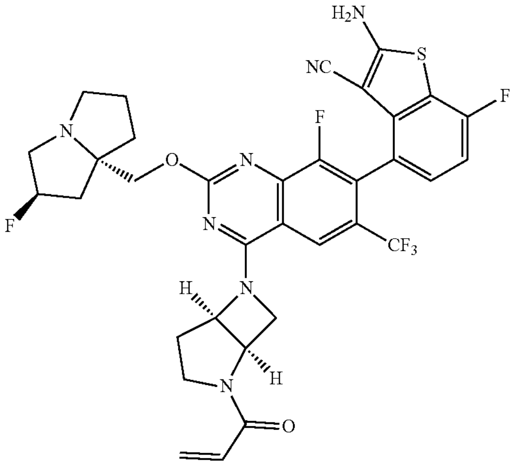 [SMILES: C=CC(=O)N1CC[C@@H]2[C@H]1CN2c1nc(OC[C@@]23CCCN2C[C@H](F)C3)nc2c(F)c(-c3ccc(F)c4sc(N)c(C#N)c34)c(C(F)(F)F)cc12] | LCMS m/z [M + 1]: 714.2 $^1$HNMR (400 MHz, $CD_3OD$) δ 8.09 (s, 1H), 7.17-7.26 (m, 1H), 7.02 (t, J = 9.2 Hz, 1H), 6.59-6.79 (m, 1H), 6.32-6.41 (m, 1H), 5.82-5.87 (m, 2H), 5.45-5.75 (m, 2H), 4.91-5.15 (m, 2H), 4.42-4.81 (m, 3H), 4.21-4.40 (m, 1H), 3.70-4.11 (m, 4H), 3.39-3.51 (m, 1H), 2.52-2.73 (m, 3H), 2.02-2.49 (m, 5H). |
| 339a | 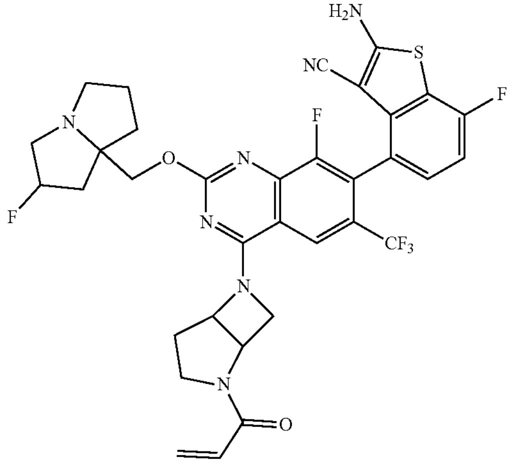 [SMILES: C=CC(=O)N1CCC2C1CN2c1nc(OCC23CCCN2CC(F)C3)nc2c(F)c(-c3ccc(F)c4sc(N)c(C#N)c34)c(C(F)(F)F)cc12] | |
| 340 | 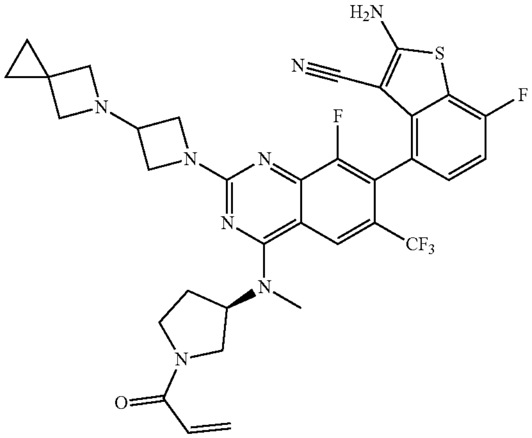 [SMILES: C=CC(=O)N1CC[C@@H](N(C)c2nc(N3CC(N4CC5(CC5)C4)C3)nc3c(F)c(-c4ccc(F)c5sc(N)c(C#N)c45)c(C(F)(F)F)cc23)C1] | LCMS m/z [M + 1]: 695.4 $^1$HNMR (400 MHz, $CD_3OD$) δ 8.31 (s, 1H), 7.18-7.23 (m, 1H), 7.04 (t, J = 8.8 Hz, 1H), 6.63-6.67 (m, 1H), 6.30-6.34 (m, 1H), 5.78-5.81 (m, 1H), 5.31-5.41 (m, 1H), 4.61-4.73 (m, 3H), 4.43-4.49 (m, 6H), 3.52-4.15 (m, 4H), 3.30 (s, 3H), 2.40-2.52 (m, 2H), 0.85 (s, 4H). |

TABLE 4-continued
| Selected compounds of the present disclosure. | | |
|---|---|---|
| Compound No. | Structure | Analytical data |
| 340a | 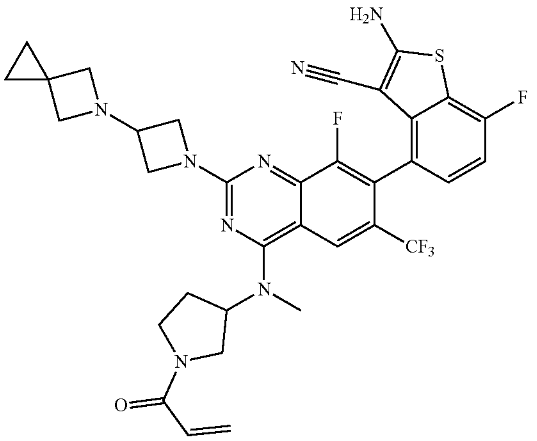 [SMILES: C=CC(=O)N1CCC(N(C)c2nc(N3CC(N4CC5(CC5)C4)C3)nc3c(F)c(-c4ccc(F)c5sc(N)c(C#N)c45)c(C(F)(F)F)cc23)C1] | |
| 341 | 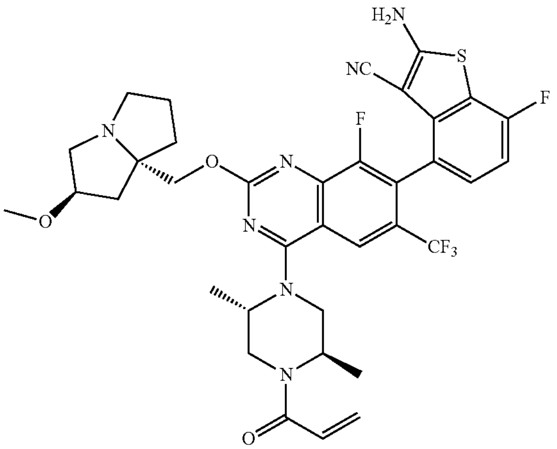 [SMILES: C=CC(=O)N1C[C@H](C)N(c2nc(OC[C@@]34CCCN3C[C@H](OC)C4)nc3c(F)c(-c4ccc(F)c5sc(N)c(C#N)c45)c(C(F)(F)F)cc23)C[C@H]1C] | LCMS m/z [M + 1]: 742.2 $^1$HNMR (400 MHz, $CD_3OD$) δ 8.18 (s, 1H), 7.20-7.28 (m, 1H), 7.03 (t, J = 8.8 Hz, 1H), 6.72-6.90 (m, 1H), 6.23-6.35 (m, 1H), 5.80-5.90 (m, 1H), 4.90-5.05 (m, 2H), 4.61-4.69 (m, 2H), 4.26-4.58 (m, 2H), 3.73-4.08 (m, 4H), 3.61-3.68 (m, 1H), 3.49-3.55 (m, 2H), 3.39 (s, 3H), 2.26-2.50 (m, 5H), 2.07-2.16 (m, 1H) 1.45-1.56 (m, 3H), 1.27-1.39 (m, 3H). |
| 341a | 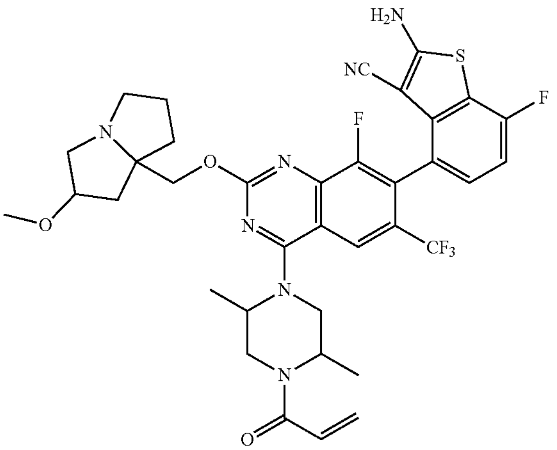 [SMILES: C=CC(=O)N1CC(C)N(c2nc(OCC34CCCN3CC(OC)C4)nc3c(F)c(-c4ccc(F)c5sc(N)c(C#N)c45)c(C(F)(F)F)cc23)CC1C] | |

TABLE 4-continued
| Selected compounds of the present disclosure. | | |
|---|---|---|
| Compound No. | Structure | Analytical data |
| 342 | 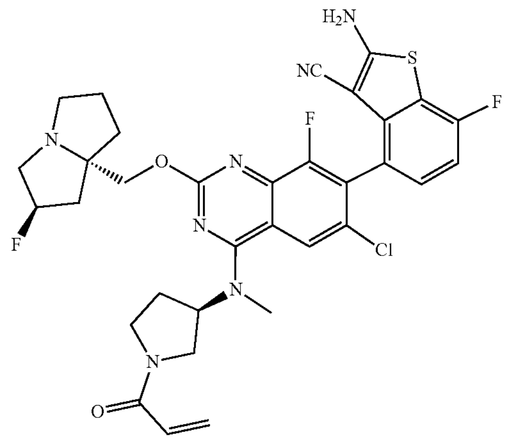 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(Cl)cc23)C1] | LCMS m/z [M + 1]: 682.3<br>$^1$HNMR (400 MHz, $CD_3OD$) δ 8.15 (s, 1H), 7.21-7.26 (m, 1H), 7.06 (d, J = 8.8 Hz, 1H), 6.65-6.69 (m, 1H), 6.32 (d, J = 16.8 Hz, 1H), 5.79 (t, J = 8.4 Hz, 1H), 5.56 (d, J = 51.6 Hz, 1H), 5.21-5.41 (m, 1H), 4.62-4.77 (m, 2H), 3.72-4.04 (m, 6H), 3.49-3.65 (m, 5H), 3.45-3.54 (m, 6H), 2.02-2.62 (m, 8H). |
| 342a | 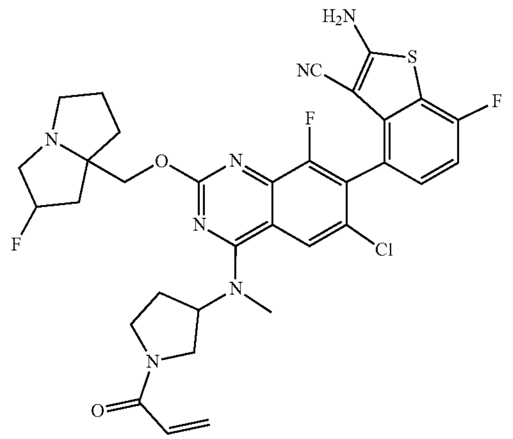 [SMILES: C=CC(=O)N1CCC(N(C)c2nc(OCC34CCCN3CC(F)C4)nc3c(F)c(-c4ccc(F)c5sc(N)c(C#N)c45)c(Cl)cc23)C1] | |
| 343 | 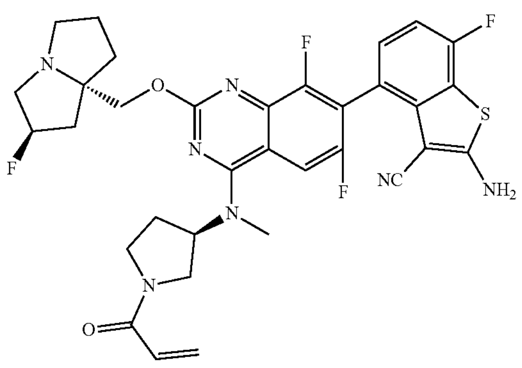 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(F)cc23)C1] | LCMS m/z [M + 1]: 666.3<br>$^1$HNMR (400 MHz, $CD_3OD$) δ 7.83 (d, J = 9.5 Hz, 1H), 7.27-7.33 (m, 1H), 7.06 (t, J = 8.8 Hz 1H), 6.60-6.71 (m, 1H), 6.32 (d, J = 16.8 Hz, 1H), 5.79 (t, J = 8.8 Hz, 1H), 5.54 (d, J = 51.2 Hz, 1H), 5.18-5.34 (m, 1H), 4.66 (s, 2H), 3.63-4.21 (m, 6H), 3.40-3.62 (m, 5H), 2.28-2.73 (m, 7H), 2.11-2.21 (m, 1H). |

TABLE 4-continued
| Selected compounds of the present disclosure. | | |
|---|---|---|
| Compound No. | Structure | Analytical data |
| 343a | 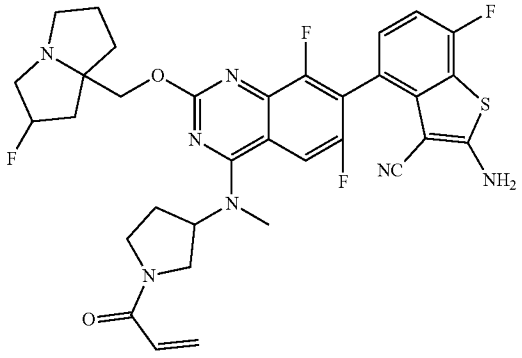 | |
| 345 | 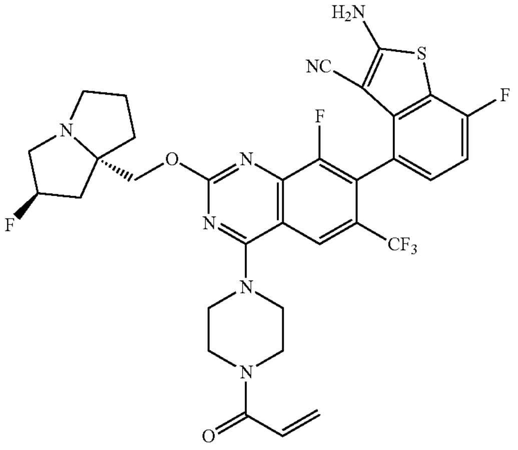 [SMILES: C=CC(=O)N1CCN(c2nc(OC[C@@]34CCCN3C[C@H](F)C4)nc3c(F)c(-c4ccc(F)c5sc(N)c(C#N)c45)c(C(F)(F)F)cc23)CC1] | LCMS m/z [M + 1]: 702.3 $^1$HNMR (400 MHz, $CD_3OD$) δ 8.26 (s, 1H), 7.19-7.29 (m, 1H), 7.03 (t, J = 8.8 Hz, 1H), 6.75-6.86 (m, 1H), 6.30 (d, J = 16.8 Hz, 1H), 5.82 (d, J = 10.4 Hz, 1H), 5.56 (d, J = 51.6 Hz, 1H), 4.59-4.80 (m, 2H), 4.17 (s, 4H), 3.84-4.10 (m, 7H), 3.41-3.52 (m, 1H), 2.53-2.80 (m, 2H), 2.29-2.48 (m, 3H), 2.07-2.23 (m, 1H). |
| 345a | 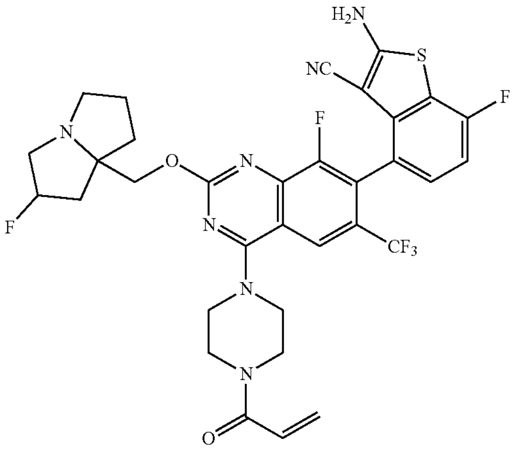 [SMILES: C=CC(=O)N1CCN(c2nc(OCC34CCCN3CC(F)C4)nc3c(F)c(-c4ccc(F)c5sc(N)c(C#N)c45)c(C(F)(F)F)cc23)CC1] | |

TABLE 4-continued
| Selected compounds of the present disclosure. | | |
|---|---|---|
| Compound No. | Structure | Analytical data |
| 346 | 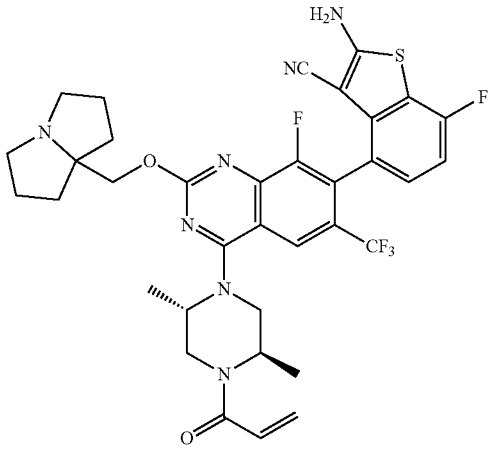 [SMILES: C=CC(=O)N1C[C@H](C)N(c2nc(OCC34CCCN3CCC4)nc3c(F)c(-c4ccc(F)c5sc(N)c(C#N)c45)c(C(F)(F)F)cc23)C[C@H]1C] | LCMS m/z [M + 1]: 712.2<br>$^1$HNMR (400 MHz, $CD_3OD$) δ 8.16 (s, 1H), 7.20-7.27 (m, 1H), 7.03 (t, J = 9.2 Hz, 1H), 6.75-6.89 (m, 1H), 6.29 (dd, J = 16.8, 6.8 Hz, 1H), 5.76-5.84 (m, 1H), 4.92-5.02 (m, 1H), 4.26-4.61 (m, 5H), 3.86-4.05 (m, 2H), 3.45-3.55 (m, 2H), 3.03-3.13 (s, 2H), 1.95-2.26 (m, 8H), 1.45-1.55 (m, 3H), 1.25-1.38 (m, 3H). |
| 346a | 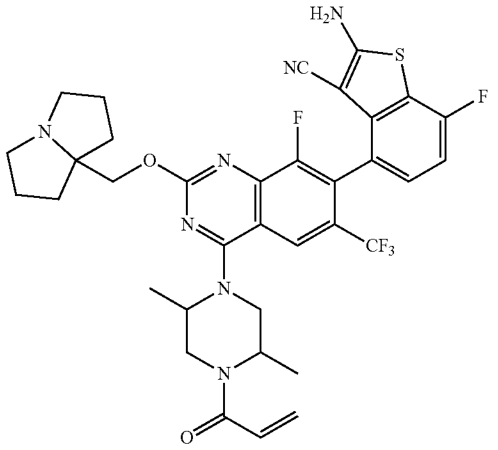 [SMILES: C=CC(=O)N1CC(C)N(c2nc(OCC34CCCN3CCC4)nc3c(F)c(-c4ccc(F)c5sc(N)c(C#N)c45)c(C(F)(F)F)cc23)CC1C] | |
| 347 | 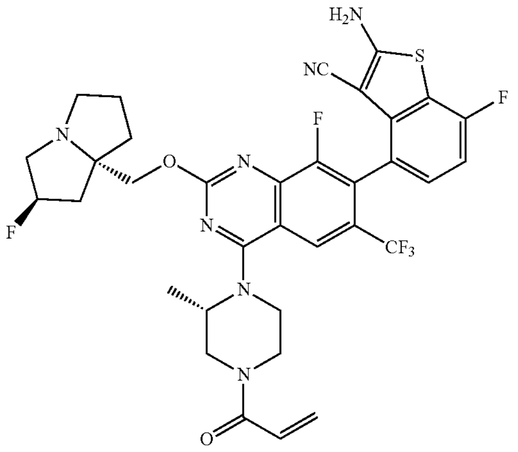 [SMILES: C=CC(=O)N1CCN(c2nc(OC[C@@]34CCCN3C[C@H](F)C4)nc3c(F)c(-c4ccc(F)c5sc(N)c(C#N)c45)c(C(F)(F)F)cc23)[C@@H](C)C1] | LCMS m/z [M + 1]: 716.4<br>$^1$HNMR (400 MHz, $CD_3OD$) δ 8.13 (s, 1H), 7.20-7.23 (m, 1H), 7.02 (t, J = 8.8 Hz, 1H), 6.76-6.89 (m, 1H), 6.30 (d, J = 16.8 Hz, 1H), 5.82 (d, J = 10.6 Hz, 1H), 5.38 (d, J = 54 Hz, 1H), 4.02-4.53 (m, 5H), 3.35-3.85 (m, 6H), 3.14-3.25 (m, 2H), 1.92-2.49 (m, 6H), 1.48-1.52 (m, 3H). |

TABLE 4-continued
Selected compounds of the present disclosure.
| Compound No. | Structure | Analytical data |
|---|---|---|
| 347a | 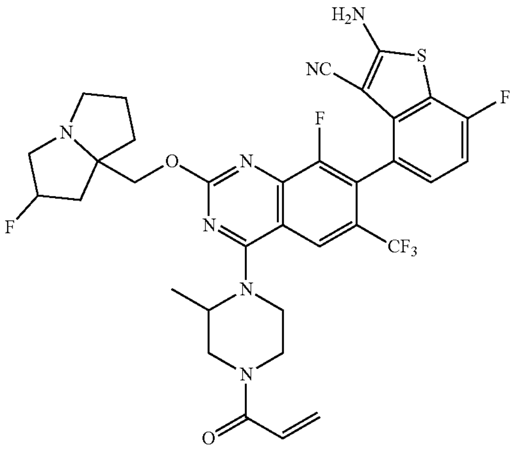 [SMILES: C=CC(=O)N1CCN(c2nc(OCC34CCCN3CC(F)C4)nc3c(F)c(-c4ccc(F)c5sc(N)c(C#N)c45)c(C(F)(F)F)cc23)C(C)C1] | |
| 348 | 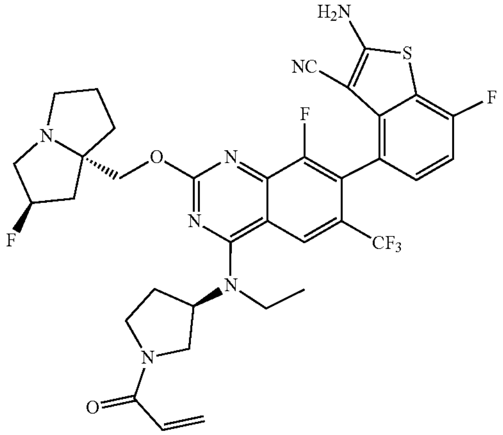 [SMILES: C=CC(=O)N1CC[C@@H](N(CC)c2nc(OC[C@@]34CCCN3C[C@H](F)C4)nc3c(F)c(-c4ccc(F)c5sc(N)c(C#N)c45)c(C(F)(F)F)cc23)C1] | LCMS m/z [M + 1]: 730.2 $^1$HNMR (400 MHz, $CD_3OD$) δ 8.27-8.32 (m, 1H), 7.20-7.27 (m, 1H), 7.03 (t, J = 9.2 Hz, 1H), 6.57-6.74 (m, 1H), 6.28-6.37 (m, 1H), 5.75-5.84 (m, 1H), 5.55 (d, J = 51.6 Hz, 1H), 4.97-5.07 (m, 1H), 4.52-4.74 (m, 2H), 3.39-4.18 (m, 10H), 2.04-2.76 (m, 8H), 1.45-1.58 (m, 3H). |
| 348a | 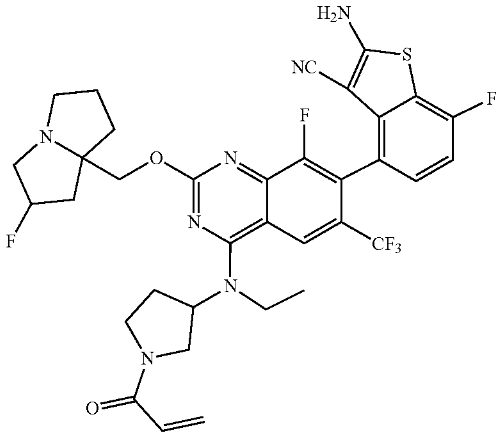 [SMILES: C=CC(=O)N1CCC(N(CC)c2nc(OCC34CCCN3CC(F)C4)nc3c(F)c(-c4ccc(F)c5sc(N)c(C#N)c45)c(C(F)(F)F)cc23)C1] | |

TABLE 4-continued
| Selected compounds of the present disclosure. | | |
|---|---|---|
| Compound No. | Structure | Analytical data |
| 349 | 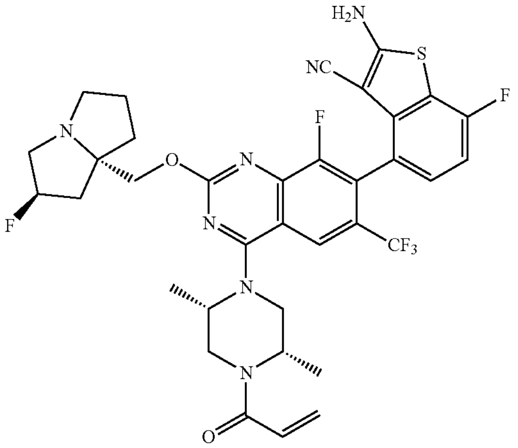 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)c(C(F)(F)F)cc23)C[C@@H]1C] | LCMS m/z [M + 1]: 730.2 $^1$HNMR (400 MHz, $CD_3OD$) δ 8.25 (s, 1H), 7.20-7.25 (m, 1H), 7.00-7.05 (m, 1H), 6.65-6.72 (m, 1H), 6.15-6.19 (m, 1H), 5.70-5.73 (m, 1H), 5.56 (d, J = 52 Hz, 1H), 4.58-4.74 (m, 5H), 3.83-4.08 (m, 3H), 3.44-3.47 (m, 2H), 2.13-2.77 (m, 6H), 1.28-1.62 (m, 6H). |
| 394a | 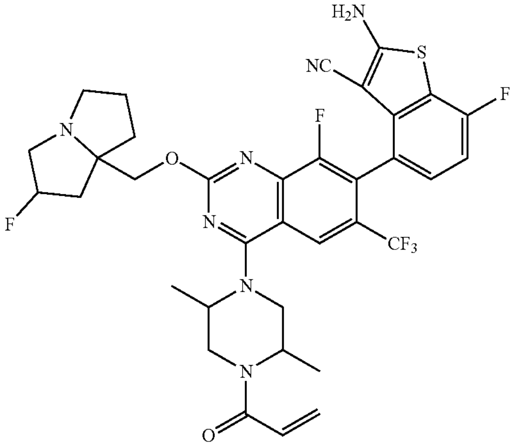 [SMILES: C=CC(=O)N1CC(C)N(c2nc(OCC34CCCN3CC(F)C4)nc3c(F)c(-c4ccc(F)c5sc(N)c(C#N)c45)c(C(F)(F)F)cc23)CC1C] | |
| 350 | 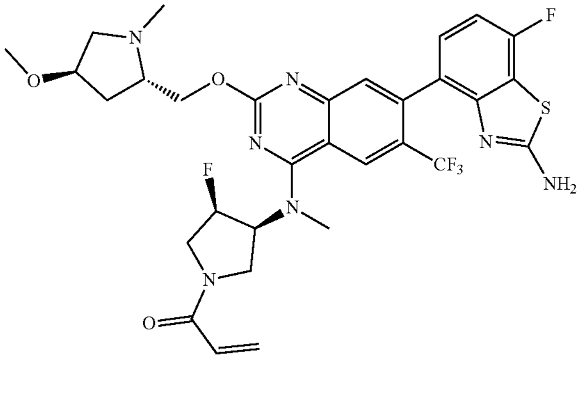 [SMILES: C=CC(=O)N1C[C@@H](F)[C@@H](N(C)c2nc(OC[C@@H]3C[C@@H](OC)CN3C)nc3cc(-c4ccc(F)c5sc(N)nc45)c(C(F)(F)F)cc23)C1] | LCMS m/z [M + 1]: 678.2 $^1$HNMR (400 MHz, $CD_3OD$) δ 8.78 (s, 1H), 7.63 (s, 1H), 7.25-7.30 (m, 1H), 7.02 (t, J = 9.0 Hz, 1H), 6.61-6.77 (m, 1H), 6.37 (d, J = 16.8 Hz, 1H), 5.80-5.86 (m, 1H), 5.67-5.71 (m, 1H), 5.26-5.49 (m, 1H), 4.95-5.0 (m, 1H),, 4.75-4.80 (m, 1H), 3.85-4.36 (m, 7H), 3.76 (s, 3H), 3.42-3.45 (m, 1H), 3.40 (s, 3H), 3.14 (s, 3H), 2.51-2.55 (m, 1H), 2.05-2.20 (m, 1H). |

TABLE 4-continued
| Selected compounds of the present disclosure. | | |
|---|---|---|
| Compound No. | Structure | Analytical data |
| 350a | 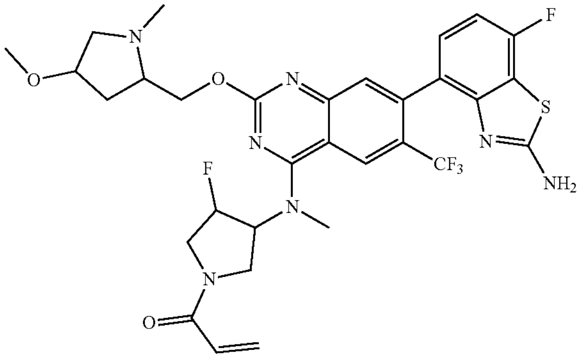 [SMILES: C=CC(=O)N1CC(F)C(N(C)c2nc(OCC3CC(OC)CN3C)nc3cc(-c4ccc(F)c5sc(N)nc45)c(C(F)(F)F)cc23)C1] | |
| 351 | 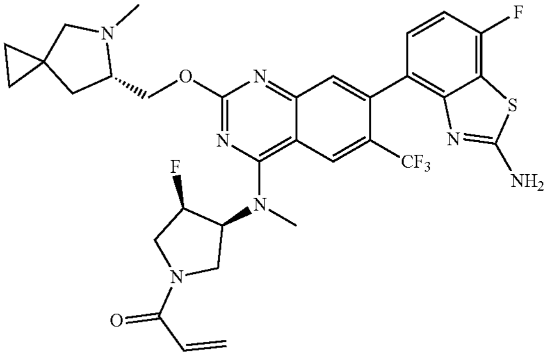 [SMILES: C=CC(=O)N1C[C@@H](F)[C@@H](N(C)c2nc(OC[C@@H]3CC4(CC4)CN3C)nc3cc(-c4ccc(F)c5sc(N)nc45)c(C(F)(F)F)cc23)C1] | LCMS m/z [M + 1]: 674.3 $^1$HNMR (400 MHz, $CD_3OD$) δ 8.66 (s, 1H), 7.62 (s, 1H), 7.21-7.25 (m, 1H), 7.00 (t, J = 8.8 Hz, 1H), 6.61-6.72 (m, 1H), 6.37 (d, J = 16.8 Hz, 1H), 5.83 (d, J = 10.6 Hz, 1H), 5.65-5.75 (m, 1H), 5.13-5.49 (m, 1H), 4.85-4.90 (m, 1H), 4.71-4.76 (m, 1H), 4.31-4.36 (m, 1H), 3.89-4.19 (m, 4H), 3.71 (s, 3H), 3.45 (d, J = 10.8 Hz, 1H), 3.36 (d, J = 11.6 Hz, 1H), 3.13 (s, 3H), 2.36-2.50 (m, 1H), 1.87-2.03 (m, 1H), 0.74-0.86 (m, 4H). |
| 351a | 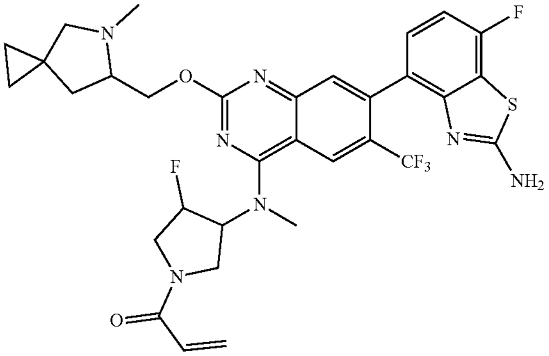 [SMILES: C=CC(=O)N1CC(F)C(N(C)c2nc(OCC3CC4(CC4)CN3C)nc3cc(-c4ccc(F)c5sc(N)nc45)c(C(F)(F)F)cc23)C1] | |
| 352 | 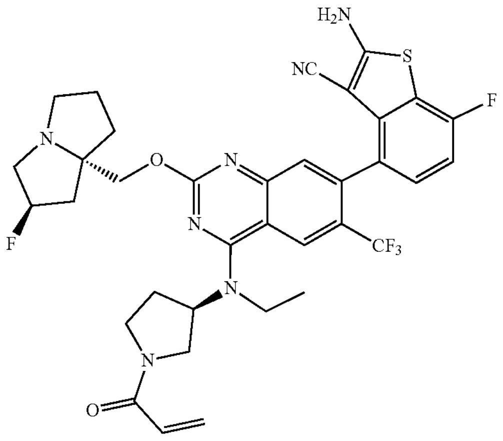 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(C(F)(F)F)cc23)C1] | LCMS m/z [M + 1]: 712.0 $^1$HNMR (400 MHz, $CD_3OD$) δ 8.47 (d, J = 9.5 Hz, 1H), 7.56 (s, 1H), 7.16-7.26 (m, 1H), 6.99 (t, J = 8.8 Hz, 1H), 6.58-6.77 (m, 1H), 6.33 (dd, J = 16.8, 4.4 Hz, 1H), 5.72-5.87 (m, 1H), 5.51 (d, J = 52 Hz, 1H), 5.00-5.13 (m, 1H), 4.53-4.72 (m, 2H), 3.38-4.24 (m, 10H), 2.06-2.82 (m, 8H), 1.48-1.56 (m, 3H). |

TABLE 4-continued
| Selected compounds of the present disclosure. | | |
|---|---|---|
| Compound No. | Structure | Analytical data |
| 352a | 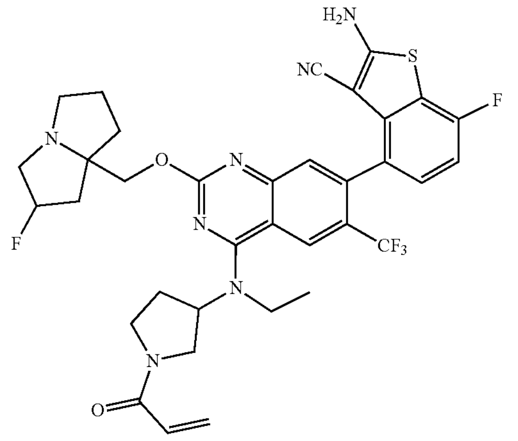 [SMILES: C=CC(=O)N1CCC(N(CC)c2nc(OCC34CCCN3CC(F)C4)nc3cc(-c4ccc(F)c5sc(N)c(C#N)c45)c(C(F)(F)F)cc23)C1] | |
| 353 | 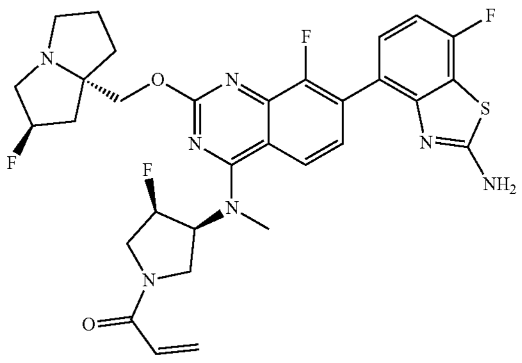 [SMILES: C=CC(=O)N1C[C@@H](F)[C@@H](N(C)c2nc(OC[C@@]34CCCN3C[C@H](F)C4)nc3c(F)c(-c4ccc(F)c5sc(N)nc45)ccc23)C1] | LCMS m/z [M + 1]: 642.3 $^1$HNMR (400 MHz, $CD_3OD$) δ 8.11 (d, J = 8.8 Hz, 1H), 7.57-7.61 (m, 1H), 7.35-7.45 (m, 1H), 7.03 (t, J = 8.8 Hz, 1H), 6.59-6.77 (m, 1H), 6.37 (d, J = 16.8 Hz, 1H), 5.65-5.86 (m, 2H), 5.55 (d, J = 52.0 Hz, 1H), 5.12-5.36 (m, 1H), 4.64-4.77 (m, 2H), 4.26-4.38 (m, 1H), 3.85-4.19 (m, 6H), 3.67 (d, J = 2.8 Hz, 3H), 3.41-3.52 (m, 1H), 2.55-2.72 (m, 2H), 2.29-2.50 (m, 3H), 2.07-2.20 (m, 1H). |
| 353a | 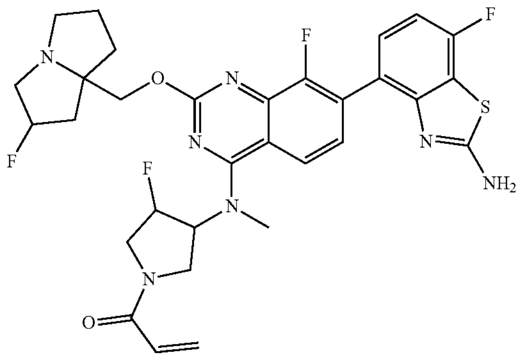 [SMILES: C=CC(=O)N1CC(F)C(N(C)c2nc(OCC34CCCN3CC(F)C4)nc3c(F)c(-c4ccc(F)c5sc(N)nc45)ccc23)C1] | |

TABLE 4-continued
| Selected compounds of the present disclosure. | | |
|---|---|---|
| Compound No. | Structure | Analytical data |
| 354 | 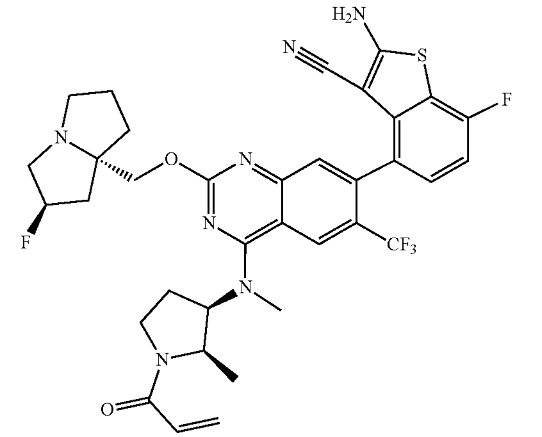 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(C(F)(F)F)cc23)[C@H]1C] | LCMS m/z [M + 1]: 712.2<br>$^1$HNMR (400 MHz, $CD_3OD$) δ 8.58-8.62 (m, 1H), 7.55-7.58 (m, 1H), 7.18-7.24 (m, 1H), 7.00 (t, J = 8.8 Hz, 1H), 6.62-6.74 (m, 1H), 6.29-6.40 (m, 1H), 5.80 (d, J = 10.4 Hz, 1H), 5.58 (d, J = 52.4 Hz, 1H), 4.90-5.13 (m, 2H), 4.63-4.77 (m, 2H), 3.85-4.04 (m, 4H), 3.55-3.84 (m, 4H), 3.44-3.53 (m, 1H), 2.11-2.81 (m, 8H), 1.09-1.22 (m, 3H). |
| 354a | 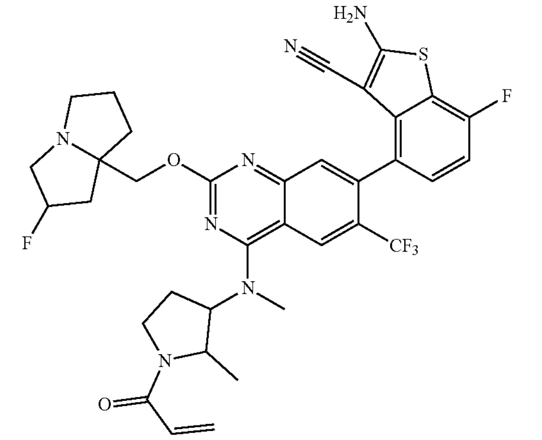 [SMILES: C=CC(=O)N1CCC(N(C)c2nc(OCC34CCCN3CC(F)C4)nc3cc(-c4ccc(F)c5sc(N)c(C#N)c45)c(C(F)(F)F)cc23)C1C] | |
| 355 | 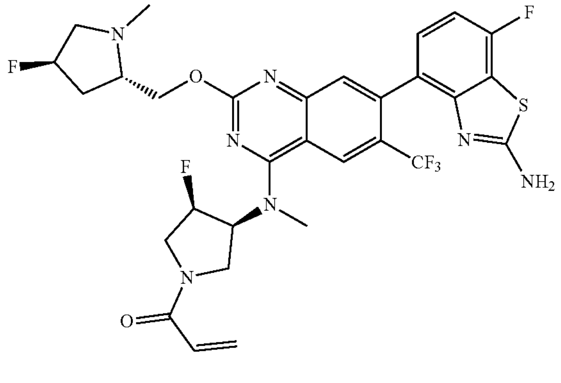 [SMILES: C=CC(=O)N1C[C@@H](F)[C@@H](N(C)c2nc(OC[C@@H]3C[C@@H](F)CN3C)nc3cc(-c4ccc(F)c5sc(N)nc45)c(C(F)(F)F)cc23)C1] | LCMS m/z [M + 1]: 666.2<br>$^1$HNMR (400 MHz, $CD_3OD$) δ 7.60 (s, 1H), 7.19-7.25 (m, 1H), 6.98 (t, J = 8.8 Hz, 1H), 6.62-6.76 (m, 1H), 6.32-6.44 (m, 1H), 5.66-5.88 (m, 2H), 5.42-5.55 (m, 1H), 5.15-5.35 (m, 1H), 4.92-5.02 (m, 2H), 4.70-4.78 (m, 1H), 4.24-4.37 (m, 2H), 3.90-4.21 (m, 4H), 3.63-3.81 (m, 4H), 3.18 (s, 3H), 2.63-2.73 (m, 1H), 2.33-2.45 (m, 1H). |

TABLE 4-continued
| Selected compounds of the present disclosure. | | |
|---|---|---|
| Compound No. | Structure | Analytical data |
| 355a | 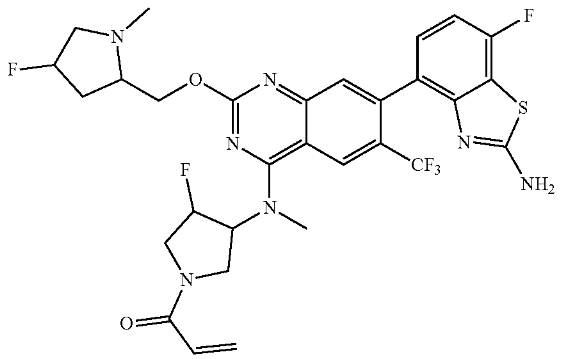 [SMILES: C=CC(=O)N1CC(F)C(N(C)c2nc(OCC3CC(F)CN3C)nc3cc(-c4ccc(F)c5sc(N)nc45)c(C(F)(F)F)cc23)C1] | |
| 356 | 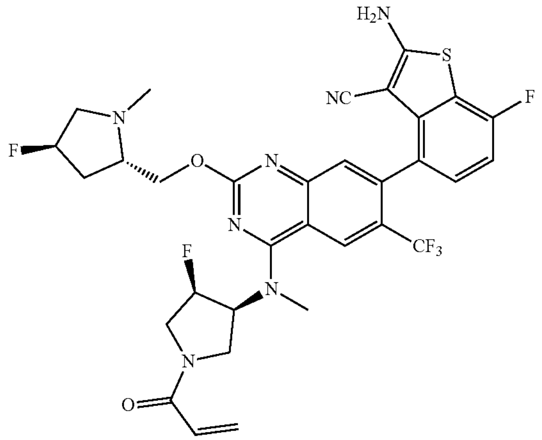 [SMILES: C=CC(=O)N1C[C@@H](F)[C@@H](N(C)c2nc(OC[C@@H]3C[C@@H](F)CN3C)nc3cc(-c4ccc(F)c5sc(N)c(C#N)c45)c(C(F)(F)F)cc23)C1] | LCMS m/z [M + 1]: 690.20 $^1$HNMR (400 MHz, $CD_3OD$) δ 7.59 (s, 1H), 7.18-7.25 (m, 1H), 7.00 (t, J = 8.8 Hz, 1H), 6.62-6.77 (m, 1H), 6.37 (d, J = 16.8 Hz, 1H), 5.67-5.86 (m, 2H), 5.49 (d, J = 52 Hz, 1H), 5.17-5.37 (m, 1H), 4.94-5.03 (m, 1H), 4.69-4.70 (m, 1H), 4.25-4.38 (m, 2H), 4.24-3.87 (m, 4H), 3.62-3.85 (m, 4H), 3.18 (s, 3H), 2.62-2.74 (m, 1H), 2.32-2.52 (m, 1H). |
| 356a | 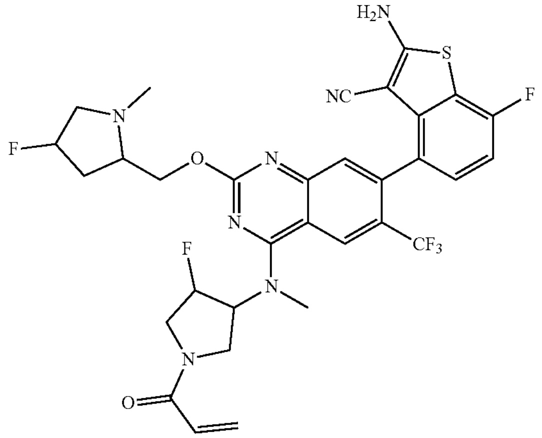 [SMILES: C=CC(=O)N1CC(F)C(N(C)c2nc(OCC3CC(F)CN3C)nc3cc(-c4ccc(F)c5sc(N)c(C#N)c45)c(C(F)(F)F)cc23)C1] | |

TABLE 4-continued
| Selected compounds of the present disclosure. | | |
|---|---|---|
| Compound No. | Structure | Analytical data |
| 357 | 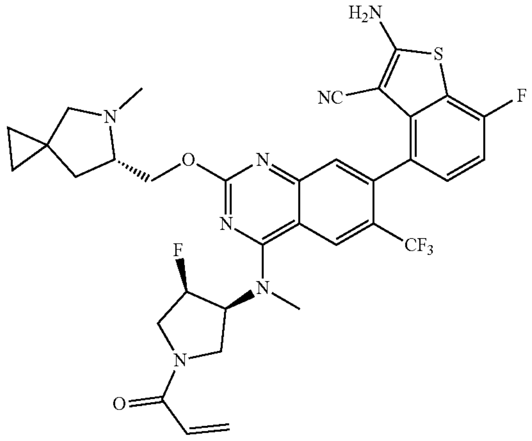 [SMILES: C=CC(=O)N1C[C@@H](F)[C@@H](N(C)c2nc(OC[C@@H]3CC4(CC4)CN3C)nc3cc(-c4ccc(F)c5sc(N)c(C#N)c45)c(C(F)(F)F)cc23)C1] | LCMS m/z [M + 1]: 698.3<br>$^1$HNMR (400 MHz, $CD_3OD$) δ 8.61 (d, J = 4.70 Hz, 1H), 7.61 (s, 1H), 7.20-7.25 (m, 1H), 7.00 (t, J = 8.8 Hz, 1H), 6.61-6.76 (m, 1H), 6.37 (d, J = 16.8 Hz, 1H), 5.67-5.89 (m, 2H), 5.23-5.49 (m, 1H), 4.80-4.96 (m, 1H), 4.71-4.81 (m, 1H), 4.28-4.40 (m, 1H), 3.89-4.22 (m, 4H), 3.71 (s, 3H), 3.45-3.49 (m, 1H), 3.36 (d, J = 10.4 Hz, 1H), 3.14 (s, 3H), 2.41-2.45 (m, 1H), 1.85-1.95 (m, 1H), 0.77-0.85 (m, 4H). |
| 357a | 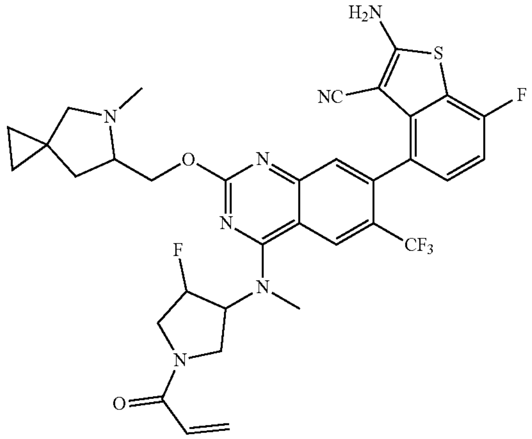 [SMILES: C=CC(=O)N1CC(F)C(N(C)c2nc(OCC3CC4(CC4)CN3C)nc3cc(-c4ccc(F)c5sc(N)c(C#N)c45)c(C(F)(F)F)cc23)C1] | |
| 358 | 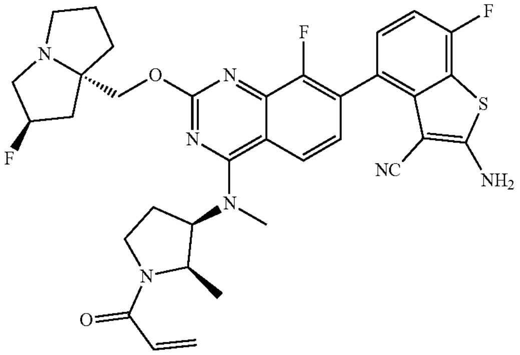 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)ccc23)[C@H]1C] | LCMS m/z [M + 1]: 662.24<br>$^1$HNMR (400 MHz, $CD_3OD$) δ 8.10-8.20 (m, 1H), 7.35-7.46 (m, 1H), 7.29 (dd, J = 8.4, 5.6 Hz, 1H), 7.05 (t, J = 8.8 Hz, 1H), 6.60-6.71 (m, 1H), 6.34 (t, J = 16.8 Hz, 1H), 5.79 (d, J = 10.4 Hz, 1H), 5.55 (d, J = 52.8 Hz, 1H), 4.90-5.12 (m, 2H), 4.59-4.87 (m, 3H), 3.78-4.10 (m, 4H), 3.64-3.73 (m, 3H), 3.42-3.54 (m, 1H), 2.55-2.78 (m, 3H), 2.27-2.54 (m, 4H), 2.05-2.22 (m, 1H), 1.05-1.22 (m, 3H). |

TABLE 4-continued
| Selected compounds of the present disclosure. | | |
|---|---|---|
| Compound No. | Structure | Analytical data |
| 358a | 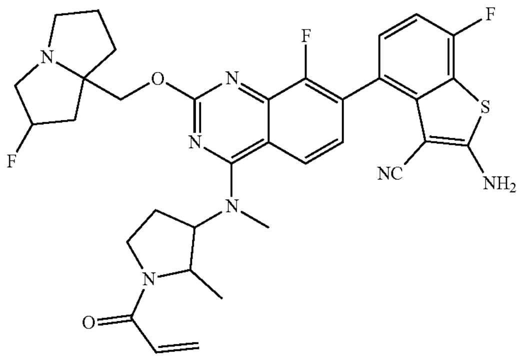 [SMILES: C=CC(=O)N1CCC(N(C)c2nc(OCC34CCCN3CC(F)C4)nc3c(F)c(-c4ccc(F)c5sc(N)c(C#N)c45)ccc23)C1C] | |
| 359 | 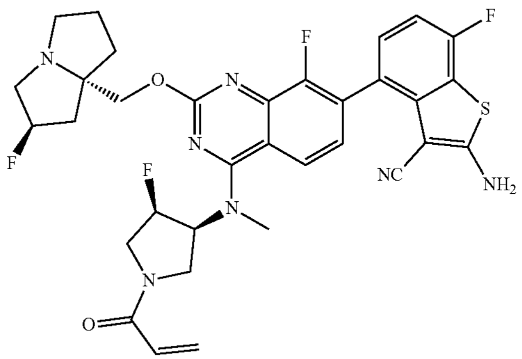 [SMILES: C=CC(=O)N1C[C@@H](F)[C@@H](N(C)c2nc(OC[C@@]34CCCN3C[C@H](F)C4)nc3c(F)c(-c4ccc(F)c5sc(N)c(C#N)c45)ccc23)C1] | LCMS m/z [M + 1]: 666.0 $^1$HNMR (400 MHz, $CD_3OD$) δ 8.13 (d, J = 7.6 Hz, 1H), 7.35-7.45 (m, 1H), 7.24-7.34 (m, 1H), 7.05 (t, J = 8.8 Hz, 1H), 6.56-6.77 (m, 1H), 6.36 (d, J = 16.8 Hz, 1H), 5.63-5.86 (m, 2H), 5.54 (d, J = 51.6 Hz, 1H), 5.10-5.32 (m, 1H), 4.73-4.85 (m, 1H), 4.54-4.69 (m, 1H), 4.23-4.37 (m, 1H), 3.73-4.18 (m, 6H), 3.67 (d, J = 3.2 Hz, 3H), 3.41-3.53 (m, 1H), 2.02-2.68 (m, 6H) |
| 359a | 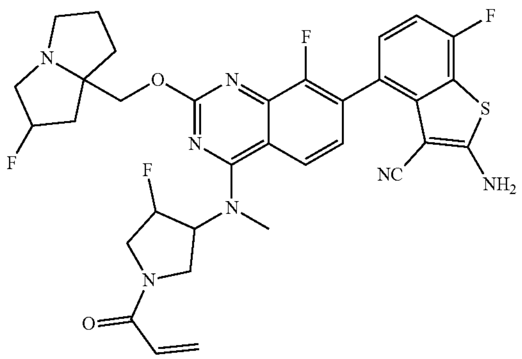 [SMILES: C=CC(=O)N1CC(F)C(N(C)c2nc(OCC34CCCN3CC(F)C4)nc3c(F)c(-c4ccc(F)c5sc(N)c(C#N)c45)ccc23)C1] | |
| 360 | 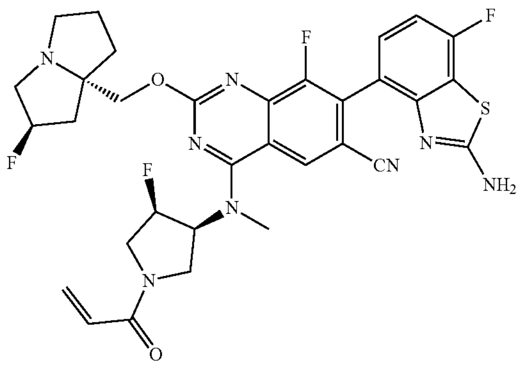 [SMILES: C=CC(=O)N1C[C@@H](F)[C@@H](N(C)c2nc(OC[C@@]34CCCN3C[C@H](F)C4)nc3c(F)c(-c4ccc(F)c5sc(N)nc45)c(C#N)cc23)C1] | LCMS m/z [M + 1]: 667 $^1$HNMR (400 MHz, $CD_3OD$) δ 8.49-8.58 (d, 1H), 7.35-7.45 (m, 1H), 7.05 (t, 1H), 6.61-6.79 (m, 1H), 6.38 (d, 1H), 5.78-5.93 (m, 1H), 5.65-5.75 (m, 1H), 5.48-5.59 (m, 1H), 5.36-5.47 (m, 1H), 5.12-5.37 (m, 2H), 4.52-4.66 (m, 1H), 4.41-4.52 (m, 1H), 4.26-4.41 (m, 1H), 4.12-4.25 (m, 1H), 3.97-4.11 (m, 1H), 3.74-3.96 (m, 2H), 3.45-3.75 (m, 3H), 3.54-3.65 (m, 1H), 2.42-2.63 (m, 2H), 2.26-2.41 (m, 1H), 2.12-2.25 (m, 2H), 1.99-2.11 (m, 1H). |

TABLE 4-continued
| Selected compounds of the present disclosure. | | |
|---|---|---|
| Compound No. | Structure | Analytical data |
| 360a | 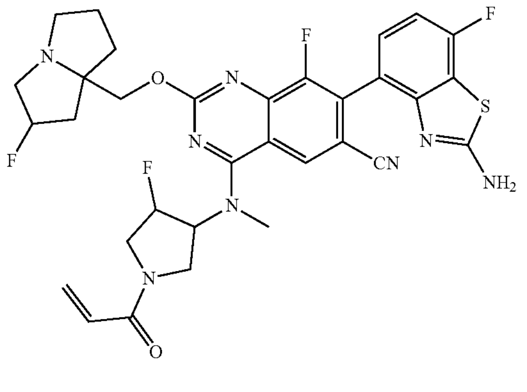 [SMILES: C=CC(=O)N1CC(F)C(N(C)c2nc(OCC34CCCN3CC(F)C4)nc3c(F)c(-c4ccc(F)c5sc(N)nc45)c(C#N)cc23)C1] | |
| 361 | 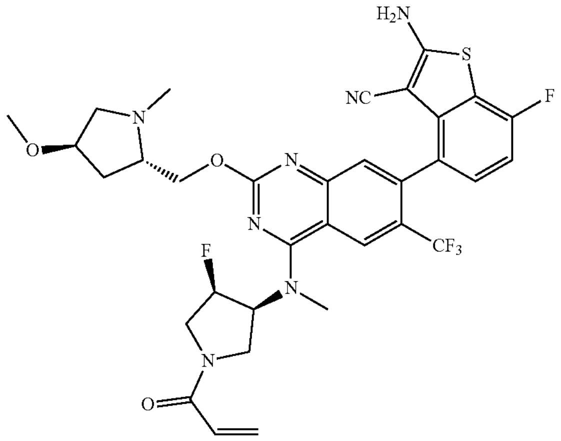 [SMILES: C=CC(=O)N1C[C@@H](F)[C@@H](N(C)c2nc(OC[C@@H]3C[C@@H](OC)CN3C)nc3cc(-c4ccc(F)c5sc(N)c(C#N)c45)c(C(F)(F)F)cc23)C1] | LCMS m/z [M + 1]: 702.3 $^1$HNMR (400 MHz, $CD_3OD$) δ 8.59 (s, 1H), 7.59 (s, 1H), 7.19-7.30 (m, 1H), 6.99-7.10 (m, 1H), 6.61-6.75 (m, 1H), 6.30-6.39 (m, 1H), 5.70-5.90 (m, 2H), 5.17-5.35 (m, 1H), 4.68-4.80 (m, 1H), 3.85-4.32 (m, 7H), 3.69 (s, 3H), 3.41 (s, 3H), 3.35-3.38 (m, 2H), 3.15 (s, 3H), 2.45-2.60 (m, 1H), 2.10-2.18 (m, 1H). |
| 361a | 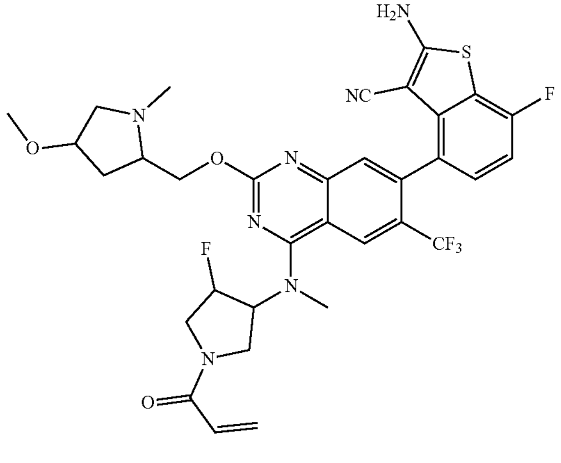 [SMILES: C=CC(=O)N1CC(F)C(N(C)c2nc(OCC3CC(OC)CN3C)nc3cc(-c4ccc(F)c5sc(N)c(C#N)c45)c(C(F)(F)F)cc23)C1] | |

TABLE 4-continued
| Selected compounds of the present disclosure. | | |
|---|---|---|
| Compound No. | Structure | Analytical data |
| 362 | 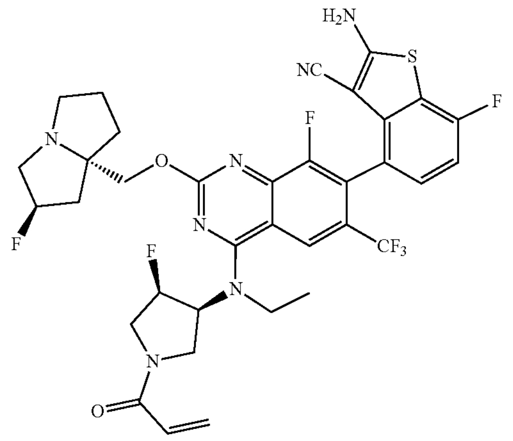 [SMILES: C=CC(=O)N1C[C@@H](F)[C@@H](N(CC)c2nc(OC[C@@]34CCCN3C[C@H](F)C4)nc3c(F)c(-c4ccc(F)c5sc(N)c(C#N)c45)c(C(F)(F)F)cc23)C1] | LCMS m/z [M + 1]: 748.0 $^1$HNMR (400 MHz, $CD_3OD$) δ 8.38 (s, 1H), 7.24 (s, 1H), 7.03 (t, J = 8.56 Hz, 1H), 6.60-6.76 (m, 1H), 6.36 (d, J = 16.9 Hz, 1H), 5.62-5.84 (m, 2H), 5.56 (d, J = 52.92 Hz, 1H), 5.02-5.22 (m, 2H), 3.47-4.77 (m, 11H), 2.16-2.71 (m, 6H), 1.44-1.45 (m, 3H). |
| 362a | 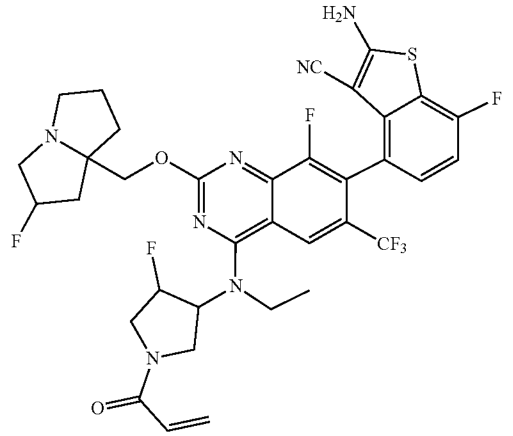 [SMILES: C=CC(=O)N1CC(F)C(N(CC)c2nc(OCC34CCCN3CC(F)C4)nc3c(F)c(-c4ccc(F)c5sc(N)c(C#N)c45)c(C(F)(F)F)cc23)C1] | |
| 363 | 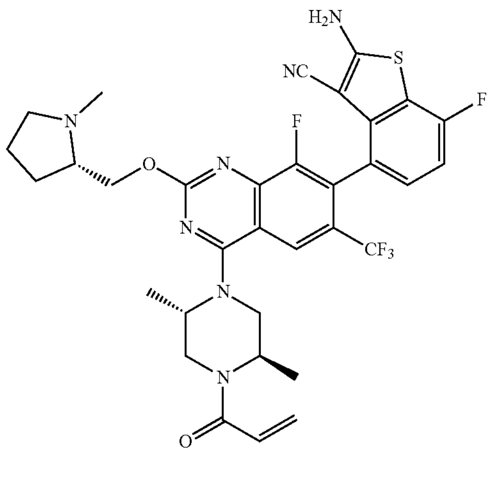 [SMILES: C=CC(=O)N1C[C@H](C)N(c2nc(OC[C@@H]3CCCN3C)nc3c(F)c(-c4ccc(F)c5sc(N)c(C#N)c45)c(C(F)(F)F)cc23)C[C@H]1C] | LCMS m/z [M + 1]: 686.3 $^1$HNMR (400 MHz, $CD_3OD$) δ 8.18 (s, 1H), 7.22-7.25 (m, 1H), 7.03 (t, J = 8 Hz, 1H), 6.73-6.90 (m, 1H), 6.26-6.32 (m, 1H), 5.80-5.82 (m, 1H), 4.89-4.97 (m, 2H), 4.29-4.69 (m, 3H), 3.84-4.07 (m, 3H), 3.51-3.73 (m, 3H), 3.09 (s, 3H), 2.09-2.40 (m, 4H), 1.48-1.51 (m, 3H), 1.26-1.33 (m, 3H). |

TABLE 4-continued
| Selected compounds of the present disclosure. | | |
|---|---|---|
| Compound No. | Structure | Analytical data |
| 363a | 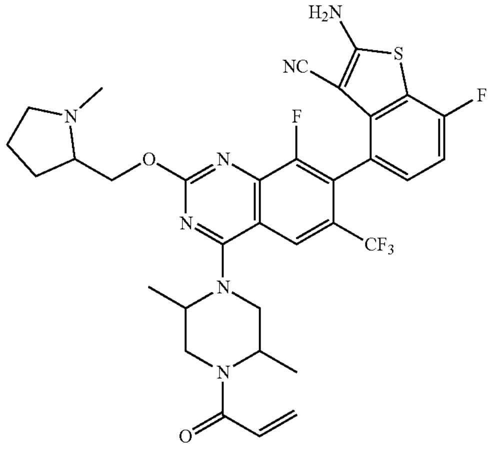 [SMILES: C=CC(=O)N1CC(C)N(c2nc(OCC3CCCN3C)nc3c(F)c(-c4ccc(F)c5sc(N)c(C#N)c45)c(C(F)(F)F)cc23)CC1C] | |
| 364 | 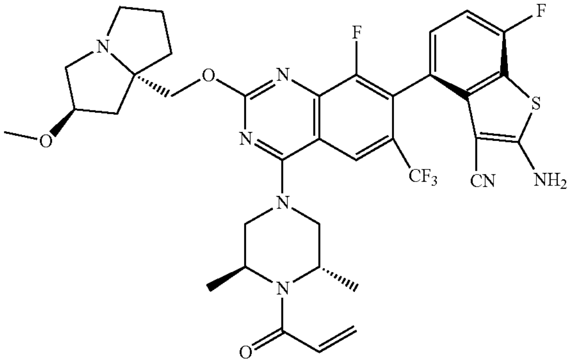 | LCMS m/z [M + 1]: 742.0 $^1$HNMR (400 MHz, $CD_3OD$) δ 8.38 (s, 1H), 7.20-7.26 (m, 1H), 7.03 (t, J = 9.0 Hz, 1H), 6.82 (dd, J = 16.5, 10.3 Hz, 1H), 6.38 (d, J = 16.3 Hz, 1H), 5.84 (d, J = 10.2 Hz, 1H), 4.43-4.78 (m, 5H), 4.26-4.31 (m, 1H), 4.16 (d, J = 13.6 Hz, 2H), 3.63-3.83 (m, 4H), 3.46-3.52 (m, 1H), 3.39 (s, 3H), 2.39-2.48 (m, 2H), 2.22-2.37 (m, 3H), 2.02-2.10 (m, 1H), 1.33-1.50 (m, 6H). |
| 364a | 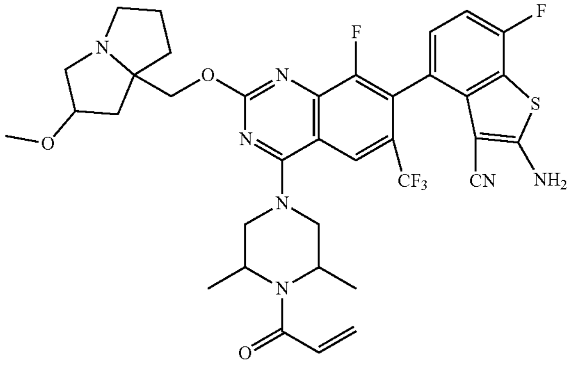 [SMILES: C=CC(=O)N1C(C)CN(c2nc(OCC34CCCN3CC(OC)C4)nc3c(F)c(-c4ccc(F)c5sc(N)c(C#N)c45)c(C(F)(F)F)cc23)CC1C] | |

TABLE 4-continued
| Selected compounds of the present disclosure. | | |
|---|---|---|
| Compound No. | Structure | Analytical data |
| 365 | 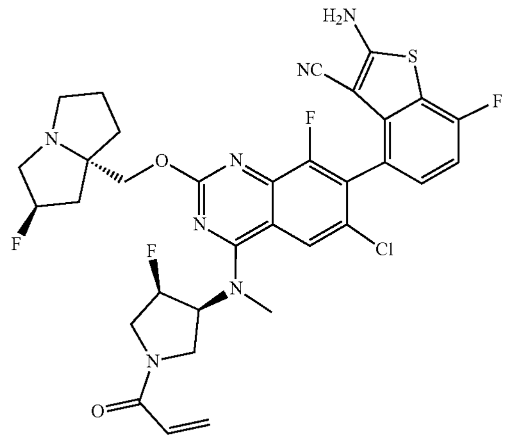 [SMILES: C=CC(=O)N1C[C@@H](F)[C@@H](N(C)c2nc(OC[C@@]34CCCN3C[C@H](F)C4)nc3c(F)c(-c4ccc(F)c5sc(N)c(C#N)c45)c(Cl)cc23)C1] | LCMS m/z [M + 1]: 700.2<br>$^1$HNMR (400 MHz, $CD_3OD$) δ 8.10 (s, 1H), 7.20-7.22 (m, 1H), 7.04 (t, J = 9.00 Hz, 1H), 6.60-6.74 (m, 1H), 6.33-6.37 (m, 1H), 5.62-5.83 (m, 2H), 5.36 (d, J = 51.30 Hz, 1H), 5.00-5.17 (m, 1H), 4.25-4.36 (m, 3H), 3.85-4.12 (m, 3H), 3.60 (s, 3H), 3.37-3.47 (m, 3H), 3.10-3.12 (m, 1H), 1.93-2.41 (m, 6H). |
| 365a | 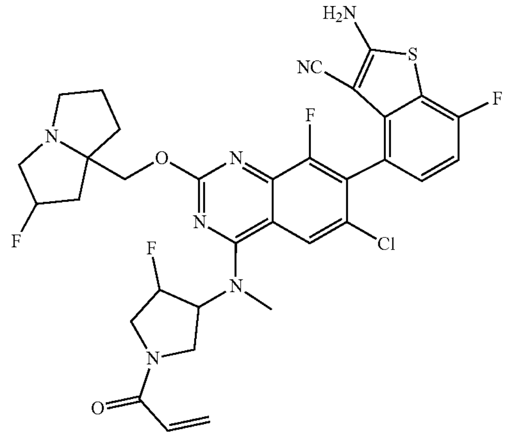 [SMILES: C=CC(=O)N1CC(F)C(N(C)c2nc(OCC34CCCN3CC(F)C4)nc3c(F)c(-c4ccc(F)c5sc(N)c(C#N)c45)c(Cl)cc23)C1] | |
| 366 | 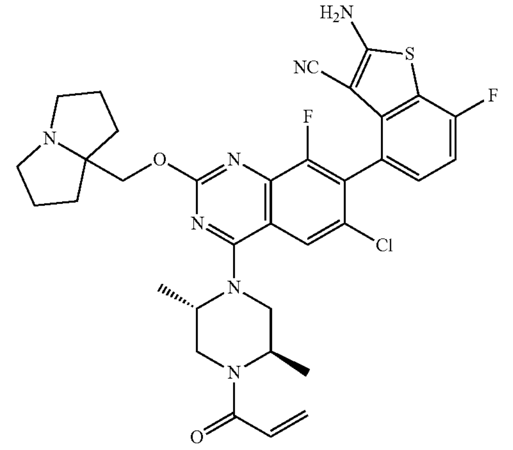 [SMILES: C=CC(=O)N1C[C@H](C)N(c2nc(OCC34CCCN3CCC4)nc3c(F)c(-c4ccc(F)c5sc(N)c(C#N)c45)c(Cl)cc23)C[C@H]1C] | LCMS m/z [M + 1]: 678.0<br>$^1$HNMR (400 MHz, $CD_3OD$) δ 7.97 (s, 1H), 7.24-7.28 (m, 1H), 7.06-7.10 (m, 1H), 6.76-6.91 (m, 1H), 6.28-6.34 (m, 1H), 5.80-5.85 (m, 1H), 4.91-5.09 (m, 2H), 4.56-4.80 (m, 2H), 4.27-4.50 (m, 2H), 3.96-4.12 (m, 1H), 3.85-3.94 (m, 1H), 3.50-3.79 (m, 3H), 3.20-3.30 (m, 1H), 2.08-2.42 (m, 8H), 1.40-1.52 (m, 3H), 1.22-1.37 (m, 3H). |

TABLE 4-continued
| Selected compounds of the present disclosure. | | |
|---|---|---|
| Compound No. | Structure | Analytical data |
| 366a | 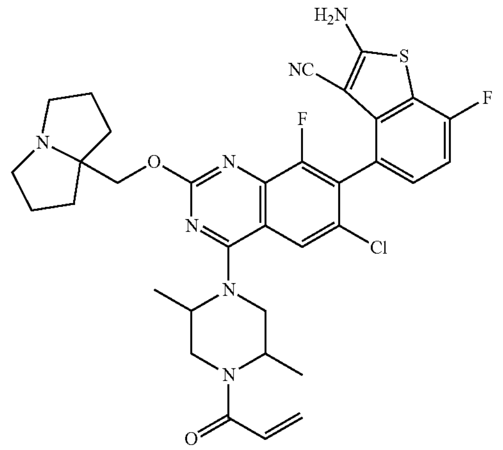 [SMILES: C=CC(=O)N1CC(C)N(c2nc(OCC34CCCN3CCC4)nc3c(F)c(-c4ccc(F)c5sc(N)c(C#N)c45)c(Cl)cc23)CC1C] | |
| 367 | 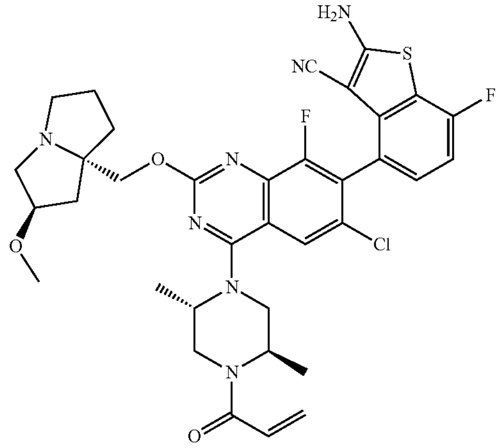 [SMILES: C=CC(=O)N1C[C@H](C)N(c2nc(OC[C@@]34CCCN3C[C@H](OC)C4)nc3c(F)c(-c4ccc(F)c5sc(N)c(C#N)c45)c(Cl)cc23)C[C@H]1C] | LCMS m/z [M + 1]: 708.0 $^1$HNMR (400 MHz, $CD_3OD$) δ 7.97 (s, 1H), 7.23-7.27 (m, 1H), 7.06-7.10 (m, 1H), 6.80-6.93 (m, 1H), 6.28-6.34 (m, 1H), 5.80-5.88 (m, 1H), 4.88-5.05 (m, 1H), 4.56-4.75 (m, 2H), 4.25-4.55 (m, 3H), 3.36-4.41 (m, 7H), 3.41 (s, 3H), 2.04-2.52 (m, 6H), 1.39-1.53 (m, 3H), 1.25-1.38 (m, 3H). |
| 367a | 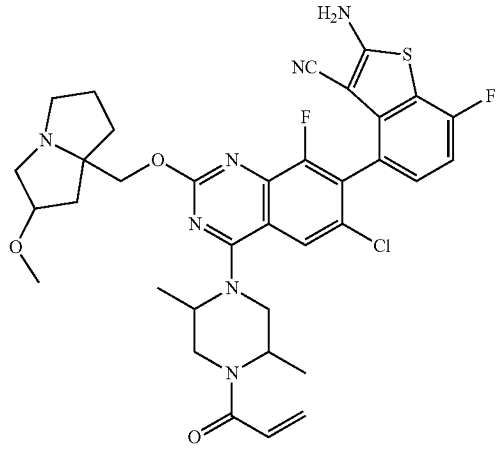 [SMILES: C=CC(=O)N1CC(C)N(c2nc(OCC34CCCN3CC(OC)C4)nc3c(F)c(-c4ccc(F)c5sc(N)c(C#N)c45)c(Cl)cc23)CC1C] | |

TABLE 4-continued
| Selected compounds of the present disclosure. | | |
|---|---|---|
| Compound No. | Structure | Analytical data |
| 368 | 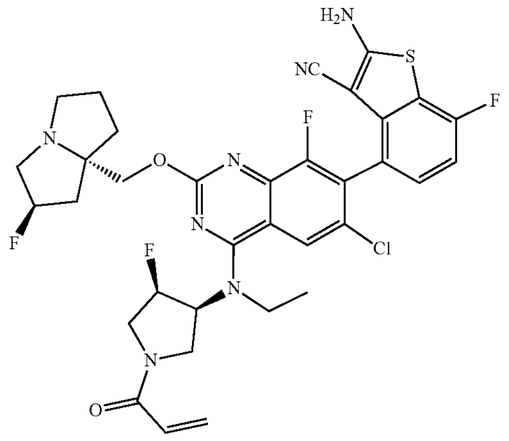 [SMILES: C=CC(=O)N1C[C@@H](F)[C@@H](N(CC)c2nc(OC[C@@]34CCCN3C[C@H](F)C4)nc3c(F)c(-c4ccc(F)c5sc(N)c(C#N)c45)c(Cl)cc23)C1] | LCMS m/z [M + 1]: 714.2 $^1$HNMR (400 MHz, $CD_3OD$) δ 8.10 (s, 1H), 7.20-7.29 (m, 1H), 7.06 (t, J = 9.2 Hz, 1H), 6.58-6.75 (m, 1H), 6.32-6.39 (m, 1H), 5.65-5.85 (m, 2H), 5.56 (d, J = 54.8 Hz, 1H), 4.99-5.16 (m, 1H), 4.56-4.77 (m, 2H), 4.34-4.44 (m, 1H), 3.70-4.15 (m, 8H), 3.41-3.52 (m, 1H), 2.52-2.77 (m, 2H), 2.28-2.50 (m, 3H), 2.06-2.25 (m, 1H), 1.26-1.40 (m, 3H). |
| 368a | 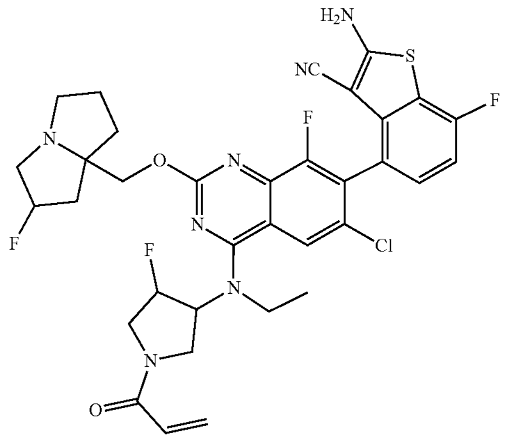 | |
| 369 | 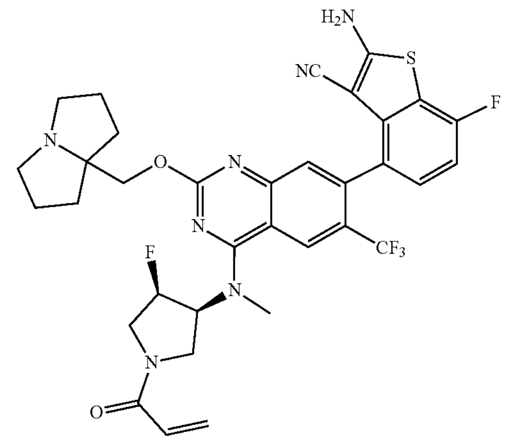 [SMILES: C=CC(=O)N1C[C@@H](F)[C@@H](N(C)c2nc(OCC34CCCN3CCC4)nc3cc(-c4ccc(F)c5sc(N)c(C#N)c45)c(C(F)(F)F)cc23)C1] | LCMS m/z [M + 1]: 698.3 $^1$HNMR (400 MHz, $CD_3OD$) δ 8.62 (s, 1H), 7.61 (s, 1H), 7.20-7.27 (m, 1H), 7.00-7.10 (m, 1H), 6.63-6.78 (m, 1H), 6.36-6.42 (m, 1H), 5.70-5.88 (m, 2H), 5.19-5.39 (m, 1H), 4.61-4.76 (m, 2H), 4.31-4.39 (m, 1H), 3.82-4.23 (m, 4H), 3.74 (s, 3H), 3.60-3.69 (m, 2H), 3.32-3.28 (m, 1H), 2.07-2.40 (m, 8H). |

TABLE 4-continued
| Selected compounds of the present disclosure. | | |
|---|---|---|
| Compound No. | Structure | Analytical data |
| 369a | 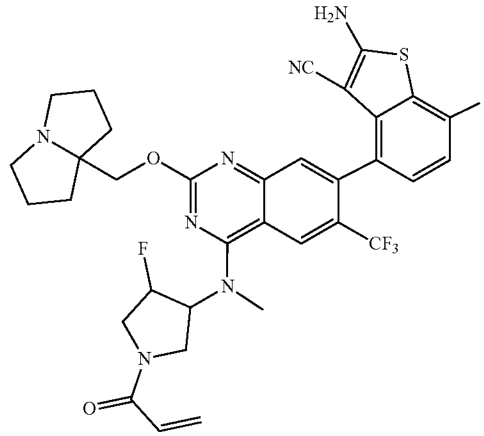 | |
| 370 | 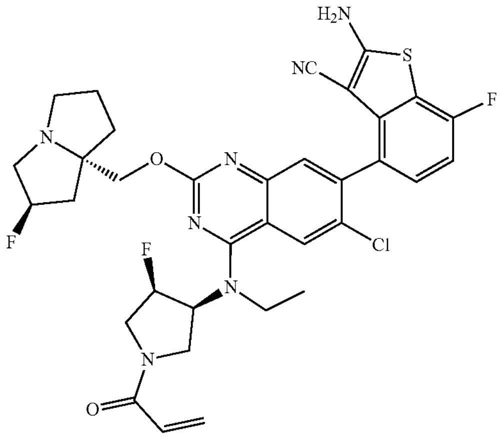 [SMILES: C=CC(=O)N1C[C@@H](F)[C@@H](N(CC)c2nc(OC[C@@]34CCCN3C[C@H](F)C4)nc3cc(-c4ccc(F)c5sc(N)c(C#N)c45)c(Cl)cc23)C1] | LCMS m/z [M + 1]: 696.2<br>$^1$HNMR (400 MHz, $CD_3OD$) δ 8.22-8.26 (m, 1H), 7.66 (s, 1H), 7.16-7.24 (m, 1H), 7.02 (t, J = 8.8 Hz, 1H), 6.59-6.78 (m, 1H), 6.32-6.40 (m, 1H), 5.50-5.90 (m, 3H), 5.00-5.20 (m, 1H), 4.59-4.76 (m, 2H), 4.35-4.45 (m, 1H), 3.70-4.20 (m, 8H), 3.41-3.52 (m, 1H), 2.53-2.80 (m, 2H), 2.27-2.48 (m, 3H), 2.12-2.25 (m, 1H), 1.25-1.41 (m, 3H). |
| 370a | 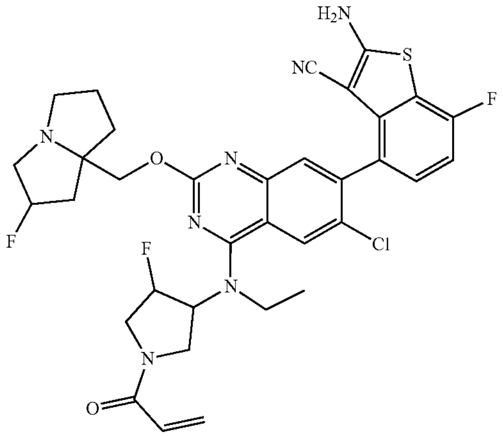 [SMILES: C=CC(=O)N1CC(F)C(N(CC)c2nc(OCC34CCCN3CC(F)C4)nc3cc(-c4ccc(F)c5sc(N)c(C#N)c45)c(Cl)cc23)C1] | |

TABLE 4-continued
| Selected compounds of the present disclosure. | | |
|---|---|---|
| Compound No. | Structure | Analytical data |
| 371 | 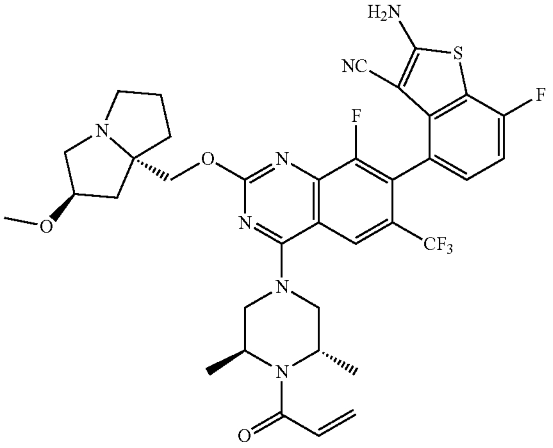 [SMILES: C=CC(=O)N1[C@@H](C)CN(c2nc(OC[C@@]34CCCN3C[C@H](OC)C4)nc3c(F)c(-c4ccc(F)c5sc(N)c(C#N)c45)c(C(F)(F)F)cc23)C[C@@H]1C] | LCMS m/z [M + 1]: 742.0 $^1$HNMR (400 MHz, $CD_3OD$) δ 8.37 (m, 1H), 7.18-7.27 (m, 1H), 7.03 (t, J = 8.9 Hz, 1H), 6.82 (dd, J = 16.8, 10.4 Hz, 1H), 6.38 (d, J = 16.7 Hz, 1H), 5.84 (d, J = 10.4 Hz, 1H), 4.34-4.82 (m, 6H), 4.24-4.32 (m, 1H), 4.11-4.21 (m, 2H), 3.74-3.86 (m, 2H), 3.60-3.69 (m, 1H), 3.45-3.56 (m, 1H), 3.39 (s, 3H), 2.38-2.52 (m, 2H), 2.20-2.37 (m, 3H), 2.00-2.14 (m, 1H), 1.21-1.52 (m, 6H). |
| 371a | 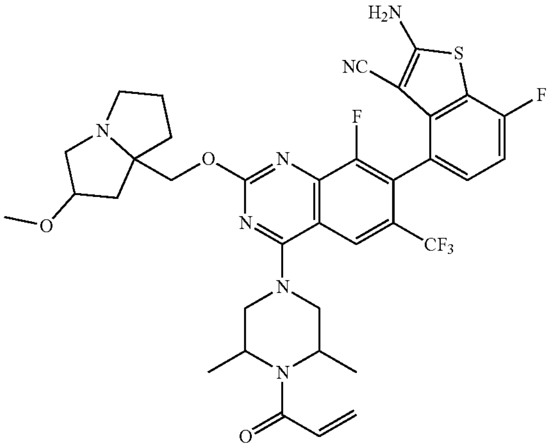 [SMILES: C=CC(=O)N1C(C)CN(c2nc(OCC34CCCN3CC(OC)C4)nc3c(F)c(-c4ccc(F)c5sc(N)c(C#N)c45)c(C(F)(F)F)cc23)CC1C] | |
| 372 | 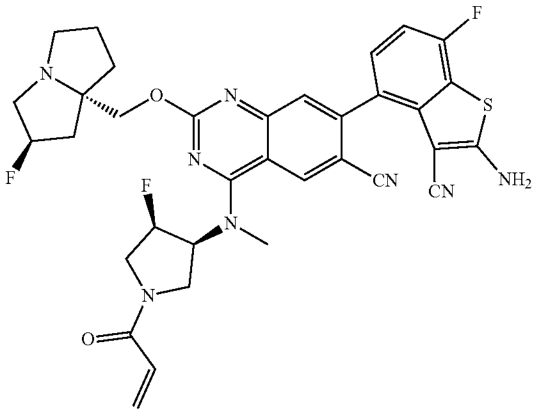 [SMILES: C=CC(=O)N1C[C@@H](F)[C@@H](N(C)c2nc(OC[C@@]34CCCN3C[C@H](F)C4)nc3cc(-c4ccc(F)c5sc(N)c(C#N)c45)c(C#N)cc23)C1] | LCMS m/z [M + 1]: 673.1 $^1$HNMR (400 MHz, $CD_3OD$) δ 8.70-8.64 (m, 1H), 8.49 (s, 1H), 7.63 (s, 1H), 7.32-7.28 (m, 1H), 7.07-7.03 (m, 1H), 6.76-6.61 (m, 1H), 6.39-6.34 (m, 1H), 5.85-5.65 (m, 2H), 5.45-5.11 (m, 2H), 4.37-4.25 (m, 3H), 4.11-3.80 (m, 3H), 3.66 (s, 2H), 3.46-3.39 (m, 3H), 3.16-3.13 (m, 1H), 2.47-1.97 (m, 6H). |

TABLE 4-continued
| Selected compounds of the present disclosure. | | |
|---|---|---|
| Compound No. | Structure | Analytical data |
| 372a | 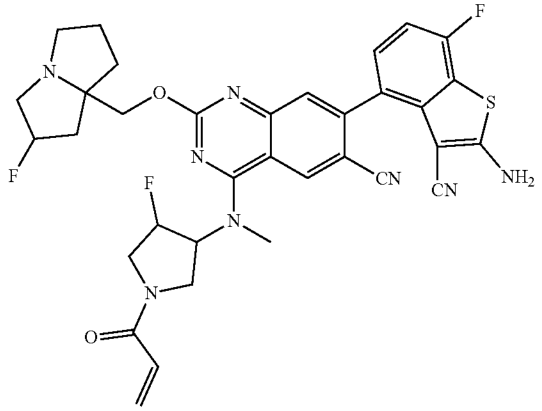 [SMILES: C=CC(=O)N1CC(F)C(N(C)c2nc(OCC34CCCN3CC(F)C4)nc3cc(-c4ccc(F)c5sc(N)c(C#N)c45)c(C#N)cc23)C1] | |
| 373 | 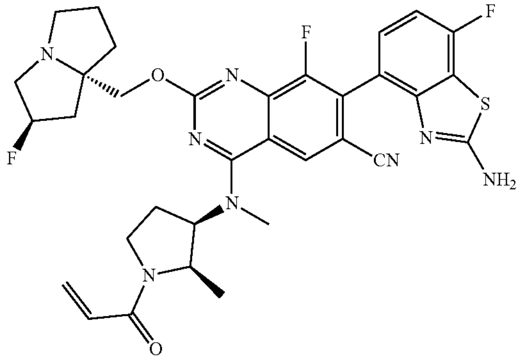 [SMILES: C=CC(=O)N1CC[C@@H](N(C)c2nc(OC[C@@]34CCCN3C[C@H](F)C4)nc3c(F)c(-c4ccc(F)c5sc(N)nc45)c(C#N)cc23)[C@H]1C] | LCMS m/z [M + 1]: 663.1 $^1$HNMR (400 MHz, $CD_3OD$) δ 8.51 (s, 1H), 7.35 (t, 1H), 7.01 (t, 1H), 6.62 (t, 1H), 6.33 (t, 1H), 5.80 (d, 1H), 5.53 (s, 0.5H), 5.33 (s, 0.5H), 5.06-5.02 (m, 1H), 4.58-4.45 (m, 2H), 3.97 (t, 1H), 3.78-3.47 (m, 7H), 2.78-2.37 (m, 5H), 2.20-2.01 (m, 5H), 1.11 (d, 3H). |
| 373a | 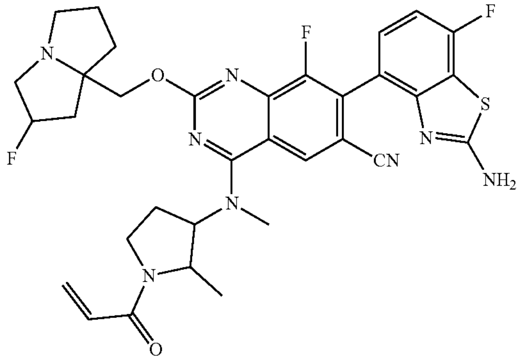 [SMILES: C=CC(=O)N1CCC(N(C)c2nc(OCC34CCCN3CC(F)C4)nc3c(F)c(-c4ccc(F)c5sc(N)nc45)c(C#N)cc23)C1C] | |
| 374 | 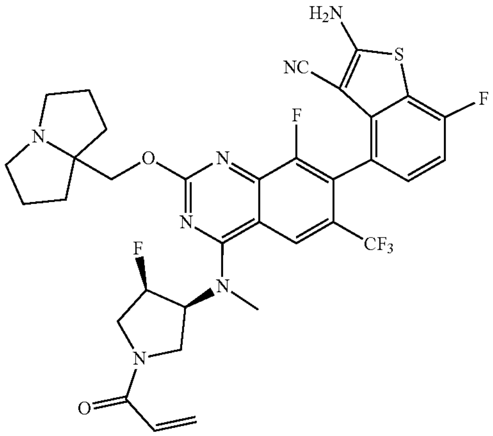 [SMILES: C=CC(=O)N1C[C@@H](F)[C@@H](N(C)c2nc(OCC34CCCN3CCC4)nc3c(F)c(-c4ccc(F)c5sc(N)c(C#N)c45)c(C(F)(F)F)cc23)C1] | LCMS m/z [M + 1]: 716.3 $^1$HNMR (400 MHz, $CD_3OD$) δ 8.41 (s, 1H), 7.23-7.25 (m, 1H), 7.03 (t, J = 8.90 Hz, 1H), 6.60-6.75 (m, 1H), 6.34-6.38 (m, 1H), 5.67-5.84 (m, 2H), 5.10-5.33 (m, 2H), 4.59-4.71 (m, 2H), 4.30-4.35 (m, 1H), 3.67-4.18 (m, 9H), 2.11-2.43 (m, 8H). |

TABLE 4-continued
| Selected compounds of the present disclosure. | | |
|---|---|---|
| Compound No. | Structure | Analytical data |
| 374a | 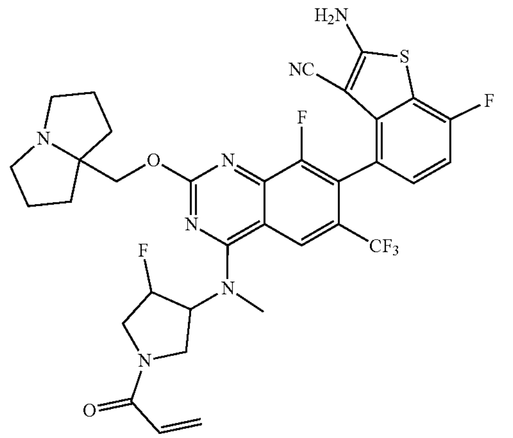 [SMILES: C=CC(=O)N1CC(F)C(N(C)c2nc(OCC34CCCN3CCC4)nc3c(F)c(-c4ccc(F)c5sc(N)c(C#N)c45)c(C(F)(F)F)cc23)C1] | |
| 375 | 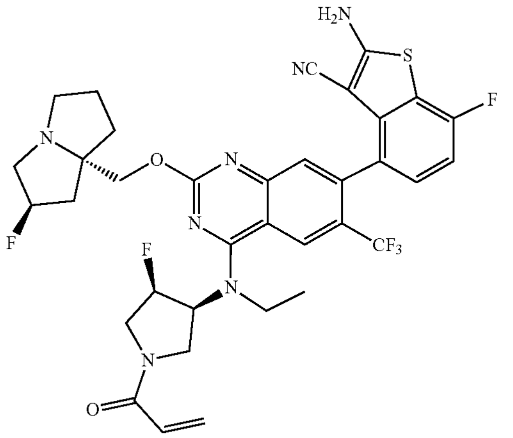 [SMILES: C=CC(=O)N1C[C@@H](F)[C@@H](N(CC)c2nc(OC[C@@]34CCCN3C[C@H](F)C4)nc3cc(-c4ccc(F)c5sc(N)c(C#N)c45)c(C(F)(F)F)cc23)C1] | LCMS m/z [M + 1]: 730.0 $^1$HNMR (400 MHz, $CD_3OD$) δ 8.54 (s, 1H), 7.44-7.78 (m, 1H), 7.17-7.23 (m, 1H), 6.99 (t, J = 8.94 Hz, 1H), 6.60-6.76 (m, 1H), 6.36 (d, J = 16.76 Hz, 1H), 5.52-5.85 (m, 3H), 5.00-5.20 (m, 1H), 4.59-4.74 (m, 2H), 4.37-4.42 (m, 1H), 3.78-4.18 (m, 8H), 3.44-3.51 (m, 1H), 2.19-2.75 (m, 6H), 1.41-1.47 (m, 3H). |
| 375a | 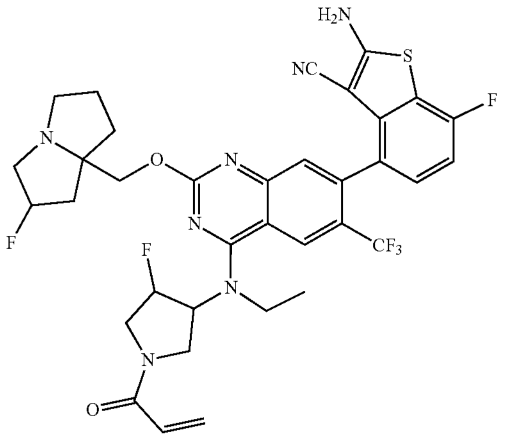 | |

TABLE 4-continued
| Selected compounds of the present disclosure. | | |
|---|---|---|
| Compound No. | Structure | Analytical data |
| 376 | 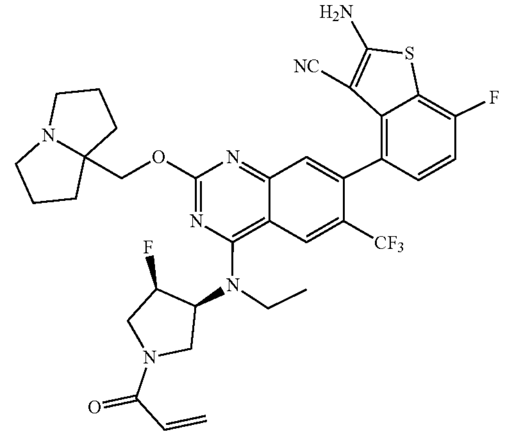 [SMILES: C=CC(=O)N1C[C@@H](F)[C@@H](N(CC)c2nc(OCC34CCCN3CCC4)nc3cc(-c4ccc(F)c5sc(N)c(C#N)c45)c(C(F)(F)F)cc23)C1] | LCMS m/z [M + 1]: 712.2<br>$^1$HNMR (400 MHz, $CD_3OD$) δ 8.54 (s, 1H), 7.62 (s, 1H), 7.17-7.25 (m, 1H), 6.95-7.05 (m, 1H), 6.59-6.77 (m, 1H), 6.32-6.40 (m, 1H), 5.65-5.88 (m, 2H), 5.00-5.20 (m, 1H), 4.58-4.72 (m, 2H), 4.35-4.44 (m, 1H), 3.78-4.17 (m, 5H), 3.60-3.74 (m, 3H), 2.06-2.43 (m, 8H), 1.36-1.48 (m, 3H). |
| 376a | 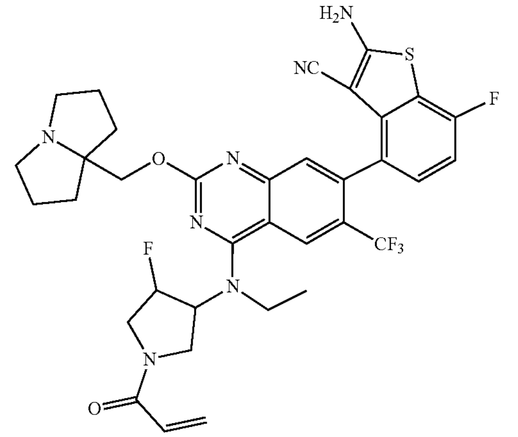 [SMILES: C=CC(=O)N1CC(F)C(N(CC)c2nc(OCC34CCCN3CCC4)nc3cc(-c4ccc(F)c5sc(N)c(C#N)c45)c(C(F)(F)F)cc23)C1] | |
| 377 | 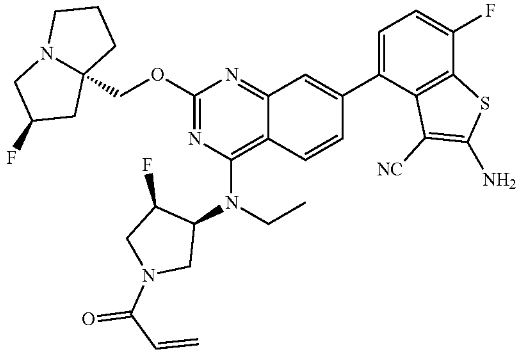 [SMILES: C=CC(=O)N1C[C@@H](F)[C@@H](N(CC)c2nc(OC[C@@]34CCCN3C[C@H](F)C4)nc3cc(-c4ccc(F)c5sc(N)c(C#N)c45)ccc23)C1] | LCMS m/z [M + 1]: 662.2<br>$^1$HNMR (400 MHz, $CD_3OD$) δ 8.26-8.29 (m, 1H), 7.68 (s, 1H), 7.55-7.61 (m, 1H), 7.27-7.31 (m, 1H), 7.01-7.06 (m, 1H), 6.65-6.80 (m, 1H), 6.34-6.38 (m, 1H), 5.82-5.90 (m, 2H), 5.48-5.75 (m, 1H), 5.10-5.32 (m, 1H), 4.71-4.80 (m, 2H), 4.30-4.48 (m, 1H), 3.87-4.17 (m, 8H), 3.48-3.58 (m, 1H), 2.61-2.72 (m, 2H), 2.23-2.48 (m, 4H), 1.40-1.44 (m, 3H). |

TABLE 4-continued
| Selected compounds of the present disclosure. | | |
|---|---|---|
| Compound No. | Structure | Analytical data |
| 377a | 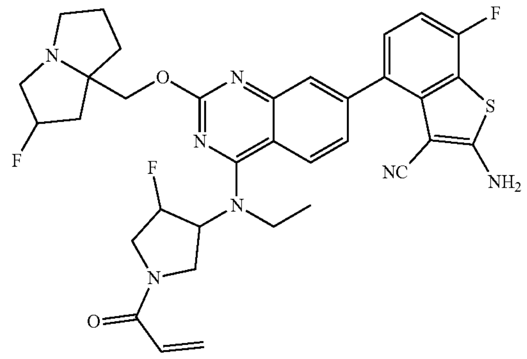 [SMILES: C=CC(=O)N1CC(F)C(N(CC)c2nc(OCC34CCCN3CC(F)C4)nc3cc(-c4ccc(F)c5sc(N)c(C#N)c45)ccc23)C1] | |
| 378 | 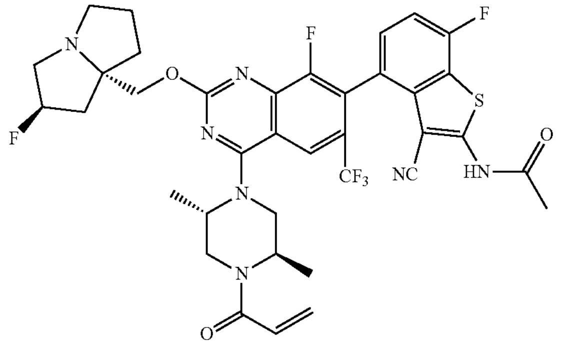 [SMILES: C=CC(=O)N1C[C@H](C)N(c2nc(OC[C@@]34CCCN3C[C@H](F)C4)nc3c(F)c(-c4ccc(F)c5sc(NC(C)=O)c(C#N)c45)c(C(F)(F)F)cc23)C[C@H]1C] | LCMS m/z [M + 1]: 772.0 $^1$HNMR (400 MHz, $CD_3OD$) δ 8.21 (s, 1H), 7.40-7.46 (m, 1H), 7.25-7.33 (m, 1H), 6.74-6.90 (m, 1H), 6.25-6.35 (m, 1H), 5.78-5.86 (m, 1H), 5.57 (d, J = 51.6 Hz, 1H), 4.90-5.08 (m, 2H), 4.24-4.75 (m, 4H), 3.82-4.14 (m, 4H), 3.40-3.57 (m, 2H), 2.55-2.80 (m, 2H), 2.31-2.50 (m, 3H), 2.30 (s, 3H), 2.10-2.22 (m, 1H), 1.47-1.56 (m, 3H), 1.23-1.39 (m, 3H). |
| 378a | 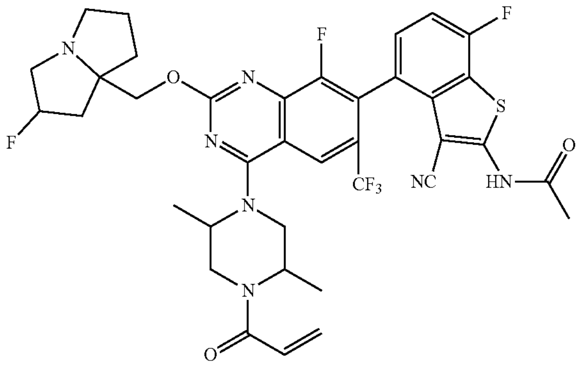 [SMILES: C=CC(=O)N1CC(C)N(c2nc(OCC34CCCN3CC(F)C4)nc3c(F)c(-c4ccc(F)c5sc(NC(C)=O)c(C#N)c45)c(C(F)(F)F)cc23)CC1C] | |
| 379 | 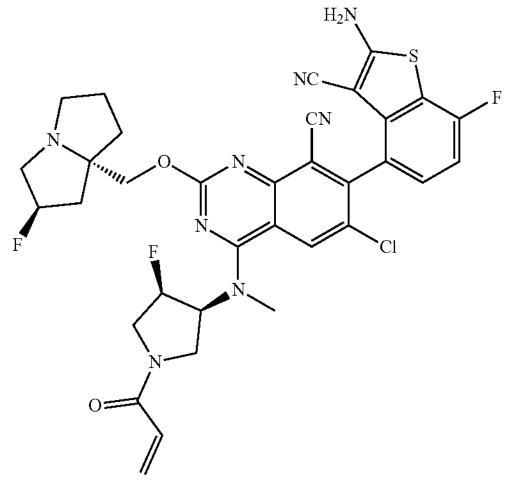 [SMILES: C=CC(=O)N1C[C@@H](F)[C@@H](N(C)c2nc(OC[C@@]34CCCN3C[C@H](F)C4)nc3c(C#N)c(-c4ccc(F)c5sc(N)c(C#N)c45)c(Cl)cc23)C1] | LCMS m/z [M + 1]: 707.1 $^1$HNMR (400 MHz, $CD_3OD$) δ 8.51 (t, 1H), 7.25-7.29 (m, 1H), 7.08 (t, 1H), 6.60-6.74 (t, 1H), 6.35 (d, 1H), 5.81-5.84 (m, 1H), 5.78-5.81 (m, 0.5H), 5.64-5.69 (m, 0.5H), 5.42 (s, 0.5H), 5.29 (s, 0.5H), 5.08-5.16 (m, 1H), 4.26-4.48 (m, 3H), 3.86-4.11 (m, 3H), 3.61 (s, 3H), 3.36-3.47 (m, 3H), 3.12 (s, 1H), 2.21-2.42 (m, 3H), 2.08 (s, 2H), 1.96 (s, 1H). |

TABLE 4-continued
| Selected compounds of the present disclosure. | | |
|---|---|---|
| Compound No. | Structure | Analytical data |
| 379a | 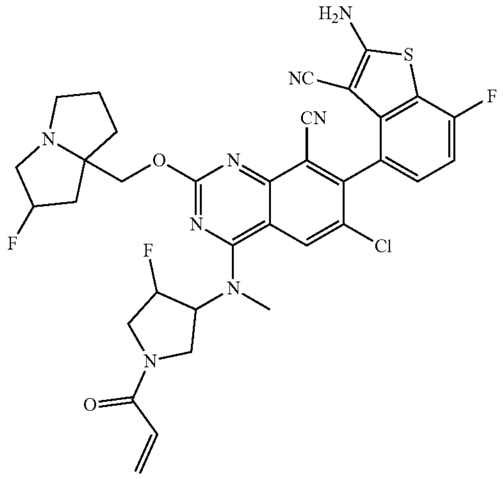 [SMILES: C=CC(=O)N1CC(F)C(N(C)c2nc(OCC34CCCN3CC(F)C4)nc3c(C#N)c(-c4ccc(F)c5sc(N)c(C#N)c45)c(Cl)cc23)C1] | |
| 380 | 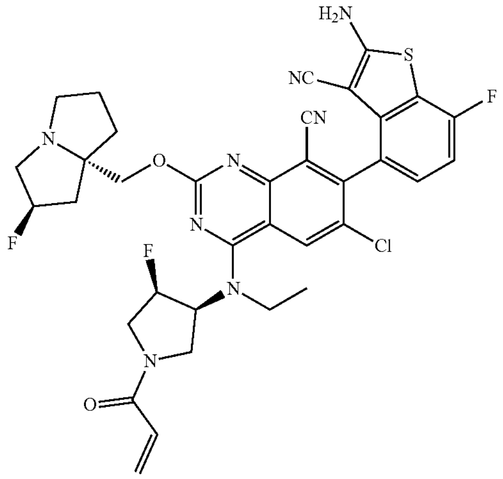 [SMILES: C=CC(=O)N1C[C@@H](F)[C@@H](N(CC)c2nc(OC[C@@]34CCCN3C[C@H](F)C4)nc3c(C#N)c(-c4ccc(F)c5sc(N)c(C#N)c45)c(Cl)cc23)C1] | LCMS m/z [M + 1]: 721.1 $^1$HNMR (400 MHz, $CD_3OD$) δ 8.43-8.45 (m, 2H), 7.27-7.30 (m, 1H), 7.08 (t, 1H), 6.59-6.73 (m, 1H), 6.34 (d, 1H), 5.80-5.83 (m, 1H), 5.76-5.78 (m, 0.5H), 5.62-5.68 (m, 0.5H), 5.54-5.55 (m, 0.5H), 5.41 (s, 0.5H), 4.93-5.06 (m, 1H), 4.51-4.66 (m, 2H), 4.35-4.43 (m, 1H), 3.89-4.11 (m, 4H), 3.65-3.75 (m, 4H), 2.44-2.59 (m, 2H), 2.35-2.38 (m, 1H), 2.18-2.27 (m, 2H), 2.08 (s, 1H), 1.28-1.35 (m, 4H). |
| 380a | 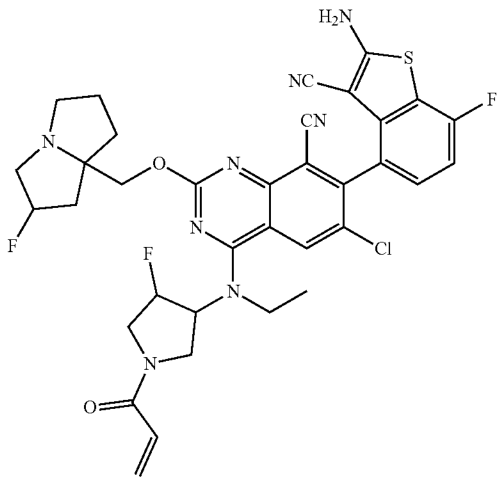 [SMILES: C=CC(=O)N1CC(F)C(N(CC)c2nc(OCC34CCCN3CC(F)C4)nc3c(C#N)c(-c4ccc(F)c5sc(N)c(C#N)c45)c(Cl)cc23)C1] | |

TABLE 4-continued
| Selected compounds of the present disclosure. | | |
|---|---|---|
| Compound No. | Structure | Analytical data |
| 381 | 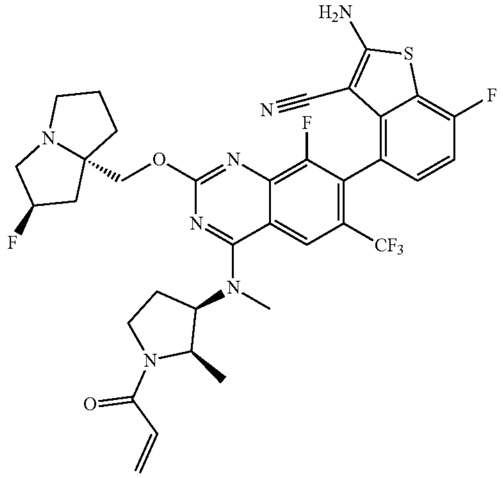 | LCMS m/z [M + 1]: 703.2 $^1$HNMR (400 MHz, $CD_3OD$) δ 8.37 (s, 1H), 7.22 (t, 1H), 7.01 (t, 1H), 6.68-6.61 (m, 1H), 6.32 (t, 1H), 5.78 (d, 1H), 5.50-5.31 (m, 1H), 5.06-5.04 (m, 1H), 4.56-4.39 (m, 2H), 3.8-3.67 (m, 1H), 3.63 (s, 4H), 3.58 (t, 2H), 3.44 (t, 1H), 2.46-2.09 (m, 8H), 1.28 (s, 1H), 1.16-1.09 (m, 4H). |
| 381a | 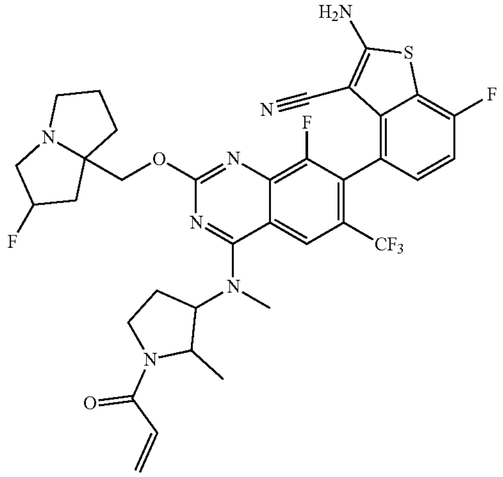 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1C] | |
| 382 | 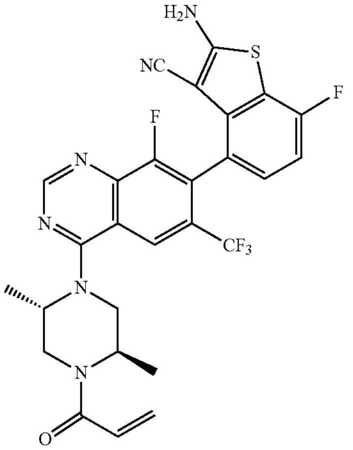 [SMILES: C=CC(=O)N1C[C@H](C)N(c2ncnc3c(F)c(-c4ccc(F)c5sc(N)c(C#N)c45)c(C(F)(F)F)cc23)C[C@H]1C] | LCMS m/z [M + 1]: 573 $^1$HNMR (400 MHz, $CD_3OD$) δ 8.73 (s, 1H), 8.20 (s, 1H), 7.19-7.32 (m, 1H), 7.03 (t, 1H), 6.73-6.91 (m, 1H), 6.22-6.37 (m, 1H), 5.75-5.88 (m, 1H), 5.01 (s, 1H), 4.20-4.65 (m, 2H), 3.76-4.14 (m, 2H), 3.33-3.68 (m, 1H), 1.14-1.43 (m, 6H). |

TABLE 4-continued
| Selected compounds of the present disclosure. | | |
|---|---|---|
| Compound No. | Structure | Analytical data |
| 382a | 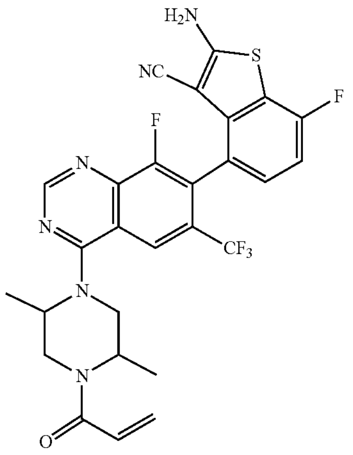 [SMILES: C=CC(=O)N1CC(C)N(c2ncnc3c(F)c(-c4ccc(F)c5sc(N)c(C#N)c45)c(C(F)(F)F)cc23)CC1C] | |
TABLE 5
| Selected compounds of the present disclosure. | | |
|---|---|---|
| Compound No. | Structure | Analytical data |
| 383 | 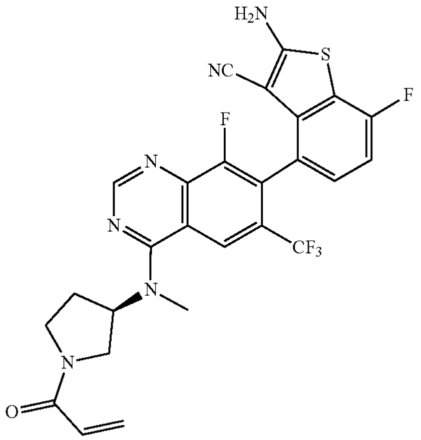 [SMILES: C=CC(=O)N1CC[C@@H](N(C)c2ncnc3c(F)c(-c4ccc(F)c5sc(N)c(C#N)c45)c(C(F)(F)F)cc23)C1] | LCMS m/z [M + 1]: 559<br>$^{1}$HNMR (400 MHz, $CD_3OD$) δ 8.73 (s, 1H), 8.42 (s, 1H), 7.28 (t, 1H), 7.06 (t, 1H), 6.63-6.77 (m, 1H), 6.34 (d, 1H), 5.76-5.88 (m, 1H), 5.34-5.54 (m, 1H), 3.89-4.35 (m, 2H), 3.53-3.88 (m, 2H), 3.48-3.54 (m, 3H), 2.36-2.65 (m, 2H). |
| 383a | 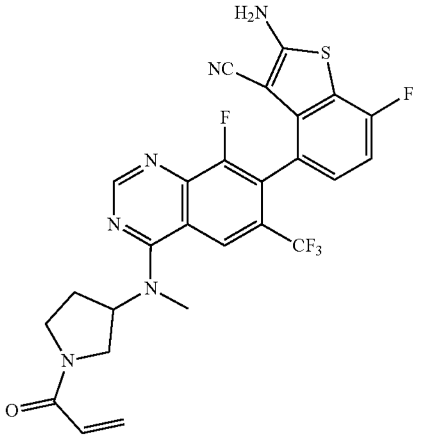 [SMILES: C=CC(=O)N1CCC(N(C)c2ncnc3c(F)c(-c4ccc(F)c5sc(N)c(C#N)c45)c(C(F)(F)F)cc23)C1] | |

TABLE 5-continued
| Selected compounds of the present disclosure. | | |
|---|---|---|
| Compound No. | Structure | Analytical data |
| 384 | 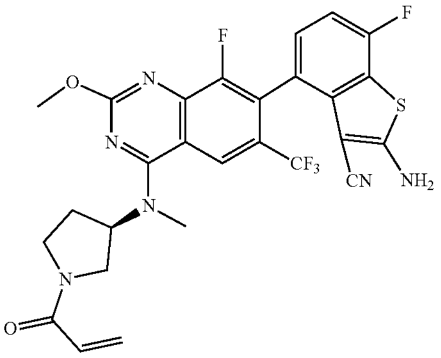 [SMILES: C=CC(=O)N1CC[C@@H](N(C)c2nc(OC)nc3c(F)c(-c4ccc(F)c5sc(N)c(C#N)c45)c(C(F)(F)F)cc23)C1] | LCMS m/z [M + 1]: 589 $^1$HNMR (400 MHz, $CD_3OD$) δ 8.31 (s, 1H), 7.20-7.31 (m, 1H), 6.99-7.03 (t, 1H), 6.63-6.71 (m, 1H), 6.29-6.33 (m, 1H), 5.76-5.80 (m, 1H), 5.33-5.35 (m, 1H), 4.06-4.24 (m, 4H), 3.91-3.99 (m, 1H), 3.74-3.82 (m, 1H), 3.63-3.69 (m, 1H), 3.45-3.46 (m, 3H), 2.35-2.51 (m, 2H), 2.02-2.03 (m, 1H), 1.60 (m, 1H). |
| 384a | 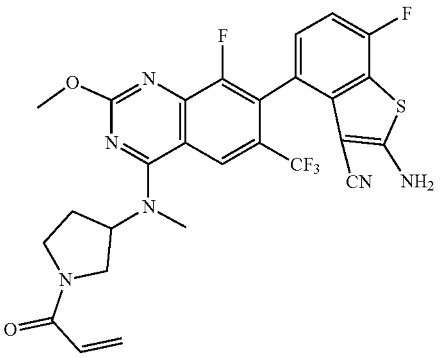 [SMILES: C=CC(=O)N1CCC(N(C)c2nc(OC)nc3c(F)c(-c4ccc(F)c5sc(N)c(C#N)c45)c(C(F)(F)F)cc23)C1] | |
| 385 | 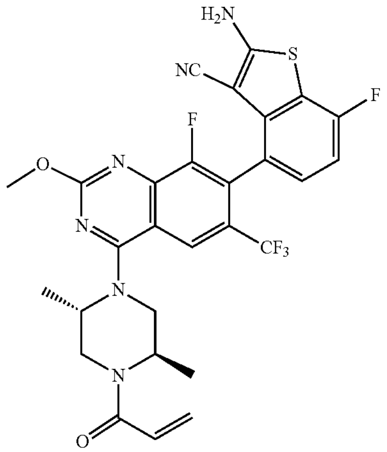 [SMILES: C=CC(=O)N1C[C@H](C)N(c2nc(OC)nc3c(F)c(-c4ccc(F)c5sc(N)c(C#N)c45)c(C(F)(F)F)cc23)C[C@H]1C] | LCMS m/z [M + 1]: 603 $^1$HNMR (400 MHz, $CD_3OD$) δ 8.09-8.16 (m, 1H), 7.19-7.26 (m, 1H), 7.014 (t, 1H), 6.757-6.897 (m, 1H), 6.255-6.325 (m, 1H), 5.78-5.83 (m, 1H), 4.23-4.61 (m, 3H), 4.02-4.12 (m, 3H), 3.86-3.94 (m, 1H), 3.43-3.57 (m, 1H), 1.42-1.56 (m, 3H), 1.22-1.42 (m, 4 H). |

TABLE 5-continued
| Selected compounds of the present disclosure. | | |
|---|---|---|
| Compound No. | Structure | Analytical data |
| 385a | 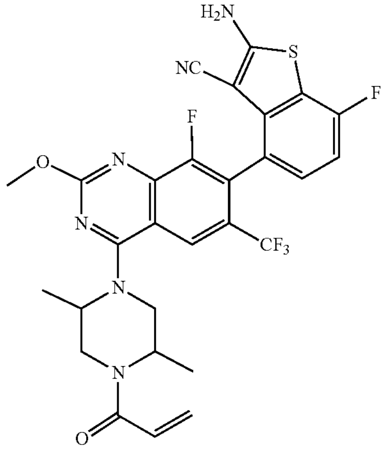 [SMILES: C=CC(=O)N1CC(C)N(c2nc(OC)nc3c(F)c(-c4ccc(F)c5sc(N)c(C#N)c45)c(C(F)(F)F)cc23)CC1C] | |
| 386 | 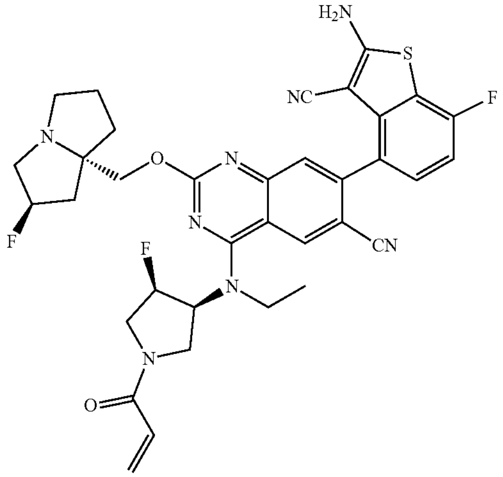 [SMILES: C=CC(=O)N1C[C@@H](F)[C@@H](N(CC)c2nc(OC[C@@]34CCCN3C[C@H](F)C4)nc3cc(-c4ccc(F)c5sc(N)c(C#N)c45)c(C#N)cc23)C1] | LCMS m/z [M + 1]: 687.4 $^1$HNMR (400 MHz, $CD_3OD$) δ 8.58-8.56 (m, 1H), 7.74-7.68 (m, 1H), 7.31-7.29 (m, 1H), 7.08-7.03 (m, 1H), 6.69-6.60 (m, 1H), 6.38-6.33 (m, 1H), 5.83-5.63 (m, 2H), 5.52-5.39 (m, 1H), 5.13-4.99 (m, 1H), 2.52-2.04 (m, 7H), 1.36-1.29 (m, 3H). |
| 386a | 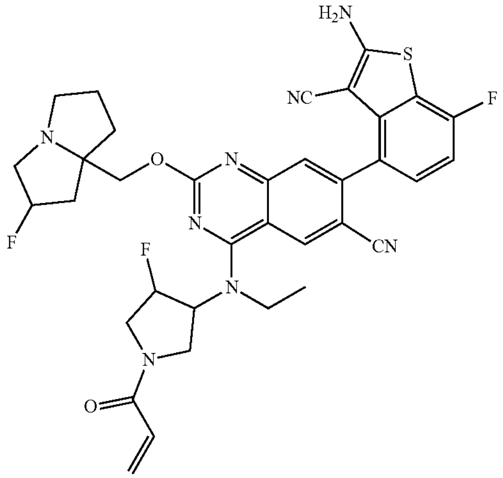 [SMILES: C=CC(=O)N1CC(F)C(N(CC)c2nc(OCC34CCCN3CC(F)C4)nc3cc(-c4ccc(F)c5sc(N)c(C#N)c45)c(C#N)cc23)C1] | |

TABLE 5-continued
Selected compounds of the present disclosure.
| Compound No. | Structure | Analytical data |
|---|---|---|
| 387 | 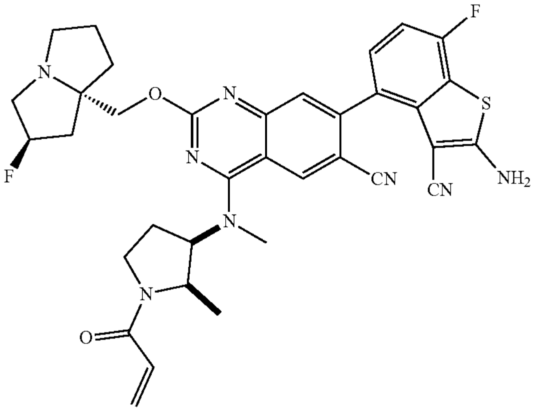 | LCMS m/z [M + 1]: 669.3 $^1$HNMR (400 MHz, $CD_3OD$) δ 8.64-8.63 (m, 1H), 7.60-7.58 (m, 1H), 7.30-7.27 (m, 1H), 7.06-7.01 (m, 1H), 6.71-6.62 (m, 1H), 6.37-6.28 (m, 1H), 5.79-5.76 (m, 1H), 5.37-5.24 (d, 1H), 5.03-5.01 (m, 1H), 4.31-4.20 (m, 2H), 3.98-3.54 (m, 5H), 3.25-3.17 (m, 2H), 3.01-3.00 (m, 1H), 2.69-1.89 (m, 9H), 1.28 (s, 1H), 1.12-1.07 (m, 3H). |
| 387a | 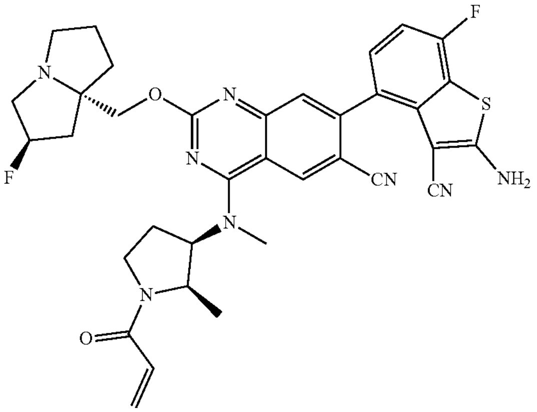 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(C#N)cc23)[C@H]1C] | |
| 387b | 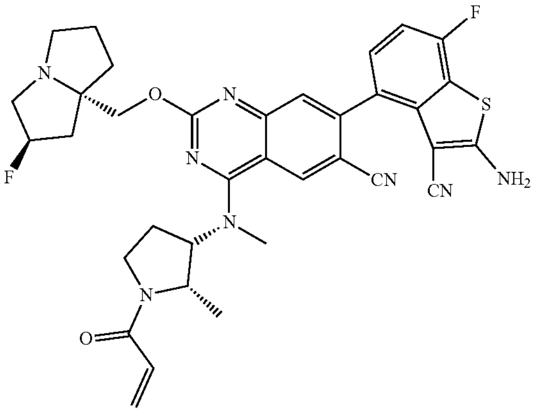 | |

TABLE 5-continued
| Selected compounds of the present disclosure. | | |
|---|---|---|
| Compound No. | Structure | Analytical data |
| 387c | 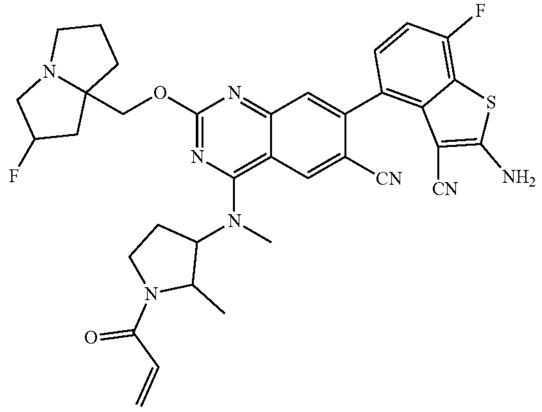 [SMILES: C=CC(=O)N1CCC(N(C)c2nc(OCC34CCCN3CC(F)C4)nc3cc(-c4ccc(F)c5sc(N)c(C#N)c45)c(C#N)cc23)C1C] | |
| 388 | 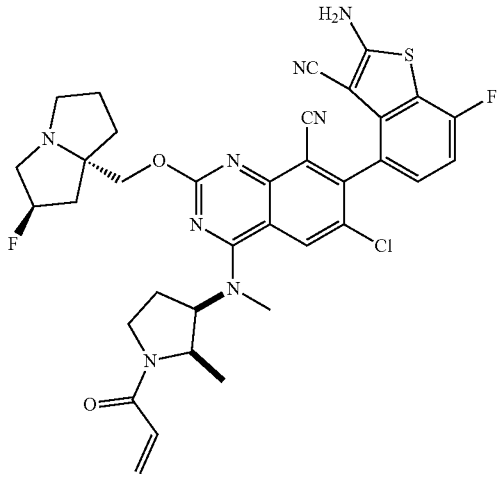 | LCMS m/z [M + 1]: 703.3 $^1$HNMR (400 MHz, $CD_3OD$) δ 8.35 (s, 1H), 8.17 (d, 1H), 7.87 (s, 1H), 7.29-7.25 (m, 1H), 7.10-7.06 (t, 1H), 6.68-6.61 (m,1H), 6.58 (s, 1H), 6.37-6.29 (m, 1H), 5.79 (d, 1H), 5.52 (d, 0.5H), 5.38 (d, 0.5H), 5.06-5.01 (m, 1H), 4.66-4.45 (m, 2H), 3.95-3.53 (m, 7H), 2.92-2.85 (m, 1H), 2.69-2.03 (m, 8H), 1.37-1.29 (m, 3H). |
| 388a | 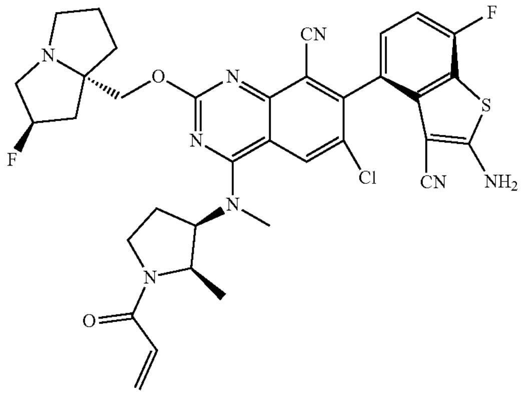 | |

TABLE 5-continued
Selected compounds of the present disclosure.
| Compound No. | Structure | Analytical data |
|---|---|---|
| 388b | 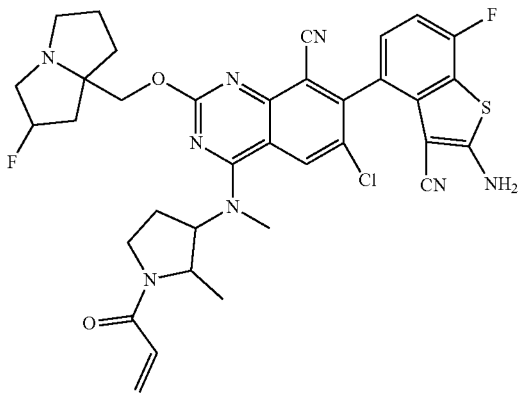 [SMILES: C=CC(=O)N1CCC(N(C)c2nc(OCC34CCCN3CC(F)C4)nc3c(C#N)c(-c4ccc(F)c5sc(N)c(C#N)c45)c(Cl)cc23)C1C] | |
| 389 | 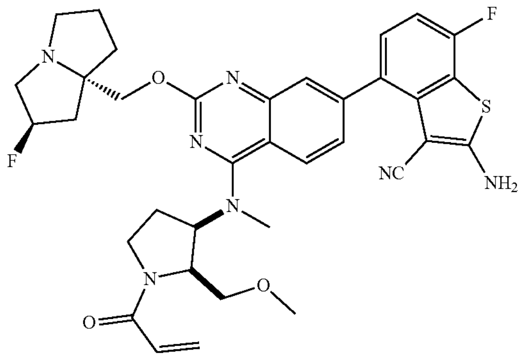 | LCMS m/z [M + 1]: 674.2<br>$^1$HNMR (400 MHz, $CD_3OD$) δ 8.46 (d, J = 8.74 Hz, 1H), 7.63-7.67 (m, 2H), 7.30-7.33 (m, 1H), 7.06 (t, J = 9.00 Hz, 1H), 6.68-6.83 (m, 1H), 6.35-6.39 (m, 1H), 5.81-5.86 (m, 1H), 5.62 (d, J = 50.30 Hz, 1H), 5.14-5.26 (m, 1H), 4.95-5.00 (m, 1H), 3.91-4.03 (m, 4H), 3.36-3.84 (m, 8H), 3.27-3.29 (m, 4H), 2.25-2.95 (m, 8H). |
| 389a | 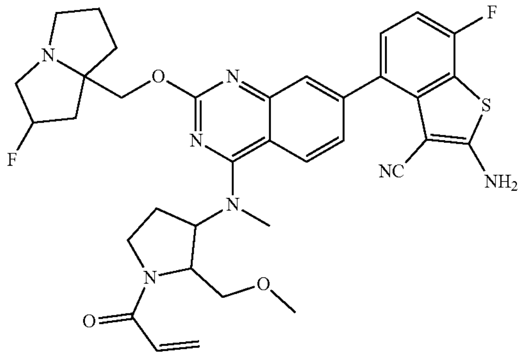 [SMILES: C=CC(=O)N1CCC(N(C)c2nc(OCC34CCCN3CC(F)C4)nc3cc(-c4ccc(F)c5sc(N)c(C#N)c45)ccc23)C1COC] | |
| 390 | 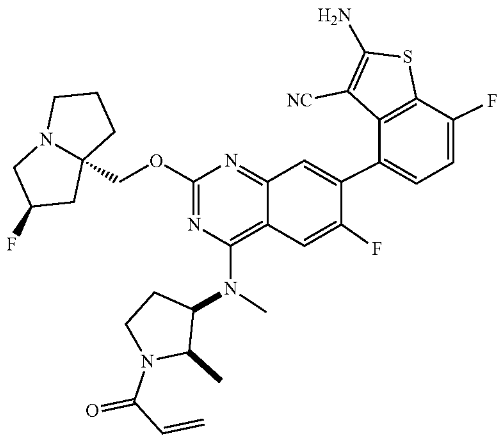 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@H]1C] | LCMS m/z [M + 1]: 662.2<br>$^1$HNMR (400 MHz, $CD_3OD$) δ 8.09 (t, J = 9.54 Hz, 1H), 7.66-7.68 (m, 1H), 7.28-7.32 (m, 1H), 7.06 (t, J = 9.04 Hz, 1H), 6.64-6.73 (m, 1H), 6.32-6.40 (m, 1H), 5.80-5.83 (m, 1H), 5.61 (d, J = 51.60 Hz, 1H), 4.98-5.09 (m, 1H), 4.71-4.78 (m, 2H), 3.90-4.00 (m, 4H), 3.61-3.75 (m, 4H), 3.47-3.54 (m, 1H), 2.21-2.99 (m, 9H), 1.10-1.19 (m, 3H) |

TABLE 5-continued
| Selected compounds of the present disclosure. | | |
|---|---|---|
| Compound No. | Structure | Analytical data |
| 390a | 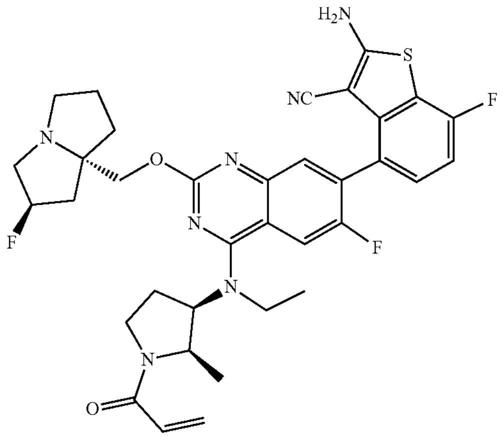 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@H]1C] | |
| 390b | 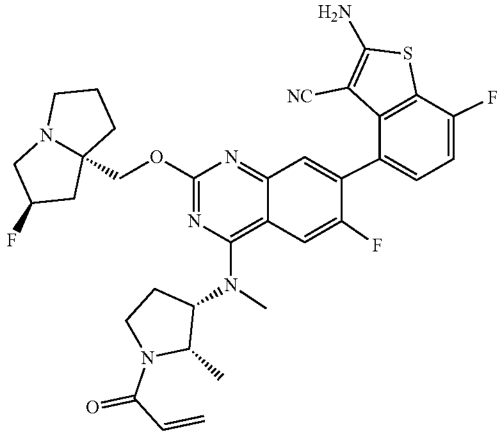 [SMILES: C=CC(=O)N1CC[C@H](N(C)c2nc(OC[C@@]34CCCN3C[C@H](F)C4)nc3cc(-c4ccc(F)c5sc(N)c(C#N)c45)c(F)cc23)[C@@H]1C] | |
| 390c | 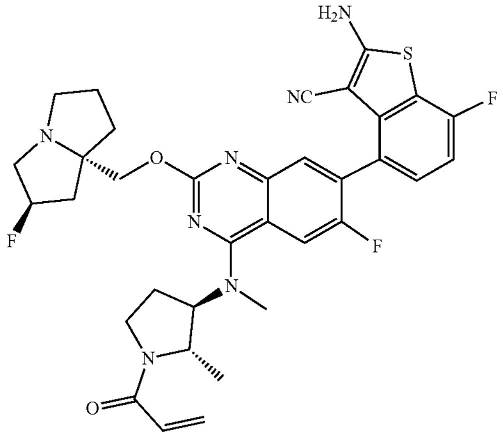 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@@H]1C] | |

TABLE 5-continued
| Selected compounds of the present disclosure. | | |
|---|---|---|
| Compound No. | Structure | Analytical data |
| 390d | 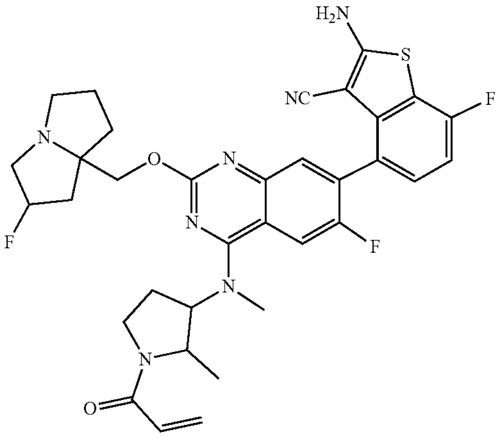 [SMILES: C=CC(=O)N1CCC(N(C)c2nc(OCC34CCCN3CC(F)C4)nc3cc(-c4ccc(F)c5sc(N)c(C#N)c45)c(F)cc23)C1C] | |
| 391 | 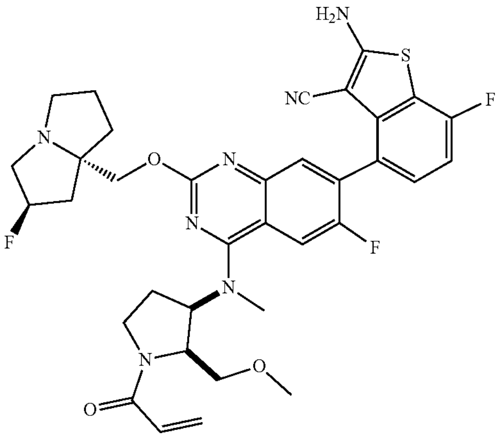 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@H]1COC] | LCMS m/z [M + 1]: 692.3 HNMR (400 MHz, CD3OD) δ 8.17 (d, J = 10.36 Hz, 1H), 7.69 (d, J = 6.34 Hz, 1H), 7.30-7.33 (m, 1H), 7.07 (t, J = 8.78 Hz, 1H), 6.68-6.89 (m, 1H), 6.37 (d, J = 16.56 Hz, 1H), 5.81-5.86 (m, 1H), 5.61 (d, J = 52.20 Hz, 1H), 4.98-5.16 (m, 2H), 4.71-4.81 (m, 2H), 3.36-4.04 (m, 11H), 3.27 (s, 3H), 2.25-2.95 (m, 8H). |
| 391a | 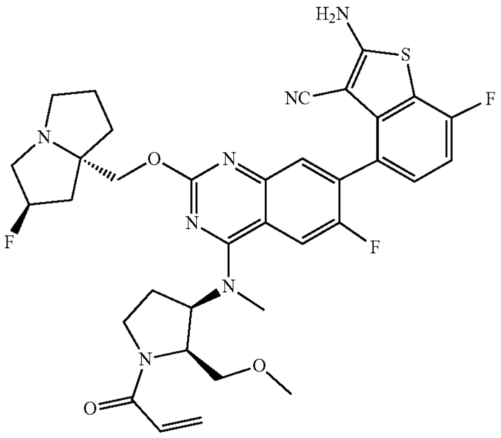 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@H]1COC] | |

TABLE 5-continued
| Selected compounds of the present disclosure. | | |
|---|---|---|
| Compound No. | Structure | Analytical data |
| 391b | 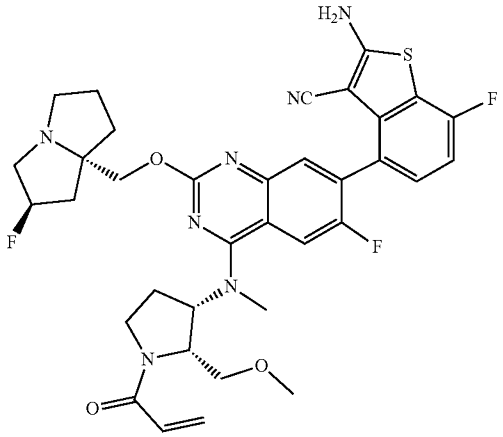 [SMILES: C=CC(=O)N1CC[C@H](N(C)c2nc(OC[C@@]34CCCN3C[C@H](F)C4)nc3cc(-c4ccc(F)c5sc(N)c(C#N)c45)c(F)cc23)[C@@H]1COC] | |
| 391c | 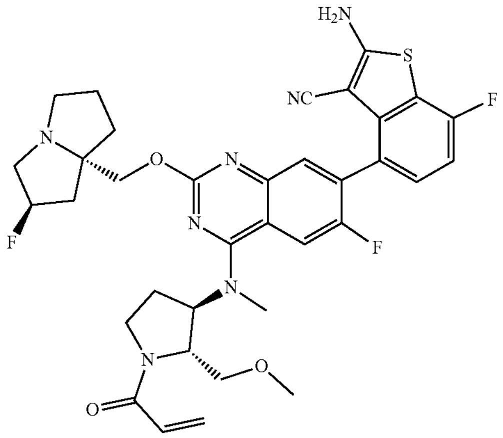 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@@H]1COC] | |
| 391d | 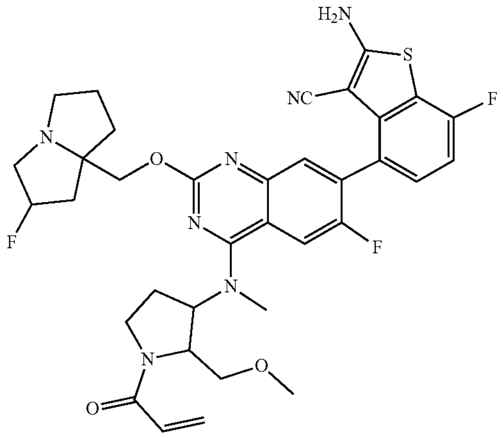 [SMILES: C=CC(=O)N1CCC(N(C)c2nc(OCC34CCCN3CC(F)C4)nc3cc(-c4ccc(F)c5sc(N)c(C#N)c45)c(F)cc23)C1COC] | |

TABLE 5-continued
| Selected compounds of the present disclosure. | | |
|---|---|---|
| Compound No. | Structure | Analytical data |
| 392 | 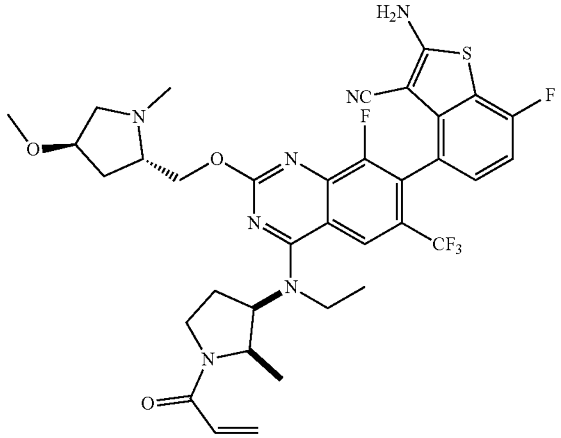 | LCMS m/z [M + 1]: 730.1<br>$^1$HNMR (400 MHz, $CD_3OD$) δ 8.34 (s, 1H), 7.23 (t, 1H), 7.02 (t, 1H), 6.61-6.68 (m, 1H), 6.32 (s, 1H), 5.76 (d, 1H), 4.99-5.06 (m, 1H), 4.70-4.80 (m, 1H), 4.56-4.61 (m, 2H), 3.94-4.10 (m, 3H), 3.68-3.78 (m, 1H), 3.47-3.59 (m, 2H), 3.33 (s, 3H), 2.51-2.79 (m, 7H), 2.16-2.26 (m, 1H), 2.00-2.03 (m, 1H), 1.40-1.45 (m, 3H), 1.03-1.05 (m, 3H). |
| 392a | 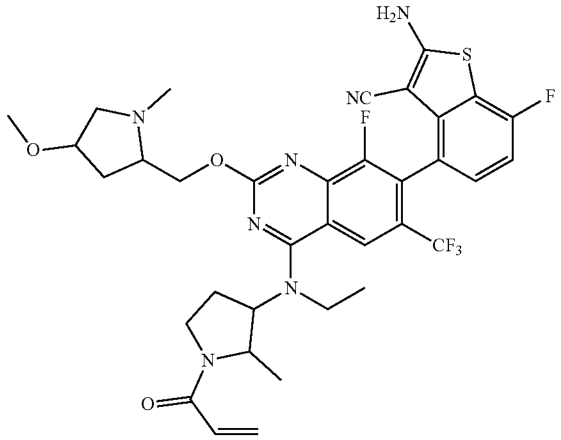 [SMILES: C=CC(=O)N1CCC(N(CC)c2nc(OCC3CC(OC)CN3C)nc3c(F)c(-c4ccc(F)c5sc(N)c(C#N)c45)c(C(F)(F)F)cc23)C1C] | |
| 393 | 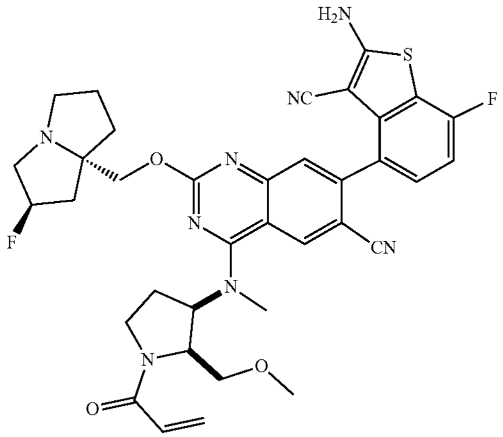 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(C#N)cc23)[C@H]1COC] | LCMS m/z [M + 1]: 699.0<br>$^1$HNMR (400 MHz, $CD_3OD$) δ 8.77 (s, 1H), 7.67 (s, 1H), 7.27-7.35 (m, 1H), 7.09 (t, J = 8.9 Hz, 1H), 6.69-6.80 (m, 1H), 6.31-6.43 (m, 1H), 5.77-5.89 (m, 1H), 5.60 (d, J = 50.9 Hz, 1H), 4.95-5.08 (m, 2H), 4.65-4.77 (m, 2H), 3.88-4.05 (m, 4H), 3.66-3.80 (m, 5H), 3.42-3.64 (m, 2H), 3.27 (d, J = 8.7 Hz, 3H), 2.81-2.93 (m, 1H), 2.59-2.76 (m, 2H), 2.31-2.48 (m, 4H), 2.14-2.27 (m, 1H). |

TABLE 5-continued
Selected compounds of the present disclosure.
| Compound No. | Structure | Analytical data |
|---|---|---|
| 393a | 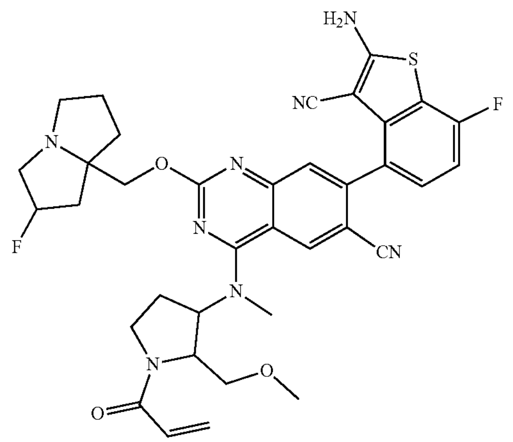 [SMILES: C=CC(=O)N1CCC(N(C)c2nc(OCC34CCCN3CC(F)C4)nc3cc(-c4ccc(F)c5sc(N)c(C#N)c45)c(C#N)cc23)C1COC] | |
| 394 | 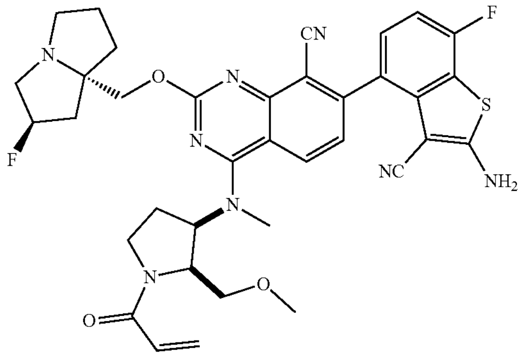 | LCMS m/z [M + 1]: 699.0 $^1$HNMR (400 MHz, $CD_3OD$) δ 8.47-8.49 (m, 1H), 7.40-7.43 (m, 1H), 7.29-7.32 (m, 1H), 7.06 (t, J = 8.92 Hz, 1H), 6.66-6.75 (m, 1H), 6.33 (d, J = 16.32 Hz, 1H), 5.75-5.81 (m, 1H), 5.41 (d, J = 52.48 Hz, 1H), 4.94-4.98 (m, 2H), 4.38-4.57 (m, 3H), 3.36-3.95 (m, 9H), 3.13-3.22 (m, 4H), 1.98-2.83 (m, 8H). |
| 394a | 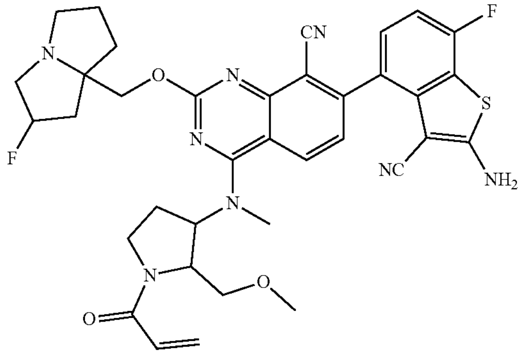 [SMILES: C=CC(=O)N1CCC(N(C)c2nc(OCC34CCCN3CC(F)C4)nc3c(C#N)c(-c4ccc(F)c5sc(N)c(C#N)c45)ccc23)C1COC] | |

TABLE 5-continued
| Selected compounds of the present disclosure. | | |
|---|---|---|
| Compound No. | Structure | Analytical data |
| 395 | 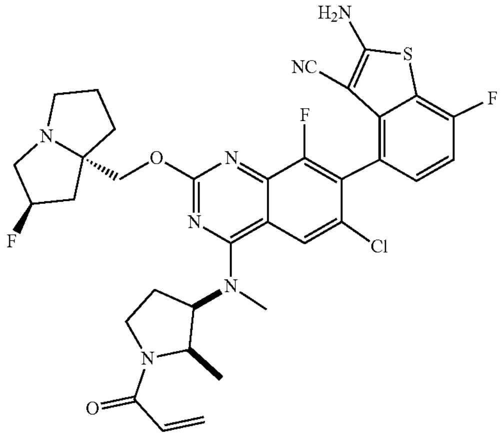 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(Cl)cc23)[C@H]1C] | LCMS m/z [M + 1]: 696.0<br>$^1$HNMR (400 MHz, $CD_3OD$) δ 8.19 (s, 1H), 7.23-7.27 (m, 1H), 7.08 (t, J = 8.94 Hz, 1H), 6.64-6.71 (m, 1H), 6.31-6.40 (m, 1H), 5.79-5.82 (m, 1H), 5.58 (d, J = 51.98 Hz, 1H), 4.98-5.09 (m, 1H), 4.60-4.79 (m, 3H), 3.46-4.04 (m, 9H), 2.16-2.71 (m, 8H), 1.16-1.19 (m, 3H). |
| 395a | 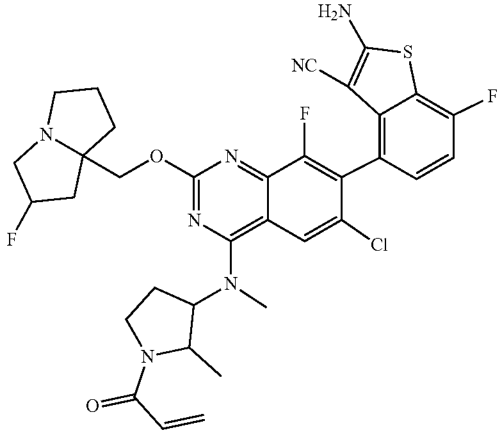 [SMILES: C=CC(=O)N1CCC(N(C)c2nc(OCC34CCCN3CC(F)C4)nc3c(F)c(-c4ccc(F)c5sc(N)c(C#N)c45)c(Cl)cc23)C1C] | |
| 396 | 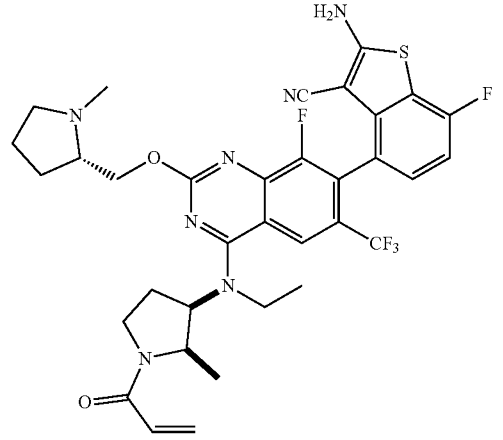 | LCMS m/z [M + 1]: 701.2<br>$^1$HNMR (400 MHz, $CD_3OD$) δ 8.33 (s, 1H), 7.21-7.24 (m, 1H), 7.01 (t, 1H), 6.60-6.67 (m, 1H), 6.31 (t, 1H), 5.76 (d, 1H), 4.99-5.05 (m, 1H), 4.77 (t, 1H), 4.48-4.56 (m, 2H), 3.93-4.09 (m, 2H), 3.57-3.78 (m, 2H), 3.12-3.20 (m, 2H), 2.43-2.62 (m, 6H), 2.11-2.16 (m, 1H), 1.73-1.90 (m, 3H), 1.39-1.44 (m, 3H), 1.03-1.10 (m, 3H). |

TABLE 5-continued
| Selected compounds of the present disclosure. | | |
|---|---|---|
| Compound No. | Structure | Analytical data |
| 396a | 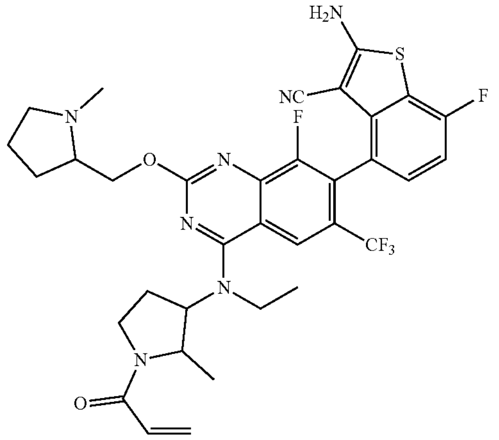 [SMILES: C=CC(=O)N1CCC(N(CC)c2nc(OCC3CCCN3C)nc3c(F)c(-c4ccc(F)c5sc(N)c(C#N)c45)c(C(F)(F)F)cc23)C1C] | |
| 397 | 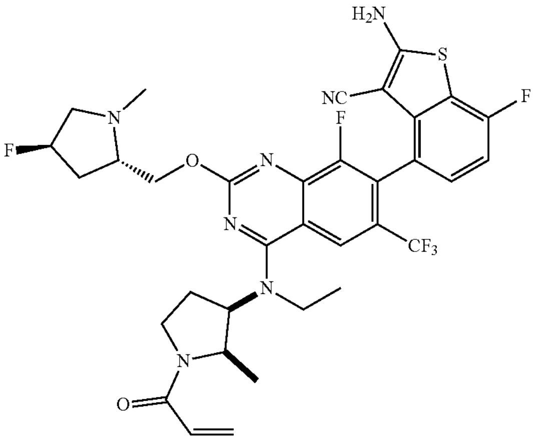 | LCMS m/z [M + 1]: 719.2<br>$^{1}$HNMR (400 MHz, $CD_3OD$) δ 8.32 (s, 1H), 7.22-7.24 (m, 1H), 7.01 (t, 1H), 6.60-6.70 (m, 1H), 6.31 (t, 1H), 5.74-5.78 (m, 1H), 4.99-5.24 (m, 2H), 4.82 (s, 1H), 4.48-4.56 (m, 2H), 3.90-4.07 (m, 2H), 3.45-3.77 (m, 3H), 3.16-3.21 (m, 1H), 2.47-2.64 (m, 6H), 2.26-2.29 (m, 1H), 1.96-2.04 (m, 1H), 1.37-1.42 (m, 3H), 1.03-1.10 (m, 3H). |
| 397a | 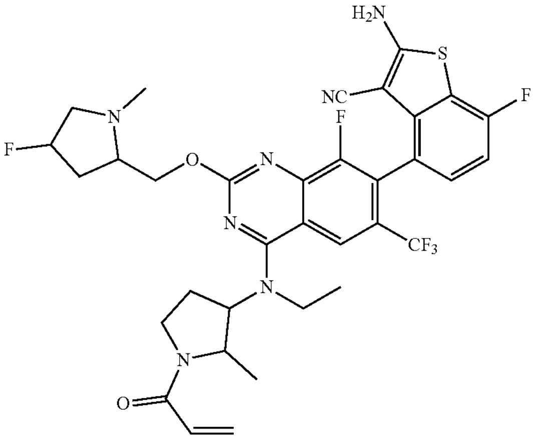 [SMILES: C=CC(=O)N1CCC(N(CC)c2nc(OCC3CC(F)CN3C)nc3c(F)c(-c4ccc(F)c5sc(N)c(C#N)c45)c(C(F)(F)F)cc23)C1C] | |

TABLE 5-continued
| Selected compounds of the present disclosure. | | |
|---|---|---|
| Compound No. | Structure | Analytical data |
| 398 | 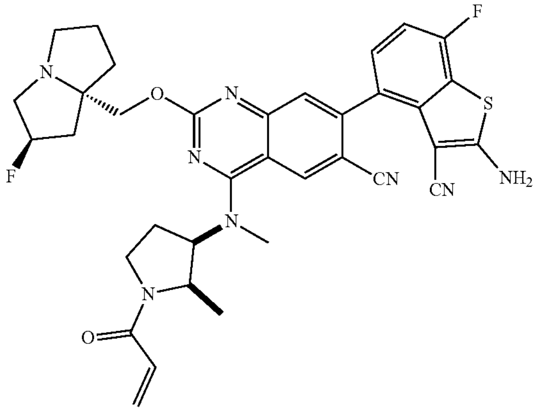 | LCMS m/z [M + 1]: 683.1<br>$^1$HNMR (400 MHz, $CD_3OD$) δ 8.56 (d, 1H), 7.65 (d, 1H), 7.32-7.27 (m, 1H), 7.07-7.02 (m, 1H), 6.67-6.61 (m, 1H), 6.30 (t, 1H), 5.57 (d, 1H), 5.39 (d, 0.5H), 5.25 (d, 0.5H), 5.06-4.98 (m, 1H), 4.78-4.68 (m, 1H), 4.39-4.28 (m, 2H), 4.13-4.07 (m, 1H), 3.97-3.40 (m, 5H), 3.20-2.91 (m, 2H), 2.60-1.93 (m, 8H), 1.38-1.28 (m, 3H), 1.13-0.98 (m, 3H). |
| 398a | 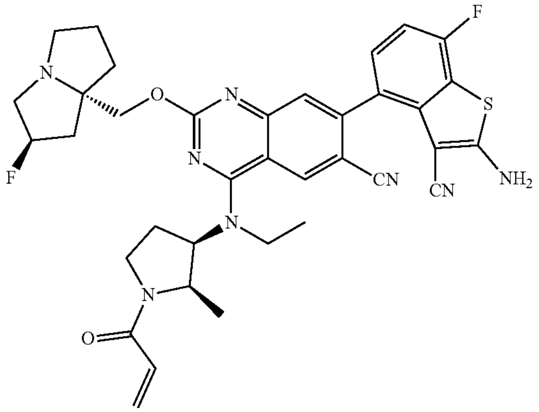 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(C#N)cc23)[C@H]1C] | |
| 398b | 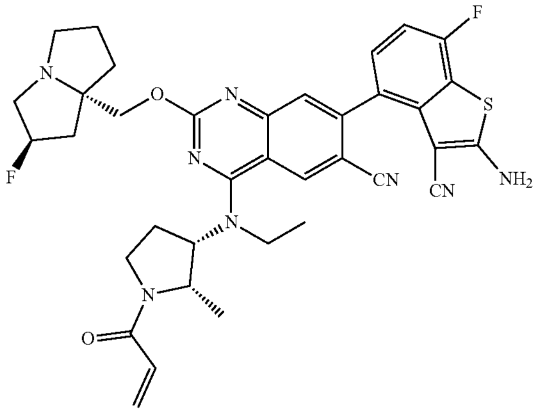 [SMILES: C=CC(=O)N1CC[C@H](N(CC)c2nc(OC[C@@]34CCCN3C[C@H](F)C4)nc3cc(-c4ccc(F)c5sc(N)c(C#N)c45)c(C#N)cc23)[C@@H]1C] | |

TABLE 5-continued
| Selected compounds of the present disclosure. | | |
|---|---|---|
| Compound No. | Structure | Analytical data |
| 398c | 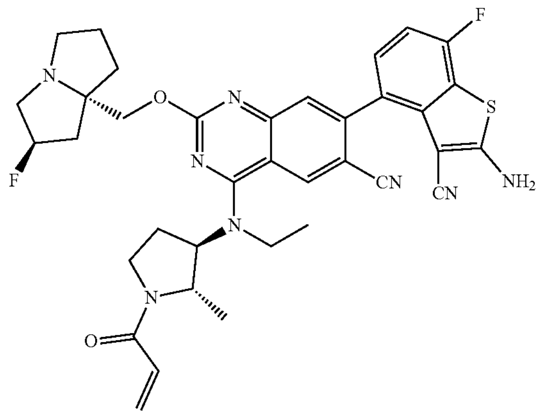 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(C#N)cc23)[C@@H]1C] | |
| 398d | 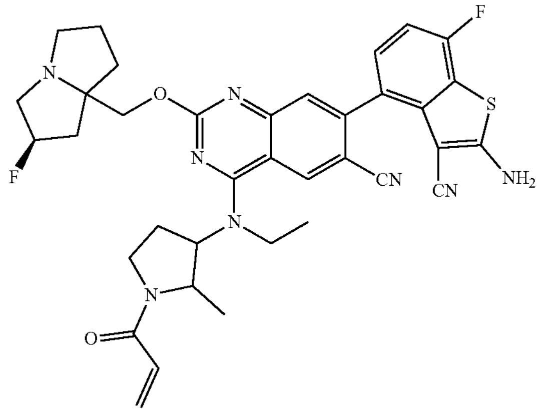 [SMILES: C=CC(=O)N1CCC(N(CC)c2nc(OCC34CCCN3C[C@H](F)C4)nc3cc(-c4ccc(F)c5sc(N)c(C#N)c45)c(C#N)cc23)C1C] | |
| 399 | 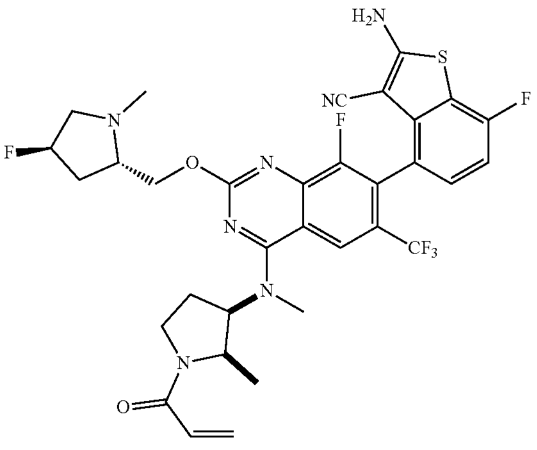 | LCMS m/z [M + 1]: 704.1<br>$^1$HNMR (400 MHz, $CD_3OD$) δ 8.35 (s, 1H), 7.26-7.18 (m, 1H), 7.01 (t, 1H), 6.69-6.60 (m, 1H), 6.32 (t, 1H), 5.77 (d, 1H), 5.25 (s, 0.5H), 5.10 (s, 0.5H), 5.06-5.01 (m, 1H), 4.53-4.50 (m, 2H), 3.96-3.93 (m, 1H), 3.77-3.74 (m, 1H), 3.73-3.44 (m, 6H), 3.24-3.14 (m, 1H), 2.72-2.65 (m, 1H), 2.55 (d, 3H), 2.49-2.41 (m, 1H), 2.08-1.93 (m, 1H), 1.17-1.11 (m, 3H). |

TABLE 5-continued
| Selected compounds of the present disclosure. | | |
|---|---|---|
| Compound No. | Structure | Analytical data |
| 399a | 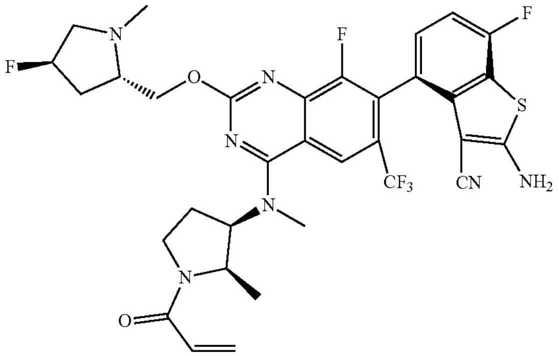 | |
| 399b | 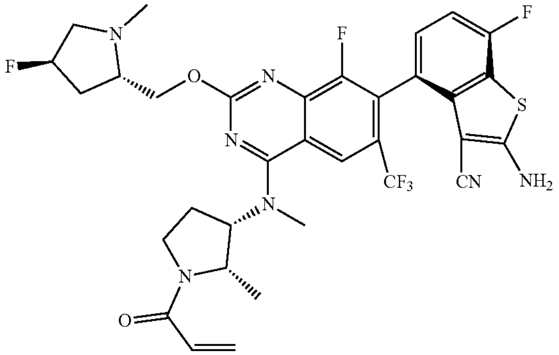 | |
| 399c | 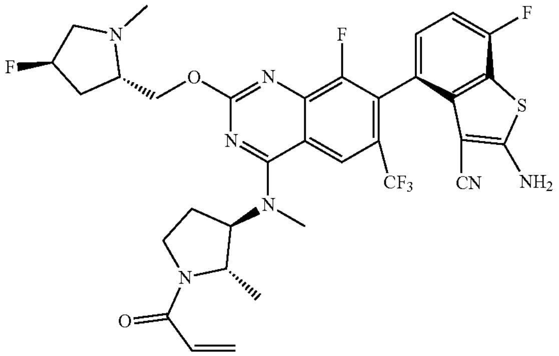 | |
| 399d | 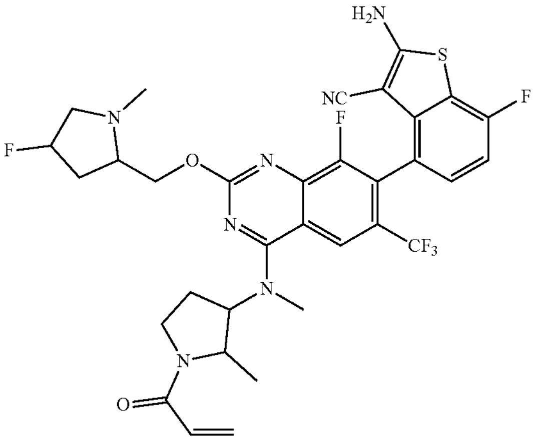 [SMILES: C=CC(=O)N1CCC(N(C)c2nc(OCC3CC(F)CN3C)nc3c(F)c(-c4ccc(F)c5sc(N)c(C#N)c45)c(C(F)(F)F)cc23)C1C] | |

TABLE 5-continued
Selected compounds of the present disclosure.
| Compound No. | Structure | Analytical data |
|---|---|---|
| 400 | 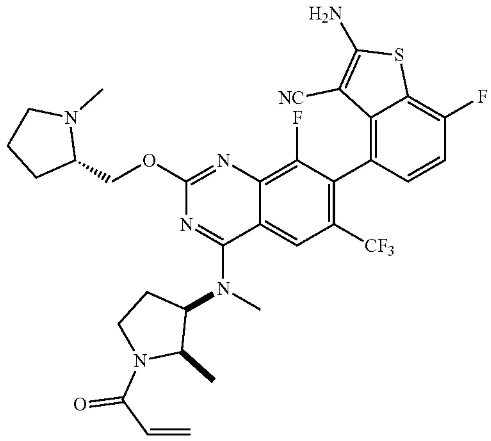 | LCMS m/z [M + 1]: 686.2 $^1$HNMR (400 MHz, $CD_3OD$) δ 8.36 (S, 1H), 7.24-7.20 (m, 1H), 7.01 (t, 1H), 6.68-6.62 (m, 1H), 6.32 (t, 1H), 5.77 (d, 1H), 5.04 (m, 1H), 4.59 (m, 2H), 3.96 (t, 1H), 3.78 (t, 1H), 3.62 (d, 3H), 3.47 (m, 1H), 3.17-3.12 (m, 2H), 2.78 (m, 2H), 2.66 (m, 2H), 2.45 (m, 1H), 2.23 (m, 2H), 1.92 (m, 3H), 1.18-1.10 (m, 3H). |
| 400a | 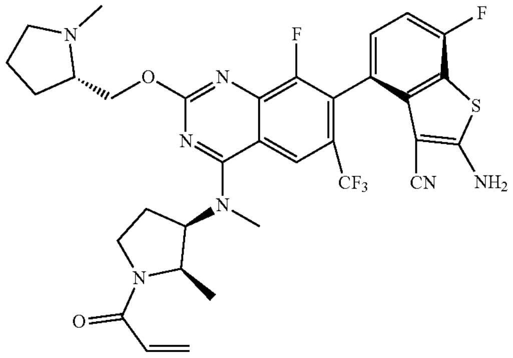 | |
| 400b | 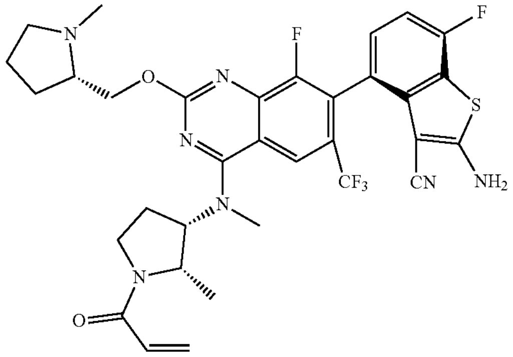 | |
| 400c | 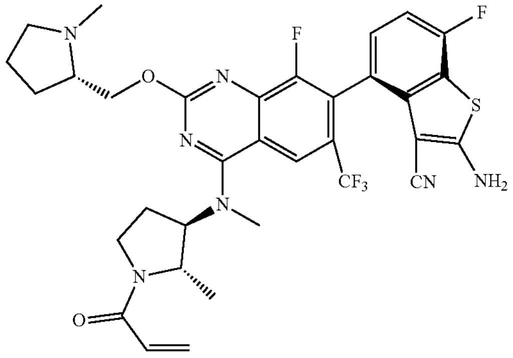 | |

TABLE 5-continued
| Compound No. | Structure | Analytical data |
|---|---|---|
| Selected compounds of the present disclosure. | | |
| 400d | 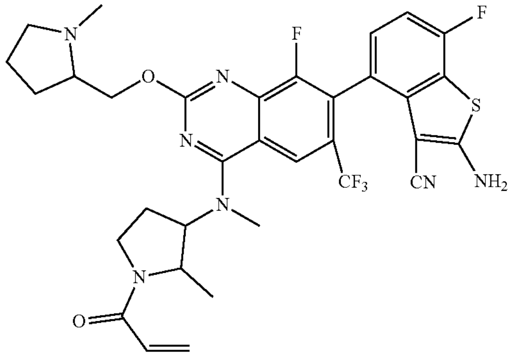 [SMILES: C=CC(=O)N1CCC(N(C)c2nc(OCC3CCCN3C)nc3c(F)c(-c4ccc(F)c5sc(N)c(C#N)c45)c(C(F)(F)F)cc23)C1C] | |
| 401 | 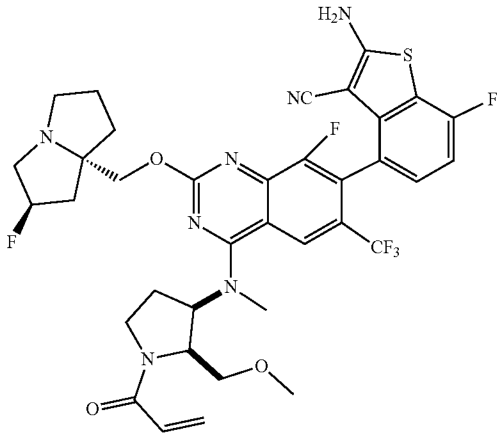 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(C(F)(F)F)cc23)[C@H]1COC] | LCMS m/z [M + 1]: 760.0 $^1$HNMR (400 MHz, $CD_3OD$) δ 8.47 (d, J = 4.88 Hz, 1H), 7.24-7.28 (m, 1H), 7.06 (t, J = 8.78 Hz, 1H), 6.69-6.80 (m, 1H), 6.34-6.41 (m, 1H), 5.80-5.86 (m, 1H), 5.58 (d, J = 52.32 Hz, 1H), 4.99-5.09 (m, 2H), 4.62-4.79 (m, 2H), 3.45-4.05 (m, 11H), 3.25-3.29 (m, 3H), 2.18-2.90 (m, 8H). |
| 401a | 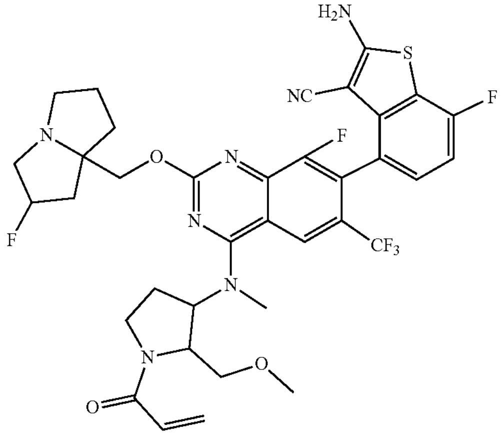 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1COC] | |

TABLE 5-continued
| Selected compounds of the present disclosure. | | |
|---|---|---|
| Compound No. | Structure | Analytical data |
| 402 | 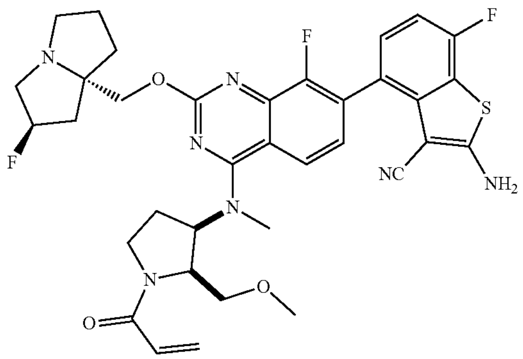 | LCMS m/z [M + 1]: 692.0<br>$^1$HNMR (400 MHz, $CD_3OD$) δ 8.22 (d, J = 9.00 Hz, 1H), 7.43-7.46 (m, 1H), 7.30-7.34 (m, 1H), 7.08 (t, J = 8.74 Hz, 1H), 6.68-6.75 (m, 1H), 6.34-6.38 (m, 1H), 5.82-5.85 (m, 1H), 5.58 (d, J = 51.34 Hz, 1H), 4.96-5.05 (m, 2H), 4.79-4.83 (m, 1H), 4.63-4.71 (m, 1H), 3.46-4.06 (m, 11H), 3.25-3.26 (m, 3H), 2.15-2.90 (m, 8H). |
| 402a | 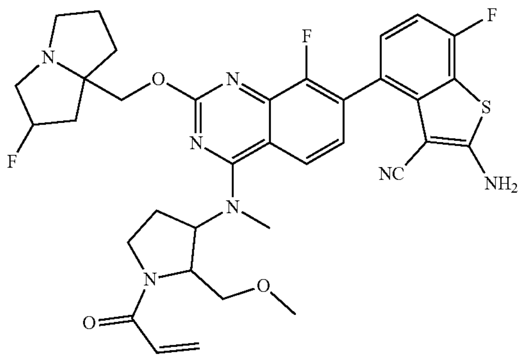 [SMILES: C=CC(=O)N1CCC(N(C)c2nc(OCC34CCCN3CC(F)C4)nc3c(F)c(-c4ccc(F)c5sc(N)c(C#N)c45)ccc23)C1COC] | |
| 403 | 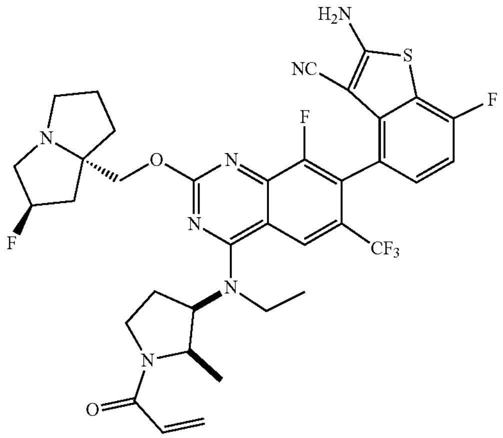 [SMILES: C=CC(=O)N1CC[C@@H](N(CC)c2nc(OC[C@@]34CCCN3C[C@H](F)C4)nc3c(F)c(-c4ccc(F)c5sc(N)c(C#N)c45)c(C(F)(F)F)cc23)[C@H]1C] | LCMS m/z [M + 1]: 744.0<br>$^1$HNMR (400 MHz, $CD_3OD$) δ 8.40 (s, 1H), 7.24-7.28 (m, 1H), 7.05 (t, J = 8.68 Hz, 1H), 6.64-6.71 (m, 1H), 6.31-6.40 (m, 1H), 5.80-5.83 (m, 1H), 5.58 (d, J = 51.54 Hz, 1H), 5.00-5.15 (m, 1H), 4.74-4.78 (m, 1H), 3.59-4.16 (m, 7H), 3.43-3.52 (m, 1H), 2.19-2.76 (m, 8H), 1.49-1.52 (m, 3H), 1.31-1.35 (m, 3H). |

TABLE 5-continued
| Selected compounds of the present disclosure. | | |
|---|---|---|
| Compound No. | Structure | Analytical data |
| 403a | 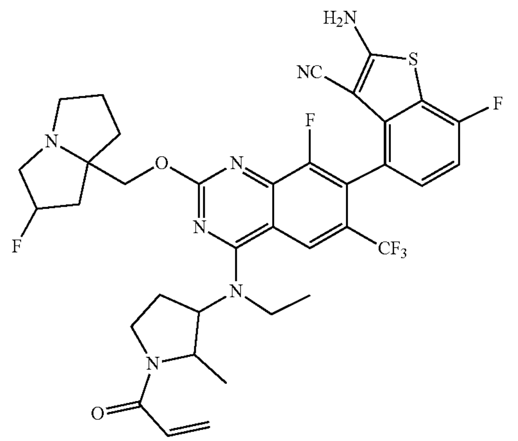 [SMILES: C=CC(=O)N1CCC(N(CC)c2nc(OCC34CCCN3CC(F)C4)nc3c(F)c(-c4ccc(F)c5sc(N)c(C#N)c45)c(C(F)(F)F)cc23)C1C] | |
| 404 | 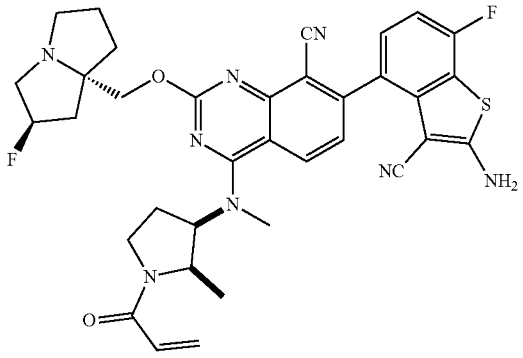 | LCMS m/z [M + 1]: 669.0<br>$^1$HNMR (400 MHz, $CD_3OD$) δ 8.45-8.48 (m, 1H), 7.41-7.44 (m, 1H), 7.29-7.32 (m, 1H), 7.06 (t, J = 9.28, 1H), 6.62-6.68 (m, 1H), 6.33 (t, J = 17.44, 1H), 5.78 (d, J = 10.6 Hz, 1H), 5.32-5.50 (m, 1H), 5.01-5.06 (m, 1H), 4.40-4.63 (m, 4H), 3.13-3.98 (m, 8H), 2.00-2.67 (m, 8H), 1.06-1.14 (m, 3H). |
| 404a | 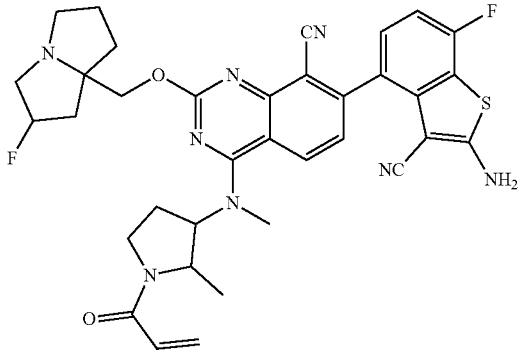 [SMILES: C=CC(=O)N1CCC(N(C)c2nc(OCC34CCCN3CC(F)C4)nc3c(C#N)c(-c4ccc(F)c5sc(N)c(C#N)c45)ccc23)C1C] | |

TABLE 5-continued
| Selected compounds of the present disclosure. | | |
|---|---|---|
| Compound No. | Structure | Analytical data |
| 405 | 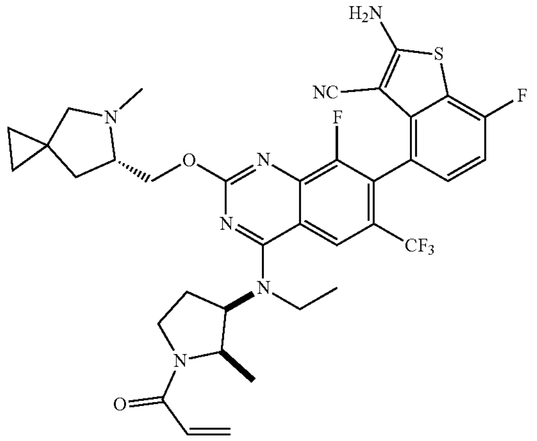 | LCMS m/z [M + 1]: 726 $^1$HNMR (400 MHz, $CD_3OD$) δ 8.33 (s, 1H), 7.21-7.24 (m, 1H), 7.01 (t, 1H), 6.59-6.67 (m, 1H), 6.26-6.36 (m, 1H), 5.74-5.77 (m, 1H), 4.98-5.06 (m, 1H), 4.74-4.79 (m, 1H), 4.52-4.65 (m, 2H), 3.90-4.10 (m, 2H), 3.457-3.78 (m, 2H), 3.12-3.19 (m, 1H), 2.50-2.87 (m, 7H), 2.13-2.23 (m, 1H), 1.69-1.78 (m, 1H), 1.38-1.45 (m, 3H), 1.03-1.11 (m, 3H), 0.55-0.66 (m, 4H). |
| 405a | 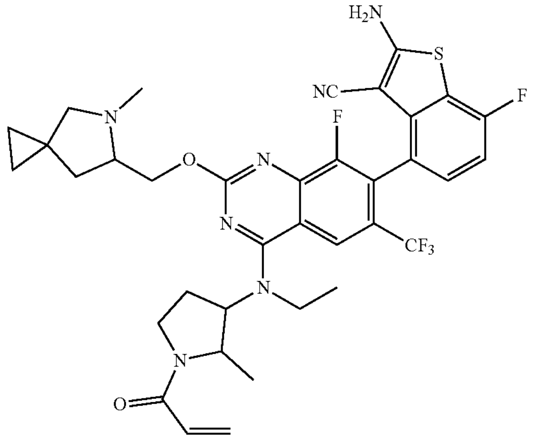 [SMILES: C=CC(=O)N1CCC(N(CC)c2nc(OCC3CC4(CC4)CN3C)nc3c(F)c(-c4ccc(F)c5sc(N)c(C#N)c45)c(C(F)(F)F)cc23)C1C] | |
| 406 | 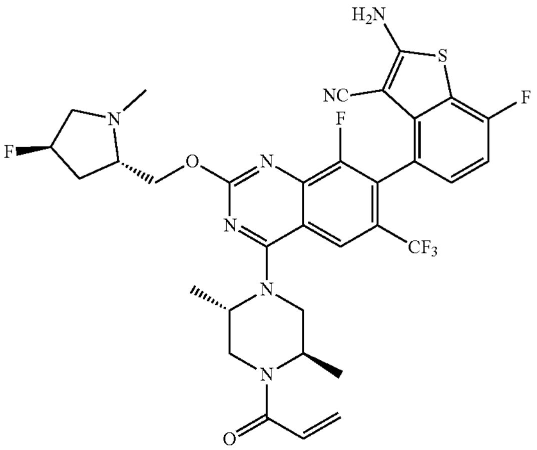 [SMILES: C=CC(=O)N1C[C@H](C)N(c2nc(OC[C@@H]3C[C@@H](F)CN3C)nc3c(F)c(-c4ccc(F)c5sc(N)c(C#N)c45)c(C(F)(F)F)cc23)C[C@H]1C] | LCMS m/z [M + 1]: 704.1 $^1$HNMR (400 MHz, $CD_3OD$) δ 8.142 (s, 1H), 7.198-7.261 (m, 1H), 7.016 (t, 1H), 6.75-6.84 (m, 1H), 6.249-6.327 (m, 1H), 5.78-5.846 (m, 1H), 5.273 (s, 0.5H), 5.136 (s, 0.5H), 4.506-4.606 (m, 2H), 4.237-4.409 (m, 2H), 3.866-4.025 (m, 2H), 3.507-3.59 (m, 1H), 2.672-2.817 (m, 2H), 2.607 (s, 3H), 2.225-2.406 (m, 2H), 1.962-2.145 (m, 2H), 1.381-1.524 (m, 3H), 1.228-1.336 (m, 3H). |

TABLE 5-continued
Selected compounds of the present disclosure.
| Compound No. | Structure | Analytical data |
| --- | --- | --- |
| 406a | 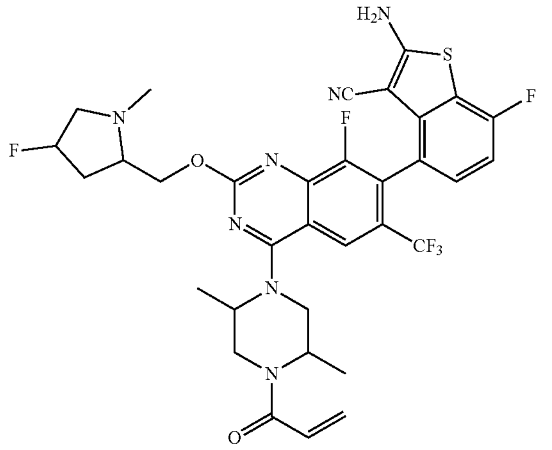 [SMILES: C=CC(=O)N1CC(C)N(c2nc(OCC3CC(F)CN3C)nc3c(F)c(-c4ccc(F)c5sc(N)c(C#N)c45)c(C(F)(F)F)cc23)CC1C] | |
| 407 | 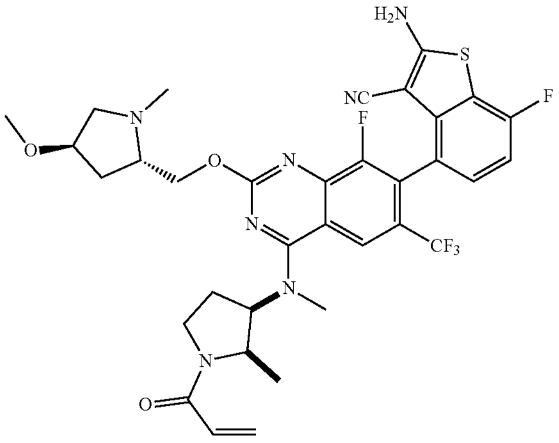 | LCMS m/z [M + 1]: 716.1 $^1$HNMR (400 MHz, $CD_3OD$) δ 8.36 (s, 1H), 7.22 (s, 1H), 7.01 (t, 1H), 6.61-6.68 (m, 1H), 6.32 (t, 1H), 5.76-5.78 (m, 1H), 5.03 (m, 2H), 4.51-4.55 (m, 2H), 3.96 (s, 1H), 3.57-3.61 (m, 5H), 3.47-3.48 (m, 2H), 3.12-3.14 (m, 2H), 2.46-2.64 (m, 6H), 1.93-2.18 (m, 3H), 1.11-1.18 (m, 3H). |
| 407a | 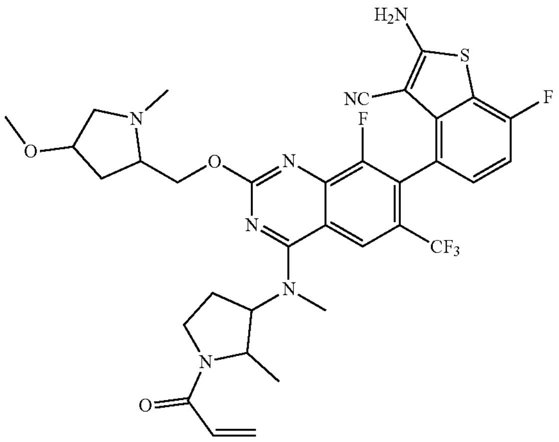 [SMILES: C=CC(=O)N1CCC(N(C)c2nc(OCC3CC(OC)CN3C)nc3c(F)c(-c4ccc(F)c5sc(N)c(C#N)c45)c(C(F)(F)F)cc23)C1C] | |

TABLE 5-continued
| Selected compounds of the present disclosure. | | |
|---|---|---|
| Compound No. | Structure | Analytical data |
| 408 | 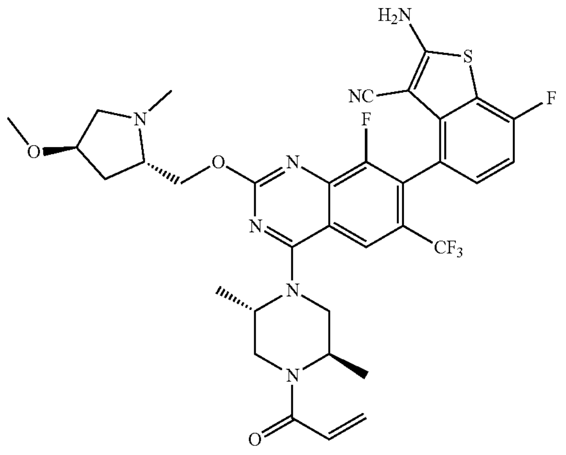 [SMILES: C=CC(=O)N1C[C@H](C)N(c2nc(OC[C@@H]3C[C@@H](OC)CN3C)nc3c(F)c(-c4ccc(F)c5sc(N)c(C#N)c45)c(C(F)(F)F)cc23)C[C@H]1C] | LCMS m/z [M + 1]: 716.2<br>$^1$HNMR (400 MHz, $CD_3OD$) δ 8.14 (s, 1H), 7.21-7.23 (m, 1H), 7.01 (t, 1H), 6.75-6.86 (m, 1H), 6.25-6.31 (m, 1H), 5.78-5.83 (m, 1H), 4.89-4.95 (m, 1H), 4.27-4.60 (m, 4H), 3.83-4.05 (m, 3H), 3.38-3.61 (m, 2H), 3.28 (s, 1H), 3.10-3.16 (m, 1H), 2.41-2.61 (m, 4H), 2.11-2.20 (m, 1H), 1.91-2.01 (m, 1H), 1.22-1.52 (m, 8H). |
| 408a | 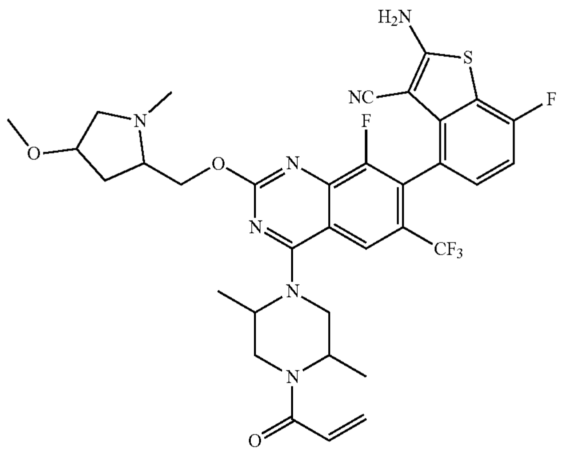 [SMILES: C=CC(=O)N1CC(C)N(c2nc(OCC3CC(OC)CN3C)nc3c(F)c(-c4ccc(F)c5sc(N)c(C#N)c45)c(C(F)(F)F)cc23)CC1C] | |
| 409 | 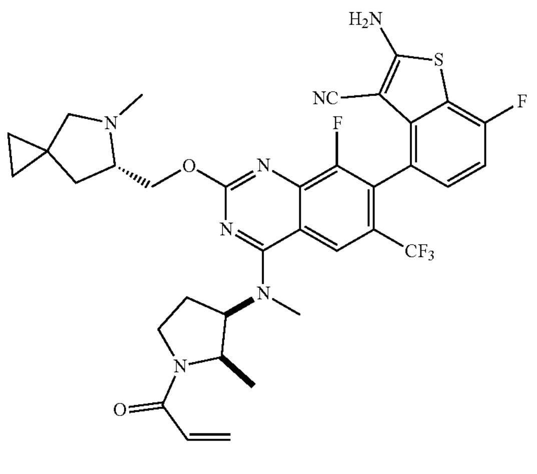 | LCMS m/z [M + 1]: 712.2<br>$^1$HNMR (400 MHz, $CD_3OD$) δ 8.36 (d, 1H), 7.23-7.20 (m, 1H), 7.01 (t, 1H), 6.70-6.61 (m, 1H), 6.36-6.27 (m, 1H), 5.77 (d, 1H), 5.04-5.02 (m, 1H), 4.94-4.91 (m, 1H), 4.58-4.54 (m, 2H), 3.96 (t, 1H), 3.78 (t, 1H), 3.62 (d, 3H), 3.59-3.57 (m, 1H), 2.67-2.56 (m, 7H), 2.49-2.44 (m, 1H), 2.16-2.14 (m, 1H), 1.72-1.67 (m, 1H), 1.16-1.10 (m, 3H), 0.61 (d, 3H). |

TABLE 5-continued
Selected compounds of the present disclosure.
| Compound No. | Structure | Analytical data |
| --- | --- | --- |
| 409a | 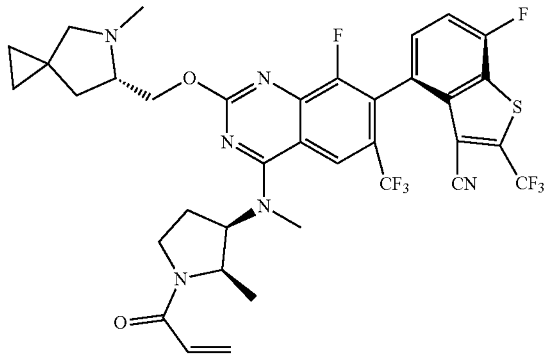 | |
| 409b | 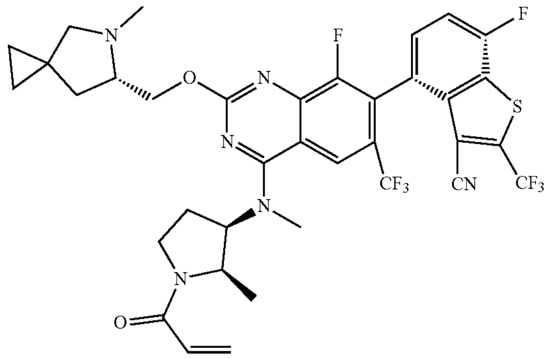 | |
| 409c | 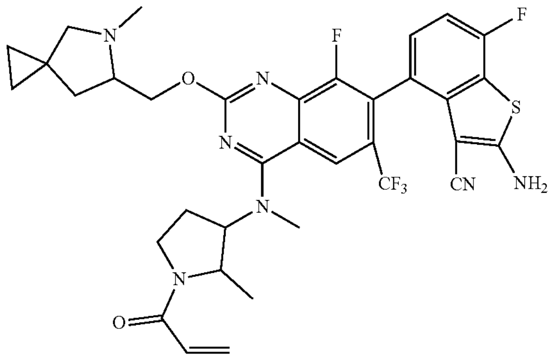 [SMILES: C=CC(=O)N1CCC(N(C)c2nc(OCC3CC4(CC4)CN3C)nc3c(F)c(-c4ccc(F)c5sc(N)c(C#N)c45)c(C(F)(F)F)cc23)C1C] | |
| 410 | 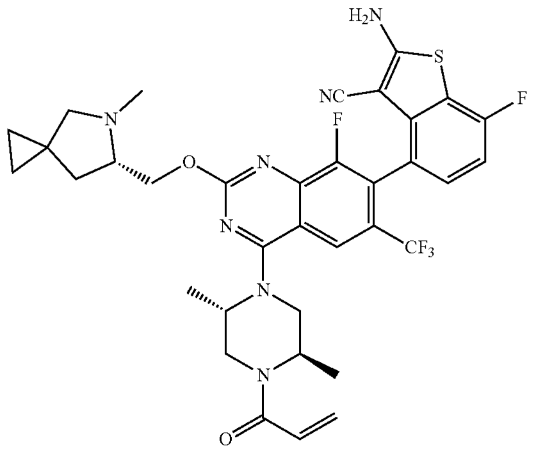 [SMILES: C=CC(=O)N1C[C@H](C)N(c2nc(OC[C@@H]3CC4(CC4)CN3C)nc3c(F)c(-c4ccc(F)c5sc(N)c(C#N)c45)c(C(F)(F)F)cc23)C[C@H]1C] | LCMS m/z [M + 1]: 712.2 $^1$HNMR (400 MHz, $CD_3OD$) δ 8.13 (d, 1H), 7.24-7.21 (m, 1H), 7.01 (t, 1H), 6.85-6.75 (m, 1H), 6.31-6.25 (m, 1H), 5.83-5.78 (m, 1H), 4.89 (m, 1H), 4.58 (d, 3H), 4.27 (d, 1H), 4.01-3.88 (m, 2H), 2.82 (d, 1H), 2.71 (d, 1H), 2.60 (d, 3H), 2.21-2.16 (m, 1H), 1.79-1.74 (m, 1H), 1.52-1.46 (m, 3H), 1.32-1.28 (m, 5H), 0.67-0.56 (m, 4H). |

TABLE 5-continued
| Selected compounds of the present disclosure. | | |
|---|---|---|
| Compound No. | Structure | Analytical data |
| 410a | 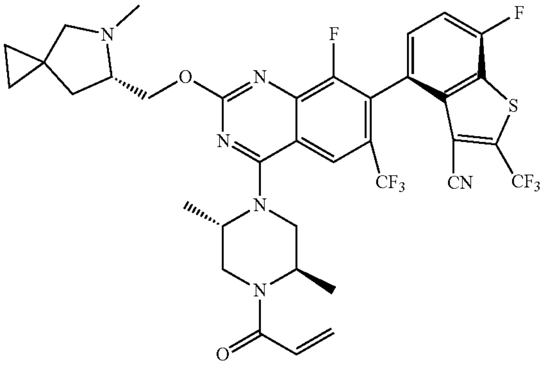 | LCMS m/z [M + 1]: 712.4 $^1$HNMR (400 MHz, $CD_3OD$) δ 8.16 (s, 1H), 7.22-7.27 (m, 1H), 7.01-7.07 (m, 1H), 6.72-6.95 (m, 1H), 6.27-6.34 (m, 1H), 5.81-5.84 (m, 1H), 4.90 (m, 1H), 4.60 (d, 3H), 4.27-4.42 (m, 1H), 3.88-3.97 (m, 2H), 2.83 (d, 1H), 2.74 (d, 1H), 2.62 (s, 3H), 2.17-2.24 (m, 1H), 1.75-1.82 (m, 1H), 1.50-1.54 (m, 3H), 1.32-1.42 (m, 5H), 0.68-0.70 (m, 4H). |
| 410b | 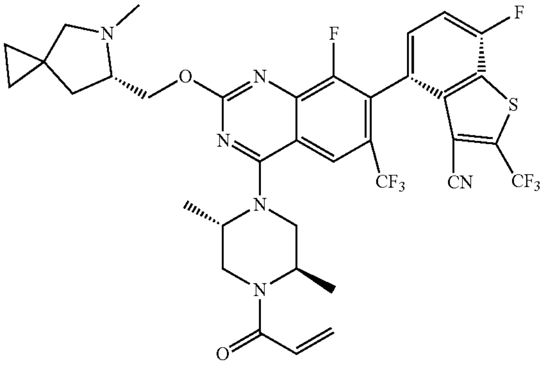 | LCMS m/z [M + 1]: 712.4 $^1$HNMR (400 MHz, $CD_3OD$) δ 8.15 (s, 1H), 7.23-7.27 (m, 1H), 7.00-7.06 (m, 1H), 6.77-6.93 (m, 1H), 6.27-6.34 (m, 1H), 5.81-5.84 (m, 1H), 4.97 (m, 1H), 4.22-4.63 (m, 4H), (m, 1H), 3.90-4.12 (m, 2H), 3.10 (m, 1H), 2.77 (d, 1H), 2.66 (d, 1H), 2.55 (s, 3H), 2.14-2.21 (m, 1H), 1.73-1.80 (m, 1H), 1.49 (m, 3H), 1.25-1.34 (m, 5H), 0.55-0.69 (m, 4H). |
| 410c | 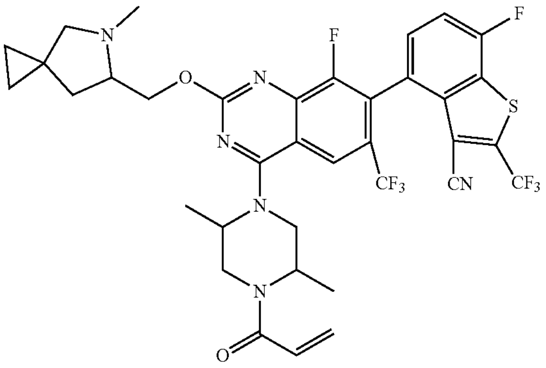 [SMILES: C=CC(=O)N1CC(C)N(c2nc(OCC3CC4(CC4)CN3C)nc3c(F)c(-c4ccc(F)c5sc(C(F)(F)F)c(C#N)c45)c(C(F)(F)F)cc23)CC1C] | |

TABLE 5-continued
Selected compounds of the present disclosure.
| Compound No. | Structure | Analytical data |
| --- | --- | --- |
| 411 | 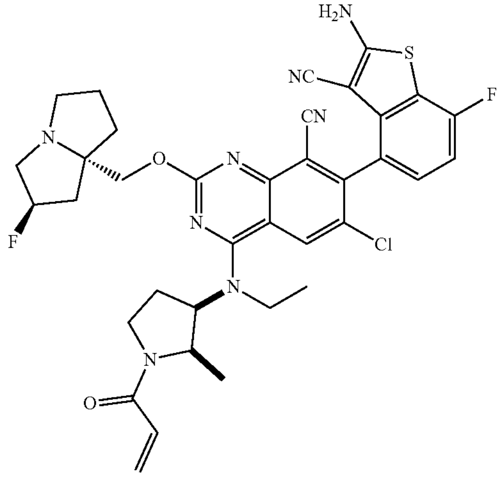 | LCMS m/z [M + 1]: 717.1 $^1$HNMR (400 MHz, $CD_3OD$) δ 8.42 (s, 1H), 7.27 (s, 1H), 7.08 (t, 1H), 6.66-6.595 (m, 1H), 6.3 (t, 1H), 5.75 (d,1H), 5.37 (s, 0.5H), 5.24 (s, 0.5H), 4.99 (s, 1H), 4.75-4.56 (m, 2H), 4.43-4.33 (m, 2H), 4.05-3.57 (m, 5H), 3.02 (s, 1H), 2.47-1.91 (m, 9H), 1.31-1.25 (m, 3H), 1.00 (t, 3H). |
| 411a | 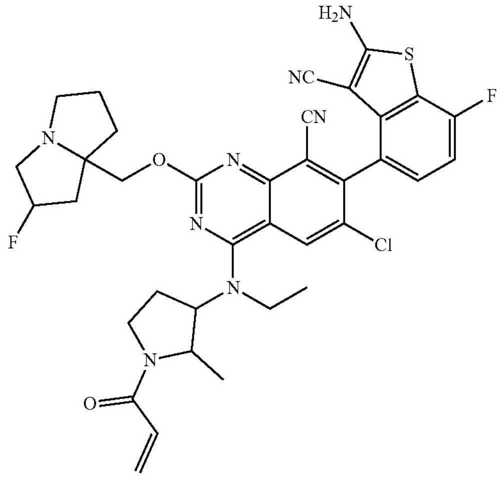 [SMILES: C=CC(=O)N1CCC(N(CC)c2nc(OCC34CCCN3CC(F)C4)nc3c(C#N)c(-c4ccc(F)c5sc(N)c(C#N)c45)c(Cl)cc23)C1C] | |
| 412 | 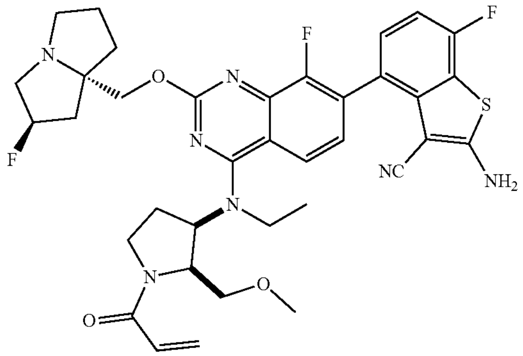 | LCMS m/z [M + 1]: 706.2 $^1$HNMR (400 MHz, $CD_3OD$) δ 8.9-8.18 (m, 1H), 7.44-7.53 (m, 1H), 7.28-7.35 (m, 1H), 7.06 (t, J = 8.8 Hz, 1H), 6.65-6.83 (m, 1H), 6.28-6.43 (m, 1H), 5.75-5.88 (m, 1H), 5.58 (d, J = 48.8 Hz, 1H), 4.91-5.12 (m, 2H), 4.72-4.86 (m, 1H), 4.57-4.71 (m, 1H), 3.39-4.35 (m, 9H), 3.11-3.28 (m, 4H), 2.08-2.91 (m, 8H), 1.40-1.59 (m, 3H). |

TABLE 5-continued
| Selected compounds of the present disclosure. | | |
|---|---|---|
| Compound No. | Structure | Analytical data |
| 412a | 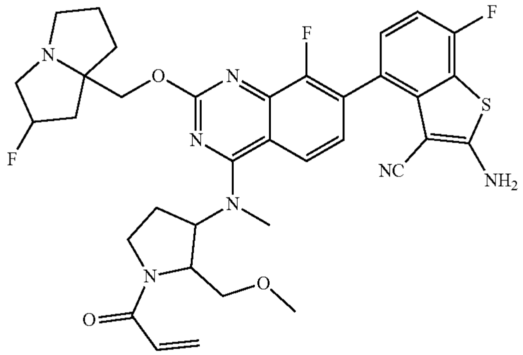 [SMILES: C=CC(=O)N1CCC(N(C)c2nc(OCC34CCCN3CC(F)C4)nc3c(F)c(-c4ccc(F)c5sc(N)c(C#N)c45)ccc23)C1COC] | |
| 413 | 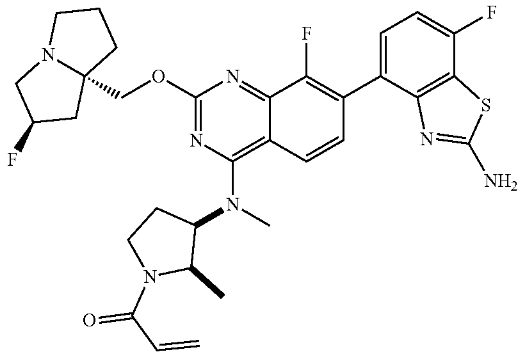 | LCMS m/z [M + 1]: 638.2 $^{1}$HNMR (400 MHz, $CD_3OD$) δ 8.15 (d, J = 9.0 Hz, 1H), 7.63 (s, 1H), 7.47-7.38 (m, 1H), 7.05 (t, J = 8.8 Hz, 1H), 6.64-6.71 (m, 1H), 6.32-6.40 (m, 1H), 5.82 (d, J = 10.5, 1H), 5.59 (d, J = 51.8 Hz, 1H), 5.00-5.13 (m, 2H), 4.75 (s, 2H), 4.11-3.70 (m, 5H), 3.69 (s, 3H), 3.45-3.55 (m, 1H), 2.80-2.56 (m, 3H), 2.56-2.28 (m, 4H), 2.21 (s, 1H), 1.24-1.05 (m, 3H). |
| 413a | 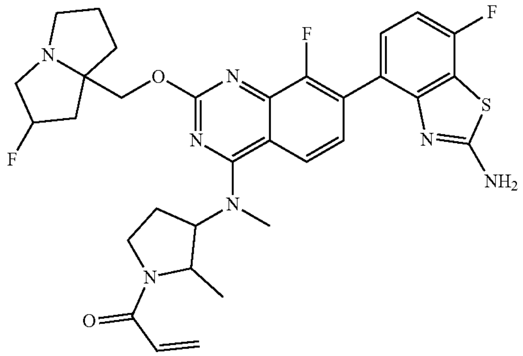 [SMILES: C=CC(=O)N1CCC(N(C)c2nc(OCC34CCCN3CC(F)C4)nc3c(F)c(-c4ccc(F)c5sc(N)nc45)ccc23)C1C] | |
| 414 | 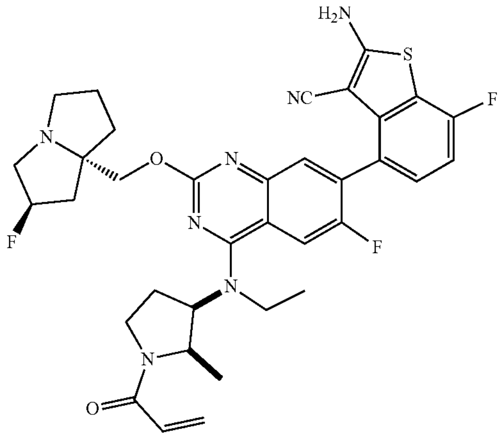 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@H]1C] | LCMS m/z [M + 1]: 676.2 $^{1}$HNMR (400 MHz, $CD_3OD$) δ 7.96-8.04 (m, 1H), 7.69-7.75 (m, 1H), 7.27-7.35 (m, 1H), 7.07 (t, J = 8.9 Hz, 1H), 6.68-6.75 (m, 1H), 6.36 (t, J = 17.7 Hz, 1H), 5.82 (d, J = 10.3 Hz, 1H), 5.62 (d, J = 52.3 Hz, 1H), 5.06-5.17 (m, 1H), 4.92-5.03 (m, 1H), 4.69-4.82 (m, 2H), 4.19-4.31 (m, 1H), 3.62-4.06 (m, 6H), 3.46-3.54 (m, 1H), 2.33-2.79 (m, 7H), 2.19-2.28 (m, 1H), 1.40-1.54 (m, 3H), 1.00-1.19 (m, 3H). |

TABLE 5-continued
Selected compounds of the present disclosure.
| Compound No. | Structure | Analytical data |
| --- | --- | --- |
| 414a | 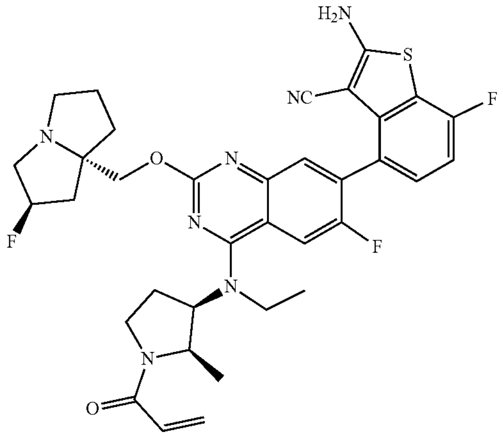 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@H]1C] | |
| 414b | 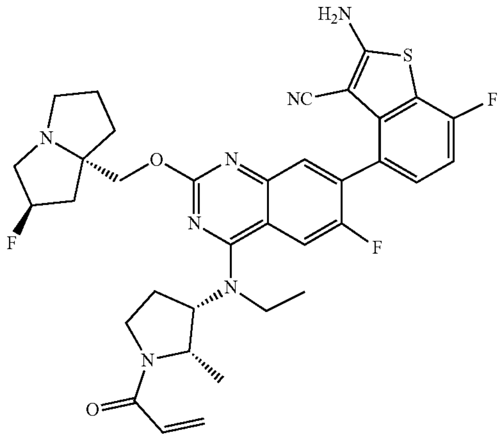 [SMILES: C=CC(=O)N1CC[C@H](N(CC)c2nc(OC[C@@]34CCCN3C[C@H](F)C4)nc3cc(-c4ccc(F)c5sc(N)c(C#N)c45)c(F)cc23)[C@@H]1C] | |
| 414c | 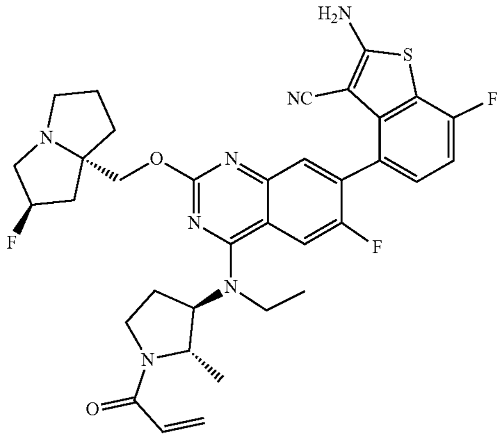 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@@H]1C] | |

TABLE 5-continued
| Selected compounds of the present disclosure. | | |
|---|---|---|
| Compound No. | Structure | Analytical data |
| 414d | 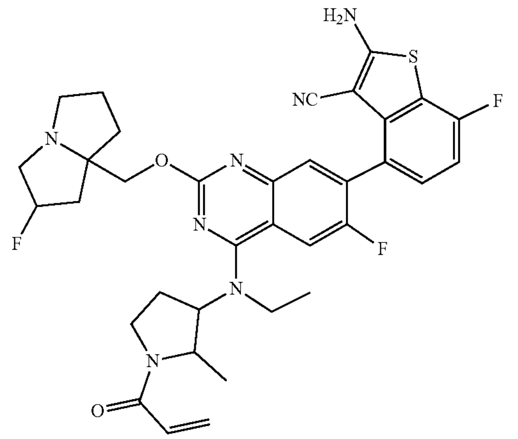 [SMILES: C=CC(=O)N1CCC(N(CC)c2nc(OCC34CCCN3CC(F)C4)nc3cc(-c4ccc(F)c5sc(N)c(C#N)c45)c(F)cc23)C1C] | |
| 415 | 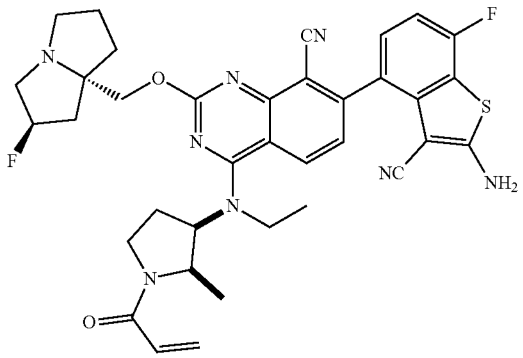 | LCMS m/z [M + 1]: 683.0<br>$^1$HNMR (400 MHz, $CD_3OD$) δ 8.49 (dd, J = 11.7, 6.0 Hz, 1H), 7.50-7.60 (m, 1H), 7.30-7.39 (m, 1H), 7.06-7.15 (m, 1H), 6.61-6.74 (m, 1H), 6.28-6.40 (m, 1H), 5.77-5.86 (m, 1H), 5.59 (d, J = 52.1 Hz, 1H), 4.98-5.14 (m, 1H), 4.58-4.81 (m, 3H), 4.10-4.22 (m, 1H), 3.91-4.04 (m, 4H), 3.45-3.78 (m, 3H), 2.46-2.73 (m, 5H), 2.32-2.41 (m, 2H), 2.11-2.24 (m, 1H), 1.34-1.43 (m, 3H), 1.06 (dt, J = 13.8, 7.6 Hz, 3H) |
| 415a | 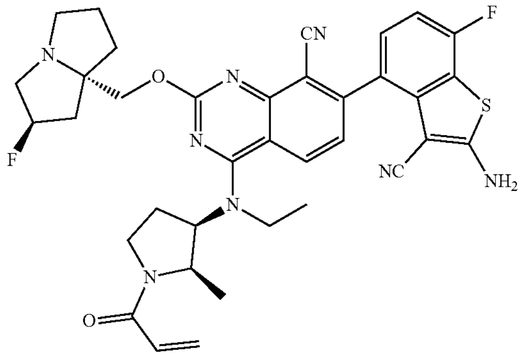 [SMILES: C=CC(=O)N1CC[C@@H](N(CC)c2nc(OC[C@@]34CCCN3C[C@H](F)C4)nc3c(C#N)c(-c4ccc(F)c5sc(N)c(C#N)c45)ccc23)[C@H]1C] | |
| 415b | 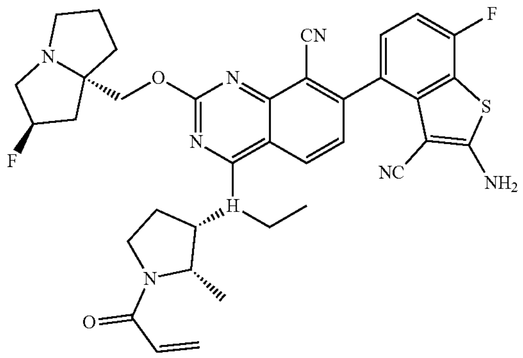 | |

TABLE 5-continued
| Selected compounds of the present disclosure. | | |
|---|---|---|
| Compound No. | Structure | Analytical data |
| 415c | 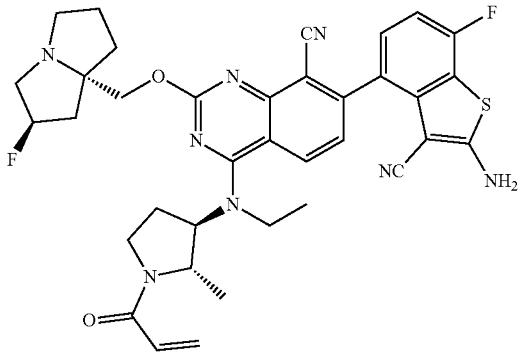 [SMILES: C=CC(=O)N1CC[C@@H](N(CC)c2nc(OC[C@@]34CCCN3C[C@H](F)C4)nc3c(C#N)c(-c4ccc(F)c5sc(N)c(C#N)c45)ccc23)[C@@H]1C] | |
| 415d | 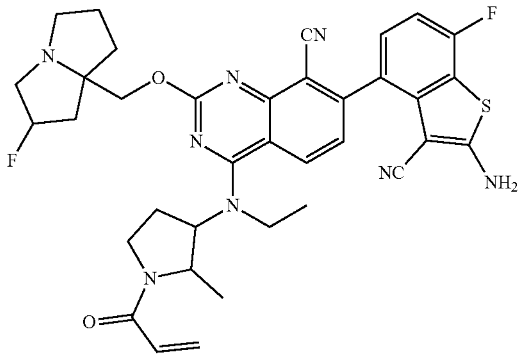 [SMILES: C=CC(=O)N1CCC(N(CC)c2nc(OCC34CCCN3CC(F)C4)nc3c(C#N)c(-c4ccc(F)c5sc(N)c(C#N)c45)ccc23)C1C] | |
| 416 | 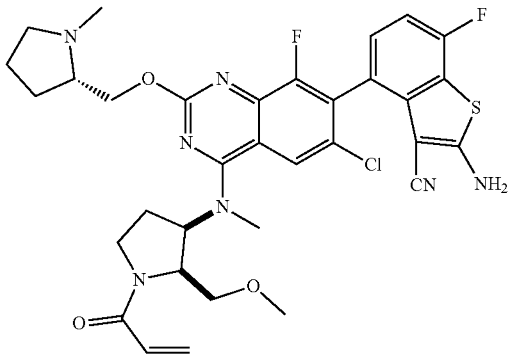 | LCMS m/z [M + 1]: 682.2<br>$^1$HNMR (400 MHz, $CD_3OD$) δ 8.22 (d, J = 1.6 Hz, 1H), 7.22-7.30 (m, 1H), 7.08 (t, J = 8.9 Hz, 1H), 6.72 (dd, J = 16.8, 10.5 Hz, 1H), 6.36 (d, J = 16.7 Hz, 1H), 5.81 (dd, J = 19.2, 10.9 Hz, 1H), 4.92-5.01 (m, 3H), 4.57-4.70 (m, 1H), 3.85-4.04 (m, 2H), 3.62-3.83 (m, 6H), 3.37-3.61 (m, 2H), 3.22-3.31 (m, 3H), 3.06-3.17 (m, 3H), 2.72-2.89 (m, 1H), 2.36-2.47 (m, 2H), 2.03-2.25 (m, 3H). |
| 416a | 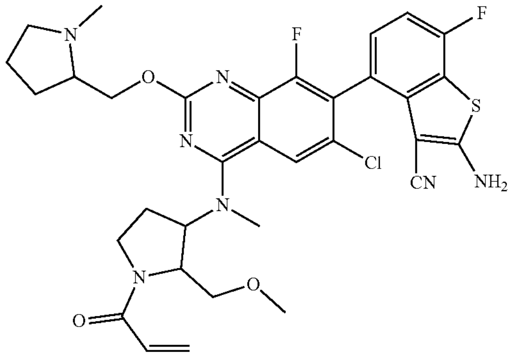 [SMILES: C=CC(=O)N1CCC(N(C)c2nc(OCC3CCCN3C)nc3c(F)c(-c4ccc(F)c5sc(N)c(C#N)c45)c(Cl)cc23)C1COC] | |

TABLE 5-continued
| Selected compounds of the present disclosure. | | |
|---|---|---|
| Compound No. | Structure | Analytical data |
| 417 | 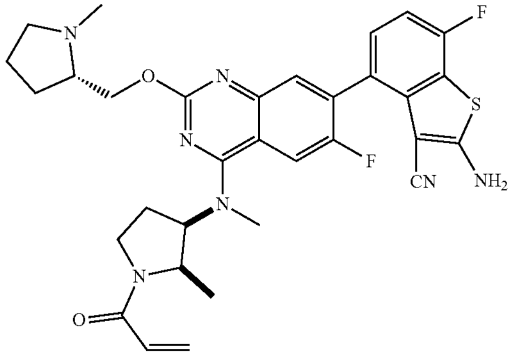 | LCMS m/z [M + 1]: 618.0 $^1$HNMR (400 MHz, $CD_3OD$) δ 7.88-7.92 (m, 1H), 7.59-7.62 (m, 1H), 7.24-7.27 (m, 1H), 7.02 (t, J = 9.2 Hz, 1H), 6.61-6.68 (m, 1H), 6.32 (t, J = 18.68 Hz, 1H), 5.77 (d, J = 10.48 Hz, 1H), 4.71-5.04 (m, 2H), 4.46-4.58 (m, 3H), 3.53-3.97 (m, 5H), 3.13-3.32 (m, 1H), 1.74-2.72 (m, 10H), 1.04-1.14 (m, 3H). |
| 417a | 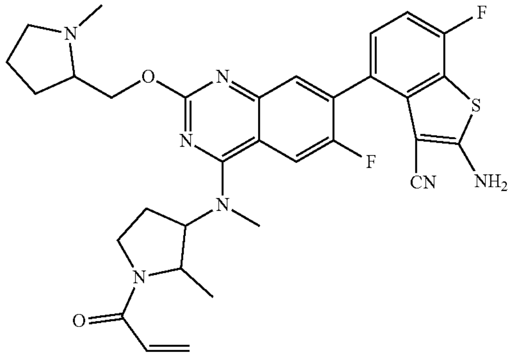 [SMILES: C=CC(=O)N1CCC(N(C)c2nc(OCC3CCCN3C)nc3cc(-c4ccc(F)c5sc(N)c(C#N)c45)c(F)cc23)C1C] | |
| 418 | 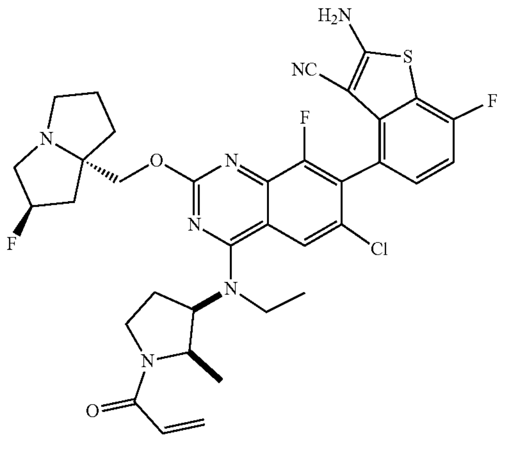 [SMILES: C=CC(=O)N1CC[C@@H](N(CC)c2nc(OC[C@@]34CCCN3C[C@H](F)C4)nc3c(F)c(-c4ccc(F)c5sc(N)c(C#N)c45)c(Cl)cc23)[C@H]1C] | LCMS m/z [M + 1]: 710.0 $^1$HNMR (400 MHz, $CD_3OD$) δ 8.12 (s, 1H), 7.24-7.27 (m, 1H), 7.08 (t, J = 8.68 Hz, 1H), 6.63-6.70 (m, 1H), 6.30-6.39 (m, 1H), 5.79-5.82 (m, 1H), 5.58 (d, J = 50.04 Hz, 1H), 5.05-5.07 (m, 1H), 4.66-4.70 (m, 1H), 3.90-4.17 (m, 6H), 3.62-3.79 (m, 1H), 3.46-3.51 (m, 1H), 2.19-2.74 (m, 8H), 1.31-1.38 (m, 6H). |

TABLE 5-continued
Selected compounds of the present disclosure.
| Compound No. | Structure | Analytical data |
| --- | --- | --- |
| 418a | 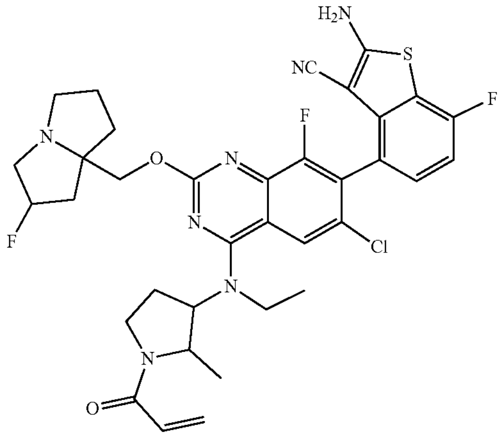 [SMILES: C=CC(=O)N1CCC(N(CC)c2nc(OCC34CCCN3CC(F)C4)nc3c(F)c(-c4ccc(F)c5sc(N)c(C#N)c45)c(Cl)cc23)C1C] | |
| 419 | 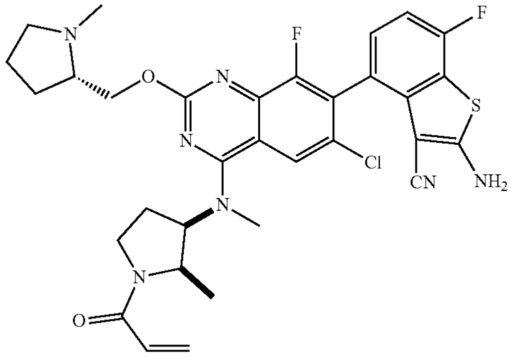 | LCMS m/z [M + 1]: 652.2<br>$^1$HNMR (400 MHz, $CD_3OD$) δ 8.18 (s, 1H), 7.23-7.26 (m, 1H), 7.07 (t, J = 8.54 Hz, 1H), 6.64-6.71 (m, 1H), 6.31-6.42 (m, 1H), 5.79-5.82 (m, 1H), 4.96-5.08 (m, 2H), 4.72-4.78 (m, 2H), 3.53-4.03 (m, 8H), 3.10-3.15 (m, 3H), 2.05-2.79 (m, 6H), 1.07-1.19 (m, 3H). |
| 419a | 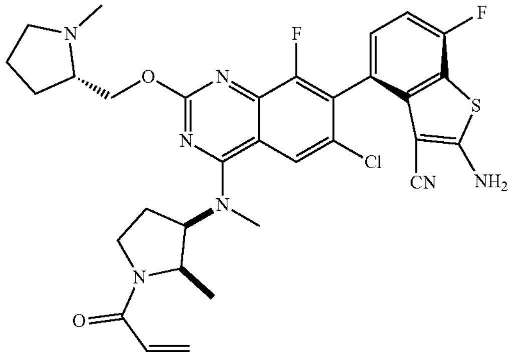 | |
| 419b | 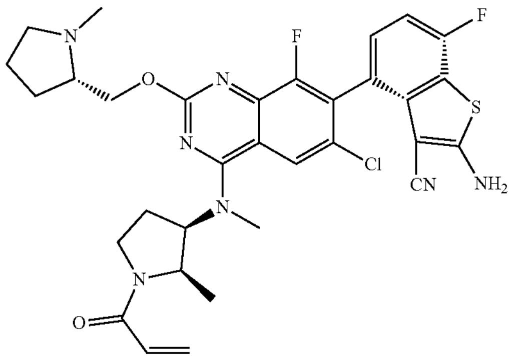 | |

TABLE 5-continued
| Selected compounds of the present disclosure. | | |
|---|---|---|
| Compound No. | Structure | Analytical data |
| 419c | 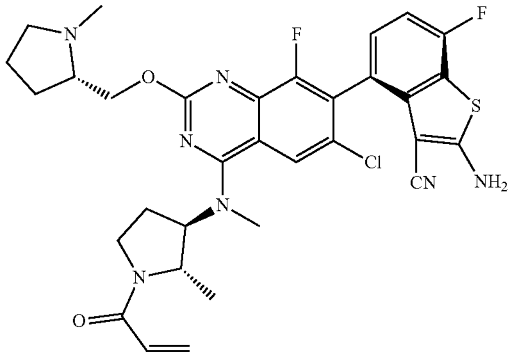 | |
| 419d | 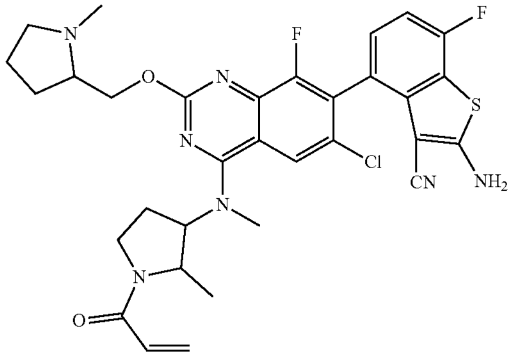 [SMILES: C=CC(=O)N1CCC(N(C)c2nc(OCC3CCCN3C)nc3c(F)c(-c4ccc(F)c5sc(N)c(C#N)c45)c(Cl)cc23)C1C] | |
| 420 | 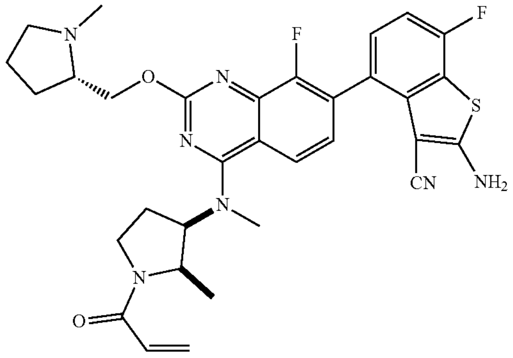 | LCMS m/z [M + 1]: 618.2<br>$^1$HNMR (400 MHz, $CD_3OD$) δ 8.15-8.17 (m, 1H), 7.40-7.44 (m, 1H), 7.29-7.33 (m, 1H), 7.07 (t, J = 8.78 Hz, 1H), 6.64-6.71 (m, 1H), 6.31-6.39 (m, 1H), 5.80-5.82 (m, 1H), 4.93-5.08 (m, 4H), 4.64-4.74 (m, 1H), 3.49-4.02 (m, 7H), 3.11-3.12 (m, 3H), 2.05-2.77 (m, 6H), 1.12-1.16 (m, 3H). |
| 420a | 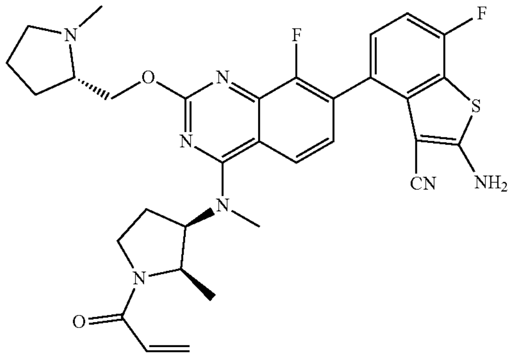 [SMILES: C=CC(=O)N1CC[C@@H](N(C)c2nc(OC[C@@H]3CCCN3C)nc3c(F)c(-c4ccc(F)c5sc(N)c(C#N)c45)ccc23)[C@H]1C] | |

TABLE 5-continued
| Selected compounds of the present disclosure. | | |
|---|---|---|
| Compound No. | Structure | Analytical data |
| 420b | 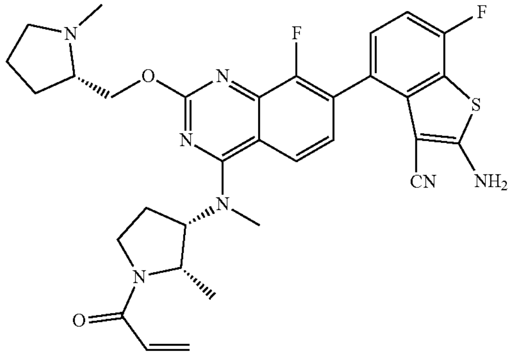 [SMILES: C=CC(=O)N1CC[C@H](N(C)c2nc(OC[C@@H]3CCCN3C)nc3c(F)c(-c4ccc(F)c5sc(N)c(C#N)c45)ccc23)[C@@H]1C] | |
| 420c | 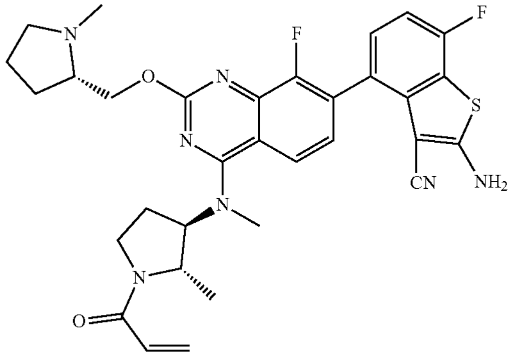 [SMILES: C=CC(=O)N1CC[C@@H](N(C)c2nc(OC[C@@H]3CCCN3C)nc3c(F)c(-c4ccc(F)c5sc(N)c(C#N)c45)ccc23)[C@@H]1C] | |
| 420d | 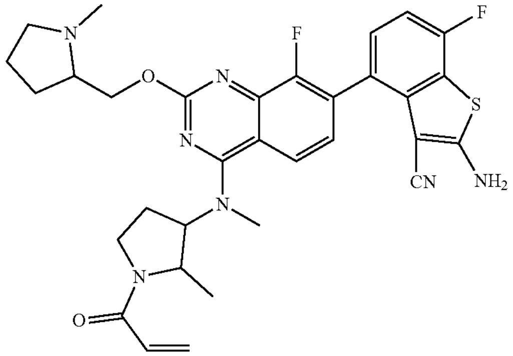 [SMILES: C=CC(=O)N1CCC(N(C)c2nc(OCC3CCCN3C)nc3c(F)c(-c4ccc(F)c5sc(N)c(C#N)c45)ccc23)C1C] | |
| 421 | 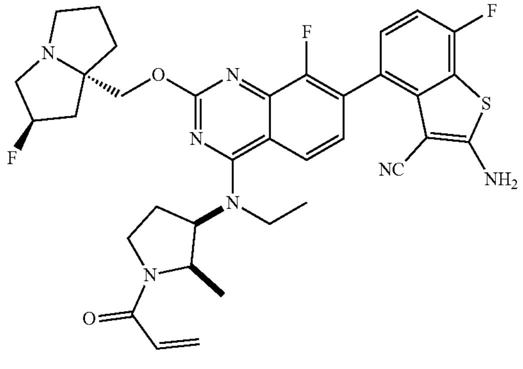 | LCMS m/z [M + 1]: 676.0 $^1$HNMR (400 MHz, $CD_3OD$) δ 8.08-8.11 (m, 1H), 7.47 (t, J = 8.02 Hz, 1H), 7.30-7.34 (m, 1H), 7.08 (t, J = 8.84 Hz, 1H), 6.64-6.71 (m, 1H), 6.31-6.40 (m, 1H), 5.80-5.82 (m, 1H), 5.58 (d, J = 52.12 Hz, 1H), 4.96-5.11 (m, 1H), 4.64-4.85 (m, 3H), 3.50-4.27 (m, 8H), 2.12-2.79 (m, 8H), 1.41-1.47 (m, 3H), 1.03-1.14 (m, 3H). |

TABLE 5-continued
| Selected compounds of the present disclosure. | | |
|---|---|---|
| Compound No. | Structure | Analytical data |
| 421a | 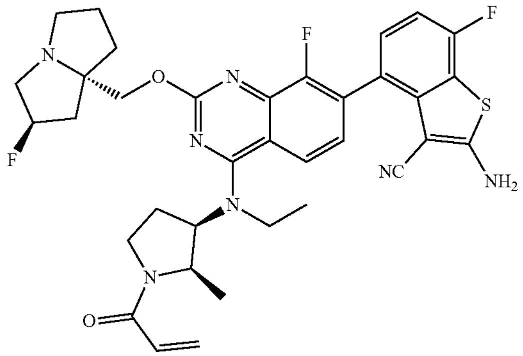 [SMILES: C=CC(=O)N1CC[C@@H](N(CC)c2nc(OC[C@@]34CCCN3C[C@H](F)C4)nc3c(F)c(-c4ccc(F)c5sc(N)c(C#N)c45)ccc23)[C@H]1C] | |
| 421b | 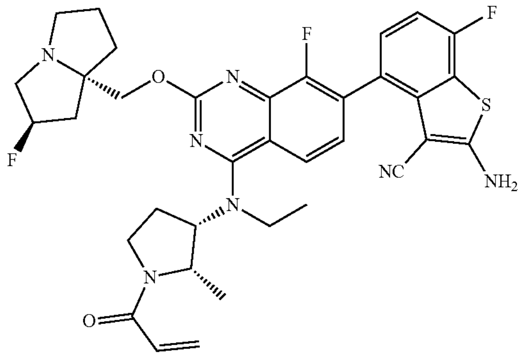 [SMILES: C=CC(=O)N1CC[C@H](N(CC)c2nc(OC[C@@]34CCCN3C[C@H](F)C4)nc3c(F)c(-c4ccc(F)c5sc(N)c(C#N)c45)ccc23)[C@@H]1C] | |
| 421c | 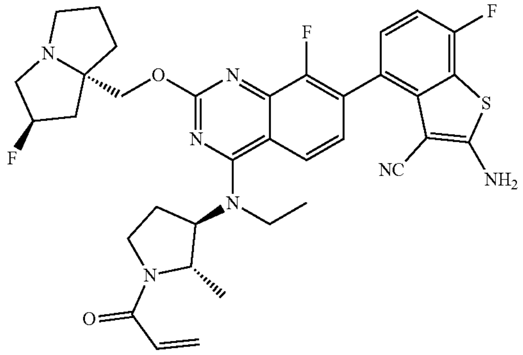 [SMILES: C=CC(=O)N1CC[C@@H](N(CC)c2nc(OC[C@@]34CCCN3C[C@H](F)C4)nc3c(F)c(-c4ccc(F)c5sc(N)c(C#N)c45)ccc23)[C@@H]1C] | |
| 421d | 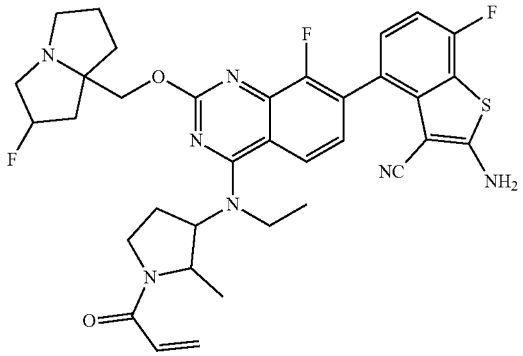 [SMILES: C=CC(=O)N1CCC(N(CC)c2nc(OCC34CCCN3CC(F)C4)nc3c(F)c(-c4ccc(F)c5sc(N)c(C#N)c45)ccc23)C1C] | |

TABLE 5-continued
Selected compounds of the present disclosure.
| Compound No. | Structure | Analytical data |
|---|---|---|
| 422 | 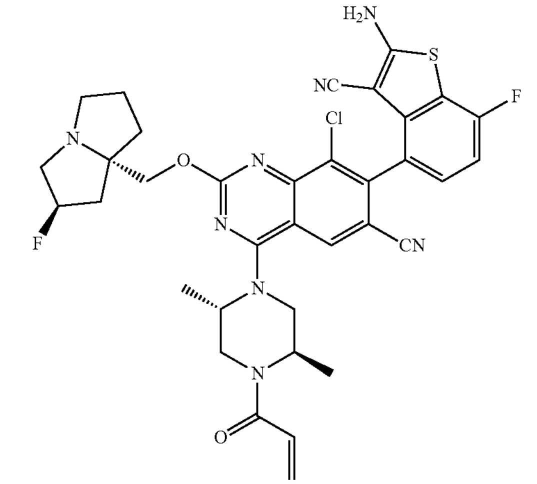 [SMILES: C=CC(=O)N1C[C@H](C)N(c2nc(OC[C@@]34CCCN3C[C@H](F)C4)nc3c(Cl)c(-c4ccc(F)c5sc(N)c(C#N)c45)c(C#N)cc23)C[C@H]1C] | LCMS m/z [M + 1]: 703.0 $^1$HNMR (400 MHz, $CD_3OD$) δ 8.44 (s, 1H), 7.27-7.32 (m, 1H), 7.11 (t, J = 8.82 Hz, 1H), 6.77-6.90 (m, 1H), 6.28-6.34 (m, 1H), 5.82-5.86 (m, 1H), 5.52-5.66 (m, 1H), 4.97-5.01 (m, 1H), 4.68-4.82 (m, 2H), 3.48-4.51 (m, 9H), 2.16-2.82 (m, 6H), 1.46-1.50 (m, 3H), 1.18-1.32 (m, 3H). |
| 422a | 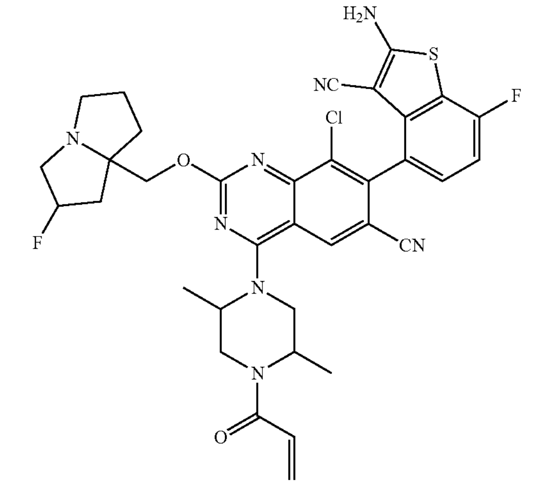 [SMILES: C=CC(=O)N1CC(C)N(c2nc(OCC34CCCN3CC(F)C4)nc3c(Cl)c(-c4ccc(F)c5sc(N)c(C#N)c45)c(C#N)cc23)CC1C] | |
| 423 | 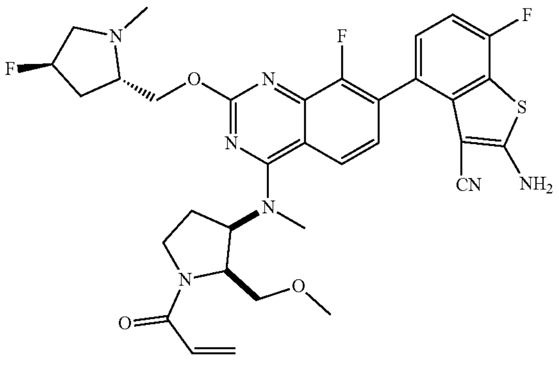 | LCMS m/z [M + 1]: 666.0 $^1$HNMR (400 MHz, $CD_3OD$) δ 8.22 (d, J = 8.62 Hz, 1H), 7.43-7.47 (m, 1H), 7.30-7.34 (m, 1H), 7.05-7.10 (m, 1H), 6.68-6.79 (m, 1H), 6.37 (d, J = 16.80 Hz, 1H), 5.79-5.85 (m, 1H), 5.49 (d, J = 50.84 Hz, 1H), 4.96-5.14 (m, 3H), 4.68-4.84 (m, 1H), 3.39-4.28 (m, 10H), 3.21-3.27 (m, 6H), 2.31-2.93 (m, 4H). |

TABLE 5-continued
| Selected compounds of the present disclosure. | | |
|---|---|---|
| Compound No. | Structure | Analytical data |
| 423a | 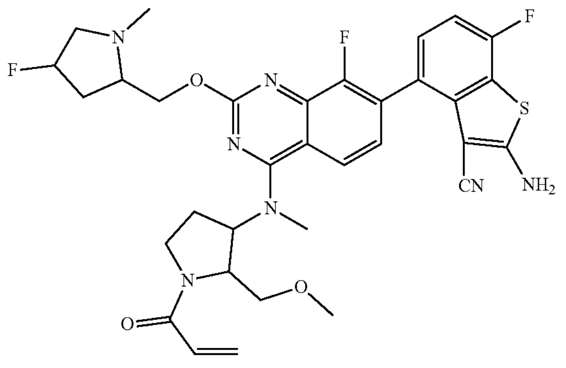 [SMILES: C=CC(=O)N1CCC(N(C)c2nc(OCC3CC(F)CN3C)nc3c(F)c(-c4ccc(F)c5sc(N)c(C#N)c45)ccc23)C1COC] | |
| 424 | 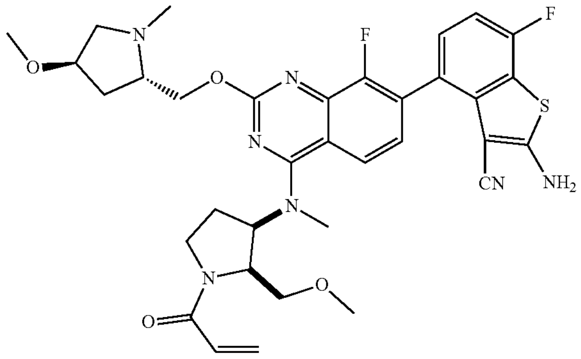 | LCMS m/z [M + 1]: 678.1 $^{1}$HNMR (400 MHz, $CD_3OD$) δ 8.22 (d, J = 8.62 Hz, 1H), 7.43-7.48 (m, 1H), 7.30-7.34 (m, 1H), 7.08 (t, J = 8.82 Hz, 1H), 6.68-6.79 (m, 1H), 6.34-6.39 (m, 1H), 5.79-5.85 (m, 1H), 4.93-5.09 (m, 4H), 4.65-4.80 (m, 1H), 3.42-4.21 (m, 13H), 3.26-3.27 (m, 3H), 3.16 (s, 3H), 2.15-2.93 (m, 4H). |
| 424a | 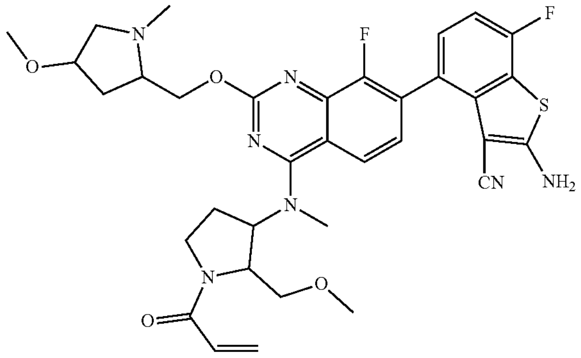 [SMILES: C=CC(=O)N1CCC(N(C)c2nc(OCC3CC(OC)CN3C)nc3c(F)c(-c4ccc(F)c5sc(N)c(C#N)c45)ccc23)C1COC] | |
| 425 | 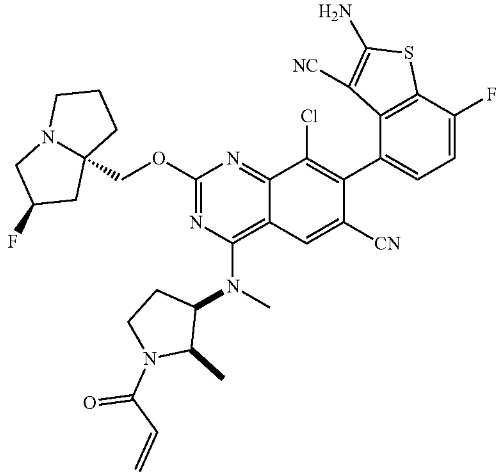 | LCMS m/z [M + 1]: 703.2 $^{1}$HNMR (400 MHz, $CD_3OD$) δ 8.67 (s, 1H), 7.27-7.28 (m, 1H), 7.11 (t, J = 8.82 Hz, 1H), 6.64-6.67 (m, 1H), 6.32-6.36 (m, 1H), 5.80-5.83 (m, 1H), 5.20-5.65 (m, 1H), 5.10-3.94 (m, 13H), 2.16-2.74 (m, 8H), 1.13-1.32 (m, 3H). |

TABLE 5-continued
| Selected compounds of the present disclosure. | | |
|---|---|---|
| Compound No. | Structure | Analytical data |
| 425a | 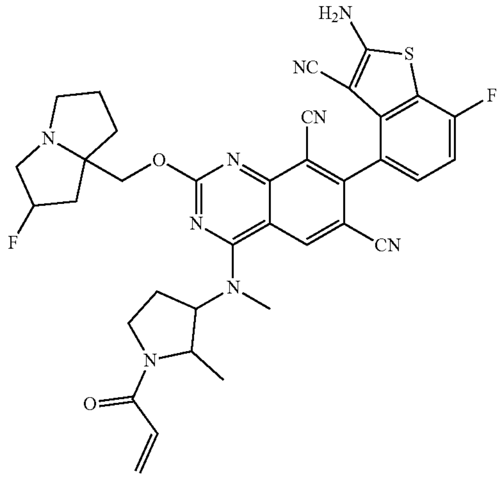 [SMILES: C=CC(=O)N1CCC(N(C)c2nc(OCC34CCCN3CC(F)C4)nc3c(C#N)c(-c4ccc(F)c5sc(N)c(C#N)c45)c(C#N)cc23)C1C] | |
| 426 | 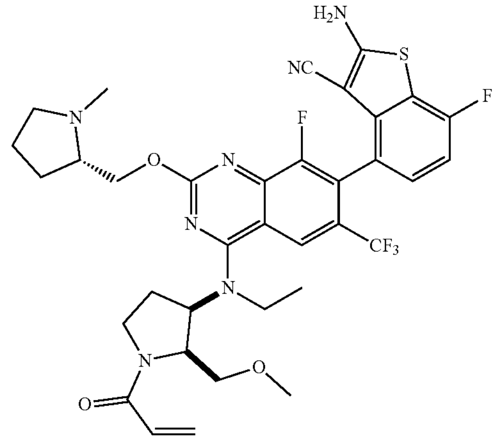 | LCMS m/z [M + 1]: 716<br>$^{1}$HNMR (400 MHz, $CD_3OD$) δ 8.39 (s, 1H), 7.22 (t, 1H), 7.01 (t, 1H), 6.65-6.77 (m, 1H), 6.29-6.36 (m, 1H), 5.75-5.80 (m, 1H), 4.95-5.05 (m, 2H), 4.42-4.54 (m, 2H), 3.69-3.95 (m, 2H), 3.56-3.67 (m, 4H), 3.06-3.27 (m, 5H), 2.88-2.96 (m, 1H), 2.66-2.84 (m, 1H), 2.54-2.58 (m, 3H), 2.37-2.50 (m, 2H), 2.07-2.16 (m, 1H), 1.68-1.89 (m, 3H). |
| 426a | 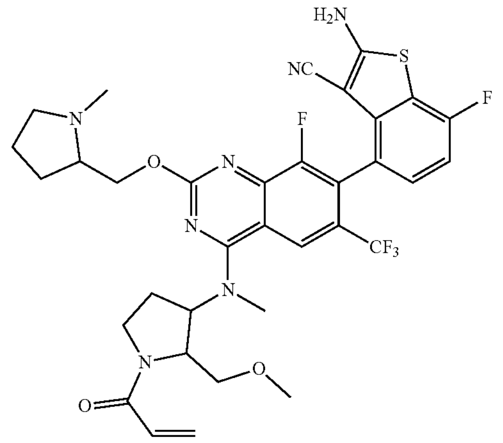 [SMILES: C=CC(=O)N1CCC(N(C)c2nc(OCC3CCCN3C)nc3c(F)c(-c4ccc(F)c5sc(N)c(C#N)c45)c(C(F)(F)F)cc23)C1COC] | |

TABLE 5-continued
| Selected compounds of the present disclosure. | | |
|---|---|---|
| Compound No. | Structure | Analytical data |
| 427 | 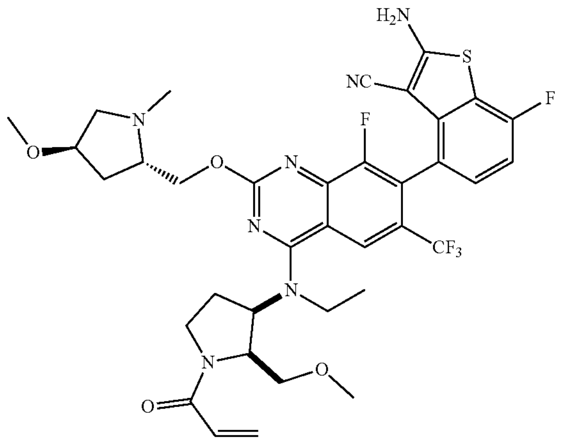 | LCMS m/z [M + 1]: 760.3<br>$^{1}$HNMR (400 MHz, $CD_3OD$) δ 8.27-8.23 (t, 1H), 8.08 (s, 1H), 7.27 (t, 1H), 7.17-7.12 (m, 1H), 6.68-6.60 (m, 1H),6.18 (d, 1H), 5.71 (t, 1H), 4.83-4.73 (m, 2H), 4.41-4.22 (m, 2H), 3.99-3.84 (m, 3H), 3.61-3.52 (m, 2H), 3.27 (m, 5H), 3.17 (s, 2H), 3.12-2.92 (m, 4H), 2.82-2.75 (m, 1H), 2.31 (s, 4H), 2.16-2.15 (m, 1H), 1.87-1.83 (m, 2H), 1.37-1.29 (m, 3H). |
| 427a | 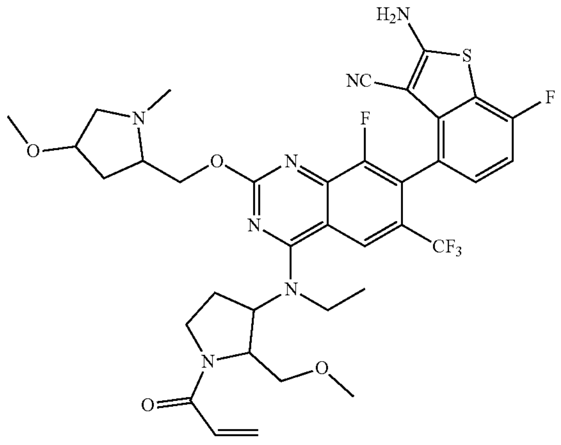 [SMILES: C=CC(=O)N1CCC(N(CC)c2nc(OCC3CC(OC)CN3C)nc3c(F)c(-c4ccc(F)c5sc(N)c(C#N)c45)c(C(F)(F)F)cc23)C1COC] | |
| 428 | 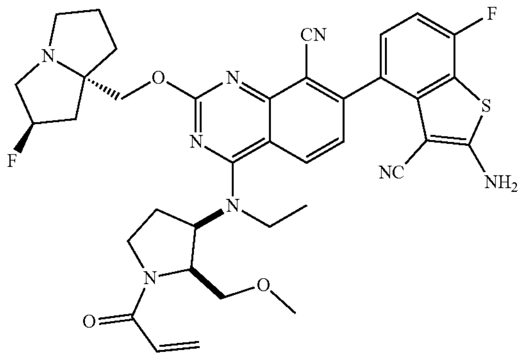 | LCMS m/z [M + 1]: 713.0<br>$^{1}$HNMR (400 MHz, $CD_3OD$) δ 8.40 (d, J = 8.56 Hz, 1H), 7.42-7.46 (m, 1H), 7.28-7.33 (m, 1H), 7.02-7.08 (m, 1H), 6.64-6.75 (m, 1H), 6.29-6.34 (m, 1H), 5.72-5.80 (m, 1H), 5.23-5.40 (m, 1H), 4.97-5.00 (m, 1H), 3.33-4.46 (m, 9H), 3.03-3.34 (m, 7H), 1.93-2.76 (m, 8H), 1.28-1.40 (m, 3H). |

TABLE 5-continued
| Selected compounds of the present disclosure. | | |
|---|---|---|
| Compound No. | Structure | Analytical data |
| 428a | 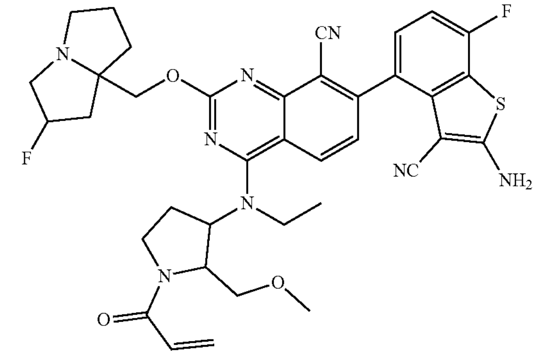 [SMILES: C=CC(=O)N1CCC(N(CC)c2nc(OCC34CCCN3CC(F)C4)nc3c(C#N)c(-c4ccc(F)c5sc(N)c(C#N)c45)ccc23)C1COC] | |
| 429 | 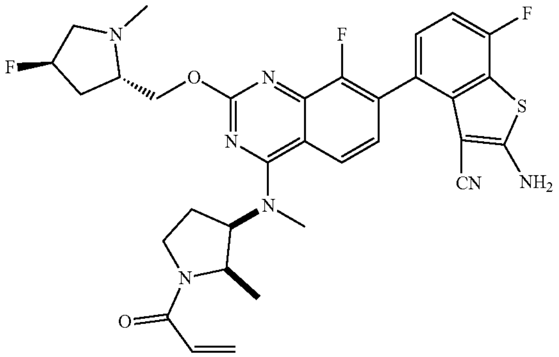 | LCMS m/z [M + 1]: 636.2<br>$^{1}$HNMR (400 MHz, $CD_3OD$) δ 8.14 (s, 1H), 7.40 (t, J = 7.2 Hz, 1H), 7.33-7.25 (m, 1H), 7.02-7.07 (m, 1H), 6.62-6.69 (m, 1H), 6.29-6.37 (m, 1H), 5.79 (d, J = 10.8 Hz, 1H), 5.47 (d, J = 51.7 Hz, 1H), 5.10-4.92 (m, 3H), 4.65-4.72 (m, 1H), 4.20-4.30 (m, 1H), 3.95-4.07 (m, 1H), 3.82-3.52 (m, 6H), 3.20 (s, 3H), 2.67-2.48 (m, 4H), 1.24-1.03 (m, 3H). |
| 429a | 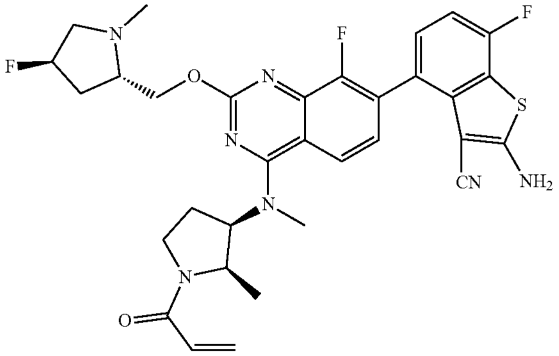 [SMILES: C=CC(=O)N1CC[C@@H](N(C)c2nc(OC[C@@H]3C[C@@H](F)CN3C)nc3c(F)c(-c4ccc(F)c5sc(N)c(C#N)c45)ccc23)[C@H]1C] | |
| 429b | 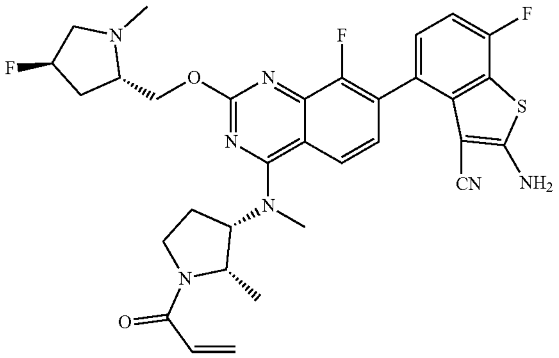 [SMILES: C=CC(=O)N1CC[C@H](N(C)c2nc(OC[C@@H]3C[C@@H](F)CN3C)nc3c(F)c(-c4ccc(F)c5sc(N)c(C#N)c45)ccc23)[C@@H]1C] | |

TABLE 5-continued
| Selected compounds of the present disclosure. | | |
|---|---|---|
| Compound No. | Structure | Analytical data |
| 429c | 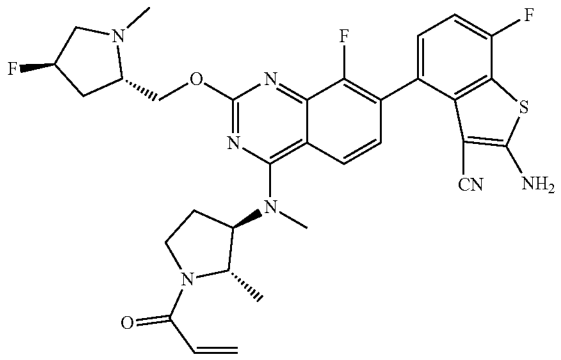 [SMILES: C=CC(=O)N1CC[C@@H](N(C)c2nc(OC[C@@H]3C[C@@H](F)CN3C)nc3c(F)c(-c4ccc(F)c5sc(N)c(C#N)c45)ccc23)[C@@H]1C] | |
| 429d | 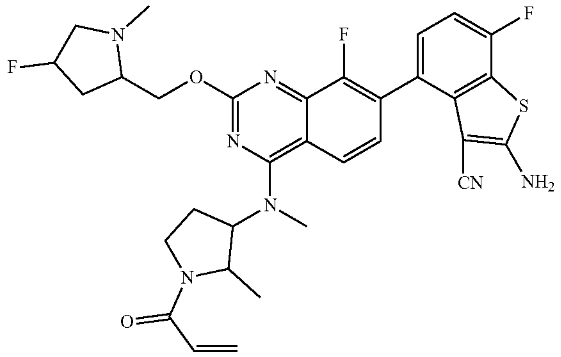 [SMILES: C=CC(=O)N1CCC(N(C)c2nc(OCC3CC(F)CN3C)nc3c(F)c(-c4ccc(F)c5sc(N)c(C#N)c45)ccc23)C1C] | |
| 430 | 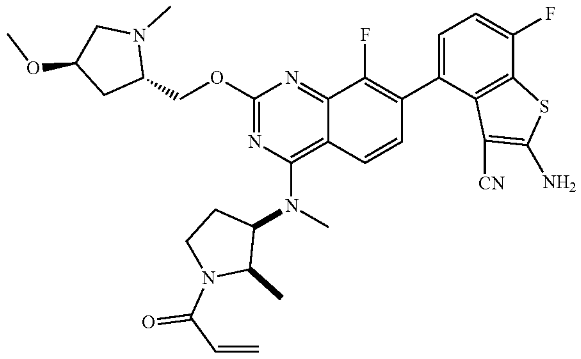 | LCMS m/z [M + 1]: 648.2 $^{1}$HNMR (400 MHz, $CD_3OD$) δ 8.13 (s, 1H), 7.40 (t, J = 7.9 Hz, 1H), 7.33-7.22 (m, 1H), 7.10-6.98 (m, 1H), 6.62-6.69 (m, 1H), 6.29-6.37 (m, 1H), 5.79 (d, J = 10.5 Hz, 1H), 5.10-4.89 (m, 3H), 4.69-4.71 (m, 1H), 4.09-4.17 (m, 2H), 4.01-3.45 (m, 2H), 3.74-3.50 (m, 4H), 3.39-3.47 (m, 4H), 3.15 (s, 3H), 2.81-2.32 (m, 3H), 2.20 (m, 1H), 1.2-1.04 (m, 3H). |
| 430a | 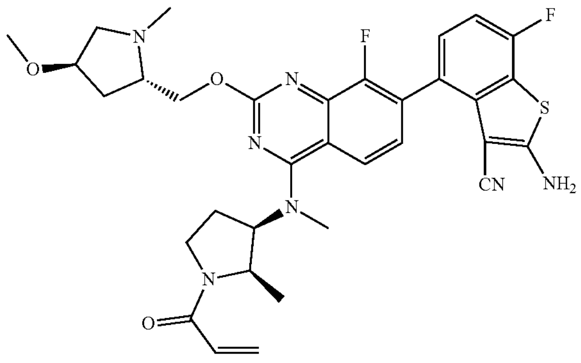 [SMILES: C=CC(=O)N1CC[C@@H](N(C)c2nc(OC[C@@H]3C[C@@H](OC)CN3C)nc3c(F)c(-c4ccc(F)c5sc(N)c(C#N)c45)ccc23)[C@H]1C] | |

TABLE 5-continued
| Selected compounds of the present disclosure. | | |
|---|---|---|
| Compound No. | Structure | Analytical data |
| 430b | 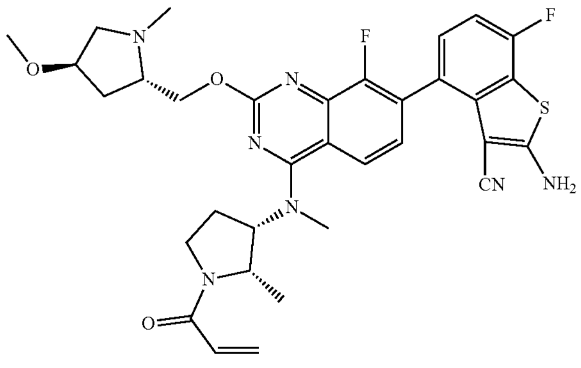 [SMILES: C=CC(=O)N1CC[C@H](N(C)c2nc(OC[C@@H]3C[C@@H](OC)CN3C)nc3c(F)c(-c4ccc(F)c5sc(N)c(C#N)c45)ccc23)[C@@H]1C] | |
| 430c | 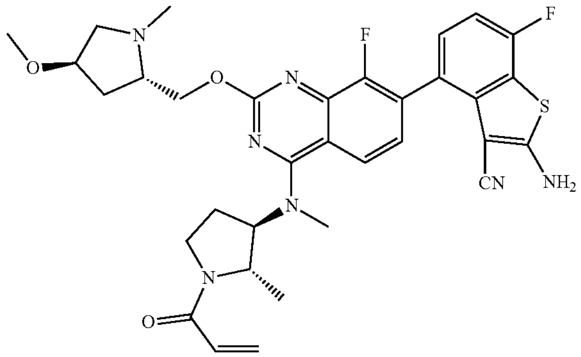 [SMILES: C=CC(=O)N1CC[C@@H](N(C)c2nc(OC[C@@H]3C[C@@H](OC)CN3C)nc3c(F)c(-c4ccc(F)c5sc(N)c(C#N)c45)ccc23)[C@@H]1C] | |
| 430d | 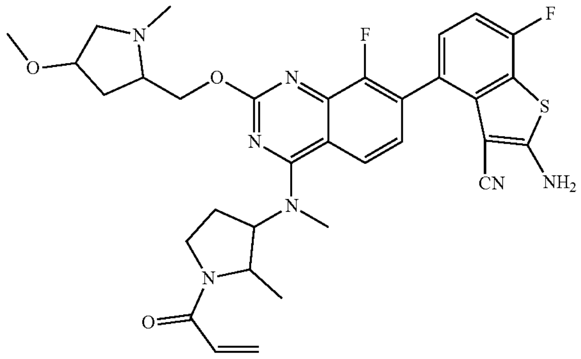 [SMILES: C=CC(=O)N1CCC(N(C)c2nc(OCC3CC(OC)CN3C)nc3c(F)c(-c4ccc(F)c5sc(N)c(C#N)c45)ccc23)C1C] | |
| 431 | 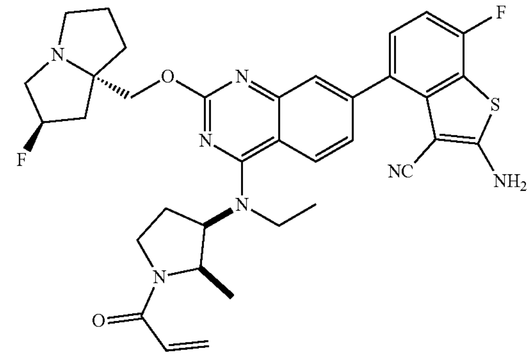 | LCMS m/z [M + 1]: 658.1 $^{1}$HNMR (400 MHz, $CD_3OD$) δ 8.35 (d, J = 8.8 Hz, 1H), 7.71 (s, 1H), 7.60-7.67 (m, 1H), 7.28-7.34 (m, 1H), 7.04-7.11 (m, 1H), 6.65-6.77 (m, 1H), 6.31-6.43 (m, 1H), 5.83 (d, J = 11.3 Hz, 1H), 5.62 (d, J = 52.1 Hz, 1H), 4.97-5.19 (m, 2H), 4.70-4.84 (m, 2H), 4.22-4.37 (m, 1H), 3.92-4.11 (m, 4H), 3.48-3.83 (m, 3H), 2.53-2.82 (m, 4H), 2.21-2.47 (m, 4H), 1.48-1.61 (m, 3H), 1.04-1.21 (m, 3H). |

TABLE 5-continued
| Selected compounds of the present disclosure. | | |
|---|---|---|
| Compound No. | Structure | Analytical data |
| 431a | 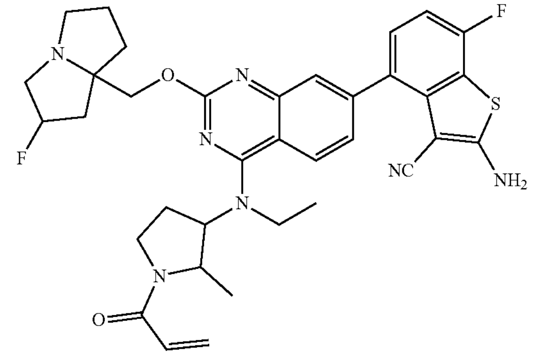 [SMILES: C=CC(=O)N1CCC(N(CC)c2nc(OCC34CCCN3CC(F)C4)nc3cc(-c4ccc(F)c5sc(N)c(C#N)c45)ccc23)C1C] | |
| 432 | 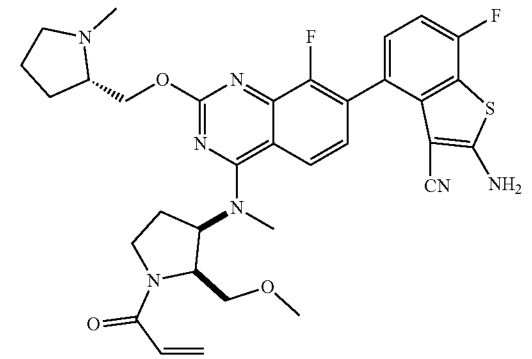 | LCMS m/z [M + 1]: 648.3<br>$^1$HNMR (400 MHz, $CD_3OD$) δ 8.17 (d, J = 8.5 Hz, 1H), 7.40 (t, J = 7.8 Hz, 1H), 7.26-7.32 (m, 1H), 7.05 (t, J = 8.9 Hz, 1H), 6.70 (dd, J = 16.7, 10.4 Hz, 1H), 6.34 (d, J = 16.7 Hz, 1H), 5.73-5.86 (m, 1H), 4.92-5.06 (m, 3H), 4.53-4.73 (m, 1H), 3.38-4.02 (m, 9H), 3.17-3.29 (m, 4H), 3.09 (d, J = 3.8 Hz, 3H), 2.78-2.93 (m, 1H), 1.99-2.41 (m, 5H). |
| 432a | 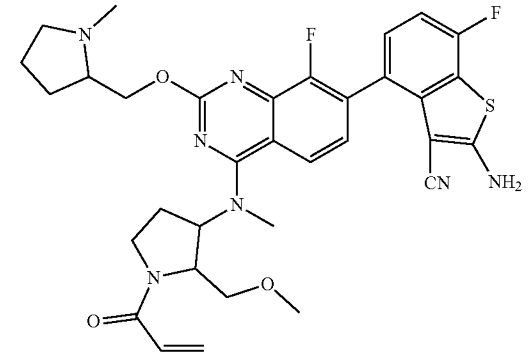 [SMILES: C=CC(=O)N1CCC(N(C)c2nc(OCC3CCCN3C)nc3c(F)c(-c4ccc(F)c5sc(N)c(C#N)c45)ccc23)C1COC] | |
| 433 | 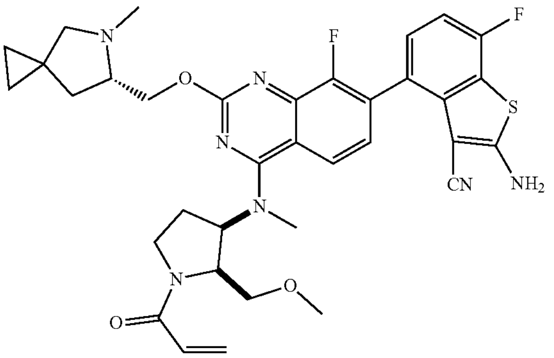 | LCMS m/z [M + 1]: 674<br>$^1$HNMR (400 MHz, $CD_3OD$) δ 21 (d, J = 8.7 Hz, 1H), 7.37-7.50 (m, 1H), 7.25-7.34 (m, 1H), 7.05 (t, J = 8.9 Hz, 1H), 6.69 (dd, J = 16.8, 10.4 Hz, 1H), 6.26-6.41 (m, 1H), 5.72-5.86 (m, 1H), 4.90-5.10 (m, 3H), 4.51-4.80 (m, 1H), 4.05-4.20 (m, 1H), 3.91-4.00 (m, 1H), 3.56-3.82 (m, 5H), 3.41-3.53 (m, 1H), 3.31-3.38 (m, 2H), 3.19-3.27 (m, 3H), 3.14 (s, 3H), 2.65-2.93 (m, 1H), 2.31-2.54 (m, 2H), 1.87-2.06 (m, 1H), 0.51-0.87 (m, 4H). |

TABLE 5-continued
| Selected compounds of the present disclosure. | | |
|---|---|---|
| Compound No. | Structure | Analytical data |
| 433a | 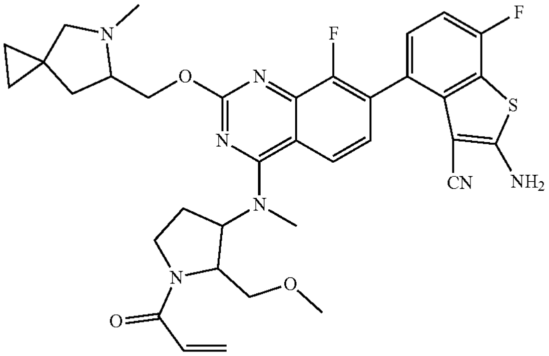 [SMILES: C=CC(=O)N1CCC(N(C)c2nc(OCC3CC4(CC4)CN3C)nc3c(F)c(-c4ccc(F)c5sc(N)c(C#N)c45)ccc23)C1COC] | |
| 434 | 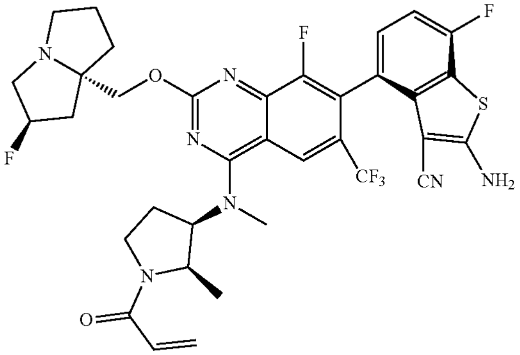 | LCMS m/z [M + 1]: 730.0 $^1$HNMR (400 MHz, $CD_3OD$) δ 8.34 (s, 1H), 7.19-7.27 (m, 1H), 6.99-7.05 (m, 1H), 6.62-6.70 (m, 1H), 6.28-6.39 (m, 1H), 5.77 (d, J = 10.5 Hz, 1H), 5.29 (d, J = 52.2 Hz, 1H), 5.02-5.09 (m, 1H), 4.87-4.92 (m, 1H), 4.20-4.36 (m, 2H), 3.55-4.05 (m, 5H), 3.11-3.26 (m, 3H), 2.94-3.04 (m, 1H), 1.80-2.80 (m, 8H), 1.11 (dd, J = 10.0, 6.7 Hz, 3H). |
| 435 | 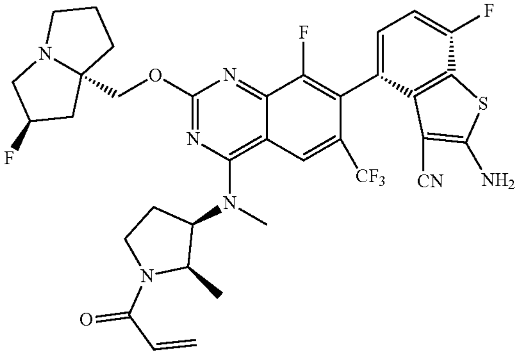 | LCMS m/z [M + 1]: 730.0 $^1$HNMR (400 MHz, $CD_3OD$) δ 8.35 (s, 1H), 7.19-7.25 (m, 1H), 7.01 (t, J = 8.9 Hz, 1H), 6.61-6.71 (m, 1H), 6.30-6.41 (m, 1H), 5.78 (d, J = 12.2 Hz, 1H), 5.30 (d, J = 53.4 Hz, 1H), 5.01-5.07 (m, 1H), 4.87-4.94 (m, 1H), 4.21-4.36 (m, 2H), 3.55-4.05 (m, 5H), 3.13-3.27 (m, 3H), 2.97-3.06 (m, 1H), 1.80-2.80 (m, 8H), 1.14 (t, J = 7.1 Hz, 3H). |
| 435a | 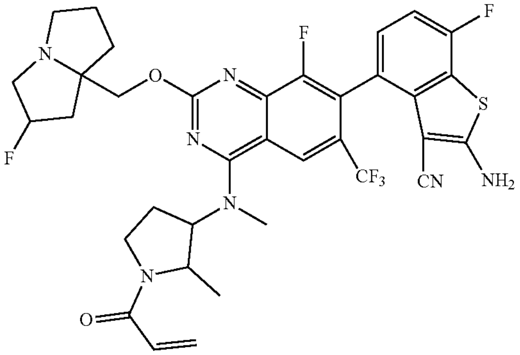 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1C] | |

TABLE 5-continued
| Selected compounds of the present disclosure. | | |
|---|---|---|
| Compound No. | Structure | Analytical data |
| 436 | 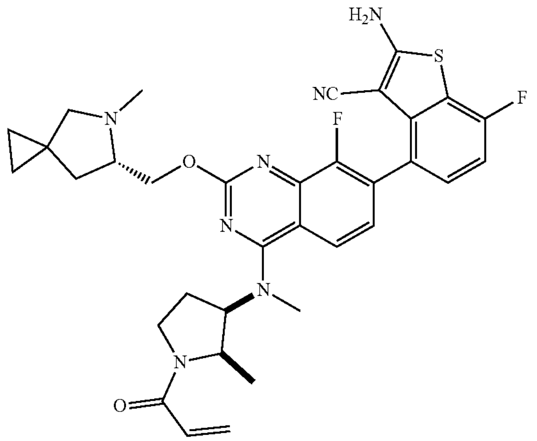 | LCMS m/z [M + 1]: 644.0<br>$^1$HNMR (400 MHz, $CD_3OD$) δ 8.13-8.16 (m, 1H), 7.39-7.43 (m, 1H), 7.27-7.30 (m, 1H), 7.05 (t, J = 8.54 Hz, 1H), 6.62-6.68 (m, 1H), 6.28-6.37 (m, 1H), 5.77-5.79 (m, 1H), 4.88-5.06 (m, 3H), 4.60-4.79 (m, 1H), 4.08-4.15 (m, 1H), 3.44-4.00 (m, 6H), 3.34-3.36 (m, 1H), 3.14 (s, 3H), 2.46-2.77 (m, 3H), 1.97-1.98 (m, 1H), 1.09-1.16 (m, 3H), 0.64-0.84 (m, 4H), |
| 436a | 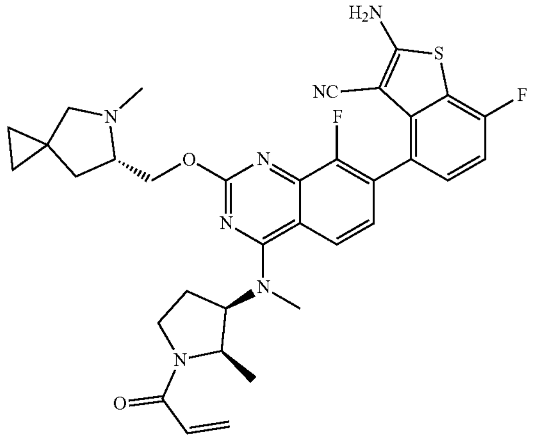 [SMILES: C=CC(=O)N1CC[C@@H](N(C)c2nc(OC[C@@H]3CC4(CC4)CN3C)nc3c(F)c(-c4ccc(F)c5sc(N)c(C#N)c45)ccc23)[C@H]1C] | |
| 436b | 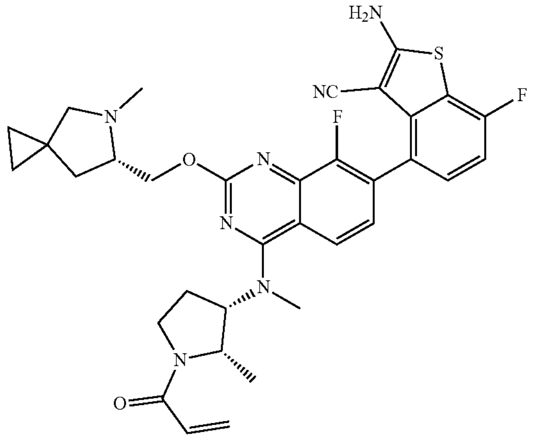 [SMILES: C=CC(=O)N1CC[C@H](N(C)c2nc(OC[C@@H]3CC4(CC4)CN3C)nc3c(F)c(-c4ccc(F)c5sc(N)c(C#N)c45)ccc23)[C@@H]1C] | |

TABLE 5-continued
| Selected compounds of the present disclosure. | | |
|---|---|---|
| Compound No. | Structure | Analytical data |
| 436c | 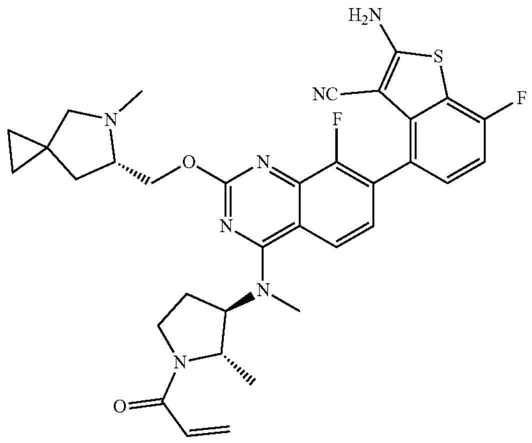 [SMILES: C=CC(=O)N1CC[C@@H](N(C)c2nc(OC[C@@H]3CC4(CC4)CN3C)nc3c(F)c(-c4ccc(F)c5sc(N)c(C#N)c45)ccc23)[C@@H]1C] | |
| 436d | 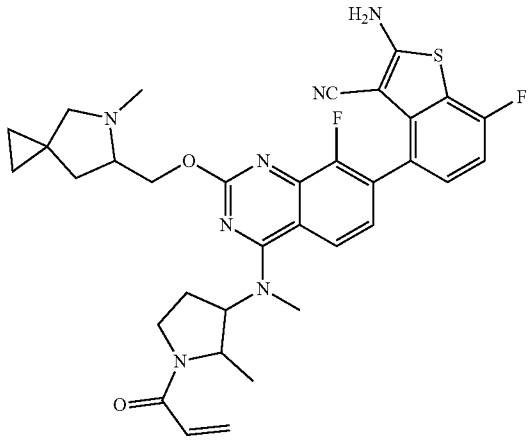 [SMILES: C=CC(=O)N1CCC(N(C)c2nc(OCC3CC4(CC4)CN3C)nc3c(F)c(-c4ccc(F)c5sc(N)c(C#N)c45)ccc23)C1C] | |
| 437 | 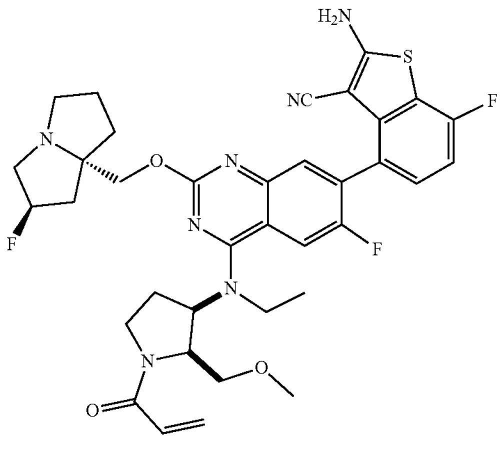 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@H]1COC] | LCMS m/z [M + 1]: 706.6 $^{1}$HNMR (400 MHz, $CD_3OD$) δ 8.02-8.06 (m, 1H), 7.69-7.71 (m, 1H), 7.28-7.31 (m, 1H), 7.05 (t, J = 8.96 Hz, 1H), 6.65-6.72(m, 1H), 6.31-6.39 (m, 1H), 5.77-5.83 (m, 1H), 5.59 (d, J = 81.84 Hz, 1H), 4.99-5.03 (m, 2H), 4.67-4.82 (m, 2H), 3.28-4.31 (m, 10H), 3.20 (s, 3H), 2.23-2.89 (m, 8H), 1.46-1.58 (m, 3H). |

TABLE 5-continued
Selected compounds of the present disclosure.
| Compound No. | Structure | Analytical data |
| --- | --- | --- |
| 437a | 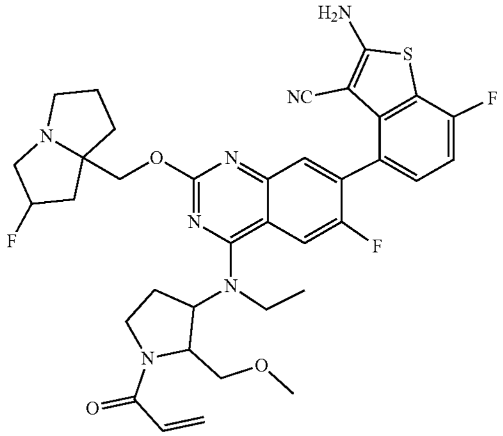 [SMILES: C=CC(=O)N1CCC(N(CC)c2nc(OCC34CCCN3CC(F)C4)nc3cc(-c4ccc(F)c5sc(N)c(C#N)c45)c(F)cc23)C1COC] | |
| 438 | 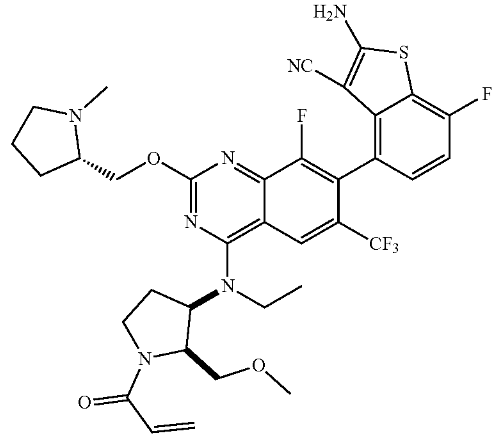 | LCMS m/z [M + 1]: 730.4 $^1$HNMR (400 MHz, $CD_3OD$) δ 8.28-8.45 (m, 1H), 7.18-7.27 (m, 1H), 7.01 (t, 1H), 6.63-6.79 (m, 1H), 6.26-6.38 (m, 1H), 5.69-5.85 (m, 1H), 4.88-5.03 (m, 2H), 4.42-4.62 (m, 2H), 4.06-4.14 (m, 1H), 3.93 (t, 1H), 3.45-3.78 (m, 3H), 3.31-3.42 (m, 1H), 3.14-3.26 (m, 4H), 2.91-3.09 (m, 1H), 2.72-2.85 (m, 1H), 2.41-2.71 (m, 5H), 2.08-2.23 (m, 1H), 1.70-2.00 (m, 3H), 1.33-1.57 (m, 3H). |
| 438a | 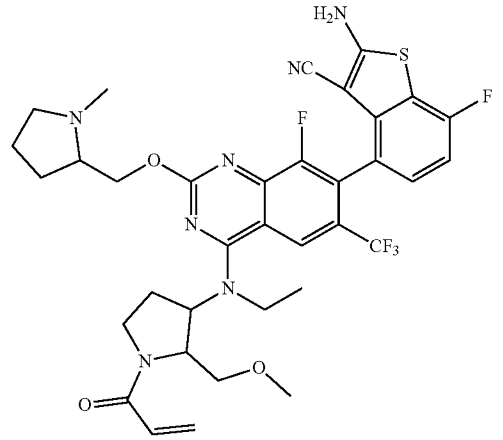 [SMILES: C=CC(=O)N1CCC(N(CC)c2nc(OCC3CCCN3C)nc3c(F)c(-c4ccc(F)c5sc(N)c(C#N)c45)c(C(F)(F)F)cc23)C1COC] | |

TABLE 5-continued
| Selected compounds of the present disclosure. | | |
|---|---|---|
| Compound No. | Structure | Analytical data |
| 439 | 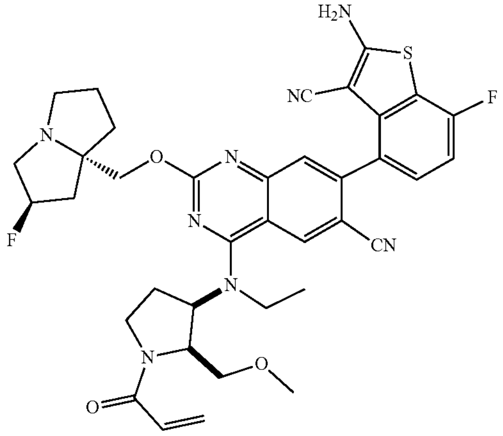 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(C#N)cc23)[C@H]1COC] | LCMS m/z [M + 1]: 713.0 $^1$HNMR (400 MHz, $CD_3OD$) δ 8.56-8.57 (m, 1H), 7.62-7.65 (m, 1H), 7.27-7.31 (m, 1H), 7.05 (t, J = 8.96 Hz, 1H), 6.64-6.77 (m, 1H), 6.29-6.35 (m, 1H), 5.73-5.80 (m, 1H), 5.23-5.39 (m, 1H), 4.57-4.99 (m, 3H), 4.17-4.35 (m, 2H), 3.90-4.12 (m, 2H), 2.99-3.76 (m, 10H), 1.88-3.05 (m, 8H), 1.36-1.47 (m, 3H). |
| 439a | 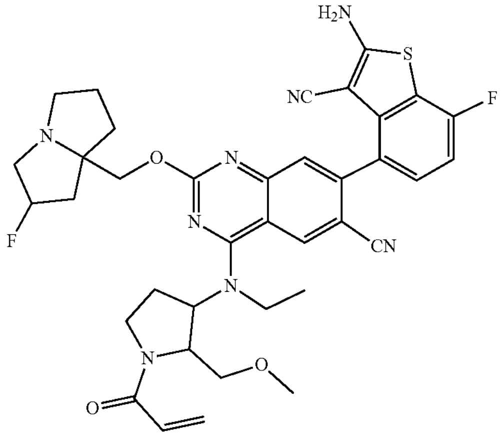 [SMILES: C=CC(=O)N1CCC(N(CC)c2nc(OCC34CCCN3CC(F)C4)nc3cc(-c4ccc(F)c5sc(N)c(C#N)c45)c(C#N)cc23)C1COC] | |
| 440 | 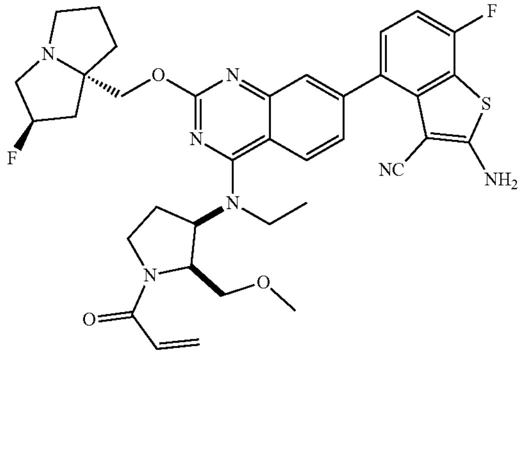 | LCMS m/z [M + 1]: 688.0 $^1$HNMR (400 MHz, $CD_3OD$) δ 8.38 (d, J = 9.08 Hz, 1H), 7.67-7.69 (m, 2H), 7.29-7.32 (m, 1H), 7.05 (t, J = 9.08 Hz, 1H), 6.65-6.72 (m, 1H), 6.32-6.36 (m, 1H), 5.81-5.84 (m, 1H), 5.52-5.67 (m, 1H), 4.94-5.25 (m, 2H), 4.75-4.83 (m, 2H), 3.33-4.37 (m, 10H), 3.22-3.25 (m, 3H), 2.24-2.94 (m, 8H), 1.57-1.65 (m, 3H). |

TABLE 5-continued
| Compound No. | Structure | Analytical data |
|---|---|---|
| 440a | 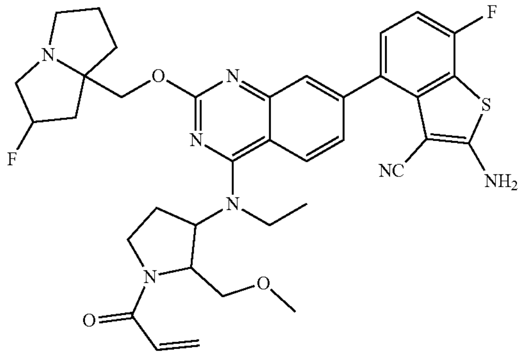 [SMILES: C=CC(=O)N1CCC(N(CC)c2nc(OCC34CCCN3CC(F)C4)nc3cc(-c4ccc(F)c5sc(N)c(C#N)c45)ccc23)C1COC] | |
| 441 | 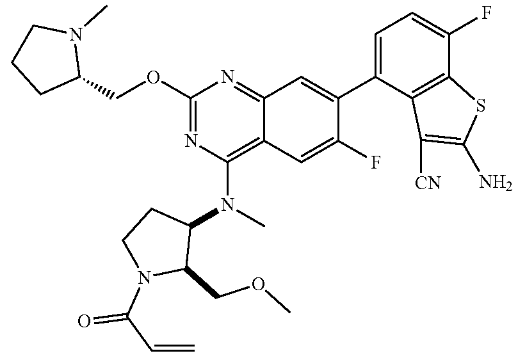 | LCMS m/z [M + 1]: 648.0 $^1$HNMR (400 MHz, $CD_3OD$) δ 8.15-8.17 (m, 1H), 7.65-7.67 (m, 1H), 7.28-7.32 (m, 1H), 7.05 (t, J = 9.08 Hz, 1H), 6.66-6.73 (m, 1H), 6.33-6.37 (m, 1H), 5.77-5.84 (m, 1H), 5.07-5.15 (m, 1H), 4.89-5.00 (m, 2H), 4.70-4.81 (m, 1H), 3.58-4.00 (m, 8H), 3.26-3.45 (m, 5H), 3.09-3.10 (m, 3H), 2.72-2.93 (m, 1H), 2.40-2.44 (m, 2H), 2.00-2.22 (m, 3H). |
| 441a | 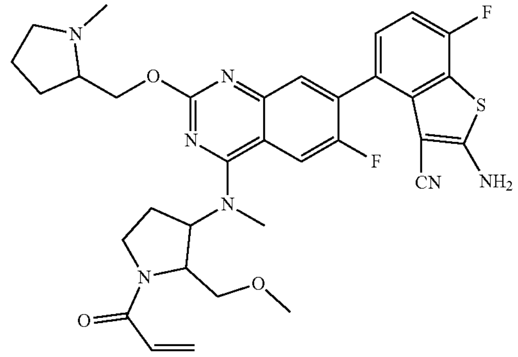 [SMILES: C=CC(=O)N1CCC(N(C)c2nc(OCC3CCCN3C)nc3cc(-c4ccc(F)c5sc(N)c(C#N)c45)c(F)cc23)C1COC] | |
| 442 | 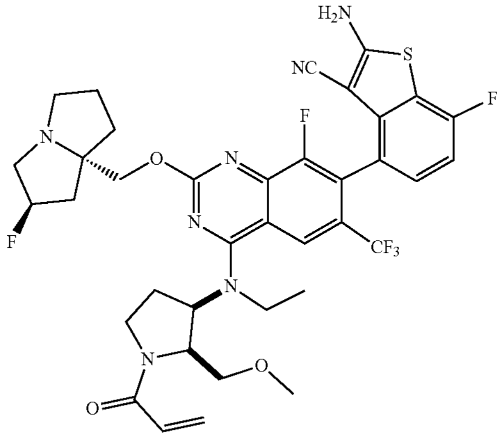 [SMILES: C=CC(=O)N1CC[C@@H](N(CC)c2nc(OC[C@@]34CCCN3C[C@H](F)C4)nc3c(F)c(-c4ccc(F)c5sc(N)c(C#N)c45)c(C(F)(F)F)cc23)[C@H]1COC] | LCMS m/z [M + 1]: 774 $^1$HNMR (400 MHz, $CD_3OD$) δ 8.34-8.44 (m, 1H), 7.23 (t, 1H), 7.02 (t, 1H), 6.64-6.79 (m, 1H), 6.28-6.39 (m, 1H), 5.72-5.85 (m, 1H), 5.50 (s, 0.3H), 5.44 (s, 0.2H), 5.37 (s, 0.3H), 5.30 (s, 0.2H), 4.88-5.07 (m, 2H), 4.30-4.55 (m, 2H), 4.07-4.15 (m, 1H), 3.93 (t, 1H), 3.33-3.82 (m, 6H), 3.12-3.26 (m, 4H), 2.62-2.88 (m, 2H), 2.24-2.58 (m, 4H), 1.98-2.20 (m, 3H), 1.39-1.58 (m, 3H). |
Selected compounds of the present disclosure.

TABLE 5-continued
| Selected compounds of the present disclosure. | | |
|---|---|---|
| Compound No. | Structure | Analytical data |
| 442a | 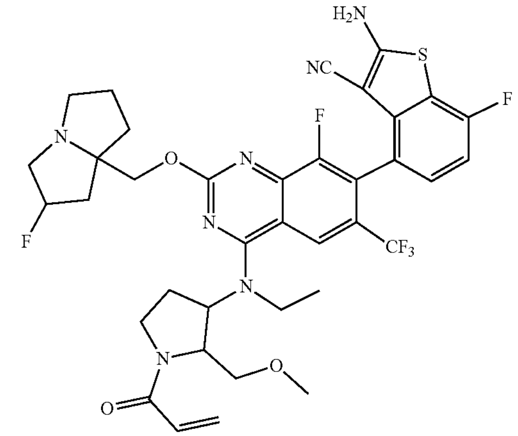 [SMILES: C=CC(=O)N1CCC(N(CC)c2nc(OCC34CCCN3CC(F)C4)nc3c(F)c(-c4ccc(F)c5sc(N)c(C#N)c45)c(C(F)(F)F)cc23)C1COC] | |
| 443 | 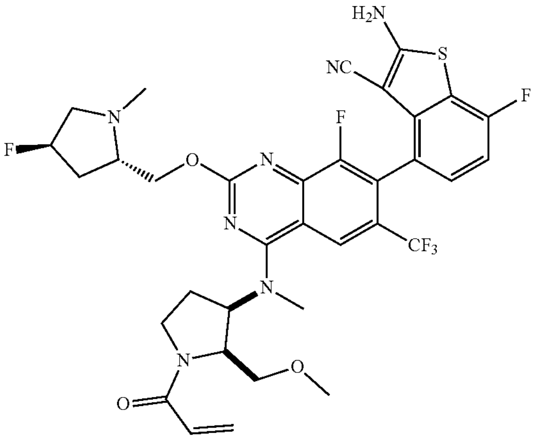 | LCMS m/z [M + 1]: 734.1<br>$^1$HNMR (400 MHz, $CD_3OD$) δ 8.39 (s, 1H), 7.16-7.28 (m, 1H), 7.01 (t, 1H), 6.63-6.82 (m, 1H), 6.26-6.39 (m, 1H), 5.72-5.84 (m, 1H), 5.24 (s, 0.5H), 5.10 (s, 0.5H), 4.88-5.07 (s, 2H), 4.34-4.65 (m, 2H), 3.37-3.98 (m, 7H), 3.09-3.28 (m, 4H), 2.45-2.94 (m, 5H), 1.68-2.43 (m, 4H). |
| 443a | 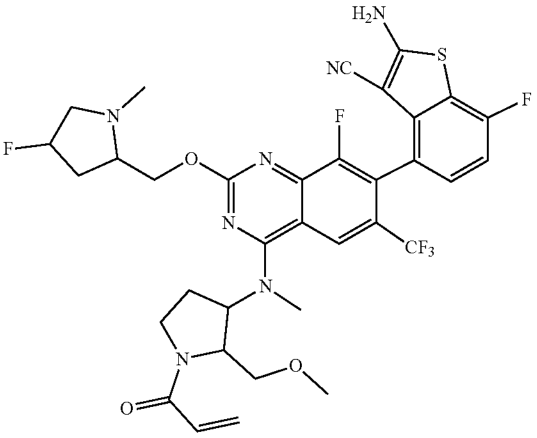 [SMILES: C=CC(=O)N1CCC(N(C)c2nc(OCC3CC(F)CN3C)nc3c(F)c(-c4ccc(F)c5sc(N)c(C#N)c45)c(C(F)(F)F)cc23)C1COC] | |

TABLE 5-continued
Selected compounds of the present disclosure.
| Compound No. | Structure | Analytical data |
|---|---|---|
| 444 | 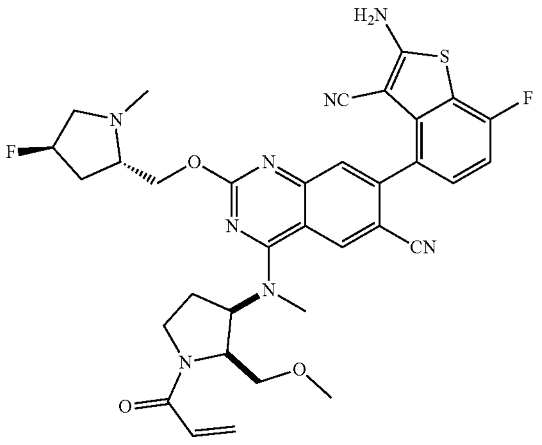 | LCMS m/z [M + 1]: 673.1 $^1$HNMR (400 MHz, $CD_3OD$) δ 8.52 (s, 1H), 7.60 (s, 1H), 7.28 (m, 1H), 7.05 (m, 1H), 6.78-6.66 (m, 1H), 6.31 (m, 1H), 5.82-5.75 (m, 1H), 5.14 (s, 0.6H), 5.00 (s, 0.6H), 4.94 (m, 2H), 4.30 (m, 2H), 3.75-3.31 (m, 8H), 3.13 (m, 4H), 2.82-2.61 (m, 2H), 2.37 (m, 3H), 2.30-2.26 (m, 2H), 1.98 (m, 1H). |
| 444a | 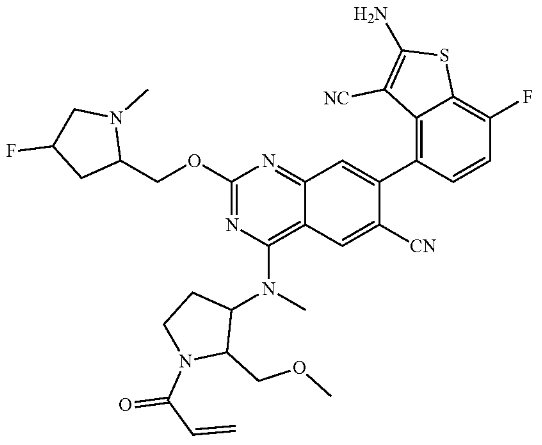 [SMILES: C=CC(=O)N1CCC(N(C)c2nc(OCC3CC(F)CN3C)nc3cc(-c4ccc(F)c5sc(N)c(C#N)c45)c(C#N)cc23)C1COC] | |
| 445 | 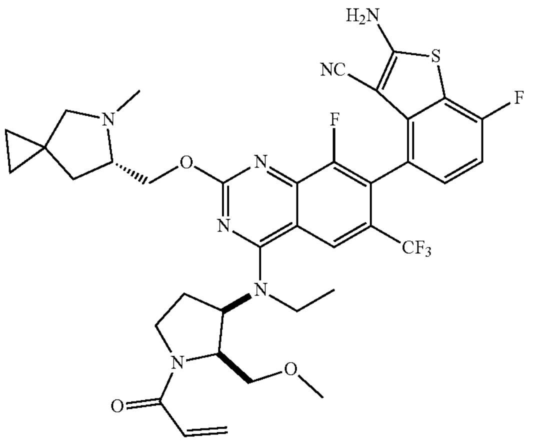 | LCMS m/z [M + 1]: 756.2 $^1$HNMR (400 MHz, $CD_3OD$) δ 8.37 (d, 1H), 7.23 (m, 1H), 7.01 (t, 1H), 6.73-6.64 (m, 1H), 6.32 (t, 1H), 5.80-5.72 (m, 1H), 4.99-4.91 (m, 2H), 4.62-4.52 (m, 2H), 4.09-4.00 (m, 2H), 3.95 (t, 1H), 3.72-3.65 (m, 3H), 3.30 (d, 1H), 3.29(d, 1H), 3.17(d, 3H), 2.79 (t, 2H), 2.55 (d, 3H), 2.46-2.44 (m, 1H), 2.20-2.13 (m, 1H), 1.75-1.70 (m, 1H), 1.49-1.44 (t, 3H), 0.62-0.54 (m, 4H). |

TABLE 5-continued
| Selected compounds of the present disclosure. | | |
|---|---|---|
| Compound No. | Structure | Analytical data |
| 445a | 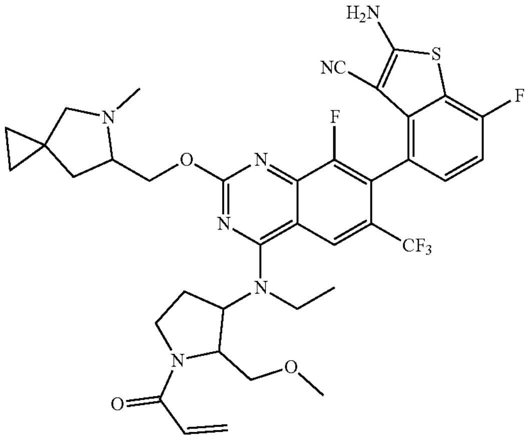 [SMILES: C=CC(=O)N1CCC(N(CC)c2nc(OCC3CC4(CC4)CN3C)nc3c(F)c(-c4ccc(F)c5sc(N)c(C#N)c45)c(C(F)(F)F)cc23)C1COC] | |
| 446 | 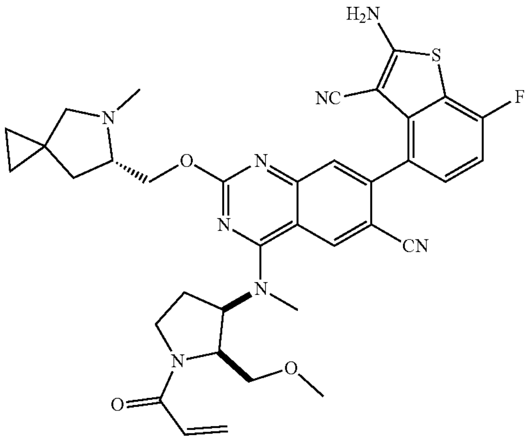 | LCMS m/z [M + 1]: 681.2 $^1$HNMR (400 MHz, $CD_3OD$) δ 8.67 (s, 1H), 7.61-7.59 (m, 1H), 7.31-7.27 (m, 1H), 7.06-7.02 (m, 1H), 6.82-6.65 (m, 1H), 6.36-6.29 (m, 1H), 5.81-5.74 (m, 1H), 5.05-4.94 (m, 2H), 4.56-4.45 (m, 2H), 3.96-3.42 (m, 7H), 3.25 (s, 3H), 3.13-3.09 (m, 1H), 2.88-2.63 (m, 3H), 2.53 (m, 3H), 2.37 (m, 1H), 2.18-2.04 (m, 1H), 1.73-1.59 (m, 1H), 0.66-0.53 (m, 4H). |
| 446a | 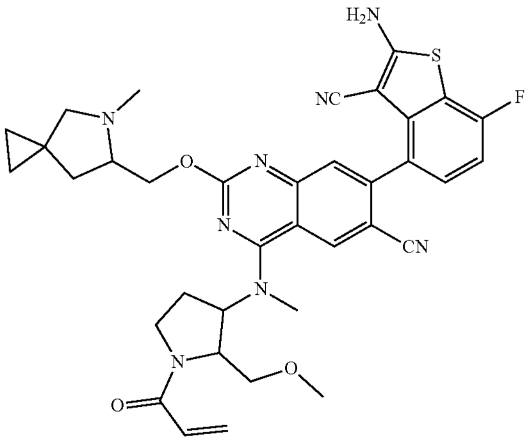 [SMILES: C=CC(=O)N1CCC(N(C)c2nc(OCC3CC4(CC4)CN3C)nc3cc(-c4ccc(F)c5sc(N)c(C#N)c45)c(C#N)cc23)C1COC] | |

TABLE 5-continued
| Compound No. | Structure | Analytical data |
|---|---|---|
| 447 | 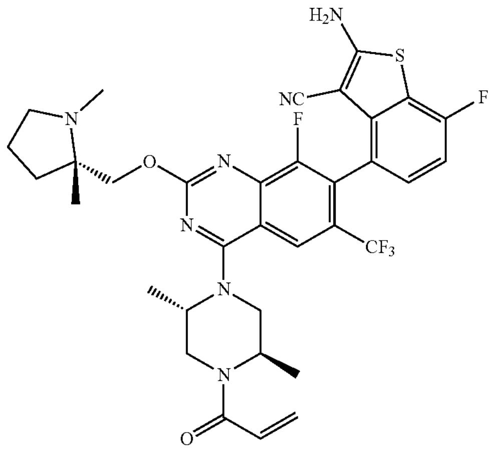 [SMILES: C=CC(=O)N1C[C@H](C)N(c2nc(OC[C@]3(C)CCCN3C)nc3c(F)c(-c4ccc(F)c5sc(N)c(C#N)c45)c(C(F)(F)F)cc23)C[C@H]1C] | LCMS m/z [M + 1]: 700.1<br>$^1$HNMR (400 MHz, $CD_3OD$) δ 8.14 (s, 1H), 7.20-7.25 (m, 1H), 6.99-7.04 (m, 1H), 6.77-6.87 (m, 1H), 6.25-6.32 (m, 1H), 5.78-5.84 (m, 1H), 4.90-4.96 (m, 1H), 4.25-4.58 (m, 4H), 3.83-4.02 (m, 2H), 3.39-3.61 (m, 1H), 3.16-3.23 (m, 1H), 2.91-2.99(m, 1H), 2.64 (s, 3H), 2.11-2.19 (m, 1H), 1.81-1.99 (m, 3H), 1.43-1.56 (m, 3H), 1.27-1.31 (m, 6H). |
| 447a | 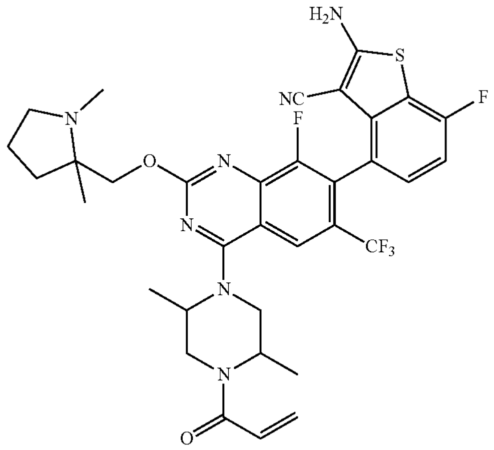 [SMILES: C=CC(=O)N1CC(C)N(c2nc(OCC3(C)CCCN3C)nc3c(F)c(-c4ccc(F)c5sc(N)c(C#N)c45)c(C(F)(F)F)cc23)CC1C] | |
| 448 | 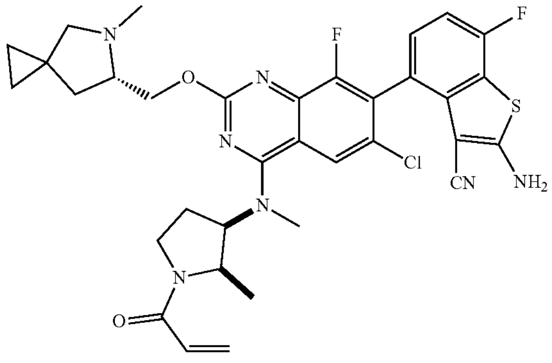 | LCMS m/z [M + 1]: 678.2<br>$^1$HNMR (400 MHz, $CD_3OD$) δ 8.18 (d, J = 8.5 Hz, 1H), 7.21-7.25 (m, 1H), 7.05 (t, J = 9.0 Hz, 1H), 6.68-6.58 (m, 1H), 6.33 (t, J = 17.8 Hz, 1H), 5.78 (d, J = 10.5 Hz, 1H), 5.06-4.94 (m, 2H), 4.72-4.57 (m, 1H), 4.16-4.06 (m, 1H), 3.83-3.64 (m, 1H), 3.60-3.62 (m, 4H), 3.59-3.33 (m, 3H), 3.12 (s, 3H), 2.76-2.54 (m, 1H), 2.54-2.35 (m, 2H), 1.99-1.90 (m, 1H), 1.20-1.04 (m, 3H), 0.8-0.6 (m, 4H). |
Selected compounds of the present disclosure.

TABLE 5-continued
| Selected compounds of the present disclosure. | | |
|---|---|---|
| Compound No. | Structure | Analytical data |
| 448a | 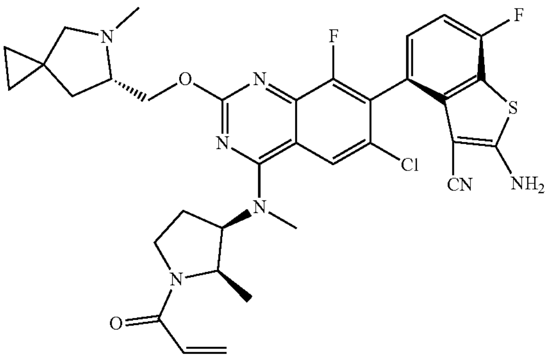 | |
| 448b | 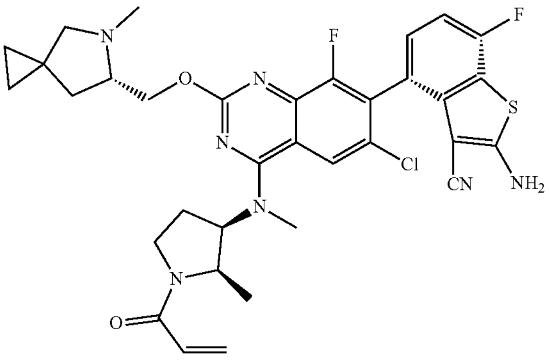 | |
| 448c | 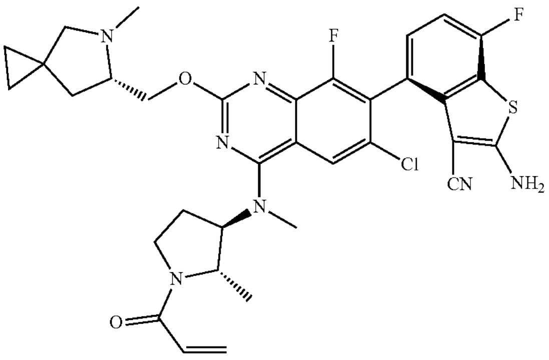 | |
| 448d | 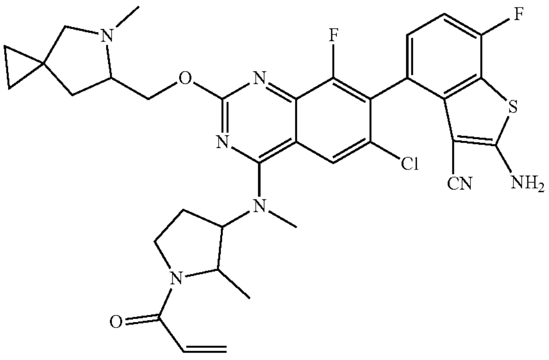 [SMILES: C=CC(=O)N1CCC(N(C)c2nc(OCC3CC4(CC4)CN3C)nc3c(F)c(-c4ccc(F)c5sc(N)c(C#N)c45)c(Cl)cc23)C1C] | |

TABLE 5-continued
| Selected compounds of the present disclosure. | | |
|---|---|---|
| Compound No. | Structure | Analytical data |
| 449 | 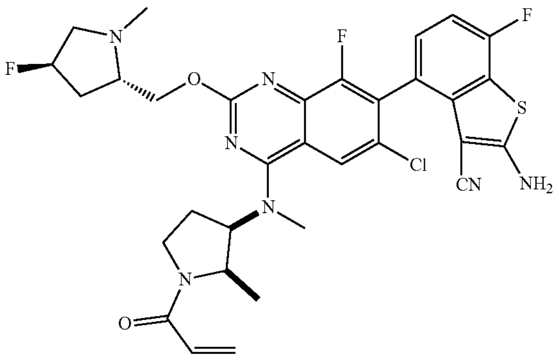 | LCMS m/z [M + 1]: 670.1 $^1$HNMR (400 MHz, $CD_3OD$) δ 8.18 (s, 1H), 7.27-7.19 (m, 1H), 7.06 (t, J = 8.9 Hz, 1H), 6.69-6.59 (m, 1H), 6.33 (t, J = 15.1 Hz, 1H), 5.79 (d, J = 10.4 Hz, 1H), 5.47 (d, J = 52.1 Hz, 1H), 5.08-4.90 (m, 3H), 4.80-4.61 (m, 2H), 4.28-4.20 (m, 1H), 3.99-3.94 (m, 1H), 3.84-3.64 (m, 2H), 3.62 (s, 3H), 3.18 (d, J = 3.2 Hz, 3H), 2.71-2.61 (m, 2H), 2.50-2.35 (m, 2H), 1.20-1.06 (m, 3H). |
| 449a | 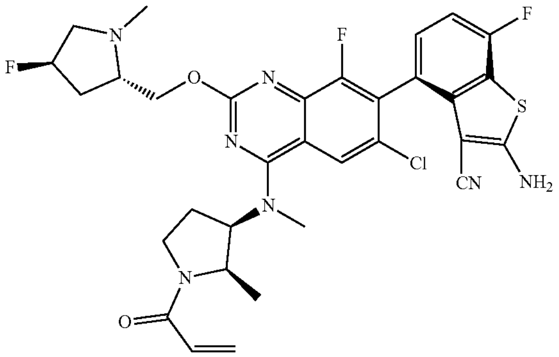 | |
| 449b | 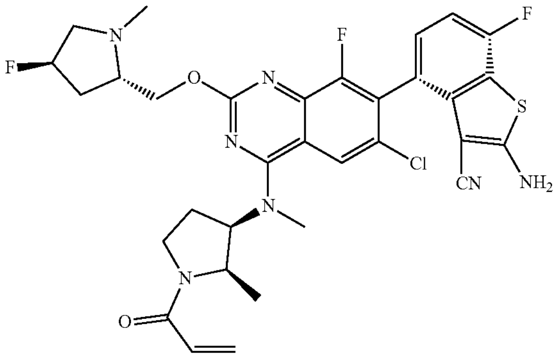 | |
| 449c | 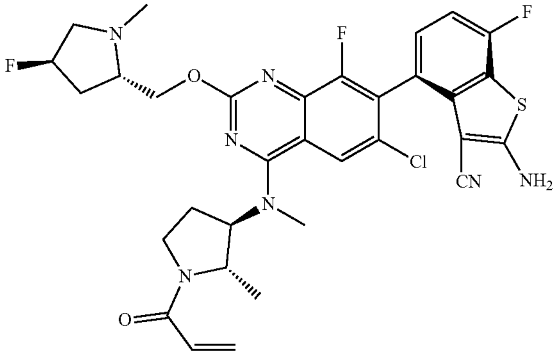 | |

TABLE 5-continued
| Selected compounds of the present disclosure. | | |
|---|---|---|
| Compound No. | Structure | Analytical data |
| 449d | 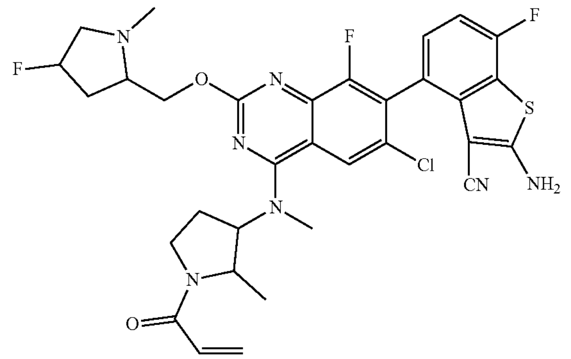 [SMILES: C=CC(=O)N1CCC(N(C)c2nc(OCC3CC(F)CN3C)nc3c(F)c(-c4ccc(F)c5sc(N)c(C#N)c45)c(Cl)cc23)C1C] | |
| 450 | 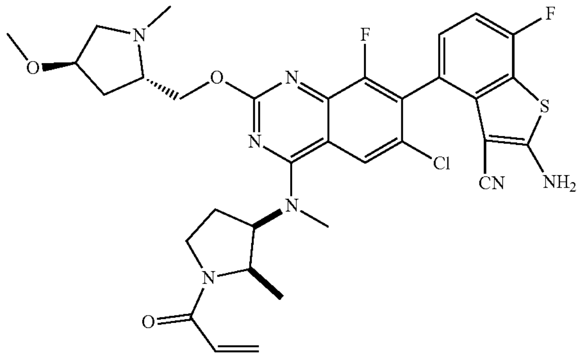 | LCMS m/z [M + 1]: 682.2<br>$^1$HNMR (400 MHz, $CD_3OD$) δ 8.17 (s, 1H), 7.27-7.41 (m, 2H), 7.06 (t, J = 8.9 Hz, 1H), 6.68-6.62 (m, 1H), 6.33 (t, J = 15.3 Hz, 1H), 5.79 (d, J = 10.4 Hz, 1H), 5.09-4.89 (m, 2H), 4.80-4.59 (m, 2H), 4.18-4.09 (m, 2H), 3.90-3.64 (m, 3H), 3.61 (s, 3H), 3.56-3.42 (m, 1H), 3.39 (s, 3H), 3.13 (s, 3H), 2.76-2.34 (m, 3H), 2.21-2.10 (m, 1H), 1.15-1.07 (m, 3H). |
| 450a | 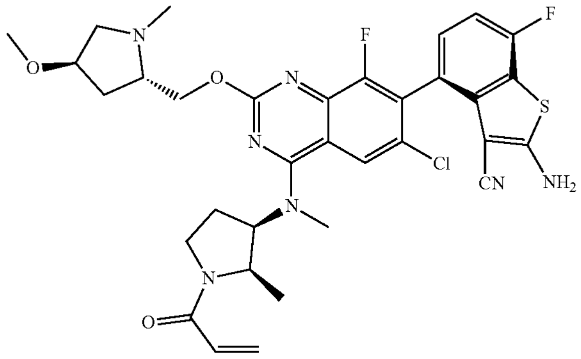 | |
| 450b | 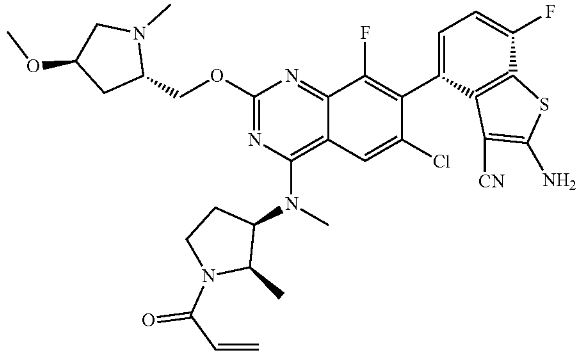 | |

TABLE 5-continued
| Selected compounds of the present disclosure. | | |
|---|---|---|
| Compound No. | Structure | Analytical data |
| 450c | 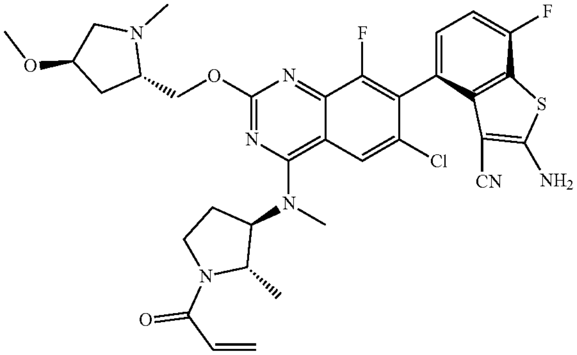 | |
| 450d | 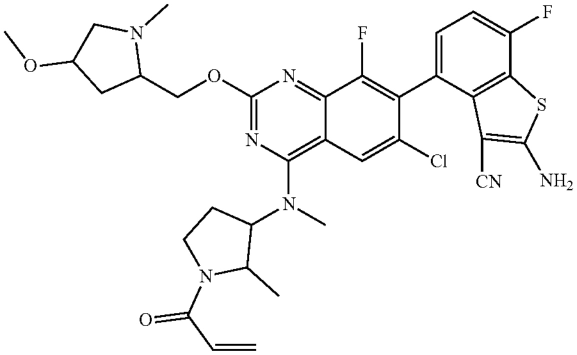 [SMILES: C=CC(=O)N1CCC(N(C)c2nc(OCC3CC(OC)CN3C)nc3c(F)c(-c4ccc(F)c5sc(N)c(C#N)c45)c(Cl)cc23)C1C] | |
| 451 | 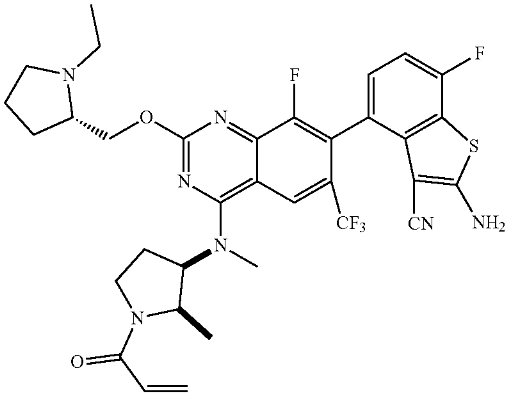 | LCMS m/z [M + 1]: 700.0<br>$^1$HNMR (400 MHz, $CD_3OD$) δ 8.40 (s, 1H), 7.21-7.27 (m, 1H), 7.03 (t, J = 8.8 Hz, 1H), 6.62-6.73 (m, 1H), 6.34 (t, J = 18.1 Hz, 1H), 5.79 (d, J = 10.5 Hz, 1H), 4.86-5.12 (m, 3H), 4.58-4.70 (m, 1H), 3.90-4.06 (m, 2H), 3.57-3.85 (m, 6H), 3.19-3.28 (m, 2H), 2.63-2.77 (m, 1H), 2.33-2.52 (m, 2H), 2.01-2.21 (m, 3H), 1.34-1.43 (m, 3H), 1.10-1.21 (m, 3H). |
| 451a | 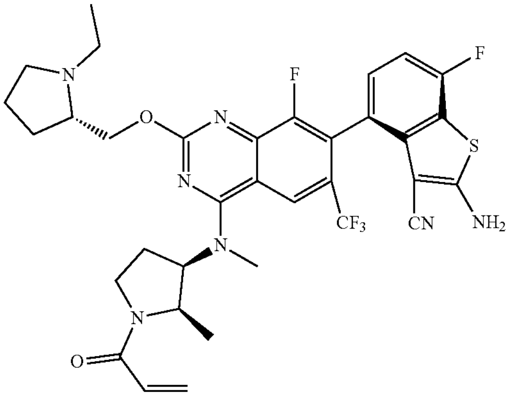 | |

TABLE 5-continued
| Selected compounds of the present disclosure. | | |
| --- | --- | --- |
| Compound No. | Structure | Analytical data |
| 451b | 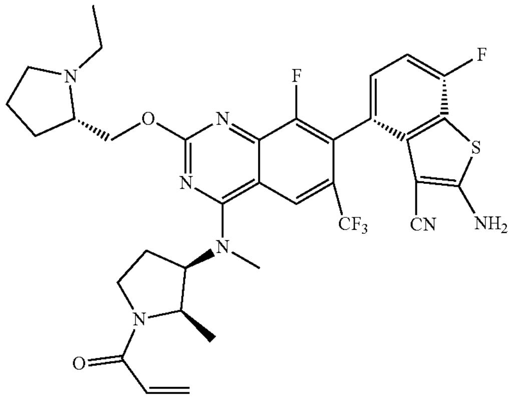 | |
| 451c | 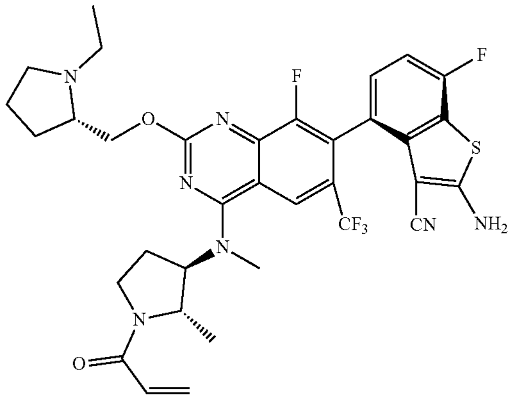 | |
| 451d | 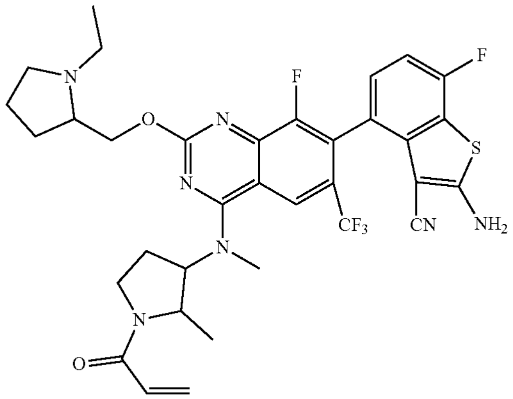 | |

TABLE 5-continued
Selected compounds of the present disclosure.
| Compound No. | Structure | Analytical data |
| --- | --- | --- |
| 453 | 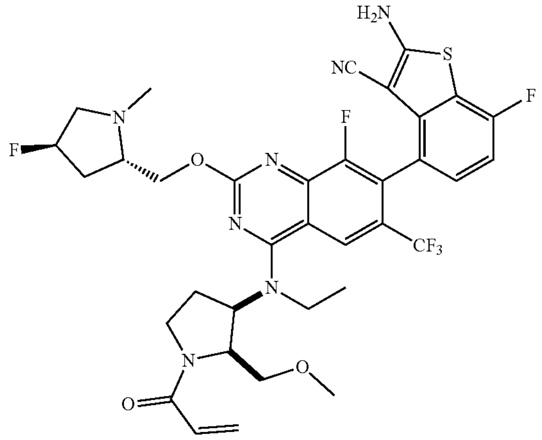 | LCMS m/z [M + 1]: 748.1<br>$^1$HNMR (400 MHz, $CD_3OD$) δ 8.37 (s, 1H), 7.22 (t, 1H), 7.01 (t, 1H), 6.77-6.44 (m, 1H), 6.34-6.29 (m, 1H), 5.80-5.73 (m,1H), 5.22 (s, 0.5H), 5.09 (s, 0.5H), 5.03-4.92 (m, 2H), 4.4.58-4.42 (m, 2H), 4.12-3.90 (m, 2H), 3.78-3.36 (m, 4H), 3.18-3.13 (m, 3H), 2.81-2.45 (m, 6H), 2.32-2.17 (m, 1), 2.01-1.92 (m, 1H), 1.48-1.44 (m, 3H), 1.35 (d, 2H). |
| 453a | 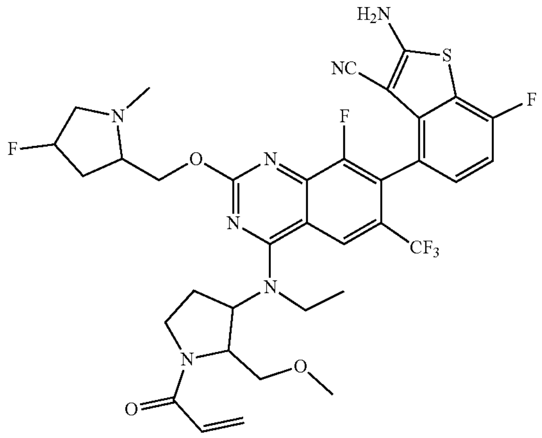 [SMILES: C=CC(=O)N1CCC(N(CC)c2nc(OCC3CC(F)CN3C)nc3c(F)c(-c4ccc(F)c5sc(N)c(C#N)c45)c(C(F)(F)F)cc23)C1COC] | |
| 454 | 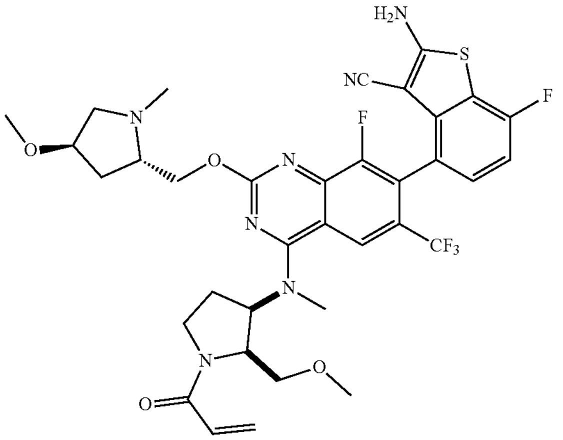 | LCMS m/z [M + 1]: 747<br>$^1$HNMR (400 MHz, $CD_3OD$) δ 8.38 (s, 1H), 7.22 (t, 1H), 7.01 (t, 1H), 6.63-6.83 (m, 1H), 6.27-6.39 (m, 1H), 5.73-5.83 (m, 1H), 4.90-5.09 (m, 2H), 4.38-4.60 (m, 2H), 3.52-4.03 (m, 7H), 3.36-3.45 (m, 1H), 3.27-3.29 (m, 2H), 3.15-3.27 (m, 4H), 2.98-3.12 (m, 1H), 2.61-2.94 (m, 2H), 2.27-2.58 (m, 5H), 1.83-2.18 (m, 2H). |

TABLE 5-continued
| Selected compounds of the present disclosure. | | |
|---|---|---|
| Compound No. | Structure | Analytical data |
| 454a | 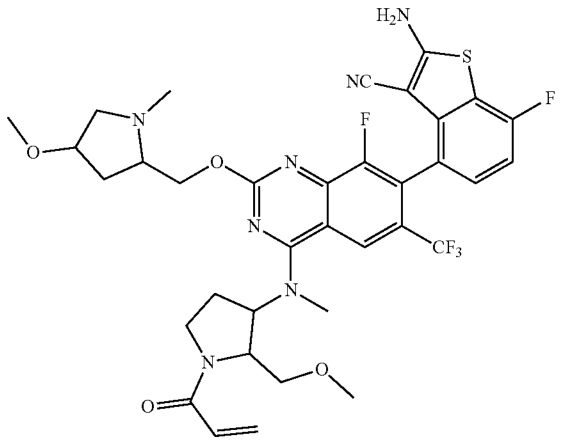 [SMILES: C=CC(=O)N1CCC(N(C)c2nc(OCC3CC(OC)CN3C)nc3c(F)c(-c4ccc(F)c5sc(N)c(C#N)c45)c(C(F)(F)F)cc23)C1COC] | |
| 455 | 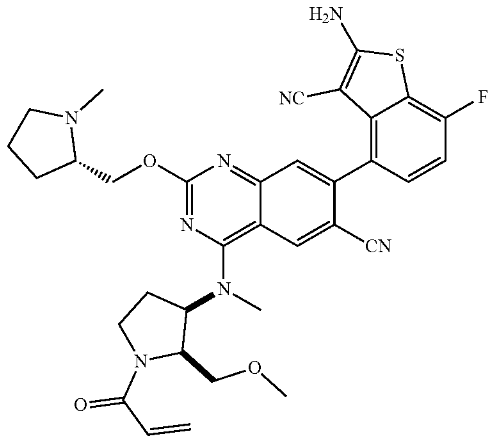 | LCMS m/z [M + 1]: 655 $^1$HNMR (400 MHz, $CD_3OD$) δ 8.68 (s, 1H), 7.63-7.61 (m, 1H), 7.30-7.27 (m, 1H), 7.06-7.02 (m, 1H), 6.78-6.65 (m, 1H), 6.35-6.30 (m, 1H), 5.82-5.74(m, 1H), 5.01-4.93 (m, 2H), 4.72-4.49 (m, 2H), 3.96-3.41 (m, 9H), 3.23 (m, 3H), 2.98-2.66 (m, 5H), 2.38-2.21 (m, 2H), 2.05-1.91 (m, 3H). |
| 456 | 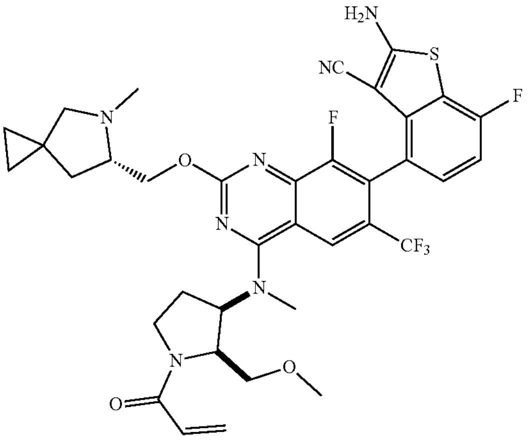 | LCMS m/z [M + 1]: 742.4 $^1$HNMR (400 MHz, $CD_3OD$) δ 8.39 (d, 1H), 7.22 (t, 1H), 7.01 (t, 1H), 6.72-6.65 (m, 1H), 6.33 (t, 1H), 5.80-5.78 (m, 1H), 5.07-4.94 (m, 3H), 4.61-4.53 (m, 2H), 3.93 (t, 1H), 3.82-3.80 (m, 1H), 3.66 (d, 3H), 3.42-3.36 (m, 1H), 3.24 (s, 3H), 2.82-2.69 (m, 4H), 2.58 (d, 3H), 2.39 (m, 1H), 2.23-2.17 (m, 1H), 1.72 (m, 1H), 0.63-0.54 (m, 4H). |

TABLE 5-continued
| Selected compounds of the present disclosure. | | |
|---|---|---|
| Compound No. | Structure | Analytical data |
| 456a | 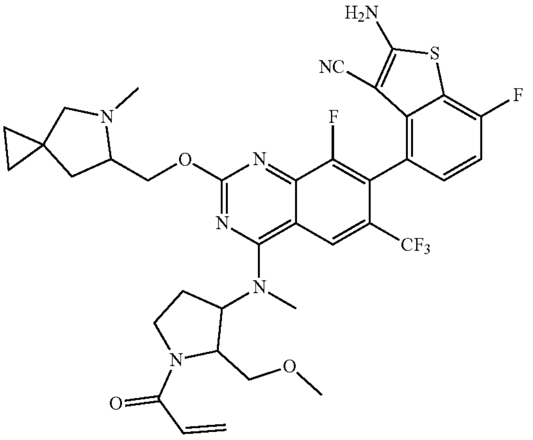 [SMILES: C=CC(=O)N1CCC(N(C)c2nc(OCC3CC4(CC4)CN3C)nc3c(F)c(-c4ccc(F)c5sc(N)c(C#N)c45)c(C(F)(F)F)cc23)C1COC] | |
| 457 | 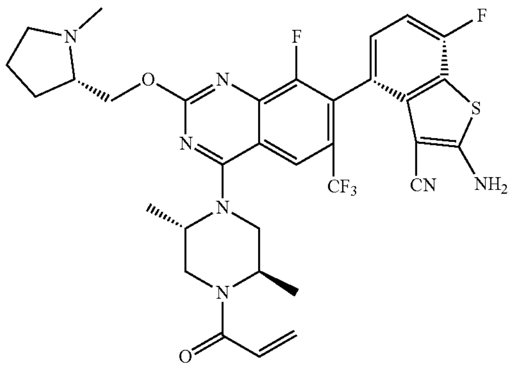 | LCMS m/z [M + 1]: 686.1 $^1$HNMR (400 MHz, $CD_3OD$) δ 8.14 (s, 1H), 7.20-7.25 (m, 1H), 6.99-7.04 (m, 1H), 6.75-6.87 (m, 1H), 6.25-6.32 (m, 1H), 5.78-5.84 (m, 1H), 4.89-4.94 (m, 1H), 4.49 (d, 2H), 4.25-4.45 (m, 2H), 3.86-3.97 (m, 2H), 3.43-3.58 (m, 1H), 3.06-3.13 (m, 1H), 2.77-2.83 (m, 1H), 2.52 (s, 3H), 2.32-2.39 (m, 1H), 2.08-2.16 (m, 1H), 1.72-1.86 (m, 3H), 1.46-1.53 (m, 3H), 1.40 (d, 1H), 1.27-1.35 (m, 2H). |
| 458 | 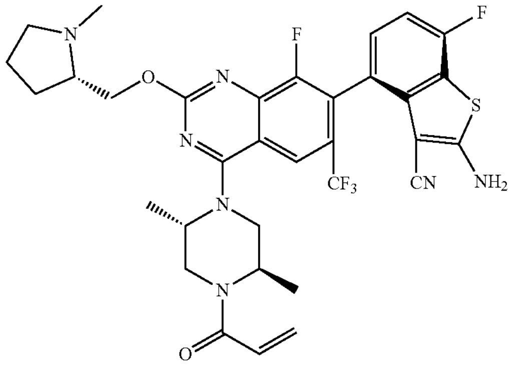 | LCMS m/z [M + 1]: 686.1 $^1$HNMR (400 MHz, $CD_3OD$) δ 8.13 (s, 1H), 7.19-7.25 (m, 1H), 6.98-7.04 (m, 1H), 6.76-6.87 (m, 1H), 6.24-6.32 (m, 1H), 5.77-5.84 (m, 1H), 4.90-4.96 (m, 1H), 4.46-4.53 (m, 2H), 4.14-4.40 (m, 2H), 3.88-4.06 (m, 2H), 3.48-3.65 (m, 1H), 3.09-3.16 (m, 1H), 2.81-2.90 (m, 2H), 2.55 (s, 3H), 2.35-2.45 (m, 1H), 2.09-2.18 (m, 1H), 1.73-1.91 (m, 3H), 1.475 (t, 3H), 1.22-1.32 (m, 3H). |
| 458a | 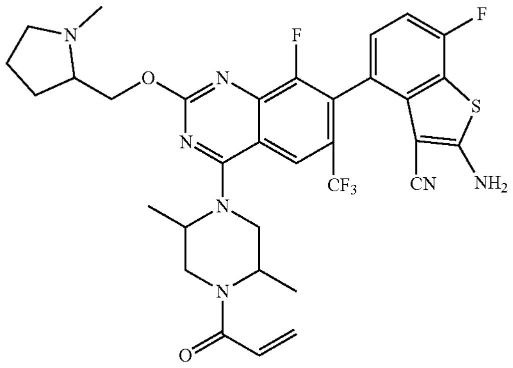 [SMILES: C=CC(=O)N1CC(C)N(c2nc(OCC3CCCN3C)nc3c(F)c(-c4ccc(F)c5sc(N)c(C#N)c45)c(C(F)(F)F)cc23)CC1C] | |

TABLE 5-continued
| Selected compounds of the present disclosure. | | |
|---|---|---|
| Compound No. | Structure | Analytical data |
| 459 | 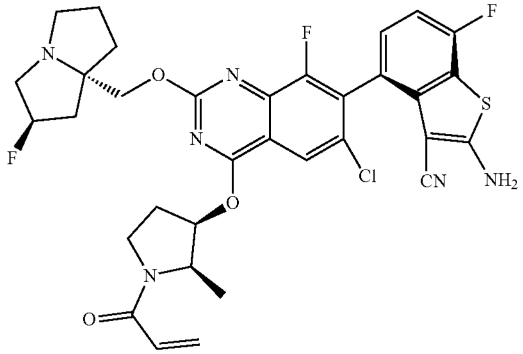 | |
| 459a | 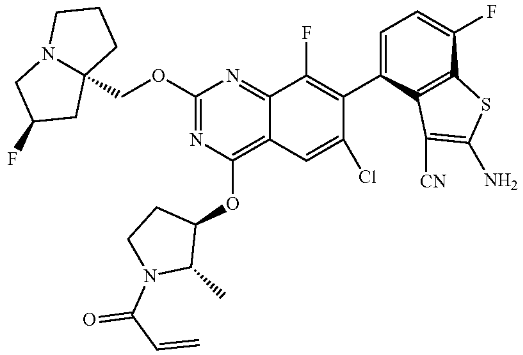 | |
| 460 | 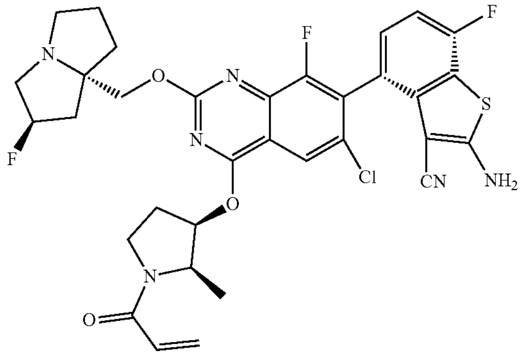 | |
| 461 | 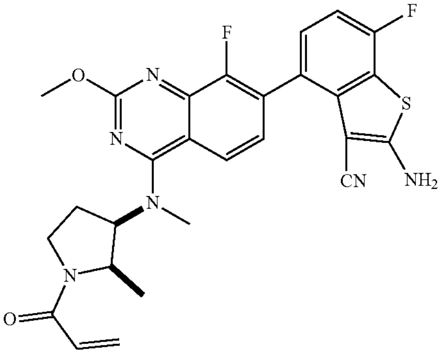 | LCMS m/z [M + 1]: 535.1 $^1$HNMR (400 MHz, $CD_3S(O)CD_3$) δ 8.05 (s, 2H), 7.99 (s, 1H), 7.27 (s, 2H), 7.11-7.17 (m, 1H), 6.58-6.64 (m, 1H), 6.16-6.22 (m, 1H), 5.70 (d, J = 9.24 Hz, 1H), 4.60-4.80 (m, 2H), 3.94 (d, J = 3.16 Hz, 3H), 3.46-3.84 (m, 5H), 2.33-2.43 (m, 2H), 0.99-1.02 (m, 3H). |

TABLE 5-continued
| Selected compounds of the present disclosure. | | |
|---|---|---|
| Compound No. | Structure | Analytical data |
| 461a | 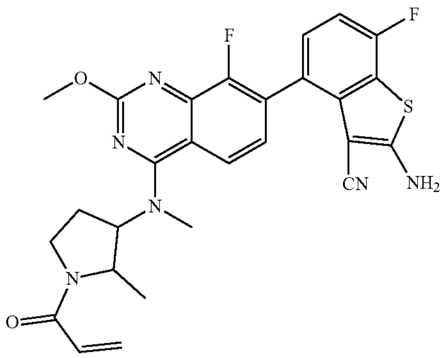 [SMILES: C=CC(=O)N1CCC(N(C)c2nc(OC)nc3c(F)c(-c4ccc(F)c5sc(N)c(C#N)c45)ccc23)C1C] | |
| 462 | 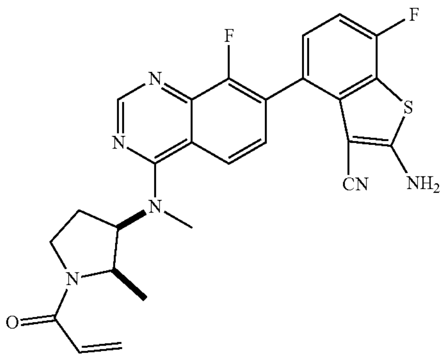 | LCMS m/z [M + 1]: 505.0 $^1$HNMR (400 MHz, $CD_3OD$) δ 8.78 (s, 1H), 8.33 (d, J = 8.78 Hz, 1H), 7.72-7.77 (m, 1H), 7.33-7.36 (m, 1H), 7.08 (t, J = 8.94 Hz, 1H), 6.62-6.68 (m, 1H), 6.30-6.38 (m, 1H), 5.77-5.80 (m, 1H), 5.19-5.27 (m, 1H), 4.98-5.02 (m, 1H), 3.81-4.03 (m, 4H), 3.53-3.73 (m, 1H), 2.70-2.80 (m, 1H), 2.46-2.52 (m, 1H), 1.18-1.20 (m, 3H). |
| 462a | 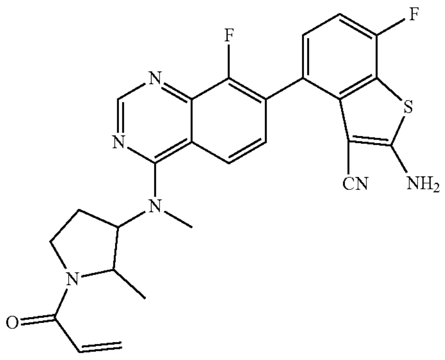 [SMILES: C=CC(=O)N1CCC(N(C)c2ncnc3c(F)c(-c4ccc(F)c5sc(N)c(C#N)c45)ccc23)C1C] | |
| 463 | 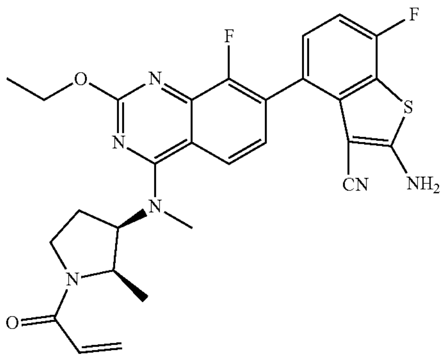 [SMILES: C=CC(=O)N1CC[C@@H](N(C)c2nc(OCC)nc3c(F)c(-c4ccc(F)c5sc(N)c(C#N)c45)ccc23)[C@H]1C] | LCMS m/z [M + 1]: 549.0 $^1$HNMR (400 MHz, $CD_3OD$) δ 7.99 (d, J = 8.82 Hz, 1H), 7.23-7.28 (m, 2H), 7.01 (t, J = 8.86 Hz, 1H), 6.61-6.68 (m, 1H), 6.28-6.35 (m, 1H), 5.76 (d, J = 10.08 Hz, 1H), 4.97-5.06 (m, 1H), 4.73-4.77 (m, 1H), 4.47-4.51 (m, 2H), 3.54-3.96 (m, 5H), 2.41-2.70 (m, 2H), 1.40-1.44 (m, 3H), 1.07-1.15 (m, 3H). |

TABLE 5-continued
| Compound No. | Structure | Analytical data |
|---|---|---|
| 463a | 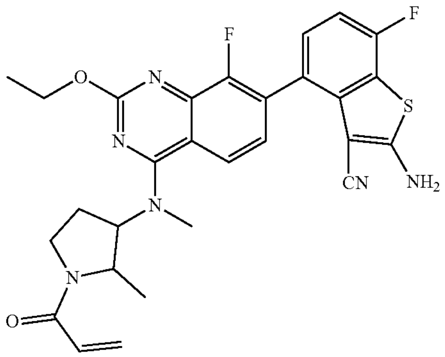 [SMILES: C=CC(=O)N1CCC(N(C)c2nc(OCC)nc3c(F)c(-c4ccc(F)c5sc(N)c(C#N)c45)ccc23)C1C] | |
| 464 | 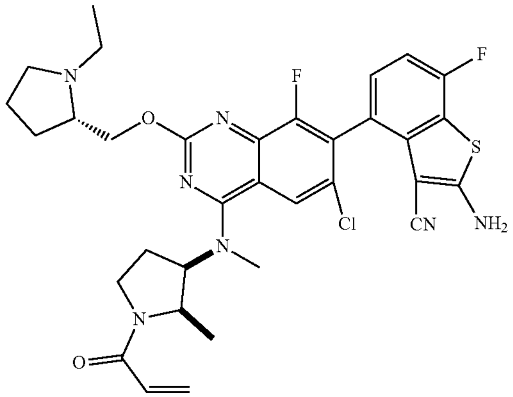 | LCMS m/z [M + 1]: 666.0 $^1$HNMR (400 MHz, $CD_3OD$) δ 8.17 (s, 1H), 7.20-7.27 (m, 1H), 7.05 (t, J = 8.9 Hz, 1H), 6.60-6.70 (m, 1H), 6.33 (t, J = 17.6 Hz, 1H), 5.79 (d, J = 10.5 Hz, 1H), 4.88-5.10 (m, 2H), 4.72-4.81 (m, 1H), 4.57-4.68 (m, 1H), 3.78-4.05 (m, 2H), 3.54-3.79 (m, 6H), 3.18-3.28 (m, 2H), 2.58-2.75 (m, 1H), 2.32-2.52 (m, 2H), 1.99-2.24 (m, 3H), 1.31-1.43 (m, 3H), 1.04-1.19 (m, 3H). |
| 464a | 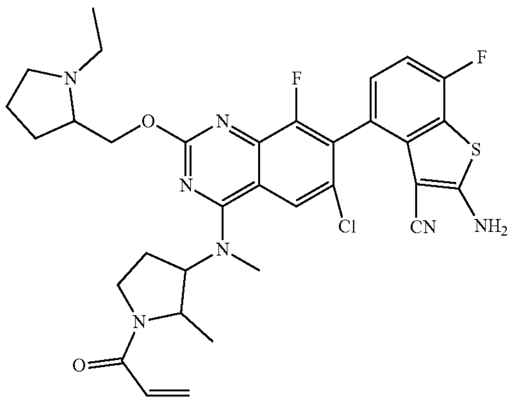 [SMILES: C=CC(=O)N1CCC(N(C)c2nc(OCC3CCCN3CC)nc3c(F)c(-c4ccc(F)c5sc(N)c(C#N)c45)c(Cl)cc23)C1C] | |
Selected compounds of the present disclosure.

TABLE 5-continued
| Compound No. | Structure | Analytical data |
| --- | --- | --- |
| 465 | 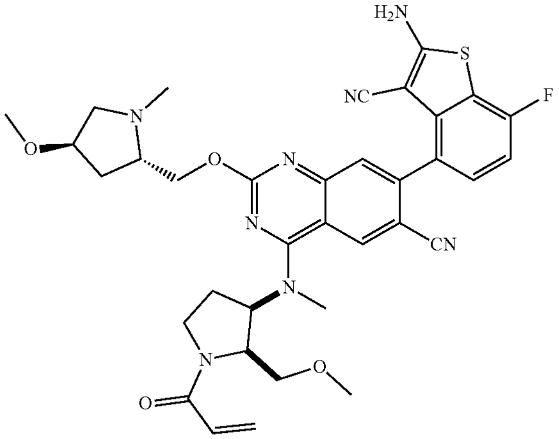 | LCMS m/z [M + 1]: 685.2 $^1$HNMR (400 MHz, $CD_3OD$) δ 8.67 (s, 1H), 7.60-7.59 (m, 1H), 7.33-7.27 (m, 1H), 7.06-7.02 (m, 1H), 6.79-6.65 (m, 1H), 6.36-6.30 (m, 1H), 5.81-5.76 (m, 1H), 5.01-4.93 (m, 2H), 4.58-4.37 (m, 2H), 3.96-3.39 (m, 8H), 3.26-3.07 (m, 7H), 2.85-2.80 (m, 1H), 2.69-2.37 (m, 5H), 2.17-1.75 (m, 3H), 1.31-1.24 (m, 1H). |
| 465a | 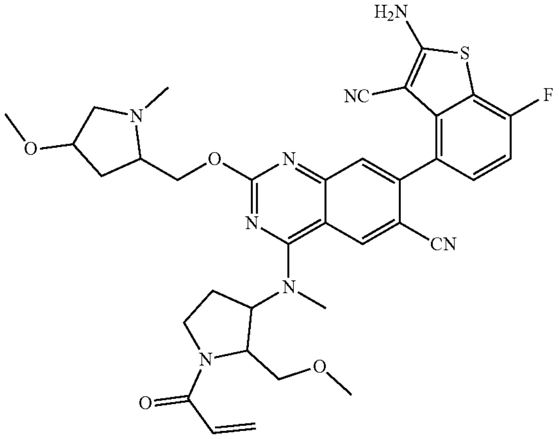 [SMILES: C=CC(=O)N1CCC(N(C)c2nc(OCC3CC(OC)CN3C)nc3cc(-c4ccc(F)c5sc(N)c(C#N)c45)c(C#N)cc23)C1COC] | |
| 466 | 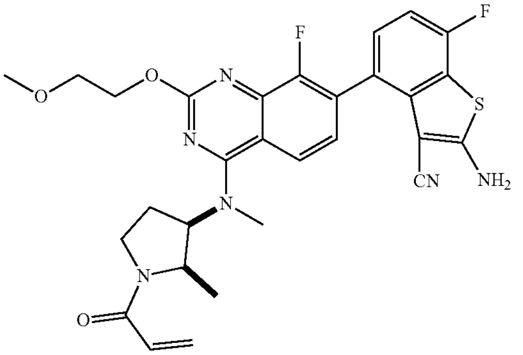 | LCMS m/z [M + 1]: 579.0 $^1$HNMR (400 MHz, $CD_3OD$) δ 8.25 (d, J = 8.78 Hz, 1H), 7.52-7.55 (m, 1H), 7.29-7.33 (m, 1H), 7.06 (t, J = 8.78 Hz, 1H), 6.62-6.69 (m, 1H), 6.30-6.37 (m, 1H), 5.78-5.80 (m, 1H), 5.00-5.15 (m, 2H), 4.67-4.77 (m, 1H), 3.46-4.02 (m, 8H), 3.41 (s, 3H), 2.68-2.80 (m, 1H), 2.47-2.50 (m, 1H), 1.18-1.22 (m, 3H). |
Selected compounds of the present disclosure.

TABLE 5-continued
| Selected compounds of the present disclosure. | | |
|---|---|---|
| Compound No. | Structure | Analytical data |
| 466a | 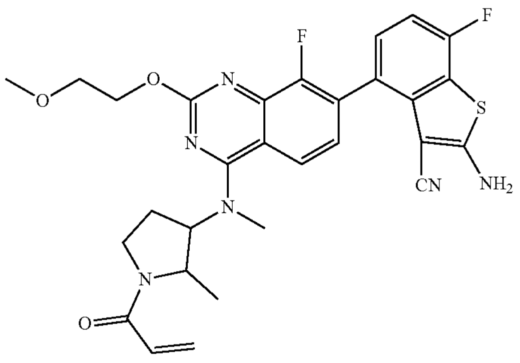 [SMILES: C=CC(=O)N1CCC(N(C)c2nc(OCCOC)nc3c(F)c(-c4ccc(F)c5sc(N)c(C#N)c45)ccc23)C1C] | |
| 467 | 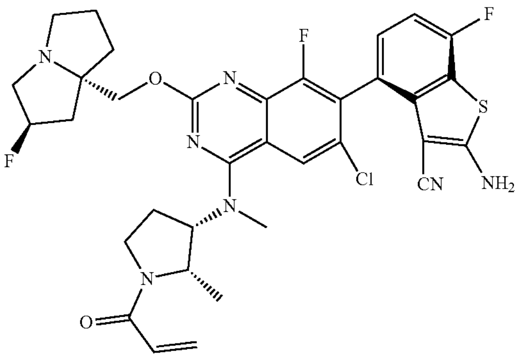 | LCMS m/z [M + 1]: 696.3 $^1$HNMR (400 MHz, $CD_3OD$) δ 8.08 (d, J = 3.58 Hz, 1H), 7.19-7.23 (m, 1H), 7.03 (t, J = 8.40 Hz, 1H), 6.61-6.71 (m, 1H), 6.27-6.36 (m, 1H), 5.76 (d, J = 10.32 Hz, 1H), 5.30 (d, J = 54.20 Hz, 1H), 4.98-5.07 (m, 1H), 4.73-4.82 (m, 1H), 4.17-4.30 (m, 2H), 3.55-3.97 (m, 5H), 3.13-3.26 (m, 3H), 2.97-3.03 (m, 1H), 1.84-2.66 (m, 8H), 1.06-1.16 (m, 3H). |
| 468 | 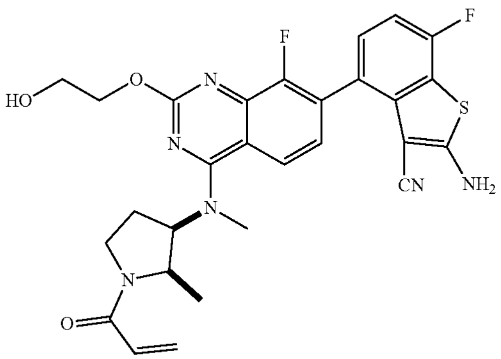 | LCMS m/z [M + 1]: 565.0 $^1$HNMR (400 MHz, $CD_3OD$) δ 8.00 (d, J = 5.40 Hz, 1H), 7.23-7.28 (m, 2H), 7.01 (t, J = 9.02 Hz, 1H), 6.61-6.72 (m, 1H), 6.28-6.35 (m, 1H), 5.75-5.78 m, 1H),5.00-5.05 (m, 1H), 4.73-4.81 (m, 1H), 4.46-4.55 (m, 2H), 3.55-3.96 (m, 7H), 2.41-2.64 (m, 2H), 1.06-1.13 (m, 3H). |
| 468a | 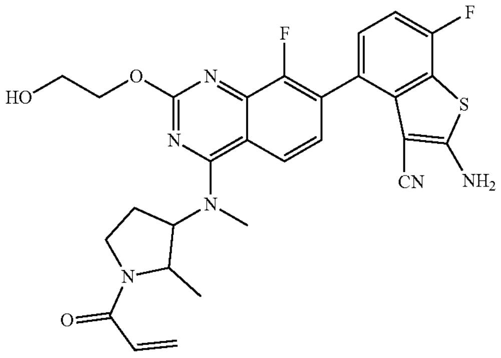 [SMILES: C=CC(=O)N1CCC(N(C)c2nc(OCCO)nc3c(F)c(-c4ccc(F)c5sc(N)c(C#N)c45)ccc23)C1C] | |

TABLE 5-continued
Selected compounds of the present disclosure.
| Compound No. | Structure | Analytical data |
| --- | --- | --- |
| 469 | 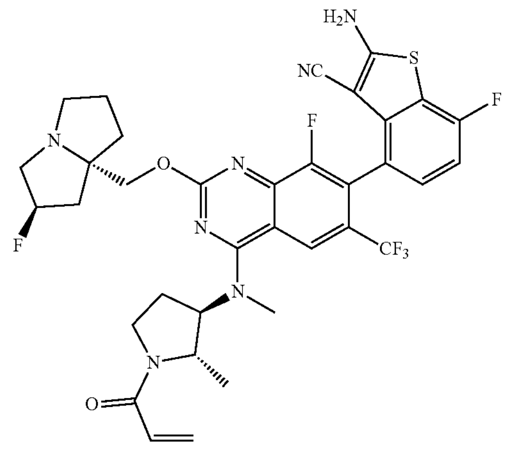 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)c(C(F)(F)F)cc23)[C@@H]1C] | LCMS m/z [M + 1]: 730.1<br>$^1$HNMR (400 MHz, $CD_3OD$) δ 8.29 (s, 1H), 7.21 (t, 1H), 7.00 (t, 1H), 6.75-6.62 (m, 1H), 6.31 (t, 1H), 5.77 (d, 1H), 5.37 (s, 0.5H), 5.24 (s, 0.5H), 5.14-5.01 (m, 1H), 4.50-4.44 (m, 1H), 4.34-4.24 (m, 2H), 4.10-4.00 (m, 1H), 3.83-3.59 (m, 1H), 3.42 (t, 3H), 3.26-3.21 (m, 2H), 3.06-3.00 (m, 1H), 2.64-2.53 (m, 1H), 2.38-1.88 (m, 8H), 1.48-1.41 (m, 3H). |
| 469a | 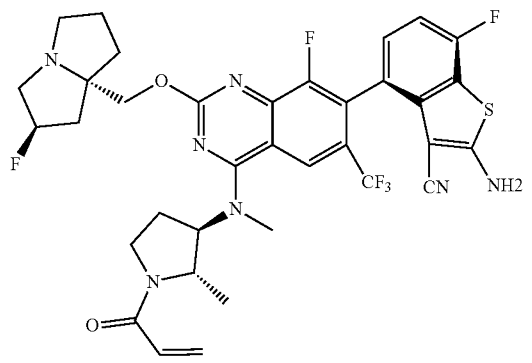 | |
| 469b | 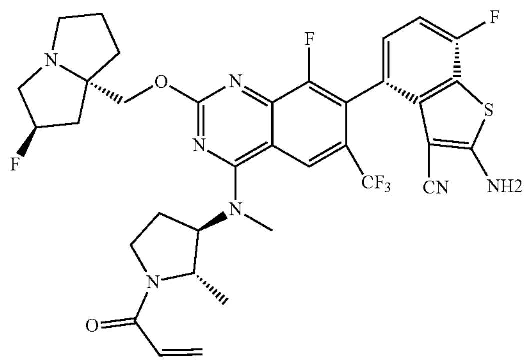 | |

TABLE 5-continued
| Selected compounds of the present disclosure. | | |
|---|---|---|
| Compound No. | Structure | Analytical data |
| 470 | 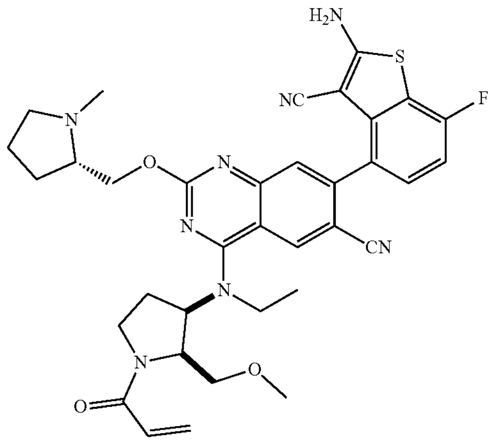 | LCMS m/z [M + 1]: 669.1 $^1$HNMR (400 MHz, $CD_3OD$) δ 8.59 (d, J = 4.4 Hz, 1H), 7.67 (d, J = 6.4 Hz, 1H), 7.29 (d, J = 4.8 Hz, 1H), 6.32 (d, J = 16.8 Hz, 1H), 5.82-5.73 (m, 1H), 4.98-4.94 (m, 2H), 4.71-4.51 (m, 3H), 4.12-3.91 (m, 3H), 3.71-3.63 (m, 2H), 3.52-3.38 (m, 3H), 3.26-3.22 (m, 1H), 3.16-3.14 (m, 3H), 2.97 (s, 1H), 2.88 (s, 2H), 2.79-2.69 (m, 2H), 2.47-2.25 (m, 2H), 2.03-1.94 (m, 3H), 1.46-1.28 (m, 3H). |
| 470a | 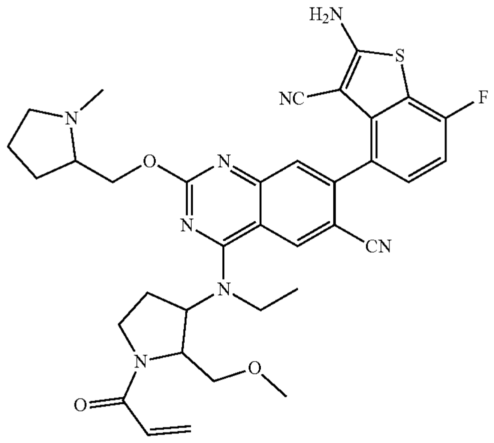 [SMILES: C=CC(=O)N1CCC(N(CC)c2nc(OCC3CCCN3C)nc3cc(-c4ccc(F)c5sc(N)c(C#N)c45)c(C#N)cc23)C1COC] | |
| 471 | 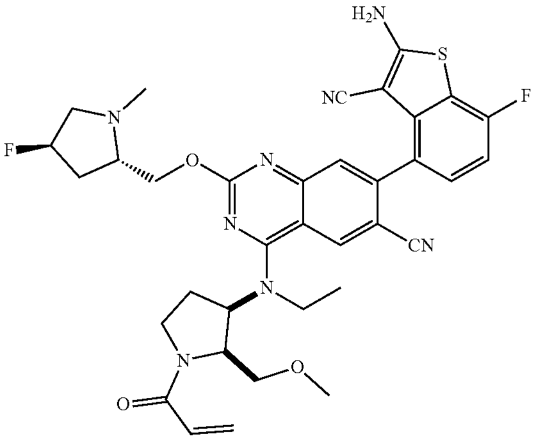 | LCMS m/z [M + 1]: 687.1 $^1$HNMR (400 MHz, $CD_3OD$) δ 8.58 (d, J = 4.4 Hz, 1H), 7.67-7.64 (m, 1H), 7.32-7.27 (m, 1H), 7.07-7.02 (m, 1H), 6.76-6.64 (m, 1H), 6.34-6.29 (m, 1H), 5.81-5.73 (m, 1H), 5.30 (d, J = 17.6 Hz, 0.5H), 5.16 (d, J = 18.4 Hz, 0.5H), 4.97-4.94 (m, 2H), 4.62-4.49 (m, 2H), 4.12-3.90 (m, 3H), 3.76-3.34 (m, 5H), 3.24-3.13 (m, 4H), 2.98-2.30 (m, 2H), 2.70-2.63 (m, 3H), 2.45-2.34 (m, 2H), 2.14-2.03 (m, 1H), 1.45-1.28 (m, 3H). |

TABLE 5-continued
| Selected compounds of the present disclosure. | | |
|---|---|---|
| Compound No. | Structure | Analytical data |
| 471a | 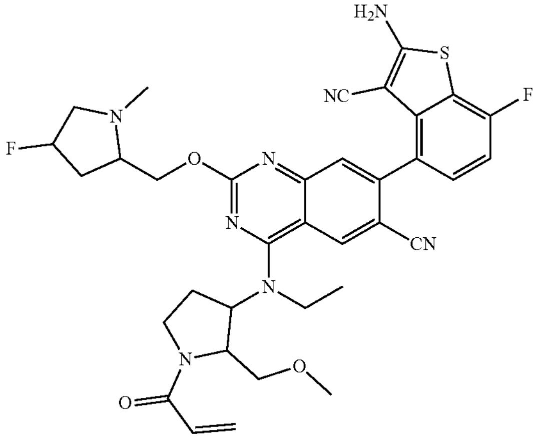 [SMILES: C=CC(=O)N1CCC(N(CC)c2nc(OCC3CC(F)CN3C)nc3cc(-c4ccc(F)c5sc(N)c(C#N)c45)c(C#N)cc23)C1COC] | |
| 472 | 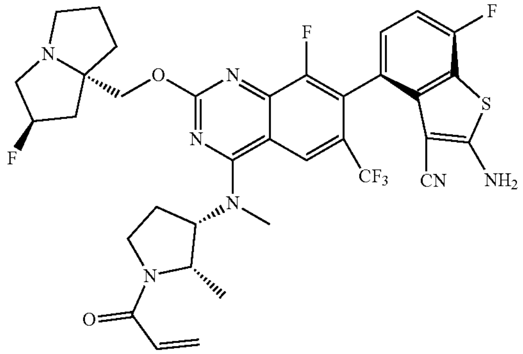 | LCMS m/z [M + 1]: 730.0 $^1$HNMR (400 MHz, $CD_3OD$) δ 8.35 (s, 1H), 7.18-7.26 (m, 1H), 7.01 (t, J = 9.0 Hz, 1H), 6.61-6.74 (m, 1H), 6.26-6.39 (m, 1H), 5.77 (d, J = 10.7 Hz, 1H), 5.31 (d, J = 54.6 Hz, 1H), 4.98-5.10 (m, 1H), 4.87-4.94 (m, 1H), 4.21-4.37 (m, 2H), 3.55-3.97 (m, 5H), 3.14-3.29 (m, 3H), 2.96-3.06 (m, 1H), 2.57-2.75 (m, 1H), 1.87-2.48 (m, 7H), 1.07-1.18 (m, 3H). |
| 473 | 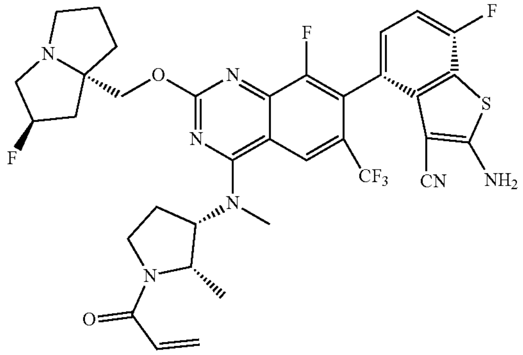 | LCMS m/z [M + 1]: 730.0 $^1$HNMR (400 MHz, $CD_3OD$) δ 8.35 (s, 1H), 7.20-7.27 (m, 1H), 6.98-7.06 (m, 1H), 6.59-6.73 (m, 1H), 6.26-6.40 (m, 1H), 5.73-5.81 (m, 1H), 5.32 (d, J = 53.2 Hz, 1H), 5.01-5.12 (m, 1H), 4.87-4.94 (m, 1H), 4.19-4.36 (m, 3H), 3.54-4.01 (m, 5H), 3.19-3.28 (m, 3H), 2.98-3.10 (m, 1H), 1.93-2.67 (m, 8H), 1.06-1.18 (m, 3H). |
| 473a | 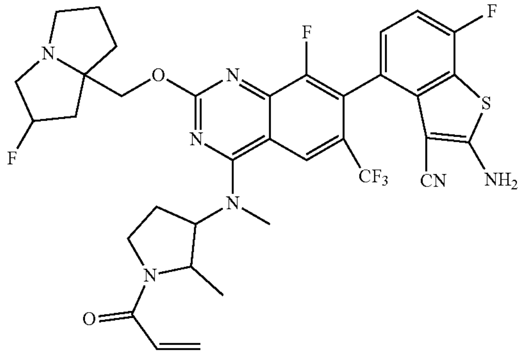 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1C] | |

TABLE 5-continued
Selected compounds of the present disclosure.
| Compound No. | Structure | Analytical data |
| --- | --- | --- |
| 474 | 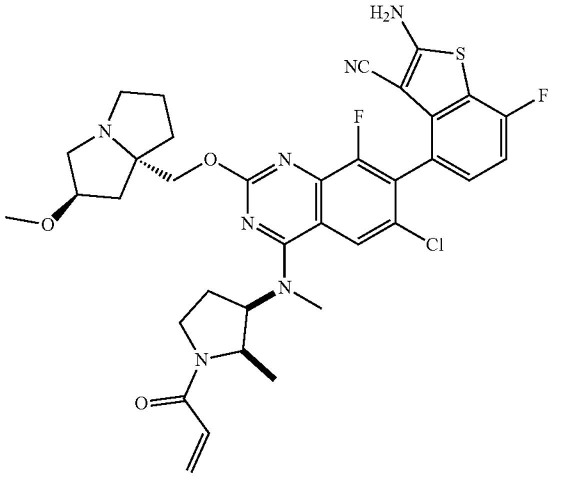 | LCMS m/z [M + 1]: 708.0<br>$^1$HNMR (400 MHz, $CD_3OD$) δ 8.18 (s, 1H), 7.23 (dd, J = 8.3, 5.1 Hz, 1H), 7.06 (t, J = 8.9 Hz, 1H), 6.60-6.73 (m, 1H), 6.34 (t, J = 18.4 Hz, 1H), 5.79 (d, J = 10.4 Hz, 1H), 4.96-5.11 (m, 1H), 4.75-4.83 (m, 1H), 4.54-4.73 (m, 2H), 4.23-4.31 (m, 1H), 3.47-4.00 (m, 9H), 3.39 (s, 3H), 2.58-2.77 (m, 1H), 2.38-2.52 (m, 3H), 2.24-2.35 (m, 3H), 2.02-2.17 (m, 1H), 1.06-1.20 (m, 3H). |
| 474a | 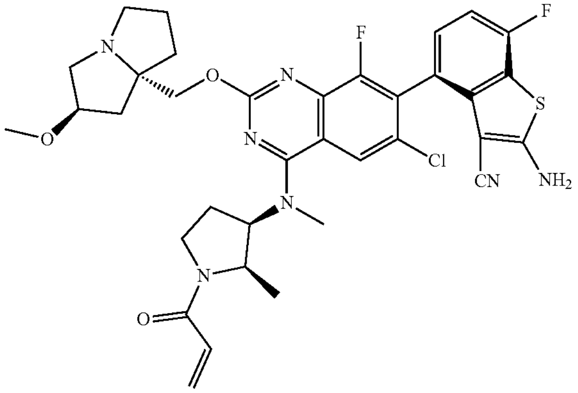 | |
| 474b | 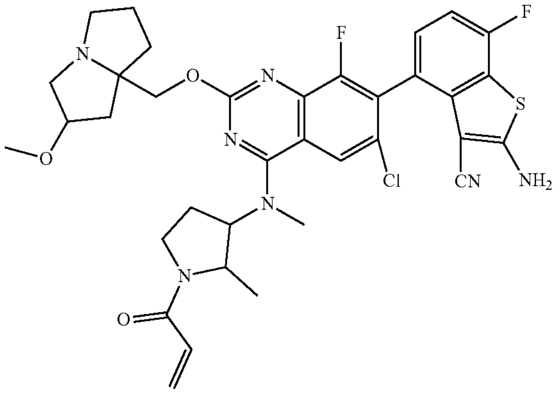 [SMILES: C=CC(=O)N1CCC(N(C)c2nc(OCC34CCCN3CC(OC)C4)nc3c(F)c(-c4ccc(F)c5sc(N)c(C#N)c45)c(Cl)cc23)C1C] | |

TABLE 5-continued
Selected compounds of the present disclosure.
| Compound No. | Structure | Analytical data |
|---|---|---|
| 475 | 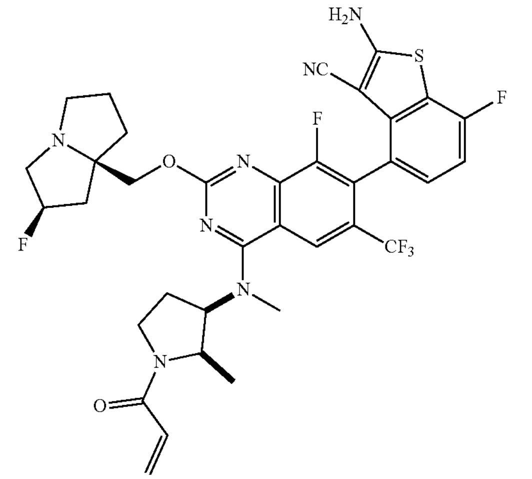 | LCMS m/z [M + 1]: 696.3 $^1$HNMR (400 MHz, $CD_3OD$) δ 8.18 (s, 1H), 7.21-7.27 (m, 1H), 7.06 (t, J = 8.9 Hz, 1H), 6.57-6.70 (m, 1H), 6.27-6.38 (m, 1H), 5.74-5.83 (m, 1H), 5.40-5.60 (m, 1H), 4.97-5.09 (m, 1H), 4.66-4.83 (m, 3H), 3.91-4.13 (m, 2H), 3.44-3.77 (m, 7H), 2.36-2.72 (m, 5H), 2.10-2.30 (m, 3H), 1.06-1.18 (m, 3H). |
| 475a | 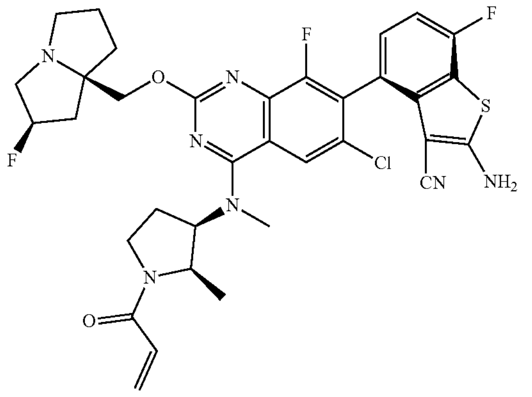 | |
| 475b | 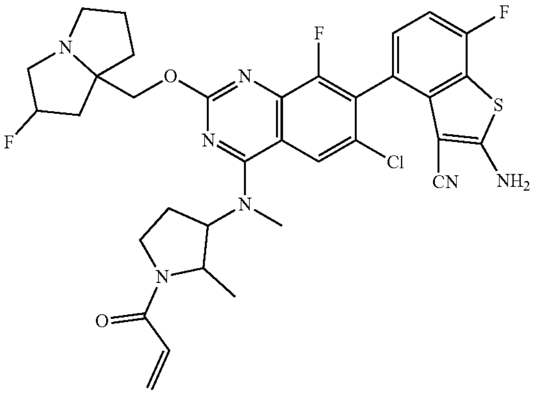 [SMILES: C=CC(=O)N1CCC(N(C)c2nc(OCC34CCCN3CC(F)C4)nc3c(F)c(-c4ccc(F)c5sc(N)c(C#N)c45)c(Cl)cc23)C1C] | |

TABLE 5-continued
| Selected compounds of the present disclosure. | | |
|---|---|---|
| Compound No. | Structure | Analytical data |
| 476 | 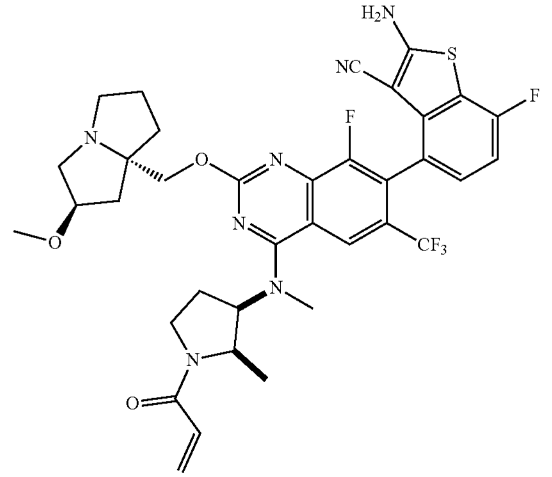 | LCMS m/z [M + 1]: 742.0 ¹HNMR (400 MHz, $CD_3OD$) δ 8.43 (s, 1H), 7.28-7.22 (m, 1H), 7.05 (t, J = 9.0 Hz, 1H), 6.63-6.73 (m, 1H), 6.30-6.43 (m, 1H), 5.80-5.85 (m, 1H), 5.00-5.15 (m, 1H), 4.72-4.55 (m, 3H), 4.28-4.33 (m, 1H), 3.97-4.03 (M, 1h), 3.84-3.51 (m, 8H), 3.41 (s, 3H), 2.66-2.78 (m, 1H), 2.25-2.55 (m, 6H), 2.00-2.20 (m, 1H), 1.12-1.23 (m, 3H). |
| 476a | 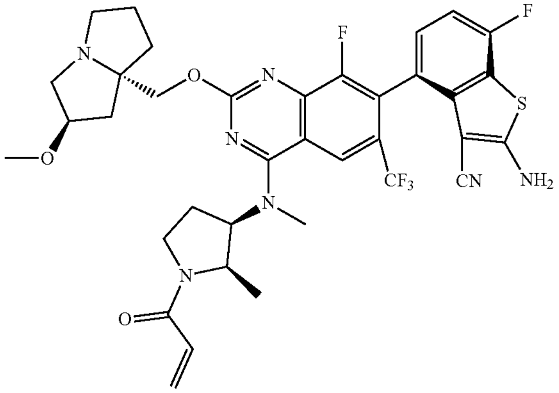 | |
| 476b | 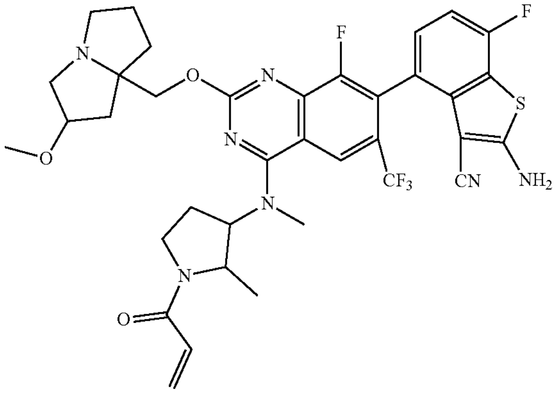 [SMILES: C=CC(=O)N1CCC(N(C)c2nc(OCC34CCCN3CC(OC)C4)nc3c(F)c(-c4ccc(F)c5sc(N)c(C#N)c45)c(C(F)(F)F)cc23)C1C] | |

TABLE 5-continued
| Compound No. | Structure | Analytical data |
|---|---|---|
| | Selected compounds of the present disclosure. | |
| 477 | 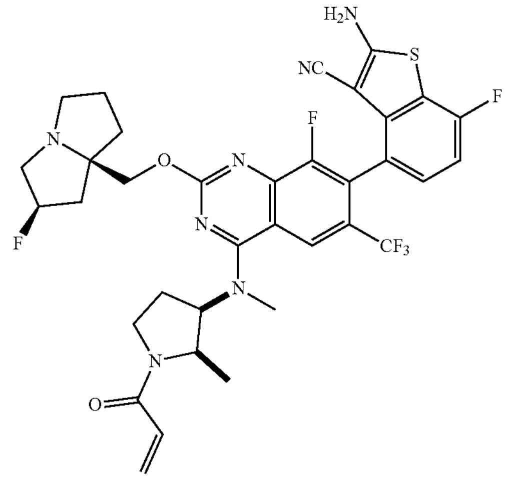 | LCMS m/z [M + 1]: 730.0<br>$^{1}$HNMR (400 MHz, $CD_3OD$) δ 8.41 (s, 1H), 7.20-7.25 (m, 1H), 7.03 (t, J = 9.0 Hz, 1H), 6.58-6.75 (m, 1H), 6.25-6.40 (m, 1H), 5.75-5.82 (m, 1H), 5.48 (d, J = 51.2 Hz, 1H), 5.00-5.11 (m, 1H), 4.76-4.65 (m, 2H), 3.95-4.07 (m, 2H), 3.80-3.44 (m, 8H), 2.60-2.72 (m, 2H), 2.42-2.51 (m, 3H), 2.22-2.33 (m, 2H), 2.12-2.18(m, 1H), 1.10-1.20 (m, 3H). |
| 477a | 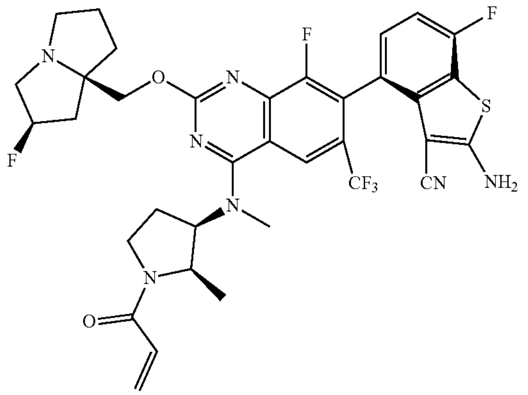 | |
| 477b | 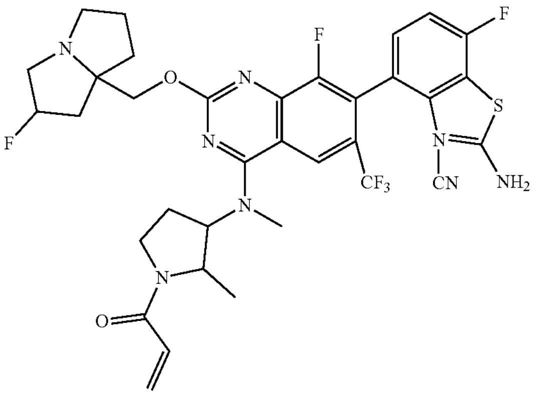 | |

TABLE 5-continued
| Selected compounds of the present disclosure. | | |
|---|---|---|
| Compound No. | Structure | Analytical data |
| 478 | 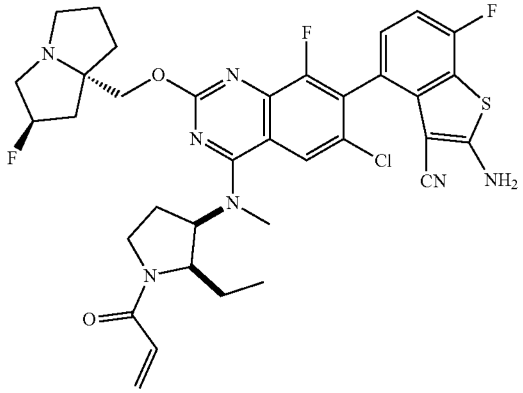 | |
| 478a | 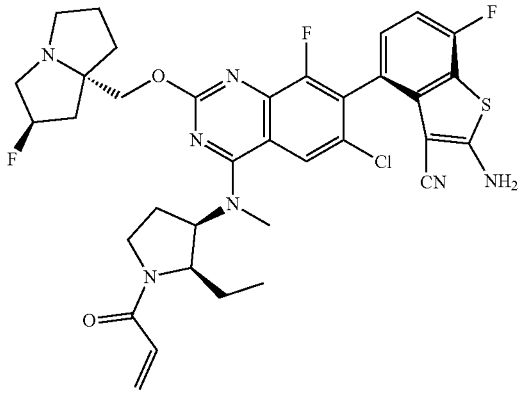 | |
| 478b | 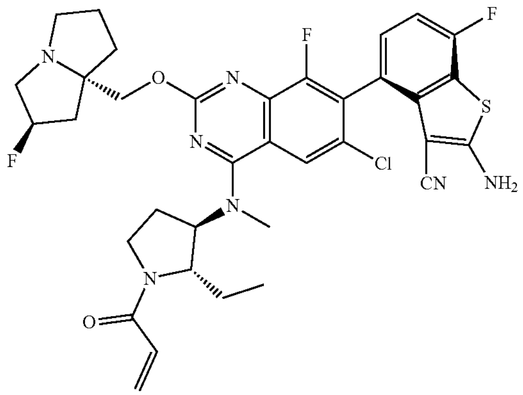 | |

TABLE 5-continued
| Selected compounds of the present disclosure. | | |
|---|---|---|
| Compound No. | Structure | Analytical data |
| 478c | 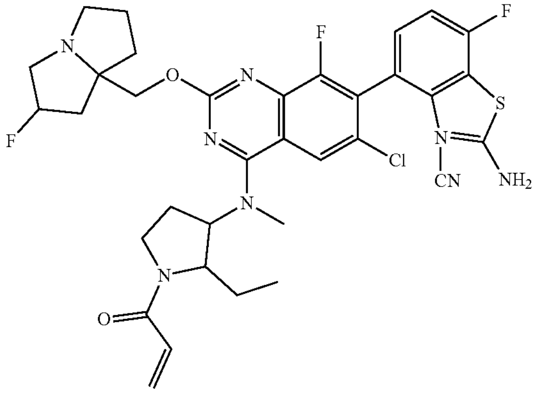 | |
| 479 | 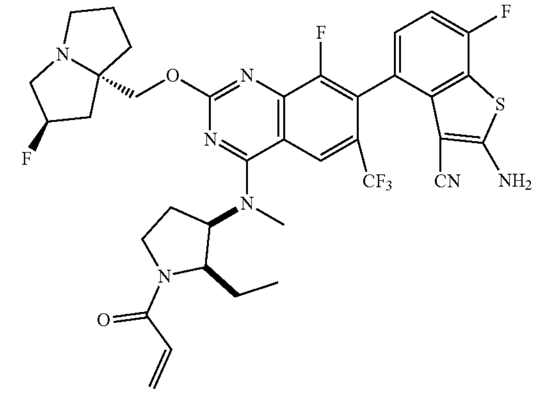 | |
| 479a | 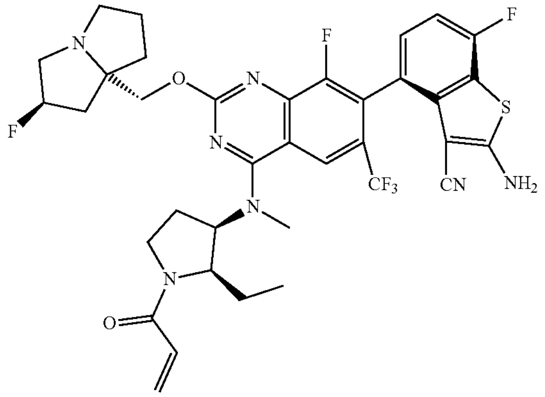 | |

TABLE 5-continued
| Selected compounds of the present disclosure. | | |
|---|---|---|
| Compound No. | Structure | Analytical data |
| 479b | 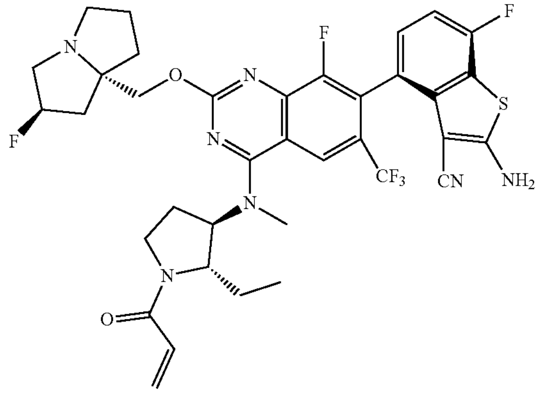 | |
| 479c | 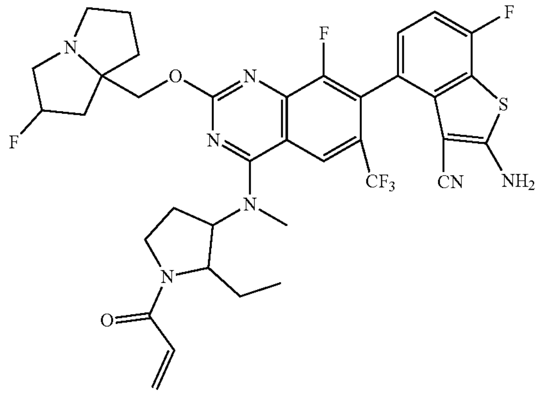 [SMILES: C=CC(=O)N1CCC(N(C)c2nc(OCC34CCCN3CC(F)C4)nc3c(F)c(-c4ccc(F)c5sc(N)c(C#N)c45)c(C(F)(F)F)cc23)C1CC] | |
| 480 | 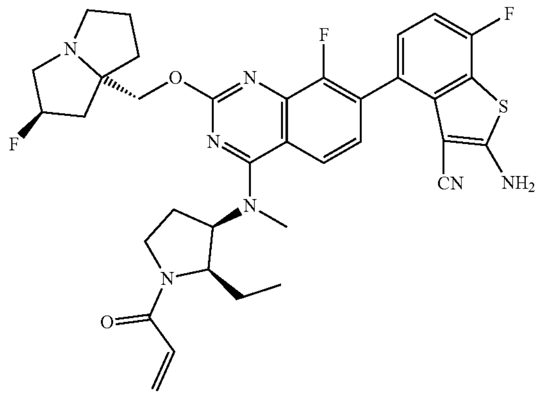 | |

TABLE 5-continued
| Selected compounds of the present disclosure. | | |
|---|---|---|
| Compound No. | Structure | Analytical data |
| 480a | 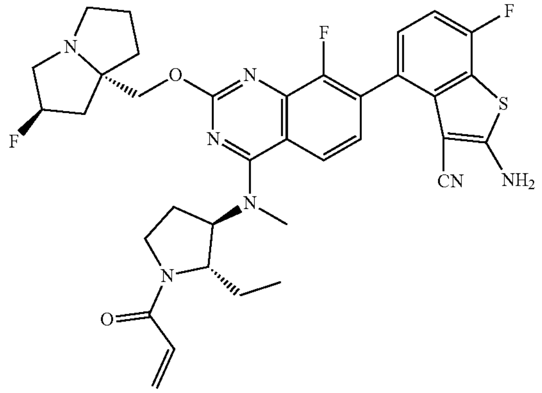 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)ccc23)[C@@H]1CC] | |
| 480b | 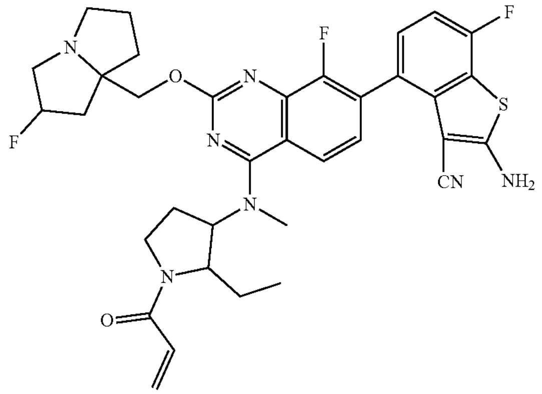 [SMILES: C=CC(=O)N1CCC(N(C)c2nc(OCC34CCCN3CC(F)C4)nc3c(F)c(-c4ccc(F)c5sc(N)c(C#N)c45)ccc23)C1CC] | |
| 481 | 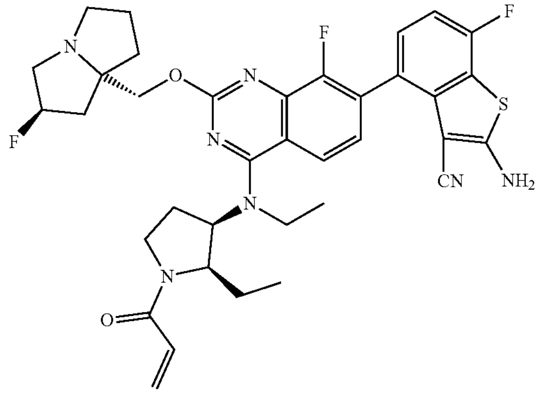 | |

TABLE 5-continued
| Selected compounds of the present disclosure. | | |
|---|---|---|
| Compound No. | Structure | Analytical data |
| 481a | 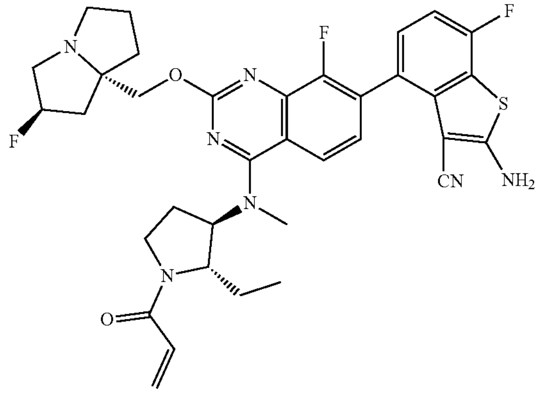 [SMILES: C=CC(=O)N1CC[C@@H](N(C)c2nc(OC[C@@]34CCCN3C[C@H](F)C4)nc3c(F)c(-c4ccc(F)c5sc(N)c(C#N)c45)ccc23)[C@@H]1CC] | |
| 481b | 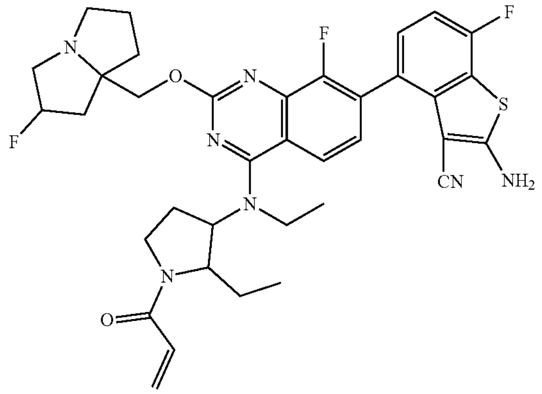 [SMILES: C=CC(=O)N1CCC(N(CC)c2nc(OCC34CCCN3CC(F)C4)nc3c(F)c(-c4ccc(F)c5sc(N)c(C#N)c45)ccc23)C1CC] | |
| 482 | 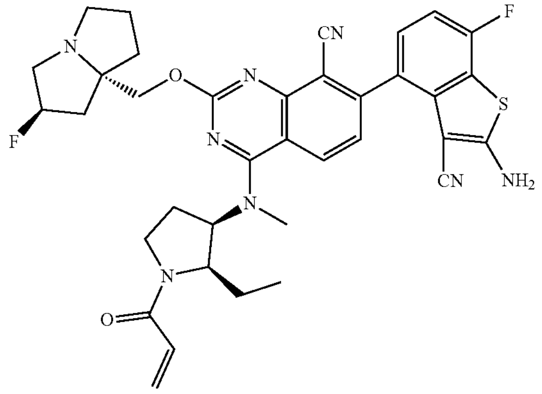 [SMILES: C=CC(=O)N1CC[C@@H](N(C)c2nc(OC[C@@]34CCCN3C[C@H](F)C4)nc3c(C#N)c(-c4ccc(F)c5sc(N)c(C#N)c45)ccc23)[C@H]1CC] | |

TABLE 5-continued
| Selected compounds of the present disclosure. | | |
|---|---|---|
| Compound No. | Structure | Analytical data |
| 482a | 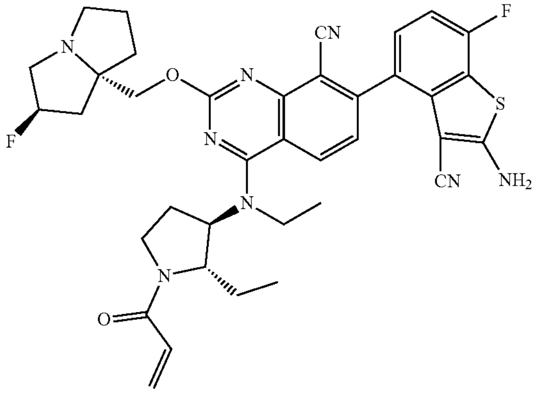 [SMILES: C=CC(=O)N1CC[C@@H](N(CC)c2nc(OC[C@@]34CCCN3C[C@H](F)C4)nc3c(C#N)c(-c4ccc(F)c5sc(N)c(C#N)c45)ccc23)[C@@H]1CC] | |
| 482b | 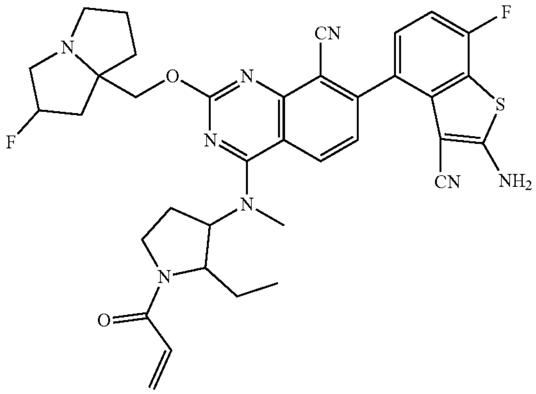 [SMILES: C=CC(=O)N1CCC(N(C)c2nc(OCC34CCCN3CC(F)C4)nc3c(C#N)c(-c4ccc(F)c5sc(N)c(C#N)c45)ccc23)C1CC] | |
| 483 | 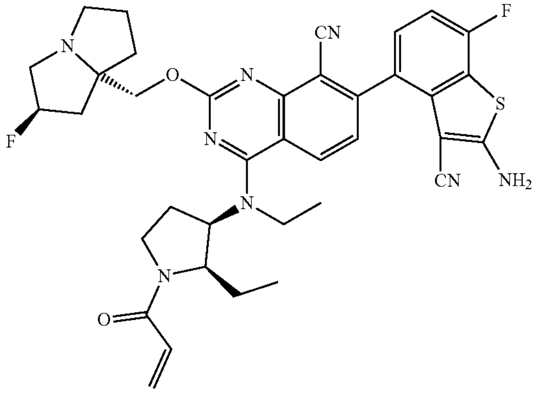 | |

TABLE 5-continued
| Selected compounds of the present disclosure. | | |
|---|---|---|
| Compound No. | Structure | Analytical data |
| 483a | 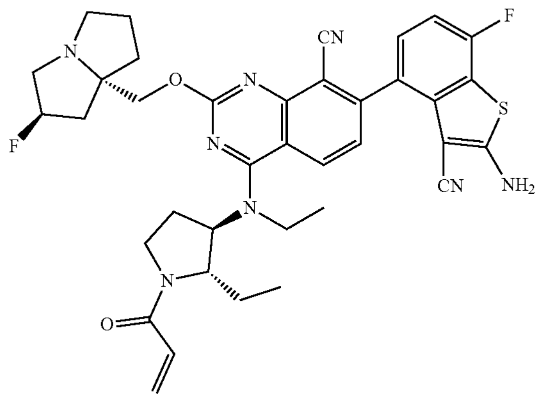 [SMILES: C=CC(=O)N1CC[C@@H](N(CC)c2nc(OC[C@@]34CCCN3C[C@H](F)C4)nc3c(C#N)c(-c4ccc(F)c5sc(N)c(C#N)c45)ccc23)[C@@H]1CC] | |
| 483b | 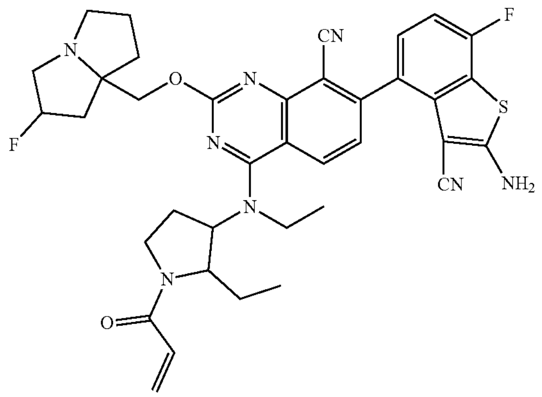 [SMILES: C=CC(=O)N1CCC(N(CC)c2nc(OCC34CCCN3CC(F)C4)nc3c(C#N)c(-c4ccc(F)c5sc(N)c(C#N)c45)ccc23)C1CC] | |
| 484 | 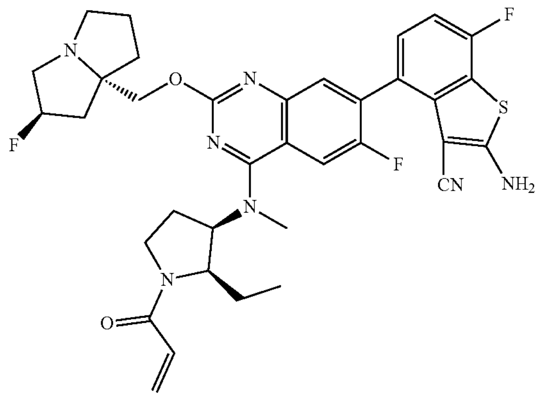 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@H]1CC] | |

TABLE 5-continued
| Selected compounds of the present disclosure. | | |
|---|---|---|
| Compound No. | Structure | Analytical data |
| 484a | 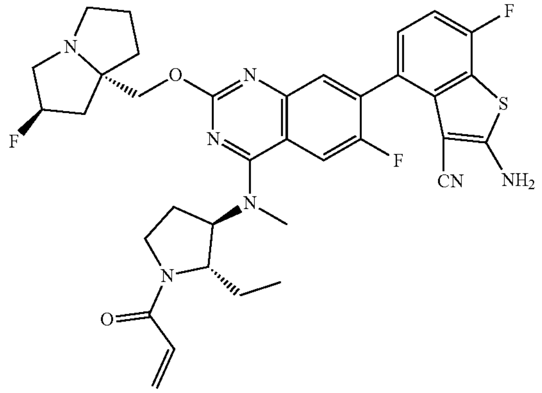 [SMILES: C=CC(=O)N1CC[C@@H](N(C)c2nc(OC[C@@]34CCCN3C[C@H](F)C4)nc3cc(-c4ccc(F)c5sc(N)c(C#N)c45)c(F)cc23)[C@@H]1CC] | |
| 484b | 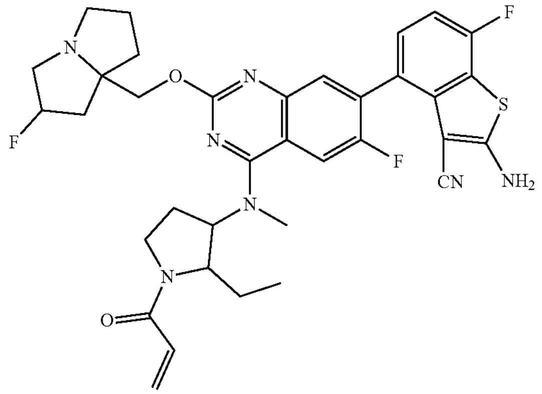 [SMILES: C=CC(=O)N1CCC(N(C)c2nc(OCC34CCCN3CC(F)C4)nc3cc(-c4ccc(F)c5sc(N)c(C#N)c45)c(F)cc23)C1CC] | |
| 485 | 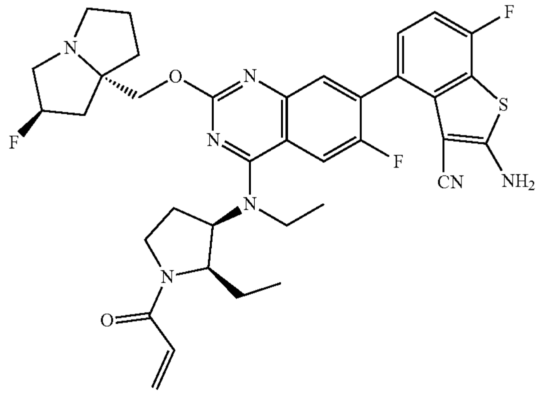 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@H]1CC] | |

TABLE 5-continued
| Selected compounds of the present disclosure. | | |
|---|---|---|
| Compound No. | Structure | Analytical data |
| 485a | 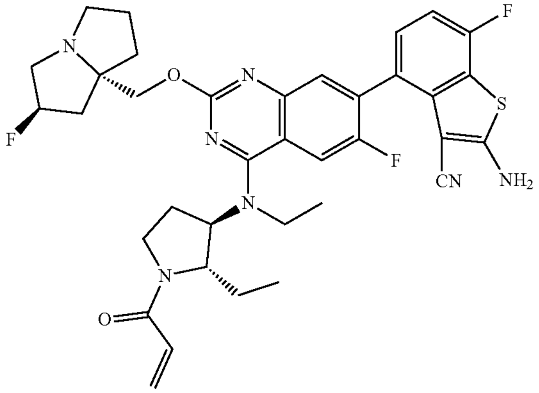 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(F)cc23)[C@@H]1CC] | |
| 485b | 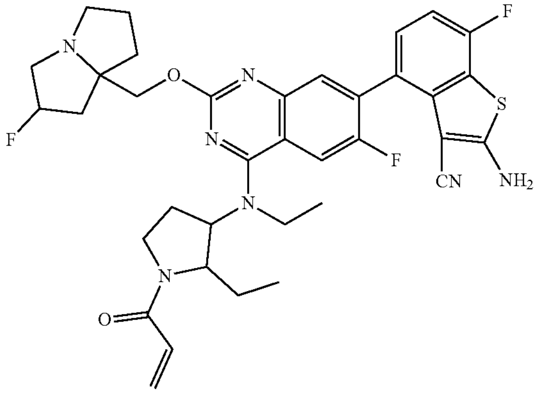 | |
| 486 | 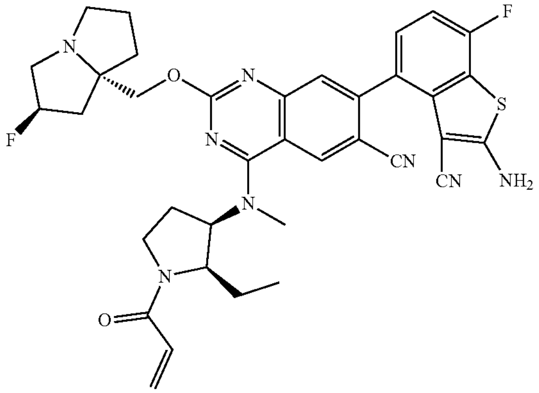 | |

TABLE 5-continued
| Selected compounds of the present disclosure. | | |
|---|---|---|
| Compound No. | Structure | Analytical data |
| 486a | 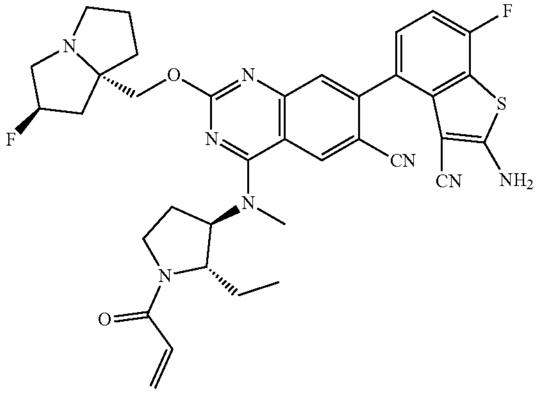 | |
| 486b | 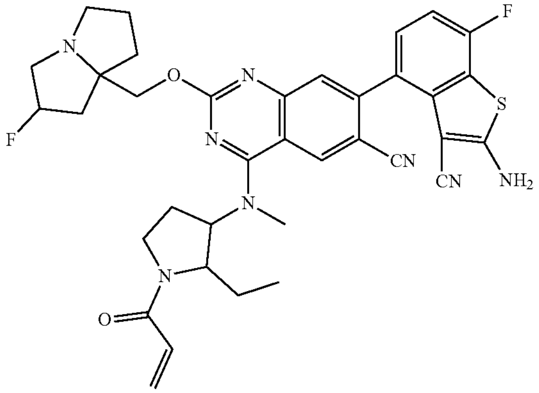 | |
| 487 | 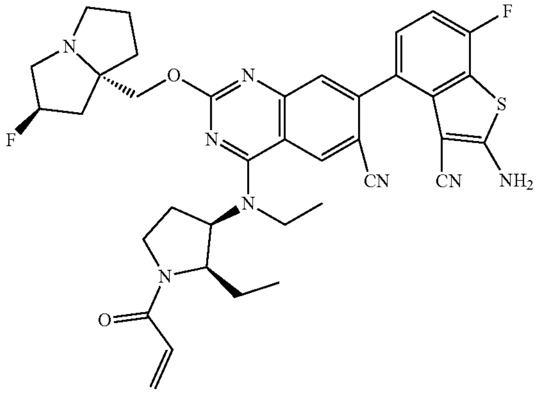 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(C#N)cc23)[C@H]1CC] | |

TABLE 5-continued
Selected compounds of the present disclosure.
| Compound No. | Structure | Analytical data |
|---|---|---|
| 487a | 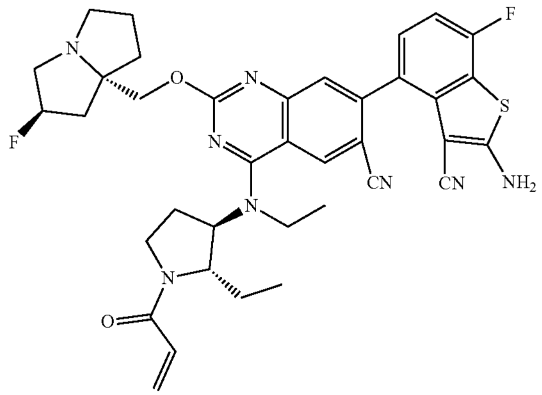 [SMILES: C=CC(=O)N1CC[C@@H](N(CC)c2nc(OC[C@@]34CCCN3C[C@H](F)C4)nc3cc(-c4ccc(F)c5sc(N)c(C#N)c45)c(C#N)cc23)[C@@H]1CC] | |
| 487b | 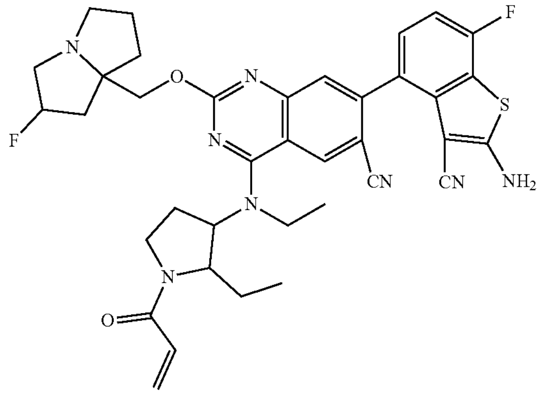 [SMILES: C=CC(=O)N1CCC(N(CC)c2nc(OCC34CCCN3CC(F)C4)nc3cc(-c4ccc(F)c5sc(N)c(C#N)c45)c(C#N)cc23)C1CC] | |
| 488 | 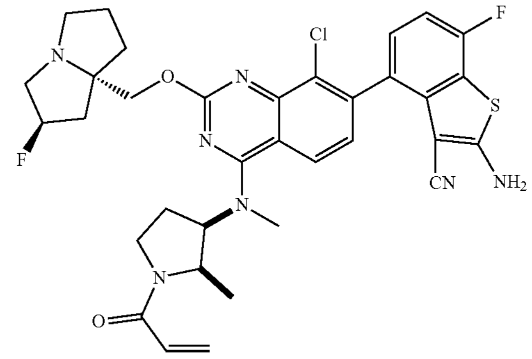 | LCMS m/z [M + 1]: 678.0 $^1$HNMR (400 MHz, $CD_3OD$) δ 8.24 (m, 1 H), 7.41 (d, 1H), 7.22 (m 1H), 7.03 (m, 1H), 6.62-6.69 (m, 1H), 6.30-6.37 (m, 1H), 5.79 (dd, 1H), 5.48 & 5.60 (s, 1H), 4.95-5.11 (m, 2H), 4.56-4.86 (m, 3H), 3.63-4.15 (m, 5H), 3.62 (d, 3H), 3.43-3.52 (m, 1H), 1.92-2.79 (m, 8H), 1.08-2.15 (m, 3H). |
| 489 | 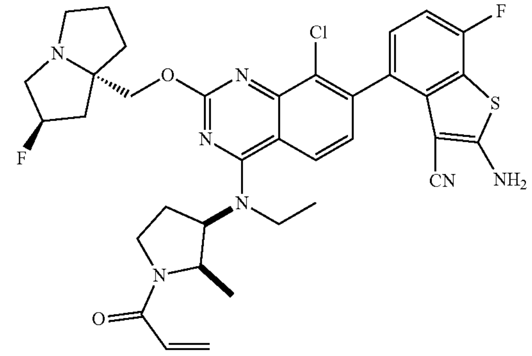 | LCMS m/z [M + 1]: 692.0 $^1$HNMR (400 MHz, $CD_3OD$) δ 8.17 (m, 1H), 7.44 (m, 1H), 7.21 (m, 1H), 7.04 (m, 1H), 6.56-6.67 (m, 1H), 6.28-6.37 (m, 1H), 5.78 (d, 1H), 5.47 & 5.61 (s, 1H), 4.81-5.06 (m, 2H), 4.60-4.82 (m, 3H), 3.41-4.19 (m, 8H), 1.95-2.68 (m, 8H), 1.05-1.09 (m, 3H), 0.98-1.02 (m, 3H). |

TABLE 5-continued

| Selected compounds of the present disclosure. | | |
|---|---|---|
| Compound No. | Structure | Analytical data |
| 489a | 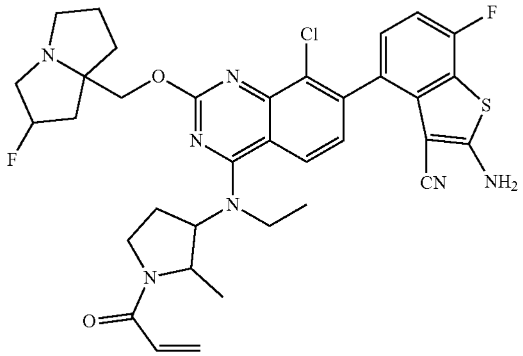 [SMILES: C=CC(=O)N1CCC(N(CC)c2nc(OCC34CCCN3CC(F)C4)nc3c(Cl)c(-c4ccc(F)c5sc(N)c(C#N)c45)ccc23)C1C] | |

Biological Example 1: Covalent Cysteine 12 Modification Analysis Using Matrix Assisted Laser Desorption Ionization—Time of Flight Mass Spectrometry (MALDI-TOF MS)

MALDI-TOF MS analysis was performed using two sets of conditions. Initially, 5 μM protein target, and 1:2.5 protein to compound ratio was used. Later, when compounds become more potent, the target protein concentration was adjusted to 1 μM, with 1:2.5 protein to compound ratio.

Reaction: 5 μM or 1 μM of GppNHp, GTP, or GDP-loaded KRAS4b (amino acids 1-169) G12C/C118S protein (produced in-house by Protein Expression Laboratory, FNLCR/Leidos Biomed) in 20 mM 4-(2-hydroxyethyl)-1-piperazineethanesulfonic acid (HEPES) buffer containing 150 mM NaCl, 1 mM $MgCl_2$, pH 7.3 was prepared freshly before assay. Ten-μL aliquots of protein were dispensed onto low volume 384-well plate, then 375 nL DMSO, and 25 nL of tested compounds from 5 mM DMSO stocks were added to appropriate wells using ECHO 555 acoustic liquid handler (Labcyte Inc.). For each reaction/assay, three blanks were prepared by mixing 10 μL of protein solution with 400 nL DMSO. The contents of the wells were carefully mixed by aspiration, and then each plate was sealed with an adhesive cover, centrifuged at 2000 g for 1 minute, and kept in the dark at room temperature until 5 min, 15 min, 30 min, 2 h, or 6 h collections.

Target pretreatment: Before each assay MALDI target (Bruker MPT 384 ground steel BC) was pre-treated by pipetting on each spot 0.75 μL of saturated sinapinic acid in acetonitrile (ACN). This step significantly improves uniformity of sample crystallization across the plate resulting in enhanced sensitivity.

Sample preparation: At collection time point, 2 μL of reaction mixtures were pipetted out into 20 μL MALDI matrix solution (saturated solution of sinapinic acid in 1:1 ACN:water solution containing 0.75% trifluoroacetic acid (TFA)) deposited on 384 well polypropylene plate. Resulting solution was mixed by aspiration, centrifuged at 2000 g for 1 minute, then 1 μL aliquots were dispensed on pre-treated MALDI target using Beckman Coulter Biomek $FX^P$ 96/384-Span-8 Laboratory Automation Workstation. Finally, the MALDI target was dried under mild vacuum to produce spots with fine crystalline structure.

Measurements: MALDI-TOF measurements were performed on a Bruker Daltonics rapifleX Tissuetyper TOF-TOF mass spectrometer using linear mode and mass range from 18.6 to 21.6 kDa. Detector gain was set to 3.3×(483 V), sample rate to 5 GS/s, real time smoothing to medium (175 MHz), laser smart beam pattern was set to: "MS Thin Layer M5", and the laser frequency was 10000 Hz. Spectra were automatically collected using custom AutoXecute method. Laser power was auto adjusted using fuzzy control. The peak selection range was set to be between 19000 and 21500 Da. Peak evaluation uses half width parameter set to be smaller than 40 Da for processed spectrograms (centroid peak detection; smoothed by SavitzkyGolay algorithm using 7 m/z width and 2 cycles; baseline was subtracted using median algorithm with flatness 1 and median level 0.01). Fuzzy control used Proteins/Oligonucleotides protocol with minimum half width 1/10 times above threshold. Up to 40000 satisfactory shots were collected in 10000 shot steps. Dynamic termination was implemented to finish data collection when peak signal/noise ratio was reaching value of 50.

Spectra processing: Spectra were smoothed by Savitzky-Golay algorithm using 7 m/z width and three cycles. Centroid peak detection algorithm was used with signal to noise threshold set to 6, relative intensity threshold 4%, peak width 10 m/z and median baseline subtraction using flatness of 1 and median level of 0.01. Peak intensity and area under the peak were evaluated and recorded for all peaks between 19,300 Da and 21,550 Da.

Calculation of percent modification: Percent modification was calculated as a ratio of peak height for protein modified by compound to sum of peak height of remaining protein plus peak height for protein modified by compound. If multiple modifications were observed each was calculated as a ratio of peak height for given modification versus sum of peak heights for all observed protein species. Data reported in Table 7 are from 15 minutes reaction time point.

Biological Example 2: Disrupting KRAS G12C-Effector Binding (Protein:Protein Interaction HTRF Assay)

A protein:protein interaction (PPI) Homogeneous Time Resolved Fluorescence (HTRF) assay was used to determine the effectiveness of compounds of the present disclosure in disrupting KRAS G12C protein and effector (RAF1) binding.

The HTRF assay used the following reagents and proteins: 50 nM Avi-KRAS G12C Q25A (1-169) GppNHp/3xFLAG-PI3K CA (157-299); 50 nM Avi-KRAS G12C (1-169) GppNHp/RAF1 RBD-3xFLAG (52-151); 35 nM Avi-PI3K RBD-3xFLAG; Assay Buffer: 50 mM Tris pH 7.5, 100 mM NaCl, 5 mM $MgCl_2$, 0.1% BSA, 0.01% Tween 20, 10% DMSO; Bead Buffer: 50 mM Tris pH 7.5, 0.01% Tween 20; Assay volume: 20 μL (384 well plate-low volume format); and Compound titration: 30-0.02 μM, 3×dilution series.

The HTRF assay employed the following protocol:

Compounds were dispensed in assay plate (384-well, Grenier Bione #784075) using Echo (model 555) with dose response settings: 200 nL final volume, titration from 100 μM as a 10-point dilution series. KRAS proteins were prepared in assay buffer, and dispensed on plates, 5 μL per well, then incubated for 1 h at room temperature, with 700 rpm shaking. RAF1 RBD were prepared in assay buffer, dispensed onto plates, 5 μL per well, and then incubated for 1 h at room temperature, with 700 rpm shaking. Reagent mix was then prepared and dispensed on plates, 10 μL per well, and then incubated for 1 h at room temperature, with 700 rpm shaking.

Plates were analyzed on an Envision plate reader using the following setting: Excitation 320 nm, Bandwidth 75 nm; Emission 615 nm, Bandwidth 85 nm; Gain 100%; Flashes 100; Lag 60 μs. Data was reported as percentage of activity, with DMSO as 100%. Data was plotted and analyzed using Prism 8. Table 6 summarizes parameters used with the Envision plate reader.

TABLE 6

Envision plate reader settings.

| | |
|---|---|
| Top Mirror | TRF LANCE/DELFIA dual enh (D400/630) |
| Excitation Filter | UV2 (TRF) 320 (Bandwith: 75 nm) |
| Emission Filter | APC 665 (Bandwith: 75 nm) |
| 2nd Emission Filter | Europium 615 (Bandwith: 85 nM) |
| Cycle | 2000 |
| Gain (%) | 100 |
| Number of Flashes | 100 |
| Delay (μs) | 60 |
| Total time of windows (μs) | 400 |
| | Flash Lamp |

Biological Example 3: Cell-Based pERK HTRF Assay pERK HTRF assays (Perkin Elmer) were used to determine the effectiveness of compounds of the present disclosure in disrupting KRAS G12C protein/effector signaling in cells.

On Day 1, cells (NCI-H358) were seeded into 96-well plates at $4\times10^4$ cells/well in complete growth media (RPMI, 10% FBS).

On Day 2, cells were treated with compounds at 0.25% DMSO. The source plate was created with compounds diluted in media at 5-fold the final assay concentration. The compounds were run in a 9-point concentration curve starting at 75 μM, with a 3-fold dilution between concentrations. 20 μL was transferred onto the cell plates (final volume in wells was 100 μL). Plates were harvested after 30 min incubation by aspirating media and adding kit-supplied 1× supplemented lysis buffer to all wells (75 μl per well). Plates were then placed on a plate shaker and incubated at 850 rpm for an additional 30 min.

Antibody mixture solution was prepared by diluting aliquoted d2 and Eu Cryptate antibodies 1:20 in kit supplied detection buffer, then mixed the diluted antibodies solutions (1:1 v:v). 4 μL of this solution was then added to a 384-well detection plate (Perkin Elmer; 6008230).

Samples were homogenized by pipetting up and down and then transferred (16 μL of cell lysates) from the 96-well cell culture plate to two wells of the HTRF 384-well detection plate containing the antibody solution. Plates were centrifuged (524 g for 1 min) and allowed to incubate between 4 and 24 h at room temperature. Maximum signal is reached after 4 h incubation time and remains stable over a period of 24 hours. Therefore, readings can be made between 4 and 24 h of incubation. Plates were centrifuged again (524 g for 1 min), and analyzed on the EnVision plate reader using the following settings: Excitation 320 nm, Bandwidth 75 nm; Emission 615 nm, Bandwidth 85 nm; Gain 100%; Flashes 100; Lag 60 μs.

The percent of modification of GppNHp, GTP, or GDP loaded KRAS G12C by MALDI-TOF MS, biochemical Raf1 RBD-KRAS G12C-GppNHp disruption assay $IC_{50}$, and pERK inhibition $IC_{50}$ of selected compounds described herein are shown in Table 7. For percent of modification at 15 minutes (MALDI-TOF MS) of GppNHp, GTP, or GDP loaded KRAS G12C (compounds 94 or before using 5 μM proteins; compound 95 or later using 1 μM proteins): A: percent of modification ≥70%; B: 50≤percent of modification <70%; C: 10%≤percent of modification <50%; D: percent of modification <10%. For Raf1 RBD-KRAS G12C-GppNHp disruption assay: A: $IC_{50}$≤0.5 μM; B: 0.5 μM<$IC_{50}$≤5 μM; C: 5 μM<$IC_{50}$≤20 μM; D: $IC_{50}$>20 μM. For pERK inhibition in H358 cell assay: A: $IC_{50}$≤0.1 μM; B: 0.1 μM<$IC_{50}$≤1 μM; C: $IC_{50}$>1 μM. Blanks in the table represent that compound was not tested in the indicated assay.

TABLE 7

Biological characterization of selected compounds of the present disclosure.

| Compound No. | GppNHp-KRAS G12C percent of modification | GTP-KRAS G12C percent of modification | GDP-KRAS G12C percent of modification | Raf1-GppNHp-KRAS G12C disruption | PERK in H358 cell |
|---|---|---|---|---|---|
| 1 | D | | A | | |
| 2 | C | | A | | |
| 3 | D | | A | | |
| 4 | D | | A | C | |
| 5 | A | | A | B | |
| 7 | D | | A | D | |
| 8 | A | | A | B | |
| 9 | D | | C | | |
| 10 | D | | A | | |
| 11 | D | | A | | |
| 12 | C | | A | | |
| 13 | B | | A | | |
| 14 | D | | C | | |
| 15 | D | | D | | |
| 16 | B | | A | C | |
| 17 | D | | C | | |
| 18 | D | | A | | |
| 19 | D | | C | | |
| 20 | D | | C | D | |
| 21 | D | | D | D | |
| 22 | C | | A | C | |

TABLE 7-continued

Biological characterization of selected compounds of the present disclosure.

| Compound No. | GppNHp-KRAS G12C percent of modification | GTP-KRAS G12C percent of modification | GDP-KRAS G12C percent of modification | Raf1-GppNHp-KRAS G12C disruption | PERK in H358 cell |
|---|---|---|---|---|---|
| 23 | A | | A | A | C |
| 24 | B | | A | B | |
| 25 | D | | A | D | |
| 26 | D | | A | D | |
| 27 | C | | B | C | |
| 28 | D | | A | D | |
| 29 | C | | B | B | |
| 30 | A | | A | A | A |
| 31 | B | | A | B | |
| 32 | D | | A | D | |
| 33 | C | | A | B | |
| 34 | D | | A | D | |
| 36 | A | | A | A | |
| 37 | C | | A | B | |
| 38 | C | | A | C | |
| 39 | C | | A | B | |
| 40 | A | | A | A | B |
| 41 | A | | A | B | |
| 42 | D | | A | C | |
| 43 | C | | A | D | C |
| 44 | C | | A | B | A |
| 45 | A | | A | A | A |
| 46 | D | | B | D | |
| 47 | C | | A | C | |
| 48 | D | | B | D | |
| 49 | A | | A | A | C |
| 50 | D | | C | D | |
| 51 | B | | B | A | B |
| 52 | B | | A | A | C |
| 53 | D | | C | C | C |
| 54 | C | | B | B | B |
| 55 | C | | B | B | C |
| 56 | C | | A | B | |
| 57 | D | | A | D | |
| 58 | A | | A | A | B |
| 59 | D | | A | D | |
| 60 | B | | A | B | C |
| 61 | D | | B | D | |
| 62 | D | | C | D | |
| 63 | A | | A | A | B |
| 64 | D | | B | D | C |
| 65 | C | | A | B | B |
| 66 | C | | A | B | A |
| 67 | A | | A | A | A |
| 68 | D | | B | D | |
| 69 | D | | B | D | C |
| 70 | A | | A | A | C |
| 71 | C | | A | B | A |
| 72 | D | | A | D | C |
| 73 | C | | A | C | |
| 74 | C | | A | C | |
| 75 | D | | A | D | |
| 76 | A | | A | A | |
| 77 | A | | A | A | |
| 78 | D | | D | D | |
| 79 | A | | A | A | C |
| 80 | A | | A | A | A |
| 81 | A | | A | A | B |
| 82 | D | | A | D | A |
| 83 | D | | B | D | |
| 84 | A | | A | A | B |
| 85 | C | | A | B | |
| 86 | C | | A | B | |
| 87 | A | | A | A | |
| 88 | C | | A | B | C |
| 89 | C | | A | B | A |
| 90 | D | | A | D | C |
| 91 | A | | A | A | C |
| 92 | B | | A | A | C |
| 93 | A | | A | A | C |
| 94 | C | | B | B | |
| 95 | A | | A | A | |
| 96 | D | | A | | |
| 97 | C | | A | B | |
| 98 | C | | A | B | |
| 99 | D | | B | B | |
| 106 | C | | A | A | |
| 109 | B | | A | A | |
| 114 | D | | D | D | |
| 118 | D | | C | | C |
| 119 | C | | A | B | C |
| 120 | D | | B | | C |
| 121 | C | | A | B | C |
| 122 | D | | C | | C |
| 126 | D | | D | D | |
| 127 | D | | A | C | |
| 128 | D | | A | B | |
| 129 | D | | A | B | B |
| 131 | D | | B | B | A |
| 132 | D | | C | D | C |
| 133 | D | | A | B | C |
| 134 | D | | B | B | B |
| 138 | D | | A | B | A |
| 139 | C | | A | B | B |
| 140 | D | | B | B | B |
| 141 | D | | A | B | C |
| 142 | D | | D | D | |
| 143 | D | | A | D | |
| 144 | D | | A | D | |
| 145 | D | | C | B | |
| 146 | D | | A | B | |
| 149 | D | | B | B | A |
| 150 | C | | B | B | A |
| 151 | D | | A | B | C |
| 152 | C | | A | B | C |
| 153 | D | | B | B | A |
| 154 | D | | B | D | B |
| 156 | D | | C | D | A |
| 158 | D | | C | D | |
| 159 | C | | C | B | C |
| 160 | | | | C | |
| 161 | D | | A | C | C |
| 162 | C | | A | B | B |
| 163 | D | | A | | B |
| 164 | C | | B | B | |
| 165 | C | | A | A | A |
| 166 | C | | A | A | B |
| 167 | C | | A | B | C |
| 169 | C | | B | B | B |
| 170 | D | | B | C | B |
| 171 | C | | A | B | A |
| 172 | D | | B | B | C |
| 176 | D | | C | B | |
| 177 | C | | A | A | A |
| 178 | D | | C | B | B |
| 180 | D | | C | B | C |
| 181 | D | | B | B | C |
| 183 | D | | C | C | |
| 184 | | | | C | |
| 185 | C | | C | A | B |
| 186 | D | | B | C | B |
| 187 | D | | C | B | B |
| 188 | C | | C | A | B |
| 189 | C | | B | A | A |
| 190 | C | | A | A | A |
| 191 | D | | A | C | B |
| 192 | D | | C | B | A |
| 193 | D | | C | D | C |

TABLE 7-continued

Biological characterization of selected compounds of the present disclosure.

| Compound No. | GppNHp-KRAS G12C percent of modification | GTP-KRAS G12C percent of modification | GDP-KRAS G12C percent of modification | Raf1-GppNHp-KRAS G12C disruption | PERK in H358 cell |
|---|---|---|---|---|---|
| 194 | C | | A | A | A |
| 195 | C | | C | A | A |
| 196 | D | | A | B | A |
| 197 | C | | C | A | C |
| 198 | A | A | A | A | A |
| 199 | D | | B | D | B |
| 200 | D | | B | B | A |
| 201 | C | | A | A | B |
| 202 | A | C | A | A | A |
| 203 | D | | B | B | B |
| 204 | C | | B | A | A |
| 205 | D | | B | B | B |
| 206 | C | | C | A | B |
| 207 | C | | A | A | A |
| 208 | D | | B | C | B |
| 209 | C | | A | B | A |
| 210 | D | | C | D | C |
| 211 | D | | A | C | |
| 212 | C | | A | D | |
| 213 | C | | C | | C |
| 215 | C | | B | A | A |
| 216 | D | | A | B | |
| 217 | D | | B | B | B |
| 218 | C | | A | A | A |
| 219 | C | | A | A | A |
| 220 | D | | D | B | A |
| 221 | D | | D | B | C |
| 222 | A | | A | A | B |
| 223 | B | | A | A | A |
| 224 | D | | A | B | A |
| 225 | D | | A | C | B |
| 226 | A | | A | A | B |
| 227 | C | | A | B | C |
| 228 | C | | A | B | A |
| 229 | D | | D | D | C |
| 230 | C | | C | A | B |
| 231 | D | | A | A | B |
| 232 | D | | D | B | B |
| 233 | D | | A | D | B |
| 234 | D | | C | D | C |
| 235 | C | | A | A | A |
| 236 | B | | A | A | A |
| 237 | D | | D | B | C |
| 238 | B | | A | A | B |
| 239 | A | A | A | A | A |
| 240 | D | | D | B | B |
| 241 | C | | A | A | A |
| 242 | C | | C | A | B |
| 243 | D | | D | B | |
| 244 | B | | A | A | A |
| 245 | D | | D | B | C |
| 246 | C | | A | A | B |
| 247 | C | | A | A | A |
| 248 | D | | A | B | B |
| 249 | A | | A | A | B |
| 250 | D | | A | B | B |
| 251 | D | | D | D | C |
| 252 | A | B | A | A | A |
| 253 | A | A | A | A | A |
| 254 | C | | A | A | B |
| 255 | A | | A | A | A |
| 256 | C | | C | B | A |
| 257 | A | | A | A | A |
| 258 | A | | A | B | A |
| 259 | D | | D | D | |
| 260 | D | | A | D | |
| 261 | D | | B | C | C |
| 262 | D | | D | D | C |
| 263 | D | | B | D | C |

TABLE 7-continued

Biological characterization of selected compounds of the present disclosure.

| Compound No. | GppNHp-KRAS G12C percent of modification | GTP-KRAS G12C percent of modification | GDP-KRAS G12C percent of modification | Raf1-GppNHp-KRAS G12C disruption | PERK in H358 cell |
|---|---|---|---|---|---|
| 264 | D | | D | D | C |
| 265 | C | | A | A | A |
| 266 | C | | A | A | A |
| 267 | A | B | A | A | A |
| 268 | D | D | D | B | A |
| 269 | B | | A | A | A |
| 270 | A | | A | A | A |
| 271 | A | | A | A | A |
| 272 | D | | D | B | C |
| 273 | D | | C | B | B |
| 274 | A | A | A | A | A |
| 275 | A | A | A | A | A |
| 276 | C | | A | A | A |
| 277 | A | A | A | A | A |
| 278 | D | D | D | B | B |
| 279 | A | A | A | A | A |
| 280 | C | | A | | A |
| 281 | B | | A | A | A |
| 282 | D | | B | C | C |
| 283 | D | | A | B | C |
| 284 | D | | D | B | C |
| 285 | D | | B | B | A |
| 286 | D | | B | A | A |
| 287 | A | B | B | A | A |
| 288 | B | B | A | A | A |
| 289 | C | | C | A | A |
| 290 | A | A | A | A | A |
| 291 | B | | A | A | A |
| 292 | C | C | B | A | B |
| 293 | A | C | A | A | A |
| 294 | C | C | A | B | A |
| 295 | C | D | B | A | A |
| 296 | A | | A | A | A |
| 297 | A | C | A | A | A |
| 298 | B | C | A | A | A |
| 299 | C | D | A | A | A |
| 300 | A | A | A | A | A |
| 301 | C | D | A | B | A |
| 302 | A | A | A | A | A |
| 303 | D | D | D | C | B |
| 304 | A | C | A | A | A |
| 305 | A | A | A | A | A |
| 306 | A | B | B | A | A |
| 307 | D | D | C | D | A |
| 308 | C | C | C | A | A |
| 309 | A | B | A | A | A |
| 310 | D | D | C | D | C |
| 311 | A | A | A | A | A |
| 312 | B | D | A | A | A |
| 313 | A | A | A | A | A |
| 314 | D | D | D | C | B |
| 315 | A | A | A | A | A |
| 316 | A | A | A | A | A |
| 317 | A | A | A | A | A |
| 318 | A | B | A | A | A |
| 319 | A | A | A | A | A |
| 320 | A | A | A | A | A |
| 321 | A | B | A | A | A |
| 322 | C | C | B | A | A |
| 323 | A | B | A | A | A |
| 324 | A | C | A | A | A |
| 325 | A | A | A | A | A |
| 326 | D | D | A | B | A |
| 327 | A | A | A | A | A |
| 328 | C | D | C | A | A |
| 329 | A | B | A | A | A |
| 330 | D | D | C | B | B |
| 331 | C | D | B | A | A |
| 332 | D | D | D | D | C |

TABLE 7-continued

Biological characterization of selected compounds of the present disclosure.

| Compound No. | GppNHp-KRAS G12C percent of modification | GTP-KRAS G12C percent of modification | GDP-KRAS G12C percent of modification | Raf1-GppNHp-KRAS G12C disruption | PERK in H358 cell |
|---|---|---|---|---|---|
| 333 | A | C | A | A | A |
| 334 | A | C | B | A | A |
| 335 | A | A | A | A | A |
| 336 | D | D | D | B | B |
| 337 | B | C | B | A | A |
| 338 | C | D | C | A | A |
| 339 | A | A | A | A | A |
| 340 | C | C | C | A | A |
| 341 | A | A | A | A | A |
| 342 | A | A | A | A | A |
| 343 | C | C | C | A | A |
| 345 | A | A | A | A | A |
| 346 | A | A | A | A | A |
| 347 | A | A | A | A | A |
| 348 | A | A | A | A | A |
| 349 | C | C | B | A | A |
| 350 | A | C | A | A | A |
| 351 | A | A | A | A | A |
| 352 | A | A | A | A | A |
| 353 | A | A | A | A | A |
| 354 | A | A | A | A | A |
| 355 | B | C | A | A | A |
| 356 | A | B | A | A | A |
| 357 | A | A | A | A | A |
| 358 | A | A | A | A | A |
| 359 | A | A | A | A | A |
| 360 | A | B | A | A | B |
| 361 | B | B | A | A | A |
| 362 | B | B | B | A | A |
| 363 | A | C | A | A | A |
| 364 | A | C | A | A | A |
| 365 | A | B | A | A | A |
| 366 | A | B | A | A | A |
| 367 | A | B | A | A | A |
| 368 | A | A | A | A | A |
| 369 | A | A | A | A | A |
| 370 | B | B | B | A | A |
| 372 | A | A | A | A | A |
| 373 | A | A | A | A | B |
| 374 | A | A | A | A | A |
| 375 | B | B | B | A | A |
| 376 | A | A | A | A | A |
| 377 | A | B | A | A | A |
| 378 | D | D | B | D | B |
| 379 | A | A | A | A | A |
| 380 | B | C | C | A | A |
| 381 | A | B | A | A | A |
| 382 | C | D | A | A | A |
| 383 | C | C | A | A | A |
| 384 | C | D | B | B | A |
| 385 | D | D | C | B | A |
| 386 | A | B | A | A | A |
| 387 | A | A | A | A | A |
| 388 | A | A | A | A | A |
| 389 | A | A | A | A | A |
| 390 | A | A | A | A | A |
| 391 | A | A | A | A | A |
| 392 | C | C | B | A | A |
| 393 | A | A | A | A | A |
| 394 | A | A | A | A | B |
| 395 | A | A | A | A | A |
| 396 | B | B | A | A | A |
| 397 | C | C | C | A | A |
| 398 | A | A | A | A | A |
| 399 | A | B | B | A | A |
| 400 | A | A | A | A | A |
| 401 | C | C | A | A | A |
| 402 | A | A | A | A | A |
| 403 | C | D | C | A | A |
| 404 | A | A | A | A | B |
| 405 | B | C | A | A | A |
| 406 | C | C | C | A | A |
| 407 | C | C | C | A | A |
| 408 | C | C | B | A | A |
| 409 | A | A | A | A | A |
| 410 | A | B | A | A | A |
| 411 | C | C | B | A | A |
| 412 | A | A | A | A | B |
| 413 | A | A | A | A | B |
| 414 | A | A | A | A | A |
| 415 | A | A | A | A | A |
| 416 | A | A | A | A | A |
| 417 | A | A | A | A | B |
| 418 | B | C | B | A | B |
| 419 | B | C | A | A | A |
| 420 | A | A | A | A | A |
| 421 | A | A | A | A | A |
| 422 | B | C | A | A | A |
| 423 | A | A | A | A | A |
| 424 | A | A | A | A | A |
| 425 | D | D | C | B | B |
| 426 | B | B | B | A | A |
| 427 | C | C | C | A | A |
| 428 | B | C | A | A | B |
| 429 | A | A | A | A | A |
| 430 | A | A | A | A | A |
| 431 | A | A | A | A | A |
| 432 | A | A | A | A | B |
| 433 | A | A | A | A | A |
| 434 | A | A | A | A | A |
| 435 | D | D | D | D | C |
| 436 | A | A | A | A | A |
| 437 | A | B | A | A | B |
| 438 | A | B | A | A | A |
| 439 | A | A | A | A | B |
| 440 | B | C | A | A | B |
| 441 | A | B | A | A | B |
| 442 | B | B | A | A | A |
| 443 | C | C | B | A | A |
| 444 | A | C | A | A | A |
| 445 | B | B | B | A | A |
| 446 | A | A | A | A | B |
| 447 | A | C | A | A | A |
| 448 | D | D | A | B | B |
| 449 | D | D | B | B | B |
| 450 | A | A | A | A | A |
| 451 | B | B | A | A | A |
| 453 | C | C | C | A | A |
| 454 | B | B | A | A | A |
| 455 | A | A | A | A | B |
| 456 | A | A | A | A | A |
| 457 | D | D | D | D | D |
| 458 | A | B | A | A | A |
| 461 | D | D | C | B | C |
| 462 | D | D | C | B | C |
| 463 | D | D | C | B | C |
| 464 | B | C | A | B | A |
| 465 | A | A | A | A | B |
| 466 | D | D | C | B | C |
| 467 | B | C | A | A | A |
| 468 | D | D | C | B | B |
| 469 | A | A | A | A | A |
| 470 | B | C | A | A | B |
| 471 | C | D | C | A | B |
| 472 | B | C | A | A | A |
| 473 | C | D | C | A | A |
| 474 | A | C | A | A | A |
| 475 | A | B | A | A | A |

TABLE 7-continued

Biological characterization of selected compounds of the present disclosure.

| Compound No. | GppNHp-KRAS G12C percent of modification | GTP-KRAS G12C percent of modification | GDP-KRAS G12C percent of modification | Raf1-GppNHp-KRAS G12C disruption | PERK in H358 cell |
|---|---|---|---|---|---|
| 476 | C | C | A | A | A |
| 477 | B | C | A | A | A |

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations, and equivalents. It is intended that the following claims define the scope of the invention and that methods and structures within the scope of these claims and their equivalents be covered thereby.

The invention claimed is:

1. A compound selected from:

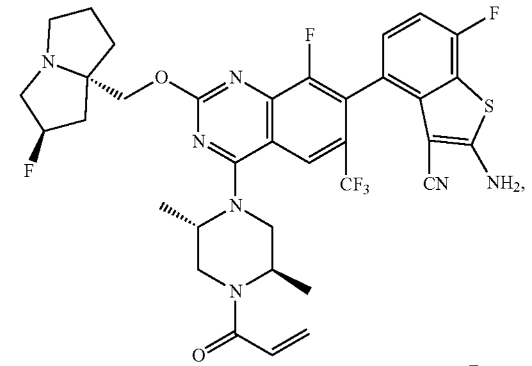

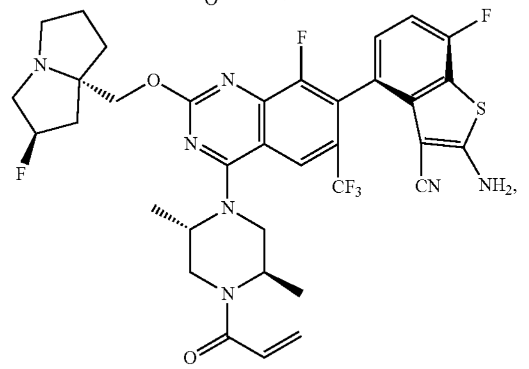

and

-continued

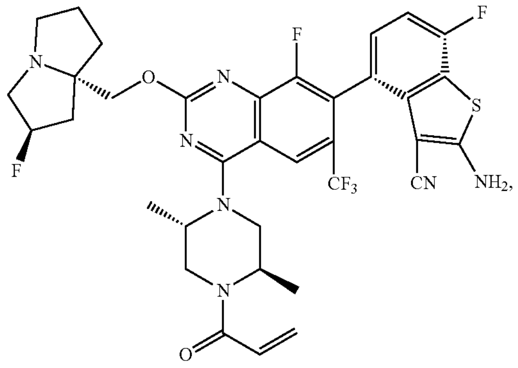

or a pharmaceutically acceptable salt thereof.

2. A compound having the structure:

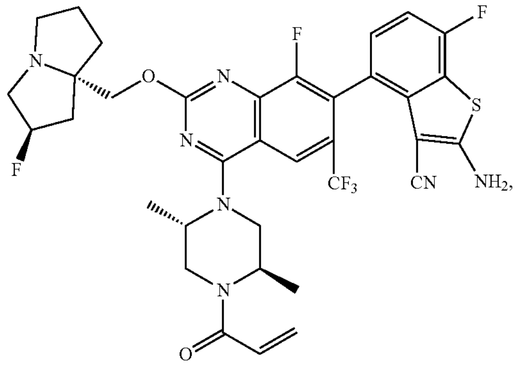 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)c(C(F)(F)F)cc23)C[C@H]1C]

or a pharmaceutically acceptable salt thereof.

3. A compound having the structure:

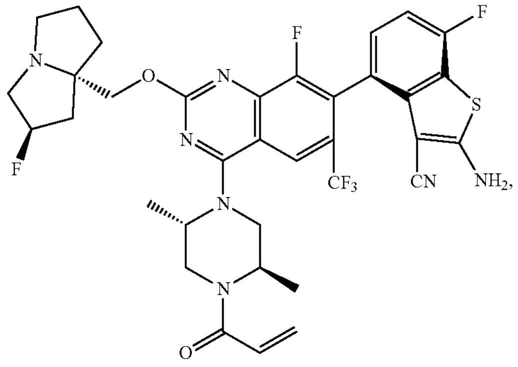

or a pharmaceutically acceptable salt thereof.

4. A compound having the structure:

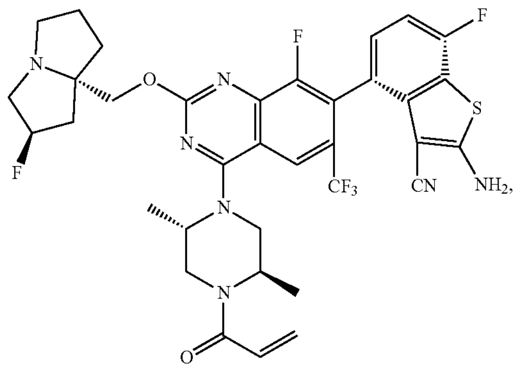

or a pharmaceutically acceptable salt thereof.

5. A compound of claim 1, wherein the compound is selected from:

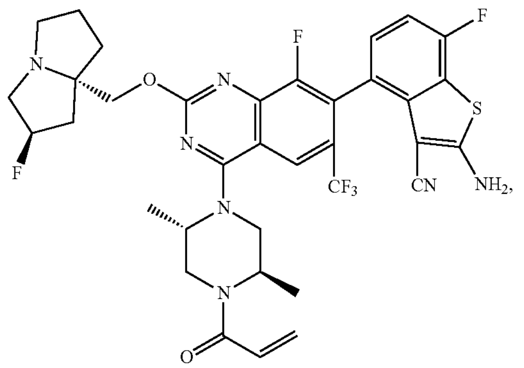

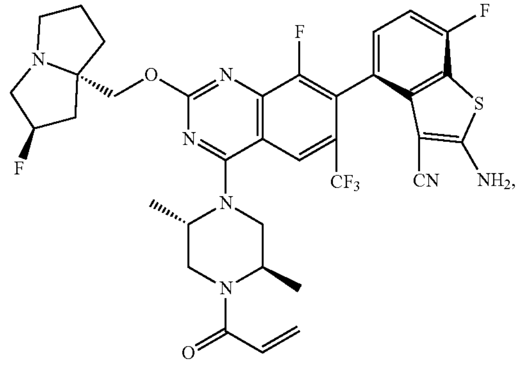

and

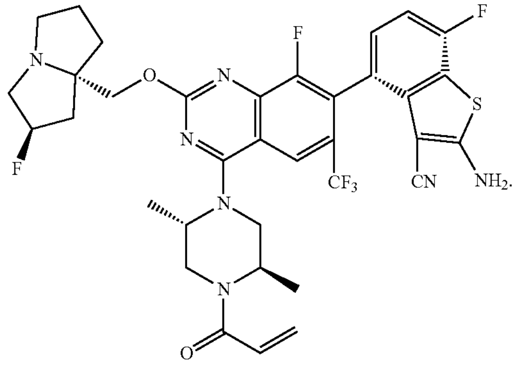

6. The compound of claim 2, wherein the compound is

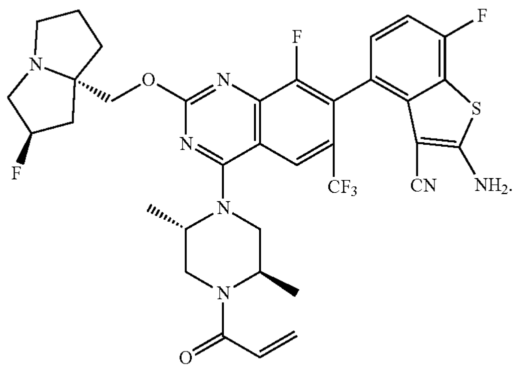 [SMILES: C=CC(=O)N1C[C@H](C)N(c2nc(OC[C@@]34CCCN3C[C@H](F)C4)nc3c(F)c(-c4ccc(F)c5sc(N)c(C#N)c45)c(C(F)(F)F)cc23)C[C@H]1C]

7. The compound of claim 3, wherein the compound is

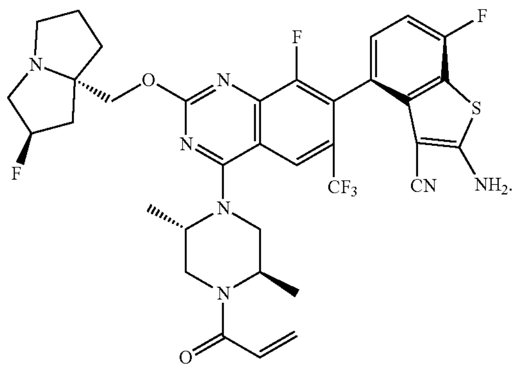

8. The compound of claim 4, wherein the compound is

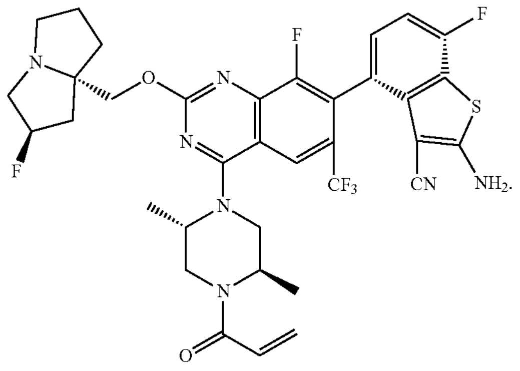

9. A pharmaceutical composition comprising a compound of claim 1, or a pharmaceutically acceptable salt thereof.

10. The pharmaceutical composition of claim 9, wherein the compound is

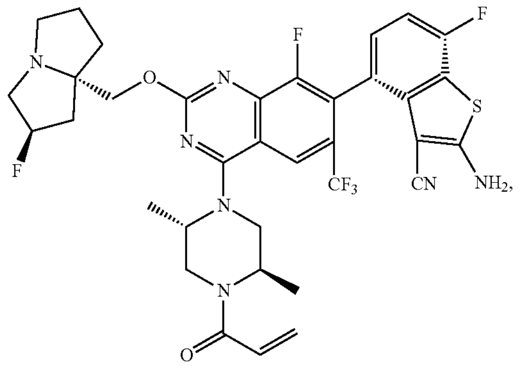

or a pharmaceutically acceptable salt thereof.

11. The pharmaceutical composition of claim 9, wherein the compound is

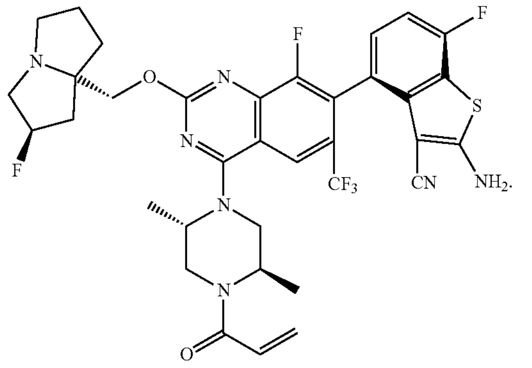

or a pharmaceutically acceptable salt thereof.

12. The pharmaceutical composition of claim 9, wherein the compound is

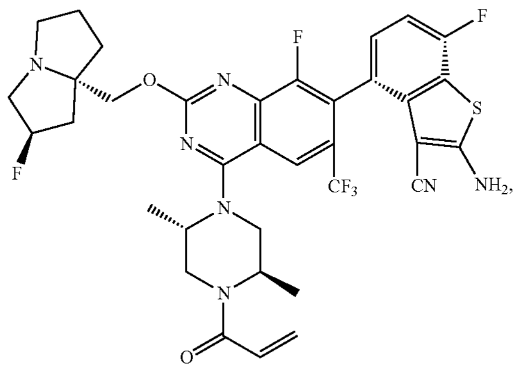

or a pharmaceutically acceptable salt thereof.

13. A pharmaceutical composition comprising a compound of claim 5.

14. The pharmaceutical composition of claim 13, wherein the compound is

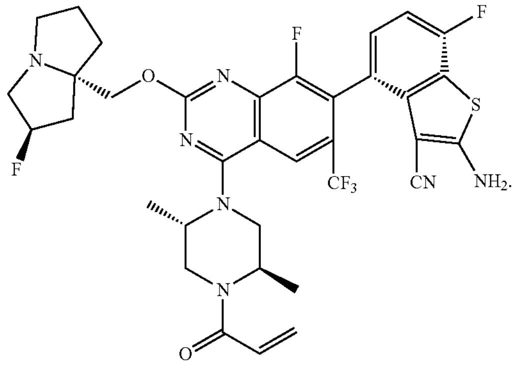

15. The pharmaceutical composition of claim 13, wherein the compound is

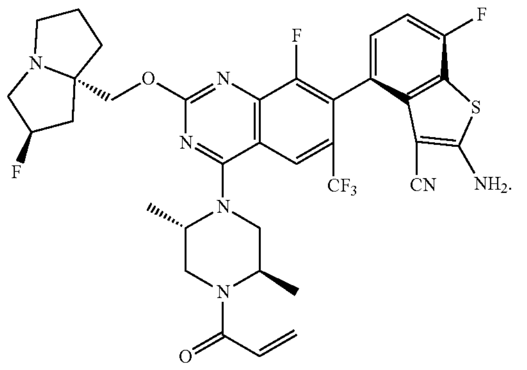

16. The pharmaceutical composition of claim 13, wherein the compound is

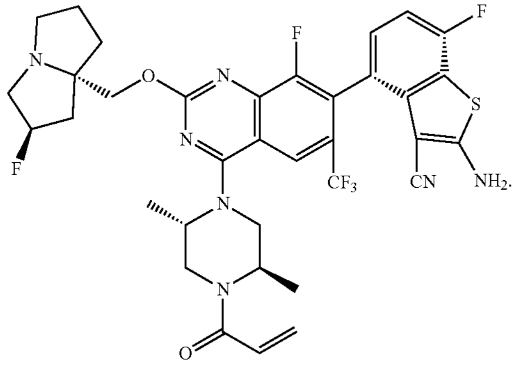

* * * * *